US008798939B2

(12) United States Patent
Leonard et al.

(10) Patent No.: US 8,798,939 B2
(45) Date of Patent: Aug. 5, 2014

(54) METHODS FOR DESIGNING, SELECTING AND/OR OPTIMIZING ALLOSTERIC PROCESSING INHIBITORS FOR MATRIX METALLOPROTEINASES

(75) Inventors: Kristi A. Leonard, Lansdale, PA (US); Richard Scott Alexander, Newark, DE (US); Joseph Kent Barbay, Flourtown, PA (US); Roger F. Bone, Bridgewater, NJ (US); Ingrid Christa Deckman, Berwyn, PA (US); Paul F. Jackson, Furlong, PA (US); Lawrence C. Kuo, Gwynedd Valley, PA (US); Frank A. Lewandowski, Philadelphia, PA (US); Diane M. Maguire, Downingtown, PA (US); Cynthia M. Milligan, Rutledge, PA (US); Kenneth J. Rhodes, Belmont, MA (US); Robert H. Scannevin, Hopkinton, MA (US); Celine Schalk-Hihi, Phoenixville, PA (US); Barry Springer, Wilmington, DE (US); John C. Spurlino, Downingtown, PA (US); Matthew J. Todd, Ambler, PA (US); Brett A. Tounge, Blue Bell, PA (US); Aihua Wang, Jamison, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 13/533,201

(22) Filed: Jun. 26, 2012

(65) Prior Publication Data

US 2013/0166268 A1    Jun. 27, 2013

Related U.S. Application Data

(60) Provisional application No. 61/502,516, filed on Jun. 29, 2011.

(51) Int. Cl.
*G01N 33/48* (2006.01)
*G01N 33/50* (2006.01)
*G01N 31/00* (2006.01)

(52) U.S. Cl.
USPC .............................................. 702/27; 702/19

(58) Field of Classification Search
None
See application file for complete search history.

(56) References Cited

U.S. PATENT DOCUMENTS

| | | |
|---|---|---|
| 4,906,122 A | 3/1990 | Barrett et al. |
| 5,030,103 A | 7/1991 | Buist et al. |
| 5,200,910 A | 4/1993 | Subbiah |
| 5,365,456 A | 11/1994 | Subbiah |
| 5,583,973 A | 12/1996 | DeLisi et al. |
| 5,612,894 A | 3/1997 | Wertz |
| 5,733,720 A | 3/1998 | Olivo |
| 5,763,263 A | 6/1998 | Dehlinger |
| 5,942,428 A | 8/1999 | Mohammadi et al. |
| 5,994,503 A | 11/1999 | Xu et al. |
| 5,998,593 A | 12/1999 | Huff et al. |
| 6,037,117 A | 3/2000 | Qiu et al. |
| 6,071,700 A | 6/2000 | He et al. |
| 6,075,014 A | 6/2000 | Weston et al. |
| 6,075,123 A | 6/2000 | Lahti et al. |
| 6,080,576 A | 6/2000 | Zambrowicz et al. |
| 6,093,573 A | 7/2000 | Beamer et al. |
| 2013/0040360 A1 | 2/2013 | Leonard et al. |
| 2013/0040994 A1 | 2/2013 | Leonard et al. |

FOREIGN PATENT DOCUMENTS

| | | |
|---|---|---|
| WO | WO 03/067219 A2 | 8/2003 |
| WO | WO 2006/101740 A2 | 9/2006 |

OTHER PUBLICATIONS

International Search Report relating to co-pending International Patent Application No. PCT/US2012/044217, filed Jun. 26, 2012. Date of Mailing of International Search Report: Aug. 9, 2013.
Written Opinion of the International Search Authority relating to co-pending International Patent Applcation No. PCT/US2012/044217, filed Jun. 26, 2012. Date of Mailing of Written Opinion: Aug. 9, 2013.
International Search Report relating to International Patent Application No. PCT/US2012/044205, filed Jun. 26, 2012; which relates to co-pending U.S. Patent Publication No. 2013-0040360. Date of Mailing of International Search Report: Nov. 21, 2012.
Written Opinion of the International Search Authority relating to International Patent Applcation No. PCT/US2012/044205, filed Jun. 26, 2012; which relates to co-pending U.S. Patent Publication No. 2013-004036. Date of Mailing of Written Opinion: Nov. 21, 2012.
International Search Report relating to International Patent Application No. PCT/US2012/044221, filed Jun. 26, 2012; which relates to co-pending U.S. Patent Publication No. 2013-0040994. Date of Mailing of International Search Report: Nov. 19, 2012.

(Continued)

*Primary Examiner* — Michael Borin

(57) ABSTRACT

The present invention includes a crystal comprising a complex of the pro form of a matrix metalloprotease (proMMP) and a small-molecule allosteric processing inhibitor that inhibits that activation of the proMMP, methods for identifying small-molecule allosteric processing inhibitors that inhibit the activation of a proMMP, and methods of treatment using small-molecule allosteric processing inhibitors that inhibit the activation of a proMMP. The present invention relates to the crystal structure of a complex of proMMP9 bound to a small-molecule allosteric processing inhibitor that inhibits activation of proMMP9. The invention further relates to the use of the methods and the crystal and related structural information for designing, selecting and/or optimizing small-molecule allosteric processing inhibitors that inhibit activation of proMMP9 and proMMP9 homologues. The present invention also relates to the use of small-molecule allosteric processing inhibitors for the treatment of diseases mediated by inappropriate matrix metalloproteinase (MMP) activity.

4 Claims, 12 Drawing Sheets

(56) References Cited

OTHER PUBLICATIONS

Written Opinion of the International Search Authority relating to International Patent Applcation No. PCT/US2012/044221, filed Jun. 26, 2012; which relates to co-pending U.S. Patent Publication No. 2013-0040994. Date of Mailing of Written Opinion: Nov. 19, 2012.
Adair et al., "Measurement of gelatinase B (MMP-9) in the cerebrospinal fluid of patients with vascular dementia and Alzheimer disease.", *Stroke*, 2004, pp. e159-162, vol. 35(6).
Adams et al., "PHENIX: building new software for automated crystallographic structure determination.", *Acta Crystallogr D Biol Crystallogr*, 2002, pp. 1948-1954, vol. 58(Pt 11).
Altschul et al., "Issues in searching molecular sequence databases.", *Nature Genetics*, 1994, pp. 119-129, vol. 6.
Altschul, S. F., "A protein alignment scoring system sensitive at all evolutionary distances.", *J. Mol. Evol.*, 1993, pp. 290-300, vol. 36.
Asahi et al. (2000). "Role for matrix metalloproteinase 9 after focal cerebral ischemia: effects of gene knockout and enzyme inhibition with BB-94.", *J Cereb Blood Flow Metab*, 2000, pp. 1681-1690, vol. 20(12).
Bacon et al., "Docking by Least-squares Fitting of Molecular Surface Patterns.", *J.Mol.Biol.*, 1992, pp. 849-858, vol. 225.
Bartlett et al., "CAVEAT: A Program to Facilitate the Structure-Derived Design of Biologically Active Molecules.", in *Molecular Recognition in Chemical and Biological Problems*, 1989, pp. 182-196, vol. 78, Special Pub., Royal Chem. Soc.
Becker et al., "Stromelysin-1: three-dimensional structure of the inhibited catalytic domain and of the C-truncated proenzyme.", *Protein Sci*, 1995, pp. 1966-1976, vol. 4(10).
Berge et al., "Pharmaceutical salts.", *J Pharm Sci.*, 1977, pp. 1-19, vol. 66(1).
Bohm, H.-J., "The Computer Program LUDI: A New Method for the De Novo Design of Enzyme Inhibitors.", *J. Computer-Aided Molecular Design*, 1992, pp. 61-78, vol. 6.
Cohen et al., "Molecular Modeling Software and Methods for Medicinal Chemistry.", *J. Med. Chem.*, 1990, pp. 883-894, vol. 33.
Cromartie et al., "Arthritis in rats after systemic injection of *Streptococcal* cells or cell walls.", *J Exp Med.*, 1977, pp. 1585-1602, vol. 146(6).
Cunningham et al., "Multiple roles for MMPs and TIMPs in cerebral ischemia.", *Glia*, 2005, pp. 329-339, vol. 50(4).
Doherty et al., "Therapeutic developments in matrix metalloproteinase inhibition.", *Expert Opinion on Therapeutic Patents*, 2002, pp. 665-707, vol. 12(5).
Duncan et al., "Human matrix metalloproteinase-9: activation by limited trypsin treatment and generation of monoclonal antibodies specific for the activated form.", *Eur J Biochem*, 1998, pp. 37-43, vol. 258(1).
Elkins et al., "Structure of the C-terminally truncated human ProMMP9, a gelatin-binding matrix metalloproteinase.", *Acta Crystallogr D Biol Crystallogr*, 2002, pp. 1182-1192, vol. 58(Pt 7).
Emsley et al., "Coot: model-building tools for molecular graphics.", *Acta Crystallogr D, Biol Crystallogr*, 2004, pp. 2126-2132, vol. D60.
Fang et al., "Dog mast cell α-chymase activates progelatinase B by cleaving the Phe[88]-Gln89 and Phe91-Glu92 bonds of the catalytic domain.", *J Biol Chem*, 1997, pp. 25628-25835, vol. 272(41).
Frederiks et al., "Metabolic mapping of proteinase activity with emphasis on in situ zymography of gelatinases: review and protocols.", *J Histochem Cytochem*, 2004, pp. 711-722, vol. 52(6).
George, S. J., "Therapeutic potential of matrix metalloproteinase inhibitors in atherosclerosis.", *Expert Opin Investig Drugs*, 2000, pp. 993-1007, vol. 9(5).
Goodford, P. J., "A Computational Procedure for Determining Energetically Favorable Binding Sites on Biologically Important Macromolecules.", *J. Med. Chem.*, 1985, pp. 849-857, vol. 28.
Goodsell et al., "Automated Docking of Substrates to Proteins by Simulated Annealing.", *Proteins: Structure. Function, and Genetics*, 1990, pp. 195-202, vol. 8.
Gould, P. L., "Salt selection for basic drugs.", *International Journal of Pharmaceutics*, 1986, pp. 201-2017, vol. 33(1-3).

Gruber et al., "Markedly elevated serum MMP-9 (gelatinase B) levels in rheumatoid arthritis: a potentially useful laboratory marker.", *Clin Immunol Immunopathol*, 1996 pp. 161-171, vol. 78(2).
Gu et al., "A highly specific inhibitor of matrix metalloproteinase-9 rescues laminin from proteolysis and neurons from apoptosis in transient focal cerebral ischemia.", *J Neurosci*, 2005, pp. 6401-6408, vol. 25(27).
Gursoy-Ozdemir et al., "Cortical spreading depression activates and upregulates MMP-9.", *J Clin Invest*, 1004, 2004, pp. 1447-1455, vol. 113(10).
Handsley et al., "Metalloproteinases and their inhibitors in tumor angiogenesis.", *Int J Cancer*, 2005, pp. 849-860, vol. 115(6).
Haringman et al., "Synovial tissue macrophages: a sensitive biomarker for response to treatment in patients with rheumatoid arthritis.", *Ann Rheum Dis*, 2005, pp. 834-838, vol. 64(6).
Henikoff, J. G., "Amino acid substitution matrices from protein blocks.", *Proc. Natl. Acad. Sci.*, 1992, pp. 10915-10919, vol. 89.
Iannone et al., "The pathophysiology of osteoarthritis.", *Aging Clin Exp Res*, 2003, pp. 264-372, vol. 15(5).
Jozic et al., "X-ray structure of human proMMP-1: new insights into procollagenase activation and collagen binding.", *J Biol Chem*, 2005, pp. 9578-9585, vol. 280(10).
Jung et al., "Pathogenic Aβ induces the expression and activation of matrix metalloproteinase-2 in human cerebrovascular smooth muscle cells.", *J Neurochem*, 2003, pp. 1208-1215, vol. 85(5).
Karlin et al., "Methods for assessing the statistical significance of molecular sequence features by using general scoring schemes.", *Proc. Natl. Acad. Sci.*, 1990, pp. 2264-2268, vol. 87, USA.
Kissinger et al., "Rapid automated molecular replacement by evolutionary search.", *Acta Crystallogr D Biol Crystallogr*, 1999, pp. 484-491, vol. 55(2).
Klostermeier et al., "Time-resolved fluorescence resonance energy transfer: a versatile tool for the analysis of nucleic acids.", *Biopolymers*, 2001, pp. 159-179, vol. 61(3).
Kuntz et al., "A geometric approach to macromolecule-ligand interactions.", *J Mol Biol*, 1982, pp. 269-288, vol. 161(2).
Lang et al., "Crystal Structure of the Catalytic Domain of MMP-16/MT3-MMP: Characterization of MT-MMP Specific Features.", *J. Mol. Biol.*, 2004, pp. 213-225, vol. 336.
Leach, A., "Molecular Modelling, Principles and Application; The use of molecular modelling and chemoinformatics to discover and design new molecules.", *Molecular Modelling: Principles and Applications*, Jan. 1, 2001, pp. 640-726, XP002444241.
Lipinski et al., "Experimental and computational approaches to estimate solubility and permeability in drug discovery and development settings", *Advanced Drug Delivery Reviews*, 1997, pp. 3-25, vol. 23(1-3).
Lorenzl et al., "Increased plasma levels of matrix metalloproteinase-9 in patients with Alzheimer's disease.", *Neurochem Int*, 2003, pp. 191-196, vol. 43(3).
Lorenzl et al., "Matrix metalloproteinase-9 is elevated in 1-methyl-4-phenyl-1,2,3,6-tetrahydropyridine-induced parkinsonism in mice.", *Neuromolecular Med*, 2004, pp. 119-131, vol. 5(2).
Losso et al., "Inhibition of matrix metalloproteinase-1 activity by the soybean Bowman-Birk inhibitor.", *Biotechnol Lett*, 2004, pp. 901-905, vol. 26(11).
Martin, Y. C., "3D Database Searching in Drug Design.", *J. Med. Chem.*, 1992, pp. 2145-2154, vol. 35.
Matteucci et al., "Synthesis of Deoxyoligonucleotides on a Polymer Support.", *J. Am. Chem. Soc.*, 1981, pp. 3185, vol. 103.
Matulis et al., "Thermodynamic stability of carbonic anhydrase: measurements of binding affinity and stoichiometry using ThermoFluor.", *Biochemistry*, 2005, pp. 5258-5266, vol. 44(13).
Meng et al., "Automated docking with grid-based energy evaluation.", *J. Comp. Chem.*, 1992, pp. 505-524, vol. 13.
Miranker et al., "Functionality Maps of Binding Sites: A Multiple Copy Simultaneous Search Method.", *Proteins: Structure, Function and Genetics*, 1991, pp. 29-34, vol. 1.
Morgunova et al., "Structure insight into the complex formation or latent matrix metalloproteinase 2 with tissue inhibitor of metallproteinase 2.", *PNAS*, May 28, 2002, pp. 7414-7419, vol. 99(11).

(56) References Cited

OTHER PUBLICATIONS

Morgunova et al., "Structure of human pro-matrix metalloproteinase-2: activation mechanism revealed.", Science, 1999, pp. 1667-1670, vol. 284(5420).
Nagase, H., "Activation mechanisms of matrix metalloproteinases.", Biol Chem, 1997, pp. 151-160, vol. 378(3-4).
Navia et al., "The Use of Structural Information in Drug Design.", Current Opinions in Structural Biology, 1992, pp. 202-210, vol. 2.
Nishibata et al., "Automatic creation of drug candidate structures based on receptor structure. Starting point for artificial lead generation.", Tetrahedron, 1991, pp. 8985-8990, vol. 47.
Norton, P. A. and J. M. Coffin (1985). "Bacterial beta-galactosidase as a marker of *Rous sarcoma virus* gene expression and replication.", Mol Cell Biol, 1985, pp. 281-291, vol. 5(2).
Ogata et al., "Matrix metalloproteinase 3 (stromelysin) activates the precursor for the human matrix metalloproteinase 9.", J Biol Chem, 1992, pp. 2581-2584, vol. 267(6).
Opdenakker et al., "Functional roles and therapeutic targeting of gelatinase B and chemokines in multiple sclerosis.", Lancet Neurol, 2003, pp. 747-756, vol. 2(12).
Pantoliano et al., "High-density miniaturized thermal shift assays as a general strategy for drug discovery.", J Biomol Screen, 2001, pp. 429-440, vol. 6(6).
Pflugrath, J. W., "The finer things in X-ray diffraction data collection.", Acta Crystallogr D Biol Crystallogr, 1999, pp. 1718-1725, vol. 55(10).
Ra et al., "Control of matrix metalloproteinase catalytic activity.", Matrix Biology, Oct. 1, 2007, pp. 587-596, vol. 26(8), Elsevier, NL, XP022369657.
Ramos-Desimone et al., "Inhibition of matrix metalloproteinase 9 activation by a specific monoclonal antibody.", Hybridoma, 1993, pp. 349-363, vol. 12(4).
Richards et al., "Suppression of chronic *streptococcal* cell wall-induced arthritis in Lewis rats by liposomal clodronate.", Rheumatology, 2001, pp. 978-987, vol. 40(9).
Rosenblum et al., "Molecular Structures and Dynamics of the Stepwise Activation Mechanism of a Matris Metalloproteinase Xymogen: Challenging the Cysteine Switch Dogma.", Journal of the American Chemical Society, Nov. 1, 2007,pp. 13566-13574, vol. 129(44), XP55042621.
Rotstein et al., "GroupBuild: a fragment-based method for de novo drug design.", J Med Chem, 1993, pp. 1700-1710, vol. 36(12).
Rowsell et al., "Crystal structure of human MMP9 in complex with a reverse hydroxamate inhibitor.", J Mol Biol., 2002, pp. 173-181, vol. 319(1).
Rundhaug, J. E., "Matrix metalloproteinases and angiogenesis.", J Cell Mol Med., 2005, pp. 267-285, vol. 9(2).
Sela-Passwell et al., "Structural and functional bases for allosteric control of MMP activities: Can it pave the path for selective inhibition ?", Biochimica et Biophysica Acta, Molecular Cell Research, Jan. 1, 2010, pp. 29-38, vol. 1803(1), Elsevier Science Publishers, Amsterdam, NL, XP02694661.

Skold et al., "Human neutrophil elastase augments fibroblast-mediated contraction of released collagen gels.", Am J Respir Crit Care Med, 1999, pp. 1138-1146, vol. 159.
Sung et al., "Proteolytic cleavage of extracellular secreted {alpha}-synuclein via matrix metalloproteinases.", J Biol Chem, 2005, pp. 25216-25224, vol. 280(26).
Tayebjee et al., "Matrix metalloproteinases in coronary artery disease: clinical and therapeutic implications and pathological significance.", Curr Med Chem, 2005, pp. 917-925, vol. 12(8).
Taylor et al., "Role for matrix metalloproteinase 9 in granuloma formation during pulmonary Mycobacterium tuberculosis infection.", Infect Immun, 2006, pp. 6135-6144, vol. 74(11).
Tchougounova et al., "A key role for mast cell chymase in the activation of pro-matrix metalloprotease-9 and pro-matrix metalloprotease-2.", *J Biol Chem*, 2005, pp. 9291-9296, vol. 280(10).
Tochowicz et al., "Crystal structures of MMP-9 complexes with five inhibitors: contribution of the flexible Arg424 side-chain to selectivity.", J Mol Biol, 2007, pp. 989-1006, vol. 371(4).
Travis, J., "Proteins and Organic Solvents Make an Eye-Opening Mix.", Science, 1993, pp. 1374, vol. 262.
Van Wart et al., "The cysteine switch: a principle of regulation of metalloproteinase activity with potential applicability to the entire matrix metalloproteinase gene family.", Proc Natl Acad Sci, 1990, pp. 5578-5582, vol. 87(14).
Vihinen et al., "Matrix metalloproteinases as therapeutic targets in cancer.", Curr Cancer Drug Targets , 2005, pp. 203-220, vol. 5(3).
Wahl et al., "T lymphocyte-dependent evolution of bacterial cell wall-induced hepatic granulomas.", J Immunol, 1986, pp. 2199-2209, vol. 137(7).
Wang et al.,"Secretion of matrix metalloproteinase-2 and -9 after mechanical trauma injury in rat cortical cultures and involvement of MAP kinase.", J Neurotrauma, 2002, pp. 615-625, vol. 19(5).
Yong, V. W., "The potential use of MMP inhibitors to treat CNS diseases.", Expert Opin Investig Drugs 1999, pp. 255-268, vol. 8(3).
Yoo et al., "4'-Methyl-4, 5'-bithiazole-based correctors of defective DELTAF508-CFTR cellular processing.", Biooganic & Medical Chemistry Letters, Apr. 15, 2008, vol. 18(8), Pergamon, Elsevier Science, GB, XP022606357.
Benevenuti et al., "Crystallizaiton of Soluble Proteins in Vapor Diffusion for X-ray Crystallography.", Nature Protocols, published on-line Jun. 28, 2007, pp. 1663-1651, vol. 2(7).
Cudney, R., "Protein Cyrstallization and Dumb Luck.", The Rigaku Journal, 1999, pp. 1-7, vol. 16(1).
Drenth, J., "Principles of Protein X-Ray Crystallography", 2nd edition, 1999, Spring-Verlag New York Inc., Chapter 1, p. 1-21.
Kundrot, C.E., "Which Strategy for a Protein Crystallization Project?", Cellular Molecular Life Science, 2004, pp. 525-536, vol. 61.
McPherson, A., "Current Approaches to Macromolecular Crystallization.", European Journal of Biochemistry, 1990, pp. 1-23, vol. 189.
Moon et al., "A synergistic approach to proein crystallization: Combination of a fixed-arm carrier with surface entropy reduction.", Protein Science, 2010, pp. 901-913, vol. 19.

SEQUENCE LISTING

<160> NUMBER OF SEQ ID NOS: 12

<210> SEQ ID NO 1
<211> LENGTH: 707
<212> TYPE: PRT
<213> ORGANISM: Homo sapiens

<400> SEQUENCE: 1

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr

```
            35                  40                  45
Leu Tyr Arg Tyr Gly Tyr Thr Arg Val Ala Glu Met Arg Gly Glu Ser
 50                  55                  60

Lys Ser Leu Gly Pro Ala Leu Leu Leu Gln Lys Gln Leu Ser Leu
 65                  70                  75                  80

Pro Glu Thr Gly Glu Leu Asp Ser Ala Thr Leu Lys Ala Met Arg Thr
                     85                  90                  95

Pro Arg Cys Gly Val Pro Asp Leu Gly Arg Phe Gln Thr Phe Glu Gly
                    100                 105                 110

Asp Leu Lys Trp His His His Asn Ile Thr Tyr Trp Ile Gln Asn Tyr
                    115                 120                 125

Ser Glu Asp Leu Pro Arg Ala Val Ile Asp Ala Phe Ala Arg Ala
                130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                    165                 170                 175

Asp Gly Tyr Pro Phe Asp Gly Lys Asp Gly Leu Leu Ala His Ala Phe
                    180                 185                 190

Pro Pro Gly Pro Gly Ile Gln Gly Asp Ala His Phe Asp Asp Asp Glu
                    195                 200                 205

Leu Trp Ser Leu Gly Lys Gly Val Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                    245                 250                 255

Ser Thr Thr Ala Asn Tyr Asp Thr Asp Asp Arg Phe Gly Phe Cys Pro
                    260                 265                 270

Ser Glu Arg Leu Tyr Thr Gln Asp Gly Asn Ala Asp Gly Lys Pro Cys
                    275                 280                 285

Gln Phe Pro Phe Ile Phe Gln Gly Gln Ser Tyr Ser Ala Cys Thr Thr
                    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                    325                 330                 335

Val Met Gly Gly Asn Ser Ala Gly Glu Leu Cys Val Phe Pro Phe Thr
                    340                 345                 350

Phe Leu Gly Lys Glu Tyr Ser Thr Cys Thr Ser Glu Gly Arg Gly Asp
                    355                 360                 365

Gly Arg Leu Trp Cys Ala Thr Thr Ser Asn Phe Asp Ser Asp Lys Lys
                    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                    405                 410                 415

Ala Leu Met Tyr Pro Met Tyr Arg Phe Thr Glu Gly Pro Pro Leu His
                    420                 425                 430

Lys Asp Asp Val Asn Gly Ile Arg His Leu Tyr Gly Pro Arg Pro Glu
                    435                 440                 445

Pro Glu Pro Arg Pro Pro Thr Thr Thr Thr Pro Gln Pro Thr Ala Pro
450                 455                 460
```

```
Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
                515                 520                 525

Asn Gln Leu Tyr Leu Phe Lys Asp Gly Lys Tyr Trp Arg Phe Ser Glu
530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
                595                 600                 605

Asp Val Ala Gln Val Thr Gly Ala Leu Arg Ser Gly Arg Gly Lys Met
                610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
                690                 695                 700

Pro Glu Asp
705

<210> SEQ ID NO 2
<211> LENGTH: 427
<212> TYPE: PRT
<213> ORGANISM: Homo sapiens

<400> SEQUENCE: 2

Met Ala Pro Arg Gln Arg Gln Ser Thr Leu Val Leu Phe Pro Gly Asp
1               5                   10                  15

Leu Arg Thr Asn Leu Thr Asp Arg Gln Leu Ala Glu Glu Tyr Leu Tyr
                20                  25                  30

Arg Tyr Gly Tyr Thr Arg Val Ala Glu Met Arg Gly Glu Ser Lys Ser
                35                  40                  45

Leu Gly Pro Ala Leu Leu Leu Leu Gln Lys Gln Leu Ser Leu Pro Glu
            50                  55                  60

Thr Gly Glu Leu Asp Ser Ala Thr Leu Lys Ala Met Arg Thr Pro Arg
65                  70                  75                  80

Cys Gly Val Pro Asp Leu Gly Arg Phe Gln Thr Phe Glu Gly Asp Leu
                85                  90                  95

Lys Trp His His His Asn Ile Thr Tyr Trp Ile Gln Asn Tyr Ser Glu
                100                 105                 110

Asp Leu Pro Arg Ala Val Ile Asp Asp Ala Phe Ala Arg Ala Phe Ala
```

```
            115                 120                 125
Leu Trp Ser Ala Val Thr Pro Leu Thr Phe Thr Arg Val Tyr Ser Arg
    130                 135                 140

Asp Ala Asp Ile Val Ile Gln Phe Gly Val Ala Glu His Gly Asp Gly
145                 150                 155                 160

Tyr Pro Phe Asp Gly Lys Asp Gly Leu Leu Ala His Ala Phe Pro Pro
                165                 170                 175

Gly Pro Gly Ile Gln Gly Asp Ala His Phe Asp Asp Glu Leu Trp
            180                 185                 190

Ser Leu Gly Lys Gly Val Val Pro Thr Arg Phe Gly Asn Ala Asp
        195                 200                 205

Gly Ala Ala Cys His Phe Pro Phe Ile Phe Glu Gly Arg Ser Tyr Ser
    210                 215                 220

Ala Cys Thr Thr Asp Gly Arg Ser Asp Gly Leu Pro Trp Cys Ser Thr
225                 230                 235                 240

Thr Ala Asn Tyr Asp Thr Asp Arg Phe Gly Phe Cys Pro Ser Glu
                245                 250                 255

Arg Leu Tyr Thr Gln Asp Gly Asn Ala Asp Gly Lys Pro Cys Gln Phe
            260                 265                 270

Pro Phe Ile Phe Gln Gly Gln Ser Tyr Ser Ala Cys Thr Thr Asp Gly
        275                 280                 285

Arg Ser Asp Gly Tyr Arg Trp Cys Ala Thr Thr Ala Asn Tyr Asp Arg
    290                 295                 300

Asp Lys Leu Phe Gly Phe Cys Pro Thr Arg Ala Asp Ser Thr Val Met
305                 310                 315                 320

Gly Gly Asn Ser Ala Gly Glu Leu Cys Val Phe Pro Phe Thr Phe Leu
                325                 330                 335

Gly Lys Glu Tyr Ser Thr Cys Thr Ser Glu Gly Arg Gly Asp Gly Arg
            340                 345                 350

Leu Trp Cys Ala Thr Thr Ser Asn Phe Asp Ser Asp Lys Lys Trp Gly
        355                 360                 365

Phe Cys Pro Asp Gln Gly Tyr Ser Leu Phe Leu Val Ala Ala His Glu
    370                 375                 380

Phe Gly His Ala Leu Gly Leu Asp His Ser Ser Val Pro Glu Ala Leu
385                 390                 395                 400

Met Tyr Pro Met Tyr Arg Phe Thr Glu Gly Pro Pro Leu His Lys Asp
                405                 410                 415

Asp Val Asn Gly Ile Arg His Leu Tyr Gly Pro
            420                 425

<210> SEQ ID NO 3
<211> LENGTH: 417
<212> TYPE: PRT
<213> ORGANISM: Homo sapiens

<400> SEQUENCE: 3

Met Val Leu Phe Pro Gly Asp Leu Arg Thr Asn Leu Thr Asp Arg Gln
1               5                   10                  15

Leu Ala Glu Glu Tyr Leu Tyr Arg Tyr Gly Tyr Thr Arg Val Ala Glu
            20                  25                  30

Met Arg Gly Glu Ser Lys Ser Leu Gly Pro Ala Leu Leu Leu Leu Gln
        35                  40                  45

Lys Gln Leu Ser Leu Pro Glu Thr Gly Glu Leu Asp Ser Ala Thr Leu
    50                  55                  60
```

```
Lys Ala Met Arg Thr Pro Arg Cys Gly Val Pro Asp Leu Gly Arg Phe
 65                  70                  75                  80

Gln Thr Phe Glu Gly Asp Leu Lys Trp His His Asn Ile Thr Tyr
                 85                  90                  95

Trp Ile Gln Asn Tyr Ser Glu Asp Leu Pro Arg Ala Val Ile Asp Asp
            100                 105                 110

Ala Phe Ala Arg Ala Phe Ala Leu Trp Ser Ala Val Thr Pro Leu Thr
            115                 120                 125

Phe Thr Arg Val Tyr Ser Arg Asp Ala Asp Ile Val Ile Gln Phe Gly
            130                 135                 140

Val Ala Glu His Gly Asp Gly Tyr Pro Phe Asp Gly Lys Asp Gly Leu
145                 150                 155                 160

Leu Ala His Ala Phe Pro Pro Gly Pro Gly Ile Gln Gly Asp Ala His
                165                 170                 175

Phe Asp Asp Asp Glu Leu Trp Ser Leu Gly Lys Gly Val Val Val Pro
            180                 185                 190

Thr Arg Phe Gly Asn Ala Asp Gly Ala Ala Cys His Phe Pro Phe Ile
            195                 200                 205

Phe Glu Gly Arg Ser Tyr Ser Ala Cys Thr Thr Asp Gly Arg Ser Asp
210                 215                 220

Gly Leu Pro Trp Cys Ser Thr Thr Ala Asn Tyr Asp Thr Asp Asp Arg
225                 230                 235                 240

Phe Gly Phe Cys Pro Ser Glu Arg Leu Tyr Thr Gln Asp Gly Asn Ala
                245                 250                 255

Asp Gly Lys Pro Cys Gln Phe Pro Phe Ile Phe Gln Gly Gln Ser Tyr
            260                 265                 270

Ser Ala Cys Thr Thr Asp Gly Arg Ser Asp Gly Tyr Arg Trp Cys Ala
            275                 280                 285

Thr Thr Ala Asn Tyr Asp Arg Asp Lys Leu Phe Gly Phe Cys Pro Thr
            290                 295                 300

Arg Ala Asp Ser Thr Val Met Gly Gly Asn Ser Ala Gly Glu Leu Cys
305                 310                 315                 320

Val Phe Pro Phe Thr Phe Leu Gly Lys Glu Tyr Ser Thr Cys Thr Ser
                325                 330                 335

Glu Gly Arg Gly Asp Gly Arg Leu Trp Cys Ala Thr Thr Ser Asn Phe
            340                 345                 350

Asp Ser Asp Lys Lys Trp Gly Phe Cys Pro Asp Gln Gly Tyr Ser Leu
            355                 360                 365

Phe Leu Val Ala Ala His Glu Phe Gly His Ala Leu Gly Leu Asp His
            370                 375                 380

Ser Ser Val Pro Glu Ala Leu Met Tyr Pro Met Tyr Arg Phe Thr Glu
385                 390                 395                 400

Gly Pro Pro Leu His Lys Asp Asp Val Asn Gly Ile Arg His Leu Tyr
                405                 410                 415

Gly

<210> SEQ ID NO 4
<211> LENGTH: 242
<212> TYPE: PRT
<213> ORGANISM: Homo sapiens

<400> SEQUENCE: 4

Met Val Leu Phe Pro Gly Asp Leu Arg Thr Asn Leu Thr Asp Arg Gln
 1               5                  10                  15
```

```
Leu Ala Glu Glu Tyr Leu Tyr Arg Tyr Gly Tyr Thr Arg Val Ala Glu
                20                  25                  30

Met Arg Gly Glu Ser Lys Ser Leu Gly Pro Ala Leu Leu Leu Leu Gln
            35                  40                  45

Lys Gln Leu Ser Leu Pro Glu Thr Gly Glu Leu Asp Ser Ala Thr Leu
 50                  55                  60

Lys Ala Met Arg Thr Pro Arg Cys Gly Val Pro Asp Leu Gly Arg Phe
 65                  70                  75                  80

Gln Thr Phe Glu Gly Asp Leu Lys Trp His His His Asn Ile Thr Tyr
                85                  90                  95

Trp Ile Gln Asn Tyr Ser Glu Asp Leu Pro Arg Ala Val Ile Asp Asp
            100                 105                 110

Ala Phe Ala Arg Ala Phe Ala Leu Trp Ser Ala Val Thr Pro Leu Thr
        115                 120                 125

Phe Thr Arg Val Tyr Ser Arg Asp Ala Asp Ile Val Ile Gln Phe Gly
    130                 135                 140

Val Ala Glu His Gly Asp Gly Tyr Pro Phe Asp Gly Lys Asp Gly Leu
145                 150                 155                 160

Leu Ala His Ala Phe Pro Pro Gly Pro Gly Ile Gln Gly Asp Ala His
                165                 170                 175

Phe Asp Asp Asp Glu Leu Trp Ser Leu Gly Lys Gly Gln Gly Tyr Ser
            180                 185                 190

Leu Phe Leu Val Ala Ala His Glu Phe Gly His Ala Leu Gly Leu Asp
        195                 200                 205

His Ser Ser Val Pro Glu Ala Leu Met Tyr Pro Met Tyr Arg Phe Thr
    210                 215                 220

Glu Gly Pro Pro Leu His Lys Asp Asp Val Asn Gly Ile Arg His Leu
225                 230                 235                 240

Tyr Gly

<210> SEQ ID NO 5
<211> LENGTH: 204
<212> TYPE: PRT
<213> ORGANISM: Homo sapiens

<400> SEQUENCE: 5

Met Leu Gly Pro Ala Leu Leu Leu Leu Gln Lys Gln Leu Ser Leu Pro
 1               5                  10                  15

Glu Thr Gly Glu Leu Asp Ser Ala Thr Leu Lys Ala Met Arg Thr Pro
                20                  25                  30

Arg Cys Gly Val Pro Asp Leu Gly Arg Phe Gln Thr Phe Glu Gly Asp
            35                  40                  45

Leu Lys Trp His His His Asn Ile Thr Tyr Trp Ile Gln Asn Tyr Ser
 50                  55                  60

Glu Asp Leu Pro Arg Ala Val Ile Asp Asp Ala Phe Ala Arg Ala Phe
 65                  70                  75                  80

Ala Leu Trp Ser Ala Val Thr Pro Leu Thr Phe Thr Arg Val Tyr Ser
                85                  90                  95

Arg Asp Ala Asp Ile Val Ile Gln Phe Gly Val Ala Glu His Gly Asp
            100                 105                 110

Gly Tyr Pro Phe Asp Gly Lys Asp Gly Leu Leu Ala His Ala Phe Pro
        115                 120                 125

Pro Gly Pro Gly Ile Gln Gly Asp Ala His Phe Asp Asp Asp Glu Leu
    130                 135                 140
```

-continued

Trp Ser Leu Gly Lys Gly Gln Gly Tyr Ser Leu Phe Leu Val Ala Ala
145                 150                 155                 160

His Glu Phe Gly His Ala Leu Gly Leu Asp His Ser Ser Val Pro Glu
                165                 170                 175

Ala Leu Met Tyr Pro Met Tyr Arg Phe Thr Glu Gly Pro Pro Leu His
            180                 185                 190

Lys Asp Asp Val Asn Gly Ile Arg His Leu Tyr Gly
        195                 200

<210> SEQ ID NO 6
<211> LENGTH: 251
<212> TYPE: PRT
<213> ORGANISM: Homo sapiens

<400> SEQUENCE: 6

Met Ala Pro Arg Gln Arg Gln Ser Thr Leu Val Leu Phe Pro Gly Asp
1               5                   10                  15

Leu Arg Thr Asn Leu Thr Asp Arg Gln Leu Ala Glu Glu Tyr Leu Tyr
            20                  25                  30

Arg Tyr Gly Tyr Thr Arg Val Ala Glu Met Arg Gly Glu Ser Lys Ser
        35                  40                  45

Leu Gly Pro Ala Leu Leu Leu Leu Gln Lys Gln Leu Ser Leu Pro Glu
    50                  55                  60

Thr Gly Glu Leu Asp Ser Ala Thr Leu Lys Ala Met Arg Thr Pro Arg
65                  70                  75                  80

Cys Gly Val Pro Asp Leu Gly Arg Phe Gln Thr Phe Glu Gly Asp Leu
                85                  90                  95

Lys Trp His His His Asn Ile Thr Tyr Trp Ile Gln Asn Tyr Ser Glu
            100                 105                 110

Asp Leu Pro Arg Ala Val Ile Asp Asp Ala Phe Ala Arg Ala Phe Ala
        115                 120                 125

Leu Trp Ser Ala Val Thr Pro Leu Thr Phe Thr Arg Val Tyr Ser Arg
    130                 135                 140

Asp Ala Asp Ile Val Ile Gln Phe Gly Val Ala Glu His Gly Asp Gly
145                 150                 155                 160

Tyr Pro Phe Asp Gly Lys Asp Gly Leu Leu Ala His Ala Phe Pro Pro
                165                 170                 175

Gly Pro Gly Ile Gln Gly Asp Ala His Phe Asp Asp Asp Glu Leu Trp
            180                 185                 190

Ser Leu Gly Lys Gly Gln Gly Tyr Ser Leu Phe Leu Val Ala Ala His
        195                 200                 205

Glu Phe Gly His Ala Leu Gly Leu Asp His Ser Ser Val Pro Glu Ala
    210                 215                 220

Leu Met Tyr Pro Met Tyr Arg Phe Thr Glu Gly Pro Pro Leu His Lys
225                 230                 235                 240

Asp Asp Val Asn Gly Ile Arg His Leu Tyr Gly
                245                 250

<210> SEQ ID NO 7
<211> LENGTH: 268
<212> TYPE: PRT
<213> ORGANISM: Homo sapiens

<400> SEQUENCE: 7

Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Leu Ser
            20                  25                  30

Glu Glu Asp Leu Gln Phe Ala Glu Arg Tyr Leu Arg Ser Tyr Tyr His
         35                  40                  45

Pro Thr Asn Leu Ala Gly Ile Leu Lys Glu Asn Ala Ala Ser Ser Met
 50                  55                  60

Thr Glu Arg Leu Arg Glu Met Gln Ser Phe Phe Gly Leu Glu Val Thr
 65                  70                  75                  80

Gly Lys Leu Asp Asp Asn Thr Leu Asp Val Met Lys Lys Pro Arg Cys
                 85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Ala Phe Lys Val
130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
        195                 200                 205

Ser Ser Ser Lys Gly Tyr Asn Leu Phe Leu Val Ala Ala His Glu Phe
210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro
            260                 265

<210> SEQ ID NO 8
<211> LENGTH: 167
<212> TYPE: PRT
<213> ORGANISM: Homo sapiens

<400> SEQUENCE: 8

Met Phe Arg Thr Phe Pro Gly Ile Pro Lys Trp Arg Lys Thr His Leu
1               5                   10                  15

Thr Tyr Arg Ile Val Asn Tyr Thr Pro Asp Leu Pro Lys Asp Ala Val
            20                  25                  30

Asp Ser Ala Val Glu Lys Ala Leu Lys Val Trp Glu Glu Val Thr Pro
         35                  40                  45

Leu Thr Phe Ser Arg Leu Tyr Glu Gly Glu Ala Asp Ile Met Ile Ser
 50                  55                  60

Phe Ala Val Arg Glu His Gly Asp Phe Tyr Pro Phe Asp Gly Pro Gly
65                  70                  75                  80

Asn Val Leu Ala His Ala Tyr Ala Pro Gly Pro Gly Ile Asn Gly Asp
                 85                  90                  95

Ala His Phe Asp Asp Asp Glu Gln Trp Thr Lys Asp Thr Thr Gly Thr
            100                 105                 110

Asn Leu Phe Leu Val Ala Ala His Glu Ile Gly His Ser Leu Gly Leu
        115                 120                 125

```
Phe His Ser Ala Asn Thr Glu Ala Leu Met Tyr Pro Leu Tyr His Ser
    130                 135                 140

Leu Thr Asp Leu Thr Arg Phe Arg Leu Ser Gln Asp Asp Ile Asn Gly
145                 150                 155                 160

Ile Gln Ser Leu Tyr Gly Pro
                165

<210> SEQ ID NO 9
<211> LENGTH: 7
<212> TYPE: PRT
<213> ORGANISM: Homo sapiens

<400> SEQUENCE: 9

Phe Gln Thr Phe Glu Gly Asp
1               5

<210> SEQ ID NO 10
<211> LENGTH: 15
<212> TYPE: PRT
<213> ORGANISM: Homo sapiens

<400> SEQUENCE: 10

Cys Gly Val Pro Asp Leu Gly Arg Phe Gln Thr Phe Glu Gly Asp
1               5                   10                  15

<210> SEQ ID NO 11
<211> LENGTH: 708
<212> TYPE: PRT
<213> ORGANISM: Rattus norvegicus

<400> SEQUENCE: 11

Met Ser Pro Trp Gln Pro Leu Leu Val Leu Leu Ala Leu Gly Tyr
1               5                   10                  15

Ser Phe Ala Ala Pro His Gln Arg Gln Pro Thr Tyr Val Val Phe Pro
                20                  25                  30

Arg Asp Leu Lys Thr Ser Asn Leu Thr Asp Thr Gln Leu Ala Glu Asp
                35                  40                  45

Tyr Leu Tyr Arg Tyr Gly Tyr Thr Arg Ala Ala Gln Met Met Gly Glu
    50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Glu Thr Leu Lys Ala Ile Arg
                85                  90                  95

Ser Pro Arg Cys Gly Val Pro Asp Val Gly Lys Phe Gln Thr Phe Asp
                100                 105                 110

Gly Asp Leu Lys Trp His His His Asn Ile Thr Tyr Trp Ile Gln Ser
                115                 120                 125

Tyr Thr Glu Asp Leu Pro Arg Asp Val Ile Asp Asp Ser Phe Ala Arg
    130                 135                 140

Ala Phe Ala Val Trp Ser Ala Val Thr Pro Leu Thr Phe Thr Arg Val
145                 150                 155                 160

Tyr Gly Leu Glu Ala Asp Ile Val Ile Gln Phe Gly Val Ala Glu His
                165                 170                 175

Gly Asp Gly Tyr Pro Phe Asp Gly Lys Asp Gly Leu Leu Ala His Ala
                180                 185                 190

Phe Pro Pro Gly Pro Gly Ile Gln Gly Asp Ala His Phe Asp Asp Asp
                195                 200                 205
```

```
Glu Leu Trp Ser Leu Gly Lys Gly Ala Val Val Pro Thr Tyr Phe Gly
210                 215                 220

Asn Ala Asn Gly Ala Pro Cys His Phe Pro Phe Thr Phe Glu Gly Arg
225                 230                 235                 240

Ser Tyr Leu Ser Cys Thr Thr Asp Gly Arg Asn Asp Gly Lys Pro Trp
                245                 250                 255

Cys Gly Thr Thr Ala Asp Tyr Asp Thr Asp Arg Lys Tyr Gly Phe Cys
                260                 265                 270

Pro Ser Glu Asn Leu Tyr Thr Glu His Gly Asn Gly Asp Gly Lys Pro
            275                 280                 285

Cys Val Phe Pro Phe Ile Phe Glu Gly His Ser Tyr Ser Ala Cys Thr
290                 295                 300

Thr Lys Gly Arg Ser Asp Gly Tyr Arg Trp Cys Ala Thr Thr Ala Asn
305                 310                 315                 320

Tyr Asp Gln Asp Lys Ala Asp Gly Phe Cys Pro Thr Arg Ala Asp Val
                325                 330                 335

Thr Val Thr Gly Gly Asn Ser Ala Gly Glu Met Cys Val Phe Pro Phe
                340                 345                 350

Val Phe Leu Gly Lys Gln Tyr Ser Thr Cys Thr Ser Glu Gly Arg Ser
            355                 360                 365

Asp Gly Arg Leu Trp Cys Ala Thr Thr Ser Asn Phe Asp Ala Asp Lys
370                 375                 380

Lys Trp Gly Phe Cys Pro Asp Gln Gly Tyr Ser Leu Phe Leu Val Ala
385                 390                 395                 400

Ala His Glu Phe Gly His Ala Leu Gly Leu Asp His Ser Ser Val Pro
                405                 410                 415

Glu Ala Leu Met Tyr Pro Met Tyr His Tyr His Glu Asp Ser Pro Leu
            420                 425                 430

His Glu Asp Asp Ile Lys Gly Ile His His Leu Tyr Gly Arg Gly Ser
            435                 440                 445

Lys Pro Asp Pro Arg Pro Ala Thr Thr Ala Ala Glu Pro Gln Pro
450                 455                 460

Thr Ala Pro Pro Thr Met Cys Ser Thr Ala Pro Pro Met Ala Tyr Pro
465                 470                 475                 480

Thr Gly Gly Pro Thr Val Ala Pro Thr Gly Ala Pro Ser Pro Gly Pro
                485                 490                 495

Thr Gly Pro Pro Thr Ala Gly Pro Ser Glu Ala Pro Thr Glu Ser Ser
            500                 505                 510

Thr Pro Asp Asp Pro Cys Asn Val Asp Val Phe Asp Ala Ile Ala
            515                 520                 525

Asp Ile Gln Gly Ala Leu His Phe Phe Lys Asp Gly Arg Tyr Trp Lys
530                 535                 540

Phe Ser Asn His Gly Gly Asn Gln Leu Gln Gly Pro Phe Leu Ile Ala
545                 550                 555                 560

Arg Thr Trp Pro Ala Phe Pro Ser Lys Leu Asn Ser Ala Phe Glu Asp
                565                 570                 575

Pro Gln Pro Lys Lys Ile Phe Phe Leu Trp Ala Gln Met Trp Val
            580                 585                 590

Tyr Thr Gly Gln Ser Val Leu Gly Pro Arg Ser Leu Asp Lys Leu Gly
            595                 600                 605

Leu Gly Ser Glu Val Thr Leu Val Thr Gly Leu Leu Pro Arg Arg Gly
610                 615                 620

Gly Lys Ala Leu Leu Ile Ser Arg Glu Arg Ile Trp Lys Phe Asp Leu
```

```
                625                 630                 635                 640
Lys Ser Gln Lys Val Asp Pro Gln Ser Val Thr Arg Leu Asp Asn Glu
                    645                 650                 655

Phe Ser Gly Val Pro Trp Asn Ser His Asn Val Phe Gln Tyr Gln Asp
                    660                 665                 670

Lys Ala Tyr Phe Cys His Asp Lys Tyr Phe Trp Arg Val Ser Phe His
                675                 680                 685

Asn Arg Val Asn Gln Val Asp His Val Ala Tyr Val Thr Tyr Asp Leu
                690                 695                 700

Leu Gln Cys Pro
705

<210> SEQ ID NO 12
<211> LENGTH: 235
<212> TYPE: PRT
<213> ORGANISM: Homo sapiens

<400> SEQUENCE: 12

Leu Arg Thr Asn Leu Thr Asp Arg Gln Leu Ala Glu Glu Tyr Leu Tyr
1               5                   10                  15

Arg Tyr Gly Tyr Thr Arg Val Ala Glu Met Arg Gly Glu Ser Lys Ser
                20                  25                  30

Leu Gly Pro Ala Leu Leu Leu Leu Gln Lys Gln Leu Ser Leu Pro Glu
                35                  40                  45

Thr Gly Glu Leu Asp Ser Ala Thr Leu Lys Ala Met Arg Thr Pro Arg
            50                  55                  60

Cys Gly Val Pro Asp Leu Gly Arg Phe Gln Thr Phe Glu Gly Asp Leu
65                  70                  75                  80

Lys Trp His His His Asn Ile Thr Tyr Trp Ile Gln Asn Tyr Ser Glu
                85                  90                  95

Asp Leu Pro Arg Ala Val Ile Asp Asp Ala Phe Ala Arg Ala Phe Ala
                100                 105                 110

Leu Trp Ser Ala Val Thr Pro Leu Thr Phe Thr Arg Val Tyr Ser Arg
                115                 120                 125

Asp Ala Asp Ile Val Ile Gln Phe Gly Val Ala Glu His Gly Asp Gly
            130                 135                 140

Tyr Pro Phe Asp Gly Lys Asp Gly Leu Leu Ala His Ala Phe Pro Pro
145                 150                 155                 160

Gly Pro Gly Ile Gln Gly Asp Ala His Phe Asp Asp Asp Glu Leu Trp
                165                 170                 175

Ser Leu Gly Lys Gly Gln Gly Tyr Ser Leu Phe Leu Val Ala Ala His
                180                 185                 190

Glu Phe Gly His Ala Leu Gly Leu Asp His Ser Ser Val Pro Glu Ala
                195                 200                 205

Leu Met Tyr Pro Met Tyr Arg Phe Thr Glu Gly Pro Pro Leu His Lys
            210                 215                 220

Asp Asp Val Asn Gly Ile Arg His Leu Tyr Gly
225                 230                 235
```

METHODS FOR DESIGNING, SELECTING AND/OR OPTIMIZING ALLOSTERIC PROCESSING INHIBITORS FOR MATRIX METALLOPROTEINASES

CROSS REFERENCE TO RELATED APPLICATION

This application claims priority to provisional application Ser. No. 61/502,516, filed Jun. 29, 2011, which is incorporated herein by reference in its entirety.

TECHNICAL FIELD

The present invention generally pertains to the fields of high-throughput screening, protein crystallization, X-ray diffraction analysis, three-dimensional structure determination, molecular modeling, and structure based rational drug design. More particularly, the present invention pertains to methods for selecting ligands that are allosteric processing inhibitors that inhibit activation of the pro form of matrix metalloproteinases (proMMPs) and to the therapeutic and prophylactic uses of the selected ligands. Examples of relevant therapeutic areas generally include inflammation, oncology, cardiovascular disease, and neurological disorders.

BACKGROUND OF THE INVENTION

Various publications, which may include patents, published applications, technical articles and scholarly articles, are cited throughout the specification in parentheses, and full citations of each may be found at the end of the specification. Each of these cited publications is incorporated by reference herein, in its entirety.

Matrix metalloproteinases (MMPs) are a family of structurally related zinc-dependent proteolytic enzymes that digest extracellular matrix proteins such as collagen, elastin, laminin and fibronectin. Currently, at least 28 different mammalian MMP proteins have been identified and they are grouped based on substrate specificity and domain structure. Enzymatic activities of the MMPs are precisely controlled, not only by their gene expression in various cell types, but also by activation of their inactive zymogen precursors (proMMPs) and inhibition by endogenous inhibitors and tissue inhibitors of metalloproteinases (TIMPs). The enzymes play a key role in normal homeostatic tissue remodeling events, but are also considered to play a key role in pathological destruction of the matrix in many connective tissue diseases such as arthritis, periodontitis, and tissue ulceration and also in cancer cell invasion and metastasis.

A role for MMPs in oncology is well established, as up-regulation of any number of MMPs are one mechanism by which malignant cells can overcome connective tissue barriers and metastasize (Vihinen, Ala-aho et al. 2005). MMPs also appear to have a direct role in angiogenesis, which is another reason they have been an important target for oncology indications (Handsley and Edwards 2005; Rundhaug 2005). Several different classes of MMPs are involved in these processes, including for example MMP9, MMP2, and MT1-MMP.

Other MMP mediated indications include the cartilage and bone degeneration that results in osteoarthritis and rheumatoid arthritis. The degeneration is due primarily to MMP digestion of the extracellular matrix (ECM) in bone and joints (Iannone and Lapadula 2003). MMP1, MMP3, MMP9, and MMP13 have all been found to be elevated in the tissues and body fluids surrounding the damaged areas.

MMPs may also have a role in cardiovascular diseases, in that they are believed to be involved in atherosclerotic plaque rupture, aneurysm and vascular and myocardial tissue morphogenesis (George 2000; Tayebjee, Lip et al. 2005). Elevated levels of MMP1, MMP2, MMP9, and MMP13 have often been associated with these conditions. Several other pathologies such as gastric ulcers, pulmonary hypertension, chronic obstructive pulmonary disease, inflammatory bowel disease, periodontal disease, skin ulcers, liver fibrosis, emphysema, and Marfan syndrome all appear to have an MMP component as well (Shah, Wilkin et al. 2002).

Within the central nervous system, altered MMP expression has been linked to several neurodegenerative disease states (Yong 1999), most notably in stroke (Cunningham, Wetzel et al. 2005). In particular, MMP2 and MMP9 appear to have the significant impact in propagating the brain tissue damage that occurs following an ischemic or hemorrhagic insult. Studies in human stroke patients and in animal stroke models have demonstrated that both MMP2 and MMP9 expression levels and activity increase sharply over a 24 hour period following an ischemic event. Within the brain, the microvascular endothelial cell tight junctions are broken down by activated MMP2 and MMP9, which results in increased permeability of the blood-brain barrier (BBB). This breakdown in the integrity of the BBB then leads to edema and infiltration of inflammatory agents, both of which cause increased cell death around the infarct core (the penumbra) and increase the possibility of hemorrhagic transformation. Administration of MMP inhibitors has been shown to be protective in animal models of stroke (Yong 1999; Gu, Cui et al. 2005). In addition, MMP9 knockout animals also demonstrate significant neuroprotection in similar stroke models (Asahi, Asahi et al. 2000). In the US, stroke is the third leading cause of mortality, and the leading cause of disability. Thus this area has a large unmet medical need for acute interventional therapy that could potentially be addressed with MMP inhibitors.

It has also been suggested that MMP9 may play a role in the progression of multiple sclerosis (MS). Studies have indicated that serum levels of MMP9 are elevated in active patients, and are concentrated around MS lesions (Opdenakker, Nelissen et al. 2003). Increased serum MMP9 activity would promote infiltration of leukocytes into the CNS, a causal factor and one of the hallmarks of the disease. MMPs may also contribute to severity and prolongation of migraines. In animal models of migraine (cortical spreading depression), MMP9 is rapidly upregulated and activated leading to a breakdown in the BBB, which results in mild to moderate edema (Gursoy-Ozdemir, Qiu et al. 2004). It is this brain swelling and subsequent vasoconstriction which causes the debilitating headaches and other symptoms associated with migraine. In the cortical spreading depression model, MMP inhibitors have been shown to prevent the opening of the BBB (Gursoy-Ozdemir, Qiu et al. 2004). Related research has shown that MMP9 is specifically upregulated in damaged brain tissues following traumatic brain injury (Wang, Mori et al. 2002), which would be predicted to lead to further brain damage due to edema and immune cell infiltration. MMPs may also have additional roles in additional chronic CNS disorders. In an animal model of Parkinson's disease, MMP9 was found to be rapidly upregulated after striatal injection of a dopaminergic neuron poison (MPTP) (Lorenzl, Calingasan et al. 2004), and MMP3 has been shown to process α-synuclein to an aggregation-prone form (Sung, Park et al. 2005). This implicates MMPs in both the neuronal remodeling that occurs upon cell loss and one of the potential causative factors of the disease. In patients with Alzheimer's disease, MMP9 was found to be upregulated in postmortem plasma samples compared to normal controls (Yong 1999; Lorenzl, Albers et al. 2003). Furthermore, pathologic expression of amyloid beta peptides induces expression and activation of MMP2, which may contribute to cerebral amyloid angiopathy, a major pathological feature of Alzheimer's disease (Jung, Zhang et al. 2003). MMPs may also have a role in vascular dementia, as MMP9 levels have been found to be elevated in the cerebrospinal fluid from demented patients (Adair, Charlie et al. 2004).

With regard to structure and activation of the inactive zymogen form, a prototypical MMP is matrix metalloproteinase 9 (MMP9). MMP9 is also known as macrophage gelatinase, gelatinase B, 92 kDa gelatinase, 92 kDa type IV collagenase, and type V collagenase. The inactive form of MMP9, proMMP9, is expressed with several different domains including a signal sequence for secretion, a propeptide domain which inhibits activity of proMMP9, a catalytic domain for protein cleavage, a fibronectin type-II (FnII) domain consisting of three fibronectin-type II repeats, and a hemopexin-like domain thought to assist in substrate docking. The hemopexin-like domain also serves as a binding domain for interaction with Tissue Inhibitors of Metalloproteinases (TIMPs). The inactive zymogen form of MMP9, proMMP9, is maintained through a cysteine-switch mechanism, in which a Cys in the propeptide forms a complex with the catalytic zinc in the catalytic domain and occludes the active site (Van Wart and Birkedal-Hansen 1990). Activation of proMMP9 occurs in a two-step process. A protease cleaves an initial site after Met 60, disrupting the zinc coordination and destabilizing the propeptide interaction with the catalytic domain. This initial cleavage allows access to the second cleavage site at Phe 107, after which the propeptide is removed and the mature active form of the enzyme is released (Nagase 1997). The identity of the MMP9 activating proteases is unknown in vivo, although there is evidence that activation can occur through the actions of MMP3, chymase and trypsin (Ogata, Enghild et al. 1992; Fang, Raymond et al. 1997; Tchougounova, Lundequist et al. 2005).

Crystal structures of MMP9 and proMMP9 have been reported. A structure of the C-terminally truncated proMMP9 was reported to 2.5 Å resolution (Elkins, Ho et al. 2002). The structure contained the pro domain, the catalytic domain and the fibronectin-type II (FnII) repeats, but the structure did not contain active site inhibitors or allosteric processing inhibitors. Two additional publications reported the structure of the catalytic domain of MMP9 without the FnII repeats (Rowsell, Hawtin et al. 2002; Tochowicz, Maskos et al. 2007). The structures of the MMP9 catalytic domain showed both the apo and active site inhibited forms of the protein. The structures solved to date show a high degree of structural homology. No large difference in structure was noted due to the presence or lack of the FnII repeats. No structure reported to date identifies compounds binding to the region near residue Phe 107. In addition to the proMMP9 structure, the structures of proMMP1 (Jozic, Bourenkov et al. 2005), proMMP2 (Morgunova, Tuuttila et al. 1999), and proMMP3 (Becker, Marcy et al. 1995) have also been reported.

Based on the demonstrated involvement in numerous pathological conditions, inhibitors of matrix metalloproteases (MMPs) have been widely sought for their therapeutic potential in a range of disease states. However, non-selective active site MMP inhibitors have performed poorly in clinical trials. The failures have often been caused by dose-limiting toxicity and the manifestation of significant side effects, including the development of musculoskeletal syndrome (MSS). It has been suggested that development of more selective MMP inhibitors might help to overcome some of the problems that hindered clinical success in the past, but there are a number of obstacles to developing more selective MMP active site inhibitors. MMPs share a catalytically important Zn2+ ion in the active site and a highly conserved zinc-binding motif. In addition, there is considerable sequence conservation across the entire catalytic domain for members of the MMP family.

Herein is described a novel approach to developing more selective MMP inhibitors by targeting the pro domain of the inactive zymogens, proMMPs, with small-molecule allosteric processing inhibitors that bind and stabilize the inactive pro form of the protein and inhibit processing to the active enzyme. There is significantly less sequence identity within the pro domains of MMP proteins, no catalytically important Zn2+ ion, and no highly conserved zinc-binding motif. Thus targeting the pro domain of proMMPs is an attractive mechanism of action for inhibiting the activity of the MMP proteins Inhibition of proMMP9 activation has been observed with a specific monoclonal antibody (Ramos-DeSimone, Moll et al. 1993). The activation of proMMP9 by trypsin has also been shown to be inhibited by Bowman-Birk inhibitor proteins and derived peptide inhibitors (Losso, Munene et al. 2004). There are no reports, however, of small-molecule allosteric processing inhibitors that inhibit the proteolytic activation of proMMP9 or any other proMMP. The present invention provides methods of identifying such small-molecule allosteric processing inhibitors and methods of treatment using such inhibitors.

SUMMARY OF THE INVENTION

In one embodiment, the present invention comprises a crystal comprising the pro form of a matrix metalloproteinase (proMMP), or a fragment, or target structural motif or derivative thereof, and a chemical entity, wherein said chemical entity is a small-molecule allosteric processing inhibitor of the proMMP.

In another embodiment, the present invention comprises a crystal comprising proMMP9, or a fragment, or target structural motif or derivative thereof, and a chemical entity, wherein said chemical entity is a small-molecule allosteric processing inhibitor of proMMP9.

In another embodiment, the present invention comprises a crystal comprising proMMP9, or a fragment, or target structural motif or derivative thereof, and a chemical entity, wherein said chemical entity is a small-molecule allosteric processing inhibitor of proMMP9, and wherein said small-molecule allosteric processing inhibitor binds in an allosteric binding site comprising a region of space that is occupied by phenylalanine (Phe) 107 in the apo form of proMMP9, numbering taken from full-length human matrix metalloproteinase-9 precursor, proMMP9(1-707) (SEQ ID NO:1).

In another embodiment, the present invention comprises a crystal comprising proMMP9, or a fragment, or target structural motif or derivative thereof, and a chemical entity, wherein said chemical entity is a small-molecule allosteric processing inhibitor of proMMP9, and wherein said small-molecule allosteric processing inhibitor binds in an allosteric binding site comprising amino acid residues 100-102, 110, 114, 177-179, 190-193, and 405-410, numbering taken from full-length human matrix metalloproteinase-9 precursor, proMMP9(1-707) (SEQ ID NO:1).

In another embodiment, the present invention comprises a crystal comprising a homologue of proMMP9, or a fragment, or target structural motif or derivative thereof, and a chemical entity, wherein said chemical entity is a small-molecule allosteric processing inhibitor of the homologue of proMMP9, and wherein said small-molecule allosteric processing inhibitor binds in an allosteric binding site comprising a region of space that is homologous to the region of space occupied by Phe 107 in the apo form of proMMP9.

In another embodiment, the present invention comprises a crystal comprising the proMMP9 or a fragment, or target structural motif or derivative thereof, and a small-molecule allosteric processing inhibitor of proMMP9, wherein said fragment or derivative thereof is a peptide comprising SEQ ID NO:12 or a peptide having at least 95% sequence identity to SEQ ID NO:12.

In another embodiment, the present invention comprises a crystal comprising a proMMP, or a fragment, or target structural motif or derivative thereof, and a chemical entity, wherein said chemical entity is a small-molecule allosteric processing inhibitor of the proMMP, and wherein said crystal has a spacegroup of C2.

In another embodiment, the present invention comprises a crystal comprising a proMMP, or a fragment, or target structural motif or derivative thereof, and a chemical entity, wherein said chemical entity is a small-molecule allosteric processing inhibitor of the proMMP, and wherein said chemical entity is selected from the group consisting of the following structures:

Example 1

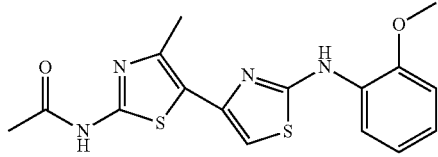 [SMILES: COc1ccccc1Nc1nc(-c2sc(NC(C)=O)nc2C)cs1]

Example 2

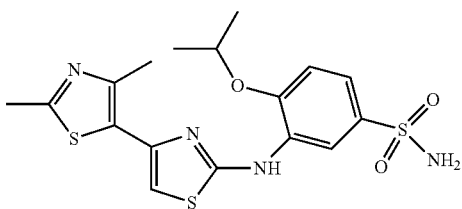 [SMILES: Cc1nc(C)c(-c2csc(Nc3cc(S(N)(=O)=O)ccc3OC(C)C)n2)s1]

Example 3

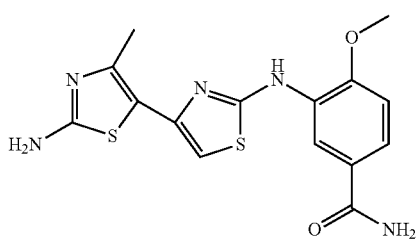 [SMILES: COc1ccc(C(N)=O)cc1Nc1nc(-c2sc(N)nc2C)cs1]

Example 4

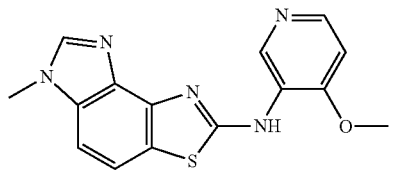

In another embodiment, the present invention comprises a crystal comprising a proMMP, or a fragment, or target structural motif or derivative thereof, and a chemical entity, wherein said chemical entity is a small-molecule allosteric processing inhibitor of the proMMP, and wherein said crystal comprises a unit cell having dimensions selected from the group consisting of: the unit cell dimensions of a=91.7 (Å), b=73.7 (Å), c=79.4 (Å), the unit cell dimensions of a=90.7 (Å), b=73.0 (Å), c=78.2 (Å), the unit cell dimensions of a=91.0 (Å), b=73.6 (Å), c=78.0 (Å), and the unit cell dimensions of a=90.0 (Å), b=77.1 (Å), c=75.0 (Å).

In another embodiment, the present invention comprises an atomic structure of a proMMP, or a fragment, or target structural motif or derivative thereof, and a chemical entity, wherein said chemical entity is a small-molecule allosteric processing inhibitor of the proMMP, and wherein said atomic structure comprises coordinates selected form the group consisting of: the coordinates of Table 11, the coordinates of Table 12, the coordinates of Table 13, and the coordinates of Table 14.

In another embodiment, the present invention comprises an atomic structure of a proMMP, or a fragment, or target structural motif or derivative thereof, and a chemical entity, wherein said chemical entity is a small-molecule allosteric processing inhibitor of the proMMP, and wherein said proMMP is proMMP9.

In another embodiment, the present invention comprises an atomic structure of proMMP9, or a fragment, or target structural motif or derivative thereof, and a chemical entity, wherein said chemical entity is a small-molecule allosteric processing inhibitor of proMMP9, and wherein said small-molecule allosteric processing inhibitor binds in an allosteric binding site comprising a region of space that is occupied by Phe 107 in the apo form of proMMP9.

In another embodiment, the present invention comprises an atomic structure of proMMP9, or a fragment, or target structural motif or derivative thereof, and a chemical entity, wherein said chemical entity is a small-molecule allosteric processing inhibitor of proMMP9, and wherein said small-molecule allosteric processing inhibitor binds in an allosteric binding site comprising amino acid residues 100-102, 110, 114, 177-179, 190-193, and 405-410, numbering taken from full-length human matrix metalloproteinase-9 precursor, proMMP9(1-707) (SEQ ID NO:1).

In another embodiment, the present invention comprises an atomic structure of a proMMP, or a fragment, or target structural motif or derivative thereof, and a chemical entity, wherein said chemical entity is a small-molecule allosteric processing inhibitor of the proMMP, and wherein said proMMP is a homologue of proMMP9 selected from the group consisting of: proMMP1, proMMP2, proMMP3, and proMMP13.

In another embodiment, the present invention comprises an atomic structure of a homologue of proMMP9, or a fragment, or target structural motif or derivative thereof, and a chemical entity, wherein said chemical entity is a small-molecule allosteric processing inhibitor of the homologue of proMMP9, and wherein said small-molecule allosteric processing inhibitor binds in an allosteric binding site comprising a region of space that is homologous to the region of space occupied by Phe 107 in the apo form of proMMP9.

In another embodiment, the present invention comprises a method for designing, selecting and/or optimizing a chemical entity that binds to an allosteric binding site of proMMP9 comprising the steps of: (a.) employing the structural coordinates of the allosteric binding site of proMMP9 according to any one of Tables 11-14 to generate a three-dimensional model of said allosteric binding pocket on a computer, wherein said computer comprises the means for generating said three-dimensional model; (b.) identifying said allosteric binding site of proMMP9, wherein said allosteric binding site comprises a region of space that is occupied by phenylalanine (Phe) 107 in the apo form of proMMP9, numbering taken from full-length human matrix metalloproteinase-9 precursor, proMMP9(1-707) (SEQ ID NO:1); (c.) employing the residues identified in (b) to design, select and/or optimize said chemical entity by performing a fitting operation between said chemical entity and said three-dimensional structural information of all or part of said allosteric binding site.

In another embodiment, the present invention comprises a method for designing, selecting and/or optimizing a chemical entity that binds to an allosteric binding site of proMMP9 comprising the steps of: (a.) employing the structural coordinates of the allosteric binding site of proMMP9 according to any one of Tables 11-14 to generate a three-dimensional model of said allosteric binding pocket on a computer, wherein said computer comprises the means for generating said three-dimensional model; (b.) identifying said allosteric binding site of proMMP9, wherein said allosteric binding site comprises amino acid residues 100-102, 110, 114, 177-179, 190-193, and 405-410, numbering taken from full-length human matrix metalloproteinase-9 precursor, proMMP9(1-707) (SEQ ID NO:1); (c.) employing the residues identified in (b) to design, select and/or optimize said chemical entity by performing a fitting operation between said chemical entity and said three-dimensional structural information of all or part of said allosteric binding site.

In another embodiment, the present invention comprises a method for designing, selecting and/or optimizing a chemical entity that binds to an allosteric binding site of a homologue of proMMP9 comprising the steps of: (a.) employing the structural coordinates of proMMP9 according to any one of Tables 11-14 to generate a three-dimensional model of said allosteric binding site of said homologue of proMMP9 on a computer, wherein said computer comprises the means for generating said three-dimensional model; (b.) identifying said allosteric binding site of the homologue of proMMP9, wherein said allosteric binding site comprises a region that is homologous to the region of space that is occupied by Phe 107 in the apo form of proMMP9; (c.) employing the residues identified in (b) to design, select and/or optimize said chemical entity by performing a fitting operation between said chemical entity and said three-dimensional structural information of all or part of said allosteric binding site.

In another embodiment, the present invention comprises a method for designing, selecting and/or optimizing a chemical entity that binds to an allosteric binding site of a homologue of proMMP9 comprising the steps of: (a.) employing the structural coordinates of proMMP9 according to any one of Tables 11-14 to generate a three-dimensional model of said allosteric binding site of said homologue of proMMP9 on a computer, wherein said computer comprises the means for generating said three-dimensional model; (b.) identifying said allosteric binding site of the homologue of proMMP9, wherein said allosteric binding site comprises amino acid residues 100-102, 110, 114, 177-179, 190-193, and 405-410, numbering taken from full-length human matrix metalloproteinase-9 precursor, proMMP9(1-707) (SEQ ID NO:1); (c.) employing the residues identified in (b) to design, select and/or optimize said chemical entity by performing a fitting operation between said chemical entity and said three-dimensional structural information of all or part of said allosteric binding site.

In another embodiment, the present invention comprises a method for designing, selecting and/or optimizing a chemical entity that binds to an allosteric binding site of a homologue of proMMP9, wherein said homologue of proMMP9 is selected from the group consisting of: proMMP1, proMMP2, proMMP3, and proMMP13, and wherein said method comprises the steps of: (a.) employing the structural coordinates of proMMP9 according to any one of Tables 11-14 to generate a three-dimensional model of said allosteric binding site of said homologue of proMMP9 on a computer, wherein said computer comprises the means for generating said three-dimensional model; (b.) identifying said allosteric binding site of the homologue of proMMP9, wherein said allosteric binding site comprises a region that is homologous to the region of space that is occupied by Phe 107 in the apo form of proMMP9; (c.) employing the residues identified in (b) to design, select and/or optimize said chemical entity by performing a fitting operation between said chemical entity and said three-dimensional structural information of all or part of said allosteric binding site.

In another embodiment, the present invention comprises a method for evaluating the ability of a chemical entity to associate with all or part of an allosteric binding site of proMMP9 comprising the steps of: (a.) employing the structural coordinates of said allosteric binding site of proMMP9 according to any to any one of Tables 11-14 to generate a three-dimensional model of said allosteric binding site of proMMP9 on a computer, wherein said computer comprises the means for generating said three-dimensional model; (b.) identifying a binding site for said chemical entity, wherein said binding site comprises a region of space that is occupied by Phe 107 in the apo form of proMMP9; (c.) employing computational means to perform a fitting operation between the chemical entity and all or part of the allosteric binding site identified in (b); and (d.) analyzing the results of said fitting operation to quantitate the association between the chemical entity and all or part of the allosteric binding site.

In another embodiment, the present invention comprises a method for evaluating the ability of a chemical entity to associate with all or part of an allosteric binding site of proMMP9 comprising the steps of: (a.) employing the structural coordinates of said allosteric binding site of proMMP9 according to any to any one of Tables 11-14 to generate a three-dimensional model of said allosteric binding site of proMMP9 on a computer, wherein said computer comprises the means for generating said three-dimensional model; (b.) identifying a binding site for said chemical entity, wherein said binding site comprises amino acid residues 100-102, 110, 114, 177-179, 190-193, and 405-410, numbering taken from full-length human matrix metalloproteinase-9 precursor, proMMP9(1-707) (SEQ ID NO:1); (c.) employing computational means to perform a fitting operation between the chemical entity and all or part of the allosteric binding site identified in (b); and (d.) analyzing the results of said fitting operation to quantitate the association between the chemical entity and all or part of the allosteric binding site.

In another embodiment, the present invention comprises a method for evaluating the ability of a chemical entity to associate with all or part of an allosteric binding site of a homologue of proMMP9 comprising the steps of: (a.) employing the structural coordinates of proMMP9 according to any to any one of Tables 11-14 to generate a three-dimensional model of said allosteric binding site of the homologue of proMMP9 on a computer, wherein said computer comprises the means for generating said three-dimensional model; (b.) identifying a binding site for said chemical entity, wherein said binding site comprises a region that is homologous to the region of space that is occupied by Phe 107 in the apo form of proMMP9; (c.) employing computational means to perform a fitting operation between the chemical entity and all or part of the allosteric binding site identified in (b); and (d.) analyzing the results of said fitting operation to quantitate the association between the chemical entity and all or part of the allosteric binding site.

In another embodiment, the present invention comprises a method of employing a computer for evaluating the ability of a chemical entity to associate with all or part of an allosteric binding site of proMMP9, wherein said computer comprises a machine-readable data storage medium comprising a data storage material encoded with the structure coordinates of the allosteric binding site according to any one of Tables 11-14 and means for generating a three-dimensional graphical representation of the allosteric binding site, and wherein said method comprises the steps of: (a.) employing the structural coordinates of said allosteric binding site of proMMP9 according to any one of Tables 11-14 to generate a three-dimensional model of said allosteric binding site of proMMP9 on said computer; (b.) identifying an allosteric binding site for said chemical entity, wherein said binding site comprises a region of space that is occupied by Phe 107 in the apo form of proMMP9; (c.) employing computational means to perform a fitting operation between the chemical entity and all or part of the allosteric binding site identified in (b); and (d.) analyzing the results of said fitting operation to quantitate the association between said chemical entity and all or part of the allosteric binding site.

In another embodiment, the present invention comprises a method of employing a computer for evaluating the ability of a chemical entity to associate with all or part of an allosteric binding site of proMMP9, wherein said computer comprises a machine-readable data storage medium comprising a data storage material encoded with the structure coordinates of the allosteric binding site according to any one of Tables 11-14 and means for generating a three-dimensional graphical representation of the allosteric binding site, and wherein said method comprises the steps of: (a.) employing the structural coordinates of said allosteric binding site of proMMP9 according to any one of Tables 11-14 to generate a three-dimensional model of said allosteric binding site of proMMP9 on said computer; (b.) identifying an allosteric binding site for said chemical entity, wherein said binding site comprises a region of space that is occupied by Phe 107 in the apo form of proMMP9; (c.) employing computational means to perform a fitting operation between the chemical entity and all or part of the allosteric binding site identified in (b); (d.) analyzing the results of said fitting operation to quantitate the association between said chemical entity and all or part of the allosteric binding site, (e) repeating steps (a) through (d) with a second chemical entity; and (f) selecting at least one part of said first or second chemical entity that associates with said all or part of said allosteric binding site based on said quantitated association of said first or second chemical entity.

In another embodiment, the present invention comprises a method of employing a computer for evaluating the ability of a chemical entity to associate with all or part of an allosteric binding site of a homologue of proMMP9, wherein said computer comprises a machine-readable data storage medium comprising a data storage material encoded with the structure coordinates of the allosteric binding site according to any one of Tables 11-14 and means for generating a three-dimensional graphical representation of the allosteric binding site, and wherein said method comprises the steps of: (a.) employing the structural coordinates of proMMP9 according to any one of Tables 11-14 to generate a three-dimensional model of said allosteric binding site of the homologue of proMMP9 on said computer; (b.) identifying an allosteric binding site for said chemical entity, wherein said binding site comprises a region that is homologous to the region of space that is occupied by Phe 107 in the apo form of proMMP9; (c.) employing computational means to perform a fitting operation between the chemical entity and all or part of the allosteric binding site identified in (b); and (d.) analyzing the results of said fitting operation to quantitate the association between said chemical entity and all or part of the allosteric binding site.

In another embodiment, the present invention comprises a method of employing a computer for evaluating the ability of a chemical entity to associate with all or part of an allosteric binding site of a homologue of proMMP9, wherein said computer comprises a machine-readable data storage medium comprising a data storage material encoded with the structure coordinates of the allosteric binding site according to any one of Tables 11-14 and means for generating a three-dimensional graphical representation of the allosteric binding site, and wherein said method comprises the steps of: (a.) employing the structural coordinates of proMMP9 according to any one of Tables 11-14 to generate a three-dimensional model of said allosteric binding site of the homologue of proMMP9 on said computer; (b.) identifying an allosteric binding site for said chemical entity, wherein said binding site comprises a region that is homologous to the region of space that is occupied by Phe 107 in the apo form of proMMP9; (c.) employing computational means to perform a fitting operation between the chemical entity and all or part of the allosteric binding site identified in (b); (d.) analyzing the results of said fitting operation to quantitate the association between said chemical entity and all or part of the allosteric binding site; (e) repeating steps (a) through (d) with a second chemical entity; and (f) selecting at least one part of said first or second chemical entity that associates with said all or part of said allosteric binding site based on said quantitated association of said first or second chemical entity.

In another embodiment, the present invention comprises a method of employing a computer for evaluating the ability of a chemical entity to associate with all or part of an allosteric binding site of a homologue of proMMP9, wherein said homologue of MMP9 is selected from the group consisting of: proMMP1, proMMP2, proMMP3, and proMMP13, and wherein said computer comprises a machine-readable data storage medium comprising a data storage material encoded with the structure coordinates of the allosteric binding site according to any one of Tables 11-14 and means for generating a three-dimensional graphical representation of the allosteric binding site, and wherein said method comprises the steps of: (a.) employing the structural coordinates of proMMP9 according to any one of Tables 11-14 to generate a three-dimensional model of said allosteric binding site of the homologue of proMMP9 on said computer; (b.) identifying an allosteric binding site for said chemical entity, wherein said binding site comprises a region that is homologous to the region of space that is occupied by Phe 107 in the apo form of proMMP9; (c.) employing computational means to perform a fitting operation between the chemical entity and all or part of the allosteric binding site identified in (b); and (d.) analyzing the results of said fitting operation to quantitate the association between said chemical entity and all or part of the allosteric binding site.

In another embodiment, the present invention comprises a method of employing a computer for evaluating the ability of a chemical entity to associate with all or part of an allosteric binding site of a homologue of proMMP9, wherein said homologue of MMP9 is selected from the group consisting of: proMMP1, proMMP2, proMMP3, and proMMP13, and wherein said computer comprises a machine-readable data storage medium comprising a data storage material encoded with the structure coordinates of the allosteric binding site according to any one of Tables 11-14 and means for generating a three-dimensional graphical representation of the allosteric binding site, wherein said method comprises the steps of: (a.) employing the structural coordinates of proMMP9 according to any one of Tables 11-14 to generate a three-dimensional model of said allosteric binding site of the homologue of proMMP9 on said computer; (b.) identifying an allosteric binding site for said chemical entity, wherein said binding site comprises a region that is homologous to the region of space that is occupied by Phe 107 in the apo form of proMMP9; (c.) employing computational means to perform a fitting operation between the chemical entity and all or part of the allosteric binding site identified in (b); (d.) analyzing the results of said fitting operation to quantitate the association between said chemical entity and all or part of the allosteric binding site; (e) repeating steps (a) through (d) with a second chemical entity; and (f) selecting at least one part of said first or second chemical entity that associates with said all or part of said allosteric binding site based on said quantitated association of said first or second chemical entity.

In another embodiment, the present invention comprises a method of inhibiting activation of a pro matrix metalloprotease (proMMP) using a chemical entity selected from the group consisting of: a small-molecule allosteric processing inhibitor and solvates, hydrates, tautomers, or pharmaceutically acceptable salts thereof.

In another embodiment, the present invention comprises a method of inhibiting activation of a proMMP using a pharmaceutical composition, comprising a small-molecule allosteric processing inhibitor and a pharmaceutically acceptable carrier.

In another embodiment, the present invention comprises a method of inhibiting activation of a proMMP using a chemical entity selected from the group consisting of: a small-molecule allosteric processing inhibitor and solvates, hydrates, tautomers, or pharmaceutically acceptable salts thereof; wherein said proMMP is proMMP9; and wherein said chemical entity binds in an allosteric binding site comprising a region of space that is occupied by phenylalanine (Phe) 107 in the apo form of proMMP9, numbering taken from full-length human matrix metalloproteinase-9 precursor, proMMP9(1-707) (SEQ ID NO:1).

In another embodiment, the present invention comprises a method of inhibiting activation of a proMMP using a chemical entity selected from the group consisting of: a small-molecule allosteric processing inhibitor and solvates, hydrates, tautomers, or pharmaceutically acceptable salts thereof; wherein said proMMP is proMMP9; and wherein said chemical entity binds in an allosteric binding site comprising amino acid residues 100-102, 110, 114, 177-179, 190-193, and 405-410, numbering taken from full-length human matrix metalloproteinase-9 precursor, proMMP9(1-707) (SEQ ID NO:1).

In another embodiment, the present invention comprises a method of inhibiting activation of a proMMP using a pharmaceutical composition, comprising a small-molecule allosteric processing inhibitor and a pharmaceutically acceptable carrier; wherein said proMMP is proMMP9; and wherein said chemical entity binds in an allosteric binding site comprising a region of space that is occupied by Phe 107 in the apo form of proMMP9.

In another embodiment, the present invention comprises a method of inhibiting activation of a pro matrix metalloprotease (proMMP) using a chemical entity selected from the group consisting of: a small-molecule allosteric processing inhibitor and solvates, hydrates, tautomers, or pharmaceutically acceptable salts thereof; wherein said proMMP is a homologue of MMP9 selected from the group consisting of: proMMP1, proMMP2, proMMP3, and proMMP13; and wherein said chemical entity binds in an allosteric binding site comprising a region that is homologous to the region of space that is occupied by Phe 107 in the apo form of proMMP9.

In another embodiment, the present invention comprises a method of inhibiting activation of a proMMP using a pharmaceutical composition, comprising a small-molecule allosteric processing inhibitor and a pharmaceutically acceptable carrier; wherein said proMMP is a homologue of MMP9 selected from the group consisting of: proMMP1, proMMP2, proMMP3, and proMMP13; and wherein said chemical entity binds in an allosteric binding site comprising a region that is homologous to the region of space that is occupied by Phe 107 in the apo form of proMMP9.

In another embodiment, the present invention comprises a method of inhibiting matrix metalloprotease (MMP) activity in a mammal by administration of an effective amount of at least one small-molecule allosteric processing inhibitor that inhibits activation of the MMP.

In another embodiment, the present invention comprises a method of inhibiting matrix metalloprotease (MMP) activity in a mammal by administration of an effective amount of at least one small-molecule allosteric processing inhibitor that inhibits activation of the MMP; wherein said MMP is MMP9; and wherein said small-molecule allosteric processing inhibitor binds in an allosteric binding site comprising a region of space that is occupied by Phe 107 in the apo form of proMMP9

In another embodiment, the present invention comprises a method of inhibiting matrix metalloprotease (MMP) activity in a mammal by administration of an effective amount of at least one small-molecule allosteric processing inhibitor that inhibits activation of the MMP; wherein said MMP is MMP9; and wherein said small-molecule allosteric processing inhibitor binds in an allosteric binding site comprising amino acid residues 100-102, 110, 114, 177-179, 190-193, and 405-410, numbering taken from full-length human matrix metalloproteinase-9 precursor, proMMP9(1-707) (SEQ ID NO:1).

In another embodiment, the present invention comprises a method of inhibiting matrix metalloprotease (MMP) activity in a mammal by administration of an effective amount of at least one small-molecule allosteric processing inhibitor that inhibits activation of the MMP; wherein said MMP is a homologue of MMP9 selected from the group consisting of: MMP1, MMP2, MMP3, and MMP13; and wherein said small-molecule allosteric processing inhibitor binds in an allosteric binding site comprising a region that is homologous to the region of space that is occupied by Phe 107 in the apo form of proMMP9.

In another embodiment, the present invention comprises a method for preventing, treating or ameliorating an MMP mediated syndrome, disorder or disease comprising administering to a subject in need thereof an effective amount of a small-molecule allosteric processing inhibitor that inhibits activation of the MMP, or a form, composition or medicament comprising the allosteric processing inhibitor.

In another embodiment, the present invention comprises a method for preventing, treating or ameliorating an MMP mediated syndrome, disorder or disease wherein said syndrome, disorder or disease is associated with elevated MMP expression or MMP overexpression, or is a condition that accompanies syndromes, disorders or diseases associated with elevated MMP expression or MMP overexpression comprising administering to a subject in need thereof an effective amount of a small-molecule allosteric processing inhibitor that inhibits activation of the MMP, or a form, composition or medicament comprising the allosteric processing inhibitor.

In another embodiment, the present invention comprises a method of preventing, treating or ameliorating a syndrome, disorder or disease, wherein said syndrome, disorder or disease is selected from the group consisting of: neoplastic disorders, osteoarthritis, rheumatoid arthritis, cardiovascular diseases, gastric ulcer, pulmonary hypertension, chronic obstructive pulmonary disease, inflammatory bowel syndrome, periodontal disease, skin ulcers, liver fibrosis, emphysema, Marfan syndrome, stroke, multiple sclerosis, asthma, abdominal aortic aneurysm, coronary artery disease, idiopathic pulmonary fibrosis, renal fibrosis, and migraine, comprising administering to a subject in need thereof an effective amount of a small-molecule allosteric processing inhibitor that inhibits activation of an MMP, or a form, composition or medicament comprising the allosteric processing inhibitor.

In another embodiment, the present invention comprises a method of inhibiting matrix metalloprotease (MMP) activity in a mammal by administration of an effective amount of at least one small-molecule allosteric processing inhibitor that inhibits activation of the MMP; wherein said MMP is a homologue of MMP9 selected from the group consisting of: MMP1, MMP2, MMP3, and MMP13; and wherein said small-molecule allosteric processing inhibitor binds in an allosteric binding site comprising a region that is homologous to the region of space that is occupied by Phe 107 in the apo form of proMMP9.

In another embodiment, the present invention comprises a method for preventing, treating or ameliorating an MMP mediated syndrome, disorder or disease comprising administering to a subject in need thereof an effective amount of a small-molecule allosteric processing inhibitor that inhibits activation of the MMP, or a form, composition or medicament comprising the allosteric processing inhibitor; wherein said MMP is MMP9; and wherein said small-molecule allosteric processing inhibitor binds in an allosteric binding site comprising a region of space that is occupied by Phe 107 in the apo form of proMMP9.

In another embodiment, the present invention comprises a method for preventing, treating or ameliorating an MMP mediated syndrome, disorder or disease wherein said syndrome, disorder or disease is associated with elevated MMP expression or MMP overexpression, or is a condition that accompanies syndromes, disorders or diseases associated with elevated MMP expression or MMP overexpression comprising administering to a subject in need thereof an effective amount of a small-molecule allosteric processing inhibitor that inhibits activation of the MMP, or a form, composition or medicament comprising the allosteric processing inhibitor; wherein said MMP is MMP9; and wherein said small-molecule allosteric processing inhibitor binds in an allosteric binding site comprising a region of space that is occupied by Phe 107 in the apo form of proMMP9.

In another embodiment, the present invention comprises a method of preventing, treating or ameliorating a syndrome, disorder or disease, wherein said syndrome, disorder or disease is selected from the group consisting of: neoplastic disorders, osteoarthritis, rheumatoid arthritis, cardiovascular diseases, gastric ulcer, pulmonary hypertension, chronic obstructive pulmonary disease, inflammatory bowel syndrome, periodontal disease, skin ulcers, liver fibrosis, emphysema, Marfan syndrome, stroke, multiple sclerosis, asthma, abdominal aortic aneurysm, coronary artery disease, idiopathic pulmonary fibrosis, renal fibrosis, and migraine, comprising administering to a subject in need thereof an effective amount of a small-molecule allosteric processing inhibitor that inhibits activation of an MMP, or a form, composition or medicament comprising the allosteric processing inhibitor; wherein said MMP is MMP9; and wherein said small-molecule allosteric processing inhibitor binds in an allosteric binding site comprising a region of space that is occupied by Phe 107 in the apo form of proMMP9.

In another embodiment, the present invention comprises a method for preventing, treating or ameliorating an MMP mediated syndrome, disorder or disease comprising administering to a subject in need thereof an effective amount of a small-molecule allosteric processing inhibitor that inhibits activation of the MMP, or a form, composition or medicament comprising the allosteric processing inhibitor; wherein said MMP is a homologue of MMP9 selected from the group consisting of: MMP1, MMP2, MMP3, and MMP13; and wherein said small-molecule allosteric processing inhibitor binds in an allosteric binding site comprising a region that is homologous to the region of space that is occupied by Phe 107 in the apo form of proMMP9.

In another embodiment, the present invention comprises a method for preventing, treating or ameliorating an MMP mediated syndrome, disorder or disease wherein said syndrome, disorder or disease is associated with elevated MMP expression or MMP overexpression, or is a condition that accompanies syndromes, disorders or diseases associated with elevated MMP expression or MMP overexpression comprising administering to a subject in need thereof an effective amount of a small-molecule allosteric processing inhibitor that inhibits activation of the MMP, or a form, composition or medicament comprising the allosteric processing inhibitor; wherein said MMP is a homologue of MMP9 selected from the group consisting of: MMP1, MMP2, MMP3, and MMP13; and wherein said small-molecule allosteric processing inhibitor binds in an allosteric binding site comprising a region that is homologous to the region of space that is occupied by Phe 107 in the apo form of proMMP9.

In another embodiment, the present invention comprises a method of preventing, treating or ameliorating a syndrome, disorder or disease, wherein said syndrome, disorder or disease is selected from the group consisting of: neoplastic disorders, osteoarthritis, rheumatoid arthritis, cardiovascular diseases, gastric ulcer, pulmonary hypertension, chronic obstructive pulmonary disease, inflammatory bowel syndrome, periodontal disease, skin ulcers, liver fibrosis, emphysema, Marfan syndrome, stroke, multiple sclerosis, asthma, abdominal aortic aneurysm, coronary artery disease, idiopathic pulmonary fibrosis, renal fibrosis, and migraine, comprising administering to a subject in need thereof an effective amount of a small-molecule allosteric processing inhibitor that inhibits activation of an MMP, or a form, composition or medicament comprising the allosteric processing inhibitor; wherein said MMP is a homologue of MMP9 selected from the group consisting of: MMP1, MMP2, MMP3, and MMP13; and wherein said small-molecule allosteric processing inhibitor binds in an allosteric binding site comprising a region that is homologous to the region of space that is occupied by Phe 107 in the apo form of proMMP9.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; wherein said syndrome, disorder or disease is a neoplastic disorder, which is ovarian cancer.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; wherein said syndrome, disorder or disease is a cardiovascular disease, and wherein said cardiovascular disease is selected from the group consisting of: atherosclerotic plaque rupture, aneurysm, vascular tissue morphogenesis, coronary artery disease, and myocardial tissue morphogenesis.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; and wherein said syndrome, disorder or disease is a cardiovascular disease, and wherein said cardiovascular disease is atherosclerotic plaque rupture.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; and wherein said syndrome, disorder or disease is rheumatoid arthritis.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; and wherein said syndrome, disorder or disease is asthma.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; and wherein said syndrome, disorder or disease is chronic obstructive pulmonary disease.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; and wherein said syndrome, disorder or disease is inflammatory bowel syndrome.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; and wherein said syndrome, disorder or disease is abdominal aortic aneurism.

In another embodiment, the present invention comprises a method of preventing, treating or ameliorating a syndrome, disorder or disease, wherein said method comprises administering to a subject in need thereof an effective amount of a small-molecule allosteric processing inhibitor that inhibits activation of an MMP, or a form, composition or medicament comprising the allosteric processing inhibitor; and wherein said syndrome, disorder or disease is osteoarthritis.

Additional embodiments and advantages of the invention will become apparent from the detailed discussion, schemes, examples, and claims included herein.

BRIEF DESCRIPTION OF THE DRAWINGS

Embodiments of the present invention will now be described, by way of an example only, with reference to the accompanying drawings wherein.

DEFINITIONS

Figure 1:
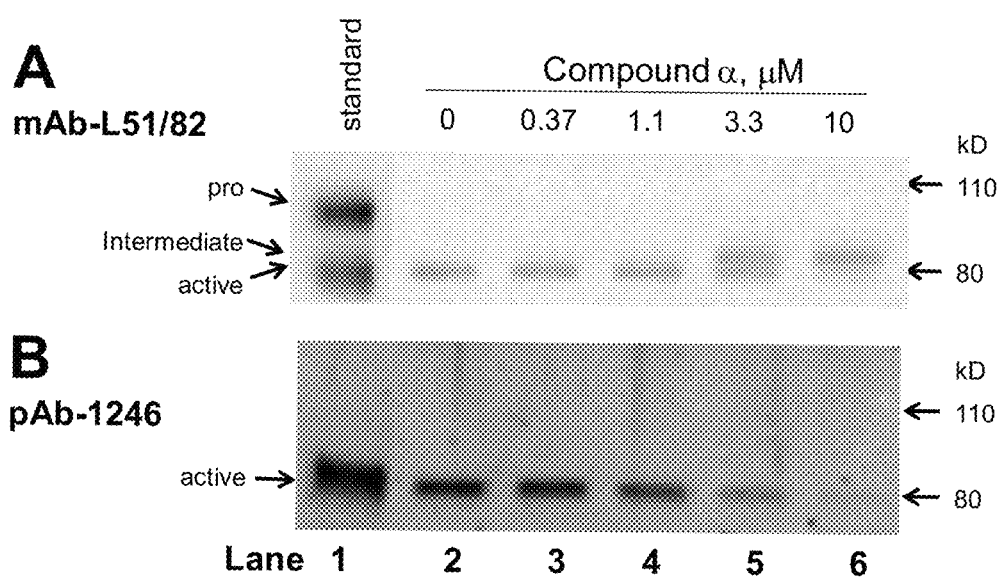
FIG. 1: Shown are western blots with two different antibodies illustrating the effects of a small-molecule allosteric processing inhibitor, Example 2, on the activation of proMMP9 in synoviocytes harvested from female Lewis rats after inducing arthritis with i.p. administration of Streptococcal cell wall peptidoglycan polysaccharides. A mouse monoclonal antibody, mAb L51/82, detected pro and processed forms of MMP9. The mouse monoclonal antibody showed that Example 2 caused a dose-dependent reduction in the appearance of the 80 kD active form of MMP9 and the appearance of an 86 kD form of the protein (FIG. 1A, lanes 3-6). A rabbit polyclonal antibody, pAb-1246, detected the 80 kD active form of MMP9, but did not recognize the 100 kD form of proMMP9. The rabbit polyclonal antibody showed that the small-molecule allosteric processing inhibitor caused a dose-dependent reduction in the appearance of the 80 kD active form of MMP9 (FIG. 1B, lanes 2-6).

As is generally the case in biotechnology and chemistry, the description of the present invention has required the use of a number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which this invention belongs. Definitions for other terms may also appear elsewhere herein. However, the definitions provided here and elsewhere herein should always be considered in determining the intended scope and meaning of the defined terms. Although any methods and materials similar or equivalent to those described herein can be used in the practice of the present invention, the preferred methods and materials are described.

The term "comprising" means "including principally, but not necessarily solely". Furthermore, variations of the word "comprising", such as "comprise" and "comprises", have correspondingly varied meanings.

As used herein, the terms "containing", "having" and "including" are used in their open, non-limiting sense.

As used herein, "sequence" means the linear order in which monomers occur in a polymer, for example, the order of amino acids in a polypeptide or the order of nucleotides in a polynucleotide.

The terms "polypeptide", "protein", and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide", "protein", and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking Further, amino acids other than the conventional twenty amino acids encoded by the codons of genes may also be included in a polypeptide.

As used herein, a protein or nucleic acid molecule is said to be "isolated" when the protein or nucleic acid molecule is substantially separated from contaminants from the source of the protein or nucleic acid.

As used herein, the term "native protein" refers to a protein comprising an amino acid sequence identical to that of a protein isolated from its natural source or organism.

As used herein, the term "amino acids" refers to the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, and lysine. Unless specifically indicated, all amino acids are referred to in this application are in the L-form.

As used herein, the term "normatural amino acids" refers to amino acids that are not naturally found in proteins. For example, selenomethionine.

As used herein, the term "positively charged amino acid" includes any amino acids having a positively charged side chain under normal physiological conditions. Examples of positively charged naturally occurring amino acids are arginine, lysine, and histidine.

As used herein, the term "negatively charged amino acid" includes any amino acids having a negatively charged side chains under normal physiological conditions. Examples of negatively charged naturally occurring amino acids are aspartic acid and glutamic acid.

As used herein, the term "hydrophobic amino acid" includes any amino acids having an uncharged, nonpolar side chain that is relatively insoluble in water. Examples of naturally occurring hydrophobic amino acids are alanine, leucine, isoleucine, valine, proline, phenylalanine, tryptophan, and methionine.

As used herein, the term "hydrophilic amino acid" refers to any amino acids having an uncharged, polar side chain that is relatively soluble in water. Examples of naturally occurring hydrophilic amino acids are serine, threonine, tyrosine, asparagine, glutamine and cysteine.

As used herein, "nucleic acid" is defined as RNA or DNA that encodes a protein or peptide as defined herein, or is complementary to nucleic acid sequence encoding such peptides, or hybridizes to such nucleic acid and remains stably bound to it under appropriate stringency conditions. Nucleic acid sequences can be composed of natural nucleotides of the following bases: thymidine, adenine, cytosine, guanine, and uracil; abbreviated T, A, C, G, and U, respectively, and/or synthetic analogs of the natural nucleotides.

The term "oligonucleotide" or "oligo" refers to a single-stranded DNA or RNA sequence of a relatively short length, for example, less than 100 residues long. For many methods, oligonucleotides of about 16-25 nucleotides in length are useful, although longer oligonucleotides of greater than about 25 nucleotides may sometimes be utilized. Some oligonucleotides can be used as "primers" for the synthesis of complimentary nucleic acid strands. For example, DNA primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation.

The term "high stringency" as used herein refers to the conditions under which two nucleic acids may be hybridized, and may include, for example, the concentration of salts and/or detergents in a solution, the temperature of a solution that is used during the hybridization of the two nucleic acids and time period of the hybridization. Accordingly, the term "high stringency" as used herein refers to conditions in a solution that are conducive to hybridization of two nucleic acids only where such nucleic acids share a high degree of complementarity. The degree of complementarity may include, but not be limited to, a range of from about 90% to 100%. Thus, "high stringency" conditions may involve, but are not limited to, the use of a varying temperature and a buffer comprising various concentrations of detergents, salts, and divalent cations.

As used herein, "vector" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, "proMMP" is used to mean a protein obtained as a result of expression of the pro form of a matrix metalloproteinase (also known as a matrix metalloprotease). Within the meaning of this term, it will be understood that a proMMP encompasses all proteins encoded by a proMMP gene or cDNA, mutants thereof, including deletions, substitutions, and truncations, as well as modified forms thereof. As used herein, the term "proMMP" also includes partially processed forms of a proMMP that have not yet been completely processed to the active form.

As used herein, the term "homologue of MMP9" or "MMP9 homologue" refers to a molecule that is homologous to human proMMP9 by structure or sequence and has the activity of a matrix metalloprotease (MMP) protein when processed to the active form. Examples of human MMP9 homologues include but are not limited to, human proMMP1, human proMMP2, human proMMP3, human proMMP9, human proMMP13, and proMMPs from other species, including proMMPs with conservative substitutions, additions, deletions or combinations thereof. As a non-limiting example, human proMMP9 comprises SEQ ID NO:12 and variants thereof comprising at least about 70% amino acid sequence identity to SEQ ID NO:12, or preferably 80%, 85%, 90% and 95% sequence identity to SEQ ID NO:12, or more preferably, at least about 95% or more sequence identity to SEQ ID NO:12.

As used herein, the terms "homologous region" and "regions homologous to" refer to regions of a protein that may have different primary amino acid sequences but have similar overall secondary and tertiary structures. Homologous regions contemplated for use in the present invention include, but are not limited to, regions homologous to the allosteric binding site of proMMP9 that includes the region occupied by Phe 107 in the apo form of proMMP9.

As used herein, the term "activation" refers to the processing that occurs to change from an inactive pro form of a matrix metalloproteinase (proMMP) to an active form of a matrix metalloproteinase (MMP).

As used herein, the term "activity" or "active form" refers to an activity exerted by a matrix metalloproteinase (MMP) as determined in vivo or in vitro, according to standard techniques. Examples of such activity include, but are not limited to, direct activity such as catalytic activity or the ability to bind to a ligand or an analog thereof, changes in transcriptional activity or changes in the levels of genes or gene products that are regulated directly or indirectly by MMP activity, changes in enzymatic activity for another protein whose expression may be affected directly or indirectly by MMP activity, or functional changes of cell physiology that result from changes in MMP activity.

As used herein, the term "allosteric" relates to binding at a binding site other than the active site.

As used herein, the term "active site" refers to regions on an active MMP or a structural motif of an active MMP that are directly involved in the catalytic activity of a human MMP or a homolog.

As used herein, the terms "processing inhibitor", "activation inhibitor", and "inhibitor of activation" all refer to ligands with the ability to inhibit processing of a proMMP to an active form and thus modulate a measurable amount of MMP activity in vitro or in vivo. Preferred processing inhibitors are small-molecules, preferably less than about 1,000 daltons.

As used herein, the term "small-molecule" refers to any molecule, or chemical entity, with a molecular weight of less than about 1,000 daltons.

As used herein, the term "chemical entity" refers to chemical compounds, complexes of at least two chemical compounds, and fragments of such compounds or complexes. The chemical entity may be, for example, a ligand, a substrate, a nucleotide triphosphate, a nucleotide diphosphate, phosphate, a nucleotide, an agonist, antagonist, inhibitor, antibody, drug, peptide, protein or compound.

As used herein, the term "ligand" refers to any molecule, or chemical entity, which binds with or to a human MMP or proMMP, a subunit of an MMP or proMMP, a domain of an MMP or proMMP, a target structural motif of an MMP or proMMP, or a fragment of an MMP or proMMP. Thus, ligands include, but are not limited to, processing inhibitors that bind to a proMMP and inhibit processing of the proMMP to the active MMP form. Preferred ligands are small-molecules, preferably less than about 1,000 daltons.

As used herein, the terms "apo" and "apo form" when used in reference to a proMMP protein, refer to a proMMP protein that does not have an allosteric processing inhibitor bound in an allosteric binding site.

As used herein the terms "bind", "binding", "bond", "bonded" or "bound" when used in reference to the association of atoms, molecules, or chemical groups, refer to any physical contact or association of two or more atoms, molecules, or chemical groups.

As used herein, the terms "binding site" or "binding pocket" refer to a region of an MMP or proMMP, and a molecular complex comprising a ligand and an MMP or proMMP that, as a result of the primary amino acid sequence of the MMP or proMMP and/or its three-dimensional shape, favourably associates with another chemical entity or compound including ligands, cofactors, inhibitors, or other types of modulators.

As used herein, "target structural motif", "target motif", or "domain" refer to any rationally selected sequence or combination of sequences in which the sequence(s) are chosen based on a three-dimensional configuration or electron density map which is formed upon the folding of a proMMP or MMP. There are a variety of target motifs known in the art. Protein target motifs include, but are not limited to, enzymatic active sites, inhibitor binding sites, allosteric binding sites, structural subdomains, epitopes, functional domains and signal sequences. A variety of structural formats for the input and output means can be used to input and output the information in the computer-based systems of the present invention.

By the term "selecting", "select", "selected", "identifying", "identify", or "identified" compounds it is intended to encompass both (a) choosing compounds from a group previously unknown to be modulators of a protein complex or interacting protein members thereof and (b) testing compounds that are known to be capable of binding, or modulating the functions and activities of, a protein complex or interacting protein members thereof. The compounds encompass numerous chemical classes, including but not limited to, small organic or inorganic compounds and natural or synthetic molecules. Preferably, they are small organic compounds, i.e., those having a molecular weight of no greater than about 1,000 daltons.

The term "high-throughput assay" or "high-throughput screening" refers to assay designs that allow easy screening of multiple samples simultaneously and/or in rapid succession, and may include the capacity for robotic manipulation. Another desired feature of high-throughput assays is an assay design that is optimized to reduce reagent usage, or minimize the number of manipulations in order to achieve the analysis desired. Examples of high-throughput assay formats include, but are not limited to, formats that utilize 96-well, 384-well, and 1536-well plates, or "lab on a chip" microchannel chips used for liquid handling experiments. It is well known by those in the art that as miniaturization of plastic molds and liquid handling devices are advanced, or as improved assay devices are designed, greater numbers of samples can be processed using the forms of the present invention. The present invention includes any high-throughput screening method utilized to test new compounds which are identified or designed for their ability to interact with a proMMP. For general information on high-throughput screening see, for example, (Devlin (editor) 1998); and U.S. Pat. No. 5,763, 263).

As used herein, the term "atomic coordinates" or "structure coordinates" refers to mathematical coordinates that describe the positions of atoms in crystals of a proMMP or MMP in Protein Data Bank (PDB) format, including X, Y, Z and B, for each atom. The diffraction data obtained from the crystals are used to calculate an electron density map of the repeating unit of the crystal. The electron density maps may be used to establish the positions (i.e. coordinates X, Y and Z) of the individual atoms within the crystal. Those of skill in the art understand that a set of structure coordinates determined by X-ray crystallography is not without standard error.

The term "atom type" refers to the chemical element whose coordinates are measured.

The terms "X," "Y" and "Z" refer to the crystallographically-defined atomic position of the element measured with respect to the chosen crystallographic origin. The term "B" refers to a thermal factor that measures the mean variation of an atom's position with respect to its average position.

As used herein, the term "crystal" refers to any three-dimensional ordered array of molecules that diffracts X-rays.

As used herein, the term "carrier" in a composition refers to a diluent, adjuvant, excipient, or vehicle with which the product is mixed.

As used herein, the term "SAR", an abbreviation for Structure-Activity Relationships, collectively refers to the structure-activity/structure property relationships pertaining to the relationship(s) between a compound's activity/properties and its chemical structure.

As used herein, the term "molecular structure" refers to the three dimensional arrangement of molecules of a particular compound or complex of molecules (e.g., the three dimensional structure of a complex of a proMMP and an allosteric processing inhibitor As used herein, the term "molecular modeling" refers to the use of computational methods, preferably computer assisted methods, to draw realistic models of what molecules look like and to make predictions about structure activity relationships of ligands. The methods used in molecular modeling range from molecular graphics to computational chemistry.

As used herein, the term "molecular model" refers to the three dimensional arrangement of the atoms of a molecule connected by covalent bonds or the three dimensional arrangement of the atoms of a complex comprising more than one molecule, e.g., a protein:ligand complex.

As used herein, the term "molecular graphics" refers to three dimensional (3D) representations of the molecules; for instance, a 3D representation produced using computer assisted computational methods.

As used herein, "computer readable medium" refers to any medium, which can be read and accessed directly by a computer. Such media include, but are not limited to: magnetic storage media, such as floppy discs, hard disc storage media, and magnetic tape; optical storage media such as optical discs or CD-ROM; electrical storage media such as RAM and ROM; and hybrids of these categories such as magnetic/optical storage media.

As used herein, "recorded" refers to a process for storing information on computer readable media. A skilled artisan can readily adopt any of the presently known methods for recording information on computer readable media to generate manufactures comprising an amino acid sequence and/or atomic coordinate/X-ray diffraction data information of the present invention.

As used herein, "a computer-based system" refers to the hardware means, software means, and data storage means used to analyze the sequence and/or X-ray diffraction data of the present invention. The minimum hardware means of the computer-based systems of the present invention comprises a central processing unit (CPU), input means, output means, and data storage means. A skilled artisan can readily appreciate which of the currently available computer-based systems are suitable for use in the present invention. A visualization device, such as a monitor, is optionally provided to visualize structure data.

As stated above, the computer-based systems of the present invention comprise a data storage means having stored therein sequence and/or atomic coordinate/X-ray diffraction data of the present invention and the necessary hardware means and software means for supporting and implementing an analysis means. As used herein, "data storage means" refers to memory which can store sequence or atomic coordinate/X-ray diffraction data of the present invention, or a memory access means which can access manufactures having recorded thereon the sequence or X-ray data of the present invention.

As used herein, "search means" or "analysis means" refers to one or more programs which are implemented on the computer-based system to compare a target sequence or target structural motif with the sequence or X-ray data stored within the data storage means. Search means are used to identify fragments or regions of a protein which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses can be adapted for use in the present computer-based systems.

As used herein, the term "computational chemistry" refers to calculations of the physical and chemical properties of the molecules.

As used herein, the term "molecular replacement" refers to a method that involves generating a preliminary model of a crystal of a complex of a proMMP and an allosteric processing inhibitor whose coordinates are unknown, by orienting and positioning the said atomic coordinates described in the present invention so as best to account for the observed diffraction pattern of the unknown crystal. Phases can then be calculated from this model and combined with the observed amplitudes to give an approximate Fourier synthesis of the structure whose coordinates are unknown. (Rossmann 1972)

As used herein, the term "homolog" refers to a proMMP molecule or the nucleic acid molecule which encodes the protein, or a functional domain from said protein from a first source having at least about 70% or 75% sequence identity, or at least about 80% sequence identity, or more preferably at least about 85% sequence identity, or even more preferably at least about 90% sequence identity, and most preferably at least about 95%, 97% or 99% amino acid or nucleotide sequence identity, with the protein, encoding nucleic acid molecule or any functional domain thereof, from a second source. The second source may be a version of the molecule from the first source that has been genetically altered by any available means to change the primary amino acid or nucleotide sequence or may be from the same or a different species than that of the first source.

The term "root mean square deviation" means the square root of the arithmetic mean of the squares of the deviations from the mean.

As used herein, the term "hydrogen bond" refers to two hydrophilic atoms (either O or N), which share a hydrogen that is covalently bonded to only one atom, while interacting with the other.

As used herein, the term "hydrophobic interaction" refers to interactions made by two hydrophobic residues or atoms (such as Carbon).

As used herein, the term "conjugated system" refers to more than two double bonds adjacent to each other, in which electrons are completely delocalized with the entire system. This also includes aromatic residues.

As used herein, the term "aromatic residue" refers to amino acids with side chains having a delocalized conjugated system. Examples of aromatic residues are phenylalanine, tryptophan, and tyrosine.

As used herein, the term "R or S-isomer" refers to two possible stereoisomers of a chiral carbon according to the Cahn-Ingold-Prelog system adopted by International Union of Pure and Applied Chemistry (IUPAC). Each group attached to the chiral carbon is first assigned to a preference or priority a, b, c, or d on the basis of the atomic number of the atom that is directly attached to the chiral carbon. The group with the highest atomic number is given the highest preference a, the group with next highest atomic number is given the next highest preference b, and so on. The group with the lowest preference (d) is then directed away from the viewer. If the trace of a path from a to b to c is counter clockwise, the isomer is designated (S); in the opposite direction, clockwise, the isomer is designated (R).

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

As used herein, the term "chiral center" refers to a carbon atom to which four different groups are attached.

As used herein, the term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

As used herein, the term "racemic" refers to a mixture of equal parts of enantiomers and which is optically active.

As used herein, the term "resolution" refers to the separation or concentration or depletion of one of the two enantiomeric forms of a molecule. In the context of this application, The term "resolution" also refers to the amount of detail, which can be resolved by the diffraction experiment. Or in other terms, since the inherent disorder of a protein crystal diffraction pattern fades away at some diffraction angle theta$_{max}$, the corresponding distance d$_{min}$, of the reciprocal lattices is determined by Bragg's law. In practice in protein crystallography it is usual to quote the nominal resolution of a protein electron density in terms of d$_{min}$, the minimum lattice distance to which data is included in the calculation of the map.

As used herein, the terms "covalent bond" or "valence bond" refer to a chemical bond between two atoms in a molecule created by the sharing of electrons, usually in pairs, by the bonded atoms.

As used herein, "noncovalent bond" refers to an interaction between atoms and/or molecules that does not involve the formation of a covalent bond between them.

The term "composition" is intended to encompass a product comprising the specified ingredients in the specified amounts, as well as any product which results, directly or indirectly, from combinations of the specified ingredients in the specified amounts. For the purposes of this invention, a composition will often, but not always comprise a carrier.

The term "subject" as used herein, refers to an animal, preferably a mammal, most preferably a human, who is the object of treatment, observation or experiment.

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "pharmaceutically acceptable salt" refers to non-toxic pharmaceutically acceptable salts (Berge, Bighley et al. 1977; Gould 1986). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxy-ethanesulfonic, benzenesulfonic, oxalic, pamoic, 2-naphthalenesulfonic, p-toluenesulfonic, cyclohexane- sulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

DETAILED DESCRIPTION OF ILLUSTRATIVE EMBODIMENTS

It is to be understood at the outset, that the figures and examples provided herein are to exemplify, and not to limit the invention and its various embodiments.

The present invention includes a crystal comprising a complex of a proMMP and an allosteric processing inhibitor that inhibits that activation of the proMMP, methods for identifying allosteric processing inhibitors that inhibit the activation of proMMPs, and methods of inhibiting the activation of proMMPs with allosteric processing inhibitors. In a non-limiting example, the proMMP is human proMMP9 and the allosteric processing inhibitor is a small-molecule with a molecular weight of no greater than about 1,000 daltons.

Engineered Forms and Fragments

Engineered forms of a proMMP or fragments thereof, for instance engineered forms or fragments comprising the pro domain defined by two or more amino acids may be prepared by any available means including synthetic or recombinant means. Such fragments may then be used in the assays as described herein, for example, but not limited to, high-throughput assays to detect interactions between prospective ligands and the pro domain within the fragment.

For recombinant expression or production of the forms or fragments of the invention, nucleic acid molecules encoding the form or fragment may be prepared. Nucleic acid molecules encoding engineered forms or fragments of the invention may differ in sequence because of the degeneracy in the genetic code or may differ in sequence as they encode proteins or protein fragments that differ in amino acid sequence. Homology or sequence identity between two or more such nucleic acid molecules is determined by BLAST (Basic Local Alignment Search Tool) analysis using the algorithm employed by the programs blastp, blastn, blastx, tblastn and tblastx (Karlin and Altschul 1990) and (Altschul 1993), which are tailored for sequence similarity searching.

The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see (Altschul, Boguski et al. 1994). The search parameters for histogram, descriptions, alignments, expect (i.e., the statistical significance threshold for reporting matches against database sequences), cutoff, matrix and filter are at the default settings. For a discussion of default scoring matrix used by blastp, blastx, tblastn, and tblastx, see (Henikoff 1992).

The encoding nucleic acid molecules of the present invention or fragments thereof (i.e., synthetic oligonucleotides) and those that are used as probes or specific primers for polymerase chain reaction (PCR) or to synthesize gene sequences encoding proteins of the invention can easily be synthesized by chemical techniques, for example, the phosphotriester method of (Matteucci and Caruthers 1981) or using automated synthesis methods. In addition, larger DNA segments can readily be prepared by well-known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. There are a variety of such labels known in the art that can readily be employed with the encoding molecules herein described. Suitable labels include, but are not limited to, biotin, radiolabeled nucleotides and the like. A skilled artisan can employ any of the art-known labels to obtain a labeled encoding nucleic acid molecule.

The present invention further provides recombinant DNA molecules (rDNA) that contain a coding sequence for a protein or protein fragment as described herein. As used herein, an rDNA molecule is a DNA molecule that has been subjected to molecular manipulation. Methods for generating rDNA molecules are well known in the art, for example, see (Sambrook, Fritsch et al. 1989). In the preferred rDNA molecules, a coding DNA sequence is operably linked to expression control sequences and/or vector sequences.

The choice of vector and expression control sequences to which one of the protein encoding sequences of the present invention is operably linked depends directly, as is well known in the art, on the functional properties desired (e.g., protein expression, and the host cell to be transformed). A vector of the present invention may be capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

The present invention further provides host cells transformed with a nucleic acid molecule that encodes a protein or protein fragment of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, insect, yeast, and mammalian cells. Preferred eukaryotic host cells include *Spodoptera frugiperda* (Sf9 or Sf21) insect cells and human embryonic kidney cells (HEK cells).

Transformed host cells of the invention may be cultured under conditions that allow the production of the recombinant protein. Optionally the recombinant protein is isolated from the medium or from the cells; recovery and purification of the protein may not be necessary in some instances where some impurities may be tolerated.

Kits may also be prepared with any of the described nucleic acid molecules, proteins, protein fragments, vector and/or host cells optionally packaged with the reagents needed for a specific assay. In such kits, the protein, protein fragments, or other reagents may be attached to a solid support, such as glass or plastic beads.

High-Throughput Assays

Compound identification methods can be performed using conventional laboratory assay formats or in high-throughput assays, including, but not limited to, those described below.

Immunoassays

Immunoassays are a group of techniques used for the measurement of specific biochemical substances, commonly at low concentrations in complex mixtures such as biological fluids. The assays depend upon suitably prepared and selected antibodies with specificity and high affinity for their complementary antigens. A substance to be measured must, of necessity, be antigenic, either an immunogenic macromolecule or a haptenic small-molecule. To each sample a known limited amount of specific antibody is added and the fraction of the antigen combining with it, often expressed as the bound:free ratio, is estimated by quantifying the signal from the antibody. Quantification can be achieved with a number of readily identifiable labels and used for various types of assays, including, but not limited to, radioisotopes for radioimmunoassays (RIA), fluorescent molecules for fluoroimmunoassays (FIA), stable free radicals for spin immunoassays, chemiluminescent molecules for chemiluminescent immunoassays (CLIA), colloidal gold particles for immunogold assays, and enzymes for enzyme-linked immunosorbent assays (ELISA).

A common immunoassay format is the ELISA, which avoids the hazards of radiochemicals and the expense of fluorescence detection systems. Instead, an ELISA is a form of quantitative immunoassay based on the use of antibodies (or antigens) that may be linked to an insoluble carrier surface, which is then used to "capture" the relevant antigen (or antibody) in the test solution. The antigen-antibody complex is then detected by measuring the activity of an appropriate enzyme that can be covalently attached to the capture antigen (or antibody) or to a subsequent "detection" antibody (or antigen). For more information on ELISA techniques, see, for example, (Crowther 1995); (Kemeny (editor) and Challacombe (editor) 1988), (Kemeny 1991), and (Ishikawa 1999).

Colorimetric Assays

Colorimetric assays for enzymes are methods of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically. For example, standard colorimetric assays of beta-galactosidase enzymatic activity are well known to those skilled in the art, see e.g., (Norton and Coffin 1985). A colorimetric assay can be performed with purified components or on whole cell lysates, using for example, O-nitrophenyl-beta-D-galactopyranoside (ONPG, Sigma) as the substrate in a standard colorimetric beta-galactosidase assay (Sambrook, Fritsch et al. 1989). Automated colorimetric assays are also available, see for example, detection of beta-galactosidase activity as described in U.S. Pat. No. 5,733,720.

Fluorescence Assays

Enzymatic substrates that become fluorescent after being acted upon by an enzyme generally are well known. Such fluorescent substrates typically have two components that are bound to one another through, for example, a covalent chemical bond. One component is a fluorescent molecule that is capable of fluorescing by first accepting light energy and then emitting light energy. The other component is an entity that prevents the fluorescent molecule from accepting or emitting light energy when the two components are covalently bound to one another. In the presence of an appropriate enzyme, the enzyme cleaves the covalent bond between the two components and separates one component from the other to permit the fluorescent molecule to accept and emit light energy. In other words, the enzyme frees the fluorescent molecule and allows it to fluoresce. Ideally, fluorescent substrates should be soluble and stable in aqueous buffers, should have a high affinity for the enzymes that act upon them, and should yield a strong signal upon enzymatic action (U.S. Pat. No. 5,998, 593A).

Detecting fluorescence emitted from the fluorescent component of a fluorescent enzyme substrate is typically achieved in two steps. The fluorescent molecule is first excited with light energy and subsequently the fluorescence emitted from the fluorescent component is then detected. Generally, fluorescent molecules can be excited with light energy from, for example, a laser or another suitable light source. Fluorescence is detected with a device designed to detect light energy of a wavelength that is emitted by the fluorescent molecule. Such excitation and emission detection systems generally are designed to operate at particular wavelength ranges (U.S. Pat. No. 5,998,593A).

Time-resolved Fluorescence resonance energy transfer (TR-FRET) unites TRF (Time-Resolved Fluorescence) and FRET (Fluorescence Resonance Energy Transfer) principles. This combination brings together the low background benefits of TRF with the homogeneous assay format of FRET. Time-resolved fluorometry (TRF) takes advantage of the unique properties of the rare earth elements called lanthanides. Specifically, lanthanides have large Stoke's shifts and extremely long emission half-lives compared to more traditional fluorophores. The commonly used lanthanides in TRF assays are samarium (Sm), europium (Eu), terbium (Tb), and dysprosium (Dy). Lanthanides are complexed with organic moieties that harvest light and transfer it to the lanthanide through intramolecular processes. FRET uses two fluorophores, a donor and an acceptor. Excitation of the donor by an energy source (e.g. flash lamp or fluorometer laser) triggers an energy transfer to the acceptor if they are within a given proximity to each other. The acceptor in turn emits light at its given wavelength. Because of this energy transfer, molecular interactions between biomolecules can be assessed by coupling each partner with a fluorescent label and detecting the level of energy transfer. More importantly acceptor emissions, as a measure of energy transfer, can be detected without the need to separate bound from unbound assay components (Klostermeier and Millar 2001).

Thermofluor® Assays

ThermoFluor® assays are based on a classical method for estimating ligand binding affinities, by measuring the effect of a ligand on stability using chemical or thermal denaturation methods (Pantoliano, Petrella et al. 2001). This approach is general, applicable to a wide variety of systems, and rigorous in theoretical interpretation through quantitation of equilibrium binding constants (i.e. true $K_D$ values). The technique monitors changes in the fluorescent intensity of dyes such as 1-anilinonaphthalene-8-sulfonic acid (1,8-ANS). The fluorescent dyes are quenched in aqueous environments but increase in fluorescence on binding to the hydrophobic core of denatured proteins.

In an experiment where stability is monitored as the temperature is steadily increased, either kinetic or equilibrium theory would dictate that equilibrium binding ligands would cause the midpoint of an unfolding transition to occur at a higher temperature, described as a $\Delta T_m$. The dependence of $\Delta T_m$ on added ligand is a function of the equilibrium constant for both ligand binding and protein stability. In addition, the results of compound binding may be compared based on the magnitude of $\Delta T_m$ at a fixed, single concentration of ligand, as the contribution of binding energy to protein stability is determined by the product of the binding constant and ligand concentration. Thus, compound potency may be compared as a rank order of either $\Delta T_m$ values ("screening" mode) or in terms of $K_D$ values (complete concentration response curves).

The dynamic range of measurable $K_D$ values spans ~200 uM to <10 pM; resolution is limited only be the upper limit on ligand solubility.

Homogenous, 384-well plate-based assays run in a Thermofluor® instrument, were developed by 3-Dimensional Pharmaceuticals (Pantoliano, Petrella et al. 2001; Matulis, Kranz et al. 2005). Assay components typically include a protein (1-5 µM) with dye (25-100 µM, typically 1,8-ANS or dapoxylsulfonamide) in buffer, with or without ligand. Assay volumes are typically 2-4 uL with 1 uL silicone oil overlay to limit evaporation, dispensed into an appropriate 384-well thermocycler assay plate. The assay measures dye fluorescence on a plate-basis via CCD camera, ramping temperature of the 384-well plate from ambient to high temperature, imaging the change in dye fluorescence upon increasing the temperature incrementally. Protein unfolding energetics and ligand binding energetics are quantitated based on proven biophysical principles.

Modeling the Three-Dimensional Structure

The atomic coordinate data provided herein, or the coordinate data derived from homologous proteins may be used to build a three-dimensional model of a complex of a proMMP and an allosteric processing inhibitor that inhibits the activation of a proMMP. Any available computational methods may be used to build the three dimensional model. As a starting point, the X-ray diffraction pattern obtained from the assemblage of the molecules or atoms in a crystalline version of a proMMP or a proMMP homolog can be used to build an electron density map using tools well known to those skilled in the art of crystallography and X-ray diffraction techniques. Additional phase information extracted either from the diffraction data and available in the published literature and/or from supplementing experiments may then be used to complete the reconstruction.

For basic concepts and procedures of collecting, analyzing, and utilizing X-ray diffraction data for the construction of electron densities see, for example, (Campbell 1984), (Cantor and Schimmel 1980), (Brunger 1993), (Woolfson 1997), (Drenth 1999), (Tsirelson and Ozerov 1996), and (U.S. Pat. No. 5,942,428A); (U.S. Pat. No. 6,037,117A); (U.S. Pat. No. 5,200,910A); and (U.S. Pat. No. 5,365,456A).

For basic information on molecular modeling, see, for example, (Schlecht 1998); (Gans, Amann et al. 1996); (Cohen (editor) 1996); and (Smith 1996). U.S. Patents which provide detailed information on molecular modeling include (U.S. Pat. No. 4,906,122A; U.S. Pat. No. 5,030,103A; U.S. Pat. No. 5,583,973A; U.S. Pat. No. 5,612,894A; U.S. Pat. No. 5,994, 503A; U.S. Pat. No. 6,071,700A; U.S. Pat. No. 6,075,014A; U.S. Pat. No. 6,075,123A; U.S. Pat. No. 6,080,576A; U.S. Pat. No. 6,093,573A).

Methods of Using the Atomic Coordinates to Identify and Design Ligands

The atomic coordinates described herein, or coordinates substantially identical to or homologous to those described herein may be used with any available methods to prepare three dimensional models of a complex of a proMMP and an allosteric processing inhibitor that inhibits the activation of a proMMP, as well as to identify and design allosteric processing inhibitors that inhibit the activation of a proMMP. Such methods provide the amino acid sequence and/or X-ray diffraction data in a form which allows a skilled artisan to analyze and molecular model the three-dimensional structure of a complex of a proMMP and an allosteric processing inhibitor that inhibits the activation of a proMMP or related molecules, including a subdomain thereof.

For instance, three-dimensional modeling may be performed using the experimentally determined coordinates derived from X-ray diffraction patterns, such as those described herein. For example, wherein such modeling includes, but is not limited to, drawing pictures of the actual structures, building physical models of the actual structures, and determining the structures of related subunits and proMMP:ligand and proMMP subunit:ligand complexes using the coordinates. Such molecular modeling can utilize known X-ray diffraction molecular modeling algorithms or molecular modeling software to generate atomic coordinates corresponding to the three-dimensional structure of a complex of a proMMP and a ligand that inhibits the activation of a proMMP.

As described above, molecular modeling involves the use of computational methods, preferably computer assisted methods, to build realistic models of molecules that are identifiably related in sequence to the known crystal structure. It also involves modeling new small-molecules bound to a proMMP starting with the structures of a proMMP and or a proMMP complexed with known ligands or other molecules. The methods utilized in ligand modeling range from molecular graphics (i.e., 3D representations) to computational chemistry (i.e., calculations of the physical and chemical properties) to make predictions about the binding of ligands or activities of ligands; to design new ligands; and to predict novel molecules, including ligands such as drugs, for chemical synthesis, collectively referred to as rational drug design.

One approach to rational drug design is to search for known molecular structures that might bind to an active site or allosteric binding site. Using molecular modeling, rational drug design programs can look at a range of different molecular structures of drugs that may fit into the site, and by moving them in a three-dimensional environment it can be decided which structures actually fit the site well.

An alternative but related rational drug design approach starts with the known structure of a complex with a small-molecule ligand and models modifications of that small-molecule in an effort to make additional favourable interactions with a proMMP.

The present invention includes the use of molecular and computer modeling techniques to design and select ligands, such as small-molecule ligands that act as allosteric processing inhibitors of a proMMP. For example, the invention as herein described includes the design of ligands that bind a proMMP and inhibit processing of the proMMP to a catalytically active form of the protein. In a preferred, but non limiting embodiment, the ligands bind to proMMP9 and inhibit processing of proMMP9 to the catalytically active form of MMP9. In another nonlimiting embodiment, the present invention provides a method to design allosteric processing inhibitors using the atomic coordinates of a complex of proMMP9 and an allosteric processing inhibitor of the present invention.

The atomic coordinates of the present invention also provide the needed information to probe a crystal of a proMMP with different molecules composed of a variety of different chemical features to determine optimal sites of interaction on the proMMP to identify potential allosteric processing inhibitors of a proMMP. For example, high resolution X-ray diffraction data collected from crystals saturated with solvent allows the determination of where each type of solvent molecule sticks. Small molecules that bind to those sites can then be designed and synthesized and tested for their ability to modulate activity (Travis 1993).

The present invention also includes methods for computationally screening small-molecule databases and libraries for chemical entities, agents, ligands, or compounds that can bind in whole, or in part, to a proMMP. In this screening, the quality of fit of such entities or compounds to the binding site or sites may be judged either by shape complementarity or by estimated interaction energy (Meng, Shoichet et al. 1992).

The design of ligands that bind to or inhibit the activation of a proMMP according to this invention generally involves consideration of two factors. First, the compound must be capable of physically and structurally associating with a proMMP. In addition to the covalent interaction described herein, non-covalent molecular interactions important in the association of a proMMP with the ligand include hydrogen bonding, van der Waals and hydrophobic interactions. Second, the ligand must be able to assume a conformation that allows it to associate with a proMMP. Although certain portions of the ligand may not directly participate in the association with a proMMP, those portions may still influence the overall conformation of the molecule. This, in turn, may have a significant impact on binding affinities, therapeutic efficacy, drug-like qualities and potency of the ligand. Such conformational requirements include the overall three-dimensional structure and orientation of the ligand in relation to all or a portion of the binding site or other region of the proMMP, or the spacing between functional groups of a ligand comprising several chemical entities that directly interact with the proMMP.

The potential or predicted ability of a ligand to bind to a proMMP and inhibit activation of the proMMP may be analyzed prior to its actual synthesis and testing by the use of computer modeling techniques. If the theoretical structure of the given ligand suggests insufficient interaction and association between it and a proMMP, synthesis and testing of the ligand may be obviated. If computer modeling indicates a strong interaction, however, the molecule may then be synthesized and tested for its ability to interact with a proMMP. In this manner, synthesis of inoperative ligands may be avoided. In other cases, inactive ligands can be synthesized based on modeling and then tested to help develop SAR (structure-activity relationship) that can be used to design other compounds that interact with a specific region of a proMMP.

One skilled in the art may use one of several methods to screen chemical entities, fragments, compounds, or other agents for use as ligands based on their ability to associate with a proMMP and more particularly their ability to associate with the individual binding pocket of a proMMP as described in the present invention. In a nonlimiting example, the proMMP is human proMMP9. This process may begin by visual inspection of, for example, the allosteric binding site on the computer screen based on the atomic coordinates of a proMMP or a proMMP complexed with a ligand. Selected chemical entities, compounds, or agents may then be positioned in a variety of orientations, or docked within an individual binding pocket of a proMMP. Docking may be accomplished using software such as, but not limited to, QUANTA, available from Accelrys, Inc., San Diego, Calif.; and SYBYL, available for Tripos, St. Louis, Mo.; followed by energy minimization and molecular dynamics with standard molecular mechanics forcefields, such as CHARMm; available from Accelrys, Inc., San Diego, Calif.; and AMBER, University of California, San Francisco.

Specialized computer programs may also assist in the process of selecting chemical entities. These include but are not limited to: GRID (Goodford 1985), available from Oxford University, Oxford, UK); MCSS (Miranker and Karplus 1991), available from Molecular Simulations, Burlington, Mass.; AUTODOCK (Goodsell and Olsen 1990), available from Scripps Research Institute, La Jolla, Calif.; and DOCK (Kuntz, Blaney et al. 1982), available from University of California, San Francisco, Calif.

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. The program DOCK may be used to analyze an active site or ligand-binding site and suggest ligands with complementary steric properties.

Once suitable chemical entities, compounds, or agents have been selected as potential ligands, they can be assembled into a single ligand, compound, antagonist (inhibitor), agonist (activator), or inverse agonist. Assembly may proceed by visual inspection of the relationship of the fragments to each other on the three-dimensional image. This may be followed by manual model building using software such as QUANTA or SYBYL.

Useful programs to aid in connecting the individual chemical entities, compounds, or agents include but are not limited to: CAVEAT (Bartlett, Shea et al. 1989); 3D Database systems such as MACCS-3D (Martin 1992), available from MDL Information Systems, San Leandro, Calif.; and HOOK, available from Molecular Simulations, Burlington, Mass.

Several methodologies for searching three-dimensional databases to test pharmacophore hypotheses and select compounds for screening are available. These include the program CAVEAT (Bacon and Moult 1992). For instance, CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding.

Instead of proceeding to build an allosteric processing inhibitor of a proMMP in a step-wise fashion, one chemical entity at a time as described above, such ligands may be designed as a whole or "de novo" using either an empty binding site or optionally including some portion(s) of a known molecule(s). These methods include: LUDI (Bohm 1992), available from Biosym Technologies, San Diego, Calif.; LEGEND (Nishibata and Itai 1991), available from Molecular Simulations, Burlington, Mass.; and LeapFrog, available from Tripos Associates, St. Louis, Mo., USA.

For example, the program LUDI can determine a list of interaction sites into which to place both hydrogen bonding and hydrophobic fragments. LUDI then uses a library of linkers to connect up to four different interaction sites into fragments. Then smaller "bridging" groups such as —$CH_2$— and —COO— are used to connect these fragments. For the enzyme DHFR, the placements of key functional groups in the well-known inhibitor methotrexate were reproduced by LUDI. See also, (Rotstein and Murcko 1993).

Other molecular modeling techniques may also be employed in accordance with this invention. See, e.g., (Cohen, Blaney et al. 1990). See also, (Navia and Murcko 1992).

Once a ligand has been designed or selected by the above methods, the affinity with which that ligand may bind or associate with a proMMP may be tested and optimized by computational evaluation and/or by testing biological activity after synthesizing the compound. Ligands may interact with the proMMP in more than one conformation that is similar in overall binding energy. In those cases, the deformation energy of binding is taken to be the difference between the energy of the free ligand and the average energy of the conformations observed when the ligand binds to the proMMP.

A ligand designed or selected as binding or associating with a proMMP may be further computationally optimized so that in its bound state it would preferably lack repulsive electrostatic interaction with the proMMP. Such non-complementary (e.g., electrostatic) interactions include repulsive charge-charge, dipole-dipole and charge-dipole interactions. Specifically, the sum of all electrostatic interactions between the compound and the proMMP when the compound is bound, preferably make a neutral or favourable contribution to the enthalpy of binding. Weak binding compounds will also be designed by these methods so as to determine SAR.

Specific computer software is available in the art to evaluate compound deformation energy and electrostatic interaction. Examples of programs designed for such uses include: Gaussian 92, revision C (Frisch, Trucks et al. 1992); AMBER, University of California, San Francisco; QUANTA and CHARMm, available from Accelrys, Inc., San Diego, Calif.; and Insight II/Discover, from Biosysm Technologies Inc., San Diego, Calif., USA. Other hardware systems and software packages will be known to those skilled in the art.

Once a ligand that associates with a proMMP has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted ligands may then be analyzed for efficiency of fit to the proMMP by the same computer methods described in detail above.

Use of Homology Structure Modeling to Design Ligands

The present invention includes the use of the atomic coordinates and structures of a proMMP and a proMMP complexed with an allosteric processing inhibitor to design modifications to starting ligands and derivatives thereof that will bind more tightly or interact more specifically to a proMMP or other related proMMP proteins to design an allosteric processing inhibitor. The structure of the complex between proMMP and the starting ligand can be used to guide the modification of that ligand to produce new ligands that have other desirable properties for applicable industrial and other uses (e.g., as pharmaceuticals), such as chemical stability, solubility or membrane permeability. (Lipinski, Lombardo et al. 1997).

Ligands known and unknown in the art can be diffused into or soaked with the stabilized crystals of a proMMP to form a complex for collecting X-ray diffraction data. Alternatively, ligands known and unknown in the art can be cocrystallized with a proMMP, by mixing the ligand with the proMMP before crystallization. In a nonlimiting example, the proMMP is human proMMP9.

To produce custom high affinity and very specific compounds, the structure of the present invention of human proMMP9 complexed with an allosteric processing inhibitor can be compared to the structure of a selected non-targeted proMMP molecule and a hybrid structure can be constructed by changing the structure of the non-targeted proMMP molecule to include structural features described at the allosteric binding site provided in the present invention. The process whereby this modeling is achieved is referred to as homology structure modeling. This can be done computationally by removing the side chains from the known structure of the present invention and systematically replacing them with the chains of the non-targeted proMMP molecule, such that the side chains are placed in sterically plausible positions. In this way it can be understood how the shapes of the binding site cavities of the targeted and non-targeted molecules differ. This process, therefore, provides information concerning how a bound ligand can be chemically altered in order to produce compounds that will bind tightly and specifically to the desired target but will simultaneously be sterically prevented from binding to the non-targeted molecule. Likewise, knowledge of portions of the bound ligands that are facing to the solvent allows introduction of other functional groups for additional pharmaceutical purposes. The use of homology structure modeling to design ligands that bind more tightly to the target enzyme than to the non-target enzyme has wide spread applicability. In particular, in a non-limiting example, homology structure modeling has applicability to designing compounds with high specificity for a targeted proMMP such as human proMMP9.

Databases and Computer Systems

An amino acid sequence or nucleotide sequence of a proMMP and/or X-ray diffraction data, useful for computer molecular modeling of the proMMP or a portion thereof, can be provided in a variety of mediums to facilitate use thereof. In one application of this embodiment, databases comprising data pertaining to X-ray diffraction data for a complex of a proMMP and an allosteric processing inhibitor, or at least one proMMP subdomain thereof, is recorded on computer readable medium. A skilled artisan can readily appreciate how any of the presently known computer readable media can be used to create a manufacture comprising computer readable medium having recorded thereon data pertaining to X-ray diffraction data of the present invention.

A variety of data storage structures are available to a skilled artisan for creating a computer readable medium having recorded thereon an amino acid sequence and/or atomic coordinate/X-ray diffraction data of the present invention. The choice of the data storage structure will generally be based on the means chosen to access the stored information. In addition, a variety of data processor programs and formats can be used to store the sequence and X-ray data information of the present invention on computer readable media. The sequence information can be represented in a word processing text file, formatted in commercially-available software such as WordPerfect and MICROSOFT Word, or represented in the form of an ASCII file, stored in a database application, such as DB2, Sybase, Oracle, or the like. A skilled artisan can readily adapt any number of data processor structuring formats (e.g., text file or database) in order to obtain computer readable media having recorded thereon the information of the present invention.

By providing computer readable media having sequence and/or atomic coordinates based on X-ray diffraction data, a skilled artisan can routinely access the sequence and atomic coordinates or X-ray diffraction data to model a related molecule, a subdomain, mimetic, or a ligand thereof. Computer algorithms are publicly and commercially available which allow a skilled artisan to access this data provided in a computer readable medium and analyze it for molecular modeling and/or RDD (rational drug design). See, e.g., (Mary Ann Liebert (Publishers) 1995).

The present invention further provides systems, particularly computer-based systems, which contain the sequence and/or diffraction data described herein. Such systems are designed to do structure determination and rational drug design (RDD) using information such as a complex of a ligand that inhibits the activation of the proMMP and a proMMP, or at least one subdomain thereof. Non-limiting examples are microcomputer workstations available from Silicon Graphics Incorporated and Sun Microsystems running UNIX based software, Windows NT or IBM OS/2 operating systems.

A variety of comparing means can also be used to compare a target sequence or target motif with the data storage means to identify structural motifs or electron density maps derived in part from the atomic coordinate/X-ray diffraction data. A skilled artisan can readily recognize that any one of the publicly available computer modeling programs can be used as the search means for the computer-based systems of the present invention.

Integrated Procedures Which Utilize the Present Invention

Molecular modeling is provided by the present invention for rational drug design (RDD) of ligands that inhibit the activation of a proMMP. As described above, the drug design paradigm uses computer-modeling programs to determine potential ligands which are expected to interact with sites on the protein. The potential ligands are then screened for activity and/or binding and/or interaction. For proMMP related ligands, screening methods can be selected from an assay of at least one biological activity of an MMP.

Thus, the tools and methodologies provided by the present invention may be used in procedures for identifying and designing ligands which bind in desirable ways with the target. Such procedures utilize an iterative process whereby ligands are synthesized, tested and characterized. New ligands can be designed based on the information gained in the testing and characterization of the initial ligands and then such newly identified ligands can themselves be tested and characterized. This series of processes may be repeated as many times as necessary to obtain ligands with the desirable binding properties.

It is to be understood that the present invention is considered to include stereoisomers as well as optical isomers, e.g., mixtures of enantiomers as well as individual enantiomers and diastereomers, which arise as a consequence of structural asymmetry in selected compounds of the present invention.

Some of the ligands disclosed or discovered by the methods herein may contain one or more asymmetric centers and thus give rise to enantiomers, diastereomers, and other stereoisomeric forms. The present invention is also meant to encompass all such possible forms as well as their racemic and resolved forms and mixtures thereof. When the ligands described or discovered herein contain olefinic double bonds or other centers of geometric asymmetry, and unless otherwise specified, it is intended to include both E and Z geometric isomers. All tautomers are intended to be encompassed by the present invention as well.

EXAMPLES

Without further description, it is believed that one of ordinary skill in the art can, using the preceding description and the following illustrative examples, make and utilize the present invention and practice the claimed methods. The following working examples therefore, specifically point out preferred embodiments of the present invention, and are not to be construed as limiting in any way the remainder of the disclosure.

Example Compounds

Example 1

N-[2-(2-Methoxy-phenylamino)-4'-methyl-[4,5']bithiazolyl-2'-yl]-acetamide)

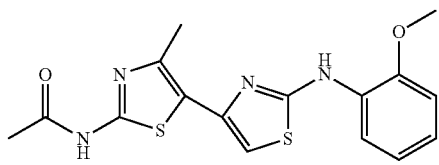 [SMILES: COc1ccccc1Nc1nc(-c2sc(NC(C)=O)nc2C)cs1]

Example 1 is a commercially available compound from ChemBridge.

Example 2

3-(2',4'-Dimethyl-[4,5']bithiazolyl-2-ylamino)-4-isopropoxy-benzenesulfonamide.HBr

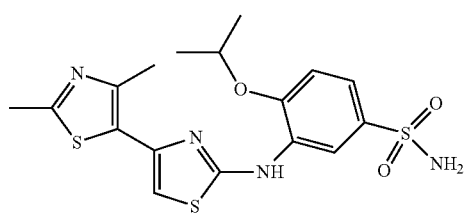 [SMILES: Cc1nc(C)c(-c2csc(Nc3cc(S(N)(=O)=O)ccc3OC(C)C)n2)s1]

Example 2

Step a 2-Bromo-1-(2,4-dimethyl-thiazol-5-yl)-ethanone.HBr

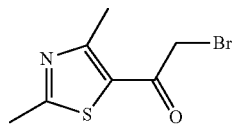

A suspension of bromine (11.9 mL, 231.5 mmol) in 1,4-dioxane (200 mL) was added to a stirred solution of 1-(2,4-dimethyl-thiazol-5-yl)-ethanone (28.75 g, 185.2 mmol, Alfa) in 1,4-dioxane (200 mL). The mixture was stirred for 25 h at 50° C. and the resulting cream-colored suspension was allowed to cool to room temperature and was filtered and washed with 2:1 heptane:EtOAc (v/v). The resulting white powder was recrystallized from EtOH, affording the title compound.

Example 2

Step b

4-Fluoro-3-nitro-benzenesulfonamide

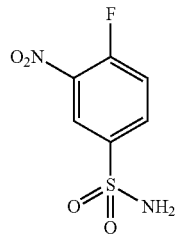 [SMILES: NS(=O)(=O)c1ccc(F)c([N+](=O)[O-])c1]

Following the procedure of *J. Med. Chem.* 2006, 49, 1173, a solution of commercially available 2-fluoronitrobenzene (10.00 g, 70.87 mmol) and chlorosulfonic acid (21 mL) were heated to reflux for 18 hours at 95° C. and then cooled to room temperature. The solution was then added dropwise over a 1 hour period to a solution of iPrOH (225 mL) and concentrated aqueous NH$_4$OH (54 mL) at −35° C. and stirred for 0.5 hours. The solution was maintained at −35° C. while concentrated aqueous HCl was added until the pH was acidic. The solution was then evaporated to remove some iPrOH, water was added and the solution was evaporated again to remove most of the iPrOH. More water was added, the solution was filtered and the solid was washed with 1 N aqueous HCl and water to give the title compound.

Example 2

Step c

4-Isopropoxy-3-nitro-benzenesulfonamide

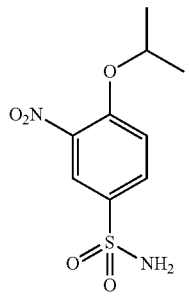

A solution of isopropanol (225 mL) and small chunks of sodium metal (1.92 g, 83.6 mmol) were heated to reflux for 2.5 hours, until the sodium was consumed. The resulting solution was added while still hot to a solution of 4-fluoro-3-nitro-benzenesulfonamide (8.37 g, 38.0 mmol, example 2, step b) in THF/iPrOH (1/1, v/v, 150 mL) over a 10 minute period and stirred at room temperature for 3.5 hours. The reaction mixture was partitioned between EtOAc and brine and 1 N aqueous HCl. The organic phase was then washed with brine, dried with Na$_2$SO$_4$ and evaporated to give the title compound.

Example 2

Step d

3-Amino-4-isopropoxy-benzenesulfonamide

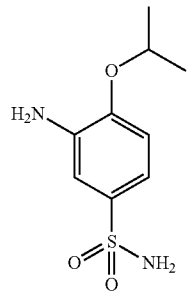 [SMILES: CC(C)Oc1ccc(S(N)(=O)=O)cc1[N+](=O)[O-]]

Sodium borohydride (1.88 g, 49.6 mmol) was added slowly to a solution of nickel (II) chloride hexahydrate (3.93 g, 16.5 mmol) in methanol (60 mL) at 0° C. and the resulting black suspension was stirred for 30 min at 23° C. The mixture was cooled to 0° C. and 4-isopropoxy-3-nitro-benzenesulfonamide (8.6 g, 33.0 mmol, example 2, step c) was added followed by sodium borohydride (4.38 g, 115.6 mmol). The resulting black suspension was stirred for 30 min at 23° C. Water was added to the reaction mixture to quench excess $NaBH_4$, followed by addition of saturated aqueous $NaHCO_3$. The product was extracted with dichloromethane and the organic phase was washed with brine, dried with $Na_2SO_4$ and evaporated to give the title compound.

Example 2

Step e

4-Isopropoxy-3-isothiocyanato-benzenesulfonamide

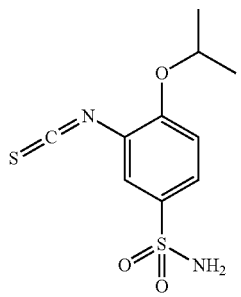 [SMILES: CC(C)Oc1ccc(S(N)(=O)=O)cc1N=C=S]

A solution of sodium bicarbonate (16.8 g, 199.5 mmol) in water (400 mL) was added to 3-amino-4-isopropoxy-benzenesulfonamide (15.3 g, 66.5 mmol, example 2, step d) in a mixture of chloroform (200 mL) and water (200 mL). Thiophosgene (6.37 mL, 83.1 mmol) was then added. The biphasic solution was stirred at room temperature for 1.5 h. The phases were separated and the aqueous phase was extracted with $CH_2Cl_2$. The organic phase was washed with water, dried ($Na_2SO_4$), filtered, and concentrated, yielding the crude title compound as a tan solid.

Example 2

Step f

4-Isopropoxy-3-thioureido-benzenesulfonamide

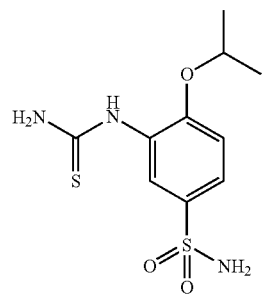 [SMILES: CC(C)Oc1ccc(S(N)(=O)=O)cc1NC(N)=S]

Crude 4-isopropoxy-3-isothiocyanato-benzenesulfonamide (17.8 g, 65.2 mmol, example 2, step e) was treated with a 2 M solution of ammonia in MeOH (250 mL) and the resulting solution was stirred at room temperature for 18 h. The reaction mixture was then concentrated to about half the volume until a large amount of tan solid precipitated. The suspension was cooled to 0° C. for 30 minutes and was filtered. The solid was washed with methanol and ether to give the title compound as a cream colored solid.

Example 2

3-(2',4'-Dimethyl-[4,5']bithiazolyl-2-ylamino)-4-isopropoxy-benzenesulfonamide.HBr

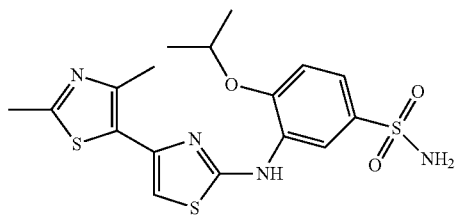 [SMILES: Cc1nc(C)c(-c2csc(Nc3cc(S(N)(=O)=O)ccc3OC(C)C)n2)s1]

A mixture of 2-bromo-1-(2,4-dimethyl-thiazol-5-yl)-ethanone.HBr (1.07 g, 3.39 mmol, example 2, step a) and 4-isopropoxy-3-thioureido-benzenesulfonamide (0.98 g, 3.39 mmol, example 2, step f) in ethanol (15 mL) was stirred at room temperature for 2 d. The mixture was filtered, washed with cold EtOH, and air-dried, affording the title compound as a white powder. $^1$H NMR (300 MHz, DMSO-$d_6$) δ 9.67 (s, 1H), 9.00 (d, J=2.26 Hz, 1H), 7.43 (dd, J=2.07, 8.48 Hz, 1H), 7.21 (d, J=8.67 Hz, 1H), 7.14 (br. s, 2H), 7.07 (s, 1H), 4.80 (sept, J=6.03 Hz, 1H), 2.65 (s, 3H), 1.36 (d, J=6.03 Hz, 6H); MS m/e 425.1 (M+H).

Example 3

3-(2'-Amino-4'-methyl-[4,5]bithiazolyl-2-ylamino)-4-methoxy-benzamide.HBr

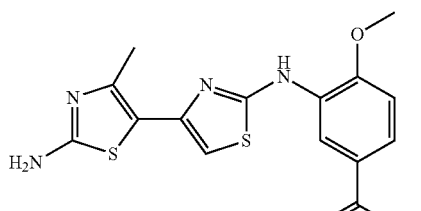

Example 3

Step a 1-(2-Amino-4-methyl-thiazol-5-yl)-2-bromo-ethanone

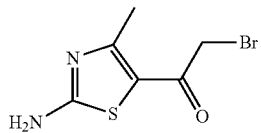

1-(2-Amino-4-methyl-thiazol-5-yl)-2-bromo-ethanone. HBr was prepared as described in WO 2005/068444. To convert to the corresponding free base, the crude reaction mixture was slowly added to ice-cold sat. aq. NaHCO₃ solution. The precipitate was collected by vacuum filtration and washed with Et₂O. The crude product was recrystallized from EtOH, affording the title compound as an orange powder.

Example 3

Step b

4-Methoxy-3-thioureido-benzamide

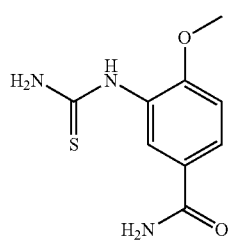

To a solution of 3-amino-4-methoxybenzamide (2.49 g, 15.0 mmol, Alfa) in acetone (30 mL) at reflux was added benzoyl isothiocyanate (2.22 mL, 16.5 mmol) and the mixture was stirred at reflux for 30 min, then was poured into water. The precipitate was collected by vacuum filtration and was treated with 10% aq. NaOH (15 mL). The mixture was heated to reflux for 40 min, cooled to room temperature, and poured into a mixture of ice and 6 N aq. HCl. The mixture was basified to pH 10 with conc. aq. NH₄OH and the resulting white solid precipitate was collected by vacuum filtration, affording the crude title compound, which was used without further purification.

Example 3

3-(2'-Amino-4'-methyl-[4,5']bithiazolyl-2-ylamino)-4-methoxy-benzamide.HBr

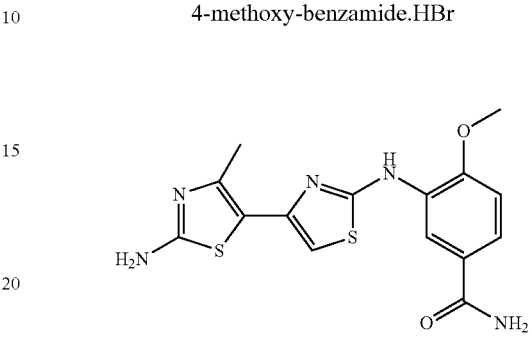

A mixture of 1-(2-amino-4-methyl-thiazol-5-yl)-2-bromo-ethanone (270 mg, 1.15 mmol, example 3, step a) and 4-methoxy-3-thioureido-benzamide (259 mg, 1.15 mmol, example 3, step b) in ethanol (5 mL) was stirred at room temperature for 18 h. The mixture was filtered, washed with EtOH, and air-dried. The crude product was recrystallized from a mixture of EtOH and water. ¹H NMR (300 MHz, DMSO-$d_6$) δ ppm 9.82 (s, 1H), 9.25 (br. s, 2H), 8.79 (s, 1H), 7.80 (br. s, 1H), 7.57 (d, J=7.9 Hz, 1H), 7.00-7.17 (m, 3H), 3.92 (s, 3H), 2.45 (s, 3H). MS m/e 362.1 (M+H).

Example 4

(4-Methoxy-pyridin-3-yl)-(6-methyl-6H-imidazo[4',5':3,4]benzo[2,1-d]thiazol-2-yl)-amine.TFA

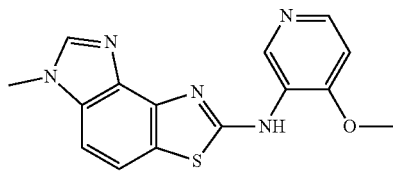

Example 4

Step a

3-Isothiocyanato-4-methoxy-pyridine

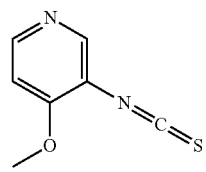

To a stirred mixture of 3-amino-4-methoxypyridine (2.01 g, 16.2 mmol) and NaHCO₃ (4.08 g, 48.6 mmol) in CHCl₃ and water (1:1, 50 mL) at 4° C. was added thiophosgene (1.5 mL, 19.6 mmol) dropwise. After completion of the addition, the ice bath was removed. The mixture was stirred for 4 hours, the organic layer was separated, and the aqueous layer was extracted with $CH_2Cl_2$. The combined organic phases were washed with water, dried over $Na_2SO_4$, filtered, and concentrated to give the title compound as brown solid.

Example 4

Step b 1-(4-Methoxy-pyridin-3-yl)-3-(1-methyl-1H-benzoimidazol-4-yl)-thiourea

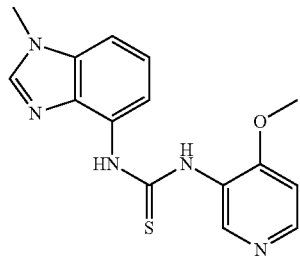 [SMILES: COc1ccncc1NC(=S)Nc1cccc2c1ncn2C]

A mixture of 4-amino-1-methylbenzimidazole (0.100 g, 0.679 mmol) and 3-isothiocyanato-4-methoxy-pyridine (0.113 mg, 0.680 mmol, example 4, step a) in DMF was stirred at room temperature for 64 hours. After removal of DMF in vacuo, the residue was treated with water. The precipitated solid was filtered, washed with water, and dried to give a portion of the title compound. The filtrate was concentrated and the oily brown residue was dried under vacuum to provide a second potion of the title compound.

Example 4

(4-Methoxy-pyridin-3-yl)-(6-methyl-6H-imidazo[4',5':3,4]benzo[2,1-d]thiazol-2-yl)-amine.TFA

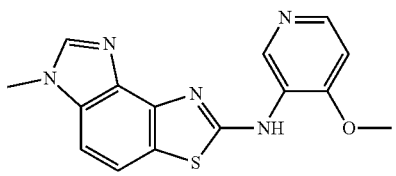

1-(4-M ethoxy-pyridin-3-yl)-3-(1-methyl-1H-benzoimidazol-4-yl)-thiourea (213 mg, 0.68 mmol, example 4, step b) in acetic acid (1 mL) was treated with 0.50 M $Br_2$ (1.09 mL, 0.544 mmol) in acetic acid overnight. After evaporation of HOAc in vacuo, $CF_3CO_2H$ was added and then removed in vacuo. The residue was dissolved in a small amount of DMSO and purified by HPLC eluting with water/acetonitrile/0.2% trifluoroacetic acid to provide the title compound as a brown solid. $^1$H NMR (400 MHz, MeOH-$d_4$) δ=10.47 (d, J=1.0 Hz, 1H), 9.41 (s, 1H), 8.50 (dd, J=1.2, 6.6 Hz, 1H), 7.99 (d, J=8.8 Hz, 1H), 7.71 (d, J=8.8 Hz, 1H), 7.66 (d, J=6.6 Hz, 1H), 4.30 (s, 3H), 4.19 (s, 3H); MS m/e 312 (M+H).

Cloning, Expression and Purification

Cloning of Human proMMP9

Amino acid numbering for all human proMMP9 constructs was based on UniProtKB/Swiss-Prot P14780, full-length human matrix metalloproteinase-9 precursor, proMMP9(1-707) (SEQ ID NO:1). One construct, proMMP9(20-445) (SEQ ID NO:2), was based on the previously published crystal structure (Elkins, Ho et al. 2002). The construct lacked the signal peptide at the N-terminus and also lacked the four hemopexin-like domains at the C-terminus. An N-terminal truncated construct was also designed with an N-terminus truncation after the first observable electron density in the previously published proMMP9 structure and a single amino acid was removed from the C-terminus to produce proMMP9 (29-444) (SEQ ID NO:3). Other truncated constructs were also synthesized without the three fibronectin type-II domains (ΔFnII), amino acids 216-390. The ΔFnII constructs were proMMP9(29-444; ΔFnII) (SEQ ID NO:4), proMMP9 (67-444; ΔFnII) (SEQ ID NO:5) and proMMP9(20-445; ΔFnII) (SEQ ID NO:6). Binding studies with the proMMP9 proteins without the FnII domains showed that compounds bound with similar affinity compared to the wild-type protein (data not shown).

In order to make the constructs with the FnII domains deleted, proMMP9(29-444; ΔFnII) (SEQ ID NO:4), proMMP9(67-444; ΔFnII) (SEQ ID NO:5) and proMMP9 (20-445; ΔFnII) (SEQ ID NO:6), plasmids encoding the different proMMP9 truncations were used as templates for PCR to create two fragments of DNA corresponding to amino acid pairs including: 29-215/391-444, 67-215/391-444, and 20-215/391-445, respectively. Overlapping PCR was used to join the fragments. The 5' primers had an Nde1 site and a start methionine and the 3' primers had a stop codon and a Bgl2 site. The final PCR products were cloned into the TOPO TA cloning vector (Invitrogen) and the sequences were confirmed. Subsequently the vectors were digested with Nde1 and Bgl2 and the sequences were subcloned into Nde1 and BamH1 sites of the T7 expression vector pET11a (Novagen).

Expression of Truncated Forms of Human proMMP9

For expression in E. coli, all of the truncated proMMP9 constructs were transformed into BL21(DE3) RIL cells (Stratagene). Cells were initiated for an overnight culture from glycerol stocks in LB+Ampicillin (100 µg/ml) @ 37° C. shaking at 220 rpms. The overnight culture was subcultured 1:100 in LB+Ampicillin (100 ug/ml) and maintained at 37° C. shaking at 220 rpms. Samples were taken and A600 readings were monitored until an OD of 0.6 was achieved. The culture was induced with 1 mM IPTG and maintained under present growth conditions. Cultures were harvested 3 hours post induction at 6000×g for 10 min. Pellets were washed in 1×PBS with protease inhibitors and stored at −80° C.

Purification of Truncated Forms of Human proMMP9

To purify the truncated proMMP9 proteins from E. coli, cell pellets were suspended in 25 mM $Na_2HPO_4$ pH 7, 150 mM NaCl, 10 mL/gram cell pellet. The cells were homogenized in a Dounce homogenizer, and then processed twice through a microfluidizer (Microfluidics International Corporation, model M-110Y). The lysate was centrifuged at 32,000×g for 45 minutes at 4° C. The supernatant was discarded. The pellet was suspended in 25 mM $Na_2HPO_4$ pH 7, 150 mM NaCl, 10 mM DTT, 1 mM EDTA, 10 mL/gram cell pellet. The pellet was homogenized in a Dounce homogenizer, and then centrifuged at 32,000×g for 45 minutes at 4° C. The supernatant was discarded. The pellet was suspended in 7 M urea, 25 mM Tris pH 7.5, 10 mM DTT, 1 mM EDTA, 6.5 mL/gram cell pellet, and then solubilized in a Dounce homogenizer and stirred for approximately 16 hours at ambient temperature. The solubilized protein solution was adjusted to pH 7.5, centrifuged at 45,000×g, 45 minutes at 4°

C., and the supernatant, containing the denatured proMMP9, was filtered to 0.8 micron. A 5 mL HiTrap Q Sepharose HP column (GE Healthcare) was prepared according to manufacturer's instructions using Buffer A: 7 M urea, 25 mM Tris pH 7.5 and Buffer B: 7 M urea, 25 mM Tris pH 7.5, 1.0 M NaCl. The protein solution was applied to the HiTrap at 2.5 mL/minute. The column was washed to baseline absorbance with approximately 3.5 CV Buffer A. The proMMP9 was eluted in a 12CV linear gradient from 0% Buffer B to 12% Buffer B. Fractions were collected, analyzed on SDS-PAGE (Novex) and pooled based on purity. The pooled protein was re-natured by drop-wise addition to a solution, stirring and at ambient temperature, of 20 mM Tris pH 7.5, 200 mM NaCl, 5 mM $CaCl_2$, 1 mM $ZnCl_2$, 0.7 M L-arginine, 10 mM reduced and 1 mM oxidized glutathione, and was stirred for approximately 16 hours at 4° C. The refolded protein was concentrated to approximately 2.5 mg/mL in Jumbo Sep centrifugal concentrators (Pall) with 10,000 MWCO membranes. The concentrated protein solution was dialyzed at 4° C. for approximately 16 hours against 20 mM Tris pH 7.5, 150 mM NaCl. The dialyzed protein solution was clarified by filtration to 0.8 micron, concentrated to 2 mg/mL as before, centrifuged at 45,000×g for 15 minutes at 4° C. and filtered to 0.2 micron. It was purified on a HiLoad 26/60 Superdex 200 column (GE Healthcare) equilibrated in 20 mM Tris pH 7.5, 200 mM NaCl. Fractions were analyzed by SDS-PAGE and pooled based on purity. The pooled protein was concentrated in a Jumbo Sep concentrator as before and centrifuged at 16,000×g for 10 minutes at 4° C. The protein concentration was determined using Bio-Rad Protein Assay (Bio-Rad Laboratories, Inc.) with bovine serum albumin as a standard. The supernatant was aliquoted, frozen in liquid nitrogen and stored at −80° C.

Full-Length Human proMMP9

Full-length proMMP9(1-707) (SEQ ID NO:1) was expressed in HEK293 cells or in COS-1 cells as a secreted protein using a pcDNA3.1 expression vector. When expressed as a secreted protein in HEK293 cells or COS-1 cells, there is cotranslational removal of the signal peptide, amino acids 1-19 of full-length proMMP9(1-707) (SEQ ID NO:1). The final purified proMMP9(1-707) (SEQ ID NO:1) protein lacks the signal peptide.

Prior to transfection with the proMMP9(1-707) (SEQ ID NO:1) construct, the HEK293 cells were suspension adapted (shake flasks) in a serum free media (Freestyle 293) supplemented with pluronic acid (F-68) at a final concentration of 0.1%. Once cells reached a density of $1.2 \times 10^6$/mL they were transiently transfected using standard methods. Transient transfection of COS-1 cells was done in flasks with adherent cell cultures and serum free media. For both HEK293 and COS-1 cells, the conditioned media was collected for purification of the proMMP9(1-707) (SEQ ID NO:1) protein. 1.0 M HEPES pH 7.5 was added to 9 L of conditioned media for a final concentration of 50 mM. The media was concentrated to 600 mL in a Kvicklab concentrator fitted with a hollow fiber cartridge of 10,000 MWCO (GE Healthcare). This was clarified by centrifugation at 6,000×g, 15 minutes, at 4° C. and then further concentrated to 400 mL in Jumbo Sep centrifugal concentrators (Pall) with 10,000 MWCO membranes. The concentrated protein was dialyzed against 50 mM HEPES pH 7.5, 10 mM $CaCl_2$, 0.05% Brij 35, overnight at 4° C. and then dialysis was continued for several hours at 4° C. in fresh dialysis buffer. The dialyzed protein was centrifuged at 6,000×g, 15 minutes, at 4° C., and filtered to 0.45 micron. 12 mL of Gelatin Sepharose 4B resin (GE Healthcare) was equilibrated in 50 mM HEPES pH 7.5, 10 mM $CaCl_2$, 0.05% Brij 35 in a 2.5 cm diameter Econo-Column (Bio-Rad Laboratories). The filtered protein solution was loaded onto the Gelatin Sepharose resin using gravity flow at approximately 3 mL/minute. The resin was washed with 10CV 50 mM HEPES pH 7.5, 10 mM $CaCl_2$, 0.05% Brij 35 and eluted with 30 mL 50 mM HEPES pH 7.5, 10 mM $CaCl_2$, 0.05% Brij 35, 10% DMSO, collected in 5 mL fractions. Fractions containing protein, confirmed by A280 absorbance, were dialyzed, in 500 times the volume of the fractions, against 50 mM HEPES pH 7.5, 10 mM $CaCl_2$, 0.05% Brij 35, overnight at 4° C. Dialysis was continued for an additional 24 hours in two fresh buffer changes. The dialyzed fractions were analyzed on SDS-PAGE and pooled based on purity. The pooled protein was concentrated to 1.2 mg/mL in Jumbo Sep centrifugal concentrators with 10,000 MWCO membranes. Protein concentration was determined with DC™ protein assay (Bio-Rad Laboratories, Inc.). The protein was aliquoted, frozen in liquid nitrogen and stored at −80° C.

Full-Length Rat proMMP9

Amino acid numbering for full-length rat proMMP9 was based on UniProtKB/Swiss-Prot P50282, full-length rat matrix metalloproteinase-9 precursor, proMMP9(1-708) (SEQ ID NO:11). The full-length rat proMMP9 was produced with the same methods as described for full-length human proMMP9. In brief, full-length rat proMMP9(1-708) (SEQ ID NO:11) was expressed in HEK293 cells as a secreted protein using a pcDNA3.1 expression vector. When expressed in HEK293 cells and secreted into the media, there is cotranslational removal of the signal peptide, so the final purified full-length rat proMMP9(1-708) (SEQ ID NO:11) protein lacks the signal peptide.

Human proMMP13

The sequence for proMMP13 was amino acids 1-268 from UniProtKB/Swiss-Prot P45452, proMMP13(1-268) (SEQ ID NO:7). The expression construct included a C-terminal Tev cleavage sequence flanking recombination sequences for use in the Invitrogen Gateway system. The construct was recombined into an entry vector using the Invitrogen Gateway recombination reagents. The resulting construct was transferred into a HEK293 expression vector containing a C-terminal 6×-histidine tag. Protein was expressed via transient transfection utilizing HEK293 cells and secreted into the media. When expressed in HEK293 cells and secreted into the media, there is cotranslational removal of the signal peptide, amino acids 1-19 of proMMP13(1-268) (SEQ ID NO:7). The final purified proMMP13(1-268) (SEQ ID NO:7) protein lacks the signal peptide. HEK293 media were harvested and centrifuged. Media were loaded on GE Healthcare HisTrap FF columns, washed with buffer A (20 mM Tris pH 7.5, 200 mM NaCl, 2 mM $CaCl_2$, 10 mM imidazole), and eluted with buffer B (20 mM Tris pH 7.5, 200 mM NaCl, 2 mM $CaCl_2$ 200 mM imidazole). The eluted protein was loaded on a Superdex 200 column equilibrated with buffer C (20 mM HEPES pH 7.4, 100 mM NaCl, 0.5 mM $CaCl_2$). Fractions containing proMMP13(1-268) (SEQ ID NO:7) were pooled and concentrated to >2 mg/mL.

Human Catalytic MMP3

Catalytic MMP3 was amino acids 100-265 of human MMP3 from UniProtKB/Swiss-Prot P08254, MMP3(100-265) (SEQ ID NO:8). The corresponding nucleotide sequence was subcloned into a pET28b vector to add a C-terminal 6×-Histidine tag and the construct was used for expression in *E. coli*. The protein was purified to >95% purity from 4.5 M urea solubilized inclusion bodies by standard techniques. Aliquots of purified protein were stored at −70° C. Purified recombinant human catalytic MMP3 is also available from commercial sources (e.g., Calbiochem®, 444217).

Biological Assays
ThermoFluor® Assays
Generalized ThermoFluor® Methods

The ThermoFluor® (TF) assay is a 384-well plate-based binding assay that measures thermal stability of proteins (Pantoliano, Petrella et al. 2001; Matulis, Kranz et al. 2005). The experiments were carried out using instruments available from Johnson & Johnson Pharmaceutical Research & Development, LLC. TF dye used in all experiments was 1,8-anilinonaphthalene-8-sulfonic acid (1,8-ANS) (Invitrogen: A-47).

Compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For multiple compound concentration-response experiments, the compound aliquots (50 mL) were robotically predispensed directly into black 384-well polypropylene PCR microplates (Abgene: TF-0384/k) using a Cartesian Hummingbird liquid handler (DigiLab, Holliston, Mass.). Following compound dispense, protein and dye solutions were added to achieve the final assay volume of 3 µL. The assay solutions were overlayed with 1 µL of silicone oil (Fluka, type DC 200: 85411) to prevent evaporation.

Assay plates were robotically loaded onto a thermostatically controlled PCR-type thermal block and then heated from 40 to 90° C. at a ramp-rate of 1° C./min for all experiments. Fluorescence was measured by continuous illumination with UV light (Hamamatsu LC6) supplied via fiber optics and filtered through a band-pass filter (380-400 nm; >60D cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m$ (Pantoliano, Petrella et al. 2001).

Thermodynamic parameters necessary for fitting compound binding for each proMMP were estimated by differential scanning calorimetry (DSC) and from ThermoFluor® data. The heat capacity of unfolding for each protein was estimated from the molecular weight and from ThermoFluor® dosing data. Unfolding curves were fit singly, then in groups of 12 ligand concentrations the data were fit to a single $K_D$ for each compound.

ThermoFluor® with proMMP9(67-444; ΔFnII) (SEQ ID NO:5)

The protein sample preparations had to include a desalting buffer exchange step via a PD-10 gravity column (GE Healthcare). The desalting buffer exchange was performed prior to diluting the protein to the final assay concentration of 3.5 µM proMMP9(67-444; ΔFnII) (SEQ ID NO:5). The concentration of proMMP9(67-444; ΔFnII) (SEQ ID NO:5) was determined spectrophotometrically based on a calculated extinction coefficient of $\epsilon_{280}=33900$ M$^{-1}$ cm$^{-1}$, a calculated molecular weight of 22.6 kDa, and calculated pI of 5.20. ThermoFluor® reference conditions were defined as follows: 80 µg/mL (3.5 µM) proMMP9(67-444; ΔFnII) (SEQ ID NO:5), 50 µM 1,8-ANS, pH 7.0 Buffer (50 mM HEPES pH 7.0, 100 mM NaCl, 0.001% Tween-20, 2.5 mM MgCl$_2$, 300 µM CaCl$_2$). The thermodynamic parameters for proMMP9(67-444; ΔFnII) (SEQ ID NO:5) are as follows: $T_m$ (° C.)=63 (+/−0.1), $\Delta_U H_{(Tm)}$ (cal mol$^{-1}$)=105000(+/−5000), $\Delta_U S_{(Tm)}$ (cal mol$^{-1}$ K$^{-1}$)=450, $\Delta_U C_p$ (cal mol$^{-1}$ K$^{-1}$)=2000.

ThermoFluor® with proMMP9(20-445; ΔFnII) (SEQ ID NO:6)

The protein sample preparations included a desalting buffer exchange step via a PD-10 gravity column (GE Healthcare). The desalting buffer exchange was performed prior to diluting the protein to the final assay concentration of 2.8 µM proMMP9(20-445; ΔFnII) (SEQ ID NO:6). The concentration of proMMP9(20-445; ΔFnII) (SEQ ID NO:6) was determined spectrophotometrically based on a calculated extinction coefficient of $\epsilon_{280}=39880$ M$^{-1}$ cm$^{-1}$, a calculated molecular weight of 28.2 kDa, and calculated pI of 5.5. ThermoFluor® reference conditions were define as follows: 80 µg/mL (2.8 µM) proMMP9(20-445; ΔFnII) (SEQ ID NO:6), 50 µM 1,8-ANS, pH 7.0 Buffer (50 mM HEPES pH 7.0, 100 mM NaCl, 0.001% Tween-20, 2.5 mM MgCl$_2$, 300 µM CaCl$_2$). The thermodynamic parameters for proMMP9(20-445; ΔFnII) (SEQ ID NO:6) are as follows: $T_m$ (° C.)=72 (+/−0.1), $\Delta_U H_{(Tm)}$ (cal mol$^{-1}$)=160000(+/−5000), $\Delta_U S_{(Tm)}$ (cal mol$^{-1}$ K$^{-1}$)=434, $\Delta_U C_p$ (cal mol$^{-1}$ K$^{-1}$)=2400.

ThermoFluor® with proMMP13(1-268) (SEQ ID NO:7)

The proMMP13(1-268) (SEQ ID NO:7) protein sample preparations included a desalting buffer exchange step via a PD-10 gravity column (GE Healthcare). The desalting buffer exchange was performed prior to diluting the protein to the final assay concentration of 3.5 µM. The concentration of proMMP13(1-268) (SEQ ID NO:7) was estimated spectrophotometrically based on a calculated extinction coefficient of $\epsilon_{280}=37000$ M$^{-1}$ cm$^{-1}$, a calculated molecular weight of 30.8 kDa, and calculated pI of 5.33. ThermoFluor® reference conditions were defined as follows: 100 µg/mL proMMP13 (1-268) (SEQ ID NO:7), 25 µM 1,8-ANS, pH 7.0 Buffer (50 mM HEPES pH 7.0, 100 mM NaCl, 0.001% Tween-20, 2.5 mM MgCl$_2$, 300 µM CaCl$_2$). The thermodynamic parameters for proMMP13(1-268) (SEQ ID NO:7) are as follows: $T_m$(° C.)=67 (+/−0.1), $\Delta_U H_{(Tm)}$ (cal mol$^{-1}$)=107000(+/−5000), $\Delta_U S_{(Tm)}$ (cal mol$^{-1}$c)=318, $\Delta_U C_p$ (cal mol$^{-1}$c)=2600.

TABLE 1

Representative Thermofluor data for selected compounds

| Example | proMMP9(20-445; ΔFnII) (SEQ ID NO: 6) binding, Kd (µM) | proMMP9(67-444; ΔFnII) (SEQ ID NO: 5) binding, Kd (µM) | proMMP13(1-268) (SEQ ID NO: 7) binding, Kd (µM) |
| --- | --- | --- | --- |
| 1 | 1.75 | 0.388 | 37.48 |
| 2 | 0.10 | 0.26 | 0.14 |
| 3 | 0.27 | 0.56 | 4.9 |
| 4 | 1.0 | 0.039 | ND |

Enzyme Assays
proMMP9/MMP3 P126 Activation Assay

Compounds were assessed for inhibition of proMMP9 activation by catalytic MMP3, MMP3(100-265) (SEQ ID NO:8) using full-length proMMP9(1-707) (SEQ ID NO:1) purified from HEK293 cells and a peptide (Mca-PLGL-Dpa-AR-NH$_2$, BioMol P-126) that fluoresces upon cleavage by catalytic MMP9. The assay buffer employed was 50 mM Hepes, pH 7.5, 10 mM CaCl$_2$, 0.05% Brij-35. DMSO was included at a final concentration of 2%, arising from the test compound addition. On the day of assay, proMMP9(1-707) (SEQ ID NO:1) purified from HEK293 cells and MMP3(100-265) (SEQ ID NO:8) were diluted to 400 nM in assay buffer. The reaction volume was 50 µL. In 96-well black plates (Costar 3915), 44 µL of assay buffer was mixed with 1.0 µL of test compound, 2.5 µL of 400 nM proMMP9(1-707) (SEQ ID NO:1) purified from HEK293 cells and the reaction was initiated with 2.5 µL of 400 nM MMP3(100-265) (SEQ ID NO:8). The plate was sealed and incubated for 80 min at 37° C. Final concentrations were 20 nM proMMP9(1-707) (SEQ ID NO:1) purified from HEK293 cells and 20 nM MMP3 (100-265) (SEQ ID NO:8), and concentrations of test compounds were varied to fully bracket the IC$_{50}$. Immediately following the 80 min incubation, 50 µL of 40 µM P-126 substrate was added (freshly diluted in assay buffer), and the resulting activity associated with catalytic MMP9 was kinetically monitored at 328 nm excitation, 393 nm emission for 10-15 min at 37° C., using a Spectramax Gemini XPS reader (Molecular Devices). Reactivity of residual MMP3 towards P-126 substrate was minimal under these conditions. Initial velocities were plotted by use of a four-parameter logistics equation (GraphPad Prism® software) for determination of IC$_{50}$.

ProMMP13/Plasmin P126 Activation Assay

Compounds were assessed for inhibition of proMMP13 activation by plasmin using a peptide (Mca-PLGL-Dpa-AR-NH$_2$, BioMol P-126) that fluoresces upon cleavage by catalytic MMP13. The assay buffer employed was 50 mM Hepes, pH 7.5, 10 mM CaCl$_2$, 0.05% Brij-35. DMSO was included at a final concentration of 2%, arising from the test compound addition. On the day of assay, proMMP13(1-268) (SEQ ID NO:7) purified from HEK293 cells and plasmin were diluted to 160 nM and 320 nM, respectively, in assay buffer. The reaction volume was 50 µL. In 96-well black plates (Costar 3915), 44 µL of assay buffer was mixed with 1.0 µL of test compound, 2.5 µL of 160 nM proMMP13(1-268) (SEQ ID NO:7), and the reaction was initiated with 2.5 µL of 320 nM plasmin. The plate was sealed and incubated for 40 min at 37° C. Final concentrations were 8 nM proMMP13(1-268) (SEQ ID NO:7) and 16 nM plasmin, and concentrations of test compounds were varied to fully bracket the IC$_{50}$. Immediately following the 40 min incubation, 50 µL of 40 µM P-126 substrate was added (freshly diluted in assay buffer), and the resulting activity associated with catalytic MMP13 was kinetically monitored at 328 nm excitation, 393 nm emission for 10-15 min at 37° C., using a Spectramax Gemini XPS reader (Molecular Devices). Plasmin was not reactive towards P-126 substrate under these conditions. Initial velocities were plotted by use of a four-parameter logistics equation (GraphPad Prism® software) for determination of IC$_{50}$.

ProMMP9/MMP3 DQ Gelatin Activation Assay

Compounds were assessed for inhibition of proMMP9 activation by catalytic MMP3 using a quenched fluorescein gelatin substrate (DQ gelatin, Invitrogen D12054) that fluoresces upon cleavage by activated MMP9. The assay buffer employed was 50 mM Hepes, pH 7.5, 10 mM CaCl$_2$, 0.05% Brij-35. DMSO was included at a final concentration of 0.2%, arising from the test compound addition. On the day of assay, full-length proMMP9(1-707) (SEQ ID NO:1) from COS-1 cells and catalytic MMP3(100-265) (SEQ ID NO:8) were diluted to 60 nM and 30 nM, respectively, in assay buffer. Test compounds in DMSO were diluted 250-fold in assay buffer at 4× the final concentration. The reaction volume was 12 µL, and all reactions were conducted in triplicate. In 384-well half-volume plates (Perkin Elmer ProxiPlate 384 F Plus, 6008260), 4 µL of test compound in assay buffer was mixed with 4 µL of 60 nM full-length proMMP9(1-707) (SEQ ID NO:1) from COS-1 cells. The plate was sealed and incubated for 30 min at 37° C. Final concentrations were 20 nM full-length proMMP9(1-707) (SEQ ID NO:1) from COS-1 cells and 10 nM MMP3(100-265) (SEQ ID NO:8), and concentrations of test compounds were varied to fully bracket the IC$_{50}$. Immediately following the 30 min incubation, 4 µL of 40 µg/ml DQ gelatin substrate was added (freshly diluted in assay buffer), and incubated for 10 min at room temperature. The reaction was stopped by the addition of 4 µL of 50 mM EDTA, and the resulting activity associated with catalytic MMP9 was determined at 485 nm excitation, 535 nm emission using an Envision fluorescent reader (Perkin Elmer). Reactivity of residual MMP3 towards DQ gelatin was minimal under these conditions. Percent inhibition of test compounds were determined from suitable positive (DMSO only in assay buffer) and negative (EDTA added prior to reaction initiation) controls. Plots of % inhibition vs. test compound concentration were fit to a four-parameter logistics equation (GraphPad Prism® software) for determination of IC$_{50}$.

Catalytic Enzyme Assays

Selected compounds that were active in the proMMP9 activation assays were subsequently tested in catalytic MMP3 and catalytic MMP9 assays. Compounds that inhibited catalytic MMP3 or catalytic MMP9 were considered false positives in the proMMP9 activation assay.

Catalytic MMP3

Compounds were assessed for inhibition of human catalytic MMP3, MMP3(100-265) (SEQ ID NO:8), using a peptide (Mca-RPKPVE-Nva-WRK(Dnp)-NH$_2$, Bachem M2110) that fluoresces upon cleavage by catalytic MMP3. The assay buffer employed was 50 mM Hepes, pH 7.5, 10 mM CaCl$_2$, 0.05% Brij-35. DMSO was included at a final concentration of 2%, arising from the test compound addition. The reaction volume was 100 µL. In 96-well black plates (Costar 3915), 44 µL of assay buffer was mixed with 1.0 µL of test compound, and 5 µL of 400 nM human catalytic MMP3 and the mixture was preincubated at 37° C. for 10 minutes. The reaction was initiated with 50 µL of 40 µM M-2110 substrate (freshly diluted in assay buffer), and the resulting activity associated with catalytic MMP3 was kinetically monitored at 328 nm excitation, 393 nm emission for 5-15 min at 37° C., using a Spectramax Gemini XPS reader (Molecular Devices). Initial velocities were plotted by use of a four-parameter logistics equation (GraphPad Prism® software) for determination of IC50, if required. Final concentrations employed were 20 nM catalytic MMP3 and 20 µM M2110 substrate.

Catalytic MMP9

Compounds were assessed for inhibition of human catalytic MMP9 (BioMol SE-244), using a peptide (Mca-PLGL-Dpa-AR-NH$_2$, BioMol P-126) that fluoresces upon cleavage by catalytic MMP9. The assay buffer employed was 50 mM Hepes, pH 7.5, 10 mM CaCl$_2$, 0.05% Brij-35. DMSO was included at a final concentration of 2%, arising from the test compound addition. The reaction volume was 100 µL. In 96-well black plates (Costar 3915), 44 µL of assay buffer was mixed with 1.0 µL of test compound, and 5 µL of 100 nM human catalytic MMP9 and the mixture was preincubated at 37° C. for 10 minutes. The reaction was initiated with 50 µL of 40 µM P-126 substrate (freshly diluted in assay buffer), and the resulting activity associated with catalytic MMP9 was kinetically monitored at 328 nm excitation, 393 nm emission for 5-15 min at 37° C., using a Spectramax Gemini XPS reader (Molecular Devices). Initial velocities were plotted by use of a four-parameter logistics equation (GraphPad Prism® software) for determination of IC50, if required. Final concentrations employed were 5 nM catalytic MMP9 and 20 µM P-126 substrate.

TABLE 2

Representative enzyme assay data for selected compounds

| Example | proMMP9/MMP3 P126 Activation Assay, IC$_{50}$ (μM) | ProMMP9/MMP3 DQ gel Activation Assay, IC$_{50}$ (μM) | ProMMP13/Plasmin P126 Activation Assay, IC$_{50}$ (μM) |
|---|---|---|---|
| 1 | 1.3 | 1.5 | ND |
| 2 | 0.18 | ND | 3.3 |
| 3 | 0.85 | ND | ND |
| 4 | 0.11 | ND | ND |

| Example | Catalytic MMP9 IC50 (μM) | Catalytic MMP3 IC50 (μM) |
|---|---|---|
| 1 | ~40 | >50 |

Cell-Based Assays
Activation of proMMP9 in Rat Synoviocyte Cultures

A primary synoviocytes line was derived from the periarticular tissue of arthritic rats. Arthritis was induced in female Lewis rats following an i.p. administration of streptococcal cell wall peptidoglycan polysaccharides (Cromartie, Craddock et al. 1977). Rats with established arthritis were sacrificed, and hind-limbs were severed, immersed briefly in 70% ethanol, and placed in a sterile hood. The skin was removed and the inflamed tissue surrounding the tibia-tarsal joint was harvested using a scalpel. Tissue from six rats was pooled, minced to approximately 8 mm$^3$ pieces, and cultured in Dulbecco's Modified Eagle's Medium (DMEM) containing 15% fetal calf serum (FCS). In the following weeks, cells migrated out of the tissue piece, proliferated, and formed a monolayer of adherent cells. The synoviocytes were lifted from culture plates with 0.05% trypsin and passaged weekly at 1:4 ratios in DMEM containing 10% FCS. Synoviocytes were used at passage 9 to investigate the ability of Example 2 to inhibit the maturation of MMP9 to active form.

Rat synoviocytes spontaneously expressed and activated MMP9 when cultured in collagen gels and stimulated with tumor necrosis factor-alpha (TNFα) (FIG. 1 and Table 3). Eight volumes of an ice-cold solution of 3.8 mg/mL rat tail collagen (Sigma Cat #C3867-1VL) were mixed with 1 volume of 1 M sodium bicarbonate and 1 volume of 10× Roswell Park Memorial Institute medium. The pH of the mixture was adjusted to pH 7 with 1 N sodium hydroxide and equal volumes of the pH-adjusted collagen solution were mixed with DMEM containing 0.8 million synoviocytes per mL. One half mL volumes were dispensed into Costar 24-well culture dishes and placed for one hr at 37° C. and 5% CO$_2$, during which time the collagen solution formed a gel. Individual gels were dislodged into wells of 12-well Costar plates containing 1 mL/well of DMEM adjusted to contain 0.05% BSA and 100 ng/mL mouse TNFα (R&D Systems Cat #410-MT-010). The plates were agitated 10 seconds to ensure that the collagen gels did not adhere to the well bottoms. After overnight culture at 37° C. and 5% CO$_2$, wells were adjusted to contain an additional 0.5 mL of DMEM containing 0.05% BSA and Example 2 at 4× the final desired concentration (final culture volumes were 2 mL). The plates were cultured an additional 48 hrs, at which time 1 mL of conditioned media were harvested into fresh eppendorf tubes containing 40 μL/mL of a 50% slurry of gelatin-conjugated sepharose (GE Healthcare Cat #17-0956-01). Samples were rotated for 2 hrs at 4° C. before centrifugation 1 min×200 g. Supernatants were discarded. The gelatin-sepharose pellets were washed once with 1 mL of ice cold DMEM, resuspended in 50 μL of 2× reducing Leamli buffer and heated 5 min at 95° C. Fifteen μL of eluted proteins were resolved on 4-12% NuPAGE gels and transferred to 0.45 μm pore-sized nitrocellose blots. Next, blots were incubated in blocking buffer (5% milk in Tris-buffered saline containing 0.1% Tween-20) for 1 hr at RT and probed overnight (4° C.) with blocking buffer containing 1 μg/mL primary antibodies. Blots were next probed 1 hr at RT with 1/10,000 dilutions of goat anti-mouse IgG-HRP or goat anti-rabbit IgG-HRP (Santa Cruz) in blocking buffer and developed using SuperSignal® West Fempto Maximum Sensitivity Substrate. Chemiluminesence signal was analyzed using a ChemiDoc imaging system (BioRad Laboratories) and Quantity One® image software. Electrophoretic mobility was estimated based on the mobility of standards (Novex Sharp Pre-Stained Protein Standards P/N 57318).

Mouse mAb-L51/82 (UC Davis/NIH NeuroMab Facility, Antibody Incorporated) was used to detect pro and processed forms of MMP9. Synoviocyte-conditioned media contained an approximately 80 kD form of MMP9 (FIG. 1A, lane 2). In the presence of 0.37-10 μM Example 2 (FIG. 1A, lanes 3-6), the 80 kD active MMP9 form was reduced in a dose dependent fashion, and a form of approximately 86 kD appeared. The 86 kD form was predominant in the presence of 10 μM Example 2 (FIG. 1A, lane 6). Lane 1 was loaded with a standard containing 3 ng of full-length rat proMMP9(1-708) (SEQ ID NO:11) and 3 ng of full-length rat proMMP9(1-708) (SEQ ID NO:11) converted to catalytic rat MMP9 by catalytic MMP3. The electrophoretic mobility of the 80 kD form present in synoviocyte conditioned medium was the same as the active MMP9 standard. The 86 kD form produced by synoviocytes in the presence of Example 2 demonstrated greater mobility than the full-length rat proMMP9(1-708) (SEQ ID NO:11) standard which ran with a mobility of approximately 100 kD. The 86 kD form demonstrated a mobility similar to an incompletely processed intermediate form described previously that retains the cysteine switch and lacks catalytic activity (Ogata, Enghild et al. 1992).

ProMMP9 is activated when cleaved between R106 and F107 (Ogata, Enghild et al. 1992). A rabbit polyclonal antibody (pAb-1246) was generated to the active MMP9 N-terminal neoepitope using an approach similar to that reported previously (Duncan, Richardson et al. 1998). Rabbits were immunized and boosted with a peptide, human MMP9(107-113) (SEQ ID NO:9) conjugated to keyhole limpet hemocyanin, and antibodies were affinity purified from serum using FQTFEGD-conjugated agarose affinity resin and 100 mM glycine (pH 2.5) elution. To resolve N-terminal neoepitope antibodies from antibodies directed to other epitopes within the sequence, eluted antibody was dialyzed in PBS and cross-absorbed by mixing with a peptide, human proMMP9(99-113) (SEQ ID NO:10), that was conjugated to agarose. The unbound fraction containing N-terminal neoepitope antibodies was recovered and was designated pAb-1246.

FIG. 1B, lane 1 demonstrated that pAb-1246 bound the 80 kD active MMP9 standard, but did not recognize the 100 kD proMMP9 standard. pAb-1246 detected 80 kD active MMP9 in synoviocyte conditioned medium, and Example 2 caused a dose-dependent reduction in active MMP9 (FIG. 1B, lanes 2-6). Band chemiluminescence intensities were measured directly and reported in Table 3. The production of active MMP9 was inhibited by Example 2 with an IC$_{50}$ of approximately 1.1 μM. pAb-1246 did not recognize the 86 kD form, providing further evidence that this likely represented an intermediate form whose further maturation was blocked by Example 2.

TABLE 3

Example 2 blocked production of
active MMP9 by rat synoviocytes [a]

| Example 2, µM | Signal of 80 kD band (INT*mm$^2$) [b] | % Inhibition [c] |
|---|---|---|
| 0 | 84384 | 0 |
| 0.37 µM | 74381 | 12 |
| 1.1 µM | 45381 | 46 |
| 3.3 µM | 11554 | 86 |
| 10 µM | 2578 | 97 |

[a] Rat synoviocytes embedded in collagen gels were stimulated 72 hrs with TNFα. Cultures were supplemented with the indicated concentrations of Example 2 for the final 48 hrs and conditioned media were assessed for the 80 kD active form of MMP9 by Western blotting with pAb-1246 developed against the N-terminal activation neoepitope.
[b] Chemiluminesence captured during a 30 s exposure was analyzed using a ChemiDoc imaging system (BioRad Laboratories) and Quantity One ® image software. Signals were measured within uniform sized boxes drawn to circumscribe the 80 kD bands and were the product of the average intensity (INT) and the box area (mm$^2$). Values given have been corrected for background signal.
[c] Percent signal reduction relative to the signal generated by synoviocytes cultured in the absence of Example 2.

Activation of proMMP9 by Human Fetal Lung Fibroblast Cultures

Example 2 was assessed additionally for ability to block the maturation of proMMP9 to active MMP9 in cultures of human fetal lung fibroblasts (HFL-1, American Type Culture Collection #CCL-153). Unlike rat synoviocytes, HFL-1 cells were unable to process proMMP9 to the active form without addition of neutrophil elastase. Elastase did not directly cause processing of recombinant proMMP9 (data not shown). Rather, the function of elastase in this assay may be to inactivate tissue inhibitors of matrix metalloproteinases (TIMPs) that repress endogenous pathways of MMP9 activation (Skold, Liu et al. 1999).

HLF-1 were maintained in monolayer culture in DMEM with 10% FCS and were used between passage numbers 5-15. HLF-1 were embedded in collagen gels as described for rat SCW synoviocytes (vida supra). Half mL gels containing 0.4 million cells were dislodged into wells of 12 well Costar plates containing 1 mL/well of DMEM adjusted to contain 0.05% BSA and 100 ng/mL human TNFα (R&D Systems Cat #210-TA/CF). After overnight culture (37° C. and 5% CO$_2$) wells were adjusted to contain an additional 0.5 mL of DMEM containing 0.05% BSA and with or without 13.2 µM Example 2 (final concentration was 3.3 µM Example 2). Next, cultures were adjusted to contain 30 nM human elastase (Innovative Research). The plates were cultured an additional 72 hrs, at which time MMP9 secreted into the conditioned media was bound to gelatin-sepharose and evaluated by Western blot analysis as described for the rat synoviocyte cultures (vida supra). mAb-51/82 detected three forms of MMP9 in HFL-1 cultures.

These included a form of approximately 100 kD with mobility similar to recombinant rat proMMP9, an approximately 80 kD form with mobility similar to rat active MMP9, and an approximately 86 kD intermediate form. The band intensities are provided in Table 4. In the absence of Example 2, most of the MMP9 was present as the 80 kD form. In the presence of Example 2, the 80 kD form was a minor fraction of the total signal while nearly half of the signal were contributed each by the 100 kD and 86 kD forms. The total signal of the three bands was similar with or without Example 2. These data indicate that the 100 kD and 86 kD forms of MMP9 were effectively stabilized by Example 2 and the formation of the 80 kD form was suppressed.

TABLE 4

Example 2 blocked processing of MMP9 by HFL-1 cells [a]

| Example 2, 3.3 µM | Signal (INT * mm$^2$) [b] | | | | Percent of total signal | | |
|---|---|---|---|---|---|---|---|
| | 100 kD | 86 kD | 80 kD | Total | 100 kD | 86 kD | 80 kD |
| − | 17190 | 24858 | 61925 | 103973 | 16 | 24 | 60 |
| + | 42107 | 43147 | 6092 | 91346 | 46 | 47 | 7 |

[a] Human fetal lung fibroblasts (HFL-1) embedded in collagen gels were stimulated 90 hrs with TNFα. Cultures were supplemented with or without 3.3 µM Example 2 and with 30 nM elastase for the final 72 hrs and conditioned media were assessed for the MMP9 forms by Western blotting with mAb-L51/82.
[b] Chemiluminesence captured during a 150 s exposure was analyzed using a ChemiDoc imaging system (BioRad Laboratories) and Quantity One ® image software. Signals were measured within uniform sized boxes drawn to circumscribe the bands and were the product of the average intensity (INT) and the box area (mm$^2$). Values given have been corrected for background signal.

A second experiment was performed to determine if the 80 kD form was mature active MMP9 and to determine the potency of Example 2 as an inhibitor of MMP9 maturation in this assay. HFL-1 cells embedded in collagen gels were cultured as described above in the presence of TNFα overnight and the cultures were then adjusted to contain 30 nM elastase and graded concentrations of Example 2 for an additional 72 hrs at which time MMP9 secreted into the conditioned media was bound to gelatin-sepharose and evaluated by Western blot analysis for active MMP9 using pAb-1246 raised against the N-terminal neoepitope of active MMP9 (Table 5). In the absence of Example 2, pAb-1246 readily detected MMP9 with an electrophoretic mobility of approximately 80 kD. Example 2 effectively inhibited the ability of HFL-1 cultures to process proMMP9 to active MMP9. Inhibition occurred over a dose range with an IC$_{50}$ of approximately 0.3 µM Example 2.

TABLE 5

Example 2 blocked production of active
MMP9 by human fetal lung fibroblasts [a]

| Example 2, µM | Signal of 80 kD band (INT*mm$^2$) [b] | % Inhibition [c] |
|---|---|---|
| 0 | 168781 | 0 |
| 0.12 µM | 168211 | 0 |
| 0.37 µM | 45996 | 73 |
| 1.1 µM | 1747 | 99 |
| 3.3 µM | 152 | 100 |
| 10 µM | 0 | 100 |

[a] Human fetal lung fibroblasts (HFL-1) embedded in collagen gels were stimulated 90 hrs with TNFα. Cultures were supplemented with the indicated concentrations of Example 2 and 30 nM elastase for the final 72 hrs and conditioned media were assessed for active MMP9 by Western blotting with pAb-1246 developed against the N-terminal activation neoepitope.
[b] Chemiluminesence captured during a 10 s exposure was analyzed using a ChemiDoc imaging system (BioRad Laboratories) and Quantity One ® image software. Signals were measured within uniform sized boxes drawn to circumscribe the 80 kD bands and were the product of the average intensity (INT) and the box area (mm$^2$). Values given have been corrected for background signal.
[c] Percent signal reduction relative to the signal generated by HFL-1 cells cultured in the absence of Example 2.

In Vivo Studies
Expression and Activation of proMMP9 In Vivo is Associated with Rat SCW-Arthritis MMP9 protein expression was reportedly increased in the synovial fluid of patients with rheumatoid arthritis (Gruber, Sorbi et al. 1996). A preliminary study was performed to assess MMP9 expression and activation in a rat model of arthritis.

A polyarthritis can be induced in female Lewis rats following i.p. administration of streptococcal cell wall (SCW) proteoglycan-polysaccharides (PG-PS) (Cromartie, Craddock et al. 1977). The model has an acute phase (days 3-7) that is complement and neutrophil-dependent and that resolves. A chronic erosive phase begins at about day ten and is dependent on the development of specific T cell immunity to the PG-GS, which resists digestion and remains present in synovial macrophages for months. Like rheumatoid arthritis, SCW-induced arthritis is reduced by TNF inhibitors, and the dependence of SCW-induced arthritis on macrophages (Richards, Williams et al. 2001) and the strong association of rheumatoid arthritis severity with synovial-tissue macrophage counts (Haringman, Gerlag et al. 2005) makes SCW-arthritis an attractive model for testing potential therapeutic agents.

SCW PG-PS 10S (Beckton Dickinson Cat #210866) suspended in saline was vortexed for 30 seconds and sonicated for 3 min with a probe type sonicator prior to injection. Female Lewis (LEW/N) rats, 5-6 weeks of age (80-100 g) were injected (i.p.) with SCW PG-PS (15 μg of rhamnose/gram BW) in the lower left quadrant of the abdomen using a 1 mL syringe fitted with a 23-gauge needle. Control (disease-free) rats were treated in a similar manner with sterile saline. Control rats were sacrificed on day 5 and groups of SCW-injected rats were sacrificed on day 5 when acute inflammation was maximal or on day 18 when chronic inflammation was established.

Hind-limbs were skinned, severed just above the tibia-tarsus joint and below the metatarsals, and the tibia-tarsus joints (ankles) were weighed, snap frozen and pulverized on dry ice using a hammer and anvil. The pulverized tissue was suspended in 3 volumes (w:v) of ice-cold homogenization buffer containing 50 mM Tris pH 7.5, 150 mM NaCl, 5 mM EDTA, 1% Triton X100, 0.05% Brij 30, 10% dimethylsulfoxide and Complete EDTA-free Protease Inhibitor Cocktail (Roche Diagnostics). The suspended tissue was homogenized sequentially with a Kinematica AG Polytron and a Dounce homogenizer. Homogenates were centrifuged at 16,000×g for 10 min at 4° C. and the soluble fractions were saved. Dimethylsulfoxide was removed from a portion of each soluble fraction using PD MiniTrap™ G-25 desalting columns (GE Healthcare). Homogenates (0.25 mL), free of DMSO, were diluted with an equal volume of binding buffer (i.e., homogenization buffer without dimethylsufoxide) and adjusted to contain 50 μL of a 50% slurry of gelatin-conjugated sepharose. Following 2 hours of rotation at 4° C. the beads were washed twice in binding buffer and eluted in 100 μL 2×-reducing Laemmli buffer with heating to 95° C. for 5 minutes. Eluates (20 μL) were resolved on 4-12% NuPAGE gels, transferred to 0.45 μm pore-sized nitrocellose and immunoblotted for detection of proMMP9, active MMP9, and other processed forms using mAb-L51/82 and pAb-1246 as described above for detection of MMP9 forms in synoviocyte and HFL-1 cell conditioned media.

Figure 2:
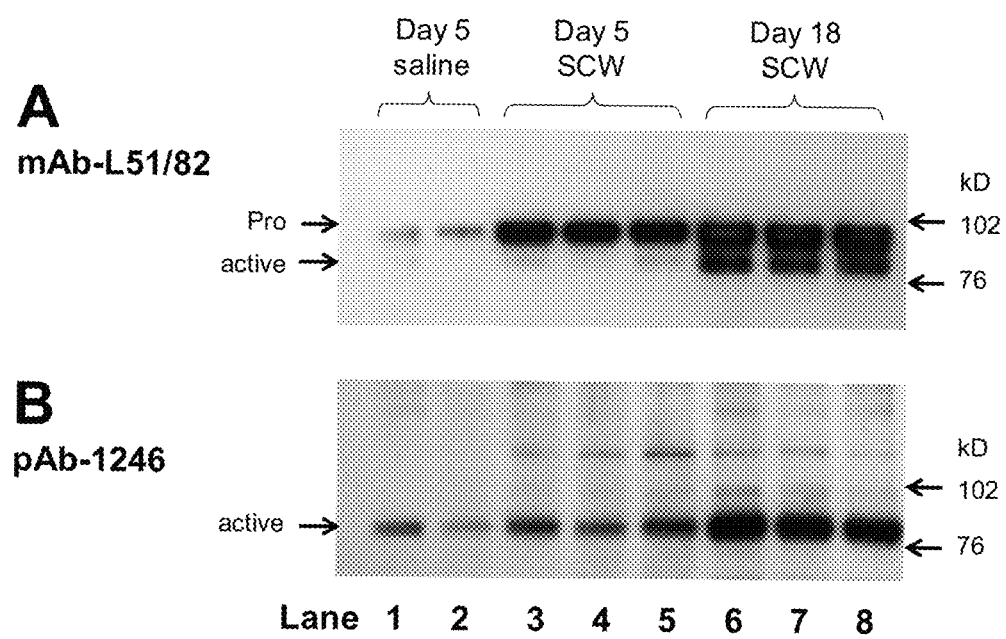
FIG. 2: Shown are western blots illustrating increased proMMP9 and increased active MMP9 in tibia-tarsus joints (ankles) from female Lewis rats after inducing arthritis with i.p. administration of Streptococcal cell wall peptidoglycan polysaccharides (SCW). In healthy ankles of rats administered saline, mAb-L51/82 detected small amounts of an approximately 100 kD proMMP9 and an approximately 80 kD form of active MMP9 (FIG. 2A, lanes 1 and 2). The amount of proMMP9 increased markedly in ankle homogenates 5 and 18 days after SCW-administration (FIG. 2A, lanes 3-5 and 6-8, respectively). The amount of active 80 kD MMP9 increased mildly 5 days after SCW-administration (FIG. 2A, lanes 3-5) and increased markedly 18 days after SCW-administration (FIG. 2A, lanes 6-8). In healthy ankles of rats administered saline, mAb-1246 detected small amounts active 80 kD MMP9 (FIG. 2B, lanes 1 and 2). The 80 kD active MMP9 increased mildly 5 days after SCW-administration (FIG. 2A, lanes 3-5) and increased markedly 18 days after SCW-administration (FIG. 2A, lanes 6-8).

In healthy ankles of rats administered saline, mAb-L51/82 detected small amounts of an approximately 100 kD (proMMP9) and an approximately 80 kD form of MMP9 (FIG. 2A, lanes 1 and 2). proMMP9 was increased markedly in ankle homogenates 5 and 18 days after SCW-administration (FIG. 2A, lanes 3-5 and 6-8, respectively). The 80 kD MMP9 was increased mildly 5 days after SCW-administration (FIG. 2A, lanes 3-5) and was increased markedly 18 days after SCW-administration (FIG. 2A, lanes 6-8). In healthy ankles of rats administered saline, mAb-1246 detected small amounts active MMP9 at 80 kD (FIG. 2B, lanes 1 and 2). The 80 kD active MMP9 was increased mildly 5 days after SCW-administration (FIG. 2A, lanes 3-5) and was increased markedly 18 days after SCW-administration (FIG. 2A, lanes 6-8). Efficacy of Example 2 in Rats with SCW Arthritis Having shown that active MMP9 is increased in rats with SCW-induced arthritis, we next sought to determine the ability of Example 2 to reduce disease severity and to reduce active MMP9.

Example 2 Reduced Ankle Swelling of Rats with SCW-Induced Arthritis.

To induce arthritis, Female Lewis (LEW/N) rats, 5-6 weeks of age (80-100 g) were injected (i.p.) with SCW PG-PS as described above. Eighteen days later, arthritis was well established. Calipers were used to measure the width (anterior to posterior surface) of the left and right hind ankles of each rat. Each ankle was measured 3 times and averaged, and treatment groups were randomized based on ankle thickness (Table 6). Commencing on day 18, randomized groups of arthritic rats (n=5 rats/group) received vehicle or 5, 20, or 50 mg/kg Example 2 BID by oral gavage. Vehicle consisted of an aqueous mixture containing 2% (v:v) N-methylpyrrolidone, 5% (v:v) glycerine, and 20% (w:v) captisol. Treatment continued daily through the morning of day 26.

By day 18 mean ankle thickness was increased an average of >4.4 mm compared to disease free rats. Rats treated with vehicle alone continued to gradually develop a more severe arthritis based on ankle thickness measurements over the eight-day treatment period (Table 6). Treatment with Example 2 induced a dose-dependent decrease in ankle thickness measurements. By day 26, the disease associated increase in ankle thickness had been reduced 27, 37, and 46 percent by 5, 20, and 50 mg/kg Example 2, respectively.

TABLE 6

Ankle thickness of rats with SCW-arthritis dosed with vehicle vs. Example 2

| Treatment | | Ankle thickness (mm)[a] | | Day 26 Δ mm (vs. group 1) | % Inh |
|---|---|---|---|---|---|
| | | Day 18 | Day 26 | | |
| Group 1: Sterile Saline Vehicle Day 18-26 | mean (n = 4) SD p-value[b] | 7.20 0.043 0.0000 | 7.26 0.012 0.0001 | 0 | 100 |
| Group 2: PG-PS (15 μg/gramBW) Vehicle Day 18-26 | mean (n = 5) SD p-value* | 11.86 0.77 na | 12.31 1.26 na | 5.04 | 0 |
| Group 3: PG-PS (15 μg/gramBW) Example 2 (5 mg/kg) Day 18-26 | mean (n = 5) SD p value* | 11.79 0.56 0.88 | 10.93 0.21 0.043 | 3.67 | 27 |
| Group 4: PG-PS (15 μg/gramBW) Example 2 (20 mg/kg) Day 18-26 | mean (n = 5) SD p-value* | 11.76 0.73 0.85 | 10.42 0.93 0.028 | 3.15 | 37 |
| Group 5: PG-PS (15 μg/gramBW) Example 2 (50 mg/kg) Day 18-26 | mean (n = 5) SD p-value* | 11.68 0.62 0.71 | 9.99 0.73 0.0075 | 2.73 | 46 |

[a]Calipers were used to measure the width (anterior to posterior surface) of the left and right hind ankles of each rat. Each ankle was measured 3 times and averaged.
[b]Student's t-test vs. group 2

Hind paw inflammation clinical scores were assigned based on swelling and erythema. By day 18, nearly all rats induced with SCW PG-PS had a clinical score of 8 based on an 8-point scale (Table 7). Treatment with Example 2 induced a dose dependent decrease in clinical score measurements with significant effects emerging at the 20 mg/kg dose (Table 7).

TABLE 7

Clinical Scores of rats with SCW-arthritis dosed with vehicle vs. Example 2

| Treatment | | Clinical Scores (0-8) [a] | | Δ Day 18 |
|---|---|---|---|---|
| | | Day 18 | Day 26 | vs. day 26 |
| Group 1: Sterile Saline Vehicle Day 18-26 | mean (n = 4) SD p-value [b] | 0 0 | 0 0 <0.0001 | 0 |
| Group 2: PG-PS (15 μg/gramBW) Vehicle Day 18-26 | mean (n = 5) SD p-value | 7.80 0.45 | 7.80 0.45 na | 0 |
| Group 3: PG-PS (15 μg/gramBW) Example 2 (5 mg/kg) Day 18-26 | mean (n = 5) SD p-value | 8.00 0.00 | 6.80 1.09 0.095 | −1.20 |
| Group 4: PG-PS (15 μg/gramBW) Example 2 (20 mg/kg) Day 18-26 | mean (n = 5) SD p-value | 8.00 0.00 | 5.20 1.79 0.014 | −2.80 |
| Group 5: PG-PS (15 μg/gramBW) Example 2 (50 mg/kg) Day 18-26 | mean (n = 5) SD p-value | 7.80 0.45 | 4.40 1.67 0.0023 | −3.40 |

[a] Hind paw inflammation clinical scores were assigned based on swelling and erythema as follows: 1 = ankle involvement only; 2 = involvement of ankle and proximal ½ of tarsal joint; 3 = involvement of the ankle and entire tarsal joint down to the metatarsal joints; and 4 = involvement of the entire paw including the digits. Scores of both hind-paws were summed for a maximal score of 8.
[b] Student's t-test vs. group 2

Figure 3:
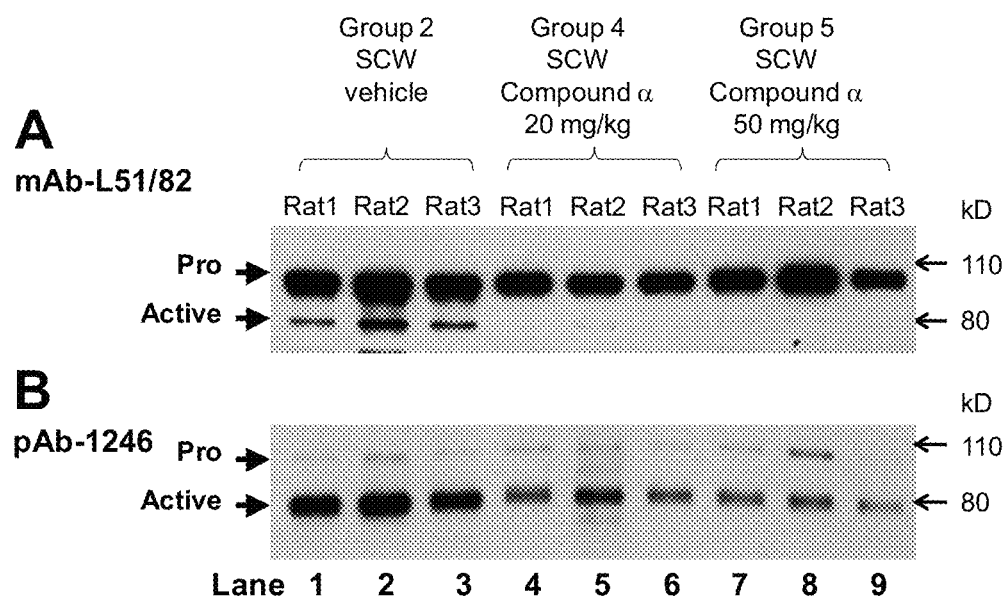
FIG. 3: Shown are western blots with two different antibodies illustrating the effects of a small-molecule allosteric processing inhibitor, Example 2, on the activation of proMMP9 in tibia-tarsus joints (ankles) from female Lewis rats after inducing arthritis with i.p. administration of Streptococcal cell wall peptidoglycan polysaccharides (SCW). Both proMMP9 and active MMP9 were abundantly present in ankles of SCW-induced vehicle-treated rats (FIGS. 3A and 3B, lanes 1-3). Treatment of rats with Example 2 did not reduce the abundance of proMMP-9 (FIG. 3A, lanes 4-9). However, treatment of rats with Example 2 resulted in a notable reduction in the active 80 kD form of MMP9 detected with pAb-1246 (FIG. 3B, lanes 4-9) and also with mAb-L51/82 (FIG. 3A, lanes 4-9).
Figure 4:
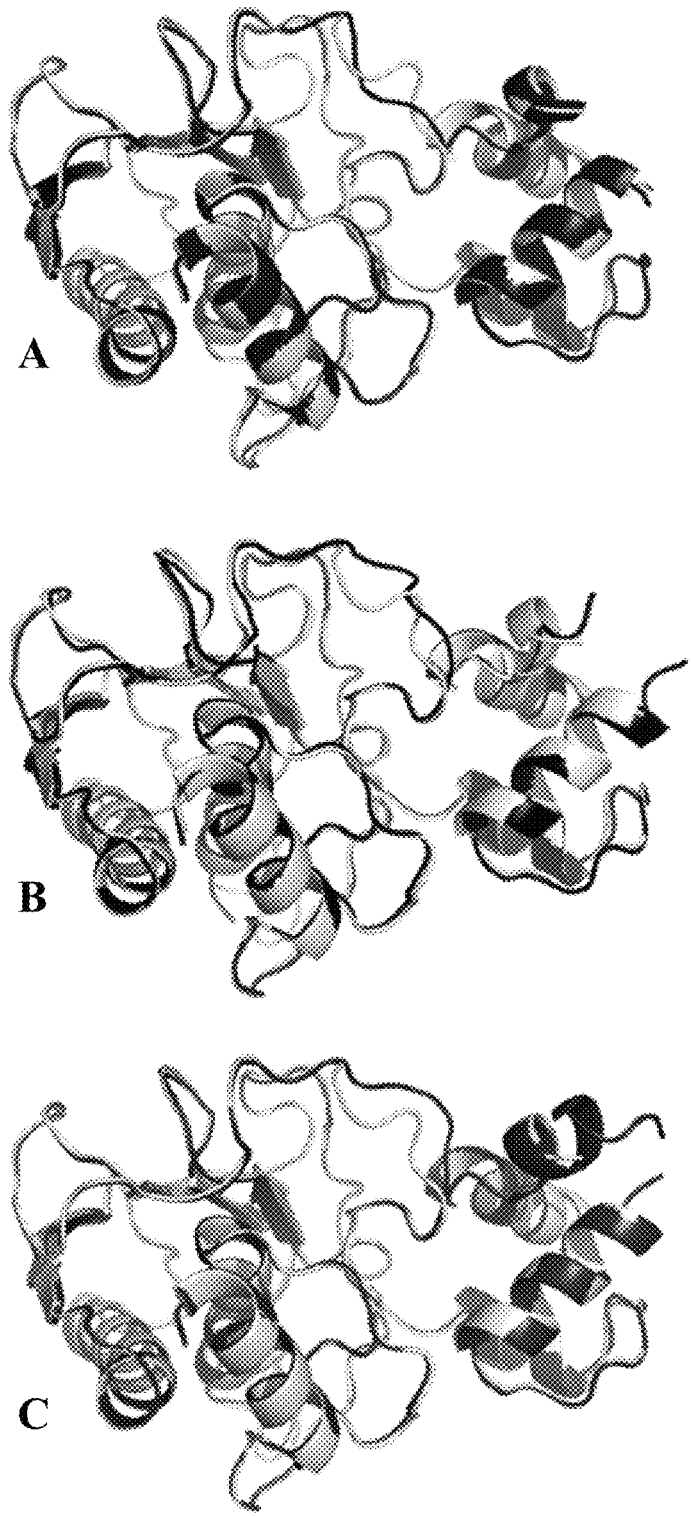
FIGS. 4 (A, B, and C): Shown are three separate superpositions of inhibited proMMP9 (dark structure) with apo proMMP9 (light structure). While the exact location of the displaced loop can vary with the different inhibitors, all of the inhibitors bind in the same pocket and prevent the cleavage of the bond to form an active enzyme. A is the proMMP9 complex with Example 2, B is the proMMP9 complex with Example 3, and C is the proMMP9 complex with Example 4.
Figure 5:
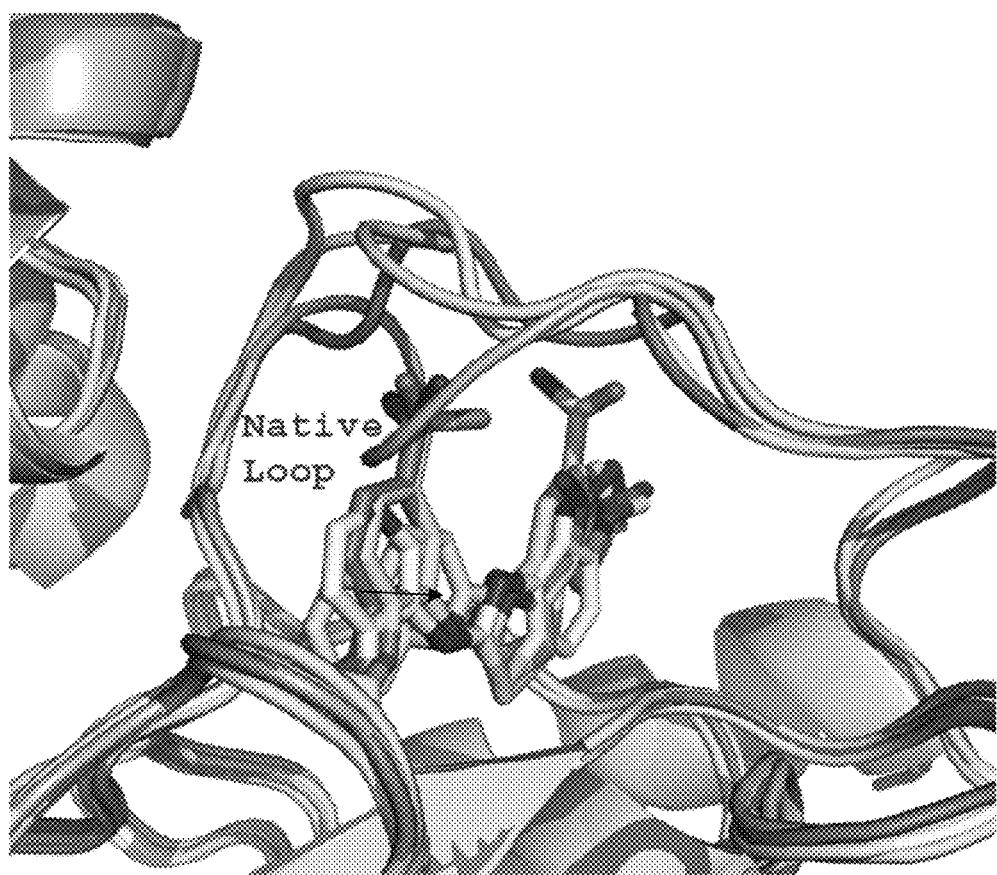
FIG. 5: Shown are the superpositions of the structures for inhibited proMMP9 with apo proMMP9 (marked structure). The structures are shown as ribbon cartoons with the inhibitors shown as ball and stick figures. While the exact location of the displaced loop can vary with the different inhibitors, all of the inhibitors bind in the same pocket and prevent the cleavage of the bond to form an active enzyme. The inhibitors shown are Example 2, Example 3, and Example 4.
Figure 6:
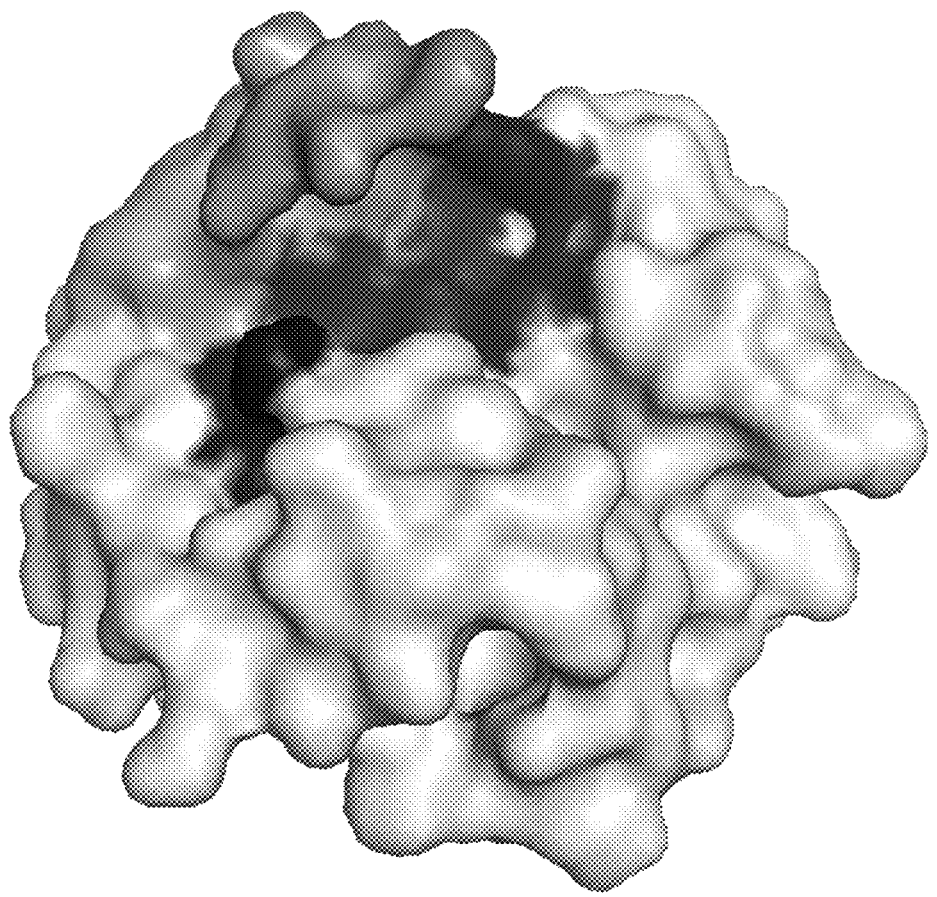
FIG. 6: Shown is the accessible surface of the proMMP9 structure. The surface of contact for the residues in the catalytic domain are colored a dark gray and the contact surface from the residues of the pro domain are colored a medium gray.

Example 2 Reduced Active MMP9 in Ankles of Rats with SCW-Induced Arthritis Demonstrated by Western Blot Analysis Rats in the study reported in Tables 6 and 7 were sacrificed on day 26 four hours after the AM dose Ankles harvested from the right-hind-limbs were processed by the method described above. Pro and active MMP9 were abundantly present in ankles of SCW-induced vehicle-treated rats (FIGS. 3A and 3B, lanes 1-3). Treatment of rats with Example 2 did not reduce the abundance of proMMP9 (FIG. 3A, lanes 4-9). However, treatment of rats with Example 2 resulted in a notable reduction in the active 80 kD form of MMP9 detected with pAb-1246 (FIG. 3B, lanes 4-9 vs. 1-3) and with mAb-L51/82 (FIG. 3A, lanes 4-9 vs. 1-3).

Example 2 Reduced MMP9 Mediated Gelatinase Activity in the Livers of Rats with SCW Arthritis In situ zymography provides an alternative approach to assess active MMP9 in tissues (Frederiks and Mook 2004). Tissue sections are overlain with fluorescein-conjugated gelatin wherein the conjugation is sufficiently dense to cause the fluorescein to be dye-quenched (DQ). Proteolytic degradation of the DQ-gelatin releases the fluorescein from the quenching effect giving rise to bright green fluorescence at the site of degradation. Because in situ zymography requires the use of frozen sections, calcified tissues are problematic. However, an additional feature of the SCW arthritis model is the development of hepatic granulomatous disease (Wahl, Allen et al. 1986), and MMP9 reportedly plays a role in macrophage recruitment in the granulomas response to mycobacteria (Taylor, Hattle et al. 2006). Consequently, granulomatous livers from SCW-treated rats were assessed for active MMP9 by in situ zymography.

As described above, Female Lewis (LEW/N) rats, 5-6 weeks of age (80-100 g) were injected (i.p.) with saline or SCW PG-PS. On day 28, when the granulomatous response was well established, animals were sacrificed and livers were frozen in OCT cryo-sectioning medium and 10 μm sections were cut on a Cryome HM 500 M cryotome and mounted on glass microscope slides. Sections were air dried briefly. MMP9 was confirmed as the source of the gelatinase activity in the liver by treating liver sections with monoclonal antibodies directed against the active site of the two major gelatinases MMP9 and MMP2. Liver sections overlain with 50 μL of 100 μg/mL neutralizing mouse monoclonal antibodies directed against MMP9 (Calbiochem, clone 6-6B), or MMP2 (Millipore, clone CA-4001), or with PBS for 1 hr at room temperature. Tissues were rinsed once with PBS, blotted, and briefly air dried and then overlain with DQ-gelatin (Invitrogen) dissolved to 1 mg/mL in deionized water and then diluted 1:10 in 1% wt/vol low gelling point agarose type VII (Sigma) in PBS. The sections were covered with coverslips, incubated in the dark at room temperature for 20 min, and imaged on an Olympus IX80 inverted microscope fitted with fluorescence optics, using SlideBook™ imaging software (Intelligent Imaging Innovations, Inc., Philadelphia, Pa.; version 5.0). Fluorescence intensity was determined (Table 8). When compared to a saline-treated rat, gelatinase activity was abundantly expressed in granulomatous liver sections obtained from a rat with SCW arthritis. The activity in the granulomatous liver sections was almost completely inhibited by treatment with anti-MMP9 monoclonal antibody but not by treatment with anti-MMP2 monoclonal antibody.

TABLE 8

Indentification of MMP9 as the gelatinase responsible for signals detected by in situ zymography in SCW-granulomatous livers

| Disease induction | Section treatment | Intensity (RLU × 10$^6$) | |
|---|---|---|---|
| | | Mean | SD |
| Saline-healthy | PBS | 11.4 | 2.91 |
| SCW-granulomatous | PBS | 109 | 19.4 |
| | Anti-MMP9 | 1.04 | 0.19 |
| | Anti-MMP2 | 128 | 36.2 |

Key: RLU = relative light units; SCW = Streptococcal cell wall peptidoglycan-polysaccharide equivalent to 15 μg rhamnose/gram BW.

Next, liver in situ zymography was used to assess the relative presence of active MMP9 in rats dosed with vehicle vs. Example 2. Female Lewis (LEW/N) rats, 5-6 weeks of age (80-100 g) were injected (i.p.) with saline or SCW PG-PS. Commencing on day 25, randomized groups of rats (n=3 rats/group) received vehicle or 20 or 50 mg/kg Example 2 BID by oral gavage. Vehicle consisted of an aqueous mixture containing 2% (v:v) N-methylpyrrolidone, 5% (v:v) glycerine, and 20% (w:v) captisol. Treatment continued daily through the morning of day 28. Four hrs after the AM dose on day 28, rats were sacrificed and livers assessed for active MMP9 by in situ zymography (Table 9). Gelatinase activity was increased markedly in SCW-induced rats, but activity was reduced by approximately 80% in animals treated with 50 mg/kg Example 2.

TABLE 9

In situ zymography determination of gelatinase activity in livers of SCW-induced rats dosed with vehicle vs. Example 2

| Treatment | Intensity (RLU × 10⁶) | | | | | t-test vs. SCW-vehicle |
|---|---|---|---|---|---|---|
| | Rat 1 | Rat 2 | Rat 3 | Mean | SD | |
| Saline Vehicle Day 25-28 | 3.3 | 1.1 | 1.6 | 2.0 | 1.14 | 0.001 |
| SCW Vehicle Day 25-28 | 65.1 | 43.4 | 58.9 | 55.8 | 11.20 | 1 |
| SCW Example 2 (20 mg/kg) Day 25-28 | 43.0 | 69.0 | 53.7 | 55.2 | 13.09 | 0.96 |
| SCW Example 2 (50 mg/kg) Day 25-28 | 3.2 | 25.6 | 4.5 | 11.1 | 12.57 | 0.010 |

Key:
RLU = relative light units;
SCW = Streptococcal cell wall peptidoglycan-polysaccharide equivalent to 15 µg rhamnose/gram BW.

Crystallization and Data Collection

Crystals of apo proMMP9(29-444 ΔFnII) (SEQ ID NO:4) were grown by adding 1 microliter of protein to 1 microliter of a solution containing: 25% PEG 8K, 1% glycerol, 0.2 M Ammonium Sulfate, and 100 mM Sodium Cacodylate, pH 5.5. A cryoprotectant solution was prepared by the addition of 20% glycerol to a stabilizing solution. X-ray data of the apo proMMP9(29-444 ΔFnII) (SEQ ID NO:4) crystals were collected at ESRF beamline ID23 via the MXpress service. Crystals diffracted to 1.7 Å. Crystals formed in a space group C2 with unit cell dimensions: a=90.3 Å b=73.2 Å c=77.5 Å, β=106.3. The structure was solved by molecular replacement methods with the program EPMR (Kissinger, Gehlhaar et al. 1999) using the previously published proMMP9 structure as the search molecule for the proMMP9(29-444 ΔFnII) structure. Two molecules of proMMP9(29-444 ΔFnII) (SEQ ID NO:4) were found in the asymmetric unit. The data were refined with the program CNX. The R-factor was 20.9 R-free 23.2. The overall fold of the protein was very similar to published structure. The first residue visible in electron density at the N-terminus was Asp 41. N-terminal sequencing of crystals of the proMMP9(29-444 ΔFnII) (SEQ ID NO:4) protein showed that the N-terminal residue of the material that crystallized was Leu 35, which indicated that the proMMP9(29-444 ΔFn) (SEQ ID NO:4) protein was further processed at the N-terminus during expression, purification, or crystallization of the protein. Mass spectrometry of the purified protein confirmed that additional processing of the N-terminus had occurred during expression or purification. Thus the crystallized form of proMMP9 was actually proMMP9(35-444 ΔFnII) (SEQ ID NO:12).

Cocrystallization trials with Example 1 did not produce crystals. A data set derived from a 24 hour soak to produce a complex of apo proMMP9(35-444 ΔFnII) (SEQ ID NO:12) crystals with Example 1 (1 mM in 5% DMSO) was collected at the IMCA-CAT beamline at the Advanced Photon Source in Chicago. The crystal diffracted to 2.9 Å resolution. The data were refined with the program CNX. The structure has R-factor of 30.0 and R-free of 34.8. Initial electron density maps indicated the presence of inhibitor and a reordering of residues near Phe 107 in one molecule of the asymmetric unit. The changes in the protein were focused around residue 107 and did not propagate through the molecule (including the zinc binding sites).

Data sets were also collected for a number of other compounds that were soaked for 24 hours to produce complexes with proMMP9(35-444 ΔFnII) (SEQ ID NO:12). Data were collected with a Rigaku 007 HF generator and a Saturn 94 CCD detector. Data were processed with the d*trek program (Pflugrath 1999) and refined with the program Phenix(Adams, Grosse-Kunstleve et al. 2002). Relevant data collection statistics for selected data sets are found in Table 10. The programs Coot(Emsley and Cowtan 2004), Pymol (DeLano Scientific), and Quanta (Accelerys) were used for inspection of the electron density maps. Figures were generated with Pymol and Moe (Schrodinger).

TABLE 10

X-ray data collection and refinement statistics for apo and complexed proMMP9(35-444 ΔFnII) (SEQ ID NO: 12)

| | apo | Example 1 |
|---|---|---|
| Space Group | C2 | C2 |
| Unit Cell Parameters | | |
| a (Å) | 90.3 | 91.7 |
| b (Å) | 73.2 | 73.7 |
| c (Å) | 77.5 | 79.4 |
| β (°) | 106.3 | 105.4 |
| Resolution Range (Å) | 49-1.7 | 38-2.7 |
| % Complete | 98.1 (97.2) | 99.7 (100) |
| R-sym | 0.048 (0.181) | 0.112 (0.325) |
| Redundancy | 3.2 | 3.6 |
| Rfact/Rfree | 20.9/23.2 | 27.9/34.9 |
| Rmsd from ideal bond length (Å) | 0.0034 | 0.0088 |
| Rmsd from ideal bond angle (°) | 0.77 | 1.1 |

| | Example 2 | Example 3 | Example 4 |
|---|---|---|---|
| Space Group | C2 | C2 | C2 |
| Unit Cell Parameters | | | |
| a (Å) | 90.7 | 91.0 | 90.0 |
| b (Å) | 73.0 | 73.6 | 77.1 |
| c (Å) | 78.2 | 78.0 | 75.0 |
| β (°) | 104.6 | 106.0 | 102.1 |
| Resolution Range (Å) | 29-2.0 | 49-2.6 | 29-2.8 |
| % Complete | 90.1 (78.2) | 94.8 (92) | 91.5 (84.5) |
| R-sym | 0.060 (0.226) | 0.112 (0.325) | 0.081 (0.301) |
| Redundancy | 2.1 | 3.6 | 3.1 |
| Rfact/Rfree | 25.0/30.1 | 27.6/35.6 | 21.9/29.1 |
| Rmsd from ideal bond length (Å) | 0.008 | 0.007 | 0.0077 |
| Rmsd from ideal bond angle (°) | 1.3 | 1.1 | 0.87 |

X-ray Structure Discussion

The apo form of proMMP9(35-444 ΔFnII) (SEQ ID NO:12) was initially crystallized. The apo structure was determined at a much higher resolution (1.7 Å versus 2.5 Å) compared to the previously published proMMP9 structure that included the FnII domains (Elkins, Ho et al. 2002), but the structure of proMMP9(35-444 ΔFnII) (SEQ ID NO:12) was essentially identical for residues present in the form of the protein that included the FnII domains. Thus removal of FnII domains in the proMMP9(35-444 ΔFnII) (SEQ ID NO:12) structure did not alter the overall structure of the catalytic domain compared to the previously published full length structure. In particular, the backbone atoms of residues surrounding the residue Phe 107 cleavage site are in similar positions in the proMMP9(35-444 ΔFnII) (SEQ ID NO:12) structure and the previously published proMMP9 structure that included the FnII domains.

Binding of Example 1

The binding of Example 1 requires the reorientation of several residues in the pro region of proMMP9(35-444 ΔFnII) (SEQ ID NO:12). The phenoxy moiety of the inhibitor binds in a region of space that was occupied by Phe 107 in the apo protein. This location is 6 Å away from the structural zinc. Cys 99 blocks the area between the compound and the zinc, so that there is no direct access to the zinc from Example 1. No hydrogen bond is observed for the phenoxy oxygen, which suggests that the role of this group may be more important in altering the electronics of the aromatic ring than in a specific hydrogen bonding interaction. The residues that are in the vicinity of the phenoxy group include: Val 101, Pro 102, Tyr 179, H is 190 (coordinated to the structural zinc), and Phe 192. The inner thiazole ring of Example 1 is located near residues Phe 110 from the pro domain and His 405 (coordinated to the catalytic zinc). A 2.8 Å distance was observed between the thiazole sulfur and the backbone carbonyl of Ala 191. In the proMMP9(35-444 ΔFnII) (SEQ ID NO:12) structure in the absence of inhibitor, five solvent molecules occupy the space occupied by the two thiazole rings in the Example 1 structure. The terminal methyl thiazole ring is located near residues Leu 114 and Asp 410. Interestingly, the acetamide group is located in the same position as the guanidino group of Arg 108 in the apo proMMP9(35-444 ΔFnII) (SEQ ID NO:12) structure.

The interactions of Cys 99 (the cysteine switch) remain consistent between inhibited and uninhibited proMMP9(35-444 ΔFnII) (SEQ ID NO:12). There were no differences in the zinc coordination of either the catalytic or structural zinc ions. Indeed, the reorientations were concentrated in the region between residues 103 and 108.

Binding of Example 2

The binding of Example 2 requires the reorientation of several residues in the pro region of proMMP9(35-444 ΔFnII) (SEQ ID NO:12). The 1-methylethoxy-benzenesulfonamide moiety of the inhibitor binds in a region of space that was occupied by Phe 107 in the apo protein. This location is 6 Å away from the structural zinc. Cys 99 blocks the area between the compound and the zinc, so that there is no direct access to the zinc from Example 2. A hydrogen bonds is observed between the aniline NH and the carbonyl oxygen of Ala 191 in the protein. The sulphonamide also makes hydrogen bonds to the protein. The nitrogen bonds to the NH of Gly 105 and one of the oxygens forms bonds with the amide nitrogens of Phe 107 and Gln 108. The residues that are in the vicinity of the 1-methylethoxy-benzenesulfonamide group include: Gly 100, Val 101, Pro 102, Leu 104, Gly 105, Arg 106, Phe 107, Gln 108, Phe 110, Tyr 179, His 190 (coordinated to the structural zinc), Ala 191 and Phe 192. The inner thiazole ring of Example 2 is located near residues Pro 192 and His 405 (coordinated to the catalytic zinc). The outer thiazole ring of Example 2 is located near residues Arg 106, Leu 114 and Asp 410. These two thiazole rings make no direct hydrogen bonds with the protein.

Binding of Example 3

The binding of Example 3 requires the reorientation of several residues in the pro region of proMMP9(35-444 ΔFnII) (SEQ ID NO:12). The methoxybenzenamide moiety of the inhibitor binds in a region of space that was occupied by Phe 107 in the apo protein. This location is 6 Å away from the structural zinc. Cys 99 blocks the area between the compound and the zinc, so that there is no direct access to the zinc from Example 2. Hydrogen bonds are observed between the aniline NH and the carbonyl oxygen of Ala 191 in the protein. The amide also makes hydrogen bonds to the protein. The nitrogen bonds to the NH of Gly 105 and one of the oxygens forms bonds with the amide nitrogens of Phe 107 and Gln 108. The residues that are in the vicinity of the methoxybenzenamide group include: Gly 100, Val 101, Pro 102, Leu 104, Gly 105, Arg 106, Phe 107, Gln 108, Phe 110, Tyr 179, His 190 (coordinated to the structural zinc), Ala 191 and Phe 192. The inner thiazole ring of Example 3 is located near residues Pro 192 and His 405 (coordinated to the catalytic zinc). The outer thiazole ring of Example 2 is located near residues Arg 106, Leu 114 and Asp 410. These two thiazole rings make no direct hydrogen bonds with the protein.

Binding of Example 4

The binding of Example 4 requires the reorientation of several residues in the pro region of proMMP9(35-444 ΔFnII) (SEQ ID NO:12). The methoxy-pyridine moiety of the inhibitor binds in a region of space that was occupied by Phe 107 in the apo protein. This location is 6 Å away from the structural zinc. Cys 99 blocks the area between the compound and the zinc, so that there is no direct access to the zinc from Example 2. A hydrogen bond is observed between the aniline NH and the carbonyl oxygen of Ala 191 in the protein. The residues that are in the vicinity of the methoxy-pyridine group include: Val 101, Pro 102, Arg 106, Gln 108, Phe 110, Tyr 179, His 190 (coordinated to the structural zinc), Ala 191 and Phe 192. The methyl-imidazo-benzothiazole ring of Example 4 is located near residues Arg 106, Leu 114, Pro 192, His 405 (coordinated to the catalytic zinc) and Asp 410. This fused ring makes no direct hydrogen bonds with the protein.

A soak of any of the above compounds proved successful in showing electron density consistent with compound binding. The loop containing residues 103-108 reorganizes to accommodate compound binding. Sometimes the loop makes direct hydrogen bonds with the compound further stabilizing the interaction. The exact orientation of this loop is seen to vary in the complexes with the various compounds. In the case of Example 1, this loop remained disordered. Electron density for the entire loop was observed in the structures for Example 2, Example 3, and Example 4. The position of the displaced Phe 107 and the Arg 106 that make up the scissile bond cleaved to form the active enzyme is seen to vary dramatically between compound bound structures. The general effect is however to keep these residues from being cleaved.

As mentioned above, the phenoxy group binds in a pocket that is occupied by Phe 107 in the apo proMMP9(35-444 ΔFnII) (SEQ ID NO:12) structure. In essence, the aromatic ring of the inhibitor replaces the aromatic ring of the phenylalanine residue. In the mature enzyme, the pocket is occupied by Phe 110. In the structure of proMMP1, the residues of the cleavage site are disordered, however, a HEPES molecule is found to bind in the same region as these inhibitors.

Although proMMP9 can be activated by several different proteases, the compounds presented here must function by making proMMP9 a less optimal substrate. Data has shown that the compounds do not inhibit the catalytic activity of MMP3 or MMP9. It is possible that the compounds function by limiting the mobility of residues near the cleavage site. If these residues are stabilized in a conformation that does not allow proMMP9 to be a productive substrate, it would lead to inhibition of the activation. As mentioned earlier, Phe 110 occupies this location in the catalytically active protein. The binding of compound at this site may prevent Phe 110 from moving into this location which could be required for catalysis and activation. In addition to motion of Phe 107, in some structures Arg 106 is in a different environment and Asp 410 rotates to form a bidentate interaction with the side-chain of Arg 106. This salt bridge may serve to lock proMMP9 in a conformation that is not able serve as a productive substrate.

Allosteric Binding Site

The core of the allosteric binding site of proMMP9 is comprised of amino acid residues 100-102, 110, 114, 177-179, 190-193, and 405-410, numbering taken from full-length human matrix metalloproteinase-9 precursor, proMMP9(1-707) (SEQ ID NO:1). This site forms the binding surface that the key residue phenylalanine (Phe) 107 occupies in the "native" proenzyme. The allosteric processing inhibitors bind in this site and also interact with the displaced loop (residue 104-108) which forms the flap of the binding site. This loop is flexible and has a number of different conformations that can make contact and interact with the inhibitors. These interactions with the loop are inhibitor specific.

Selectivity

The selectivity of these compounds for all other MMPs is yet to be determined, but it is very likely that the compounds will have much better specificity than previous MMP inhibitors that bound in the active sites of the catalytically active enzymes. Structurally, the binding of these compounds requires the dramatic movement of several residues and the sequence identity of the pro domains of MMPs at the final cleavage site is significantly less than at the active site. Given the historic difficulty in producing selective MMP inhibitors that display favorable pharmacokinetic properties, it is a significant finding to identify compounds that inhibit the activation of a proMMP.

Modeling and Other MMPs

This method of inhibition should be transferable to other MMPs based on sequence alignment of the MMPs and modeling suggesting that other proMMPs could rearrange in a similar fashion to accommodate binding of activation inhibitors. The overall secondary structure of the pro region is conserved in the proMMPs. The tertiary structure for the pro domains is a four helical bundle in the determined structures and predicted to have the same fold from the sequences for the remaining MMPs. In addition, the proMMPs have a similar pocket for the binding of the cysteine switch and while there are a variety of residues that fill the cavity in the catalytic domain the general mode of stabilization will remain the same.

Figure 7:
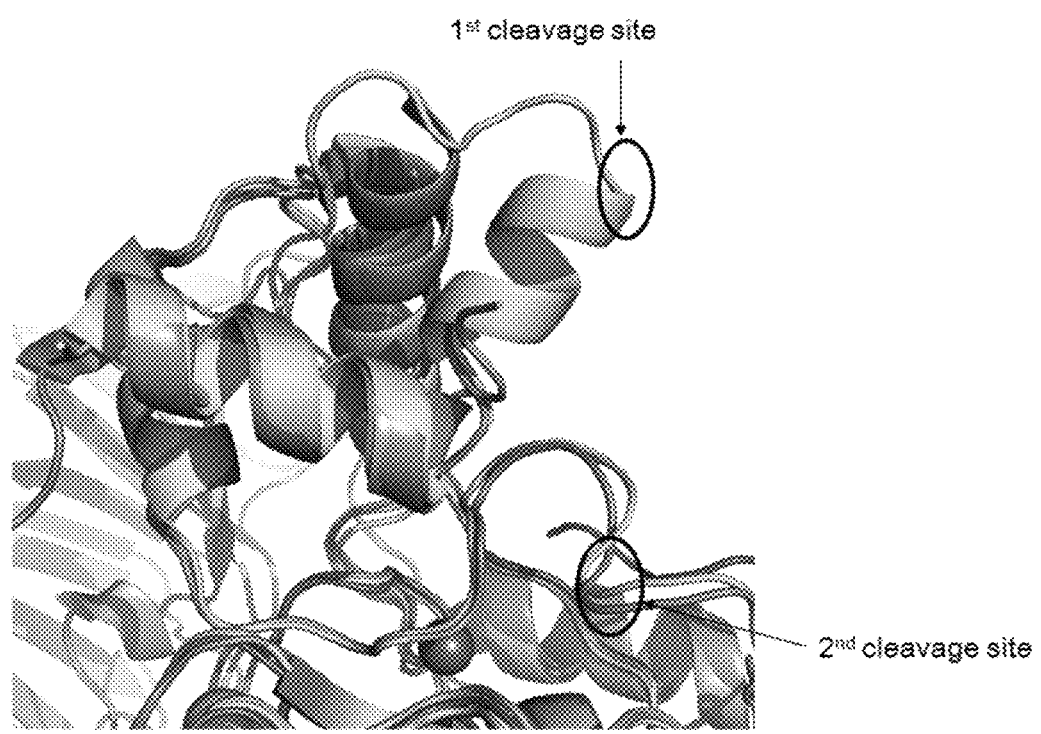
FIG. 7: Shown is the structural overlap of the proMMP structures that have been determined. The overlap demonstrates that a similar tertiary structure exists for other MMP pro domains with the final cleavage site for activation in contact with the catalytic domain.
Figure 8:
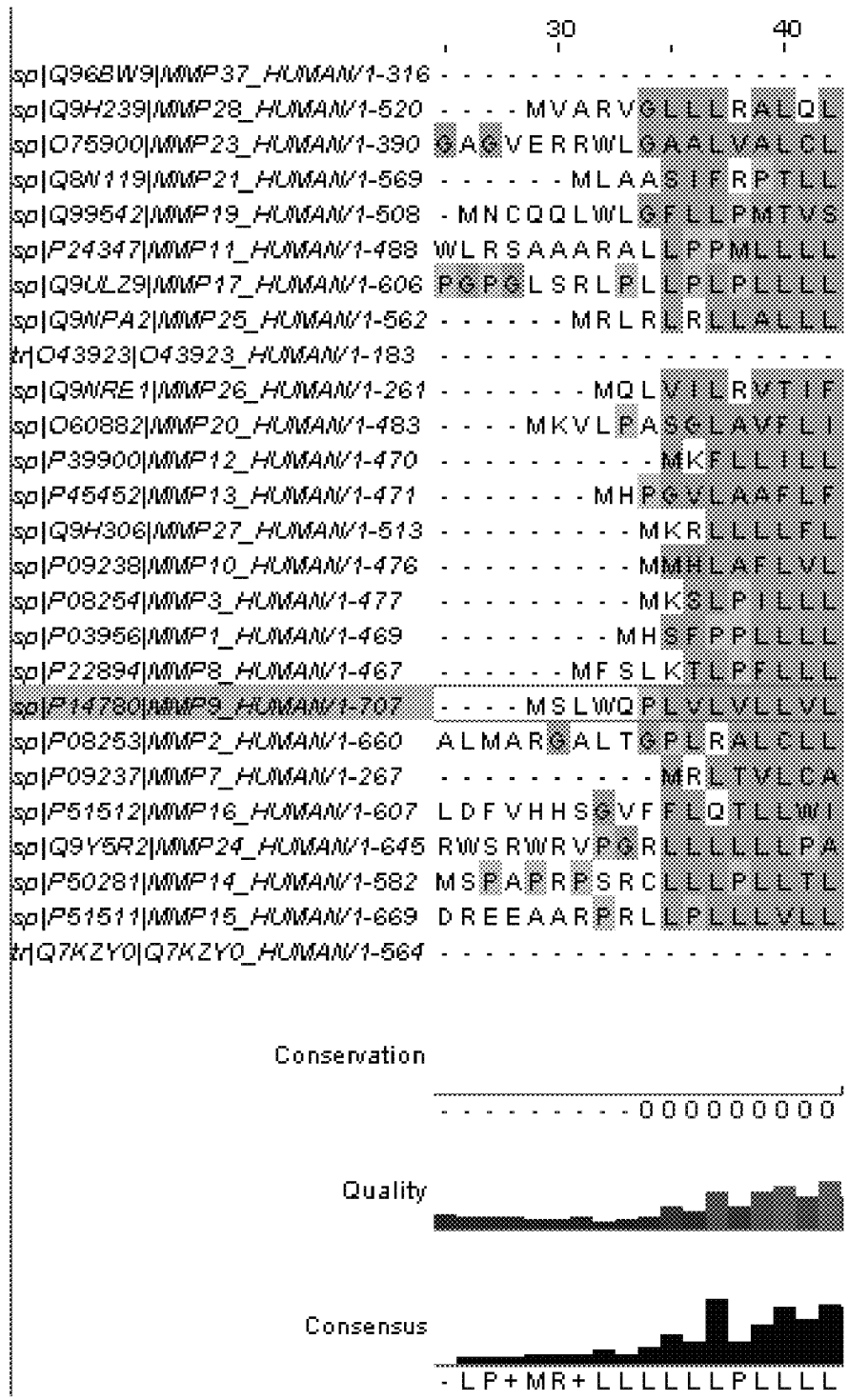
FIG. 8: Shown is the sequence alignment of the pro domains for the human MMP family. The tertiary structure for these domains is a four helical bundle in the determined structures and predicted to have the same fold from the sequence for the remaining MMPs. While there are a variety of residues that fill the cavity in the catalytic domain the general mode of stabilization will remain the same.
Figure 8:
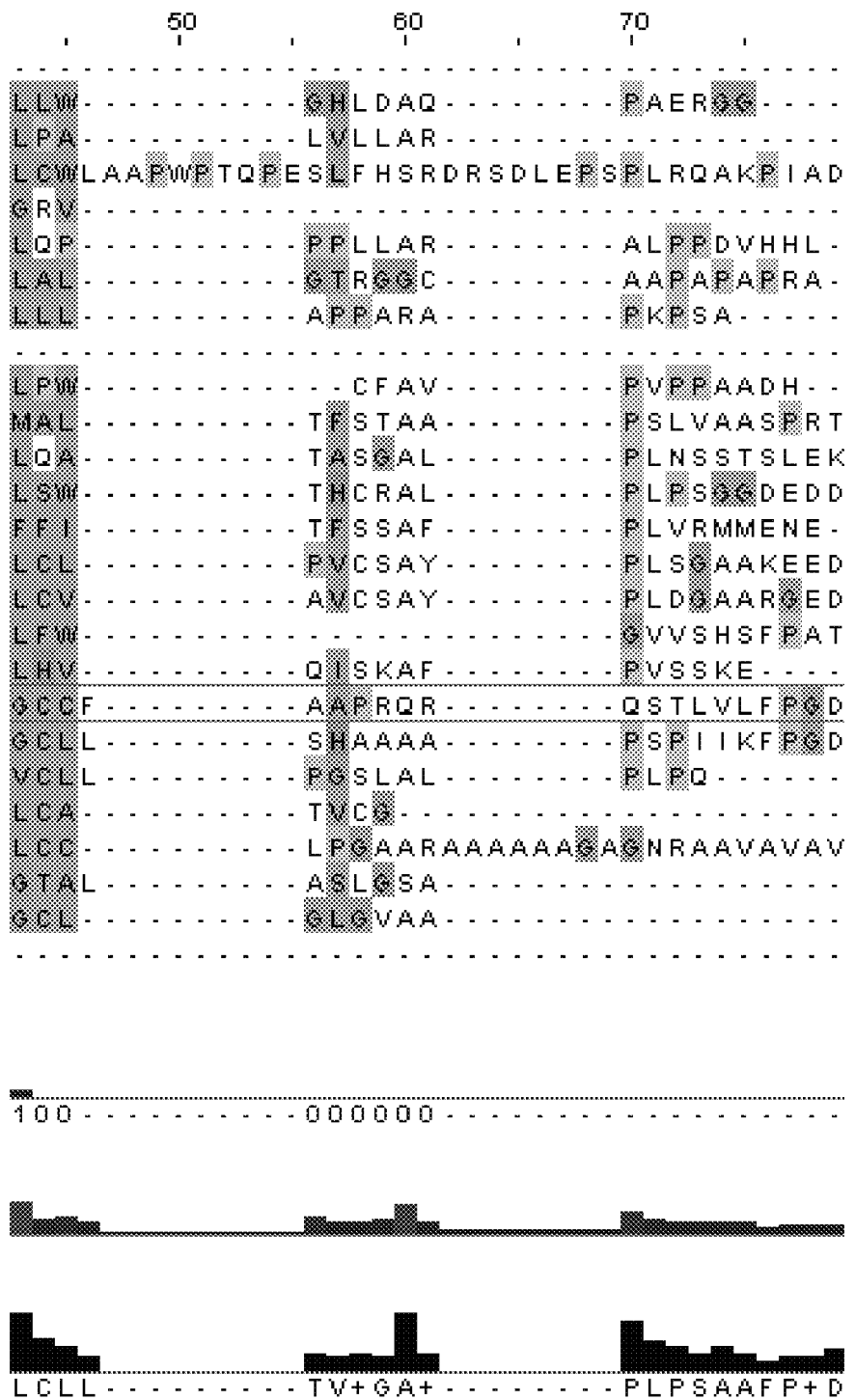
Figure 8:
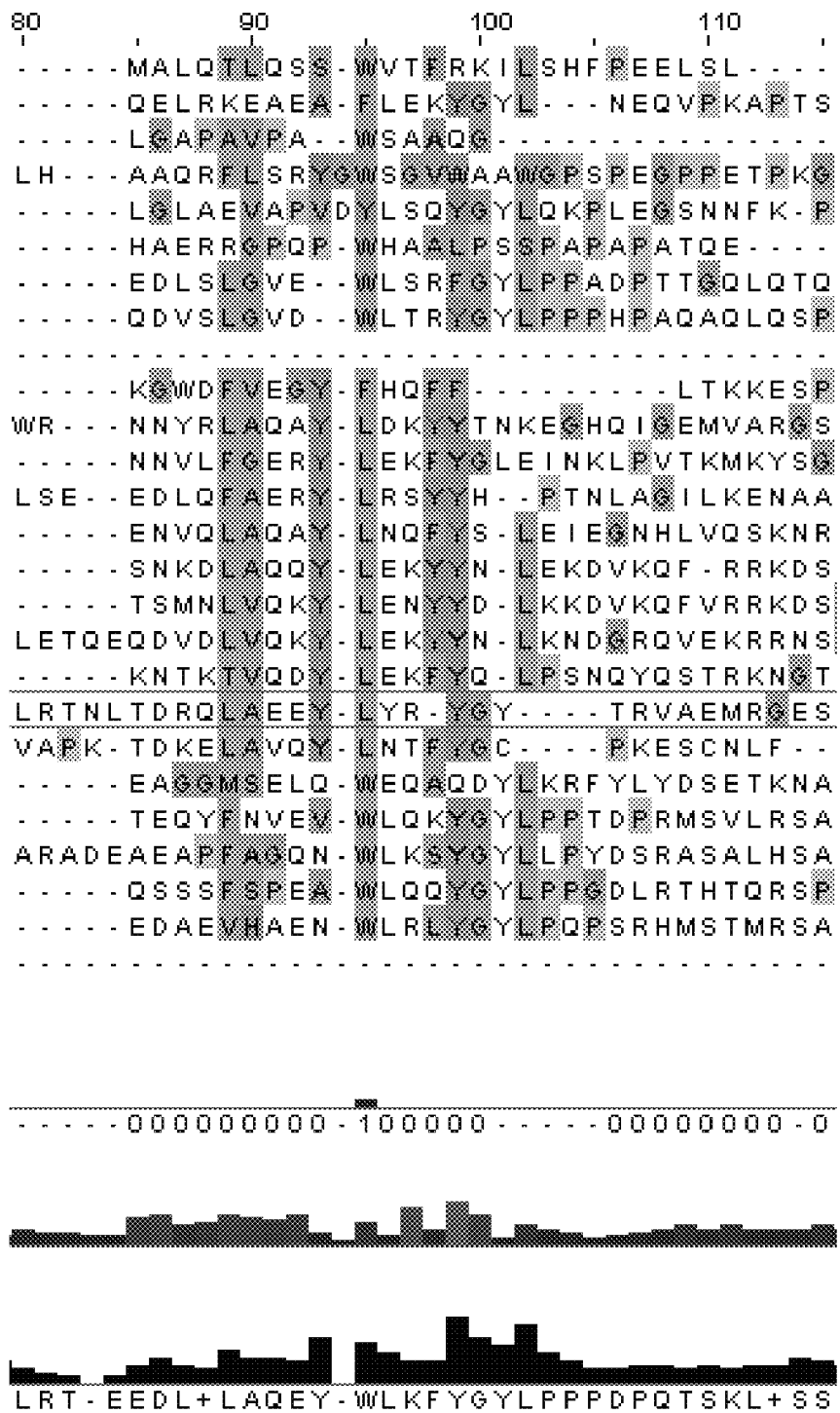
Figure 8:
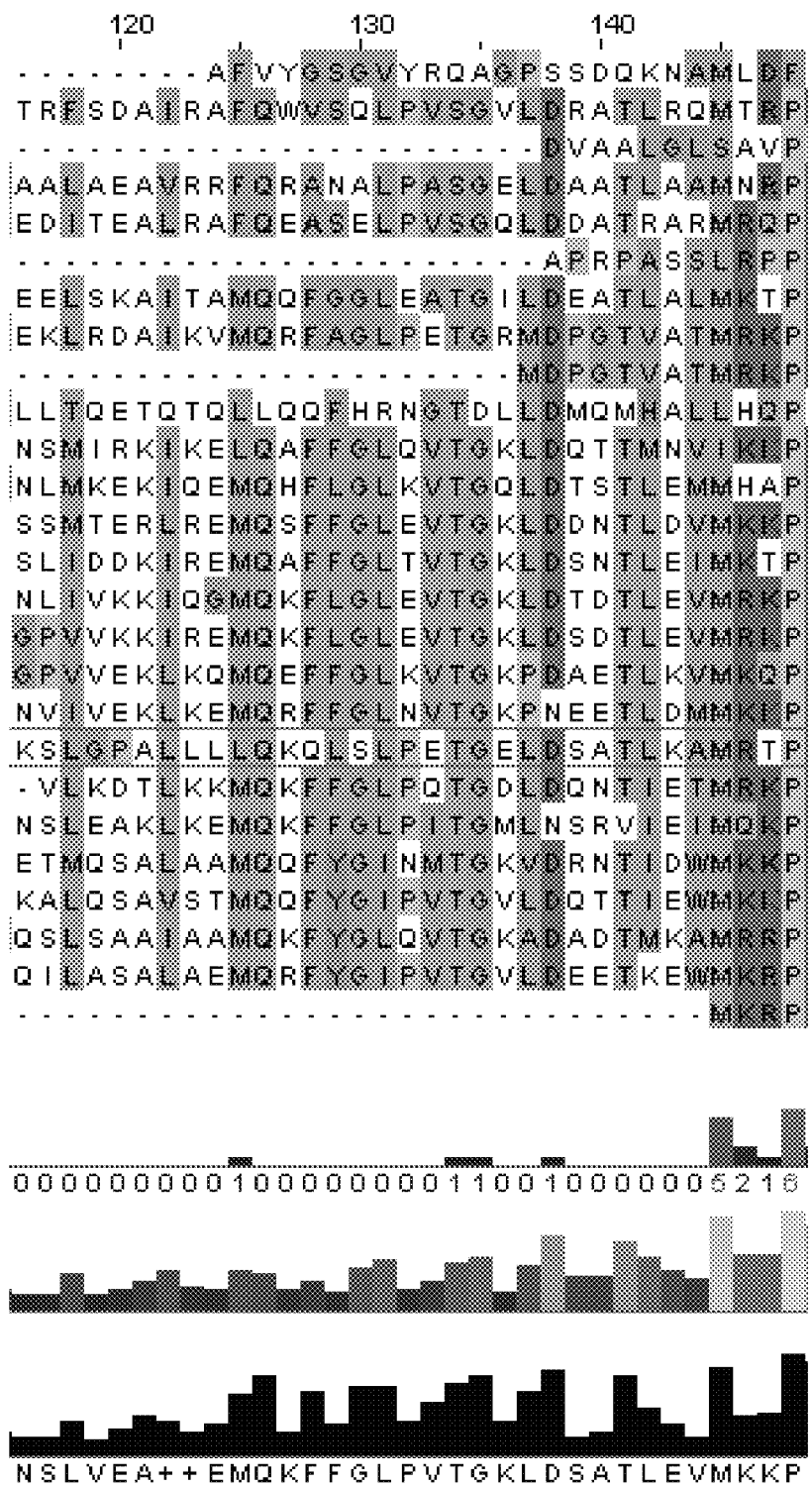
Figure 8:
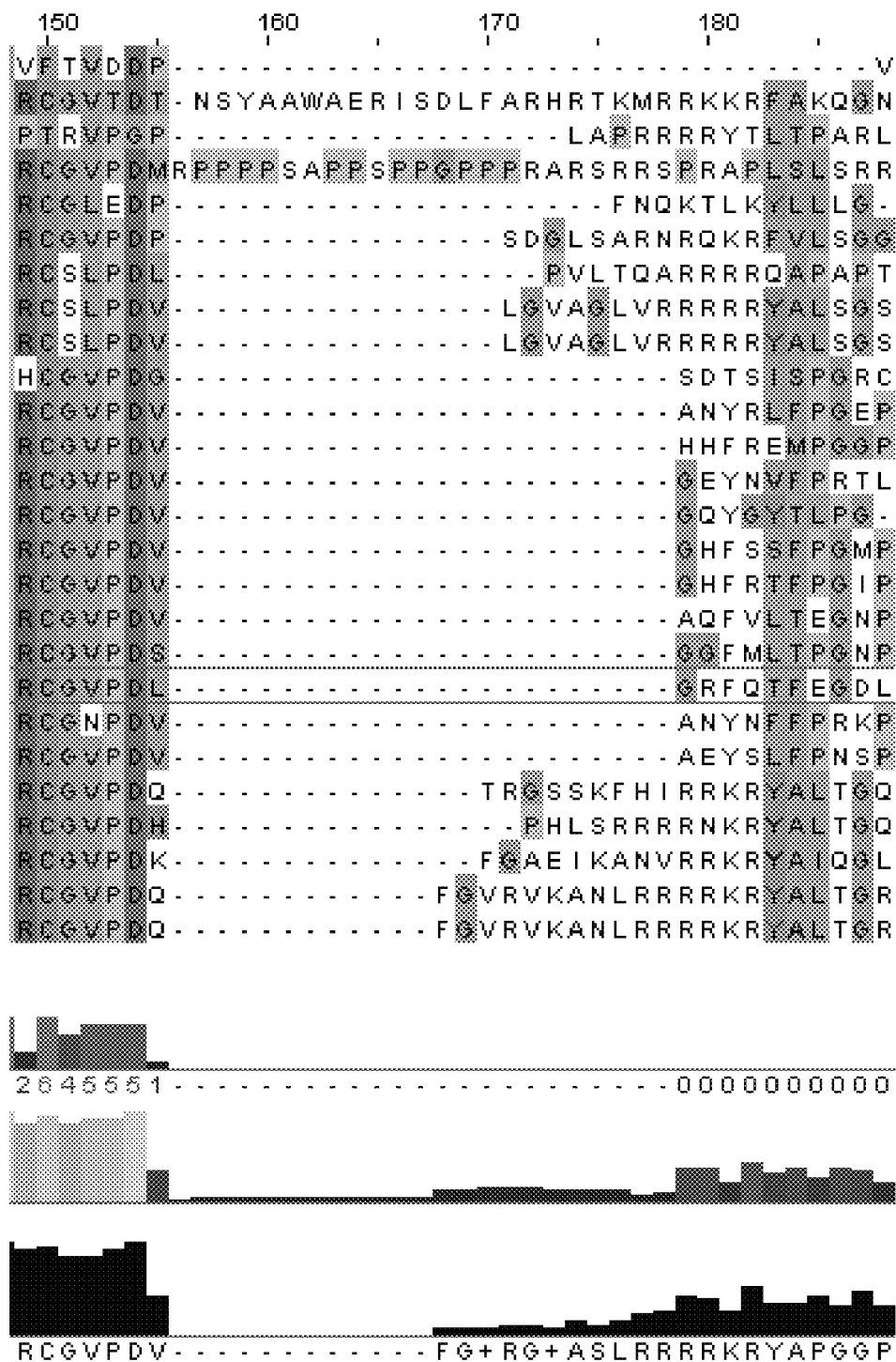

Of note is the structure of proMMP1, where the region is disordered in the area of the cleavage site, suggesting that these residues are flexible. In addition, both MMP1 and MMP3, which are cleaved to the active form by MMP3, have a cleavage site that contains an S1 hydrophilic residue and a S1' Phe residue. Indeed, the proMMP3 structure has the S1' Phe in a very similar location to Phe 107 in the apo proMMP9 structure. FIG. 7 shows the overlap of all current proMMP structures, (MMP9 (pdb1L6J), MMP1 (pdb1SU3), and MMP2 (pdb1CK7)). A sequence alignment of the pro domains for the MMP family is shown in FIG. 8.

Evidence that this method of inhibition is in fact transferable to other MMPs was demonstrated with a number of compounds that showed activity in inhibiting activation of both proMMP9 and proMMP13. See for example, Table 2, showing that Example 2 inhibited activation of both proMMP9 and proMMP13. Furthermore, it was also demonstrated with ThermoFluor® that a number of compounds bind to both proMMP9 and proMMP13. See for example, Table 1, showing ThermoFluor® data for selected compounds using proMM9 and proMMP13.

Coordinates

Tables 11, 12, 13, and 14, list the coordinates for representative structures of proMMP9 complexed with examples of different allosteric processing inhibitors. Table 15 lists the coordinates for the apo form of proMMP9.

TABLE 11

Coordinates for pro MMP9(35-444 ΔFnII) (SEQ ID NO: 12) complex with Example 1

| ATOM | 1801 | CB | ASP | B | 41 | -5.622 | 13.523 | 78.580 | 1.00 | 62.75 B | C |
|------|------|-----|-----|---|----|--------|--------|--------|------|---------|---|
| ATOM | 1802 | CG | ASP | B | 41 | -6.779 | 14.221 | 77.898 | 1.00 | 63.89 B | C |
| ATOM | 1803 | OD1 | ASP | B | 41 | -7.191 | 13.757 | 76.812 | 1.00 | 64.66 B | O |
| ATOM | 1804 | OD2 | ASP | B | 41 | -7.271 | 15.235 | 78.447 | 1.00 | 64.07 B | O |
| ATOM | 1805 | C | ASP | B | 41 | -4.493 | 15.705 | 78.723 | 1.00 | 62.33 B | C |
| ATOM | 1806 | O | ASP | B | 41 | -3.955 | 16.589 | 78.066 | 1.00 | 63.96 B | O |
| ATOM | 1807 | N | ASP | B | 41 | -3.222 | 13.602 | 79.148 | 1.00 | 61.28 B | N |
| ATOM | 1808 | CA | ASP | B | 41 | -4.305 | 14.244 | 78.357 | 1.00 | 61.88 B | C |
| ATOM | 1809 | N | ARG | B | 42 | -5.273 | 15.963 | 79.766 | 1.00 | 62.29 B | N |
| ATOM | 1810 | CA | ARG | B | 42 | -5.474 | 17.334 | 80.222 | 1.00 | 62.94 B | C |
| ATOM | 1811 | CB | ARG | B | 42 | -6.406 | 17.366 | 81.435 | 1.00 | 62.27 B | C |
| ATOM | 1812 | CG | ARG | B | 42 | -6.403 | 18.686 | 82.180 | 1.00 | 60.80 B | C |
| ATOM | 1813 | CD | ARG | B | 42 | -7.548 | 18.762 | 83.172 | 1.00 | 61.00 B | C |
| ATOM | 1814 | NE | ARG | B | 42 | -7.787 | 20.139 | 83.599 | 1.00 | 61.72 B | N |
| ATOM | 1815 | CZ | ARG | B | 42 | -8.797 | 20.900 | 83.181 | 1.00 | 62.56 B | C |
| ATOM | 1816 | NH1 | ARG | B | 42 | -9.683 | 20.418 | 82.315 | 1.00 | 60.84 B | N |
| ATOM | 1817 | NH2 | ARG | B | 42 | -8.912 | 22.151 | 83.627 | 1.00 | 63.72 B | N |
| ATOM | 1818 | C | ARG | B | 42 | -4.135 | 17.945 | 80.603 | 1.00 | 63.83 B | C |
| ATOM | 1819 | O | ARG | B | 42 | -3.902 | 19.144 | 80.411 | 1.00 | 63.99 B | O |
| ATOM | 1820 | N | GLN | B | 43 | -3.255 | 17.108 | 81.150 | 1.00 | 63.14 B | N |
| ATOM | 1821 | CA | GLN | B | 43 | -1.942 | 17.566 | 81.587 | 1.00 | 62.24 B | C |
| ATOM | 1822 | CB | GLN | B | 43 | -1.111 | 16.375 | 82.081 | 1.00 | 64.08 B | C |
| ATOM | 1823 | CG | GLN | B | 43 | -1.834 | 15.462 | 83.078 | 1.00 | 65.58 B | C |
| ATOM | 1824 | CD | GLN | B | 43 | -2.663 | 14.370 | 82.398 | 1.00 | 66.13 B | C |
| ATOM | 1825 | OE1 | GLN | B | 43 | -2.140 | 13.581 | 81.597 | 1.00 | 66.23 B | O |
| ATOM | 1826 | NE2 | GLN | B | 43 | -3.958 | 14.318 | 82.719 | 1.00 | 64.68 B | N |
| ATOM | 1827 | C | GLN | B | 43 | -1.263 | 18.232 | 80.395 | 1.00 | 61.38 B | C |
| ATOM | 1828 | O | GLN | B | 43 | -0.720 | 19.338 | 80.503 | 1.00 | 60.88 B | O |
| ATOM | 1829 | N | LEU | B | 44 | -1.321 | 17.547 | 79.254 | 1.00 | 60.44 B | N |
| ATOM | 1830 | CA | LEU | B | 44 | -0.887 | 18.113 | 77.981 | 1.00 | 60.89 B | C |
| ATOM | 1831 | CB | LEU | B | 44 | -1.102 | 17.117 | 76.836 | 1.00 | 59.48 B | C |
| ATOM | 1832 | CG | LEU | B | 44 | -1.197 | 17.711 | 75.422 | 1.00 | 59.18 B | C |
| ATOM | 1833 | CD1 | LEU | B | 44 | 0.055 | 18.519 | 75.088 | 1.00 | 59.52 B | C |
| ATOM | 1834 | CD2 | LEU | B | 44 | -1.384 | 16.586 | 74.422 | 1.00 | 58.19 B | C |
| ATOM | 1835 | C | LEU | B | 44 | -1.687 | 19.362 | 77.679 | 1.00 | 61.53 B | C |

TABLE 11-continued

Coordinates for pro MMP9(35-444 ΔFnII) (SEQ ID NO: 12) complex with Example 1

| ATOM | 1836 | O   | LEU | B | 44 | −1.161 | 20.356 | 77.176 | 1.00 | 61.91 B | O |
|------|------|-----|-----|---|----|--------|--------|--------|------|---------|---|
| ATOM | 1837 | N   | ALA | B | 45 | −2.974 | 19.296 | 77.980 | 1.00 | 61.27 B | N |
| ATOM | 1838 | CA  | ALA | B | 45 | −3.876 | 20.347 | 77.572 | 1.00 | 62.45 B | C |
| ATOM | 1839 | CB  | ALA | B | 45 | −5.315 | 19.979 | 77.940 | 1.00 | 63.46 B | C |
| ATOM | 1840 | C   | ALA | B | 45 | −3.465 | 21.626 | 78.264 | 1.00 | 62.12 B | C |
| ATOM | 1841 | O   | ALA | B | 45 | −3.493 | 22.711 | 77.674 | 1.00 | 62.26 B | O |
| ATOM | 1842 | N   | GLU | B | 46 | −3.064 | 21.490 | 79.519 | 1.00 | 62.06 B | N |
| ATOM | 1843 | CA  | GLU | B | 46 | −2.748 | 22.647 | 80.330 | 1.00 | 61.09 B | C |
| ATOM | 1844 | CB  | GLU | B | 46 | −2.990 | 22.331 | 81.802 | 1.00 | 62.73 B | C |
| ATOM | 1845 | CG  | GLU | B | 46 | −4.414 | 21.904 | 82.110 | 1.00 | 63.16 B | C |
| ATOM | 1846 | CD  | GLU | B | 46 | −4.571 | 21.442 | 83.542 | 1.00 | 64.25 B | C |
| ATOM | 1847 | OE1 | GLU | B | 46 | −5.539 | 21.882 | 84.202 | 1.00 | 64.03 B | O |
| ATOM | 1848 | OE2 | GLU | B | 46 | −3.724 | 20.642 | 84.005 | 1.00 | 64.81 B | O |
| ATOM | 1849 | C   | GLU | B | 46 | −1.304 | 23.036 | 80.107 | 1.00 | 59.85 B | C |
| ATOM | 1850 | O   | GLU | B | 46 | −0.972 | 24.222 | 80.103 | 1.00 | 59.39 B | O |
| ATOM | 1851 | N   | GLU | B | 47 | −0.447 | 22.040 | 79.905 | 1.00 | 58.45 B | N |
| ATOM | 1852 | CA  | GLU | B | 47 | 0.961  | 22.316 | 79.632 | 1.00 | 58.81 B | C |
| ATOM | 1853 | CB  | GLU | B | 47 | 1.738  | 21.004 | 79.459 | 1.00 | 60.80 B | C |
| ATOM | 1854 | CG  | GLU | B | 47 | 3.048  | 20.921 | 80.257 | 1.00 | 62.91 B | C |
| ATOM | 1855 | CD  | GLU | B | 47 | 4.243  | 21.574 | 79.565 | 1.00 | 64.06 B | C |
| ATOM | 1856 | OE1 | GLU | B | 47 | 4.785  | 20.983 | 78.599 | 1.00 | 64.66 B | O |
| ATOM | 1857 | OE2 | GLU | B | 47 | 4.649  | 22.677 | 80.000 | 1.00 | 64.03 B | O |
| ATOM | 1858 | C   | GLU | B | 47 | 1.096  | 23.175 | 78.364 | 1.00 | 57.20 B | C |
| ATOM | 1859 | O   | GLU | B | 47 | 1.731  | 24.229 | 78.388 | 1.00 | 56.69 B | O |
| ATOM | 1860 | N   | TYR | B | 48 | 0.477  | 22.713 | 77.274 | 1.00 | 54.95 B | N |
| ATOM | 1861 | CA  | TYR | B | 48 | 0.540  | 23.372 | 75.966 | 1.00 | 51.46 B | C |
| ATOM | 1862 | CB  | TYR | B | 48 | −0.245 | 22.567 | 74.929 | 1.00 | 50.46 B | C |
| ATOM | 1863 | CG  | TYR | B | 48 | −0.016 | 22.980 | 73.488 | 1.00 | 48.44 B | C |
| ATOM | 1864 | CD1 | TYR | B | 48 | −0.555 | 24.157 | 72.988 | 1.00 | 47.77 B | C |
| ATOM | 1865 | CE1 | TYR | B | 48 | −0.387 | 24.518 | 71.665 | 1.00 | 47.69 B | C |
| ATOM | 1866 | CD2 | TYR | B | 48 | 0.708  | 22.167 | 72.617 | 1.00 | 46.99 B | C |
| ATOM | 1867 | CE2 | TYR | B | 48 | 0.883  | 22.518 | 71.282 | 1.00 | 46.69 B | C |
| ATOM | 1868 | CZ  | TYR | B | 48 | 0.324  | 23.702 | 70.814 | 1.00 | 47.29 B | C |
| ATOM | 1869 | OH  | TYR | B | 48 | 0.432  | 24.077 | 69.494 | 1.00 | 46.46 B | O |
| ATOM | 1870 | C   | TYR | B | 48 | 0.006  | 24.797 | 75.992 | 1.00 | 51.37 B | C |
| ATOM | 1871 | O   | TYR | B | 48 | 0.589  | 25.693 | 75.385 | 1.00 | 51.99 B | O |
| ATOM | 1872 | N   | LEU | B | 49 | −1.101 | 25.017 | 76.685 | 1.00 | 50.67 B | N |
| ATOM | 1873 | CA  | LEU | B | 49 | −1.577 | 26.371 | 76.830 | 1.00 | 50.62 B | C |
| ATOM | 1874 | CB  | LEU | B | 49 | −2.924 | 26.403 | 77.544 | 1.00 | 50.69 B | C |
| ATOM | 1875 | CG  | LEU | B | 49 | −4.068 | 25.775 | 76.745 | 1.00 | 50.22 B | C |
| ATOM | 1876 | CD1 | LEU | B | 49 | −5.359 | 25.742 | 77.563 | 1.00 | 50.84 B | C |
| ATOM | 1877 | CD2 | LEU | B | 49 | −4.268 | 26.584 | 75.491 | 1.00 | 51.85 B | C |
| ATOM | 1878 | C   | LEU | B | 49 | −0.556 | 27.208 | 77.586 | 1.00 | 50.99 B | C |
| ATOM | 1879 | O   | LEU | B | 49 | −0.175 | 28.282 | 77.123 | 1.00 | 52.52 B | O |
| ATOM | 1880 | N   | TYR | B | 50 | −0.088 | 26.740 | 78.735 | 1.00 | 50.56 B | N |
| ATOM | 1881 | CA  | TYR | B | 50 | 0.806  | 27.589 | 79.513 | 1.00 | 52.06 B | C |
| ATOM | 1882 | CB  | TYR | B | 50 | 1.215  | 26.909 | 80.849 | 1.00 | 54.75 B | C |
| ATOM | 1883 | CG  | TYR | B | 50 | 2.356  | 27.610 | 81.595 | 1.00 | 56.49 B | C |
| ATOM | 1884 | CD1 | TYR | B | 50 | 2.132  | 28.749 | 82.369 | 1.00 | 56.67 B | C |
| ATOM | 1885 | CE1 | TYR | B | 50 | 3.196  | 29.425 | 82.983 | 1.00 | 57.25 B | C |
| ATOM | 1886 | CD2 | TYR | B | 50 | 3.669  | 27.165 | 81.465 | 1.00 | 57.57 B | C |
| ATOM | 1887 | CE2 | TYR | B | 50 | 4.733  | 27.833 | 82.071 | 1.00 | 57.73 B | C |
| ATOM | 1888 | CZ  | TYR | B | 50 | 4.492  | 28.962 | 82.822 | 1.00 | 57.73 B | C |
| ATOM | 1889 | OH  | TYR | B | 50 | 5.556  | 29.647 | 83.366 | 1.00 | 57.23 B | O |
| ATOM | 1890 | C   | TYR | B | 50 | 2.046  | 27.888 | 78.666 | 1.00 | 51.21 B | C |
| ATOM | 1891 | O   | TYR | B | 50 | 2.565  | 29.010 | 78.658 | 1.00 | 50.09 B | O |
| ATOM | 1892 | N   | ARG | B | 51 | 2.490  | 26.874 | 77.929 | 1.00 | 50.13 B | N |
| ATOM | 1893 | CA  | ARG | B | 51 | 3.795  | 26.897 | 77.285 | 1.00 | 49.14 B | C |
| ATOM | 1894 | CB  | ARG | B | 51 | 4.092  | 25.520 | 76.658 | 1.00 | 49.01 B | C |
| ATOM | 1895 | CG  | ARG | B | 51 | 5.358  | 25.464 | 75.799 | 1.00 | 49.48 B | C |
| ATOM | 1896 | CD  | ARG | B | 51 | 5.841  | 24.031 | 75.496 | 1.00 | 49.62 B | C |
| ATOM | 1897 | NE  | ARG | B | 51 | 6.502  | 23.367 | 76.633 | 1.00 | 50.14 B | N |
| ATOM | 1898 | CZ  | ARG | B | 51 | 7.815  | 23.369 | 76.872 | 1.00 | 49.61 B | C |
| ATOM | 1899 | NH1 | ARG | B | 51 | 8.656  | 24.004 | 76.064 | 1.00 | 50.15 B | N |
| ATOM | 1900 | NH2 | ARG | B | 51 | 8.289  | 22.716 | 77.921 | 1.00 | 49.36 B | N |
| ATOM | 1901 | C   | ARG | B | 51 | 3.872  | 27.995 | 76.229 | 1.00 | 48.42 B | C |
| ATOM | 1902 | O   | ARG | B | 51 | 4.867  | 28.708 | 76.133 | 1.00 | 46.51 B | O |
| ATOM | 1903 | N   | TYR | B | 52 | 2.817  | 28.146 | 75.443 | 1.00 | 47.18 B | N |
| ATOM | 1904 | CA  | TYR | B | 52 | 2.913  | 29.024 | 74.292 | 1.00 | 48.85 B | C |
| ATOM | 1905 | CB  | TYR | B | 52 | 2.407  | 28.290 | 73.038 | 1.00 | 47.39 B | C |
| ATOM | 1906 | CG  | TYR | B | 52 | 3.175  | 27.018 | 72.746 | 1.00 | 44.63 B | C |
| ATOM | 1907 | CD1 | TYR | B | 52 | 2.580  | 25.777 | 72.910 | 1.00 | 44.87 B | C |
| ATOM | 1908 | CE1 | TYR | B | 52 | 3.286  | 24.609 | 72.683 | 1.00 | 44.91 B | C |
| ATOM | 1909 | CD2 | TYR | B | 52 | 4.504  | 27.061 | 72.342 | 1.00 | 43.90 B | C |
| ATOM | 1910 | CE2 | TYR | B | 52 | 5.227  | 25.900 | 72.108 | 1.00 | 43.90 B | C |
| ATOM | 1911 | CZ  | TYR | B | 52 | 4.615  | 24.669 | 72.279 | 1.00 | 44.52 B | C |
| ATOM | 1912 | OH  | TYR | B | 52 | 5.313  | 23.494 | 72.040 | 1.00 | 43.22 B | O |
| ATOM | 1913 | C   | TYR | B | 52 | 2.162  | 30.328 | 74.533 | 1.00 | 49.58 B | C |

TABLE 11-continued

Coordinates for pro MMP9(35-444 ΔFnII) (SEQ ID NO: 12) complex with Example 1

| ATOM | 1914 | O   | TYR | B | 52 | 1.683   | 30.977 | 73.597 | 1.00 | 49.81 | B | O |
|------|------|-----|-----|---|----|---------|--------|--------|------|-------|---|---|
| ATOM | 1915 | N   | GLY | B | 53 | 2.070   | 30.691 | 75.815 | 1.00 | 51.04 | B | N |
| ATOM | 1916 | CA  | GLY | B | 53 | 1.646   | 32.024 | 76.217 | 1.00 | 50.61 | B | C |
| ATOM | 1917 | C   | GLY | B | 53 | 0.183   | 32.203 | 76.596 | 1.00 | 51.60 | B | C |
| ATOM | 1918 | O   | GLY | B | 53 | −0.182  | 33.267 | 77.088 | 1.00 | 51.76 | B | O |
| ATOM | 1919 | N   | TYR | B | 54 | −0.654  | 31.189 | 76.378 | 1.00 | 51.15 | B | N |
| ATOM | 1920 | CA  | TYR | B | 54 | −2.090  | 31.419 | 76.355 | 1.00 | 51.50 | B | C |
| ATOM | 1921 | CB  | TYR | B | 54 | −2.832  | 30.230 | 75.729 | 1.00 | 51.54 | B | C |
| ATOM | 1922 | CG  | TYR | B | 54 | −2.587  | 30.086 | 74.230 | 1.00 | 53.01 | B | C |
| ATOM | 1923 | CD1 | TYR | B | 54 | −1.779  | 29.071 | 73.732 | 1.00 | 53.74 | B | C |
| ATOM | 1924 | CE1 | TYR | B | 54 | −1.511  | 28.958 | 72.383 | 1.00 | 53.90 | B | C |
| ATOM | 1925 | CD2 | TYR | B | 54 | −3.126  | 30.990 | 73.317 | 1.00 | 53.57 | B | C |
| ATOM | 1926 | CE2 | TYR | B | 54 | −2.857  | 30.879 | 71.960 | 1.00 | 54.75 | B | C |
| ATOM | 1927 | CZ  | TYR | B | 54 | −2.048  | 29.857 | 71.508 | 1.00 | 54.89 | B | C |
| ATOM | 1928 | OH  | TYR | B | 54 | −1.767  | 29.728 | 70.171 | 1.00 | 56.35 | B | O |
| ATOM | 1929 | C   | TYR | B | 54 | −2.646  | 31.711 | 77.727 | 1.00 | 52.70 | B | C |
| ATOM | 1930 | O   | TYR | B | 54 | −3.155  | 32.801 | 77.977 | 1.00 | 52.64 | B | O |
| ATOM | 1931 | N   | THR | B | 55 | −2.546  | 30.741 | 78.623 | 1.00 | 55.09 | B | N |
| ATOM | 1932 | CA  | THR | B | 55 | −3.071  | 30.908 | 79.968 | 1.00 | 56.46 | B | C |
| ATOM | 1933 | CB  | THR | B | 55 | −2.798  | 29.652 | 80.782 | 1.00 | 55.37 | B | C |
| ATOM | 1934 | OG1 | THR | B | 55 | −1.395  | 29.404 | 80.821 | 1.00 | 56.74 | B | O |
| ATOM | 1935 | CG2 | THR | B | 55 | −3.464  | 28.459 | 80.123 | 1.00 | 56.02 | B | C |
| ATOM | 1936 | C   | THR | B | 55 | −2.463  | 32.152 | 80.632 | 1.00 | 57.54 | B | C |
| ATOM | 1937 | O   | THR | B | 55 | −3.126  | 32.853 | 81.401 | 1.00 | 58.41 | B | O |
| ATOM | 1938 | N   | ARG | B | 56 | −1.212  | 32.453 | 80.303 | 1.00 | 58.28 | B | N |
| ATOM | 1939 | CA  | ARG | B | 56 | −0.594  | 33.689 | 80.772 | 1.00 | 59.32 | B | C |
| ATOM | 1940 | CB  | ARG | B | 56 | 0.835   | 33.788 | 80.240 | 1.00 | 61.48 | B | C |
| ATOM | 1941 | CG  | ARG | B | 56 | 1.292   | 35.221 | 80.010 | 1.00 | 64.60 | B | C |
| ATOM | 1942 | CD  | ARG | B | 56 | 2.554   | 35.538 | 80.798 | 1.00 | 66.20 | B | C |
| ATOM | 1943 | NE  | ARG | B | 56 | 2.845   | 36.971 | 80.804 | 1.00 | 65.83 | B | N |
| ATOM | 1944 | CZ  | ARG | B | 56 | 3.769   | 37.554 | 80.047 | 1.00 | 65.50 | B | C |
| ATOM | 1945 | NH1 | ARG | B | 56 | 4.502   | 36.823 | 79.208 | 1.00 | 63.11 | B | N |
| ATOM | 1946 | NH2 | ARG | B | 56 | 3.962   | 38.868 | 80.143 | 1.00 | 63.67 | B | N |
| ATOM | 1947 | C   | ARG | B | 56 | −1.381  | 34.940 | 80.350 | 1.00 | 58.31 | B | C |
| ATOM | 1948 | O   | ARG | B | 56 | −1.627  | 35.818 | 81.160 | 1.00 | 58.35 | B | O |
| ATOM | 1949 | N   | VAL | B | 57 | −1.768  | 35.014 | 79.079 | 1.00 | 58.36 | B | N |
| ATOM | 1950 | CA  | VAL | B | 57 | −2.421  | 36.204 | 78.528 | 1.00 | 56.57 | B | C |
| ATOM | 1951 | CB  | VAL | B | 57 | −2.555  | 36.105 | 76.964 | 1.00 | 55.30 | B | C |
| ATOM | 1952 | CG1 | VAL | B | 57 | −3.465  | 37.191 | 76.423 | 1.00 | 54.65 | B | C |
| ATOM | 1953 | CG2 | VAL | B | 57 | −1.181  | 36.227 | 76.311 | 1.00 | 52.96 | B | C |
| ATOM | 1954 | C   | VAL | B | 57 | −3.803  | 36.421 | 79.140 | 1.00 | 57.00 | B | C |
| ATOM | 1955 | O   | VAL | B | 57 | −4.108  | 37.520 | 79.608 | 1.00 | 57.15 | B | O |
| ATOM | 1956 | N   | ALA | B | 58 | −4.626  | 35.371 | 79.141 | 1.00 | 57.18 | B | N |
| ATOM | 1957 | CA  | ALA | B | 58 | −5.993  | 35.453 | 79.651 | 1.00 | 57.73 | B | C |
| ATOM | 1958 | CB  | ALA | B | 58 | −6.619  | 34.059 | 79.691 | 1.00 | 56.30 | B | C |
| ATOM | 1959 | C   | ALA | B | 58 | −6.059  | 36.112 | 81.040 | 1.00 | 58.36 | B | C |
| ATOM | 1960 | O   | ALA | B | 58 | −7.092  | 36.671 | 81.427 | 1.00 | 58.49 | B | O |
| ATOM | 1961 | N   | GLU | B | 59 | −4.956  | 36.053 | 81.783 | 1.00 | 59.14 | B | N |
| ATOM | 1962 | CA  | GLU | B | 59 | −4.819  | 36.823 | 83.021 | 1.00 | 59.00 | B | C |
| ATOM | 1963 | CB  | GLU | B | 59 | −3.702  | 36.228 | 83.897 | 1.00 | 59.61 | B | C |
| ATOM | 1964 | CG  | GLU | B | 59 | −3.785  | 34.713 | 84.100 | 1.00 | 59.48 | B | C |
| ATOM | 1965 | CD  | GLU | B | 59 | −2.454  | 34.084 | 84.515 | 1.00 | 60.05 | B | C |
| ATOM | 1966 | OE1 | GLU | B | 59 | −1.426  | 34.801 | 84.552 | 1.00 | 60.10 | B | O |
| ATOM | 1967 | OE2 | GLU | B | 59 | −2.433  | 32.864 | 84.803 | 1.00 | 60.25 | B | O |
| ATOM | 1968 | C   | GLU | B | 59 | −4.489  | 38.290 | 82.705 | 1.00 | 59.68 | B | C |
| ATOM | 1969 | O   | GLU | B | 59 | −5.250  | 38.994 | 82.033 | 1.00 | 59.54 | B | O |
| ATOM | 1970 | N   | GLY | B | 68 | −10.715 | 26.983 | 79.395 | 1.00 | 60.34 | B | N |
| ATOM | 1971 | CA  | GLY | B | 68 | −11.961 | 27.302 | 78.719 | 1.00 | 62.09 | B | C |
| ATOM | 1972 | C   | GLY | B | 68 | −11.886 | 28.595 | 77.927 | 1.00 | 63.65 | B | C |
| ATOM | 1973 | O   | GLY | B | 68 | −12.057 | 28.587 | 76.701 | 1.00 | 64.44 | B | O |
| ATOM | 1974 | N   | PRO | B | 69 | −11.637 | 29.733 | 78.605 | 1.00 | 64.13 | B | N |
| ATOM | 1975 | CD  | PRO | B | 69 | −11.735 | 29.893 | 80.067 | 1.00 | 62.87 | B | C |
| ATOM | 1976 | CA  | PRO | B | 69 | −11.362 | 31.018 | 77.943 | 1.00 | 63.98 | B | C |
| ATOM | 1977 | CB  | PRO | B | 69 | −11.242 | 32.011 | 79.106 | 1.00 | 62.94 | B | C |
| ATOM | 1978 | CG  | PRO | B | 69 | −11.969 | 31.373 | 80.221 | 1.00 | 62.18 | B | C |
| ATOM | 1979 | C   | PRO | B | 69 | −10.081 | 30.962 | 77.115 | 1.00 | 63.67 | B | C |
| ATOM | 1980 | O   | PRO | B | 69 | −10.112 | 31.166 | 75.908 | 1.00 | 64.56 | B | O |
| ATOM | 1981 | N   | ALA | B | 70 | −8.956  | 30.678 | 77.766 | 1.00 | 63.29 | B | N |
| ATOM | 1982 | CA  | ALA | B | 70 | −7.683  | 30.598 | 77.055 | 1.00 | 63.79 | B | C |
| ATOM | 1983 | CB  | ALA | B | 70 | −6.512  | 30.560 | 78.041 | 1.00 | 61.38 | B | C |
| ATOM | 1984 | C   | ALA | B | 70 | −7.621  | 29.393 | 76.105 | 1.00 | 63.72 | B | C |
| ATOM | 1985 | O   | ALA | B | 70 | −6.629  | 29.212 | 75.404 | 1.00 | 63.83 | B | O |
| ATOM | 1986 | N   | LEU | B | 71 | −8.673  | 28.574 | 76.076 | 1.00 | 62.11 | B | N |
| ATOM | 1987 | CA  | LEU | B | 71 | −8.763  | 27.502 | 75.090 | 1.00 | 60.75 | B | C |
| ATOM | 1988 | CB  | LEU | B | 71 | −9.712  | 26.404 | 75.574 | 1.00 | 60.83 | B | C |
| ATOM | 1989 | CG  | LEU | B | 71 | −9.207  | 24.967 | 75.365 | 1.00 | 61.47 | B | C |
| ATOM | 1990 | CD1 | LEU | B | 71 | −10.006 | 24.256 | 74.294 | 1.00 | 60.61 | B | C |
| ATOM | 1991 | CD2 | LEU | B | 71 | −7.730  | 25.003 | 75.008 | 1.00 | 61.49 | B | C |

TABLE 11-continued

Coordinates for pro MMP9(35-444 ΔFnII) (SEQ ID NO: 12) complex with Example 1

| ATOM | 1992 | C   | LEU | B | 71 | −9.244  | 28.046 | 73.739 | 1.00 | 61.00 B | C |
|------|------|-----|-----|---|----|---------|--------|--------|------|---------|---|
| ATOM | 1993 | O   | LEU | B | 71 | −9.076  | 27.405 | 72.698 | 1.00 | 61.47 B | O |
| ATOM | 1994 | N   | LEU | B | 72 | −9.847  | 29.234 | 73.761 | 1.00 | 61.08 B | N |
| ATOM | 1995 | CA  | LEU | B | 72 | −10.315 | 29.898 | 72.541 | 1.00 | 59.16 B | C |
| ATOM | 1996 | CB  | LEU | B | 72 | −11.565 | 30.739 | 72.834 | 1.00 | 58.95 B | C |
| ATOM | 1997 | CG  | LEU | B | 72 | −12.880 | 30.283 | 72.191 | 1.00 | 58.78 B | C |
| ATOM | 1998 | CD1 | LEU | B | 72 | −13.748 | 31.487 | 71.866 | 1.00 | 57.47 B | C |
| ATOM | 1999 | CD2 | LEU | B | 72 | −12.577 | 29.518 | 70.926 | 1.00 | 60.36 B | C |
| ATOM | 2000 | C   | LEU | B | 72 | −9.236  | 30.795 | 71.913 | 1.00 | 58.54 B | C |
| ATOM | 2001 | O   | LEU | B | 72 | −9.124  | 30.874 | 70.694 | 1.00 | 58.48 B | O |
| ATOM | 2002 | N   | LEU | B | 73 | −8.444  | 31.468 | 72.741 | 1.00 | 56.65 B | N |
| ATOM | 2003 | CA  | LEU | B | 73 | −7.310  | 32.210 | 72.224 | 1.00 | 55.43 B | C |
| ATOM | 2004 | CB  | LEU | B | 73 | −6.502  | 32.817 | 73.357 | 1.00 | 53.30 B | C |
| ATOM | 2005 | CG  | LEU | B | 73 | −7.100  | 34.083 | 73.926 | 1.00 | 51.80 B | C |
| ATOM | 2006 | CD1 | LEU | B | 73 | −5.989  | 34.855 | 74.597 | 1.00 | 52.00 B | C |
| ATOM | 2007 | CD2 | LEU | B | 73 | −7.728  | 34.914 | 72.828 | 1.00 | 50.38 B | C |
| ATOM | 2008 | C   | LEU | B | 73 | −6.392  | 31.335 | 71.380 | 1.00 | 56.07 B | C |
| ATOM | 2009 | O   | LEU | B | 73 | −5.778  | 31.812 | 70.424 | 1.00 | 57.01 B | O |
| ATOM | 2010 | N   | LEU | B | 74 | −6.287  | 30.058 | 71.735 | 1.00 | 55.82 B | N |
| ATOM | 2011 | CA  | LEU | B | 74 | −5.412  | 29.147 | 71.002 | 1.00 | 55.30 B | C |
| ATOM | 2012 | CB  | LEU | B | 74 | −4.950  | 27.985 | 71.896 | 1.00 | 52.49 B | C |
| ATOM | 2013 | CG  | LEU | B | 74 | −4.395  | 26.749 | 71.174 | 1.00 | 49.44 B | C |
| ATOM | 2014 | CD1 | LEU | B | 74 | −3.361  | 26.095 | 72.027 | 1.00 | 47.93 B | C |
| ATOM | 2015 | CD2 | LEU | B | 74 | −5.518  | 25.774 | 70.857 | 1.00 | 48.17 B | C |
| ATOM | 2016 | C   | LEU | B | 74 | −6.090  | 28.588 | 69.759 | 1.00 | 56.92 B | C |
| ATOM | 2017 | O   | LEU | B | 74 | −5.429  | 28.302 | 68.752 | 1.00 | 57.25 B | O |
| ATOM | 2018 | N   | GLN | B | 75 | −7.405  | 28.418 | 69.830 | 1.00 | 56.80 B | N |
| ATOM | 2019 | CA  | GLN | B | 75 | −8.160  | 27.957 | 68.671 | 1.00 | 57.63 B | C |
| ATOM | 2020 | CB  | GLN | B | 75 | −9.559  | 27.514 | 69.111 | 1.00 | 56.50 B | C |
| ATOM | 2021 | CG  | GLN | B | 75 | −9.552  | 26.237 | 69.929 | 1.00 | 56.07 B | C |
| ATOM | 2022 | CD  | GLN | B | 75 | −10.933 | 25.881 | 70.474 | 1.00 | 57.52 B | C |
| ATOM | 2023 | OE1 | GLN | B | 75 | −11.716 | 26.768 | 70.851 | 1.00 | 57.77 B | O |
| ATOM | 2024 | NE2 | GLN | B | 75 | −11.240 | 24.580 | 70.524 | 1.00 | 56.66 B | N |
| ATOM | 2025 | C   | GLN | B | 75 | −8.236  | 29.058 | 67.600 | 1.00 | 57.80 B | C |
| ATOM | 2026 | O   | GLN | B | 75 | −8.572  | 28.794 | 66.440 | 1.00 | 58.35 B | O |
| ATOM | 2027 | N   | LYS | B | 76 | −7.881  | 30.282 | 67.997 | 1.00 | 56.87 B | N |
| ATOM | 2028 | CA  | LYS | B | 76 | −7.963  | 31.452 | 67.123 | 1.00 | 56.29 B | C |
| ATOM | 2029 | CB  | LYS | B | 76 | −8.367  | 32.693 | 67.938 | 1.00 | 57.72 B | C |
| ATOM | 2030 | CG  | LYS | B | 76 | −9.383  | 33.608 | 67.242 | 1.00 | 58.97 B | C |
| ATOM | 2031 | CD  | LYS | B | 76 | −10.044 | 34.604 | 68.214 | 1.00 | 59.88 B | C |
| ATOM | 2032 | CE  | LYS | B | 76 | −11.231 | 33.982 | 68.981 | 1.00 | 60.17 B | C |
| ATOM | 2033 | NZ  | LYS | B | 76 | −11.959 | 34.948 | 69.872 | 1.00 | 56.84 B | N |
| ATOM | 2034 | C   | LYS | B | 76 | −6.653  | 31.728 | 66.371 | 1.00 | 55.13 B | C |
| ATOM | 2035 | O   | LYS | B | 76 | −6.668  | 32.137 | 65.209 | 1.00 | 54.25 B | O |
| ATOM | 2036 | N   | GLN | B | 77 | −5.521  | 31.488 | 67.022 | 1.00 | 54.38 B | N |
| ATOM | 2037 | CA  | GLN | B | 77 | −4.224  | 31.627 | 66.359 | 1.00 | 53.88 B | C |
| ATOM | 2038 | CB  | GLN | B | 77 | −3.118  | 31.716 | 67.407 | 1.00 | 54.27 B | C |
| ATOM | 2039 | CG  | GLN | B | 77 | −3.404  | 32.753 | 68.460 | 1.00 | 58.53 B | C |
| ATOM | 2040 | CD  | GLN | B | 77 | −3.526  | 34.158 | 67.870 | 1.00 | 60.95 B | C |
| ATOM | 2041 | OE1 | GLN | B | 77 | −4.583  | 34.554 | 67.329 | 1.00 | 60.29 B | O |
| ATOM | 2042 | NE2 | GLN | B | 77 | −2.434  | 34.924 | 67.968 | 1.00 | 62.21 B | N |
| ATOM | 2043 | C   | GLN | B | 77 | −3.913  | 30.489 | 65.378 | 1.00 | 52.74 B | C |
| ATOM | 2044 | O   | GLN | B | 77 | −3.192  | 30.685 | 64.410 | 1.00 | 52.34 B | O |
| ATOM | 2045 | N   | LEU | B | 78 | −4.451  | 29.302 | 65.628 | 1.00 | 53.59 B | N |
| ATOM | 2046 | CA  | LEU | B | 78 | −4.130  | 28.140 | 64.805 | 1.00 | 53.81 B | C |
| ATOM | 2047 | CB  | LEU | B | 78 | −3.951  | 26.893 | 65.675 | 1.00 | 53.42 B | C |
| ATOM | 2048 | CG  | LEU | B | 78 | −3.081  | 27.072 | 66.928 | 1.00 | 53.99 B | C |
| ATOM | 2049 | CD1 | LEU | B | 78 | −3.023  | 25.774 | 67.715 | 1.00 | 54.97 B | C |
| ATOM | 2050 | CD2 | LEU | B | 78 | −1.686  | 27.524 | 66.524 | 1.00 | 52.88 B | C |
| ATOM | 2051 | C   | LEU | B | 78 | −5.271  | 27.917 | 63.839 | 1.00 | 54.05 B | C |
| ATOM | 2052 | O   | LEU | B | 78 | −5.343  | 26.891 | 63.162 | 1.00 | 53.06 B | O |
| ATOM | 2053 | N   | SER | B | 79 | −6.176  | 28.890 | 63.801 | 1.00 | 54.86 B | N |
| ATOM | 2054 | CA  | SER | B | 79 | −7.328  | 28.834 | 62.913 | 1.00 | 55.94 B | C |
| ATOM | 2055 | CB  | SER | B | 79 | −6.885  | 29.053 | 61.461 | 1.00 | 55.19 B | C |
| ATOM | 2056 | OG  | SER | B | 79 | −6.458  | 30.397 | 61.262 | 1.00 | 51.79 B | O |
| ATOM | 2057 | C   | SER | B | 79 | −8.045  | 27.498 | 63.063 | 1.00 | 56.76 B | C |
| ATOM | 2058 | O   | SER | B | 79 | −8.404  | 26.855 | 62.072 | 1.00 | 56.92 B | O |
| ATOM | 2059 | N   | LEU | B | 80 | −8.248  | 27.093 | 64.318 | 1.00 | 57.68 B | N |
| ATOM | 2060 | CA  | LEU | B | 80 | −9.006  | 25.884 | 64.654 | 1.00 | 58.01 B | C |
| ATOM | 2061 | CB  | LEU | B | 80 | −8.529  | 25.326 | 65.991 | 1.00 | 57.13 B | C |
| ATOM | 2062 | CG  | LEU | B | 80 | −7.137  | 24.718 | 65.959 | 1.00 | 57.11 B | C |
| ATOM | 2063 | CD1 | LEU | B | 80 | −6.619  | 24.572 | 67.377 | 1.00 | 56.46 B | C |
| ATOM | 2064 | CD2 | LEU | B | 80 | −7.188  | 23.376 | 65.237 | 1.00 | 56.74 B | C |
| ATOM | 2065 | C   | LEU | B | 80 | −10.506 | 26.140 | 64.739 | 1.00 | 58.76 B | C |
| ATOM | 2066 | O   | LEU | B | 80 | −10.945 | 27.273 | 64.925 | 1.00 | 58.40 B | O |
| ATOM | 2067 | N   | PRO | B | 81 | −11.317 | 25.080 | 64.604 | 1.00 | 60.19 B | N |
| ATOM | 2068 | CD  | PRO | B | 81 | −11.022 | 23.717 | 64.125 | 1.00 | 60.96 B | C |
| ATOM | 2069 | CA  | PRO | B | 81 | −12.726 | 25.240 | 64.962 | 1.00 | 61.92 B | C |

TABLE 11-continued

Coordinates for pro MMP9(35-444 ΔFnII) (SEQ ID NO: 12) complex with Example 1

| ATOM | 2070 | CB | PRO | B | 81 | −13.283 | 23.824 | 64.829 | 1.00 | 61.57 | B | C |
| ATOM | 2071 | CG | PRO | B | 81 | −12.377 | 23.164 | 63.824 | 1.00 | 60.13 | B | C |
| ATOM | 2072 | C | PRO | B | 81 | −12.822 | 25.785 | 66.389 | 1.00 | 62.95 | B | C |
| ATOM | 2073 | O | PRO | B | 81 | −12.367 | 25.138 | 67.341 | 1.00 | 63.10 | B | O |
| ATOM | 2074 | N | GLU | B | 82 | −13.408 | 26.979 | 66.520 | 1.00 | 63.96 | B | N |
| ATOM | 2075 | CA | GLU | B | 82 | −13.388 | 27.764 | 67.766 | 1.00 | 64.28 | B | C |
| ATOM | 2076 | CB | GLU | B | 82 | −13.556 | 29.252 | 67.433 | 1.00 | 65.33 | B | C |
| ATOM | 2077 | CG | GLU | B | 82 | −12.364 | 29.834 | 66.688 | 1.00 | 68.08 | B | C |
| ATOM | 2078 | CD | GLU | B | 82 | −12.538 | 31.302 | 66.311 | 1.00 | 70.16 | B | C |
| ATOM | 2079 | OE1 | GLU | B | 82 | −13.617 | 31.869 | 66.588 | 1.00 | 70.59 | B | O |
| ATOM | 2080 | OE2 | GLU | B | 82 | −11.589 | 31.890 | 65.733 | 1.00 | 71.70 | B | O |
| ATOM | 2081 | C | GLU | B | 82 | −14.447 | 27.331 | 68.789 | 1.00 | 64.05 | B | C |
| ATOM | 2082 | O | GLU | B | 82 | −15.299 | 28.123 | 69.204 | 1.00 | 63.04 | B | O |
| ATOM | 2083 | N | THR | B | 83 | −14.368 | 26.068 | 69.206 | 1.00 | 63.97 | B | N |
| ATOM | 2084 | CA | THR | B | 83 | −15.416 | 25.456 | 70.015 | 1.00 | 63.61 | B | C |
| ATOM | 2085 | CB | THR | B | 83 | −15.240 | 23.912 | 70.085 | 1.00 | 61.81 | B | C |
| ATOM | 2086 | OG1 | THR | B | 83 | −13.957 | 23.590 | 70.643 | 1.00 | 62.11 | B | O |
| ATOM | 2087 | CG2 | THR | B | 83 | −15.345 | 23.312 | 68.698 | 1.00 | 59.20 | B | C |
| ATOM | 2088 | C | THR | B | 83 | −15.429 | 26.032 | 71.430 | 1.00 | 64.78 | B | C |
| ATOM | 2089 | O | THR | B | 83 | −16.306 | 26.823 | 71.784 | 1.00 | 64.95 | B | O |
| ATOM | 2090 | N | GLY | B | 84 | −14.446 | 25.653 | 72.233 | 1.00 | 65.43 | B | N |
| ATOM | 2091 | CA | GLY | B | 84 | −14.503 | 25.989 | 73.641 | 1.00 | 67.36 | B | C |
| ATOM | 2092 | C | GLY | B | 84 | −14.296 | 24.766 | 74.510 | 1.00 | 68.60 | B | C |
| ATOM | 2093 | O | GLY | B | 84 | −14.476 | 24.825 | 75.722 | 1.00 | 69.36 | B | O |
| ATOM | 2094 | N | GLU | B | 85 | −13.918 | 23.652 | 73.898 | 1.00 | 68.54 | B | N |
| ATOM | 2095 | CA | GLU | B | 85 | −13.504 | 22.503 | 74.673 | 1.00 | 68.99 | B | C |
| ATOM | 2096 | CB | GLU | B | 85 | −14.614 | 21.453 | 74.734 | 1.00 | 71.41 | B | C |
| ATOM | 2097 | CG | GLU | B | 85 | −15.896 | 21.941 | 75.384 | 1.00 | 74.07 | B | C |
| ATOM | 2098 | CD | GLU | B | 85 | −16.716 | 22.769 | 74.430 | 1.00 | 75.29 | B | C |
| ATOM | 2099 | OE1 | GLU | B | 85 | −16.540 | 22.567 | 73.202 | 1.00 | 74.87 | B | O |
| ATOM | 2100 | OE2 | GLU | B | 85 | −17.523 | 23.612 | 74.905 | 1.00 | 77.08 | B | O |
| ATOM | 2101 | C | GLU | B | 85 | −12.268 | 21.873 | 74.088 | 1.00 | 68.03 | B | C |
| ATOM | 2102 | O | GLU | B | 85 | −11.913 | 22.139 | 72.941 | 1.00 | 67.91 | B | O |
| ATOM | 2103 | N | LEU | B | 86 | −11.617 | 21.033 | 74.888 | 1.00 | 68.12 | B | N |
| ATOM | 2104 | CA | LEU | B | 86 | −10.596 | 20.118 | 74.386 | 1.00 | 68.46 | B | C |
| ATOM | 2105 | CB | LEU | B | 86 | −9.919 | 19.384 | 75.545 | 1.00 | 67.76 | B | C |
| ATOM | 2106 | CG | LEU | B | 86 | −9.158 | 20.199 | 76.590 | 1.00 | 69.11 | B | C |
| ATOM | 2107 | CD1 | LEU | B | 86 | −8.581 | 19.262 | 77.647 | 1.00 | 68.81 | B | C |
| ATOM | 2108 | CD2 | LEU | B | 86 | −8.042 | 20.986 | 75.925 | 1.00 | 69.76 | B | C |
| ATOM | 2109 | C | LEU | B | 86 | −11.224 | 19.094 | 73.439 | 1.00 | 68.37 | B | C |
| ATOM | 2110 | O | LEU | B | 86 | −11.431 | 17.937 | 73.812 | 1.00 | 68.45 | B | O |
| ATOM | 2111 | N | ASP | B | 87 | −11.523 | 19.524 | 72.214 | 1.00 | 68.42 | B | N |
| ATOM | 2112 | CA | ASP | B | 87 | −12.189 | 18.658 | 71.243 | 1.00 | 68.29 | B | C |
| ATOM | 2113 | CB | ASP | B | 87 | −13.115 | 19.478 | 70.331 | 1.00 | 69.23 | B | C |
| ATOM | 2114 | CG | ASP | B | 87 | −12.384 | 20.100 | 69.150 | 1.00 | 70.44 | B | C |
| ATOM | 2115 | OD1 | ASP | B | 87 | −11.682 | 21.124 | 69.342 | 1.00 | 71.40 | B | O |
| ATOM | 2116 | OD2 | ASP | B | 87 | −12.519 | 19.561 | 68.028 | 1.00 | 69.66 | B | O |
| ATOM | 2117 | C | ASP | B | 87 | −11.166 | 17.906 | 70.397 | 1.00 | 67.76 | B | C |
| ATOM | 2118 | O | ASP | B | 87 | −9.971 | 18.189 | 70.449 | 1.00 | 68.23 | B | O |
| ATOM | 2119 | N | SER | B | 88 | −11.640 | 16.948 | 69.616 | 1.00 | 66.27 | B | N |
| ATOM | 2120 | CA | SER | B | 88 | −10.745 | 16.148 | 68.807 | 1.00 | 65.89 | B | C |
| ATOM | 2121 | CB | SER | B | 88 | −11.562 | 15.206 | 67.919 | 1.00 | 65.38 | B | C |
| ATOM | 2122 | OG | SER | B | 88 | −10.746 | 14.217 | 67.324 | 1.00 | 66.14 | B | O |
| ATOM | 2123 | C | SER | B | 88 | −9.817 | 17.032 | 67.952 | 1.00 | 65.57 | B | C |
| ATOM | 2124 | O | SER | B | 88 | −8.677 | 16.661 | 67.694 | 1.00 | 65.55 | B | O |
| ATOM | 2125 | N | ALA | B | 89 | −10.287 | 18.200 | 67.523 | 1.00 | 64.38 | B | N |
| ATOM | 2126 | CA | ALA | B | 89 | −9.466 | 19.052 | 66.666 | 1.00 | 64.16 | B | C |
| ATOM | 2127 | CB | ALA | B | 89 | −10.288 | 20.201 | 66.094 | 1.00 | 64.16 | B | C |
| ATOM | 2128 | C | ALA | B | 89 | −8.310 | 19.609 | 67.466 | 1.00 | 64.27 | B | C |
| ATOM | 2129 | O | ALA | B | 89 | −7.140 | 19.309 | 67.204 | 1.00 | 65.09 | B | O |
| ATOM | 2130 | N | THR | B | 90 | −8.647 | 20.428 | 68.454 | 1.00 | 63.40 | B | N |
| ATOM | 2131 | CA | THR | B | 90 | −7.634 | 21.062 | 69.283 | 1.00 | 61.60 | B | C |
| ATOM | 2132 | CB | THR | B | 90 | −8.265 | 21.824 | 70.453 | 1.00 | 60.90 | B | C |
| ATOM | 2133 | OG1 | THR | B | 90 | −9.263 | 22.727 | 69.962 | 1.00 | 61.09 | B | O |
| ATOM | 2134 | CG2 | THR | B | 90 | −7.196 | 22.606 | 71.193 | 1.00 | 59.84 | B | C |
| ATOM | 2135 | C | THR | B | 90 | −6.733 | 19.985 | 69.859 | 1.00 | 60.76 | B | C |
| ATOM | 2136 | O | THR | B | 90 | −5.541 | 20.205 | 70.039 | 1.00 | 61.25 | B | O |
| ATOM | 2137 | N | LEU | B | 91 | −7.318 | 18.822 | 70.142 | 1.00 | 60.27 | B | N |
| ATOM | 2138 | CA | LEU | B | 91 | −6.615 | 17.747 | 70.832 | 1.00 | 59.27 | B | C |
| ATOM | 2139 | CB | LEU | B | 91 | −7.592 | 16.630 | 71.212 | 1.00 | 58.33 | B | C |
| ATOM | 2140 | CG | LEU | B | 91 | −7.413 | 15.944 | 72.573 | 1.00 | 57.71 | B | C |
| ATOM | 2141 | CD1 | LEU | B | 91 | −7.680 | 16.952 | 73.663 | 1.00 | 57.34 | B | C |
| ATOM | 2142 | CD2 | LEU | B | 91 | −8.372 | 14.771 | 72.711 | 1.00 | 57.54 | B | C |
| ATOM | 2143 | C | LEU | B | 91 | −5.545 | 17.206 | 69.893 | 1.00 | 59.31 | B | C |
| ATOM | 2144 | O | LEU | B | 91 | −4.561 | 16.598 | 70.323 | 1.00 | 57.85 | B | O |
| ATOM | 2145 | N | LYS | B | 92 | −5.745 | 17.439 | 68.600 | 1.00 | 59.01 | B | N |
| ATOM | 2146 | CA | LYS | B | 92 | −4.753 | 17.059 | 67.614 | 1.00 | 59.15 | B | C |
| ATOM | 2147 | CB | LYS | B | 92 | −5.408 | 16.746 | 66.260 | 1.00 | 60.11 | B | C |

TABLE 11-continued

Coordinates for pro MMP9(35-444 ΔFnII) (SEQ ID NO: 12) complex with Example 1

| ATOM | 2148 | CG | LYS | B | 92 | −4.532 | 15.902 | 65.315 | 1.00 | 61.79 | B | C |
|------|------|-----|-----|---|-----|--------|--------|--------|------|-------|---|---|
| ATOM | 2149 | CD | LYS | B | 92 | −5.043 | 15.942 | 63.865 | 1.00 | 62.34 | B | C |
| ATOM | 2150 | CE | LYS | B | 92 | −3.922 | 16.193 | 62.854 | 1.00 | 61.30 | B | C |
| ATOM | 2151 | NZ | LYS | B | 92 | −4.480 | 16.472 | 61.504 | 1.00 | 61.09 | B | N |
| ATOM | 2152 | C | LYS | B | 92 | −3.750 | 18.188 | 67.455 | 1.00 | 58.04 | B | C |
| ATOM | 2153 | O | LYS | B | 92 | −2.541 | 17.950 | 67.379 | 1.00 | 59.11 | B | O |
| ATOM | 2154 | N | ALA | B | 93 | −4.233 | 19.422 | 67.419 | 1.00 | 56.13 | B | N |
| ATOM | 2155 | CA | ALA | B | 93 | −3.320 | 20.536 | 67.208 | 1.00 | 55.38 | B | C |
| ATOM | 2156 | CB | ALA | B | 93 | −4.052 | 21.868 | 67.404 | 1.00 | 54.41 | B | C |
| ATOM | 2157 | C | ALA | B | 93 | −2.146 | 20.426 | 68.182 | 1.00 | 54.25 | B | C |
| ATOM | 2158 | O | ALA | B | 93 | −0.984 | 20.600 | 67.800 | 1.00 | 53.19 | B | O |
| ATOM | 2159 | N | MET | B | 94 | −2.463 | 20.112 | 69.438 | 1.00 | 54.33 | B | N |
| ATOM | 2160 | CA | MET | B | 94 | −1.475 | 20.105 | 70.518 | 1.00 | 54.32 | B | C |
| ATOM | 2161 | CB | MET | B | 94 | −2.187 | 20.187 | 71.865 | 1.00 | 54.57 | B | C |
| ATOM | 2162 | CG | MET | B | 94 | −2.912 | 21.495 | 72.085 | 1.00 | 55.46 | B | C |
| ATOM | 2163 | SD | MET | B | 94 | −4.430 | 21.279 | 73.060 | 1.00 | 59.01 | B | S |
| ATOM | 2164 | CE | MET | B | 94 | −4.108 | 22.396 | 74.457 | 1.00 | 57.26 | B | C |
| ATOM | 2165 | C | MET | B | 94 | −0.593 | 18.865 | 70.478 | 1.00 | 54.68 | B | C |
| ATOM | 2166 | O | MET | B | 94 | 0.525 | 18.860 | 71.001 | 1.00 | 55.26 | B | O |
| ATOM | 2167 | N | ARG | B | 95 | −1.111 | 17.818 | 69.849 | 1.00 | 54.49 | B | N |
| ATOM | 2168 | CA | ARG | B | 95 | −0.433 | 16.528 | 69.765 | 1.00 | 53.38 | B | C |
| ATOM | 2169 | CB | ARG | B | 95 | −1.432 | 15.462 | 69.302 | 1.00 | 55.43 | B | C |
| ATOM | 2170 | CG | ARG | B | 95 | −1.275 | 14.112 | 69.962 | 1.00 | 56.55 | B | C |
| ATOM | 2171 | CD | ARG | B | 95 | −2.620 | 13.441 | 70.086 | 1.00 | 59.84 | B | C |
| ATOM | 2172 | NE | ARG | B | 95 | −3.233 | 13.690 | 71.391 | 1.00 | 64.42 | B | N |
| ATOM | 2173 | CZ | ARG | B | 95 | −4.533 | 13.562 | 71.646 | 1.00 | 65.28 | B | C |
| ATOM | 2174 | NH1 | ARG | B | 95 | −5.361 | 13.190 | 70.677 | 1.00 | 65.14 | B | N |
| ATOM | 2175 | NH2 | ARG | B | 95 | −5.004 | 13.792 | 72.868 | 1.00 | 65.12 | B | N |
| ATOM | 2176 | C | ARG | B | 95 | 0.717 | 16.627 | 68.775 | 1.00 | 51.01 | B | C |
| ATOM | 2177 | O | ARG | B | 95 | 1.780 | 16.051 | 68.987 | 1.00 | 51.64 | B | O |
| ATOM | 2178 | N | THR | B | 96 | 0.492 | 17.376 | 67.701 | 1.00 | 48.27 | B | N |
| ATOM | 2179 | CA | THR | B | 96 | 1.465 | 17.522 | 66.634 | 1.00 | 46.45 | B | C |
| ATOM | 2180 | CB | THR | B | 96 | 0.725 | 18.021 | 65.331 | 1.00 | 47.46 | B | C |
| ATOM | 2181 | OG1 | THR | B | 96 | 1.669 | 18.531 | 64.381 | 1.00 | 50.40 | B | O |
| ATOM | 2182 | CG2 | THR | B | 96 | −0.311 | 19.079 | 65.659 | 1.00 | 47.39 | B | C |
| ATOM | 2183 | C | THR | B | 96 | 2.686 | 18.406 | 66.986 | 1.00 | 44.27 | B | C |
| ATOM | 2184 | O | THR | B | 96 | 2.569 | 19.427 | 67.662 | 1.00 | 40.44 | B | O |
| ATOM | 2185 | N | PRO | B | 97 | 3.884 | 17.981 | 66.544 | 1.00 | 43.87 | B | N |
| ATOM | 2186 | CD | PRO | B | 97 | 4.038 | 16.669 | 65.894 | 1.00 | 42.64 | B | C |
| ATOM | 2187 | CA | PRO | B | 97 | 5.174 | 18.679 | 66.675 | 1.00 | 43.84 | B | C |
| ATOM | 2188 | CB | PRO | B | 97 | 6.137 | 17.815 | 65.873 | 1.00 | 43.21 | B | C |
| ATOM | 2189 | CG | PRO | B | 97 | 5.517 | 16.457 | 65.916 | 1.00 | 44.59 | B | C |
| ATOM | 2190 | C | PRO | B | 97 | 5.144 | 20.099 | 66.138 | 1.00 | 44.58 | B | C |
| ATOM | 2191 | O | PRO | B | 97 | 4.557 | 20.359 | 65.097 | 1.00 | 46.08 | B | O |
| ATOM | 2192 | N | ARG | B | 98 | 5.787 | 21.018 | 66.843 | 1.00 | 42.67 | B | N |
| ATOM | 2193 | CA | ARG | B | 98 | 5.762 | 22.407 | 66.438 | 1.00 | 41.79 | B | C |
| ATOM | 2194 | CB | ARG | B | 98 | 4.597 | 23.115 | 67.080 | 1.00 | 39.57 | B | C |
| ATOM | 2195 | CG | ARG | B | 98 | 4.658 | 23.024 | 68.585 | 1.00 | 38.84 | B | C |
| ATOM | 2196 | CD | ARG | B | 98 | 3.626 | 23.918 | 69.214 | 1.00 | 36.53 | B | C |
| ATOM | 2197 | NE | ARG | B | 98 | 4.069 | 25.297 | 69.136 | 1.00 | 37.53 | B | N |
| ATOM | 2198 | CZ | ARG | B | 98 | 3.326 | 26.340 | 69.468 | 1.00 | 38.37 | B | C |
| ATOM | 2199 | NH1 | ARG | B | 98 | 2.092 | 26.166 | 69.904 | 1.00 | 41.50 | B | N |
| ATOM | 2200 | NH2 | ARG | B | 98 | 3.824 | 27.558 | 69.369 | 1.00 | 38.22 | B | N |
| ATOM | 2201 | C | ARG | B | 98 | 7.034 | 23.102 | 66.858 | 1.00 | 42.54 | B | C |
| ATOM | 2202 | O | ARG | B | 98 | 8.035 | 22.462 | 67.193 | 1.00 | 43.92 | B | O |
| ATOM | 2203 | N | CYS | B | 99 | 6.977 | 24.427 | 66.850 | 1.00 | 40.74 | B | N |
| ATOM | 2204 | CA | CYS | B | 99 | 8.104 | 25.267 | 67.216 | 1.00 | 39.39 | B | C |
| ATOM | 2205 | CB | CYS | B | 99 | 8.134 | 26.466 | 66.263 | 1.00 | 34.48 | B | C |
| ATOM | 2206 | SG | CYS | B | 99 | 9.125 | 27.822 | 66.800 | 1.00 | 30.47 | B | S |
| ATOM | 2207 | C | CYS | B | 99 | 8.004 | 25.720 | 68.693 | 1.00 | 41.89 | B | C |
| ATOM | 2208 | O | CYS | B | 99 | 6.902 | 25.912 | 69.227 | 1.00 | 42.28 | B | O |
| ATOM | 2209 | N | GLY | B | 100 | 9.152 | 25.881 | 69.350 | 1.00 | 41.35 | B | N |
| ATOM | 2210 | CA | GLY | B | 100 | 9.154 | 26.116 | 70.785 | 1.00 | 41.80 | B | C |
| ATOM | 2211 | C | GLY | B | 100 | 8.884 | 27.560 | 71.137 | 1.00 | 41.15 | B | C |
| ATOM | 2212 | O | GLY | B | 100 | 8.399 | 27.889 | 72.211 | 1.00 | 42.29 | B | O |
| ATOM | 2213 | N | VAL | B | 101 | 9.193 | 28.444 | 70.218 | 1.00 | 40.80 | B | N |
| ATOM | 2214 | CA | VAL | B | 101 | 8.910 | 29.842 | 70.444 | 1.00 | 41.25 | B | C |
| ATOM | 2215 | CB | VAL | B | 101 | 9.397 | 30.645 | 69.242 | 1.00 | 40.41 | B | C |
| ATOM | 2216 | CG1 | VAL | B | 101 | 8.802 | 32.037 | 69.273 | 1.00 | 40.34 | B | C |
| ATOM | 2217 | CG2 | VAL | B | 101 | 10.941 | 30.708 | 69.269 | 1.00 | 39.99 | B | C |
| ATOM | 2218 | C | VAL | B | 101 | 7.428 | 30.153 | 70.721 | 1.00 | 41.68 | B | C |
| ATOM | 2219 | O | VAL | B | 101 | 6.537 | 29.692 | 70.021 | 1.00 | 43.24 | B | O |
| ATOM | 2220 | N | PRO | B | 102 | 7.146 | 30.958 | 71.747 | 1.00 | 40.72 | B | N |
| ATOM | 2221 | CD | PRO | B | 102 | 8.053 | 31.428 | 72.806 | 1.00 | 39.17 | B | C |
| ATOM | 2222 | CA | PRO | B | 102 | 5.733 | 31.226 | 72.061 | 1.00 | 39.57 | B | C |
| ATOM | 2223 | CB | PRO | B | 102 | 5.799 | 31.977 | 73.392 | 1.00 | 39.49 | B | C |
| ATOM | 2224 | CG | PRO | B | 102 | 7.129 | 31.569 | 73.987 | 1.00 | 39.01 | B | C |
| ATOM | 2225 | C | PRO | B | 102 | 4.968 | 32.010 | 70.988 | 1.00 | 36.64 | B | C |

TABLE 11-continued

Coordinates for pro MMP9(35-444 ΔFnII) (SEQ ID NO: 12) complex with Example 1

| ATOM | 2226 | O   | PRO | B | 102 | 3.737  | 32.133 | 71.049 | 1.00 | 35.95 | B | O |
|------|------|-----|-----|---|-----|--------|--------|--------|------|-------|---|---|
| ATOM | 2227 | N   | THR | B | 109 | 11.901 | 38.959 | 77.442 | 1.00 | 55.11 | B | N |
| ATOM | 2228 | CA  | THR | B | 109 | 12.364 | 40.350 | 77.502 | 1.00 | 55.36 | B | C |
| ATOM | 2229 | CB  | THR | B | 109 | 12.645 | 40.798 | 78.940 | 1.00 | 56.98 | B | C |
| ATOM | 2230 | OG1 | THR | B | 109 | 11.408 | 40.938 | 79.664 | 1.00 | 56.86 | B | O |
| ATOM | 2231 | CG2 | THR | B | 109 | 13.405 | 42.124 | 78.923 | 1.00 | 57.52 | B | C |
| ATOM | 2232 | C   | THR | B | 109 | 13.638 | 40.580 | 76.714 | 1.00 | 54.54 | B | C |
| ATOM | 2233 | O   | THR | B | 109 | 14.687 | 40.031 | 77.044 | 1.00 | 54.74 | B | O |
| ATOM | 2234 | N   | PHE | B | 110 | 13.552 | 41.420 | 75.691 | 1.00 | 53.48 | B | N |
| ATOM | 2235 | CA  | PHE | B | 110 | 14.602 | 41.495 | 74.679 | 1.00 | 51.99 | B | C |
| ATOM | 2236 | CB  | PHE | B | 110 | 14.096 | 40.918 | 73.362 | 1.00 | 48.67 | B | C |
| ATOM | 2237 | CG  | PHE | B | 110 | 14.026 | 39.453 | 73.351 | 1.00 | 46.48 | B | C |
| ATOM | 2238 | CD1 | PHE | B | 110 | 12.819 | 38.816 | 73.194 | 1.00 | 47.06 | B | C |
| ATOM | 2239 | CD2 | PHE | B | 110 | 15.177 | 38.704 | 73.503 | 1.00 | 46.90 | B | C |
| ATOM | 2240 | CE1 | PHE | B | 110 | 12.757 | 37.444 | 73.187 | 1.00 | 48.71 | B | C |
| ATOM | 2241 | CE2 | PHE | B | 110 | 15.129 | 37.335 | 73.498 | 1.00 | 48.40 | B | C |
| ATOM | 2242 | CZ  | PHE | B | 110 | 13.918 | 36.695 | 73.340 | 1.00 | 48.41 | B | C |
| ATOM | 2243 | C   | PHE | B | 110 | 15.103 | 42.897 | 74.421 | 1.00 | 52.26 | B | C |
| ATOM | 2244 | O   | PHE | B | 110 | 14.465 | 43.875 | 74.791 | 1.00 | 52.08 | B | O |
| ATOM | 2245 | N   | GLU | B | 111 | 16.244 | 42.984 | 73.756 | 1.00 | 53.92 | B | N |
| ATOM | 2246 | CA  | GLU | B | 111 | 16.878 | 44.268 | 73.512 | 1.00 | 55.45 | B | C |
| ATOM | 2247 | CB  | GLU | B | 111 | 18.330 | 44.190 | 73.972 | 1.00 | 57.42 | B | C |
| ATOM | 2248 | CG  | GLU | B | 111 | 18.977 | 45.521 | 74.243 | 1.00 | 60.30 | B | C |
| ATOM | 2249 | CD  | GLU | B | 111 | 20.374 | 45.362 | 74.804 | 1.00 | 62.77 | B | C |
| ATOM | 2250 | OE1 | GLU | B | 111 | 20.674 | 44.242 | 75.293 | 1.00 | 63.66 | B | O |
| ATOM | 2251 | OE2 | GLU | B | 111 | 21.166 | 46.345 | 74.756 | 1.00 | 62.77 | B | O |
| ATOM | 2252 | C   | GLU | B | 111 | 16.804 | 44.720 | 72.039 | 1.00 | 55.15 | B | C |
| ATOM | 2253 | O   | GLU | B | 111 | 17.178 | 43.980 | 71.122 | 1.00 | 56.14 | B | O |
| ATOM | 2254 | N   | GLY | B | 112 | 16.300 | 45.937 | 71.832 | 1.00 | 55.02 | B | N |
| ATOM | 2255 | CA  | GLY | B | 112 | 16.349 | 46.568 | 70.523 | 1.00 | 52.56 | B | C |
| ATOM | 2256 | C   | GLY | B | 112 | 15.042 | 46.656 | 69.744 | 1.00 | 51.35 | B | C |
| ATOM | 2257 | O   | GLY | B | 112 | 13.982 | 46.285 | 70.237 | 1.00 | 50.10 | B | O |
| ATOM | 2258 | N   | ASP | B | 113 | 15.138 | 47.165 | 68.517 | 1.00 | 51.06 | B | N |
| ATOM | 2259 | CA  | ASP | B | 113 | 14.068 | 47.105 | 67.533 | 1.00 | 50.58 | B | C |
| ATOM | 2260 | CB  | ASP | B | 113 | 14.523 | 47.776 | 66.243 | 1.00 | 53.82 | B | C |
| ATOM | 2261 | CG  | ASP | B | 113 | 14.107 | 49.203 | 66.180 | 1.00 | 58.14 | B | C |
| ATOM | 2262 | OD1 | ASP | B | 113 | 13.707 | 49.721 | 67.249 | 1.00 | 61.51 | B | O |
| ATOM | 2263 | OD2 | ASP | B | 113 | 14.167 | 49.805 | 65.084 | 1.00 | 59.88 | B | O |
| ATOM | 2264 | C   | ASP | B | 113 | 13.579 | 45.703 | 67.187 | 1.00 | 48.96 | B | C |
| ATOM | 2265 | O   | ASP | B | 113 | 12.497 | 45.545 | 66.610 | 1.00 | 46.57 | B | O |
| ATOM | 2266 | N   | LEU | B | 114 | 14.386 | 44.699 | 67.510 | 1.00 | 48.26 | B | N |
| ATOM | 2267 | CA  | LEU | B | 114 | 14.121 | 43.342 | 67.072 | 1.00 | 49.73 | B | C |
| ATOM | 2268 | CB  | LEU | B | 114 | 12.821 | 42.813 | 67.702 | 1.00 | 49.40 | B | C |
| ATOM | 2269 | CG  | LEU | B | 114 | 12.626 | 42.973 | 69.218 | 1.00 | 47.95 | B | C |
| ATOM | 2270 | CD1 | LEU | B | 114 | 11.433 | 42.157 | 69.698 | 1.00 | 45.23 | B | C |
| ATOM | 2271 | CD2 | LEU | B | 114 | 13.881 | 42.517 | 69.913 | 1.00 | 47.54 | B | C |
| ATOM | 2272 | C   | LEU | B | 114 | 14.017 | 43.277 | 65.537 | 1.00 | 50.53 | B | C |
| ATOM | 2273 | O   | LEU | B | 114 | 13.256 | 42.463 | 64.992 | 1.00 | 52.04 | B | O |
| ATOM | 2274 | N   | LYS | B | 115 | 14.752 | 44.168 | 64.861 | 1.00 | 51.89 | B | N |
| ATOM | 2275 | CA  | LYS | B | 115 | 15.076 | 44.076 | 63.431 | 1.00 | 49.99 | B | C |
| ATOM | 2276 | CB  | LYS | B | 115 | 14.399 | 45.186 | 62.607 | 1.00 | 51.78 | B | C |
| ATOM | 2277 | CG  | LYS | B | 115 | 12.901 | 45.018 | 62.360 | 1.00 | 52.75 | B | C |
| ATOM | 2278 | CD  | LYS | B | 115 | 12.336 | 46.045 | 61.343 | 1.00 | 52.50 | B | C |
| ATOM | 2279 | CE  | LYS | B | 115 | 12.725 | 47.494 | 61.646 | 1.00 | 49.79 | B | C |
| ATOM | 2280 | NZ  | LYS | B | 115 | 14.069 | 47.806 | 61.114 | 1.00 | 47.18 | B | N |
| ATOM | 2281 | C   | LYS | B | 115 | 16.587 | 44.231 | 63.259 | 1.00 | 49.76 | B | C |
| ATOM | 2282 | O   | LYS | B | 115 | 17.306 | 44.552 | 64.204 | 1.00 | 49.70 | B | O |
| ATOM | 2283 | N   | TRP | B | 116 | 17.063 | 44.027 | 62.037 | 1.00 | 49.31 | B | N |
| ATOM | 2284 | CA  | TRP | B | 116 | 18.464 | 44.226 | 61.742 | 1.00 | 47.10 | B | C |
| ATOM | 2285 | CB  | TRP | B | 116 | 18.895 | 43.219 | 60.708 | 1.00 | 45.52 | B | C |
| ATOM | 2286 | CG  | TRP | B | 116 | 18.903 | 41.842 | 61.269 | 1.00 | 45.03 | B | C |
| ATOM | 2287 | CD2 | TRP | B | 116 | 19.886 | 41.288 | 62.142 | 1.00 | 43.32 | B | C |
| ATOM | 2288 | CE2 | TRP | B | 116 | 19.517 | 39.946 | 62.385 | 1.00 | 44.57 | B | C |
| ATOM | 2289 | CE3 | TRP | B | 116 | 21.039 | 41.795 | 62.740 | 1.00 | 40.58 | B | C |
| ATOM | 2290 | CD1 | TRP | B | 116 | 17.994 | 40.846 | 61.027 | 1.00 | 45.95 | B | C |
| ATOM | 2291 | NE1 | TRP | B | 116 | 18.358 | 39.702 | 61.693 | 1.00 | 45.13 | B | N |
| ATOM | 2292 | CZ2 | TRP | B | 116 | 20.271 | 39.103 | 63.202 | 1.00 | 43.39 | B | C |
| ATOM | 2293 | CZ3 | TRP | B | 116 | 21.780 | 40.972 | 63.544 | 1.00 | 41.21 | B | C |
| ATOM | 2294 | CH2 | TRP | B | 116 | 21.395 | 39.629 | 63.772 | 1.00 | 42.59 | B | C |
| ATOM | 2295 | C   | TRP | B | 116 | 18.717 | 45.630 | 61.264 | 1.00 | 47.50 | B | C |
| ATOM | 2296 | O   | TRP | B | 116 | 17.860 | 46.251 | 60.631 | 1.00 | 48.31 | B | O |
| ATOM | 2297 | N   | HIS | B | 117 | 19.893 | 46.158 | 61.565 | 1.00 | 48.67 | B | N |
| ATOM | 2298 | CA  | HIS | B | 117 | 20.149 | 47.527 | 61.156 | 1.00 | 49.40 | B | C |
| ATOM | 2299 | CB  | HIS | B | 117 | 20.297 | 48.407 | 62.397 | 1.00 | 50.74 | B | C |
| ATOM | 2300 | CG  | HIS | B | 117 | 19.004 | 48.620 | 63.132 | 1.00 | 51.22 | B | C |
| ATOM | 2301 | CD2 | HIS | B | 117 | 17.884 | 49.306 | 62.792 | 1.00 | 51.17 | B | C |
| ATOM | 2302 | ND1 | HIS | B | 117 | 18.755 | 48.080 | 64.377 | 1.00 | 51.48 | B | N |
| ATOM | 2303 | CE1 | HIS | B | 117 | 17.541 | 48.425 | 64.773 | 1.00 | 51.43 | B | C |

TABLE 11-continued

Coordinates for pro MMP9(35-444 ΔFnII) (SEQ ID NO: 12) complex with Example 1

| ATOM | 2304 | NE2 | HIS | B | 117 | 16.991 | 49.170 | 63.830 | 1.00 | 51.55 | B | N |
|---|---|---|---|---|---|---|---|---|---|---|---|---|
| ATOM | 2305 | C | HIS | B | 117 | 21.335 | 47.665 | 60.205 | 1.00 | 48.49 | B | C |
| ATOM | 2306 | O | HIS | B | 117 | 21.782 | 48.778 | 59.907 | 1.00 | 48.60 | B | O |
| ATOM | 2307 | N | HIS | B | 118 | 21.821 | 46.520 | 59.718 | 1.00 | 48.21 | B | N |
| ATOM | 2308 | CA | HIS | B | 118 | 22.772 | 46.477 | 58.608 | 1.00 | 46.67 | B | C |
| ATOM | 2309 | CB | HIS | B | 118 | 24.161 | 46.088 | 59.104 | 1.00 | 46.05 | B | C |
| ATOM | 2310 | CG | HIS | B | 118 | 24.166 | 44.915 | 60.025 | 1.00 | 47.16 | B | C |
| ATOM | 2311 | CD2 | HIS | B | 118 | 24.582 | 43.639 | 59.844 | 1.00 | 48.01 | B | C |
| ATOM | 2312 | ND1 | HIS | B | 118 | 23.663 | 44.977 | 61.307 | 1.00 | 47.95 | B | N |
| ATOM | 2313 | CE1 | HIS | B | 118 | 23.765 | 43.789 | 61.876 | 1.00 | 49.06 | B | C |
| ATOM | 2314 | NE2 | HIS | B | 118 | 24.319 | 42.959 | 61.010 | 1.00 | 49.48 | B | N |
| ATOM | 2315 | C | HIS | B | 118 | 22.310 | 45.505 | 57.527 | 1.00 | 46.51 | B | C |
| ATOM | 2316 | O | HIS | B | 118 | 21.168 | 45.059 | 57.525 | 1.00 | 45.67 | B | O |
| ATOM | 2317 | N | HIS | B | 119 | 23.179 | 45.192 | 56.583 | 1.00 | 47.29 | B | N |
| ATOM | 2318 | CA | HIS | B | 119 | 22.682 | 44.564 | 55.383 | 1.00 | 48.75 | B | C |
| ATOM | 2319 | CB | HIS | B | 119 | 23.019 | 45.420 | 54.153 | 1.00 | 53.33 | B | C |
| ATOM | 2320 | CG | HIS | B | 119 | 22.176 | 46.653 | 54.035 | 1.00 | 57.38 | B | C |
| ATOM | 2321 | CD2 | HIS | B | 119 | 20.833 | 46.807 | 53.948 | 1.00 | 58.70 | B | C |
| ATOM | 2322 | ND1 | HIS | B | 119 | 22.708 | 47.927 | 54.025 | 1.00 | 59.87 | B | N |
| ATOM | 2323 | CE1 | HIS | B | 119 | 21.729 | 48.812 | 53.938 | 1.00 | 60.33 | B | C |
| ATOM | 2324 | NE2 | HIS | B | 119 | 20.581 | 48.158 | 53.891 | 1.00 | 60.33 | B | N |
| ATOM | 2325 | C | HIS | B | 119 | 23.195 | 43.158 | 55.215 | 1.00 | 47.70 | B | C |
| ATOM | 2326 | O | HIS | B | 119 | 22.442 | 42.261 | 54.841 | 1.00 | 47.36 | B | O |
| ATOM | 2327 | N | ASN | B | 120 | 24.476 | 42.959 | 55.495 | 1.00 | 47.99 | B | N |
| ATOM | 2328 | CA | ASN | B | 120 | 25.040 | 41.622 | 55.409 | 1.00 | 47.22 | B | C |
| ATOM | 2329 | CB | ASN | B | 120 | 26.483 | 41.664 | 54.911 | 1.00 | 48.97 | B | C |
| ATOM | 2330 | CG | ASN | B | 120 | 27.006 | 40.278 | 54.540 | 1.00 | 52.10 | B | C |
| ATOM | 2331 | OD1 | ASN | B | 120 | 26.227 | 39.386 | 54.163 | 1.00 | 53.12 | B | O |
| ATOM | 2332 | ND2 | ASN | B | 120 | 28.327 | 40.085 | 54.650 | 1.00 | 52.17 | B | N |
| ATOM | 2333 | C | ASN | B | 120 | 24.978 | 40.955 | 56.775 | 1.00 | 45.83 | B | C |
| ATOM | 2334 | O | ASN | B | 120 | 25.594 | 41.418 | 57.746 | 1.00 | 45.09 | B | O |
| ATOM | 2335 | N | ILE | B | 121 | 24.214 | 39.869 | 56.839 | 1.00 | 42.91 | B | N |
| ATOM | 2336 | CA | ILE | B | 121 | 24.043 | 39.138 | 58.075 | 1.00 | 41.02 | B | C |
| ATOM | 2337 | CB | ILE | B | 121 | 22.594 | 38.725 | 58.266 | 1.00 | 39.38 | B | C |
| ATOM | 2338 | CG2 | ILE | B | 121 | 22.413 | 38.098 | 59.615 | 1.00 | 38.99 | B | C |
| ATOM | 2339 | CG1 | ILE | B | 121 | 21.711 | 39.963 | 58.225 | 1.00 | 40.20 | B | C |
| ATOM | 2340 | CD1 | ILE | B | 121 | 22.095 | 40.977 | 59.271 | 1.00 | 39.34 | B | C |
| ATOM | 2341 | C | ILE | B | 121 | 24.940 | 37.927 | 58.014 | 1.00 | 40.88 | B | C |
| ATOM | 2342 | O | ILE | B | 121 | 24.981 | 37.237 | 56.999 | 1.00 | 40.80 | B | O |
| ATOM | 2343 | N | THR | B | 122 | 25.696 | 37.694 | 59.082 | 1.00 | 41.16 | B | N |
| ATOM | 2344 | CA | THR | B | 122 | 26.764 | 36.693 | 59.044 | 1.00 | 41.23 | B | C |
| ATOM | 2345 | CB | THR | B | 122 | 28.092 | 37.257 | 59.478 | 1.00 | 41.88 | B | C |
| ATOM | 2346 | OG1 | THR | B | 122 | 27.958 | 37.723 | 60.823 | 1.00 | 42.35 | B | O |
| ATOM | 2347 | CG2 | THR | B | 122 | 28.523 | 38.403 | 58.577 | 1.00 | 41.22 | B | C |
| ATOM | 2348 | C | THR | B | 122 | 26.482 | 35.590 | 60.015 | 1.00 | 39.79 | B | C |
| ATOM | 2349 | O | THR | B | 122 | 26.373 | 35.840 | 61.209 | 1.00 | 41.25 | B | O |
| ATOM | 2350 | N | TYR | B | 123 | 26.415 | 34.368 | 59.499 | 1.00 | 40.55 | B | N |
| ATOM | 2351 | CA | TYR | B | 123 | 26.026 | 33.218 | 60.296 | 1.00 | 39.60 | B | C |
| ATOM | 2352 | CB | TYR | B | 123 | 24.798 | 32.568 | 59.681 | 1.00 | 37.77 | B | C |
| ATOM | 2353 | CG | TYR | B | 123 | 25.057 | 31.795 | 58.409 | 1.00 | 37.99 | B | C |
| ATOM | 2354 | CD1 | TYR | B | 123 | 25.115 | 32.438 | 57.166 | 1.00 | 36.75 | B | C |
| ATOM | 2355 | CE1 | TYR | B | 123 | 25.226 | 31.708 | 55.993 | 1.00 | 36.06 | B | C |
| ATOM | 2356 | CD2 | TYR | B | 123 | 25.136 | 30.403 | 58.434 | 1.00 | 37.82 | B | C |
| ATOM | 2357 | CE2 | TYR | B | 123 | 25.251 | 29.669 | 57.274 | 1.00 | 36.30 | B | C |
| ATOM | 2358 | CZ | TYR | B | 123 | 25.288 | 30.316 | 56.061 | 1.00 | 37.33 | B | C |
| ATOM | 2359 | OH | TYR | B | 123 | 25.340 | 29.545 | 54.920 | 1.00 | 38.75 | B | O |
| ATOM | 2360 | C | TYR | B | 123 | 27.143 | 32.181 | 60.460 | 1.00 | 41.07 | B | C |
| ATOM | 2361 | O | TYR | B | 123 | 27.939 | 31.953 | 59.540 | 1.00 | 39.95 | B | O |
| ATOM | 2362 | N | TRP | B | 124 | 27.176 | 31.574 | 61.651 | 1.00 | 40.96 | B | N |
| ATOM | 2363 | CA | TRP | B | 124 | 28.124 | 30.537 | 62.033 | 1.00 | 41.66 | B | C |
| ATOM | 2364 | CB | TRP | B | 124 | 28.906 | 30.982 | 63.272 | 1.00 | 43.80 | B | C |
| ATOM | 2365 | CG | TRP | B | 124 | 29.970 | 30.003 | 63.712 | 1.00 | 45.96 | B | C |
| ATOM | 2366 | CD2 | TRP | B | 124 | 30.468 | 29.813 | 65.046 | 1.00 | 46.71 | B | C |
| ATOM | 2367 | CE2 | TRP | B | 124 | 31.474 | 28.815 | 64.979 | 1.00 | 45.97 | B | C |
| ATOM | 2368 | CE3 | TRP | B | 124 | 30.169 | 30.390 | 66.290 | 1.00 | 48.17 | B | C |
| ATOM | 2369 | CD1 | TRP | B | 124 | 30.679 | 29.131 | 62.911 | 1.00 | 45.99 | B | C |
| ATOM | 2370 | NE1 | TRP | B | 124 | 31.579 | 28.419 | 63.670 | 1.00 | 45.74 | B | N |
| ATOM | 2371 | CZ2 | TRP | B | 124 | 32.178 | 28.380 | 66.107 | 1.00 | 45.22 | B | C |
| ATOM | 2372 | CZ3 | TRP | B | 124 | 30.879 | 29.951 | 67.422 | 1.00 | 48.24 | B | C |
| ATOM | 2373 | CH2 | TRP | B | 124 | 31.872 | 28.954 | 67.313 | 1.00 | 46.12 | B | C |
| ATOM | 2374 | C | TRP | B | 124 | 27.409 | 29.220 | 62.343 | 1.00 | 42.06 | B | C |
| ATOM | 2375 | O | TRP | B | 124 | 26.587 | 29.154 | 63.258 | 1.00 | 43.39 | B | O |
| ATOM | 2376 | N | ILE | B | 125 | 27.721 | 28.185 | 61.569 | 1.00 | 41.65 | B | N |
| ATOM | 2377 | CA | ILE | B | 125 | 27.308 | 26.816 | 61.871 | 1.00 | 42.68 | B | C |
| ATOM | 2378 | CB | ILE | B | 125 | 27.356 | 25.931 | 60.603 | 1.00 | 43.36 | B | C |
| ATOM | 2379 | CG2 | ILE | B | 125 | 27.028 | 24.485 | 60.949 | 1.00 | 43.97 | B | C |
| ATOM | 2380 | CG1 | ILE | B | 125 | 26.401 | 26.479 | 59.545 | 1.00 | 43.65 | B | C |
| ATOM | 2381 | CD1 | ILE | B | 125 | 26.622 | 25.861 | 58.181 | 1.00 | 41.39 | B | C |

TABLE 11-continued

Coordinates for pro MMP9(35-444 ΔFnII) (SEQ ID NO: 12) complex with Example 1

| ATOM | 2382 | C   | ILE | B | 125 | 28.311 | 26.252 | 62.865 | 1.00 | 41.25 B | C |
| --- | --- | --- | --- | --- | --- | --- | --- | --- | --- | --- | --- |
| ATOM | 2383 | O   | ILE | B | 125 | 29.417 | 25.886 | 62.477 | 1.00 | 42.48 B | O |
| ATOM | 2384 | N   | GLN | B | 126 | 27.929 | 26.176 | 64.139 | 1.00 | 42.10 B | N |
| ATOM | 2385 | CA  | GLN | B | 126 | 28.896 | 25.922 | 65.205 | 1.00 | 40.20 B | C |
| ATOM | 2386 | CB  | GLN | B | 126 | 28.621 | 26.828 | 66.397 | 1.00 | 42.38 B | C |
| ATOM | 2387 | CG  | GLN | B | 126 | 27.681 | 26.225 | 67.407 | 1.00 | 50.00 B | C |
| ATOM | 2388 | CD  | GLN | B | 126 | 27.621 | 27.031 | 68.705 | 1.00 | 54.69 B | C |
| ATOM | 2389 | OE1 | GLN | B | 126 | 26.561 | 27.140 | 69.360 | 1.00 | 56.32 B | O |
| ATOM | 2390 | NE2 | GLN | B | 126 | 28.767 | 27.604 | 69.086 | 1.00 | 58.22 B | N |
| ATOM | 2391 | C   | GLN | B | 126 | 28.992 | 24.480 | 65.690 | 1.00 | 37.48 B | C |
| ATOM | 2392 | O   | GLN | B | 126 | 29.901 | 24.147 | 66.436 | 1.00 | 37.51 B | O |
| ATOM | 2393 | N   | ASN | B | 127 | 28.079 | 23.616 | 65.276 | 0.50 | 38.49 B | N |
| ATOM | 2394 | CA  | ASN | B | 127 | 28.297 | 22.193 | 65.480 | 0.50 | 38.69 B | C |
| ATOM | 2395 | CB  | ASN | B | 127 | 28.032 | 21.790 | 66.928 | 0.50 | 37.72 B | C |
| ATOM | 2396 | CG  | ASN | B | 127 | 26.736 | 22.337 | 67.446 | 0.50 | 37.87 B | C |
| ATOM | 2397 | OD1 | ASN | B | 127 | 26.115 | 23.192 | 66.815 | 0.50 | 39.08 B | O |
| ATOM | 2398 | ND2 | ASN | B | 127 | 26.315 | 21.858 | 68.602 | 0.50 | 36.28 B | N |
| ATOM | 2399 | C   | ASN | B | 127 | 27.397 | 21.426 | 64.550 | 0.50 | 40.83 B | C |
| ATOM | 2400 | O   | ASN | B | 127 | 26.567 | 22.021 | 63.874 | 0.50 | 41.26 B | O |
| ATOM | 2401 | N   | TYR | B | 128 | 27.565 | 20.108 | 64.507 | 1.00 | 43.09 B | N |
| ATOM | 2402 | CA  | TYR | B | 128 | 26.925 | 19.295 | 63.478 | 1.00 | 43.60 B | C |
| ATOM | 2403 | CB  | TYR | B | 128 | 27.962 | 18.825 | 62.466 | 1.00 | 45.04 B | C |
| ATOM | 2404 | CG  | TYR | B | 128 | 28.287 | 19.841 | 61.391 | 1.00 | 47.51 B | C |
| ATOM | 2405 | CD1 | TYR | B | 128 | 27.538 | 19.905 | 60.215 | 1.00 | 48.05 B | C |
| ATOM | 2406 | CE1 | TYR | B | 128 | 27.866 | 20.800 | 59.199 | 1.00 | 48.73 B | C |
| ATOM | 2407 | CD2 | TYR | B | 128 | 29.373 | 20.707 | 61.528 | 1.00 | 47.75 B | C |
| ATOM | 2408 | CE2 | TYR | B | 128 | 29.709 | 21.604 | 60.524 | 1.00 | 47.49 B | C |
| ATOM | 2409 | CZ  | TYR | B | 128 | 28.954 | 21.645 | 59.358 | 1.00 | 48.46 B | C |
| ATOM | 2410 | OH  | TYR | B | 128 | 29.302 | 22.512 | 58.346 | 1.00 | 45.74 B | O |
| ATOM | 2411 | C   | TYR | B | 128 | 26.162 | 18.082 | 63.985 | 1.00 | 44.90 B | C |
| ATOM | 2412 | O   | TYR | B | 128 | 26.713 | 17.211 | 64.664 | 1.00 | 46.03 B | O |
| ATOM | 2413 | N   | SER | B | 129 | 24.890 | 18.001 | 63.624 | 1.00 | 45.04 B | N |
| ATOM | 2414 | CA  | SER | B | 129 | 24.155 | 16.768 | 63.859 | 1.00 | 45.77 B | C |
| ATOM | 2415 | CB  | SER | B | 129 | 22.674 | 16.953 | 63.543 | 1.00 | 43.66 B | C |
| ATOM | 2416 | OG  | SER | B | 129 | 22.025 | 15.702 | 63.584 | 1.00 | 41.28 B | O |
| ATOM | 2417 | C   | SER | B | 129 | 24.727 | 15.646 | 62.994 | 1.00 | 47.15 B | C |
| ATOM | 2418 | O   | SER | B | 129 | 25.471 | 15.883 | 62.041 | 1.00 | 47.19 B | O |
| ATOM | 2419 | N   | GLU | B | 130 | 24.371 | 14.415 | 63.320 | 1.00 | 49.17 B | N |
| ATOM | 2420 | CA  | GLU | B | 130 | 25.013 | 13.284 | 62.676 | 1.00 | 51.22 B | C |
| ATOM | 2421 | CB  | GLU | B | 130 | 25.649 | 12.380 | 63.734 | 1.00 | 53.34 B | C |
| ATOM | 2422 | CG  | GLU | B | 130 | 26.603 | 13.112 | 64.677 | 1.00 | 57.56 B | C |
| ATOM | 2423 | CD  | GLU | B | 130 | 28.058 | 12.690 | 64.510 | 1.00 | 60.18 B | C |
| ATOM | 2424 | OE1 | GLU | B | 130 | 28.325 | 11.467 | 64.547 | 1.00 | 62.12 B | O |
| ATOM | 2425 | OE2 | GLU | B | 130 | 28.937 | 13.582 | 64.348 | 1.00 | 61.07 B | O |
| ATOM | 2426 | C   | GLU | B | 130 | 24.074 | 12.475 | 61.795 | 1.00 | 50.78 B | C |
| ATOM | 2427 | O   | GLU | B | 130 | 24.471 | 11.444 | 61.258 | 1.00 | 50.80 B | O |
| ATOM | 2428 | N   | ASP | B | 131 | 22.834 | 12.940 | 61.643 | 1.00 | 51.25 B | N |
| ATOM | 2429 | CA  | ASP | B | 131 | 21.857 | 12.245 | 60.793 | 1.00 | 50.61 B | C |
| ATOM | 2430 | CB  | ASP | B | 131 | 20.439 | 12.644 | 61.187 | 1.00 | 50.45 B | C |
| ATOM | 2431 | CG  | ASP | B | 131 | 20.181 | 12.454 | 62.666 | 1.00 | 51.11 B | C |
| ATOM | 2432 | OD1 | ASP | B | 131 | 20.983 | 11.731 | 63.312 | 1.00 | 51.11 B | O |
| ATOM | 2433 | OD2 | ASP | B | 131 | 19.184 | 13.026 | 63.174 | 1.00 | 48.43 B | O |
| ATOM | 2434 | C   | ASP | B | 131 | 22.085 | 12.536 | 59.313 | 1.00 | 51.33 B | C |
| ATOM | 2435 | O   | ASP | B | 131 | 21.681 | 11.754 | 58.444 | 1.00 | 51.91 B | O |
| ATOM | 2436 | N   | LEU | B | 132 | 22.736 | 13.667 | 59.044 | 1.00 | 49.15 B | N |
| ATOM | 2437 | CA  | LEU | B | 132 | 23.142 | 14.041 | 57.700 | 1.00 | 46.80 B | C |
| ATOM | 2438 | CB  | LEU | B | 132 | 22.478 | 15.363 | 57.317 | 1.00 | 45.75 B | C |
| ATOM | 2439 | CG  | LEU | B | 132 | 20.949 | 15.419 | 57.303 | 1.00 | 43.95 B | C |
| ATOM | 2440 | CD1 | LEU | B | 132 | 20.505 | 16.844 | 57.096 | 1.00 | 43.72 B | C |
| ATOM | 2441 | CD2 | LEU | B | 132 | 20.407 | 14.557 | 56.180 | 1.00 | 44.26 B | C |
| ATOM | 2442 | C   | LEU | B | 132 | 24.665 | 14.187 | 57.632 | 1.00 | 46.69 B | C |
| ATOM | 2443 | O   | LEU | B | 132 | 25.318 | 14.447 | 58.640 | 1.00 | 47.59 B | O |
| ATOM | 2444 | N   | PRO | B | 133 | 25.251 | 14.007 | 56.437 | 1.00 | 46.39 B | N |
| ATOM | 2445 | CD  | PRO | B | 133 | 24.677 | 13.251 | 55.310 | 1.00 | 46.66 B | C |
| ATOM | 2446 | CA  | PRO | B | 133 | 26.642 | 14.402 | 56.146 | 1.00 | 46.99 B | C |
| ATOM | 2447 | CB  | PRO | B | 133 | 26.891 | 13.923 | 54.747 | 1.00 | 45.70 B | C |
| ATOM | 2448 | CG  | PRO | B | 133 | 25.892 | 12.823 | 54.539 | 1.00 | 45.43 B | C |
| ATOM | 2449 | C   | PRO | B | 133 | 26.803 | 15.915 | 56.303 | 1.00 | 47.78 B | C |
| ATOM | 2450 | O   | PRO | B | 133 | 25.861 | 16.666 | 56.022 | 1.00 | 47.82 B | O |
| ATOM | 2451 | N   | ARG | B | 134 | 27.993 | 16.360 | 56.717 | 1.00 | 49.83 B | N |
| ATOM | 2452 | CA  | ARG | B | 134 | 28.256 | 17.789 | 56.990 | 1.00 | 49.68 B | C |
| ATOM | 2453 | CB  | ARG | B | 134 | 29.678 | 17.987 | 57.528 | 1.00 | 51.29 B | C |
| ATOM | 2454 | CG  | ARG | B | 134 | 29.844 | 17.752 | 59.007 | 1.00 | 53.28 B | C |
| ATOM | 2455 | CD  | ARG | B | 134 | 31.135 | 18.400 | 59.511 | 1.00 | 54.49 B | C |
| ATOM | 2456 | NE  | ARG | B | 134 | 31.377 | 18.104 | 60.919 | 1.00 | 55.78 B | N |
| ATOM | 2457 | CZ  | ARG | B | 134 | 32.244 | 18.751 | 61.689 | 1.00 | 56.23 B | C |
| ATOM | 2458 | NH1 | ARG | B | 134 | 32.965 | 19.747 | 61.183 | 1.00 | 55.60 B | N |
| ATOM | 2459 | NH2 | ARG | B | 134 | 32.382 | 18.404 | 62.968 | 1.00 | 57.18 B | N |

TABLE 11-continued

Coordinates for pro MMP9(35-444 ΔFnII) (SEQ ID NO: 12) complex with Example 1

| ATOM | 2460 | C   | ARG | B | 134 | 28.072 | 18.738 | 55.801 | 1.00 | 47.81 | B | C |
| --- | --- | --- | --- | --- | --- | --- | --- | --- | --- | --- | --- | --- |
| ATOM | 2461 | O   | ARG | B | 134 | 27.721 | 19.909 | 55.987 | 1.00 | 47.97 | B | O |
| ATOM | 2462 | N   | ALA | B | 135 | 28.339 | 18.241 | 54.594 | 1.00 | 45.58 | B | N |
| ATOM | 2463 | CA  | ALA | B | 135 | 28.066 | 19.001 | 53.376 | 1.00 | 43.47 | B | C |
| ATOM | 2464 | CB  | ALA | B | 135 | 28.692 | 18.306 | 52.175 | 1.00 | 41.20 | B | C |
| ATOM | 2465 | C   | ALA | B | 135 | 26.554 | 19.162 | 53.163 | 1.00 | 42.31 | B | C |
| ATOM | 2466 | O   | ALA | B | 135 | 26.078 | 20.250 | 52.846 | 1.00 | 41.35 | B | O |
| ATOM | 2467 | N   | VAL | B | 136 | 25.806 | 18.080 | 53.347 | 1.00 | 40.97 | B | N |
| ATOM | 2468 | CA  | VAL | B | 136 | 24.359 | 18.140 | 53.233 | 1.00 | 40.01 | B | C |
| ATOM | 2469 | CB  | VAL | B | 136 | 23.724 | 16.771 | 53.518 | 1.00 | 39.78 | B | C |
| ATOM | 2470 | CG1 | VAL | B | 136 | 22.241 | 16.920 | 53.732 | 1.00 | 40.96 | B | C |
| ATOM | 2471 | CG2 | VAL | B | 136 | 23.987 | 15.841 | 52.361 | 1.00 | 38.01 | B | C |
| ATOM | 2472 | C   | VAL | B | 136 | 23.735 | 19.176 | 54.169 | 1.00 | 41.05 | B | C |
| ATOM | 2473 | O   | VAL | B | 136 | 22.717 | 19.784 | 53.832 | 1.00 | 40.50 | B | O |
| ATOM | 2474 | N   | ILE | B | 137 | 24.353 | 19.382 | 55.331 | 1.00 | 40.89 | B | N |
| ATOM | 2475 | CA  | ILE | B | 137 | 23.826 | 20.294 | 56.349 | 1.00 | 41.02 | B | C |
| ATOM | 2476 | CB  | ILE | B | 137 | 24.449 | 19.984 | 57.752 | 1.00 | 40.35 | B | C |
| ATOM | 2477 | CG2 | ILE | B | 137 | 24.170 | 21.111 | 58.731 | 1.00 | 41.40 | B | C |
| ATOM | 2478 | CG1 | ILE | B | 137 | 23.889 | 18.653 | 58.288 | 1.00 | 40.52 | B | C |
| ATOM | 2479 | CD1 | ILE | B | 137 | 24.456 | 18.215 | 59.633 | 1.00 | 37.58 | B | C |
| ATOM | 2480 | C   | ILE | B | 137 | 24.076 | 21.750 | 55.957 | 1.00 | 41.91 | B | C |
| ATOM | 2481 | O   | ILE | B | 137 | 23.139 | 22.560 | 55.856 | 1.00 | 41.25 | B | O |
| ATOM | 2482 | N   | ASP | B | 138 | 25.335 | 22.083 | 55.707 | 1.00 | 43.24 | B | N |
| ATOM | 2483 | CA  | ASP | B | 138 | 25.661 | 23.413 | 55.207 | 1.00 | 44.74 | B | C |
| ATOM | 2484 | CB  | ASP | B | 138 | 27.081 | 23.431 | 54.632 | 1.00 | 46.86 | B | C |
| ATOM | 2485 | CG  | ASP | B | 138 | 28.139 | 23.229 | 55.695 | 1.00 | 51.02 | B | C |
| ATOM | 2486 | OD1 | ASP | B | 138 | 28.783 | 22.145 | 55.717 | 1.00 | 53.15 | B | O |
| ATOM | 2487 | OD2 | ASP | B | 138 | 28.326 | 24.162 | 56.515 | 1.00 | 53.20 | B | O |
| ATOM | 2488 | C   | ASP | B | 138 | 24.666 | 23.811 | 54.133 | 1.00 | 43.68 | B | C |
| ATOM | 2489 | O   | ASP | B | 138 | 24.167 | 24.932 | 54.115 | 1.00 | 44.60 | B | O |
| ATOM | 2490 | N   | ASP | B | 139 | 24.373 | 22.870 | 53.245 | 1.00 | 43.96 | B | N |
| ATOM | 2491 | CA  | ASP | B | 139 | 23.570 | 23.162 | 52.075 | 1.00 | 42.60 | B | C |
| ATOM | 2492 | CB  | ASP | B | 139 | 23.605 | 21.991 | 51.104 | 1.00 | 43.34 | B | C |
| ATOM | 2493 | CG  | ASP | B | 139 | 22.905 | 22.304 | 49.796 | 1.00 | 45.53 | B | C |
| ATOM | 2494 | OD1 | ASP | B | 139 | 23.533 | 22.958 | 48.928 | 1.00 | 47.55 | B | O |
| ATOM | 2495 | OD2 | ASP | B | 139 | 21.727 | 21.902 | 49.624 | 1.00 | 47.31 | B | O |
| ATOM | 2496 | C   | ASP | B | 139 | 22.137 | 23.444 | 52.476 | 1.00 | 42.21 | B | C |
| ATOM | 2497 | O   | ASP | B | 139 | 21.474 | 24.312 | 51.899 | 1.00 | 41.13 | B | O |
| ATOM | 2498 | N   | ALA | B | 140 | 21.638 | 22.707 | 53.455 | 1.00 | 41.74 | B | N |
| ATOM | 2499 | CA  | ALA | B | 140 | 20.251 | 22.911 | 53.814 | 1.00 | 43.53 | B | C |
| ATOM | 2500 | CB  | ALA | B | 140 | 19.774 | 21.844 | 54.800 | 1.00 | 42.75 | B | C |
| ATOM | 2501 | C   | ALA | B | 140 | 20.154 | 24.302 | 54.427 | 1.00 | 43.95 | B | C |
| ATOM | 2502 | O   | ALA | B | 140 | 19.243 | 25.067 | 54.105 | 1.00 | 43.98 | B | O |
| ATOM | 2503 | N   | PHE | B | 141 | 21.116 | 24.642 | 55.281 | 1.00 | 43.60 | B | N |
| ATOM | 2504 | CA  | PHE | B | 141 | 21.097 | 25.952 | 55.908 | 1.00 | 42.93 | B | C |
| ATOM | 2505 | CB  | PHE | B | 141 | 22.229 | 26.088 | 56.940 | 1.00 | 42.04 | B | C |
| ATOM | 2506 | CG  | PHE | B | 141 | 21.943 | 25.377 | 58.239 | 1.00 | 40.59 | B | C |
| ATOM | 2507 | CD1 | PHE | B | 141 | 20.633 | 25.118 | 58.620 | 1.00 | 38.33 | B | C |
| ATOM | 2508 | CD2 | PHE | B | 141 | 22.972 | 24.926 | 59.048 | 1.00 | 39.63 | B | C |
| ATOM | 2509 | CE1 | PHE | B | 141 | 20.353 | 24.422 | 59.768 | 1.00 | 36.71 | B | C |
| ATOM | 2510 | CE2 | PHE | B | 141 | 22.700 | 24.226 | 60.205 | 1.00 | 38.82 | B | C |
| ATOM | 2511 | CZ  | PHE | B | 141 | 21.385 | 23.974 | 60.561 | 1.00 | 37.71 | B | C |
| ATOM | 2512 | C   | PHE | B | 141 | 21.169 | 27.081 | 54.881 | 1.00 | 43.11 | B | C |
| ATOM | 2513 | O   | PHE | B | 141 | 20.305 | 27.968 | 54.878 | 1.00 | 45.28 | B | O |
| ATOM | 2514 | N   | ALA | B | 142 | 22.165 | 27.052 | 53.998 | 1.00 | 40.49 | B | N |
| ATOM | 2515 | CA  | ALA | B | 142 | 22.291 | 28.095 | 52.978 | 1.00 | 37.84 | B | C |
| ATOM | 2516 | CB  | ALA | B | 142 | 23.506 | 27.826 | 52.118 | 1.00 | 36.79 | B | C |
| ATOM | 2517 | C   | ALA | B | 142 | 21.042 | 28.192 | 52.104 | 1.00 | 37.51 | B | C |
| ATOM | 2518 | O   | ALA | B | 142 | 20.496 | 29.278 | 51.894 | 1.00 | 33.84 | B | O |
| ATOM | 2519 | N   | ARG | B | 143 | 20.594 | 27.043 | 51.609 | 1.00 | 39.12 | B | N |
| ATOM | 2520 | CA  | ARG | B | 143 | 19.342 | 26.941 | 50.867 | 1.00 | 41.61 | B | C |
| ATOM | 2521 | CB  | ARG | B | 143 | 18.945 | 25.480 | 50.719 | 1.00 | 42.92 | B | C |
| ATOM | 2522 | CG  | ARG | B | 143 | 19.025 | 24.996 | 49.296 | 1.00 | 43.85 | B | C |
| ATOM | 2523 | CD  | ARG | B | 143 | 19.110 | 23.488 | 49.216 | 1.00 | 43.74 | B | C |
| ATOM | 2524 | NE  | ARG | B | 143 | 17.872 | 22.828 | 49.588 | 1.00 | 43.94 | B | N |
| ATOM | 2525 | CZ  | ARG | B | 143 | 17.839 | 21.799 | 50.418 | 1.00 | 43.07 | B | C |
| ATOM | 2526 | NH1 | ARG | B | 143 | 18.975 | 21.359 | 50.933 | 1.00 | 44.72 | B | N |
| ATOM | 2527 | NH2 | ARG | B | 143 | 16.693 | 21.201 | 50.722 | 1.00 | 45.28 | B | N |
| ATOM | 2528 | C   | ARG | B | 143 | 18.209 | 27.681 | 51.548 | 1.00 | 42.45 | B | C |
| ATOM | 2529 | O   | ARG | B | 143 | 17.360 | 28.288 | 50.902 | 1.00 | 44.06 | B | O |
| ATOM | 2530 | N   | ALA | B | 144 | 18.194 | 27.606 | 52.869 | 1.00 | 41.78 | B | N |
| ATOM | 2531 | CA  | ALA | B | 144 | 17.174 | 28.269 | 53.642 | 1.00 | 39.35 | B | C |
| ATOM | 2532 | CB  | ALA | B | 144 | 17.194 | 27.756 | 55.055 | 1.00 | 38.33 | B | C |
| ATOM | 2533 | C   | ALA | B | 144 | 17.392 | 29.778 | 53.613 | 1.00 | 39.06 | B | C |
| ATOM | 2534 | O   | ALA | B | 144 | 16.445 | 30.545 | 53.416 | 1.00 | 40.22 | B | O |
| ATOM | 2535 | N   | PHE | B | 145 | 18.629 | 30.218 | 53.803 | 1.00 | 38.92 | B | N |
| ATOM | 2536 | CA  | PHE | B | 145 | 18.899 | 31.645 | 53.717 | 1.00 | 38.87 | B | C |
| ATOM | 2537 | CB  | PHE | B | 145 | 20.370 | 31.944 | 54.065 | 1.00 | 35.84 | B | C |

TABLE 11-continued

Coordinates for pro MMP9(35-444 ΔFnII) (SEQ ID NO: 12) complex with Example 1

| ATOM | 2538 | CG | PHE | B | 145 | 20.636 | 32.010 | 55.545 | 1.00 | 35.24 | B | C |
|---|---|---|---|---|---|---|---|---|---|---|---|---|
| ATOM | 2539 | CD1 | PHE | B | 145 | 19.991 | 32.956 | 56.334 | 1.00 | 34.91 | B | C |
| ATOM | 2540 | CD2 | PHE | B | 145 | 21.497 | 31.109 | 56.161 | 1.00 | 35.25 | B | C |
| ATOM | 2541 | CE1 | PHE | B | 145 | 20.193 | 33.004 | 57.713 | 1.00 | 33.99 | B | C |
| ATOM | 2542 | CE2 | PHE | B | 145 | 21.709 | 31.147 | 57.550 | 1.00 | 34.41 | B | C |
| ATOM | 2543 | CZ | PHE | B | 145 | 21.054 | 32.098 | 58.326 | 1.00 | 34.36 | B | C |
| ATOM | 2544 | C | PHE | B | 145 | 18.544 | 32.158 | 52.314 | 1.00 | 39.05 | B | C |
| ATOM | 2545 | O | PHE | B | 145 | 18.129 | 33.312 | 52.141 | 1.00 | 38.80 | B | O |
| ATOM | 2546 | N | ALA | B | 146 | 18.669 | 31.290 | 51.313 | 1.00 | 39.50 | B | N |
| ATOM | 2547 | CA | ALA | B | 146 | 18.423 | 31.722 | 49.943 | 1.00 | 39.75 | B | C |
| ATOM | 2548 | CB | ALA | B | 146 | 18.784 | 30.621 | 48.958 | 1.00 | 39.43 | B | C |
| ATOM | 2549 | C | ALA | B | 146 | 16.960 | 32.128 | 49.777 | 1.00 | 41.33 | B | C |
| ATOM | 2550 | O | ALA | B | 146 | 16.659 | 33.076 | 49.048 | 1.00 | 42.06 | B | O |
| ATOM | 2551 | N | LEU | B | 147 | 16.053 | 31.437 | 50.467 | 1.00 | 39.32 | B | N |
| ATOM | 2552 | CA | LEU | B | 147 | 14.652 | 31.848 | 50.455 | 1.00 | 39.31 | B | C |
| ATOM | 2553 | CB | LEU | B | 147 | 13.828 | 31.069 | 51.490 | 1.00 | 38.14 | B | C |
| ATOM | 2554 | CG | LEU | B | 147 | 13.308 | 29.668 | 51.134 | 1.00 | 37.99 | B | C |
| ATOM | 2555 | CD1 | LEU | B | 147 | 12.598 | 29.101 | 52.332 | 1.00 | 36.24 | B | C |
| ATOM | 2556 | CD2 | LEU | B | 147 | 12.366 | 29.718 | 49.943 | 1.00 | 35.55 | B | C |
| ATOM | 2557 | C | LEU | B | 147 | 14.568 | 33.332 | 50.773 | 1.00 | 39.71 | B | C |
| ATOM | 2558 | O | LEU | B | 147 | 14.128 | 34.133 | 49.946 | 1.00 | 41.25 | B | O |
| ATOM | 2559 | N | TRP | B | 148 | 15.025 | 33.702 | 51.966 | 1.00 | 40.57 | B | N |
| ATOM | 2560 | CA | TRP | B | 148 | 14.739 | 35.024 | 52.514 | 1.00 | 39.24 | B | C |
| ATOM | 2561 | CB | TRP | B | 148 | 15.092 | 35.062 | 54.013 | 1.00 | 37.40 | B | C |
| ATOM | 2562 | CG | TRP | B | 148 | 14.107 | 34.282 | 54.858 | 1.00 | 35.82 | B | C |
| ATOM | 2563 | CD2 | TRP | B | 148 | 12.705 | 34.558 | 55.040 | 1.00 | 35.94 | B | C |
| ATOM | 2564 | CE2 | TRP | B | 148 | 12.160 | 33.496 | 55.794 | 1.00 | 35.14 | B | C |
| ATOM | 2565 | CE3 | TRP | B | 148 | 11.856 | 35.593 | 54.634 | 1.00 | 36.07 | B | C |
| ATOM | 2566 | CD1 | TRP | B | 148 | 14.342 | 33.103 | 55.507 | 1.00 | 36.48 | B | C |
| ATOM | 2567 | NE1 | TRP | B | 148 | 13.179 | 32.622 | 56.067 | 1.00 | 34.94 | B | N |
| ATOM | 2568 | CZ2 | TRP | B | 148 | 10.807 | 33.442 | 56.146 | 1.00 | 34.07 | B | C |
| ATOM | 2569 | CZ3 | TRP | B | 148 | 10.505 | 35.532 | 54.990 | 1.00 | 34.15 | B | C |
| ATOM | 2570 | CH2 | TRP | B | 148 | 10.001 | 34.465 | 55.735 | 1.00 | 32.87 | B | C |
| ATOM | 2571 | C | TRP | B | 148 | 15.472 | 36.102 | 51.741 | 1.00 | 38.45 | B | C |
| ATOM | 2572 | O | TRP | B | 148 | 15.024 | 37.247 | 51.651 | 1.00 | 37.45 | B | O |
| ATOM | 2573 | N | SER | B | 149 | 16.593 | 35.719 | 51.153 | 1.00 | 40.24 | B | N |
| ATOM | 2574 | CA | SER | B | 149 | 17.411 | 36.683 | 50.423 | 1.00 | 41.85 | B | C |
| ATOM | 2575 | CB | SER | B | 149 | 18.724 | 36.031 | 49.987 | 1.00 | 41.87 | B | C |
| ATOM | 2576 | OG | SER | B | 149 | 19.580 | 36.991 | 49.410 | 1.00 | 41.32 | B | O |
| ATOM | 2577 | C | SER | B | 149 | 16.677 | 37.238 | 49.198 | 1.00 | 41.91 | B | C |
| ATOM | 2578 | O | SER | B | 149 | 16.827 | 38.413 | 48.855 | 1.00 | 41.42 | B | O |
| ATOM | 2579 | N | ALA | B | 150 | 15.892 | 36.392 | 48.539 | 1.00 | 40.50 | B | N |
| ATOM | 2580 | CA | ALA | B | 150 | 15.229 | 36.802 | 47.308 | 1.00 | 40.10 | B | C |
| ATOM | 2581 | CB | ALA | B | 150 | 14.543 | 35.603 | 46.663 | 1.00 | 38.16 | B | C |
| ATOM | 2582 | C | ALA | B | 150 | 14.208 | 37.913 | 47.577 | 1.00 | 40.91 | B | C |
| ATOM | 2583 | O | ALA | B | 150 | 13.878 | 38.705 | 46.693 | 1.00 | 42.62 | B | O |
| ATOM | 2584 | N | VAL | B | 151 | 13.730 | 37.987 | 48.814 | 1.00 | 40.84 | B | N |
| ATOM | 2585 | CA | VAL | B | 151 | 12.567 | 38.794 | 49.133 | 1.00 | 37.46 | B | C |
| ATOM | 2586 | CB | VAL | B | 151 | 11.454 | 37.871 | 49.680 | 1.00 | 36.12 | B | C |
| ATOM | 2587 | CG1 | VAL | B | 151 | 11.031 | 36.897 | 48.607 | 1.00 | 33.40 | B | C |
| ATOM | 2588 | CG2 | VAL | B | 151 | 11.967 | 37.085 | 50.873 | 1.00 | 34.67 | B | C |
| ATOM | 2589 | C | VAL | B | 151 | 12.870 | 39.950 | 50.115 | 1.00 | 38.29 | B | C |
| ATOM | 2590 | O | VAL | B | 151 | 11.972 | 40.728 | 50.466 | 1.00 | 37.85 | B | O |
| ATOM | 2591 | N | THR | B | 152 | 14.130 | 40.062 | 50.545 | 1.00 | 39.26 | B | N |
| ATOM | 2592 | CA | THR | B | 152 | 14.560 | 41.107 | 51.499 | 1.00 | 41.68 | B | C |
| ATOM | 2593 | CB | THR | B | 152 | 14.935 | 40.509 | 52.908 | 1.00 | 43.62 | B | C |
| ATOM | 2594 | OG1 | THR | B | 152 | 16.052 | 39.614 | 52.784 | 1.00 | 45.98 | B | O |
| ATOM | 2595 | CG2 | THR | B | 152 | 13.760 | 39.741 | 53.510 | 1.00 | 44.83 | B | C |
| ATOM | 2596 | C | THR | B | 152 | 15.777 | 41.879 | 50.995 | 1.00 | 40.45 | B | C |
| ATOM | 2597 | O | THR | B | 152 | 16.537 | 41.373 | 50.178 | 1.00 | 42.39 | B | O |
| ATOM | 2598 | N | PRO | B | 153 | 15.976 | 43.115 | 51.478 | 1.00 | 39.85 | B | N |
| ATOM | 2599 | CD | PRO | B | 153 | 15.048 | 43.869 | 52.338 | 1.00 | 39.76 | B | C |
| ATOM | 2600 | CA | PRO | B | 153 | 17.180 | 43.895 | 51.167 | 1.00 | 40.14 | B | C |
| ATOM | 2601 | CB | PRO | B | 153 | 16.796 | 45.315 | 51.588 | 1.00 | 39.40 | B | C |
| ATOM | 2602 | CG | PRO | B | 153 | 15.814 | 45.113 | 52.696 | 1.00 | 39.26 | B | C |
| ATOM | 2603 | C | PRO | B | 153 | 18.436 | 43.385 | 51.914 | 1.00 | 40.82 | B | C |
| ATOM | 2604 | O | PRO | B | 153 | 19.340 | 44.161 | 52.241 | 1.00 | 41.47 | B | O |
| ATOM | 2605 | N | LEU | B | 154 | 18.474 | 42.085 | 52.198 | 1.00 | 39.77 | B | N |
| ATOM | 2606 | CA | LEU | B | 154 | 19.538 | 41.496 | 53.006 | 1.00 | 39.27 | B | C |
| ATOM | 2607 | CB | LEU | B | 154 | 18.925 | 40.962 | 54.305 | 1.00 | 40.72 | B | C |
| ATOM | 2608 | CG | LEU | B | 154 | 18.391 | 42.040 | 55.261 | 1.00 | 41.77 | B | C |
| ATOM | 2609 | CD1 | LEU | B | 154 | 17.327 | 41.461 | 56.196 | 1.00 | 40.29 | B | C |
| ATOM | 2610 | CD2 | LEU | B | 154 | 19.552 | 42.631 | 56.062 | 1.00 | 42.82 | B | C |
| ATOM | 2611 | C | LEU | B | 154 | 20.317 | 40.385 | 52.267 | 1.00 | 39.28 | B | C |
| ATOM | 2612 | O | LEU | B | 154 | 19.750 | 39.649 | 51.465 | 1.00 | 39.83 | B | O |
| ATOM | 2613 | N | THR | B | 155 | 21.621 | 40.285 | 52.521 | 1.00 | 39.08 | B | N |
| ATOM | 2614 | CA | THR | B | 155 | 22.404 | 39.155 | 52.039 | 1.00 | 39.68 | B | C |
| ATOM | 2615 | CB | THR | B | 155 | 23.542 | 39.567 | 51.028 | 1.00 | 39.54 | B | C |

TABLE 11-continued

Coordinates for pro MMP9(35-444 ΔFnII) (SEQ ID NO: 12) complex with Example 1

| ATOM | 2616 | OG1 | THR | B | 155 | 24.547 | 40.331 | 51.705 | 1.00 | 40.29 | B | O |
|------|------|-----|-----|---|-----|--------|--------|--------|------|-------|---|---|
| ATOM | 2617 | CG2 | THR | B | 155 | 22.979 | 40.375 | 49.866 | 1.00 | 38.14 | B | C |
| ATOM | 2618 | C | THR | B | 155 | 23.046 | 38.450 | 53.237 | 1.00 | 40.60 | B | C |
| ATOM | 2619 | O | THR | B | 155 | 23.384 | 39.084 | 54.234 | 1.00 | 42.13 | B | O |
| ATOM | 2620 | N | PHE | B | 156 | 23.210 | 37.136 | 53.128 | 1.00 | 41.65 | B | N |
| ATOM | 2621 | CA | PHE | B | 156 | 23.739 | 36.328 | 54.208 | 1.00 | 42.33 | B | C |
| ATOM | 2622 | CB | PHE | B | 156 | 22.738 | 35.217 | 54.556 | 1.00 | 40.59 | B | C |
| ATOM | 2623 | CG | PHE | B | 156 | 21.398 | 35.740 | 54.968 | 1.00 | 39.96 | B | C |
| ATOM | 2624 | CD1 | PHE | B | 156 | 20.447 | 36.075 | 54.009 | 1.00 | 39.88 | B | C |
| ATOM | 2625 | CD2 | PHE | B | 156 | 21.118 | 35.991 | 56.297 | 1.00 | 39.43 | B | C |
| ATOM | 2626 | CE1 | PHE | B | 156 | 19.236 | 36.665 | 54.362 | 1.00 | 40.60 | B | C |
| ATOM | 2627 | CE2 | PHE | B | 156 | 19.912 | 36.580 | 56.659 | 1.00 | 40.90 | B | C |
| ATOM | 2628 | CZ | PHE | B | 156 | 18.967 | 36.920 | 55.684 | 1.00 | 40.26 | B | C |
| ATOM | 2629 | C | PHE | B | 156 | 25.079 | 35.749 | 53.790 | 1.00 | 42.95 | B | C |
| ATOM | 2630 | O | PHE | B | 156 | 25.253 | 35.335 | 52.641 | 1.00 | 44.03 | B | O |
| ATOM | 2631 | N | THR | B | 157 | 26.028 | 35.750 | 54.723 | 1.00 | 44.29 | B | N |
| ATOM | 2632 | CA | THR | B | 157 | 27.359 | 35.204 | 54.488 | 1.00 | 44.28 | B | C |
| ATOM | 2633 | CB | THR | B | 157 | 28.413 | 36.302 | 54.369 | 1.00 | 45.00 | B | C |
| ATOM | 2634 | OG1 | THR | B | 157 | 28.275 | 36.971 | 53.108 | 1.00 | 45.30 | B | O |
| ATOM | 2635 | CG2 | THR | B | 157 | 29.819 | 35.699 | 54.484 | 1.00 | 46.04 | B | C |
| ATOM | 2636 | C | THR | B | 157 | 27.761 | 34.329 | 55.650 | 1.00 | 46.00 | B | C |
| ATOM | 2637 | O | THR | B | 157 | 27.568 | 34.698 | 56.814 | 1.00 | 48.07 | B | O |
| ATOM | 2638 | N | ARG | B | 158 | 28.340 | 33.177 | 55.331 | 1.00 | 45.97 | B | N |
| ATOM | 2639 | CA | ARG | B | 158 | 28.732 | 32.198 | 56.345 | 1.00 | 45.91 | B | C |
| ATOM | 2640 | CB | ARG | B | 158 | 28.703 | 30.790 | 55.748 | 1.00 | 45.97 | B | C |
| ATOM | 2641 | CG | ARG | B | 158 | 29.564 | 29.786 | 56.478 | 1.00 | 47.19 | B | C |
| ATOM | 2642 | CD | ARG | B | 158 | 28.717 | 28.727 | 57.140 | 1.00 | 48.18 | B | C |
| ATOM | 2643 | NE | ARG | B | 158 | 29.417 | 27.447 | 57.202 | 1.00 | 48.81 | B | N |
| ATOM | 2644 | CZ | ARG | B | 158 | 29.872 | 26.799 | 56.137 | 1.00 | 48.20 | B | C |
| ATOM | 2645 | NH1 | ARG | B | 158 | 29.703 | 27.318 | 54.926 | 1.00 | 46.73 | B | N |
| ATOM | 2646 | NH2 | ARG | B | 158 | 30.483 | 25.630 | 56.285 | 1.00 | 49.45 | B | N |
| ATOM | 2647 | C | ARG | B | 158 | 30.126 | 32.502 | 56.858 | 1.00 | 44.47 | B | C |
| ATOM | 2648 | O | ARG | B | 158 | 31.044 | 32.724 | 56.070 | 1.00 | 43.24 | B | O |
| ATOM | 2649 | N | VAL | B | 159 | 30.273 | 32.504 | 58.181 | 1.00 | 44.42 | B | N |
| ATOM | 2650 | CA | VAL | B | 159 | 31.552 | 32.805 | 58.823 | 1.00 | 43.12 | B | C |
| ATOM | 2651 | CB | VAL | B | 159 | 31.486 | 34.138 | 59.549 | 1.00 | 41.66 | B | C |
| ATOM | 2652 | CG1 | VAL | B | 159 | 31.244 | 35.274 | 58.553 | 1.00 | 39.64 | B | C |
| ATOM | 2653 | CG2 | VAL | B | 159 | 30.378 | 34.081 | 60.563 | 1.00 | 42.97 | B | C |
| ATOM | 2654 | C | VAL | B | 159 | 31.936 | 31.740 | 59.837 | 1.00 | 44.11 | B | C |
| ATOM | 2655 | O | VAL | B | 159 | 31.071 | 31.034 | 60.362 | 1.00 | 44.87 | B | O |
| ATOM | 2656 | N | TYR | B | 160 | 33.235 | 31.640 | 60.129 | 1.00 | 46.71 | B | N |
| ATOM | 2657 | CA | TYR | B | 160 | 33.757 | 30.559 | 60.981 | 1.00 | 46.55 | B | C |
| ATOM | 2658 | CB | TYR | B | 160 | 34.877 | 29.819 | 60.227 | 1.00 | 44.82 | B | C |
| ATOM | 2659 | CG | TYR | B | 160 | 34.410 | 29.269 | 58.894 | 1.00 | 45.07 | B | C |
| ATOM | 2660 | CD1 | TYR | B | 160 | 34.407 | 30.059 | 57.753 | 1.00 | 44.90 | B | C |
| ATOM | 2661 | CE1 | TYR | B | 160 | 33.886 | 29.584 | 56.549 | 1.00 | 45.04 | B | C |
| ATOM | 2662 | CD2 | TYR | B | 160 | 33.890 | 27.988 | 58.795 | 1.00 | 45.45 | B | C |
| ATOM | 2663 | CE2 | TYR | B | 160 | 33.367 | 27.505 | 57.601 | 1.00 | 44.31 | B | C |
| ATOM | 2664 | CZ | TYR | B | 160 | 33.364 | 28.309 | 56.485 | 1.00 | 44.88 | B | C |
| ATOM | 2665 | OH | TYR | B | 160 | 32.807 | 27.847 | 55.314 | 1.00 | 43.80 | B | O |
| ATOM | 2666 | C | TYR | B | 160 | 34.234 | 30.941 | 62.399 | 1.00 | 46.43 | B | C |
| ATOM | 2667 | O | TYR | B | 160 | 34.797 | 30.111 | 63.090 | 1.00 | 48.62 | B | O |
| ATOM | 2668 | N | SER | B | 161 | 34.004 | 32.171 | 62.845 | 1.00 | 48.41 | B | N |
| ATOM | 2669 | CA | SER | B | 161 | 34.298 | 32.519 | 64.234 | 1.00 | 48.84 | B | C |
| ATOM | 2670 | CB | SER | B | 161 | 35.204 | 33.755 | 64.314 | 1.00 | 46.65 | B | C |
| ATOM | 2671 | OG | SER | B | 161 | 34.447 | 34.953 | 64.250 | 1.00 | 40.38 | B | O |
| ATOM | 2672 | C | SER | B | 161 | 32.971 | 32.820 | 64.924 | 1.00 | 52.40 | B | C |
| ATOM | 2673 | O | SER | B | 161 | 31.902 | 32.553 | 64.369 | 1.00 | 53.60 | B | O |
| ATOM | 2674 | N | ARG | B | 162 | 33.042 | 33.401 | 66.120 | 1.00 | 53.85 | B | N |
| ATOM | 2675 | CA | ARG | B | 162 | 31.844 | 33.737 | 66.882 | 1.00 | 54.08 | B | C |
| ATOM | 2676 | CB | ARG | B | 162 | 32.078 | 33.516 | 68.385 | 1.00 | 56.45 | B | C |
| ATOM | 2677 | CG | ARG | B | 162 | 32.989 | 34.540 | 69.074 | 1.00 | 58.02 | B | C |
| ATOM | 2678 | CD | ARG | B | 162 | 33.214 | 34.200 | 70.560 | 1.00 | 59.85 | B | C |
| ATOM | 2679 | NE | ARG | B | 162 | 34.239 | 33.173 | 70.762 | 1.00 | 64.12 | B | N |
| ATOM | 2680 | CZ | ARG | B | 162 | 33.990 | 31.878 | 70.969 | 1.00 | 65.95 | B | C |
| ATOM | 2681 | NH1 | ARG | B | 162 | 32.739 | 31.439 | 71.004 | 1.00 | 68.19 | B | N |
| ATOM | 2682 | NH2 | ARG | B | 162 | 34.994 | 31.020 | 71.150 | 1.00 | 65.71 | B | N |
| ATOM | 2683 | C | ARG | B | 162 | 31.420 | 35.175 | 66.615 | 1.00 | 53.39 | B | C |
| ATOM | 2684 | O | ARG | B | 162 | 30.364 | 35.607 | 67.074 | 1.00 | 53.56 | B | O |
| ATOM | 2685 | N | ASP | B | 163 | 32.255 | 35.914 | 65.880 | 1.00 | 53.54 | B | N |
| ATOM | 2686 | CA | ASP | B | 163 | 31.819 | 37.154 | 65.216 | 1.00 | 53.03 | B | C |
| ATOM | 2687 | CB | ASP | B | 163 | 33.017 | 37.881 | 64.564 | 1.00 | 55.49 | B | C |
| ATOM | 2688 | CG | ASP | B | 163 | 32.591 | 39.013 | 63.591 | 1.00 | 59.41 | B | C |
| ATOM | 2689 | OD1 | ASP | B | 163 | 31.453 | 39.532 | 63.704 | 1.00 | 59.92 | B | O |
| ATOM | 2690 | OD2 | ASP | B | 163 | 33.407 | 39.386 | 62.708 | 1.00 | 60.18 | B | O |
| ATOM | 2691 | C | ASP | B | 163 | 30.815 | 36.738 | 64.146 | 1.00 | 50.79 | B | C |
| ATOM | 2692 | O | ASP | B | 163 | 31.195 | 36.351 | 63.038 | 1.00 | 49.93 | B | O |
| ATOM | 2693 | N | ALA | B | 164 | 29.535 | 36.799 | 64.495 | 1.00 | 48.01 | B | N |

TABLE 11-continued

Coordinates for pro MMP9(35-444 ΔFnII) (SEQ ID NO: 12) complex with Example 1

| ATOM | 2694 | CA | ALA | B | 164 | 28.495 | 36.312 | 63.609 | 1.00 | 46.93 B | C |
|---|---|---|---|---|---|---|---|---|---|---|---|
| ATOM | 2695 | CB | ALA | B | 164 | 28.576 | 34.790 | 63.494 | 1.00 | 46.17 B | C |
| ATOM | 2696 | C | ALA | B | 164 | 27.118 | 36.726 | 64.097 | 1.00 | 46.34 B | C |
| ATOM | 2697 | O | ALA | B | 164 | 26.702 | 36.385 | 65.205 | 1.00 | 46.04 B | O |
| ATOM | 2698 | N | ASP | B | 165 | 26.414 | 37.473 | 63.258 | 1.00 | 46.17 B | N |
| ATOM | 2699 | CA | ASP | B | 165 | 25.096 | 37.965 | 63.609 | 1.00 | 46.11 B | C |
| ATOM | 2700 | CB | ASP | B | 165 | 24.430 | 38.609 | 62.399 | 1.00 | 46.15 B | C |
| ATOM | 2701 | CG | ASP | B | 165 | 25.151 | 39.853 | 61.943 | 1.00 | 48.04 B | C |
| ATOM | 2702 | OD1 | ASP | B | 165 | 25.656 | 40.595 | 62.827 | 1.00 | 48.57 B | O |
| ATOM | 2703 | OD2 | ASP | B | 165 | 25.209 | 40.086 | 60.711 | 1.00 | 46.91 B | O |
| ATOM | 2704 | C | ASP | B | 165 | 24.246 | 36.818 | 64.101 | 1.00 | 45.99 B | C |
| ATOM | 2705 | O | ASP | B | 165 | 23.613 | 36.937 | 65.132 | 1.00 | 48.67 B | O |
| ATOM | 2706 | N | ILE | B | 166 | 24.233 | 35.711 | 63.363 | 1.00 | 44.71 B | N |
| ATOM | 2707 | CA | ILE | B | 166 | 23.473 | 34.538 | 63.769 | 1.00 | 42.89 B | C |
| ATOM | 2708 | CB | ILE | B | 166 | 22.426 | 34.150 | 62.681 | 1.00 | 44.84 B | C |
| ATOM | 2709 | CG2 | ILE | B | 166 | 21.816 | 32.761 | 63.004 | 1.00 | 45.20 B | C |
| ATOM | 2710 | CG1 | ILE | B | 166 | 21.356 | 35.258 | 62.580 | 1.00 | 45.57 B | C |
| ATOM | 2711 | CD1 | ILE | B | 166 | 20.201 | 35.018 | 61.572 | 1.00 | 43.21 B | C |
| ATOM | 2712 | C | ILE | B | 166 | 24.357 | 33.321 | 64.090 | 1.00 | 41.58 B | C |
| ATOM | 2713 | O | ILE | B | 166 | 25.116 | 32.838 | 63.246 | 1.00 | 40.06 B | O |
| ATOM | 2714 | N | VAL | B | 167 | 24.254 | 32.833 | 65.328 | 1.00 | 41.03 B | N |
| ATOM | 2715 | CA | VAL | B | 167 | 24.960 | 31.620 | 65.738 | 1.00 | 38.97 B | C |
| ATOM | 2716 | CB | VAL | B | 167 | 25.578 | 31.786 | 67.127 | 1.00 | 36.64 B | C |
| ATOM | 2717 | CG1 | VAL | B | 167 | 26.258 | 30.504 | 67.544 | 1.00 | 35.82 B | C |
| ATOM | 2718 | CG2 | VAL | B | 167 | 26.572 | 32.919 | 67.104 | 1.00 | 34.72 B | C |
| ATOM | 2719 | C | VAL | B | 167 | 24.016 | 30.424 | 65.741 | 1.00 | 41.07 B | C |
| ATOM | 2720 | O | VAL | B | 167 | 22.954 | 30.463 | 66.367 | 1.00 | 40.50 B | O |
| ATOM | 2721 | N | ILE | B | 168 | 24.404 | 29.368 | 65.028 | 1.00 | 40.78 B | N |
| ATOM | 2722 | CA | ILE | B | 168 | 23.550 | 28.193 | 64.882 | 1.00 | 41.64 B | C |
| ATOM | 2723 | CB | ILE | B | 168 | 23.434 | 27.802 | 63.402 | 1.00 | 42.63 B | C |
| ATOM | 2724 | CG2 | ILE | B | 168 | 22.669 | 26.500 | 63.266 | 1.00 | 41.44 B | C |
| ATOM | 2725 | CG1 | ILE | B | 168 | 22.754 | 28.943 | 62.631 | 1.00 | 42.77 B | C |
| ATOM | 2726 | CD1 | ILE | B | 168 | 22.265 | 28.557 | 61.246 | 1.00 | 42.40 B | C |
| ATOM | 2727 | C | ILE | B | 168 | 24.038 | 26.988 | 65.693 | 1.00 | 43.33 B | C |
| ATOM | 2728 | O | ILE | B | 168 | 25.211 | 26.647 | 65.639 | 1.00 | 45.09 B | O |
| ATOM | 2729 | N | GLN | B | 169 | 23.147 | 26.344 | 66.444 | 1.00 | 43.40 B | N |
| ATOM | 2730 | CA | GLN | B | 169 | 23.568 | 25.262 | 67.335 | 1.00 | 44.15 B | C |
| ATOM | 2731 | CB | GLN | B | 169 | 23.865 | 25.840 | 68.716 | 1.00 | 45.30 B | C |
| ATOM | 2732 | CG | GLN | B | 169 | 24.242 | 24.804 | 69.757 | 1.00 | 47.04 B | C |
| ATOM | 2733 | CD | GLN | B | 169 | 23.776 | 25.194 | 71.163 | 1.00 | 48.16 B | C |
| ATOM | 2734 | OE1 | GLN | B | 169 | 23.775 | 26.375 | 71.519 | 1.00 | 48.37 B | O |
| ATOM | 2735 | NE2 | GLN | B | 169 | 23.376 | 24.201 | 71.962 | 1.00 | 47.14 B | N |
| ATOM | 2736 | C | GLN | B | 169 | 22.579 | 24.091 | 67.478 | 1.00 | 44.06 B | C |
| ATOM | 2737 | O | GLN | B | 169 | 21.396 | 24.285 | 67.758 | 1.00 | 44.73 B | O |
| ATOM | 2738 | N | PHE | B | 170 | 23.070 | 22.870 | 67.303 | 1.00 | 43.03 B | N |
| ATOM | 2739 | CA | PHE | B | 170 | 22.287 | 21.705 | 67.695 | 1.00 | 43.87 B | C |
| ATOM | 2740 | CB | PHE | B | 170 | 22.693 | 20.476 | 66.874 | 1.00 | 42.71 B | C |
| ATOM | 2741 | CG | PHE | B | 170 | 22.324 | 20.549 | 65.416 | 1.00 | 42.43 B | C |
| ATOM | 2742 | CD1 | PHE | B | 170 | 23.231 | 21.053 | 64.483 | 1.00 | 41.71 B | C |
| ATOM | 2743 | CD2 | PHE | B | 170 | 21.098 | 20.041 | 64.966 | 1.00 | 42.38 B | C |
| ATOM | 2744 | CE1 | PHE | B | 170 | 22.934 | 21.045 | 63.129 | 1.00 | 40.51 B | C |
| ATOM | 2745 | CE2 | PHE | B | 170 | 20.781 | 20.025 | 63.613 | 1.00 | 40.13 B | C |
| ATOM | 2746 | CZ | PHE | B | 170 | 21.703 | 20.526 | 62.689 | 1.00 | 41.47 B | C |
| ATOM | 2747 | C | PHE | B | 170 | 22.521 | 21.424 | 69.191 | 1.00 | 44.46 B | C |
| ATOM | 2748 | O | PHE | B | 170 | 23.639 | 21.549 | 69.683 | 1.00 | 42.66 B | O |
| ATOM | 2749 | N | GLY | B | 171 | 21.476 | 21.045 | 69.913 | 1.00 | 44.65 B | N |
| ATOM | 2750 | CA | GLY | B | 171 | 21.653 | 20.759 | 71.323 | 1.00 | 47.14 B | C |
| ATOM | 2751 | C | GLY | B | 171 | 20.581 | 19.819 | 71.838 | 1.00 | 49.17 B | C |
| ATOM | 2752 | O | GLY | B | 171 | 19.590 | 19.563 | 71.144 | 1.00 | 50.35 B | O |
| ATOM | 2753 | N | VAL | B | 172 | 20.767 | 19.297 | 73.049 | 1.00 | 48.87 B | N |
| ATOM | 2754 | CA | VAL | B | 172 | 19.712 | 18.527 | 73.723 | 1.00 | 49.12 B | C |
| ATOM | 2755 | CB | VAL | B | 172 | 20.075 | 17.016 | 73.816 | 1.00 | 46.61 B | C |
| ATOM | 2756 | CG1 | VAL | B | 172 | 20.014 | 16.374 | 72.446 | 1.00 | 43.45 B | C |
| ATOM | 2757 | CG2 | VAL | B | 172 | 21.447 | 16.846 | 74.433 | 1.00 | 43.17 B | C |
| ATOM | 2758 | C | VAL | B | 172 | 19.386 | 19.032 | 75.142 | 1.00 | 50.61 B | C |
| ATOM | 2759 | O | VAL | B | 172 | 20.224 | 19.655 | 75.804 | 1.00 | 51.06 B | O |
| ATOM | 2760 | N | ALA | B | 173 | 18.161 | 18.771 | 75.603 | 1.00 | 51.57 B | N |
| ATOM | 2761 | CA | ALA | B | 173 | 17.776 | 19.118 | 76.975 | 1.00 | 51.58 B | C |
| ATOM | 2762 | CB | ALA | B | 173 | 18.551 | 18.256 | 77.959 | 1.00 | 49.61 B | C |
| ATOM | 2763 | C | ALA | B | 173 | 18.056 | 20.599 | 77.236 | 1.00 | 52.82 B | C |
| ATOM | 2764 | O | ALA | B | 173 | 17.649 | 21.465 | 76.456 | 1.00 | 53.31 B | O |
| ATOM | 2765 | N | GLU | B | 174 | 18.759 | 20.887 | 78.331 | 1.00 | 54.71 B | N |
| ATOM | 2766 | CA | GLU | B | 174 | 19.239 | 22.242 | 78.621 | 1.00 | 53.26 B | C |
| ATOM | 2767 | CB | GLU | B | 174 | 19.364 | 22.464 | 80.128 | 1.00 | 55.77 B | C |
| ATOM | 2768 | CG | GLU | B | 174 | 19.588 | 23.911 | 80.497 | 1.00 | 59.80 B | C |
| ATOM | 2769 | CD | GLU | B | 174 | 18.461 | 24.802 | 79.988 | 1.00 | 62.99 B | C |
| ATOM | 2770 | OE1 | GLU | B | 174 | 17.729 | 25.374 | 80.837 | 1.00 | 63.97 B | O |
| ATOM | 2771 | OE2 | GLU | B | 174 | 18.304 | 24.924 | 78.740 | 1.00 | 64.84 B | O |

TABLE 11-continued

Coordinates for pro MMP9(35-444 ΔFnII) (SEQ ID NO: 12) complex with Example 1

| ATOM | 2772 | C   | GLU | B | 174 | 20.601 | 22.443 | 77.984 | 1.00 | 51.98 | B | C |
|------|------|-----|-----|---|-----|--------|--------|--------|------|-------|---|---|
| ATOM | 2773 | O   | GLU | B | 174 | 21.539 | 21.678 | 78.229 | 1.00 | 51.97 | B | O |
| ATOM | 2774 | N   | HIS | B | 175 | 20.705 | 23.483 | 77.170 | 1.00 | 50.90 | B | N |
| ATOM | 2775 | CA  | HIS | B | 175 | 21.874 | 23.670 | 76.329 | 1.00 | 49.30 | B | C |
| ATOM | 2776 | CB  | HIS | B | 175 | 21.481 | 23.505 | 74.857 | 1.00 | 48.17 | B | C |
| ATOM | 2777 | CG  | HIS | B | 175 | 20.173 | 24.143 | 74.493 | 1.00 | 47.43 | B | C |
| ATOM | 2778 | CD2 | HIS | B | 175 | 19.772 | 25.435 | 74.508 | 1.00 | 46.86 | B | C |
| ATOM | 2779 | ND1 | HIS | B | 175 | 19.101 | 23.416 | 74.017 | 1.00 | 47.66 | B | N |
| ATOM | 2780 | CE1 | HIS | B | 175 | 18.097 | 24.234 | 73.757 | 1.00 | 45.86 | B | C |
| ATOM | 2781 | NE2 | HIS | B | 175 | 18.478 | 25.464 | 74.046 | 1.00 | 45.27 | B | N |
| ATOM | 2782 | C   | HIS | B | 175 | 22.530 | 25.023 | 76.575 | 1.00 | 48.32 | B | C |
| ATOM | 2783 | O   | HIS | B | 175 | 23.354 | 25.492 | 75.783 | 1.00 | 48.12 | B | O |
| ATOM | 2784 | N   | GLY | B | 176 | 22.152 | 25.649 | 77.685 | 1.00 | 48.13 | B | N |
| ATOM | 2785 | CA  | GLY | B | 176 | 22.850 | 26.839 | 78.134 | 1.00 | 47.35 | B | C |
| ATOM | 2786 | C   | GLY | B | 176 | 22.174 | 28.125 | 77.725 | 1.00 | 46.62 | B | C |
| ATOM | 2787 | O   | GLY | B | 176 | 22.850 | 29.094 | 77.393 | 1.00 | 46.34 | B | O |
| ATOM | 2788 | N   | ASP | B | 177 | 20.841 | 28.129 | 77.740 | 1.00 | 47.01 | B | N |
| ATOM | 2789 | CA  | ASP | B | 177 | 20.078 | 29.362 | 77.589 | 1.00 | 47.08 | B | C |
| ATOM | 2790 | CB  | ASP | B | 177 | 19.735 | 29.622 | 76.118 | 1.00 | 46.99 | B | C |
| ATOM | 2791 | CG  | ASP | B | 177 | 18.773 | 28.599 | 75.530 | 1.00 | 47.26 | B | C |
| ATOM | 2792 | OD1 | ASP | B | 177 | 18.264 | 27.725 | 76.281 | 1.00 | 46.52 | B | O |
| ATOM | 2793 | OD2 | ASP | B | 177 | 18.532 | 28.689 | 74.295 | 1.00 | 45.00 | B | O |
| ATOM | 2794 | C   | ASP | B | 177 | 18.814 | 29.351 | 78.428 | 1.00 | 47.30 | B | C |
| ATOM | 2795 | O   | ASP | B | 177 | 17.958 | 30.237 | 78.315 | 1.00 | 46.18 | B | O |
| ATOM | 2796 | N   | GLY | B | 178 | 18.709 | 28.334 | 79.273 | 1.00 | 47.82 | B | N |
| ATOM | 2797 | CA  | GLY | B | 178 | 17.617 | 28.293 | 80.219 | 1.00 | 49.94 | B | C |
| ATOM | 2798 | C   | GLY | B | 178 | 16.286 | 28.034 | 79.543 | 1.00 | 50.90 | B | C |
| ATOM | 2799 | O   | GLY | B | 178 | 15.233 | 28.089 | 80.179 | 1.00 | 53.83 | B | O |
| ATOM | 2800 | N   | TYR | B | 179 | 16.319 | 27.755 | 78.246 | 1.00 | 50.73 | B | N |
| ATOM | 2801 | CA  | TYR | B | 179 | 15.105 | 27.377 | 77.531 | 1.00 | 48.38 | B | C |
| ATOM | 2802 | CB  | TYR | B | 179 | 14.805 | 28.371 | 76.421 | 1.00 | 47.06 | B | C |
| ATOM | 2803 | CG  | TYR | B | 179 | 14.385 | 29.736 | 76.919 | 1.00 | 46.64 | B | C |
| ATOM | 2804 | CD1 | TYR | B | 179 | 15.332 | 30.699 | 77.249 | 1.00 | 45.72 | B | C |
| ATOM | 2805 | CE1 | TYR | B | 179 | 14.955 | 31.971 | 77.632 | 1.00 | 45.55 | B | C |
| ATOM | 2806 | CD2 | TYR | B | 179 | 13.043 | 30.083 | 76.996 | 1.00 | 47.09 | B | C |
| ATOM | 2807 | CE2 | TYR | B | 179 | 12.657 | 31.353 | 77.375 | 1.00 | 46.89 | B | C |
| ATOM | 2808 | CZ  | TYR | B | 179 | 13.616 | 32.294 | 77.688 | 1.00 | 46.35 | B | C |
| ATOM | 2809 | OH  | TYR | B | 179 | 13.216 | 33.569 | 78.027 | 1.00 | 47.43 | B | O |
| ATOM | 2810 | C   | TYR | B | 179 | 15.293 | 25.993 | 76.952 | 1.00 | 47.71 | B | C |
| ATOM | 2811 | O   | TYR | B | 179 | 15.416 | 25.816 | 75.741 | 1.00 | 46.97 | B | O |
| ATOM | 2812 | N   | PRO | B | 180 | 15.308 | 24.987 | 77.831 | 1.00 | 46.25 | B | N |
| ATOM | 2813 | CD  | PRO | B | 180 | 14.864 | 25.149 | 79.224 | 1.00 | 44.90 | B | C |
| ATOM | 2814 | CA  | PRO | B | 180 | 15.677 | 23.606 | 77.531 | 1.00 | 45.55 | B | C |
| ATOM | 2815 | CB  | PRO | B | 180 | 15.724 | 22.955 | 78.897 | 1.00 | 45.49 | B | C |
| ATOM | 2816 | CG  | PRO | B | 180 | 14.725 | 23.743 | 79.694 | 1.00 | 45.12 | B | C |
| ATOM | 2817 | C   | PRO | B | 180 | 14.697 | 22.902 | 76.604 | 1.00 | 45.86 | B | C |
| ATOM | 2818 | O   | PRO | B | 180 | 13.485 | 23.098 | 76.697 | 1.00 | 45.57 | B | O |
| ATOM | 2819 | N   | PHE | B | 181 | 15.245 | 22.074 | 75.719 | 1.00 | 47.00 | B | N |
| ATOM | 2820 | CA  | PHE | B | 181 | 14.468 | 21.166 | 74.874 | 1.00 | 48.31 | B | C |
| ATOM | 2821 | CB  | PHE | B | 181 | 15.341 | 20.615 | 73.750 | 1.00 | 48.17 | B | C |
| ATOM | 2822 | CG  | PHE | B | 181 | 15.771 | 21.647 | 72.757 | 1.00 | 46.35 | B | C |
| ATOM | 2823 | CD1 | PHE | B | 181 | 14.948 | 22.722 | 72.466 | 1.00 | 46.24 | B | C |
| ATOM | 2824 | CD2 | PHE | B | 181 | 16.989 | 21.530 | 72.103 | 1.00 | 45.59 | B | C |
| ATOM | 2825 | CE1 | PHE | B | 181 | 15.328 | 23.661 | 71.542 | 1.00 | 46.10 | B | C |
| ATOM | 2826 | CE2 | PHE | B | 181 | 17.372 | 22.463 | 71.181 | 1.00 | 45.25 | B | C |
| ATOM | 2827 | CZ  | PHE | B | 181 | 16.537 | 23.536 | 70.896 | 1.00 | 45.48 | B | C |
| ATOM | 2828 | C   | PHE | B | 181 | 13.872 | 19.985 | 75.633 | 1.00 | 49.27 | B | C |
| ATOM | 2829 | O   | PHE | B | 181 | 14.165 | 19.765 | 76.810 | 1.00 | 50.37 | B | O |
| ATOM | 2830 | N   | ASP | B | 182 | 13.050 | 19.209 | 74.931 | 1.00 | 50.07 | B | N |
| ATOM | 2831 | CA  | ASP | B | 182 | 12.195 | 18.204 | 75.559 | 1.00 | 50.05 | B | C |
| ATOM | 2832 | CB  | ASP | B | 182 | 10.727 | 18.648 | 75.470 | 1.00 | 50.98 | B | C |
| ATOM | 2833 | CG  | ASP | B | 182 | 10.241 | 18.813 | 74.021 | 1.00 | 51.83 | B | C |
| ATOM | 2834 | OD1 | ASP | B | 182 | 10.998 | 19.352 | 73.189 | 1.00 | 51.17 | B | O |
| ATOM | 2835 | OD2 | ASP | B | 182 | 9.095  | 18.401 | 73.712 | 1.00 | 53.43 | B | O |
| ATOM | 2836 | C   | ASP | B | 182 | 12.344 | 16.823 | 74.924 | 1.00 | 50.10 | B | C |
| ATOM | 2837 | O   | ASP | B | 182 | 11.355 | 16.154 | 74.641 | 1.00 | 51.84 | B | O |
| ATOM | 2838 | N   | GLY | B | 183 | 13.573 | 16.392 | 74.689 | 1.00 | 50.20 | B | N |
| ATOM | 2839 | CA  | GLY | B | 183 | 13.758 | 15.078 | 74.108 | 1.00 | 50.19 | B | C |
| ATOM | 2840 | C   | GLY | B | 183 | 13.178 | 14.962 | 72.715 | 1.00 | 49.89 | B | C |
| ATOM | 2841 | O   | GLY | B | 183 | 13.595 | 15.669 | 71.802 | 1.00 | 50.71 | B | O |
| ATOM | 2842 | N   | LYS | B | 184 | 12.213 | 14.072 | 72.539 | 1.00 | 50.71 | B | N |
| ATOM | 2843 | CA  | LYS | B | 184 | 11.888 | 13.601 | 71.198 | 1.00 | 52.14 | B | C |
| ATOM | 2844 | CB  | LYS | B | 184 | 12.177 | 12.100 | 71.113 | 1.00 | 53.44 | B | C |
| ATOM | 2845 | CG  | LYS | B | 184 | 11.745 | 11.449 | 69.825 | 1.00 | 54.99 | B | C |
| ATOM | 2846 | CD  | LYS | B | 184 | 11.534 | 9.963  | 70.043 | 1.00 | 57.13 | B | C |
| ATOM | 2847 | CE  | LYS | B | 184 | 10.660 | 9.365  | 68.948 | 1.00 | 59.13 | B | C |
| ATOM | 2848 | NZ  | LYS | B | 184 | 9.301  | 9.995  | 68.879 | 1.00 | 58.76 | B | N |
| ATOM | 2849 | C   | LYS | B | 184 | 10.444 | 13.888 | 70.802 | 1.00 | 52.58 | B | C |

TABLE 11-continued

Coordinates for pro MMP9(35-444 ΔFnII) (SEQ ID NO: 12) complex with Example 1

| ATOM | 2850 | O   | LYS | B | 184 | 9.513  | 13.508 | 71.515 | 1.00 | 52.82 B | O |
|------|------|-----|-----|---|-----|--------|--------|--------|------|---------|---|
| ATOM | 2851 | N   | ASP | B | 185 | 10.274 | 14.553 | 69.658 | 1.00 | 52.06 B | N |
| ATOM | 2852 | CA  | ASP | B | 185 | 8.982  | 15.084 | 69.236 | 1.00 | 51.37 B | C |
| ATOM | 2853 | CB  | ASP | B | 185 | 7.925  | 13.981 | 69.214 | 1.00 | 53.88 B | C |
| ATOM | 2854 | CG  | ASP | B | 185 | 8.316  | 12.818 | 68.309 | 1.00 | 56.84 B | C |
| ATOM | 2855 | OD1 | ASP | B | 185 | 9.288  | 12.977 | 67.523 | 1.00 | 58.84 B | O |
| ATOM | 2856 | OD2 | ASP | B | 185 | 7.649  | 11.756 | 68.378 | 1.00 | 56.58 B | O |
| ATOM | 2857 | C   | ASP | B | 185 | 8.560  | 16.181 | 70.195 | 1.00 | 50.45 B | C |
| ATOM | 2858 | O   | ASP | B | 185 | 9.216  | 16.418 | 71.203 | 1.00 | 51.04 B | O |
| ATOM | 2859 | N   | GLY | B | 186 | 7.452  | 16.846 | 69.903 | 1.00 | 49.96 B | N |
| ATOM | 2860 | CA  | GLY | B | 186 | 7.085  | 18.002 | 70.702 | 1.00 | 47.71 B | C |
| ATOM | 2861 | C   | GLY | B | 186 | 7.642  | 19.243 | 70.041 | 1.00 | 47.77 B | C |
| ATOM | 2862 | O   | GLY | B | 186 | 7.371  | 19.508 | 68.868 | 1.00 | 47.87 B | O |
| ATOM | 2863 | N   | LEU | B | 187 | 8.424  | 20.023 | 70.770 | 1.00 | 47.62 B | N |
| ATOM | 2864 | CA  | LEU | B | 187 | 9.015  | 21.181 | 70.132 | 1.00 | 48.61 B | C |
| ATOM | 2865 | CB  | LEU | B | 187 | 9.212  | 22.329 | 71.139 | 1.00 | 48.72 B | C |
| ATOM | 2866 | CG  | LEU | B | 187 | 9.704  | 22.063 | 72.556 | 1.00 | 47.44 B | C |
| ATOM | 2867 | CD1 | LEU | B | 187 | 10.320 | 23.325 | 73.114 | 1.00 | 46.61 B | C |
| ATOM | 2868 | CD2 | LEU | B | 187 | 8.549  | 21.590 | 73.422 | 1.00 | 47.68 B | C |
| ATOM | 2869 | C   | LEU | B | 187 | 10.343 | 20.788 | 69.473 | 1.00 | 48.13 B | C |
| ATOM | 2870 | O   | LEU | B | 187 | 11.238 | 20.268 | 70.126 | 1.00 | 48.94 B | O |
| ATOM | 2871 | N   | LEU | B | 188 | 10.446 | 21.037 | 68.171 | 1.00 | 45.28 B | N |
| ATOM | 2872 | CA  | LEU | B | 188 | 11.602 | 20.655 | 67.386 | 1.00 | 41.64 B | C |
| ATOM | 2873 | CB  | LEU | B | 188 | 11.213 | 20.591 | 65.914 | 1.00 | 42.63 B | C |
| ATOM | 2874 | CG  | LEU | B | 188 | 10.040 | 19.662 | 65.583 | 1.00 | 42.15 B | C |
| ATOM | 2875 | CD1 | LEU | B | 188 | 9.613  | 19.869 | 64.137 | 1.00 | 41.06 B | C |
| ATOM | 2876 | CD2 | LEU | B | 188 | 10.453 | 18.223 | 65.820 | 1.00 | 41.02 B | C |
| ATOM | 2877 | C   | LEU | B | 188 | 12.775 | 21.614 | 67.562 | 1.00 | 40.89 B | C |
| ATOM | 2878 | O   | LEU | B | 188 | 13.928 | 21.182 | 67.610 | 1.00 | 41.38 B | O |
| ATOM | 2879 | N   | ALA | B | 189 | 12.480 | 22.911 | 67.653 | 1.00 | 38.67 B | N |
| ATOM | 2880 | CA  | ALA | B | 189 | 13.506 | 23.949 | 67.762 | 1.00 | 35.47 B | C |
| ATOM | 2881 | CB  | ALA | B | 189 | 14.267 | 24.049 | 66.475 | 1.00 | 35.61 B | C |
| ATOM | 2882 | C   | ALA | B | 189 | 12.925 | 25.307 | 68.105 | 1.00 | 35.91 B | C |
| ATOM | 2883 | O   | ALA | B | 189 | 11.715 | 25.504 | 68.113 | 1.00 | 35.15 B | O |
| ATOM | 2884 | N   | HIS | B | 190 | 13.796 | 26.257 | 68.394 | 1.00 | 37.57 B | N |
| ATOM | 2885 | CA  | HIS | B | 190 | 13.361 | 27.640 | 68.431 | 1.00 | 39.50 B | C |
| ATOM | 2886 | CB  | HIS | B | 190 | 12.932 | 28.027 | 69.847 | 1.00 | 41.66 B | C |
| ATOM | 2887 | CG  | HIS | B | 190 | 13.970 | 27.777 | 70.897 | 1.00 | 42.26 B | C |
| ATOM | 2888 | CD2 | HIS | B | 190 | 15.203 | 28.309 | 71.084 | 1.00 | 43.73 B | C |
| ATOM | 2889 | ND1 | HIS | B | 190 | 13.762 | 26.918 | 71.952 | 1.00 | 42.74 B | N |
| ATOM | 2890 | CE1 | HIS | B | 190 | 14.818 | 26.930 | 72.745 | 1.00 | 42.32 B | C |
| ATOM | 2891 | NE2 | HIS | B | 190 | 15.707 | 27.768 | 72.242 | 1.00 | 42.46 B | N |
| ATOM | 2892 | C   | HIS | B | 190 | 14.431 | 28.587 | 67.920 | 1.00 | 40.35 B | C |
| ATOM | 2893 | O   | HIS | B | 190 | 15.446 | 28.153 | 67.374 | 1.00 | 41.11 B | O |
| ATOM | 2894 | N   | ALA | B | 191 | 14.194 | 29.883 | 68.085 | 1.00 | 40.39 B | N |
| ATOM | 2895 | CA  | ALA | B | 191 | 15.114 | 30.906 | 67.584 | 1.00 | 42.00 B | C |
| ATOM | 2896 | CB  | ALA | B | 191 | 14.919 | 31.093 | 66.073 | 1.00 | 39.51 B | C |
| ATOM | 2897 | C   | ALA | B | 191 | 14.896 | 32.236 | 68.308 | 1.00 | 42.12 B | C |
| ATOM | 2898 | O   | ALA | B | 191 | 13.780 | 32.559 | 68.685 | 1.00 | 42.59 B | O |
| ATOM | 2899 | N   | PHE | B | 192 | 15.961 | 33.005 | 68.494 | 1.00 | 42.45 B | N |
| ATOM | 2900 | CA  | PHE | B | 192 | 15.841 | 34.290 | 69.168 | 1.00 | 43.53 B | C |
| ATOM | 2901 | CB  | PHE | B | 192 | 17.054 | 34.519 | 70.047 | 1.00 | 44.53 B | C |
| ATOM | 2902 | CG  | PHE | B | 192 | 17.060 | 33.651 | 71.249 | 1.00 | 44.83 B | C |
| ATOM | 2903 | CD1 | PHE | B | 192 | 16.503 | 34.091 | 72.433 | 1.00 | 44.75 B | C |
| ATOM | 2904 | CD2 | PHE | B | 192 | 17.578 | 32.374 | 71.188 | 1.00 | 46.15 B | C |
| ATOM | 2905 | CE1 | PHE | B | 192 | 16.457 | 33.277 | 73.537 | 1.00 | 43.76 B | C |
| ATOM | 2906 | CE2 | PHE | B | 192 | 17.537 | 31.548 | 72.291 | 1.00 | 46.52 B | C |
| ATOM | 2907 | CZ  | PHE | B | 192 | 16.973 | 32.004 | 73.469 | 1.00 | 45.40 B | C |
| ATOM | 2908 | C   | PHE | B | 192 | 15.658 | 35.462 | 68.212 | 1.00 | 44.86 B | C |
| ATOM | 2909 | O   | PHE | B | 192 | 15.971 | 35.359 | 67.016 | 1.00 | 46.32 B | O |
| ATOM | 2910 | N   | PRO | B | 193 | 15.128 | 36.590 | 68.716 | 1.00 | 43.32 B | N |
| ATOM | 2911 | CD  | PRO | B | 193 | 14.565 | 36.775 | 70.062 | 1.00 | 41.27 B | C |
| ATOM | 2912 | CA  | PRO | B | 193 | 14.904 | 37.751 | 67.841 | 1.00 | 43.10 B | C |
| ATOM | 2913 | CB  | PRO | B | 193 | 13.970 | 38.654 | 68.662 | 1.00 | 42.03 B | C |
| ATOM | 2914 | CG  | PRO | B | 193 | 14.175 | 38.223 | 70.076 | 1.00 | 42.25 B | C |
| ATOM | 2915 | C   | PRO | B | 193 | 16.218 | 38.450 | 67.422 | 1.00 | 42.87 B | C |
| ATOM | 2916 | O   | PRO | B | 193 | 17.269 | 38.244 | 68.029 | 1.00 | 43.53 B | O |
| ATOM | 2917 | N   | PRO | B | 194 | 16.174 | 39.275 | 66.359 | 1.00 | 43.68 B | N |
| ATOM | 2918 | CD  | PRO | B | 194 | 15.074 | 39.523 | 65.401 | 1.00 | 42.33 B | C |
| ATOM | 2919 | CA  | PRO | B | 194 | 17.422 | 39.943 | 65.956 | 1.00 | 42.55 B | C |
| ATOM | 2920 | CB  | PRO | B | 194 | 17.030 | 40.707 | 64.687 | 1.00 | 42.22 B | C |
| ATOM | 2921 | CG  | PRO | B | 194 | 15.808 | 39.991 | 64.166 | 1.00 | 41.34 B | C |
| ATOM | 2922 | C   | PRO | B | 194 | 17.915 | 40.878 | 67.054 | 1.00 | 43.26 B | C |
| ATOM | 2923 | O   | PRO | B | 194 | 17.140 | 41.677 | 67.586 | 1.00 | 43.12 B | O |
| ATOM | 2924 | N   | GLY | B | 195 | 19.196 | 40.797 | 67.397 | 1.00 | 43.58 B | N |
| ATOM | 2925 | CA  | GLY | B | 195 | 19.711 | 41.704 | 68.415 | 1.00 | 45.49 B | C |
| ATOM | 2926 | C   | GLY | B | 195 | 21.146 | 41.435 | 68.819 | 1.00 | 45.92 B | C |
| ATOM | 2927 | O   | GLY | B | 195 | 21.861 | 40.753 | 68.099 | 1.00 | 45.73 B | O |

TABLE 11-continued

Coordinates for pro MMP9(35-444 ΔFnII) (SEQ ID NO: 12) complex with Example 1

| ATOM | 2928 | N   | PRO | B | 196 | 21.600 | 41.969 | 69.961 | 1.00 | 45.58 | B | N |
|------|------|-----|-----|---|-----|--------|--------|--------|------|-------|---|---|
| ATOM | 2929 | CD  | PRO | B | 196 | 20.900 | 42.984 | 70.772 | 1.00 | 45.79 | B | C |
| ATOM | 2930 | CA  | PRO | B | 196 | 22.896 | 41.592 | 70.542 | 1.00 | 46.21 | B | C |
| ATOM | 2931 | CB  | PRO | B | 196 | 23.109 | 42.623 | 71.649 | 1.00 | 46.39 | B | C |
| ATOM | 2932 | CG  | PRO | B | 196 | 21.708 | 43.024 | 72.048 | 1.00 | 46.25 | B | C |
| ATOM | 2933 | C   | PRO | B | 196 | 22.868 | 40.176 | 71.099 | 1.00 | 46.39 | B | C |
| ATOM | 2934 | O   | PRO | B | 196 | 21.806 | 39.662 | 71.438 | 1.00 | 47.42 | B | O |
| ATOM | 2935 | N   | GLY | B | 197 | 24.035 | 39.541 | 71.181 | 1.00 | 47.78 | B | N |
| ATOM | 2936 | CA  | GLY | B | 197 | 24.197 | 38.358 | 72.030 | 1.00 | 47.25 | B | C |
| ATOM | 2937 | C   | GLY | B | 197 | 23.617 | 37.024 | 71.570 | 1.00 | 46.37 | B | C |
| ATOM | 2938 | O   | GLY | B | 197 | 23.979 | 36.490 | 70.532 | 1.00 | 46.15 | B | O |
| ATOM | 2939 | N   | ILE | B | 198 | 22.732 | 36.467 | 72.386 | 1.00 | 47.41 | B | N |
| ATOM | 2940 | CA  | ILE | B | 198 | 21.989 | 35.272 | 72.021 | 1.00 | 47.27 | B | C |
| ATOM | 2941 | CB  | ILE | B | 198 | 21.327 | 34.638 | 73.229 | 1.00 | 48.66 | B | C |
| ATOM | 2942 | CG2 | ILE | B | 198 | 20.259 | 35.587 | 73.787 | 1.00 | 47.22 | B | C |
| ATOM | 2943 | CG1 | ILE | B | 198 | 20.660 | 33.327 | 72.818 | 1.00 | 50.98 | B | C |
| ATOM | 2944 | CD1 | ILE | B | 198 | 21.583 | 32.439 | 71.983 | 1.00 | 52.70 | B | C |
| ATOM | 2945 | C   | ILE | B | 198 | 20.855 | 35.671 | 71.088 | 1.00 | 47.61 | B | C |
| ATOM | 2946 | O   | ILE | B | 198 | 20.154 | 34.819 | 70.538 | 1.00 | 48.77 | B | O |
| ATOM | 2947 | N   | GLN | B | 199 | 20.638 | 36.972 | 70.946 | 1.00 | 46.21 | B | N |
| ATOM | 2948 | CA  | GLN | B | 199 | 19.559 | 37.416 | 70.098 | 1.00 | 44.85 | B | C |
| ATOM | 2949 | CB  | GLN | B | 199 | 19.221 | 38.882 | 70.387 | 1.00 | 44.49 | B | C |
| ATOM | 2950 | CG  | GLN | B | 199 | 18.401 | 39.075 | 71.676 | 1.00 | 44.73 | B | C |
| ATOM | 2951 | CD  | GLN | B | 199 | 18.210 | 40.553 | 72.065 | 1.00 | 47.27 | B | C |
| ATOM | 2952 | OE1 | GLN | B | 199 | 17.855 | 41.390 | 71.223 | 1.00 | 47.82 | B | O |
| ATOM | 2953 | NE2 | GLN | B | 199 | 18.452 | 40.874 | 73.345 | 1.00 | 46.28 | B | N |
| ATOM | 2954 | C   | GLN | B | 199 | 20.022 | 37.216 | 68.664 | 1.00 | 43.90 | B | C |
| ATOM | 2955 | O   | GLN | B | 199 | 20.925 | 37.893 | 68.208 | 1.00 | 44.67 | B | O |
| ATOM | 2956 | N   | GLY | B | 200 | 19.429 | 36.248 | 67.973 | 1.00 | 42.93 | B | N |
| ATOM | 2957 | CA  | GLY | B | 200 | 19.710 | 36.075 | 66.561 | 1.00 | 43.21 | B | C |
| ATOM | 2958 | C   | GLY | B | 200 | 20.076 | 34.639 | 66.248 | 1.00 | 45.16 | B | C |
| ATOM | 2959 | O   | GLY | B | 200 | 20.135 | 34.211 | 65.081 | 1.00 | 44.33 | B | O |
| ATOM | 2960 | N   | ASP | B | 201 | 20.318 | 33.893 | 67.319 | 1.00 | 44.98 | B | N |
| ATOM | 2961 | CA  | ASP | B | 201 | 20.574 | 32.462 | 67.249 | 1.00 | 45.36 | B | C |
| ATOM | 2962 | CB  | ASP | B | 201 | 21.110 | 31.974 | 68.601 | 1.00 | 46.30 | B | C |
| ATOM | 2963 | CG  | ASP | B | 201 | 22.549 | 32.343 | 68.829 | 1.00 | 47.35 | B | C |
| ATOM | 2964 | OD1 | ASP | B | 201 | 22.987 | 33.427 | 68.369 | 1.00 | 49.22 | B | O |
| ATOM | 2965 | OD2 | ASP | B | 201 | 23.247 | 31.537 | 69.483 | 1.00 | 47.81 | B | O |
| ATOM | 2966 | C   | ASP | B | 201 | 19.339 | 31.623 | 66.867 | 1.00 | 45.46 | B | C |
| ATOM | 2967 | O   | ASP | B | 201 | 18.182 | 32.007 | 67.101 | 1.00 | 45.37 | B | O |
| ATOM | 2968 | N   | ALA | B | 202 | 19.619 | 30.459 | 66.286 | 1.00 | 44.34 | B | N |
| ATOM | 2969 | CA  | ALA | B | 202 | 18.613 | 29.449 | 65.994 | 1.00 | 41.65 | B | C |
| ATOM | 2970 | CB  | ALA | B | 202 | 18.272 | 29.478 | 64.501 | 1.00 | 40.80 | B | C |
| ATOM | 2971 | C   | ALA | B | 202 | 19.153 | 28.075 | 66.393 | 1.00 | 39.53 | B | C |
| ATOM | 2972 | O   | ALA | B | 202 | 20.170 | 27.618 | 65.876 | 1.00 | 38.32 | B | O |
| ATOM | 2973 | N   | HIS | B | 203 | 18.460 | 27.429 | 67.321 | 1.00 | 40.41 | B | N |
| ATOM | 2974 | CA  | HIS | B | 203 | 18.867 | 26.133 | 67.860 | 1.00 | 40.01 | B | C |
| ATOM | 2975 | CB  | HIS | B | 203 | 18.806 | 26.181 | 69.386 | 1.00 | 39.51 | B | C |
| ATOM | 2976 | CG  | HIS | B | 203 | 19.661 | 27.258 | 69.979 | 1.00 | 40.38 | B | C |
| ATOM | 2977 | CD2 | HIS | B | 203 | 20.905 | 27.682 | 69.655 | 1.00 | 40.75 | B | C |
| ATOM | 2978 | ND1 | HIS | B | 203 | 19.260 | 28.030 | 71.048 | 1.00 | 41.15 | B | N |
| ATOM | 2979 | CE1 | HIS | B | 203 | 20.222 | 28.879 | 71.358 | 1.00 | 41.02 | B | C |
| ATOM | 2980 | NE2 | HIS | B | 203 | 21.232 | 28.689 | 70.529 | 1.00 | 40.36 | B | N |
| ATOM | 2981 | C   | HIS | B | 203 | 17.971 | 25.019 | 67.352 | 1.00 | 39.63 | B | C |
| ATOM | 2982 | O   | HIS | B | 203 | 16.814 | 25.252 | 67.005 | 1.00 | 40.31 | B | O |
| ATOM | 2983 | N   | PHE | B | 204 | 18.501 | 23.804 | 67.317 | 1.00 | 39.56 | B | N |
| ATOM | 2984 | CA  | PHE | B | 204 | 17.739 | 22.667 | 66.816 | 1.00 | 38.07 | B | C |
| ATOM | 2985 | CB  | PHE | B | 204 | 18.260 | 22.272 | 65.432 | 1.00 | 38.92 | B | C |
| ATOM | 2986 | CG  | PHE | B | 204 | 18.193 | 23.388 | 64.433 | 1.00 | 38.34 | B | C |
| ATOM | 2987 | CD1 | PHE | B | 204 | 19.191 | 24.339 | 64.372 | 1.00 | 36.69 | B | C |
| ATOM | 2988 | CD2 | PHE | B | 204 | 17.098 | 23.519 | 63.593 | 1.00 | 38.44 | B | C |
| ATOM | 2989 | CE1 | PHE | B | 204 | 19.090 | 25.394 | 63.500 | 1.00 | 37.05 | B | C |
| ATOM | 2990 | CE2 | PHE | B | 204 | 17.005 | 24.583 | 62.721 | 1.00 | 37.27 | B | C |
| ATOM | 2991 | CZ  | PHE | B | 204 | 17.996 | 25.518 | 62.673 | 1.00 | 35.10 | B | C |
| ATOM | 2992 | C   | PHE | B | 204 | 17.848 | 21.491 | 67.758 | 1.00 | 37.48 | B | C |
| ATOM | 2993 | O   | PHE | B | 204 | 18.947 | 21.099 | 68.146 | 1.00 | 35.94 | B | O |
| ATOM | 2994 | N   | ASP | B | 205 | 16.705 | 20.923 | 68.122 | 1.00 | 38.68 | B | N |
| ATOM | 2995 | CA  | ASP | B | 205 | 16.696 | 19.754 | 68.994 | 1.00 | 41.03 | B | C |
| ATOM | 2996 | CB  | ASP | B | 205 | 15.271 | 19.463 | 69.466 | 1.00 | 41.80 | B | C |
| ATOM | 2997 | CG  | ASP | B | 205 | 15.238 | 18.467 | 70.599 | 1.00 | 43.94 | B | C |
| ATOM | 2998 | OD1 | ASP | B | 205 | 16.122 | 17.573 | 70.622 | 1.00 | 45.36 | B | O |
| ATOM | 2999 | OD2 | ASP | B | 205 | 14.343 | 18.577 | 71.462 | 1.00 | 42.56 | B | O |
| ATOM | 3000 | C   | ASP | B | 205 | 17.293 | 18.500 | 68.327 | 1.00 | 42.68 | B | C |
| ATOM | 3001 | O   | ASP | B | 205 | 16.708 | 17.927 | 67.405 | 1.00 | 41.40 | B | O |
| ATOM | 3002 | N   | ASP | B | 206 | 18.459 | 18.076 | 68.807 | 1.00 | 44.32 | B | N |
| ATOM | 3003 | CA  | ASP | B | 206 | 19.223 | 17.038 | 68.122 | 1.00 | 46.24 | B | C |
| ATOM | 3004 | CB  | ASP | B | 206 | 20.738 | 17.279 | 68.282 | 1.00 | 48.63 | B | C |
| ATOM | 3005 | CG  | ASP | B | 206 | 21.580 | 16.503 | 67.249 | 1.00 | 51.32 | B | C |

TABLE 11-continued

Coordinates for pro MMP9(35-444 ΔFnII) (SEQ ID NO: 12) complex with Example 1

| ATOM | 3006 | OD1 | ASP | B | 206 | 20.999 | 15.689 | 66.498 | 1.00 | 54.26 | B | O |
|---|---|---|---|---|---|---|---|---|---|---|---|---|
| ATOM | 3007 | OD2 | ASP | B | 206 | 22.821 | 16.702 | 67.186 | 1.00 | 52.05 | B | O |
| ATOM | 3008 | C | ASP | B | 206 | 18.847 | 15.681 | 68.688 | 1.00 | 46.87 | B | C |
| ATOM | 3009 | O | ASP | B | 206 | 19.464 | 14.666 | 68.367 | 1.00 | 47.41 | B | O |
| ATOM | 3010 | N | ASP | B | 207 | 17.830 | 15.673 | 69.542 | 1.00 | 47.41 | B | N |
| ATOM | 3011 | CA | ASP | B | 207 | 17.226 | 14.428 | 69.984 | 1.00 | 48.07 | B | C |
| ATOM | 3012 | CB | ASP | B | 207 | 16.445 | 14.649 | 71.290 | 1.00 | 48.89 | B | C |
| ATOM | 3013 | CG | ASP | B | 207 | 17.312 | 14.441 | 72.543 | 1.00 | 51.54 | B | C |
| ATOM | 3014 | OD1 | ASP | B | 207 | 18.193 | 13.540 | 72.516 | 1.00 | 51.22 | B | O |
| ATOM | 3015 | OD2 | ASP | B | 207 | 17.101 | 15.171 | 73.552 | 1.00 | 51.89 | B | O |
| ATOM | 3016 | C | ASP | B | 207 | 16.307 | 13.941 | 68.866 | 1.00 | 48.06 | B | C |
| ATOM | 3017 | O | ASP | B | 207 | 15.897 | 12.776 | 68.826 | 1.00 | 48.72 | B | O |
| ATOM | 3018 | N | GLU | B | 208 | 16.014 | 14.844 | 67.940 | 1.00 | 47.98 | B | N |
| ATOM | 3019 | CA | GLU | B | 208 | 15.233 | 14.519 | 66.753 | 1.00 | 48.39 | B | C |
| ATOM | 3020 | CB | GLU | B | 208 | 14.458 | 15.767 | 66.311 | 1.00 | 49.39 | B | C |
| ATOM | 3021 | CG | GLU | B | 208 | 13.792 | 16.504 | 67.460 | 1.00 | 49.24 | B | C |
| ATOM | 3022 | CD | GLU | B | 208 | 12.541 | 15.811 | 67.926 | 1.00 | 50.52 | B | C |
| ATOM | 3023 | OE1 | GLU | B | 208 | 12.505 | 14.559 | 67.947 | 1.00 | 50.44 | B | O |
| ATOM | 3024 | OE2 | GLU | B | 208 | 11.577 | 16.522 | 68.264 | 1.00 | 52.60 | B | O |
| ATOM | 3025 | C | GLU | B | 208 | 16.106 | 14.011 | 65.593 | 1.00 | 47.48 | B | C |
| ATOM | 3026 | O | GLU | B | 208 | 17.298 | 14.311 | 65.522 | 1.00 | 48.26 | B | O |
| ATOM | 3027 | N | LEU | B | 209 | 15.494 | 13.244 | 64.691 | 1.00 | 47.58 | B | N |
| ATOM | 3028 | CA | LEU | B | 209 | 16.144 | 12.776 | 63.464 | 1.00 | 47.23 | B | C |
| ATOM | 3029 | CB | LEU | B | 209 | 15.552 | 11.449 | 63.026 | 1.00 | 46.79 | B | C |
| ATOM | 3030 | CG | LEU | B | 209 | 15.925 | 11.064 | 61.600 | 1.00 | 47.21 | B | C |
| ATOM | 3031 | CD1 | LEU | B | 209 | 17.374 | 10.535 | 61.572 | 1.00 | 46.54 | B | C |
| ATOM | 3032 | CD2 | LEU | B | 209 | 14.949 | 10.004 | 61.090 | 1.00 | 45.83 | B | C |
| ATOM | 3033 | C | LEU | B | 209 | 15.965 | 13.778 | 62.330 | 1.00 | 47.66 | B | C |
| ATOM | 3034 | O | LEU | B | 209 | 14.837 | 14.106 | 61.952 | 1.00 | 48.63 | B | O |
| ATOM | 3035 | N | TRP | B | 210 | 17.074 | 14.261 | 61.784 | 1.00 | 46.14 | B | N |
| ATOM | 3036 | CA | TRP | B | 210 | 17.006 | 15.306 | 60.781 | 1.00 | 44.12 | B | C |
| ATOM | 3037 | CB | TRP | B | 210 | 18.008 | 16.427 | 61.118 | 1.00 | 41.71 | B | C |
| ATOM | 3038 | CG | TRP | B | 210 | 17.540 | 17.268 | 62.318 | 1.00 | 40.65 | B | C |
| ATOM | 3039 | CD2 | TRP | B | 210 | 16.409 | 18.162 | 62.359 | 1.00 | 38.29 | B | C |
| ATOM | 3040 | CE2 | TRP | B | 210 | 16.272 | 18.611 | 63.690 | 1.00 | 38.00 | B | C |
| ATOM | 3041 | CE3 | TRP | B | 210 | 15.495 | 18.619 | 61.398 | 1.00 | 35.91 | B | C |
| ATOM | 3042 | CD1 | TRP | B | 210 | 18.035 | 17.232 | 63.602 | 1.00 | 39.20 | B | C |
| ATOM | 3043 | NE1 | TRP | B | 210 | 17.274 | 18.032 | 64.428 | 1.00 | 37.89 | B | N |
| ATOM | 3044 | CZ2 | TRP | B | 210 | 15.267 | 19.484 | 64.082 | 1.00 | 38.51 | B | C |
| ATOM | 3045 | CZ3 | TRP | B | 210 | 14.499 | 19.484 | 61.782 | 1.00 | 35.66 | B | C |
| ATOM | 3046 | CH2 | TRP | B | 210 | 14.387 | 19.909 | 63.112 | 1.00 | 38.82 | B | C |
| ATOM | 3047 | C | TRP | B | 210 | 17.271 | 14.683 | 59.428 | 1.00 | 45.10 | B | C |
| ATOM | 3048 | O | TRP | B | 210 | 17.912 | 13.641 | 59.337 | 1.00 | 45.75 | B | O |
| ATOM | 3049 | N | SER | B | 211 | 16.736 | 15.292 | 58.378 | 1.00 | 46.33 | B | N |
| ATOM | 3050 | CA | SER | B | 211 | 16.876 | 14.753 | 57.023 | 1.00 | 47.47 | B | C |
| ATOM | 3051 | CB | SER | B | 211 | 16.144 | 13.395 | 56.893 | 1.00 | 45.60 | B | C |
| ATOM | 3052 | OG | SER | B | 211 | 14.821 | 13.410 | 57.408 | 1.00 | 40.76 | B | O |
| ATOM | 3053 | C | SER | B | 211 | 16.334 | 15.751 | 56.007 | 1.00 | 48.99 | B | C |
| ATOM | 3054 | O | SER | B | 211 | 16.057 | 16.900 | 56.357 | 1.00 | 50.58 | B | O |
| ATOM | 3055 | N | LEU | B | 212 | 16.200 | 15.318 | 54.755 | 1.00 | 50.28 | B | N |
| ATOM | 3056 | CA | LEU | B | 212 | 15.498 | 16.095 | 53.731 | 1.00 | 50.77 | B | C |
| ATOM | 3057 | CB | LEU | B | 212 | 15.735 | 15.478 | 52.359 | 1.00 | 52.04 | B | C |
| ATOM | 3058 | CG | LEU | B | 212 | 17.216 | 15.348 | 51.978 | 1.00 | 52.93 | B | C |
| ATOM | 3059 | CD1 | LEU | B | 212 | 17.352 | 14.601 | 50.637 | 1.00 | 51.42 | B | C |
| ATOM | 3060 | CD2 | LEU | B | 212 | 17.837 | 16.749 | 51.914 | 1.00 | 51.71 | B | C |
| ATOM | 3061 | C | LEU | B | 212 | 13.995 | 16.183 | 53.994 | 1.00 | 52.40 | B | C |
| ATOM | 3062 | O | LEU | B | 212 | 13.399 | 17.230 | 53.780 | 1.00 | 52.79 | B | O |
| ATOM | 3063 | N | GLY | B | 213 | 13.379 | 15.092 | 54.448 | 1.00 | 54.59 | B | N |
| ATOM | 3064 | CA | GLY | B | 213 | 12.034 | 15.190 | 54.997 | 1.00 | 55.70 | B | C |
| ATOM | 3065 | C | GLY | B | 213 | 10.977 | 14.294 | 54.373 | 1.00 | 57.19 | B | C |
| ATOM | 3066 | O | GLY | B | 213 | 9.774 | 14.422 | 54.672 | 1.00 | 58.02 | B | O |
| ATOM | 3067 | N | LYS | B | 389 | 11.424 | 13.383 | 53.506 | 1.00 | 58.33 | B | N |
| ATOM | 3068 | CA | LYS | B | 389 | 10.526 | 12.481 | 52.752 | 1.00 | 58.43 | B | C |
| ATOM | 3069 | CB | LYS | B | 389 | 11.027 | 12.329 | 51.305 | 1.00 | 57.68 | B | C |
| ATOM | 3070 | CG | LYS | B | 389 | 11.006 | 13.614 | 50.488 | 1.00 | 58.29 | B | C |
| ATOM | 3071 | CD | LYS | B | 389 | 12.100 | 13.633 | 49.414 | 1.00 | 59.54 | B | C |
| ATOM | 3072 | CE | LYS | B | 389 | 13.481 | 13.295 | 50.009 | 1.00 | 62.11 | B | C |
| ATOM | 3073 | NZ | LYS | B | 389 | 14.656 | 13.669 | 49.143 | 1.00 | 63.74 | B | N |
| ATOM | 3074 | C | LYS | B | 389 | 10.393 | 11.088 | 53.384 | 1.00 | 58.26 | B | C |
| ATOM | 3075 | O | LYS | B | 389 | 9.598 | 10.278 | 52.920 | 1.00 | 57.88 | B | O |
| ATOM | 3076 | N | GLY | B | 390 | 11.192 | 10.819 | 54.419 | 1.00 | 59.12 | B | N |
| ATOM | 3077 | CA | GLY | B | 390 | 11.110 | 9.553 | 55.125 | 1.00 | 58.22 | B | C |
| ATOM | 3078 | C | GLY | B | 390 | 10.361 | 9.707 | 56.439 | 1.00 | 58.66 | B | C |
| ATOM | 3079 | O | GLY | B | 390 | 9.157 | 9.954 | 56.453 | 1.00 | 58.16 | B | O |
| ATOM | 3080 | N | GLN | B | 391 | 11.073 | 9.568 | 57.553 | 1.00 | 59.44 | B | N |
| ATOM | 3081 | CA | GLN | B | 391 | 10.466 | 9.734 | 58.868 | 1.00 | 57.42 | B | C |
| ATOM | 3082 | CB | GLN | B | 391 | 10.500 | 8.419 | 59.651 | 1.00 | 58.76 | B | C |
| ATOM | 3083 | CG | GLN | B | 391 | 9.828 | 7.242 | 58.956 | 1.00 | 59.52 | B | C |

TABLE 11-continued

Coordinates for pro MMP9(35-444 ΔFnII) (SEQ ID NO: 12) complex with Example 1

| ATOM | 3084 | CD | GLN | B | 391 | 10.305 | 5.906 | 59.504 | 1.00 | 60.24 | B | C |
|---|---|---|---|---|---|---|---|---|---|---|---|---|
| ATOM | 3085 | OE1 | GLN | B | 391 | 11.045 | 5.857 | 60.492 | 1.00 | 60.63 | B | O |
| ATOM | 3086 | NE2 | GLN | B | 391 | 9.886 | 4.814 | 58.863 | 1.00 | 60.01 | B | N |
| ATOM | 3087 | C | GLN | B | 391 | 11.234 | 10.802 | 59.624 | 1.00 | 56.14 | B | C |
| ATOM | 3088 | O | GLN | B | 391 | 11.093 | 10.957 | 60.838 | 1.00 | 57.99 | B | O |
| ATOM | 3089 | N | GLY | B | 392 | 12.063 | 11.538 | 58.893 | 1.00 | 55.06 | B | N |
| ATOM | 3090 | CA | GLY | B | 392 | 12.725 | 12.696 | 59.473 | 1.00 | 52.23 | B | C |
| ATOM | 3091 | C | GLY | B | 392 | 11.951 | 13.997 | 59.302 | 1.00 | 48.64 | B | C |
| ATOM | 3092 | O | GLY | B | 392 | 11.120 | 14.125 | 58.405 | 1.00 | 48.02 | B | O |
| ATOM | 3093 | N | TYR | B | 393 | 12.218 | 14.962 | 60.176 | 1.00 | 45.86 | B | N |
| ATOM | 3094 | CA | TYR | B | 393 | 11.784 | 16.326 | 59.934 | 1.00 | 44.61 | B | C |
| ATOM | 3095 | CB | TYR | B | 393 | 11.750 | 17.145 | 61.246 | 1.00 | 45.06 | B | C |
| ATOM | 3096 | CG | TYR | B | 393 | 10.907 | 16.536 | 62.371 | 1.00 | 45.65 | B | C |
| ATOM | 3097 | CD1 | TYR | B | 393 | 9.515 | 16.424 | 62.256 | 1.00 | 45.93 | B | C |
| ATOM | 3098 | CE1 | TYR | B | 393 | 8.752 | 15.818 | 63.259 | 1.00 | 44.94 | B | C |
| ATOM | 3099 | CD2 | TYR | B | 393 | 11.509 | 16.031 | 63.532 | 1.00 | 44.52 | B | C |
| ATOM | 3100 | CE2 | TYR | B | 393 | 10.754 | 15.424 | 64.533 | 1.00 | 43.76 | B | C |
| ATOM | 3101 | CZ | TYR | B | 393 | 9.377 | 15.318 | 64.390 | 1.00 | 44.07 | B | C |
| ATOM | 3102 | OH | TYR | B | 393 | 8.624 | 14.691 | 65.357 | 1.00 | 42.13 | B | O |
| ATOM | 3103 | C | TYR | B | 393 | 12.811 | 16.903 | 58.955 | 1.00 | 44.17 | B | C |
| ATOM | 3104 | O | TYR | B | 393 | 13.982 | 16.508 | 58.977 | 1.00 | 43.47 | B | O |
| ATOM | 3105 | N | SER | B | 394 | 12.368 | 17.807 | 58.081 | 1.00 | 42.34 | B | N |
| ATOM | 3106 | CA | SER | B | 394 | 13.252 | 18.424 | 57.091 | 1.00 | 41.62 | B | C |
| ATOM | 3107 | CB | SER | B | 394 | 12.421 | 18.988 | 55.919 | 1.00 | 42.32 | B | C |
| ATOM | 3108 | OG | SER | B | 394 | 13.201 | 19.732 | 54.983 | 1.00 | 38.26 | B | O |
| ATOM | 3109 | C | SER | B | 394 | 14.021 | 19.543 | 57.772 | 1.00 | 41.53 | B | C |
| ATOM | 3110 | O | SER | B | 394 | 13.432 | 20.539 | 58.208 | 1.00 | 42.13 | B | O |
| ATOM | 3111 | N | LEU | B | 395 | 15.334 | 19.382 | 57.876 | 1.00 | 41.12 | B | N |
| ATOM | 3112 | CA | LEU | B | 395 | 16.147 | 20.402 | 58.527 | 1.00 | 40.33 | B | C |
| ATOM | 3113 | CB | LEU | B | 395 | 17.585 | 19.907 | 58.715 | 1.00 | 39.97 | B | C |
| ATOM | 3114 | CG | LEU | B | 395 | 18.648 | 20.950 | 59.054 | 1.00 | 39.72 | B | C |
| ATOM | 3115 | CD1 | LEU | B | 395 | 18.241 | 21.741 | 60.268 | 1.00 | 38.53 | B | C |
| ATOM | 3116 | CD2 | LEU | B | 395 | 19.986 | 20.245 | 59.278 | 1.00 | 40.49 | B | C |
| ATOM | 3117 | C | LEU | B | 395 | 16.121 | 21.661 | 57.676 | 1.00 | 38.64 | B | C |
| ATOM | 3118 | O | LEU | B | 395 | 16.325 | 22.764 | 58.173 | 1.00 | 39.14 | B | O |
| ATOM | 3119 | N | PHE | B | 396 | 15.842 | 21.498 | 56.390 | 1.00 | 37.85 | B | N |
| ATOM | 3120 | CA | PHE | B | 396 | 15.764 | 22.651 | 55.498 | 1.00 | 37.23 | B | C |
| ATOM | 3121 | CB | PHE | B | 396 | 15.773 | 22.182 | 54.036 | 1.00 | 36.26 | B | C |
| ATOM | 3122 | CG | PHE | B | 396 | 15.257 | 23.208 | 53.066 | 1.00 | 35.23 | B | C |
| ATOM | 3123 | CD1 | PHE | B | 396 | 15.938 | 24.401 | 52.866 | 1.00 | 35.91 | B | C |
| ATOM | 3124 | CD2 | PHE | B | 396 | 14.078 | 22.984 | 52.373 | 1.00 | 34.75 | B | C |
| ATOM | 3125 | CE1 | PHE | B | 396 | 15.454 | 25.349 | 52.000 | 1.00 | 37.25 | B | C |
| ATOM | 3126 | CE2 | PHE | B | 396 | 13.590 | 23.924 | 51.507 | 1.00 | 36.35 | B | C |
| ATOM | 3127 | CZ | PHE | B | 396 | 14.277 | 25.117 | 51.316 | 1.00 | 37.39 | B | C |
| ATOM | 3128 | C | PHE | B | 396 | 14.517 | 23.497 | 55.781 | 1.00 | 35.29 | B | C |
| ATOM | 3129 | O | PHE | B | 396 | 14.613 | 24.705 | 55.900 | 1.00 | 33.37 | B | O |
| ATOM | 3130 | N | LEU | B | 397 | 13.363 | 22.839 | 55.875 | 1.00 | 36.13 | B | N |
| ATOM | 3131 | CA | LEU | B | 397 | 12.102 | 23.475 | 56.215 | 1.00 | 35.65 | B | C |
| ATOM | 3132 | CB | LEU | B | 397 | 10.958 | 22.451 | 56.112 | 1.00 | 35.58 | B | C |
| ATOM | 3133 | CG | LEU | B | 397 | 10.473 | 22.032 | 54.717 | 1.00 | 33.31 | B | C |
| ATOM | 3134 | CD1 | LEU | B | 397 | 9.276 | 21.108 | 54.811 | 1.00 | 29.11 | B | C |
| ATOM | 3135 | CD2 | LEU | B | 397 | 10.115 | 23.268 | 53.932 | 1.00 | 32.98 | B | C |
| ATOM | 3136 | C | LEU | B | 397 | 12.107 | 24.123 | 57.617 | 1.00 | 36.85 | B | C |
| ATOM | 3137 | O | LEU | B | 397 | 11.841 | 25.323 | 57.749 | 1.00 | 38.10 | B | O |
| ATOM | 3138 | N | VAL | B | 398 | 12.408 | 23.343 | 58.658 | 1.00 | 36.57 | B | N |
| ATOM | 3139 | CA | VAL | B | 398 | 12.544 | 23.893 | 60.016 | 1.00 | 35.45 | B | C |
| ATOM | 3140 | CB | VAL | B | 398 | 13.014 | 22.817 | 61.039 | 1.00 | 34.25 | B | C |
| ATOM | 3141 | CG1 | VAL | B | 398 | 13.410 | 23.481 | 62.342 | 1.00 | 33.37 | B | C |
| ATOM | 3142 | CG2 | VAL | B | 398 | 11.900 | 21.820 | 61.297 | 1.00 | 31.49 | B | C |
| ATOM | 3143 | C | VAL | B | 398 | 13.496 | 25.094 | 60.091 | 1.00 | 35.83 | B | C |
| ATOM | 3144 | O | VAL | B | 398 | 13.177 | 26.080 | 60.752 | 1.00 | 37.16 | B | O |
| ATOM | 3145 | N | ALA | B | 399 | 14.643 | 25.029 | 59.414 | 1.00 | 34.37 | B | N |
| ATOM | 3146 | CA | ALA | B | 399 | 15.609 | 26.130 | 59.467 | 1.00 | 34.75 | B | C |
| ATOM | 3147 | CB | ALA | B | 399 | 16.924 | 25.726 | 58.814 | 1.00 | 32.68 | B | C |
| ATOM | 3148 | C | ALA | B | 399 | 15.075 | 27.397 | 58.808 | 1.00 | 35.42 | B | C |
| ATOM | 3149 | O | ALA | B | 399 | 15.168 | 28.487 | 59.373 | 1.00 | 36.22 | B | O |
| ATOM | 3150 | N | ALA | B | 400 | 14.506 | 27.246 | 57.616 | 1.00 | 36.86 | B | N |
| ATOM | 3151 | CA | ALA | B | 400 | 13.953 | 28.374 | 56.869 | 1.00 | 36.50 | B | C |
| ATOM | 3152 | CB | ALA | B | 400 | 13.720 | 27.992 | 55.441 | 1.00 | 35.95 | B | C |
| ATOM | 3153 | C | ALA | B | 400 | 12.659 | 28.844 | 57.499 | 1.00 | 38.11 | B | C |
| ATOM | 3154 | O | ALA | B | 400 | 11.953 | 29.679 | 56.947 | 1.00 | 38.84 | B | O |
| ATOM | 3155 | N | HIS | B | 401 | 12.347 | 28.299 | 58.665 | 1.00 | 40.38 | B | N |
| ATOM | 3156 | CA | HIS | B | 401 | 11.249 | 28.822 | 59.463 | 1.00 | 39.90 | B | C |
| ATOM | 3157 | CB | HIS | B | 401 | 10.449 | 27.689 | 60.060 | 1.00 | 39.12 | B | C |
| ATOM | 3158 | CG | HIS | B | 401 | 9.433 | 28.134 | 61.056 | 1.00 | 38.70 | B | C |
| ATOM | 3159 | CD2 | HIS | B | 401 | 9.498 | 28.262 | 62.401 | 1.00 | 38.50 | B | C |
| ATOM | 3160 | ND1 | HIS | B | 401 | 8.143 | 28.463 | 60.699 | 1.00 | 38.17 | B | N |
| ATOM | 3161 | CE1 | HIS | B | 401 | 7.456 | 28.771 | 61.784 | 1.00 | 38.22 | B | C |

TABLE 11-continued

Coordinates for pro MMP9(35-444 ΔFnII) (SEQ ID NO: 12) complex with Example 1

| ATOM | 3162 | NE2 | HIS | B | 401 | 8.255 | 28.655 | 62.830 | 1.00 | 37.46 | B | N |
|---|---|---|---|---|---|---|---|---|---|---|---|---|
| ATOM | 3163 | C | HIS | B | 401 | 11.808 | 29.658 | 60.586 | 1.00 | 40.09 | B | C |
| ATOM | 3164 | O | HIS | B | 401 | 11.367 | 30.791 | 60.817 | 1.00 | 39.85 | B | O |
| ATOM | 3165 | N | GLU | B | 402 | 12.777 | 29.084 | 61.290 | 1.00 | 38.99 | B | N |
| ATOM | 3166 | CA | GLU | B | 402 | 13.382 | 29.749 | 62.436 | 1.00 | 40.24 | B | C |
| ATOM | 3167 | CB | GLU | B | 402 | 14.317 | 28.790 | 63.209 | 1.00 | 42.12 | B | C |
| ATOM | 3168 | CG | GLU | B | 402 | 13.709 | 27.437 | 63.658 | 1.00 | 43.49 | B | C |
| ATOM | 3169 | CD | GLU | B | 402 | 12.629 | 27.563 | 64.746 | 1.00 | 44.10 | B | C |
| ATOM | 3170 | OE1 | GLU | B | 402 | 11.993 | 28.641 | 64.878 | 1.00 | 44.47 | B | O |
| ATOM | 3171 | OE2 | GLU | B | 402 | 12.415 | 26.567 | 65.471 | 1.00 | 43.52 | B | O |
| ATOM | 3172 | C | GLU | B | 402 | 14.186 | 30.929 | 61.937 | 1.00 | 39.71 | B | C |
| ATOM | 3173 | O | GLU | B | 402 | 14.435 | 31.875 | 62.687 | 1.00 | 39.05 | B | O |
| ATOM | 3174 | N | PHE | B | 403 | 14.600 | 30.851 | 60.670 | 1.00 | 38.09 | B | N |
| ATOM | 3175 | CA | PHE | B | 403 | 15.400 | 31.895 | 60.027 | 1.00 | 36.23 | B | C |
| ATOM | 3176 | CB | PHE | B | 403 | 15.928 | 31.398 | 58.685 | 1.00 | 37.44 | B | C |
| ATOM | 3177 | CG | PHE | B | 403 | 17.169 | 30.572 | 58.796 | 1.00 | 38.52 | B | C |
| ATOM | 3178 | CD1 | PHE | B | 403 | 17.716 | 30.296 | 60.034 | 1.00 | 38.45 | B | C |
| ATOM | 3179 | CD2 | PHE | B | 403 | 17.792 | 30.076 | 57.660 | 1.00 | 39.02 | B | C |
| ATOM | 3180 | CE1 | PHE | B | 403 | 18.869 | 29.529 | 60.143 | 1.00 | 41.58 | B | C |
| ATOM | 3181 | CE2 | PHE | B | 403 | 18.949 | 29.307 | 57.756 | 1.00 | 41.27 | B | C |
| ATOM | 3182 | CZ | PHE | B | 403 | 19.492 | 29.031 | 58.997 | 1.00 | 41.84 | B | C |
| ATOM | 3183 | C | PHE | B | 403 | 14.548 | 33.119 | 59.802 | 1.00 | 36.17 | B | C |
| ATOM | 3184 | O | PHE | B | 403 | 15.058 | 34.219 | 59.624 | 1.00 | 35.80 | B | O |
| ATOM | 3185 | N | GLY | B | 404 | 13.236 | 32.908 | 59.797 | 1.00 | 38.73 | B | N |
| ATOM | 3186 | CA | GLY | B | 404 | 12.310 | 34.020 | 59.755 | 1.00 | 38.07 | B | C |
| ATOM | 3187 | C | GLY | B | 404 | 12.253 | 34.707 | 61.100 | 1.00 | 38.39 | B | C |
| ATOM | 3188 | O | GLY | B | 404 | 12.197 | 35.932 | 61.172 | 1.00 | 39.00 | B | O |
| ATOM | 3189 | N | HIS | B | 405 | 12.275 | 33.926 | 62.175 | 1.00 | 38.03 | B | N |
| ATOM | 3190 | CA | HIS | B | 405 | 12.199 | 34.514 | 63.504 | 1.00 | 36.49 | B | C |
| ATOM | 3191 | CB | HIS | B | 405 | 12.159 | 33.436 | 64.591 | 1.00 | 35.77 | B | C |
| ATOM | 3192 | CG | HIS | B | 405 | 10.821 | 32.784 | 64.763 | 1.00 | 35.75 | B | C |
| ATOM | 3193 | CD2 | HIS | B | 405 | 10.480 | 31.499 | 65.025 | 1.00 | 34.81 | B | C |
| ATOM | 3194 | ND1 | HIS | B | 405 | 9.639 | 33.490 | 64.707 | 1.00 | 35.73 | B | N |
| ATOM | 3195 | CE1 | HIS | B | 405 | 8.627 | 32.670 | 64.930 | 1.00 | 34.91 | B | C |
| ATOM | 3196 | NE2 | HIS | B | 405 | 9.111 | 31.457 | 65.125 | 1.00 | 34.25 | B | N |
| ATOM | 3197 | C | HIS | B | 405 | 13.448 | 35.345 | 63.668 | 1.00 | 36.30 | B | C |
| ATOM | 3198 | O | HIS | B | 405 | 13.403 | 36.423 | 64.256 | 1.00 | 37.02 | B | O |
| ATOM | 3199 | N | ALA | B | 406 | 14.554 | 34.826 | 63.131 | 1.00 | 35.46 | B | N |
| ATOM | 3200 | CA | ALA | B | 406 | 15.878 | 35.409 | 63.313 | 1.00 | 34.36 | B | C |
| ATOM | 3201 | CB | ALA | B | 406 | 16.944 | 34.429 | 62.852 | 1.00 | 33.78 | B | C |
| ATOM | 3202 | C | ALA | B | 406 | 15.983 | 36.701 | 62.526 | 1.00 | 33.76 | B | C |
| ATOM | 3203 | O | ALA | B | 406 | 16.986 | 37.412 | 62.598 | 1.00 | 33.68 | B | O |
| ATOM | 3204 | N | LEU | B | 407 | 14.933 | 37.004 | 61.775 | 1.00 | 35.53 | B | N |
| ATOM | 3205 | CA | LEU | B | 407 | 14.878 | 38.249 | 61.020 | 1.00 | 37.10 | B | C |
| ATOM | 3206 | CB | LEU | B | 407 | 14.484 | 37.984 | 59.563 | 1.00 | 37.14 | B | C |
| ATOM | 3207 | CG | LEU | B | 407 | 15.480 | 37.229 | 58.680 | 1.00 | 37.76 | B | C |
| ATOM | 3208 | CD1 | LEU | B | 407 | 15.079 | 37.383 | 57.211 | 1.00 | 35.92 | B | C |
| ATOM | 3209 | CD2 | LEU | B | 407 | 16.875 | 37.778 | 58.922 | 1.00 | 37.13 | B | C |
| ATOM | 3210 | C | LEU | B | 407 | 13.890 | 39.235 | 61.623 | 1.00 | 37.69 | B | C |
| ATOM | 3211 | O | LEU | B | 407 | 13.910 | 40.406 | 61.274 | 1.00 | 38.30 | B | O |
| ATOM | 3212 | N | GLY | B | 408 | 13.026 | 38.763 | 62.519 | 1.00 | 37.38 | B | N |
| ATOM | 3213 | CA | GLY | B | 408 | 12.012 | 39.642 | 63.082 | 1.00 | 38.09 | B | C |
| ATOM | 3214 | C | GLY | B | 408 | 10.558 | 39.216 | 62.882 | 1.00 | 37.69 | B | C |
| ATOM | 3215 | O | GLY | B | 408 | 9.632 | 40.014 | 63.050 | 1.00 | 36.71 | B | O |
| ATOM | 3216 | N | LEU | B | 409 | 10.349 | 37.954 | 62.540 | 1.00 | 37.60 | B | N |
| ATOM | 3217 | CA | LEU | B | 409 | 9.016 | 37.498 | 62.209 | 1.00 | 38.95 | B | C |
| ATOM | 3218 | CB | LEU | B | 409 | 9.050 | 36.615 | 60.959 | 1.00 | 39.90 | B | C |
| ATOM | 3219 | CG | LEU | B | 409 | 9.482 | 37.357 | 59.687 | 1.00 | 39.78 | B | C |
| ATOM | 3220 | CD1 | LEU | B | 409 | 9.922 | 36.343 | 58.682 | 1.00 | 39.89 | B | C |
| ATOM | 3221 | CD2 | LEU | B | 409 | 8.359 | 38.243 | 59.148 | 1.00 | 36.86 | B | C |
| ATOM | 3222 | C | LEU | B | 409 | 8.352 | 36.751 | 63.348 | 1.00 | 39.36 | B | C |
| ATOM | 3223 | O | LEU | B | 409 | 9.001 | 36.023 | 64.096 | 1.00 | 39.60 | B | O |
| ATOM | 3224 | N | ASP | B | 410 | 7.043 | 36.972 | 63.469 | 1.00 | 41.86 | B | N |
| ATOM | 3225 | CA | ASP | B | 410 | 6.167 | 36.259 | 64.401 | 1.00 | 42.77 | B | C |
| ATOM | 3226 | CB | ASP | B | 410 | 5.061 | 37.187 | 64.879 | 1.00 | 46.54 | B | C |
| ATOM | 3227 | CG | ASP | B | 410 | 5.392 | 37.837 | 66.185 | 1.00 | 51.71 | B | C |
| ATOM | 3228 | OD1 | ASP | B | 410 | 6.083 | 37.159 | 66.994 | 1.00 | 53.97 | B | O |
| ATOM | 3229 | OD2 | ASP | B | 410 | 4.963 | 39.014 | 66.404 | 1.00 | 53.93 | B | O |
| ATOM | 3230 | C | ASP | B | 410 | 5.530 | 35.049 | 63.759 | 1.00 | 41.80 | B | C |
| ATOM | 3231 | O | ASP | B | 410 | 5.751 | 34.762 | 62.592 | 1.00 | 42.23 | B | O |
| ATOM | 3232 | N | HIS | B | 411 | 4.709 | 34.349 | 64.516 | 1.00 | 40.00 | B | N |
| ATOM | 3233 | CA | HIS | B | 411 | 3.974 | 33.251 | 63.928 | 1.00 | 41.44 | B | C |
| ATOM | 3234 | CB | HIS | B | 411 | 3.489 | 32.309 | 65.029 | 1.00 | 41.80 | B | C |
| ATOM | 3235 | CG | HIS | B | 411 | 4.542 | 31.352 | 65.492 | 1.00 | 41.57 | B | C |
| ATOM | 3236 | CD2 | HIS | B | 411 | 5.474 | 30.654 | 64.799 | 1.00 | 40.83 | B | C |
| ATOM | 3237 | ND1 | HIS | B | 411 | 4.743 | 31.050 | 66.821 | 1.00 | 41.15 | B | N |
| ATOM | 3238 | CE1 | HIS | B | 411 | 5.756 | 30.205 | 66.926 | 1.00 | 41.26 | B | C |
| ATOM | 3239 | NE2 | HIS | B | 411 | 6.216 | 29.950 | 65.715 | 1.00 | 39.79 | B | N |

TABLE 11-continued

Coordinates for pro MMP9(35-444 ΔFnII) (SEQ ID NO: 12) complex with Example 1

| ATOM | 3240 | C   | HIS | B | 411 | 2.809  | 33.677 | 63.016 | 1.00 | 41.49 B | C |
|------|------|-----|-----|---|-----|--------|--------|--------|------|---------|---|
| ATOM | 3241 | O   | HIS | B | 411 | 2.488  | 34.853 | 62.909 | 1.00 | 42.10 B | O |
| ATOM | 3242 | N   | SER | B | 412 | 2.202  | 32.707 | 62.340 | 1.00 | 42.34 B | N |
| ATOM | 3243 | CA  | SER | B | 412 | 1.137  | 32.966 | 61.381 | 1.00 | 42.56 B | C |
| ATOM | 3244 | CB  | SER | B | 412 | 1.636  | 32.628 | 59.963 | 1.00 | 41.67 B | C |
| ATOM | 3245 | OG  | SER | B | 412 | 0.577  | 32.533 | 59.026 | 1.00 | 39.29 B | O |
| ATOM | 3246 | C   | SER | B | 412 | −0.114 | 32.128 | 61.734 | 1.00 | 43.55 B | C |
| ATOM | 3247 | O   | SER | B | 412 | −0.019 | 31.017 | 62.280 | 1.00 | 43.23 B | O |
| ATOM | 3248 | N   | SER | B | 413 | −1.289 | 32.668 | 61.423 | 1.00 | 42.94 B | N |
| ATOM | 3249 | CA  | SER | B | 413 | −2.522 | 31.942 | 61.641 | 1.00 | 41.70 B | C |
| ATOM | 3250 | CB  | SER | B | 413 | −3.663 | 32.903 | 61.856 | 1.00 | 39.34 B | C |
| ATOM | 3251 | OG  | SER | B | 413 | −3.512 | 33.523 | 63.104 | 1.00 | 36.89 B | O |
| ATOM | 3252 | C   | SER | B | 413 | −2.814 | 31.071 | 60.455 | 1.00 | 44.76 B | C |
| ATOM | 3253 | O   | SER | B | 413 | −3.429 | 30.013 | 60.591 | 1.00 | 48.13 B | O |
| ATOM | 3254 | N   | VAL | B | 414 | −2.373 | 31.523 | 59.283 | 1.00 | 46.09 B | N |
| ATOM | 3255 | CA  | VAL | B | 414 | −2.557 | 30.769 | 58.053 | 1.00 | 45.07 B | C |
| ATOM | 3256 | CB  | VAL | B | 414 | −1.994 | 31.512 | 56.849 | 1.00 | 43.16 B | C |
| ATOM | 3257 | CG1 | VAL | B | 414 | −2.035 | 30.603 | 55.630 | 1.00 | 42.06 B | C |
| ATOM | 3258 | CG2 | VAL | B | 414 | −2.782 | 32.769 | 56.618 | 1.00 | 39.39 B | C |
| ATOM | 3259 | C   | VAL | B | 414 | −1.843 | 29.443 | 58.164 | 1.00 | 45.83 B | C |
| ATOM | 3260 | O   | VAL | B | 414 | −0.625 | 29.386 | 58.324 | 1.00 | 48.07 B | O |
| ATOM | 3261 | N   | PRO | B | 415 | −2.599 | 28.348 | 58.101 | 1.00 | 45.54 B | N |
| ATOM | 3262 | CD  | PRO | B | 415 | −4.068 | 28.298 | 58.112 | 1.00 | 45.41 B | C |
| ATOM | 3263 | CA  | PRO | B | 415 | −2.003 | 27.028 | 58.319 | 1.00 | 46.74 B | C |
| ATOM | 3264 | CB  | PRO | B | 415 | −3.192 | 26.080 | 58.210 | 1.00 | 44.77 B | C |
| ATOM | 3265 | CG  | PRO | B | 415 | −4.345 | 26.933 | 58.671 | 1.00 | 45.49 B | C |
| ATOM | 3266 | C   | PRO | B | 415 | −0.898 | 26.689 | 57.338 | 1.00 | 46.87 B | C |
| ATOM | 3267 | O   | PRO | B | 415 | 0.059  | 25.992 | 57.690 | 1.00 | 47.32 B | O |
| ATOM | 3268 | N   | GLU | B | 416 | −1.021 | 27.184 | 56.110 | 1.00 | 46.57 B | N |
| ATOM | 3269 | CA  | GLU | B | 416 | −0.177 | 26.682 | 55.030 | 1.00 | 47.52 B | C |
| ATOM | 3270 | CB  | GLU | B | 416 | −0.982 | 26.450 | 53.753 | 1.00 | 50.88 B | C |
| ATOM | 3271 | CG  | GLU | B | 416 | −2.084 | 27.477 | 53.529 | 1.00 | 55.90 B | C |
| ATOM | 3272 | CD  | GLU | B | 416 | −3.283 | 27.255 | 54.442 | 1.00 | 55.98 B | C |
| ATOM | 3273 | OE1 | GLU | B | 416 | −3.408 | 26.121 | 54.982 | 1.00 | 58.26 B | O |
| ATOM | 3274 | OE2 | GLU | B | 416 | −4.088 | 28.206 | 54.612 | 1.00 | 56.24 B | O |
| ATOM | 3275 | C   | GLU | B | 416 | 0.963  | 27.612 | 54.748 | 1.00 | 45.16 B | C |
| ATOM | 3276 | O   | GLU | B | 416 | 1.859  | 27.282 | 53.971 | 1.00 | 45.99 B | O |
| ATOM | 3277 | N   | ALA | B | 417 | 0.948  | 28.771 | 55.394 | 1.00 | 42.47 B | N |
| ATOM | 3278 | CA  | ALA | B | 417 | 2.106  | 29.655 | 55.347 | 1.00 | 39.34 B | C |
| ATOM | 3279 | CB  | ALA | B | 417 | 1.781  | 30.973 | 56.039 | 1.00 | 39.49 B | C |
| ATOM | 3280 | C   | ALA | B | 417 | 3.288  | 28.970 | 56.023 | 1.00 | 37.24 B | C |
| ATOM | 3281 | O   | ALA | B | 417 | 3.112  | 28.084 | 56.851 | 1.00 | 35.98 B | O |
| ATOM | 3282 | N   | LEU | B | 418 | 4.491  | 29.386 | 55.641 | 1.00 | 37.53 B | N |
| ATOM | 3283 | CA  | LEU | B | 418 | 5.736  | 28.846 | 56.192 | 1.00 | 37.45 B | C |
| ATOM | 3284 | CB  | LEU | B | 418 | 6.929  | 29.491 | 55.489 | 1.00 | 34.04 B | C |
| ATOM | 3285 | CG  | LEU | B | 418 | 8.221  | 29.452 | 56.291 | 1.00 | 34.17 B | C |
| ATOM | 3286 | CD1 | LEU | B | 418 | 8.663  | 28.014 | 56.446 | 1.00 | 34.24 B | C |
| ATOM | 3287 | CD2 | LEU | B | 418 | 9.284  | 30.283 | 55.621 | 1.00 | 32.08 B | C |
| ATOM | 3288 | C   | LEU | B | 418 | 5.854  | 29.079 | 57.708 | 1.00 | 39.55 B | C |
| ATOM | 3289 | O   | LEU | B | 418 | 6.279  | 28.196 | 58.463 | 1.00 | 38.65 B | O |
| ATOM | 3290 | N   | MET | B | 419 | 5.480  | 30.285 | 58.132 | 1.00 | 40.95 B | N |
| ATOM | 3291 | CA  | MET | B | 419 | 5.600  | 30.716 | 59.521 | 1.00 | 43.11 B | C |
| ATOM | 3292 | CB  | MET | B | 419 | 5.850  | 32.219 | 59.569 | 1.00 | 42.55 B | C |
| ATOM | 3293 | CG  | MET | B | 419 | 7.101  | 32.635 | 58.841 | 1.00 | 42.76 B | C |
| ATOM | 3294 | SD  | MET | B | 419 | 8.597  | 32.262 | 59.783 | 1.00 | 41.81 B | S |
| ATOM | 3295 | CE  | MET | B | 419 | 8.084  | 32.797 | 61.378 | 1.00 | 41.82 B | C |
| ATOM | 3296 | C   | MET | B | 419 | 4.378  | 30.370 | 60.391 | 1.00 | 44.74 B | C |
| ATOM | 3297 | O   | MET | B | 419 | 4.127  | 31.032 | 61.394 | 1.00 | 45.93 B | O |
| ATOM | 3298 | N   | TYR | B | 420 | 3.619  | 29.348 | 59.997 | 1.00 | 44.36 B | N |
| ATOM | 3299 | CA  | TYR | B | 420 | 2.710  | 28.651 | 60.907 | 1.00 | 43.02 B | C |
| ATOM | 3300 | CB  | TYR | B | 420 | 1.887  | 27.627 | 60.131 | 1.00 | 44.47 B | C |
| ATOM | 3301 | CG  | TYR | B | 420 | 0.668  | 27.112 | 60.854 | 1.00 | 45.27 B | C |
| ATOM | 3302 | CD1 | TYR | B | 420 | −0.445 | 27.925 | 61.027 | 1.00 | 45.02 B | C |
| ATOM | 3303 | CE1 | TYR | B | 420 | −1.572 | 27.467 | 61.675 | 1.00 | 45.09 B | C |
| ATOM | 3304 | CD2 | TYR | B | 420 | 0.619  | 25.813 | 61.354 | 1.00 | 44.86 B | C |
| ATOM | 3305 | CE2 | TYR | B | 420 | −0.513 | 25.346 | 62.005 | 1.00 | 44.84 B | C |
| ATOM | 3306 | CZ  | TYR | B | 420 | −1.602 | 26.186 | 62.161 | 1.00 | 45.37 B | C |
| ATOM | 3307 | OH  | TYR | B | 420 | −2.724 | 25.761 | 62.822 | 1.00 | 46.41 B | O |
| ATOM | 3308 | C   | TYR | B | 420 | 3.585  | 27.929 | 61.918 | 1.00 | 41.28 B | C |
| ATOM | 3309 | O   | TYR | B | 420 | 4.591  | 27.342 | 61.557 | 1.00 | 40.84 B | O |
| ATOM | 3310 | N   | PRO | B | 421 | 3.214  | 27.972 | 63.205 | 1.00 | 41.13 B | N |
| ATOM | 3311 | CD  | PRO | B | 421 | 2.037  | 28.685 | 63.739 | 1.00 | 40.73 B | C |
| ATOM | 3312 | CA  | PRO | B | 421 | 4.030  | 27.369 | 64.276 | 1.00 | 42.31 B | C |
| ATOM | 3313 | CB  | PRO | B | 421 | 3.344  | 27.838 | 65.567 | 1.00 | 39.38 B | C |
| ATOM | 3314 | CG  | PRO | B | 421 | 1.965  | 28.205 | 65.171 | 1.00 | 39.38 B | C |
| ATOM | 3315 | C   | PRO | B | 421 | 4.178  | 25.847 | 64.220 | 1.00 | 42.81 B | C |
| ATOM | 3316 | O   | PRO | B | 421 | 4.953  | 25.260 | 64.975 | 1.00 | 41.12 B | O |
| ATOM | 3317 | N   | MET | B | 422 | 3.442  | 25.213 | 63.313 | 1.00 | 44.16 B | N |

TABLE 11-continued

Coordinates for pro MMP9(35-444 ΔFnII) (SEQ ID NO: 12) complex with Example 1

| ATOM | 3318 | CA  | MET | B | 422 | 3.293  | 23.756 | 63.339 | 1.00 | 47.55 | B | C |
| ATOM | 3319 | CB  | MET | B | 422 | 1.818  | 23.413 | 63.392 | 1.00 | 50.08 | B | C |
| ATOM | 3320 | CG  | MET | B | 422 | 1.469  | 22.267 | 64.297 | 1.00 | 51.22 | B | C |
| ATOM | 3321 | SD  | MET | B | 422 | −0.240 | 22.505 | 64.750 | 1.00 | 54.14 | B | S |
| ATOM | 3322 | CE  | MET | B | 422 | −0.021 | 23.424 | 66.264 | 1.00 | 51.99 | B | C |
| ATOM | 3323 | C   | MET | B | 422 | 3.906  | 23.068 | 62.126 | 1.00 | 47.80 | B | C |
| ATOM | 3324 | O   | MET | B | 422 | 3.647  | 23.467 | 60.997 | 1.00 | 50.19 | B | O |
| ATOM | 3325 | N   | TYR | B | 423 | 4.691  | 22.019 | 62.343 | 1.00 | 48.30 | B | N |
| ATOM | 3326 | CA  | TYR | B | 423 | 5.393  | 21.384 | 61.231 | 1.00 | 46.72 | B | C |
| ATOM | 3327 | CB  | TYR | B | 423 | 6.378  | 20.348 | 61.739 | 1.00 | 43.78 | B | C |
| ATOM | 3328 | CG  | TYR | B | 423 | 7.074  | 19.604 | 60.635 | 1.00 | 41.33 | B | C |
| ATOM | 3329 | CD1 | TYR | B | 423 | 6.433  | 18.602 | 59.941 | 1.00 | 40.57 | B | C |
| ATOM | 3330 | CE1 | TYR | B | 423 | 7.086  | 17.882 | 58.969 | 1.00 | 42.30 | B | C |
| ATOM | 3331 | CD2 | TYR | B | 423 | 8.393  | 19.875 | 60.321 | 1.00 | 40.44 | B | C |
| ATOM | 3332 | CE2 | TYR | B | 423 | 9.061  | 19.158 | 59.347 | 1.00 | 42.17 | B | C |
| ATOM | 3333 | CZ  | TYR | B | 423 | 8.402  | 18.151 | 58.673 | 1.00 | 42.31 | B | C |
| ATOM | 3334 | OH  | TYR | B | 423 | 9.064  | 17.366 | 57.745 | 1.00 | 42.36 | B | O |
| ATOM | 3335 | C   | TYR | B | 423 | 4.485  | 20.716 | 60.213 | 1.00 | 48.86 | B | C |
| ATOM | 3336 | O   | TYR | B | 423 | 3.702  | 19.827 | 60.546 | 1.00 | 49.99 | B | O |
| ATOM | 3337 | N   | ARG | B | 424 | 4.615  | 21.128 | 58.959 | 1.00 | 50.79 | B | N |
| ATOM | 3338 | CA  | ARG | B | 424 | 4.068  | 20.346 | 57.856 | 1.00 | 51.55 | B | C |
| ATOM | 3339 | CB  | ARG | B | 424 | 2.796  | 20.998 | 57.304 | 1.00 | 53.44 | B | C |
| ATOM | 3340 | CG  | ARG | B | 424 | 1.794  | 19.993 | 56.722 | 1.00 | 56.55 | B | C |
| ATOM | 3341 | CD  | ARG | B | 424 | 1.514  | 18.812 | 57.673 | 1.00 | 59.43 | B | C |
| ATOM | 3342 | NE  | ARG | B | 424 | 1.031  | 19.228 | 58.997 | 1.00 | 61.75 | B | N |
| ATOM | 3343 | CZ  | ARG | B | 424 | 0.013  | 18.661 | 59.648 | 1.00 | 62.85 | B | C |
| ATOM | 3344 | NH1 | ARG | B | 424 | −0.650 | 17.645 | 59.109 | 1.00 | 64.88 | B | N |
| ATOM | 3345 | NH2 | ARG | B | 424 | −0.346 | 19.112 | 60.842 | 1.00 | 61.29 | B | N |
| ATOM | 3346 | C   | ARG | B | 424 | 5.103  | 20.220 | 56.755 | 1.00 | 49.31 | B | C |
| ATOM | 3347 | O   | ARG | B | 424 | 5.635  | 21.220 | 56.289 | 1.00 | 49.65 | B | O |
| ATOM | 3348 | N   | PHE | B | 425 | 5.388  | 18.984 | 56.360 | 1.00 | 48.81 | B | N |
| ATOM | 3349 | CA  | PHE | B | 425 | 6.248  | 18.719 | 55.218 | 1.00 | 48.21 | B | C |
| ATOM | 3350 | CB  | PHE | B | 425 | 6.653  | 17.233 | 55.185 | 1.00 | 46.50 | B | C |
| ATOM | 3351 | CG  | PHE | B | 425 | 7.528  | 16.878 | 54.024 | 1.00 | 45.66 | B | C |
| ATOM | 3352 | CD1 | PHE | B | 425 | 8.892  | 17.117 | 54.070 | 1.00 | 44.90 | B | C |
| ATOM | 3353 | CD2 | PHE | B | 425 | 6.981  | 16.381 | 52.853 | 1.00 | 45.21 | B | C |
| ATOM | 3354 | CE1 | PHE | B | 425 | 9.698  | 16.878 | 52.961 | 1.00 | 42.93 | B | C |
| ATOM | 3355 | CE2 | PHE | B | 425 | 7.783  | 16.140 | 51.738 | 1.00 | 43.79 | B | C |
| ATOM | 3356 | CZ  | PHE | B | 425 | 9.141  | 16.392 | 51.796 | 1.00 | 42.38 | B | C |
| ATOM | 3357 | C   | PHE | B | 425 | 5.500  | 19.088 | 53.930 | 1.00 | 48.36 | B | C |
| ATOM | 3358 | O   | PHE | B | 425 | 4.297  | 18.821 | 53.804 | 1.00 | 48.48 | B | O |
| ATOM | 3359 | N   | THR | B | 426 | 6.214  | 19.731 | 53.002 | 1.00 | 48.10 | B | N |
| ATOM | 3360 | CA  | THR | B | 426 | 5.763  | 19.930 | 51.619 | 1.00 | 46.98 | B | C |
| ATOM | 3361 | CB  | THR | B | 426 | 5.228  | 21.360 | 51.383 | 1.00 | 46.58 | B | C |
| ATOM | 3362 | OG1 | THR | B | 426 | 6.262  | 22.318 | 51.654 | 1.00 | 43.73 | B | O |
| ATOM | 3363 | CG2 | THR | B | 426 | 4.028  | 21.640 | 52.273 | 1.00 | 45.59 | B | C |
| ATOM | 3364 | C   | THR | B | 426 | 6.922  | 19.701 | 50.649 | 1.00 | 47.26 | B | C |
| ATOM | 3365 | O   | THR | B | 426 | 8.078  | 19.578 | 51.059 | 1.00 | 48.31 | B | O |
| ATOM | 3366 | N   | GLU | B | 427 | 6.618  | 19.638 | 49.359 | 1.00 | 49.22 | B | N |
| ATOM | 3367 | CA  | GLU | B | 427 | 7.677  | 19.620 | 48.351 | 1.00 | 49.60 | B | C |
| ATOM | 3368 | CB  | GLU | B | 427 | 7.545  | 18.378 | 47.455 | 1.00 | 51.62 | B | C |
| ATOM | 3369 | CG  | GLU | B | 427 | 7.546  | 17.039 | 48.208 | 1.00 | 54.42 | B | C |
| ATOM | 3370 | CD  | GLU | B | 427 | 8.922  | 16.385 | 48.335 | 1.00 | 56.16 | B | C |
| ATOM | 3371 | OE1 | GLU | B | 427 | 9.766  | 16.918 | 49.087 | 1.00 | 57.67 | B | O |
| ATOM | 3372 | OE2 | GLU | B | 427 | 9.155  | 15.330 | 47.695 | 1.00 | 56.41 | B | O |
| ATOM | 3373 | C   | GLU | B | 427 | 7.592  | 20.903 | 47.521 | 1.00 | 49.73 | B | C |
| ATOM | 3374 | O   | GLU | B | 427 | 8.525  | 21.268 | 46.789 | 1.00 | 48.93 | B | O |
| ATOM | 3375 | N   | GLY | B | 428 | 6.463  | 21.589 | 47.667 | 1.00 | 48.23 | B | N |
| ATOM | 3376 | CA  | GLY | B | 428 | 6.252  | 22.833 | 46.962 | 1.00 | 47.39 | B | C |
| ATOM | 3377 | C   | GLY | B | 428 | 7.173  | 23.918 | 47.478 | 1.00 | 47.18 | B | C |
| ATOM | 3378 | O   | GLY | B | 428 | 7.890  | 23.712 | 48.474 | 1.00 | 48.18 | B | O |
| ATOM | 3379 | N   | PRO | B | 429 | 7.185  | 25.089 | 46.811 | 1.00 | 45.73 | B | N |
| ATOM | 3380 | CD  | PRO | B | 429 | 6.567  | 25.277 | 45.485 | 1.00 | 43.52 | B | C |
| ATOM | 3381 | CA  | PRO | B | 429 | 7.883  | 26.301 | 47.272 | 1.00 | 42.96 | B | C |
| ATOM | 3382 | CB  | PRO | B | 429 | 7.508  | 27.339 | 46.218 | 1.00 | 41.89 | B | C |
| ATOM | 3383 | CG  | PRO | B | 429 | 7.208  | 26.523 | 44.994 | 1.00 | 42.80 | B | C |
| ATOM | 3384 | C   | PRO | B | 429 | 7.460  | 26.726 | 48.688 | 1.00 | 41.18 | B | C |
| ATOM | 3385 | O   | PRO | B | 429 | 6.287  | 27.031 | 48.930 | 1.00 | 40.84 | B | O |
| ATOM | 3386 | N   | PRO | B | 430 | 8.414  | 26.752 | 49.633 | 1.00 | 38.62 | B | N |
| ATOM | 3387 | CD  | PRO | B | 430 | 9.845  | 26.536 | 49.390 | 1.00 | 37.43 | B | C |
| ATOM | 3388 | CA  | PRO | B | 430 | 8.127  | 26.962 | 51.052 | 1.00 | 38.33 | B | C |
| ATOM | 3389 | CB  | PRO | B | 430 | 9.490  | 26.884 | 51.717 | 1.00 | 38.36 | B | C |
| ATOM | 3390 | CG  | PRO | B | 430 | 10.354 | 26.157 | 50.729 | 1.00 | 37.82 | B | C |
| ATOM | 3391 | C   | PRO | B | 430 | 7.446  | 28.280 | 51.361 | 1.00 | 39.82 | B | C |
| ATOM | 3392 | O   | PRO | B | 430 | 6.697  | 28.359 | 52.315 | 1.00 | 41.50 | B | O |
| ATOM | 3393 | N   | LEU | B | 431 | 7.713  | 29.323 | 50.580 | 1.00 | 41.49 | B | N |
| ATOM | 3394 | CA  | LEU | B | 431 | 7.182  | 30.660 | 50.872 | 1.00 | 41.20 | B | C |
| ATOM | 3395 | CB  | LEU | B | 431 | 8.052  | 31.735 | 50.222 | 1.00 | 41.28 | B | C |

TABLE 11-continued

Coordinates for pro MMP9(35-444 ΔFnII) (SEQ ID NO: 12) complex with Example 1

| ATOM | 3396 | CG | LEU | B | 431 | 9.244 | 32.297 | 50.996 | 1.00 | 41.59 | B | C |
|---|---|---|---|---|---|---|---|---|---|---|---|---|
| ATOM | 3397 | CD1 | LEU | B | 431 | 9.893 | 33.397 | 50.177 | 1.00 | 41.94 | B | C |
| ATOM | 3398 | CD2 | LEU | B | 431 | 8.785 | 32.854 | 52.337 | 1.00 | 41.92 | B | C |
| ATOM | 3399 | C | LEU | B | 431 | 5.757 | 30.875 | 50.403 | 1.00 | 41.77 | B | C |
| ATOM | 3400 | O | LEU | B | 431 | 5.380 | 30.454 | 49.307 | 1.00 | 43.80 | B | O |
| ATOM | 3401 | N | HIS | B | 432 | 4.974 | 31.567 | 51.224 | 1.00 | 42.91 | B | N |
| ATOM | 3402 | CA | HIS | B | 432 | 3.638 | 32.014 | 50.825 | 1.00 | 42.55 | B | C |
| ATOM | 3403 | CB | HIS | B | 432 | 2.586 | 31.296 | 51.659 | 1.00 | 44.07 | B | C |
| ATOM | 3404 | CG | HIS | B | 432 | 2.554 | 29.822 | 51.426 | 1.00 | 45.33 | B | C |
| ATOM | 3405 | CD2 | HIS | B | 432 | 1.622 | 29.031 | 50.846 | 1.00 | 46.03 | B | C |
| ATOM | 3406 | ND1 | HIS | B | 432 | 3.604 | 28.999 | 51.764 | 1.00 | 46.05 | B | N |
| ATOM | 3407 | CE1 | HIS | B | 432 | 3.322 | 27.761 | 51.399 | 1.00 | 45.57 | B | C |
| ATOM | 3408 | NE2 | HIS | B | 432 | 2.126 | 27.753 | 50.839 | 1.00 | 46.60 | B | N |
| ATOM | 3409 | C | HIS | B | 432 | 3.443 | 33.514 | 50.960 | 1.00 | 41.63 | B | C |
| ATOM | 3410 | O | HIS | B | 432 | 4.303 | 34.222 | 51.489 | 1.00 | 40.80 | B | O |
| ATOM | 3411 | N | LYS | B | 433 | 2.296 | 33.992 | 50.484 | 1.00 | 41.62 | B | N |
| ATOM | 3412 | CA | LYS | B | 433 | 2.013 | 35.429 | 50.480 | 1.00 | 41.87 | B | C |
| ATOM | 3413 | CB | LYS | B | 433 | 0.588 | 35.710 | 49.969 | 1.00 | 41.51 | B | C |
| ATOM | 3414 | CG | LYS | B | 433 | 0.378 | 35.422 | 48.491 | 1.00 | 41.14 | B | C |
| ATOM | 3415 | CD | LYS | B | 433 | −1.031 | 35.778 | 48.017 | 1.00 | 40.10 | B | C |
| ATOM | 3416 | CE | LYS | B | 433 | −1.329 | 35.169 | 46.632 | 1.00 | 39.04 | B | C |
| ATOM | 3417 | NZ | LYS | B | 433 | −1.514 | 36.171 | 45.540 | 1.00 | 37.46 | B | N |
| ATOM | 3418 | C | LYS | B | 433 | 2.170 | 36.008 | 51.881 | 1.00 | 41.45 | B | C |
| ATOM | 3419 | O | LYS | B | 433 | 2.827 | 37.038 | 52.075 | 1.00 | 40.46 | B | O |
| ATOM | 3420 | N | ASP | B | 434 | 1.580 | 35.326 | 52.857 | 1.00 | 42.17 | B | N |
| ATOM | 3421 | CA | ASP | B | 434 | 1.585 | 35.796 | 54.243 | 1.00 | 43.34 | B | C |
| ATOM | 3422 | CB | ASP | B | 434 | 0.827 | 34.802 | 55.135 | 1.00 | 45.45 | B | C |
| ATOM | 3423 | CG | ASP | B | 434 | 0.357 | 35.425 | 56.429 | 1.00 | 48.43 | B | C |
| ATOM | 3424 | OD1 | ASP | B | 434 | 0.014 | 36.639 | 56.435 | 1.00 | 49.73 | B | O |
| ATOM | 3425 | OD2 | ASP | B | 434 | 0.327 | 34.704 | 57.450 | 1.00 | 50.16 | B | O |
| ATOM | 3426 | C | ASP | B | 434 | 3.012 | 35.990 | 54.769 | 1.00 | 42.84 | B | C |
| ATOM | 3427 | O | ASP | B | 434 | 3.309 | 37.000 | 55.393 | 1.00 | 42.51 | B | O |
| ATOM | 3428 | N | ASP | B | 435 | 3.887 | 35.022 | 54.499 | 1.00 | 43.41 | B | N |
| ATOM | 3429 | CA | ASP | B | 435 | 5.293 | 35.103 | 54.897 | 1.00 | 41.10 | B | C |
| ATOM | 3430 | CB | ASP | B | 435 | 6.019 | 33.827 | 54.495 | 1.00 | 41.22 | B | C |
| ATOM | 3431 | CG | ASP | B | 435 | 5.259 | 32.583 | 54.897 | 1.00 | 42.48 | B | C |
| ATOM | 3432 | OD1 | ASP | B | 435 | 4.820 | 32.506 | 56.073 | 1.00 | 41.48 | B | O |
| ATOM | 3433 | OD2 | ASP | B | 435 | 5.105 | 31.686 | 54.039 | 1.00 | 42.11 | B | O |
| ATOM | 3434 | C | ASP | B | 435 | 6.007 | 36.293 | 54.276 | 1.00 | 41.27 | B | C |
| ATOM | 3435 | O | ASP | B | 435 | 6.922 | 36.853 | 54.881 | 1.00 | 41.88 | B | O |
| ATOM | 3436 | N | VAL | B | 436 | 5.601 | 36.664 | 53.062 | 1.00 | 41.22 | B | N |
| ATOM | 3437 | CA | VAL | B | 436 | 6.276 | 37.719 | 52.286 | 1.00 | 40.06 | B | C |
| ATOM | 3438 | CB | VAL | B | 436 | 5.978 | 37.561 | 50.744 | 1.00 | 40.46 | B | C |
| ATOM | 3439 | CG1 | VAL | B | 436 | 6.850 | 38.511 | 49.925 | 1.00 | 38.14 | B | C |
| ATOM | 3440 | CG2 | VAL | B | 436 | 6.206 | 36.116 | 50.311 | 1.00 | 40.30 | B | C |
| ATOM | 3441 | C | VAL | B | 436 | 5.792 | 39.091 | 52.768 | 1.00 | 40.00 | B | C |
| ATOM | 3442 | O | VAL | B | 436 | 6.590 | 39.992 | 53.036 | 1.00 | 39.11 | B | O |
| ATOM | 3443 | N | ASN | B | 437 | 4.474 | 39.224 | 52.893 | 1.00 | 40.26 | B | N |
| ATOM | 3444 | CA | ASN | B | 437 | 3.874 | 40.419 | 53.488 | 1.00 | 40.91 | B | C |
| ATOM | 3445 | CB | ASN | B | 437 | 2.360 | 40.224 | 53.679 | 1.00 | 40.47 | B | C |
| ATOM | 3446 | CG | ASN | B | 437 | 1.615 | 40.011 | 52.353 | 1.00 | 42.55 | B | C |
| ATOM | 3447 | OD1 | ASN | B | 437 | 2.021 | 40.523 | 51.305 | 1.00 | 39.43 | B | O |
| ATOM | 3448 | ND2 | ASN | B | 437 | 0.513 | 39.247 | 52.404 | 1.00 | 44.70 | B | N |
| ATOM | 3449 | C | ASN | B | 437 | 4.542 | 40.694 | 54.835 | 1.00 | 39.96 | B | C |
| ATOM | 3450 | O | ASN | B | 437 | 4.910 | 41.829 | 55.144 | 1.00 | 39.69 | B | O |
| ATOM | 3451 | N | GLY | B | 438 | 4.703 | 39.639 | 55.620 | 1.00 | 38.71 | B | N |
| ATOM | 3452 | CA | GLY | B | 438 | 5.215 | 39.805 | 56.952 | 1.00 | 38.08 | B | C |
| ATOM | 3453 | C | GLY | B | 438 | 6.547 | 40.484 | 56.865 | 1.00 | 38.65 | B | C |
| ATOM | 3454 | O | GLY | B | 438 | 6.814 | 41.458 | 57.573 | 1.00 | 39.81 | B | O |
| ATOM | 3455 | N | ILE | B | 439 | 7.384 | 39.980 | 55.970 | 1.00 | 38.30 | B | N |
| ATOM | 3456 | CA | ILE | B | 439 | 8.783 | 40.352 | 55.971 | 1.00 | 37.86 | B | C |
| ATOM | 3457 | CB | ILE | B | 439 | 9.644 | 39.291 | 55.249 | 1.00 | 37.09 | B | C |
| ATOM | 3458 | CG2 | ILE | B | 439 | 9.522 | 39.465 | 53.762 | 1.00 | 37.08 | B | C |
| ATOM | 3459 | CG1 | ILE | B | 439 | 11.116 | 39.431 | 55.654 | 1.00 | 36.30 | B | C |
| ATOM | 3460 | CD1 | ILE | B | 439 | 11.429 | 38.993 | 57.077 | 1.00 | 35.31 | B | C |
| ATOM | 3461 | C | ILE | B | 439 | 8.912 | 41.685 | 55.264 | 1.00 | 38.23 | B | C |
| ATOM | 3462 | O | ILE | B | 439 | 9.743 | 42.503 | 55.627 | 1.00 | 38.46 | B | O |
| ATOM | 3463 | N | ARG | B | 440 | 8.087 | 41.919 | 54.256 | 1.00 | 40.44 | B | N |
| ATOM | 3464 | CA | ARG | B | 440 | 8.193 | 43.177 | 53.549 | 1.00 | 42.16 | B | C |
| ATOM | 3465 | CB | ARG | B | 440 | 7.332 | 43.173 | 52.284 | 1.00 | 42.50 | B | C |
| ATOM | 3466 | CG | ARG | B | 440 | 8.094 | 42.845 | 50.995 | 1.00 | 44.01 | B | C |
| ATOM | 3467 | CD | ARG | B | 440 | 7.147 | 42.525 | 49.842 | 1.00 | 45.03 | B | C |
| ATOM | 3468 | NE | ARG | B | 440 | 7.892 | 42.116 | 48.652 | 1.00 | 44.27 | B | N |
| ATOM | 3469 | CZ | ARG | B | 440 | 7.355 | 41.879 | 47.460 | 1.00 | 44.07 | B | C |
| ATOM | 3470 | NH1 | ARG | B | 440 | 6.045 | 41.999 | 47.263 | 1.00 | 41.72 | B | N |
| ATOM | 3471 | NH2 | ARG | B | 440 | 8.148 | 41.535 | 46.458 | 1.00 | 41.34 | B | N |
| ATOM | 3472 | C | ARG | B | 440 | 7.736 | 44.263 | 54.490 | 1.00 | 42.91 | B | C |
| ATOM | 3473 | O | ARG | B | 440 | 8.082 | 45.422 | 54.316 | 1.00 | 44.99 | B | O |

TABLE 11-continued

Coordinates for pro MMP9(35-444 ΔFnII) (SEQ ID NO: 12) complex with Example 1

| ATOM | 3474 | N | HIS | B | 441 | 6.957 | 43.890 | 55.498 | 1.00 | 45.56 | B | N |
|---|---|---|---|---|---|---|---|---|---|---|---|---|
| ATOM | 3475 | CA | HIS | B | 441 | 6.543 | 44.860 | 56.501 | 1.00 | 46.08 | B | C |
| ATOM | 3476 | CB | HIS | B | 441 | 5.364 | 44.325 | 57.330 | 1.00 | 48.10 | B | C |
| ATOM | 3477 | CG | HIS | B | 441 | 4.987 | 45.210 | 58.482 | 1.00 | 50.89 | B | C |
| ATOM | 3478 | CD2 | HIS | B | 441 | 3.859 | 45.921 | 58.729 | 1.00 | 51.69 | B | C |
| ATOM | 3479 | ND1 | HIS | B | 441 | 5.846 | 45.482 | 59.528 | 1.00 | 50.80 | B | N |
| ATOM | 3480 | CE1 | HIS | B | 441 | 5.267 | 46.326 | 60.364 | 1.00 | 50.74 | B | C |
| ATOM | 3481 | NE2 | HIS | B | 441 | 4.061 | 46.609 | 59.902 | 1.00 | 51.91 | B | N |
| ATOM | 3482 | C | HIS | B | 441 | 7.719 | 45.191 | 57.421 | 1.00 | 45.64 | B | C |
| ATOM | 3483 | O | HIS | B | 441 | 7.747 | 46.245 | 58.038 | 1.00 | 46.37 | B | O |
| ATOM | 3484 | N | LEU | B | 442 | 8.692 | 44.297 | 57.525 | 1.00 | 46.18 | B | N |
| ATOM | 3485 | CA | LEU | B | 442 | 9.865 | 44.605 | 58.328 | 1.00 | 46.63 | B | C |
| ATOM | 3486 | CB | LEU | B | 442 | 10.508 | 43.325 | 58.837 | 1.00 | 45.09 | B | C |
| ATOM | 3487 | CG | LEU | B | 442 | 9.675 | 42.675 | 59.926 | 1.00 | 44.22 | B | C |
| ATOM | 3488 | CD1 | LEU | B | 442 | 9.929 | 41.190 | 59.944 | 1.00 | 46.17 | B | C |
| ATOM | 3489 | CD2 | LEU | B | 442 | 10.005 | 43.316 | 61.252 | 1.00 | 44.60 | B | C |
| ATOM | 3490 | C | LEU | B | 442 | 10.900 | 45.421 | 57.577 | 1.00 | 46.92 | B | C |
| ATOM | 3491 | O | LEU | B | 442 | 11.390 | 46.431 | 58.082 | 1.00 | 48.54 | B | O |
| ATOM | 3492 | N | TYR | B | 443 | 11.222 | 44.986 | 56.365 | 1.00 | 46.18 | B | N |
| ATOM | 3493 | CA | TYR | B | 443 | 12.377 | 45.501 | 55.657 | 1.00 | 45.03 | B | C |
| ATOM | 3494 | CB | TYR | B | 443 | 13.332 | 44.347 | 55.321 | 1.00 | 44.32 | B | C |
| ATOM | 3495 | CG | TYR | B | 443 | 13.878 | 43.642 | 56.550 | 1.00 | 42.42 | B | C |
| ATOM | 3496 | CD1 | TYR | B | 443 | 13.424 | 42.373 | 56.912 | 1.00 | 40.39 | B | C |
| ATOM | 3497 | CE1 | TYR | B | 443 | 13.880 | 41.760 | 58.051 | 1.00 | 40.28 | B | C |
| ATOM | 3498 | CD2 | TYR | B | 443 | 14.815 | 44.273 | 57.372 | 1.00 | 40.30 | B | C |
| ATOM | 3499 | CE2 | TYR | B | 443 | 15.279 | 43.676 | 58.513 | 1.00 | 40.12 | B | C |
| ATOM | 3500 | CZ | TYR | B | 443 | 14.808 | 42.420 | 58.854 | 1.00 | 41.05 | B | C |
| ATOM | 3501 | OH | TYR | B | 443 | 15.245 | 41.832 | 60.027 | 1.00 | 42.54 | B | O |
| ATOM | 3502 | C | TYR | B | 443 | 11.986 | 46.242 | 54.389 | 1.00 | 45.86 | B | C |
| ATOM | 3503 | O | TYR | B | 443 | 12.793 | 46.977 | 53.818 | 1.00 | 46.88 | B | O |
| ATOM | 3504 | N | GLY | B | 444 | 10.752 | 46.043 | 53.941 | 1.00 | 46.03 | B | N |
| ATOM | 3505 | CA | GLY | B | 444 | 10.288 | 46.729 | 52.750 | 1.00 | 45.07 | B | C |
| ATOM | 3506 | C | GLY | B | 444 | 10.067 | 45.826 | 51.559 | 1.00 | 45.52 | B | C |
| ATOM | 3507 | O | GLY | B | 444 | 9.299 | 46.176 | 50.662 | 1.00 | 45.69 | B | O |
| ATOM | 3508 | ZN | ZN | B | 500 | 8.315 | 29.493 | 65.204 | 1.00 | 35.51 | B | ZN |
| ATOM | 3509 | ZN | ZN | B | 501 | 18.046 | 27.204 | 72.671 | 1.00 | 46.18 | B | ZN |
| ATOM | 3510 | CA | CA | B | 502 | 11.649 | 17.628 | 70.817 | 1.00 | 47.54 | B | CA |
| ATOM | 3512 | CA | CA | B | 504 | 23.285 | 36.518 | 67.728 | 1.00 | 67.08 | B | CA |
| TER | 3513 |  | CA | B | 504 |  |  |  |  |  | B |  |
| ATOM | 3514 | C1 | INH | R | 1 | 10.624 | 34.268 | 74.963 | 1.00 | 70.23 | A996 | C |
| ATOM | 3515 | O2 | INH | R | 1 | 10.379 | 33.340 | 73.866 | 1.00 | 70.69 | A996 | O |
| ATOM | 3516 | C3 | INH | R | 1 | 11.393 | 32.717 | 73.262 | 1.00 | 70.19 | A996 | C |
| ATOM | 3517 | C4 | INH | R | 1 | 11.867 | 31.470 | 73.736 | 1.00 | 70.00 | A996 | C |
| ATOM | 3518 | C5 | INH | R | 1 | 12.946 | 30.835 | 73.081 | 1.00 | 69.99 | A996 | C |
| ATOM | 3519 | C6 | INH | R | 1 | 13.551 | 31.439 | 71.963 | 1.00 | 71.13 | A996 | C |
| ATOM | 3520 | C7 | INH | R | 1 | 13.076 | 32.686 | 71.488 | 1.00 | 71.11 | A996 | C |
| ATOM | 3521 | C8 | INH | R | 1 | 11.995 | 33.317 | 72.144 | 1.00 | 69.78 | A996 | C |
| ATOM | 3522 | N9 | INH | R | 1 | 11.487 | 34.500 | 71.755 | 1.00 | 68.26 | A996 | N |
| ATOM | 3523 | C10 | INH | R | 1 | 11.271 | 35.069 | 70.580 | 1.00 | 68.35 | A996 | C |
| ATOM | 3524 | N11 | INH | R | 1 | 10.757 | 36.230 | 70.278 | 1.00 | 69.95 | A996 | N |
| ATOM | 3525 | C12 | INH | R | 1 | 10.610 | 36.638 | 69.076 | 1.00 | 70.47 | A996 | C |
| ATOM | 3526 | C13 | INH | R | 1 | 11.033 | 35.751 | 68.036 | 1.00 | 68.94 | A996 | C |
| ATOM | 3527 | S14 | INH | R | 1 | 11.620 | 34.388 | 68.967 | 1.00 | 66.10 | A996 | S |
| ATOM | 3528 | C15 | INH | R | 1 | 10.010 | 37.982 | 68.744 | 1.00 | 71.40 | A996 | C |
| ATOM | 3529 | S16 | INH | R | 1 | 8.847 | 38.671 | 69.857 | 1.00 | 71.95 | A996 | S |
| ATOM | 3530 | C17 | INH | R | 1 | 8.573 | 40.162 | 68.901 | 1.00 | 72.74 | A996 | C |
| ATOM | 3531 | N18 | INH | R | 1 | 9.362 | 40.000 | 67.873 | 1.00 | 73.50 | A996 | N |
| ATOM | 3532 | C19 | INH | R | 1 | 10.099 | 38.922 | 67.755 | 1.00 | 72.77 | A996 | C |
| ATOM | 3533 | C20 | INH | R | 1 | 11.074 | 38.642 | 66.561 | 1.00 | 75.19 | A996 | C |
| ATOM | 3534 | N21 | INH | R | 1 | 7.733 | 41.028 | 69.365 | 1.00 | 73.74 | A996 | N |
| ATOM | 3535 | C22 | INH | R | 1 | 7.941 | 42.002 | 70.266 | 1.00 | 75.95 | A996 | C |
| ATOM | 3536 | C23 | INH | R | 1 | 7.893 | 43.470 | 69.865 | 1.00 | 74.12 | A996 | C |
| ATOM | 3537 | O24 | INH | R | 1 | 8.179 | 41.677 | 71.436 | 1.00 | 78.08 | A996 | O |
| TER | 3538 |  | INH | R | 1 |  |  |  |  |  | A996 |  |
| END |  |  |  |  |  |  |  |  |  |  |  |  |

TABLE 12

Coordinates for pro MMP9(35-444 ΔFnII) (SEQ ID NO: 12) complex with Example 2

| ATOM | 1 | CB | ASP | A | 41 | 42.276 | 26.353 | −23.632 | 1.00 | 56.15 | C |
|---|---|---|---|---|---|---|---|---|---|---|---|
| ATOM | 2 | CG | ASP | A | 41 | 42.803 | 26.503 | −22.206 | 1.00 | 50.47 | C |
| ATOM | 3 | OD1 | ASP | A | 41 | 42.470 | 25.682 | −21.319 | 1.00 | 47.03 | O |
| ATOM | 4 | OD2 | ASP | A | 41 | 43.570 | 27.449 | −21.982 | 1.00 | 45.65 | O |

TABLE 12-continued

Coordinates for pro MMP9(35-444 ΔFnII) (SEQ ID NO: 12) complex with Example 2

| ATOM | 5 | C | ASP | A | 41 | 40.793 | 28.391 | −23.790 | 1.00 | 54.63 | C |
|---|---|---|---|---|---|---|---|---|---|---|---|
| ATOM | 6 | O | ASP | A | 41 | 40.058 | 28.991 | −23.000 | 1.00 | 50.61 | O |
| ATOM | 7 | N | ASP | A | 41 | 40.263 | 26.359 | −25.026 | 1.00 | 44.97 | N |
| ATOM | 8 | CA | ASP | A | 41 | 40.844 | 26.864 | −23.792 | 1.00 | 52.91 | C |
| ATOM | 9 | N | ARG | A | 42 | 41.566 | 29.018 | −24.676 | 1.00 | 55.47 | N |
| ATOM | 10 | CA | ARG | A | 42 | 41.378 | 30.443 | −24.971 | 1.00 | 58.48 | C |
| ATOM | 11 | CB | ARG | A | 42 | 42.482 | 30.990 | −25.883 | 1.00 | 57.59 | C |
| ATOM | 12 | CG | ARG | A | 42 | 42.313 | 32.466 | −26.221 | 1.00 | 52.05 | C |
| ATOM | 13 | CD | ARG | A | 42 | 43.192 | 32.899 | −27.398 | 1.00 | 59.22 | C |
| ATOM | 14 | NE | ARG | A | 42 | 43.453 | 34.343 | −27.390 | 1.00 | 55.57 | N |
| ATOM | 15 | CZ | ARG | A | 42 | 42.592 | 35.269 | −27.807 | 1.00 | 62.43 | C |
| ATOM | 16 | NH1 | ARG | A | 42 | 41.400 | 34.910 | −28.294 | 1.00 | 53.74 | N |
| ATOM | 17 | NH2 | ARG | A | 42 | 42.925 | 36.557 | −27.740 | 1.00 | 64.55 | N |
| ATOM | 18 | C | ARG | A | 42 | 40.025 | 30.666 | −25.646 | 1.00 | 54.38 | C |
| ATOM | 19 | O | ARG | A | 42 | 39.562 | 31.798 | −25.739 | 1.00 | 47.98 | O |
| ATOM | 20 | N | GLN | A | 43 | 39.389 | 29.634 | −26.165 | 1.00 | 60.65 | N |
| ATOM | 21 | CA | GLN | A | 43 | 38.064 | 29.757 | −26.734 | 1.00 | 57.04 | C |
| ATOM | 22 | CB | GLN | A | 43 | 37.827 | 28.639 | −27.718 | 1.00 | 56.67 | C |
| ATOM | 23 | CG | GLN | A | 43 | 38.645 | 28.624 | −29.000 | 1.00 | 66.89 | C |
| ATOM | 24 | CD | GLN | A | 43 | 38.123 | 27.575 | −29.986 | 1.00 | 70.35 | C |
| ATOM | 25 | OE1 | GLN | A | 43 | 37.246 | 27.873 | −30.789 | 1.00 | 54.17 | O |
| ATOM | 26 | NE2 | GLN | A | 43 | 38.630 | 26.351 | −29.902 | 1.00 | 55.05 | N |
| ATOM | 27 | C | GLN | A | 43 | 36.991 | 29.635 | −25.677 | 1.00 | 57.85 | C |
| ATOM | 28 | O | GLN | A | 43 | 35.937 | 30.169 | −25.849 | 1.00 | 48.29 | O |
| ATOM | 29 | N | LEU | A | 44 | 37.255 | 28.856 | −24.621 | 1.00 | 60.48 | N |
| ATOM | 30 | CA | LEU | A | 44 | 36.400 | 28.775 | −23.447 | 1.00 | 50.39 | C |
| ATOM | 31 | CB | LEU | A | 44 | 36.960 | 27.705 | −22.510 | 1.00 | 44.19 | C |
| ATOM | 32 | CG | LEU | A | 44 | 36.286 | 27.347 | −21.181 | 1.00 | 62.86 | C |
| ATOM | 33 | CD1 | LEU | A | 44 | 36.859 | 26.035 | −20.627 | 1.00 | 62.47 | C |
| ATOM | 34 | CD2 | LEU | A | 44 | 36.443 | 28.455 | −20.150 | 1.00 | 50.97 | C |
| ATOM | 35 | C | LEU | A | 44 | 36.286 | 30.121 | −22.738 | 1.00 | 48.55 | C |
| ATOM | 36 | O | LEU | A | 44 | 35.241 | 30.449 | −22.188 | 1.00 | 50.86 | O |
| ATOM | 37 | N | ALA | A | 45 | 37.349 | 30.909 | −22.766 | 1.00 | 48.16 | N |
| ATOM | 38 | CA | ALA | A | 45 | 37.357 | 32.184 | −22.062 | 1.00 | 48.97 | C |
| ATOM | 39 | CB | ALA | A | 45 | 38.768 | 32.635 | −21.805 | 1.00 | 48.86 | C |
| ATOM | 40 | C | ALA | A | 45 | 36.644 | 33.214 | −22.896 | 1.00 | 49.69 | C |
| ATOM | 41 | O | ALA | A | 45 | 36.076 | 34.173 | −22.389 | 1.00 | 53.64 | O |
| ATOM | 42 | N | GLU | A | 46 | 36.692 | 33.017 | −24.198 | 1.00 | 50.58 | N |
| ATOM | 43 | CA | GLU | A | 46 | 36.048 | 33.941 | −25.095 | 1.00 | 54.09 | C |
| ATOM | 44 | CB | GLU | A | 46 | 36.589 | 33.717 | −26.512 | 1.00 | 58.02 | C |
| ATOM | 45 | CG | GLU | A | 46 | 36.014 | 34.627 | −27.554 | 1.00 | 67.50 | C |
| ATOM | 46 | CD | GLU | A | 46 | 34.615 | 34.224 | −27.919 | 1.00 | 68.42 | C |
| ATOM | 47 | OE1 | GLU | A | 46 | 34.399 | 33.031 | −28.214 | 1.00 | 70.96 | O |
| ATOM | 48 | OE2 | GLU | A | 46 | 33.728 | 35.094 | −27.886 | 1.00 | 70.00 | O |
| ATOM | 49 | C | GLU | A | 46 | 34.525 | 33.745 | −24.950 | 1.00 | 53.11 | C |
| ATOM | 50 | O | GLU | A | 46 | 33.777 | 34.703 | −24.719 | 1.00 | 48.28 | O |
| ATOM | 51 | N | GLU | A | 47 | 34.090 | 32.490 | −25.038 | 1.00 | 51.62 | N |
| ATOM | 52 | CA | GLU | A | 47 | 32.707 | 32.090 | −24.762 | 1.00 | 51.50 | C |
| ATOM | 53 | CB | GLU | A | 47 | 32.580 | 30.564 | −24.906 | 1.00 | 52.04 | C |
| ATOM | 54 | CG | GLU | A | 47 | 31.789 | 29.849 | −23.808 | 1.00 | 55.06 | C |
| ATOM | 55 | CD | GLU | A | 47 | 30.304 | 29.730 | −24.120 | 1.00 | 59.81 | C |
| ATOM | 56 | OE1 | GLU | A | 47 | 29.954 | 29.385 | −25.273 | 1.00 | 67.96 | O |
| ATOM | 57 | OE2 | GLU | A | 47 | 29.488 | 29.973 | −23.208 | 1.00 | 58.49 | O |
| ATOM | 58 | C | GLU | A | 47 | 32.204 | 32.554 | −23.379 | 1.00 | 53.40 | C |
| ATOM | 59 | O | GLU | A | 47 | 31.130 | 33.171 | −23.268 | 1.00 | 46.34 | O |
| ATOM | 60 | N | TYR | A | 48 | 32.990 | 32.254 | −22.343 | 1.00 | 45.68 | N |
| ATOM | 61 | CA | TYR | A | 48 | 32.674 | 32.638 | −20.977 | 1.00 | 40.55 | C |
| ATOM | 62 | CB | TYR | A | 48 | 33.824 | 32.221 | −20.042 | 1.00 | 41.85 | C |
| ATOM | 63 | CG | TYR | A | 48 | 33.554 | 32.352 | −18.560 | 1.00 | 36.21 | C |
| ATOM | 64 | CD1 | TYR | A | 48 | 33.767 | 33.557 | −17.893 | 1.00 | 39.38 | C |
| ATOM | 65 | CE1 | TYR | A | 48 | 33.541 | 33.679 | −16.526 | 1.00 | 34.44 | C |
| ATOM | 66 | CD2 | TYR | A | 48 | 33.108 | 31.270 | −17.821 | 1.00 | 35.15 | C |
| ATOM | 67 | CE2 | TYR | A | 48 | 32.876 | 31.381 | −16.441 | 1.00 | 35.84 | C |
| ATOM | 68 | CZ | TYR | A | 48 | 33.092 | 32.585 | −15.805 | 1.00 | 33.64 | C |
| ATOM | 69 | OH | TYR | A | 48 | 32.851 | 32.704 | −14.454 | 1.00 | 33.43 | O |
| ATOM | 70 | C | TYR | A | 48 | 32.486 | 34.136 | −20.906 | 1.00 | 38.10 | C |
| ATOM | 71 | O | TYR | A | 48 | 31.445 | 34.617 | −20.495 | 1.00 | 41.53 | O |
| ATOM | 72 | N | LEU | A | 49 | 33.516 | 34.870 | −21.305 | 1.00 | 44.92 | N |
| ATOM | 73 | CA | LEU | A | 49 | 33.488 | 36.329 | −21.282 | 1.00 | 45.61 | C |
| ATOM | 74 | CB | LEU | A | 49 | 34.752 | 36.901 | −21.932 | 1.00 | 40.51 | C |
| ATOM | 75 | CG | LEU | A | 49 | 36.024 | 36.932 | −21.086 | 1.00 | 40.89 | C |
| ATOM | 76 | CD1 | LEU | A | 49 | 37.222 | 37.355 | −21.932 | 1.00 | 46.73 | C |
| ATOM | 77 | CD2 | LEU | A | 49 | 35.857 | 37.878 | −19.910 | 1.00 | 47.61 | C |
| ATOM | 78 | C | LEU | A | 49 | 32.230 | 36.940 | −21.917 | 1.00 | 48.03 | C |
| ATOM | 79 | O | LEU | A | 49 | 31.664 | 37.889 | −21.373 | 1.00 | 53.13 | O |
| ATOM | 80 | N | TYR | A | 50 | 31.809 | 36.403 | −23.062 | 1.00 | 47.81 | N |
| ATOM | 81 | CA | TYR | A | 50 | 30.587 | 36.842 | −23.737 | 1.00 | 52.81 | C |

TABLE 12-continued

Coordinates for pro MMP9(35-444 ΔFnII) (SEQ ID NO: 12) complex with Example 2

| ATOM | 82 | CB | TYR | A | 50 | 30.497 | 36.221 | −25.133 | 1.00 | 53.67 | C |
|---|---|---|---|---|---|---|---|---|---|---|---|
| ATOM | 83 | CG | TYR | A | 50 | 29.158 | 36.438 | −25.809 | 1.00 | 65.03 | C |
| ATOM | 84 | CD1 | TYR | A | 50 | 28.848 | 37.661 | −26.411 | 1.00 | 65.29 | C |
| ATOM | 85 | CE1 | TYR | A | 50 | 27.621 | 37.868 | −27.034 | 1.00 | 62.49 | C |
| ATOM | 86 | CD2 | TYR | A | 50 | 28.202 | 35.422 | −25.854 | 1.00 | 64.43 | C |
| ATOM | 87 | CE2 | TYR | A | 50 | 26.973 | 35.619 | −26.479 | 1.00 | 59.37 | C |
| ATOM | 88 | CZ | TYR | A | 50 | 26.688 | 36.844 | −27.067 | 1.00 | 64.66 | C |
| ATOM | 89 | OH | TYR | A | 50 | 25.468 | 37.052 | −27.690 | 1.00 | 67.01 | O |
| ATOM | 90 | C | TYR | A | 50 | 29.329 | 36.482 | −22.934 | 1.00 | 54.74 | C |
| ATOM | 91 | O | TYR | A | 50 | 28.572 | 37.362 | −22.497 | 1.00 | 54.26 | O |
| ATOM | 92 | N | ARG | A | 51 | 29.134 | 35.178 | −22.746 | 1.00 | 50.49 | N |
| ATOM | 93 | CA | ARG | A | 51 | 28.027 | 34.608 | −21.986 | 1.00 | 46.69 | C |
| ATOM | 94 | CB | ARG | A | 51 | 28.366 | 33.163 | −21.635 | 1.00 | 48.10 | C |
| ATOM | 95 | CG | ARG | A | 51 | 27.303 | 32.419 | −20.887 | 1.00 | 46.09 | C |
| ATOM | 96 | CD | ARG | A | 51 | 27.692 | 30.960 | −20.761 | 1.00 | 46.35 | C |
| ATOM | 97 | NE | ARG | A | 51 | 26.971 | 30.092 | −21.694 | 1.00 | 54.53 | N |
| ATOM | 98 | CZ | ARG | A | 51 | 25.649 | 29.904 | −21.675 | 1.00 | 56.77 | C |
| ATOM | 99 | NH1 | ARG | A | 51 | 24.903 | 30.545 | −20.782 | 1.00 | 59.68 | N |
| ATOM | 100 | NH2 | ARG | A | 51 | 25.066 | 29.085 | −22.548 | 1.00 | 50.23 | N |
| ATOM | 101 | C | ARG | A | 51 | 27.656 | 35.384 | −20.718 | 1.00 | 51.85 | C |
| ATOM | 102 | O | ARG | A | 51 | 26.521 | 35.871 | −20.608 | 1.00 | 42.92 | O |
| ATOM | 103 | N | TYR | A | 52 | 28.601 | 35.502 | −19.775 | 1.00 | 43.77 | N |
| ATOM | 104 | CA | TYR | A | 52 | 28.342 | 36.197 | −18.505 | 1.00 | 42.06 | C |
| ATOM | 105 | CB | TYR | A | 52 | 29.169 | 35.602 | −17.352 | 1.00 | 43.74 | C |
| ATOM | 106 | CG | TYR | A | 52 | 28.937 | 34.109 | −17.256 | 1.00 | 46.12 | C |
| ATOM | 107 | CD1 | TYR | A | 52 | 29.836 | 33.215 | −17.823 | 1.00 | 44.19 | C |
| ATOM | 108 | CE1 | TYR | A | 52 | 29.609 | 31.850 | −17.787 | 1.00 | 40.96 | C |
| ATOM | 109 | CD2 | TYR | A | 52 | 27.772 | 33.591 | −16.673 | 1.00 | 42.36 | C |
| ATOM | 110 | CE2 | TYR | A | 52 | 27.537 | 32.224 | −16.631 | 1.00 | 39.48 | C |
| ATOM | 111 | CZ | TYR | A | 52 | 28.472 | 31.362 | −17.201 | 1.00 | 42.45 | C |
| ATOM | 112 | OH | TYR | A | 52 | 28.294 | 30.002 | −17.200 | 1.00 | 46.29 | O |
| ATOM | 113 | C | TYR | A | 52 | 28.494 | 37.707 | −18.618 | 1.00 | 47.87 | C |
| ATOM | 114 | O | TYR | A | 52 | 28.609 | 38.418 | −17.618 | 1.00 | 51.07 | O |
| ATOM | 115 | N | GLY | A | 53 | 28.485 | 38.186 | −19.856 | 1.00 | 47.98 | N |
| ATOM | 116 | CA | GLY | A | 53 | 28.323 | 39.597 | −20.145 | 1.00 | 52.80 | C |
| ATOM | 117 | C | GLY | A | 53 | 29.533 | 40.498 | −20.004 | 1.00 | 58.35 | C |
| ATOM | 118 | O | GLY | A | 53 | 29.370 | 41.703 | −19.815 | 1.00 | 58.84 | O |
| ATOM | 119 | N | TYR | A | 54 | 30.740 | 39.945 | −20.123 | 1.00 | 52.60 | N |
| ATOM | 120 | CA | TYR | A | 54 | 31.941 | 40.741 | −19.884 | 1.00 | 51.98 | C |
| ATOM | 121 | CB | TYR | A | 54 | 33.050 | 39.903 | −19.244 | 1.00 | 53.02 | C |
| ATOM | 122 | CG | TYR | A | 54 | 32.808 | 39.518 | −17.789 | 1.00 | 53.03 | C |
| ATOM | 123 | CD1 | TYR | A | 54 | 32.262 | 38.283 | −17.454 | 1.00 | 47.86 | C |
| ATOM | 124 | CE1 | TYR | A | 54 | 32.066 | 37.924 | −16.137 | 1.00 | 50.84 | C |
| ATOM | 125 | CD2 | TYR | A | 54 | 33.154 | 40.377 | −16.755 | 1.00 | 54.20 | C |
| ATOM | 126 | CE2 | TYR | A | 54 | 32.941 | 40.033 | −15.434 | 1.00 | 50.67 | C |
| ATOM | 127 | CZ | TYR | A | 54 | 32.408 | 38.805 | −15.133 | 1.00 | 50.09 | C |
| ATOM | 128 | OH | TYR | A | 54 | 32.207 | 38.459 | −13.824 | 1.00 | 52.44 | O |
| ATOM | 129 | C | TYR | A | 54 | 32.464 | 41.463 | −21.130 | 1.00 | 58.22 | C |
| ATOM | 130 | O | TYR | A | 54 | 33.103 | 42.522 | −21.032 | 1.00 | 58.02 | O |
| ATOM | 131 | N | THR | A | 55 | 32.211 | 40.924 | −22.313 | 1.00 | 57.96 | N |
| ATOM | 132 | CA | THR | A | 55 | 32.713 | 41.636 | −23.483 | 1.00 | 57.85 | C |
| ATOM | 133 | CB | THR | A | 55 | 32.602 | 40.788 | −24.721 | 1.00 | 51.99 | C |
| ATOM | 134 | OG1 | THR | A | 55 | 31.245 | 40.792 | −25.158 | 1.00 | 57.89 | O |
| ATOM | 135 | CG2 | THR | A | 55 | 33.036 | 39.356 | −24.389 | 1.00 | 45.18 | C |
| ATOM | 136 | C | THR | A | 55 | 32.061 | 43.049 | −23.622 | 1.00 | 62.84 | C |
| ATOM | 137 | O | THR | A | 55 | 30.824 | 43.205 | −23.594 | 1.00 | 53.73 | O |
| ATOM | 138 | O | ALA | A | 56 | 34.917 | 46.072 | −23.270 | 1.00 | 53.72 | O |
| ATOM | 139 | N | ALA | A | 56 | 32.939 | 44.053 | −23.742 | 1.00 | 63.37 | N |
| ATOM | 140 | CA | ALA | A | 56 | 32.661 | 45.472 | −23.500 | 1.00 | 62.65 | C |
| ATOM | 141 | C | ALA | A | 56 | 33.898 | 46.252 | −23.918 | 1.00 | 55.47 | C |
| ATOM | 142 | CB | ALA | A | 56 | 32.419 | 45.703 | −21.996 | 1.00 | 50.66 | C |
| ATOM | 143 | O | ALA | A | 57 | 31.201 | 48.765 | −24.400 | 1.00 | 50.51 | O |
| ATOM | 144 | N | ALA | A | 57 | 33.864 | 47.138 | −24.924 | 1.00 | 47.35 | N |
| ATOM | 145 | CA | ALA | A | 57 | 32.743 | 47.472 | −25.843 | 1.00 | 51.42 | C |
| ATOM | 146 | C | ALA | A | 57 | 31.789 | 48.658 | −25.493 | 1.00 | 50.81 | C |
| ATOM | 147 | CB | ALA | A | 57 | 31.981 | 46.225 | −26.304 | 1.00 | 51.59 | C |
| ATOM | 148 | N | LEU | A | 67 | 41.431 | 41.501 | −25.811 | 1.00 | 50.48 | N |
| ATOM | 149 | CA | LEU | A | 67 | 40.825 | 40.408 | −25.059 | 1.00 | 49.24 | C |
| ATOM | 150 | CB | LEU | A | 67 | 41.313 | 39.066 | −25.619 | 1.00 | 52.47 | C |
| ATOM | 151 | CG | LEU | A | 67 | 40.611 | 37.752 | −25.252 | 1.00 | 51.62 | C |
| ATOM | 152 | CD1 | LEU | A | 67 | 41.093 | 37.224 | −23.911 | 1.00 | 53.59 | C |
| ATOM | 153 | CD2 | LEU | A | 67 | 39.104 | 37.905 | −25.270 | 1.00 | 42.29 | C |
| ATOM | 154 | C | LEU | A | 67 | 41.135 | 40.526 | −23.553 | 1.00 | 52.25 | C |
| ATOM | 155 | O | LEU | A | 67 | 40.495 | 39.889 | −22.719 | 1.00 | 51.49 | O |
| ATOM | 156 | N | GLY | A | 68 | 42.108 | 41.355 | −23.207 | 1.00 | 44.21 | N |
| ATOM | 157 | CA | GLY | A | 68 | 42.499 | 41.492 | −21.817 | 1.00 | 51.82 | C |
| ATOM | 158 | C | GLY | A | 68 | 41.699 | 42.482 | −20.978 | 1.00 | 49.01 | C |

TABLE 12-continued

Coordinates for pro MMP9(35-444 ΔFnII) (SEQ ID NO: 12) complex with Example 2

| ATOM | 159 | O | GLY | A | 68 | 41.576 | 42.332 | −19.758 | 1.00 | 46.88 | O |
|---|---|---|---|---|---|---|---|---|---|---|---|
| ATOM | 160 | N | PRO | A | 69 | 41.173 | 43.526 | −21.615 | 1.00 | 48.90 | N |
| ATOM | 161 | CD | PRO | A | 69 | 41.370 | 44.024 | −22.990 | 1.00 | 50.41 | C |
| ATOM | 162 | CA | PRO | A | 69 | 40.419 | 44.461 | −20.790 | 1.00 | 41.43 | C |
| ATOM | 163 | CB | PRO | A | 69 | 40.065 | 45.579 | −21.770 | 1.00 | 46.02 | C |
| ATOM | 164 | CG | PRO | A | 69 | 41.121 | 45.494 | −22.838 | 1.00 | 52.10 | C |
| ATOM | 165 | C | PRO | A | 69 | 39.175 | 43.784 | −20.216 | 1.00 | 50.73 | C |
| ATOM | 166 | O | PRO | A | 69 | 38.725 | 44.144 | −19.111 | 1.00 | 55.70 | O |
| ATOM | 167 | N | ALA | A | 70 | 38.647 | 42.797 | −20.938 | 1.00 | 48.84 | N |
| ATOM | 168 | CA | ALA | A | 70 | 37.525 | 41.983 | −20.449 | 1.00 | 46.83 | C |
| ATOM | 169 | CB | ALA | A | 70 | 36.891 | 41.183 | −21.592 | 1.00 | 42.15 | C |
| ATOM | 170 | C | ALA | A | 70 | 37.973 | 41.038 | −19.343 | 1.00 | 44.77 | C |
| ATOM | 171 | O | ALA | A | 70 | 37.242 | 40.785 | −18.399 | 1.00 | 41.81 | O |
| ATOM | 172 | N | LEU | A | 71 | 39.175 | 40.496 | −19.481 | 1.00 | 49.85 | N |
| ATOM | 173 | CA | LEU | A | 71 | 39.723 | 39.629 | −18.448 | 1.00 | 48.87 | C |
| ATOM | 174 | CB | LEU | A | 71 | 41.056 | 39.026 | −18.885 | 1.00 | 45.26 | C |
| ATOM | 175 | CG | LEU | A | 71 | 40.989 | 37.851 | −19.854 | 1.00 | 45.37 | C |
| ATOM | 176 | CD1 | LEU | A | 71 | 42.400 | 37.365 | −20.197 | 1.00 | 46.93 | C |
| ATOM | 177 | CD2 | LEU | A | 71 | 40.150 | 36.735 | −19.279 | 1.00 | 32.21 | C |
| ATOM | 178 | C | LEU | A | 71 | 39.919 | 40.408 | −17.155 | 1.00 | 45.54 | C |
| ATOM | 179 | O | LEU | A | 71 | 39.809 | 39.853 | −16.065 | 1.00 | 46.62 | O |
| ATOM | 180 | N | LEU | A | 72 | 40.207 | 41.694 | −17.281 | 1.00 | 45.20 | N |
| ATOM | 181 | CA | LEU | A | 72 | 40.512 | 42.504 | −16.115 | 1.00 | 46.18 | C |
| ATOM | 182 | CB | LEU | A | 72 | 41.199 | 43.787 | −16.553 | 1.00 | 51.43 | C |
| ATOM | 183 | CG | LEU | A | 72 | 42.266 | 44.410 | −15.660 | 1.00 | 59.35 | C |
| ATOM | 184 | CD1 | LEU | A | 72 | 43.328 | 43.388 | −15.238 | 1.00 | 55.19 | C |
| ATOM | 185 | CD2 | LEU | A | 72 | 42.896 | 45.591 | −16.382 | 1.00 | 50.31 | C |
| ATOM | 186 | C | LEU | A | 72 | 39.186 | 42.799 | −15.433 | 1.00 | 50.47 | C |
| ATOM | 187 | O | LEU | A | 72 | 39.066 | 42.742 | −14.204 | 1.00 | 54.25 | O |
| ATOM | 188 | N | LEU | A | 73 | 38.185 | 43.089 | −16.257 | 1.00 | 49.79 | N |
| ATOM | 189 | CA | LEU | A | 73 | 36.799 | 43.246 | −15.817 | 1.00 | 47.42 | C |
| ATOM | 190 | CB | LEU | A | 73 | 35.893 | 43.391 | −17.047 | 1.00 | 48.53 | C |
| ATOM | 191 | CG | LEU | A | 73 | 35.894 | 44.754 | −17.717 | 1.00 | 49.08 | C |
| ATOM | 192 | CD1 | LEU | A | 73 | 34.906 | 44.755 | −18.874 | 1.00 | 43.60 | C |
| ATOM | 193 | CD2 | LEU | A | 73 | 35.559 | 45.820 | −16.669 | 1.00 | 33.83 | C |
| ATOM | 194 | C | LEU | A | 73 | 36.316 | 42.040 | −15.038 | 1.00 | 44.79 | C |
| ATOM | 195 | O | LEU | A | 73 | 35.661 | 42.164 | −14.006 | 1.00 | 40.16 | O |
| ATOM | 196 | N | LEU | A | 74 | 36.604 | 40.872 | −15.597 | 1.00 | 48.28 | N |
| ATOM | 197 | CA | LEU | A | 74 | 36.196 | 39.614 | −15.028 | 1.00 | 46.79 | C |
| ATOM | 198 | CB | LEU | A | 74 | 36.563 | 38.469 | −15.958 | 1.00 | 47.70 | C |
| ATOM | 199 | CG | LEU | A | 74 | 36.593 | 37.086 | −15.310 | 1.00 | 46.82 | C |
| ATOM | 200 | CD1 | LEU | A | 74 | 35.348 | 36.898 | −14.484 | 1.00 | 57.65 | C |
| ATOM | 201 | CD2 | LEU | A | 74 | 36.671 | 36.009 | −16.377 | 1.00 | 48.43 | C |
| ATOM | 202 | C | LEU | A | 74 | 36.910 | 39.442 | −13.722 | 1.00 | 49.49 | C |
| ATOM | 203 | O | LEU | A | 74 | 36.323 | 38.996 | −12.742 | 1.00 | 47.78 | O |
| ATOM | 204 | N | GLN | A | 75 | 38.182 | 39.812 | −13.703 | 1.00 | 45.60 | N |
| ATOM | 205 | CA | GLN | A | 75 | 38.980 | 39.565 | −12.520 | 1.00 | 42.88 | C |
| ATOM | 206 | CB | GLN | A | 75 | 40.461 | 39.761 | −12.820 | 1.00 | 42.13 | C |
| ATOM | 207 | CG | GLN | A | 75 | 40.980 | 38.701 | −13.768 | 1.00 | 45.31 | C |
| ATOM | 208 | CD | GLN | A | 75 | 42.396 | 38.949 | −14.260 | 1.00 | 47.87 | C |
| ATOM | 209 | OE1 | GLN | A | 75 | 42.849 | 40.092 | −14.379 | 1.00 | 47.74 | O |
| ATOM | 210 | NE2 | GLN | A | 75 | 43.095 | 37.869 | −14.557 | 1.00 | 44.05 | N |
| ATOM | 211 | C | GLN | A | 75 | 38.503 | 40.411 | −11.358 | 1.00 | 45.35 | C |
| ATOM | 212 | O | GLN | A | 75 | 38.478 | 39.951 | −10.213 | 1.00 | 44.47 | O |
| ATOM | 213 | N | LYS | A | 76 | 38.098 | 41.640 | −11.654 | 1.00 | 48.78 | N |
| ATOM | 214 | CA | LYS | A | 76 | 37.544 | 42.501 | −10.618 | 1.00 | 52.94 | C |
| ATOM | 215 | CB | LYS | A | 76 | 37.239 | 43.899 | −11.157 | 1.00 | 52.22 | C |
| ATOM | 216 | CG | LYS | A | 76 | 38.457 | 44.656 | −11.646 | 1.00 | 56.96 | C |
| ATOM | 217 | CD | LYS | A | 76 | 39.165 | 45.386 | −10.509 | 1.00 | 59.79 | C |
| ATOM | 218 | CE | LYS | A | 76 | 40.449 | 46.038 | −11.002 | 1.00 | 58.27 | C |
| ATOM | 219 | NZ | LYS | A | 76 | 40.377 | 46.234 | −12.481 | 1.00 | 56.38 | N |
| ATOM | 220 | C | LYS | A | 76 | 36.268 | 41.860 | −10.104 | 1.00 | 50.11 | C |
| ATOM | 221 | O | LYS | A | 76 | 36.130 | 41.593 | −8.919 | 1.00 | 55.41 | O |
| ATOM | 222 | N | GLN | A | 77 | 35.344 | 41.601 | −11.013 | 1.00 | 46.14 | N |
| ATOM | 223 | CA | GLN | A | 77 | 34.047 | 41.050 | −10.649 | 1.00 | 48.65 | C |
| ATOM | 224 | CB | GLN | A | 77 | 33.248 | 40.705 | −11.913 | 1.00 | 50.45 | C |
| ATOM | 225 | CG | GLN | A | 77 | 31.825 | 40.252 | −11.641 | 1.00 | 55.05 | C |
| ATOM | 226 | CD | GLN | A | 77 | 31.037 | 41.306 | −10.893 | 1.00 | 59.69 | C |
| ATOM | 227 | OE1 | GLN | A | 77 | 31.208 | 42.509 | −11.138 | 1.00 | 65.43 | O |
| ATOM | 228 | NE2 | GLN | A | 77 | 30.188 | 40.871 | −9.961 | 1.00 | 52.87 | N |
| ATOM | 229 | C | GLN | A | 77 | 34.123 | 39.828 | −9.726 | 1.00 | 50.42 | C |
| ATOM | 230 | O | GLN | A | 77 | 33.234 | 39.614 | −8.888 | 1.00 | 52.32 | O |
| ATOM | 231 | N | LEU | A | 78 | 35.165 | 39.017 | −9.875 | 1.00 | 46.29 | N |
| ATOM | 232 | CA | LEU | A | 78 | 35.248 | 37.790 | −9.080 | 1.00 | 49.32 | C |
| ATOM | 233 | CB | LEU | A | 78 | 35.608 | 36.597 | −9.954 | 1.00 | 49.30 | C |
| ATOM | 234 | CG | LEU | A | 78 | 34.584 | 36.252 | −11.027 | 1.00 | 50.88 | C |
| ATOM | 235 | CD1 | LEU | A | 78 | 34.919 | 34.924 | −11.642 | 1.00 | 40.69 | C |

TABLE 12-continued

Coordinates for pro MMP9(35-444 ΔFnII) (SEQ ID NO: 12) complex with Example 2

| ATOM | 236 | CD2 | LEU | A | 78 | 33.197 | 36.222 | −10.391 | 1.00 | 52.27 | C |
| --- | --- | --- | --- | --- | --- | --- | --- | --- | --- | --- | --- |
| ATOM | 237 | C | LEU | A | 78 | 36.237 | 37.912 | −7.931 | 1.00 | 51.33 | C |
| ATOM | 238 | O | LEU | A | 78 | 36.388 | 36.991 | −7.121 | 1.00 | 46.25 | O |
| ATOM | 239 | N | SER | A | 79 | 36.910 | 39.057 | −7.864 | 1.00 | 55.21 | N |
| ATOM | 240 | CA | SER | A | 79 | 37.895 | 39.300 | −6.820 | 1.00 | 46.54 | C |
| ATOM | 241 | CB | SER | A | 79 | 37.287 | 39.051 | −5.438 | 1.00 | 48.23 | C |
| ATOM | 242 | OG | SER | A | 79 | 36.149 | 39.870 | −5.230 | 1.00 | 45.62 | O |
| ATOM | 243 | C | SER | A | 79 | 39.058 | 38.364 | −7.046 | 1.00 | 43.75 | C |
| ATOM | 244 | O | SER | A | 79 | 39.441 | 37.623 | −6.154 | 1.00 | 48.33 | O |
| ATOM | 245 | N | LEU | A | 80 | 39.571 | 38.351 | −8.268 | 1.00 | 46.43 | N |
| ATOM | 246 | CA | LEU | A | 80 | 40.758 | 37.584 | −8.589 | 1.00 | 44.62 | C |
| ATOM | 247 | CB | LEU | A | 80 | 40.558 | 36.764 | −9.869 | 1.00 | 42.78 | C |
| ATOM | 248 | CG | LEU | A | 80 | 39.411 | 35.738 | −9.924 | 1.00 | 44.28 | C |
| ATOM | 249 | CD1 | LEU | A | 80 | 39.186 | 35.209 | −11.343 | 1.00 | 45.45 | C |
| ATOM | 250 | CD2 | LEU | A | 80 | 39.648 | 34.574 | −8.985 | 1.00 | 43.56 | C |
| ATOM | 251 | C | LEU | A | 80 | 41.860 | 38.620 | −8.769 | 1.00 | 45.84 | C |
| ATOM | 252 | O | LEU | A | 80 | 41.572 | 39.817 | −8.872 | 1.00 | 41.52 | O |
| ATOM | 253 | N | PRO | A | 81 | 43.127 | 38.179 | −8.766 | 1.00 | 42.24 | N |
| ATOM | 254 | CD | PRO | A | 81 | 43.703 | 36.902 | −8.305 | 1.00 | 41.32 | C |
| ATOM | 255 | CA | PRO | A | 81 | 44.151 | 39.186 | −9.040 | 1.00 | 45.24 | C |
| ATOM | 256 | CB | PRO | A | 81 | 45.456 | 38.387 | −8.992 | 1.00 | 45.38 | C |
| ATOM | 257 | CG | PRO | A | 81 | 45.168 | 37.251 | −8.041 | 1.00 | 43.68 | C |
| ATOM | 258 | C | PRO | A | 81 | 43.900 | 39.779 | −10.415 | 1.00 | 47.46 | C |
| ATOM | 259 | O | PRO | A | 81 | 43.649 | 39.043 | −11.373 | 1.00 | 49.07 | O |
| ATOM | 260 | N | GLU | A | 82 | 43.952 | 41.105 | −10.494 | 1.00 | 48.97 | N |
| ATOM | 261 | CA | GLU | A | 82 | 43.652 | 41.834 | −11.728 | 1.00 | 54.87 | C |
| ATOM | 262 | CB | GLU | A | 82 | 43.154 | 43.246 | −11.385 | 1.00 | 51.05 | C |
| ATOM | 263 | CG | GLU | A | 82 | 41.723 | 43.252 | −10.916 | 1.00 | 51.92 | C |
| ATOM | 264 | CD | GLU | A | 82 | 41.585 | 43.503 | −9.435 | 1.00 | 60.23 | C |
| ATOM | 265 | OE1 | GLU | A | 82 | 40.438 | 43.499 | −8.931 | 1.00 | 57.29 | O |
| ATOM | 266 | OE2 | GLU | A | 82 | 42.624 | 43.702 | −8.767 | 1.00 | 73.34 | O |
| ATOM | 267 | C | GLU | A | 82 | 44.814 | 41.871 | −12.733 | 1.00 | 49.48 | C |
| ATOM | 268 | O | GLU | A | 82 | 45.359 | 42.935 | −13.042 | 1.00 | 52.18 | O |
| ATOM | 269 | N | THR | A | 83 | 45.173 | 40.702 | −13.256 | 1.00 | 51.21 | N |
| ATOM | 270 | CA | THR | A | 83 | 46.378 | 40.574 | −14.083 | 1.00 | 42.40 | C |
| ATOM | 271 | CB | THR | A | 83 | 46.946 | 39.157 | −14.052 | 1.00 | 43.39 | C |
| ATOM | 272 | OG1 | THR | A | 83 | 46.026 | 38.262 | −14.683 | 1.00 | 41.77 | O |
| ATOM | 273 | CG2 | THR | A | 83 | 47.225 | 38.707 | −12.615 | 1.00 | 35.23 | C |
| ATOM | 274 | C | THR | A | 83 | 46.125 | 40.930 | −15.528 | 1.00 | 45.49 | C |
| ATOM | 275 | O | THR | A | 83 | 47.045 | 41.320 | −16.243 | 1.00 | 53.64 | O |
| ATOM | 276 | N | GLY | A | 84 | 44.883 | 40.798 | −15.973 | 1.00 | 44.45 | N |
| ATOM | 277 | CA | GLY | A | 84 | 44.561 | 41.158 | −17.337 | 1.00 | 46.34 | C |
| ATOM | 278 | C | GLY | A | 84 | 45.161 | 40.140 | −18.268 | 1.00 | 49.04 | C |
| ATOM | 279 | O | GLY | A | 84 | 45.047 | 40.245 | −19.483 | 1.00 | 55.46 | O |
| ATOM | 280 | N | GLU | A | 85 | 45.798 | 39.139 | −17.679 | 1.00 | 49.40 | N |
| ATOM | 281 | CA | GLU | A | 85 | 46.332 | 38.014 | −18.420 | 1.00 | 47.91 | C |
| ATOM | 282 | CB | GLU | A | 85 | 47.777 | 37.754 | −17.993 | 1.00 | 50.84 | C |
| ATOM | 283 | CG | GLU | A | 85 | 48.709 | 37.452 | −19.157 | 1.00 | 60.46 | C |
| ATOM | 284 | CD | GLU | A | 85 | 49.177 | 38.710 | −19.866 | 1.00 | 59.52 | C |
| ATOM | 285 | OE1 | GLU | A | 85 | 49.412 | 38.654 | −21.098 | 1.00 | 71.10 | O |
| ATOM | 286 | OE2 | GLU | A | 85 | 49.308 | 39.752 | −19.186 | 1.00 | 58.26 | O |
| ATOM | 287 | C | GLU | A | 85 | 45.475 | 36.792 | −18.112 | 1.00 | 52.94 | C |
| ATOM | 288 | O | GLU | A | 85 | 44.944 | 36.668 | −16.996 | 1.00 | 51.20 | O |
| ATOM | 289 | N | LEU | A | 86 | 45.330 | 35.892 | −19.088 | 1.00 | 53.71 | N |
| ATOM | 290 | CA | LEU | A | 86 | 44.615 | 34.635 | −18.861 | 1.00 | 45.10 | C |
| ATOM | 291 | CB | LEU | A | 86 | 44.094 | 34.036 | −20.168 | 1.00 | 41.02 | C |
| ATOM | 292 | CG | LEU | A | 86 | 43.395 | 32.680 | −20.026 | 1.00 | 42.08 | C |
| ATOM | 293 | CD1 | LEU | A | 86 | 42.171 | 32.782 | −19.134 | 1.00 | 44.13 | C |
| ATOM | 294 | CD2 | LEU | A | 86 | 43.009 | 32.104 | −21.378 | 1.00 | 38.66 | C |
| ATOM | 295 | C | LEU | A | 86 | 45.523 | 33.642 | −18.135 | 1.00 | 45.66 | C |
| ATOM | 296 | O | LEU | A | 86 | 46.212 | 32.835 | −18.761 | 1.00 | 48.83 | O |
| ATOM | 297 | N | ASP | A | 87 | 45.499 | 33.708 | −16.808 | 1.00 | 44.76 | N |
| ATOM | 298 | CA | ASP | A | 87 | 46.417 | 32.964 | −15.952 | 1.00 | 43.31 | C |
| ATOM | 299 | CB | ASP | A | 87 | 46.990 | 33.892 | −14.872 | 1.00 | 40.58 | C |
| ATOM | 300 | CG | ASP | A | 87 | 45.903 | 34.734 | −14.183 | 1.00 | 46.62 | C |
| ATOM | 301 | OD1 | ASP | A | 87 | 44.792 | 34.189 | −13.973 | 1.00 | 47.61 | O |
| ATOM | 302 | OD2 | ASP | A | 87 | 46.157 | 35.930 | −13.859 | 1.00 | 35.47 | O |
| ATOM | 303 | C | ASP | A | 87 | 45.738 | 31.772 | −15.300 | 1.00 | 42.01 | C |
| ATOM | 304 | O | ASP | A | 87 | 44.688 | 31.307 | −15.751 | 1.00 | 43.57 | O |
| ATOM | 305 | N | SER | A | 88 | 46.330 | 31.282 | −14.223 | 1.00 | 36.92 | N |
| ATOM | 306 | CA | SER | A | 88 | 45.838 | 30.057 | −13.611 | 1.00 | 42.88 | C |
| ATOM | 307 | CB | SER | A | 88 | 46.944 | 29.313 | −12.862 | 1.00 | 42.49 | C |
| ATOM | 308 | OG | SER | A | 88 | 47.471 | 28.286 | −13.691 | 1.00 | 45.31 | O |
| ATOM | 309 | C | SER | A | 88 | 44.644 | 30.293 | −12.714 | 1.00 | 39.25 | C |
| ATOM | 310 | O | SER | A | 88 | 43.713 | 29.494 | −12.681 | 1.00 | 43.63 | O |
| ATOM | 311 | N | ALA | A | 89 | 44.659 | 31.389 | −11.983 | 1.00 | 42.63 | N |
| ATOM | 312 | CA | ALA | A | 89 | 43.492 | 31.718 | −11.189 | 1.00 | 38.69 | C |

TABLE 12-continued

Coordinates for pro MMP9(35-444 ΔFnII) (SEQ ID NO: 12) complex with Example 2

| ATOM | 313 | CB  | ALA | A | 89 | 43.718 | 32.981 | −10.433 | 1.00 | 35.53 | C |
|------|-----|-----|-----|---|----|--------|--------|---------|------|-------|---|
| ATOM | 314 | C   | ALA | A | 89 | 42.353 | 31.886 | −12.173 | 1.00 | 41.99 | C |
| ATOM | 315 | O   | ALA | A | 89 | 41.343 | 31.201 | −12.090 | 1.00 | 45.73 | O |
| ATOM | 316 | N   | THR | A | 90 | 42.537 | 32.786 | −13.131 | 1.00 | 41.39 | N |
| ATOM | 317 | CA  | THR | A | 90 | 41.489 | 33.069 | −14.095 | 1.00 | 42.56 | C |
| ATOM | 318 | CB  | THR | A | 90 | 41.940 | 34.084 | −15.151 | 1.00 | 40.77 | C |
| ATOM | 319 | OG1 | THR | A | 90 | 42.141 | 35.353 | −14.512 | 1.00 | 38.65 | O |
| ATOM | 320 | CG2 | THR | A | 90 | 40.893 | 34.244 | −16.217 | 1.00 | 35.44 | C |
| ATOM | 321 | C   | THR | A | 90 | 40.942 | 31.793 | −14.729 | 1.00 | 42.52 | C |
| ATOM | 322 | O   | THR | A | 90 | 39.752 | 31.508 | −14.588 | 1.00 | 44.47 | O |
| ATOM | 323 | N   | LEU | A | 91 | 41.797 | 31.007 | −15.376 | 1.00 | 37.83 | N |
| ATOM | 324 | CA  | LEU | A | 91 | 41.316 | 29.813 | −16.082 | 1.00 | 44.43 | C |
| ATOM | 325 | CB  | LEU | A | 91 | 42.453 | 29.070 | −16.796 | 1.00 | 42.17 | C |
| ATOM | 326 | CG  | LEU | A | 91 | 42.067 | 27.673 | −17.298 | 1.00 | 40.90 | C |
| ATOM | 327 | CD1 | LEU | A | 91 | 41.115 | 27.764 | −18.474 | 1.00 | 44.17 | C |
| ATOM | 328 | CD2 | LEU | A | 91 | 43.288 | 26.844 | −17.672 | 1.00 | 39.48 | C |
| ATOM | 329 | C   | LEU | A | 91 | 40.591 | 28.849 | −15.156 | 1.00 | 42.26 | C |
| ATOM | 330 | O   | LEU | A | 91 | 39.640 | 28.168 | −15.562 | 1.00 | 43.65 | O |
| ATOM | 331 | N   | LYS | A | 92 | 41.058 | 28.771 | −13.919 | 1.00 | 38.49 | N |
| ATOM | 332 | CA  | LYS | A | 92 | 40.490 | 27.827 | −12.971 | 1.00 | 40.03 | C |
| ATOM | 333 | CB  | LYS | A | 92 | 41.364 | 27.743 | −11.714 | 1.00 | 43.16 | C |
| ATOM | 334 | CG  | LYS | A | 92 | 40.718 | 27.075 | −10.489 | 1.00 | 47.06 | C |
| ATOM | 335 | CD  | LYS | A | 92 | 41.191 | 27.751 | −9.207  | 1.00 | 47.31 | C |
| ATOM | 336 | CE  | LYS | A | 92 | 40.335 | 27.373 | −8.002  | 1.00 | 61.33 | C |
| ATOM | 337 | NZ  | LYS | A | 92 | 40.604 | 25.978 | −7.546  | 1.00 | 65.27 | N |
| ATOM | 338 | C   | LYS | A | 92 | 39.077 | 28.283 | −12.624 | 1.00 | 45.13 | C |
| ATOM | 339 | O   | LYS | A | 92 | 38.138 | 27.471 | −12.580 | 1.00 | 42.72 | O |
| ATOM | 340 | N   | ALA | A | 93 | 38.936 | 29.587 | −12.384 | 1.00 | 39.88 | N |
| ATOM | 341 | CA  | ALA | A | 93 | 37.633 | 30.184 | −12.157 | 1.00 | 35.94 | C |
| ATOM | 342 | CB  | ALA | A | 93 | 37.764 | 31.672 | −11.945 | 1.00 | 34.88 | C |
| ATOM | 343 | C   | ALA | A | 93 | 36.688 | 29.876 | −13.323 | 1.00 | 40.37 | C |
| ATOM | 344 | O   | ALA | A | 93 | 35.568 | 29.443 | −13.099 | 1.00 | 46.23 | O |
| ATOM | 345 | N   | MET | A | 94 | 37.147 | 30.068 | −14.556 | 1.00 | 36.12 | N |
| ATOM | 346 | CA  | MET | A | 94 | 36.295 | 29.866 | −15.735 | 1.00 | 42.70 | C |
| ATOM | 347 | CB  | MET | A | 94 | 37.002 | 30.285 | −17.039 | 1.00 | 42.32 | C |
| ATOM | 348 | CG  | MET | A | 94 | 37.206 | 31.778 | −17.209 | 1.00 | 44.94 | C |
| ATOM | 349 | SD  | MET | A | 94 | 37.991 | 32.191 | −18.788 | 1.00 | 48.36 | S |
| ATOM | 350 | CE  | MET | A | 94 | 38.485 | 33.888 | −18.502 | 1.00 | 36.87 | C |
| ATOM | 351 | C   | MET | A | 94 | 35.851 | 28.430 | −15.876 | 1.00 | 40.24 | C |
| ATOM | 352 | O   | MET | A | 94 | 34.840 | 28.153 | −16.530 | 1.00 | 41.43 | O |
| ATOM | 353 | N   | ARG | A | 95 | 36.612 | 27.512 | −15.287 | 1.00 | 40.36 | N |
| ATOM | 354 | CA  | ARG | A | 95 | 36.301 | 26.084 | −15.399 | 1.00 | 41.60 | C |
| ATOM | 355 | CB  | ARG | A | 95 | 37.583 | 25.247 | −15.534 | 1.00 | 44.90 | C |
| ATOM | 356 | CG  | ARG | A | 95 | 38.453 | 25.599 | −16.736 | 1.00 | 51.62 | C |
| ATOM | 357 | CD  | ARG | A | 95 | 39.062 | 24.356 | −17.390 | 1.00 | 52.15 | C |
| ATOM | 358 | NE  | ARG | A | 95 | 40.474 | 24.148 | −17.057 | 1.00 | 63.27 | N |
| ATOM | 359 | CZ  | ARG | A | 95 | 41.417 | 23.817 | −17.948 | 1.00 | 66.87 | C |
| ATOM | 360 | NH1 | ARG | A | 95 | 41.097 | 23.666 | −19.232 | 1.00 | 58.28 | N |
| ATOM | 361 | NH2 | ARG | A | 95 | 42.683 | 23.643 | −17.564 | 1.00 | 56.25 | N |
| ATOM | 362 | C   | ARG | A | 95 | 35.458 | 25.569 | −14.227 | 1.00 | 38.86 | C |
| ATOM | 363 | O   | ARG | A | 95 | 35.278 | 24.364 | −14.065 | 1.00 | 40.60 | O |
| ATOM | 364 | N   | THR | A | 96 | 34.952 | 26.494 | −13.416 | 1.00 | 46.44 | N |
| ATOM | 365 | CA  | THR | A | 96 | 34.200 | 26.173 | −12.202 | 1.00 | 47.00 | C |
| ATOM | 366 | CB  | THR | A | 96 | 34.654 | 27.089 | −11.031 | 1.00 | 44.80 | C |
| ATOM | 367 | OG1 | THR | A | 96 | 35.882 | 26.603 | −10.500 | 1.00 | 45.65 | O |
| ATOM | 368 | CG2 | THR | A | 96 | 33.633 | 27.117 | −9.916  | 1.00 | 43.95 | C |
| ATOM | 369 | C   | THR | A | 96 | 32.691 | 26.330 | −12.444 | 1.00 | 47.66 | C |
| ATOM | 370 | O   | THR | A | 96 | 32.245 | 27.372 | −12.926 | 1.00 | 48.40 | O |
| ATOM | 371 | N   | PRO | A | 97 | 31.902 | 25.297 | −12.112 | 1.00 | 48.66 | N |
| ATOM | 372 | CD  | PRO | A | 97 | 32.262 | 24.034 | −11.449 | 1.00 | 53.35 | C |
| ATOM | 373 | CA  | PRO | A | 97 | 30.471 | 25.355 | −12.432 | 1.00 | 52.48 | C |
| ATOM | 374 | CB  | PRO | A | 97 | 29.932 | 24.007 | −11.930 | 1.00 | 51.20 | C |
| ATOM | 375 | CG  | PRO | A | 97 | 31.125 | 23.118 | −11.849 | 1.00 | 56.36 | C |
| ATOM | 376 | C   | PRO | A | 97 | 29.824 | 26.499 | −11.688 | 1.00 | 46.86 | C |
| ATOM | 377 | O   | PRO | A | 97 | 30.240 | 26.790 | −10.579 | 1.00 | 45.12 | O |
| ATOM | 378 | N   | ARG | A | 98 | 28.830 | 27.138 | −12.297 | 1.00 | 48.63 | N |
| ATOM | 379 | CA  | ARG | A | 98 | 28.278 | 28.366 | −11.747 | 1.00 | 46.36 | C |
| ATOM | 380 | CB  | ARG | A | 98 | 29.136 | 29.559 | −12.171 | 1.00 | 47.90 | C |
| ATOM | 381 | CG  | ARG | A | 98 | 29.286 | 29.693 | −13.701 | 1.00 | 41.67 | C |
| ATOM | 382 | CD  | ARG | A | 98 | 29.790 | 31.085 | −14.087 | 1.00 | 38.11 | C |
| ATOM | 383 | NE  | ARG | A | 98 | 28.752 | 32.100 | −13.901 | 1.00 | 38.62 | N |
| ATOM | 384 | CZ  | ARG | A | 98 | 28.989 | 33.394 | −13.688 | 1.00 | 42.69 | C |
| ATOM | 385 | NH1 | ARG | A | 98 | 27.985 | 34.236 | −13.541 | 1.00 | 43.15 | N |
| ATOM | 386 | NH2 | ARG | A | 98 | 30.232 | 33.854 | −13.621 | 1.00 | 49.47 | N |
| ATOM | 387 | C   | ARG | A | 98 | 26.862 | 28.632 | −12.199 | 1.00 | 42.34 | C |
| ATOM | 388 | O   | ARG | A | 98 | 26.263 | 27.889 | −12.973 | 1.00 | 48.21 | O |
| ATOM | 389 | N   | CYS | A | 99 | 26.355 | 29.751 | −11.732 | 1.00 | 42.22 | N |

TABLE 12-continued

Coordinates for pro MMP9(35-444 ΔFnII) (SEQ ID NO: 12) complex with Example 2

| ATOM | 390 | CA | CYS | A | 99 | 24.988 | 30.145 | −11.961 | 1.00 | 41.05 | C |
| ATOM | 391 | CB | CYS | A | 99 | 24.590 | 31.106 | −10.846 | 1.00 | 38.15 | C |
| ATOM | 392 | SG | CYS | A | 99 | 23.146 | 32.072 | −11.120 | 1.00 | 40.30 | S |
| ATOM | 393 | C | CYS | A | 99 | 24.922 | 30.804 | −13.323 | 1.00 | 42.83 | C |
| ATOM | 394 | O | CYS | A | 99 | 25.788 | 31.600 | −13.661 | 1.00 | 42.16 | O |
| ATOM | 395 | N | GLY | A | 100 | 23.900 | 30.465 | −14.104 | 1.00 | 43.32 | N |
| ATOM | 396 | CA | GLY | A | 100 | 23.759 | 30.974 | −15.459 | 1.00 | 40.61 | C |
| ATOM | 397 | C | GLY | A | 100 | 23.418 | 32.450 | −15.608 | 1.00 | 43.87 | C |
| ATOM | 398 | O | GLY | A | 100 | 23.334 | 32.966 | −16.722 | 1.00 | 51.82 | O |
| ATOM | 399 | N | VAL | A | 101 | 23.200 | 33.138 | −14.497 | 1.00 | 44.50 | N |
| ATOM | 400 | CA | VAL | A | 101 | 22.865 | 34.560 | −14.536 | 1.00 | 43.99 | C |
| ATOM | 401 | CB | VAL | A | 101 | 22.181 | 34.992 | −13.230 | 1.00 | 39.39 | C |
| ATOM | 402 | CG1 | VAL | A | 101 | 21.917 | 36.489 | −13.216 | 1.00 | 45.01 | C |
| ATOM | 403 | CG2 | VAL | A | 101 | 20.895 | 34.239 | −13.052 | 1.00 | 45.33 | C |
| ATOM | 404 | C | VAL | A | 101 | 24.113 | 35.410 | −14.783 | 1.00 | 43.04 | C |
| ATOM | 405 | O | VAL | A | 101 | 25.158 | 35.170 | −14.186 | 1.00 | 44.26 | O |
| ATOM | 406 | N | PRO | A | 102 | 24.010 | 36.398 | −15.679 | 1.00 | 43.05 | N |
| ATOM | 407 | CD | PRO | A | 102 | 22.833 | 36.657 | −16.526 | 1.00 | 47.10 | C |
| ATOM | 408 | CA | PRO | A | 102 | 25.155 | 37.235 | −16.058 | 1.00 | 49.00 | C |
| ATOM | 409 | CB | PRO | A | 102 | 24.610 | 38.065 | −17.237 | 1.00 | 51.38 | C |
| ATOM | 410 | CG | PRO | A | 102 | 23.426 | 37.291 | −17.744 | 1.00 | 46.31 | C |
| ATOM | 411 | C | PRO | A | 102 | 25.632 | 38.156 | −14.933 | 1.00 | 45.19 | C |
| ATOM | 412 | O | PRO | A | 102 | 24.822 | 38.654 | −14.151 | 1.00 | 49.20 | O |
| ATOM | 413 | N | ASP | A | 103 | 26.933 | 38.417 | −14.900 | 1.00 | 49.15 | N |
| ATOM | 414 | CA | ASP | A | 103 | 27.559 | 39.173 | −13.816 | 1.00 | 52.26 | C |
| ATOM | 415 | CB | ASP | A | 103 | 28.964 | 38.644 | −13.590 | 1.00 | 47.96 | C |
| ATOM | 416 | CG | ASP | A | 103 | 28.975 | 37.167 | −13.403 | 1.00 | 48.49 | C |
| ATOM | 417 | OD1 | ASP | A | 103 | 28.033 | 36.667 | −12.753 | 1.00 | 48.84 | O |
| ATOM | 418 | OD2 | ASP | A | 103 | 29.903 | 36.507 | −13.904 | 1.00 | 45.43 | O |
| ATOM | 419 | C | ASP | A | 103 | 27.641 | 40.665 | −14.082 | 1.00 | 53.86 | C |
| ATOM | 420 | O | ASP | A | 103 | 28.014 | 41.432 | −13.194 | 1.00 | 54.69 | O |
| ATOM | 421 | N | LEU | A | 104 | 27.340 | 41.064 | −15.315 | 1.00 | 53.14 | N |
| ATOM | 422 | CA | LEU | A | 104 | 27.282 | 42.473 | −15.687 | 1.00 | 52.80 | C |
| ATOM | 423 | CB | LEU | A | 104 | 28.643 | 42.985 | −16.157 | 1.00 | 54.70 | C |
| ATOM | 424 | CG | LEU | A | 104 | 29.819 | 43.106 | −15.185 | 1.00 | 58.44 | C |
| ATOM | 425 | CD1 | LEU | A | 104 | 31.122 | 43.300 | −15.925 | 1.00 | 54.26 | C |
| ATOM | 426 | CD2 | LEU | A | 104 | 29.616 | 44.237 | −14.197 | 1.00 | 65.64 | C |
| ATOM | 427 | C | LEU | A | 104 | 26.267 | 42.623 | −16.802 | 1.00 | 59.65 | C |
| ATOM | 428 | O | LEU | A | 104 | 26.575 | 42.330 | −17.965 | 1.00 | 48.70 | O |
| ATOM | 429 | N | GLY | A | 105 | 25.051 | 43.046 | −16.430 | 1.00 | 72.75 | N |
| ATOM | 430 | CA | GLY | A | 105 | 23.947 | 43.258 | −17.361 | 1.00 | 62.05 | C |
| ATOM | 431 | C | GLY | A | 105 | 24.428 | 43.999 | −18.595 | 1.00 | 63.30 | C |
| ATOM | 432 | O | GLY | A | 105 | 25.626 | 44.201 | −18.752 | 1.00 | 65.09 | O |
| ATOM | 433 | N | ARG | A | 106 | 23.532 | 44.389 | −19.473 | 1.00 | 65.16 | N |
| ATOM | 434 | CA | ARG | A | 106 | 22.131 | 44.290 | −19.253 | 1.00 | 64.41 | C |
| ATOM | 435 | CB | ARG | A | 106 | 21.601 | 45.688 | −18.879 | 1.00 | 67.33 | C |
| ATOM | 436 | CG | ARG | A | 106 | 22.057 | 46.222 | −17.443 | 1.00 | 70.75 | C |
| ATOM | 437 | CD | ARG | A | 106 | 22.747 | 47.660 | −17.300 | 1.00 | 72.23 | C |
| ATOM | 438 | NE | ARG | A | 106 | 23.449 | 48.161 | −18.486 | 1.00 | 70.98 | N |
| ATOM | 439 | CZ | ARG | A | 106 | 23.300 | 49.367 | −19.008 | 1.00 | 63.39 | C |
| ATOM | 440 | NH1 | ARG | A | 106 | 23.938 | 49.687 | −20.095 | 1.00 | 57.67 | N |
| ATOM | 441 | NH2 | ARG | A | 106 | 22.497 | 50.250 | −18.463 | 1.00 | 66.94 | N |
| ATOM | 442 | C | ARG | A | 106 | 21.535 | 43.756 | −20.536 | 1.00 | 64.99 | C |
| ATOM | 443 | O | ARG | A | 106 | 20.939 | 44.493 | −21.242 | 1.00 | 68.51 | O |
| ATOM | 444 | N | PHE | A | 107 | 21.735 | 42.464 | −20.822 | 1.00 | 67.13 | N |
| ATOM | 445 | CA | PHE | A | 107 | 21.277 | 41.753 | −22.027 | 1.00 | 62.44 | C |
| ATOM | 446 | CB | PHE | A | 107 | 21.498 | 40.238 | −21.852 | 1.00 | 65.46 | C |
| ATOM | 447 | CG | PHE | A | 107 | 22.903 | 39.768 | −22.184 | 1.00 | 76.56 | C |
| ATOM | 448 | CD1 | PHE | A | 107 | 23.114 | 38.523 | −22.786 | 1.00 | 74.75 | C |
| ATOM | 449 | CD2 | PHE | A | 107 | 24.009 | 40.566 | −21.906 | 1.00 | 70.17 | C |
| ATOM | 450 | CE1 | PHE | A | 107 | 24.399 | 38.086 | −23.101 | 1.00 | 67.24 | C |
| ATOM | 451 | CE2 | PHE | A | 107 | 25.294 | 40.136 | −22.221 | 1.00 | 64.72 | C |
| ATOM | 452 | CZ | PHE | A | 107 | 25.488 | 38.893 | −22.819 | 1.00 | 61.90 | C |
| ATOM | 453 | C | PHE | A | 107 | 19.813 | 42.009 | −22.433 | 1.00 | 64.24 | C |
| ATOM | 454 | O | PHE | A | 107 | 19.531 | 42.458 | −23.538 | 1.00 | 65.19 | O |
| ATOM | 455 | N | GLN | A | 108 | 18.884 | 41.839 | −21.526 | 1.00 | 65.81 | N |
| ATOM | 456 | CA | GLN | A | 108 | 17.505 | 42.099 | −21.856 | 1.00 | 62.44 | C |
| ATOM | 457 | CB | GLN | A | 108 | 16.775 | 40.779 | −22.002 | 1.00 | 56.04 | C |
| ATOM | 458 | CG | GLN | A | 108 | 15.772 | 40.507 | −20.967 | 1.00 | 58.40 | C |
| ATOM | 459 | CD | GLN | A | 108 | 15.921 | 39.164 | −20.399 | 1.00 | 56.87 | C |
| ATOM | 460 | OE1 | GLN | A | 108 | 16.839 | 38.450 | −20.731 | 1.00 | 50.61 | O |
| ATOM | 461 | NE2 | GLN | A | 108 | 15.032 | 38.801 | −19.531 | 1.00 | 61.84 | N |
| ATOM | 462 | C | GLN | A | 108 | 16.795 | 43.022 | −20.867 | 1.00 | 66.02 | C |
| ATOM | 463 | O | GLN | A | 108 | 17.330 | 43.370 | −19.834 | 1.00 | 66.14 | O |
| ATOM | 464 | N | THR | A | 109 | 15.576 | 43.412 | −21.209 | 1.00 | 70.09 | N |
| ATOM | 465 | CA | THR | A | 109 | 14.765 | 44.299 | −20.394 | 1.00 | 64.64 | C |
| ATOM | 466 | CB | THR | A | 109 | 14.199 | 45.448 | −21.247 | 1.00 | 64.13 | C |

TABLE 12-continued

Coordinates for pro MMP9(35-444 ΔFnII) (SEQ ID NO: 12) complex with Example 2

| ATOM | 467 | OG1 | THR | A | 109 | 14.890 | 46.647 | −20.934 | 1.00 | 74.30 | O |
|------|-----|-----|-----|---|-----|--------|--------|---------|------|-------|---|
| ATOM | 468 | CG2 | THR | A | 109 | 12.773 | 45.669 | −20.966 | 1.00 | 62.52 | C |
| ATOM | 469 | C   | THR | A | 109 | 13.646 | 43.570 | −19.649 | 1.00 | 58.59 | C |
| ATOM | 470 | O   | THR | A | 109 | 12.999 | 42.713 | −20.188 | 1.00 | 56.43 | O |
| ATOM | 471 | N   | PHE | A | 110 | 13.463 | 43.932 | −18.386 | 1.00 | 65.55 | N |
| ATOM | 472 | CA  | PHE | A | 110 | 12.364 | 43.439 | −17.546 | 1.00 | 55.85 | C |
| ATOM | 473 | CB  | PHE | A | 110 | 12.897 | 42.806 | −16.255 | 1.00 | 57.28 | C |
| ATOM | 474 | CG  | PHE | A | 110 | 13.920 | 41.724 | −16.469 | 1.00 | 57.21 | C |
| ATOM | 475 | CD1 | PHE | A | 110 | 15.278 | 42.019 | −16.436 | 1.00 | 49.31 | C |
| ATOM | 476 | CD2 | PHE | A | 110 | 13.525 | 40.408 | −16.681 | 1.00 | 53.55 | C |
| ATOM | 477 | CE1 | PHE | A | 110 | 16.212 | 41.030 | −16.623 | 1.00 | 50.76 | C |
| ATOM | 478 | CE2 | PHE | A | 110 | 14.462 | 39.409 | −16.875 | 1.00 | 49.90 | C |
| ATOM | 479 | CZ  | PHE | A | 110 | 15.809 | 39.719 | −16.843 | 1.00 | 50.00 | C |
| ATOM | 480 | C   | PHE | A | 110 | 11.413 | 44.576 | −17.166 | 1.00 | 57.19 | C |
| ATOM | 481 | O   | PHE | A | 110 | 11.739 | 45.749 | −17.319 | 1.00 | 58.76 | O |
| ATOM | 482 | N   | GLU | A | 111 | 10.239 | 44.225 | −16.652 | 1.00 | 59.56 | N |
| ATOM | 483 | CA  | GLU | A | 111 | 9.271  | 45.230 | −16.206 | 1.00 | 64.27 | C |
| ATOM | 484 | CB  | GLU | A | 111 | 7.842  | 44.812 | −16.564 | 1.00 | 67.04 | C |
| ATOM | 485 | CG  | GLU | A | 111 | 7.562  | 44.650 | −18.036 | 1.00 | 67.63 | C |
| ATOM | 486 | CD  | GLU | A | 111 | 6.117  | 44.294 | −18.279 | 1.00 | 76.56 | C |
| ATOM | 487 | OE1 | GLU | A | 111 | 5.281  | 44.656 | −17.429 | 1.00 | 75.91 | O |
| ATOM | 488 | OE2 | GLU | A | 111 | 5.814  | 43.651 | −19.307 | 1.00 | 89.70 | O |
| ATOM | 489 | C   | GLU | A | 111 | 9.336  | 45.508 | −14.700 | 1.00 | 64.45 | C |
| ATOM | 490 | O   | GLU | A | 111 | 9.612  | 44.615 | −13.885 | 1.00 | 53.57 | O |
| ATOM | 491 | N   | GLY | A | 112 | 9.058  | 46.756 | −14.338 | 1.00 | 64.70 | N |
| ATOM | 492 | CA  | GLY | A | 112 | 8.932  | 47.110 | −12.943 | 1.00 | 61.35 | C |
| ATOM | 493 | C   | GLY | A | 112 | 10.265 | 47.065 | −12.239 | 1.00 | 62.25 | C |
| ATOM | 494 | O   | GLY | A | 112 | 11.272 | 46.713 | −12.838 | 1.00 | 54.45 | O |
| ATOM | 495 | N   | ASP | A | 113 | 10.251 | 47.391 | −10.949 | 1.00 | 57.75 | N |
| ATOM | 496 | CA  | ASP | A | 113 | 11.461 | 47.718 | −10.219 | 1.00 | 53.51 | C |
| ATOM | 497 | CB  | ASP | A | 113 | 11.123 | 48.684 | −9.076  | 1.00 | 60.72 | C |
| ATOM | 498 | CG  | ASP | A | 113 | 10.223 | 48.053 | −8.006  | 1.00 | 60.18 | C |
| ATOM | 499 | OD1 | ASP | A | 113 | 9.528  | 47.056 | −8.296  | 1.00 | 54.01 | O |
| ATOM | 500 | OD2 | ASP | A | 113 | 10.220 | 48.559 | −6.862  | 1.00 | 60.39 | O |
| ATOM | 501 | C   | ASP | A | 113 | 12.244 | 46.512 | −9.689  | 1.00 | 55.92 | C |
| ATOM | 502 | O   | ASP | A | 113 | 13.122 | 46.672 | −8.838  | 1.00 | 57.96 | O |
| ATOM | 503 | N   | LEU | A | 114 | 11.932 | 45.319 | −10.194 | 1.00 | 57.92 | N |
| ATOM | 504 | CA  | LEU | A | 114 | 12.630 | 44.072 | −9.811  | 1.00 | 60.26 | C |
| ATOM | 505 | CB  | LEU | A | 114 | 14.058 | 44.030 | −10.380 | 1.00 | 54.16 | C |
| ATOM | 506 | CG  | LEU | A | 114 | 14.170 | 44.204 | −11.894 | 1.00 | 56.72 | C |
| ATOM | 507 | CD1 | LEU | A | 114 | 15.454 | 43.573 | −12.423 | 1.00 | 55.13 | C |
| ATOM | 508 | CD2 | LEU | A | 114 | 12.962 | 43.582 | −12.572 | 1.00 | 58.94 | C |
| ATOM | 509 | C   | LEU | A | 114 | 12.661 | 43.766 | −8.306  | 1.00 | 52.92 | C |
| ATOM | 510 | O   | LEU | A | 114 | 13.595 | 43.139 | −7.811  | 1.00 | 50.32 | O |
| ATOM | 511 | N   | LYS | A | 115 | 11.630 | 44.202 | −7.593  | 1.00 | 57.50 | N |
| ATOM | 512 | CA  | LYS | A | 115 | 11.486 | 43.925 | −6.166  | 1.00 | 52.92 | C |
| ATOM | 513 | CB  | LYS | A | 115 | 11.657 | 45.221 | −5.376  | 1.00 | 56.69 | C |
| ATOM | 514 | CG  | LYS | A | 115 | 11.810 | 45.054 | −3.881  | 1.00 | 54.39 | C |
| ATOM | 515 | CD  | LYS | A | 115 | 12.147 | 46.384 | −3.219  | 1.00 | 57.30 | C |
| ATOM | 516 | CE  | LYS | A | 115 | 10.905 | 47.253 | −3.090  | 1.00 | 62.66 | C |
| ATOM | 517 | NZ  | LYS | A | 115 | 10.833 | 47.923 | −1.757  | 1.00 | 54.06 | N |
| ATOM | 518 | C   | LYS | A | 115 | 10.081 | 43.391 | −5.970  | 1.00 | 51.29 | C |
| ATOM | 519 | O   | LYS | A | 115 | 9.166  | 43.810 | −6.676  | 1.00 | 53.25 | O |
| ATOM | 520 | N   | TRP | A | 116 | 9.885  | 42.462 | −5.042  | 1.00 | 51.25 | N |
| ATOM | 521 | CA  | TRP | A | 116 | 8.521  | 42.034 | −4.749  | 1.00 | 48.90 | C |
| ATOM | 522 | CB  | TRP | A | 116 | 8.481  | 40.707 | −4.008  | 1.00 | 47.77 | C |
| ATOM | 523 | CG  | TRP | A | 116 | 8.902  | 39.522 | −4.819  | 1.00 | 50.21 | C |
| ATOM | 524 | CD2 | TRP | A | 116 | 8.359  | 39.096 | −6.074  | 1.00 | 50.95 | C |
| ATOM | 525 | CE2 | TRP | A | 116 | 9.049  | 37.935 | −6.454  | 1.00 | 50.48 | C |
| ATOM | 526 | CE3 | TRP | A | 116 | 7.347  | 39.581 | −6.908  | 1.00 | 56.19 | C |
| ATOM | 527 | CD1 | TRP | A | 116 | 9.877  | 38.627 | −4.506  | 1.00 | 51.21 | C |
| ATOM | 528 | NE1 | TRP | A | 116 | 9.973  | 37.670 | −5.481  | 1.00 | 50.39 | N |
| ATOM | 529 | CZ2 | TRP | A | 116 | 8.767  | 37.254 | −7.631  | 1.00 | 54.20 | C |
| ATOM | 530 | CZ3 | TRP | A | 116 | 7.069  | 38.902 | −8.081  | 1.00 | 50.06 | C |
| ATOM | 531 | CH2 | TRP | A | 116 | 7.774  | 37.753 | −8.430  | 1.00 | 54.63 | C |
| ATOM | 532 | C   | TRP | A | 116 | 7.827  | 43.107 | −3.926  | 1.00 | 54.26 | C |
| ATOM | 533 | O   | TRP | A | 116 | 8.440  | 43.731 | −3.068  | 1.00 | 52.01 | O |
| ATOM | 534 | N   | HIS | A | 117 | 6.544  | 43.328 | −4.195  | 1.00 | 57.36 | N |
| ATOM | 535 | CA  | HIS | A | 117 | 5.802  | 44.359 | −3.484  | 1.00 | 51.37 | C |
| ATOM | 536 | CB  | HIS | A | 117 | 5.376  | 45.478 | −4.436  | 1.00 | 53.71 | C |
| ATOM | 537 | CG  | HIS | A | 117 | 6.527  | 46.265 | −4.972  | 1.00 | 52.27 | C |
| ATOM | 538 | CD2 | HIS | A | 117 | 7.487  | 46.982 | −4.339  | 1.00 | 54.85 | C |
| ATOM | 539 | ND1 | HIS | A | 117 | 6.809  | 46.350 | −6.318  | 1.00 | 50.63 | N |
| ATOM | 540 | CE1 | HIS | A | 117 | 7.887  | 47.094 | −6.492  | 1.00 | 51.48 | C |
| ATOM | 541 | NE2 | HIS | A | 117 | 8.323  | 47.486 | −5.307  | 1.00 | 51.19 | N |
| ATOM | 542 | C   | HIS | A | 117 | 4.619  | 43.835 | −2.672  | 1.00 | 50.90 | C |
| ATOM | 543 | O   | HIS | A | 117 | 3.770  | 44.622 | −2.259  | 1.00 | 52.08 | O |

TABLE 12-continued

Coordinates for pro MMP9(35-444 ΔFnII) (SEQ ID NO: 12) complex with Example 2

| ATOM | 544 | N | HIS | A | 118 | 4.563 | 42.514 | −2.469 | 1.00 | 49.23 | N |
|---|---|---|---|---|---|---|---|---|---|---|---|
| ATOM | 545 | CA | HIS | A | 118 | 3.759 | 41.906 | −1.392 | 1.00 | 51.08 | C |
| ATOM | 546 | CB | HIS | A | 118 | 2.670 | 40.937 | −1.898 | 1.00 | 42.24 | C |
| ATOM | 547 | CG | HIS | A | 118 | 3.122 | 40.018 | −2.991 | 1.00 | 51.95 | C |
| ATOM | 548 | CD2 | HIS | A | 118 | 3.056 | 38.671 | −3.105 | 1.00 | 51.19 | C |
| ATOM | 549 | ND1 | HIS | A | 118 | 3.688 | 40.474 | −4.164 | 1.00 | 49.61 | N |
| ATOM | 550 | CE1 | HIS | A | 118 | 3.978 | 39.445 | −4.940 | 1.00 | 53.96 | C |
| ATOM | 551 | NE2 | HIS | A | 118 | 3.604 | 38.338 | −4.321 | 1.00 | 48.37 | N |
| ATOM | 552 | C | HIS | A | 118 | 4.705 | 41.226 | −0.417 | 1.00 | 52.56 | C |
| ATOM | 553 | O | HIS | A | 118 | 5.912 | 41.427 | −0.496 | 1.00 | 58.59 | O |
| ATOM | 554 | N | HIS | A | 119 | 4.182 | 40.425 | 0.499 | 1.00 | 50.43 | N |
| ATOM | 555 | CA | HIS | A | 119 | 5.037 | 39.887 | 1.556 | 1.00 | 61.41 | C |
| ATOM | 556 | CB | HIS | A | 119 | 4.831 | 40.645 | 2.880 | 1.00 | 55.66 | C |
| ATOM | 557 | CG | HIS | A | 119 | 5.653 | 41.896 | 2.984 | 1.00 | 53.06 | C |
| ATOM | 558 | CD2 | HIS | A | 119 | 6.223 | 42.668 | 2.029 | 1.00 | 54.39 | C |
| ATOM | 559 | ND1 | HIS | A | 119 | 5.989 | 42.471 | 4.192 | 1.00 | 60.46 | N |
| ATOM | 560 | CE1 | HIS | A | 119 | 6.725 | 43.549 | 3.976 | 1.00 | 57.96 | C |
| ATOM | 561 | NE2 | HIS | A | 119 | 6.884 | 43.689 | 2.672 | 1.00 | 62.70 | N |
| ATOM | 562 | C | HIS | A | 119 | 4.936 | 38.378 | 1.739 | 1.00 | 58.18 | C |
| ATOM | 563 | O | HIS | A | 119 | 5.818 | 37.750 | 2.339 | 1.00 | 55.13 | O |
| ATOM | 564 | N | ASN | A | 120 | 3.871 | 37.798 | 1.206 | 1.00 | 55.11 | N |
| ATOM | 565 | CA | ASN | A | 120 | 3.793 | 36.352 | 1.120 | 1.00 | 52.35 | C |
| ATOM | 566 | CB | ASN | A | 120 | 2.450 | 35.825 | 1.601 | 1.00 | 60.37 | C |
| ATOM | 567 | CG | ASN | A | 120 | 2.417 | 34.314 | 1.637 | 1.00 | 61.21 | C |
| ATOM | 568 | OD1 | ASN | A | 120 | 3.472 | 33.662 | 1.601 | 1.00 | 51.04 | O |
| ATOM | 569 | ND2 | ASN | A | 120 | 1.208 | 33.743 | 1.701 | 1.00 | 60.23 | N |
| ATOM | 570 | C | ASN | A | 120 | 4.024 | 35.906 | −0.298 | 1.00 | 53.76 | C |
| ATOM | 571 | O | ASN | A | 120 | 3.088 | 35.780 | −1.086 | 1.00 | 49.50 | O |
| ATOM | 572 | N | ILE | A | 121 | 5.294 | 35.690 | −0.600 | 1.00 | 54.06 | N |
| ATOM | 573 | CA | ILE | A | 121 | 5.752 | 35.208 | −1.883 | 1.00 | 47.54 | C |
| ATOM | 574 | CB | ILE | A | 121 | 7.274 | 35.255 | −1.921 | 1.00 | 49.06 | C |
| ATOM | 575 | CG2 | ILE | A | 121 | 7.794 | 34.367 | −3.012 | 1.00 | 55.34 | C |
| ATOM | 576 | CG1 | ILE | A | 121 | 7.761 | 36.684 | −2.153 | 1.00 | 51.75 | C |
| ATOM | 577 | CD1 | ILE | A | 121 | 7.224 | 37.679 | −1.182 | 1.00 | 54.18 | C |
| ATOM | 578 | C | ILE | A | 121 | 5.291 | 33.769 | −2.100 | 1.00 | 50.94 | C |
| ATOM | 579 | O | ILE | A | 121 | 5.475 | 32.924 | −1.223 | 1.00 | 51.60 | O |
| ATOM | 580 | N | THR | A | 122 | 4.690 | 33.488 | −3.262 | 1.00 | 49.74 | N |
| ATOM | 581 | CA | THR | A | 122 | 4.093 | 32.175 | −3.500 | 1.00 | 51.71 | C |
| ATOM | 582 | CB | THR | A | 122 | 2.632 | 32.282 | −4.033 | 1.00 | 51.20 | C |
| ATOM | 583 | OG1 | THR | A | 122 | 2.643 | 32.547 | −5.434 | 1.00 | 52.96 | O |
| ATOM | 584 | CG2 | THR | A | 122 | 1.881 | 33.401 | −3.343 | 1.00 | 54.13 | C |
| ATOM | 585 | C | THR | A | 122 | 4.929 | 31.398 | −4.494 | 1.00 | 45.98 | C |
| ATOM | 586 | O | THR | A | 122 | 5.441 | 31.974 | −5.445 | 1.00 | 49.02 | O |
| ATOM | 587 | N | TYR | A | 123 | 5.070 | 30.094 | −4.283 | 1.00 | 44.26 | N |
| ATOM | 588 | CA | TYR | A | 123 | 5.886 | 29.286 | −5.187 | 1.00 | 46.58 | C |
| ATOM | 589 | CB | TYR | A | 123 | 7.326 | 29.176 | −4.680 | 1.00 | 49.58 | C |
| ATOM | 590 | CG | TYR | A | 123 | 7.525 | 28.290 | −3.469 | 1.00 | 46.90 | C |
| ATOM | 591 | CD1 | TYR | A | 123 | 7.638 | 28.838 | −2.203 | 1.00 | 47.55 | C |
| ATOM | 592 | CE1 | TYR | A | 123 | 7.842 | 28.041 | −1.089 | 1.00 | 50.74 | C |
| ATOM | 593 | CD2 | TYR | A | 123 | 7.632 | 26.912 | −3.597 | 1.00 | 47.13 | C |
| ATOM | 594 | CE2 | TYR | A | 123 | 7.827 | 26.100 | −2.489 | 1.00 | 50.65 | C |
| ATOM | 595 | CZ | TYR | A | 123 | 7.931 | 26.674 | −1.236 | 1.00 | 52.18 | C |
| ATOM | 596 | OH | TYR | A | 123 | 8.138 | 25.895 | −0.127 | 1.00 | 40.34 | O |
| ATOM | 597 | C | TYR | A | 123 | 5.321 | 27.896 | −5.473 | 1.00 | 55.80 | C |
| ATOM | 598 | O | TYR | A | 123 | 4.635 | 27.296 | −4.640 | 1.00 | 60.09 | O |
| ATOM | 599 | N | TRP | A | 124 | 5.629 | 27.389 | −6.662 | 1.00 | 52.93 | N |
| ATOM | 600 | CA | TRP | A | 124 | 5.097 | 26.126 | −7.147 | 1.00 | 53.19 | C |
| ATOM | 601 | CB | TRP | A | 124 | 4.119 | 26.426 | −8.293 | 1.00 | 61.88 | C |
| ATOM | 602 | CG | TRP | A | 124 | 3.491 | 25.242 | −9.004 | 1.00 | 56.85 | C |
| ATOM | 603 | CD2 | TRP | A | 124 | 3.178 | 25.167 | −10.393 | 1.00 | 54.75 | C |
| ATOM | 604 | CE2 | TRP | A | 124 | 2.589 | 23.906 | −10.623 | 1.00 | 56.63 | C |
| ATOM | 605 | CE3 | TRP | A | 124 | 3.351 | 26.041 | −11.474 | 1.00 | 57.81 | C |
| ATOM | 606 | CD1 | TRP | A | 124 | 3.082 | 24.059 | −8.453 | 1.00 | 58.27 | C |
| ATOM | 607 | NE1 | TRP | A | 124 | 2.549 | 23.245 | −9.425 | 1.00 | 56.38 | N |
| ATOM | 608 | CZ2 | TRP | A | 124 | 2.172 | 23.498 | −11.888 | 1.00 | 54.12 | C |
| ATOM | 609 | CZ3 | TRP | A | 124 | 2.932 | 25.641 | −12.725 | 1.00 | 60.01 | C |
| ATOM | 610 | CH2 | TRP | A | 124 | 2.354 | 24.373 | −12.924 | 1.00 | 61.31 | C |
| ATOM | 611 | C | TRP | A | 124 | 6.266 | 25.287 | −7.641 | 1.00 | 56.70 | C |
| ATOM | 612 | O | TRP | A | 124 | 7.090 | 25.760 | −8.423 | 1.00 | 54.36 | O |
| ATOM | 613 | N | ILE | A | 125 | 6.352 | 24.048 | −7.178 | 1.00 | 55.69 | N |
| ATOM | 614 | CA | ILE | A | 125 | 7.392 | 23.148 | −7.657 | 1.00 | 46.99 | C |
| ATOM | 615 | CB | ILE | A | 125 | 7.750 | 22.096 | −6.575 | 1.00 | 51.68 | C |
| ATOM | 616 | CG2 | ILE | A | 125 | 8.874 | 21.162 | −7.040 | 1.00 | 48.21 | C |
| ATOM | 617 | CG1 | ILE | A | 125 | 8.103 | 22.792 | −5.249 | 1.00 | 53.66 | C |
| ATOM | 618 | CD1 | ILE | A | 125 | 8.335 | 21.833 | −4.073 | 1.00 | 49.89 | C |
| ATOM | 619 | C | ILE | A | 125 | 6.908 | 22.489 | −8.944 | 1.00 | 49.22 | C |
| ATOM | 620 | O | ILE | A | 125 | 6.578 | 21.310 | −8.951 | 1.00 | 54.48 | O |

TABLE 12-continued

Coordinates for pro MMP9(35-444 ΔFnII) (SEQ ID NO: 12) complex with Example 2

| ATOM | 621 | N | GLN | A | 126 | 6.855 | 23.270 | −10.024 | 1.00 | 48.65 | N |
|---|---|---|---|---|---|---|---|---|---|---|---|
| ATOM | 622 | CA | GLN | A | 126 | 6.315 | 22.836 | −11.319 | 1.00 | 50.25 | C |
| ATOM | 623 | CB | GLN | A | 126 | 6.691 | 23.830 | −12.424 | 1.00 | 51.85 | C |
| ATOM | 624 | CG | GLN | A | 126 | 6.292 | 23.387 | −13.842 | 1.00 | 50.44 | C |
| ATOM | 625 | CD | GLN | A | 126 | 6.339 | 24.538 | −14.855 | 1.00 | 56.36 | C |
| ATOM | 626 | OE1 | GLN | A | 126 | 7.253 | 24.626 | −15.685 | 1.00 | 57.60 | O |
| ATOM | 627 | NE2 | GLN | A | 126 | 5.351 | 25.427 | −14.784 | 1.00 | 52.75 | N |
| ATOM | 628 | C | GLN | A | 126 | 6.692 | 21.418 | −11.767 | 1.00 | 51.12 | C |
| ATOM | 629 | O | GLN | A | 126 | 5.941 | 20.774 | −12.496 | 1.00 | 52.04 | O |
| ATOM | 630 | N | ASN | A | 127 | 7.859 | 20.945 | −11.355 | 1.00 | 52.03 | N |
| ATOM | 631 | CA | ASN | A | 127 | 8.276 | 19.584 | −11.670 | 1.00 | 52.89 | C |
| ATOM | 632 | CB | ASN | A | 127 | 8.531 | 19.401 | −13.172 | 1.00 | 55.37 | C |
| ATOM | 633 | CG | ASN | A | 127 | 9.537 | 20.391 | −13.733 | 1.00 | 54.56 | C |
| ATOM | 634 | OD1 | ASN | A | 127 | 9.732 | 21.478 | −13.192 | 0.47 | 55.18 | O |
| ATOM | 635 | ND2 | ASN | A | 127 | 10.175 | 20.019 | −14.836 | 1.00 | 56.55 | N |
| ATOM | 636 | C | ASN | A | 127 | 9.487 | 19.157 | −10.852 | 0.65 | 55.64 | C |
| ATOM | 637 | O | ASN | A | 127 | 10.063 | 19.970 | −10.124 | 1.00 | 55.14 | O |
| ATOM | 638 | N | TYR | A | 128 | 9.860 | 17.885 | −10.980 | 1.00 | 53.40 | N |
| ATOM | 639 | CA | TYR | A | 128 | 10.940 | 17.307 | −10.189 | 1.00 | 55.06 | C |
| ATOM | 640 | CB | TYR | A | 128 | 10.379 | 16.241 | −9.247 | 1.00 | 55.84 | C |
| ATOM | 641 | CG | TYR | A | 128 | 9.488 | 16.809 | −8.155 | 1.00 | 63.24 | C |
| ATOM | 642 | CD1 | TYR | A | 128 | 9.992 | 17.072 | −6.884 | 1.00 | 61.81 | C |
| ATOM | 643 | CE1 | TYR | A | 128 | 9.189 | 17.588 | −5.892 | 1.00 | 60.10 | C |
| ATOM | 644 | CD2 | TYR | A | 128 | 8.148 | 17.086 | −8.400 | 1.00 | 58.51 | C |
| ATOM | 645 | CE2 | TYR | A | 128 | 7.343 | 17.601 | −7.419 | 1.00 | 61.09 | C |
| ATOM | 646 | CZ | TYR | A | 128 | 7.866 | 17.854 | −6.163 | 1.00 | 62.92 | C |
| ATOM | 647 | OH | TYR | A | 128 | 7.052 | 18.372 | −5.181 | 1.00 | 62.43 | O |
| ATOM | 648 | C | TYR | A | 128 | 12.102 | 16.711 | −10.997 | 1.00 | 60.61 | C |
| ATOM | 649 | O | TYR | A | 128 | 11.926 | 16.247 | −12.116 | 1.00 | 57.50 | O |
| ATOM | 650 | N | SER | A | 129 | 13.296 | 16.742 | −10.416 | 1.00 | 63.01 | N |
| ATOM | 651 | CA | SER | A | 129 | 14.400 | 15.948 | −10.918 | 1.00 | 56.03 | C |
| ATOM | 652 | CB | SER | A | 129 | 15.734 | 16.489 | −10.400 | 1.00 | 59.89 | C |
| ATOM | 653 | OG | SER | A | 129 | 16.839 | 15.849 | −11.022 | 1.00 | 61.43 | O |
| ATOM | 654 | C | SER | A | 129 | 14.148 | 14.558 | −10.374 | 1.00 | 61.89 | C |
| ATOM | 655 | O | SER | A | 129 | 13.574 | 14.407 | −9.296 | 1.00 | 67.24 | O |
| ATOM | 656 | N | GLU | A | 130 | 14.546 | 13.540 | −11.123 | 1.00 | 66.36 | N |
| ATOM | 657 | CA | GLU | A | 130 | 14.322 | 12.171 | −10.683 | 1.00 | 69.32 | C |
| ATOM | 658 | CB | GLU | A | 130 | 14.110 | 11.237 | −11.875 | 1.00 | 72.68 | C |
| ATOM | 659 | CG | GLU | A | 130 | 12.643 | 10.895 | −12.113 | 1.00 | 80.39 | C |
| ATOM | 660 | CD | GLU | A | 130 | 11.925 | 10.456 | −10.831 | 1.00 | 84.49 | C |
| ATOM | 661 | OE1 | GLU | A | 130 | 11.990 | 9.252 | −10.484 | 1.00 | 88.58 | O |
| ATOM | 662 | OE2 | GLU | A | 130 | 11.301 | 11.319 | −10.169 | 1.00 | 79.70 | O |
| ATOM | 663 | C | GLU | A | 130 | 15.491 | 11.719 | −9.847 | 1.00 | 63.71 | C |
| ATOM | 664 | O | GLU | A | 130 | 15.492 | 10.618 | −9.291 | 1.00 | 62.78 | O |
| ATOM | 665 | N | ASP | A | 131 | 16.487 | 12.594 | −9.770 | 1.00 | 65.00 | N |
| ATOM | 666 | CA | ASP | A | 131 | 17.679 | 12.362 | −8.965 | 1.00 | 63.52 | C |
| ATOM | 667 | CB | ASP | A | 131 | 18.635 | 13.541 | −9.106 | 1.00 | 57.78 | C |
| ATOM | 668 | CG | ASP | A | 131 | 19.204 | 13.644 | −10.483 | 1.00 | 58.59 | C |
| ATOM | 669 | OD1 | ASP | A | 131 | 18.960 | 12.714 | −11.274 | 1.00 | 56.65 | O |
| ATOM | 670 | OD2 | ASP | A | 131 | 19.901 | 14.638 | −10.776 | 1.00 | 63.56 | O |
| ATOM | 671 | C | ASP | A | 131 | 17.369 | 12.131 | −7.495 | 1.00 | 56.89 | C |
| ATOM | 672 | O | ASP | A | 131 | 18.045 | 11.341 | −6.841 | 1.00 | 65.85 | O |
| ATOM | 673 | N | LEU | A | 132 | 16.357 | 12.819 | −6.976 | 1.00 | 54.41 | N |
| ATOM | 674 | CA | LEU | A | 132 | 16.058 | 12.756 | −5.550 | 1.00 | 58.87 | C |
| ATOM | 675 | CB | LEU | A | 132 | 16.554 | 14.020 | −4.836 | 1.00 | 57.96 | C |
| ATOM | 676 | CG | LEU | A | 132 | 18.055 | 14.218 | −4.597 | 1.00 | 60.62 | C |
| ATOM | 677 | CD1 | LEU | A | 132 | 18.344 | 15.614 | −4.041 | 1.00 | 58.05 | C |
| ATOM | 678 | CD2 | LEU | A | 132 | 18.596 | 13.156 | −3.666 | 1.00 | 56.51 | C |
| ATOM | 679 | C | LEU | A | 132 | 14.573 | 12.561 | −5.291 | 1.00 | 60.00 | C |
| ATOM | 680 | O | LEU | A | 132 | 13.741 | 12.949 | −6.117 | 1.00 | 61.71 | O |
| ATOM | 681 | N | PRO | A | 133 | 14.238 | 11.962 | −4.132 | 1.00 | 57.32 | N |
| ATOM | 682 | CD | PRO | A | 133 | 15.202 | 11.583 | −3.079 | 1.00 | 58.89 | C |
| ATOM | 683 | CA | PRO | A | 133 | 12.846 | 11.726 | −3.733 | 1.00 | 50.66 | C |
| ATOM | 684 | CB | PRO | A | 133 | 12.960 | 11.323 | −2.266 | 1.00 | 53.17 | C |
| ATOM | 685 | CG | PRO | A | 133 | 14.363 | 10.818 | −2.100 | 1.00 | 58.39 | C |
| ATOM | 686 | C | PRO | A | 133 | 12.061 | 13.021 | −3.842 | 1.00 | 58.70 | C |
| ATOM | 687 | O | PRO | A | 133 | 12.621 | 14.083 | −3.595 | 1.00 | 56.85 | O |
| ATOM | 688 | N | ARG | A | 134 | 10.786 | 12.934 | −4.202 | 1.00 | 59.56 | N |
| ATOM | 689 | CA | ARG | A | 134 | 9.987 | 14.128 | −4.415 | 1.00 | 54.62 | C |
| ATOM | 690 | CB | ARG | A | 134 | 8.615 | 13.771 | −4.975 | 1.00 | 56.38 | C |
| ATOM | 691 | CG | ARG | A | 134 | 8.556 | 13.834 | −6.485 | 1.00 | 62.19 | C |
| ATOM | 692 | CD | ARG | A | 134 | 7.170 | 13.544 | −7.025 | 1.00 | 60.70 | C |
| ATOM | 693 | NE | ARG | A | 134 | 7.137 | 13.801 | −8.459 | 1.00 | 63.59 | N |
| ATOM | 694 | CZ | ARG | A | 134 | 6.123 | 13.495 | −9.261 | 1.00 | 69.57 | C |
| ATOM | 695 | NH1 | ARG | A | 134 | 5.035 | 12.901 | −8.776 | 1.00 | 69.93 | N |
| ATOM | 696 | NH2 | ARG | A | 134 | 6.204 | 13.781 | −10.555 | 1.00 | 64.83 | N |
| ATOM | 697 | C | ARG | A | 134 | 9.842 | 14.982 | −3.167 | 1.00 | 58.11 | C |

TABLE 12-continued

Coordinates for pro MMP9(35-444 ΔFnII) (SEQ ID NO: 12) complex with Example 2

| ATOM | 698 | O | ARG | A | 134 | 9.566 | 16.178 | −3.261 | 1.00 | 63.16 | O |
|---|---|---|---|---|---|---|---|---|---|---|---|
| ATOM | 699 | N | ALA | A | 135 | 10.024 | 14.381 | −2.000 | 1.00 | 56.02 | N |
| ATOM | 700 | CA | ALA | A | 135 | 9.810 | 15.109 | −0.759 | 1.00 | 52.35 | C |
| ATOM | 701 | CB | ALA | A | 135 | 9.305 | 14.186 | 0.327 | 1.00 | 43.52 | C |
| ATOM | 702 | C | ALA | A | 135 | 11.099 | 15.775 | −0.325 | 1.00 | 55.56 | C |
| ATOM | 703 | O | ALA | A | 135 | 11.077 | 16.863 | 0.245 | 1.00 | 54.92 | O |
| ATOM | 704 | N | VAL | A | 136 | 12.223 | 15.117 | −0.593 | 1.00 | 52.58 | N |
| ATOM | 705 | CA | VAL | A | 136 | 13.517 | 15.667 | −0.232 | 1.00 | 50.72 | C |
| ATOM | 706 | CB | VAL | A | 136 | 14.635 | 14.651 | −0.451 | 1.00 | 52.90 | C |
| ATOM | 707 | CG1 | VAL | A | 136 | 16.001 | 15.310 | −0.270 | 1.00 | 42.40 | C |
| ATOM | 708 | CG2 | VAL | A | 136 | 14.457 | 13.494 | 0.527 | 1.00 | 52.44 | C |
| ATOM | 709 | C | VAL | A | 136 | 13.776 | 16.938 | −1.021 | 1.00 | 50.44 | C |
| ATOM | 710 | O | VAL | A | 136 | 14.432 | 17.863 | −0.550 | 1.00 | 51.17 | O |
| ATOM | 711 | N | ILE | A | 137 | 13.227 | 16.992 | −2.224 | 1.00 | 53.51 | N |
| ATOM | 712 | CA | ILE | A | 137 | 13.340 | 18.187 | −3.039 | 1.00 | 52.94 | C |
| ATOM | 713 | CB | ILE | A | 137 | 13.025 | 17.888 | −4.516 | 1.00 | 51.55 | C |
| ATOM | 714 | CG2 | ILE | A | 137 | 12.849 | 19.176 | −5.292 | 1.00 | 45.79 | C |
| ATOM | 715 | CG1 | ILE | A | 137 | 14.147 | 17.037 | −5.113 | 1.00 | 52.71 | C |
| ATOM | 716 | CD1 | ILE | A | 137 | 13.687 | 16.080 | −6.214 | 1.00 | 54.01 | C |
| ATOM | 717 | C | ILE | A | 137 | 12.429 | 19.286 | −2.496 | 1.00 | 51.67 | C |
| ATOM | 718 | O | ILE | A | 137 | 12.824 | 20.454 | −2.451 | 1.00 | 48.38 | O |
| ATOM | 719 | N | ASP | A | 138 | 11.216 | 18.911 | −2.087 | 1.00 | 48.65 | N |
| ATOM | 720 | CA | ASP | A | 138 | 10.272 | 19.868 | −1.517 | 1.00 | 46.45 | C |
| ATOM | 721 | CB | ASP | A | 138 | 8.965 | 19.184 | −1.096 | 1.00 | 55.18 | C |
| ATOM | 722 | CG | ASP | A | 138 | 8.173 | 18.642 | −2.277 | 1.00 | 55.74 | C |
| ATOM | 723 | OD1 | ASP | A | 138 | 8.740 | 18.525 | −3.381 | 1.00 | 56.81 | O |
| ATOM | 724 | OD2 | ASP | A | 138 | 6.984 | 18.320 | −2.090 | 1.00 | 55.45 | O |
| ATOM | 725 | C | ASP | A | 138 | 10.886 | 20.523 | −0.303 | 1.00 | 47.83 | C |
| ATOM | 726 | O | ASP | A | 138 | 10.815 | 21.735 | −0.140 | 1.00 | 48.09 | O |
| ATOM | 727 | N | ASP | A | 139 | 11.475 | 19.693 | 0.555 | 1.00 | 47.28 | N |
| ATOM | 728 | CA | ASP | A | 139 | 12.128 | 20.146 | 1.769 | 1.00 | 41.04 | C |
| ATOM | 729 | CB | ASP | A | 139 | 12.678 | 18.932 | 2.530 | 1.00 | 44.11 | C |
| ATOM | 730 | CG | ASP | A | 139 | 13.262 | 19.292 | 3.899 | 1.00 | 48.61 | C |
| ATOM | 731 | OD1 | ASP | A | 139 | 12.597 | 20.034 | 4.658 | 1.00 | 51.68 | O |
| ATOM | 732 | OD2 | ASP | A | 139 | 14.374 | 18.811 | 4.231 | 1.00 | 44.98 | O |
| ATOM | 733 | C | ASP | A | 139 | 13.267 | 21.093 | 1.390 | 1.00 | 52.33 | C |
| ATOM | 734 | O | ASP | A | 139 | 13.434 | 22.167 | 1.981 | 1.00 | 52.55 | O |
| ATOM | 735 | N | ALA | A | 140 | 14.052 | 20.702 | 0.393 | 1.00 | 43.10 | N |
| ATOM | 736 | CA | ALA | A | 140 | 15.226 | 21.478 | 0.050 | 1.00 | 47.68 | C |
| ATOM | 737 | CB | ALA | A | 140 | 15.971 | 20.821 | −1.077 | 1.00 | 51.10 | C |
| ATOM | 738 | C | ALA | A | 140 | 14.902 | 22.946 | −0.283 | 1.00 | 52.75 | C |
| ATOM | 739 | O | ALA | A | 140 | 15.555 | 23.861 | 0.218 | 1.00 | 52.15 | O |
| ATOM | 740 | N | PHE | A | 141 | 13.899 | 23.184 | −1.120 | 1.00 | 50.14 | N |
| ATOM | 741 | CA | PHE | A | 141 | 13.520 | 24.566 | −1.404 | 1.00 | 53.45 | C |
| ATOM | 742 | CB | PHE | A | 141 | 12.498 | 24.650 | −2.531 | 1.00 | 54.87 | C |
| ATOM | 743 | CG | PHE | A | 141 | 12.913 | 23.950 | −3.781 | 1.00 | 48.87 | C |
| ATOM | 744 | CD1 | PHE | A | 141 | 14.196 | 24.058 | −4.252 | 1.00 | 51.65 | C |
| ATOM | 745 | CD2 | PHE | A | 141 | 12.003 | 23.192 | −4.494 | 1.00 | 49.59 | C |
| ATOM | 746 | CE1 | PHE | A | 141 | 14.568 | 23.415 | −5.417 | 1.00 | 53.48 | C |
| ATOM | 747 | CE2 | PHE | A | 141 | 12.364 | 22.549 | −5.649 | 1.00 | 50.79 | C |
| ATOM | 748 | CZ | PHE | A | 141 | 13.648 | 22.661 | −6.115 | 1.00 | 49.43 | C |
| ATOM | 749 | C | PHE | A | 141 | 12.926 | 25.192 | −0.153 | 1.00 | 50.30 | C |
| ATOM | 750 | O | PHE | A | 141 | 13.056 | 26.392 | 0.096 | 1.00 | 52.28 | O |
| ATOM | 751 | N | ALA | A | 142 | 12.261 | 24.377 | 0.642 | 1.00 | 48.19 | N |
| ATOM | 752 | CA | ALA | A | 142 | 11.694 | 24.894 | 1.871 | 1.00 | 53.15 | C |
| ATOM | 753 | CB | ALA | A | 142 | 10.948 | 23.796 | 2.616 | 1.00 | 52.48 | C |
| ATOM | 754 | C | ALA | A | 142 | 12.791 | 25.523 | 2.746 | 1.00 | 50.60 | C |
| ATOM | 755 | O | ALA | A | 142 | 12.665 | 26.676 | 3.151 | 1.00 | 50.34 | O |
| ATOM | 756 | N | ARG | A | 143 | 13.863 | 24.774 | 3.021 | 1.00 | 49.08 | N |
| ATOM | 757 | CA | ARG | A | 143 | 14.978 | 25.284 | 3.835 | 1.00 | 42.49 | C |
| ATOM | 758 | CB | ARG | A | 143 | 15.932 | 24.161 | 4.193 | 1.00 | 34.70 | C |
| ATOM | 759 | CG | ARG | A | 143 | 15.318 | 23.148 | 5.122 | 1.00 | 41.26 | C |
| ATOM | 760 | CD | ARG | A | 143 | 15.649 | 21.724 | 4.719 | 1.00 | 46.44 | C |
| ATOM | 761 | NE | ARG | A | 143 | 17.023 | 21.376 | 5.042 | 1.00 | 46.63 | N |
| ATOM | 762 | CZ | ARG | A | 143 | 17.998 | 21.284 | 4.144 | 1.00 | 45.17 | C |
| ATOM | 763 | NH1 | ARG | A | 143 | 17.746 | 21.480 | 2.861 | 1.00 | 49.07 | N |
| ATOM | 764 | NH2 | ARG | A | 143 | 19.220 | 20.973 | 4.529 | 1.00 | 43.86 | N |
| ATOM | 765 | C | ARG | A | 143 | 15.730 | 26.401 | 3.110 | 1.00 | 48.00 | C |
| ATOM | 766 | O | ARG | A | 143 | 16.179 | 27.366 | 3.736 | 1.00 | 45.35 | O |
| ATOM | 767 | N | ALA | A | 144 | 15.859 | 26.267 | 1.788 | 1.00 | 46.04 | N |
| ATOM | 768 | CA | ALA | A | 144 | 16.364 | 27.345 | 0.953 | 1.00 | 44.10 | C |
| ATOM | 769 | CB | ALA | A | 144 | 16.292 | 26.966 | −0.518 | 1.00 | 46.85 | C |
| ATOM | 770 | C | ALA | A | 144 | 15.540 | 28.603 | 1.212 | 1.00 | 49.14 | C |
| ATOM | 771 | O | ALA | A | 144 | 16.090 | 29.694 | 1.361 | 1.00 | 47.79 | O |
| ATOM | 772 | N | PHE | A | 145 | 14.219 | 28.448 | 1.287 | 1.00 | 47.35 | N |
| ATOM | 773 | CA | PHE | A | 145 | 13.342 | 29.588 | 1.564 | 1.00 | 46.16 | C |
| ATOM | 774 | CB | PHE | A | 145 | 11.908 | 29.284 | 1.154 | 1.00 | 41.62 | C |

TABLE 12-continued

Coordinates for pro MMP9(35-444 ΔFnII) (SEQ ID NO: 12) complex with Example 2

| ATOM | 775 | CG  | PHE | A | 145 | 11.686 | 29.430 | −0.318 | 1.00 | 48.58 | C |
| ---- | --- | --- | --- | - | --- | ------ | ------ | ------ | ---- | ----- | - |
| ATOM | 776 | CD1 | PHE | A | 145 | 12.144 | 30.555 | −0.974 | 1.00 | 43.41 | C |
| ATOM | 777 | CD2 | PHE | A | 145 | 11.048 | 28.445 | −1.048 | 1.00 | 48.39 | C |
| ATOM | 778 | CE1 | PHE | A | 145 | 11.957 | 30.709 | −2.325 | 1.00 | 46.76 | C |
| ATOM | 779 | CE2 | PHE | A | 145 | 10.864 | 28.581 | −2.402 | 1.00 | 46.25 | C |
| ATOM | 780 | CZ  | PHE | A | 145 | 11.320 | 29.717 | −3.048 | 1.00 | 50.47 | C |
| ATOM | 781 | C   | PHE | A | 145 | 13.420 | 30.113 | 2.998  | 1.00 | 40.67 | C |
| ATOM | 782 | O   | PHE | A | 145 | 13.259 | 31.310 | 3.241  | 1.00 | 38.32 | O |
| ATOM | 783 | N   | ALA | A | 146 | 13.708 | 29.226 | 3.937  | 1.00 | 40.24 | N |
| ATOM | 784 | CA  | ALA | A | 146 | 13.761 | 29.628 | 5.337  | 1.00 | 42.13 | C |
| ATOM | 785 | CB  | ALA | A | 146 | 13.827 | 28.422 | 6.218  | 1.00 | 40.37 | C |
| ATOM | 786 | C   | ALA | A | 146 | 14.942 | 30.558 | 5.599  | 1.00 | 40.98 | C |
| ATOM | 787 | O   | ALA | A | 146 | 14.968 | 31.286 | 6.590  | 1.00 | 40.58 | O |
| ATOM | 788 | N   | LEU | A | 147 | 15.914 | 30.530 | 4.695  | 1.00 | 43.94 | N |
| ATOM | 789 | CA  | LEU | A | 147 | 17.032 | 31.465 | 4.736  | 1.00 | 40.50 | C |
| ATOM | 790 | CB  | LEU | A | 147 | 18.075 | 31.034 | 3.719  | 1.00 | 40.68 | C |
| ATOM | 791 | CG  | LEU | A | 147 | 18.563 | 29.622 | 4.016  | 1.00 | 46.09 | C |
| ATOM | 792 | CD1 | LEU | A | 147 | 19.561 | 29.146 | 2.962  | 1.00 | 41.15 | C |
| ATOM | 793 | CD2 | LEU | A | 147 | 19.175 | 29.560 | 5.444  | 1.00 | 41.82 | C |
| ATOM | 794 | C   | LEU | A | 147 | 16.624 | 32.933 | 4.498  | 1.00 | 43.00 | C |
| ATOM | 795 | O   | LEU | A | 147 | 17.091 | 33.838 | 5.188  | 1.00 | 41.55 | O |
| ATOM | 796 | N   | TRP | A | 148 | 15.775 | 33.195 | 3.536  | 1.00 | 40.29 | N |
| ATOM | 797 | CA  | TRP | A | 148 | 15.367 | 34.532 | 3.259  | 1.00 | 35.66 | C |
| ATOM | 798 | CB  | TRP | A | 148 | 15.089 | 34.675 | 1.785  | 1.00 | 46.95 | C |
| ATOM | 799 | CG  | TRP | A | 148 | 16.165 | 34.135 | 0.929  | 1.00 | 43.32 | C |
| ATOM | 800 | CD2 | TRP | A | 148 | 17.402 | 34.757 | 0.630  | 1.00 | 39.54 | C |
| ATOM | 801 | CE2 | TRP | A | 148 | 18.109 | 33.892 | −0.181 | 1.00 | 37.83 | C |
| ATOM | 802 | CE3 | TRP | A | 148 | 17.987 | 35.962 | 0.994  | 1.00 | 44.81 | C |
| ATOM | 803 | CD1 | TRP | A | 148 | 16.172 | 32.964 | 0.295  | 1.00 | 39.40 | C |
| ATOM | 804 | NE1 | TRP | A | 148 | 17.328 | 32.801 | −0.381 | 1.00 | 41.00 | N |
| ATOM | 805 | CZ2 | TRP | A | 148 | 19.338 | 34.188 | −0.658 | 1.00 | 40.65 | C |
| ATOM | 806 | CZ3 | TRP | A | 148 | 19.203 | 36.244 | 0.529  | 1.00 | 46.86 | C |
| ATOM | 807 | CH2 | TRP | A | 148 | 19.874 | 35.368 | −0.297 | 1.00 | 43.87 | C |
| ATOM | 808 | C   | TRP | A | 148 | 14.167 | 34.901 | 4.060  | 1.00 | 42.66 | C |
| ATOM | 809 | O   | TRP | A | 148 | 13.978 | 36.017 | 4.386  | 1.00 | 46.11 | O |
| ATOM | 810 | N   | SER | A | 149 | 13.346 | 33.948 | 4.401  | 1.00 | 42.98 | N |
| ATOM | 811 | CA  | SER | A | 149 | 12.210 | 34.201 | 5.260  | 1.00 | 41.79 | C |
| ATOM | 812 | CB  | SER | A | 149 | 11.547 | 32.891 | 5.575  | 1.00 | 40.04 | C |
| ATOM | 813 | OG  | SER | A | 149 | 10.170 | 33.005 | 5.609  | 1.00 | 50.50 | O |
| ATOM | 814 | C   | SER | A | 149 | 12.555 | 34.872 | 6.565  | 1.00 | 42.14 | C |
| ATOM | 815 | O   | SER | A | 149 | 11.781 | 35.610 | 7.097  | 1.00 | 45.42 | O |
| ATOM | 816 | N   | ALA | A | 150 | 13.714 | 34.587 | 7.096  | 1.00 | 42.48 | N |
| ATOM | 817 | CA  | ALA | A | 150 | 14.053 | 34.954 | 8.443  | 1.00 | 46.15 | C |
| ATOM | 818 | CB  | ALA | A | 150 | 14.933 | 33.940 | 8.999  | 1.00 | 41.25 | C |
| ATOM | 819 | C   | ALA | A | 150 | 14.716 | 36.305 | 8.507  | 1.00 | 47.05 | C |
| ATOM | 820 | O   | ALA | A | 150 | 14.711 | 36.983 | 9.500  | 1.00 | 49.66 | O |
| ATOM | 821 | N   | VAL | A | 151 | 15.279 | 36.705 | 7.405  | 1.00 | 45.53 | N |
| ATOM | 822 | CA  | VAL | A | 151 | 15.974 | 37.994 | 7.336  | 1.00 | 50.74 | C |
| ATOM | 823 | CB  | VAL | A | 151 | 17.377 | 37.835 | 6.745  | 1.00 | 41.06 | C |
| ATOM | 824 | CG1 | VAL | A | 151 | 18.277 | 37.086 | 7.723  | 1.00 | 39.90 | C |
| ATOM | 825 | CG2 | VAL | A | 151 | 17.286 | 37.100 | 5.442  | 1.00 | 39.94 | C |
| ATOM | 826 | C   | VAL | A | 151 | 15.198 | 38.984 | 6.484  | 1.00 | 48.07 | C |
| ATOM | 827 | O   | VAL | A | 151 | 15.746 | 39.963 | 5.980  | 1.00 | 43.98 | O |
| ATOM | 828 | N   | THR | A | 152 | 13.905 | 38.733 | 6.352  | 1.00 | 48.63 | N |
| ATOM | 829 | CA  | THR | A | 152 | 13.091 | 39.489 | 5.432  | 1.00 | 44.47 | C |
| ATOM | 830 | CB  | THR | A | 152 | 12.989 | 38.740 | 4.103  | 1.00 | 45.61 | C |
| ATOM | 831 | OG1 | THR | A | 152 | 14.257 | 38.772 | 3.433  | 1.00 | 56.33 | O |
| ATOM | 832 | CG2 | THR | A | 152 | 12.021 | 39.407 | 3.245  | 1.00 | 50.13 | C |
| ATOM | 833 | C   | THR | A | 152 | 11.689 | 39.638 | 5.972  | 1.00 | 50.10 | C |
| ATOM | 834 | O   | THR | A | 152 | 11.172 | 38.734 | 6.641  | 1.00 | 53.26 | O |
| ATOM | 835 | N   | PRO | A | 153 | 11.048 | 40.773 | 5.676  | 1.00 | 54.38 | N |
| ATOM | 836 | CD  | PRO | A | 153 | 11.596 | 42.013 | 5.102  | 1.00 | 52.17 | C |
| ATOM | 837 | CA  | PRO | A | 153 | 9.617  | 40.876 | 5.986  | 1.00 | 56.42 | C |
| ATOM | 838 | CB  | PRO | A | 153 | 9.277  | 42.322 | 5.602  | 1.00 | 56.68 | C |
| ATOM | 839 | CG  | PRO | A | 153 | 10.605 | 43.037 | 5.511  | 1.00 | 57.40 | C |
| ATOM | 840 | C   | PRO | A | 153 | 8.774  | 39.915 | 5.136  | 1.00 | 48.71 | C |
| ATOM | 841 | O   | PRO | A | 153 | 7.585  | 40.155 | 4.998  | 1.00 | 52.07 | O |
| ATOM | 842 | N   | LEU | A | 154 | 9.371  | 38.856 | 4.592  | 1.00 | 45.44 | N |
| ATOM | 843 | CA  | LEU | A | 154 | 8.689  | 37.990 | 3.636  | 1.00 | 42.28 | C |
| ATOM | 844 | CB  | LEU | A | 154 | 9.524  | 37.836 | 2.367  | 1.00 | 47.45 | C |
| ATOM | 845 | CG  | LEU | A | 154 | 9.814  | 39.088 | 1.528  | 1.00 | 45.20 | C |
| ATOM | 846 | CD1 | LEU | A | 154 | 10.676 | 38.713 | 0.349  | 1.00 | 48.79 | C |
| ATOM | 847 | CD2 | LEU | A | 154 | 8.539  | 39.788 | 1.079  | 1.00 | 49.22 | C |
| ATOM | 848 | C   | LEU | A | 154 | 8.392  | 36.613 | 4.199  | 1.00 | 46.05 | C |
| ATOM | 849 | O   | LEU | A | 154 | 9.013  | 36.188 | 5.175  | 1.00 | 49.29 | O |
| ATOM | 850 | N   | THR | A | 155 | 7.446  | 35.919 | 3.567  | 1.00 | 46.78 | N |
| ATOM | 851 | CA  | THR | A | 155 | 7.081  | 34.545 | 3.913  | 1.00 | 43.49 | C |

TABLE 12-continued

Coordinates for pro MMP9(35-444 ΔFnII) (SEQ ID NO: 12) complex with Example 2

| ATOM | 852 | CB | THR | A | 155 | 5.749 | 34.491 | 4.664 | 1.00 | 47.19 | C |
|------|-----|-----|-----|---|-----|-------|--------|-------|------|-------|---|
| ATOM | 853 | OG1 | THR | A | 155 | 4.734 | 35.083 | 3.842 | 1.00 | 49.71 | O |
| ATOM | 854 | CG2 | THR | A | 155 | 5.826 | 35.230 | 6.015 | 1.00 | 33.55 | C |
| ATOM | 855 | C | THR | A | 155 | 6.885 | 33.797 | 2.603 | 1.00 | 44.20 | C |
| ATOM | 856 | O | THR | A | 155 | 6.467 | 34.394 | 1.616 | 1.00 | 51.76 | O |
| ATOM | 857 | N | PHE | A | 156 | 7.162 | 32.500 | 2.583 | 1.00 | 39.99 | N |
| ATOM | 858 | CA | PHE | A | 156 | 7.125 | 31.740 | 1.330 | 1.00 | 46.29 | C |
| ATOM | 859 | CB | PHE | A | 156 | 8.523 | 31.287 | 0.894 | 1.00 | 38.38 | C |
| ATOM | 860 | CG | PHE | A | 156 | 9.489 | 32.412 | 0.740 | 1.00 | 41.91 | C |
| ATOM | 861 | CD1 | PHE | A | 156 | 10.369 | 32.729 | 1.759 | 1.00 | 40.06 | C |
| ATOM | 862 | CD2 | PHE | A | 156 | 9.493 | 33.175 | −0.409 | 1.00 | 40.58 | C |
| ATOM | 863 | CE1 | PHE | A | 156 | 11.240 | 33.776 | 1.629 | 1.00 | 42.24 | C |
| ATOM | 864 | CE2 | PHE | A | 156 | 10.372 | 34.228 | −0.557 | 1.00 | 45.33 | C |
| ATOM | 865 | CZ | PHE | A | 156 | 11.250 | 34.530 | 0.465 | 1.00 | 46.60 | C |
| ATOM | 866 | C | PHE | A | 156 | 6.251 | 30.532 | 1.509 | 1.00 | 53.18 | C |
| ATOM | 867 | O | PHE | A | 156 | 6.548 | 29.650 | 2.318 | 1.00 | 57.07 | O |
| ATOM | 868 | N | THR | A | 157 | 5.165 | 30.489 | 0.758 | 1.00 | 47.16 | N |
| ATOM | 869 | CA | THR | A | 157 | 4.156 | 29.479 | 0.998 | 1.00 | 50.89 | C |
| ATOM | 870 | CB | THR | A | 157 | 2.885 | 30.109 | 1.563 | 1.00 | 51.48 | C |
| ATOM | 871 | OG1 | THR | A | 157 | 2.140 | 30.730 | 0.511 | 1.00 | 53.11 | O |
| ATOM | 872 | CG2 | THR | A | 157 | 3.246 | 31.162 | 2.566 | 1.00 | 47.51 | C |
| ATOM | 873 | C | THR | A | 157 | 3.862 | 28.781 | −0.312 | 1.00 | 61.69 | C |
| ATOM | 874 | O | THR | A | 157 | 3.648 | 29.428 | −1.341 | 1.00 | 61.07 | O |
| ATOM | 875 | N | ARG | A | 158 | 3.884 | 27.457 | −0.270 | 1.00 | 60.04 | N |
| ATOM | 876 | CA | ARG | A | 158 | 3.744 | 26.656 | −1.469 | 1.00 | 54.30 | C |
| ATOM | 877 | CB | ARG | A | 158 | 4.073 | 25.202 | −1.169 | 1.00 | 54.29 | C |
| ATOM | 878 | CG | ARG | A | 158 | 4.130 | 24.345 | −2.397 | 1.00 | 59.50 | C |
| ATOM | 879 | CD | ARG | A | 158 | 4.631 | 22.975 | −2.036 | 1.00 | 62.36 | C |
| ATOM | 880 | NE | ARG | A | 158 | 5.045 | 22.226 | −3.212 | 1.00 | 68.40 | N |
| ATOM | 881 | CZ | ARG | A | 158 | 5.204 | 20.907 | −3.227 | 1.00 | 70.93 | C |
| ATOM | 882 | NH1 | ARG | A | 158 | 4.967 | 20.200 | −2.121 | 1.00 | 59.90 | N |
| ATOM | 883 | NH2 | ARG | A | 158 | 5.589 | 20.300 | −4.350 | 1.00 | 62.22 | N |
| ATOM | 884 | C | ARG | A | 158 | 2.349 | 26.767 | −2.064 | 1.00 | 60.56 | C |
| ATOM | 885 | O | ARG | A | 158 | 1.359 | 26.931 | −1.350 | 1.00 | 60.65 | O |
| ATOM | 886 | N | VAL | A | 159 | 2.290 | 26.694 | −3.388 | 1.00 | 62.86 | N |
| ATOM | 887 | CA | VAL | A | 159 | 1.033 | 26.775 | −4.122 | 1.00 | 63.91 | C |
| ATOM | 888 | CB | VAL | A | 159 | 0.758 | 28.237 | −4.619 | 1.00 | 62.39 | C |
| ATOM | 889 | CG1 | VAL | A | 159 | −0.184 | 28.276 | −5.818 | 1.00 | 61.38 | C |
| ATOM | 890 | CG2 | VAL | A | 159 | 0.211 | 29.098 | −3.474 | 1.00 | 65.00 | C |
| ATOM | 891 | C | VAL | A | 159 | 1.119 | 25.771 | −5.271 | 1.00 | 60.80 | C |
| ATOM | 892 | O | VAL | A | 159 | 2.189 | 25.234 | −5.558 | 1.00 | 58.76 | O |
| ATOM | 893 | N | TYR | A | 160 | −0.006 | 25.494 | −5.910 | 1.00 | 62.31 | N |
| ATOM | 894 | CA | TYR | A | 160 | −0.004 | 24.563 | −7.022 | 1.00 | 62.15 | C |
| ATOM | 895 | CB | TYR | A | 160 | −0.613 | 23.239 | −6.585 | 1.00 | 63.25 | C |
| ATOM | 896 | CG | TYR | A | 160 | 0.103 | 22.654 | −5.393 | 1.00 | 65.40 | C |
| ATOM | 897 | CD1 | TYR | A | 160 | −0.421 | 22.771 | −4.115 | 1.00 | 62.84 | C |
| ATOM | 898 | CE1 | TYR | A | 160 | 0.247 | 22.231 | −3.015 | 1.00 | 68.16 | C |
| ATOM | 899 | CD2 | TYR | A | 160 | 1.318 | 22.002 | −5.547 | 1.00 | 63.13 | C |
| ATOM | 900 | CE2 | TYR | A | 160 | 1.986 | 21.458 | −4.467 | 1.00 | 66.36 | C |
| ATOM | 901 | CZ | TYR | A | 160 | 1.454 | 21.575 | −3.201 | 1.00 | 71.07 | C |
| ATOM | 902 | OH | TYR | A | 160 | 2.133 | 21.031 | −2.127 | 1.00 | 67.08 | O |
| ATOM | 903 | C | TYR | A | 160 | −0.713 | 25.133 | −8.240 | 1.00 | 58.69 | C |
| ATOM | 904 | O | TYR | A | 160 | −1.575 | 24.490 | −8.822 | 1.00 | 65.06 | O |
| ATOM | 905 | N | SER | A | 161 | −0.342 | 26.350 | −8.615 | 1.00 | 59.67 | N |
| ATOM | 906 | CA | SER | A | 161 | −0.844 | 26.962 | −9.836 | 1.00 | 61.50 | C |
| ATOM | 907 | CB | SER | A | 161 | −1.983 | 27.916 | −9.521 | 1.00 | 68.69 | C |
| ATOM | 908 | OG | SER | A | 161 | −1.477 | 29.100 | −8.931 | 1.00 | 70.11 | O |
| ATOM | 909 | C | SER | A | 161 | 0.267 | 27.758 | −10.486 | 1.00 | 62.83 | C |
| ATOM | 910 | O | SER | A | 161 | 1.244 | 28.117 | −9.835 | 1.00 | 67.08 | O |
| ATOM | 911 | N | ARG | A | 162 | 0.106 | 28.048 | −11.767 | 1.00 | 65.92 | N |
| ATOM | 912 | CA | ARG | A | 162 | 1.047 | 28.885 | −12.497 | 1.00 | 66.39 | C |
| ATOM | 913 | CB | ARG | A | 162 | 0.758 | 28.795 | −14.004 | 1.00 | 68.03 | C |
| ATOM | 914 | CG | ARG | A | 162 | 1.509 | 29.799 | −14.845 | 1.00 | 65.55 | C |
| ATOM | 915 | CD | ARG | A | 162 | 0.672 | 30.276 | −16.024 | 1.00 | 69.12 | C |
| ATOM | 916 | NE | ARG | A | 162 | 1.114 | 31.596 | −16.473 | 1.00 | 71.45 | N |
| ATOM | 917 | CZ | ARG | A | 162 | 0.317 | 32.654 | −16.593 | 1.00 | 68.81 | C |
| ATOM | 918 | NH1 | ARG | A | 162 | −0.976 | 32.543 | −16.316 | 1.00 | 61.94 | N |
| ATOM | 919 | NH2 | ARG | A | 162 | 0.814 | 33.820 | −16.999 | 1.00 | 67.09 | N |
| ATOM | 920 | C | ARG | A | 162 | 0.944 | 30.333 | −12.013 | 1.00 | 60.96 | C |
| ATOM | 921 | O | ARG | A | 162 | 1.595 | 31.234 | −12.538 | 1.00 | 66.32 | O |
| ATOM | 922 | N | ASP | A | 163 | 0.116 | 30.554 | −11.000 | 1.00 | 62.31 | N |
| ATOM | 923 | CA | ASP | A | 163 | −0.090 | 31.903 | −10.487 | 1.00 | 64.42 | C |
| ATOM | 924 | CB | ASP | A | 163 | −1.554 | 32.094 | −10.055 | 1.00 | 68.30 | C |
| ATOM | 925 | CG | ASP | A | 163 | −2.500 | 32.344 | −11.246 | 1.00 | 78.68 | C |
| ATOM | 926 | OD1 | ASP | A | 163 | −3.737 | 32.356 | −11.036 | 1.00 | 79.69 | O |
| ATOM | 927 | OD2 | ASP | A | 163 | −2.007 | 32.536 | −12.389 | 1.00 | 71.29 | O |
| ATOM | 928 | C | ASP | A | 163 | 0.890 | 32.261 | −9.354 | 1.00 | 63.28 | C |

TABLE 12-continued

Coordinates for pro MMP9(35-444 ΔFnII) (SEQ ID NO: 12) complex with Example 2

| ATOM | 929 | O | ASP | A | 163 | 0.757 | 33.294 | −8.698 | 1.00 | 59.58 | O |
|---|---|---|---|---|---|---|---|---|---|---|---|
| ATOM | 930 | N | ALA | A | 164 | 1.886 | 31.412 | −9.138 | 1.00 | 54.14 | N |
| ATOM | 931 | CA | ALA | A | 164 | 2.888 | 31.700 | −8.134 | 1.00 | 51.79 | C |
| ATOM | 932 | CB | ALA | A | 164 | 3.650 | 30.438 | −7.776 | 1.00 | 50.49 | C |
| ATOM | 933 | C | ALA | A | 164 | 3.838 | 32.808 | −8.604 | 1.00 | 55.68 | C |
| ATOM | 934 | O | ALA | A | 164 | 4.110 | 32.944 | −9.801 | 1.00 | 49.33 | O |
| ATOM | 935 | N | ASP | A | 165 | 4.319 | 33.610 | −7.655 | 1.00 | 55.23 | N |
| ATOM | 936 | CA | ASP | A | 165 | 5.347 | 34.615 | −7.933 | 1.00 | 55.28 | C |
| ATOM | 937 | CB | ASP | A | 165 | 5.639 | 35.452 | −6.687 | 1.00 | 51.88 | C |
| ATOM | 938 | CG | ASP | A | 165 | 4.381 | 35.971 | −6.020 | 1.00 | 50.57 | C |
| ATOM | 939 | OD1 | ASP | A | 165 | 4.337 | 35.977 | −4.777 | 1.00 | 51.31 | O |
| ATOM | 940 | OD2 | ASP | A | 165 | 3.432 | 36.361 | −6.727 | 1.00 | 52.39 | O |
| ATOM | 941 | C | ASP | A | 165 | 6.632 | 33.934 | −8.399 | 1.00 | 55.38 | C |
| ATOM | 942 | O | ASP | A | 165 | 7.375 | 34.462 | −9.239 | 1.00 | 51.18 | O |
| ATOM | 943 | N | ILE | A | 166 | 6.885 | 32.752 | −7.849 | 1.00 | 51.66 | N |
| ATOM | 944 | CA | ILE | A | 166 | 8.071 | 31.989 | −8.201 | 1.00 | 50.35 | C |
| ATOM | 945 | CB | ILE | A | 166 | 9.007 | 31.837 | −6.988 | 1.00 | 48.22 | C |
| ATOM | 946 | CG2 | ILE | A | 166 | 10.308 | 31.145 | −7.393 | 1.00 | 41.37 | C |
| ATOM | 947 | CG1 | ILE | A | 166 | 9.264 | 33.203 | −6.346 | 1.00 | 50.60 | C |
| ATOM | 948 | CD1 | ILE | A | 166 | 9.997 | 33.131 | −5.032 | 1.00 | 47.43 | C |
| ATOM | 949 | C | ILE | A | 166 | 7.730 | 30.600 | −8.709 | 1.00 | 46.18 | C |
| ATOM | 950 | O | ILE | A | 166 | 7.395 | 29.718 | −7.929 | 1.00 | 49.23 | O |
| ATOM | 951 | N | VAL | A | 167 | 7.831 | 30.398 | −10.015 | 1.00 | 49.37 | N |
| ATOM | 952 | CA | VAL | A | 167 | 7.687 | 29.057 | −10.583 | 1.00 | 48.82 | C |
| ATOM | 953 | CB | VAL | A | 167 | 7.080 | 29.106 | −11.989 | 1.00 | 47.51 | C |
| ATOM | 954 | CG1 | VAL | A | 167 | 7.039 | 27.711 | −12.586 | 1.00 | 44.72 | C |
| ATOM | 955 | CG2 | VAL | A | 167 | 5.685 | 29.721 | −11.922 | 1.00 | 52.98 | C |
| ATOM | 956 | C | VAL | A | 167 | 9.036 | 28.332 | −10.623 | 1.00 | 45.84 | C |
| ATOM | 957 | O | VAL | A | 167 | 10.023 | 28.886 | −11.089 | 1.00 | 48.16 | O |
| ATOM | 958 | N | ILE | A | 168 | 9.068 | 27.096 | −10.136 | 1.00 | 44.26 | N |
| ATOM | 959 | CA | ILE | A | 168 | 10.304 | 26.333 | −10.007 | 1.00 | 44.87 | C |
| ATOM | 960 | CB | ILE | A | 168 | 10.465 | 25.760 | −8.577 | 1.00 | 35.26 | C |
| ATOM | 961 | CG2 | ILE | A | 168 | 11.492 | 24.665 | −8.534 | 1.00 | 36.99 | C |
| ATOM | 962 | CG1 | ILE | A | 168 | 10.842 | 26.881 | −7.608 | 1.00 | 46.12 | C |
| ATOM | 963 | CD1 | ILE | A | 168 | 11.068 | 26.411 | −6.160 | 1.00 | 49.98 | C |
| ATOM | 964 | C | ILE | A | 168 | 10.296 | 25.196 | −11.015 | 1.00 | 50.66 | C |
| ATOM | 965 | O | ILE | A | 168 | 9.410 | 24.341 | −10.986 | 1.00 | 50.30 | O |
| ATOM | 966 | N | GLN | A | 169 | 11.291 | 25.173 | −11.897 | 1.00 | 50.08 | N |
| ATOM | 967 | CA | GLN | A | 169 | 11.284 | 24.211 | −12.995 | 1.00 | 53.72 | C |
| ATOM | 968 | CB | GLN | A | 169 | 10.750 | 24.882 | −14.265 | 1.00 | 46.79 | C |
| ATOM | 969 | CG | GLN | A | 169 | 10.689 | 23.991 | −15.480 | 1.00 | 64.45 | C |
| ATOM | 970 | CD | GLN | A | 169 | 10.465 | 24.772 | −16.777 | 1.00 | 59.89 | C |
| ATOM | 971 | OE1 | GLN | A | 169 | 10.985 | 24.401 | −17.845 | 1.00 | 49.02 | O |
| ATOM | 972 | NE2 | GLN | A | 169 | 9.703 | 25.867 | −16.682 | 1.00 | 49.76 | N |
| ATOM | 973 | C | GLN | A | 169 | 12.652 | 23.570 | −13.233 | 1.00 | 56.08 | C |
| ATOM | 974 | O | GLN | A | 169 | 13.702 | 24.217 | −13.117 | 1.00 | 55.18 | O |
| ATOM | 975 | N | PHE | A | 170 | 12.641 | 22.282 | −13.548 | 1.00 | 59.25 | N |
| ATOM | 976 | CA | PHE | A | 170 | 13.869 | 21.614 | −13.962 | 1.00 | 62.40 | C |
| ATOM | 977 | CB | PHE | A | 170 | 13.971 | 20.214 | −13.346 | 1.00 | 61.44 | C |
| ATOM | 978 | CG | PHE | A | 170 | 14.337 | 20.221 | −11.883 | 1.00 | 54.84 | C |
| ATOM | 979 | CD1 | PHE | A | 170 | 13.368 | 20.400 | −10.911 | 1.00 | 61.39 | C |
| ATOM | 980 | CD2 | PHE | A | 170 | 15.649 | 20.053 | −11.484 | 1.00 | 55.53 | C |
| ATOM | 981 | CE1 | PHE | A | 170 | 13.703 | 20.404 | −9.557 | 1.00 | 58.71 | C |
| ATOM | 982 | CE2 | PHE | A | 170 | 15.993 | 20.059 | −10.138 | 1.00 | 56.87 | C |
| ATOM | 983 | CZ | PHE | A | 170 | 15.015 | 20.234 | −9.174 | 1.00 | 51.70 | C |
| ATOM | 984 | C | PHE | A | 170 | 13.924 | 21.569 | −15.485 | 1.00 | 55.03 | C |
| ATOM | 985 | O | PHE | A | 170 | 12.983 | 21.109 | −16.119 | 1.00 | 64.02 | O |
| ATOM | 986 | N | GLY | A | 171 | 15.020 | 22.071 | −16.049 | 1.00 | 54.40 | N |
| ATOM | 987 | CA | GLY | A | 171 | 15.187 | 22.244 | −17.484 | 1.00 | 55.97 | C |
| ATOM | 988 | C | GLY | A | 171 | 16.429 | 21.561 | −18.042 | 1.00 | 60.39 | C |
| ATOM | 989 | O | GLY | A | 171 | 17.487 | 21.515 | −17.402 | 1.00 | 53.11 | O |
| ATOM | 990 | N | VAL | A | 172 | 16.298 | 21.041 | −19.257 | 1.00 | 58.51 | N |
| ATOM | 991 | CA | VAL | A | 172 | 17.267 | 20.098 | −19.785 | 1.00 | 59.94 | C |
| ATOM | 992 | CB | VAL | A | 172 | 16.546 | 18.809 | −20.296 | 1.00 | 61.75 | C |
| ATOM | 993 | CG1 | VAL | A | 172 | 15.878 | 19.052 | −21.640 | 1.00 | 65.46 | C |
| ATOM | 994 | CG2 | VAL | A | 172 | 17.494 | 17.614 | −20.351 | 1.00 | 58.11 | C |
| ATOM | 995 | C | VAL | A | 172 | 18.202 | 20.734 | −20.838 | 1.00 | 65.80 | C |
| ATOM | 996 | O | VAL | A | 172 | 19.381 | 20.358 | −20.936 | 1.00 | 66.45 | O |
| ATOM | 997 | N | ALA | A | 173 | 17.698 | 21.708 | −21.598 | 1.00 | 56.07 | N |
| ATOM | 998 | CA | ALA | A | 173 | 18.553 | 22.465 | −22.520 | 1.00 | 58.21 | C |
| ATOM | 999 | CB | ALA | A | 173 | 18.967 | 21.603 | −23.695 | 1.00 | 63.37 | C |
| ATOM | 1000 | C | ALA | A | 173 | 17.858 | 23.742 | −23.000 | 1.00 | 58.73 | C |
| ATOM | 1001 | O | ALA | A | 173 | 17.923 | 24.769 | −22.338 | 1.00 | 58.63 | O |
| ATOM | 1002 | N | GLU | A | 174 | 17.209 | 23.694 | −24.156 | 1.00 | 56.78 | N |
| ATOM | 1003 | CA | GLU | A | 174 | 16.247 | 24.739 | −24.484 | 1.00 | 58.60 | C |
| ATOM | 1004 | CB | GLU | A | 174 | 15.962 | 24.808 | −25.989 | 1.00 | 58.47 | C |
| ATOM | 1005 | CG | GLU | A | 174 | 17.176 | 25.064 | −26.864 | 1.00 | 57.98 | C |

TABLE 12-continued

Coordinates for pro MMP9(35-444 ΔFnII) (SEQ ID NO: 12) complex with Example 2

| ATOM | 1006 | CD  | GLU | A | 174 | 17.883 | 23.774 | −27.249 | 1.00 | 61.53 | C |
| --- | --- | --- | --- | --- | --- | --- | --- | --- | --- | --- | --- |
| ATOM | 1007 | OE1 | GLU | A | 174 | 19.101 | 23.818 | −27.554 | 1.00 | 53.03 | O |
| ATOM | 1008 | OE2 | GLU | A | 174 | 17.210 | 22.715 | −27.247 | 1.00 | 61.26 | O |
| ATOM | 1009 | C   | GLU | A | 174 | 14.980 | 24.374 | −23.728 | 1.00 | 59.08 | C |
| ATOM | 1010 | O   | GLU | A | 174 | 14.461 | 23.267 | −23.899 | 1.00 | 60.24 | O |
| ATOM | 1011 | N   | HIS | A | 175 | 14.485 | 25.279 | −22.885 | 1.00 | 56.10 | N |
| ATOM | 1012 | CA  | HIS | A | 175 | 13.386 | 24.912 | −21.984 | 1.00 | 54.26 | C |
| ATOM | 1013 | CB  | HIS | A | 175 | 13.923 | 24.495 | −20.603 | 1.00 | 56.94 | C |
| ATOM | 1014 | CG  | HIS | A | 175 | 14.908 | 25.455 | −20.011 | 1.00 | 56.06 | C |
| ATOM | 1015 | CD2 | HIS | A | 175 | 14.922 | 26.102 | −18.820 | 1.00 | 57.78 | C |
| ATOM | 1016 | ND1 | HIS | A | 175 | 16.074 | 25.814 | −20.653 | 1.00 | 56.52 | N |
| ATOM | 1017 | CE1 | HIS | A | 175 | 16.760 | 26.645 | −19.887 | 1.00 | 53.82 | C |
| ATOM | 1018 | NE2 | HIS | A | 175 | 16.084 | 26.834 | −18.769 | 1.00 | 52.52 | N |
| ATOM | 1019 | C   | HIS | A | 175 | 12.273 | 25.945 | −21.833 | 1.00 | 53.30 | C |
| ATOM | 1020 | O   | HIS | A | 175 | 11.758 | 26.165 | −20.737 | 1.00 | 52.33 | O |
| ATOM | 1021 | N   | GLY | A | 176 | 11.886 | 26.565 | −22.940 | 1.00 | 59.44 | N |
| ATOM | 1022 | CA  | GLY | A | 176 | 10.732 | 27.439 | −22.933 | 1.00 | 57.49 | C |
| ATOM | 1023 | C   | GLY | A | 176 | 11.028 | 28.874 | −22.563 | 1.00 | 57.21 | C |
| ATOM | 1024 | O   | GLY | A | 176 | 10.099 | 29.659 | −22.348 | 1.00 | 46.99 | O |
| ATOM | 1025 | N   | ASP | A | 177 | 12.318 | 29.202 | −22.463 | 1.00 | 55.71 | N |
| ATOM | 1026 | CA  | ASP | A | 177 | 12.781 | 30.594 | −22.355 | 1.00 | 49.16 | C |
| ATOM | 1027 | CB  | ASP | A | 177 | 12.958 | 31.049 | −20.901 | 1.00 | 53.35 | C |
| ATOM | 1028 | CG  | ASP | A | 177 | 14.239 | 30.511 | −20.254 | 1.00 | 59.24 | C |
| ATOM | 1029 | OD1 | ASP | A | 177 | 15.041 | 29.832 | −20.952 | 1.00 | 56.28 | O |
| ATOM | 1030 | OD2 | ASP | A | 177 | 14.443 | 30.785 | −19.037 | 1.00 | 55.75 | O |
| ATOM | 1031 | C   | ASP | A | 177 | 14.078 | 30.760 | −23.137 | 1.00 | 54.31 | C |
| ATOM | 1032 | O   | ASP | A | 177 | 14.553 | 29.804 | −23.776 | 1.00 | 49.71 | O |
| ATOM | 1033 | N   | GLY | A | 178 | 14.651 | 31.963 | −23.069 | 1.00 | 53.23 | N |
| ATOM | 1034 | CA  | GLY | A | 178 | 15.790 | 32.332 | −23.901 | 1.00 | 53.76 | C |
| ATOM | 1035 | C   | GLY | A | 178 | 17.185 | 31.993 | −23.391 | 1.00 | 51.89 | C |
| ATOM | 1036 | O   | GLY | A | 178 | 18.190 | 32.474 | −23.923 | 1.00 | 51.16 | O |
| ATOM | 1037 | N   | TYR | A | 179 | 17.254 | 31.149 | −22.369 | 1.00 | 54.02 | N |
| ATOM | 1038 | CA  | TYR | A | 179 | 18.527 | 30.874 | −21.715 | 1.00 | 54.93 | C |
| ATOM | 1039 | CB  | TYR | A | 179 | 18.624 | 31.689 | −20.427 | 1.00 | 50.33 | C |
| ATOM | 1040 | CG  | TYR | A | 179 | 18.518 | 33.183 | −20.654 | 1.00 | 48.16 | C |
| ATOM | 1041 | CD1 | TYR | A | 179 | 17.292 | 33.834 | −20.634 | 1.00 | 44.22 | C |
| ATOM | 1042 | CE1 | TYR | A | 179 | 17.208 | 35.217 | −20.836 | 1.00 | 46.44 | C |
| ATOM | 1043 | CD2 | TYR | A | 179 | 19.657 | 33.940 | −20.901 | 1.00 | 51.78 | C |
| ATOM | 1044 | CE2 | TYR | A | 179 | 19.589 | 35.315 | −21.106 | 1.00 | 48.83 | C |
| ATOM | 1045 | CZ  | TYR | A | 179 | 18.369 | 35.953 | −21.072 | 1.00 | 49.80 | C |
| ATOM | 1046 | OH  | TYR | A | 179 | 18.344 | 37.323 | −21.285 | 1.00 | 46.18 | O |
| ATOM | 1047 | C   | TYR | A | 179 | 18.686 | 29.373 | −21.452 | 1.00 | 57.76 | C |
| ATOM | 1048 | O   | TYR | A | 179 | 18.311 | 28.867 | −20.385 | 1.00 | 49.73 | O |
| ATOM | 1049 | N   | PRO | A | 180 | 19.255 | 28.662 | −22.436 | 1.00 | 52.97 | N |
| ATOM | 1050 | CD  | PRO | A | 180 | 20.033 | 29.239 | −23.544 | 1.00 | 46.49 | C |
| ATOM | 1051 | CA  | PRO | A | 180 | 19.266 | 27.202 | −22.465 | 1.00 | 47.45 | C |
| ATOM | 1052 | CB  | PRO | A | 180 | 19.731 | 26.886 | −23.896 | 1.00 | 53.37 | C |
| ATOM | 1053 | CG  | PRO | A | 180 | 19.863 | 28.224 | −24.606 | 1.00 | 47.28 | C |
| ATOM | 1054 | C   | PRO | A | 180 | 20.314 | 26.714 | −21.509 | 1.00 | 46.35 | C |
| ATOM | 1055 | O   | PRO | A | 180 | 21.287 | 27.442 | −21.343 | 1.00 | 49.14 | O |
| ATOM | 1056 | N   | PHE | A | 181 | 20.136 | 25.540 | −20.900 | 1.00 | 46.81 | N |
| ATOM | 1057 | CA  | PHE | A | 181 | 21.193 | 24.946 | −20.082 | 1.00 | 47.61 | C |
| ATOM | 1058 | CB  | PHE | A | 181 | 20.636 | 24.069 | −18.954 | 1.00 | 47.78 | C |
| ATOM | 1059 | CG  | PHE | A | 181 | 19.750 | 24.816 | −17.997 | 1.00 | 48.71 | C |
| ATOM | 1060 | CD1 | PHE | A | 181 | 20.162 | 26.015 | −17.453 | 1.00 | 47.19 | C |
| ATOM | 1061 | CD2 | PHE | A | 181 | 18.503 | 24.324 | −17.655 | 1.00 | 55.33 | C |
| ATOM | 1062 | CE1 | PHE | A | 181 | 19.347 | 26.711 | −16.590 | 1.00 | 52.30 | C |
| ATOM | 1063 | CE2 | PHE | A | 181 | 17.677 | 25.016 | −16.790 | 1.00 | 55.32 | C |
| ATOM | 1064 | CZ  | PHE | A | 181 | 18.099 | 26.213 | −16.258 | 1.00 | 54.58 | C |
| ATOM | 1065 | C   | PHE | A | 181 | 22.165 | 24.179 | −20.974 | 1.00 | 51.29 | C |
| ATOM | 1066 | O   | PHE | A | 181 | 21.806 | 23.716 | −22.057 | 1.00 | 46.73 | O |
| ATOM | 1067 | N   | ASP | A | 182 | 23.400 | 24.054 | −20.510 | 1.00 | 51.87 | N |
| ATOM | 1068 | CA  | ASP | A | 182 | 24.493 | 23.716 | −21.404 | 1.00 | 52.12 | C |
| ATOM | 1069 | CB  | ASP | A | 182 | 25.698 | 24.611 | −21.095 | 1.00 | 45.01 | C |
| ATOM | 1070 | CG  | ASP | A | 182 | 26.265 | 24.369 | −19.709 | 1.00 | 54.41 | C |
| ATOM | 1071 | OD1 | ASP | A | 182 | 25.716 | 23.521 | −18.966 | 1.00 | 51.77 | O |
| ATOM | 1072 | OD2 | ASP | A | 182 | 27.271 | 25.025 | −19.372 | 1.00 | 49.48 | O |
| ATOM | 1073 | C   | ASP | A | 182 | 24.890 | 22.238 | −21.402 | 1.00 | 52.35 | C |
| ATOM | 1074 | O   | ASP | A | 182 | 25.909 | 21.869 | −21.980 | 1.00 | 54.14 | O |
| ATOM | 1075 | N   | GLY | A | 183 | 24.082 | 21.389 | −20.782 | 1.00 | 48.83 | N |
| ATOM | 1076 | CA  | GLY | A | 183 | 24.471 | 20.007 | −20.612 | 1.00 | 47.30 | C |
| ATOM | 1077 | C   | GLY | A | 183 | 25.030 | 19.784 | −19.218 | 1.00 | 56.45 | C |
| ATOM | 1078 | O   | GLY | A | 183 | 24.578 | 20.389 | −18.248 | 1.00 | 58.00 | O |
| ATOM | 1079 | N   | LYS | A | 184 | 26.019 | 18.913 | −19.102 | 1.00 | 48.37 | N |
| ATOM | 1080 | CA  | LYS | A | 184 | 26.504 | 18.527 | −17.779 | 1.00 | 59.51 | C |
| ATOM | 1081 | CB  | LYS | A | 184 | 26.891 | 17.044 | −17.775 | 1.00 | 57.49 | C |
| ATOM | 1082 | CG  | LYS | A | 184 | 27.575 | 16.579 | −16.506 | 1.00 | 58.19 | C |

TABLE 12-continued

Coordinates for pro MMP9(35-444 ΔFnII) (SEQ ID NO: 12) complex with Example 2

| ATOM | 1083 | CD  | LYS | A | 184 | 28.083 | 15.157 | −16.684 | 1.00 | 63.70 | C |
|------|------|-----|-----|---|-----|--------|--------|---------|------|-------|---|
| ATOM | 1084 | CE  | LYS | A | 184 | 29.148 | 14.783 | −15.648 | 1.00 | 65.63 | C |
| ATOM | 1085 | NZ  | LYS | A | 184 | 28.581 | 14.438 | −14.298 | 1.00 | 63.05 | N |
| ATOM | 1086 | C   | LYS | A | 184 | 27.670 | 19.386 | −17.272 | 1.00 | 57.03 | C |
| ATOM | 1087 | O   | LYS | A | 184 | 28.541 | 19.780 | −18.037 | 1.00 | 63.33 | O |
| ATOM | 1088 | N   | ASP | A | 185 | 27.669 | 19.675 | −15.978 | 1.00 | 59.84 | N |
| ATOM | 1089 | CA  | ASP | A | 185 | 28.799 | 20.343 | −15.317 | 1.00 | 63.87 | C |
| ATOM | 1090 | CB  | ASP | A | 185 | 30.119 | 19.620 | −15.622 | 1.00 | 61.03 | C |
| ATOM | 1091 | CG  | ASP | A | 185 | 30.367 | 18.439 | −14.707 | 1.00 | 63.09 | C |
| ATOM | 1092 | OD1 | ASP | A | 185 | 30.080 | 18.556 | −13.492 | 1.00 | 64.82 | O |
| ATOM | 1093 | OD2 | ASP | A | 185 | 30.860 | 17.396 | −15.206 | 1.00 | 57.74 | O |
| ATOM | 1094 | C   | ASP | A | 185 | 28.987 | 21.837 | −15.598 | 1.00 | 59.82 | C |
| ATOM | 1095 | O   | ASP | A | 185 | 29.849 | 22.466 | −14.986 | 1.00 | 63.67 | O |
| ATOM | 1096 | N   | GLY | A | 186 | 28.217 | 22.408 | −16.515 | 1.00 | 52.41 | N |
| ATOM | 1097 | CA  | GLY | A | 186 | 28.471 | 23.783 | −16.907 | 1.00 | 53.95 | C |
| ATOM | 1098 | C   | GLY | A | 186 | 27.817 | 24.797 | −15.992 | 1.00 | 50.83 | C |
| ATOM | 1099 | O   | GLY | A | 186 | 28.177 | 24.949 | −14.837 | 1.00 | 50.90 | O |
| ATOM | 1100 | N   | LEU | A | 187 | 26.859 | 25.530 | −16.522 | 1.00 | 47.72 | N |
| ATOM | 1101 | CA  | LEU | A | 187 | 26.072 | 26.384 | −15.676 | 1.00 | 52.35 | C |
| ATOM | 1102 | CB  | LEU | A | 187 | 25.600 | 27.634 | −16.431 | 1.00 | 53.00 | C |
| ATOM | 1103 | CG  | LEU | A | 187 | 24.775 | 27.624 | −17.718 | 1.00 | 45.22 | C |
| ATOM | 1104 | CD1 | LEU | A | 187 | 23.292 | 27.677 | −17.413 | 1.00 | 50.82 | C |
| ATOM | 1105 | CD2 | LEU | A | 187 | 25.183 | 28.833 | −18.553 | 1.00 | 45.36 | C |
| ATOM | 1106 | C   | LEU | A | 187 | 24.922 | 25.529 | −15.162 | 1.00 | 56.71 | C |
| ATOM | 1107 | O   | LEU | A | 187 | 24.288 | 24.805 | −15.934 | 1.00 | 53.21 | O |
| ATOM | 1108 | N   | LEU | A | 188 | 24.672 | 25.611 | −13.857 | 1.00 | 52.34 | N |
| ATOM | 1109 | CA  | LEU | A | 188 | 23.799 | 24.667 | −13.160 | 1.00 | 54.15 | C |
| ATOM | 1110 | CB  | LEU | A | 188 | 24.305 | 24.446 | −11.725 | 1.00 | 51.02 | C |
| ATOM | 1111 | CG  | LEU | A | 188 | 25.794 | 24.155 | −11.523 | 1.00 | 54.04 | C |
| ATOM | 1112 | CD1 | LEU | A | 188 | 26.560 | 25.421 | −11.723 | 1.00 | 54.79 | C |
| ATOM | 1113 | CD2 | LEU | A | 188 | 26.084 | 23.617 | −10.124 | 1.00 | 51.54 | C |
| ATOM | 1114 | C   | LEU | A | 188 | 22.331 | 25.098 | −13.112 | 1.00 | 51.19 | C |
| ATOM | 1115 | O   | LEU | A | 188 | 21.432 | 24.261 | −12.963 | 1.00 | 49.46 | O |
| ATOM | 1116 | N   | ALA | A | 189 | 22.101 | 26.404 | −13.207 | 1.00 | 47.21 | N |
| ATOM | 1117 | CA  | ALA | A | 189 | 20.765 | 26.961 | −13.054 | 1.00 | 45.26 | C |
| ATOM | 1118 | CB  | ALA | A | 189 | 20.189 | 26.541 | −11.731 | 1.00 | 47.46 | C |
| ATOM | 1119 | C   | ALA | A | 189 | 20.786 | 28.480 | −13.155 | 1.00 | 46.31 | C |
| ATOM | 1120 | O   | ALA | A | 189 | 21.849 | 29.100 | −13.154 | 1.00 | 46.78 | O |
| ATOM | 1121 | N   | HIS | A | 190 | 19.602 | 29.071 | −13.245 | 1.00 | 47.54 | N |
| ATOM | 1122 | CA  | HIS | A | 190 | 19.457 | 30.518 | −13.284 | 1.00 | 45.40 | C |
| ATOM | 1123 | CB  | HIS | A | 190 | 19.669 | 31.035 | −14.686 | 1.00 | 46.58 | C |
| ATOM | 1124 | CG  | HIS | A | 190 | 18.770 | 30.395 | −15.689 | 1.00 | 48.95 | C |
| ATOM | 1125 | CD2 | HIS | A | 190 | 17.471 | 30.020 | −15.602 | 1.00 | 46.62 | C |
| ATOM | 1126 | ND1 | HIS | A | 190 | 19.197 | 30.024 | −16.945 | 1.00 | 50.60 | N |
| ATOM | 1127 | CE1 | HIS | A | 190 | 18.191 | 29.476 | −17.601 | 1.00 | 54.86 | C |
| ATOM | 1128 | NE2 | HIS | A | 190 | 17.136 | 29.451 | −16.804 | 1.00 | 53.33 | N |
| ATOM | 1129 | C   | HIS | A | 190 | 18.046 | 30.861 | −12.876 | 1.00 | 45.60 | C |
| ATOM | 1130 | O   | HIS | A | 190 | 17.288 | 29.981 | −12.458 | 1.00 | 40.73 | O |
| ATOM | 1131 | N   | ALA | A | 191 | 17.685 | 32.132 | −13.056 | 1.00 | 45.00 | N |
| ATOM | 1132 | CA  | ALA | A | 191 | 16.467 | 32.680 | −12.467 | 1.00 | 45.71 | C |
| ATOM | 1133 | CB  | ALA | A | 191 | 16.546 | 32.557 | −10.941 | 1.00 | 44.61 | C |
| ATOM | 1134 | C   | ALA | A | 191 | 16.281 | 34.147 | −12.857 | 1.00 | 47.09 | C |
| ATOM | 1135 | O   | ALA | A | 191 | 17.248 | 34.884 | −12.943 | 1.00 | 52.05 | O |
| ATOM | 1136 | N   | PHE | A | 192 | 15.041 | 34.577 | −13.074 | 1.00 | 47.51 | N |
| ATOM | 1137 | CA  | PHE | A | 192 | 14.765 | 35.977 | −13.398 | 1.00 | 46.69 | C |
| ATOM | 1138 | CB  | PHE | A | 192 | 13.613 | 36.088 | −14.418 | 1.00 | 50.27 | C |
| ATOM | 1139 | CG  | PHE | A | 192 | 13.759 | 35.208 | −15.646 | 1.00 | 44.25 | C |
| ATOM | 1140 | CD1 | PHE | A | 192 | 14.260 | 35.719 | −16.827 | 1.00 | 49.72 | C |
| ATOM | 1141 | CD2 | PHE | A | 192 | 13.346 | 33.890 | −15.627 | 1.00 | 48.08 | C |
| ATOM | 1142 | CE1 | PHE | A | 192 | 14.381 | 34.925 | −17.957 | 1.00 | 48.94 | C |
| ATOM | 1143 | CE2 | PHE | A | 192 | 13.460 | 33.097 | −16.756 | 1.00 | 51.61 | C |
| ATOM | 1144 | CZ  | PHE | A | 192 | 13.980 | 33.615 | −17.922 | 1.00 | 45.92 | C |
| ATOM | 1145 | C   | PHE | A | 192 | 14.420 | 36.817 | −12.135 | 1.00 | 52.44 | C |
| ATOM | 1146 | O   | PHE | A | 192 | 14.043 | 36.278 | −11.082 | 1.00 | 50.67 | O |
| ATOM | 1147 | N   | PRO | A | 193 | 14.522 | 38.149 | −12.245 | 1.00 | 51.08 | N |
| ATOM | 1148 | CD  | PRO | A | 193 | 14.872 | 38.912 | −13.453 | 1.00 | 50.04 | C |
| ATOM | 1149 | CA  | PRO | A | 193 | 14.186 | 39.030 | −11.117 | 1.00 | 53.51 | C |
| ATOM | 1150 | CB  | PRO | A | 193 | 14.710 | 40.407 | −11.572 | 1.00 | 54.61 | C |
| ATOM | 1151 | CG  | PRO | A | 193 | 15.401 | 40.185 | −12.887 | 1.00 | 53.64 | C |
| ATOM | 1152 | C   | PRO | A | 193 | 12.677 | 39.128 | −10.898 | 1.00 | 53.09 | C |
| ATOM | 1153 | O   | PRO | A | 193 | 11.922 | 38.822 | −11.822 | 1.00 | 50.49 | O |
| ATOM | 1154 | N   | PRO | A | 194 | 12.247 | 39.574 | −9.698  | 1.00 | 59.93 | N |
| ATOM | 1155 | CD  | PRO | A | 194 | 13.170 | 39.901 | −8.593  | 1.00 | 52.43 | C |
| ATOM | 1156 | CA  | PRO | A | 194 | 10.833 | 39.787 | −9.317  | 1.00 | 53.62 | C |
| ATOM | 1157 | CB  | PRO | A | 194 | 10.939 | 40.606 | −8.027  | 1.00 | 52.94 | C |
| ATOM | 1158 | CG  | PRO | A | 194 | 12.247 | 40.200 | −7.430  | 1.00 | 48.93 | C |
| ATOM | 1159 | C   | PRO | A | 194 | 10.025 | 40.573 | −10.346 | 1.00 | 54.51 | C |

TABLE 12-continued

Coordinates for pro MMP9(35-444 ΔFnII) (SEQ ID NO: 12) complex with Example 2

| | | | | | | | | | | |
|---|---|---|---|---|---|---|---|---|---|---|
| ATOM | 1160 | O | PRO | A | 194 | 10.471 | 41.603 | −10.853 | 1.00 | 57.29 | O |
| ATOM | 1161 | N | GLY | A | 195 | 8.822 | 40.094 | −10.637 | 1.00 | 56.71 | N |
| ATOM | 1162 | CA | GLY | A | 195 | 7.976 | 40.747 | −11.617 | 1.00 | 55.75 | C |
| ATOM | 1163 | C | GLY | A | 195 | 6.883 | 39.838 | −12.151 | 1.00 | 57.74 | C |
| ATOM | 1164 | O | GLY | A | 195 | 6.694 | 38.705 | −11.666 | 1.00 | 49.18 | O |
| ATOM | 1165 | N | PRO | A | 196 | 6.163 | 40.324 | −13.172 | 1.00 | 53.82 | N |
| ATOM | 1166 | CD | PRO | A | 196 | 6.644 | 41.395 | −14.058 | 1.00 | 52.78 | C |
| ATOM | 1167 | CA | PRO | A | 196 | 5.003 | 39.634 | −13.732 | 1.00 | 50.88 | C |
| ATOM | 1168 | CB | PRO | A | 196 | 4.398 | 40.673 | −14.682 | 1.00 | 58.96 | C |
| ATOM | 1169 | CG | PRO | A | 196 | 5.415 | 41.810 | −14.797 | 1.00 | 56.04 | C |
| ATOM | 1170 | C | PRO | A | 196 | 5.466 | 38.463 | −14.559 | 1.00 | 52.09 | C |
| ATOM | 1171 | O | PRO | A | 196 | 6.599 | 38.456 | −15.028 | 1.00 | 53.13 | O |
| ATOM | 1172 | N | GLY | A | 197 | 4.592 | 37.487 | −14.741 | 1.00 | 55.31 | N |
| ATOM | 1173 | CA | GLY | A | 197 | 4.855 | 36.410 | −15.666 | 1.00 | 47.45 | C |
| ATOM | 1174 | C | GLY | A | 197 | 6.042 | 35.601 | −15.239 | 1.00 | 46.08 | C |
| ATOM | 1175 | O | GLY | A | 197 | 6.044 | 35.058 | −14.157 | 1.00 | 47.42 | O |
| ATOM | 1176 | N | ILE | A | 198 | 7.050 | 35.531 | −16.101 | 1.00 | 53.53 | N |
| ATOM | 1177 | CA | ILE | A | 198 | 8.191 | 34.649 | −15.896 | 1.00 | 50.94 | C |
| ATOM | 1178 | CB | ILE | A | 198 | 8.972 | 34.432 | −17.229 | 1.00 | 51.79 | C |
| ATOM | 1179 | CG2 | ILE | A | 198 | 9.782 | 35.659 | −17.602 | 1.00 | 48.97 | C |
| ATOM | 1180 | CG1 | ILE | A | 198 | 9.866 | 33.199 | −17.147 | 1.00 | 50.21 | C |
| ATOM | 1181 | CD1 | ILE | A | 198 | 10.385 | 32.741 | −18.497 | 1.00 | 50.20 | C |
| ATOM | 1182 | C | ILE | A | 198 | 9.112 | 35.212 | −14.825 | 1.00 | 56.49 | C |
| ATOM | 1183 | O | ILE | A | 198 | 9.738 | 34.469 | −14.057 | 1.00 | 52.71 | O |
| ATOM | 1184 | N | GLN | A | 199 | 9.177 | 36.536 | −14.763 | 1.00 | 53.34 | N |
| ATOM | 1185 | CA | GLN | A | 199 | 10.068 | 37.181 | −13.819 | 1.00 | 54.53 | C |
| ATOM | 1186 | CB | GLN | A | 199 | 9.852 | 38.695 | −13.836 | 1.00 | 49.07 | C |
| ATOM | 1187 | CG | GLN | A | 199 | 10.472 | 39.351 | −15.062 | 1.00 | 47.73 | C |
| ATOM | 1188 | CD | GLN | A | 199 | 10.253 | 40.847 | −15.096 | 1.00 | 56.70 | C |
| ATOM | 1189 | OE1 | GLN | A | 199 | 10.307 | 41.522 | −14.062 | 1.00 | 60.68 | O |
| ATOM | 1190 | NE2 | GLN | A | 199 | 10.000 | 41.379 | −16.285 | 1.00 | 54.42 | N |
| ATOM | 1191 | C | GLN | A | 199 | 9.940 | 36.559 | −12.416 | 1.00 | 54.45 | C |
| ATOM | 1192 | O | GLN | A | 199 | 8.852 | 36.467 | −11.852 | 1.00 | 53.89 | O |
| ATOM | 1193 | N | GLY | A | 200 | 11.061 | 36.088 | −11.884 | 1.00 | 47.58 | N |
| ATOM | 1194 | CA | GLY | A | 200 | 11.063 | 35.445 | −10.585 | 1.00 | 50.84 | C |
| ATOM | 1195 | C | GLY | A | 200 | 11.093 | 33.925 | −10.596 | 1.00 | 44.43 | C |
| ATOM | 1196 | O | GLY | A | 200 | 11.155 | 33.288 | −9.551 | 1.00 | 50.23 | O |
| ATOM | 1197 | N | ASP | A | 201 | 11.020 | 33.325 | −11.767 | 1.00 | 45.65 | N |
| ATOM | 1198 | CA | ASP | A | 201 | 11.118 | 31.875 | −11.849 | 1.00 | 49.03 | C |
| ATOM | 1199 | CB | ASP | A | 201 | 10.638 | 31.385 | −13.216 | 1.00 | 47.76 | C |
| ATOM | 1200 | CG | ASP | A | 201 | 9.190 | 31.731 | −13.479 | 1.00 | 53.40 | C |
| ATOM | 1201 | OD1 | ASP | A | 201 | 8.454 | 31.947 | −12.478 | 1.00 | 48.96 | O |
| ATOM | 1202 | OD2 | ASP | A | 201 | 8.799 | 31.792 | −14.682 | 1.00 | 47.36 | O |
| ATOM | 1203 | C | ASP | A | 201 | 12.556 | 31.414 | −11.614 | 1.00 | 45.75 | C |
| ATOM | 1204 | O | ASP | A | 201 | 13.511 | 32.178 | −11.791 | 1.00 | 44.25 | O |
| ATOM | 1205 | N | ALA | A | 202 | 12.707 | 30.156 | −11.234 | 1.00 | 42.74 | N |
| ATOM | 1206 | CA | ALA | A | 202 | 14.017 | 29.594 | −10.988 | 1.00 | 42.72 | C |
| ATOM | 1207 | CB | ALA | A | 202 | 14.258 | 29.447 | −9.495 | 1.00 | 37.57 | C |
| ATOM | 1208 | C | ALA | A | 202 | 14.130 | 28.260 | −11.700 | 1.00 | 44.82 | C |
| ATOM | 1209 | O | ALA | A | 202 | 13.297 | 27.372 | −11.509 | 1.00 | 45.90 | O |
| ATOM | 1210 | N | HIS | A | 203 | 15.161 | 28.127 | −12.527 | 1.00 | 46.40 | N |
| ATOM | 1211 | CA | HIS | A | 203 | 15.308 | 26.963 | −13.388 | 1.00 | 46.58 | C |
| ATOM | 1212 | CB | HIS | A | 203 | 15.354 | 27.385 | −14.859 | 1.00 | 47.68 | C |
| ATOM | 1213 | CG | HIS | A | 203 | 14.053 | 27.903 | −15.385 | 1.00 | 54.88 | C |
| ATOM | 1214 | CD2 | HIS | A | 203 | 12.775 | 27.673 | −14.996 | 1.00 | 52.76 | C |
| ATOM | 1215 | ND1 | HIS | A | 203 | 13.975 | 28.777 | −16.447 | 1.00 | 57.89 | N |
| ATOM | 1216 | CE1 | HIS | A | 203 | 12.711 | 29.065 | −16.694 | 1.00 | 52.94 | C |
| ATOM | 1217 | NE2 | HIS | A | 203 | 11.961 | 28.403 | −15.830 | 1.00 | 54.03 | N |
| ATOM | 1218 | C | HIS | A | 203 | 16.576 | 26.218 | −13.042 | 1.00 | 48.67 | C |
| ATOM | 1219 | O | HIS | A | 203 | 17.647 | 26.800 | −12.958 | 1.00 | 49.53 | O |
| ATOM | 1220 | N | PHE | A | 204 | 16.457 | 24.921 | −12.832 | 1.00 | 49.15 | N |
| ATOM | 1221 | CA | PHE | A | 204 | 17.631 | 24.132 | −12.528 | 1.00 | 48.68 | C |
| ATOM | 1222 | CB | PHE | A | 204 | 17.422 | 23.302 | −11.256 | 1.00 | 49.78 | C |
| ATOM | 1223 | CG | PHE | A | 204 | 17.237 | 24.137 | −10.022 | 1.00 | 49.48 | C |
| ATOM | 1224 | CD1 | PHE | A | 204 | 16.076 | 24.866 | −9.834 | 1.00 | 46.13 | C |
| ATOM | 1225 | CD2 | PHE | A | 204 | 18.224 | 24.197 | −9.063 | 1.00 | 47.08 | C |
| ATOM | 1226 | CE1 | PHE | A | 204 | 15.907 | 25.642 | −8.721 | 1.00 | 48.78 | C |
| ATOM | 1227 | CE2 | PHE | A | 204 | 18.051 | 24.959 | −7.932 | 1.00 | 52.47 | C |
| ATOM | 1228 | CZ | PHE | A | 204 | 16.891 | 25.685 | −7.760 | 1.00 | 52.90 | C |
| ATOM | 1229 | C | PHE | A | 204 | 17.854 | 23.223 | −13.696 | 1.00 | 54.17 | C |
| ATOM | 1230 | O | PHE | A | 204 | 16.895 | 22.763 | −14.313 | 1.00 | 57.28 | O |
| ATOM | 1231 | N | ASP | A | 205 | 19.117 | 22.958 | −13.995 | 1.00 | 52.18 | N |
| ATOM | 1232 | CA | ASP | A | 205 | 19.472 | 22.096 | −15.111 | 1.00 | 52.75 | C |
| ATOM | 1233 | CB | ASP | A | 205 | 20.793 | 22.557 | −15.707 | 1.00 | 49.26 | C |
| ATOM | 1234 | CG | ASP | A | 205 | 21.334 | 21.596 | −16.701 | 1.00 | 53.77 | C |
| ATOM | 1235 | OD1 | ASP | A | 205 | 20.547 | 20.771 | −17.227 | 1.00 | 55.06 | O |
| ATOM | 1236 | OD2 | ASP | A | 205 | 22.550 | 21.669 | −16.958 | 1.00 | 55.12 | O |

TABLE 12-continued

Coordinates for pro MMP9(35-444 ΔFnII) (SEQ ID NO: 12) complex with Example 2

| ATOM | 1237 | C | ASP | A | 205 | 19.576 | 20.644 | −14.662 | 1.00 | 52.89 | C |
|---|---|---|---|---|---|---|---|---|---|---|---|
| ATOM | 1238 | O | ASP | A | 205 | 20.451 | 20.299 | −13.867 | 1.00 | 48.54 | O |
| ATOM | 1239 | N | ASP | A | 206 | 18.687 | 19.803 | −15.190 | 1.00 | 53.62 | N |
| ATOM | 1240 | CA | ASP | A | 206 | 18.602 | 18.399 | −14.784 | 1.00 | 53.41 | C |
| ATOM | 1241 | CB | ASP | A | 206 | 17.168 | 17.869 | −14.940 | 1.00 | 52.21 | C |
| ATOM | 1242 | CG | ASP | A | 206 | 16.868 | 16.693 | −14.005 | 1.00 | 59.79 | C |
| ATOM | 1243 | OD1 | ASP | A | 206 | 17.792 | 16.239 | −13.280 | 1.00 | 55.02 | O |
| ATOM | 1244 | OD2 | ASP | A | 206 | 15.701 | 16.234 | −13.992 | 1.00 | 58.60 | O |
| ATOM | 1245 | C | ASP | A | 206 | 19.593 | 17.443 | −15.466 | 1.00 | 52.94 | C |
| ATOM | 1246 | O | ASP | A | 206 | 19.596 | 16.256 | −15.163 | 1.00 | 58.03 | O |
| ATOM | 1247 | N | ASP | A | 207 | 20.419 | 17.931 | −16.386 | 1.00 | 51.13 | N |
| ATOM | 1248 | CA | ASP | A | 207 | 21.557 | 17.126 | −16.835 | 1.00 | 52.04 | C |
| ATOM | 1249 | CB | ASP | A | 207 | 22.303 | 17.803 | −17.995 | 1.00 | 52.97 | C |
| ATOM | 1250 | CG | ASP | A | 207 | 21.490 | 17.823 | −19.305 | 1.00 | 56.40 | C |
| ATOM | 1251 | OD1 | ASP | A | 207 | 20.828 | 16.811 | −19.615 | 1.00 | 48.96 | O |
| ATOM | 1252 | OD2 | ASP | A | 207 | 21.526 | 18.850 | −20.029 | 1.00 | 53.87 | O |
| ATOM | 1253 | C | ASP | A | 207 | 22.501 | 16.894 | −15.640 | 1.00 | 56.25 | C |
| ATOM | 1254 | O | ASP | A | 207 | 23.274 | 15.935 | −15.611 | 1.00 | 55.10 | O |
| ATOM | 1255 | N | GLU | A | 208 | 22.403 | 17.765 | −14.637 | 1.00 | 54.18 | N |
| ATOM | 1256 | CA | GLU | A | 208 | 23.293 | 17.707 | −13.485 | 1.00 | 53.04 | C |
| ATOM | 1257 | CB | GLU | A | 208 | 23.225 | 19.012 | −12.716 | 1.00 | 54.88 | C |
| ATOM | 1258 | CG | GLU | A | 208 | 23.728 | 20.152 | −13.513 | 1.00 | 54.89 | C |
| ATOM | 1259 | CD | GLU | A | 208 | 25.110 | 19.873 | −14.046 | 1.00 | 54.46 | C |
| ATOM | 1260 | OE1 | GLU | A | 208 | 25.762 | 18.913 | −13.578 | 1.00 | 49.20 | O |
| ATOM | 1261 | OE2 | GLU | A | 208 | 25.542 | 20.618 | −14.931 | 1.00 | 56.58 | O |
| ATOM | 1262 | C | GLU | A | 208 | 22.995 | 16.576 | −12.535 | 1.00 | 51.63 | C |
| ATOM | 1263 | O | GLU | A | 208 | 22.000 | 15.883 | −12.681 | 1.00 | 58.04 | O |
| ATOM | 1264 | N | LEU | A | 209 | 23.866 | 16.405 | −11.549 | 1.00 | 50.40 | N |
| ATOM | 1265 | CA | LEU | A | 209 | 23.633 | 15.434 | −10.486 | 1.00 | 50.87 | C |
| ATOM | 1266 | CB | LEU | A | 209 | 24.855 | 14.548 | −10.287 | 1.00 | 51.43 | C |
| ATOM | 1267 | CG | LEU | A | 209 | 24.706 | 13.513 | −9.170 | 1.00 | 49.42 | C |
| ATOM | 1268 | CD1 | LEU | A | 209 | 23.547 | 12.569 | −9.459 | 1.00 | 39.99 | C |
| ATOM | 1269 | CD2 | LEU | A | 209 | 26.019 | 12.744 | −8.968 | 1.00 | 48.33 | C |
| ATOM | 1270 | C | LEU | A | 209 | 23.273 | 16.112 | −9.166 | 1.00 | 58.35 | C |
| ATOM | 1271 | O | LEU | A | 209 | 24.154 | 16.517 | −8.397 | 1.00 | 58.84 | O |
| ATOM | 1272 | N | TRP | A | 210 | 21.976 | 16.234 | −8.898 | 1.00 | 54.16 | N |
| ATOM | 1273 | CA | TRP | A | 210 | 21.538 | 16.883 | −7.668 | 1.00 | 53.85 | C |
| ATOM | 1274 | CB | TRP | A | 210 | 20.113 | 17.430 | −7.815 | 1.00 | 52.39 | C |
| ATOM | 1275 | CG | TRP | A | 210 | 20.022 | 18.458 | −8.861 | 1.00 | 51.73 | C |
| ATOM | 1276 | CD2 | TRP | A | 210 | 20.601 | 19.759 | −8.820 | 1.00 | 49.71 | C |
| ATOM | 1277 | CE2 | TRP | A | 210 | 20.303 | 20.390 | −10.041 | 1.00 | 53.20 | C |
| ATOM | 1278 | CE3 | TRP | A | 210 | 21.343 | 20.455 | −7.866 | 1.00 | 55.71 | C |
| ATOM | 1279 | CD1 | TRP | A | 210 | 19.411 | 18.346 | −10.077 | 1.00 | 59.25 | C |
| ATOM | 1280 | NE1 | TRP | A | 210 | 19.571 | 19.510 | −10.793 | 1.00 | 56.99 | N |
| ATOM | 1281 | CZ2 | TRP | A | 210 | 20.706 | 21.686 | −10.326 | 1.00 | 52.95 | C |
| ATOM | 1282 | CZ3 | TRP | A | 210 | 21.751 | 21.747 | −8.161 | 1.00 | 54.32 | C |
| ATOM | 1283 | CH2 | TRP | A | 210 | 21.433 | 22.342 | −9.380 | 1.00 | 47.47 | C |
| ATOM | 1284 | C | TRP | A | 210 | 21.604 | 15.926 | −6.491 | 1.00 | 55.36 | C |
| ATOM | 1285 | O | TRP | A | 210 | 20.939 | 14.889 | −6.484 | 1.00 | 58.86 | O |
| ATOM | 1286 | N | SER | A | 211 | 22.420 | 16.267 | −5.501 | 1.00 | 58.89 | N |
| ATOM | 1287 | CA | SER | A | 211 | 22.329 | 15.610 | −4.198 | 1.00 | 53.76 | C |
| ATOM | 1288 | CB | SER | A | 211 | 23.497 | 14.656 | −3.944 | 1.00 | 53.66 | C |
| ATOM | 1289 | OG | SER | A | 211 | 24.739 | 15.268 | −4.231 | 1.00 | 61.99 | O |
| ATOM | 1290 | C | SER | A | 211 | 22.274 | 16.681 | −3.134 | 1.00 | 55.16 | C |
| ATOM | 1291 | O | SER | A | 211 | 22.223 | 17.865 | −3.445 | 1.00 | 57.63 | O |
| ATOM | 1292 | N | LEU | A | 212 | 22.266 | 16.275 | −1.875 | 1.00 | 56.60 | N |
| ATOM | 1293 | CA | LEU | A | 212 | 22.243 | 17.253 | −0.810 | 1.00 | 54.90 | C |
| ATOM | 1294 | CB | LEU | A | 212 | 21.029 | 17.050 | 0.106 | 1.00 | 58.38 | C |
| ATOM | 1295 | CG | LEU | A | 212 | 19.683 | 17.481 | −0.500 | 1.00 | 58.24 | C |
| ATOM | 1296 | CD1 | LEU | A | 212 | 18.584 | 17.474 | 0.557 | 1.00 | 51.11 | C |
| ATOM | 1297 | CD2 | LEU | A | 212 | 19.755 | 18.861 | −1.163 | 1.00 | 48.49 | C |
| ATOM | 1298 | C | LEU | A | 212 | 23.549 | 17.260 | −0.031 | 1.00 | 53.64 | C |
| ATOM | 1299 | O | LEU | A | 212 | 23.873 | 18.259 | 0.618 | 1.00 | 56.42 | O |
| ATOM | 1300 | N | GLY | A | 213 | 24.315 | 16.169 | −0.123 | 1.00 | 52.37 | N |
| ATOM | 1301 | CA | GLY | A | 213 | 25.583 | 16.064 | 0.598 | 1.00 | 62.80 | C |
| ATOM | 1302 | C | GLY | A | 213 | 26.828 | 15.846 | −0.249 | 1.00 | 62.66 | C |
| ATOM | 1303 | O | GLY | A | 213 | 27.775 | 15.160 | 0.164 | 1.00 | 59.90 | O |
| ATOM | 1304 | O | ALA | A | 393 | 23.210 | 18.572 | −5.818 | 1.00 | 20.00 | O |
| ATOM | 1305 | N | ALA | A | 393 | 25.435 | 20.059 | −7.947 | 1.00 | 20.00 | N |
| ATOM | 1306 | CA | ALA | A | 393 | 25.149 | 18.932 | −7.088 | 1.00 | 20.00 | C |
| ATOM | 1307 | C | ALA | A | 393 | 24.211 | 19.225 | −5.924 | 1.00 | 20.00 | C |
| ATOM | 1308 | CB | ALA | A | 393 | 26.407 | 18.306 | −6.613 | 1.00 | 20.00 | C |
| ATOM | 1309 | N | SER | A | 394 | 24.505 | 20.173 | −5.043 | 1.00 | 45.74 | N |
| ATOM | 1310 | CA | SER | A | 394 | 23.603 | 20.483 | −3.916 | 1.00 | 51.63 | C |
| ATOM | 1311 | CB | SER | A | 394 | 24.337 | 21.279 | −2.871 | 1.00 | 45.02 | C |
| ATOM | 1312 | OG | SER | A | 394 | 23.524 | 21.451 | −1.753 | 1.00 | 48.07 | O |
| ATOM | 1313 | C | SER | A | 394 | 22.350 | 21.256 | −4.269 | 1.00 | 47.42 | C |

TABLE 12-continued

Coordinates for pro MMP9(35-444 ΔFnII) (SEQ ID NO: 12) complex with Example 2

| ATOM | 1314 | O | SER | A | 394 | 22.453 | 22.376 | −4.643 | 1.00 | 43.55 | O |
|---|---|---|---|---|---|---|---|---|---|---|---|
| ATOM | 1315 | N | LEU | A | 395 | 21.171 | 20.665 | −4.157 | 1.00 | 48.81 | N |
| ATOM | 1316 | CA | LEU | A | 395 | 19.953 | 21.315 | −4.618 | 1.00 | 49.07 | C |
| ATOM | 1317 | CB | LEU | A | 395 | 18.819 | 20.304 | −4.790 | 1.00 | 45.13 | C |
| ATOM | 1318 | CG | LEU | A | 395 | 17.497 | 20.934 | −5.220 | 1.00 | 51.30 | C |
| ATOM | 1319 | CD1 | LEU | A | 395 | 17.720 | 21.769 | −6.475 | 1.00 | 49.01 | C |
| ATOM | 1320 | CD2 | LEU | A | 395 | 16.420 | 19.877 | −5.446 | 1.00 | 52.96 | C |
| ATOM | 1321 | C | LEU | A | 395 | 19.584 | 22.389 | −3.607 | 1.00 | 48.37 | C |
| ATOM | 1322 | O | LEU | A | 395 | 18.940 | 23.383 | −3.931 | 1.00 | 47.35 | O |
| ATOM | 1323 | N | PHE | A | 396 | 20.031 | 22.184 | −2.376 | 1.00 | 45.96 | N |
| ATOM | 1324 | CA | PHE | A | 396 | 19.818 | 23.149 | −1.319 | 1.00 | 44.23 | C |
| ATOM | 1325 | CB | PHE | A | 396 | 20.205 | 22.540 | 0.025 | 1.00 | 44.30 | C |
| ATOM | 1326 | CG | PHE | A | 396 | 20.103 | 23.502 | 1.172 | 1.00 | 45.81 | C |
| ATOM | 1327 | CD1 | PHE | A | 396 | 18.946 | 24.253 | 1.355 | 1.00 | 38.27 | C |
| ATOM | 1328 | CD2 | PHE | A | 396 | 21.161 | 23.650 | 2.074 | 1.00 | 40.08 | C |
| ATOM | 1329 | CE1 | PHE | A | 396 | 18.841 | 25.135 | 2.398 | 1.00 | 38.81 | C |
| ATOM | 1330 | CE2 | PHE | A | 396 | 21.062 | 24.534 | 3.126 | 1.00 | 40.86 | C |
| ATOM | 1331 | CZ | PHE | A | 396 | 19.897 | 25.281 | 3.293 | 1.00 | 41.25 | C |
| ATOM | 1332 | C | PHE | A | 396 | 20.584 | 24.451 | −1.570 | 1.00 | 42.14 | C |
| ATOM | 1333 | O | PHE | A | 396 | 19.983 | 25.504 | −1.796 | 1.00 | 45.93 | O |
| ATOM | 1334 | N | LEU | A | 397 | 21.907 | 24.376 | −1.538 | 1.00 | 43.02 | N |
| ATOM | 1335 | CA | LEU | A | 397 | 22.741 | 25.567 | −1.695 | 1.00 | 43.37 | C |
| ATOM | 1336 | CB | LEU | A | 397 | 24.218 | 25.178 | −1.734 | 1.00 | 44.70 | C |
| ATOM | 1337 | CG | LEU | A | 397 | 24.781 | 24.463 | −0.511 | 1.00 | 45.60 | C |
| ATOM | 1338 | CD1 | LEU | A | 397 | 26.267 | 24.158 | −0.696 | 1.00 | 51.63 | C |
| ATOM | 1339 | CD2 | LEU | A | 397 | 24.547 | 25.316 | 0.715 | 1.00 | 41.22 | C |
| ATOM | 1340 | C | LEU | A | 397 | 22.386 | 26.324 | −2.962 | 1.00 | 39.74 | C |
| ATOM | 1341 | O | LEU | A | 397 | 22.189 | 27.535 | −2.933 | 1.00 | 35.91 | O |
| ATOM | 1342 | N | VAL | A | 398 | 22.334 | 25.604 | −4.085 | 1.00 | 43.48 | N |
| ATOM | 1343 | CA | VAL | A | 398 | 21.978 | 26.215 | −5.366 | 1.00 | 41.45 | C |
| ATOM | 1344 | CB | VAL | A | 398 | 21.921 | 25.192 | −6.513 | 1.00 | 45.15 | C |
| ATOM | 1345 | CG1 | VAL | A | 398 | 21.399 | 25.856 | −7.769 | 1.00 | 45.91 | C |
| ATOM | 1346 | CG2 | VAL | A | 398 | 23.300 | 24.586 | −6.769 | 1.00 | 45.64 | C |
| ATOM | 1347 | C | VAL | A | 398 | 20.636 | 26.944 | −5.284 | 1.00 | 42.18 | C |
| ATOM | 1348 | O | VAL | A | 398 | 20.541 | 28.116 | −5.630 | 1.00 | 44.42 | O |
| ATOM | 1349 | N | ALA | A | 399 | 19.609 | 26.248 | −4.815 | 1.00 | 37.38 | N |
| ATOM | 1350 | CA | ALA | A | 399 | 18.281 | 26.834 | −4.692 | 1.00 | 44.07 | C |
| ATOM | 1351 | CB | ALA | A | 399 | 17.328 | 25.842 | −4.060 | 1.00 | 43.49 | C |
| ATOM | 1352 | C | ALA | A | 399 | 18.285 | 28.135 | −3.895 | 1.00 | 44.78 | C |
| ATOM | 1353 | O | ALA | A | 399 | 17.612 | 29.105 | −4.259 | 1.00 | 41.31 | O |
| ATOM | 1354 | N | ALA | A | 400 | 19.034 | 28.151 | −2.798 | 1.00 | 40.10 | N |
| ATOM | 1355 | CA | ALA | A | 400 | 19.085 | 29.328 | −1.956 | 1.00 | 41.10 | C |
| ATOM | 1356 | CB | ALA | A | 400 | 19.949 | 29.074 | −0.724 | 1.00 | 40.45 | C |
| ATOM | 1357 | C | ALA | A | 400 | 19.618 | 30.498 | −2.769 | 1.00 | 43.50 | C |
| ATOM | 1358 | O | ALA | A | 400 | 19.033 | 31.587 | −2.775 | 1.00 | 46.11 | O |
| ATOM | 1359 | N | HIS | A | 401 | 20.712 | 30.252 | −3.484 | 1.00 | 40.98 | N |
| ATOM | 1360 | CA | HIS | A | 401 | 21.345 | 31.265 | −4.317 | 1.00 | 43.01 | C |
| ATOM | 1361 | CB | HIS | A | 401 | 22.617 | 30.675 | −4.909 | 1.00 | 38.92 | C |
| ATOM | 1362 | CG | HIS | A | 401 | 23.296 | 31.556 | −5.906 | 1.00 | 41.73 | C |
| ATOM | 1363 | CD2 | HIS | A | 401 | 23.076 | 31.728 | −7.235 | 1.00 | 44.23 | C |
| ATOM | 1364 | ND1 | HIS | A | 401 | 24.369 | 32.354 | −5.584 | 1.00 | 39.07 | N |
| ATOM | 1365 | CE1 | HIS | A | 401 | 24.765 | 33.005 | −6.663 | 1.00 | 46.09 | C |
| ATOM | 1366 | NE2 | HIS | A | 401 | 23.999 | 32.642 | −7.681 | 1.00 | 40.63 | N |
| ATOM | 1367 | C | HIS | A | 401 | 20.414 | 31.813 | −5.415 | 1.00 | 43.12 | C |
| ATOM | 1368 | O | HIS | A | 401 | 20.371 | 33.020 | −5.654 | 1.00 | 43.14 | O |
| ATOM | 1369 | N | GLU | A | 402 | 19.657 | 30.931 | −6.064 | 1.00 | 43.68 | N |
| ATOM | 1370 | CA | GLU | A | 402 | 18.701 | 31.349 | −7.104 | 1.00 | 47.19 | C |
| ATOM | 1371 | CB | GLU | A | 402 | 18.241 | 30.144 | −7.940 | 1.00 | 43.29 | C |
| ATOM | 1372 | CG | GLU | A | 402 | 19.382 | 29.302 | −8.525 | 1.00 | 40.69 | C |
| ATOM | 1373 | CD | GLU | A | 402 | 20.130 | 30.016 | −9.639 | 1.00 | 48.11 | C |
| ATOM | 1374 | OE1 | GLU | A | 402 | 21.122 | 29.450 | −10.170 | 1.00 | 40.42 | O |
| ATOM | 1375 | OE2 | GLU | A | 402 | 19.717 | 31.146 | −9.987 | 1.00 | 48.18 | O |
| ATOM | 1376 | C | GLU | A | 402 | 17.487 | 32.094 | −6.522 | 1.00 | 43.44 | C |
| ATOM | 1377 | O | GLU | A | 402 | 16.944 | 33.002 | −7.147 | 1.00 | 37.75 | O |
| ATOM | 1378 | N | PHE | A | 403 | 17.078 | 31.715 | −5.316 | 1.00 | 41.53 | N |
| ATOM | 1379 | CA | PHE | A | 403 | 15.947 | 32.360 | −4.680 | 1.00 | 39.12 | C |
| ATOM | 1380 | CB | PHE | A | 403 | 15.511 | 31.580 | −3.445 | 1.00 | 39.28 | C |
| ATOM | 1381 | CG | PHE | A | 403 | 14.961 | 30.224 | −3.752 | 1.00 | 39.09 | C |
| ATOM | 1382 | CD1 | PHE | A | 403 | 14.761 | 29.823 | −5.061 | 1.00 | 40.95 | C |
| ATOM | 1383 | CD2 | PHE | A | 403 | 14.629 | 29.346 | −2.727 | 1.00 | 47.14 | C |
| ATOM | 1384 | CE1 | PHE | A | 403 | 14.243 | 28.571 | −5.345 | 1.00 | 44.64 | C |
| ATOM | 1385 | CE2 | PHE | A | 403 | 14.111 | 28.081 | −2.996 | 1.00 | 45.88 | C |
| ATOM | 1386 | CZ | PHE | A | 403 | 13.921 | 27.692 | −4.299 | 1.00 | 48.91 | C |
| ATOM | 1387 | C | PHE | A | 403 | 16.338 | 33.784 | −4.324 | 1.00 | 45.90 | C |
| ATOM | 1388 | O | PHE | A | 403 | 15.514 | 34.705 | −4.379 | 1.00 | 43.30 | O |
| ATOM | 1389 | N | GLY | A | 404 | 17.610 | 33.961 | −3.969 | 1.00 | 46.50 | N |
| ATOM | 1390 | CA | GLY | A | 404 | 18.174 | 35.287 | −3.798 | 1.00 | 46.49 | C |

TABLE 12-continued

Coordinates for pro MMP9(35-444 ΔFnII) (SEQ ID NO: 12) complex with Example 2

| ATOM | 1391 | C   | GLY | A | 404 | 17.957 | 36.102 | −5.060  | 1.00 | 45.07 | C |
|------|------|-----|-----|---|-----|--------|--------|---------|------|-------|---|
| ATOM | 1392 | O   | GLY | A | 404 | 17.574 | 37.268 | −5.006  | 1.00 | 47.36 | O |
| ATOM | 1393 | N   | HIS | A | 405 | 18.189 | 35.478 | −6.205  | 1.00 | 44.78 | N |
| ATOM | 1394 | CA  | HIS | A | 405 | 17.898 | 36.112 | −7.491  | 1.00 | 45.23 | C |
| ATOM | 1395 | CB  | HIS | A | 405 | 18.324 | 35.209 | −8.642  | 1.00 | 40.84 | C |
| ATOM | 1396 | CG  | HIS | A | 405 | 19.786 | 35.249 | −8.932  | 1.00 | 44.94 | C |
| ATOM | 1397 | CD2 | HIS | A | 405 | 20.623 | 34.315 | −9.438  | 1.00 | 43.23 | C |
| ATOM | 1398 | ND1 | HIS | A | 405 | 20.553 | 36.375 | −8.718  | 1.00 | 48.52 | N |
| ATOM | 1399 | CE1 | HIS | A | 405 | 21.803 | 36.125 | −9.065  | 1.00 | 47.56 | C |
| ATOM | 1400 | NE2 | HIS | A | 405 | 21.872 | 34.883 | −9.510  | 1.00 | 45.91 | N |
| ATOM | 1401 | C   | HIS | A | 405 | 16.413 | 36.417 | −7.632  | 1.00 | 48.50 | C |
| ATOM | 1402 | O   | HIS | A | 405 | 16.034 | 37.504 | −8.079  | 1.00 | 48.44 | O |
| ATOM | 1403 | N   | ALA | A | 406 | 15.582 | 35.447 | −7.250  | 1.00 | 45.85 | N |
| ATOM | 1404 | CA  | ALA | A | 406 | 14.134 | 35.553 | −7.404  | 1.00 | 45.01 | C |
| ATOM | 1405 | CB  | ALA | A | 406 | 13.467 | 34.185 | −7.215  | 1.00 | 43.56 | C |
| ATOM | 1406 | C   | ALA | A | 406 | 13.543 | 36.570 | −6.444  | 1.00 | 48.01 | C |
| ATOM | 1407 | O   | ALA | A | 406 | 12.327 | 36.695 | −6.338  | 1.00 | 47.67 | O |
| ATOM | 1408 | N   | LEU | A | 407 | 14.406 | 37.282 | −5.728  | 1.00 | 49.18 | N |
| ATOM | 1409 | CA  | LEU | A | 407 | 13.942 | 38.343 | −4.843  | 1.00 | 45.44 | C |
| ATOM | 1410 | CB  | LEU | A | 407 | 14.226 | 38.001 | −3.379  | 1.00 | 44.39 | C |
| ATOM | 1411 | CG  | LEU | A | 407 | 13.660 | 36.654 | −2.927  | 1.00 | 44.73 | C |
| ATOM | 1412 | CD1 | LEU | A | 407 | 13.728 | 36.501 | −1.424  | 1.00 | 36.77 | C |
| ATOM | 1413 | CD2 | LEU | A | 407 | 12.243 | 36.500 | −3.383  | 1.00 | 47.55 | C |
| ATOM | 1414 | C   | LEU | A | 407 | 14.562 | 39.692 | −5.218  | 1.00 | 47.20 | C |
| ATOM | 1415 | O   | LEU | A | 407 | 14.140 | 40.718 | −4.713  | 1.00 | 52.35 | O |
| ATOM | 1416 | N   | GLY | A | 408 | 15.556 | 39.696 | −6.106  | 1.00 | 43.70 | N |
| ATOM | 1417 | CA  | GLY | A | 408 | 16.163 | 40.939 | −6.554  | 1.00 | 41.72 | C |
| ATOM | 1418 | C   | GLY | A | 408 | 17.665 | 41.014 | −6.351  | 1.00 | 51.56 | C |
| ATOM | 1419 | O   | GLY | A | 408 | 18.299 | 42.013 | −6.686  | 1.00 | 50.41 | O |
| ATOM | 1420 | N   | LEU | A | 409 | 18.245 | 39.953 | −5.803  | 1.00 | 51.53 | N |
| ATOM | 1421 | CA  | LEU | A | 409 | 19.683 | 39.928 | −5.561  | 1.00 | 53.22 | C |
| ATOM | 1422 | CB  | LEU | A | 409 | 20.030 | 38.963 | −4.421  | 1.00 | 51.23 | C |
| ATOM | 1423 | CG  | LEU | A | 409 | 19.477 | 39.259 | −3.022  | 1.00 | 52.31 | C |
| ATOM | 1424 | CD1 | LEU | A | 409 | 20.182 | 38.387 | −1.999  | 1.00 | 46.17 | C |
| ATOM | 1425 | CD2 | LEU | A | 409 | 19.632 | 40.735 | −2.659  | 1.00 | 48.56 | C |
| ATOM | 1426 | C   | LEU | A | 409 | 20.487 | 39.559 | −6.809  | 1.00 | 54.16 | C |
| ATOM | 1427 | O   | LEU | A | 409 | 20.382 | 38.437 | −7.307  | 1.00 | 54.30 | O |
| ATOM | 1428 | N   | ASP | A | 410 | 21.293 | 40.493 | −7.308  | 1.00 | 52.06 | N |
| ATOM | 1429 | CA  | ASP | A | 410 | 22.279 | 40.148 | −8.333  | 1.00 | 54.31 | C |
| ATOM | 1430 | CB  | ASP | A | 410 | 22.765 | 41.387 | −9.099  | 1.00 | 55.59 | C |
| ATOM | 1431 | CG  | ASP | A | 410 | 23.166 | 42.519 | −8.184  | 1.00 | 59.15 | C |
| ATOM | 1432 | OD1 | ASP | A | 410 | 23.728 | 43.523 | −8.688  | 1.00 | 54.50 | O |
| ATOM | 1433 | OD2 | ASP | A | 410 | 22.906 | 42.405 | −6.961  | 1.00 | 61.03 | O |
| ATOM | 1434 | C   | ASP | A | 410 | 23.453 | 39.397 | −7.698  | 1.00 | 50.52 | C |
| ATOM | 1435 | O   | ASP | A | 410 | 23.286 | 38.710 | −6.691  | 1.00 | 50.53 | O |
| ATOM | 1436 | N   | HIS | A | 411 | 24.643 | 39.523 | −8.275  | 1.00 | 49.09 | N |
| ATOM | 1437 | CA  | HIS | A | 411 | 25.749 | 38.703 | −7.807  | 1.00 | 44.99 | C |
| ATOM | 1438 | CB  | HIS | A | 411 | 26.591 | 38.183 | −8.959  | 1.00 | 40.09 | C |
| ATOM | 1439 | CG  | HIS | A | 411 | 26.067 | 36.917 | −9.550  | 1.00 | 44.17 | C |
| ATOM | 1440 | CD2 | HIS | A | 411 | 25.485 | 35.843 | −8.968  | 1.00 | 42.50 | C |
| ATOM | 1441 | ND1 | HIS | A | 411 | 26.100 | 36.650 | −10.903 | 1.00 | 45.00 | N |
| ATOM | 1442 | CE1 | HIS | A | 411 | 25.566 | 35.465 | −11.128 | 1.00 | 42.71 | C |
| ATOM | 1443 | NE2 | HIS | A | 411 | 25.177 | 34.960 | −9.971  | 1.00 | 45.55 | N |
| ATOM | 1444 | C   | HIS | A | 411 | 26.620 | 39.421 | −6.810  | 1.00 | 44.48 | C |
| ATOM | 1445 | O   | HIS | A | 411 | 26.749 | 40.641 | −6.856  | 1.00 | 50.53 | O |
| ATOM | 1446 | N   | SER | A | 412 | 27.203 | 38.659 | −5.894  | 1.00 | 35.99 | N |
| ATOM | 1447 | CA  | SER | A | 412 | 28.255 | 39.196 | −5.039  | 1.00 | 41.02 | C |
| ATOM | 1448 | CB  | SER | A | 412 | 28.128 | 38.650 | −3.631  | 1.00 | 43.53 | C |
| ATOM | 1449 | OG  | SER | A | 412 | 29.377 | 38.710 | −2.985  | 1.00 | 44.46 | O |
| ATOM | 1450 | C   | SER | A | 412 | 29.663 | 38.895 | −5.571  | 1.00 | 41.96 | C |
| ATOM | 1451 | O   | SER | A | 412 | 29.874 | 37.948 | −6.332  | 1.00 | 43.62 | O |
| ATOM | 1452 | N   | SER | A | 413 | 30.620 | 39.711 | −5.143  | 1.00 | 47.75 | N |
| ATOM | 1453 | CA  | SER | A | 413 | 32.019 | 39.546 | −5.517  | 1.00 | 41.57 | C |
| ATOM | 1454 | CB  | SER | A | 413 | 32.576 | 40.857 | −6.079  | 1.00 | 45.15 | C |
| ATOM | 1455 | OG  | SER | A | 413 | 31.879 | 41.251 | −7.269  | 1.00 | 49.36 | O |
| ATOM | 1456 | C   | SER | A | 413 | 32.831 | 39.050 | −4.318  | 1.00 | 45.13 | C |
| ATOM | 1457 | O   | SER | A | 413 | 34.002 | 38.655 | −4.454  | 1.00 | 41.95 | O |
| ATOM | 1458 | N   | VAL | A | 414 | 32.191 | 39.056 | −3.144  | 1.00 | 38.89 | N |
| ATOM | 1459 | CA  | VAL | A | 414 | 32.760 | 38.420 | −1.961  | 1.00 | 39.07 | C |
| ATOM | 1460 | CB  | VAL | A | 414 | 31.897 | 38.658 | −0.691  | 1.00 | 37.42 | C |
| ATOM | 1461 | CG1 | VAL | A | 414 | 32.604 | 38.155 |  0.526  | 1.00 | 40.27 | C |
| ATOM | 1462 | CG2 | VAL | A | 414 | 31.568 | 40.109 | −0.510  | 1.00 | 33.45 | C |
| ATOM | 1463 | C   | VAL | A | 414 | 32.752 | 36.920 | −2.225  | 1.00 | 43.72 | C |
| ATOM | 1464 | O   | VAL | A | 414 | 31.675 | 36.315 | −2.252  | 1.00 | 44.14 | O |
| ATOM | 1465 | N   | PRO | A | 415 | 33.941 | 36.299 | −2.372  | 1.00 | 42.29 | N |
| ATOM | 1466 | CD  | PRO | A | 415 | 35.275 | 36.862 | −2.092  | 1.00 | 45.11 | C |
| ATOM | 1467 | CA  | PRO | A | 415 | 34.018 | 34.882 | −2.770  | 1.00 | 45.06 | C |

TABLE 12-continued

Coordinates for pro MMP9(35-444 ΔFnII) (SEQ ID NO: 12) complex with Example 2

| ATOM | 1468 | CB | PRO | A | 415 | 35.523 | 34.570 | −2.734 | 1.00 | 47.73 | C |
|---|---|---|---|---|---|---|---|---|---|---|---|
| ATOM | 1469 | CG | PRO | A | 415 | 36.196 | 35.899 | −2.816 | 1.00 | 50.28 | C |
| ATOM | 1470 | C | PRO | A | 415 | 33.242 | 33.891 | −1.886 | 1.00 | 47.68 | C |
| ATOM | 1471 | O | PRO | A | 415 | 32.822 | 32.844 | −2.389 | 1.00 | 52.28 | O |
| ATOM | 1472 | N | GLU | A | 416 | 33.042 | 34.191 | −0.607 | 1.00 | 45.64 | N |
| ATOM | 1473 | CA | GLU | A | 416 | 32.297 | 33.257 | 0.244 | 1.00 | 40.43 | C |
| ATOM | 1474 | CB | GLU | A | 416 | 32.860 | 33.229 | 1.667 | 1.00 | 42.18 | C |
| ATOM | 1475 | CG | GLU | A | 416 | 34.376 | 33.415 | 1.756 | 1.00 | 53.36 | C |
| ATOM | 1476 | CD | GLU | A | 416 | 34.788 | 34.883 | 1.751 | 1.00 | 56.65 | C |
| ATOM | 1477 | OE1 | GLU | A | 416 | 35.535 | 35.284 | 0.836 | 1.00 | 50.58 | O |
| ATOM | 1478 | OE2 | GLU | A | 416 | 34.354 | 35.637 | 2.657 | 1.00 | 58.81 | O |
| ATOM | 1479 | C | GLU | A | 416 | 30.791 | 33.552 | 0.262 | 1.00 | 43.70 | C |
| ATOM | 1480 | O | GLU | A | 416 | 29.995 | 32.714 | 0.677 | 1.00 | 38.87 | O |
| ATOM | 1481 | N | ALA | A | 417 | 30.400 | 34.735 | −0.205 | 1.00 | 46.04 | N |
| ATOM | 1482 | CA | ALA | A | 417 | 28.985 | 35.093 | −0.242 | 1.00 | 47.70 | C |
| ATOM | 1483 | CB | ALA | A | 417 | 28.791 | 36.472 | −0.867 | 1.00 | 41.04 | C |
| ATOM | 1484 | C | ALA | A | 417 | 28.193 | 34.047 | −1.010 | 1.00 | 47.56 | C |
| ATOM | 1485 | O | ALA | A | 417 | 28.671 | 33.534 | −2.018 | 1.00 | 39.78 | O |
| ATOM | 1486 | N | LEU | A | 418 | 26.986 | 33.735 | −0.532 | 1.00 | 44.74 | N |
| ATOM | 1487 | CA | LEU | A | 418 | 26.121 | 32.783 | −1.225 | 1.00 | 42.49 | C |
| ATOM | 1488 | CB | LEU | A | 418 | 24.800 | 32.586 | −0.466 | 1.00 | 44.08 | C |
| ATOM | 1489 | CG | LEU | A | 418 | 23.716 | 31.749 | −1.171 | 1.00 | 42.99 | C |
| ATOM | 1490 | CD1 | LEU | A | 418 | 24.155 | 30.320 | −1.365 | 1.00 | 36.84 | C |
| ATOM | 1491 | CD2 | LEU | A | 418 | 22.418 | 31.767 | −0.391 | 1.00 | 44.69 | C |
| ATOM | 1492 | C | LEU | A | 418 | 25.835 | 33.254 | −2.657 | 1.00 | 43.93 | C |
| ATOM | 1493 | O | LEU | A | 418 | 25.603 | 32.436 | −3.539 | 1.00 | 39.69 | O |
| ATOM | 1494 | N | MET | A | 419 | 25.846 | 34.572 | −2.876 | 1.00 | 44.25 | N |
| ATOM | 1495 | CA | MET | A | 419 | 25.506 | 35.126 | −4.187 | 1.00 | 44.65 | C |
| ATOM | 1496 | CB | MET | A | 419 | 24.845 | 36.500 | −4.087 | 1.00 | 40.96 | C |
| ATOM | 1497 | CG | MET | A | 419 | 23.449 | 36.456 | −3.486 | 1.00 | 44.77 | C |
| ATOM | 1498 | SD | MET | A | 419 | 22.400 | 35.063 | −3.977 | 1.00 | 40.90 | S |
| ATOM | 1499 | CE | MET | A | 419 | 21.580 | 35.762 | −5.417 | 1.00 | 46.71 | C |
| ATOM | 1500 | C | MET | A | 419 | 26.700 | 35.198 | −5.114 | 1.00 | 50.22 | C |
| ATOM | 1501 | O | MET | A | 419 | 26.603 | 35.734 | −6.227 | 1.00 | 47.11 | O |
| ATOM | 1502 | N | TYR | A | 420 | 27.833 | 34.675 | −4.646 | 1.00 | 49.40 | N |
| ATOM | 1503 | CA | TYR | A | 420 | 28.975 | 34.483 | −5.525 | 1.00 | 46.15 | C |
| ATOM | 1504 | CB | TYR | A | 420 | 30.164 | 33.897 | −4.767 | 1.00 | 39.25 | C |
| ATOM | 1505 | CG | TYR | A | 420 | 31.477 | 34.166 | −5.443 | 1.00 | 46.65 | C |
| ATOM | 1506 | CD1 | TYR | A | 420 | 31.885 | 35.472 | −5.719 | 1.00 | 45.71 | C |
| ATOM | 1507 | CE1 | TYR | A | 420 | 33.093 | 35.722 | −6.349 | 1.00 | 43.70 | C |
| ATOM | 1508 | CD2 | TYR | A | 420 | 32.316 | 33.121 | −5.814 | 1.00 | 44.36 | C |
| ATOM | 1509 | CE2 | TYR | A | 420 | 33.530 | 33.365 | −6.436 | 1.00 | 43.93 | C |
| ATOM | 1510 | CZ | TYR | A | 420 | 33.913 | 34.666 | −6.706 | 1.00 | 43.91 | C |
| ATOM | 1511 | OH | TYR | A | 420 | 35.127 | 34.902 | −7.339 | 1.00 | 49.08 | O |
| ATOM | 1512 | C | TYR | A | 420 | 28.523 | 33.539 | −6.641 | 1.00 | 47.87 | C |
| ATOM | 1513 | O | TYR | A | 420 | 27.847 | 32.535 | −6.365 | 1.00 | 41.13 | O |
| ATOM | 1514 | N | PRO | A | 421 | 28.884 | 33.868 | −7.899 | 1.00 | 45.06 | N |
| ATOM | 1515 | CD | PRO | A | 421 | 29.830 | 34.955 | −8.199 | 1.00 | 47.69 | C |
| ATOM | 1516 | CA | PRO | A | 421 | 28.490 | 33.142 | −9.109 | 1.00 | 39.96 | C |
| ATOM | 1517 | CB | PRO | A | 421 | 29.335 | 33.788 | −10.207 | 1.00 | 40.80 | C |
| ATOM | 1518 | CG | PRO | A | 421 | 29.684 | 35.118 | −9.696 | 1.00 | 47.40 | C |
| ATOM | 1519 | C | PRO | A | 421 | 28.845 | 31.673 | −9.019 | 1.00 | 39.82 | C |
| ATOM | 1520 | O | PRO | A | 421 | 28.011 | 30.820 | −9.319 | 1.00 | 45.20 | O |
| ATOM | 1521 | N | MET | A | 422 | 30.069 | 31.382 | −8.605 | 1.00 | 40.21 | N |
| ATOM | 1522 | CA | MET | A | 422 | 30.573 | 30.014 | −8.651 | 1.00 | 43.33 | C |
| ATOM | 1523 | CB | MET | A | 422 | 32.099 | 29.987 | −8.608 | 1.00 | 35.61 | C |
| ATOM | 1524 | CG | MET | A | 422 | 32.759 | 31.130 | −9.313 | 1.00 | 36.89 | C |
| ATOM | 1525 | SD | MET | A | 422 | 34.543 | 30.882 | −9.282 | 1.00 | 50.38 | S |
| ATOM | 1526 | CE | MET | A | 422 | 34.776 | 30.296 | −7.613 | 1.00 | 52.91 | C |
| ATOM | 1527 | C | MET | A | 422 | 30.031 | 29.127 | −7.542 | 1.00 | 44.93 | C |
| ATOM | 1528 | O | MET | A | 422 | 29.760 | 29.590 | −6.423 | 1.00 | 37.87 | O |
| ATOM | 1529 | N | TYR | A | 423 | 29.931 | 27.845 | −7.836 | 1.00 | 47.07 | N |
| ATOM | 1530 | CA | TYR | A | 423 | 29.474 | 26.847 | −6.883 | 1.00 | 49.47 | C |
| ATOM | 1531 | CB | TYR | A | 423 | 28.934 | 25.617 | −7.637 | 1.00 | 44.82 | C |
| ATOM | 1532 | CG | TYR | A | 423 | 28.490 | 24.499 | −6.748 | 1.00 | 44.32 | C |
| ATOM | 1533 | CD1 | TYR | A | 423 | 29.269 | 23.418 | −6.544 | 1.00 | 43.33 | C |
| ATOM | 1534 | CE1 | TYR | A | 423 | 28.890 | 22.443 | −5.727 | 1.00 | 47.51 | C |
| ATOM | 1535 | CD2 | TYR | A | 423 | 27.314 | 24.551 | −6.095 | 1.00 | 44.64 | C |
| ATOM | 1536 | CE2 | TYR | A | 423 | 26.936 | 23.582 | −5.276 | 1.00 | 51.10 | C |
| ATOM | 1537 | CZ | TYR | A | 423 | 27.723 | 22.530 | −5.094 | 1.00 | 51.96 | C |
| ATOM | 1538 | OH | TYR | A | 423 | 27.331 | 21.550 | −4.266 | 1.00 | 53.25 | O |
| ATOM | 1539 | C | TYR | A | 423 | 30.557 | 26.485 | −5.850 | 1.00 | 53.41 | C |
| ATOM | 1540 | O | TYR | A | 423 | 31.669 | 26.164 | −6.189 | 1.00 | 57.20 | O |
| ATOM | 1541 | N | ARG | A | 424 | 30.218 | 26.564 | −4.577 | 1.00 | 52.95 | N |
| ATOM | 1542 | CA | ARG | A | 424 | 31.138 | 26.277 | −3.496 | 1.00 | 57.51 | C |
| ATOM | 1543 | CB | ARG | A | 424 | 31.431 | 27.571 | −2.744 | 1.00 | 67.76 | C |
| ATOM | 1544 | CG | ARG | A | 424 | 30.369 | 27.952 | −1.633 | 1.00 | 79.56 | C |

TABLE 12-continued

Coordinates for pro MMP9(35-444 ΔFnII) (SEQ ID NO: 12) complex with Example 2

| ATOM | 1545 | CD  | ARG | A | 424 | 29.288 | 29.071 | −2.008 | 1.00 | 81.71 | C |
|------|------|-----|-----|---|-----|--------|--------|--------|------|-------|---|
| ATOM | 1546 | NE  | ARG | A | 424 | 28.344 | 28.724 | −3.102 | 1.00 | 91.27 | N |
| ATOM | 1547 | CZ  | ARG | A | 424 | 27.187 | 28.091 | −2.952 | 1.00 | 94.43 | C |
| ATOM | 1548 | NH1 | ARG | A | 424 | 26.804 | 27.731 | −1.755 | 1.00 | 88.26 | N |
| ATOM | 1549 | NH2 | ARG | A | 424 | 26.420 | 27.824 | −3.989 | 1.00 | 87.21 | N |
| ATOM | 1550 | C   | ARG | A | 424 | 30.393 | 25.424 | −2.548 | 1.00 | 58.53 | C |
| ATOM | 1551 | O   | ARG | A | 424 | 29.453 | 25.877 | −2.005 | 1.00 | 63.27 | O |
| ATOM | 1552 | N   | PHE | A | 425 | 30.768 | 24.185 | −2.326 | 1.00 | 56.35 | N |
| ATOM | 1553 | CA  | PHE | A | 425 | 30.015 | 23.408 | −1.369 | 1.00 | 55.76 | C |
| ATOM | 1554 | CB  | PHE | A | 425 | 30.055 | 21.920 | −1.686 | 1.00 | 49.34 | C |
| ATOM | 1555 | CG  | PHE | A | 425 | 29.442 | 21.080 | −0.630 | 1.00 | 51.59 | C |
| ATOM | 1556 | CD1 | PHE | A | 425 | 28.098 | 20.882 | −0.586 | 1.00 | 51.14 | C |
| ATOM | 1557 | CD2 | PHE | A | 425 | 30.200 | 20.512 | 0.334  | 1.00 | 51.54 | C |
| ATOM | 1558 | CE1 | PHE | A | 425 | 27.539 | 20.152 | 0.388  | 1.00 | 55.19 | C |
| ATOM | 1559 | CE2 | PHE | A | 425 | 29.632 | 19.778 | 1.297  | 1.00 | 51.23 | C |
| ATOM | 1560 | CZ  | PHE | A | 425 | 28.299 | 19.608 | 1.324  | 1.00 | 55.45 | C |
| ATOM | 1561 | C   | PHE | A | 425 | 30.515 | 23.664 | 0.025  | 1.00 | 56.54 | C |
| ATOM | 1562 | O   | PHE | A | 425 | 31.662 | 23.462 | 0.317  | 1.00 | 58.86 | O |
| ATOM | 1563 | N   | THR | A | 426 | 29.648 | 24.150 | 0.883  | 1.00 | 49.43 | N |
| ATOM | 1564 | CA  | THR | A | 426 | 29.984 | 24.214 | 2.300  | 1.00 | 49.12 | C |
| ATOM | 1565 | CB  | THR | A | 426 | 29.851 | 25.636 | 2.884  | 1.00 | 48.52 | C |
| ATOM | 1566 | OG1 | THR | A | 426 | 28.908 | 26.395 | 2.115  | 1.00 | 38.32 | O |
| ATOM | 1567 | CG2 | THR | A | 426 | 31.211 | 26.345 | 2.948  | 1.00 | 51.03 | C |
| ATOM | 1568 | C   | THR | A | 426 | 29.062 | 23.344 | 3.130  | 1.00 | 51.69 | C |
| ATOM | 1569 | O   | THR | A | 426 | 28.023 | 22.878 | 2.666  | 1.00 | 57.10 | O |
| ATOM | 1570 | N   | GLU | A | 427 | 29.445 | 23.146 | 4.382  | 1.00 | 55.18 | N |
| ATOM | 1571 | CA  | GLU | A | 427 | 28.548 | 22.560 | 5.358  | 1.00 | 48.84 | C |
| ATOM | 1572 | CB  | GLU | A | 427 | 29.282 | 21.488 | 6.136  | 1.00 | 52.05 | C |
| ATOM | 1573 | CG  | GLU | A | 427 | 29.761 | 20.380 | 5.259  | 1.00 | 59.43 | C |
| ATOM | 1574 | CD  | GLU | A | 427 | 29.319 | 19.054 | 5.786  | 1.00 | 66.49 | C |
| ATOM | 1575 | OE1 | GLU | A | 427 | 28.635 | 18.308 | 5.042  | 1.00 | 64.41 | O |
| ATOM | 1576 | OE2 | GLU | A | 427 | 29.640 | 18.782 | 6.964  | 1.00 | 66.87 | O |
| ATOM | 1577 | C   | GLU | A | 427 | 28.073 | 23.669 | 6.286  | 1.00 | 43.30 | C |
| ATOM | 1578 | O   | GLU | A | 427 | 27.211 | 23.463 | 7.141  | 1.00 | 40.52 | O |
| ATOM | 1579 | N   | GLY | A | 428 | 28.637 | 24.858 | 6.085  | 1.00 | 45.34 | N |
| ATOM | 1580 | CA  | GLY | A | 428 | 28.368 | 25.990 | 6.954  | 1.00 | 44.83 | C |
| ATOM | 1581 | C   | GLY | A | 428 | 27.153 | 26.804 | 6.576  | 1.00 | 40.75 | C |
| ATOM | 1582 | O   | GLY | A | 428 | 26.628 | 26.689 | 5.454  | 1.00 | 39.15 | O |
| ATOM | 1583 | N   | PRO | A | 429 | 26.695 | 27.649 | 7.512  | 1.00 | 41.92 | N |
| ATOM | 1584 | CD  | PRO | A | 429 | 27.244 | 27.873 | 8.860  | 1.00 | 40.56 | C |
| ATOM | 1585 | CA  | PRO | A | 429 | 25.536 | 28.506 | 7.230  | 1.00 | 40.32 | C |
| ATOM | 1586 | CB  | PRO | A | 429 | 25.517 | 29.479 | 8.413  | 1.00 | 38.23 | C |
| ATOM | 1587 | CG  | PRO | A | 429 | 26.169 | 28.709 | 9.526  | 1.00 | 38.10 | C |
| ATOM | 1588 | C   | PRO | A | 429 | 25.765 | 29.235 | 5.912  | 1.00 | 42.90 | C |
| ATOM | 1589 | O   | PRO | A | 429 | 26.716 | 29.999 | 5.803  | 1.00 | 42.60 | O |
| ATOM | 1590 | N   | PRO | A | 430 | 24.899 | 28.979 | 4.919  | 1.00 | 41.39 | N |
| ATOM | 1591 | CD  | PRO | A | 430 | 23.692 | 28.147 | 5.091  | 1.00 | 37.51 | C |
| ATOM | 1592 | CA  | PRO | A | 430 | 25.033 | 29.482 | 3.549  | 1.00 | 38.22 | C |
| ATOM | 1593 | CB  | PRO | A | 430 | 23.752 | 28.979 | 2.856  | 1.00 | 39.94 | C |
| ATOM | 1594 | CG  | PRO | A | 430 | 23.331 | 27.789 | 3.669  | 1.00 | 50.66 | C |
| ATOM | 1595 | C   | PRO | A | 430 | 25.130 | 31.004 | 3.468  | 1.00 | 41.99 | C |
| ATOM | 1596 | O   | PRO | A | 430 | 25.955 | 31.540 | 2.710  | 1.00 | 43.61 | O |
| ATOM | 1597 | N   | LEU | A | 431 | 24.295 | 31.705 | 4.226  | 1.00 | 40.62 | N |
| ATOM | 1598 | CA  | LEU | A | 431 | 24.316 | 33.161 | 4.156  | 1.00 | 40.86 | C |
| ATOM | 1599 | CB  | LEU | A | 431 | 23.070 | 33.774 | 4.781  | 1.00 | 37.06 | C |
| ATOM | 1600 | CG  | LEU | A | 431 | 21.782 | 33.392 | 4.048  | 1.00 | 43.42 | C |
| ATOM | 1601 | CD1 | LEU | A | 431 | 20.546 | 33.798 | 4.870  | 1.00 | 32.77 | C |
| ATOM | 1602 | CD2 | LEU | A | 431 | 21.731 | 33.957 | 2.617  | 1.00 | 33.88 | C |
| ATOM | 1603 | C   | LEU | A | 431 | 25.586 | 33.774 | 4.749  | 1.00 | 42.26 | C |
| ATOM | 1604 | O   | LEU | A | 431 | 26.273 | 33.179 | 5.577  | 1.00 | 39.50 | O |
| ATOM | 1605 | N   | HIS | A | 432 | 25.939 | 34.924 | 4.201  | 1.00 | 41.64 | N |
| ATOM | 1606 | CA  | HIS | A | 432 | 26.995 | 35.770 | 4.691  | 1.00 | 47.91 | C |
| ATOM | 1607 | CB  | HIS | A | 432 | 28.235 | 35.676 | 3.832  | 1.00 | 45.37 | C |
| ATOM | 1608 | CG  | HIS | A | 432 | 28.913 | 34.357 | 3.923  | 1.00 | 55.67 | C |
| ATOM | 1609 | CD2 | HIS | A | 432 | 28.627 | 33.179 | 3.343  | 1.00 | 58.20 | C |
| ATOM | 1610 | ND1 | HIS | A | 432 | 30.017 | 34.139 | 4.702  | 1.00 | 67.58 | N |
| ATOM | 1611 | CE1 | HIS | A | 432 | 30.384 | 32.884 | 4.594  | 1.00 | 66.58 | C |
| ATOM | 1612 | NE2 | HIS | A | 432 | 29.563 | 32.284 | 3.766  | 1.00 | 63.94 | N |
| ATOM | 1613 | C   | HIS | A | 432 | 26.499 | 37.187 | 4.735  | 1.00 | 45.33 | C |
| ATOM | 1614 | O   | HIS | A | 432 | 25.458 | 37.486 | 4.231  | 1.00 | 38.00 | O |
| ATOM | 1615 | N   | LYS | A | 433 | 27.251 | 38.061 | 5.365  | 1.00 | 50.54 | N |
| ATOM | 1616 | CA  | LYS | A | 433 | 26.705 | 39.395 | 5.630  | 1.00 | 45.92 | C |
| ATOM | 1617 | CB  | LYS | A | 433 | 27.481 | 40.096 | 6.747  | 1.00 | 42.92 | C |
| ATOM | 1618 | CG  | LYS | A | 433 | 28.964 | 40.101 | 6.555  | 1.00 | 49.67 | C |
| ATOM | 1619 | CD  | LYS | A | 433 | 29.611 | 40.482 | 7.859  | 1.00 | 52.67 | C |
| ATOM | 1620 | CE  | LYS | A | 433 | 31.107 | 40.267 | 7.859  | 1.00 | 57.25 | C |
| ATOM | 1621 | NZ  | LYS | A | 433 | 31.623 | 40.785 | 9.151  | 1.00 | 52.97 | N |

TABLE 12-continued

Coordinates for pro MMP9(35-444 ΔFnII) (SEQ ID NO: 12) complex with Example 2

| ATOM | 1622 | C | LYS | A | 433 | 26.558 | 40.315 | 4.420 | 1.00 | 43.22 | C |
|------|------|------|-----|---|-----|--------|--------|--------|------|-------|---|
| ATOM | 1623 | O | LYS | A | 433 | 25.932 | 41.360 | 4.543 | 1.00 | 43.46 | O |
| ATOM | 1624 | N | ASP | A | 434 | 27.122 | 39.940 | 3.271 | 1.00 | 44.72 | N |
| ATOM | 1625 | CA | ASP | A | 434 | 26.905 | 40.689 | 2.014 | 1.00 | 45.48 | C |
| ATOM | 1626 | CB | ASP | A | 434 | 28.074 | 40.498 | 1.032 | 1.00 | 42.84 | C |
| ATOM | 1627 | CG | ASP | A | 434 | 27.928 | 41.343 | −0.252 | 1.00 | 44.04 | C |
| ATOM | 1628 | OD1 | ASP | A | 434 | 28.099 | 42.582 | −0.183 | 1.00 | 41.46 | O |
| ATOM | 1629 | OD2 | ASP | A | 434 | 27.660 | 40.770 | −1.336 | 1.00 | 38.31 | O |
| ATOM | 1630 | C | ASP | A | 434 | 25.594 | 40.286 | 1.335 | 1.00 | 43.67 | C |
| ATOM | 1631 | O | ASP | A | 434 | 24.973 | 41.092 | 0.652 | 1.00 | 42.15 | O |
| ATOM | 1632 | N | ASP | A | 435 | 25.200 | 39.026 | 1.501 | 1.00 | 44.58 | N |
| ATOM | 1633 | CA | ASP | A | 435 | 23.889 | 38.575 | 1.052 | 1.00 | 45.58 | C |
| ATOM | 1634 | CB | ASP | A | 435 | 23.722 | 37.071 | 1.250 | 1.00 | 39.87 | C |
| ATOM | 1635 | CG | ASP | A | 435 | 24.860 | 36.275 | 0.656 | 1.00 | 46.73 | C |
| ATOM | 1636 | OD1 | ASP | A | 435 | 25.037 | 36.295 | −0.582 | 1.00 | 45.92 | O |
| ATOM | 1637 | OD2 | ASP | A | 435 | 25.570 | 35.611 | 1.431 | 1.00 | 47.44 | O |
| ATOM | 1638 | C | ASP | A | 435 | 22.839 | 39.275 | 1.887 | 1.00 | 48.85 | C |
| ATOM | 1639 | O | ASP | A | 435 | 21.787 | 39.676 | 1.373 | 1.00 | 53.54 | O |
| ATOM | 1640 | N | VAL | A | 436 | 23.123 | 39.414 | 3.180 | 1.00 | 40.69 | N |
| ATOM | 1641 | CA | VAL | A | 436 | 22.126 | 39.929 | 4.110 | 1.00 | 46.32 | C |
| ATOM | 1642 | CB | VAL | A | 436 | 22.425 | 39.584 | 5.586 | 1.00 | 41.27 | C |
| ATOM | 1643 | CG1 | VAL | A | 436 | 21.587 | 40.458 | 6.485 | 1.00 | 46.28 | C |
| ATOM | 1644 | CG2 | VAL | A | 436 | 22.128 | 38.126 | 5.866 | 1.00 | 39.91 | C |
| ATOM | 1645 | C | VAL | A | 436 | 21.984 | 41.431 | 3.969 | 1.00 | 50.38 | C |
| ATOM | 1646 | O | VAL | A | 436 | 20.876 | 41.977 | 4.029 | 1.00 | 49.50 | O |
| ATOM | 1647 | N | ASN | A | 437 | 23.109 | 42.102 | 3.772 | 1.00 | 46.09 | N |
| ATOM | 1648 | CA | ASN | A | 437 | 23.058 | 43.533 | 3.585 | 1.00 | 45.78 | C |
| ATOM | 1649 | CB | ASN | A | 437 | 24.462 | 44.130 | 3.585 | 1.00 | 43.52 | C |
| ATOM | 1650 | CG | ASN | A | 437 | 25.192 | 43.898 | 4.908 | 1.00 | 41.74 | C |
| ATOM | 1651 | OD1 | ASN | A | 437 | 24.573 | 43.585 | 5.917 | 1.00 | 45.75 | O |
| ATOM | 1652 | ND2 | ASN | A | 437 | 26.506 | 44.039 | 4.898 | 1.00 | 42.01 | N |
| ATOM | 1653 | C | ASN | A | 437 | 22.338 | 43.749 | 2.276 | 1.00 | 50.16 | C |
| ATOM | 1654 | O | ASN | A | 437 | 21.483 | 44.630 | 2.157 | 1.00 | 54.05 | O |
| ATOM | 1655 | N | GLY | A | 438 | 22.647 | 42.890 | 1.314 | 1.00 | 43.26 | N |
| ATOM | 1656 | CA | GLY | A | 438 | 22.002 | 42.935 | 0.017 | 1.00 | 45.61 | C |
| ATOM | 1657 | C | GLY | A | 438 | 20.494 | 42.877 | 0.131 | 1.00 | 48.54 | C |
| ATOM | 1658 | O | GLY | A | 438 | 19.805 | 43.777 | −0.337 | 1.00 | 58.28 | O |
| ATOM | 1659 | N | ILE | A | 439 | 19.974 | 41.823 | 0.754 | 1.00 | 50.56 | N |
| ATOM | 1660 | CA | ILE | A | 439 | 18.513 | 41.668 | 0.918 | 1.00 | 54.74 | C |
| ATOM | 1661 | CB | ILE | A | 439 | 18.120 | 40.285 | 1.482 | 1.00 | 48.10 | C |
| ATOM | 1662 | CG2 | ILE | A | 439 | 18.209 | 40.274 | 3.004 | 1.00 | 42.43 | C |
| ATOM | 1663 | CG1 | ILE | A | 439 | 16.724 | 39.901 | 1.004 | 1.00 | 42.02 | C |
| ATOM | 1664 | CD1 | ILE | A | 439 | 16.749 | 39.086 | −0.216 | 1.00 | 42.34 | C |
| ATOM | 1665 | C | ILE | A | 439 | 17.866 | 42.738 | 1.801 | 1.00 | 50.17 | C |
| ATOM | 1666 | O | ILE | A | 439 | 16.760 | 43.185 | 1.513 | 1.00 | 49.03 | O |
| ATOM | 1667 | N | ARG | A | 440 | 18.547 | 43.136 | 2.875 | 1.00 | 50.95 | N |
| ATOM | 1668 | CA | ARG | A | 440 | 18.048 | 44.194 | 3.752 | 1.00 | 49.73 | C |
| ATOM | 1669 | CB | ARG | A | 440 | 19.038 | 44.472 | 4.902 | 1.00 | 51.52 | C |
| ATOM | 1670 | CG | ARG | A | 440 | 18.525 | 44.129 | 6.314 | 1.00 | 55.60 | C |
| ATOM | 1671 | CD | ARG | A | 440 | 19.348 | 43.061 | 7.070 | 1.00 | 54.50 | C |
| ATOM | 1672 | NE | ARG | A | 440 | 20.458 | 43.614 | 7.857 | 1.00 | 62.11 | N |
| ATOM | 1673 | CZ | ARG | A | 440 | 20.972 | 43.063 | 8.967 | 1.00 | 58.10 | C |
| ATOM | 1674 | NH1 | ARG | A | 440 | 20.480 | 41.930 | 9.468 | 1.00 | 48.42 | N |
| ATOM | 1675 | NH2 | ARG | A | 440 | 21.989 | 43.660 | 9.588 | 1.00 | 51.77 | N |
| ATOM | 1676 | C | ARG | A | 440 | 17.770 | 45.470 | 2.943 | 1.00 | 49.30 | C |
| ATOM | 1677 | O | ARG | A | 440 | 16.751 | 46.130 | 3.133 | 1.00 | 46.23 | O |
| ATOM | 1678 | N | HIS | A | 441 | 18.663 | 45.799 | 2.015 | 1.00 | 54.49 | N |
| ATOM | 1679 | CA | HIS | A | 441 | 18.551 | 47.053 | 1.281 | 1.00 | 54.42 | C |
| ATOM | 1680 | CB | HIS | A | 441 | 19.814 | 47.352 | 0.477 | 1.00 | 56.24 | C |
| ATOM | 1681 | CG | HIS | A | 441 | 19.583 | 48.310 | −0.647 | 1.00 | 62.48 | C |
| ATOM | 1682 | CD2 | HIS | A | 441 | 19.308 | 49.636 | −0.646 | 1.00 | 62.48 | C |
| ATOM | 1683 | ND1 | HIS | A | 441 | 19.570 | 47.920 | −1.969 | 1.00 | 68.84 | N |
| ATOM | 1684 | CE1 | HIS | A | 441 | 19.322 | 48.967 | −2.736 | 1.00 | 68.76 | C |
| ATOM | 1685 | NE2 | HIS | A | 441 | 19.152 | 50.021 | −1.957 | 1.00 | 66.17 | N |
| ATOM | 1686 | C | HIS | A | 441 | 17.333 | 47.052 | 0.366 | 1.00 | 61.50 | C |
| ATOM | 1687 | O | HIS | A | 441 | 16.874 | 48.103 | −0.081 | 1.00 | 61.00 | O |
| ATOM | 1688 | N | LEU | A | 442 | 16.807 | 45.868 | 0.082 | 1.00 | 61.18 | N |
| ATOM | 1689 | CA | LEU | A | 442 | 15.534 | 45.791 | −0.614 | 1.00 | 60.02 | C |
| ATOM | 1690 | CB | LEU | A | 442 | 15.490 | 44.604 | −1.593 | 1.00 | 57.15 | C |
| ATOM | 1691 | CG | LEU | A | 442 | 16.549 | 44.520 | −2.703 | 1.00 | 62.61 | C |
| ATOM | 1692 | CD1 | LEU | A | 442 | 17.570 | 43.429 | −2.385 | 1.00 | 60.59 | C |
| ATOM | 1693 | CD2 | LEU | A | 442 | 15.935 | 44.266 | −4.089 | 1.00 | 54.09 | C |
| ATOM | 1694 | C | LEU | A | 442 | 14.361 | 45.740 | 0.375 | 1.00 | 53.53 | C |
| ATOM | 1695 | O | LEU | A | 442 | 13.409 | 46.509 | 0.257 | 1.00 | 65.07 | O |
| ATOM | 1696 | N | TYR | A | 443 | 14.418 | 44.857 | 1.361 | 1.00 | 51.44 | N |
| ATOM | 1697 | CA | TYR | A | 443 | 13.205 | 44.593 | 2.135 | 1.00 | 54.18 | C |
| ATOM | 1698 | CB | TYR | A | 443 | 12.864 | 43.111 | 2.072 | 1.00 | 51.32 | C |

TABLE 12-continued

Coordinates for pro MMP9(35-444 ΔFnII) (SEQ ID NO: 12) complex with Example 2

| | | | | | | | | | | |
|---|---|---|---|---|---|---|---|---|---|---|
| ATOM | 1699 | CG | TYR | A | 443 | 12.546 | 42.682 | 0.656 | 1.00 | 53.72 | C |
| ATOM | 1700 | CD1 | TYR | A | 443 | 13.546 | 42.246 | −0.205 | 1.00 | 49.74 | C |
| ATOM | 1701 | CE1 | TYR | A | 443 | 13.253 | 41.863 | −1.503 | 1.00 | 52.63 | C |
| ATOM | 1702 | CD2 | TYR | A | 443 | 11.249 | 42.754 | 0.167 | 1.00 | 58.07 | C |
| ATOM | 1703 | CE2 | TYR | A | 443 | 10.944 | 42.376 | −1.129 | 1.00 | 54.06 | C |
| ATOM | 1704 | CZ | TYR | A | 443 | 11.945 | 41.932 | −1.962 | 1.00 | 55.04 | C |
| ATOM | 1705 | OH | TYR | A | 443 | 11.624 | 41.560 | −3.254 | 1.00 | 46.47 | O |
| ATOM | 1706 | C | TYR | A | 443 | 13.129 | 45.157 | 3.554 | 1.00 | 58.93 | C |
| ATOM | 1707 | O | TYR | A | 443 | 12.354 | 46.073 | 3.808 | 1.00 | 63.59 | O |
| ATOM | 1708 | N | GLY | A | 444 | 13.924 | 44.617 | 4.470 | 1.00 | 69.46 | N |
| ATOM | 1709 | CA | GLY | A | 444 | 13.893 | 45.029 | 5.870 | 1.00 | 71.62 | C |
| ATOM | 1710 | C | GLY | A | 444 | 13.256 | 46.389 | 6.115 | 1.00 | 76.12 | C |
| ATOM | 1711 | O | GLY | A | 444 | 13.172 | 46.871 | 7.251 | 1.00 | 81.53 | O |
| ATOM | 1712 | ZN | ZN | A | 500 | 23.548 | 33.554 | −9.605 | 1.00 | 47.65 | Zn |
| ATOM | 1713 | ZN | ZN | A | 501 | 15.454 | 28.916 | −18.118 | 1.00 | 56.09 | Zn |
| ATOM | 1714 | CA | CA | A | 502 | 25.015 | 22.335 | −16.543 | 1.00 | 57.10 | Ca |
| ATOM | 1715 | CA | CA | A | 503 | 20.280 | 13.825 | −13.592 | 1.00 | 80.84 | Ca |
| ATOM | 1716 | CA | CA | A | 504 | 5.589 | 33.639 | −11.998 | 1.00 | 82.70 | Ca |
| TER | 1717 | | CA | A | 504 | | | | | | |
| ATOM | 1718 | CB | ASP | B | 41 | 4.270 | 13.968 | 42.643 | 1.00 | 83.25 | C |
| ATOM | 1719 | CG | ASP | B | 41 | 4.825 | 14.696 | 43.798 | 1.00 | 88.72 | C |
| ATOM | 1720 | OD1 | ASP | B | 41 | 6.018 | 14.510 | 44.020 | 1.00 | 87.83 | O |
| ATOM | 1721 | OD2 | ASP | B | 41 | 4.114 | 15.457 | 44.457 | 1.00 | 76.09 | O |
| ATOM | 1722 | C | ASP | B | 41 | 4.907 | 15.486 | 40.853 | 1.00 | 70.69 | C |
| ATOM | 1723 | O | ASP | B | 41 | 4.925 | 15.724 | 39.660 | 1.00 | 70.32 | O |
| ATOM | 1724 | N | ASP | B | 41 | 6.530 | 13.834 | 41.841 | 1.00 | 67.79 | N |
| ATOM | 1725 | CA | ASP | B | 41 | 5.159 | 14.095 | 41.428 | 1.00 | 73.66 | C |
| ATOM | 1726 | N | ARG | B | 42 | 4.624 | 16.604 | 41.486 | 1.00 | 72.48 | N |
| ATOM | 1727 | CA | ARG | B | 42 | 4.368 | 18.018 | 41.604 | 1.00 | 66.91 | C |
| ATOM | 1728 | CB | ARG | B | 42 | 3.125 | 18.271 | 42.425 | 1.00 | 66.94 | C |
| ATOM | 1729 | CG | ARG | B | 42 | 2.746 | 19.692 | 42.596 | 1.00 | 65.17 | C |
| ATOM | 1730 | CD | ARG | B | 42 | 1.469 | 19.767 | 43.362 | 1.00 | 66.64 | C |
| ATOM | 1731 | NE | ARG | B | 42 | 0.970 | 21.110 | 43.583 | 1.00 | 68.09 | N |
| ATOM | 1732 | CZ | ARG | B | 42 | −0.234 | 21.365 | 44.068 | 1.00 | 68.75 | C |
| ATOM | 1733 | NH1 | ARG | B | 42 | −1.011 | 20.363 | 44.393 | 1.00 | 69.89 | N |
| ATOM | 1734 | NH2 | ARG | B | 42 | −0.655 | 22.603 | 44.239 | 1.00 | 58.10 | N |
| ATOM | 1735 | C | ARG | B | 42 | 5.593 | 18.530 | 42.289 | 1.00 | 69.25 | C |
| ATOM | 1736 | O | ARG | B | 42 | 5.654 | 19.646 | 42.712 | 1.00 | 63.57 | O |
| ATOM | 1737 | N | GLN | B | 43 | 6.337 | 17.655 | 42.776 | 1.00 | 73.86 | N |
| ATOM | 1738 | CA | GLN | B | 43 | 7.693 | 18.098 | 43.056 | 1.00 | 74.11 | C |
| ATOM | 1739 | CB | GLN | B | 43 | 8.548 | 16.887 | 43.488 | 1.00 | 75.05 | C |
| ATOM | 1740 | CG | GLN | B | 43 | 7.888 | 15.506 | 43.204 | 1.00 | 79.14 | C |
| ATOM | 1741 | CD | GLN | B | 43 | 8.888 | 14.379 | 42.888 | 1.00 | 82.69 | C |
| ATOM | 1742 | OE1 | GLN | B | 43 | 8.519 | 13.323 | 42.348 | 1.00 | 68.25 | O |
| ATOM | 1743 | NE2 | GLN | B | 43 | 10.155 | 14.604 | 43.222 | 1.00 | 85.37 | N |
| ATOM | 1744 | C | GLN | B | 43 | 8.255 | 18.689 | 41.763 | 1.00 | 67.21 | C |
| ATOM | 1745 | O | GLN | B | 43 | 8.653 | 19.852 | 41.702 | 1.00 | 62.35 | O |
| ATOM | 1746 | N | LEU | B | 44 | 8.259 | 17.865 | 40.724 | 1.00 | 66.90 | N |
| ATOM | 1747 | CA | LEU | B | 44 | 8.830 | 18.229 | 39.439 | 1.00 | 61.56 | C |
| ATOM | 1748 | CB | LEU | B | 44 | 8.398 | 17.214 | 38.381 | 1.00 | 60.82 | C |
| ATOM | 1749 | CG | LEU | B | 44 | 8.962 | 17.369 | 36.968 | 1.00 | 60.80 | C |
| ATOM | 1750 | CD1 | LEU | B | 44 | 9.017 | 16.027 | 36.251 | 1.00 | 66.89 | C |
| ATOM | 1751 | CD2 | LEU | B | 44 | 8.155 | 18.363 | 36.179 | 1.00 | 52.17 | C |
| ATOM | 1752 | C | LEU | B | 44 | 8.450 | 19.645 | 39.023 | 1.00 | 62.06 | C |
| ATOM | 1753 | O | LEU | B | 44 | 9.276 | 20.392 | 38.498 | 1.00 | 62.99 | O |
| ATOM | 1754 | N | ALA | B | 45 | 7.204 | 20.017 | 39.276 | 1.00 | 55.23 | N |
| ATOM | 1755 | CA | ALA | B | 45 | 6.685 | 21.285 | 38.797 | 1.00 | 56.21 | C |
| ATOM | 1756 | CB | ALA | B | 45 | 5.150 | 21.292 | 38.865 | 1.00 | 60.81 | C |
| ATOM | 1757 | C | ALA | B | 45 | 7.253 | 22.481 | 39.544 | 1.00 | 54.77 | C |
| ATOM | 1758 | O | ALA | B | 45 | 7.650 | 23.471 | 38.929 | 1.00 | 54.65 | O |
| ATOM | 1759 | N | GLU | B | 46 | 7.261 | 22.391 | 40.872 | 1.00 | 61.93 | N |
| ATOM | 1760 | CA | GLU | B | 46 | 7.696 | 23.487 | 41.734 | 1.00 | 55.24 | C |
| ATOM | 1761 | CB | GLU | B | 46 | 7.400 | 23.160 | 43.201 | 1.00 | 58.14 | C |
| ATOM | 1762 | CG | GLU | B | 46 | 5.936 | 23.307 | 43.594 | 1.00 | 62.59 | C |
| ATOM | 1763 | CD | GLU | B | 46 | 5.546 | 22.425 | 44.775 | 1.00 | 71.15 | C |
| ATOM | 1764 | OE1 | GLU | B | 46 | 6.399 | 21.625 | 45.222 | 1.00 | 74.21 | O |
| ATOM | 1765 | OE2 | GLU | B | 46 | 4.383 | 22.527 | 45.248 | 1.00 | 68.52 | O |
| ATOM | 1766 | C | GLU | B | 46 | 9.176 | 23.748 | 41.562 | 1.00 | 54.94 | C |
| ATOM | 1767 | O | GLU | B | 46 | 9.633 | 24.876 | 41.731 | 1.00 | 51.82 | O |
| ATOM | 1768 | N | GLU | B | 47 | 9.921 | 22.697 | 41.232 | 1.00 | 53.12 | N |
| ATOM | 1769 | CA | GLU | B | 47 | 11.359 | 22.820 | 41.033 | 1.00 | 59.30 | C |
| ATOM | 1770 | CB | GLU | B | 47 | 12.017 | 21.438 | 41.015 | 1.00 | 60.13 | C |
| ATOM | 1771 | CG | GLU | B | 47 | 11.327 | 20.415 | 41.906 | 1.00 | 67.81 | C |
| ATOM | 1772 | CD | GLU | B | 47 | 12.047 | 20.161 | 43.225 | 1.00 | 67.34 | C |
| ATOM | 1773 | OE1 | GLU | B | 47 | 12.832 | 19.181 | 43.298 | 1.00 | 61.50 | O |
| ATOM | 1774 | OE2 | GLU | B | 47 | 11.813 | 20.928 | 44.189 | 1.00 | 63.79 | O |
| ATOM | 1775 | C | GLU | B | 47 | 11.633 | 23.551 | 39.720 | 1.00 | 54.56 | C |

TABLE 12-continued

Coordinates for pro MMP9(35-444 ΔFnII) (SEQ ID NO: 12) complex with Example 2

| ATOM | 1776 | O   | GLU | B | 47 | 12.476 | 24.462 | 39.640 | 1.00 | 45.94 | O |
|------|------|-----|-----|---|----|--------|--------|--------|------|-------|---|
| ATOM | 1777 | N   | TYR | B | 48 | 10.901 | 23.145 | 38.690 | 1.00 | 48.82 | N |
| ATOM | 1778 | CA  | TYR | B | 48 | 11.002 | 23.762 | 37.389 | 1.00 | 44.30 | C |
| ATOM | 1779 | CB  | TYR | B | 48 | 10.026 | 23.096 | 36.440 | 1.00 | 47.32 | C |
| ATOM | 1780 | CG  | TYR | B | 48 | 10.226 | 23.495 | 35.005 | 1.00 | 48.59 | C |
| ATOM | 1781 | CD1 | TYR | B | 48 | 9.803  | 24.733 | 34.538 | 1.00 | 43.08 | C |
| ATOM | 1782 | CE1 | TYR | B | 48 | 10.006 | 25.101 | 33.215 | 1.00 | 46.15 | C |
| ATOM | 1783 | CD2 | TYR | B | 48 | 10.849 | 22.629 | 34.105 | 1.00 | 53.64 | C |
| ATOM | 1784 | CE2 | TYR | B | 48 | 11.038 | 22.984 | 32.769 | 1.00 | 44.88 | C |
| ATOM | 1785 | CZ  | TYR | B | 48 | 10.620 | 24.222 | 32.340 | 1.00 | 40.08 | C |
| ATOM | 1786 | OH  | TYR | B | 48 | 10.791 | 24.564 | 31.030 | 1.00 | 40.71 | O |
| ATOM | 1787 | C   | TYR | B | 48 | 10.669 | 25.238 | 37.470 | 1.00 | 48.17 | C |
| ATOM | 1788 | O   | TYR | B | 48 | 11.444 | 26.083 | 37.027 | 1.00 | 46.89 | O |
| ATOM | 1789 | N   | LEU | B | 49 | 9.503  | 25.541 | 38.031 | 1.00 | 46.26 | N |
| ATOM | 1790 | CA  | LEU | B | 49 | 9.016  | 26.911 | 38.098 | 1.00 | 47.36 | C |
| ATOM | 1791 | CB  | LEU | B | 49 | 7.646  | 26.960 | 38.778 | 1.00 | 46.06 | C |
| ATOM | 1792 | CG  | LEU | B | 49 | 6.470  | 26.402 | 37.990 | 1.00 | 43.84 | C |
| ATOM | 1793 | CD1 | LEU | B | 49 | 5.267  | 26.210 | 38.894 | 1.00 | 43.47 | C |
| ATOM | 1794 | CD2 | LEU | B | 49 | 6.140  | 27.330 | 36.833 | 1.00 | 44.24 | C |
| ATOM | 1795 | C   | LEU | B | 49 | 9.984  | 27.802 | 38.858 | 1.00 | 48.64 | C |
| ATOM | 1796 | O   | LEU | B | 49 | 10.182 | 28.966 | 38.508 | 1.00 | 48.13 | O |
| ATOM | 1797 | N   | TYR | B | 50 | 10.580 | 27.262 | 39.910 | 1.00 | 45.69 | N |
| ATOM | 1798 | CA  | TYR | B | 50 | 11.397 | 28.073 | 40.779 | 1.00 | 46.32 | C |
| ATOM | 1799 | CB  | TYR | B | 50 | 11.600 | 27.396 | 42.136 | 1.00 | 52.89 | C |
| ATOM | 1800 | CG  | TYR | B | 50 | 12.746 | 28.002 | 42.887 | 1.00 | 54.48 | C |
| ATOM | 1801 | CD1 | TYR | B | 50 | 12.568 | 29.162 | 43.619 | 1.00 | 57.66 | C |
| ATOM | 1802 | CE1 | TYR | B | 50 | 13.612 | 29.750 | 44.300 | 1.00 | 62.99 | C |
| ATOM | 1803 | CD2 | TYR | B | 50 | 14.020 | 27.443 | 42.827 | 1.00 | 56.12 | C |
| ATOM | 1804 | CE2 | TYR | B | 50 | 15.083 | 28.024 | 43.506 | 1.00 | 58.75 | C |
| ATOM | 1805 | CZ  | TYR | B | 50 | 14.868 | 29.183 | 44.242 | 1.00 | 66.04 | C |
| ATOM | 1806 | OH  | TYR | B | 50 | 15.897 | 29.789 | 44.931 | 1.00 | 78.56 | O |
| ATOM | 1807 | C   | TYR | B | 50 | 12.732 | 28.301 | 40.107 | 1.00 | 51.65 | C |
| ATOM | 1808 | O   | TYR | B | 50 | 13.260 | 29.415 | 40.098 | 1.00 | 54.52 | O |
| ATOM | 1809 | N   | ARG | B | 51 | 13.274 | 27.236 | 39.534 | 1.00 | 47.08 | N |
| ATOM | 1810 | CA  | ARG | B | 51 | 14.536 | 27.335 | 38.832 | 1.00 | 44.97 | C |
| ATOM | 1811 | CB  | ARG | B | 51 | 14.938 | 25.976 | 38.252 | 1.00 | 38.91 | C |
| ATOM | 1812 | CG  | ARG | B | 51 | 16.260 | 26.000 | 37.517 | 1.00 | 43.42 | C |
| ATOM | 1813 | CD  | ARG | B | 51 | 16.567 | 24.668 | 36.823 | 1.00 | 51.87 | C |
| ATOM | 1814 | NE  | ARG | B | 51 | 17.211 | 23.707 | 37.715 | 1.00 | 47.88 | N |
| ATOM | 1815 | CZ  | ARG | B | 51 | 18.477 | 23.812 | 38.097 | 1.00 | 50.79 | C |
| ATOM | 1816 | NH1 | ARG | B | 51 | 19.197 | 24.838 | 37.655 | 1.00 | 46.27 | N |
| ATOM | 1817 | NH2 | ARG | B | 51 | 19.020 | 22.907 | 38.911 | 1.00 | 46.92 | N |
| ATOM | 1818 | C   | ARG | B | 51 | 14.505 | 28.418 | 37.743 | 1.00 | 44.89 | C |
| ATOM | 1819 | O   | ARG | B | 51 | 15.386 | 29.275 | 37.701 | 1.00 | 39.72 | O |
| ATOM | 1820 | N   | TYR | B | 52 | 13.499 | 28.393 | 36.869 | 1.00 | 41.41 | N |
| ATOM | 1821 | CA  | TYR | B | 52 | 13.527 | 29.280 | 35.700 | 1.00 | 46.41 | C |
| ATOM | 1822 | CB  | TYR | B | 52 | 13.024 | 28.570 | 34.428 | 1.00 | 43.16 | C |
| ATOM | 1823 | CG  | TYR | B | 52 | 13.796 | 27.299 | 34.159 | 1.00 | 42.17 | C |
| ATOM | 1824 | CD1 | TYR | B | 52 | 13.255 | 26.071 | 34.476 | 1.00 | 44.16 | C |
| ATOM | 1825 | CE1 | TYR | B | 52 | 13.964 | 24.904 | 34.275 | 1.00 | 44.97 | C |
| ATOM | 1826 | CD2 | TYR | B | 52 | 15.093 | 27.333 | 33.644 | 1.00 | 44.33 | C |
| ATOM | 1827 | CE2 | TYR | B | 52 | 15.815 | 26.160 | 33.424 | 1.00 | 43.97 | C |
| ATOM | 1828 | CZ  | TYR | B | 52 | 15.235 | 24.943 | 33.747 | 1.00 | 45.65 | C |
| ATOM | 1829 | OH  | TYR | B | 52 | 15.890 | 23.747 | 33.543 | 1.00 | 42.35 | O |
| ATOM | 1830 | C   | TYR | B | 52 | 12.864 | 30.639 | 35.929 | 1.00 | 46.67 | C |
| ATOM | 1831 | O   | TYR | B | 52 | 12.796 | 31.471 | 35.020 | 1.00 | 45.72 | O |
| ATOM | 1832 | N   | GLY | B | 53 | 12.412 | 30.868 | 37.158 | 1.00 | 47.04 | N |
| ATOM | 1833 | CA  | GLY | B | 53 | 11.966 | 32.191 | 37.563 | 1.00 | 50.93 | C |
| ATOM | 1834 | C   | GLY | B | 53 | 10.470 | 32.429 | 37.737 | 1.00 | 51.15 | C |
| ATOM | 1835 | O   | GLY | B | 53 | 10.061 | 33.549 | 38.040 | 1.00 | 55.14 | O |
| ATOM | 1836 | N   | TYR | B | 54 | 9.648  | 31.400 | 37.560 | 1.00 | 45.82 | N |
| ATOM | 1837 | CA  | TYR | B | 54 | 8.197  | 31.606 | 37.536 | 1.00 | 50.84 | C |
| ATOM | 1838 | CB  | TYR | B | 54 | 7.476  | 30.424 | 36.867 | 1.00 | 46.17 | C |
| ATOM | 1839 | CG  | TYR | B | 54 | 7.907  | 30.281 | 35.434 | 1.00 | 49.04 | C |
| ATOM | 1840 | CD1 | TYR | B | 54 | 9.091  | 29.622 | 35.111 | 1.00 | 44.96 | C |
| ATOM | 1841 | CE1 | TYR | B | 54 | 9.505  | 29.521 | 33.809 | 1.00 | 44.46 | C |
| ATOM | 1842 | CD2 | TYR | B | 54 | 7.170  | 30.856 | 34.404 | 1.00 | 49.21 | C |
| ATOM | 1843 | CE2 | TYR | B | 54 | 7.589  | 30.764 | 33.095 | 1.00 | 44.23 | C |
| ATOM | 1844 | CZ  | TYR | B | 54 | 8.749  | 30.090 | 32.809 | 1.00 | 39.77 | C |
| ATOM | 1845 | OH  | TYR | B | 54 | 9.163  | 29.990 | 31.517 | 1.00 | 45.61 | O |
| ATOM | 1846 | C   | TYR | B | 54 | 7.601  | 31.948 | 38.907 | 1.00 | 54.91 | C |
| ATOM | 1847 | O   | TYR | B | 54 | 6.565  | 32.621 | 38.978 | 1.00 | 53.64 | O |
| ATOM | 1848 | N   | THR | B | 55 | 8.279  | 31.495 | 39.933 | 1.00 | 45.28 | N |
| ATOM | 1849 | CA  | THR | B | 55 | 7.952  | 31.752 | 41.313 | 1.00 | 48.27 | C |
| ATOM | 1850 | CB  | THR | B | 55 | 8.643  | 30.702 | 42.150 | 1.00 | 51.17 | C |
| ATOM | 1851 | OG1 | THR | B | 55 | 7.943  | 29.471 | 41.996 | 1.00 | 57.40 | O |
| ATOM | 1852 | CG2 | THR | B | 55 | 8.663  | 31.059 | 43.547 | 1.00 | 41.80 | C |

TABLE 12-continued

Coordinates for pro MMP9(35-444 ΔFnII) (SEQ ID NO: 12) complex with Example 2

| ATOM | 1853 | C | THR | B | 55 | 8.202 | 33.224 | 41.761 | 1.00 | 54.15 | C |
|---|---|---|---|---|---|---|---|---|---|---|---|
| ATOM | 1854 | O | THR | B | 55 | 7.374 | 33.820 | 42.397 | 1.00 | 54.77 | O |
| ATOM | 1855 | O | ALA | B | 56 | 7.930 | 36.420 | 39.499 | 1.00 | 20.00 | O |
| ATOM | 1856 | N | ALA | B | 56 | 9.209 | 33.911 | 41.294 | 1.00 | 20.00 | N |
| ATOM | 1857 | CA | ALA | B | 56 | 9.058 | 35.336 | 41.378 | 1.00 | 20.00 | C |
| ATOM | 1858 | C | ALA | B | 56 | 7.833 | 35.788 | 40.545 | 1.00 | 20.00 | C |
| ATOM | 1859 | CB | ALA | B | 56 | 10.290 | 36.015 | 40.958 | 1.00 | 20.00 | C |
| ATOM | 1860 | O | ALA | B | 57 | 3.377 | 36.169 | 42.068 | 1.00 | 20.00 | O |
| ATOM | 1861 | N | ALA | B | 57 | 6.673 | 35.394 | 41.043 | 1.00 | 20.00 | N |
| ATOM | 1862 | CA | ALA | B | 57 | 5.344 | 35.856 | 40.648 | 1.00 | 20.00 | C |
| ATOM | 1863 | C | ALA | B | 57 | 4.592 | 36.007 | 41.993 | 1.00 | 20.00 | C |
| ATOM | 1864 | CB | ALA | B | 57 | 4.689 | 34.836 | 39.793 | 1.00 | 20.00 | C |
| ATOM | 1865 | O | ALA | B | 58 | 5.796 | 38.448 | 43.683 | 1.00 | 20.00 | O |
| ATOM | 1866 | N | ALA | B | 58 | 5.388 | 35.913 | 43.055 | 1.00 | 20.00 | N |
| ATOM | 1867 | CA | ALA | B | 58 | 5.052 | 36.266 | 44.405 | 1.00 | 20.00 | C |
| ATOM | 1868 | C | ALA | B | 58 | 5.398 | 37.735 | 44.609 | 1.00 | 20.00 | C |
| ATOM | 1869 | CB | ALA | B | 58 | 5.844 | 35.404 | 45.357 | 1.00 | 20.00 | C |
| ATOM | 1870 | O | ALA | B | 66 | −2.608 | 27.406 | 43.594 | 1.00 | 20.00 | O |
| ATOM | 1871 | N | ALA | B | 66 | −3.236 | 29.115 | 45.678 | 1.00 | 20.00 | N |
| ATOM | 1872 | CA | ALA | B | 66 | −2.373 | 29.544 | 44.603 | 1.00 | 20.00 | C |
| ATOM | 1873 | C | ALA | B | 66 | −1.920 | 28.387 | 43.703 | 1.00 | 20.00 | C |
| ATOM | 1874 | CB | ALA | B | 66 | −1.188 | 30.347 | 45.181 | 1.00 | 20.00 | C |
| ATOM | 1875 | N | LEU | B | 67 | −0.772 | 28.537 | 43.064 | 1.00 | 42.04 | N |
| ATOM | 1876 | CA | LEU | B | 67 | −0.196 | 27.655 | 42.033 | 1.00 | 50.92 | C |
| ATOM | 1877 | CB | LEU | B | 67 | −0.050 | 26.184 | 42.414 | 1.00 | 58.64 | C |
| ATOM | 1878 | CG | LEU | B | 67 | 1.407 | 25.790 | 42.126 | 1.00 | 52.48 | C |
| ATOM | 1879 | CD1 | LEU | B | 67 | 2.269 | 25.653 | 43.349 | 1.00 | 52.32 | C |
| ATOM | 1880 | CD2 | LEU | B | 67 | 1.668 | 24.742 | 41.150 | 1.00 | 54.42 | C |
| ATOM | 1881 | C | LEU | B | 67 | −0.630 | 27.803 | 40.596 | 1.00 | 50.20 | C |
| ATOM | 1882 | O | LEU | B | 67 | 0.186 | 27.950 | 39.746 | 1.00 | 51.48 | O |
| ATOM | 1883 | N | GLY | B | 68 | −1.905 | 27.772 | 40.313 | 1.00 | 51.51 | N |
| ATOM | 1884 | CA | GLY | B | 68 | −2.343 | 27.911 | 38.944 | 1.00 | 45.43 | C |
| ATOM | 1885 | C | GLY | B | 68 | −1.844 | 29.096 | 38.168 | 1.00 | 49.61 | C |
| ATOM | 1886 | O | GLY | B | 68 | −1.860 | 29.081 | 36.972 | 1.00 | 52.97 | O |
| ATOM | 1887 | N | PRO | B | 69 | −1.426 | 30.139 | 38.846 | 1.00 | 46.55 | N |
| ATOM | 1888 | CD | PRO | B | 69 | −2.344 | 30.493 | 39.922 | 1.00 | 41.74 | C |
| ATOM | 1889 | CA | PRO | B | 69 | −0.968 | 31.336 | 38.172 | 1.00 | 50.55 | C |
| ATOM | 1890 | CB | PRO | B | 69 | −1.186 | 32.406 | 39.231 | 1.00 | 50.74 | C |
| ATOM | 1891 | CG | PRO | B | 69 | −1.834 | 31.761 | 40.342 | 1.00 | 42.79 | C |
| ATOM | 1892 | C | PRO | B | 69 | 0.481 | 31.322 | 37.737 | 1.00 | 49.09 | C |
| ATOM | 1893 | O | PRO | B | 69 | 0.855 | 32.092 | 36.899 | 1.00 | 53.14 | O |
| ATOM | 1894 | N | ALA | B | 70 | 1.283 | 30.464 | 38.320 | 1.00 | 51.50 | N |
| ATOM | 1895 | CA | ALA | B | 70 | 2.663 | 30.349 | 37.974 | 1.00 | 46.90 | C |
| ATOM | 1896 | CB | ALA | B | 70 | 3.392 | 29.707 | 39.087 | 1.00 | 48.79 | C |
| ATOM | 1897 | C | ALA | B | 70 | 2.749 | 29.499 | 36.751 | 1.00 | 47.70 | C |
| ATOM | 1898 | O | ALA | B | 70 | 3.560 | 29.729 | 35.913 | 1.00 | 47.05 | O |
| ATOM | 1899 | N | LEU | B | 71 | 1.897 | 28.496 | 36.670 | 1.00 | 39.58 | N |
| ATOM | 1900 | CA | LEU | B | 71 | 1.761 | 27.681 | 35.469 | 1.00 | 51.55 | C |
| ATOM | 1901 | CB | LEU | B | 71 | 0.720 | 26.584 | 35.709 | 1.00 | 49.02 | C |
| ATOM | 1902 | CG | LEU | B | 71 | 1.002 | 25.752 | 36.960 | 1.00 | 51.84 | C |
| ATOM | 1903 | CD1 | LEU | B | 71 | −0.212 | 24.923 | 37.328 | 1.00 | 54.73 | C |
| ATOM | 1904 | CD2 | LEU | B | 71 | 2.215 | 24.870 | 36.750 | 1.00 | 50.67 | C |
| ATOM | 1905 | C | LEU | B | 71 | 1.386 | 28.516 | 34.232 | 1.00 | 46.05 | C |
| ATOM | 1906 | O | LEU | B | 71 | 1.909 | 28.306 | 33.143 | 1.00 | 37.81 | O |
| ATOM | 1907 | N | LEU | B | 72 | 0.478 | 29.459 | 34.424 | 1.00 | 44.27 | N |
| ATOM | 1908 | CA | LEU | B | 72 | 0.014 | 30.305 | 33.356 | 1.00 | 44.08 | C |
| ATOM | 1909 | CB | LEU | B | 72 | −1.115 | 31.192 | 33.843 | 1.00 | 46.39 | C |
| ATOM | 1910 | CG | LEU | B | 72 | −2.411 | 30.390 | 33.822 | 1.00 | 49.30 | C |
| ATOM | 1911 | CD1 | LEU | B | 72 | −3.418 | 31.009 | 34.735 | 1.00 | 48.38 | C |
| ATOM | 1912 | CD2 | LEU | B | 72 | −2.941 | 30.268 | 32.390 | 1.00 | 50.63 | C |
| ATOM | 1913 | C | LEU | B | 72 | 1.113 | 31.139 | 32.743 | 1.00 | 51.67 | C |
| ATOM | 1914 | O | LEU | B | 72 | 1.151 | 31.310 | 31.527 | 1.00 | 52.00 | O |
| ATOM | 1915 | N | LEU | B | 73 | 2.007 | 31.654 | 33.581 | 1.00 | 52.72 | N |
| ATOM | 1916 | CA | LEU | B | 73 | 3.142 | 32.454 | 33.113 | 1.00 | 48.71 | C |
| ATOM | 1917 | CB | LEU | B | 73 | 3.898 | 32.972 | 34.322 | 1.00 | 43.97 | C |
| ATOM | 1918 | CG | LEU | B | 73 | 2.996 | 33.888 | 35.119 | 1.00 | 53.68 | C |
| ATOM | 1919 | CD1 | LEU | B | 73 | 3.068 | 33.562 | 36.626 | 1.00 | 54.42 | C |
| ATOM | 1920 | CD2 | LEU | B | 73 | 3.357 | 35.337 | 34.800 | 1.00 | 48.14 | C |
| ATOM | 1921 | C | LEU | B | 73 | 4.077 | 31.616 | 32.246 | 1.00 | 50.60 | C |
| ATOM | 1922 | O | LEU | B | 73 | 4.693 | 32.094 | 31.283 | 1.00 | 46.57 | O |
| ATOM | 1923 | N | LEU | B | 74 | 4.175 | 30.354 | 32.639 | 1.00 | 48.06 | N |
| ATOM | 1924 | CA | LEU | B | 74 | 4.967 | 29.358 | 31.964 | 1.00 | 44.38 | C |
| ATOM | 1925 | CB | LEU | B | 74 | 5.073 | 28.142 | 32.881 | 1.00 | 43.61 | C |
| ATOM | 1926 | CG | LEU | B | 74 | 5.523 | 26.794 | 32.345 | 1.00 | 43.90 | C |
| ATOM | 1927 | CD1 | LEU | B | 74 | 6.656 | 26.981 | 31.376 | 1.00 | 50.89 | C |
| ATOM | 1928 | CD2 | LEU | B | 74 | 5.960 | 25.976 | 33.533 | 1.00 | 48.19 | C |
| ATOM | 1929 | C | LEU | B | 74 | 4.300 | 29.013 | 30.641 | 1.00 | 46.62 | C |

TABLE 12-continued

Coordinates for pro MMP9(35-444 ΔFnII) (SEQ ID NO: 12) complex with Example 2

| ATOM | 1930 | O | LEU | B | 74 | 4.932 | 29.030 | 29.594 | 1.00 | 49.23 | O |
|---|---|---|---|---|---|---|---|---|---|---|---|
| ATOM | 1931 | N | GLN | B | 75 | 3.005 | 28.739 | 30.692 | 1.00 | 47.87 | N |
| ATOM | 1932 | CA | GLN | B | 75 | 2.248 | 28.447 | 29.492 | 1.00 | 45.65 | C |
| ATOM | 1933 | CB | GLN | B | 75 | 0.797 | 28.120 | 29.846 | 1.00 | 49.31 | C |
| ATOM | 1934 | CG | GLN | B | 75 | 0.622 | 26.713 | 30.421 | 1.00 | 47.10 | C |
| ATOM | 1935 | CD | GLN | B | 75 | −0.503 | 26.624 | 31.440 | 1.00 | 49.82 | C |
| ATOM | 1936 | OE1 | GLN | B | 75 | −1.314 | 27.541 | 31.576 | 1.00 | 49.78 | O |
| ATOM | 1937 | NE2 | GLN | B | 75 | −0.555 | 25.514 | 32.163 | 1.00 | 48.43 | N |
| ATOM | 1938 | C | GLN | B | 75 | 2.359 | 29.606 | 28.512 | 1.00 | 47.55 | C |
| ATOM | 1939 | O | GLN | B | 75 | 2.631 | 29.390 | 27.343 | 1.00 | 48.73 | O |
| ATOM | 1940 | N | LYS | B | 76 | 2.194 | 30.836 | 28.992 | 1.00 | 46.78 | N |
| ATOM | 1941 | CA | LYS | B | 76 | 2.385 | 31.999 | 28.131 | 1.00 | 49.72 | C |
| ATOM | 1942 | CB | LYS | B | 76 | 2.146 | 33.306 | 28.896 | 1.00 | 47.68 | C |
| ATOM | 1943 | CG | LYS | B | 76 | 0.885 | 33.330 | 29.735 | 1.00 | 59.50 | C |
| ATOM | 1944 | CD | LYS | B | 76 | −0.252 | 34.109 | 29.087 | 1.00 | 63.81 | C |
| ATOM | 1945 | CE | LYS | B | 76 | −1.331 | 34.426 | 30.128 | 1.00 | 64.47 | C |
| ATOM | 1946 | NZ | LYS | B | 76 | −0.700 | 34.859 | 31.426 | 1.00 | 58.06 | N |
| ATOM | 1947 | C | LYS | B | 76 | 3.813 | 32.007 | 27.581 | 1.00 | 57.61 | C |
| ATOM | 1948 | O | LYS | B | 76 | 4.032 | 32.222 | 26.378 | 1.00 | 56.86 | O |
| ATOM | 1949 | N | GLN | B | 77 | 4.778 | 31.773 | 28.472 | 1.00 | 51.59 | N |
| ATOM | 1950 | CA | GLN | B | 77 | 6.196 | 31.856 | 28.137 | 1.00 | 51.45 | C |
| ATOM | 1951 | CB | GLN | B | 77 | 7.048 | 31.678 | 29.384 | 1.00 | 52.37 | C |
| ATOM | 1952 | CG | GLN | B | 77 | 8.521 | 31.870 | 29.125 | 1.00 | 50.47 | C |
| ATOM | 1953 | CD | GLN | B | 77 | 8.887 | 33.336 | 29.014 | 1.00 | 58.07 | C |
| ATOM | 1954 | OE1 | GLN | B | 77 | 8.309 | 34.183 | 29.706 | 1.00 | 55.27 | O |
| ATOM | 1955 | NE2 | GLN | B | 77 | 9.858 | 33.648 | 28.152 | 1.00 | 56.93 | N |
| ATOM | 1956 | C | GLN | B | 77 | 6.634 | 30.821 | 27.120 | 1.00 | 50.91 | C |
| ATOM | 1957 | O | GLN | B | 77 | 7.419 | 31.116 | 26.226 | 1.00 | 49.86 | O |
| ATOM | 1958 | N | LEU | B | 78 | 6.132 | 29.603 | 27.268 | 1.00 | 49.35 | N |
| ATOM | 1959 | CA | LEU | B | 78 | 6.502 | 28.521 | 26.371 | 1.00 | 49.59 | C |
| ATOM | 1960 | CB | LEU | B | 78 | 6.524 | 27.209 | 27.139 | 1.00 | 45.14 | C |
| ATOM | 1961 | CG | LEU | B | 78 | 7.607 | 27.155 | 28.192 | 1.00 | 48.66 | C |
| ATOM | 1962 | CD1 | LEU | B | 78 | 7.851 | 25.719 | 28.571 | 1.00 | 52.12 | C |
| ATOM | 1963 | CD2 | LEU | B | 78 | 8.863 | 27.786 | 27.619 | 1.00 | 51.85 | C |
| ATOM | 1964 | C | LEU | B | 78 | 5.572 | 28.381 | 25.162 | 1.00 | 50.72 | C |
| ATOM | 1965 | O | LEU | B | 78 | 5.739 | 27.464 | 24.354 | 1.00 | 48.94 | O |
| ATOM | 1966 | N | SER | B | 79 | 4.600 | 29.284 | 25.043 | 1.00 | 51.27 | N |
| ATOM | 1967 | CA | SER | B | 79 | 3.581 | 29.192 | 23.993 | 1.00 | 52.03 | C |
| ATOM | 1968 | CB | SER | B | 79 | 4.180 | 29.447 | 22.611 | 1.00 | 46.44 | C |
| ATOM | 1969 | OG | SER | B | 79 | 4.538 | 30.809 | 22.488 | 1.00 | 50.15 | O |
| ATOM | 1970 | C | SER | B | 79 | 2.866 | 27.845 | 24.025 | 1.00 | 50.70 | C |
| ATOM | 1971 | O | SER | B | 79 | 2.884 | 27.092 | 23.050 | 1.00 | 50.22 | O |
| ATOM | 1972 | N | LEU | B | 80 | 2.277 | 27.553 | 25.178 | 1.00 | 49.94 | N |
| ATOM | 1973 | CA | LEU | B | 80 | 1.455 | 26.382 | 25.403 | 1.00 | 50.88 | C |
| ATOM | 1974 | CB | LEU | B | 80 | 2.020 | 25.579 | 26.568 | 1.00 | 47.88 | C |
| ATOM | 1975 | CG | LEU | B | 80 | 3.430 | 25.011 | 26.591 | 1.00 | 53.46 | C |
| ATOM | 1976 | CD1 | LEU | B | 80 | 3.654 | 24.342 | 27.960 | 1.00 | 54.07 | C |
| ATOM | 1977 | CD2 | LEU | B | 80 | 3.660 | 24.025 | 25.442 | 1.00 | 54.57 | C |
| ATOM | 1978 | C | LEU | B | 80 | 0.051 | 26.871 | 25.790 | 1.00 | 55.38 | C |
| ATOM | 1979 | O | LEU | B | 80 | −0.100 | 28.003 | 26.265 | 1.00 | 48.86 | O |
| ATOM | 1980 | N | PRO | B | 81 | −0.977 | 26.016 | 25.615 | 1.00 | 55.87 | N |
| ATOM | 1981 | CD | PRO | B | 81 | −0.902 | 24.595 | 25.234 | 1.00 | 57.85 | C |
| ATOM | 1982 | CA | PRO | B | 81 | −2.336 | 26.401 | 25.999 | 1.00 | 55.92 | C |
| ATOM | 1983 | CB | PRO | B | 81 | −3.119 | 25.089 | 25.858 | 1.00 | 56.90 | C |
| ATOM | 1984 | CG | PRO | B | 81 | −2.324 | 24.243 | 24.943 | 1.00 | 43.55 | C |
| ATOM | 1985 | C | PRO | B | 81 | −2.375 | 26.847 | 27.460 | 1.00 | 52.47 | C |
| ATOM | 1986 | O | PRO | B | 81 | −2.129 | 26.015 | 28.329 | 1.00 | 50.16 | O |
| ATOM | 1987 | N | GLU | B | 82 | −2.647 | 28.128 | 27.710 | 1.00 | 53.49 | N |
| ATOM | 1988 | CA | GLU | B | 82 | −2.826 | 28.647 | 29.061 | 1.00 | 50.62 | C |
| ATOM | 1989 | CB | GLU | B | 82 | −2.993 | 30.172 | 29.047 | 1.00 | 56.07 | C |
| ATOM | 1990 | CG | GLU | B | 82 | −1.728 | 30.963 | 28.744 | 1.00 | 55.60 | C |
| ATOM | 1991 | CD | GLU | B | 82 | −1.644 | 31.361 | 27.296 | 1.00 | 63.99 | C |
| ATOM | 1992 | OE1 | GLU | B | 82 | −0.860 | 32.276 | 26.959 | 1.00 | 62.82 | O |
| ATOM | 1993 | OE2 | GLU | B | 82 | −2.381 | 30.758 | 26.485 | 1.00 | 74.92 | O |
| ATOM | 1994 | C | GLU | B | 82 | −4.045 | 28.011 | 29.737 | 1.00 | 53.29 | C |
| ATOM | 1995 | O | GLU | B | 82 | −5.130 | 28.598 | 29.781 | 1.00 | 51.58 | O |
| ATOM | 1996 | N | THR | B | 83 | −3.867 | 26.804 | 30.252 | 1.00 | 48.74 | N |
| ATOM | 1997 | CA | THR | B | 83 | −4.947 | 26.103 | 30.900 | 1.00 | 42.52 | C |
| ATOM | 1998 | CB | THR | B | 83 | −4.840 | 24.597 | 30.715 | 1.00 | 41.01 | C |
| ATOM | 1999 | OG1 | THR | B | 83 | −3.788 | 24.102 | 31.543 | 1.00 | 45.14 | O |
| ATOM | 2000 | CG2 | THR | B | 83 | −4.562 | 24.236 | 29.280 | 1.00 | 43.07 | C |
| ATOM | 2001 | C | THR | B | 83 | −4.837 | 26.339 | 32.387 | 1.00 | 49.10 | C |
| ATOM | 2002 | O | THR | B | 83 | −5.675 | 25.865 | 33.154 | 1.00 | 48.31 | O |
| ATOM | 2003 | N | GLY | B | 84 | −3.786 | 27.048 | 32.795 | 1.00 | 49.76 | N |
| ATOM | 2004 | CA | GLY | B | 84 | −3.467 | 27.205 | 34.207 | 1.00 | 50.96 | C |
| ATOM | 2005 | C | GLY | B | 84 | −3.413 | 25.890 | 34.967 | 1.00 | 47.75 | C |
| ATOM | 2006 | O | GLY | B | 84 | −3.328 | 25.877 | 36.189 | 1.00 | 58.69 | O |

TABLE 12-continued

Coordinates for pro MMP9(35-444 ΔFnII) (SEQ ID NO: 12) complex with Example 2

| ATOM | 2007 | N   | GLU | B | 85 | −3.435  | 24.780 | 34.239 | 1.00 | 49.08 | N |
|------|------|-----|-----|---|----|---------|--------|--------|------|-------|---|
| ATOM | 2008 | CA  | GLU | B | 85 | −3.564  | 23.457 | 34.835 | 1.00 | 51.07 | C |
| ATOM | 2009 | CB  | GLU | B | 85 | −4.746  | 22.727 | 34.196 | 1.00 | 50.40 | C |
| ATOM | 2010 | CG  | GLU | B | 85 | −5.505  | 21.833 | 35.160 | 1.00 | 56.50 | C |
| ATOM | 2011 | CD  | GLU | B | 85 | −6.104  | 22.608 | 36.314 | 1.00 | 54.88 | C |
| ATOM | 2012 | OE1 | GLU | B | 85 | −5.922  | 22.170 | 37.472 | 1.00 | 55.52 | O |
| ATOM | 2013 | OE2 | GLU | B | 85 | −6.738  | 23.658 | 36.062 | 1.00 | 53.99 | O |
| ATOM | 2014 | C   | GLU | B | 85 | −2.293  | 22.635 | 34.640 | 1.00 | 54.43 | C |
| ATOM | 2015 | O   | GLU | B | 85 | −1.627  | 22.735 | 33.606 | 1.00 | 52.41 | O |
| ATOM | 2016 | N   | LEU | B | 86 | −1.955  | 21.816 | 35.632 | 1.00 | 55.34 | N |
| ATOM | 2017 | CA  | LEU | B | 86 | −0.776  | 20.965 | 35.527 | 1.00 | 48.00 | C |
| ATOM | 2018 | CB  | LEU | B | 86 | −0.290  | 20.538 | 36.908 | 1.00 | 47.31 | C |
| ATOM | 2019 | CG  | LEU | B | 86 | 1.065   | 19.844 | 36.916 | 1.00 | 55.60 | C |
| ATOM | 2020 | CD1 | LEU | B | 86 | 1.944   | 20.450 | 35.862 | 1.00 | 46.17 | C |
| ATOM | 2021 | CD2 | LEU | B | 86 | 1.704   | 19.951 | 38.294 | 1.00 | 66.48 | C |
| ATOM | 2022 | C   | LEU | B | 86 | −1.108  | 19.756 | 34.661 | 1.00 | 49.70 | C |
| ATOM | 2023 | O   | LEU | B | 86 | −1.050  | 18.618 | 35.111 | 1.00 | 47.88 | O |
| ATOM | 2024 | N   | ASP | B | 87 | −1.438  | 20.030 | 33.401 | 1.00 | 53.60 | N |
| ATOM | 2025 | CA  | ASP | B | 87 | −1.930  | 19.032 | 32.454 | 1.00 | 46.03 | C |
| ATOM | 2026 | CB  | ASP | B | 87 | −2.799  | 19.747 | 31.442 | 1.00 | 43.25 | C |
| ATOM | 2027 | CG  | ASP | B | 87 | −2.117  | 20.984 | 30.884 | 1.00 | 48.52 | C |
| ATOM | 2028 | OD1 | ASP | B | 87 | −0.867  | 21.011 | 30.871 | 1.00 | 48.99 | O |
| ATOM | 2029 | OD2 | ASP | B | 87 | −2.818  | 21.927 | 30.457 | 1.00 | 47.11 | O |
| ATOM | 2030 | C   | ASP | B | 87 | −0.810  | 18.286 | 31.725 | 1.00 | 50.42 | C |
| ATOM | 2031 | O   | ASP | B | 87 | 0.373   | 18.501 | 31.987 | 1.00 | 52.06 | O |
| ATOM | 2032 | N   | SER | B | 88 | −1.189  | 17.412 | 30.798 | 1.00 | 48.58 | N |
| ATOM | 2033 | CA  | SER | B | 88 | −0.212  | 16.609 | 30.059 | 1.00 | 52.39 | C |
| ATOM | 2034 | CB  | SER | B | 88 | −0.909  | 15.626 | 29.111 | 1.00 | 51.95 | C |
| ATOM | 2035 | OG  | SER | B | 88 | −1.724  | 14.706 | 29.809 | 1.00 | 57.77 | O |
| ATOM | 2036 | C   | SER | B | 88 | 0.774   | 17.460 | 29.257 | 1.00 | 53.32 | C |
| ATOM | 2037 | O   | SER | B | 88 | 1.969   | 17.182 | 29.243 | 1.00 | 60.80 | O |
| ATOM | 2038 | N   | ALA | B | 89 | 0.275   | 18.481 | 28.577 | 1.00 | 48.03 | N |
| ATOM | 2039 | CA  | ALA | B | 89 | 1.131   | 19.295 | 27.730 | 1.00 | 45.61 | C |
| ATOM | 2040 | CB  | ALA | B | 89 | 0.287   | 20.216 | 26.876 | 1.00 | 36.83 | C |
| ATOM | 2041 | C   | ALA | B | 89 | 2.160   | 20.096 | 28.551 | 1.00 | 52.29 | C |
| ATOM | 2042 | O   | ALA | B | 89 | 3.283   | 20.328 | 28.090 | 1.00 | 52.62 | O |
| ATOM | 2043 | N   | THR | B | 90 | 1.776   | 20.506 | 29.763 | 1.00 | 49.75 | N |
| ATOM | 2044 | CA  | THR | B | 90 | 2.633   | 21.324 | 30.627 | 1.00 | 46.94 | C |
| ATOM | 2045 | CB  | THR | B | 90 | 1.802   | 22.076 | 31.705 | 1.00 | 53.89 | C |
| ATOM | 2046 | OG1 | THR | B | 90 | 1.050   | 23.140 | 31.088 | 1.00 | 53.18 | O |
| ATOM | 2047 | CG2 | THR | B | 90 | 2.695   | 22.645 | 32.803 | 1.00 | 46.14 | C |
| ATOM | 2048 | C   | THR | B | 90 | 3.710   | 20.468 | 31.287 | 1.00 | 53.06 | C |
| ATOM | 2049 | O   | THR | B | 90 | 4.884   | 20.852 | 31.367 | 1.00 | 49.03 | O |
| ATOM | 2050 | N   | LEU | B | 91 | 3.361   | 19.279 | 31.719 | 1.00 | 53.98 | N |
| ATOM | 2051 | CA  | LEU | B | 91 | 4.349   | 18.365 | 32.267 | 1.00 | 54.98 | C |
| ATOM | 2052 | CB  | LEU | B | 91 | 3.643   | 17.205 | 32.911 | 1.00 | 55.84 | C |
| ATOM | 2053 | CG  | LEU | B | 91 | 3.193   | 17.406 | 34.325 | 1.00 | 62.72 | C |
| ATOM | 2054 | CD1 | LEU | B | 91 | 2.079   | 16.476 | 34.560 | 1.00 | 69.76 | C |
| ATOM | 2055 | CD2 | LEU | B | 91 | 4.320   | 17.096 | 35.201 | 1.00 | 58.96 | C |
| ATOM | 2056 | C   | LEU | B | 91 | 5.303   | 17.834 | 31.221 | 1.00 | 57.62 | C |
| ATOM | 2057 | O   | LEU | B | 91 | 6.425   | 17.520 | 31.490 | 1.00 | 51.02 | O |
| ATOM | 2058 | N   | LYS | B | 92 | 4.816   | 17.698 | 30.015 | 1.00 | 56.12 | N |
| ATOM | 2059 | CA  | LYS | B | 92 | 5.666   | 17.271 | 28.912 | 1.00 | 49.79 | C |
| ATOM | 2060 | CB  | LYS | B | 92 | 4.839   | 17.103 | 27.637 | 1.00 | 47.78 | C |
| ATOM | 2061 | CG  | LYS | B | 92 | 5.651   | 16.958 | 26.381 | 1.00 | 46.22 | C |
| ATOM | 2062 | CD  | LYS | B | 92 | 5.383   | 18.130 | 25.452 | 1.00 | 54.69 | C |
| ATOM | 2063 | CE  | LYS | B | 92 | 6.350   | 18.149 | 24.248 | 1.00 | 61.93 | C |
| ATOM | 2064 | NZ  | LYS | B | 92 | 6.198   | 16.986 | 23.320 | 1.00 | 46.05 | N |
| ATOM | 2065 | C   | LYS | B | 92 | 6.775   | 18.283 | 28.709 | 1.00 | 52.62 | C |
| ATOM | 2066 | O   | LYS | B | 92 | 7.951   | 17.927 | 28.694 | 1.00 | 54.23 | O |
| ATOM | 2067 | N   | ALA | B | 93 | 6.399   | 19.553 | 28.590 | 1.00 | 55.23 | N |
| ATOM | 2068 | CA  | ALA | B | 93 | 7.374   | 20.626 | 28.415 | 1.00 | 47.69 | C |
| ATOM | 2069 | CB  | ALA | B | 93 | 6.678   | 21.962 | 28.280 | 1.00 | 48.60 | C |
| ATOM | 2070 | C   | ALA | B | 93 | 8.355   | 20.654 | 29.580 | 1.00 | 50.34 | C |
| ATOM | 2071 | O   | ALA | B | 93 | 9.569   | 20.700 | 29.382 | 1.00 | 52.21 | O |
| ATOM | 2072 | N   | MET | B | 94 | 7.817   | 20.614 | 30.793 | 1.00 | 51.09 | N |
| ATOM | 2073 | CA  | MET | B | 94 | 8.637   | 20.661 | 31.997 | 1.00 | 51.97 | C |
| ATOM | 2074 | CB  | MET | B | 94 | 7.762   | 20.596 | 33.237 | 1.00 | 49.57 | C |
| ATOM | 2075 | CG  | MET | B | 94 | 6.923   | 21.833 | 33.468 | 1.00 | 51.26 | C |
| ATOM | 2076 | SD  | MET | B | 94 | 6.156   | 21.678 | 35.084 | 1.00 | 47.56 | S |
| ATOM | 2077 | CE  | MET | B | 94 | 5.723   | 23.391 | 35.442 | 1.00 | 40.60 | C |
| ATOM | 2078 | C   | MET | B | 94 | 9.662   | 19.538 | 32.054 | 1.00 | 53.18 | C |
| ATOM | 2079 | O   | MET | B | 94 | 10.717  | 19.698 | 32.658 | 1.00 | 49.72 | O |
| ATOM | 2080 | N   | ARG | B | 95 | 9.356   | 18.410 | 31.417 | 1.00 | 56.06 | N |
| ATOM | 2081 | CA  | ARG | B | 95 | 10.259  | 17.258 | 31.422 | 1.00 | 50.30 | C |
| ATOM | 2082 | CB  | ARG | B | 95 | 9.470   | 15.950 | 31.469 | 1.00 | 56.50 | C |
| ATOM | 2083 | CG  | ARG | B | 95 | 9.273   | 15.394 | 32.870 | 1.00 | 62.34 | C |

TABLE 12-continued

Coordinates for pro MMP9(35-444 ΔFnII) (SEQ ID NO: 12) complex with Example 2

| ATOM | 2084 | CD  | ARG | B | 95  | 8.979  | 13.902 | 32.824 | 1.00 | 62.36 | C |
|------|------|-----|-----|---|-----|--------|--------|--------|------|-------|---|
| ATOM | 2085 | NE  | ARG | B | 95  | 7.557  | 13.609 | 32.989 | 1.00 | 72.70 | N |
| ATOM | 2086 | CZ  | ARG | B | 95  | 6.992  | 13.273 | 34.145 | 1.00 | 72.52 | C |
| ATOM | 2087 | NH1 | ARG | B | 95  | 7.720  | 13.184 | 35.251 | 1.00 | 68.51 | N |
| ATOM | 2088 | NH2 | ARG | B | 95  | 5.696  | 13.019 | 34.189 | 1.00 | 75.03 | N |
| ATOM | 2089 | C   | ARG | B | 95  | 11.207 | 17.209 | 30.231 | 1.00 | 51.21 | C |
| ATOM | 2090 | O   | ARG | B | 95  | 12.065 | 16.334 | 30.172 | 1.00 | 48.41 | O |
| ATOM | 2091 | N   | THR | B | 96  | 11.049 | 18.115 | 29.268 | 1.00 | 47.61 | N |
| ATOM | 2092 | CA  | THR | B | 96  | 11.957 | 18.096 | 28.129 | 1.00 | 51.48 | C |
| ATOM | 2093 | CB  | THR | B | 96  | 11.266 | 18.478 | 26.794 | 1.00 | 47.32 | C |
| ATOM | 2094 | OG1 | THR | B | 96  | 12.101 | 19.379 | 26.059 | 1.00 | 48.87 | O |
| ATOM | 2095 | CG2 | THR | B | 96  | 9.959  | 19.140 | 27.045 | 1.00 | 48.06 | C |
| ATOM | 2096 | C   | THR | B | 96  | 13.201 | 18.951 | 28.391 | 1.00 | 49.48 | C |
| ATOM | 2097 | O   | THR | B | 96  | 13.094 | 20.032 | 28.979 | 1.00 | 42.82 | O |
| ATOM | 2098 | N   | PRO | B | 97  | 14.378 | 18.455 | 27.950 | 1.00 | 46.85 | N |
| ATOM | 2099 | CD  | PRO | B | 97  | 14.467 | 17.278 | 27.071 | 1.00 | 46.16 | C |
| ATOM | 2100 | CA  | PRO | B | 97  | 15.698 | 19.056 | 28.175 | 1.00 | 43.98 | C |
| ATOM | 2101 | CB  | PRO | B | 97  | 16.660 | 18.109 | 27.448 | 1.00 | 44.20 | C |
| ATOM | 2102 | CG  | PRO | B | 97  | 15.899 | 16.857 | 27.224 | 1.00 | 47.91 | C |
| ATOM | 2103 | C   | PRO | B | 97  | 15.758 | 20.414 | 27.532 | 1.00 | 44.23 | C |
| ATOM | 2104 | O   | PRO | B | 97  | 15.194 | 20.625 | 26.461 | 1.00 | 43.63 | O |
| ATOM | 2105 | N   | ARG | B | 98  | 16.451 | 21.328 | 28.192 | 1.00 | 47.24 | N |
| ATOM | 2106 | CA  | ARG | B | 98  | 16.443 | 22.717 | 27.792 | 1.00 | 47.91 | C |
| ATOM | 2107 | CB  | ARG | B | 98  | 15.295 | 23.433 | 28.480 | 1.00 | 40.48 | C |
| ATOM | 2108 | CG  | ARG | B | 98  | 15.423 | 23.430 | 29.999 | 1.00 | 44.00 | C |
| ATOM | 2109 | CD  | ARG | B | 98  | 14.477 | 24.439 | 30.636 | 1.00 | 42.89 | C |
| ATOM | 2110 | NE  | ARG | B | 98  | 15.016 | 25.796 | 30.570 | 1.00 | 40.97 | N |
| ATOM | 2111 | CZ  | ARG | B | 98  | 14.272 | 26.895 | 30.496 | 1.00 | 40.29 | C |
| ATOM | 2112 | NH1 | ARG | B | 98  | 12.949 | 26.810 | 30.450 | 1.00 | 36.03 | N |
| ATOM | 2113 | NH2 | ARG | B | 98  | 14.854 | 28.080 | 30.445 | 1.00 | 41.17 | N |
| ATOM | 2114 | C   | ARG | B | 98  | 17.735 | 23.410 | 28.182 | 1.00 | 44.27 | C |
| ATOM | 2115 | O   | ARG | B | 98  | 18.654 | 22.794 | 28.726 | 1.00 | 44.27 | O |
| ATOM | 2116 | N   | CYS | B | 99  | 17.781 | 24.704 | 27.885 | 1.00 | 41.10 | N |
| ATOM | 2117 | CA  | CYS | B | 99  | 18.846 | 25.575 | 28.335 | 1.00 | 39.98 | C |
| ATOM | 2118 | CB  | CYS | B | 99  | 18.827 | 26.869 | 27.540 | 1.00 | 42.96 | C |
| ATOM | 2119 | SG  | CYS | B | 99  | 19.942 | 28.076 | 28.253 | 1.00 | 46.56 | S |
| ATOM | 2120 | C   | CYS | B | 99  | 18.678 | 25.920 | 29.811 | 1.00 | 44.32 | C |
| ATOM | 2121 | O   | CYS | B | 99  | 17.564 | 26.000 | 30.312 | 1.00 | 41.65 | O |
| ATOM | 2122 | N   | GLY | B | 100 | 19.797 | 26.145 | 30.491 | 1.00 | 45.28 | N |
| ATOM | 2123 | CA  | GLY | B | 100 | 19.794 | 26.518 | 31.887 | 1.00 | 39.07 | C |
| ATOM | 2124 | C   | GLY | B | 100 | 19.355 | 27.946 | 32.133 | 1.00 | 43.31 | C |
| ATOM | 2125 | O   | GLY | B | 100 | 18.754 | 28.248 | 33.164 | 1.00 | 50.02 | O |
| ATOM | 2126 | N   | VAL | B | 101 | 19.644 | 28.843 | 31.204 | 1.00 | 40.78 | N |
| ATOM | 2127 | CA  | VAL | B | 101 | 19.275 | 30.227 | 31.436 | 1.00 | 44.42 | C |
| ATOM | 2128 | CB  | VAL | B | 101 | 19.655 | 31.119 | 30.261 | 1.00 | 43.99 | C |
| ATOM | 2129 | CG1 | VAL | B | 101 | 19.245 | 32.570 | 30.556 | 1.00 | 47.54 | C |
| ATOM | 2130 | CG2 | VAL | B | 101 | 21.148 | 31.033 | 30.010 | 1.00 | 43.85 | C |
| ATOM | 2131 | C   | VAL | B | 101 | 17.779 | 30.385 | 31.786 | 1.00 | 47.40 | C |
| ATOM | 2132 | O   | VAL | B | 101 | 16.918 | 29.884 | 31.058 | 1.00 | 45.60 | O |
| ATOM | 2133 | N   | PRO | B | 102 | 17.477 | 31.061 | 32.919 | 1.00 | 43.88 | N |
| ATOM | 2134 | CD  | PRO | B | 102 | 18.509 | 31.419 | 33.908 | 1.00 | 44.31 | C |
| ATOM | 2135 | CA  | PRO | B | 102 | 16.128 | 31.448 | 33.375 | 1.00 | 48.59 | C |
| ATOM | 2136 | CB  | PRO | B | 102 | 16.421 | 32.416 | 34.530 | 1.00 | 45.73 | C |
| ATOM | 2137 | CG  | PRO | B | 102 | 17.719 | 31.967 | 35.075 | 1.00 | 42.92 | C |
| ATOM | 2138 | C   | PRO | B | 102 | 15.289 | 32.174 | 32.306 | 1.00 | 51.27 | C |
| ATOM | 2139 | O   | PRO | B | 102 | 15.873 | 32.816 | 31.426 | 1.00 | 51.78 | O |
| ATOM | 2140 | N   | ASP | B | 103 | 13.956 | 32.087 | 32.396 | 1.00 | 52.15 | N |
| ATOM | 2141 | CA  | ASP | B | 103 | 13.042 | 32.752 | 31.449 | 1.00 | 48.21 | C |
| ATOM | 2142 | CB  | ASP | B | 103 | 11.892 | 31.815 | 31.058 | 1.00 | 45.24 | C |
| ATOM | 2143 | CG  | ASP | B | 103 | 12.359 | 30.421 | 30.748 | 1.00 | 44.34 | C |
| ATOM | 2144 | OD1 | ASP | B | 103 | 13.469 | 30.274 | 30.198 | 1.00 | 46.82 | O |
| ATOM | 2145 | OD2 | ASP | B | 103 | 11.612 | 29.473 | 31.037 | 1.00 | 38.32 | O |
| ATOM | 2146 | C   | ASP | B | 103 | 12.435 | 34.061 | 31.981 | 1.00 | 45.02 | C |
| ATOM | 2147 | O   | ASP | B | 103 | 12.082 | 34.938 | 31.208 | 1.00 | 45.25 | O |
| ATOM | 2148 | N   | LEU | B | 104 | 12.261 | 34.161 | 33.296 | 1.00 | 50.42 | N |
| ATOM | 2149 | CA  | LEU | B | 104 | 11.806 | 35.399 | 33.926 | 1.00 | 49.12 | C |
| ATOM | 2150 | CB  | LEU | B | 104 | 10.384 | 35.255 | 34.468 | 1.00 | 48.54 | C |
| ATOM | 2151 | CG  | LEU | B | 104 | 9.277  | 34.781 | 33.525 | 1.00 | 50.78 | C |
| ATOM | 2152 | CD1 | LEU | B | 104 | 7.999  | 34.511 | 34.319 | 1.00 | 57.37 | C |
| ATOM | 2153 | CD2 | LEU | B | 104 | 9.009  | 35.790 | 32.423 | 1.00 | 53.26 | C |
| ATOM | 2154 | C   | LEU | B | 104 | 12.749 | 35.798 | 35.067 | 1.00 | 59.64 | C |
| ATOM | 2155 | O   | LEU | B | 104 | 13.551 | 34.981 | 35.546 | 1.00 | 56.14 | O |
| ATOM | 2156 | N   | GLY | B | 105 | 12.616 | 37.020 | 35.519 | 1.00 | 60.65 | N |
| ATOM | 2157 | CA  | GLY | B | 105 | 13.252 | 37.429 | 36.736 | 1.00 | 56.94 | C |
| ATOM | 2158 | C   | GLY | B | 105 | 14.666 | 37.886 | 36.576 | 1.00 | 65.63 | C |
| ATOM | 2159 | O   | GLY | B | 105 | 15.353 | 37.483 | 35.666 | 1.00 | 64.02 | O |
| ATOM | 2160 | N   | ARG | B | 106 | 15.074 | 38.742 | 37.498 | 1.00 | 64.07 | N |

TABLE 12-continued

Coordinates for pro MMP9(35-444 ΔFnII) (SEQ ID NO: 12) complex with Example 2

| ATOM | 2161 | CA | ARG | B | 106 | 16.433 | 39.156 | 37.640 | 1.00 | 72.26 | C |
|---|---|---|---|---|---|---|---|---|---|---|---|
| ATOM | 2162 | CB | ARG | B | 106 | 16.541 | 40.668 | 37.678 | 1.00 | 76.42 | C |
| ATOM | 2163 | CG | ARG | B | 106 | 16.794 | 41.317 | 36.331 | 1.00 | 65.95 | C |
| ATOM | 2164 | CD | ARG | B | 106 | 17.360 | 40.345 | 35.303 | 1.00 | 68.91 | C |
| ATOM | 2165 | NE | ARG | B | 106 | 17.183 | 40.824 | 33.932 | 1.00 | 71.94 | N |
| ATOM | 2166 | CZ | ARG | B | 106 | 17.853 | 41.837 | 33.387 | 1.00 | 63.90 | C |
| ATOM | 2167 | NH1 | ARG | B | 106 | 17.623 | 42.201 | 32.141 | 1.00 | 57.67 | N |
| ATOM | 2168 | NH2 | ARG | B | 106 | 18.751 | 42.488 | 34.095 | 1.00 | 65.93 | N |
| ATOM | 2169 | C | ARG | B | 106 | 16.882 | 38.590 | 38.949 | 1.00 | 73.21 | C |
| ATOM | 2170 | O | ARG | B | 106 | 17.078 | 39.286 | 39.879 | 1.00 | 76.40 | O |
| ATOM | 2171 | N | PHE | B | 107 | 17.040 | 37.296 | 39.026 | 1.00 | 71.68 | N |
| ATOM | 2172 | CA | PHE | B | 107 | 17.601 | 36.761 | 40.205 | 1.00 | 75.30 | C |
| ATOM | 2173 | CB | PHE | B | 107 | 17.712 | 35.271 | 40.107 | 1.00 | 79.20 | C |
| ATOM | 2174 | CG | PHE | B | 107 | 16.406 | 34.595 | 40.270 | 1.00 | 87.63 | C |
| ATOM | 2175 | CD1 | PHE | B | 107 | 16.023 | 34.095 | 41.492 | 1.00 | 89.90 | C |
| ATOM | 2176 | CD2 | PHE | B | 107 | 15.533 | 34.509 | 39.220 | 1.00 | 84.20 | C |
| ATOM | 2177 | CE1 | PHE | B | 107 | 14.811 | 33.497 | 41.646 | 1.00 | 85.03 | C |
| ATOM | 2178 | CE2 | PHE | B | 107 | 14.335 | 33.919 | 39.385 | 1.00 | 71.70 | C |
| ATOM | 2179 | CZ | PHE | B | 107 | 13.975 | 33.411 | 40.603 | 1.00 | 71.75 | C |
| ATOM | 2180 | C | PHE | B | 107 | 18.922 | 37.394 | 40.334 | 1.00 | 70.91 | C |
| ATOM | 2181 | O | PHE | B | 107 | 19.163 | 38.091 | 41.291 | 1.00 | 65.04 | O |
| ATOM | 2182 | N | GLN | B | 108 | 19.790 | 37.205 | 39.363 | 1.00 | 70.72 | N |
| ATOM | 2183 | CA | GLN | B | 108 | 21.087 | 37.834 | 39.468 | 1.00 | 67.59 | C |
| ATOM | 2184 | CB | GLN | B | 108 | 22.190 | 36.976 | 38.957 | 1.00 | 57.57 | C |
| ATOM | 2185 | CG | GLN | B | 108 | 23.455 | 37.672 | 39.141 | 1.00 | 57.57 | C |
| ATOM | 2186 | CD | GLN | B | 108 | 24.595 | 36.778 | 38.968 | 1.00 | 68.33 | C |
| ATOM | 2187 | OE1 | GLN | B | 108 | 25.731 | 37.200 | 39.035 | 1.00 | 61.07 | O |
| ATOM | 2188 | NE2 | GLN | B | 108 | 24.313 | 35.523 | 38.717 | 1.00 | 57.45 | N |
| ATOM | 2189 | C | GLN | B | 108 | 21.238 | 39.181 | 38.826 | 1.00 | 67.96 | C |
| ATOM | 2190 | O | GLN | B | 108 | 20.581 | 39.525 | 37.873 | 1.00 | 67.24 | O |
| ATOM | 2191 | N | THR | B | 109 | 22.158 | 39.936 | 39.366 | 1.00 | 60.34 | N |
| ATOM | 2192 | CA | THR | B | 109 | 22.378 | 41.300 | 38.900 | 1.00 | 64.84 | C |
| ATOM | 2193 | CB | THR | B | 109 | 22.268 | 42.324 | 40.076 | 1.00 | 72.36 | C |
| ATOM | 2194 | OG1 | THR | B | 109 | 21.541 | 43.486 | 39.653 | 1.00 | 76.39 | O |
| ATOM | 2195 | CG2 | THR | B | 109 | 23.650 | 42.732 | 40.614 | 1.00 | 67.41 | C |
| ATOM | 2196 | C | THR | B | 109 | 23.740 | 41.401 | 38.181 | 1.00 | 69.53 | C |
| ATOM | 2197 | O | THR | B | 109 | 24.797 | 41.063 | 38.737 | 1.00 | 64.83 | O |
| ATOM | 2198 | N | PHE | B | 110 | 23.706 | 41.853 | 36.933 | 1.00 | 58.71 | N |
| ATOM | 2199 | CA | PHE | B | 110 | 24.897 | 41.865 | 36.104 | 1.00 | 57.37 | C |
| ATOM | 2200 | CB | PHE | B | 110 | 24.610 | 41.172 | 34.764 | 1.00 | 54.27 | C |
| ATOM | 2201 | CG | PHE | B | 110 | 24.374 | 39.687 | 34.883 | 1.00 | 52.46 | C |
| ATOM | 2202 | CD1 | PHE | B | 110 | 23.095 | 39.185 | 35.073 | 1.00 | 58.35 | C |
| ATOM | 2203 | CD2 | PHE | B | 110 | 25.433 | 38.793 | 34.795 | 1.00 | 48.15 | C |
| ATOM | 2204 | CE1 | PHE | B | 110 | 22.877 | 37.807 | 35.180 | 1.00 | 59.78 | C |
| ATOM | 2205 | CE2 | PHE | B | 110 | 25.224 | 37.420 | 34.900 | 1.00 | 50.73 | C |
| ATOM | 2206 | CZ | PHE | B | 110 | 23.945 | 36.923 | 35.096 | 1.00 | 50.94 | C |
| ATOM | 2207 | C | PHE | B | 110 | 25.424 | 43.286 | 35.888 | 1.00 | 57.96 | C |
| ATOM | 2208 | O | PHE | B | 110 | 24.781 | 44.272 | 36.274 | 1.00 | 57.41 | O |
| ATOM | 2209 | N | GLU | B | 111 | 26.606 | 43.382 | 35.287 | 1.00 | 53.58 | N |
| ATOM | 2210 | CA | GLU | B | 111 | 27.199 | 44.672 | 34.937 | 1.00 | 58.58 | C |
| ATOM | 2211 | CB | GLU | B | 111 | 28.713 | 44.633 | 35.144 | 1.00 | 64.39 | C |
| ATOM | 2212 | CG | GLU | B | 111 | 29.169 | 44.670 | 36.583 | 1.00 | 69.04 | C |
| ATOM | 2213 | CD | GLU | B | 111 | 30.638 | 45.040 | 36.698 | 1.00 | 83.84 | C |
| ATOM | 2214 | OE1 | GLU | B | 111 | 31.147 | 45.705 | 35.765 | 1.00 | 78.89 | O |
| ATOM | 2215 | OE2 | GLU | B | 111 | 31.280 | 44.671 | 37.712 | 1.00 | 102.30 | O |
| ATOM | 2216 | C | GLU | B | 111 | 26.918 | 45.105 | 33.489 | 1.00 | 58.27 | C |
| ATOM | 2217 | O | GLU | B | 111 | 27.021 | 44.298 | 32.552 | 1.00 | 58.98 | O |
| ATOM | 2218 | N | GLY | B | 112 | 26.589 | 46.384 | 33.311 | 1.00 | 48.61 | N |
| ATOM | 2219 | CA | GLY | B | 112 | 26.435 | 46.964 | 31.989 | 1.00 | 47.65 | C |
| ATOM | 2220 | C | GLY | B | 112 | 25.051 | 46.770 | 31.387 | 1.00 | 49.32 | C |
| ATOM | 2221 | O | GLY | B | 112 | 24.196 | 46.125 | 31.981 | 1.00 | 47.60 | O |
| ATOM | 2222 | N | ASP | B | 113 | 24.837 | 47.330 | 30.199 | 1.00 | 49.94 | N |
| ATOM | 2223 | CA | ASP | B | 113 | 23.565 | 47.209 | 29.489 | 1.00 | 49.91 | C |
| ATOM | 2224 | CB | ASP | B | 113 | 23.419 | 48.327 | 28.457 | 1.00 | 51.80 | C |
| ATOM | 2225 | CG | ASP | B | 113 | 24.621 | 48.416 | 27.527 | 1.00 | 54.63 | C |
| ATOM | 2226 | OD1 | ASP | B | 113 | 25.702 | 47.935 | 27.931 | 1.00 | 56.67 | O |
| ATOM | 2227 | OD2 | ASP | B | 113 | 24.498 | 48.965 | 26.411 | 1.00 | 50.07 | O |
| ATOM | 2228 | C | ASP | B | 113 | 23.432 | 45.876 | 28.768 | 1.00 | 49.47 | C |
| ATOM | 2229 | O | ASP | B | 113 | 22.656 | 45.771 | 27.823 | 1.00 | 51.04 | O |
| ATOM | 2230 | N | LEU | B | 114 | 24.208 | 44.880 | 29.199 | 1.00 | 50.60 | N |
| ATOM | 2231 | CA | LEU | B | 114 | 24.105 | 43.507 | 28.697 | 1.00 | 48.83 | C |
| ATOM | 2232 | CB | LEU | B | 114 | 22.786 | 42.879 | 29.139 | 1.00 | 45.04 | C |
| ATOM | 2233 | CG | LEU | B | 114 | 22.476 | 42.831 | 30.639 | 1.00 | 48.40 | C |
| ATOM | 2234 | CD1 | LEU | B | 114 | 21.217 | 42.009 | 30.882 | 1.00 | 41.98 | C |
| ATOM | 2235 | CD2 | LEU | B | 114 | 23.640 | 42.262 | 31.439 | 1.00 | 48.44 | C |
| ATOM | 2236 | C | LEU | B | 114 | 24.246 | 43.397 | 27.180 | 1.00 | 52.83 | C |
| ATOM | 2237 | O | LEU | B | 114 | 23.557 | 42.597 | 26.540 | 1.00 | 55.57 | O |

TABLE 12-continued

Coordinates for pro MMP9(35-444 ΔFnII) (SEQ ID NO: 12) complex with Example 2

| ATOM | 2238 | N | LYS | B | 115 | 25.153 | 44.189 | 26.617 | 1.00 | 53.08 | N |
|---|---|---|---|---|---|---|---|---|---|---|---|
| ATOM | 2239 | CA | LYS | B | 115 | 25.312 | 44.307 | 25.176 | 1.00 | 50.45 | C |
| ATOM | 2240 | CB | LYS | B | 115 | 24.413 | 45.436 | 24.678 | 1.00 | 55.68 | C |
| ATOM | 2241 | CG | LYS | B | 115 | 24.418 | 45.651 | 23.183 | 1.00 | 56.29 | C |
| ATOM | 2242 | CD | LYS | B | 115 | 23.475 | 46.780 | 22.794 | 1.00 | 59.92 | C |
| ATOM | 2243 | CE | LYS | B | 115 | 24.233 | 48.072 | 22.546 | 1.00 | 63.82 | C |
| ATOM | 2244 | NZ | LYS | B | 115 | 23.318 | 49.122 | 22.009 | 1.00 | 71.06 | N |
| ATOM | 2245 | C | LYS | B | 115 | 26.768 | 44.631 | 24.858 | 1.00 | 51.76 | C |
| ATOM | 2246 | O | LYS | B | 115 | 27.409 | 45.381 | 25.598 | 1.00 | 50.92 | O |
| ATOM | 2247 | N | TRP | B | 116 | 27.303 | 44.065 | 23.778 | 1.00 | 48.24 | N |
| ATOM | 2248 | CA | TRP | B | 116 | 28.677 | 44.378 | 23.394 | 1.00 | 47.21 | C |
| ATOM | 2249 | CB | TRP | B | 116 | 29.253 | 43.363 | 22.396 | 1.00 | 48.87 | C |
| ATOM | 2250 | CG | TRP | B | 116 | 29.385 | 41.983 | 22.971 | 1.00 | 47.35 | C |
| ATOM | 2251 | CD2 | TRP | B | 116 | 30.165 | 41.597 | 24.115 | 1.00 | 45.81 | C |
| ATOM | 2252 | CE2 | TRP | B | 116 | 29.978 | 40.217 | 24.302 | 1.00 | 44.11 | C |
| ATOM | 2253 | CE3 | TRP | B | 116 | 31.010 | 42.290 | 24.995 | 1.00 | 51.76 | C |
| ATOM | 2254 | CD1 | TRP | B | 116 | 28.769 | 40.847 | 22.531 | 1.00 | 45.26 | C |
| ATOM | 2255 | NE1 | TRP | B | 116 | 29.118 | 39.781 | 23.327 | 1.00 | 48.12 | N |
| ATOM | 2256 | CZ2 | TRP | B | 116 | 30.606 | 39.512 | 25.324 | 1.00 | 41.15 | C |
| ATOM | 2257 | CZ3 | TRP | B | 116 | 31.630 | 41.586 | 26.019 | 1.00 | 40.46 | C |
| ATOM | 2258 | CH2 | TRP | B | 116 | 31.426 | 40.214 | 26.169 | 1.00 | 43.92 | C |
| ATOM | 2259 | C | TRP | B | 116 | 28.788 | 45.794 | 22.853 | 1.00 | 50.49 | C |
| ATOM | 2260 | O | TRP | B | 116 | 27.826 | 46.341 | 22.319 | 1.00 | 59.00 | O |
| ATOM | 2261 | N | HIS | B | 117 | 29.962 | 46.393 | 23.003 | 1.00 | 55.60 | N |
| ATOM | 2262 | CA | HIS | B | 117 | 30.180 | 47.746 | 22.513 | 1.00 | 52.47 | C |
| ATOM | 2263 | CB | HIS | B | 117 | 30.273 | 48.740 | 23.680 | 1.00 | 47.92 | C |
| ATOM | 2264 | CG | HIS | B | 117 | 28.950 | 49.104 | 24.288 | 1.00 | 58.43 | C |
| ATOM | 2265 | CD2 | HIS | B | 117 | 28.112 | 50.143 | 24.047 | 1.00 | 63.59 | C |
| ATOM | 2266 | ND1 | HIS | B | 117 | 28.361 | 48.368 | 25.301 | 1.00 | 59.86 | N |
| ATOM | 2267 | CE1 | HIS | B | 117 | 27.213 | 48.930 | 25.645 | 1.00 | 56.04 | C |
| ATOM | 2268 | NE2 | HIS | B | 117 | 27.039 | 50.010 | 24.901 | 1.00 | 63.81 | N |
| ATOM | 2269 | C | HIS | B | 117 | 31.436 | 47.805 | 21.641 | 1.00 | 53.33 | C |
| ATOM | 2270 | O | HIS | B | 117 | 32.079 | 48.850 | 21.542 | 1.00 | 53.58 | O |
| ATOM | 2271 | N | HIS | B | 118 | 31.787 | 46.683 | 21.015 | 1.00 | 56.76 | N |
| ATOM | 2272 | CA | HIS | B | 118 | 32.915 | 46.642 | 20.068 | 1.00 | 57.51 | C |
| ATOM | 2273 | CB | HIS | B | 118 | 34.257 | 46.506 | 20.793 | 1.00 | 49.63 | C |
| ATOM | 2274 | CG | HIS | B | 118 | 34.383 | 45.259 | 21.613 | 1.00 | 52.76 | C |
| ATOM | 2275 | CD2 | HIS | B | 118 | 35.196 | 44.182 | 21.482 | 1.00 | 50.89 | C |
| ATOM | 2276 | ND1 | HIS | B | 118 | 33.622 | 45.029 | 22.737 | 1.00 | 52.44 | N |
| ATOM | 2277 | CE1 | HIS | B | 118 | 33.958 | 43.861 | 23.260 | 1.00 | 59.24 | C |
| ATOM | 2278 | NE2 | HIS | B | 118 | 34.912 | 43.327 | 22.517 | 1.00 | 48.83 | N |
| ATOM | 2279 | C | HIS | B | 118 | 32.717 | 45.521 | 19.045 | 1.00 | 58.44 | C |
| ATOM | 2280 | O | HIS | B | 118 | 32.095 | 44.505 | 19.356 | 1.00 | 59.48 | O |
| ATOM | 2281 | N | HIS | B | 119 | 33.241 | 45.701 | 17.832 | 1.00 | 54.94 | N |
| ATOM | 2282 | CA | HIS | B | 119 | 32.838 | 44.841 | 16.708 | 1.00 | 58.12 | C |
| ATOM | 2283 | CB | HIS | B | 119 | 32.868 | 45.589 | 15.362 | 1.00 | 64.74 | C |
| ATOM | 2284 | CG | HIS | B | 119 | 31.659 | 46.438 | 15.116 | 1.00 | 69.89 | C |
| ATOM | 2285 | CD2 | HIS | B | 119 | 30.337 | 46.141 | 15.172 | 1.00 | 64.51 | C |
| ATOM | 2286 | ND1 | HIS | B | 119 | 31.735 | 47.778 | 14.801 | 1.00 | 79.66 | N |
| ATOM | 2287 | CE1 | HIS | B | 119 | 30.515 | 48.268 | 14.660 | 1.00 | 74.17 | C |
| ATOM | 2288 | NE2 | HIS | B | 119 | 29.649 | 47.294 | 14.880 | 1.00 | 69.12 | N |
| ATOM | 2289 | C | HIS | B | 119 | 33.534 | 43.487 | 16.577 | 1.00 | 56.14 | C |
| ATOM | 2290 | O | HIS | B | 119 | 32.932 | 42.544 | 16.056 | 1.00 | 57.74 | O |
| ATOM | 2291 | N | ASN | B | 120 | 34.787 | 43.371 | 17.014 | 1.00 | 55.52 | N |
| ATOM | 2292 | CA | ASN | B | 120 | 35.449 | 42.063 | 16.927 | 1.00 | 56.15 | C |
| ATOM | 2293 | CB | ASN | B | 120 | 36.857 | 42.116 | 16.333 | 1.00 | 55.69 | C |
| ATOM | 2294 | CG | ASN | B | 120 | 37.506 | 40.721 | 16.268 | 1.00 | 62.63 | C |
| ATOM | 2295 | OD1 | ASN | B | 120 | 36.809 | 39.698 | 16.150 | 1.00 | 54.59 | O |
| ATOM | 2296 | ND2 | ASN | B | 120 | 38.839 | 40.677 | 16.358 | 1.00 | 62.85 | N |
| ATOM | 2297 | C | ASN | B | 120 | 35.481 | 41.274 | 18.219 | 1.00 | 53.49 | C |
| ATOM | 2298 | O | ASN | B | 120 | 36.444 | 41.345 | 18.992 | 1.00 | 44.51 | O |
| ATOM | 2299 | N | ILE | B | 121 | 34.416 | 40.503 | 18.409 | 1.00 | 54.81 | N |
| ATOM | 2300 | CA | ILE | B | 121 | 34.255 | 39.629 | 19.550 | 1.00 | 44.74 | C |
| ATOM | 2301 | CB | ILE | B | 121 | 32.795 | 39.274 | 19.722 | 1.00 | 43.20 | C |
| ATOM | 2302 | CG2 | ILE | B | 121 | 32.636 | 38.132 | 20.731 | 1.00 | 48.08 | C |
| ATOM | 2303 | CG1 | ILE | B | 121 | 32.030 | 40.521 | 20.181 | 1.00 | 44.23 | C |
| ATOM | 2304 | CD1 | ILE | B | 121 | 31.359 | 41.284 | 19.088 | 1.00 | 42.66 | C |
| ATOM | 2305 | C | ILE | B | 121 | 35.123 | 38.373 | 19.410 | 1.00 | 50.08 | C |
| ATOM | 2306 | O | ILE | B | 121 | 35.116 | 37.692 | 18.380 | 1.00 | 47.10 | O |
| ATOM | 2307 | N | THR | B | 122 | 35.889 | 38.093 | 20.457 | 1.00 | 50.32 | N |
| ATOM | 2308 | CA | THR | B | 122 | 36.860 | 37.016 | 20.435 | 1.00 | 44.97 | C |
| ATOM | 2309 | CB | THR | B | 122 | 38.241 | 37.521 | 20.915 | 1.00 | 45.93 | C |
| ATOM | 2310 | OG1 | THR | B | 122 | 38.117 | 38.151 | 22.198 | 1.00 | 50.15 | O |
| ATOM | 2311 | CG2 | THR | B | 122 | 38.815 | 38.534 | 19.928 | 1.00 | 50.31 | C |
| ATOM | 2312 | C | THR | B | 122 | 36.393 | 35.891 | 21.350 | 1.00 | 43.95 | C |
| ATOM | 2313 | O | THR | B | 122 | 35.836 | 36.154 | 22.413 | 1.00 | 48.37 | O |
| ATOM | 2314 | N | TYR | B | 123 | 36.602 | 34.643 | 20.948 | 1.00 | 39.95 | N |

TABLE 12-continued

Coordinates for pro MMP9(35-444 ΔFnII) (SEQ ID NO: 12) complex with Example 2

| ATOM | 2315 | CA | TYR | B | 123 | 36.327 | 33.543 | 21.859 | 1.00 | 44.47 | C |
|---|---|---|---|---|---|---|---|---|---|---|---|
| ATOM | 2316 | CB | TYR | B | 123 | 35.088 | 32.770 | 21.441 | 1.00 | 45.41 | C |
| ATOM | 2317 | CG | TYR | B | 123 | 35.186 | 32.084 | 20.112 | 1.00 | 41.45 | C |
| ATOM | 2318 | CD1 | TYR | B | 123 | 34.887 | 32.770 | 18.951 | 1.00 | 40.60 | C |
| ATOM | 2319 | CE1 | TYR | B | 123 | 34.949 | 32.156 | 17.717 | 1.00 | 46.20 | C |
| ATOM | 2320 | CD2 | TYR | B | 123 | 35.534 | 30.740 | 20.015 | 1.00 | 41.71 | C |
| ATOM | 2321 | CE2 | TYR | B | 123 | 35.598 | 30.107 | 18.771 | 1.00 | 44.35 | C |
| ATOM | 2322 | CZ | TYR | B | 123 | 35.302 | 30.834 | 17.629 | 1.00 | 42.99 | C |
| ATOM | 2323 | OH | TYR | B | 123 | 35.346 | 30.269 | 16.387 | 1.00 | 44.70 | O |
| ATOM | 2324 | C | TYR | B | 123 | 37.496 | 32.591 | 22.055 | 1.00 | 47.17 | C |
| ATOM | 2325 | O | TYR | B | 123 | 38.448 | 32.582 | 21.272 | 1.00 | 46.04 | O |
| ATOM | 2326 | N | TRP | B | 124 | 37.411 | 31.784 | 23.106 | 1.00 | 44.83 | N |
| ATOM | 2327 | CA | TRP | B | 124 | 38.516 | 30.910 | 23.482 | 1.00 | 43.67 | C |
| ATOM | 2328 | CB | TRP | B | 124 | 39.288 | 31.550 | 24.629 | 1.00 | 42.57 | C |
| ATOM | 2329 | CG | TRP | B | 124 | 40.384 | 30.691 | 25.172 | 1.00 | 48.16 | C |
| ATOM | 2330 | CD2 | TRP | B | 124 | 40.673 | 30.425 | 26.556 | 1.00 | 47.91 | C |
| ATOM | 2331 | CE2 | TRP | B | 124 | 41.805 | 29.584 | 26.595 | 1.00 | 43.35 | C |
| ATOM | 2332 | CE3 | TRP | B | 124 | 40.077 | 30.822 | 27.757 | 1.00 | 38.08 | C |
| ATOM | 2333 | CD1 | TRP | B | 124 | 41.332 | 30.014 | 24.451 | 1.00 | 42.71 | C |
| ATOM | 2334 | NE1 | TRP | B | 124 | 42.177 | 29.337 | 25.300 | 1.00 | 43.45 | N |
| ATOM | 2335 | CZ2 | TRP | B | 124 | 42.353 | 29.121 | 27.782 | 1.00 | 41.16 | C |
| ATOM | 2336 | CZ3 | TRP | B | 124 | 40.625 | 30.364 | 28.941 | 1.00 | 46.98 | C |
| ATOM | 2337 | CH2 | TRP | B | 124 | 41.746 | 29.520 | 28.948 | 1.00 | 51.92 | C |
| ATOM | 2338 | C | TRP | B | 124 | 38.022 | 29.538 | 23.910 | 1.00 | 45.39 | C |
| ATOM | 2339 | O | TRP | B | 124 | 37.501 | 29.375 | 25.028 | 1.00 | 46.79 | O |
| ATOM | 2340 | N | ILE | B | 125 | 38.163 | 28.544 | 23.038 | 1.00 | 39.45 | N |
| ATOM | 2341 | CA | ILE | B | 125 | 37.711 | 27.216 | 23.425 | 1.00 | 47.85 | C |
| ATOM | 2342 | CB | ILE | B | 125 | 37.801 | 26.158 | 22.306 | 1.00 | 46.33 | C |
| ATOM | 2343 | CG2 | ILE | B | 125 | 37.741 | 24.769 | 22.938 | 1.00 | 42.99 | C |
| ATOM | 2344 | CG1 | ILE | B | 125 | 36.615 | 26.242 | 21.334 | 1.00 | 50.58 | C |
| ATOM | 2345 | CD1 | ILE | B | 125 | 36.370 | 27.596 | 20.682 | 1.00 | 50.31 | C |
| ATOM | 2346 | C | ILE | B | 125 | 38.624 | 26.792 | 24.548 | 1.00 | 46.90 | C |
| ATOM | 2347 | O | ILE | B | 125 | 39.748 | 26.357 | 24.301 | 1.00 | 49.91 | O |
| ATOM | 2348 | N | GLN | B | 126 | 38.172 | 26.927 | 25.787 | 1.00 | 43.94 | N |
| ATOM | 2349 | CA | GLN | B | 126 | 39.073 | 26.654 | 26.893 | 1.00 | 43.84 | C |
| ATOM | 2350 | CB | GLN | B | 126 | 38.649 | 27.416 | 28.147 | 1.00 | 46.15 | C |
| ATOM | 2351 | CG | GLN | B | 126 | 39.480 | 27.087 | 29.365 | 1.00 | 43.96 | C |
| ATOM | 2352 | CD | GLN | B | 126 | 38.840 | 27.573 | 30.655 | 1.00 | 51.22 | C |
| ATOM | 2353 | OE1 | GLN | B | 126 | 37.670 | 27.978 | 30.676 | 1.00 | 51.22 | O |
| ATOM | 2354 | NE2 | GLN | B | 126 | 39.607 | 27.537 | 31.740 | 1.00 | 41.09 | N |
| ATOM | 2355 | C | GLN | B | 126 | 39.259 | 25.162 | 27.186 | 1.00 | 44.44 | C |
| ATOM | 2356 | O | GLN | B | 126 | 40.190 | 24.779 | 27.894 | 1.00 | 49.63 | O |
| ATOM | 2357 | N | ASN | B | 127 | 38.385 | 24.314 | 26.663 | 1.00 | 37.34 | N |
| ATOM | 2358 | CA | ASN | B | 127 | 38.598 | 22.871 | 26.791 | 0.00 | 43.20 | C |
| ATOM | 2359 | CB | ASN | B | 127 | 38.532 | 22.418 | 28.253 | 1.00 | 34.70 | C |
| ATOM | 2360 | CG | ASN | B | 127 | 37.124 | 22.468 | 28.812 | 1.00 | 46.20 | C |
| ATOM | 2361 | OD1 | ASN | B | 127 | 36.300 | 23.262 | 28.365 | 1.00 | 45.53 | O |
| ATOM | 2362 | ND2 | ASN | B | 127 | 36.837 | 21.612 | 29.790 | 0.96 | 43.78 | N |
| ATOM | 2363 | C | ASN | B | 127 | 37.644 | 22.046 | 25.944 | 1.00 | 44.11 | C |
| ATOM | 2364 | O | ASN | B | 127 | 36.782 | 22.580 | 25.255 | 1.00 | 45.78 | O |
| ATOM | 2365 | N | TYR | B | 128 | 37.797 | 20.732 | 25.997 | 1.00 | 45.10 | N |
| ATOM | 2366 | CA | TYR | B | 128 | 37.048 | 19.880 | 25.095 | 1.00 | 47.36 | C |
| ATOM | 2367 | CB | TYR | B | 128 | 37.978 | 19.324 | 24.012 | 1.00 | 51.19 | C |
| ATOM | 2368 | CG | TYR | B | 128 | 38.523 | 20.400 | 23.106 | 1.00 | 46.90 | C |
| ATOM | 2369 | CD1 | TYR | B | 128 | 37.912 | 20.681 | 21.899 | 1.00 | 49.16 | C |
| ATOM | 2370 | CE1 | TYR | B | 128 | 38.384 | 21.671 | 21.069 | 1.00 | 54.48 | C |
| ATOM | 2371 | CD2 | TYR | B | 128 | 39.620 | 21.161 | 23.478 | 1.00 | 48.89 | C |
| ATOM | 2372 | CE2 | TYR | B | 128 | 40.111 | 22.161 | 22.645 | 1.00 | 48.28 | C |
| ATOM | 2373 | CZ | TYR | B | 128 | 39.481 | 22.410 | 21.444 | 1.00 | 51.79 | C |
| ATOM | 2374 | OH | TYR | B | 128 | 39.935 | 23.392 | 20.604 | 1.00 | 49.69 | O |
| ATOM | 2375 | C | TYR | B | 128 | 36.333 | 18.757 | 25.820 | 1.00 | 52.51 | C |
| ATOM | 2376 | O | TYR | B | 128 | 36.806 | 18.258 | 26.841 | 1.00 | 53.09 | O |
| ATOM | 2377 | N | SER | B | 129 | 35.163 | 18.400 | 25.304 | 1.00 | 51.10 | N |
| ATOM | 2378 | CA | SER | B | 129 | 34.520 | 17.160 | 25.685 | 1.00 | 51.43 | C |
| ATOM | 2379 | CB | SER | B | 129 | 33.008 | 17.224 | 25.436 | 1.00 | 49.79 | C |
| ATOM | 2380 | OG | SER | B | 129 | 32.468 | 15.951 | 25.101 | 1.00 | 43.12 | O |
| ATOM | 2381 | C | SER | B | 129 | 35.164 | 16.151 | 24.771 | 1.00 | 46.57 | C |
| ATOM | 2382 | O | SER | B | 129 | 35.695 | 16.532 | 23.741 | 1.00 | 50.11 | O |
| ATOM | 2383 | N | GLU | B | 130 | 35.114 | 14.874 | 25.147 | 1.00 | 53.25 | N |
| ATOM | 2384 | CA | GLU | B | 130 | 35.689 | 13.795 | 24.343 | 1.00 | 55.46 | C |
| ATOM | 2385 | CB | GLU | B | 130 | 36.219 | 12.696 | 25.261 | 1.00 | 56.42 | C |
| ATOM | 2386 | CG | GLU | B | 130 | 37.285 | 13.152 | 26.241 | 1.00 | 63.08 | C |
| ATOM | 2387 | CD | GLU | B | 130 | 38.669 | 13.228 | 25.616 | 1.00 | 67.90 | C |
| ATOM | 2388 | OE1 | GLU | B | 130 | 39.607 | 12.599 | 26.164 | 1.00 | 65.20 | O |
| ATOM | 2389 | OE2 | GLU | B | 130 | 38.816 | 13.911 | 24.576 | 1.00 | 70.06 | O |
| ATOM | 2390 | C | GLU | B | 130 | 34.716 | 13.178 | 23.311 | 1.00 | 54.41 | C |
| ATOM | 2391 | O | GLU | B | 130 | 35.123 | 12.389 | 22.453 | 1.00 | 54.32 | O |

TABLE 12-continued

Coordinates for pro MMP9(35-444 ΔFnII) (SEQ ID NO: 12) complex with Example 2

| ATOM | 2392 | N | ASP | B | 131 | 33.439 | 13.533 | 23.388 | 1.00 | 48.60 | N |
|---|---|---|---|---|---|---|---|---|---|---|---|
| ATOM | 2393 | CA | ASP | B | 131 | 32.438 | 12.883 | 22.556 | 1.00 | 48.15 | C |
| ATOM | 2394 | CB | ASP | B | 131 | 31.037 | 13.305 | 22.998 | 1.00 | 50.07 | C |
| ATOM | 2395 | CG | ASP | B | 131 | 30.845 | 13.205 | 24.498 | 1.00 | 53.01 | C |
| ATOM | 2396 | OD1 | ASP | B | 131 | 31.627 | 12.477 | 25.144 | 1.00 | 58.57 | O |
| ATOM | 2397 | OD2 | ASP | B | 131 | 29.910 | 13.848 | 25.034 | 1.00 | 53.80 | O |
| ATOM | 2398 | C | ASP | B | 131 | 32.643 | 13.170 | 21.059 | 1.00 | 55.06 | C |
| ATOM | 2399 | O | ASP | B | 131 | 32.058 | 12.503 | 20.193 | 1.00 | 50.86 | O |
| ATOM | 2400 | N | LEU | B | 132 | 33.469 | 14.169 | 20.757 | 1.00 | 51.43 | N |
| ATOM | 2401 | CA | LEU | B | 132 | 33.677 | 14.590 | 19.377 | 1.00 | 47.27 | C |
| ATOM | 2402 | CB | LEU | B | 132 | 32.676 | 15.693 | 18.992 | 1.00 | 49.16 | C |
| ATOM | 2403 | CG | LEU | B | 132 | 31.170 | 15.386 | 19.048 | 1.00 | 46.90 | C |
| ATOM | 2404 | CD1 | LEU | B | 132 | 30.335 | 16.658 | 18.986 | 1.00 | 40.32 | C |
| ATOM | 2405 | CD2 | LEU | B | 132 | 30.763 | 14.434 | 17.940 | 1.00 | 39.45 | C |
| ATOM | 2406 | C | LEU | B | 132 | 35.105 | 15.081 | 19.146 | 1.00 | 48.95 | C |
| ATOM | 2407 | O | LEU | B | 132 | 35.708 | 15.710 | 20.015 | 1.00 | 49.32 | O |
| ATOM | 2408 | N | PRO | B | 133 | 35.647 | 14.803 | 17.957 | 1.00 | 48.74 | N |
| ATOM | 2409 | CD | PRO | B | 133 | 34.979 | 14.137 | 16.828 | 1.00 | 45.76 | C |
| ATOM | 2410 | CA | PRO | B | 133 | 36.993 | 15.256 | 17.615 | 1.00 | 49.75 | C |
| ATOM | 2411 | CB | PRO | B | 133 | 37.144 | 14.832 | 16.155 | 1.00 | 49.94 | C |
| ATOM | 2412 | CG | PRO | B | 133 | 36.111 | 13.763 | 15.953 | 1.00 | 47.50 | C |
| ATOM | 2413 | C | PRO | B | 133 | 37.087 | 16.766 | 17.723 | 1.00 | 49.32 | C |
| ATOM | 2414 | O | PRO | B | 133 | 36.204 | 17.473 | 17.245 | 1.00 | 52.24 | O |
| ATOM | 2415 | N | ARG | B | 134 | 38.154 | 17.238 | 18.352 | 1.00 | 47.71 | N |
| ATOM | 2416 | CA | ARG | B | 134 | 38.411 | 18.650 | 18.563 | 1.00 | 49.45 | C |
| ATOM | 2417 | CB | ARG | B | 134 | 39.869 | 18.840 | 18.986 | 1.00 | 53.99 | C |
| ATOM | 2418 | CG | ARG | B | 134 | 40.255 | 18.119 | 20.264 | 1.00 | 54.34 | C |
| ATOM | 2419 | CD | ARG | B | 134 | 41.625 | 18.588 | 20.753 | 1.00 | 50.57 | C |
| ATOM | 2420 | NE | ARG | B | 134 | 41.770 | 18.375 | 22.182 | 1.00 | 51.99 | N |
| ATOM | 2421 | CZ | ARG | B | 134 | 42.404 | 19.207 | 22.998 | 1.00 | 55.19 | C |
| ATOM | 2422 | NH1 | ARG | B | 134 | 42.955 | 20.313 | 22.512 | 1.00 | 55.84 | N |
| ATOM | 2423 | NH2 | ARG | B | 134 | 42.486 | 18.935 | 24.295 | 1.00 | 44.15 | N |
| ATOM | 2424 | C | ARG | B | 134 | 38.163 | 19.487 | 17.322 | 1.00 | 48.83 | C |
| ATOM | 2425 | O | ARG | B | 134 | 37.600 | 20.575 | 17.403 | 1.00 | 49.69 | O |
| ATOM | 2426 | N | ALA | B | 135 | 38.634 | 19.003 | 16.182 | 1.00 | 48.31 | N |
| ATOM | 2427 | CA | ALA | B | 135 | 38.412 | 19.702 | 14.935 | 1.00 | 48.68 | C |
| ATOM | 2428 | CB | ALA | B | 135 | 39.044 | 18.939 | 13.792 | 1.00 | 42.64 | C |
| ATOM | 2429 | C | ALA | B | 135 | 36.900 | 19.878 | 14.715 | 1.00 | 50.13 | C |
| ATOM | 2430 | O | ALA | B | 135 | 36.433 | 20.961 | 14.356 | 1.00 | 44.39 | O |
| ATOM | 2431 | N | VAL | B | 136 | 36.146 | 18.807 | 14.949 | 1.00 | 43.69 | N |
| ATOM | 2432 | CA | VAL | B | 136 | 34.695 | 18.834 | 14.782 | 1.00 | 46.53 | C |
| ATOM | 2433 | CB | VAL | B | 136 | 34.112 | 17.449 | 15.044 | 1.00 | 47.28 | C |
| ATOM | 2434 | CG1 | VAL | B | 136 | 32.628 | 17.530 | 15.305 | 1.00 | 38.87 | C |
| ATOM | 2435 | CG2 | VAL | B | 136 | 34.443 | 16.527 | 13.887 | 1.00 | 43.43 | C |
| ATOM | 2436 | C | VAL | B | 136 | 34.038 | 19.848 | 15.717 | 1.00 | 46.79 | C |
| ATOM | 2437 | O | VAL | B | 136 | 33.172 | 20.616 | 15.305 | 1.00 | 47.65 | O |
| ATOM | 2438 | N | ILE | B | 137 | 34.471 | 19.848 | 16.974 | 1.00 | 45.80 | N |
| ATOM | 2439 | CA | ILE | B | 137 | 33.979 | 20.790 | 17.975 | 1.00 | 41.88 | C |
| ATOM | 2440 | CB | ILE | B | 137 | 34.586 | 20.487 | 19.352 | 1.00 | 43.18 | C |
| ATOM | 2441 | CG2 | ILE | B | 137 | 34.525 | 21.719 | 20.259 | 1.00 | 40.79 | C |
| ATOM | 2442 | CG1 | ILE | B | 137 | 33.879 | 19.285 | 19.989 | 1.00 | 43.56 | C |
| ATOM | 2443 | CD1 | ILE | B | 137 | 34.569 | 18.761 | 21.260 | 1.00 | 49.33 | C |
| ATOM | 2444 | C | ILE | B | 137 | 34.296 | 22.228 | 17.589 | 1.00 | 45.35 | C |
| ATOM | 2445 | O | ILE | B | 137 | 33.403 | 23.083 | 17.573 | 1.00 | 43.72 | O |
| ATOM | 2446 | N | ASP | B | 138 | 35.570 | 22.482 | 17.278 | 1.00 | 45.82 | N |
| ATOM | 2447 | CA | ASP | B | 138 | 36.023 | 23.789 | 16.794 | 1.00 | 45.90 | C |
| ATOM | 2448 | CB | ASP | B | 138 | 37.480 | 23.735 | 16.342 | 1.00 | 46.71 | C |
| ATOM | 2449 | CG | ASP | B | 138 | 38.437 | 23.479 | 17.486 | 1.00 | 50.08 | C |
| ATOM | 2450 | OD1 | ASP | B | 138 | 37.961 | 23.220 | 18.614 | 1.00 | 53.35 | O |
| ATOM | 2451 | OD2 | ASP | B | 138 | 39.666 | 23.534 | 17.256 | 1.00 | 51.07 | O |
| ATOM | 2452 | C | ASP | B | 138 | 35.178 | 24.261 | 15.627 | 1.00 | 48.51 | C |
| ATOM | 2453 | O | ASP | B | 138 | 34.762 | 25.413 | 15.568 | 1.00 | 52.06 | O |
| ATOM | 2454 | N | ASP | B | 139 | 34.920 | 23.370 | 14.687 | 1.00 | 46.87 | N |
| ATOM | 2455 | CA | ASP | B | 139 | 34.096 | 23.754 | 13.571 | 1.00 | 43.14 | C |
| ATOM | 2456 | CB | ASP | B | 139 | 34.283 | 22.818 | 12.380 | 1.00 | 36.90 | C |
| ATOM | 2457 | CG | ASP | B | 139 | 33.158 | 22.951 | 11.380 | 1.00 | 45.32 | C |
| ATOM | 2458 | OD1 | ASP | B | 139 | 33.270 | 23.802 | 10.470 | 1.00 | 44.79 | O |
| ATOM | 2459 | OD2 | ASP | B | 139 | 32.136 | 22.238 | 11.536 | 1.00 | 47.81 | O |
| ATOM | 2460 | C | ASP | B | 139 | 32.624 | 23.832 | 13.977 | 1.00 | 44.22 | C |
| ATOM | 2461 | O | ASP | B | 139 | 31.870 | 24.625 | 13.417 | 1.00 | 48.03 | O |
| ATOM | 2462 | N | ALA | B | 140 | 32.189 | 23.026 | 14.933 | 1.00 | 37.96 | N |
| ATOM | 2463 | CA | ALA | B | 140 | 30.820 | 23.215 | 15.437 | 1.00 | 42.58 | C |
| ATOM | 2464 | CB | ALA | B | 140 | 30.464 | 22.161 | 16.451 | 1.00 | 39.25 | C |
| ATOM | 2465 | C | ALA | B | 140 | 30.627 | 24.627 | 16.024 | 1.00 | 37.23 | C |
| ATOM | 2466 | O | ALA | B | 140 | 29.729 | 25.348 | 15.639 | 1.00 | 38.31 | O |
| ATOM | 2467 | N | PHE | B | 141 | 31.481 | 25.036 | 16.944 | 1.00 | 44.23 | N |
| ATOM | 2468 | CA | PHE | B | 141 | 31.399 | 26.403 | 17.451 | 1.00 | 44.73 | C |

TABLE 12-continued

Coordinates for pro MMP9(35-444 ΔFnII) (SEQ ID NO: 12) complex with Example 2

| ATOM | 2469 | CB  | PHE | B | 141 | 32.452 | 26.611 | 18.520 | 1.00 | 41.79 | C |
| ---- | ---- | --- | --- | - | --- | ------ | ------ | ------ | ---- | ----- | - |
| ATOM | 2470 | CG  | PHE | B | 141 | 32.239 | 25.779 | 19.737 | 1.00 | 50.31 | C |
| ATOM | 2471 | CD1 | PHE | B | 141 | 30.974 | 25.644 | 20.286 | 1.00 | 44.88 | C |
| ATOM | 2472 | CD2 | PHE | B | 141 | 33.302 | 25.149 | 20.359 | 1.00 | 53.74 | C |
| ATOM | 2473 | CE1 | PHE | B | 141 | 30.773 | 24.894 | 21.422 | 1.00 | 43.47 | C |
| ATOM | 2474 | CE2 | PHE | B | 141 | 33.099 | 24.394 | 21.508 | 1.00 | 49.33 | C |
| ATOM | 2475 | CZ  | PHE | B | 141 | 31.829 | 24.268 | 22.039 | 1.00 | 36.41 | C |
| ATOM | 2476 | C   | PHE | B | 141 | 31.588 | 27.451 | 16.342 | 1.00 | 44.73 | C |
| ATOM | 2477 | O   | PHE | B | 141 | 30.865 | 28.449 | 16.286 | 1.00 | 44.66 | O |
| ATOM | 2478 | N   | ALA | B | 142 | 32.564 | 27.220 | 15.470 | 1.00 | 32.97 | N |
| ATOM | 2479 | CA  | ALA | B | 142 | 32.870 | 28.132 | 14.360 | 1.00 | 38.54 | C |
| ATOM | 2480 | CB  | ALA | B | 142 | 33.921 | 27.497 | 13.403 | 1.00 | 30.62 | C |
| ATOM | 2481 | C   | ALA | B | 142 | 31.622 | 28.525 | 13.576 | 1.00 | 38.46 | C |
| ATOM | 2482 | O   | ALA | B | 142 | 31.325 | 29.712 | 13.430 | 1.00 | 39.38 | O |
| ATOM | 2483 | N   | ARG | B | 143 | 30.916 | 27.514 | 13.062 | 1.00 | 33.55 | N |
| ATOM | 2484 | CA  | ARG | B | 143 | 29.659 | 27.673 | 12.327 | 1.00 | 36.65 | C |
| ATOM | 2485 | CB  | ARG | B | 143 | 29.195 | 26.320 | 11.750 | 1.00 | 35.14 | C |
| ATOM | 2486 | CG  | ARG | B | 143 | 30.245 | 25.606 | 10.897 | 1.00 | 37.72 | C |
| ATOM | 2487 | CD  | ARG | B | 143 | 30.128 | 24.072 | 10.933 | 1.00 | 35.29 | C |
| ATOM | 2488 | NE  | ARG | B | 143 | 28.763 | 23.644 | 10.691 | 1.00 | 44.12 | N |
| ATOM | 2489 | CZ  | ARG | B | 143 | 28.015 | 23.016 | 11.598 | 1.00 | 53.32 | C |
| ATOM | 2490 | NH1 | ARG | B | 143 | 28.539 | 22.707 | 12.785 | 1.00 | 52.29 | N |
| ATOM | 2491 | NH2 | ARG | B | 143 | 26.752 | 22.690 | 11.327 | 1.00 | 41.29 | N |
| ATOM | 2492 | C   | ARG | B | 143 | 28.536 | 28.285 | 13.177 | 1.00 | 38.29 | C |
| ATOM | 2493 | O   | ARG | B | 143 | 27.765 | 29.109 | 12.686 | 1.00 | 36.85 | O |
| ATOM | 2494 | N   | ALA | B | 144 | 28.423 | 27.887 | 14.440 | 1.00 | 31.21 | N |
| ATOM | 2495 | CA  | ALA | B | 144 | 27.404 | 28.521 | 15.287 | 1.00 | 42.39 | C |
| ATOM | 2496 | CB  | ALA | B | 144 | 27.402 | 27.939 | 16.719 | 1.00 | 42.74 | C |
| ATOM | 2497 | C   | ALA | B | 144 | 27.609 | 30.039 | 15.326 | 1.00 | 42.18 | C |
| ATOM | 2498 | O   | ALA | B | 144 | 26.650 | 30.804 | 15.444 | 1.00 | 38.97 | O |
| ATOM | 2499 | N   | PHE | B | 145 | 28.873 | 30.456 | 15.246 | 1.00 | 42.18 | N |
| ATOM | 2500 | CA  | PHE | B | 145 | 29.223 | 31.870 | 15.228 | 1.00 | 36.63 | C |
| ATOM | 2501 | CB  | PHE | B | 145 | 30.671 | 32.094 | 15.657 | 1.00 | 39.89 | C |
| ATOM | 2502 | CG  | PHE | B | 145 | 30.851 | 32.174 | 17.157 | 1.00 | 40.77 | C |
| ATOM | 2503 | CD1 | PHE | B | 145 | 30.193 | 33.141 | 17.893 | 1.00 | 37.31 | C |
| ATOM | 2504 | CD2 | PHE | B | 145 | 31.696 | 31.297 | 17.824 | 1.00 | 43.42 | C |
| ATOM | 2505 | CE1 | PHE | B | 145 | 30.355 | 33.218 | 19.271 | 1.00 | 44.18 | C |
| ATOM | 2506 | CE2 | PHE | B | 145 | 31.865 | 31.373 | 19.201 | 1.00 | 40.50 | C |
| ATOM | 2507 | CZ  | PHE | B | 145 | 31.198 | 32.337 | 19.921 | 1.00 | 42.50 | C |
| ATOM | 2508 | C   | PHE | B | 145 | 28.954 | 32.478 | 13.873 | 1.00 | 39.76 | C |
| ATOM | 2509 | O   | PHE | B | 145 | 28.315 | 33.517 | 13.791 | 1.00 | 42.12 | O |
| ATOM | 2510 | N   | ALA | B | 146 | 29.421 | 31.821 | 12.813 | 1.00 | 39.28 | N |
| ATOM | 2511 | CA  | ALA | B | 146 | 29.077 | 32.230 | 11.459 | 1.00 | 36.57 | C |
| ATOM | 2512 | CB  | ALA | B | 146 | 29.392 | 31.131 | 10.493 | 1.00 | 30.77 | C |
| ATOM | 2513 | C   | ALA | B | 146 | 27.594 | 32.593 | 11.362 | 1.00 | 40.40 | C |
| ATOM | 2514 | O   | ALA | B | 146 | 27.213 | 33.507 | 10.633 | 1.00 | 37.27 | O |
| ATOM | 2515 | N   | LEU | B | 147 | 26.764 | 31.876 | 12.115 | 1.00 | 38.07 | N |
| ATOM | 2516 | CA  | LEU | B | 147 | 25.322 | 32.052 | 12.042 | 1.00 | 35.40 | C |
| ATOM | 2517 | CB  | LEU | B | 147 | 24.647 | 30.989 | 12.895 | 1.00 | 36.54 | C |
| ATOM | 2518 | CG  | LEU | B | 147 | 23.281 | 30.439 | 12.519 | 1.00 | 43.73 | C |
| ATOM | 2519 | CD1 | LEU | B | 147 | 23.313 | 29.720 | 11.151 | 1.00 | 32.23 | C |
| ATOM | 2520 | CD2 | LEU | B | 147 | 22.772 | 29.512 | 13.639 | 1.00 | 35.78 | C |
| ATOM | 2521 | C   | LEU | B | 147 | 24.903 | 33.462 | 12.464 | 1.00 | 39.12 | C |
| ATOM | 2522 | O   | LEU | B | 147 | 24.035 | 34.066 | 11.853 | 1.00 | 41.56 | O |
| ATOM | 2523 | N   | TRP | B | 148 | 25.551 | 33.988 | 13.501 | 1.00 | 40.82 | N |
| ATOM | 2524 | CA  | TRP | B | 148 | 25.323 | 35.353 | 13.969 | 1.00 | 36.38 | C |
| ATOM | 2525 | CB  | TRP | B | 148 | 25.625 | 35.430 | 15.475 | 1.00 | 45.02 | C |
| ATOM | 2526 | CG  | TRP | B | 148 | 24.677 | 34.592 | 16.297 | 1.00 | 41.66 | C |
| ATOM | 2527 | CD2 | TRP | B | 148 | 23.291 | 34.864 | 16.536 | 1.00 | 32.30 | C |
| ATOM | 2528 | CE2 | TRP | B | 148 | 22.789 | 33.816 | 17.331 | 1.00 | 35.29 | C |
| ATOM | 2529 | CE3 | TRP | B | 148 | 22.420 | 35.887 | 16.139 | 1.00 | 37.95 | C |
| ATOM | 2530 | CD1 | TRP | B | 148 | 24.957 | 33.421 | 16.947 | 1.00 | 41.88 | C |
| ATOM | 2531 | NE1 | TRP | B | 148 | 23.829 | 32.957 | 17.584 | 1.00 | 35.92 | N |
| ATOM | 2532 | CZ2 | TRP | B | 148 | 21.455 | 33.769 | 17.755 | 1.00 | 39.02 | C |
| ATOM | 2533 | CZ3 | TRP | B | 148 | 21.084 | 35.836 | 16.557 | 1.00 | 41.39 | C |
| ATOM | 2534 | CH2 | TRP | B | 148 | 20.623 | 34.785 | 17.366 | 1.00 | 34.28 | C |
| ATOM | 2535 | C   | TRP | B | 148 | 26.123 | 36.428 | 13.201 | 1.00 | 41.47 | C |
| ATOM | 2536 | O   | TRP | B | 148 | 25.636 | 37.547 | 12.995 | 1.00 | 41.59 | O |
| ATOM | 2537 | N   | SER | B | 149 | 27.349 | 36.096 | 12.787 | 1.00 | 35.70 | N |
| ATOM | 2538 | CA  | SER | B | 149 | 28.158 | 37.019 | 11.985 | 1.00 | 41.16 | C |
| ATOM | 2539 | CB  | SER | B | 149 | 29.321 | 36.301 | 11.260 | 1.00 | 43.67 | C |
| ATOM | 2540 | OG  | SER | B | 149 | 30.109 | 35.478 | 12.106 | 1.00 | 47.58 | O |
| ATOM | 2541 | C   | SER | B | 149 | 27.286 | 37.658 | 10.917 | 1.00 | 39.00 | C |
| ATOM | 2542 | O   | SER | B | 149 | 27.248 | 38.874 | 10.779 | 1.00 | 41.47 | O |
| ATOM | 2543 | N   | ALA | B | 150 | 26.594 | 36.813 | 10.160 | 1.00 | 37.36 | N |
| ATOM | 2544 | CA  | ALA | B | 150 | 25.899 | 37.235 | 8.956  | 1.00 | 37.94 | C |
| ATOM | 2545 | CB  | ALA | B | 150 | 25.360 | 36.034 | 8.228  | 1.00 | 38.47 | C |

TABLE 12-continued

Coordinates for pro MMP9(35-444 ΔFnII) (SEQ ID NO: 12) complex with Example 2

| ATOM | 2546 | C   | ALA | B | 150 | 24.794 | 38.254 | 9.194  | 1.00 | 41.07 | C |
|------|------|-----|-----|---|-----|--------|--------|--------|------|-------|---|
| ATOM | 2547 | O   | ALA | B | 150 | 24.509 | 39.071 | 8.307  | 1.00 | 38.81 | O |
| ATOM | 2548 | N   | VAL | B | 151 | 24.174 | 38.208 | 10.378 | 1.00 | 43.33 | N |
| ATOM | 2549 | CA  | VAL | B | 151 | 23.034 | 39.097 | 10.681 | 1.00 | 48.91 | C |
| ATOM | 2550 | CB  | VAL | B | 151 | 21.782 | 38.323 | 11.143 | 1.00 | 40.98 | C |
| ATOM | 2551 | CG1 | VAL | B | 151 | 21.211 | 37.534 | 9.978  | 1.00 | 42.92 | C |
| ATOM | 2552 | CG2 | VAL | B | 151 | 22.134 | 37.393 | 12.267 | 1.00 | 38.84 | C |
| ATOM | 2553 | C   | VAL | B | 151 | 23.399 | 40.161 | 11.698 | 1.00 | 43.37 | C |
| ATOM | 2554 | O   | VAL | B | 151 | 22.578 | 40.584 | 12.507 | 1.00 | 42.70 | O |
| ATOM | 2555 | N   | THR | B | 152 | 24.641 | 40.613 | 11.616 | 1.00 | 47.40 | N |
| ATOM | 2556 | CA  | THR | B | 152 | 25.211 | 41.458 | 12.650 | 1.00 | 47.88 | C |
| ATOM | 2557 | CB  | THR | B | 152 | 25.653 | 40.580 | 13.828 | 1.00 | 38.22 | C |
| ATOM | 2558 | OG1 | THR | B | 152 | 24.516 | 40.263 | 14.632 | 1.00 | 41.99 | O |
| ATOM | 2559 | CG2 | THR | B | 152 | 26.590 | 41.300 | 14.664 | 1.00 | 46.10 | C |
| ATOM | 2560 | C   | THR | B | 152 | 26.395 | 42.278 | 12.119 | 1.00 | 49.13 | C |
| ATOM | 2561 | O   | THR | B | 152 | 27.029 | 41.917 | 11.111 | 1.00 | 46.38 | O |
| ATOM | 2562 | N   | PRO | B | 153 | 26.669 | 43.412 | 12.770 | 1.00 | 48.99 | N |
| ATOM | 2563 | CD  | PRO | B | 153 | 25.619 | 44.193 | 13.439 | 1.00 | 52.39 | C |
| ATOM | 2564 | CA  | PRO | B | 153 | 27.901 | 44.190 | 12.555 | 1.00 | 52.22 | C |
| ATOM | 2565 | CB  | PRO | B | 153 | 27.537 | 45.572 | 13.102 | 1.00 | 52.87 | C |
| ATOM | 2566 | CG  | PRO | B | 153 | 26.012 | 45.598 | 13.107 | 1.00 | 57.75 | C |
| ATOM | 2567 | C   | PRO | B | 153 | 29.109 | 43.617 | 13.322 | 1.00 | 52.65 | C |
| ATOM | 2568 | O   | PRO | B | 153 | 30.187 | 44.209 | 13.316 | 1.00 | 52.62 | O |
| ATOM | 2569 | N   | LEU | B | 154 | 28.917 | 42.473 | 13.972 | 1.00 | 47.57 | N |
| ATOM | 2570 | CA  | LEU | B | 154 | 29.976 | 41.828 | 14.747 | 1.00 | 56.79 | C |
| ATOM | 2571 | CB  | LEU | B | 154 | 29.421 | 41.133 | 16.000 | 1.00 | 49.00 | C |
| ATOM | 2572 | CG  | LEU | B | 154 | 28.426 | 41.904 | 16.878 | 1.00 | 52.80 | C |
| ATOM | 2573 | CD1 | LEU | B | 154 | 28.022 | 41.133 | 18.146 | 1.00 | 44.26 | C |
| ATOM | 2574 | CD2 | LEU | B | 154 | 28.964 | 43.282 | 17.209 | 1.00 | 53.90 | C |
| ATOM | 2575 | C   | LEU | B | 154 | 30.714 | 40.797 | 13.909 | 1.00 | 55.83 | C |
| ATOM | 2576 | O   | LEU | B | 154 | 30.192 | 40.313 | 12.902 | 1.00 | 51.73 | O |
| ATOM | 2577 | N   | THR | B | 155 | 31.921 | 40.454 | 14.352 | 1.00 | 45.67 | N |
| ATOM | 2578 | CA  | THR | B | 155 | 32.683 | 39.376 | 13.739 | 1.00 | 49.59 | C |
| ATOM | 2579 | CB  | THR | B | 155 | 33.717 | 39.899 | 12.716 | 1.00 | 54.49 | C |
| ATOM | 2580 | OG1 | THR | B | 155 | 34.876 | 40.399 | 13.401 | 1.00 | 45.06 | O |
| ATOM | 2581 | CG2 | THR | B | 155 | 33.111 | 41.009 | 11.881 | 1.00 | 55.61 | C |
| ATOM | 2582 | C   | THR | B | 155 | 33.408 | 38.638 | 14.851 | 1.00 | 50.68 | C |
| ATOM | 2583 | O   | THR | B | 155 | 33.709 | 39.221 | 15.902 | 1.00 | 53.32 | O |
| ATOM | 2584 | N   | PHE | B | 156 | 33.696 | 37.365 | 14.624 | 1.00 | 42.59 | N |
| ATOM | 2585 | CA  | PHE | B | 156 | 34.262 | 36.527 | 15.666 | 1.00 | 39.96 | C |
| ATOM | 2586 | CB  | PHE | B | 156 | 33.304 | 35.395 | 16.017 | 1.00 | 37.92 | C |
| ATOM | 2587 | CG  | PHE | B | 156 | 31.924 | 35.884 | 16.288 | 1.00 | 43.08 | C |
| ATOM | 2588 | CD1 | PHE | B | 156 | 31.051 | 36.124 | 15.234 | 1.00 | 43.49 | C |
| ATOM | 2589 | CD2 | PHE | B | 156 | 31.522 | 36.190 | 17.577 | 1.00 | 38.99 | C |
| ATOM | 2590 | CE1 | PHE | B | 156 | 29.790 | 36.613 | 15.465 | 1.00 | 44.62 | C |
| ATOM | 2591 | CE2 | PHE | B | 156 | 30.259 | 36.684 | 17.820 | 1.00 | 40.31 | C |
| ATOM | 2592 | CZ  | PHE | B | 156 | 29.392 | 36.901 | 16.768 | 1.00 | 48.27 | C |
| ATOM | 2593 | C   | PHE | B | 156 | 35.566 | 36.004 | 15.176 | 1.00 | 43.57 | C |
| ATOM | 2594 | O   | PHE | B | 156 | 35.683 | 35.570 | 14.032 | 1.00 | 44.94 | O |
| ATOM | 2595 | N   | THR | B | 157 | 36.568 | 36.113 | 16.028 | 1.00 | 39.48 | N |
| ATOM | 2596 | CA  | THR | B | 157 | 37.826 | 35.464 | 15.777 | 1.00 | 42.41 | C |
| ATOM | 2597 | CB  | THR | B | 157 | 38.958 | 36.469 | 15.546 | 1.00 | 38.47 | C |
| ATOM | 2598 | OG1 | THR | B | 157 | 39.296 | 37.106 | 16.777 | 1.00 | 54.30 | O |
| ATOM | 2599 | CG2 | THR | B | 157 | 38.504 | 37.544 | 14.592 | 1.00 | 50.07 | C |
| ATOM | 2600 | C   | THR | B | 157 | 38.087 | 34.610 | 17.004 | 1.00 | 46.17 | C |
| ATOM | 2601 | O   | THR | B | 157 | 37.925 | 35.062 | 18.156 | 1.00 | 37.93 | O |
| ATOM | 2602 | N   | ARG | B | 158 | 38.449 | 33.361 | 16.744 | 1.00 | 38.99 | N |
| ATOM | 2603 | CA  | ARG | B | 158 | 38.887 | 32.471 | 17.785 | 1.00 | 41.15 | C |
| ATOM | 2604 | CB  | ARG | B | 158 | 39.138 | 31.082 | 17.205 | 1.00 | 42.10 | C |
| ATOM | 2605 | CG  | ARG | B | 158 | 39.307 | 30.007 | 18.237 | 1.00 | 47.12 | C |
| ATOM | 2606 | CD  | ARG | B | 158 | 39.304 | 28.649 | 17.594 | 1.00 | 41.09 | C |
| ATOM | 2607 | NE  | ARG | B | 158 | 39.870 | 27.665 | 18.500 | 1.00 | 47.78 | N |
| ATOM | 2608 | CZ  | ARG | B | 158 | 40.263 | 26.455 | 18.128 | 1.00 | 48.00 | C |
| ATOM | 2609 | NH1 | ARG | B | 158 | 40.146 | 26.088 | 16.863 | 1.00 | 45.99 | N |
| ATOM | 2610 | NH2 | ARG | B | 158 | 40.782 | 25.618 | 19.018 | 1.00 | 50.44 | N |
| ATOM | 2611 | C   | ARG | B | 158 | 40.180 | 33.070 | 18.296 | 1.00 | 41.36 | C |
| ATOM | 2612 | O   | ARG | B | 158 | 40.970 | 33.581 | 17.511 | 1.00 | 41.75 | O |
| ATOM | 2613 | N   | VAL | B | 159 | 40.382 | 33.045 | 19.603 | 1.00 | 39.91 | N |
| ATOM | 2614 | CA  | VAL | B | 159 | 41.652 | 33.472 | 20.185 | 1.00 | 44.14 | C |
| ATOM | 2615 | CB  | VAL | B | 159 | 41.495 | 34.834 | 20.864 | 1.00 | 43.08 | C |
| ATOM | 2616 | CG1 | VAL | B | 159 | 42.708 | 35.178 | 21.681 | 1.00 | 49.76 | C |
| ATOM | 2617 | CG2 | VAL | B | 159 | 41.240 | 35.909 | 19.790 | 1.00 | 41.83 | C |
| ATOM | 2618 | C   | VAL | B | 159 | 42.175 | 32.366 | 21.111 | 1.00 | 38.34 | C |
| ATOM | 2619 | O   | VAL | B | 159 | 41.502 | 31.363 | 21.315 | 1.00 | 45.28 | O |
| ATOM | 2620 | N   | TYR | B | 160 | 43.377 | 32.498 | 21.635 | 1.00 | 42.84 | N |
| ATOM | 2621 | CA  | TYR | B | 160 | 43.908 | 31.415 | 22.464 | 1.00 | 46.30 | C |
| ATOM | 2622 | CB  | TYR | B | 160 | 44.995 | 30.641 | 21.703 | 1.00 | 41.91 | C |

TABLE 12-continued

Coordinates for pro MMP9(35-444 ΔFnII) (SEQ ID NO: 12) complex with Example 2

| ATOM | 2623 | CG | TYR | B | 160 | 44.435 | 29.980 | 20.467 | 1.00 | 36.51 | C |
|---|---|---|---|---|---|---|---|---|---|---|---|
| ATOM | 2624 | CD1 | TYR | B | 160 | 44.287 | 30.692 | 19.293 | 1.00 | 42.24 | C |
| ATOM | 2625 | CE1 | TYR | B | 160 | 43.737 | 30.111 | 18.161 | 1.00 | 43.41 | C |
| ATOM | 2626 | CD2 | TYR | B | 160 | 43.997 | 28.665 | 20.493 | 1.00 | 40.59 | C |
| ATOM | 2627 | CE2 | TYR | B | 160 | 43.436 | 28.068 | 19.371 | 1.00 | 39.73 | C |
| ATOM | 2628 | CZ | TYR | B | 160 | 43.313 | 28.799 | 18.203 | 1.00 | 44.58 | C |
| ATOM | 2629 | OH | TYR | B | 160 | 42.782 | 28.216 | 17.063 | 1.00 | 48.09 | O |
| ATOM | 2630 | C | TYR | B | 160 | 44.354 | 31.804 | 23.883 | 1.00 | 42.41 | C |
| ATOM | 2631 | O | TYR | B | 160 | 45.160 | 31.111 | 24.487 | 1.00 | 42.25 | O |
| ATOM | 2632 | N | SER | B | 161 | 43.795 | 32.874 | 24.436 | 1.00 | 45.05 | N |
| ATOM | 2633 | CA | SER | B | 161 | 44.065 | 33.206 | 25.849 | 1.00 | 50.83 | C |
| ATOM | 2634 | CB | SER | B | 161 | 45.028 | 34.387 | 25.957 | 1.00 | 46.11 | C |
| ATOM | 2635 | OG | SER | B | 161 | 44.544 | 35.500 | 25.211 | 1.00 | 52.41 | O |
| ATOM | 2636 | C | SER | B | 161 | 42.811 | 33.548 | 26.642 | 1.00 | 46.38 | C |
| ATOM | 2637 | O | SER | B | 161 | 41.805 | 33.971 | 26.079 | 1.00 | 45.28 | O |
| ATOM | 2638 | N | ARG | B | 162 | 42.896 | 33.385 | 27.956 | 1.00 | 52.45 | N |
| ATOM | 2639 | CA | ARG | B | 162 | 41.860 | 33.844 | 28.879 | 1.00 | 51.61 | C |
| ATOM | 2640 | CB | ARG | B | 162 | 42.469 | 34.069 | 30.270 | 1.00 | 49.34 | C |
| ATOM | 2641 | CG | ARG | B | 162 | 42.309 | 32.890 | 31.244 | 1.00 | 65.82 | C |
| ATOM | 2642 | CD | ARG | B | 162 | 43.603 | 32.582 | 32.018 | 1.00 | 49.54 | C |
| ATOM | 2643 | NE | ARG | B | 162 | 44.583 | 31.981 | 31.122 | 1.00 | 59.77 | N |
| ATOM | 2644 | CZ | ARG | B | 162 | 44.723 | 30.672 | 30.944 | 1.00 | 59.68 | C |
| ATOM | 2645 | NH1 | ARG | B | 162 | 43.957 | 29.828 | 31.631 | 1.00 | 47.87 | N |
| ATOM | 2646 | NH2 | ARG | B | 162 | 45.630 | 30.210 | 30.081 | 1.00 | 54.39 | N |
| ATOM | 2647 | C | ARG | B | 162 | 41.197 | 35.138 | 28.384 | 1.00 | 53.50 | C |
| ATOM | 2648 | O | ARG | B | 162 | 39.988 | 35.334 | 28.551 | 1.00 | 53.34 | O |
| ATOM | 2649 | N | ASP | B | 163 | 41.997 | 36.007 | 27.768 | 1.00 | 43.29 | N |
| ATOM | 2650 | CA | ASP | B | 163 | 41.545 | 37.317 | 27.288 | 1.00 | 56.43 | C |
| ATOM | 2651 | CB | ASP | B | 163 | 42.594 | 37.909 | 26.329 | 1.00 | 60.87 | C |
| ATOM | 2652 | CG | ASP | B | 163 | 43.042 | 39.310 | 26.735 | 1.00 | 65.30 | C |
| ATOM | 2653 | OD1 | ASP | B | 163 | 44.020 | 39.826 | 26.145 | 1.00 | 60.90 | O |
| ATOM | 2654 | OD2 | ASP | B | 163 | 42.409 | 39.897 | 27.643 | 1.00 | 72.49 | O |
| ATOM | 2655 | C | ASP | B | 163 | 40.129 | 37.383 | 26.646 | 1.00 | 59.61 | C |
| ATOM | 2656 | O | ASP | B | 163 | 39.329 | 38.249 | 26.995 | 1.00 | 60.23 | O |
| ATOM | 2657 | N | ALA | B | 164 | 39.844 | 36.472 | 25.715 | 1.00 | 55.26 | N |
| ATOM | 2658 | CA | ALA | B | 164 | 38.604 | 36.467 | 24.908 | 1.00 | 50.58 | C |
| ATOM | 2659 | CB | ALA | B | 164 | 38.414 | 35.083 | 24.242 | 1.00 | 44.38 | C |
| ATOM | 2660 | C | ALA | B | 164 | 37.290 | 36.891 | 25.587 | 1.00 | 49.22 | C |
| ATOM | 2661 | O | ALA | B | 164 | 36.920 | 36.350 | 26.620 | 1.00 | 47.88 | O |
| ATOM | 2662 | N | ASP | B | 165 | 36.582 | 37.833 | 24.962 | 1.00 | 50.27 | N |
| ATOM | 2663 | CA | ASP | B | 165 | 35.216 | 38.196 | 25.342 | 1.00 | 44.63 | C |
| ATOM | 2664 | CB | ASP | B | 165 | 34.498 | 38.953 | 24.206 | 1.00 | 45.52 | C |
| ATOM | 2665 | CG | ASP | B | 165 | 35.289 | 40.165 | 23.676 | 1.00 | 51.92 | C |
| ATOM | 2666 | OD1 | ASP | B | 165 | 35.223 | 40.425 | 22.450 | 1.00 | 50.47 | O |
| ATOM | 2667 | OD2 | ASP | B | 165 | 35.962 | 40.862 | 24.464 | 1.00 | 45.35 | O |
| ATOM | 2668 | C | ASP | B | 165 | 34.395 | 36.944 | 25.671 | 1.00 | 44.86 | C |
| ATOM | 2669 | O | ASP | B | 165 | 33.687 | 36.883 | 26.674 | 1.00 | 39.38 | O |
| ATOM | 2670 | N | ILE | B | 166 | 34.476 | 35.940 | 24.809 | 1.00 | 45.32 | N |
| ATOM | 2671 | CA | ILE | B | 166 | 33.668 | 34.749 | 25.013 | 1.00 | 47.66 | C |
| ATOM | 2672 | CB | ILE | B | 166 | 32.779 | 34.420 | 23.805 | 1.00 | 47.15 | C |
| ATOM | 2673 | CG2 | ILE | B | 166 | 32.051 | 33.119 | 24.057 | 1.00 | 39.55 | C |
| ATOM | 2674 | CG1 | ILE | B | 166 | 31.801 | 35.560 | 23.528 | 1.00 | 45.07 | C |
| ATOM | 2675 | CD1 | ILE | B | 166 | 30.838 | 35.263 | 22.393 | 1.00 | 39.87 | C |
| ATOM | 2676 | C | ILE | B | 166 | 34.510 | 33.529 | 25.327 | 1.00 | 46.59 | C |
| ATOM | 2677 | O | ILE | B | 166 | 35.129 | 32.931 | 24.438 | 1.00 | 41.09 | O |
| ATOM | 2678 | N | VAL | B | 167 | 34.528 | 33.165 | 26.605 | 1.00 | 46.44 | N |
| ATOM | 2679 | CA | VAL | B | 167 | 35.243 | 31.985 | 27.033 | 1.00 | 45.54 | C |
| ATOM | 2680 | CB | VAL | B | 167 | 35.837 | 32.153 | 28.434 | 1.00 | 47.68 | C |
| ATOM | 2681 | CG1 | VAL | B | 167 | 36.183 | 30.799 | 29.035 | 1.00 | 45.14 | C |
| ATOM | 2682 | CG2 | VAL | B | 167 | 37.049 | 33.040 | 28.365 | 1.00 | 44.51 | C |
| ATOM | 2683 | C | VAL | B | 167 | 34.253 | 30.849 | 27.019 | 1.00 | 47.23 | C |
| ATOM | 2684 | O | VAL | B | 167 | 33.202 | 30.933 | 27.648 | 1.00 | 47.05 | O |
| ATOM | 2685 | N | ILE | B | 168 | 34.592 | 29.798 | 26.280 | 1.00 | 43.73 | N |
| ATOM | 2686 | CA | ILE | B | 168 | 33.720 | 28.653 | 26.091 | 1.00 | 40.59 | C |
| ATOM | 2687 | CB | ILE | B | 168 | 33.640 | 28.285 | 24.585 | 1.00 | 43.09 | C |
| ATOM | 2688 | CG2 | ILE | B | 168 | 33.041 | 26.896 | 24.400 | 1.00 | 35.97 | C |
| ATOM | 2689 | CG1 | ILE | B | 168 | 32.858 | 29.367 | 23.835 | 1.00 | 39.54 | C |
| ATOM | 2690 | CD1 | ILE | B | 168 | 32.964 | 29.288 | 22.340 | 1.00 | 40.13 | C |
| ATOM | 2691 | C | ILE | B | 168 | 34.263 | 27.487 | 26.889 | 1.00 | 38.60 | C |
| ATOM | 2692 | O | ILE | B | 168 | 35.482 | 27.272 | 26.927 | 1.00 | 47.70 | O |
| ATOM | 2693 | N | GLN | B | 169 | 33.388 | 26.719 | 27.520 | 1.00 | 34.54 | N |
| ATOM | 2694 | CA | GLN | B | 169 | 33.878 | 25.711 | 28.467 | 1.00 | 40.05 | C |
| ATOM | 2695 | CB | GLN | B | 169 | 34.188 | 26.389 | 29.813 | 1.00 | 41.85 | C |
| ATOM | 2696 | CG | GLN | B | 169 | 34.307 | 25.495 | 31.036 | 1.00 | 46.92 | C |
| ATOM | 2697 | CD | GLN | B | 169 | 34.463 | 26.328 | 32.306 | 1.00 | 51.78 | C |
| ATOM | 2698 | OE1 | GLN | B | 169 | 34.104 | 25.900 | 33.407 | 1.00 | 46.07 | O |
| ATOM | 2699 | NE2 | GLN | B | 169 | 34.996 | 27.539 | 32.149 | 1.00 | 56.59 | N |

TABLE 12-continued

Coordinates for pro MMP9(35-444 ΔFnII) (SEQ ID NO: 12) complex with Example 2

| ATOM | 2700 | C | GLN | B | 169 | 32.965 | 24.500 | 28.642 | 1.00 | 40.63 | C |
|------|------|------|-----|---|-----|--------|--------|--------|------|-------|---|
| ATOM | 2701 | O | GLN | B | 169 | 31.747 | 24.617 | 28.669 | 1.00 | 49.42 | O |
| ATOM | 2702 | N | PHE | B | 170 | 33.559 | 23.325 | 28.744 | 1.00 | 44.35 | N |
| ATOM | 2703 | CA | PHE | B | 170 | 32.780 | 22.132 | 29.010 | 1.00 | 49.07 | C |
| ATOM | 2704 | CB | PHE | B | 170 | 33.313 | 20.961 | 28.209 | 1.00 | 46.98 | C |
| ATOM | 2705 | CG | PHE | B | 170 | 32.917 | 20.984 | 26.785 | 1.00 | 46.12 | C |
| ATOM | 2706 | CD1 | PHE | B | 170 | 33.660 | 21.685 | 25.860 | 1.00 | 50.30 | C |
| ATOM | 2707 | CD2 | PHE | B | 170 | 31.799 | 20.301 | 26.361 | 1.00 | 48.43 | C |
| ATOM | 2708 | CE1 | PHE | B | 170 | 33.299 | 21.698 | 24.527 | 1.00 | 45.87 | C |
| ATOM | 2709 | CE2 | PHE | B | 170 | 31.438 | 20.303 | 25.044 | 1.00 | 46.67 | C |
| ATOM | 2710 | CZ | PHE | B | 170 | 32.191 | 21.007 | 24.119 | 1.00 | 44.42 | C |
| ATOM | 2711 | C | PHE | B | 170 | 32.919 | 21.836 | 30.484 | 1.00 | 45.77 | C |
| ATOM | 2712 | O | PHE | B | 170 | 34.008 | 21.971 | 31.021 | 1.00 | 47.32 | O |
| ATOM | 2713 | N | GLY | B | 171 | 31.824 | 21.450 | 31.131 | 1.00 | 45.24 | N |
| ATOM | 2714 | CA | GLY | B | 171 | 31.828 | 21.182 | 32.565 | 1.00 | 50.33 | C |
| ATOM | 2715 | C | GLY | B | 171 | 30.826 | 20.107 | 32.926 | 1.00 | 51.23 | C |
| ATOM | 2716 | O | GLY | B | 171 | 30.096 | 19.640 | 32.061 | 1.00 | 54.72 | O |
| ATOM | 2717 | N | VAL | B | 172 | 30.758 | 19.723 | 34.193 | 1.00 | 50.00 | N |
| ATOM | 2718 | CA | VAL | B | 172 | 29.923 | 18.593 | 34.568 | 1.00 | 49.97 | C |
| ATOM | 2719 | CB | VAL | B | 172 | 30.790 | 17.395 | 34.964 | 1.00 | 57.79 | C |
| ATOM | 2720 | CG1 | VAL | B | 172 | 30.058 | 16.509 | 35.957 | 1.00 | 59.47 | C |
| ATOM | 2721 | CG2 | VAL | B | 172 | 31.216 | 16.620 | 33.706 | 1.00 | 48.17 | C |
| ATOM | 2722 | C | VAL | B | 172 | 28.864 | 18.881 | 35.644 | 1.00 | 60.01 | C |
| ATOM | 2723 | O | VAL | B | 172 | 27.659 | 18.688 | 35.414 | 1.00 | 63.69 | O |
| ATOM | 2724 | N | ALA | B | 173 | 29.293 | 19.330 | 36.816 | 1.00 | 50.32 | N |
| ATOM | 2725 | CA | ALA | B | 173 | 28.337 | 19.660 | 37.865 | 1.00 | 44.24 | C |
| ATOM | 2726 | CB | ALA | B | 173 | 28.433 | 18.678 | 39.002 | 1.00 | 40.20 | C |
| ATOM | 2727 | C | ALA | B | 173 | 28.617 | 21.076 | 38.336 | 1.00 | 47.33 | C |
| ATOM | 2728 | O | ALA | B | 173 | 28.365 | 22.020 | 37.598 | 1.00 | 43.53 | O |
| ATOM | 2729 | N | GLU | B | 174 | 29.153 | 21.234 | 39.547 | 1.00 | 45.48 | N |
| ATOM | 2730 | CA | GLU | B | 174 | 29.634 | 22.550 | 39.968 | 1.00 | 48.12 | C |
| ATOM | 2731 | CB | GLU | B | 174 | 29.926 | 22.604 | 41.478 | 1.00 | 47.78 | C |
| ATOM | 2732 | CG | GLU | B | 174 | 29.132 | 23.667 | 42.258 | 1.00 | 43.07 | C |
| ATOM | 2733 | CD | GLU | B | 174 | 29.432 | 25.112 | 41.849 | 1.00 | 50.86 | C |
| ATOM | 2734 | OE1 | GLU | B | 174 | 30.539 | 25.405 | 41.334 | 1.00 | 51.30 | O |
| ATOM | 2735 | OE2 | GLU | B | 174 | 28.549 | 25.971 | 42.067 | 1.00 | 54.43 | O |
| ATOM | 2736 | C | GLU | B | 174 | 30.911 | 22.815 | 39.179 | 1.00 | 47.74 | C |
| ATOM | 2737 | O | GLU | B | 174 | 31.951 | 22.205 | 39.442 | 1.00 | 47.90 | O |
| ATOM | 2738 | N | HIS | B | 175 | 30.838 | 23.695 | 38.190 | 1.00 | 46.43 | N |
| ATOM | 2739 | CA | HIS | B | 175 | 32.013 | 23.921 | 37.355 | 1.00 | 51.77 | C |
| ATOM | 2740 | CB | HIS | B | 175 | 31.691 | 23.828 | 35.851 | 1.00 | 50.72 | C |
| ATOM | 2741 | CG | HIS | B | 175 | 30.315 | 24.286 | 35.497 | 1.00 | 42.77 | C |
| ATOM | 2742 | CD2 | HIS | B | 175 | 29.887 | 25.309 | 34.720 | 1.00 | 44.80 | C |
| ATOM | 2743 | ND1 | HIS | B | 175 | 29.182 | 23.657 | 35.958 | 1.00 | 50.90 | N |
| ATOM | 2744 | CE1 | HIS | B | 175 | 28.112 | 24.269 | 35.485 | 1.00 | 51.82 | C |
| ATOM | 2745 | NE2 | HIS | B | 175 | 28.512 | 25.273 | 34.727 | 1.00 | 52.15 | N |
| ATOM | 2746 | C | HIS | B | 175 | 32.709 | 25.222 | 37.713 | 1.00 | 50.14 | C |
| ATOM | 2747 | O | HIS | B | 175 | 33.626 | 25.654 | 37.020 | 1.00 | 51.80 | O |
| ATOM | 2748 | N | GLY | B | 176 | 32.265 | 25.837 | 38.805 | 1.00 | 52.97 | N |
| ATOM | 2749 | CA | GLY | B | 176 | 32.970 | 26.971 | 39.370 | 1.00 | 49.35 | C |
| ATOM | 2750 | C | GLY | B | 176 | 32.364 | 28.316 | 39.036 | 1.00 | 55.22 | C |
| ATOM | 2751 | O | GLY | B | 176 | 33.094 | 29.281 | 38.812 | 1.00 | 55.51 | O |
| ATOM | 2752 | N | ASP | B | 177 | 31.036 | 28.394 | 39.002 | 1.00 | 50.37 | N |
| ATOM | 2753 | CA | ASP | B | 177 | 30.384 | 29.661 | 38.719 | 1.00 | 41.44 | C |
| ATOM | 2754 | CB | ASP | B | 177 | 30.270 | 29.885 | 37.212 | 1.00 | 45.44 | C |
| ATOM | 2755 | CG | ASP | B | 177 | 29.129 | 29.115 | 36.581 | 1.00 | 45.46 | C |
| ATOM | 2756 | OD1 | ASP | B | 177 | 28.604 | 28.148 | 37.180 | 1.00 | 46.45 | O |
| ATOM | 2757 | OD2 | ASP | B | 177 | 28.761 | 29.494 | 35.452 | 1.00 | 47.77 | O |
| ATOM | 2758 | C | ASP | B | 177 | 29.024 | 29.816 | 39.396 | 1.00 | 48.73 | C |
| ATOM | 2759 | O | ASP | B | 177 | 28.288 | 30.780 | 39.118 | 1.00 | 47.25 | O |
| ATOM | 2760 | N | GLY | B | 178 | 28.704 | 28.875 | 40.284 | 1.00 | 49.40 | N |
| ATOM | 2761 | CA | GLY | B | 178 | 27.518 | 28.976 | 41.122 | 1.00 | 48.06 | C |
| ATOM | 2762 | C | GLY | B | 178 | 26.244 | 28.601 | 40.382 | 1.00 | 51.59 | C |
| ATOM | 2763 | O | GLY | B | 178 | 25.150 | 28.952 | 40.810 | 1.00 | 52.16 | O |
| ATOM | 2764 | N | TYR | B | 179 | 26.391 | 27.903 | 39.259 | 1.00 | 51.51 | N |
| ATOM | 2765 | CA | TYR | B | 179 | 25.247 | 27.382 | 38.520 | 1.00 | 49.71 | C |
| ATOM | 2766 | CB | TYR | B | 179 | 24.874 | 28.311 | 37.362 | 1.00 | 43.33 | C |
| ATOM | 2767 | CG | TYR | B | 179 | 24.265 | 29.635 | 37.791 | 1.00 | 47.22 | C |
| ATOM | 2768 | CD1 | TYR | B | 179 | 25.058 | 30.759 | 38.007 | 1.00 | 50.29 | C |
| ATOM | 2769 | CE1 | TYR | B | 179 | 24.505 | 31.979 | 38.388 | 1.00 | 45.13 | C |
| ATOM | 2770 | CD2 | TYR | B | 179 | 22.899 | 29.767 | 37.965 | 1.00 | 43.61 | C |
| ATOM | 2771 | CE2 | TYR | B | 179 | 22.340 | 30.989 | 38.340 | 1.00 | 48.53 | C |
| ATOM | 2772 | CZ | TYR | B | 179 | 23.147 | 32.086 | 38.549 | 1.00 | 50.90 | C |
| ATOM | 2773 | OH | TYR | B | 179 | 22.580 | 33.284 | 38.924 | 1.00 | 53.58 | O |
| ATOM | 2774 | C | TYR | B | 179 | 25.601 | 25.995 | 38.007 | 1.00 | 48.24 | C |
| ATOM | 2775 | O | TYR | B | 179 | 25.953 | 25.825 | 36.845 | 1.00 | 49.75 | O |
| ATOM | 2776 | N | PRO | B | 180 | 25.529 | 24.992 | 38.887 | 1.00 | 45.68 | N |

TABLE 12-continued

Coordinates for pro MMP9(35-444 ΔFnII) (SEQ ID NO: 12) complex with Example 2

| ATOM | 2777 | CD  | PRO | B | 180 | 24.882 | 24.996 | 40.208 | 1.00 | 49.14 | C |
| ATOM | 2778 | CA  | PRO | B | 180 | 25.996 | 23.661 | 38.502 | 1.00 | 44.76 | C |
| ATOM | 2779 | CB  | PRO | B | 180 | 25.899 | 22.845 | 39.804 | 1.00 | 43.44 | C |
| ATOM | 2780 | CG  | PRO | B | 180 | 25.504 | 23.821 | 40.885 | 1.00 | 51.17 | C |
| ATOM | 2781 | C   | PRO | B | 180 | 25.077 | 23.038 | 37.468 | 1.00 | 47.80 | C |
| ATOM | 2782 | O   | PRO | B | 180 | 23.865 | 23.267 | 37.502 | 1.00 | 55.51 | O |
| ATOM | 2783 | N   | PHE | B | 181 | 25.651 | 22.256 | 36.563 | 1.00 | 47.21 | N |
| ATOM | 2784 | CA  | PHE | B | 181 | 24.864 | 21.402 | 35.701 | 1.00 | 50.02 | C |
| ATOM | 2785 | CB  | PHE | B | 181 | 25.691 | 20.947 | 34.512 | 1.00 | 51.95 | C |
| ATOM | 2786 | CG  | PHE | B | 181 | 25.954 | 22.038 | 33.528 | 1.00 | 48.50 | C |
| ATOM | 2787 | CD1 | PHE | B | 181 | 24.914 | 22.826 | 33.067 | 1.00 | 47.28 | C |
| ATOM | 2788 | CD2 | PHE | B | 181 | 27.233 | 22.277 | 33.063 | 1.00 | 49.14 | C |
| ATOM | 2789 | CE1 | PHE | B | 181 | 25.139 | 23.833 | 32.146 | 1.00 | 44.71 | C |
| ATOM | 2790 | CE2 | PHE | B | 181 | 27.470 | 23.276 | 32.152 | 1.00 | 46.17 | C |
| ATOM | 2791 | CZ  | PHE | B | 181 | 26.417 | 24.058 | 31.693 | 1.00 | 46.26 | C |
| ATOM | 2792 | C   | PHE | B | 181 | 24.361 | 20.221 | 36.509 | 1.00 | 48.80 | C |
| ATOM | 2793 | O   | PHE | B | 181 | 24.868 | 19.947 | 37.599 | 1.00 | 45.12 | O |
| ATOM | 2794 | N   | ASP | B | 182 | 23.352 | 19.541 | 35.973 | 1.00 | 54.26 | N |
| ATOM | 2795 | CA  | ASP | B | 182 | 22.511 | 18.640 | 36.768 | 1.00 | 51.42 | C |
| ATOM | 2796 | CB  | ASP | B | 182 | 21.021 | 19.020 | 36.642 | 1.00 | 41.18 | C |
| ATOM | 2797 | CG  | ASP | B | 182 | 20.438 | 18.703 | 35.253 | 1.00 | 53.65 | C |
| ATOM | 2798 | OD1 | ASP | B | 182 | 21.145 | 18.897 | 34.244 | 1.00 | 51.66 | O |
| ATOM | 2799 | OD2 | ASP | B | 182 | 19.271 | 18.257 | 35.163 | 1.00 | 53.92 | O |
| ATOM | 2800 | C   | ASP | B | 182 | 22.709 | 17.194 | 36.352 | 1.00 | 52.76 | C |
| ATOM | 2801 | O   | ASP | B | 182 | 21.815 | 16.364 | 36.502 | 1.00 | 56.83 | O |
| ATOM | 2802 | N   | GLY | B | 183 | 23.886 | 16.881 | 35.842 | 1.00 | 48.28 | N |
| ATOM | 2803 | CA  | GLY | B | 183 | 24.106 | 15.553 | 35.324 | 1.00 | 54.74 | C |
| ATOM | 2804 | C   | GLY | B | 183 | 23.546 | 15.400 | 33.921 | 1.00 | 58.43 | C |
| ATOM | 2805 | O   | GLY | B | 183 | 23.816 | 16.198 | 33.029 | 1.00 | 59.65 | O |
| ATOM | 2806 | N   | LYS | B | 184 | 22.748 | 14.368 | 33.726 | 1.00 | 53.68 | N |
| ATOM | 2807 | CA  | LYS | B | 184 | 22.341 | 13.962 | 32.397 | 1.00 | 53.55 | C |
| ATOM | 2808 | CB  | LYS | B | 184 | 22.506 | 12.446 | 32.293 | 1.00 | 53.83 | C |
| ATOM | 2809 | CG  | LYS | B | 184 | 21.557 | 11.752 | 31.348 | 1.00 | 57.21 | C |
| ATOM | 2810 | CD  | LYS | B | 184 | 21.399 | 10.292 | 31.751 | 1.00 | 60.16 | C |
| ATOM | 2811 | CE  | LYS | B | 184 | 20.555 | 9.543  | 30.750 | 1.00 | 61.42 | C |
| ATOM | 2812 | NZ  | LYS | B | 184 | 21.140 | 9.714  | 29.392 | 1.00 | 64.94 | N |
| ATOM | 2813 | C   | LYS | B | 184 | 20.907 | 14.383 | 32.065 | 1.00 | 54.48 | C |
| ATOM | 2814 | O   | LYS | B | 184 | 19.990 | 14.112 | 32.840 | 1.00 | 58.34 | O |
| ATOM | 2815 | N   | ASP | B | 185 | 20.726 | 15.076 | 30.941 | 1.00 | 50.25 | N |
| ATOM | 2816 | CA  | ASP | B | 185 | 19.392 | 15.312 | 30.365 | 1.00 | 53.85 | C |
| ATOM | 2817 | CB  | ASP | B | 185 | 18.608 | 13.995 | 30.280 | 1.00 | 55.73 | C |
| ATOM | 2818 | CG  | ASP | B | 185 | 19.205 | 13.045 | 29.292 | 1.00 | 54.19 | C |
| ATOM | 2819 | OD1 | ASP | B | 185 | 19.845 | 13.550 | 28.359 | 1.00 | 43.11 | O |
| ATOM | 2820 | OD2 | ASP | B | 185 | 19.046 | 11.815 | 29.450 | 1.00 | 60.16 | O |
| ATOM | 2821 | C   | ASP | B | 185 | 18.499 | 16.335 | 31.057 | 1.00 | 58.06 | C |
| ATOM | 2822 | O   | ASP | B | 185 | 17.268 | 16.216 | 31.012 | 1.00 | 58.43 | O |
| ATOM | 2823 | N   | GLY | B | 186 | 19.084 | 17.328 | 31.708 | 1.00 | 54.05 | N |
| ATOM | 2824 | CA  | GLY | B | 186 | 18.258 | 18.325 | 32.363 | 1.00 | 50.65 | C |
| ATOM | 2825 | C   | GLY | B | 186 | 18.436 | 19.614 | 31.611 | 1.00 | 51.53 | C |
| ATOM | 2826 | O   | GLY | B | 186 | 17.932 | 19.778 | 30.500 | 1.00 | 46.01 | O |
| ATOM | 2827 | N   | LEU | B | 187 | 19.179 | 20.531 | 32.212 | 1.00 | 53.10 | N |
| ATOM | 2828 | CA  | LEU | B | 187 | 19.711 | 21.637 | 31.440 | 1.00 | 53.17 | C |
| ATOM | 2829 | CB  | LEU | B | 187 | 19.917 | 22.868 | 32.324 | 1.00 | 47.91 | C |
| ATOM | 2830 | CG  | LEU | B | 187 | 20.416 | 22.602 | 33.735 | 1.00 | 51.87 | C |
| ATOM | 2831 | CD1 | LEU | B | 187 | 21.867 | 22.175 | 33.677 | 1.00 | 58.23 | C |
| ATOM | 2832 | CD2 | LEU | B | 187 | 20.244 | 23.838 | 34.620 | 1.00 | 50.75 | C |
| ATOM | 2833 | C   | LEU | B | 187 | 21.005 | 21.180 | 30.729 | 1.00 | 54.14 | C |
| ATOM | 2834 | O   | LEU | B | 187 | 21.845 | 20.481 | 31.311 | 1.00 | 53.20 | O |
| ATOM | 2835 | N   | LEU | B | 188 | 21.143 | 21.571 | 29.468 | 1.00 | 47.16 | N |
| ATOM | 2836 | CA  | LEU | B | 188 | 22.213 | 21.101 | 28.602 | 1.00 | 40.11 | C |
| ATOM | 2837 | CB  | LEU | B | 188 | 21.674 | 20.999 | 27.176 | 1.00 | 40.92 | C |
| ATOM | 2838 | CG  | LEU | B | 188 | 20.422 | 20.129 | 26.980 | 1.00 | 39.12 | C |
| ATOM | 2839 | CD1 | LEU | B | 188 | 19.842 | 20.294 | 25.595 | 1.00 | 47.00 | C |
| ATOM | 2840 | CD2 | LEU | B | 188 | 20.743 | 18.669 | 27.195 | 1.00 | 42.65 | C |
| ATOM | 2841 | C   | LEU | B | 188 | 23.413 | 22.046 | 28.635 | 1.00 | 42.63 | C |
| ATOM | 2842 | O   | LEU | B | 188 | 24.569 | 21.620 | 28.492 | 1.00 | 45.19 | O |
| ATOM | 2843 | N   | ALA | B | 189 | 23.136 | 23.336 | 28.805 | 1.00 | 38.80 | N |
| ATOM | 2844 | CA  | ALA | B | 189 | 24.186 | 24.350 | 28.830 | 1.00 | 42.55 | C |
| ATOM | 2845 | CB  | ALA | B | 189 | 24.987 | 24.330 | 27.510 | 1.00 | 41.22 | C |
| ATOM | 2846 | C   | ALA | B | 189 | 23.629 | 25.752 | 29.135 | 1.00 | 43.73 | C |
| ATOM | 2847 | O   | ALA | B | 189 | 22.411 | 25.918 | 29.283 | 1.00 | 40.33 | O |
| ATOM | 2848 | N   | HIS | B | 190 | 24.515 | 26.744 | 29.260 | 1.00 | 40.60 | N |
| ATOM | 2849 | CA  | HIS | B | 190 | 24.092 | 28.130 | 29.492 | 1.00 | 44.48 | C |
| ATOM | 2850 | CB  | HIS | B | 190 | 23.537 | 28.345 | 30.909 | 1.00 | 39.24 | C |
| ATOM | 2851 | CG  | HIS | B | 190 | 24.411 | 27.811 | 31.998 | 1.00 | 43.97 | C |
| ATOM | 2852 | CD2 | HIS | B | 190 | 25.728 | 27.992 | 32.263 | 1.00 | 47.51 | C |
| ATOM | 2853 | ND1 | HIS | B | 190 | 23.935 | 26.975 | 32.987 | 1.00 | 45.16 | N |

TABLE 12-continued

Coordinates for pro MMP9(35-444 ΔFnII) (SEQ ID NO: 12) complex with Example 2

| ATOM | 2854 | CE1 | HIS | B | 190 | 24.921 | 26.665 | 33.813 | 1.00 | 43.06 | C |
|---|---|---|---|---|---|---|---|---|---|---|---|
| ATOM | 2855 | NE2 | HIS | B | 190 | 26.019 | 27.269 | 33.396 | 1.00 | 42.91 | N |
| ATOM | 2856 | C | HIS | B | 190 | 25.173 | 29.168 | 29.177 | 1.00 | 42.83 | C |
| ATOM | 2857 | O | HIS | B | 190 | 26.229 | 28.836 | 28.653 | 1.00 | 39.94 | O |
| ATOM | 2858 | N | ALA | B | 191 | 24.890 | 30.429 | 29.497 | 1.00 | 38.14 | N |
| ATOM | 2859 | CA | ALA | B | 191 | 25.775 | 31.529 | 29.156 | 1.00 | 42.01 | C |
| ATOM | 2860 | CB | ALA | B | 191 | 25.705 | 31.840 | 27.649 | 1.00 | 41.11 | C |
| ATOM | 2861 | C | ALA | B | 191 | 25.372 | 32.750 | 29.962 | 1.00 | 45.68 | C |
| ATOM | 2862 | O | ALA | B | 191 | 24.291 | 32.785 | 30.554 | 1.00 | 43.97 | O |
| ATOM | 2863 | N | PHE | B | 192 | 26.239 | 33.756 | 29.959 | 1.00 | 45.58 | N |
| ATOM | 2864 | CA | PHE | B | 192 | 25.978 | 35.003 | 30.655 | 1.00 | 43.55 | C |
| ATOM | 2865 | CB | PHE | B | 192 | 27.116 | 35.311 | 31.626 | 1.00 | 45.45 | C |
| ATOM | 2866 | CG | PHE | B | 192 | 27.387 | 34.210 | 32.621 | 1.00 | 49.65 | C |
| ATOM | 2867 | CD1 | PHE | B | 192 | 26.863 | 34.269 | 33.897 | 1.00 | 50.50 | C |
| ATOM | 2868 | CD2 | PHE | B | 192 | 28.169 | 33.120 | 32.277 | 1.00 | 50.65 | C |
| ATOM | 2869 | CE1 | PHE | B | 192 | 27.109 | 33.272 | 34.805 | 1.00 | 45.53 | C |
| ATOM | 2870 | CE2 | PHE | B | 192 | 28.418 | 32.117 | 33.186 | 1.00 | 49.79 | C |
| ATOM | 2871 | CZ | PHE | B | 192 | 27.887 | 32.191 | 34.447 | 1.00 | 46.35 | C |
| ATOM | 2872 | C | PHE | B | 192 | 25.890 | 36.098 | 29.614 | 1.00 | 45.28 | C |
| ATOM | 2873 | O | PHE | B | 192 | 26.533 | 36.006 | 28.586 | 1.00 | 39.26 | O |
| ATOM | 2874 | N | PRO | B | 193 | 25.092 | 37.150 | 29.878 | 1.00 | 46.19 | N |
| ATOM | 2875 | CD | PRO | B | 193 | 24.435 | 37.521 | 31.132 | 1.00 | 46.14 | C |
| ATOM | 2876 | CA | PRO | B | 193 | 24.980 | 38.215 | 28.881 | 1.00 | 48.37 | C |
| ATOM | 2877 | CB | PRO | B | 193 | 24.004 | 39.210 | 29.531 | 1.00 | 45.06 | C |
| ATOM | 2878 | CG | PRO | B | 193 | 23.457 | 38.540 | 30.685 | 1.00 | 48.62 | C |
| ATOM | 2879 | C | PRO | B | 193 | 26.332 | 38.895 | 28.635 | 1.00 | 45.66 | C |
| ATOM | 2880 | O | PRO | B | 193 | 27.284 | 38.645 | 29.359 | 1.00 | 43.50 | O |
| ATOM | 2881 | N | PRO | B | 194 | 26.414 | 39.745 | 27.601 | 1.00 | 49.70 | N |
| ATOM | 2882 | CD | PRO | B | 194 | 25.437 | 39.879 | 26.511 | 1.00 | 46.95 | C |
| ATOM | 2883 | CA | PRO | B | 194 | 27.623 | 40.537 | 27.358 | 1.00 | 48.78 | C |
| ATOM | 2884 | CB | PRO | B | 194 | 27.223 | 41.419 | 26.174 | 1.00 | 48.92 | C |
| ATOM | 2885 | CG | PRO | B | 194 | 26.210 | 40.609 | 25.445 | 1.00 | 48.47 | C |
| ATOM | 2886 | C | PRO | B | 194 | 27.950 | 41.393 | 28.571 | 1.00 | 51.18 | C |
| ATOM | 2887 | O | PRO | B | 194 | 27.087 | 41.608 | 29.421 | 1.00 | 49.25 | O |
| ATOM | 2888 | N | GLY | B | 195 | 29.179 | 41.885 | 28.639 | 1.00 | 46.50 | N |
| ATOM | 2889 | CA | GLY | B | 195 | 29.650 | 42.585 | 29.812 | 1.00 | 50.47 | C |
| ATOM | 2890 | C | GLY | B | 195 | 30.954 | 41.962 | 30.263 | 1.00 | 56.57 | C |
| ATOM | 2891 | O | GLY | B | 195 | 31.405 | 40.984 | 29.668 | 1.00 | 56.94 | O |
| ATOM | 2892 | N | PRO | B | 196 | 31.566 | 42.529 | 31.311 | 1.00 | 53.57 | N |
| ATOM | 2893 | CD | PRO | B | 196 | 30.991 | 43.735 | 31.935 | 1.00 | 58.62 | C |
| ATOM | 2894 | CA | PRO | B | 196 | 32.874 | 42.179 | 31.886 | 1.00 | 51.48 | C |
| ATOM | 2895 | CB | PRO | B | 196 | 32.928 | 43.036 | 33.155 | 1.00 | 53.80 | C |
| ATOM | 2896 | CG | PRO | B | 196 | 32.087 | 44.220 | 32.847 | 1.00 | 60.70 | C |
| ATOM | 2897 | C | PRO | B | 196 | 33.105 | 40.706 | 32.264 | 1.00 | 53.61 | C |
| ATOM | 2898 | O | PRO | B | 196 | 32.178 | 39.896 | 32.312 | 1.00 | 46.46 | O |
| ATOM | 2899 | N | GLY | B | 197 | 34.377 | 40.393 | 32.527 | 1.00 | 55.28 | N |
| ATOM | 2900 | CA | GLY | B | 197 | 34.805 | 39.158 | 33.167 | 1.00 | 46.50 | C |
| ATOM | 2901 | C | GLY | B | 197 | 34.185 | 37.863 | 32.684 | 1.00 | 48.19 | C |
| ATOM | 2902 | O | GLY | B | 197 | 34.472 | 37.398 | 31.582 | 1.00 | 41.17 | O |
| ATOM | 2903 | N | ILE | B | 198 | 33.347 | 37.264 | 33.521 | 1.00 | 44.97 | N |
| ATOM | 2904 | CA | ILE | B | 198 | 32.744 | 35.998 | 33.152 | 1.00 | 48.64 | C |
| ATOM | 2905 | CB | ILE | B | 198 | 32.395 | 35.145 | 34.372 | 1.00 | 47.01 | C |
| ATOM | 2906 | CG2 | ILE | B | 198 | 31.140 | 35.660 | 35.041 | 1.00 | 42.61 | C |
| ATOM | 2907 | CG1 | ILE | B | 198 | 32.267 | 33.673 | 33.968 | 1.00 | 50.50 | C |
| ATOM | 2908 | CD1 | ILE | B | 198 | 31.770 | 32.779 | 35.096 | 1.00 | 54.16 | C |
| ATOM | 2909 | C | ILE | B | 198 | 31.524 | 36.194 | 32.246 | 1.00 | 52.60 | C |
| ATOM | 2910 | O | ILE | B | 198 | 31.172 | 35.303 | 31.464 | 1.00 | 51.85 | O |
| ATOM | 2911 | N | GLN | B | 199 | 30.893 | 37.363 | 32.328 | 1.00 | 49.89 | N |
| ATOM | 2912 | CA | GLN | B | 199 | 29.816 | 37.671 | 31.389 | 1.00 | 50.97 | C |
| ATOM | 2913 | CB | GLN | B | 199 | 29.303 | 39.105 | 31.567 | 1.00 | 50.45 | C |
| ATOM | 2914 | CG | GLN | B | 199 | 28.467 | 39.316 | 32.821 | 1.00 | 42.84 | C |
| ATOM | 2915 | CD | GLN | B | 199 | 28.166 | 40.782 | 33.093 | 1.00 | 51.99 | C |
| ATOM | 2916 | OE1 | GLN | B | 199 | 27.507 | 41.472 | 32.294 | 1.00 | 48.74 | O |
| ATOM | 2917 | NE2 | GLN | B | 199 | 28.645 | 41.267 | 34.231 | 1.00 | 54.54 | N |
| ATOM | 2918 | C | GLN | B | 199 | 30.343 | 37.453 | 29.979 | 1.00 | 49.34 | C |
| ATOM | 2919 | O | GLN | B | 199 | 31.460 | 37.838 | 29.670 | 1.00 | 47.66 | O |
| ATOM | 2920 | N | GLY | B | 200 | 29.540 | 36.819 | 29.132 | 1.00 | 53.57 | N |
| ATOM | 2921 | CA | GLY | B | 200 | 29.956 | 36.485 | 27.780 | 1.00 | 44.50 | C |
| ATOM | 2922 | C | GLY | B | 200 | 30.247 | 35.001 | 27.645 | 1.00 | 47.43 | C |
| ATOM | 2923 | O | GLY | B | 200 | 30.034 | 34.414 | 26.585 | 1.00 | 50.95 | O |
| ATOM | 2924 | N | ASP | B | 201 | 30.738 | 34.391 | 28.722 | 1.00 | 47.30 | N |
| ATOM | 2925 | CA | ASP | B | 201 | 31.079 | 32.966 | 28.710 | 1.00 | 50.73 | C |
| ATOM | 2926 | CB | ASP | B | 201 | 31.519 | 32.498 | 30.106 | 1.00 | 48.14 | C |
| ATOM | 2927 | CG | ASP | B | 201 | 32.996 | 32.713 | 30.372 | 1.00 | 54.77 | C |
| ATOM | 2928 | OD1 | ASP | B | 201 | 33.628 | 33.486 | 29.620 | 1.00 | 53.04 | O |
| ATOM | 2929 | OD2 | ASP | B | 201 | 33.523 | 32.103 | 31.344 | 1.00 | 63.32 | O |
| ATOM | 2930 | C | ASP | B | 201 | 29.907 | 32.086 | 28.284 | 1.00 | 49.83 | C |

TABLE 12-continued

Coordinates for pro MMP9(35-444 ΔFnII) (SEQ ID NO: 12) complex with Example 2

| ATOM | 2931 | O   | ASP | B | 201 | 28.736 | 32.388 | 28.577 | 1.00 | 50.33 | O |
|------|------|-----|-----|---|-----|--------|--------|--------|------|-------|---|
| ATOM | 2932 | N   | ALA | B | 202 | 30.226 | 30.973 | 27.640 | 1.00 | 38.84 | N |
| ATOM | 2933 | CA  | ALA | B | 202 | 29.231 | 29.938 | 27.395 | 1.00 | 45.51 | C |
| ATOM | 2934 | CB  | ALA | B | 202 | 28.935 | 29.833 | 25.908 | 1.00 | 43.79 | C |
| ATOM | 2935 | C   | ALA | B | 202 | 29.718 | 28.601 | 27.929 | 1.00 | 43.31 | C |
| ATOM | 2936 | O   | ALA | B | 202 | 30.811 | 28.178 | 27.580 | 1.00 | 48.48 | O |
| ATOM | 2937 | N   | HIS | B | 203 | 28.916 | 27.932 | 28.755 | 1.00 | 36.37 | N |
| ATOM | 2938 | CA  | HIS | B | 203 | 29.319 | 26.635 | 29.328 | 1.00 | 43.55 | C |
| ATOM | 2939 | CB  | HIS | B | 203 | 29.350 | 26.708 | 30.841 | 1.00 | 42.80 | C |
| ATOM | 2940 | CG  | HIS | B | 203 | 30.248 | 27.776 | 31.367 | 1.00 | 43.82 | C |
| ATOM | 2941 | CD2 | HIS | B | 203 | 31.274 | 28.438 | 30.789 | 1.00 | 45.53 | C |
| ATOM | 2942 | ND1 | HIS | B | 203 | 30.125 | 28.298 | 32.637 | 1.00 | 44.98 | N |
| ATOM | 2943 | CE1 | HIS | B | 203 | 31.041 | 29.228 | 32.820 | 1.00 | 49.72 | C |
| ATOM | 2944 | NE2 | HIS | B | 203 | 31.752 | 29.333 | 31.712 | 1.00 | 47.89 | N |
| ATOM | 2945 | C   | HIS | B | 203 | 28.425 | 25.474 | 28.916 | 1.00 | 45.12 | C |
| ATOM | 2946 | O   | HIS | B | 203 | 27.212 | 25.595 | 28.950 | 1.00 | 43.27 | O |
| ATOM | 2947 | N   | PHE | B | 204 | 29.020 | 24.344 | 28.543 | 1.00 | 45.20 | N |
| ATOM | 2948 | CA  | PHE | B | 204 | 28.239 | 23.192 | 28.083 | 1.00 | 45.81 | C |
| ATOM | 2949 | CB  | PHE | B | 204 | 28.627 | 22.759 | 26.658 | 1.00 | 47.54 | C |
| ATOM | 2950 | CG  | PHE | B | 204 | 28.499 | 23.847 | 25.630 | 1.00 | 45.00 | C |
| ATOM | 2951 | CD1 | PHE | B | 204 | 29.545 | 24.722 | 25.398 | 1.00 | 44.82 | C |
| ATOM | 2952 | CD2 | PHE | B | 204 | 27.337 | 23.982 | 24.886 | 1.00 | 45.70 | C |
| ATOM | 2953 | CE1 | PHE | B | 204 | 29.432 | 25.725 | 24.455 | 1.00 | 41.83 | C |
| ATOM | 2954 | CE2 | PHE | B | 204 | 27.209 | 24.981 | 23.948 | 1.00 | 43.12 | C |
| ATOM | 2955 | CZ  | PHE | B | 204 | 28.257 | 25.850 | 23.726 | 1.00 | 44.90 | C |
| ATOM | 2956 | C   | PHE | B | 204 | 28.407 | 22.011 | 29.032 | 1.00 | 47.33 | C |
| ATOM | 2957 | O   | PHE | B | 204 | 29.522 | 21.679 | 29.423 | 1.00 | 44.83 | O |
| ATOM | 2958 | N   | ASP | B | 205 | 27.284 | 21.379 | 29.380 | 1.00 | 51.15 | N |
| ATOM | 2959 | CA  | ASP | B | 205 | 27.266 | 20.246 | 30.301 | 1.00 | 48.93 | C |
| ATOM | 2960 | CB  | ASP | B | 205 | 25.846 | 19.992 | 30.814 | 1.00 | 46.68 | C |
| ATOM | 2961 | CG  | ASP | B | 205 | 25.780 | 18.823 | 31.782 | 1.00 | 52.68 | C |
| ATOM | 2962 | OD1 | ASP | B | 205 | 26.843 | 18.220 | 32.047 | 1.00 | 56.14 | O |
| ATOM | 2963 | OD2 | ASP | B | 205 | 24.677 | 18.503 | 32.273 | 1.00 | 45.40 | O |
| ATOM | 2964 | C   | ASP | B | 205 | 27.842 | 18.977 | 29.677 | 1.00 | 47.80 | C |
| ATOM | 2965 | O   | ASP | B | 205 | 27.213 | 18.338 | 28.838 | 1.00 | 47.36 | O |
| ATOM | 2966 | N   | ASP | B | 206 | 29.043 | 18.613 | 30.112 | 1.00 | 49.84 | N |
| ATOM | 2967 | CA  | ASP | B | 206 | 29.750 | 17.453 | 29.577 | 1.00 | 48.20 | C |
| ATOM | 2968 | CB  | ASP | B | 206 | 31.237 | 17.513 | 29.926 | 1.00 | 52.08 | C |
| ATOM | 2969 | CG  | ASP | B | 206 | 32.109 | 16.763 | 28.923 | 1.00 | 57.14 | C |
| ATOM | 2970 | OD1 | ASP | B | 206 | 31.648 | 16.509 | 27.784 | 1.00 | 55.43 | O |
| ATOM | 2971 | OD2 | ASP | B | 206 | 33.259 | 16.432 | 29.279 | 1.00 | 54.06 | O |
| ATOM | 2972 | C   | ASP | B | 206 | 29.167 | 16.156 | 30.102 | 1.00 | 54.19 | C |
| ATOM | 2973 | O   | ASP | B | 206 | 29.698 | 15.082 | 29.822 | 1.00 | 54.08 | O |
| ATOM | 2974 | N   | ASP | B | 207 | 28.087 | 16.255 | 30.876 | 1.00 | 50.28 | N |
| ATOM | 2975 | CA  | ASP | B | 207 | 27.358 | 15.065 | 31.282 | 1.00 | 46.50 | C |
| ATOM | 2976 | CB  | ASP | B | 207 | 26.516 | 15.334 | 32.538 | 1.00 | 58.98 | C |
| ATOM | 2977 | CG  | ASP | B | 207 | 27.275 | 15.069 | 33.846 | 1.00 | 57.67 | C |
| ATOM | 2978 | OD1 | ASP | B | 207 | 28.222 | 14.251 | 33.855 | 1.00 | 48.41 | O |
| ATOM | 2979 | OD2 | ASP | B | 207 | 26.896 | 15.669 | 34.875 | 1.00 | 59.10 | O |
| ATOM | 2980 | C   | ASP | B | 207 | 26.482 | 14.524 | 30.129 | 1.00 | 48.55 | C |
| ATOM | 2981 | O   | ASP | B | 207 | 26.067 | 13.364 | 30.161 | 1.00 | 49.18 | O |
| ATOM | 2982 | N   | GLU | B | 208 | 26.200 | 15.357 | 29.122 | 1.00 | 48.01 | N |
| ATOM | 2983 | CA  | GLU | B | 208 | 25.488 | 14.890 | 27.923 | 1.00 | 49.23 | C |
| ATOM | 2984 | CB  | GLU | B | 208 | 24.781 | 16.035 | 27.183 | 1.00 | 42.52 | C |
| ATOM | 2985 | CG  | GLU | B | 208 | 24.146 | 17.075 | 28.092 | 1.00 | 50.85 | C |
| ATOM | 2986 | CD  | GLU | B | 208 | 23.093 | 16.485 | 29.027 | 1.00 | 47.96 | C |
| ATOM | 2987 | OE1 | GLU | B | 208 | 22.586 | 15.371 | 28.765 | 1.00 | 40.85 | O |
| ATOM | 2988 | OE2 | GLU | B | 208 | 22.777 | 17.143 | 30.029 | 1.00 | 46.06 | O |
| ATOM | 2989 | C   | GLU | B | 208 | 26.486 | 14.266 | 26.969 | 1.00 | 48.49 | C |
| ATOM | 2990 | O   | GLU | B | 208 | 27.631 | 14.692 | 26.915 | 1.00 | 53.58 | O |
| ATOM | 2991 | N   | LEU | B | 209 | 26.057 | 13.262 | 26.211 | 1.00 | 48.92 | N |
| ATOM | 2992 | CA  | LEU | B | 209 | 26.868 | 12.774 | 25.104 | 1.00 | 52.45 | C |
| ATOM | 2993 | CB  | LEU | B | 209 | 26.543 | 11.324 | 24.766 | 1.00 | 52.12 | C |
| ATOM | 2994 | CG  | LEU | B | 209 | 27.174 | 10.960 | 23.421 | 1.00 | 58.59 | C |
| ATOM | 2995 | CD1 | LEU | B | 209 | 28.473 | 10.227 | 23.624 | 1.00 | 58.06 | C |
| ATOM | 2996 | CD2 | LEU | B | 209 | 26.219 | 10.146 | 22.563 | 1.00 | 71.72 | C |
| ATOM | 2997 | C   | LEU | B | 209 | 26.641 | 13.663 | 23.876 | 1.00 | 53.15 | C |
| ATOM | 2998 | O   | LEU | B | 209 | 25.626 | 13.554 | 23.183 | 1.00 | 57.05 | O |
| ATOM | 2999 | N   | TRP | B | 210 | 27.584 | 14.557 | 23.615 | 1.00 | 51.07 | N |
| ATOM | 3000 | CA  | TRP | B | 210 | 27.410 | 15.534 | 22.553 | 1.00 | 49.23 | C |
| ATOM | 3001 | CB  | TRP | B | 210 | 28.338 | 16.723 | 22.783 | 1.00 | 46.32 | C |
| ATOM | 3002 | CG  | TRP | B | 210 | 27.880 | 17.521 | 23.929 | 1.00 | 45.08 | C |
| ATOM | 3003 | CD2 | TRP | B | 210 | 26.733 | 18.374 | 23.965 | 1.00 | 45.20 | C |
| ATOM | 3004 | CE2 | TRP | B | 210 | 26.654 | 18.912 | 25.263 | 1.00 | 47.09 | C |
| ATOM | 3005 | CE3 | TRP | B | 210 | 25.762 | 18.733 | 23.023 | 1.00 | 46.54 | C |
| ATOM | 3006 | CD1 | TRP | B | 210 | 28.437 | 17.569 | 25.172 | 1.00 | 48.35 | C |
| ATOM | 3007 | NE1 | TRP | B | 210 | 27.709 | 18.411 | 25.982 | 1.00 | 49.39 | N |

TABLE 12-continued

Coordinates for pro MMP9(35-444 ΔFnII) (SEQ ID NO: 12) complex with Example 2

| ATOM | 3008 | CZ2 | TRP | B | 210 | 25.645 | 19.794 | 25.646 | 1.00 | 41.02 | C |
|------|------|-----|-----|---|-----|--------|--------|--------|------|-------|---|
| ATOM | 3009 | CZ3 | TRP | B | 210 | 24.761 | 19.615 | 23.406 | 1.00 | 45.27 | C |
| ATOM | 3010 | CH2 | TRP | B | 210 | 24.718 | 20.137 | 24.709 | 1.00 | 41.16 | C |
| ATOM | 3011 | C | TRP | B | 210 | 27.596 | 14.936 | 21.161 | 1.00 | 51.46 | C |
| ATOM | 3012 | O | TRP | B | 210 | 28.537 | 14.174 | 20.922 | 1.00 | 51.60 | O |
| ATOM | 3013 | N | SER | B | 211 | 26.686 | 15.296 | 20.257 | 1.00 | 48.38 | N |
| ATOM | 3014 | CA | SER | B | 211 | 26.642 | 14.757 | 18.901 | 1.00 | 48.09 | C |
| ATOM | 3015 | CB | SER | B | 211 | 25.478 | 13.769 | 18.749 | 1.00 | 57.94 | C |
| ATOM | 3016 | OG | SER | B | 211 | 24.216 | 14.427 | 18.886 | 1.00 | 56.37 | O |
| ATOM | 3017 | C | SER | B | 211 | 26.446 | 15.886 | 17.912 | 1.00 | 47.04 | C |
| ATOM | 3018 | O | SER | B | 211 | 26.480 | 17.054 | 18.285 | 1.00 | 46.26 | O |
| ATOM | 3019 | N | LEU | B | 212 | 26.237 | 15.524 | 16.647 | 1.00 | 58.09 | N |
| ATOM | 3020 | CA | LEU | B | 212 | 25.923 | 16.489 | 15.594 | 1.00 | 53.43 | C |
| ATOM | 3021 | CB | LEU | B | 212 | 27.140 | 16.772 | 14.722 | 1.00 | 48.82 | C |
| ATOM | 3022 | CG | LEU | B | 212 | 28.111 | 17.821 | 15.255 | 1.00 | 49.32 | C |
| ATOM | 3023 | CD1 | LEU | B | 212 | 29.260 | 18.066 | 14.271 | 1.00 | 40.74 | C |
| ATOM | 3024 | CD2 | LEU | B | 212 | 27.346 | 19.093 | 15.523 | 1.00 | 41.76 | C |
| ATOM | 3025 | C | LEU | B | 212 | 24.770 | 15.999 | 14.737 | 1.00 | 56.87 | C |
| ATOM | 3026 | O | LEU | B | 212 | 24.091 | 16.794 | 14.082 | 1.00 | 59.66 | O |
| ATOM | 3027 | N | GLY | B | 213 | 24.547 | 14.689 | 14.744 | 1.00 | 57.63 | N |
| ATOM | 3028 | CA | GLY | B | 213 | 23.428 | 14.117 | 14.013 | 1.00 | 64.72 | C |
| ATOM | 3029 | C | GLY | B | 213 | 22.146 | 14.079 | 14.828 | 1.00 | 62.18 | C |
| ATOM | 3030 | O | GLY | B | 213 | 21.053 | 13.903 | 14.279 | 1.00 | 69.95 | O |
| ATOM | 3031 | O | ALA | B | 393 | 24.996 | 17.016 | 21.345 | 1.00 | 20.00 | O |
| ATOM | 3032 | N | ALA | B | 393 | 21.865 | 17.049 | 22.926 | 1.00 | 20.00 | N |
| ATOM | 3033 | CA | ALA | B | 393 | 22.958 | 16.316 | 22.310 | 1.00 | 20.00 | C |
| ATOM | 3034 | C | ALA | B | 393 | 23.810 | 17.096 | 21.301 | 1.00 | 20.00 | C |
| ATOM | 3035 | CB | ALA | B | 393 | 22.453 | 15.051 | 21.688 | 1.00 | 20.00 | C |
| ATOM | 3036 | N | SER | B | 394 | 23.208 | 17.837 | 20.405 | 1.00 | 31.84 | N |
| ATOM | 3037 | CA | SER | B | 394 | 23.850 | 18.478 | 19.270 | 1.00 | 47.23 | C |
| ATOM | 3038 | CB | SER | B | 394 | 22.868 | 18.746 | 18.133 | 1.00 | 38.96 | C |
| ATOM | 3039 | OG | SER | B | 394 | 23.516 | 19.548 | 17.161 | 1.00 | 39.84 | O |
| ATOM | 3040 | C | SER | B | 394 | 24.559 | 19.780 | 19.626 | 1.00 | 44.77 | C |
| ATOM | 3041 | O | SER | B | 394 | 23.929 | 20.814 | 19.848 | 1.00 | 45.62 | O |
| ATOM | 3042 | N | LEU | B | 395 | 25.879 | 19.739 | 19.614 | 1.00 | 38.86 | N |
| ATOM | 3043 | CA | LEU | B | 395 | 26.653 | 20.863 | 20.103 | 1.00 | 44.28 | C |
| ATOM | 3044 | CB | LEU | B | 395 | 28.132 | 20.475 | 20.156 | 1.00 | 46.21 | C |
| ATOM | 3045 | CG | LEU | B | 395 | 29.184 | 21.460 | 20.651 | 1.00 | 45.64 | C |
| ATOM | 3046 | CD1 | LEU | B | 395 | 28.938 | 21.911 | 22.114 | 1.00 | 46.28 | C |
| ATOM | 3047 | CD2 | LEU | B | 395 | 30.550 | 20.815 | 20.493 | 1.00 | 43.54 | C |
| ATOM | 3048 | C | LEU | B | 395 | 26.433 | 22.082 | 19.217 | 1.00 | 39.97 | C |
| ATOM | 3049 | O | LEU | B | 395 | 26.518 | 23.218 | 19.664 | 1.00 | 45.54 | O |
| ATOM | 3050 | N | PHE | B | 396 | 26.147 | 21.846 | 17.953 | 1.00 | 43.35 | N |
| ATOM | 3051 | CA | PHE | B | 396 | 25.961 | 22.943 | 17.019 | 1.00 | 43.14 | C |
| ATOM | 3052 | CB | PHE | B | 396 | 25.917 | 22.438 | 15.572 | 1.00 | 38.68 | C |
| ATOM | 3053 | CG | PHE | B | 396 | 25.413 | 23.461 | 14.579 | 1.00 | 42.55 | C |
| ATOM | 3054 | CD1 | PHE | B | 396 | 26.056 | 24.681 | 14.427 | 1.00 | 43.36 | C |
| ATOM | 3055 | CD2 | PHE | B | 396 | 24.306 | 23.193 | 13.782 | 1.00 | 40.33 | C |
| ATOM | 3056 | CE1 | PHE | B | 396 | 25.603 | 25.623 | 13.503 | 1.00 | 43.30 | C |
| ATOM | 3057 | CE2 | PHE | B | 396 | 23.854 | 24.128 | 12.848 | 1.00 | 38.98 | C |
| ATOM | 3058 | CZ | PHE | B | 396 | 24.501 | 25.344 | 12.711 | 1.00 | 36.50 | C |
| ATOM | 3059 | C | PHE | B | 396 | 24.725 | 23.779 | 17.355 | 1.00 | 38.44 | C |
| ATOM | 3060 | O | PHE | B | 396 | 24.822 | 24.998 | 17.412 | 1.00 | 38.76 | O |
| ATOM | 3061 | N | LEU | B | 397 | 23.571 | 23.140 | 17.562 | 1.00 | 40.81 | N |
| ATOM | 3062 | CA | LEU | B | 397 | 22.360 | 23.896 | 17.891 | 1.00 | 37.99 | C |
| ATOM | 3063 | CB | LEU | B | 397 | 21.106 | 23.029 | 17.884 | 1.00 | 27.98 | C |
| ATOM | 3064 | CG | LEU | B | 397 | 20.821 | 22.297 | 16.587 | 1.00 | 36.02 | C |
| ATOM | 3065 | CD1 | LEU | B | 397 | 19.429 | 21.724 | 16.649 | 1.00 | 43.16 | C |
| ATOM | 3066 | CD2 | LEU | B | 397 | 20.926 | 23.266 | 15.429 | 1.00 | 35.77 | C |
| ATOM | 3067 | C | LEU | B | 397 | 22.547 | 24.524 | 19.263 | 1.00 | 41.97 | C |
| ATOM | 3068 | O | LEU | B | 397 | 22.441 | 25.750 | 19.415 | 1.00 | 39.38 | O |
| ATOM | 3069 | N | VAL | B | 398 | 22.835 | 23.693 | 20.261 | 1.00 | 34.24 | N |
| ATOM | 3070 | CA | VAL | B | 398 | 22.992 | 24.227 | 21.602 | 1.00 | 42.00 | C |
| ATOM | 3071 | CB | VAL | B | 398 | 23.555 | 23.188 | 22.621 | 1.00 | 42.68 | C |
| ATOM | 3072 | CG1 | VAL | B | 398 | 23.606 | 23.798 | 23.991 | 1.00 | 37.54 | C |
| ATOM | 3073 | CG2 | VAL | B | 398 | 22.715 | 21.926 | 22.647 | 1.00 | 37.57 | C |
| ATOM | 3074 | C | VAL | B | 398 | 23.930 | 25.438 | 21.512 | 1.00 | 42.79 | C |
| ATOM | 3075 | O | VAL | B | 398 | 23.595 | 26.519 | 22.005 | 1.00 | 46.44 | O |
| ATOM | 3076 | N | ALA | B | 399 | 25.085 | 25.269 | 20.861 | 1.00 | 35.97 | N |
| ATOM | 3077 | CA | ALA | B | 399 | 26.042 | 26.361 | 20.759 | 1.00 | 37.88 | C |
| ATOM | 3078 | CB | ALA | B | 399 | 27.292 | 25.946 | 20.017 | 1.00 | 33.95 | C |
| ATOM | 3079 | C | ALA | B | 399 | 25.397 | 27.591 | 20.132 | 1.00 | 42.15 | C |
| ATOM | 3080 | O | ALA | B | 399 | 25.585 | 28.701 | 20.622 | 1.00 | 44.78 | O |
| ATOM | 3081 | N | ALA | B | 400 | 24.599 | 27.393 | 19.081 | 1.00 | 43.05 | N |
| ATOM | 3082 | CA | ALA | B | 400 | 23.942 | 28.516 | 18.391 | 1.00 | 46.31 | C |
| ATOM | 3083 | CB | ALA | B | 400 | 23.166 | 28.027 | 17.145 | 1.00 | 43.26 | C |
| ATOM | 3084 | C | ALA | B | 400 | 23.023 | 29.291 | 19.328 | 1.00 | 38.49 | C |

TABLE 12-continued

Coordinates for pro MMP9(35-444 ΔFnII) (SEQ ID NO: 12) complex with Example 2

| ATOM | 3085 | O   | ALA | B | 400 | 23.013 | 30.517 | 19.342 | 1.00 | 38.90 | O |
|------|------|-----|-----|---|-----|--------|--------|--------|------|-------|---|
| ATOM | 3086 | N   | HIS | B | 401 | 22.263 | 28.556 | 20.119 | 1.00 | 38.71 | N |
| ATOM | 3087 | CA  | HIS | B | 401 | 21.397 | 29.141 | 21.141 | 1.00 | 42.18 | C |
| ATOM | 3088 | CB  | HIS | B | 401 | 20.619 | 28.010 | 21.837 | 1.00 | 40.09 | C |
| ATOM | 3089 | CG  | HIS | B | 401 | 19.659 | 28.478 | 22.884 | 1.00 | 44.46 | C |
| ATOM | 3090 | CD2 | HIS | B | 401 | 19.797 | 28.602 | 24.226 | 1.00 | 43.70 | C |
| ATOM | 3091 | ND1 | HIS | B | 401 | 18.367 | 28.862 | 22.596 | 1.00 | 42.25 | N |
| ATOM | 3092 | CE1 | HIS | B | 401 | 17.756 | 29.217 | 23.709 | 1.00 | 43.39 | C |
| ATOM | 3093 | NE2 | HIS | B | 401 | 18.598 | 29.059 | 24.715 | 1.00 | 42.08 | N |
| ATOM | 3094 | C   | HIS | B | 401 | 22.194 | 29.963 | 22.168 | 1.00 | 43.24 | C |
| ATOM | 3095 | O   | HIS | B | 401 | 21.949 | 31.154 | 22.334 | 1.00 | 40.37 | O |
| ATOM | 3096 | N   | GLU | B | 402 | 23.154 | 29.321 | 22.842 | 1.00 | 40.98 | N |
| ATOM | 3097 | CA  | GLU | B | 402 | 23.927 | 29.965 | 23.908 | 1.00 | 40.21 | C |
| ATOM | 3098 | CB  | GLU | B | 402 | 24.857 | 28.944 | 24.576 | 1.00 | 39.33 | C |
| ATOM | 3099 | CG  | GLU | B | 402 | 24.118 | 27.762 | 25.172 | 1.00 | 45.42 | C |
| ATOM | 3100 | CD  | GLU | B | 402 | 23.089 | 28.209 | 26.220 | 1.00 | 49.45 | C |
| ATOM | 3101 | OE1 | GLU | B | 402 | 22.063 | 27.508 | 26.400 | 1.00 | 39.99 | O |
| ATOM | 3102 | OE2 | GLU | B | 402 | 23.310 | 29.275 | 26.849 | 1.00 | 44.58 | O |
| ATOM | 3103 | C   | GLU | B | 402 | 24.728 | 31.170 | 23.427 | 1.00 | 42.72 | C |
| ATOM | 3104 | O   | GLU | B | 402 | 24.994 | 32.104 | 24.191 | 1.00 | 39.03 | O |
| ATOM | 3105 | N   | PHE | B | 403 | 25.135 | 31.138 | 22.160 | 1.00 | 45.60 | N |
| ATOM | 3106 | CA  | PHE | B | 403 | 25.886 | 32.241 | 21.592 | 1.00 | 41.66 | C |
| ATOM | 3107 | CB  | PHE | B | 403 | 26.538 | 31.851 | 20.272 | 1.00 | 40.39 | C |
| ATOM | 3108 | CG  | PHE | B | 403 | 27.646 | 30.853 | 20.422 | 1.00 | 42.71 | C |
| ATOM | 3109 | CD1 | PHE | B | 403 | 28.147 | 30.538 | 21.685 | 1.00 | 47.83 | C |
| ATOM | 3110 | CD2 | PHE | B | 403 | 28.182 | 30.217 | 19.309 | 1.00 | 39.21 | C |
| ATOM | 3111 | CE1 | PHE | B | 403 | 29.173 | 29.607 | 21.828 | 1.00 | 45.91 | C |
| ATOM | 3112 | CE2 | PHE | B | 403 | 29.194 | 29.292 | 19.442 | 1.00 | 40.64 | C |
| ATOM | 3113 | CZ  | PHE | B | 403 | 29.692 | 28.981 | 20.694 | 1.00 | 41.55 | C |
| ATOM | 3114 | C   | PHE | B | 403 | 24.972 | 33.428 | 21.416 | 1.00 | 39.56 | C |
| ATOM | 3115 | O   | PHE | B | 403 | 25.416 | 34.562 | 21.457 | 1.00 | 48.69 | O |
| ATOM | 3116 | N   | GLY | B | 404 | 23.692 | 33.161 | 21.212 | 1.00 | 40.58 | N |
| ATOM | 3117 | CA  | GLY | B | 404 | 22.708 | 34.220 | 21.159 | 1.00 | 40.90 | C |
| ATOM | 3118 | C   | GLY | B | 404 | 22.736 | 34.926 | 22.503 | 1.00 | 44.38 | C |
| ATOM | 3119 | O   | GLY | B | 404 | 22.888 | 36.149 | 22.553 | 1.00 | 38.02 | O |
| ATOM | 3120 | N   | HIS | B | 405 | 22.594 | 34.151 | 23.585 | 1.00 | 43.52 | N |
| ATOM | 3121 | CA  | HIS | B | 405 | 22.738 | 34.682 | 24.954 | 1.00 | 46.34 | C |
| ATOM | 3122 | CB  | HIS | B | 405 | 22.736 | 33.563 | 26.013 | 1.00 | 37.18 | C |
| ATOM | 3123 | CG  | HIS | B | 405 | 21.388 | 32.948 | 26.273 | 1.00 | 45.70 | C |
| ATOM | 3124 | CD2 | HIS | B | 405 | 21.040 | 31.699 | 26.672 | 1.00 | 43.87 | C |
| ATOM | 3125 | ND1 | HIS | B | 405 | 20.203 | 33.650 | 26.169 | 1.00 | 46.58 | N |
| ATOM | 3126 | CE1 | HIS | B | 405 | 19.189 | 32.855 | 26.462 | 1.00 | 45.43 | C |
| ATOM | 3127 | NE2 | HIS | B | 405 | 19.672 | 31.672 | 26.790 | 1.00 | 41.46 | N |
| ATOM | 3128 | C   | HIS | B | 405 | 24.006 | 35.548 | 25.104 | 1.00 | 45.29 | C |
| ATOM | 3129 | O   | HIS | B | 405 | 23.912 | 36.726 | 25.475 | 1.00 | 42.28 | O |
| ATOM | 3130 | N   | ALA | B | 406 | 25.173 | 34.978 | 24.789 | 1.00 | 41.37 | N |
| ATOM | 3131 | CA  | ALA | B | 406 | 26.456 | 35.695 | 24.957 | 1.00 | 48.05 | C |
| ATOM | 3132 | CB  | ALA | B | 406 | 27.669 | 34.791 | 24.634 | 1.00 | 36.32 | C |
| ATOM | 3133 | C   | ALA | B | 406 | 26.502 | 36.983 | 24.135 | 1.00 | 47.12 | C |
| ATOM | 3134 | O   | ALA | B | 406 | 27.387 | 37.825 | 24.319 | 1.00 | 44.62 | O |
| ATOM | 3135 | N   | LEU | B | 407 | 25.534 | 37.134 | 23.236 | 1.00 | 42.62 | N |
| ATOM | 3136 | CA  | LEU | B | 407 | 25.402 | 38.371 | 22.475 | 1.00 | 44.73 | C |
| ATOM | 3137 | CB  | LEU | B | 407 | 24.996 | 38.076 | 21.034 | 1.00 | 41.36 | C |
| ATOM | 3138 | CG  | LEU | B | 407 | 25.989 | 37.166 | 20.320 | 1.00 | 41.66 | C |
| ATOM | 3139 | CD1 | LEU | B | 407 | 25.588 | 37.075 | 18.887 | 1.00 | 39.67 | C |
| ATOM | 3140 | CD2 | LEU | B | 407 | 27.423 | 37.686 | 20.465 | 1.00 | 34.07 | C |
| ATOM | 3141 | C   | LEU | B | 407 | 24.426 | 39.363 | 23.105 | 1.00 | 46.50 | C |
| ATOM | 3142 | O   | LEU | B | 407 | 24.402 | 40.523 | 22.709 | 1.00 | 50.58 | O |
| ATOM | 3143 | N   | GLY | B | 408 | 23.628 | 38.908 | 24.075 | 1.00 | 43.26 | N |
| ATOM | 3144 | CA  | GLY | B | 408 | 22.612 | 39.748 | 24.683 | 1.00 | 41.84 | C |
| ATOM | 3145 | C   | GLY | B | 408 | 21.173 | 39.389 | 24.315 | 1.00 | 45.91 | C |
| ATOM | 3146 | O   | GLY | B | 408 | 20.294 | 40.252 | 24.317 | 1.00 | 56.09 | O |
| ATOM | 3147 | N   | LEU | B | 409 | 20.916 | 38.127 | 23.995 | 1.00 | 40.40 | N |
| ATOM | 3148 | CA  | LEU | B | 409 | 19.546 | 37.701 | 23.722 | 1.00 | 43.87 | C |
| ATOM | 3149 | CB  | LEU | B | 409 | 19.440 | 36.882 | 22.435 | 1.00 | 45.76 | C |
| ATOM | 3150 | CG  | LEU | B | 409 | 19.584 | 37.591 | 21.090 | 1.00 | 42.11 | C |
| ATOM | 3151 | CD1 | LEU | B | 409 | 19.261 | 36.606 | 20.003 | 1.00 | 40.96 | C |
| ATOM | 3152 | CD2 | LEU | B | 409 | 18.659 | 38.778 | 21.007 | 1.00 | 37.92 | C |
| ATOM | 3153 | C   | LEU | B | 409 | 18.997 | 36.886 | 24.880 | 1.00 | 48.72 | C |
| ATOM | 3154 | O   | LEU | B | 409 | 19.710 | 36.084 | 25.489 | 1.00 | 45.21 | O |
| ATOM | 3155 | N   | ASP | B | 410 | 17.726 | 37.108 | 25.191 | 1.00 | 47.24 | N |
| ATOM | 3156 | CA  | ASP | B | 410 | 17.053 | 36.332 | 26.216 | 1.00 | 50.00 | C |
| ATOM | 3157 | CB  | ASP | B | 410 | 16.075 | 37.209 | 27.000 | 1.00 | 51.87 | C |
| ATOM | 3158 | CG  | ASP | B | 410 | 15.049 | 37.866 | 26.099 | 1.00 | 55.41 | C |
| ATOM | 3159 | OD1 | ASP | B | 410 | 15.413 | 38.184 | 24.947 | 1.00 | 64.30 | O |
| ATOM | 3160 | OD2 | ASP | B | 410 | 13.892 | 38.056 | 26.525 | 1.00 | 60.17 | O |
| ATOM | 3161 | C   | ASP | B | 410 | 16.284 | 35.274 | 25.471 | 1.00 | 46.23 | C |

TABLE 12-continued

Coordinates for pro MMP9(35-444 ΔFnII) (SEQ ID NO: 12) complex with Example 2

| ATOM | 3162 | O   | ASP | B | 410 | 16.402 | 35.163 | 24.268 | 1.00 | 44.68 | O |
|------|------|-----|-----|---|-----|--------|--------|--------|------|-------|---|
| ATOM | 3163 | N   | HIS | B | 411 | 15.475 | 34.506 | 26.180 | 1.00 | 49.05 | N |
| ATOM | 3164 | CA  | HIS | B | 411 | 14.694 | 33.487 | 25.509 | 1.00 | 48.46 | C |
| ATOM | 3165 | CB  | HIS | B | 411 | 14.170 | 32.472 | 26.516 | 1.00 | 43.18 | C |
| ATOM | 3166 | CG  | HIS | B | 411 | 15.195 | 31.459 | 26.911 | 1.00 | 44.42 | C |
| ATOM | 3167 | CD2 | HIS | B | 411 | 15.960 | 30.636 | 26.157 | 1.00 | 44.83 | C |
| ATOM | 3168 | ND1 | HIS | B | 411 | 15.559 | 31.229 | 28.219 | 1.00 | 45.44 | N |
| ATOM | 3169 | CE1 | HIS | B | 411 | 16.485 | 30.289 | 28.253 | 1.00 | 47.86 | C |
| ATOM | 3170 | NE2 | HIS | B | 411 | 16.741 | 29.911 | 27.015 | 1.00 | 49.24 | N |
| ATOM | 3171 | C   | HIS | B | 411 | 13.571 | 34.038 | 24.627 | 1.00 | 48.48 | C |
| ATOM | 3172 | O   | HIS | B | 411 | 13.070 | 35.155 | 24.840 | 1.00 | 47.25 | O |
| ATOM | 3173 | N   | SER | B | 412 | 13.210 | 33.248 | 23.621 | 1.00 | 40.03 | N |
| ATOM | 3174 | CA  | SER | B | 412 | 12.075 | 33.541 | 22.751 | 1.00 | 44.24 | C |
| ATOM | 3175 | CB  | SER | B | 412 | 12.431 | 33.227 | 21.298 | 1.00 | 38.75 | C |
| ATOM | 3176 | OG  | SER | B | 412 | 11.274 | 33.166 | 20.496 | 1.00 | 39.44 | O |
| ATOM | 3177 | C   | SER | B | 412 | 10.869 | 32.703 | 23.165 | 1.00 | 48.26 | C |
| ATOM | 3178 | O   | SER | B | 412 | 11.015 | 31.629 | 23.755 | 1.00 | 48.88 | O |
| ATOM | 3179 | N   | SER | B | 413 | 9.675  | 33.188 | 22.857 | 1.00 | 42.00 | N |
| ATOM | 3180 | CA  | SER | B | 413 | 8.478  | 32.426 | 23.161 | 1.00 | 44.46 | C |
| ATOM | 3181 | CB  | SER | B | 413 | 7.368  | 33.353 | 23.681 | 1.00 | 48.01 | C |
| ATOM | 3182 | OG  | SER | B | 413 | 7.259  | 34.529 | 22.882 | 1.00 | 44.41 | O |
| ATOM | 3183 | C   | SER | B | 413 | 8.029  | 31.681 | 21.914 | 1.00 | 49.55 | C |
| ATOM | 3184 | O   | SER | B | 413 | 7.130  | 30.839 | 21.956 | 1.00 | 48.99 | O |
| ATOM | 3185 | N   | VAL | B | 414 | 8.659  | 31.990 | 20.791 | 1.00 | 45.26 | N |
| ATOM | 3186 | CA  | VAL | B | 414 | 8.329  | 31.287 | 19.569 | 1.00 | 45.71 | C |
| ATOM | 3187 | CB  | VAL | B | 414 | 8.824  | 32.045 | 18.337 | 1.00 | 51.19 | C |
| ATOM | 3188 | CG1 | VAL | B | 414 | 8.568  | 31.226 | 17.053 | 1.00 | 49.06 | C |
| ATOM | 3189 | CG2 | VAL | B | 414 | 8.166  | 33.432 | 18.279 | 1.00 | 42.82 | C |
| ATOM | 3190 | C   | VAL | B | 414 | 8.969  | 29.920 | 19.649 | 1.00 | 47.17 | C |
| ATOM | 3191 | O   | VAL | B | 414 | 10.176 | 29.819 | 19.785 | 1.00 | 51.35 | O |
| ATOM | 3192 | N   | PRO | B | 415 | 8.157  | 28.859 | 19.582 | 1.00 | 50.00 | N |
| ATOM | 3193 | CD  | PRO | B | 415 | 6.687  | 28.881 | 19.566 | 1.00 | 49.27 | C |
| ATOM | 3194 | CA  | PRO | B | 415 | 8.679  | 27.506 | 19.775 | 1.00 | 48.38 | C |
| ATOM | 3195 | CB  | PRO | B | 415 | 7.413  | 26.639 | 19.837 | 1.00 | 51.16 | C |
| ATOM | 3196 | CG  | PRO | B | 415 | 6.332  | 27.578 | 20.220 | 1.00 | 47.43 | C |
| ATOM | 3197 | C   | PRO | B | 415 | 9.620  | 27.018 | 18.684 | 1.00 | 44.25 | C |
| ATOM | 3198 | O   | PRO | B | 415 | 10.433 | 26.152 | 18.981 | 1.00 | 50.46 | O |
| ATOM | 3199 | N   | GLU | B | 416 | 9.538  | 27.527 | 17.461 | 1.00 | 45.10 | N |
| ATOM | 3200 | CA  | GLU | B | 416 | 10.539 | 27.120 | 16.457 | 1.00 | 46.77 | C |
| ATOM | 3201 | CB  | GLU | B | 416 | 9.943  | 26.908 | 15.058 | 1.00 | 46.78 | C |
| ATOM | 3202 | CG  | GLU | B | 416 | 8.798  | 27.853 | 14.704 | 1.00 | 55.40 | C |
| ATOM | 3203 | CD  | GLU | B | 416 | 7.559  | 27.549 | 15.518 | 1.00 | 48.72 | C |
| ATOM | 3204 | OE1 | GLU | B | 416 | 6.909  | 26.526 | 15.218 | 1.00 | 45.88 | O |
| ATOM | 3205 | OE2 | GLU | B | 416 | 7.260  | 28.311 | 16.469 | 1.00 | 49.92 | O |
| ATOM | 3206 | C   | GLU | B | 416 | 11.727 | 28.076 | 16.406 | 1.00 | 46.88 | C |
| ATOM | 3207 | O   | GLU | B | 416 | 12.694 | 27.837 | 15.675 | 1.00 | 42.65 | O |
| ATOM | 3208 | N   | ALA | B | 417 | 11.646 | 29.151 | 17.188 | 1.00 | 46.36 | N |
| ATOM | 3209 | CA  | ALA | B | 417 | 12.739 | 30.104 | 17.272 | 1.00 | 46.27 | C |
| ATOM | 3210 | CB  | ALA | B | 417 | 12.369 | 31.286 | 18.147 | 1.00 | 41.55 | C |
| ATOM | 3211 | C   | ALA | B | 417 | 13.918 | 29.364 | 17.853 | 1.00 | 44.35 | C |
| ATOM | 3212 | O   | ALA | B | 417 | 13.740 | 28.414 | 18.609 | 1.00 | 48.38 | O |
| ATOM | 3213 | N   | LEU | B | 418 | 15.116 | 29.779 | 17.466 | 1.00 | 42.10 | N |
| ATOM | 3214 | CA  | LEU | B | 418 | 16.360 | 29.189 | 17.950 | 1.00 | 42.90 | C |
| ATOM | 3215 | CB  | LEU | B | 418 | 17.502 | 29.705 | 17.082 | 1.00 | 34.00 | C |
| ATOM | 3216 | CG  | LEU | B | 418 | 18.965 | 29.371 | 17.371 | 1.00 | 38.38 | C |
| ATOM | 3217 | CD1 | LEU | B | 418 | 19.619 | 30.489 | 18.140 | 1.00 | 44.49 | C |
| ATOM | 3218 | CD2 | LEU | B | 418 | 19.098 | 28.066 | 18.100 | 1.00 | 34.02 | C |
| ATOM | 3219 | C   | LEU | B | 418 | 16.592 | 29.513 | 19.446 | 1.00 | 43.30 | C |
| ATOM | 3220 | O   | LEU | B | 418 | 17.064 | 28.664 | 20.238 | 1.00 | 30.24 | O |
| ATOM | 3221 | N   | MET | B | 419 | 16.232 | 30.744 | 19.815 | 1.00 | 40.37 | N |
| ATOM | 3222 | CA  | MET | B | 419 | 16.341 | 31.202 | 21.195 | 1.00 | 43.13 | C |
| ATOM | 3223 | CB  | MET | B | 419 | 16.431 | 32.727 | 21.259 | 1.00 | 38.00 | C |
| ATOM | 3224 | CG  | MET | B | 419 | 17.714 | 33.273 | 20.708 | 1.00 | 38.59 | C |
| ATOM | 3225 | SD  | MET | B | 419 | 19.140 | 32.362 | 21.329 | 1.00 | 36.55 | S |
| ATOM | 3226 | CE  | MET | B | 419 | 19.069 | 32.721 | 23.068 | 1.00 | 43.44 | C |
| ATOM | 3227 | C   | MET | B | 419 | 15.206 | 30.700 | 22.103 | 1.00 | 40.77 | C |
| ATOM | 3228 | O   | MET | B | 419 | 15.089 | 31.150 | 23.231 | 1.00 | 37.22 | O |
| ATOM | 3229 | N   | TYR | B | 420 | 14.380 | 29.790 | 21.593 | 1.00 | 41.96 | N |
| ATOM | 3230 | CA  | TYR | B | 420 | 13.399 | 29.078 | 22.387 | 1.00 | 38.40 | C |
| ATOM | 3231 | CB  | TYR | B | 420 | 12.582 | 28.191 | 21.473 | 1.00 | 38.92 | C |
| ATOM | 3232 | CG  | TYR | B | 420 | 11.326 | 27.615 | 22.096 | 1.00 | 48.58 | C |
| ATOM | 3233 | CD1 | TYR | B | 420 | 10.290 | 28.445 | 22.530 | 1.00 | 46.36 | C |
| ATOM | 3234 | CE1 | TYR | B | 420 | 9.135  | 27.912 | 23.081 | 1.00 | 50.31 | C |
| ATOM | 3235 | CD2 | TYR | B | 420 | 11.163 | 26.240 | 22.232 | 1.00 | 49.49 | C |
| ATOM | 3236 | CE2 | TYR | B | 420 | 10.014 | 25.703 | 22.786 | 1.00 | 49.34 | C |
| ATOM | 3237 | CZ  | TYR | B | 420 | 9.000  | 26.541 | 23.204 | 1.00 | 49.93 | C |
| ATOM | 3238 | OH  | TYR | B | 420 | 7.860  | 26.000 | 23.758 | 1.00 | 48.40 | O |

TABLE 12-continued

Coordinates for pro MMP9(35-444 ΔFnII) (SEQ ID NO: 12) complex with Example 2

| ATOM | 3239 | C   | TYR | B | 420 | 14.185 | 28.204 | 23.344 | 1.00 | 43.10 | C |
|------|------|-----|-----|---|-----|--------|--------|--------|------|-------|---|
| ATOM | 3240 | O   | TYR | B | 420 | 15.200 | 27.670 | 22.953 | 1.00 | 50.34 | O |
| ATOM | 3241 | N   | PRO | B | 421 | 13.724 | 28.045 | 24.599 | 1.00 | 46.87 | N |
| ATOM | 3242 | CD  | PRO | B | 421 | 12.437 | 28.533 | 25.123 | 1.00 | 43.66 | C |
| ATOM | 3243 | CA  | PRO | B | 421 | 14.513 | 27.351 | 25.632 | 1.00 | 43.05 | C |
| ATOM | 3244 | CB  | PRO | B | 421 | 13.757 | 27.656 | 26.932 | 1.00 | 46.49 | C |
| ATOM | 3245 | CG  | PRO | B | 421 | 12.702 | 28.659 | 26.585 | 1.00 | 46.73 | C |
| ATOM | 3246 | C   | PRO | B | 421 | 14.589 | 25.836 | 25.474 | 1.00 | 43.96 | C |
| ATOM | 3247 | O   | PRO | B | 421 | 15.599 | 25.259 | 25.857 | 1.00 | 50.96 | O |
| ATOM | 3248 | N   | MET | B | 422 | 13.542 | 25.195 | 24.969 | 1.00 | 45.92 | N |
| ATOM | 3249 | CA  | MET | B | 422 | 13.508 | 23.735 | 24.919 | 1.00 | 46.43 | C |
| ATOM | 3250 | CB  | MET | B | 422 | 12.085 | 23.200 | 24.727 | 1.00 | 48.11 | C |
| ATOM | 3251 | CG  | MET | B | 422 | 11.087 | 23.629 | 25.767 | 1.00 | 54.78 | C |
| ATOM | 3252 | SD  | MET | B | 422 | 9.704  | 22.487 | 25.780 | 1.00 | 60.93 | S |
| ATOM | 3253 | CE  | MET | B | 422 | 8.919  | 22.903 | 24.226 | 1.00 | 59.18 | C |
| ATOM | 3254 | C   | MET | B | 422 | 14.329 | 23.255 | 23.758 | 1.00 | 46.56 | C |
| ATOM | 3255 | O   | MET | B | 422 | 14.221 | 23.786 | 22.653 | 1.00 | 51.73 | O |
| ATOM | 3256 | N   | TYR | B | 423 | 15.141 | 22.234 | 23.995 | 1.00 | 50.18 | N |
| ATOM | 3257 | CA  | TYR | B | 423 | 15.897 | 21.631 | 22.904 | 1.00 | 54.16 | C |
| ATOM | 3258 | CB  | TYR | B | 423 | 16.888 | 20.583 | 23.422 | 1.00 | 50.11 | C |
| ATOM | 3259 | CG  | TYR | B | 423 | 17.673 | 19.867 | 22.344 | 1.00 | 47.38 | C |
| ATOM | 3260 | CD1 | TYR | B | 423 | 17.280 | 18.625 | 21.882 | 1.00 | 45.37 | C |
| ATOM | 3261 | CE1 | TYR | B | 423 | 18.001 | 17.959 | 20.908 | 1.00 | 43.64 | C |
| ATOM | 3262 | CD2 | TYR | B | 423 | 18.820 | 20.431 | 21.801 | 1.00 | 52.51 | C |
| ATOM | 3263 | CE2 | TYR | B | 423 | 19.549 | 19.779 | 20.810 | 1.00 | 47.48 | C |
| ATOM | 3264 | CZ  | TYR | B | 423 | 19.137 | 18.543 | 20.367 | 1.00 | 48.38 | C |
| ATOM | 3265 | OH  | TYR | B | 423 | 19.860 | 17.886 | 19.385 | 1.00 | 43.16 | O |
| ATOM | 3266 | C   | TYR | B | 423 | 14.925 | 21.005 | 21.916 | 1.00 | 55.79 | C |
| ATOM | 3267 | O   | TYR | B | 423 | 13.899 | 20.426 | 22.298 | 1.00 | 56.90 | O |
| ATOM | 3268 | N   | ARG | B | 424 | 15.236 | 21.154 | 20.640 | 1.00 | 54.64 | N |
| ATOM | 3269 | CA  | ARG | B | 424 | 14.504 | 20.460 | 19.597 | 1.00 | 55.63 | C |
| ATOM | 3270 | CB  | ARG | B | 424 | 13.189 | 21.168 | 19.282 | 1.00 | 60.69 | C |
| ATOM | 3271 | CG  | ARG | B | 424 | 12.322 | 20.424 | 18.275 | 1.00 | 70.01 | C |
| ATOM | 3272 | CD  | ARG | B | 424 | 10.905 | 20.180 | 18.814 | 1.00 | 84.40 | C |
| ATOM | 3273 | NE  | ARG | B | 424 | 10.117 | 21.413 | 18.927 | 1.00 | 90.01 | N |
| ATOM | 3274 | CZ  | ARG | B | 424 | 9.580  | 21.879 | 20.056 | 1.00 | 85.20 | C |
| ATOM | 3275 | NH1 | ARG | B | 424 | 9.728  | 21.216 | 21.205 | 1.00 | 73.44 | N |
| ATOM | 3276 | NH2 | ARG | B | 424 | 8.882  | 23.013 | 20.035 | 1.00 | 74.32 | N |
| ATOM | 3277 | C   | ARG | B | 424 | 15.406 | 20.449 | 18.390 | 1.00 | 53.00 | C |
| ATOM | 3278 | O   | ARG | B | 424 | 15.883 | 21.497 | 17.959 | 1.00 | 57.35 | O |
| ATOM | 3279 | N   | PHE | B | 425 | 15.651 | 19.268 | 17.846 | 1.00 | 53.36 | N |
| ATOM | 3280 | CA  | PHE | B | 425 | 16.571 | 19.132 | 16.726 | 1.00 | 55.20 | C |
| ATOM | 3281 | CB  | PHE | B | 425 | 17.329 | 17.811 | 16.871 | 1.00 | 52.73 | C |
| ATOM | 3282 | CG  | PHE | B | 425 | 18.105 | 17.417 | 15.663 | 1.00 | 52.30 | C |
| ATOM | 3283 | CD1 | PHE | B | 425 | 19.334 | 17.983 | 15.398 | 1.00 | 57.98 | C |
| ATOM | 3284 | CD2 | PHE | B | 425 | 17.610 | 16.463 | 14.792 | 1.00 | 58.13 | C |
| ATOM | 3285 | CE1 | PHE | B | 425 | 20.061 | 17.602 | 14.273 | 1.00 | 61.84 | C |
| ATOM | 3286 | CE2 | PHE | B | 425 | 18.326 | 16.080 | 13.672 | 1.00 | 59.12 | C |
| ATOM | 3287 | CZ  | PHE | B | 425 | 19.555 | 16.652 | 13.409 | 1.00 | 57.97 | C |
| ATOM | 3288 | C   | PHE | B | 425 | 15.886 | 19.196 | 15.363 | 1.00 | 56.78 | C |
| ATOM | 3289 | O   | PHE | B | 425 | 15.056 | 18.349 | 15.061 | 1.00 | 61.00 | O |
| ATOM | 3290 | N   | THR | B | 426 | 16.235 | 20.195 | 14.545 | 1.00 | 60.79 | N |
| ATOM | 3291 | CA  | THR | B | 426 | 15.917 | 20.173 | 13.102 | 1.00 | 58.67 | C |
| ATOM | 3292 | CB  | THR | B | 426 | 15.086 | 21.390 | 12.628 | 1.00 | 59.11 | C |
| ATOM | 3293 | OG1 | THR | B | 426 | 15.684 | 22.600 | 13.121 | 1.00 | 52.73 | O |
| ATOM | 3294 | CG2 | THR | B | 426 | 13.626 | 21.283 | 13.088 | 1.00 | 61.58 | C |
| ATOM | 3295 | C   | THR | B | 426 | 17.162 | 20.153 | 12.221 | 1.00 | 57.12 | C |
| ATOM | 3296 | O   | THR | B | 426 | 18.278 | 20.392 | 12.684 | 1.00 | 58.59 | O |
| ATOM | 3297 | N   | GLU | B | 427 | 16.957 | 19.878 | 10.936 | 1.00 | 61.70 | N |
| ATOM | 3298 | CA  | GLU | B | 427 | 18.023 | 19.989 | 9.952  | 1.00 | 60.13 | C |
| ATOM | 3299 | CB  | GLU | B | 427 | 17.931 | 18.868 | 8.908  | 1.00 | 54.67 | C |
| ATOM | 3300 | CG  | GLU | B | 427 | 17.960 | 17.470 | 9.518  | 1.00 | 65.42 | C |
| ATOM | 3301 | CD  | GLU | B | 427 | 18.893 | 16.515 | 8.781  | 1.00 | 72.62 | C |
| ATOM | 3302 | OE1 | GLU | B | 427 | 19.179 | 15.422 | 9.330  | 1.00 | 60.84 | O |
| ATOM | 3303 | OE2 | GLU | B | 427 | 19.338 | 16.859 | 7.659  | 1.00 | 73.29 | O |
| ATOM | 3304 | C   | GLU | B | 427 | 17.907 | 21.348 | 9.282  | 1.00 | 54.90 | C |
| ATOM | 3305 | O   | GLU | B | 427 | 18.825 | 21.782 | 8.585  | 1.00 | 45.97 | O |
| ATOM | 3306 | N   | GLY | B | 428 | 16.768 | 22.009 | 9.512  | 1.00 | 48.91 | N |
| ATOM | 3307 | CA  | GLY | B | 428 | 16.473 | 23.309 | 8.921  | 1.00 | 44.87 | C |
| ATOM | 3308 | C   | GLY | B | 428 | 17.435 | 24.395 | 9.366  | 1.00 | 46.25 | C |
| ATOM | 3309 | O   | GLY | B | 428 | 18.184 | 24.198 | 10.308 | 1.00 | 50.84 | O |
| ATOM | 3310 | N   | PRO | B | 429 | 17.439 | 25.546 | 8.676  | 1.00 | 49.06 | N |
| ATOM | 3311 | CD  | PRO | B | 429 | 16.787 | 25.806 | 7.384  | 1.00 | 41.83 | C |
| ATOM | 3312 | CA  | PRO | B | 429 | 18.223 | 26.699 | 9.132  | 1.00 | 44.60 | C |
| ATOM | 3313 | CB  | PRO | B | 429 | 17.846 | 27.781 | 8.124  | 1.00 | 42.97 | C |
| ATOM | 3314 | CG  | PRO | B | 429 | 17.441 | 27.049 | 6.925  | 1.00 | 38.99 | C |
| ATOM | 3315 | C   | PRO | B | 429 | 17.783 | 27.125 | 10.532 | 1.00 | 44.35 | C |

TABLE 12-continued

Coordinates for pro MMP9(35-444 ΔFnII) (SEQ ID NO: 12) complex with Example 2

| ATOM | 3316 | O | PRO | B | 429 | 16.614 | 27.448 | 10.734 | 1.00 | 47.95 | O |
|---|---|---|---|---|---|---|---|---|---|---|---|
| ATOM | 3317 | N | PRO | B | 430 | 18.713 | 27.144 | 11.491 | 1.00 | 41.86 | N |
| ATOM | 3318 | CD | PRO | B | 430 | 20.157 | 26.970 | 11.267 | 1.00 | 31.48 | C |
| ATOM | 3319 | CA | PRO | B | 430 | 18.360 | 27.334 | 12.914 | 1.00 | 36.00 | C |
| ATOM | 3320 | CB | PRO | B | 430 | 19.710 | 27.239 | 13.636 | 1.00 | 37.66 | C |
| ATOM | 3321 | CG | PRO | B | 430 | 20.653 | 26.555 | 12.625 | 1.00 | 45.83 | C |
| ATOM | 3322 | C | PRO | B | 430 | 17.688 | 28.677 | 13.221 | 1.00 | 35.43 | C |
| ATOM | 3323 | O | PRO | B | 430 | 16.840 | 28.739 | 14.105 | 1.00 | 38.65 | O |
| ATOM | 3324 | N | LEU | B | 431 | 18.052 | 29.734 | 12.502 | 1.00 | 31.04 | N |
| ATOM | 3325 | CA | LEU | B | 431 | 17.486 | 31.060 | 12.746 | 1.00 | 35.74 | C |
| ATOM | 3326 | CB | LEU | B | 431 | 18.314 | 32.139 | 12.058 | 1.00 | 25.12 | C |
| ATOM | 3327 | CG | LEU | B | 431 | 19.736 | 32.394 | 12.542 | 1.00 | 33.35 | C |
| ATOM | 3328 | CD1 | LEU | B | 431 | 20.207 | 33.681 | 11.914 | 1.00 | 30.44 | C |
| ATOM | 3329 | CD2 | LEU | B | 431 | 19.862 | 32.454 | 14.072 | 1.00 | 35.88 | C |
| ATOM | 3330 | C | LEU | B | 431 | 16.001 | 31.212 | 12.324 | 1.00 | 47.91 | C |
| ATOM | 3331 | O | LEU | B | 431 | 15.603 | 30.832 | 11.210 | 1.00 | 39.81 | O |
| ATOM | 3332 | N | HIS | B | 432 | 15.182 | 31.787 | 13.201 | 1.00 | 41.39 | N |
| ATOM | 3333 | CA | HIS | B | 432 | 13.831 | 32.154 | 12.774 | 1.00 | 48.82 | C |
| ATOM | 3334 | CB | HIS | B | 432 | 12.778 | 31.465 | 13.648 | 1.00 | 47.68 | C |
| ATOM | 3335 | CG | HIS | B | 432 | 11.448 | 31.296 | 12.981 | 1.00 | 56.60 | C |
| ATOM | 3336 | CD2 | HIS | B | 432 | 10.241 | 31.866 | 13.232 | 1.00 | 52.63 | C |
| ATOM | 3337 | ND1 | HIS | B | 432 | 11.250 | 30.433 | 11.922 | 1.00 | 60.75 | N |
| ATOM | 3338 | CE1 | HIS | B | 432 | 9.984 | 30.490 | 11.541 | 1.00 | 62.14 | C |
| ATOM | 3339 | NE2 | HIS | B | 432 | 9.352 | 31.352 | 12.319 | 1.00 | 53.00 | N |
| ATOM | 3340 | C | HIS | B | 432 | 13.674 | 33.681 | 12.792 | 1.00 | 48.04 | C |
| ATOM | 3341 | O | HIS | B | 432 | 14.528 | 34.388 | 13.330 | 1.00 | 42.82 | O |
| ATOM | 3342 | N | LYS | B | 433 | 12.608 | 34.193 | 12.187 | 1.00 | 47.13 | N |
| ATOM | 3343 | CA | LYS | B | 433 | 12.342 | 35.625 | 12.268 | 1.00 | 46.56 | C |
| ATOM | 3344 | CB | LYS | B | 433 | 10.928 | 35.939 | 11.766 | 1.00 | 47.48 | C |
| ATOM | 3345 | CG | LYS | B | 433 | 10.780 | 35.966 | 10.220 | 1.00 | 49.30 | C |
| ATOM | 3346 | CD | LYS | B | 433 | 9.336 | 35.717 | 9.799 | 1.00 | 51.05 | C |
| ATOM | 3347 | CE | LYS | B | 433 | 9.177 | 35.601 | 8.280 | 1.00 | 44.20 | C |
| ATOM | 3348 | NZ | LYS | B | 433 | 9.195 | 36.933 | 7.641 | 1.00 | 45.78 | N |
| ATOM | 3349 | C | LYS | B | 433 | 12.567 | 36.192 | 13.685 | 1.00 | 41.72 | C |
| ATOM | 3350 | O | LYS | B | 433 | 13.198 | 37.228 | 13.859 | 1.00 | 40.57 | O |
| ATOM | 3351 | N | ASP | B | 434 | 12.067 | 35.515 | 14.708 | 1.00 | 41.39 | N |
| ATOM | 3352 | CA | ASP | B | 434 | 12.199 | 36.063 | 16.056 | 1.00 | 41.15 | C |
| ATOM | 3353 | CB | ASP | B | 434 | 11.412 | 35.224 | 17.055 | 1.00 | 45.00 | C |
| ATOM | 3354 | CG | ASP | B | 434 | 11.112 | 35.984 | 18.340 | 1.00 | 44.21 | C |
| ATOM | 3355 | OD1 | ASP | B | 434 | 10.663 | 37.145 | 18.249 | 1.00 | 45.43 | O |
| ATOM | 3356 | OD2 | ASP | B | 434 | 11.316 | 35.415 | 19.435 | 1.00 | 42.52 | O |
| ATOM | 3357 | C | ASP | B | 434 | 13.652 | 36.235 | 16.554 | 1.00 | 43.60 | C |
| ATOM | 3358 | O | ASP | B | 434 | 13.956 | 37.172 | 17.322 | 1.00 | 41.61 | O |
| ATOM | 3359 | N | ASP | B | 435 | 14.541 | 35.329 | 16.153 | 1.00 | 34.70 | N |
| ATOM | 3360 | CA | ASP | B | 435 | 15.917 | 35.405 | 16.612 | 1.00 | 37.69 | C |
| ATOM | 3361 | CB | ASP | B | 435 | 16.635 | 34.079 | 16.428 | 1.00 | 36.39 | C |
| ATOM | 3362 | CG | ASP | B | 435 | 15.807 | 32.904 | 16.885 | 1.00 | 41.20 | C |
| ATOM | 3363 | OD1 | ASP | B | 435 | 15.189 | 32.984 | 17.970 | 1.00 | 39.14 | O |
| ATOM | 3364 | OD2 | ASP | B | 435 | 15.778 | 31.895 | 16.147 | 1.00 | 43.08 | O |
| ATOM | 3365 | C | ASP | B | 435 | 16.640 | 36.531 | 15.879 | 1.00 | 38.55 | C |
| ATOM | 3366 | O | ASP | B | 435 | 17.540 | 37.159 | 16.423 | 1.00 | 38.68 | O |
| ATOM | 3367 | N | VAL | B | 436 | 16.213 | 36.802 | 14.654 | 1.00 | 37.46 | N |
| ATOM | 3368 | CA | VAL | B | 436 | 16.787 | 37.881 | 13.869 | 1.00 | 44.09 | C |
| ATOM | 3369 | CB | VAL | B | 436 | 16.510 | 37.686 | 12.370 | 1.00 | 39.41 | C |
| ATOM | 3370 | CG1 | VAL | B | 436 | 17.004 | 38.893 | 11.581 | 1.00 | 42.07 | C |
| ATOM | 3371 | CG2 | VAL | B | 436 | 17.172 | 36.430 | 11.897 | 1.00 | 40.53 | C |
| ATOM | 3372 | C | VAL | B | 436 | 16.285 | 39.252 | 14.343 | 1.00 | 44.98 | C |
| ATOM | 3373 | O | VAL | B | 436 | 17.082 | 40.118 | 14.743 | 1.00 | 45.81 | O |
| ATOM | 3374 | N | ASN | B | 437 | 14.969 | 39.440 | 14.286 | 1.00 | 35.29 | N |
| ATOM | 3375 | CA | ASN | B | 437 | 14.342 | 40.612 | 14.872 | 1.00 | 40.68 | C |
| ATOM | 3376 | CB | ASN | B | 437 | 12.861 | 40.344 | 15.128 | 1.00 | 40.62 | C |
| ATOM | 3377 | CG | ASN | B | 437 | 12.078 | 40.078 | 13.853 | 1.00 | 39.74 | C |
| ATOM | 3378 | OD1 | ASN | B | 437 | 12.501 | 40.421 | 12.738 | 1.00 | 36.67 | O |
| ATOM | 3379 | ND2 | ASN | B | 437 | 10.914 | 39.469 | 14.015 | 1.00 | 47.43 | N |
| ATOM | 3380 | C | ASN | B | 437 | 14.995 | 40.968 | 16.195 | 1.00 | 40.69 | C |
| ATOM | 3381 | O | ASN | B | 437 | 15.279 | 42.129 | 16.462 | 1.00 | 43.71 | O |
| ATOM | 3382 | N | GLY | B | 438 | 15.234 | 39.952 | 17.018 | 1.00 | 40.21 | N |
| ATOM | 3383 | CA | GLY | B | 438 | 15.805 | 40.160 | 18.335 | 1.00 | 47.05 | C |
| ATOM | 3384 | C | GLY | B | 438 | 17.207 | 40.719 | 18.243 | 1.00 | 45.13 | C |
| ATOM | 3385 | O | GLY | B | 438 | 17.489 | 41.827 | 18.706 | 1.00 | 46.59 | O |
| ATOM | 3386 | N | ILE | B | 439 | 18.099 | 39.962 | 17.620 | 1.00 | 47.04 | N |
| ATOM | 3387 | CA | ILE | B | 439 | 19.467 | 40.444 | 17.473 | 1.00 | 47.91 | C |
| ATOM | 3388 | CB | ILE | B | 439 | 20.350 | 39.501 | 16.644 | 1.00 | 41.16 | C |
| ATOM | 3389 | CG2 | ILE | B | 439 | 19.998 | 39.575 | 15.133 | 1.00 | 38.05 | C |
| ATOM | 3390 | CG1 | ILE | B | 439 | 21.822 | 39.809 | 16.932 | 1.00 | 41.14 | C |
| ATOM | 3391 | CD1 | ILE | B | 439 | 22.212 | 39.533 | 18.344 | 1.00 | 41.71 | C |
| ATOM | 3392 | C | ILE | B | 439 | 19.506 | 41.851 | 16.884 | 1.00 | 45.15 | C |

TABLE 12-continued

Coordinates for pro MMP9(35-444 ΔFnII) (SEQ ID NO: 12) complex with Example 2

| ATOM | 3393 | O | ILE | B | 439 | 20.248 | 42.700 | 17.371 | 1.00 | 47.07 | | O |
|---|---|---|---|---|---|---|---|---|---|---|---|---|
| ATOM | 3394 | N | ARG | B | 440 | 18.690 | 42.106 | 15.866 | 1.00 | 39.41 | | N |
| ATOM | 3395 | CA | ARG | B | 440 | 18.785 | 43.373 | 15.162 | 1.00 | 43.98 | | C |
| ATOM | 3396 | CB | ARG | B | 440 | 17.818 | 43.437 | 13.983 | 1.00 | 50.48 | | C |
| ATOM | 3397 | CG | ARG | B | 440 | 18.290 | 42.715 | 12.723 | 1.00 | 51.65 | | C |
| ATOM | 3398 | CD | ARG | B | 440 | 17.251 | 42.829 | 11.605 | 1.00 | 41.78 | | C |
| ATOM | 3399 | NE | ARG | B | 440 | 17.611 | 42.024 | 10.450 | 1.00 | 52.28 | | N |
| ATOM | 3400 | CZ | ARG | B | 440 | 16.880 | 41.922 | 9.345 | 1.00 | 57.86 | | C |
| ATOM | 3401 | NH1 | ARG | B | 440 | 15.726 | 42.571 | 9.256 | 1.00 | 54.34 | | N |
| ATOM | 3402 | NH2 | ARG | B | 440 | 17.299 | 41.161 | 8.332 | 1.00 | 49.06 | | N |
| ATOM | 3403 | C | ARG | B | 440 | 18.503 | 44.489 | 16.142 | 1.00 | 51.17 | | C |
| ATOM | 3404 | O | ARG | B | 440 | 19.185 | 45.513 | 16.147 | 1.00 | 52.09 | | O |
| ATOM | 3405 | N | HIS | B | 441 | 17.503 | 44.275 | 16.987 | 1.00 | 44.90 | | N |
| ATOM | 3406 | CA | HIS | B | 441 | 17.167 | 45.241 | 18.012 | 1.00 | 47.41 | | C |
| ATOM | 3407 | CB | HIS | B | 441 | 16.132 | 44.637 | 18.953 | 1.00 | 48.60 | | C |
| ATOM | 3408 | CG | HIS | B | 441 | 15.343 | 45.651 | 19.707 | 1.00 | 55.13 | | C |
| ATOM | 3409 | CD2 | HIS | B | 441 | 14.392 | 46.522 | 19.299 | 1.00 | 59.97 | | C |
| ATOM | 3410 | ND1 | HIS | B | 441 | 15.507 | 45.864 | 21.060 | 1.00 | 60.72 | | N |
| ATOM | 3411 | CE1 | HIS | B | 441 | 14.685 | 46.822 | 21.455 | 1.00 | 64.18 | | C |
| ATOM | 3412 | NE2 | HIS | B | 441 | 13.998 | 47.239 | 20.406 | 1.00 | 71.86 | | N |
| ATOM | 3413 | C | HIS | B | 441 | 18.426 | 45.674 | 18.777 | 1.00 | 53.33 | | C |
| ATOM | 3414 | O | HIS | B | 441 | 18.737 | 46.861 | 18.857 | 1.00 | 56.08 | | O |
| ATOM | 3415 | N | LEU | B | 442 | 19.161 | 44.713 | 19.325 | 1.00 | 49.59 | | N |
| ATOM | 3416 | CA | LEU | B | 442 | 20.456 | 45.006 | 19.938 | 1.00 | 52.14 | | C |
| ATOM | 3417 | CB | LEU | B | 442 | 21.174 | 43.710 | 20.341 | 1.00 | 46.62 | | C |
| ATOM | 3418 | CG | LEU | B | 442 | 20.827 | 43.058 | 21.678 | 1.00 | 55.43 | | C |
| ATOM | 3419 | CD1 | LEU | B | 442 | 21.036 | 44.068 | 22.819 | 1.00 | 64.79 | | C |
| ATOM | 3420 | CD2 | LEU | B | 442 | 19.408 | 42.501 | 21.688 | 1.00 | 45.82 | | C |
| ATOM | 3421 | C | LEU | B | 442 | 21.388 | 45.818 | 19.028 | 1.00 | 50.90 | | C |
| ATOM | 3422 | O | LEU | B | 442 | 21.899 | 46.868 | 19.421 | 1.00 | 47.83 | | O |
| ATOM | 3423 | N | TYR | B | 443 | 21.630 | 45.299 | 17.825 | 1.00 | 51.71 | | N |
| ATOM | 3424 | CA | TYR | B | 443 | 22.635 | 45.857 | 16.921 | 1.00 | 52.80 | | C |
| ATOM | 3425 | CB | TYR | B | 443 | 23.758 | 44.838 | 16.677 | 1.00 | 51.98 | | C |
| ATOM | 3426 | CG | TYR | B | 443 | 24.266 | 44.166 | 17.945 | 1.00 | 49.74 | | C |
| ATOM | 3427 | CD1 | TYR | B | 443 | 23.865 | 42.880 | 18.289 | 1.00 | 48.37 | | C |
| ATOM | 3428 | CE1 | TYR | B | 443 | 24.311 | 42.273 | 19.444 | 1.00 | 49.63 | | C |
| ATOM | 3429 | CD2 | TYR | B | 443 | 25.135 | 44.828 | 18.801 | 1.00 | 51.18 | | C |
| ATOM | 3430 | CE2 | TYR | B | 443 | 25.596 | 44.232 | 19.963 | 1.00 | 47.29 | | C |
| ATOM | 3431 | CZ | TYR | B | 443 | 25.182 | 42.957 | 20.284 | 1.00 | 54.49 | | C |
| ATOM | 3432 | OH | TYR | B | 443 | 25.646 | 42.368 | 21.447 | 1.00 | 44.92 | | O |
| ATOM | 3433 | C | TYR | B | 443 | 21.989 | 46.287 | 15.599 | 1.00 | 49.23 | | C |
| ATOM | 3434 | O | TYR | B | 443 | 21.958 | 47.463 | 15.270 | 1.00 | 43.95 | | O |
| ATOM | 3435 | N | GLY | B | 444 | 21.472 | 45.320 | 14.849 | 1.00 | 59.32 | | N |
| ATOM | 3436 | CA | GLY | B | 444 | 20.739 | 45.603 | 13.623 | 1.00 | 60.84 | | C |
| ATOM | 3437 | C | GLY | B | 444 | 21.490 | 46.439 | 12.613 | 1.00 | 59.87 | | C |
| ATOM | 3438 | O | GLY | B | 444 | 21.628 | 46.042 | 11.453 | 1.00 | 75.23 | | O |
| ATOM | 3439 | ZN | ZN | B | 500 | 18.838 | 29.756 | 26.785 | 1.00 | 46.43 | | Zn |
| ATOM | 3440 | ZN | ZN | B | 501 | 28.420 | 27.416 | 34.020 | 1.00 | 49.83 | | Zn |
| ATOM | 3441 | CA | CA | B | 502 | 22.047 | 17.943 | 32.177 | 1.00 | 60.92 | | Ca |
| ATOM | 3442 | CA | CA | B | 503 | 29.961 | 13.344 | 27.676 | 1.00 | 68.05 | | Ca |
| ATOM | 3443 | CA | CA | B | 504 | 33.455 | 36.117 | 29.287 | 1.00 | 61.68 | | Ca |
| TER | 3444 | | CA | B | 504 | | | | | | | |
| ATOM | 3501 | C01 | LIG | E | 1 | 19.271 | 43.772 | −8.671 | 1.00 | 47.08 | A | C |
| ATOM | 3502 | C02 | LIG | E | 1 | 19.125 | 43.041 | −9.954 | 1.00 | 55.16 | A | C |
| ATOM | 3503 | N03 | LIG | E | 1 | 19.227 | 43.463 | −11.173 | 1.00 | 46.06 | A | N |
| ATOM | 3504 | C04 | LIG | E | 1 | 19.006 | 42.397 | −12.061 | 1.00 | 46.95 | A | C |
| ATOM | 3505 | C05 | LIG | E | 1 | 19.051 | 42.805 | −13.482 | 1.00 | 49.25 | A | C |
| ATOM | 3506 | C06 | LIG | E | 1 | 18.751 | 41.159 | −11.521 | 1.00 | 51.62 | A | C |
| ATOM | 3507 | S07 | LIG | E | 1 | 18.813 | 41.325 | −9.809 | 1.00 | 50.76 | A | S |
| ATOM | 3508 | C08 | LIG | E | 1 | 18.596 | 39.749 | −11.958 | 1.00 | 49.69 | A | C |
| ATOM | 3509 | C09 | LIG | E | 1 | 18.343 | 38.792 | −11.051 | 1.00 | 49.91 | A | C |
| ATOM | 3510 | S10 | LIG | E | 1 | 18.203 | 37.229 | −11.675 | 1.00 | 47.36 | A | S |
| ATOM | 3511 | C11 | LIG | E | 1 | 18.499 | 37.889 | −13.253 | 1.00 | 43.92 | A | C |
| ATOM | 3512 | N12 | LIG | E | 1 | 18.694 | 39.181 | −13.267 | 1.00 | 47.32 | A | N |
| ATOM | 3513 | N13 | LIG | E | 1 | 18.528 | 37.033 | −14.359 | 1.00 | 44.50 | A | N |
| ATOM | 3514 | C14 | LIG | E | 1 | 18.937 | 37.239 | −15.723 | 1.00 | 47.19 | A | C |
| ATOM | 3515 | C15 | LIG | E | 1 | 19.503 | 38.461 | −16.082 | 1.00 | 47.31 | A | C |
| ATOM | 3516 | C16 | LIG | E | 1 | 19.872 | 38.953 | −17.346 | 1.00 | 48.74 | A | C |
| ATOM | 3517 | C17 | LIG | E | 1 | 19.651 | 38.008 | −18.316 | 1.00 | 43.63 | A | C |
| ATOM | 3518 | C18 | LIG | E | 1 | 19.032 | 36.799 | −18.035 | 1.00 | 44.86 | A | C |
| ATOM | 3519 | C19 | LIG | E | 1 | 18.670 | 36.343 | −16.771 | 1.00 | 45.50 | A | C |
| ATOM | 3520 | O20 | LIG | E | 1 | 18.067 | 35.183 | −16.456 | 1.00 | 46.15 | A | O |
| ATOM | 3521 | C21 | LIG | E | 1 | 18.197 | 33.971 | −17.142 | 1.00 | 43.46 | A | C |
| ATOM | 3522 | C22 | LIG | E | 1 | 17.477 | 32.902 | −16.359 | 1.00 | 42.00 | A | C |
| ATOM | 3523 | C23 | LIG | E | 1 | 19.668 | 33.631 | −17.068 | 1.00 | 41.39 | A | C |
| ATOM | 3524 | S24 | LIG | E | 1 | 20.461 | 40.559 | −17.600 | 1.00 | 47.47 | A | S |
| ATOM | 3525 | N25 | LIG | E | 1 | 22.012 | 40.809 | −17.441 | 1.00 | 58.41 | A | N |

TABLE 12-continued

Coordinates for pro MMP9(35-444 ΔFnII) (SEQ ID NO: 12) complex with Example 2

| ATOM | 3526 | O26 | LIG | E | 1 | 20.251 | 40.881 | −18.886 | 1.00 | 55.02 | A | O |
|---|---|---|---|---|---|---|---|---|---|---|---|---|
| ATOM | 3527 | O27 | LIG | E | 1 | 19.967 | 41.339 | −16.632 | 1.00 | 51.32 | A | O |
| TER | 3528 | | LIG | E | 1 | | | | | | | |
| END | | | | | | | | | | | | |
| ATOM | 1 | N | THR | A | 40 | 3.580 | 62.492 | 27.428 | 1.00 | 62.75 | A | N |
| ATOM | 2 | CA | THR | A | 40 | 4.940 | 62.991 | 27.307 | 1.00 | 58.36 | A | C |
| ATOM | 3 | C | THR | A | 40 | 5.117 | 63.876 | 26.067 | 1.00 | 54.85 | A | C |
| ATOM | 4 | CB | THR | A | 40 | 5.976 | 61.829 | 27.293 | 1.00 | 57.75 | A | C |
| ATOM | 5 | OG1 | THR | A | 40 | 7.258 | 62.302 | 27.739 | 1.00 | 54.58 | A | O |
| ATOM | 6 | CG2 | THR | A | 40 | 6.092 | 61.207 | 25.896 | 1.00 | 48.26 | A | C |
| ATOM | 7 | O | THR | A | 40 | 6.225 | 64.327 | 25.793 | 1.00 | 55.72 | A | O |
| ATOM | 8 | CB | ASP | A | 41 | 2.809 | 65.010 | 23.347 | 1.00 | 40.17 | A | C |
| ATOM | 9 | CG | ASP | A | 41 | 2.532 | 63.689 | 22.660 | 1.00 | 41.78 | A | C |
| ATOM | 10 | OD1 | ASP | A | 41 | 3.353 | 62.761 | 22.802 | 1.00 | 49.03 | A | O |
| ATOM | 11 | OD2 | ASP | A | 41 | 1.490 | 63.570 | 21.983 | 1.00 | 39.34 | A | O |
| ATOM | 12 | C | ASP | A | 41 | 4.533 | 66.425 | 24.492 | 1.00 | 47.53 | A | C |
| ATOM | 13 | O | ASP | A | 41 | 5.320 | 67.049 | 23.783 | 1.00 | 49.17 | A | O |
| ATOM | 14 | N | ASP | A | 41 | 4.038 | 64.133 | 25.323 | 1.00 | 49.77 | A | N |
| ATOM | 15 | CA | ASP | A | 41 | 4.121 | 64.998 | 24.137 | 1.00 | 48.30 | A | C |
| ATOM | 16 | N | ARG | A | 42 | 3.998 | 66.946 | 25.586 | 1.00 | 49.44 | A | N |
| ATOM | 17 | CA | ARG | A | 42 | 4.430 | 68.236 | 26.098 | 1.00 | 46.62 | A | C |
| ATOM | 18 | CB | ARG | A | 42 | 3.592 | 68.603 | 27.323 | 1.00 | 52.31 | A | C |
| ATOM | 19 | CG | ARG | A | 42 | 4.021 | 69.855 | 28.074 | 1.00 | 57.05 | A | C |
| ATOM | 20 | CD | ARG | A | 42 | 3.298 | 71.093 | 27.579 | 1.00 | 54.75 | A | C |
| ATOM | 21 | NE | ARG | A | 42 | 3.613 | 72.270 | 28.393 | 1.00 | 56.94 | A | N |
| ATOM | 22 | CZ | ARG | A | 42 | 2.899 | 73.395 | 28.385 | 1.00 | 57.02 | A | C |
| ATOM | 23 | NH1 | ARG | A | 42 | 1.818 | 73.499 | 27.613 | 1.00 | 49.33 | A | N |
| ATOM | 24 | NH2 | ARG | A | 42 | 3.266 | 74.418 | 29.146 | 1.00 | 59.81 | A | N |
| ATOM | 25 | C | ARG | A | 42 | 5.924 | 68.158 | 26.444 | 1.00 | 49.20 | A | C |
| ATOM | 26 | O | ARG | A | 42 | 6.665 | 69.111 | 26.228 | 1.00 | 48.84 | A | O |
| ATOM | 27 | N | GLN | A | 43 | 6.345 | 67.010 | 26.977 | 1.00 | 52.77 | A | N |
| ATOM | 28 | CA | GLN | A | 43 | 7.743 | 66.720 | 27.320 | 1.00 | 47.89 | A | C |
| ATOM | 29 | CB | GLN | A | 43 | 7.868 | 65.301 | 27.896 | 1.00 | 52.21 | A | C |
| ATOM | 30 | CG | GLN | A | 43 | 7.332 | 65.068 | 29.329 | 1.00 | 64.15 | A | C |
| ATOM | 31 | CD | GLN | A | 43 | 5.929 | 65.615 | 29.560 | 1.00 | 63.97 | A | C |
| ATOM | 32 | OE1 | GLN | A | 43 | 4.951 | 65.191 | 28.916 | 1.00 | 60.46 | A | O |
| ATOM | 33 | NE2 | GLN | A | 43 | 5.820 | 66.557 | 30.498 | 1.00 | 67.30 | A | N |
| ATOM | 34 | C | GLN | A | 43 | 8.624 | 66.761 | 26.083 | 1.00 | 47.32 | A | C |
| ATOM | 35 | O | GLN | A | 43 | 9.743 | 67.262 | 26.111 | 1.00 | 43.62 | A | O |
| ATOM | 36 | N | LEU | A | 44 | 8.118 | 66.168 | 25.014 | 1.00 | 41.39 | A | N |
| ATOM | 37 | CA | LEU | A | 44 | 8.855 | 66.028 | 23.782 | 1.00 | 45.22 | A | C |
| ATOM | 38 | CB | LEU | A | 44 | 8.022 | 65.249 | 22.779 | 1.00 | 43.61 | A | C |
| ATOM | 39 | CG | LEU | A | 44 | 8.776 | 64.795 | 21.542 | 1.00 | 40.21 | A | C |
| ATOM | 40 | CD1 | LEU | A | 44 | 9.571 | 63.566 | 21.925 | 1.00 | 49.88 | A | C |
| ATOM | 41 | CD2 | LEU | A | 44 | 7.831 | 64.470 | 20.424 | 1.00 | 38.41 | A | C |
| ATOM | 42 | C | LEU | A | 44 | 9.135 | 67.403 | 23.219 | 1.00 | 41.41 | A | C |
| ATOM | 43 | O | LEU | A | 44 | 10.260 | 67.725 | 22.885 | 1.00 | 40.18 | A | O |
| ATOM | 44 | N | ALA | A | 45 | 8.085 | 68.203 | 23.137 | 1.00 | 35.34 | A | N |
| ATOM | 45 | CA | ALA | A | 45 | 8.145 | 69.529 | 22.572 | 1.00 | 33.60 | A | C |
| ATOM | 46 | CB | ALA | A | 45 | 6.725 | 70.126 | 22.450 | 1.00 | 38.71 | A | C |
| ATOM | 47 | C | ALA | A | 45 | 9.040 | 70.463 | 23.364 | 1.00 | 38.36 | A | C |
| ATOM | 48 | O | ALA | A | 45 | 9.706 | 71.328 | 22.792 | 1.00 | 38.44 | A | O |
| ATOM | 49 | N | GLU | A | 46 | 9.042 | 70.317 | 24.681 | 1.00 | 39.71 | A | N |
| ATOM | 50 | CA | GLU | A | 46 | 9.845 | 71.200 | 25.491 | 1.00 | 42.03 | A | C |
| ATOM | 51 | CB | GLU | A | 46 | 9.537 | 71.007 | 26.974 | 1.00 | 43.99 | A | C |
| ATOM | 52 | CG | GLU | A | 46 | 8.257 | 71.725 | 27.410 | 1.00 | 54.77 | A | C |
| ATOM | 53 | CD | GLU | A | 46 | 7.667 | 71.195 | 28.726 | 1.00 | 65.94 | A | C |
| ATOM | 54 | OE1 | GLU | A | 46 | 8.373 | 70.476 | 29.476 | 1.00 | 65.43 | A | O |
| ATOM | 55 | OE2 | GLU | A | 46 | 6.485 | 71.507 | 29.007 | 1.00 | 62.78 | A | O |
| ATOM | 56 | C | GLU | A | 46 | 11.317 | 70.953 | 25.199 | 1.00 | 40.40 | A | C |
| ATOM | 57 | O | GLU | A | 46 | 12.103 | 71.896 | 25.048 | 1.00 | 40.18 | A | O |
| ATOM | 58 | N | GLU | A | 47 | 11.676 | 69.676 | 25.121 | 1.00 | 39.60 | A | N |
| ATOM | 59 | CA | GLU | A | 47 | 13.061 | 69.268 | 24.917 | 1.00 | 42.86 | A | C |
| ATOM | 60 | CB | GLU | A | 47 | 13.202 | 67.769 | 25.178 | 1.00 | 44.76 | A | C |
| ATOM | 61 | CG | GLU | A | 47 | 13.992 | 67.017 | 24.135 | 1.00 | 52.11 | A | C |
| ATOM | 62 | CD | GLU | A | 47 | 15.436 | 66.789 | 24.537 | 1.00 | 63.02 | A | C |
| ATOM | 63 | OE1 | GLU | A | 47 | 15.692 | 66.620 | 25.756 | 1.00 | 63.91 | A | O |
| ATOM | 64 | OE2 | GLU | A | 47 | 16.304 | 66.765 | 23.628 | 1.00 | 51.14 | A | O |
| ATOM | 65 | C | GLU | A | 47 | 13.553 | 69.654 | 23.513 | 1.00 | 41.05 | A | C |
| ATOM | 66 | O | GLU | A | 47 | 14.655 | 70.174 | 23.353 | 1.00 | 41.88 | A | O |
| ATOM | 67 | N | TYR | A | 48 | 12.721 | 69.421 | 22.506 | 1.00 | 38.79 | A | N |
| ATOM | 68 | CA | TYR | A | 48 | 13.006 | 69.881 | 21.158 | 1.00 | 35.96 | A | C |
| ATOM | 69 | CB | TYR | A | 48 | 11.845 | 69.506 | 20.270 | 1.00 | 31.64 | A | C |
| ATOM | 70 | CG | TYR | A | 48 | 12.081 | 69.533 | 18.791 | 1.00 | 28.89 | A | C |
| ATOM | 71 | CD1 | TYR | A | 48 | 12.041 | 70.726 | 18.086 | 1.00 | 30.84 | A | C |
| ATOM | 72 | CE1 | TYR | A | 48 | 12.225 | 70.750 | 16.719 | 1.00 | 27.12 | A | C |
| ATOM | 73 | CD2 | TYR | A | 48 | 12.285 | 68.355 | 18.080 | 1.00 | 31.64 | A | C |

TABLE 12-continued

Coordinates for pro MMP9(35-444 ΔFnII) (SEQ ID NO: 12) complex with Example 2

| ATOM | 74 | CE2 | TYR | A | 48 | 12.467 | 68.365 | 16.710 | 1.00 | 26.48 | A | C |
|---|---|---|---|---|---|---|---|---|---|---|---|---|
| ATOM | 75 | CZ | TYR | A | 48 | 12.449 | 69.569 | 16.041 | 1.00 | 28.04 | A | C |
| ATOM | 76 | OH | TYR | A | 48 | 12.619 | 69.589 | 14.680 | 1.00 | 23.38 | A | O |
| ATOM | 77 | C | TYR | A | 48 | 13.188 | 71.396 | 21.159 | 1.00 | 39.41 | A | C |
| ATOM | 78 | O | TYR | A | 48 | 14.231 | 71.899 | 20.751 | 1.00 | 36.31 | A | O |
| ATOM | 79 | N | LEU | A | 49 | 12.183 | 72.134 | 21.616 | 1.00 | 35.31 | A | N |
| ATOM | 80 | CA | LEU | A | 49 | 12.272 | 73.587 | 21.580 | 1.00 | 36.48 | A | C |
| ATOM | 81 | CB | LEU | A | 49 | 11.069 | 74.221 | 22.273 | 1.00 | 33.93 | A | C |
| ATOM | 82 | CG | LEU | A | 49 | 9.792 | 74.029 | 21.473 | 1.00 | 37.32 | A | C |
| ATOM | 83 | CD1 | LEU | A | 49 | 8.613 | 74.395 | 22.353 | 1.00 | 33.67 | A | C |
| ATOM | 84 | CD2 | LEU | A | 49 | 9.804 | 74.825 | 20.165 | 1.00 | 33.93 | A | C |
| ATOM | 85 | C | LEU | A | 49 | 13.540 | 74.084 | 22.239 | 1.00 | 33.29 | A | C |
| ATOM | 86 | O | LEU | A | 49 | 14.088 | 75.115 | 21.869 | 1.00 | 35.00 | A | O |
| ATOM | 87 | N | TYR | A | 50 | 13.990 | 73.376 | 23.254 | 1.00 | 32.59 | A | N |
| ATOM | 88 | CA | TYR | A | 50 | 15.169 | 73.841 | 23.947 | 1.00 | 38.08 | A | C |
| ATOM | 89 | CB | TYR | A | 50 | 15.264 | 73.229 | 25.333 | 1.00 | 35.23 | A | C |
| ATOM | 90 | CG | TYR | A | 50 | 16.589 | 73.472 | 26.000 | 1.00 | 38.28 | A | C |
| ATOM | 91 | CD1 | TYR | A | 50 | 16.881 | 74.704 | 26.559 | 1.00 | 44.29 | A | C |
| ATOM | 92 | CE1 | TYR | A | 50 | 18.086 | 74.937 | 27.171 | 1.00 | 45.25 | A | C |
| ATOM | 93 | CD2 | TYR | A | 50 | 17.552 | 72.470 | 26.072 | 1.00 | 42.25 | A | C |
| ATOM | 94 | CE2 | TYR | A | 50 | 18.758 | 72.694 | 26.692 | 1.00 | 41.67 | A | C |
| ATOM | 95 | CZ | TYR | A | 50 | 19.015 | 73.931 | 27.243 | 1.00 | 43.07 | A | C |
| ATOM | 96 | OH | TYR | A | 50 | 20.219 | 74.182 | 27.860 | 1.00 | 59.73 | A | O |
| ATOM | 97 | C | TYR | A | 50 | 16.397 | 73.460 | 23.148 | 1.00 | 34.82 | A | C |
| ATOM | 98 | O | TYR | A | 50 | 17.266 | 74.285 | 22.910 | 1.00 | 34.44 | A | O |
| ATOM | 99 | N | ARG | A | 51 | 16.432 | 72.195 | 22.754 | 1.00 | 29.73 | A | N |
| ATOM | 100 | CA | ARG | A | 51 | 17.560 | 71.607 | 22.057 | 1.00 | 37.49 | A | C |
| ATOM | 101 | CB | ARG | A | 51 | 17.249 | 70.186 | 21.592 | 1.00 | 36.38 | A | C |
| ATOM | 102 | CG | ARG | A | 51 | 18.359 | 69.583 | 20.711 | 1.00 | 41.48 | A | C |
| ATOM | 103 | CD | ARG | A | 51 | 18.125 | 68.119 | 20.377 | 1.00 | 39.28 | A | C |
| ATOM | 104 | NE | ARG | A | 51 | 18.422 | 67.246 | 21.507 | 1.00 | 47.26 | A | N |
| ATOM | 105 | CZ | ARG | A | 51 | 19.632 | 66.774 | 21.808 | 1.00 | 51.36 | A | C |
| ATOM | 106 | NH1 | ARG | A | 51 | 20.688 | 67.094 | 21.059 | 1.00 | 47.31 | A | N |
| ATOM | 107 | NH2 | ARG | A | 51 | 19.784 | 65.983 | 22.867 | 1.00 | 41.13 | A | N |
| ATOM | 108 | C | ARG | A | 51 | 17.934 | 72.463 | 20.870 | 1.00 | 35.85 | A | C |
| ATOM | 109 | O | ARG | A | 51 | 19.080 | 72.873 | 20.721 | 1.00 | 35.82 | A | O |
| ATOM | 110 | N | TYR | A | 52 | 16.952 | 72.756 | 20.043 | 1.00 | 28.40 | A | N |
| ATOM | 111 | CA | TYR | A | 52 | 17.229 | 73.400 | 18.775 | 1.00 | 30.35 | A | C |
| ATOM | 112 | CB | TYR | A | 52 | 16.339 | 72.803 | 17.704 | 1.00 | 29.77 | A | C |
| ATOM | 113 | CG | TYR | A | 52 | 16.639 | 71.337 | 17.517 | 1.00 | 30.95 | A | C |
| ATOM | 114 | CD1 | TYR | A | 52 | 15.635 | 70.383 | 17.542 | 1.00 | 33.45 | A | C |
| ATOM | 115 | CE1 | TYR | A | 52 | 15.928 | 69.021 | 17.383 | 1.00 | 34.37 | A | C |
| ATOM | 116 | CD2 | TYR | A | 52 | 17.946 | 70.899 | 17.336 | 1.00 | 32.23 | A | C |
| ATOM | 117 | CE2 | TYR | A | 52 | 18.246 | 69.559 | 17.167 | 1.00 | 30.37 | A | C |
| ATOM | 118 | CZ | TYR | A | 52 | 17.239 | 68.625 | 17.194 | 1.00 | 33.71 | A | C |
| ATOM | 119 | OH | TYR | A | 52 | 17.538 | 67.296 | 17.029 | 1.00 | 31.94 | A | O |
| ATOM | 120 | C | TYR | A | 52 | 17.246 | 74.929 | 18.775 | 1.00 | 28.47 | A | C |
| ATOM | 121 | O | TYR | A | 52 | 17.289 | 75.563 | 17.712 | 1.00 | 28.92 | A | O |
| ATOM | 122 | N | GLY | A | 53 | 17.239 | 75.515 | 19.973 | 1.00 | 29.71 | A | N |
| ATOM | 123 | CA | GLY | A | 53 | 17.525 | 76.935 | 20.140 | 1.00 | 34.14 | A | C |
| ATOM | 124 | C | GLY | A | 53 | 16.334 | 77.846 | 20.366 | 1.00 | 35.57 | A | C |
| ATOM | 125 | O | GLY | A | 53 | 16.475 | 79.013 | 20.717 | 1.00 | 34.35 | A | O |
| ATOM | 126 | N | TYR | A | 54 | 15.148 | 77.289 | 20.189 | 1.00 | 34.64 | A | N |
| ATOM | 127 | CA | TYR | A | 54 | 13.912 | 78.057 | 20.159 | 1.00 | 34.62 | A | C |
| ATOM | 128 | CB | TYR | A | 54 | 12.811 | 77.139 | 19.681 | 1.00 | 32.63 | A | C |
| ATOM | 129 | CG | TYR | A | 54 | 13.009 | 76.715 | 18.256 | 1.00 | 27.29 | A | C |
| ATOM | 130 | CD1 | TYR | A | 54 | 13.411 | 75.425 | 17.930 | 1.00 | 31.05 | A | C |
| ATOM | 131 | CE1 | TYR | A | 54 | 13.596 | 75.039 | 16.592 | 1.00 | 25.11 | A | C |
| ATOM | 132 | CD2 | TYR | A | 54 | 12.813 | 77.612 | 17.226 | 1.00 | 28.46 | A | C |
| ATOM | 133 | CE2 | TYR | A | 54 | 12.981 | 77.233 | 15.903 | 1.00 | 26.56 | A | C |
| ATOM | 134 | CZ | TYR | A | 54 | 13.381 | 75.952 | 15.599 | 1.00 | 26.82 | A | C |
| ATOM | 135 | OH | TYR | A | 54 | 13.536 | 75.602 | 14.273 | 1.00 | 27.68 | A | O |
| ATOM | 136 | C | TYR | A | 54 | 13.508 | 78.745 | 21.469 | 1.00 | 34.35 | A | C |
| ATOM | 137 | O | TYR | A | 54 | 13.030 | 79.871 | 21.447 | 1.00 | 31.36 | A | O |
| ATOM | 138 | N | THR | A | 55 | 13.731 | 78.092 | 22.597 | 1.00 | 29.37 | A | N |
| ATOM | 139 | CA | THR | A | 55 | 13.290 | 78.634 | 23.869 | 1.00 | 33.75 | A | C |
| ATOM | 140 | CB | THR | A | 55 | 13.266 | 77.561 | 24.968 | 1.00 | 34.33 | A | C |
| ATOM | 141 | OG1 | THR | A | 55 | 14.591 | 77.335 | 25.462 | 1.00 | 40.91 | A | O |
| ATOM | 142 | CG2 | THR | A | 55 | 12.705 | 76.268 | 24.433 | 1.00 | 34.63 | A | C |
| ATOM | 143 | C | THR | A | 55 | 14.167 | 79.809 | 24.302 | 1.00 | 44.98 | A | C |
| ATOM | 144 | O | THR | A | 55 | 13.651 | 80.823 | 24.789 | 1.00 | 43.86 | A | O |
| ATOM | 145 | N | ARG | A | 56 | 15.482 | 79.669 | 24.107 | 1.00 | 41.30 | A | N |
| ATOM | 146 | CA | ARG | A | 56 | 16.434 | 80.747 | 24.376 | 1.00 | 40.16 | A | C |
| ATOM | 147 | CB | ARG | A | 56 | 17.855 | 80.361 | 23.923 | 1.00 | 45.94 | A | C |
| ATOM | 148 | CG | ARG | A | 56 | 18.395 | 79.035 | 24.475 | 1.00 | 55.67 | A | C |
| ATOM | 149 | CD | ARG | A | 56 | 19.480 | 78.405 | 23.552 | 1.00 | 54.23 | A | C |
| ATOM | 150 | NE | ARG | A | 56 | 19.968 | 77.121 | 24.068 | 1.00 | 50.34 | A | N |

TABLE 12-continued

Coordinates for pro MMP9(35-444 ΔFnII) (SEQ ID NO: 12) complex with Example 2

| ATOM | 151 | CZ  | ARG | A | 56 | 20.234 | 76.049 | 23.317 | 1.00 | 51.47 | A | C |
|------|-----|-----|-----|---|----|--------|--------|--------|------|-------|---|---|
| ATOM | 152 | NH1 | ARG | A | 56 | 20.078 | 76.091 | 21.997 | 1.00 | 53.10 | A | N |
| ATOM | 153 | NH2 | ARG | A | 56 | 20.656 | 74.927 | 23.888 | 1.00 | 46.27 | A | N |
| ATOM | 154 | C   | ARG | A | 56 | 16.005 | 82.025 | 23.654 | 1.00 | 38.72 | A | C |
| ATOM | 155 | O   | ARG | A | 56 | 16.059 | 83.109 | 24.213 | 1.00 | 41.62 | A | O |
| ATOM | 156 | N   | VAL | A | 57 | 15.590 | 81.893 | 22.402 | 1.00 | 36.68 | A | N |
| ATOM | 157 | CA  | VAL | A | 57 | 15.154 | 83.039 | 21.633 | 1.00 | 39.39 | A | C |
| ATOM | 158 | CB  | VAL | A | 57 | 15.055 | 82.739 | 20.127 | 1.00 | 34.24 | A | C |
| ATOM | 159 | CG1 | VAL | A | 57 | 14.592 | 83.985 | 19.382 | 1.00 | 35.58 | A | C |
| ATOM | 160 | CG2 | VAL | A | 57 | 16.415 | 82.278 | 19.578 | 1.00 | 39.71 | A | C |
| ATOM | 161 | C   | VAL | A | 57 | 13.820 | 83.571 | 22.145 | 1.00 | 39.11 | A | C |
| ATOM | 162 | O   | VAL | A | 57 | 13.612 | 84.779 | 22.167 | 1.00 | 42.74 | A | O |
| ATOM | 163 | N   | GLY | A | 58 | 12.916 | 82.678 | 22.542 | 1.00 | 42.48 | A | N |
| ATOM | 164 | CA  | GLY | A | 58 | 11.665 | 83.094 | 23.168 | 1.00 | 39.23 | A | C |
| ATOM | 165 | C   | GLY | A | 58 | 11.963 | 83.963 | 24.384 | 1.00 | 42.20 | A | C |
| ATOM | 166 | O   | GLY | A | 58 | 11.480 | 85.094 | 24.501 | 1.00 | 44.29 | A | O |
| ATOM | 167 | N   | GLU | A | 59 | 12.779 | 83.440 | 25.290 | 1.00 | 40.15 | A | N |
| ATOM | 168 | CA  | GLU | A | 59 | 13.121 | 84.162 | 26.505 | 1.00 | 40.23 | A | C |
| ATOM | 169 | C   | GLU | A | 59 | 13.691 | 85.519 | 26.178 | 1.00 | 47.82 | A | C |
| ATOM | 170 | CB  | GLU | A | 59 | 14.157 | 83.394 | 27.313 | 1.00 | 43.11 | A | C |
| ATOM | 171 | CG  | GLU | A | 59 | 13.833 | 81.938 | 27.537 | 1.00 | 46.17 | A | C |
| ATOM | 172 | CD  | GLU | A | 59 | 14.966 | 81.224 | 28.237 | 1.00 | 56.40 | A | C |
| ATOM | 173 | OE1 | GLU | A | 59 | 16.028 | 81.864 | 28.417 | 1.00 | 51.84 | A | O |
| ATOM | 174 | OE2 | GLU | A | 59 | 14.804 | 80.035 | 28.609 | 1.00 | 59.67 | A | O |
| ATOM | 175 | O   | GLU | A | 59 | 13.441 | 86.493 | 26.884 | 1.00 | 48.47 | A | O |
| ATOM | 176 | N   | MET | A | 60 | 14.487 | 85.560 | 25.110 | 1.00 | 49.65 | A | N |
| ATOM | 177 | CA  | MET | A | 60 | 15.200 | 86.754 | 24.664 | 1.00 | 46.88 | A | C |
| ATOM | 178 | C   | MET | A | 60 | 14.199 | 87.846 | 24.270 | 1.00 | 45.94 | A | C |
| ATOM | 179 | CB  | MET | A | 60 | 16.104 | 86.374 | 23.473 | 1.00 | 50.94 | A | C |
| ATOM | 180 | CG  | MET | A | 60 | 17.506 | 87.008 | 23.419 | 1.00 | 50.81 | A | C |
| ATOM | 181 | SD  | MET | A | 60 | 18.720 | 86.018 | 22.491 | 1.00 | 49.76 | A | S |
| ATOM | 182 | CE  | MET | A | 60 | 19.269 | 84.911 | 23.778 | 1.00 | 46.34 | A | C |
| ATOM | 183 | O   | MET | A | 60 | 14.477 | 89.031 | 24.400 | 1.00 | 44.71 | A | O |
| ATOM | 184 | N   | ARG | A | 61 | 13.026 | 87.432 | 23.795 | 1.00 | 45.78 | A | N |
| ATOM | 185 | CA  | ARG | A | 61 | 11.966 | 88.365 | 23.408 | 1.00 | 47.11 | A | C |
| ATOM | 186 | C   | ARG | A | 61 | 10.923 | 88.517 | 24.523 | 1.00 | 47.89 | A | C |
| ATOM | 187 | CB  | ARG | A | 61 | 11.291 | 87.912 | 22.105 | 1.00 | 44.19 | A | C |
| ATOM | 188 | CG  | ARG | A | 61 | 12.268 | 87.579 | 20.955 | 1.00 | 52.98 | A | C |
| ATOM | 189 | CD  | ARG | A | 61 | 11.536 | 87.268 | 19.642 | 1.00 | 53.56 | A | C |
| ATOM | 190 | NE  | ARG | A | 61 | 12.448 | 86.894 | 18.555 | 1.00 | 56.33 | A | N |
| ATOM | 191 | CZ  | ARG | A | 61 | 12.078 | 86.718 | 17.285 | 1.00 | 56.90 | A | C |
| ATOM | 192 | NH1 | ARG | A | 61 | 12.981 | 86.383 | 16.365 | 1.00 | 51.19 | A | N |
| ATOM | 193 | NH2 | ARG | A | 61 | 10.808 | 86.886 | 16.928 | 1.00 | 54.30 | A | N |
| ATOM | 194 | O   | ARG | A | 61 |  9.883 | 89.132 | 24.317 | 1.00 | 48.92 | A | O |
| ATOM | 195 | N   | GLY | A | 62 | 11.220 | 87.942 | 25.688 | 1.00 | 45.01 | A | N |
| ATOM | 196 | CA  | GLY | A | 62 | 10.363 | 88.009 | 26.862 | 1.00 | 52.53 | A | C |
| ATOM | 197 | C   | GLY | A | 62 |  9.103 | 87.153 | 26.787 | 1.00 | 57.24 | A | C |
| ATOM | 198 | O   | GLY | A | 62 |  8.040 | 87.553 | 27.289 | 1.00 | 55.72 | A | O |
| ATOM | 199 | N   | GLU | A | 63 |  9.224 | 85.976 | 26.177 | 1.00 | 48.75 | A | N |
| ATOM | 200 | CA  | GLU | A | 63 |  8.068 | 85.141 | 25.874 | 1.00 | 48.59 | A | C |
| ATOM | 201 | C   | GLU | A | 63 |  8.205 | 83.688 | 26.343 | 1.00 | 51.94 | A | C |
| ATOM | 202 | CB  | GLU | A | 63 |  7.753 | 85.191 | 24.381 | 1.00 | 46.88 | A | C |
| ATOM | 203 | CG  | GLU | A | 63 |  7.240 | 86.537 | 23.890 | 1.00 | 55.37 | A | C |
| ATOM | 204 | CD  | GLU | A | 63 |  7.489 | 86.752 | 22.400 | 1.00 | 56.55 | A | C |
| ATOM | 205 | OE1 | GLU | A | 63 |  8.256 | 85.961 | 21.814 | 1.00 | 60.14 | A | O |
| ATOM | 206 | OE2 | GLU | A | 63 |  6.936 | 87.710 | 21.809 | 1.00 | 55.54 | A | O |
| ATOM | 207 | O   | GLU | A | 63 |  7.897 | 82.751 | 25.600 | 1.00 | 49.43 | A | O |
| ATOM | 208 | N   | SER | A | 64 |  8.651 | 83.514 | 27.586 | 1.00 | 54.35 | A | N |
| ATOM | 209 | CA  | SER | A | 64 |  8.585 | 82.226 | 28.271 | 1.00 | 55.77 | A | C |
| ATOM | 210 | C   | SER | A | 64 |  7.170 | 82.051 | 28.845 | 1.00 | 59.60 | A | C |
| ATOM | 211 | CB  | SER | A | 64 |  9.633 | 82.179 | 29.376 | 1.00 | 61.44 | A | C |
| ATOM | 212 | OG  | SER | A | 64 |  9.845 | 83.474 | 29.921 | 1.00 | 63.00 | A | O |
| ATOM | 213 | O   | SER | A | 64 |  6.916 | 81.233 | 29.735 | 1.00 | 55.39 | A | O |
| ATOM | 214 | N   | LYS | A | 65 |  6.262 | 82.860 | 28.312 | 1.00 | 58.51 | A | N |
| ATOM | 215 | CA  | LYS | A | 65 |  4.843 | 82.801 | 28.615 | 1.00 | 60.27 | A | C |
| ATOM | 216 | C   | LYS | A | 65 |  4.209 | 81.577 | 27.974 | 1.00 | 59.18 | A | C |
| ATOM | 217 | CB  | LYS | A | 65 |  4.170 | 84.054 | 28.049 | 1.00 | 59.42 | A | C |
| ATOM | 218 | CG  | LYS | A | 65 |  4.702 | 84.468 | 26.673 | 1.00 | 55.96 | A | C |
| ATOM | 219 | CD  | LYS | A | 65 |  4.424 | 85.936 | 26.365 | 1.00 | 57.92 | A | C |
| ATOM | 220 | CE  | LYS | A | 65 |  3.085 | 86.124 | 25.664 | 1.00 | 66.70 | A | C |
| ATOM | 221 | NZ  | LYS | A | 65 |  2.640 | 87.553 | 25.620 | 1.00 | 68.66 | A | N |
| ATOM | 222 | O   | LYS | A | 65 |  3.433 | 81.710 | 27.020 | 1.00 | 58.45 | A | O |
| ATOM | 223 | N   | SER | A | 66 |  4.535 | 80.394 | 28.486 | 1.00 | 55.49 | A | N |
| ATOM | 224 | CA  | SER | A | 66 |  4.076 | 79.151 | 27.863 | 1.00 | 56.36 | A | C |
| ATOM | 225 | C   | SER | A | 66 |  4.816 | 78.852 | 26.554 | 1.00 | 51.99 | A | C |
| ATOM | 226 | CB  | SER | A | 66 |  2.571 | 79.204 | 27.589 | 1.00 | 50.96 | A | C |
| ATOM | 227 | OG  | SER | A | 66 |  2.306 | 79.735 | 26.300 | 1.00 | 48.57 | A | O |

TABLE 12-continued

Coordinates for pro MMP9(35-444 ΔFnII) (SEQ ID NO: 12) complex with Example 2

| ATOM | 228 | O | SER | A | 66 | 5.694 | 79.610 | 26.129 | 1.00 | 49.63 | A | O |
|---|---|---|---|---|---|---|---|---|---|---|---|---|
| ATOM | 229 | N | LEU | A | 67 | 4.428 | 77.756 | 25.907 | 1.00 | 50.77 | A | N |
| ATOM | 230 | CA | LEU | A | 67 | 5.094 | 77.286 | 24.696 | 1.00 | 47.17 | A | C |
| ATOM | 231 | C | LEU | A | 67 | 4.764 | 78.116 | 23.456 | 1.00 | 46.77 | A | C |
| ATOM | 232 | CB | LEU | A | 67 | 4.754 | 75.809 | 24.451 | 1.00 | 40.25 | A | C |
| ATOM | 233 | CG | LEU | A | 67 | 5.725 | 74.825 | 25.090 | 1.00 | 40.79 | A | C |
| ATOM | 234 | CD1 | LEU | A | 67 | 5.944 | 75.156 | 26.552 | 1.00 | 51.23 | A | C |
| ATOM | 235 | CD2 | LEU | A | 67 | 5.226 | 73.407 | 24.934 | 1.00 | 47.13 | A | C |
| ATOM | 236 | O | LEU | A | 67 | 5.507 | 78.117 | 22.459 | 1.00 | 38.25 | A | O |
| ATOM | 237 | N | GLY | A | 68 | 3.649 | 78.826 | 23.524 | 1.00 | 42.27 | A | N |
| ATOM | 238 | CA | GLY | A | 68 | 3.117 | 79.496 | 22.359 | 1.00 | 38.62 | A | C |
| ATOM | 239 | C | GLY | A | 68 | 4.145 | 80.148 | 21.448 | 1.00 | 40.35 | A | C |
| ATOM | 240 | O | GLY | A | 68 | 4.326 | 79.740 | 20.313 | 1.00 | 39.02 | A | O |
| ATOM | 241 | N | PRO | A | 69 | 4.815 | 81.189 | 21.936 | 1.00 | 38.18 | A | N |
| ATOM | 242 | CD | PRO | A | 69 | 4.841 | 81.740 | 23.296 | 1.00 | 45.19 | A | C |
| ATOM | 243 | CA | PRO | A | 69 | 5.683 | 81.928 | 21.029 | 1.00 | 42.35 | A | C |
| ATOM | 244 | CB | PRO | A | 69 | 6.177 | 83.092 | 21.896 | 1.00 | 46.27 | A | C |
| ATOM | 245 | CG | PRO | A | 69 | 5.198 | 83.165 | 23.038 | 1.00 | 46.52 | A | C |
| ATOM | 246 | C | PRO | A | 69 | 6.838 | 81.057 | 20.482 | 1.00 | 37.74 | A | C |
| ATOM | 247 | O | PRO | A | 69 | 7.115 | 81.154 | 19.301 | 1.00 | 36.74 | A | O |
| ATOM | 248 | N | ALA | A | 70 | 7.456 | 80.208 | 21.303 | 1.00 | 39.94 | A | N |
| ATOM | 249 | CA | ALA | A | 70 | 8.501 | 79.288 | 20.826 | 1.00 | 32.70 | A | C |
| ATOM | 250 | CB | ALA | A | 70 | 9.008 | 78.430 | 21.967 | 1.00 | 34.38 | A | C |
| ATOM | 251 | C | ALA | A | 70 | 8.015 | 78.405 | 19.691 | 1.00 | 38.37 | A | C |
| ATOM | 252 | O | ALA | A | 70 | 8.718 | 78.218 | 18.692 | 1.00 | 33.60 | A | O |
| ATOM | 253 | N | LEU | A | 71 | 6.810 | 77.858 | 19.828 | 1.00 | 31.85 | A | N |
| ATOM | 254 | CA | LEU | A | 71 | 6.265 | 77.010 | 18.777 | 1.00 | 29.15 | A | C |
| ATOM | 255 | CB | LEU | A | 71 | 4.876 | 76.523 | 19.148 | 1.00 | 31.24 | A | C |
| ATOM | 256 | CG | LEU | A | 71 | 4.912 | 75.458 | 20.219 | 1.00 | 30.49 | A | C |
| ATOM | 257 | CD1 | LEU | A | 71 | 3.508 | 75.225 | 20.719 | 1.00 | 36.69 | A | C |
| ATOM | 258 | CD2 | LEU | A | 71 | 5.482 | 74.192 | 19.627 | 1.00 | 32.56 | A | C |
| ATOM | 259 | C | LEU | A | 71 | 6.150 | 77.788 | 17.496 | 1.00 | 32.11 | A | C |
| ATOM | 260 | O | LEU | A | 71 | 6.304 | 77.243 | 16.400 | 1.00 | 32.86 | A | O |
| ATOM | 261 | N | LEU | A | 72 | 5.827 | 79.063 | 17.632 | 1.00 | 29.99 | A | N |
| ATOM | 262 | CA | LEU | A | 72 | 5.664 | 79.892 | 16.463 | 1.00 | 35.28 | A | C |
| ATOM | 263 | CB | LEU | A | 72 | 5.068 | 81.245 | 16.839 | 1.00 | 35.51 | A | C |
| ATOM | 264 | CG | LEU | A | 72 | 4.357 | 82.045 | 15.745 | 1.00 | 43.34 | A | C |
| ATOM | 265 | CD1 | LEU | A | 72 | 3.229 | 81.267 | 15.088 | 1.00 | 42.23 | A | C |
| ATOM | 266 | CD2 | LEU | A | 72 | 3.828 | 83.344 | 16.345 | 1.00 | 51.30 | A | C |
| ATOM | 267 | C | LEU | A | 72 | 7.028 | 80.064 | 15.783 | 1.00 | 36.06 | A | C |
| ATOM | 268 | O | LEU | A | 72 | 7.140 | 79.885 | 14.584 | 1.00 | 35.34 | A | O |
| ATOM | 269 | N | LEU | A | 73 | 8.052 | 80.400 | 16.559 | 1.00 | 35.18 | A | N |
| ATOM | 270 | CA | LEU | A | 73 | 9.409 | 80.499 | 16.017 | 1.00 | 37.32 | A | C |
| ATOM | 271 | CB | LEU | A | 73 | 10.419 | 80.721 | 17.138 | 1.00 | 31.15 | A | C |
| ATOM | 272 | CG | LEU | A | 73 | 10.364 | 82.098 | 17.785 | 1.00 | 34.21 | A | C |
| ATOM | 273 | CD1 | LEU | A | 73 | 11.406 | 82.230 | 18.862 | 1.00 | 35.85 | A | C |
| ATOM | 274 | CD2 | LEU | A | 73 | 10.515 | 83.184 | 16.741 | 1.00 | 43.68 | A | C |
| ATOM | 275 | C | LEU | A | 73 | 9.723 | 79.218 | 15.259 | 1.00 | 36.24 | A | C |
| ATOM | 276 | O | LEU | A | 73 | 10.181 | 79.242 | 14.109 | 1.00 | 35.35 | A | O |
| ATOM | 277 | N | LEU | A | 74 | 9.439 | 78.091 | 15.893 | 1.00 | 32.26 | A | N |
| ATOM | 278 | CA | LEU | A | 74 | 9.656 | 76.821 | 15.238 | 1.00 | 32.19 | A | C |
| ATOM | 279 | CB | LEU | A | 74 | 9.246 | 75.669 | 16.133 | 1.00 | 26.76 | A | C |
| ATOM | 280 | CG | LEU | A | 74 | 9.508 | 74.255 | 15.620 | 1.00 | 25.39 | A | C |
| ATOM | 281 | CD1 | LEU | A | 74 | 9.922 | 73.403 | 16.785 | 1.00 | 30.67 | A | C |
| ATOM | 282 | CD2 | LEU | A | 74 | 8.270 | 73.658 | 14.932 | 1.00 | 31.59 | A | C |
| ATOM | 283 | C | LEU | A | 74 | 8.922 | 76.735 | 13.928 | 1.00 | 35.77 | A | C |
| ATOM | 284 | O | LEU | A | 74 | 9.516 | 76.429 | 12.899 | 1.00 | 36.31 | A | O |
| ATOM | 285 | N | GLN | A | 75 | 7.621 | 76.983 | 13.954 | 1.00 | 36.03 | A | N |
| ATOM | 286 | CA | GLN | A | 75 | 6.818 | 76.769 | 12.770 | 1.00 | 28.91 | A | C |
| ATOM | 287 | CB | GLN | A | 75 | 5.341 | 77.064 | 13.048 | 1.00 | 33.42 | A | C |
| ATOM | 288 | CG | GLN | A | 75 | 4.611 | 75.895 | 13.710 | 1.00 | 31.58 | A | C |
| ATOM | 289 | CD | GLN | A | 75 | 3.609 | 76.340 | 14.788 | 1.00 | 37.14 | A | C |
| ATOM | 290 | OE1 | GLN | A | 75 | 3.265 | 77.527 | 14.907 | 1.00 | 31.64 | A | O |
| ATOM | 291 | NE2 | GLN | A | 75 | 3.144 | 75.377 | 15.575 | 1.00 | 34.69 | A | N |
| ATOM | 292 | C | GLN | A | 75 | 7.303 | 77.573 | 11.579 | 1.00 | 33.24 | A | C |
| ATOM | 293 | O | GLN | A | 75 | 7.252 | 77.086 | 10.439 | 1.00 | 27.33 | A | O |
| ATOM | 294 | N | LYS | A | 76 | 7.740 | 78.805 | 11.813 | 1.00 | 31.80 | A | N |
| ATOM | 295 | CA | LYS | A | 76 | 8.254 | 79.556 | 10.675 | 1.00 | 38.51 | A | C |
| ATOM | 296 | CB | LYS | A | 76 | 8.200 | 81.066 | 10.877 | 1.00 | 40.13 | A | C |
| ATOM | 297 | CG | LYS | A | 76 | 9.046 | 81.606 | 11.980 | 1.00 | 43.14 | A | C |
| ATOM | 298 | CD | LYS | A | 76 | 8.398 | 82.892 | 12.502 | 1.00 | 51.70 | A | C |
| ATOM | 299 | CE | LYS | A | 76 | 6.910 | 82.654 | 12.788 | 1.00 | 45.31 | A | C |
| ATOM | 300 | NZ | LYS | A | 76 | 6.120 | 83.912 | 12.868 | 1.00 | 46.65 | A | N |
| ATOM | 301 | C | LYS | A | 76 | 9.647 | 79.085 | 10.260 | 1.00 | 32.73 | A | C |
| ATOM | 302 | O | LYS | A | 76 | 9.921 | 78.976 | 9.085 | 1.00 | 33.93 | A | O |
| ATOM | 303 | N | GLN | A | 77 | 10.504 | 78.768 | 11.220 | 1.00 | 30.80 | A | N |
| ATOM | 304 | CA | GLN | A | 77 | 11.797 | 78.172 | 10.882 | 1.00 | 38.13 | A | C |

TABLE 12-continued

Coordinates for pro MMP9(35-444 ΔFnII) (SEQ ID NO: 12) complex with Example 2

| | | | | | | | | | | | |
|---|---|---|---|---|---|---|---|---|---|---|---|
| ATOM | 305 | CB | GLN | A | 77 | 12.618 | 77.864 | 12.138 | 1.00 | 39.49 A | C |
| ATOM | 306 | CG | GLN | A | 77 | 14.021 | 77.262 | 11.884 | 1.00 | 43.07 A | C |
| ATOM | 307 | CD | GLN | A | 77 | 14.958 | 78.148 | 11.033 | 1.00 | 41.29 A | C |
| ATOM | 308 | OE1 | GLN | A | 77 | 15.037 | 79.379 | 11.203 | 1.00 | 30.40 A | O |
| ATOM | 309 | NE2 | GLN | A | 77 | 15.685 | 77.501 | 10.118 | 1.00 | 38.97 A | N |
| ATOM | 310 | C | GLN | A | 77 | 11.654 | 76.926 | 10.005 | 1.00 | 35.84 A | C |
| ATOM | 311 | O | GLN | A | 77 | 12.464 | 76.710 | 9.113 | 1.00 | 33.90 A | O |
| ATOM | 312 | N | LEU | A | 78 | 10.606 | 76.130 | 10.219 | 1.00 | 33.26 A | N |
| ATOM | 313 | CA | LEU | A | 78 | 10.437 | 74.902 | 9.439 | 1.00 | 29.13 A | C |
| ATOM | 314 | CB | LEU | A | 78 | 10.186 | 73.702 | 10.338 | 1.00 | 27.61 A | C |
| ATOM | 315 | CG | LEU | A | 78 | 11.234 | 73.267 | 11.358 | 1.00 | 37.20 A | C |
| ATOM | 316 | CD1 | LEU | A | 78 | 10.579 | 72.313 | 12.364 | 1.00 | 36.87 A | C |
| ATOM | 317 | CD2 | LEU | A | 78 | 12.429 | 72.594 | 10.688 | 1.00 | 34.07 A | C |
| ATOM | 318 | C | LEU | A | 78 | 9.355 | 74.994 | 8.385 | 1.00 | 26.51 A | C |
| ATOM | 319 | O | LEU | A | 78 | 9.030 | 74.010 | 7.708 | 1.00 | 30.88 A | O |
| ATOM | 320 | N | SER | A | 79 | 8.802 | 76.179 | 8.203 | 1.00 | 26.34 A | N |
| ATOM | 321 | CA | SER | A | 79 | 7.788 | 76.347 | 7.165 | 1.00 | 31.27 A | C |
| ATOM | 322 | CB | SER | A | 79 | 8.385 | 76.070 | 5.782 | 1.00 | 28.87 A | C |
| ATOM | 323 | OG | SER | A | 79 | 9.324 | 77.099 | 5.458 | 1.00 | 36.29 A | O |
| ATOM | 324 | C | SER | A | 79 | 6.557 | 75.469 | 7.438 | 1.00 | 29.75 A | C |
| ATOM | 325 | O | SER | A | 79 | 5.976 | 74.858 | 6.539 | 1.00 | 26.96 A | O |
| ATOM | 326 | N | LEU | A | 80 | 6.178 | 75.427 | 8.710 | 1.00 | 35.15 A | N |
| ATOM | 327 | CA | LEU | A | 80 | 4.909 | 74.844 | 9.131 | 1.00 | 29.28 A | C |
| ATOM | 328 | CB | LEU | A | 80 | 5.106 | 74.174 | 10.468 | 1.00 | 29.78 A | C |
| ATOM | 329 | CG | LEU | A | 80 | 6.110 | 73.031 | 10.395 | 1.00 | 30.57 A | C |
| ATOM | 330 | CD1 | LEU | A | 80 | 6.277 | 72.392 | 11.747 | 1.00 | 35.30 A | C |
| ATOM | 331 | CD2 | LEU | A | 80 | 5.640 | 72.032 | 9.377 | 1.00 | 33.55 A | C |
| ATOM | 332 | C | LEU | A | 80 | 3.905 | 75.971 | 9.285 | 1.00 | 31.11 A | C |
| ATOM | 333 | O | LEU | A | 80 | 4.282 | 77.107 | 9.595 | 1.00 | 30.26 A | O |
| ATOM | 334 | N | PRO | A | 81 | 2.611 | 75.671 | 9.099 | 1.00 | 36.05 A | N |
| ATOM | 335 | CD | PRO | A | 81 | 1.965 | 74.419 | 8.674 | 1.00 | 27.86 A | C |
| ATOM | 336 | CA | PRO | A | 81 | 1.633 | 76.744 | 9.326 | 1.00 | 30.12 A | C |
| ATOM | 337 | CB | PRO | A | 81 | 0.295 | 76.027 | 9.150 | 1.00 | 33.98 A | C |
| ATOM | 338 | CG | PRO | A | 81 | 0.639 | 74.905 | 8.172 | 1.00 | 35.05 A | C |
| ATOM | 339 | C | PRO | A | 81 | 1.813 | 77.340 | 10.722 | 1.00 | 27.32 A | C |
| ATOM | 340 | O | PRO | A | 81 | 2.050 | 76.621 | 11.689 | 1.00 | 29.98 A | O |
| ATOM | 341 | N | GLU | A | 82 | 1.775 | 78.664 | 10.800 | 1.00 | 27.37 A | N |
| ATOM | 342 | CA | GLU | A | 82 | 2.169 | 79.364 | 12.016 | 1.00 | 37.44 A | C |
| ATOM | 343 | CB | GLU | A | 82 | 2.873 | 80.672 | 11.638 | 1.00 | 37.65 A | C |
| ATOM | 344 | CG | GLU | A | 82 | 4.101 | 80.415 | 10.769 | 1.00 | 39.21 A | C |
| ATOM | 345 | CD | GLU | A | 82 | 4.512 | 81.591 | 9.886 | 1.00 | 47.26 A | C |
| ATOM | 346 | OE1 | GLU | A | 82 | 4.234 | 82.763 | 10.235 | 1.00 | 49.48 A | O |
| ATOM | 347 | OE2 | GLU | A | 82 | 5.132 | 81.327 | 8.833 | 1.00 | 47.13 A | O |
| ATOM | 348 | C | GLU | A | 82 | 0.965 | 79.586 | 12.961 | 1.00 | 39.29 A | C |
| ATOM | 349 | O | GLU | A | 82 | 0.231 | 80.563 | 12.844 | 1.00 | 36.47 A | O |
| ATOM | 350 | N | THR | A | 83 | 0.771 | 78.654 | 13.886 | 1.00 | 37.39 A | N |
| ATOM | 351 | CA | THR | A | 83 | −0.478 | 78.586 | 14.628 | 1.00 | 39.83 A | C |
| ATOM | 352 | CB | THR | A | 83 | −1.158 | 77.229 | 14.436 | 1.00 | 35.31 A | C |
| ATOM | 353 | OG1 | THR | A | 83 | −0.383 | 76.213 | 15.081 | 1.00 | 37.39 A | O |
| ATOM | 354 | CG2 | THR | A | 83 | −1.250 | 76.904 | 12.973 | 1.00 | 38.35 A | C |
| ATOM | 355 | C | THR | A | 83 | −0.201 | 78.767 | 16.090 | 1.00 | 41.33 A | C |
| ATOM | 356 | O | THR | A | 83 | −1.125 | 78.912 | 16.888 | 1.00 | 43.93 A | O |
| ATOM | 357 | N | GLY | A | 84 | 1.079 | 78.755 | 16.444 | 1.00 | 35.51 A | N |
| ATOM | 358 | CA | GLY | A | 84 | 1.465 | 78.949 | 17.822 | 1.00 | 32.99 A | C |
| ATOM | 359 | C | GLY | A | 84 | 0.877 | 77.876 | 18.721 | 1.00 | 30.57 A | C |
| ATOM | 360 | O | GLY | A | 84 | 0.932 | 77.969 | 19.943 | 1.00 | 36.11 A | O |
| ATOM | 361 | N | GLU | A | 85 | 0.362 | 76.830 | 18.101 | 1.00 | 32.47 A | N |
| ATOM | 362 | CA | GLU | A | 85 | −0.228 | 75.714 | 18.825 | 1.00 | 34.29 A | C |
| ATOM | 363 | CB | GLU | A | 85 | −1.642 | 75.444 | 18.295 | 1.00 | 30.31 A | C |
| ATOM | 364 | CG | GLU | A | 85 | −2.617 | 76.580 | 18.477 | 1.00 | 36.66 A | C |
| ATOM | 365 | CD | GLU | A | 85 | −3.097 | 76.731 | 19.913 | 1.00 | 38.33 A | C |
| ATOM | 366 | OE1 | GLU | A | 85 | −2.746 | 75.890 | 20.773 | 1.00 | 35.76 A | O |
| ATOM | 367 | OE2 | GLU | A | 85 | −3.823 | 77.709 | 20.180 | 1.00 | 37.24 A | O |
| ATOM | 368 | C | GLU | A | 85 | 0.589 | 74.445 | 18.643 | 1.00 | 33.96 A | C |
| ATOM | 369 | O | GLU | A | 85 | 1.074 | 74.168 | 17.532 | 1.00 | 35.36 A | O |
| ATOM | 370 | N | LEU | A | 86 | 0.723 | 73.673 | 19.721 | 1.00 | 31.08 A | N |
| ATOM | 371 | CA | LEU | A | 86 | 1.267 | 72.329 | 19.637 | 1.00 | 26.04 A | C |
| ATOM | 372 | CB | LEU | A | 86 | 1.671 | 71.779 | 20.998 | 1.00 | 31.02 A | C |
| ATOM | 373 | CG | LEU | A | 86 | 2.158 | 70.326 | 20.902 | 1.00 | 31.71 A | C |
| ATOM | 374 | CD1 | LEU | A | 86 | 3.230 | 70.199 | 19.829 | 1.00 | 39.17 A | C |
| ATOM | 375 | CD2 | LEU | A | 86 | 2.661 | 69.809 | 22.210 | 1.00 | 25.92 A | C |
| ATOM | 376 | C | LEU | A | 86 | 0.264 | 71.432 | 18.961 | 1.00 | 30.65 A | C |
| ATOM | 377 | O | LEU | A | 86 | −0.381 | 70.596 | 19.603 | 1.00 | 37.54 A | O |
| ATOM | 378 | N | ASP | A | 87 | 0.131 | 71.636 | 17.651 | 1.00 | 28.93 A | N |
| ATOM | 379 | CA | ASP | A | 87 | −0.803 | 70.907 | 16.814 | 1.00 | 28.52 A | C |
| ATOM | 380 | CB | ASP | A | 87 | −1.338 | 71.834 | 15.739 | 1.00 | 32.22 A | C |
| ATOM | 381 | CG | ASP | A | 87 | −0.244 | 72.433 | 14.901 | 1.00 | 37.45 A | C |

TABLE 12-continued

Coordinates for pro MMP9(35-444 ΔFnII) (SEQ ID NO: 12) complex with Example 2

| ATOM | 382 | OD1 | ASP | A | 87 | 0.840 | 71.794 | 14.831 | 1.00 | 32.18 | A | O |
|---|---|---|---|---|---|---|---|---|---|---|---|---|
| ATOM | 383 | OD2 | ASP | A | 87 | −0.483 | 73.524 | 14.311 | 1.00 | 32.30 | A | O |
| ATOM | 384 | C | ASP | A | 87 | −0.254 | 69.641 | 16.155 | 1.00 | 34.31 | A | C |
| ATOM | 385 | O | ASP | A | 87 | 0.844 | 69.177 | 16.470 | 1.00 | 35.17 | A | O |
| ATOM | 386 | N | SER | A | 88 | −1.034 | 69.093 | 15.233 | 1.00 | 28.79 | A | N |
| ATOM | 387 | CA | SER | A | 88 | −0.706 | 67.809 | 14.631 | 1.00 | 34.28 | A | C |
| ATOM | 388 | CB | SER | A | 88 | −1.924 | 67.249 | 13.879 | 1.00 | 38.31 | A | C |
| ATOM | 389 | OG | SER | A | 88 | −2.763 | 66.483 | 14.729 | 1.00 | 36.85 | A | O |
| ATOM | 390 | C | SER | A | 88 | 0.522 | 67.883 | 13.690 | 1.00 | 36.36 | A | C |
| ATOM | 391 | O | SER | A | 88 | 1.326 | 66.953 | 13.630 | 1.00 | 30.33 | A | O |
| ATOM | 392 | N | ALA | A | 89 | 0.653 | 68.985 | 12.959 | 1.00 | 30.55 | A | N |
| ATOM | 393 | CA | ALA | A | 89 | 1.768 | 69.147 | 12.029 | 1.00 | 33.00 | A | C |
| ATOM | 394 | CB | ALA | A | 89 | 1.526 | 70.337 | 11.113 | 1.00 | 27.69 | A | C |
| ATOM | 395 | C | ALA | A | 89 | 3.061 | 69.327 | 12.817 | 1.00 | 32.76 | A | C |
| ATOM | 396 | O | ALA | A | 89 | 4.093 | 68.740 | 12.498 | 1.00 | 39.05 | A | O |
| ATOM | 397 | N | THR | A | 90 | 2.966 | 70.114 | 13.879 | 1.00 | 27.95 | A | N |
| ATOM | 398 | CA | THR | A | 90 | 4.087 | 70.496 | 14.690 | 1.00 | 27.41 | A | C |
| ATOM | 399 | CB | THR | A | 90 | 3.735 | 71.689 | 15.559 | 1.00 | 27.62 | A | C |
| ATOM | 400 | OG1 | THR | A | 90 | 3.352 | 72.785 | 14.706 | 1.00 | 24.43 | A | O |
| ATOM | 401 | CG2 | THR | A | 90 | 4.913 | 72.093 | 16.404 | 1.00 | 26.71 | A | C |
| ATOM | 402 | C | THR | A | 90 | 4.650 | 69.344 | 15.501 | 1.00 | 34.37 | A | C |
| ATOM | 403 | O | THR | A | 90 | 5.861 | 69.266 | 15.724 | 1.00 | 29.75 | A | O |
| ATOM | 404 | N | LEU | A | 91 | 3.785 | 68.422 | 15.903 | 1.00 | 30.38 | A | N |
| ATOM | 405 | CA | LEU | A | 91 | 4.225 | 67.262 | 16.654 | 1.00 | 28.89 | A | C |
| ATOM | 406 | CB | LEU | A | 91 | 3.063 | 66.656 | 17.436 | 1.00 | 31.43 | A | C |
| ATOM | 407 | CG | LEU | A | 91 | 3.490 | 65.460 | 18.269 | 1.00 | 29.96 | A | C |
| ATOM | 408 | CD1 | LEU | A | 91 | 4.115 | 65.939 | 19.567 | 1.00 | 30.78 | A | C |
| ATOM | 409 | CD2 | LEU | A | 91 | 2.283 | 64.562 | 18.567 | 1.00 | 43.98 | A | C |
| ATOM | 410 | C | LEU | A | 91 | 4.775 | 66.206 | 15.713 | 1.00 | 27.77 | A | C |
| ATOM | 411 | O | LEU | A | 91 | 5.695 | 65.468 | 16.056 | 1.00 | 30.67 | A | O |
| ATOM | 412 | N | LYS | A | 92 | 4.178 | 66.105 | 14.537 | 1.00 | 25.94 | A | N |
| ATOM | 413 | CA | LYS | A | 92 | 4.706 | 65.195 | 13.540 | 1.00 | 34.75 | A | C |
| ATOM | 414 | CB | LYS | A | 92 | 3.892 | 65.329 | 12.270 | 1.00 | 32.15 | A | C |
| ATOM | 415 | CG | LYS | A | 92 | 4.251 | 64.383 | 11.159 | 1.00 | 40.74 | A | C |
| ATOM | 416 | CD | LYS | A | 92 | 3.801 | 64.951 | 9.812 | 1.00 | 46.82 | A | C |
| ATOM | 417 | CE | LYS | A | 92 | 3.619 | 63.853 | 8.773 | 1.00 | 56.66 | A | C |
| ATOM | 418 | NZ | LYS | A | 92 | 3.028 | 64.390 | 7.511 | 1.00 | 64.71 | A | N |
| ATOM | 419 | C | LYS | A | 92 | 6.192 | 65.599 | 13.337 | 1.00 | 34.15 | A | C |
| ATOM | 420 | O | LYS | A | 92 | 7.104 | 64.823 | 13.636 | 1.00 | 36.31 | A | O |
| ATOM | 421 | N | ALA | A | 93 | 6.404 | 66.835 | 12.895 | 1.00 | 29.82 | A | N |
| ATOM | 422 | CA | ALA | A | 93 | 7.727 | 67.442 | 12.787 | 1.00 | 30.52 | A | C |
| ATOM | 423 | CB | ALA | A | 93 | 7.620 | 68.956 | 12.723 | 1.00 | 32.37 | A | C |
| ATOM | 424 | C | ALA | A | 93 | 8.664 | 67.049 | 13.908 | 1.00 | 31.47 | A | C |
| ATOM | 425 | O | ALA | A | 93 | 9.730 | 66.535 | 13.652 | 1.00 | 34.91 | A | O |
| ATOM | 426 | N | MET | A | 94 | 8.260 | 67.278 | 15.152 | 1.00 | 32.27 | A | N |
| ATOM | 427 | CA | MET | A | 94 | 9.137 | 67.070 | 16.291 | 1.00 | 28.69 | A | C |
| ATOM | 428 | CB | MET | A | 94 | 8.491 | 67.585 | 17.574 | 1.00 | 31.80 | A | C |
| ATOM | 429 | CG | MET | A | 94 | 8.318 | 69.096 | 17.627 | 1.00 | 34.44 | A | C |
| ATOM | 430 | SD | MET | A | 94 | 7.363 | 69.556 | 19.088 | 1.00 | 33.84 | A | S |
| ATOM | 431 | CE | MET | A | 94 | 7.826 | 71.262 | 19.413 | 1.00 | 27.02 | A | C |
| ATOM | 432 | C | MET | A | 94 | 9.538 | 65.619 | 16.470 | 1.00 | 31.18 | A | C |
| ATOM | 433 | O | MET | A | 94 | 10.525 | 65.321 | 17.141 | 1.00 | 34.01 | A | O |
| ATOM | 434 | N | ARG | A | 95 | 8.761 | 64.721 | 15.885 | 1.00 | 27.55 | A | N |
| ATOM | 435 | CA | ARG | A | 95 | 9.067 | 63.298 | 15.969 | 1.00 | 32.87 | A | C |
| ATOM | 436 | CB | ARG | A | 95 | 7.776 | 62.465 | 15.900 | 1.00 | 40.23 | A | C |
| ATOM | 437 | CG | ARG | A | 95 | 6.920 | 62.333 | 17.183 | 1.00 | 47.14 | A | C |
| ATOM | 438 | CD | ARG | A | 95 | 5.945 | 61.138 | 17.041 | 1.00 | 43.71 | A | C |
| ATOM | 439 | NE | ARG | A | 95 | 4.902 | 61.101 | 18.066 | 1.00 | 60.66 | A | N |
| ATOM | 440 | CZ | ARG | A | 95 | 3.604 | 61.308 | 17.833 | 1.00 | 53.96 | A | C |
| ATOM | 441 | NH1 | ARG | A | 95 | 3.172 | 61.566 | 16.599 | 1.00 | 48.81 | A | N |
| ATOM | 442 | NH2 | ARG | A | 95 | 2.736 | 61.252 | 18.838 | 1.00 | 51.57 | A | N |
| ATOM | 443 | C | ARG | A | 95 | 9.944 | 62.851 | 14.796 | 1.00 | 30.91 | A | C |
| ATOM | 444 | O | ARG | A | 95 | 10.353 | 61.700 | 14.735 | 1.00 | 31.59 | A | O |
| ATOM | 445 | N | THR | A | 96 | 10.162 | 63.733 | 13.825 | 1.00 | 35.13 | A | N |
| ATOM | 446 | CA | THR | A | 96 | 10.887 | 63.341 | 12.615 | 1.00 | 35.74 | A | C |
| ATOM | 447 | CB | THR | A | 96 | 10.611 | 64.291 | 11.465 | 1.00 | 36.83 | A | C |
| ATOM | 448 | OG1 | THR | A | 96 | 9.212 | 64.264 | 11.161 | 1.00 | 36.09 | A | O |
| ATOM | 449 | CG2 | THR | A | 96 | 11.381 | 63.850 | 10.218 | 1.00 | 36.82 | A | C |
| ATOM | 450 | C | THR | A | 96 | 12.396 | 63.258 | 12.880 | 1.00 | 26.10 | A | C |
| ATOM | 451 | O | THR | A | 96 | 12.962 | 64.113 | 13.559 | 1.00 | 28.48 | A | O |
| ATOM | 452 | N | PRO | A | 97 | 13.038 | 62.186 | 12.396 | 1.00 | 32.24 | A | N |
| ATOM | 453 | CD | PRO | A | 97 | 12.419 | 60.981 | 11.820 | 1.00 | 33.02 | A | C |
| ATOM | 454 | CA | PRO | A | 97 | 14.507 | 62.066 | 12.470 | 1.00 | 26.77 | A | C |
| ATOM | 455 | CB | PRO | A | 97 | 14.786 | 60.824 | 11.636 | 1.00 | 29.53 | A | C |
| ATOM | 456 | CG | PRO | A | 97 | 13.564 | 59.989 | 11.828 | 1.00 | 35.14 | A | C |
| ATOM | 457 | C | PRO | A | 97 | 15.186 | 63.293 | 11.854 | 1.00 | 24.73 | A | C |
| ATOM | 458 | O | PRO | A | 97 | 14.630 | 63.871 | 10.927 | 1.00 | 27.34 | A | O |

TABLE 12-continued

Coordinates for pro MMP9(35-444 ΔFnII) (SEQ ID NO: 12) complex with Example 2

| ATOM | 459 | N | ARG | A | 98 | 16.347 | 63.701 | 12.365 | 1.00 | 30.20 | A | N |
|------|-----|------|------|---|-----|--------|--------|--------|------|-------|---|---|
| ATOM | 460 | CA | ARG | A | 98 | 16.959 | 64.928 | 11.865 | 1.00 | 25.00 | A | C |
| ATOM | 461 | CB | ARG | A | 98 | 16.109 | 66.137 | 12.252 | 1.00 | 27.45 | A | C |
| ATOM | 462 | CG | ARG | A | 98 | 16.117 | 66.422 | 13.778 | 1.00 | 25.11 | A | C |
| ATOM | 463 | CD | ARG | A | 98 | 15.671 | 67.865 | 14.047 | 1.00 | 32.74 | A | C |
| ATOM | 464 | NE | ARG | A | 98 | 16.776 | 68.825 | 14.005 | 1.00 | 26.80 | A | N |
| ATOM | 465 | CZ | ARG | A | 98 | 16.637 | 70.144 | 13.849 | 1.00 | 28.52 | A | C |
| ATOM | 466 | NH1 | ARG | A | 98 | 15.446 | 70.689 | 13.695 | 1.00 | 21.59 | A | N |
| ATOM | 467 | NH2 | ARG | A | 98 | 17.706 | 70.928 | 13.831 | 1.00 | 31.24 | A | N |
| ATOM | 468 | C | ARG | A | 98 | 18.371 | 65.175 | 12.359 | 1.00 | 25.55 | A | C |
| ATOM | 469 | O | ARG | A | 98 | 18.914 | 64.438 | 13.175 | 1.00 | 26.91 | A | O |
| ATOM | 470 | N | CYS | A | 99 | 18.934 | 66.268 | 11.864 | 1.00 | 27.95 | A | N |
| ATOM | 471 | CA | CYS | A | 99 | 20.286 | 66.678 | 12.162 | 1.00 | 23.49 | A | C |
| ATOM | 472 | CB | CYS | A | 99 | 20.730 | 67.683 | 11.094 | 1.00 | 28.07 | A | C |
| ATOM | 473 | SG | CYS | A | 99 | 22.327 | 68.447 | 11.402 | 1.00 | 25.26 | A | S |
| ATOM | 474 | C | CYS | A | 99 | 20.401 | 67.317 | 13.530 | 1.00 | 28.48 | A | C |
| ATOM | 475 | O | CYS | A | 99 | 19.598 | 68.169 | 13.879 | 1.00 | 26.25 | A | O |
| ATOM | 476 | N | GLY | A | 100 | 21.448 | 66.958 | 14.270 | 1.00 | 20.70 | A | N |
| ATOM | 477 | CA | GLY | A | 100 | 21.630 | 67.456 | 15.618 | 1.00 | 25.18 | A | C |
| ATOM | 478 | C | GLY | A | 100 | 22.034 | 68.905 | 15.760 | 1.00 | 25.21 | A | C |
| ATOM | 479 | O | GLY | A | 100 | 22.166 | 69.427 | 16.887 | 1.00 | 21.18 | A | O |
| ATOM | 480 | N | VAL | A | 101 | 22.271 | 69.573 | 14.637 | 1.00 | 25.63 | A | N |
| ATOM | 481 | CA | VAL | A | 101 | 22.720 | 70.960 | 14.739 | 1.00 | 29.99 | A | C |
| ATOM | 482 | CB | VAL | A | 101 | 23.422 | 71.468 | 13.442 | 1.00 | 27.85 | A | C |
| ATOM | 483 | CG1 | VAL | A | 101 | 23.647 | 73.004 | 13.520 | 1.00 | 29.85 | A | C |
| ATOM | 484 | CG2 | VAL | A | 101 | 24.747 | 70.744 | 13.213 | 1.00 | 21.36 | A | C |
| ATOM | 485 | C | VAL | A | 101 | 21.521 | 71.856 | 15.026 | 1.00 | 27.56 | A | C |
| ATOM | 486 | O | VAL | A | 101 | 20.471 | 71.664 | 14.441 | 1.00 | 27.84 | A | O |
| ATOM | 487 | N | PRO | A | 102 | 21.702 | 72.869 | 15.891 | 1.00 | 27.71 | A | N |
| ATOM | 488 | CD | PRO | A | 102 | 22.795 | 72.845 | 16.868 | 1.00 | 28.78 | A | C |
| ATOM | 489 | CA | PRO | A | 102 | 20.726 | 73.910 | 16.220 | 1.00 | 26.25 | A | C |
| ATOM | 490 | CB | PRO | A | 102 | 21.476 | 74.774 | 17.226 | 1.00 | 31.38 | A | C |
| ATOM | 491 | CG | PRO | A | 102 | 22.335 | 73.819 | 17.919 | 1.00 | 34.27 | A | C |
| ATOM | 492 | C | PRO | A | 102 | 20.221 | 74.764 | 15.075 | 1.00 | 35.16 | A | C |
| ATOM | 493 | O | PRO | A | 102 | 21.011 | 75.264 | 14.280 | 1.00 | 35.13 | A | O |
| ATOM | 494 | N | ASP | A | 103 | 18.897 | 74.947 | 15.025 | 1.00 | 31.26 | A | N |
| ATOM | 495 | CA | ASP | A | 103 | 18.251 | 75.791 | 14.036 | 1.00 | 31.08 | A | C |
| ATOM | 496 | CB | ASP | A | 103 | 16.752 | 75.465 | 13.951 | 1.00 | 26.77 | A | C |
| ATOM | 497 | CG | ASP | A | 103 | 16.517 | 74.046 | 13.650 | 1.00 | 31.77 | A | C |
| ATOM | 498 | OD1 | ASP | A | 103 | 17.475 | 73.380 | 13.186 | 1.00 | 30.48 | A | O |
| ATOM | 499 | OD2 | ASP | A | 103 | 15.385 | 73.583 | 13.857 | 1.00 | 29.34 | A | O |
| ATOM | 500 | C | ASP | A | 103 | 18.424 | 77.279 | 14.324 | 1.00 | 28.28 | A | C |
| ATOM | 501 | O | ASP | A | 103 | 18.409 | 78.076 | 13.400 | 1.00 | 29.08 | A | O |
| ATOM | 502 | N | LEU | A | 104 | 18.545 | 77.643 | 15.601 | 1.00 | 32.53 | A | N |
| ATOM | 503 | CA | LEU | A | 104 | 18.744 | 79.036 | 15.994 | 1.00 | 35.19 | A | C |
| ATOM | 504 | CB | LEU | A | 104 | 17.458 | 79.671 | 16.550 | 1.00 | 34.65 | A | C |
| ATOM | 505 | CG | LEU | A | 104 | 16.154 | 79.698 | 15.737 | 1.00 | 37.22 | A | C |
| ATOM | 506 | CD1 | LEU | A | 104 | 15.107 | 80.581 | 16.451 | 1.00 | 33.05 | A | C |
| ATOM | 507 | CD2 | LEU | A | 104 | 16.323 | 80.179 | 14.304 | 1.00 | 33.29 | A | C |
| ATOM | 508 | C | LEU | A | 104 | 19.859 | 79.141 | 17.022 | 1.00 | 33.55 | A | C |
| ATOM | 509 | O | LEU | A | 104 | 19.935 | 78.347 | 17.955 | 1.00 | 37.79 | A | O |
| ATOM | 510 | N | GLY | A | 105 | 20.741 | 80.118 | 16.847 | 1.00 | 35.96 | A | N |
| ATOM | 511 | CA | GLY | A | 105 | 21.908 | 80.191 | 17.701 | 1.00 | 43.35 | A | C |
| ATOM | 512 | C | GLY | A | 105 | 22.852 | 79.052 | 17.357 | 1.00 | 40.89 | A | C |
| ATOM | 513 | O | GLY | A | 105 | 22.741 | 78.436 | 16.288 | 1.00 | 37.69 | A | O |
| ATOM | 514 | N | ARG | A | 106 | 23.749 | 78.732 | 18.279 | 1.00 | 44.31 | A | N |
| ATOM | 515 | CA | ARG | A | 106 | 24.917 | 77.939 | 17.937 | 1.00 | 46.80 | A | C |
| ATOM | 516 | CB | ARG | A | 106 | 26.125 | 78.876 | 17.927 | 1.00 | 52.01 | A | C |
| ATOM | 517 | CG | ARG | A | 106 | 27.269 | 78.438 | 17.054 | 1.00 | 51.48 | A | C |
| ATOM | 518 | CD | ARG | A | 106 | 27.087 | 78.888 | 15.605 | 1.00 | 55.60 | A | C |
| ATOM | 519 | NE | ARG | A | 106 | 27.004 | 80.340 | 15.470 | 1.00 | 49.14 | A | N |
| ATOM | 520 | CZ | ARG | A | 106 | 26.764 | 80.958 | 14.320 | 1.00 | 55.22 | A | C |
| ATOM | 521 | NH1 | ARG | A | 106 | 26.599 | 80.243 | 13.209 | 1.00 | 48.94 | A | N |
| ATOM | 522 | NH2 | ARG | A | 106 | 26.691 | 82.287 | 14.280 | 1.00 | 55.01 | A | N |
| ATOM | 523 | C | ARG | A | 106 | 25.170 | 76.824 | 18.941 | 1.00 | 46.89 | A | C |
| ATOM | 524 | O | ARG | A | 106 | 24.764 | 76.930 | 20.095 | 1.00 | 46.93 | A | O |
| ATOM | 525 | N | PHE | A | 107 | 25.836 | 75.754 | 18.509 | 1.00 | 38.00 | A | N |
| ATOM | 526 | CA | PHE | A | 107 | 26.393 | 74.794 | 19.463 | 1.00 | 42.73 | A | C |
| ATOM | 527 | CB | PHE | A | 107 | 27.459 | 73.924 | 18.796 | 1.00 | 42.91 | A | C |
| ATOM | 528 | CG | PHE | A | 107 | 26.929 | 72.691 | 18.118 | 1.00 | 41.68 | A | C |
| ATOM | 529 | CD1 | PHE | A | 107 | 26.050 | 71.838 | 18.767 | 1.00 | 48.54 | A | C |
| ATOM | 530 | CD2 | PHE | A | 107 | 27.362 | 72.352 | 16.852 | 1.00 | 36.91 | A | C |
| ATOM | 531 | CE1 | PHE | A | 107 | 25.584 | 70.671 | 18.136 | 1.00 | 43.24 | A | C |
| ATOM | 532 | CE2 | PHE | A | 107 | 26.917 | 71.207 | 16.222 | 1.00 | 35.72 | A | C |
| ATOM | 533 | CZ | PHE | A | 107 | 26.023 | 70.360 | 16.866 | 1.00 | 41.92 | A | C |
| ATOM | 534 | C | PHE | A | 107 | 27.059 | 75.526 | 20.635 | 1.00 | 43.91 | A | C |
| ATOM | 535 | O | PHE | A | 107 | 26.775 | 75.261 | 21.809 | 1.00 | 44.08 | A | O |

TABLE 12-continued

Coordinates for pro MMP9(35-444 ΔFnII) (SEQ ID NO: 12) complex with Example 2

| ATOM | 536 | N | GLN | A | 108 | 27.960 | 76.446 | 20.307 | 1.00 | 44.68 | A | N |
|---|---|---|---|---|---|---|---|---|---|---|---|---|
| ATOM | 537 | CA | GLN | A | 108 | 28.763 | 77.137 | 21.316 | 1.00 | 43.81 | A | C |
| ATOM | 538 | CB | GLN | A | 108 | 29.946 | 76.266 | 21.704 | 1.00 | 41.88 | A | C |
| ATOM | 539 | CG | GLN | A | 108 | 30.818 | 75.953 | 20.521 | 1.00 | 41.69 | A | C |
| ATOM | 540 | CD | GLN | A | 108 | 31.846 | 74.903 | 20.825 | 1.00 | 46.11 | A | C |
| ATOM | 541 | OE1 | GLN | A | 108 | 31.511 | 73.769 | 21.175 | 1.00 | 49.23 | A | O |
| ATOM | 542 | NE2 | GLN | A | 108 | 33.114 | 75.268 | 20.693 | 1.00 | 44.02 | A | N |
| ATOM | 543 | C | GLN | A | 108 | 29.310 | 78.419 | 20.737 | 1.00 | 42.16 | A | C |
| ATOM | 544 | O | GLN | A | 108 | 28.969 | 78.792 | 19.610 | 1.00 | 42.43 | A | O |
| ATOM | 545 | N | THR | A | 109 | 30.162 | 79.097 | 21.503 | 1.00 | 40.78 | A | N |
| ATOM | 546 | CA | THR | A | 109 | 30.969 | 80.154 | 20.920 | 1.00 | 39.66 | A | C |
| ATOM | 547 | CB | THR | A | 109 | 31.512 | 81.125 | 21.963 | 1.00 | 43.06 | A | C |
| ATOM | 548 | OG1 | THR | A | 109 | 30.578 | 82.202 | 22.134 | 1.00 | 37.58 | A | O |
| ATOM | 549 | CG2 | THR | A | 109 | 32.843 | 81.699 | 21.483 | 1.00 | 44.17 | A | C |
| ATOM | 550 | C | THR | A | 109 | 32.116 | 79.521 | 20.132 | 1.00 | 42.69 | A | C |
| ATOM | 551 | O | THR | A | 109 | 32.802 | 78.624 | 20.630 | 1.00 | 37.60 | A | O |
| ATOM | 552 | N | PHE | A | 110 | 32.295 | 79.977 | 18.895 | 1.00 | 43.05 | A | N |
| ATOM | 553 | CA | PHE | A | 110 | 33.260 | 79.384 | 17.974 | 1.00 | 34.07 | A | C |
| ATOM | 554 | CB | PHE | A | 110 | 32.572 | 78.902 | 16.706 | 1.00 | 29.70 | A | C |
| ATOM | 555 | CG | PHE | A | 110 | 31.830 | 77.613 | 16.875 | 1.00 | 41.66 | A | C |
| ATOM | 556 | CD1 | PHE | A | 110 | 30.448 | 77.572 | 16.785 | 1.00 | 36.10 | A | C |
| ATOM | 557 | CD2 | PHE | A | 110 | 32.515 | 76.441 | 17.134 | 1.00 | 36.95 | A | C |
| ATOM | 558 | CE1 | PHE | A | 110 | 29.780 | 76.391 | 16.927 | 1.00 | 36.92 | A | C |
| ATOM | 559 | CE2 | PHE | A | 110 | 31.839 | 75.245 | 17.278 | 1.00 | 38.60 | A | C |
| ATOM | 560 | CZ | PHE | A | 110 | 30.474 | 75.226 | 17.179 | 1.00 | 38.96 | A | C |
| ATOM | 561 | C | PHE | A | 110 | 34.337 | 80.380 | 17.589 | 1.00 | 43.28 | A | C |
| ATOM | 562 | O | PHE | A | 110 | 34.148 | 81.594 | 17.698 | 1.00 | 42.92 | A | O |
| ATOM | 563 | N | GLU | A | 111 | 35.469 | 79.855 | 17.130 | 1.00 | 43.23 | A | N |
| ATOM | 564 | CA | GLU | A | 111 | 36.589 | 80.697 | 16.754 | 1.00 | 43.68 | A | C |
| ATOM | 565 | CB | GLU | A | 111 | 37.898 | 79.980 | 17.025 | 1.00 | 44.45 | A | C |
| ATOM | 566 | CG | GLU | A | 111 | 38.465 | 80.266 | 18.382 | 1.00 | 54.53 | A | C |
| ATOM | 567 | CD | GLU | A | 111 | 39.950 | 79.991 | 18.435 | 1.00 | 63.27 | A | C |
| ATOM | 568 | OE1 | GLU | A | 111 | 40.531 | 79.614 | 17.384 | 1.00 | 57.56 | A | O |
| ATOM | 569 | OE2 | GLU | A | 111 | 40.536 | 80.159 | 19.526 | 1.00 | 70.29 | A | O |
| ATOM | 570 | C | GLU | A | 111 | 36.540 | 81.137 | 15.302 | 1.00 | 40.37 | A | C |
| ATOM | 571 | O | GLU | A | 111 | 36.296 | 80.331 | 14.392 | 1.00 | 38.14 | A | O |
| ATOM | 572 | N | GLY | A | 112 | 36.774 | 82.427 | 15.091 | 1.00 | 39.63 | A | N |
| ATOM | 573 | CA | GLY | A | 112 | 36.947 | 82.950 | 13.752 | 1.00 | 39.53 | A | C |
| ATOM | 574 | C | GLY | A | 112 | 35.713 | 83.285 | 12.945 | 1.00 | 41.53 | A | C |
| ATOM | 575 | O | GLY | A | 112 | 34.663 | 83.644 | 13.472 | 1.00 | 46.71 | A | O |
| ATOM | 576 | N | ASP | A | 113 | 35.878 | 83.127 | 11.638 | 1.00 | 40.89 | A | N |
| ATOM | 577 | CA | ASP | A | 113 | 34.987 | 83.594 | 10.592 | 1.00 | 45.20 | A | C |
| ATOM | 578 | CB | ASP | A | 113 | 35.818 | 83.731 | 9.313 | 1.00 | 44.17 | A | C |
| ATOM | 579 | CG | ASP | A | 113 | 35.491 | 84.961 | 8.551 | 1.00 | 51.40 | A | C |
| ATOM | 580 | OD1 | ASP | A | 113 | 35.099 | 85.950 | 9.202 | 1.00 | 57.77 | A | O |
| ATOM | 581 | OD2 | ASP | A | 113 | 35.629 | 84.946 | 7.313 | 1.00 | 49.39 | A | O |
| ATOM | 582 | C | ASP | A | 113 | 33.836 | 82.627 | 10.279 | 1.00 | 43.98 | A | C |
| ATOM | 583 | O | ASP | A | 113 | 32.791 | 83.045 | 9.786 | 1.00 | 39.87 | A | O |
| ATOM | 584 | N | LEU | A | 114 | 34.070 | 81.338 | 10.516 | 1.00 | 38.94 | A | N |
| ATOM | 585 | CA | LEU | A | 114 | 33.129 | 80.280 | 10.151 | 1.00 | 39.63 | A | C |
| ATOM | 586 | CB | LEU | A | 114 | 31.706 | 80.585 | 10.611 | 1.00 | 36.54 | A | C |
| ATOM | 587 | CG | LEU | A | 114 | 31.557 | 80.974 | 12.077 | 1.00 | 35.18 | A | C |
| ATOM | 588 | CD1 | LEU | A | 114 | 30.085 | 80.957 | 12.402 | 1.00 | 44.40 | A | C |
| ATOM | 589 | CD2 | LEU | A | 114 | 32.330 | 80.038 | 13.005 | 1.00 | 37.15 | A | C |
| ATOM | 590 | C | LEU | A | 114 | 33.155 | 80.071 | 8.663 | 1.00 | 38.62 | A | C |
| ATOM | 591 | O | LEU | A | 114 | 32.226 | 79.510 | 8.084 | 1.00 | 35.10 | A | O |
| ATOM | 592 | N | LYS | A | 115 | 34.255 | 80.518 | 8.061 | 1.00 | 40.38 | A | N |
| ATOM | 593 | CA | LYS | A | 115 | 34.535 | 80.374 | 6.634 | 1.00 | 41.06 | A | C |
| ATOM | 594 | CB | LYS | A | 115 | 34.592 | 81.773 | 6.019 | 1.00 | 43.32 | A | C |
| ATOM | 595 | CG | LYS | A | 115 | 34.270 | 81.858 | 4.557 | 1.00 | 42.22 | A | C |
| ATOM | 596 | CD | LYS | A | 115 | 34.565 | 83.250 | 4.022 | 1.00 | 46.15 | A | C |
| ATOM | 597 | CE | LYS | A | 115 | 33.946 | 84.322 | 4.910 | 1.00 | 50.64 | A | C |
| ATOM | 598 | NZ | LYS | A | 115 | 34.188 | 85.701 | 4.389 | 1.00 | 57.92 | A | N |
| ATOM | 599 | C | LYS | A | 115 | 35.920 | 79.717 | 6.513 | 1.00 | 36.01 | A | C |
| ATOM | 600 | O | LYS | A | 115 | 36.787 | 79.986 | 7.335 | 1.00 | 34.55 | A | O |
| ATOM | 601 | N | TRP | A | 116 | 36.134 | 78.842 | 5.534 | 1.00 | 32.72 | A | N |
| ATOM | 602 | CA | TRP | A | 116 | 37.505 | 78.376 | 5.307 | 1.00 | 39.30 | A | C |
| ATOM | 603 | CB | TRP | A | 116 | 37.586 | 77.105 | 4.468 | 1.00 | 35.24 | A | C |
| ATOM | 604 | CG | TRP | A | 116 | 37.099 | 75.883 | 5.157 | 1.00 | 34.99 | A | C |
| ATOM | 605 | CD2 | TRP | A | 116 | 37.642 | 75.271 | 6.330 | 1.00 | 31.07 | A | C |
| ATOM | 606 | CE2 | TRP | A | 116 | 36.859 | 74.139 | 6.604 | 1.00 | 27.78 | A | C |
| ATOM | 607 | CE3 | TRP | A | 116 | 38.700 | 75.572 | 7.174 | 1.00 | 33.71 | A | C |
| ATOM | 608 | CD1 | TRP | A | 116 | 36.058 | 75.113 | 4.776 | 1.00 | 29.26 | A | C |
| ATOM | 609 | NE1 | TRP | A | 116 | 35.915 | 74.057 | 5.628 | 1.00 | 27.19 | A | N |
| ATOM | 610 | CZ2 | TRP | A | 116 | 37.101 | 73.303 | 7.675 | 1.00 | 29.81 | A | C |
| ATOM | 611 | CZ3 | TRP | A | 116 | 38.939 | 74.744 | 8.254 | 1.00 | 38.41 | A | C |
| ATOM | 612 | CH2 | TRP | A | 116 | 38.137 | 73.628 | 8.501 | 1.00 | 36.13 | A | C |

TABLE 12-continued

Coordinates for pro MMP9(35-444 ΔFnII) (SEQ ID NO: 12) complex with Example 2

| ATOM | 613 | C | TRP | A | 116 | 38.279 | 79.480 | 4.620 | 1.00 | 39.17 | A | C |
|------|-----|-----|-----|---|-----|--------|--------|-------|------|-------|---|---|
| ATOM | 614 | O | TRP | A | 116 | 37.698 | 80.306 | 3.915 | 1.00 | 44.17 | A | O |
| ATOM | 615 | N | HIS | A | 117 | 39.591 | 79.503 | 4.823 | 1.00 | 42.50 | A | N |
| ATOM | 616 | CA | HIS | A | 117 | 40.399 | 80.531 | 4.192 | 1.00 | 40.42 | A | C |
| ATOM | 617 | CB | HIS | A | 117 | 40.818 | 81.586 | 5.211 | 1.00 | 42.18 | A | C |
| ATOM | 618 | CG | HIS | A | 117 | 39.740 | 82.573 | 5.523 | 1.00 | 45.02 | A | C |
| ATOM | 619 | CD2 | HIS | A | 117 | 39.153 | 83.522 | 4.755 | 1.00 | 47.90 | A | C |
| ATOM | 620 | ND1 | HIS | A | 117 | 39.113 | 82.631 | 6.751 | 1.00 | 51.58 | A | N |
| ATOM | 621 | CE1 | HIS | A | 117 | 38.205 | 83.590 | 6.735 | 1.00 | 48.59 | A | C |
| ATOM | 622 | NE2 | HIS | A | 117 | 38.206 | 84.144 | 5.534 | 1.00 | 53.43 | A | N |
| ATOM | 623 | C | HIS | A | 117 | 41.579 | 79.933 | 3.448 | 1.00 | 40.46 | A | C |
| ATOM | 624 | O | HIS | A | 117 | 42.644 | 80.535 | 3.351 | 1.00 | 35.38 | A | O |
| ATOM | 625 | N | HIS | A | 118 | 41.362 | 78.724 | 2.945 | 1.00 | 38.35 | A | N |
| ATOM | 626 | CA | HIS | A | 118 | 42.234 | 78.102 | 1.964 | 1.00 | 38.52 | A | C |
| ATOM | 627 | CB | HIS | A | 118 | 43.338 | 77.262 | 2.615 | 1.00 | 36.85 | A | C |
| ATOM | 628 | CG | HIS | A | 118 | 42.843 | 76.138 | 3.478 | 1.00 | 38.63 | A | C |
| ATOM | 629 | CD2 | HIS | A | 118 | 42.636 | 74.828 | 3.199 | 1.00 | 36.76 | A | C |
| ATOM | 630 | ND1 | HIS | A | 118 | 42.556 | 76.297 | 4.819 | 1.00 | 35.53 | A | N |
| ATOM | 631 | CE1 | HIS | A | 118 | 42.185 | 75.131 | 5.327 | 1.00 | 36.89 | A | C |
| ATOM | 632 | NE2 | HIS | A | 118 | 42.223 | 74.225 | 4.365 | 1.00 | 32.95 | A | N |
| ATOM | 633 | C | HIS | A | 118 | 41.375 | 77.263 | 1.055 | 1.00 | 41.51 | A | C |
| ATOM | 634 | O | HIS | A | 118 | 40.261 | 76.870 | 1.420 | 1.00 | 38.65 | A | O |
| ATOM | 635 | N | HIS | A | 119 | 41.890 | 76.995 | −0.129 | 1.00 | 32.72 | A | N |
| ATOM | 636 | CA | HIS | A | 119 | 41.090 | 76.430 | −1.178 | 1.00 | 37.57 | A | C |
| ATOM | 637 | CB | HIS | A | 119 | 41.643 | 76.877 | −2.531 | 1.00 | 44.33 | A | C |
| ATOM | 638 | CG | HIS | A | 119 | 41.185 | 76.034 | −3.677 | 1.00 | 47.43 | A | C |
| ATOM | 639 | CD2 | HIS | A | 119 | 41.548 | 74.789 | −4.070 | 1.00 | 49.60 | A | C |
| ATOM | 640 | ND1 | HIS | A | 119 | 40.209 | 76.446 | −4.560 | 1.00 | 48.63 | A | N |
| ATOM | 641 | CE1 | HIS | A | 119 | 39.997 | 75.496 | −5.454 | 1.00 | 42.14 | A | C |
| ATOM | 642 | NE2 | HIS | A | 119 | 40.791 | 74.477 | −5.176 | 1.00 | 49.26 | A | N |
| ATOM | 643 | C | HIS | A | 119 | 41.046 | 74.913 | −1.096 | 1.00 | 36.29 | A | C |
| ATOM | 644 | O | HIS | A | 119 | 40.122 | 74.289 | −1.603 | 1.00 | 41.61 | A | O |
| ATOM | 645 | N | ASN | A | 120 | 42.043 | 74.293 | −0.486 | 1.00 | 37.40 | A | N |
| ATOM | 646 | CA | ASN | A | 120 | 42.062 | 72.838 | −0.543 | 1.00 | 36.57 | A | C |
| ATOM | 647 | CB | ASN | A | 120 | 43.369 | 72.284 | −1.098 | 1.00 | 36.51 | A | C |
| ATOM | 648 | CG | ASN | A | 120 | 43.344 | 70.779 | −1.185 | 1.00 | 42.43 | A | C |
| ATOM | 649 | OD1 | ASN | A | 120 | 42.299 | 70.160 | −0.954 | 1.00 | 38.80 | A | O |
| ATOM | 650 | ND2 | ASN | A | 120 | 44.488 | 70.171 | −1.500 | 1.00 | 40.90 | A | N |
| ATOM | 651 | C | ASN | A | 120 | 41.761 | 72.217 | 0.791 | 1.00 | 33.50 | A | C |
| ATOM | 652 | O | ASN | A | 120 | 42.576 | 72.251 | 1.712 | 1.00 | 34.03 | A | O |
| ATOM | 653 | N | ILE | A | 121 | 40.568 | 71.642 | 0.895 | 1.00 | 35.59 | A | N |
| ATOM | 654 | CA | ILE | A | 121 | 40.101 | 71.162 | 2.184 | 1.00 | 32.53 | A | C |
| ATOM | 655 | CB | ILE | A | 121 | 38.567 | 71.419 | 2.371 | 1.00 | 29.15 | A | C |
| ATOM | 656 | CG2 | ILE | A | 121 | 38.169 | 71.248 | 3.824 | 1.00 | 29.28 | A | C |
| ATOM | 657 | CG1 | ILE | A | 121 | 38.209 | 72.832 | 1.898 | 1.00 | 26.11 | A | C |
| ATOM | 658 | CD1 | ILE | A | 121 | 38.869 | 73.938 | 2.685 | 1.00 | 30.14 | A | C |
| ATOM | 659 | C | ILE | A | 121 | 40.478 | 69.701 | 2.305 | 1.00 | 24.26 | A | C |
| ATOM | 660 | O | ILE | A | 121 | 40.269 | 68.910 | 1.393 | 1.00 | 33.22 | A | O |
| ATOM | 661 | N | THR | A | 122 | 41.063 | 69.335 | 3.421 | 1.00 | 26.54 | A | N |
| ATOM | 662 | CA | THR | A | 122 | 41.529 | 67.971 | 3.555 | 1.00 | 30.49 | A | C |
| ATOM | 663 | CB | THR | A | 122 | 42.938 | 67.947 | 4.120 | 1.00 | 28.73 | A | C |
| ATOM | 664 | OG1 | THR | A | 122 | 42.957 | 68.701 | 5.334 | 1.00 | 28.29 | A | O |
| ATOM | 665 | CG2 | THR | A | 122 | 43.925 | 68.591 | 3.115 | 1.00 | 27.70 | A | C |
| ATOM | 666 | C | THR | A | 122 | 40.619 | 67.286 | 4.549 | 1.00 | 30.80 | A | C |
| ATOM | 667 | O | THR | A | 122 | 40.196 | 67.906 | 5.516 | 1.00 | 31.77 | A | O |
| ATOM | 668 | N | TYR | A | 123 | 40.350 | 66.010 | 4.332 | 1.00 | 27.41 | A | N |
| ATOM | 669 | CA | TYR | A | 123 | 39.517 | 65.289 | 5.270 | 1.00 | 35.48 | A | C |
| ATOM | 670 | CB | TYR | A | 123 | 38.094 | 65.147 | 4.718 | 1.00 | 22.88 | A | C |
| ATOM | 671 | CG | TYR | A | 123 | 37.921 | 64.201 | 3.548 | 1.00 | 26.64 | A | C |
| ATOM | 672 | CD1 | TYR | A | 123 | 38.073 | 64.648 | 2.251 | 1.00 | 24.67 | A | C |
| ATOM | 673 | CE1 | TYR | A | 123 | 37.886 | 63.797 | 1.180 | 1.00 | 28.01 | A | C |
| ATOM | 674 | CD2 | TYR | A | 123 | 37.576 | 62.865 | 3.747 | 1.00 | 25.90 | A | C |
| ATOM | 675 | CE2 | TYR | A | 123 | 37.372 | 62.012 | 2.690 | 1.00 | 24.39 | A | C |
| ATOM | 676 | CZ | TYR | A | 123 | 37.531 | 62.483 | 1.404 | 1.00 | 26.57 | A | C |
| ATOM | 677 | OH | TYR | A | 123 | 37.339 | 61.643 | 0.335 | 1.00 | 31.98 | A | O |
| ATOM | 678 | C | TYR | A | 123 | 40.076 | 63.932 | 5.641 | 1.00 | 33.76 | A | C |
| ATOM | 679 | O | TYR | A | 123 | 40.627 | 63.224 | 4.792 | 1.00 | 30.17 | A | O |
| ATOM | 680 | N | TRP | A | 124 | 39.913 | 63.582 | 6.917 | 1.00 | 29.77 | A | N |
| ATOM | 681 | CA | TRP | A | 124 | 40.322 | 62.287 | 7.420 | 1.00 | 30.90 | A | C |
| ATOM | 682 | CB | TRP | A | 124 | 41.338 | 62.484 | 8.536 | 1.00 | 33.31 | A | C |
| ATOM | 683 | CG | TRP | A | 124 | 41.802 | 61.213 | 9.098 | 1.00 | 32.64 | A | C |
| ATOM | 684 | CD2 | TRP | A | 124 | 42.165 | 60.971 | 10.452 | 1.00 | 33.00 | A | C |
| ATOM | 685 | CE2 | TRP | A | 124 | 42.546 | 59.630 | 10.548 | 1.00 | 30.03 | A | C |
| ATOM | 686 | CE3 | TRP | A | 124 | 42.196 | 61.767 | 11.604 | 1.00 | 38.82 | A | C |
| ATOM | 687 | CD1 | TRP | A | 124 | 41.982 | 60.046 | 8.433 | 1.00 | 35.71 | A | C |
| ATOM | 688 | NE1 | TRP | A | 124 | 42.431 | 59.079 | 9.300 | 1.00 | 35.41 | A | N |
| ATOM | 689 | CZ2 | TRP | A | 124 | 42.955 | 59.060 | 11.740 | 1.00 | 37.70 | A | C |

TABLE 12-continued

Coordinates for pro MMP9(35-444 ΔFnII) (SEQ ID NO: 12) complex with Example 2

| ATOM | 690 | CZ3 | TRP | A | 124 | 42.601 | 61.207 | 12.786 | 1.00 | 41.30 | A | C |
|------|-----|-----|-----|---|-----|--------|--------|--------|------|-------|---|---|
| ATOM | 691 | CH2 | TRP | A | 124 | 42.983 | 59.866 | 12.849 | 1.00 | 36.32 | A | C |
| ATOM | 692 | C | TRP | A | 124 | 39.161 | 61.423 | 7.939 | 1.00 | 34.90 | A | C |
| ATOM | 693 | O | TRP | A | 124 | 38.497 | 61.785 | 8.909 | 1.00 | 34.00 | A | O |
| ATOM | 694 | N | ILE | A | 125 | 38.942 | 60.280 | 7.291 | 1.00 | 37.00 | A | N |
| ATOM | 695 | CA | ILE | A | 125 | 37.977 | 59.291 | 7.741 | 1.00 | 31.41 | A | C |
| ATOM | 696 | CB | ILE | A | 125 | 37.657 | 58.299 | 6.646 | 1.00 | 34.68 | A | C |
| ATOM | 697 | CG2 | ILE | A | 125 | 36.643 | 57.275 | 7.138 | 1.00 | 36.59 | A | C |
| ATOM | 698 | CG1 | ILE | A | 125 | 37.145 | 59.020 | 5.401 | 1.00 | 29.29 | A | C |
| ATOM | 699 | CD1 | ILE | A | 125 | 36.882 | 58.081 | 4.247 | 1.00 | 34.65 | A | C |
| ATOM | 700 | C | ILE | A | 125 | 38.572 | 58.504 | 8.887 | 1.00 | 36.09 | A | C |
| ATOM | 701 | O | ILE | A | 125 | 39.229 | 57.476 | 8.672 | 1.00 | 34.90 | A | O |
| ATOM | 702 | N | GLN | A | 126 | 38.301 | 58.977 | 10.100 | 1.00 | 34.47 | A | N |
| ATOM | 703 | CA | GLN | A | 126 | 38.937 | 58.502 | 11.322 | 1.00 | 32.52 | A | C |
| ATOM | 704 | CB | GLN | A | 126 | 38.693 | 59.505 | 12.442 | 1.00 | 29.79 | A | C |
| ATOM | 705 | CG | GLN | A | 126 | 39.092 | 58.998 | 13.797 | 1.00 | 36.48 | A | C |
| ATOM | 706 | CD | GLN | A | 126 | 39.092 | 60.098 | 14.840 | 1.00 | 46.68 | A | C |
| ATOM | 707 | OE1 | GLN | A | 126 | 38.041 | 60.625 | 15.202 | 1.00 | 47.95 | A | O |
| ATOM | 708 | NE2 | GLN | A | 126 | 40.278 | 60.450 | 15.335 | 1.00 | 46.62 | A | N |
| ATOM | 709 | C | GLN | A | 126 | 38.527 | 57.088 | 11.767 | 1.00 | 38.02 | A | C |
| ATOM | 710 | O | GLN | A | 126 | 39.320 | 56.374 | 12.384 | 1.00 | 38.26 | A | O |
| ATOM | 711 | N | ASN | A | 127 | 37.304 | 56.671 | 11.452 | 1.00 | 31.21 | A | N |
| ATOM | 712 | CA | ASN | A | 127 | 36.851 | 55.338 | 11.823 | 1.00 | 33.38 | A | C |
| ATOM | 713 | CB | ASN | A | 127 | 36.541 | 55.265 | 13.322 | 1.00 | 36.21 | A | C |
| ATOM | 714 | CG | ASN | A | 127 | 35.288 | 56.048 | 13.704 | 1.00 | 35.75 | A | C |
| ATOM | 715 | OD1 | ASN | A | 127 | 34.454 | 56.351 | 12.860 | 1.00 | 35.10 | A | O |
| ATOM | 716 | ND2 | ASN | A | 127 | 35.164 | 56.374 | 14.973 | 1.00 | 36.01 | A | N |
| ATOM | 717 | C | ASN | A | 127 | 35.646 | 54.924 | 10.991 | 1.00 | 36.66 | A | C |
| ATOM | 718 | O | ASN | A | 127 | 35.153 | 55.706 | 10.183 | 1.00 | 38.05 | A | O |
| ATOM | 719 | N | TYR | A | 128 | 35.170 | 53.702 | 11.178 | 1.00 | 33.81 | A | N |
| ATOM | 720 | CA | TYR | A | 128 | 34.075 | 53.213 | 10.354 | 1.00 | 35.75 | A | C |
| ATOM | 721 | CB | TYR | A | 128 | 34.596 | 52.173 | 9.376 | 1.00 | 34.70 | A | C |
| ATOM | 722 | CG | TYR | A | 128 | 35.500 | 52.750 | 8.309 | 1.00 | 40.93 | A | C |
| ATOM | 723 | CD1 | TYR | A | 128 | 35.035 | 52.930 | 7.012 | 1.00 | 41.68 | A | C |
| ATOM | 724 | CE1 | TYR | A | 128 | 35.848 | 53.449 | 6.016 | 1.00 | 42.35 | A | C |
| ATOM | 725 | CD2 | TYR | A | 128 | 36.821 | 53.109 | 8.590 | 1.00 | 41.17 | A | C |
| ATOM | 726 | CE2 | TYR | A | 128 | 37.646 | 53.637 | 7.594 | 1.00 | 38.98 | A | C |
| ATOM | 727 | CZ | TYR | A | 128 | 37.146 | 53.800 | 6.308 | 1.00 | 40.91 | A | C |
| ATOM | 728 | OH | TYR | A | 128 | 37.913 | 54.320 | 5.296 | 1.00 | 36.87 | A | O |
| ATOM | 729 | C | TYR | A | 128 | 32.935 | 52.614 | 11.184 | 1.00 | 39.01 | A | C |
| ATOM | 730 | O | TYR | A | 128 | 33.136 | 52.232 | 12.334 | 1.00 | 40.17 | A | O |
| ATOM | 731 | N | SER | A | 129 | 31.747 | 52.522 | 10.593 | 1.00 | 32.23 | A | N |
| ATOM | 732 | CA | SER | A | 129 | 30.713 | 51.687 | 11.177 | 1.00 | 37.41 | A | C |
| ATOM | 733 | CB | SER | A | 129 | 29.349 | 52.359 | 11.119 | 1.00 | 30.18 | A | C |
| ATOM | 734 | OG | SER | A | 129 | 28.587 | 51.810 | 10.065 | 1.00 | 31.57 | A | O |
| ATOM | 735 | C | SER | A | 129 | 30.687 | 50.416 | 10.365 | 1.00 | 37.57 | A | C |
| ATOM | 736 | O | SER | A | 129 | 30.980 | 50.431 | 9.162 | 1.00 | 37.79 | A | O |
| ATOM | 737 | N | GLU | A | 130 | 30.341 | 49.322 | 11.029 | 1.00 | 34.53 | A | N |
| ATOM | 738 | CA | GLU | A | 130 | 30.345 | 48.001 | 10.421 | 1.00 | 37.20 | A | C |
| ATOM | 739 | CB | GLU | A | 130 | 30.510 | 46.941 | 11.513 | 1.00 | 37.94 | A | C |
| ATOM | 740 | CG | GLU | A | 130 | 31.854 | 46.998 | 12.217 | 1.00 | 41.66 | A | C |
| ATOM | 741 | CD | GLU | A | 130 | 33.025 | 46.755 | 11.252 | 1.00 | 48.61 | A | C |
| ATOM | 742 | OE1 | GLU | A | 130 | 32.871 | 45.961 | 10.298 | 1.00 | 43.12 | A | O |
| ATOM | 743 | OE2 | GLU | A | 130 | 34.098 | 47.363 | 11.449 | 1.00 | 53.13 | A | O |
| ATOM | 744 | C | GLU | A | 130 | 29.084 | 47.715 | 9.624 | 1.00 | 37.89 | A | C |
| ATOM | 745 | O | GLU | A | 130 | 28.899 | 46.589 | 9.146 | 1.00 | 37.01 | A | O |
| ATOM | 746 | N | ASP | A | 131 | 28.215 | 48.720 | 9.488 | 1.00 | 33.20 | A | N |
| ATOM | 747 | CA | ASP | A | 131 | 26.983 | 48.561 | 8.707 | 1.00 | 30.26 | A | C |
| ATOM | 748 | CB | ASP | A | 131 | 26.019 | 49.735 | 8.965 | 1.00 | 34.52 | A | C |
| ATOM | 749 | CG | ASP | A | 131 | 25.491 | 49.763 | 10.399 | 1.00 | 34.43 | A | C |
| ATOM | 750 | OD1 | ASP | A | 131 | 25.435 | 48.691 | 11.038 | 1.00 | 32.61 | A | O |
| ATOM | 751 | OD2 | ASP | A | 131 | 25.149 | 50.859 | 10.891 | 1.00 | 36.69 | A | O |
| ATOM | 752 | C | ASP | A | 131 | 27.211 | 48.398 | 7.195 | 1.00 | 33.84 | A | C |
| ATOM | 753 | O | ASP | A | 131 | 26.350 | 47.867 | 6.490 | 1.00 | 27.26 | A | O |
| ATOM | 754 | N | LEU | A | 132 | 28.360 | 48.865 | 6.694 | 1.00 | 33.49 | A | N |
| ATOM | 755 | CA | LEU | A | 132 | 28.676 | 48.815 | 5.256 | 1.00 | 28.02 | A | C |
| ATOM | 756 | CB | LEU | A | 132 | 28.387 | 50.178 | 4.610 | 1.00 | 32.60 | A | C |
| ATOM | 757 | CG | LEU | A | 132 | 26.962 | 50.728 | 4.447 | 1.00 | 33.16 | A | C |
| ATOM | 758 | CD1 | LEU | A | 132 | 26.938 | 52.272 | 4.335 | 1.00 | 27.49 | A | C |
| ATOM | 759 | CD2 | LEU | A | 132 | 26.255 | 50.068 | 3.243 | 1.00 | 30.78 | A | C |
| ATOM | 760 | C | LEU | A | 132 | 30.176 | 48.483 | 5.066 | 1.00 | 31.60 | A | C |
| ATOM | 761 | O | LEU | A | 132 | 30.979 | 48.683 | 5.984 | 1.00 | 30.76 | A | O |
| ATOM | 762 | N | PRO | A | 133 | 30.558 | 47.985 | 3.872 | 1.00 | 26.11 | A | N |
| ATOM | 763 | CD | PRO | A | 133 | 29.715 | 47.660 | 2.716 | 1.00 | 27.42 | A | C |
| ATOM | 764 | CA | PRO | A | 133 | 31.987 | 47.811 | 3.575 | 1.00 | 32.72 | A | C |
| ATOM | 765 | CB | PRO | A | 133 | 31.984 | 47.291 | 2.131 | 1.00 | 33.38 | A | C |
| ATOM | 766 | CG | PRO | A | 133 | 30.578 | 46.730 | 1.920 | 1.00 | 31.29 | A | C |

TABLE 12-continued

Coordinates for pro MMP9(35-444 ΔFnII) (SEQ ID NO: 12) complex with Example 2

| ATOM | 767 | C | PRO | A | 133 | 32.678 | 49.166 | 3.613 | 1.00 | 31.48 | A | C |
|---|---|---|---|---|---|---|---|---|---|---|---|---|
| ATOM | 768 | O | PRO | A | 133 | 32.057 | 50.157 | 3.249 | 1.00 | 32.54 | A | O |
| ATOM | 769 | N | ARG | A | 134 | 33.935 | 49.218 | 4.029 | 1.00 | 36.40 | A | N |
| ATOM | 770 | CA | ARG | A | 134 | 34.631 | 50.498 | 4.091 | 1.00 | 33.95 | A | C |
| ATOM | 771 | CB | ARG | A | 134 | 35.998 | 50.330 | 4.735 | 1.00 | 39.76 | A | C |
| ATOM | 772 | CG | ARG | A | 134 | 35.931 | 49.574 | 6.035 | 1.00 | 40.80 | A | C |
| ATOM | 773 | CD | ARG | A | 134 | 37.091 | 49.941 | 6.934 | 1.00 | 43.02 | A | C |
| ATOM | 774 | NE | ARG | A | 134 | 37.139 | 49.059 | 8.092 | 1.00 | 47.95 | A | N |
| ATOM | 775 | CZ | ARG | A | 134 | 38.118 | 49.065 | 8.989 | 1.00 | 56.39 | A | C |
| ATOM | 776 | NH1 | ARG | A | 134 | 39.133 | 49.911 | 8.852 | 1.00 | 53.66 | A | N |
| ATOM | 777 | NH2 | ARG | A | 134 | 38.082 | 48.226 | 10.021 | 1.00 | 63.92 | A | N |
| ATOM | 778 | C | ARG | A | 134 | 34.747 | 51.143 | 2.713 | 1.00 | 33.12 | A | C |
| ATOM | 779 | O | ARG | A | 134 | 34.786 | 52.367 | 2.582 | 1.00 | 35.74 | A | O |
| ATOM | 780 | N | ALA | A | 135 | 34.769 | 50.331 | 1.675 | 1.00 | 29.57 | A | N |
| ATOM | 781 | CA | ALA | A | 135 | 34.844 | 50.918 | 0.351 | 1.00 | 34.30 | A | C |
| ATOM | 782 | CB | ALA | A | 135 | 35.038 | 49.858 | −0.681 | 1.00 | 31.50 | A | C |
| ATOM | 783 | C | ALA | A | 135 | 33.564 | 51.717 | 0.076 | 1.00 | 38.91 | A | C |
| ATOM | 784 | O | ALA | A | 135 | 33.612 | 52.883 | −0.328 | 1.00 | 37.81 | A | O |
| ATOM | 785 | N | VAL | A | 136 | 32.414 | 51.088 | 0.302 | 1.00 | 36.67 | A | N |
| ATOM | 786 | CA | VAL | A | 136 | 31.135 | 51.769 | 0.096 | 1.00 | 34.10 | A | C |
| ATOM | 787 | CB | VAL | A | 136 | 29.937 | 50.808 | 0.327 | 1.00 | 38.81 | A | C |
| ATOM | 788 | CG1 | VAL | A | 136 | 28.624 | 51.582 | 0.514 | 1.00 | 33.80 | A | C |
| ATOM | 789 | CG2 | VAL | A | 136 | 29.826 | 49.833 | −0.833 | 1.00 | 36.47 | A | C |
| ATOM | 790 | C | VAL | A | 136 | 31.025 | 53.043 | 0.953 | 1.00 | 27.14 | A | C |
| ATOM | 791 | O | VAL | A | 136 | 30.426 | 54.016 | 0.546 | 1.00 | 32.83 | A | O |
| ATOM | 792 | N | ILE | A | 137 | 31.630 | 53.035 | 2.123 | 1.00 | 28.43 | A | N |
| ATOM | 793 | CA | ILE | A | 137 | 31.632 | 54.209 | 2.979 | 1.00 | 27.95 | A | C |
| ATOM | 794 | CB | ILE | A | 137 | 32.041 | 53.814 | 4.410 | 1.00 | 29.11 | A | C |
| ATOM | 795 | CG2 | ILE | A | 137 | 32.410 | 55.027 | 5.248 | 1.00 | 26.72 | A | C |
| ATOM | 796 | CG1 | ILE | A | 137 | 30.928 | 52.989 | 5.079 | 1.00 | 33.40 | A | C |
| ATOM | 797 | CD1 | ILE | A | 137 | 31.136 | 52.731 | 6.570 | 1.00 | 31.36 | A | C |
| ATOM | 798 | C | ILE | A | 137 | 32.591 | 55.278 | 2.437 | 1.00 | 36.02 | A | C |
| ATOM | 799 | O | ILE | A | 137 | 32.291 | 56.481 | 2.430 | 1.00 | 27.71 | A | O |
| ATOM | 800 | N | ASP | A | 138 | 33.759 | 54.848 | 1.974 | 1.00 | 33.80 | A | N |
| ATOM | 801 | CA | ASP | A | 138 | 34.672 | 55.804 | 1.371 | 1.00 | 32.70 | A | C |
| ATOM | 802 | CB | ASP | A | 138 | 35.932 | 55.102 | 0.865 | 1.00 | 33.99 | A | C |
| ATOM | 803 | CG | ASP | A | 138 | 36.727 | 54.481 | 1.966 | 1.00 | 33.09 | A | C |
| ATOM | 804 | OD1 | ASP | A | 138 | 36.580 | 54.906 | 3.127 | 1.00 | 40.74 | A | O |
| ATOM | 805 | OD2 | ASP | A | 138 | 37.523 | 53.564 | 1.667 | 1.00 | 41.65 | A | O |
| ATOM | 806 | C | ASP | A | 138 | 34.004 | 56.519 | 0.207 | 1.00 | 24.67 | A | C |
| ATOM | 807 | O | ASP | A | 138 | 34.052 | 57.726 | 0.110 | 1.00 | 30.11 | A | O |
| ATOM | 808 | N | ASP | A | 139 | 33.399 | 55.765 | −0.697 | 1.00 | 28.10 | A | N |
| ATOM | 809 | CA | ASP | A | 139 | 32.860 | 56.354 | −1.918 | 1.00 | 25.82 | A | C |
| ATOM | 810 | CB | ASP | A | 139 | 32.415 | 55.245 | −2.845 | 1.00 | 32.24 | A | C |
| ATOM | 811 | CG | ASP | A | 139 | 31.411 | 55.705 | −3.866 | 1.00 | 37.67 | A | C |
| ATOM | 812 | OD1 | ASP | A | 139 | 31.813 | 56.333 | −4.864 | 1.00 | 44.46 | A | O |
| ATOM | 813 | OD2 | ASP | A | 139 | 30.210 | 55.403 | −3.698 | 1.00 | 42.63 | A | O |
| ATOM | 814 | C | ASP | A | 139 | 31.672 | 57.246 | −1.599 | 1.00 | 35.16 | A | C |
| ATOM | 815 | O | ASP | A | 139 | 31.431 | 58.275 | −2.254 | 1.00 | 31.91 | A | O |
| ATOM | 816 | N | ALA | A | 140 | 30.916 | 56.828 | −0.588 | 1.00 | 32.89 | A | N |
| ATOM | 817 | CA | ALA | A | 140 | 29.780 | 57.607 | −0.115 | 1.00 | 33.14 | A | C |
| ATOM | 818 | CB | ALA | A | 140 | 29.081 | 56.881 | 1.045 | 1.00 | 28.65 | A | C |
| ATOM | 819 | C | ALA | A | 140 | 30.254 | 58.988 | 0.306 | 1.00 | 27.26 | A | C |
| ATOM | 820 | O | ALA | A | 140 | 29.680 | 59.993 | −0.096 | 1.00 | 31.78 | A | O |
| ATOM | 821 | N | PHE | A | 141 | 31.318 | 59.060 | 1.091 | 1.00 | 30.08 | A | N |
| ATOM | 822 | CA | PHE | A | 141 | 31.840 | 60.379 | 1.468 | 1.00 | 29.18 | A | C |
| ATOM | 823 | CB | PHE | A | 141 | 32.908 | 60.271 | 2.555 | 1.00 | 34.53 | A | C |
| ATOM | 824 | CG | PHE | A | 141 | 32.394 | 59.794 | 3.885 | 1.00 | 30.07 | A | C |
| ATOM | 825 | CD1 | PHE | A | 141 | 31.193 | 60.271 | 4.402 | 1.00 | 32.94 | A | C |
| ATOM | 826 | CD2 | PHE | A | 141 | 33.123 | 58.886 | 4.636 | 1.00 | 27.72 | A | C |
| ATOM | 827 | CE1 | PHE | A | 141 | 30.725 | 59.839 | 5.647 | 1.00 | 29.84 | A | C |
| ATOM | 828 | CE2 | PHE | A | 141 | 32.663 | 58.450 | 5.879 | 1.00 | 36.22 | A | C |
| ATOM | 829 | CZ | PHE | A | 141 | 31.456 | 58.930 | 6.381 | 1.00 | 30.44 | A | C |
| ATOM | 830 | C | PHE | A | 141 | 32.375 | 61.180 | 0.261 | 1.00 | 30.34 | A | C |
| ATOM | 831 | O | PHE | A | 141 | 32.163 | 62.393 | 0.162 | 1.00 | 28.80 | A | O |
| ATOM | 832 | N | ALA | A | 142 | 33.053 | 60.506 | −0.666 | 1.00 | 33.51 | A | N |
| ATOM | 833 | CA | ALA | A | 142 | 33.626 | 61.209 | −1.818 | 1.00 | 34.14 | A | C |
| ATOM | 834 | CB | ALA | A | 142 | 34.462 | 60.244 | −2.669 | 1.00 | 35.98 | A | C |
| ATOM | 835 | C | ALA | A | 142 | 32.533 | 61.837 | −2.664 | 1.00 | 31.34 | A | C |
| ATOM | 836 | O | ALA | A | 142 | 32.592 | 63.018 | −3.023 | 1.00 | 29.07 | A | O |
| ATOM | 837 | N | ARG | A | 143 | 31.526 | 61.024 | −2.978 | 1.00 | 30.48 | A | N |
| ATOM | 838 | CA | ARG | A | 143 | 30.402 | 61.466 | −3.786 | 1.00 | 24.34 | A | C |
| ATOM | 839 | CB | ARG | A | 143 | 29.385 | 60.351 | −3.933 | 1.00 | 25.55 | A | C |
| ATOM | 840 | CG | ARG | A | 143 | 29.802 | 59.309 | −4.940 | 1.00 | 31.09 | A | C |
| ATOM | 841 | CD | ARG | A | 143 | 29.180 | 57.984 | −4.657 | 1.00 | 32.69 | A | C |
| ATOM | 842 | NE | ARG | A | 143 | 27.737 | 58.094 | −4.638 | 1.00 | 40.43 | A | N |
| ATOM | 843 | CZ | ARG | A | 143 | 26.930 | 57.638 | −3.678 | 1.00 | 39.04 | A | C |

TABLE 12-continued

Coordinates for pro MMP9(35-444 ΔFnII) (SEQ ID NO: 12) complex with Example 2

| ATOM | 844 | NH1 | ARG | A | 143 | 27.386 | 56.971 | −2.618 | 1.00 | 32.01 | A | N |
|---|---|---|---|---|---|---|---|---|---|---|---|---|
| ATOM | 845 | NH2 | ARG | A | 143 | 25.632 | 57.833 | −3.814 | 1.00 | 36.43 | A | N |
| ATOM | 846 | C | ARG | A | 143 | 29.766 | 62.687 | −3.164 | 1.00 | 23.70 | A | C |
| ATOM | 847 | O | ARG | A | 143 | 29.383 | 63.611 | −3.873 | 1.00 | 27.78 | A | O |
| ATOM | 848 | N | ALA | A | 144 | 29.680 | 62.680 | −1.834 | 1.00 | 23.70 | A | N |
| ATOM | 849 | CA | ALA | A | 144 | 29.153 | 63.793 | −1.046 | 1.00 | 25.97 | A | C |
| ATOM | 850 | CB | ALA | A | 144 | 29.077 | 63.389 | 0.446 | 1.00 | 27.89 | A | C |
| ATOM | 851 | C | ALA | A | 144 | 29.950 | 65.092 | −1.205 | 1.00 | 28.68 | A | C |
| ATOM | 852 | O | ALA | A | 144 | 29.371 | 66.168 | −1.421 | 1.00 | 23.37 | A | O |
| ATOM | 853 | N | PHE | A | 145 | 31.276 | 64.997 | −1.080 | 1.00 | 31.53 | A | N |
| ATOM | 854 | CA | PHE | A | 145 | 32.163 | 66.143 | −1.372 | 1.00 | 24.45 | A | C |
| ATOM | 855 | CB | PHE | A | 145 | 33.610 | 65.843 | −0.986 | 1.00 | 24.66 | A | C |
| ATOM | 856 | CG | PHE | A | 145 | 33.861 | 65.844 | 0.491 | 1.00 | 27.82 | A | C |
| ATOM | 857 | CD1 | PHE | A | 145 | 33.697 | 67.002 | 1.233 | 1.00 | 25.76 | A | C |
| ATOM | 858 | CD2 | PHE | A | 145 | 34.296 | 64.692 | 1.139 | 1.00 | 28.43 | A | C |
| ATOM | 859 | CE1 | PHE | A | 145 | 33.945 | 67.005 | 2.583 | 1.00 | 24.95 | A | C |
| ATOM | 860 | CE2 | PHE | A | 145 | 34.560 | 64.692 | 2.484 | 1.00 | 26.00 | A | C |
| ATOM | 861 | CZ | PHE | A | 145 | 34.384 | 65.851 | 3.214 | 1.00 | 28.47 | A | C |
| ATOM | 862 | C | PHE | A | 145 | 32.093 | 66.539 | −2.833 | 1.00 | 20.85 | A | C |
| ATOM | 863 | O | PHE | A | 145 | 32.064 | 67.719 | −3.172 | 1.00 | 28.89 | A | O |
| ATOM | 864 | N | ALA | A | 146 | 32.008 | 65.562 | −3.715 | 1.00 | 21.83 | A | N |
| ATOM | 865 | CA | ALA | A | 146 | 31.899 | 65.877 | −5.125 | 1.00 | 20.02 | A | C |
| ATOM | 866 | CB | ALA | A | 146 | 31.807 | 64.597 | −5.918 | 1.00 | 23.54 | A | C |
| ATOM | 867 | C | ALA | A | 146 | 30.683 | 66.787 | −5.429 | 1.00 | 29.66 | A | C |
| ATOM | 868 | O | ALA | A | 146 | 30.646 | 67.499 | −6.443 | 1.00 | 21.03 | A | O |
| ATOM | 869 | N | LEU | A | 147 | 29.676 | 66.754 | −4.559 | 1.00 | 24.91 | A | N |
| ATOM | 870 | CA | LEU | A | 147 | 28.467 | 67.554 | −4.783 | 1.00 | 26.36 | A | C |
| ATOM | 871 | CB | LEU | A | 147 | 27.367 | 67.211 | −3.751 | 1.00 | 19.44 | A | C |
| ATOM | 872 | CG | LEU | A | 147 | 26.396 | 66.078 | −4.041 | 1.00 | 26.97 | A | C |
| ATOM | 873 | CD1 | LEU | A | 147 | 25.309 | 66.087 | −2.947 | 1.00 | 25.48 | A | C |
| ATOM | 874 | CD2 | LEU | A | 147 | 25.739 | 66.210 | −5.399 | 1.00 | 28.06 | A | C |
| ATOM | 875 | C | LEU | A | 147 | 28.813 | 69.010 | −4.621 | 1.00 | 18.74 | A | C |
| ATOM | 876 | O | LEU | A | 147 | 28.347 | 69.866 | −5.365 | 1.00 | 24.03 | A | O |
| ATOM | 877 | N | TRP | A | 148 | 29.611 | 69.269 | −3.609 | 1.00 | 20.20 | A | N |
| ATOM | 878 | CA | TRP | A | 148 | 29.969 | 70.612 | −3.235 | 1.00 | 26.06 | A | C |
| ATOM | 879 | CB | TRP | A | 148 | 30.372 | 70.628 | −1.772 | 1.00 | 23.77 | A | C |
| ATOM | 880 | CG | TRP | A | 148 | 29.203 | 70.424 | −0.789 | 1.00 | 33.02 | A | C |
| ATOM | 881 | CD2 | TRP | A | 148 | 28.042 | 71.260 | −0.646 | 1.00 | 31.64 | A | C |
| ATOM | 882 | CE2 | TRP | A | 148 | 27.234 | 70.693 | 0.371 | 1.00 | 35.58 | A | C |
| ATOM | 883 | CE3 | TRP | A | 148 | 27.605 | 72.432 | −1.279 | 1.00 | 30.31 | A | C |
| ATOM | 884 | CD1 | TRP | A | 148 | 29.062 | 69.415 | 0.131 | 1.00 | 31.57 | A | C |
| ATOM | 885 | NE1 | TRP | A | 148 | 27.882 | 69.571 | 0.833 | 1.00 | 31.61 | A | N |
| ATOM | 886 | CZ2 | TRP | A | 148 | 26.018 | 71.270 | 0.776 | 1.00 | 28.98 | A | C |
| ATOM | 887 | CZ3 | TRP | A | 148 | 26.377 | 73.000 | −0.881 | 1.00 | 33.29 | A | C |
| ATOM | 888 | CH2 | TRP | A | 148 | 25.614 | 72.423 | 0.138 | 1.00 | 25.14 | A | C |
| ATOM | 889 | C | TRP | A | 148 | 31.126 | 71.186 | −4.068 | 1.00 | 32.74 | A | C |
| ATOM | 890 | O | TRP | A | 148 | 31.112 | 72.364 | −4.421 | 1.00 | 32.85 | A | O |
| ATOM | 891 | N | SER | A | 149 | 32.154 | 70.381 | −4.330 | 1.00 | 29.94 | A | N |
| ATOM | 892 | CA | SER | A | 149 | 33.290 | 70.894 | −5.098 | 1.00 | 31.65 | A | C |
| ATOM | 893 | CB | SER | A | 149 | 34.344 | 69.814 | −5.318 | 1.00 | 28.83 | A | C |
| ATOM | 894 | OG | SER | A | 149 | 34.016 | 69.090 | −6.475 | 1.00 | 33.07 | A | O |
| ATOM | 895 | C | SER | A | 149 | 32.830 | 71.484 | −6.440 | 1.00 | 26.72 | A | C |
| ATOM | 896 | O | SER | A | 149 | 33.318 | 72.520 | −6.855 | 1.00 | 30.94 | A | O |
| ATOM | 897 | N | ALA | A | 150 | 31.857 | 70.864 | −7.096 | 1.00 | 22.46 | A | N |
| ATOM | 898 | CA | ALA | A | 150 | 31.381 | 71.397 | −8.356 | 1.00 | 21.16 | A | C |
| ATOM | 899 | CB | ALA | A | 150 | 30.466 | 70.430 | −9.041 | 1.00 | 24.22 | A | C |
| ATOM | 900 | C | ALA | A | 150 | 30.738 | 72.778 | −8.290 | 1.00 | 25.46 | A | C |
| ATOM | 901 | O | ALA | A | 150 | 30.531 | 73.407 | −9.321 | 1.00 | 28.00 | A | O |
| ATOM | 902 | N | VAL | A | 151 | 30.423 | 73.270 | −7.100 | 1.00 | 27.77 | A | N |
| ATOM | 903 | CA | VAL | A | 151 | 29.690 | 74.536 | −7.032 | 1.00 | 27.42 | A | C |
| ATOM | 904 | CB | VAL | A | 151 | 28.229 | 74.326 | −6.585 | 1.00 | 26.49 | A | C |
| ATOM | 905 | CG1 | VAL | A | 151 | 27.450 | 73.668 | −7.692 | 1.00 | 19.47 | A | C |
| ATOM | 906 | CG2 | VAL | A | 151 | 28.169 | 73.466 | −5.314 | 1.00 | 26.32 | A | C |
| ATOM | 907 | C | VAL | A | 151 | 30.433 | 75.499 | −6.143 | 1.00 | 25.99 | A | C |
| ATOM | 908 | O | VAL | A | 151 | 30.035 | 76.641 | −5.936 | 1.00 | 30.72 | A | O |
| ATOM | 909 | N | THR | A | 152 | 31.544 | 75.014 | −5.618 | 1.00 | 32.49 | A | N |
| ATOM | 910 | CA | THR | A | 152 | 32.448 | 75.849 | −4.854 | 1.00 | 36.18 | A | C |
| ATOM | 911 | CB | THR | A | 152 | 32.697 | 75.243 | −3.491 | 1.00 | 36.45 | A | C |
| ATOM | 912 | OG1 | THR | A | 152 | 32.922 | 73.841 | −3.663 | 1.00 | 39.67 | A | O |
| ATOM | 913 | CG2 | THR | A | 152 | 31.486 | 75.457 | −2.589 | 1.00 | 32.17 | A | C |
| ATOM | 914 | C | THR | A | 152 | 33.803 | 75.962 | −5.546 | 1.00 | 37.62 | A | C |
| ATOM | 915 | O | THR | A | 152 | 34.173 | 75.119 | −6.363 | 1.00 | 35.91 | A | O |
| ATOM | 916 | N | PRO | A | 153 | 34.542 | 77.019 | −5.215 | 1.00 | 34.09 | A | N |
| ATOM | 917 | CD | PRO | A | 153 | 34.098 | 78.153 | −4.393 | 1.00 | 43.15 | A | C |
| ATOM | 918 | CA | PRO | A | 153 | 35.939 | 77.151 | −5.603 | 1.00 | 41.47 | A | C |
| ATOM | 919 | CB | PRO | A | 153 | 36.218 | 78.642 | −5.403 | 1.00 | 45.96 | A | C |
| ATOM | 920 | CG | PRO | A | 153 | 34.903 | 79.265 | −4.940 | 1.00 | 46.62 | A | C |

TABLE 12-continued

Coordinates for pro MMP9(35-444 ΔFnII) (SEQ ID NO: 12) complex with Example 2

| ATOM | 921 | C | PRO | A | 153 | 36.729 | 76.395 | −4.571 | 1.00 | 41.21 | A | C |
|---|---|---|---|---|---|---|---|---|---|---|---|---|
| ATOM | 922 | O | PRO | A | 153 | 37.607 | 76.998 | −3.955 | 1.00 | 46.60 | A | O |
| ATOM | 923 | N | LEU | A | 154 | 36.400 | 75.126 | −4.346 | 1.00 | 36.26 | A | N |
| ATOM | 924 | CA | LEU | A | 154 | 37.089 | 74.343 | −3.324 | 1.00 | 35.56 | A | C |
| ATOM | 925 | CB | LEU | A | 154 | 36.243 | 74.223 | −2.044 | 1.00 | 35.17 | A | C |
| ATOM | 926 | CG | LEU | A | 154 | 35.900 | 75.468 | −1.205 | 1.00 | 35.37 | A | C |
| ATOM | 927 | CD1 | LEU | A | 154 | 35.239 | 75.063 | 0.094 | 1.00 | 32.76 | A | C |
| ATOM | 928 | CD2 | LEU | A | 154 | 37.114 | 76.330 | −0.887 | 1.00 | 37.91 | A | C |
| ATOM | 929 | C | LEU | A | 154 | 37.369 | 72.960 | −3.861 | 1.00 | 31.93 | A | C |
| ATOM | 930 | O | LEU | A | 154 | 36.638 | 72.472 | −4.730 | 1.00 | 31.78 | A | O |
| ATOM | 931 | N | THR | A | 155 | 38.412 | 72.323 | −3.331 | 1.00 | 28.79 | A | N |
| ATOM | 932 | CA | THR | A | 155 | 38.700 | 70.928 | −3.649 | 1.00 | 25.34 | A | C |
| ATOM | 933 | CB | THR | A | 155 | 40.087 | 70.738 | −4.318 | 1.00 | 29.53 | A | C |
| ATOM | 934 | OG1 | THR | A | 155 | 41.069 | 71.454 | −3.557 | 1.00 | 30.87 | A | O |
| ATOM | 935 | CG2 | THR | A | 155 | 40.067 | 71.228 | −5.718 | 1.00 | 31.71 | A | C |
| ATOM | 936 | C | THR | A | 155 | 38.796 | 70.197 | −2.345 | 1.00 | 24.14 | A | C |
| ATOM | 937 | O | THR | A | 155 | 39.165 | 70.785 | −1.338 | 1.00 | 27.05 | A | O |
| ATOM | 938 | N | PHE | A | 156 | 38.515 | 68.903 | −2.367 | 1.00 | 27.88 | A | N |
| ATOM | 939 | CA | PHE | A | 156 | 38.548 | 68.143 | −1.132 | 1.00 | 32.96 | A | C |
| ATOM | 940 | CB | PHE | A | 156 | 37.129 | 67.653 | −0.747 | 1.00 | 27.70 | A | C |
| ATOM | 941 | CG | PHE | A | 156 | 36.109 | 68.757 | −0.727 | 1.00 | 24.80 | A | C |
| ATOM | 942 | CD1 | PHE | A | 156 | 35.253 | 68.939 | −1.791 | 1.00 | 27.20 | A | C |
| ATOM | 943 | CD2 | PHE | A | 156 | 36.023 | 69.617 | 0.359 | 1.00 | 25.70 | A | C |
| ATOM | 944 | CE1 | PHE | A | 156 | 34.332 | 69.979 | −1.791 | 1.00 | 27.11 | A | C |
| ATOM | 945 | CE2 | PHE | A | 156 | 35.122 | 70.650 | 0.367 | 1.00 | 24.81 | A | C |
| ATOM | 946 | CZ | PHE | A | 156 | 34.272 | 70.831 | −0.710 | 1.00 | 22.28 | A | C |
| ATOM | 947 | C | PHE | A | 156 | 39.520 | 66.998 | −1.285 | 1.00 | 24.20 | A | C |
| ATOM | 948 | O | PHE | A | 156 | 39.541 | 66.341 | −2.310 | 1.00 | 28.04 | A | O |
| ATOM | 949 | N | THR | A | 157 | 40.271 | 66.728 | −0.232 | 1.00 | 25.89 | A | N |
| ATOM | 950 | CA | THR | A | 157 | 41.365 | 65.788 | −0.322 | 1.00 | 31.86 | A | C |
| ATOM | 951 | CB | THR | A | 157 | 42.709 | 66.551 | −0.442 | 1.00 | 32.50 | A | C |
| ATOM | 952 | OG1 | THR | A | 157 | 42.710 | 67.316 | −1.657 | 1.00 | 36.08 | A | O |
| ATOM | 953 | CG2 | THR | A | 157 | 43.863 | 65.593 | −0.452 | 1.00 | 33.63 | A | C |
| ATOM | 954 | C | THR | A | 157 | 41.414 | 64.881 | 0.886 | 1.00 | 27.21 | A | C |
| ATOM | 955 | O | THR | A | 157 | 41.542 | 65.355 | 2.009 | 1.00 | 30.08 | A | O |
| ATOM | 956 | N | ARG | A | 158 | 41.342 | 63.572 | 0.644 | 1.00 | 32.23 | A | N |
| ATOM | 957 | CA | ARG | A | 158 | 41.426 | 62.571 | 1.718 | 1.00 | 32.19 | A | C |
| ATOM | 958 | CB | ARG | A | 158 | 40.914 | 61.215 | 1.231 | 1.00 | 26.93 | A | C |
| ATOM | 959 | CG | ARG | A | 158 | 41.059 | 60.120 | 2.278 | 1.00 | 28.30 | A | C |
| ATOM | 960 | CD | ARG | A | 158 | 40.355 | 58.843 | 1.864 | 1.00 | 28.04 | A | C |
| ATOM | 961 | NE | ARG | A | 158 | 40.433 | 57.856 | 2.933 | 1.00 | 30.93 | A | N |
| ATOM | 962 | CZ | ARG | A | 158 | 40.130 | 56.570 | 2.780 | 1.00 | 29.89 | A | C |
| ATOM | 963 | NH1 | ARG | A | 158 | 39.727 | 56.117 | 1.605 | 1.00 | 28.69 | A | N |
| ATOM | 964 | NH2 | ARG | A | 158 | 40.235 | 55.739 | 3.804 | 1.00 | 32.90 | A | N |
| ATOM | 965 | C | ARG | A | 158 | 42.849 | 62.404 | 2.258 | 1.00 | 34.84 | A | C |
| ATOM | 966 | O | ARG | A | 158 | 43.766 | 62.117 | 1.491 | 1.00 | 38.24 | A | O |
| ATOM | 967 | N | VAL | A | 159 | 43.005 | 62.584 | 3.568 | 1.00 | 34.25 | A | N |
| ATOM | 968 | CA | VAL | A | 159 | 44.270 | 62.410 | 4.278 | 1.00 | 37.44 | A | C |
| ATOM | 969 | CB | VAL | A | 159 | 44.711 | 63.701 | 4.969 | 1.00 | 35.19 | A | C |
| ATOM | 970 | CG1 | VAL | A | 159 | 44.866 | 64.833 | 3.956 | 1.00 | 35.82 | A | C |
| ATOM | 971 | CG2 | VAL | A | 159 | 43.726 | 64.076 | 6.059 | 1.00 | 37.83 | A | C |
| ATOM | 972 | C | VAL | A | 159 | 44.160 | 61.360 | 5.389 | 1.00 | 41.92 | A | C |
| ATOM | 973 | O | VAL | A | 159 | 43.136 | 60.670 | 5.517 | 1.00 | 35.74 | A | O |
| ATOM | 974 | N | TYR | A | 160 | 45.206 | 61.270 | 6.217 | 1.00 | 42.62 | A | N |
| ATOM | 975 | CA | TYR | A | 160 | 45.280 | 60.218 | 7.221 | 1.00 | 37.36 | A | C |
| ATOM | 976 | CB | TYR | A | 160 | 46.061 | 59.037 | 6.648 | 1.00 | 37.40 | A | C |
| ATOM | 977 | CG | TYR | A | 160 | 45.340 | 58.392 | 5.486 | 1.00 | 37.03 | A | C |
| ATOM | 978 | CD1 | TYR | A | 160 | 45.572 | 58.798 | 4.168 | 1.00 | 36.62 | A | C |
| ATOM | 979 | CE1 | TYR | A | 160 | 44.888 | 58.202 | 3.099 | 1.00 | 30.90 | A | C |
| ATOM | 980 | CD2 | TYR | A | 160 | 44.401 | 57.389 | 5.704 | 1.00 | 40.75 | A | C |
| ATOM | 981 | CE2 | TYR | A | 160 | 43.721 | 56.794 | 4.652 | 1.00 | 33.36 | A | C |
| ATOM | 982 | CZ | TYR | A | 160 | 43.967 | 57.198 | 3.364 | 1.00 | 38.05 | A | C |
| ATOM | 983 | OH | TYR | A | 160 | 43.270 | 56.587 | 2.353 | 1.00 | 38.34 | A | O |
| ATOM | 984 | C | TYR | A | 160 | 45.829 | 60.660 | 8.582 | 1.00 | 39.74 | A | C |
| ATOM | 985 | O | TYR | A | 160 | 46.569 | 59.926 | 9.235 | 1.00 | 45.57 | A | O |
| ATOM | 986 | N | SER | A | 161 | 45.423 | 61.839 | 9.037 | 1.00 | 39.44 | A | N |
| ATOM | 987 | CA | SER | A | 161 | 45.941 | 62.383 | 10.289 | 1.00 | 43.72 | A | C |
| ATOM | 988 | CB | SER | A | 161 | 47.311 | 63.034 | 10.048 | 1.00 | 45.57 | A | C |
| ATOM | 989 | OG | SER | A | 161 | 47.174 | 64.396 | 9.643 | 1.00 | 42.49 | A | O |
| ATOM | 990 | C | SER | A | 161 | 45.005 | 63.416 | 10.951 | 1.00 | 44.50 | A | C |
| ATOM | 991 | O | SER | A | 161 | 44.185 | 64.049 | 10.297 | 1.00 | 39.35 | A | O |
| ATOM | 992 | N | ARG | A | 162 | 45.171 | 63.604 | 12.251 | 1.00 | 43.86 | A | N |
| ATOM | 993 | CA | ARG | A | 162 | 44.362 | 64.537 | 13.013 | 1.00 | 49.09 | A | C |
| ATOM | 994 | CB | ARG | A | 162 | 44.869 | 64.575 | 14.459 | 1.00 | 56.78 | A | C |
| ATOM | 995 | CG | ARG | A | 162 | 44.900 | 65.960 | 15.104 | 1.00 | 60.00 | A | C |
| ATOM | 226 | CD | ARG | A | 162 | 45.987 | 66.028 | 16.185 | 1.00 | 65.00 | A | C |
| ATOM | 997 | NE | ARG | A | 162 | 47.209 | 65.323 | 15.785 | 1.00 | 63.48 | A | N |

TABLE 12-continued

Coordinates for pro MMP9(35-444 ΔFnII) (SEQ ID NO: 12) complex with Example 2

| | | | | | | | | | | | |
|---|---|---|---|---|---|---|---|---|---|---|---|
| ATOM | 998 | CZ | ARG | A | 162 | 48.211 | 65.038 | 16.613 | 1.00 | 66.17 A | C |
| ATOM | 999 | NH1 | ARG | A | 162 | 48.129 | 65.400 | 17.889 | 1.00 | 66.79 A | N |
| ATOM | 1000 | NH2 | ARG | A | 162 | 49.290 | 64.391 | 16.173 | 1.00 | 54.98 A | N |
| ATOM | 1001 | C | ARG | A | 162 | 44.352 | 65.944 | 12.429 | 1.00 | 49.92 A | C |
| ATOM | 1002 | O | ARG | A | 162 | 43.561 | 66.793 | 12.844 | 1.00 | 52.42 A | O |
| ATOM | 1003 | N | ASP | A | 163 | 45.229 | 66.203 | 11.468 | 1.00 | 49.74 A | N |
| ATOM | 1004 | CA | ASP | A | 163 | 45.400 | 67.572 | 11.001 | 1.00 | 51.36 A | C |
| ATOM | 1005 | CB | ASP | A | 163 | 46.876 | 67.871 | 10.719 | 1.00 | 55.95 A | C |
| ATOM | 1006 | CG | ASP | A | 163 | 47.579 | 68.507 | 11.916 | 1.00 | 62.51 A | C |
| ATOM | 1007 | OD1 | ASP | A | 163 | 47.383 | 68.025 | 13.056 | 1.00 | 65.84 A | O |
| ATOM | 1008 | OD2 | ASP | A | 163 | 48.325 | 69.492 | 11.716 | 1.00 | 61.80 A | O |
| ATOM | 1009 | C | ASP | A | 163 | 44.528 | 67.941 | 9.804 | 1.00 | 45.41 A | C |
| ATOM | 1010 | O | ASP | A | 163 | 44.629 | 69.045 | 9.271 | 1.00 | 45.19 A | O |
| ATOM | 1011 | N | ALA | A | 164 | 43.675 | 67.022 | 9.379 | 1.00 | 41.14 A | N |
| ATOM | 1012 | CA | ALA | A | 164 | 42.716 | 67.349 | 8.341 | 1.00 | 30.81 A | C |
| ATOM | 1013 | CB | ALA | A | 164 | 41.845 | 66.161 | 8.065 | 1.00 | 31.83 A | C |
| ATOM | 1014 | C | ALA | A | 164 | 41.879 | 68.539 | 8.798 | 1.00 | 34.75 A | C |
| ATOM | 1015 | O | ALA | A | 164 | 41.721 | 68.780 | 9.990 | 1.00 | 36.03 A | O |
| ATOM | 1016 | N | ASP | A | 165 | 41.373 | 69.307 | 7.847 | 1.00 | 35.52 A | N |
| ATOM | 1017 | CA | ASP | A | 165 | 40.397 | 70.338 | 8.158 | 1.00 | 31.35 A | C |
| ATOM | 1018 | CB | ASP | A | 165 | 40.003 | 71.066 | 6.885 | 1.00 | 31.60 A | C |
| ATOM | 1019 | CG | ASP | A | 165 | 41.189 | 71.784 | 6.230 | 1.00 | 31.34 A | C |
| ATOM | 1020 | OD1 | ASP | A | 165 | 42.002 | 72.358 | 6.969 | 1.00 | 33.79 A | O |
| ATOM | 1021 | OD2 | ASP | A | 165 | 41.286 | 71.784 | 4.994 | 1.00 | 31.29 A | O |
| ATOM | 1022 | C | ASP | A | 165 | 39.161 | 69.669 | 8.747 | 1.00 | 34.46 A | C |
| ATOM | 1023 | O | ASP | A | 165 | 38.687 | 70.065 | 9.811 | 1.00 | 32.22 A | O |
| ATOM | 1024 | N | ILE | A | 166 | 38.654 | 68.655 | 8.042 | 1.00 | 26.44 A | N |
| ATOM | 1025 | CA | ILE | A | 166 | 37.435 | 67.963 | 8.431 | 1.00 | 32.49 A | C |
| ATOM | 1026 | CB | ILE | A | 166 | 36.437 | 67.909 | 7.255 | 1.00 | 34.03 A | C |
| ATOM | 1027 | CG2 | ILE | A | 166 | 35.079 | 67.373 | 7.715 | 1.00 | 34.49 A | C |
| ATOM | 1028 | CG1 | ILE | A | 166 | 36.287 | 69.280 | 6.598 | 1.00 | 29.50 A | C |
| ATOM | 1029 | CD1 | ILE | A | 166 | 35.276 | 69.300 | 5.467 | 1.00 | 33.82 A | C |
| ATOM | 1030 | C | ILE | A | 166 | 37.693 | 66.525 | 8.896 | 1.00 | 30.25 A | C |
| ATOM | 1031 | O | ILE | A | 166 | 37.920 | 65.640 | 8.084 | 1.00 | 31.28 A | O |
| ATOM | 1032 | N | VAL | A | 167 | 37.635 | 66.294 | 10.204 | 1.00 | 30.76 A | N |
| ATOM | 1033 | CA | VAL | A | 167 | 37.708 | 64.931 | 10.716 | 1.00 | 31.12 A | C |
| ATOM | 1034 | CB | VAL | A | 167 | 38.392 | 64.874 | 12.057 | 1.00 | 26.77 A | C |
| ATOM | 1035 | CG1 | VAL | A | 167 | 38.581 | 63.420 | 12.459 | 1.00 | 29.40 A | C |
| ATOM | 1036 | CG2 | VAL | A | 167 | 39.732 | 65.608 | 12.008 | 1.00 | 28.08 A | C |
| ATOM | 1037 | C | VAL | A | 167 | 36.327 | 64.257 | 10.833 | 1.00 | 35.95 A | C |
| ATOM | 1038 | O | VAL | A | 167 | 35.396 | 64.801 | 11.428 | 1.00 | 33.05 A | O |
| ATOM | 1039 | N | ILE | A | 168 | 36.225 | 63.067 | 10.263 | 1.00 | 34.26 A | N |
| ATOM | 1040 | CA | ILE | A | 168 | 34.972 | 62.330 | 10.150 | 1.00 | 34.47 A | C |
| ATOM | 1041 | CB | ILE | A | 168 | 34.782 | 61.839 | 8.726 | 1.00 | 31.38 A | C |
| ATOM | 1042 | CG2 | ILE | A | 168 | 33.608 | 60.887 | 8.610 | 1.00 | 32.51 A | C |
| ATOM | 1043 | CG1 | ILE | A | 168 | 34.567 | 63.025 | 7.802 | 1.00 | 29.00 A | C |
| ATOM | 1044 | CD1 | ILE | A | 168 | 34.199 | 62.597 | 6.407 | 1.00 | 35.00 A | C |
| ATOM | 1045 | C | ILE | A | 168 | 34.988 | 61.130 | 11.096 | 1.00 | 39.82 A | C |
| ATOM | 1046 | O | ILE | A | 168 | 35.946 | 60.331 | 11.119 | 1.00 | 31.84 A | O |
| ATOM | 1047 | N | GLN | A | 169 | 33.916 | 61.012 | 11.872 | 1.00 | 34.48 A | N |
| ATOM | 1048 | CA | GLN | A | 169 | 33.849 | 60.068 | 12.980 | 1.00 | 31.39 A | C |
| ATOM | 1049 | CB | GLN | A | 169 | 34.186 | 60.799 | 14.264 | 1.00 | 35.93 A | C |
| ATOM | 1050 | CG | GLN | A | 169 | 34.348 | 59.920 | 15.458 | 1.00 | 40.30 A | C |
| ATOM | 1051 | CD | GLN | A | 169 | 34.957 | 60.674 | 16.603 | 1.00 | 47.43 A | C |
| ATOM | 1052 | OE1 | GLN | A | 169 | 35.733 | 61.609 | 16.392 | 1.00 | 49.96 A | O |
| ATOM | 1053 | NE2 | GLN | A | 169 | 34.612 | 60.286 | 17.828 | 1.00 | 50.08 A | N |
| ATOM | 1054 | C | GLN | A | 169 | 32.461 | 59.450 | 13.109 | 1.00 | 34.84 A | C |
| ATOM | 1055 | O | GLN | A | 169 | 31.447 | 60.141 | 13.005 | 1.00 | 38.71 A | O |
| ATOM | 1056 | N | PHE | A | 170 | 32.415 | 58.143 | 13.310 | 1.00 | 30.95 A | N |
| ATOM | 1057 | CA | PHE | A | 170 | 31.185 | 57.501 | 13.725 | 1.00 | 37.19 A | C |
| ATOM | 1058 | CB | PHE | A | 170 | 31.009 | 56.153 | 13.062 | 1.00 | 31.97 A | C |
| ATOM | 1059 | CG | PHE | A | 170 | 30.914 | 56.214 | 11.568 | 1.00 | 35.47 A | C |
| ATOM | 1060 | CD1 | PHE | A | 170 | 32.041 | 56.447 | 10.796 | 1.00 | 33.00 A | C |
| ATOM | 1061 | CD2 | PHE | A | 170 | 29.701 | 56.014 | 10.929 | 1.00 | 31.61 A | C |
| ATOM | 1062 | CE1 | PHE | A | 170 | 31.963 | 56.481 | 9.416 | 1.00 | 32.08 A | C |
| ATOM | 1063 | CE2 | PHE | A | 170 | 29.615 | 56.045 | 9.550 | 1.00 | 30.52 A | C |
| ATOM | 1064 | CZ | PHE | A | 170 | 30.747 | 56.281 | 8.789 | 1.00 | 31.95 A | C |
| ATOM | 1065 | C | PHE | A | 170 | 31.289 | 57.309 | 15.222 | 1.00 | 39.74 A | C |
| ATOM | 1066 | O | PHE | A | 170 | 32.346 | 56.925 | 15.736 | 1.00 | 33.16 A | O |
| ATOM | 1067 | N | GLY | A | 171 | 30.196 | 57.572 | 15.922 | 1.00 | 31.71 A | N |
| ATOM | 1068 | CA | GLY | A | 171 | 30.187 | 57.434 | 17.372 | 1.00 | 36.21 A | C |
| ATOM | 1069 | C | GLY | A | 171 | 28.816 | 57.129 | 17.963 | 1.00 | 34.75 A | C |
| ATOM | 1070 | O | GLY | A | 171 | 27.809 | 57.086 | 17.225 | 1.00 | 35.88 A | O |
| ATOM | 1071 | N | VAL | A | 172 | 28.776 | 56.903 | 19.283 | 1.00 | 38.73 A | N |
| ATOM | 1072 | CA | VAL | A | 172 | 27.507 | 56.716 | 20.003 | 1.00 | 36.61 A | C |
| ATOM | 1073 | CB | VAL | A | 172 | 27.221 | 55.243 | 20.367 | 1.00 | 35.51 A | C |
| ATOM | 1074 | CG1 | VAL | A | 172 | 26.864 | 54.445 | 19.147 | 1.00 | 32.42 A | C |

TABLE 12-continued

Coordinates for pro MMP9(35-444 ΔFnII) (SEQ ID NO: 12) complex with Example 2

| ATOM | 1075 | CG2 | VAL | A | 172 | 28.408 | 54.650 | 21.081 | 1.00 | 41.39 | A | C |
|------|------|-----|-----|---|-----|--------|--------|--------|------|-------|---|---|
| ATOM | 1076 | C   | VAL | A | 172 | 27.474 | 57.504 | 21.294 | 1.00 | 39.89 | A | C |
| ATOM | 1077 | O   | VAL | A | 172 | 28.504 | 57.739 | 21.931 | 1.00 | 41.29 | A | O |
| ATOM | 1078 | N   | ALA | A | 173 | 26.272 | 57.919 | 21.675 | 1.00 | 41.08 | A | N |
| ATOM | 1079 | CA  | ALA | A | 173 | 26.084 | 58.517 | 22.976 | 1.00 | 42.22 | A | C |
| ATOM | 1080 | CB  | ALA | A | 173 | 26.255 | 57.473 | 24.041 | 1.00 | 41.24 | A | C |
| ATOM | 1081 | C   | ALA | A | 173 | 27.133 | 59.589 | 23.127 | 1.00 | 39.63 | A | C |
| ATOM | 1082 | O   | ALA | A | 173 | 27.348 | 60.385 | 22.217 | 1.00 | 39.45 | A | O |
| ATOM | 1083 | N   | GLU | A | 174 | 27.789 | 59.616 | 24.277 | 1.00 | 40.86 | A | N |
| ATOM | 1084 | CA  | GLU | A | 174 | 28.902 | 60.535 | 24.429 | 1.00 | 48.13 | A | C |
| ATOM | 1085 | CB  | GLU | A | 174 | 29.227 | 60.821 | 25.885 | 1.00 | 45.08 | A | C |
| ATOM | 1086 | CG  | GLU | A | 174 | 30.487 | 61.666 | 26.023 | 1.00 | 46.91 | A | C |
| ATOM | 1087 | CD  | GLU | A | 174 | 30.399 | 62.983 | 25.263 | 1.00 | 48.50 | A | C |
| ATOM | 1088 | OE1 | GLU | A | 174 | 29.808 | 63.021 | 24.153 | 1.00 | 51.41 | A | O |
| ATOM | 1089 | OE2 | GLU | A | 174 | 30.936 | 63.991 | 25.773 | 1.00 | 54.97 | A | O |
| ATOM | 1090 | C   | GLU | A | 174 | 30.136 | 59.990 | 23.724 | 1.00 | 45.16 | A | C |
| ATOM | 1091 | O   | GLU | A | 174 | 30.664 | 58.923 | 24.079 | 1.00 | 39.72 | A | O |
| ATOM | 1092 | N   | HIS | A | 175 | 30.604 | 60.746 | 22.740 | 1.00 | 42.65 | A | N |
| ATOM | 1093 | CA  | HIS | A | 175 | 31.686 | 60.295 | 21.874 | 1.00 | 39.48 | A | C |
| ATOM | 1094 | CB  | HIS | A | 175 | 31.128 | 60.040 | 20.483 | 1.00 | 42.18 | A | C |
| ATOM | 1095 | CG  | HIS | A | 175 | 30.431 | 61.225 | 19.899 | 1.00 | 40.69 | A | C |
| ATOM | 1096 | CD2 | HIS | A | 175 | 30.364 | 61.679 | 18.629 | 1.00 | 44.05 | A | C |
| ATOM | 1097 | ND1 | HIS | A | 175 | 29.699 | 62.108 | 20.661 | 1.00 | 44.14 | A | N |
| ATOM | 1098 | CE1 | HIS | A | 175 | 29.213 | 63.056 | 19.884 | 1.00 | 41.54 | A | C |
| ATOM | 1099 | NE2 | HIS | A | 175 | 29.598 | 62.816 | 18.645 | 1.00 | 38.50 | A | N |
| ATOM | 1100 | C   | HIS | A | 175 | 32.870 | 61.277 | 21.827 | 1.00 | 44.29 | A | C |
| ATOM | 1101 | O   | HIS | A | 175 | 33.678 | 61.263 | 20.896 | 1.00 | 40.22 | A | O |
| ATOM | 1102 | N   | GLY | A | 176 | 32.965 | 62.136 | 22.825 | 1.00 | 38.00 | A | N |
| ATOM | 1103 | CA  | GLY | A | 176 | 34.185 | 62.884 | 23.021 | 1.00 | 42.71 | A | C |
| ATOM | 1104 | C   | GLY | A | 176 | 34.085 | 64.380 | 22.859 | 1.00 | 45.76 | A | C |
| ATOM | 1105 | O   | GLY | A | 176 | 35.089 | 65.073 | 23.035 | 1.00 | 46.26 | A | O |
| ATOM | 1106 | N   | ASP | A | 177 | 32.898 | 64.890 | 22.528 | 1.00 | 43.51 | A | N |
| ATOM | 1107 | CA  | ASP | A | 177 | 32.777 | 66.331 | 22.270 | 1.00 | 45.89 | A | C |
| ATOM | 1108 | CB  | ASP | A | 177 | 32.415 | 66.625 | 20.808 | 1.00 | 40.81 | A | C |
| ATOM | 1109 | CG  | ASP | A | 177 | 31.151 | 65.920 | 20.348 | 1.00 | 39.85 | A | C |
| ATOM | 1110 | OD1 | ASP | A | 177 | 30.454 | 65.285 | 21.172 | 1.00 | 40.46 | A | O |
| ATOM | 1111 | OD2 | ASP | A | 177 | 30.865 | 66.016 | 19.140 | 1.00 | 28.10 | A | O |
| ATOM | 1112 | C   | ASP | A | 177 | 31.858 | 67.127 | 23.196 | 1.00 | 47.53 | A | C |
| ATOM | 1113 | O   | ASP | A | 177 | 31.838 | 68.352 | 23.111 | 1.00 | 44.07 | A | O |
| ATOM | 1114 | N   | GLY | A | 178 | 31.113 | 66.443 | 24.068 | 1.00 | 52.24 | A | N |
| ATOM | 1115 | CA  | GLY | A | 178 | 30.147 | 67.106 | 24.942 | 1.00 | 48.03 | A | C |
| ATOM | 1116 | C   | GLY | A | 178 | 28.830 | 67.454 | 24.260 | 1.00 | 45.80 | A | C |
| ATOM | 1117 | O   | GLY | A | 178 | 28.063 | 68.292 | 24.740 | 1.00 | 50.76 | A | O |
| ATOM | 1118 | N   | TYR | A | 179 | 28.592 | 66.824 | 23.118 | 1.00 | 39.99 | A | N |
| ATOM | 1119 | CA  | TYR | A | 179 | 27.320 | 66.887 | 22.433 | 1.00 | 38.05 | A | C |
| ATOM | 1120 | CB  | TYR | A | 179 | 27.426 | 67.711 | 21.150 | 1.00 | 37.84 | A | C |
| ATOM | 1121 | CG  | TYR | A | 179 | 27.826 | 69.148 | 21.387 | 1.00 | 46.63 | A | C |
| ATOM | 1122 | CD1 | TYR | A | 179 | 29.165 | 69.498 | 21.552 | 1.00 | 42.26 | A | C |
| ATOM | 1123 | CE1 | TYR | A | 179 | 29.545 | 70.804 | 21.774 | 1.00 | 45.26 | A | C |
| ATOM | 1124 | CD2 | TYR | A | 179 | 26.874 | 70.156 | 21.453 | 1.00 | 45.56 | A | C |
| ATOM | 1125 | CE2 | TYR | A | 179 | 27.249 | 71.477 | 21.672 | 1.00 | 48.97 | A | C |
| ATOM | 1126 | CZ  | TYR | A | 179 | 28.587 | 71.788 | 21.833 | 1.00 | 42.42 | A | C |
| ATOM | 1127 | OH  | TYR | A | 179 | 28.968 | 73.083 | 22.054 | 1.00 | 48.46 | A | O |
| ATOM | 1128 | C   | TYR | A | 179 | 26.941 | 65.444 | 22.108 | 1.00 | 40.86 | A | C |
| ATOM | 1129 | O   | TYR | A | 179 | 27.033 | 65.012 | 20.963 | 1.00 | 43.07 | A | O |
| ATOM | 1130 | N   | PRO | A | 180 | 26.512 | 64.694 | 23.127 | 1.00 | 41.83 | A | N |
| ATOM | 1131 | CD  | PRO | A | 180 | 26.199 | 65.239 | 24.460 | 1.00 | 44.60 | A | C |
| ATOM | 1132 | CA  | PRO | A | 180 | 26.247 | 63.256 | 23.036 | 1.00 | 42.09 | A | C |
| ATOM | 1133 | CB  | PRO | A | 180 | 25.755 | 62.897 | 24.445 | 1.00 | 43.93 | A | C |
| ATOM | 1134 | CG  | PRO | A | 180 | 26.215 | 64.020 | 25.330 | 1.00 | 46.79 | A | C |
| ATOM | 1135 | C   | PRO | A | 180 | 25.158 | 62.931 | 22.037 | 1.00 | 35.93 | A | C |
| ATOM | 1136 | O   | PRO | A | 180 | 24.256 | 63.721 | 21.827 | 1.00 | 33.90 | A | O |
| ATOM | 1137 | N   | PHE | A | 181 | 25.257 | 61.776 | 21.405 | 1.00 | 35.55 | A | N |
| ATOM | 1138 | CA  | PHE | A | 181 | 24.176 | 61.302 | 20.577 | 1.00 | 34.50 | A | C |
| ATOM | 1139 | CB  | PHE | A | 181 | 24.688 | 60.320 | 19.538 | 1.00 | 36.99 | A | C |
| ATOM | 1140 | CG  | PHE | A | 181 | 25.388 | 60.984 | 18.381 | 1.00 | 39.75 | A | C |
| ATOM | 1141 | CD1 | PHE | A | 181 | 24.748 | 61.969 | 17.642 | 1.00 | 35.92 | A | C |
| ATOM | 1142 | CD2 | PHE | A | 181 | 26.680 | 60.622 | 18.027 | 1.00 | 41.58 | A | C |
| ATOM | 1143 | CE1 | PHE | A | 181 | 25.382 | 62.579 | 16.570 | 1.00 | 42.20 | A | C |
| ATOM | 1144 | CE2 | PHE | A | 181 | 27.316 | 61.234 | 16.965 | 1.00 | 35.23 | A | C |
| ATOM | 1145 | CZ  | PHE | A | 181 | 26.669 | 62.210 | 16.233 | 1.00 | 34.90 | A | C |
| ATOM | 1146 | C   | PHE | A | 181 | 23.129 | 60.664 | 21.494 | 1.00 | 39.63 | A | C |
| ATOM | 1147 | O   | PHE | A | 181 | 23.317 | 60.617 | 22.713 | 1.00 | 36.58 | A | O |
| ATOM | 1148 | N   | ASP | A | 182 | 22.048 | 60.172 | 20.903 | 1.00 | 37.05 | A | N |
| ATOM | 1149 | CA  | ASP | A | 182 | 20.852 | 59.822 | 21.650 | 1.00 | 38.32 | A | C |
| ATOM | 1150 | CB  | ASP | A | 182 | 19.803 | 60.898 | 21.396 | 1.00 | 31.69 | A | C |
| ATOM | 1151 | CG  | ASP | A | 182 | 19.381 | 60.953 | 19.946 | 1.00 | 38.75 | A | C |

TABLE 12-continued

Coordinates for pro MMP9(35-444 ΔFnII) (SEQ ID NO: 12) complex with Example 2

| ATOM | 1152 | OD1 | ASP | A | 182 | 19.959 | 60.207 | 19.136 | 1.00 | 39.74 | A | O |
|---|---|---|---|---|---|---|---|---|---|---|---|---|
| ATOM | 1153 | OD2 | ASP | A | 182 | 18.476 | 61.735 | 19.596 | 1.00 | 41.97 | A | O |
| ATOM | 1154 | C | ASP | A | 182 | 20.276 | 58.461 | 21.261 | 1.00 | 40.11 | A | C |
| ATOM | 1155 | O | ASP | A | 182 | 19.060 | 58.275 | 21.279 | 1.00 | 39.50 | A | O |
| ATOM | 1156 | N | GLY | A | 183 | 21.135 | 57.509 | 20.905 | 1.00 | 36.64 | A | N |
| ATOM | 1157 | CA | GLY | A | 183 | 20.676 | 56.162 | 20.592 | 1.00 | 29.13 | A | C |
| ATOM | 1158 | C | GLY | A | 183 | 19.854 | 56.184 | 19.329 | 1.00 | 38.57 | A | C |
| ATOM | 1159 | O | GLY | A | 183 | 19.841 | 57.200 | 18.640 | 1.00 | 39.70 | A | O |
| ATOM | 1160 | N | LYS | A | 184 | 19.139 | 55.098 | 19.035 | 1.00 | 35.06 | A | N |
| ATOM | 1161 | CA | LYS | A | 184 | 18.525 | 54.946 | 17.717 | 1.00 | 33.16 | A | C |
| ATOM | 1162 | CB | LYS | A | 184 | 17.859 | 53.579 | 17.561 | 1.00 | 36.65 | A | C |
| ATOM | 1163 | CG | LYS | A | 184 | 17.603 | 53.207 | 16.111 | 1.00 | 38.12 | A | C |
| ATOM | 1164 | CD | LYS | A | 184 | 16.993 | 51.823 | 15.961 | 1.00 | 37.42 | A | C |
| ATOM | 1165 | CE | LYS | A | 184 | 15.551 | 51.937 | 15.526 | 1.00 | 41.09 | A | C |
| ATOM | 1166 | NZ | LYS | A | 184 | 15.044 | 50.618 | 15.091 | 1.00 | 55.97 | A | N |
| ATOM | 1167 | C | LYS | A | 184 | 17.534 | 56.047 | 17.381 | 1.00 | 39.29 | A | C |
| ATOM | 1168 | O | LYS | A | 184 | 16.788 | 56.491 | 18.248 | 1.00 | 42.90 | A | O |
| ATOM | 1169 | N | ASP | A | 185 | 17.541 | 56.476 | 16.116 | 1.00 | 38.95 | A | N |
| ATOM | 1170 | CA | ASP | A | 185 | 16.667 | 57.545 | 15.608 | 1.00 | 38.91 | A | C |
| ATOM | 1171 | CB | ASP | A | 185 | 15.197 | 57.098 | 15.592 | 1.00 | 36.81 | A | C |
| ATOM | 1172 | CG | ASP | A | 185 | 14.960 | 55.913 | 14.677 | 1.00 | 42.98 | A | C |
| ATOM | 1173 | OD1 | ASP | A | 185 | 15.496 | 55.913 | 13.542 | 1.00 | 39.11 | A | O |
| ATOM | 1174 | OD2 | ASP | A | 185 | 14.238 | 54.976 | 15.090 | 1.00 | 44.37 | A | O |
| ATOM | 1175 | C | ASP | A | 185 | 16.839 | 58.873 | 16.369 | 1.00 | 39.84 | A | C |
| ATOM | 1176 | O | ASP | A | 185 | 17.775 | 59.041 | 17.140 | 1.00 | 36.15 | A | O |
| ATOM | 1177 | N | GLY | A | 186 | 15.932 | 59.820 | 16.156 | 1.00 | 33.09 | A | N |
| ATOM | 1178 | CA | GLY | A | 186 | 16.137 | 61.144 | 16.728 | 1.00 | 38.52 | A | C |
| ATOM | 1179 | C | GLY | A | 186 | 17.212 | 61.922 | 15.966 | 1.00 | 33.48 | A | C |
| ATOM | 1180 | O | GLY | A | 186 | 17.092 | 62.088 | 14.756 | 1.00 | 30.67 | A | O |
| ATOM | 1181 | N | LEU | A | 187 | 18.218 | 62.421 | 16.687 | 1.00 | 34.59 | A | N |
| ATOM | 1182 | CA | LEU | A | 187 | 19.400 | 63.060 | 16.101 | 1.00 | 38.17 | A | C |
| ATOM | 1183 | CB | LEU | A | 187 | 20.355 | 63.500 | 17.203 | 1.00 | 33.91 | A | C |
| ATOM | 1184 | CG | LEU | A | 187 | 20.162 | 64.847 | 17.868 | 1.00 | 38.96 | A | C |
| ATOM | 1185 | CD1 | LEU | A | 187 | 18.693 | 65.047 | 18.200 | 1.00 | 42.27 | A | C |
| ATOM | 1186 | CD2 | LEU | A | 187 | 21.002 | 64.888 | 19.112 | 1.00 | 34.78 | A | C |
| ATOM | 1187 | C | LEU | A | 187 | 20.177 | 62.065 | 15.265 | 1.00 | 36.34 | A | C |
| ATOM | 1188 | O | LEU | A | 187 | 20.555 | 61.030 | 15.771 | 1.00 | 33.51 | A | O |
| ATOM | 1189 | N | LEU | A | 188 | 20.451 | 62.376 | 14.005 | 1.00 | 32.50 | A | N |
| ATOM | 1190 | CA | LEU | A | 188 | 21.205 | 61.447 | 13.174 | 1.00 | 31.84 | A | C |
| ATOM | 1191 | CB | LEU | A | 188 | 20.681 | 61.488 | 11.751 | 1.00 | 26.47 | A | C |
| ATOM | 1192 | CG | LEU | A | 188 | 19.221 | 61.053 | 11.629 | 1.00 | 26.96 | A | C |
| ATOM | 1193 | CD1 | LEU | A | 188 | 18.818 | 60.983 | 10.193 | 1.00 | 23.19 | A | C |
| ATOM | 1194 | CD2 | LEU | A | 188 | 19.012 | 59.710 | 12.340 | 1.00 | 30.11 | A | C |
| ATOM | 1195 | C | LEU | A | 188 | 22.730 | 61.679 | 13.192 | 1.00 | 36.14 | A | C |
| ATOM | 1196 | O | LEU | A | 188 | 23.502 | 60.736 | 13.011 | 1.00 | 32.78 | A | O |
| ATOM | 1197 | N | ALA | A | 189 | 23.147 | 62.915 | 13.445 | 1.00 | 34.06 | A | N |
| ATOM | 1198 | CA | ALA | A | 189 | 24.527 | 63.333 | 13.214 | 1.00 | 32.49 | A | C |
| ATOM | 1199 | CB | ALA | A | 189 | 24.919 | 63.008 | 11.803 | 1.00 | 30.03 | A | C |
| ATOM | 1200 | C | ALA | A | 189 | 24.676 | 64.824 | 13.416 | 1.00 | 35.57 | A | C |
| ATOM | 1201 | O | ALA | A | 189 | 23.695 | 65.557 | 13.455 | 1.00 | 32.73 | A | O |
| ATOM | 1202 | N | HIS | A | 190 | 25.913 | 65.290 | 13.504 | 1.00 | 35.42 | A | N |
| ATOM | 1203 | CA | HIS | A | 190 | 26.139 | 66.722 | 13.499 | 1.00 | 30.33 | A | C |
| ATOM | 1204 | CB | HIS | A | 190 | 25.971 | 67.285 | 14.892 | 1.00 | 31.73 | A | C |
| ATOM | 1205 | CG | HIS | A | 190 | 26.809 | 66.600 | 15.913 | 1.00 | 36.95 | A | C |
| ATOM | 1206 | CD2 | HIS | A | 190 | 28.070 | 66.114 | 15.844 | 1.00 | 36.72 | A | C |
| ATOM | 1207 | ND1 | HIS | A | 190 | 26.364 | 66.342 | 17.193 | 1.00 | 37.81 | A | N |
| ATOM | 1208 | CE1 | HIS | A | 190 | 27.323 | 65.734 | 17.871 | 1.00 | 38.27 | A | C |
| ATOM | 1209 | NE2 | HIS | A | 190 | 28.365 | 65.580 | 17.074 | 1.00 | 32.13 | A | N |
| ATOM | 1210 | C | HIS | A | 190 | 27.521 | 67.106 | 12.988 | 1.00 | 38.91 | A | C |
| ATOM | 1211 | O | HIS | A | 190 | 28.369 | 66.249 | 12.702 | 1.00 | 29.31 | A | O |
| ATOM | 1212 | N | ALA | A | 191 | 27.749 | 68.413 | 12.924 | 1.00 | 36.50 | A | N |
| ATOM | 1213 | CA | ALA | A | 191 | 28.993 | 68.928 | 12.384 | 1.00 | 35.36 | A | C |
| ATOM | 1214 | CB | ALA | A | 191 | 28.998 | 68.798 | 10.881 | 1.00 | 23.07 | A | C |
| ATOM | 1215 | C | ALA | A | 191 | 29.145 | 70.383 | 12.789 | 1.00 | 39.61 | A | C |
| ATOM | 1216 | O | ALA | A | 191 | 28.152 | 71.089 | 13.042 | 1.00 | 31.75 | A | O |
| ATOM | 1217 | N | PHE | A | 192 | 30.397 | 70.817 | 12.827 | 1.00 | 29.58 | A | N |
| ATOM | 1218 | CA | PHE | A | 192 | 30.746 | 72.145 | 13.282 | 1.00 | 32.07 | A | C |
| ATOM | 1219 | CB | PHE | A | 192 | 31.792 | 72.020 | 14.370 | 1.00 | 35.62 | A | C |
| ATOM | 1220 | CG | PHE | A | 192 | 31.467 | 70.987 | 15.418 | 1.00 | 37.98 | A | C |
| ATOM | 1221 | CD1 | PHE | A | 192 | 31.230 | 71.365 | 16.726 | 1.00 | 37.11 | A | C |
| ATOM | 1222 | CD2 | PHE | A | 192 | 31.407 | 69.645 | 15.095 | 1.00 | 39.76 | A | C |
| ATOM | 1223 | CE1 | PHE | A | 192 | 30.953 | 70.427 | 17.695 | 1.00 | 40.37 | A | C |
| ATOM | 1224 | CE2 | PHE | A | 192 | 31.121 | 68.701 | 16.060 | 1.00 | 40.71 | A | C |
| ATOM | 1225 | CZ | PHE | A | 192 | 30.893 | 69.096 | 17.364 | 1.00 | 41.36 | A | C |
| ATOM | 1226 | C | PHE | A | 192 | 31.275 | 73.005 | 12.123 | 1.00 | 35.65 | A | C |
| ATOM | 1227 | O | PHE | A | 192 | 31.880 | 72.497 | 11.183 | 1.00 | 36.24 | A | O |
| ATOM | 1228 | N | PRO | A | 193 | 31.055 | 74.318 | 12.201 | 1.00 | 34.67 | A | N |

TABLE 12-continued

Coordinates for pro MMP9(35-444 ΔFnII) (SEQ ID NO: 12) complex with Example 2

| ATOM | 1229 | CD  | PRO | A | 193 | 30.590 | 75.020 | 13.407 | 1.00 | 28.79 | A | C |
|------|------|-----|-----|---|-----|--------|--------|--------|------|-------|---|---|
| ATOM | 1230 | CA  | PRO | A | 193 | 31.405 | 75.248 | 11.119 | 1.00 | 34.65 | A | C |
| ATOM | 1231 | CB  | PRO | A | 193 | 30.917 | 76.588 | 11.653 | 1.00 | 29.53 | A | C |
| ATOM | 1232 | CG  | PRO | A | 193 | 31.085 | 76.424 | 13.169 | 1.00 | 36.90 | A | C |
| ATOM | 1233 | C   | PRO | A | 193 | 32.917 | 75.323 | 10.977 | 1.00 | 34.52 | A | C |
| ATOM | 1234 | O   | PRO | A | 193 | 33.626 | 74.953 | 11.913 | 1.00 | 35.07 | A | O |
| ATOM | 1235 | N   | PRO | A | 194 | 33.397 | 75.830 | 9.830  | 1.00 | 36.03 | A | N |
| ATOM | 1236 | CD  | PRO | A | 194 | 32.537 | 76.202 | 8.694  | 1.00 | 33.20 | A | C |
| ATOM | 1237 | CA  | PRO | A | 194 | 34.824 | 76.001 | 9.515  | 1.00 | 35.65 | A | C |
| ATOM | 1238 | CB  | PRO | A | 194 | 34.796 | 76.934 | 8.301  | 1.00 | 35.65 | A | C |
| ATOM | 1239 | CG  | PRO | A | 194 | 33.539 | 76.550 | 7.587  | 1.00 | 33.79 | A | C |
| ATOM | 1240 | C   | PRO | A | 194 | 35.630 | 76.636 | 10.638 | 1.00 | 33.22 | A | C |
| ATOM | 1241 | O   | PRO | A | 194 | 35.173 | 77.568 | 11.284 | 1.00 | 32.62 | A | O |
| ATOM | 1242 | N   | GLY | A | 195 | 36.840 | 76.129 | 10.853 | 1.00 | 38.40 | A | N |
| ATOM | 1243 | CA  | GLY | A | 195 | 37.747 | 76.714 | 11.824 | 1.00 | 34.27 | A | C |
| ATOM | 1244 | C   | GLY | A | 195 | 38.769 | 75.741 | 12.376 | 1.00 | 32.87 | A | C |
| ATOM | 1245 | O   | GLY | A | 195 | 38.941 | 74.647 | 11.859 | 1.00 | 35.51 | A | O |
| ATOM | 1246 | N   | PRO | A | 196 | 39.436 | 76.141 | 13.459 | 1.00 | 32.51 | A | N |
| ATOM | 1247 | CD  | PRO | A | 196 | 39.236 | 77.495 | 13.985 | 1.00 | 33.53 | A | C |
| ATOM | 1248 | CA  | PRO | A | 196 | 40.449 | 75.395 | 14.213 | 1.00 | 37.94 | A | C |
| ATOM | 1249 | CB  | PRO | A | 196 | 40.942 | 76.414 | 15.250 | 1.00 | 34.07 | A | C |
| ATOM | 1250 | CG  | PRO | A | 196 | 40.468 | 77.721 | 14.790 | 1.00 | 41.17 | A | C |
| ATOM | 1251 | C   | PRO | A | 196 | 39.869 | 74.214 | 14.971 | 1.00 | 43.64 | A | C |
| ATOM | 1252 | O   | PRO | A | 196 | 38.754 | 74.283 | 15.500 | 1.00 | 43.08 | A | O |
| ATOM | 1253 | N   | GLY | A | 197 | 40.644 | 73.143 | 15.041 | 1.00 | 39.76 | A | N |
| ATOM | 1254 | CA  | GLY | A | 197 | 40.365 | 72.059 | 15.948 | 1.00 | 40.08 | A | C |
| ATOM | 1255 | C   | GLY | A | 197 | 39.195 | 71.201 | 15.537 | 1.00 | 46.40 | A | C |
| ATOM | 1256 | O   | GLY | A | 197 | 39.235 | 70.531 | 14.514 | 1.00 | 42.59 | A | O |
| ATOM | 1257 | N   | ILE | A | 198 | 38.151 | 71.226 | 16.356 | 1.00 | 42.14 | A | N |
| ATOM | 1258 | CA  | ILE | A | 198 | 36.975 | 70.405 | 16.144 | 1.00 | 42.92 | A | C |
| ATOM | 1259 | CB  | ILE | A | 198 | 36.202 | 70.233 | 17.468 | 1.00 | 42.35 | A | C |
| ATOM | 1260 | CG2 | ILE | A | 198 | 35.684 | 71.602 | 17.982 | 1.00 | 34.79 | A | C |
| ATOM | 1261 | CG1 | ILE | A | 198 | 35.075 | 69.223 | 17.285 | 1.00 | 41.12 | A | C |
| ATOM | 1262 | CD1 | ILE | A | 198 | 34.456 | 68.762 | 18.592 | 1.00 | 46.02 | A | C |
| ATOM | 1263 | C   | ILE | A | 198 | 36.092 | 71.049 | 15.080 | 1.00 | 37.02 | A | C |
| ATOM | 1264 | O   | ILE | A | 198 | 35.412 | 70.373 | 14.300 | 1.00 | 39.58 | A | O |
| ATOM | 1265 | N   | GLN | A | 199 | 36.120 | 72.368 | 15.032 | 1.00 | 35.42 | A | N |
| ATOM | 1266 | CA  | GLN | A | 199 | 35.398 | 73.060 | 13.991 | 1.00 | 36.83 | A | C |
| ATOM | 1267 | CB  | GLN | A | 199 | 35.748 | 74.545 | 14.011 | 1.00 | 36.87 | A | C |
| ATOM | 1268 | CG  | GLN | A | 199 | 35.308 | 75.195 | 15.313 | 1.00 | 37.86 | A | C |
| ATOM | 1269 | CD  | GLN | A | 199 | 35.548 | 76.681 | 15.363 | 1.00 | 36.36 | A | C |
| ATOM | 1270 | OE1 | GLN | A | 199 | 35.268 | 77.405 | 14.407 | 1.00 | 37.90 | A | O |
| ATOM | 1271 | NE2 | GLN | A | 199 | 36.079 | 77.146 | 16.486 | 1.00 | 36.32 | A | N |
| ATOM | 1272 | C   | GLN | A | 199 | 35.709 | 72.419 | 12.647 | 1.00 | 40.12 | A | C |
| ATOM | 1273 | O   | GLN | A | 199 | 36.845 | 72.070 | 12.371 | 1.00 | 37.82 | A | O |
| ATOM | 1274 | N   | GLY | A | 200 | 34.687 | 72.257 | 11.817 | 1.00 | 35.22 | A | N |
| ATOM | 1275 | CA  | GLY | A | 200 | 34.839 | 71.574 | 10.558 | 1.00 | 27.82 | A | C |
| ATOM | 1276 | C   | GLY | A | 200 | 34.533 | 70.086 | 10.690 | 1.00 | 28.02 | A | C |
| ATOM | 1277 | O   | GLY | A | 200 | 34.218 | 69.431 | 9.701  | 1.00 | 28.40 | A | O |
| ATOM | 1278 | N   | ASP | A | 201 | 34.639 | 69.536 | 11.892 | 1.00 | 27.66 | A | N |
| ATOM | 1279 | CA  | ASP | A | 201 | 34.435 | 68.083 | 12.050 | 1.00 | 31.79 | A | C |
| ATOM | 1280 | CB  | ASP | A | 201 | 34.969 | 67.605 | 13.392 | 1.00 | 31.24 | A | C |
| ATOM | 1281 | CG  | ASP | A | 201 | 36.476 | 67.611 | 13.438 | 1.00 | 36.87 | A | C |
| ATOM | 1282 | OD1 | ASP | A | 201 | 37.093 | 67.990 | 12.411 | 1.00 | 33.76 | A | O |
| ATOM | 1283 | OD2 | ASP | A | 201 | 37.030 | 67.248 | 14.495 | 1.00 | 38.77 | A | O |
| ATOM | 1284 | C   | ASP | A | 201 | 32.986 | 67.619 | 11.872 | 1.00 | 29.98 | A | C |
| ATOM | 1285 | O   | ASP | A | 201 | 32.056 | 68.397 | 12.082 | 1.00 | 27.07 | A | O |
| ATOM | 1286 | N   | ALA | A | 202 | 32.818 | 66.359 | 11.477 | 1.00 | 28.93 | A | N |
| ATOM | 1287 | CA  | ALA | A | 202 | 31.506 | 65.788 | 11.207 | 1.00 | 33.46 | A | C |
| ATOM | 1288 | CB  | ALA | A | 202 | 31.284 | 65.693 | 9.706  | 1.00 | 31.07 | A | C |
| ATOM | 1289 | C   | ALA | A | 202 | 31.300 | 64.409 | 11.858 | 1.00 | 35.35 | A | C |
| ATOM | 1290 | O   | ALA | A | 202 | 31.980 | 63.444 | 11.508 | 1.00 | 33.67 | A | O |
| ATOM | 1291 | N   | HIS | A | 203 | 30.335 | 64.311 | 12.771 | 1.00 | 33.44 | A | N |
| ATOM | 1292 | CA  | HIS | A | 203 | 30.049 | 63.053 | 13.472 | 1.00 | 31.74 | A | C |
| ATOM | 1293 | CB  | HIS | A | 203 | 30.147 | 63.297 | 14.961 | 1.00 | 33.03 | A | C |
| ATOM | 1294 | CG  | HIS | A | 203 | 31.434 | 63.930 | 15.356 | 1.00 | 36.44 | A | C |
| ATOM | 1295 | CD2 | HIS | A | 203 | 32.677 | 63.805 | 14.840 | 1.00 | 34.93 | A | C |
| ATOM | 1296 | ND1 | HIS | A | 203 | 31.533 | 64.856 | 16.366 | 1.00 | 39.90 | A | N |
| ATOM | 1297 | CE1 | HIS | A | 203 | 32.782 | 65.264 | 16.476 | 1.00 | 39.48 | A | C |
| ATOM | 1298 | NE2 | HIS | A | 203 | 33.499 | 64.643 | 15.556 | 1.00 | 41.70 | A | N |
| ATOM | 1299 | C   | HIS | A | 203 | 28.710 | 62.387 | 13.116 | 1.00 | 33.98 | A | C |
| ATOM | 1300 | O   | HIS | A | 203 | 27.680 | 63.067 | 12.998 | 1.00 | 32.83 | A | O |
| ATOM | 1301 | N   | PHE | A | 204 | 28.744 | 61.066 | 12.944 | 1.00 | 30.19 | A | N |
| ATOM | 1302 | CA  | PHE | A | 204 | 27.564 | 60.268 | 12.598 | 1.00 | 32.67 | A | C |
| ATOM | 1303 | CB  | PHE | A | 204 | 27.809 | 59.505 | 11.309 | 1.00 | 31.59 | A | C |
| ATOM | 1304 | CG  | PHE | A | 204 | 28.164 | 60.390 | 10.182 | 1.00 | 35.12 | A | C |
| ATOM | 1305 | CD1 | PHE | A | 204 | 29.445 | 60.869 | 10.054 | 1.00 | 35.13 | A | C |

TABLE 12-continued

Coordinates for pro MMP9(35-444 ΔFnII) (SEQ ID NO: 12) complex with Example 2

| ATOM | 1306 | CD2 | PHE | A | 204 | 27.201 | 60.815 | 9.293 | 1.00 | 31.17 | A | C |
|------|------|-----|-----|---|-----|--------|--------|-------|------|-------|---|---|
| ATOM | 1307 | CE1 | PHE | A | 204 | 29.764 | 61.726 | 9.022 | 1.00 | 35.15 | A | C |
| ATOM | 1308 | CE2 | PHE | A | 204 | 27.514 | 61.656 | 8.261 | 1.00 | 29.77 | A | C |
| ATOM | 1309 | CZ  | PHE | A | 204 | 28.799 | 62.121 | 8.129 | 1.00 | 26.50 | A | C |
| ATOM | 1310 | C   | PHE | A | 204 | 27.188 | 59.274 | 13.673 | 1.00 | 33.67 | A | C |
| ATOM | 1311 | O   | PHE | A | 204 | 28.047 | 58.546 | 14.170 | 1.00 | 33.13 | A | O |
| ATOM | 1312 | N   | ASP | A | 205 | 25.894 | 59.225 | 14.005 | 1.00 | 36.16 | A | N |
| ATOM | 1313 | CA  | ASP | A | 205 | 25.402 | 58.386 | 15.093 | 1.00 | 32.51 | A | C |
| ATOM | 1314 | CB  | ASP | A | 205 | 24.018 | 58.829 | 15.599 | 1.00 | 36.04 | A | C |
| ATOM | 1315 | CG  | ASP | A | 205 | 23.601 | 58.077 | 16.888 | 1.00 | 38.97 | A | C |
| ATOM | 1316 | OD1 | ASP | A | 205 | 24.142 | 56.984 | 17.143 | 1.00 | 36.43 | A | O |
| ATOM | 1317 | OD2 | ASP | A | 205 | 22.767 | 58.585 | 17.665 | 1.00 | 38.39 | A | O |
| ATOM | 1318 | C   | ASP | A | 205 | 25.320 | 56.934 | 14.679 | 1.00 | 31.72 | A | C |
| ATOM | 1319 | O   | ASP | A | 205 | 24.396 | 56.529 | 13.962 | 1.00 | 30.03 | A | O |
| ATOM | 1320 | N   | ASP | A | 206 | 26.268 | 56.145 | 15.180 | 1.00 | 35.43 | A | N |
| ATOM | 1321 | CA  | ASP | A | 206 | 26.377 | 54.755 | 14.788 | 1.00 | 34.03 | A | C |
| ATOM | 1322 | CB  | ASP | A | 206 | 27.797 | 54.256 | 15.016 | 1.00 | 36.16 | A | C |
| ATOM | 1323 | CG  | ASP | A | 206 | 28.116 | 53.005 | 14.217 | 1.00 | 26.64 | A | C |
| ATOM | 1324 | OD1 | ASP | A | 206 | 27.469 | 52.714 | 13.181 | 1.00 | 23.12 | A | O |
| ATOM | 1325 | OD2 | ASP | A | 206 | 29.046 | 52.297 | 14.651 | 1.00 | 40.86 | A | O |
| ATOM | 1326 | C   | ASP | A | 206 | 25.354 | 53.857 | 15.485 | 1.00 | 36.31 | A | C |
| ATOM | 1327 | O   | ASP | A | 206 | 25.307 | 52.659 | 15.219 | 1.00 | 32.06 | A | O |
| ATOM | 1328 | N   | ASP | A | 207 | 24.536 | 54.437 | 16.363 | 1.00 | 35.09 | A | N |
| ATOM | 1329 | CA  | ASP | A | 207 | 23.346 | 53.743 | 16.855 | 1.00 | 36.67 | A | C |
| ATOM | 1330 | CB  | ASP | A | 207 | 22.799 | 54.358 | 18.157 | 1.00 | 35.77 | A | C |
| ATOM | 1331 | CG  | ASP | A | 207 | 23.528 | 53.849 | 19.404 | 1.00 | 35.38 | A | C |
| ATOM | 1332 | OD1 | ASP | A | 207 | 24.025 | 52.703 | 19.379 | 1.00 | 35.82 | A | O |
| ATOM | 1333 | OD2 | ASP | A | 207 | 23.627 | 54.593 | 20.405 | 1.00 | 32.10 | A | O |
| ATOM | 1334 | C   | ASP | A | 207 | 22.282 | 53.739 | 15.766 | 1.00 | 35.79 | A | C |
| ATOM | 1335 | O   | ASP | A | 207 | 21.238 | 53.130 | 15.926 | 1.00 | 40.02 | A | O |
| ATOM | 1336 | N   | GLU | A | 208 | 22.543 | 54.405 | 14.645 | 1.00 | 35.25 | A | N |
| ATOM | 1337 | CA  | GLU | A | 208 | 21.662 | 54.279 | 13.485 | 1.00 | 29.68 | A | C |
| ATOM | 1338 | CB  | GLU | A | 208 | 21.591 | 55.586 | 12.691 | 1.00 | 28.98 | A | C |
| ATOM | 1339 | CG  | GLU | A | 208 | 21.392 | 56.837 | 13.512 | 1.00 | 35.67 | A | C |
| ATOM | 1340 | CD  | GLU | A | 208 | 20.029 | 56.876 | 14.166 | 1.00 | 39.48 | A | C |
| ATOM | 1341 | OE1 | GLU | A | 208 | 19.170 | 56.020 | 13.826 | 1.00 | 31.07 | A | O |
| ATOM | 1342 | OE2 | GLU | A | 208 | 19.832 | 57.765 | 15.016 | 1.00 | 35.43 | A | O |
| ATOM | 1343 | C   | GLU | A | 208 | 22.150 | 53.202 | 12.532 | 1.00 | 31.79 | A | C |
| ATOM | 1344 | O   | GLU | A | 208 | 23.352 | 52.965 | 12.428 | 1.00 | 35.08 | A | O |
| ATOM | 1345 | N   | LEU | A | 209 | 21.230 | 52.582 | 11.796 | 1.00 | 28.93 | A | N |
| ATOM | 1346 | CA  | LEU | A | 209 | 21.631 | 51.659 | 10.746 | 1.00 | 31.71 | A | C |
| ATOM | 1347 | CB  | LEU | A | 209 | 20.506 | 50.694 | 10.361 | 1.00 | 31.99 | A | C |
| ATOM | 1348 | CG  | LEU | A | 209 | 20.775 | 49.672 | 9.251 | 1.00 | 31.34 | A | C |
| ATOM | 1349 | CD1 | LEU | A | 209 | 21.734 | 48.596 | 9.748 | 1.00 | 29.47 | A | C |
| ATOM | 1350 | CD2 | LEU | A | 209 | 19.476 | 49.047 | 8.731 | 1.00 | 32.60 | A | C |
| ATOM | 1351 | C   | LEU | A | 209 | 22.003 | 52.513 | 9.540 | 1.00 | 34.45 | A | C |
| ATOM | 1352 | O   | LEU | A | 209 | 21.140 | 53.157 | 8.930 | 1.00 | 31.60 | A | O |
| ATOM | 1353 | N   | TRP | A | 210 | 23.287 | 52.520 | 9.191 | 1.00 | 32.56 | A | N |
| ATOM | 1354 | CA  | TRP | A | 210 | 23.704 | 53.276 | 8.017 | 1.00 | 32.42 | A | C |
| ATOM | 1355 | CB  | TRP | A | 210 | 25.112 | 53.848 | 8.222 | 1.00 | 29.33 | A | C |
| ATOM | 1356 | CG  | TRP | A | 210 | 25.084 | 54.888 | 9.277 | 1.00 | 22.77 | A | C |
| ATOM | 1357 | CD2 | TRP | A | 210 | 24.497 | 56.189 | 9.161 | 1.00 | 25.25 | A | C |
| ATOM | 1358 | CE2 | TRP | A | 210 | 24.675 | 56.840 | 10.395 | 1.00 | 23.41 | A | C |
| ATOM | 1359 | CE3 | TRP | A | 210 | 23.844 | 56.871 | 8.122 | 1.00 | 30.29 | A | C |
| ATOM | 1360 | CD1 | TRP | A | 210 | 25.558 | 54.794 | 10.538 | 1.00 | 26.47 | A | C |
| ATOM | 1361 | NE1 | TRP | A | 210 | 25.343 | 55.973 | 11.220 | 1.00 | 22.82 | A | N |
| ATOM | 1362 | CZ2 | TRP | A | 210 | 24.214 | 58.140 | 10.630 | 1.00 | 25.61 | A | C |
| ATOM | 1363 | CZ3 | TRP | A | 210 | 23.393 | 58.174 | 8.355 | 1.00 | 20.72 | A | C |
| ATOM | 1364 | CH2 | TRP | A | 210 | 23.591 | 58.791 | 9.594 | 1.00 | 20.72 | A | C |
| ATOM | 1365 | C   | TRP | A | 210 | 23.561 | 52.436 | 6.758 | 1.00 | 32.67 | A | C |
| ATOM | 1366 | O   | TRP | A | 210 | 23.914 | 51.259 | 6.743 | 1.00 | 32.77 | A | O |
| ATOM | 1367 | N   | SER | A | 211 | 22.992 | 53.029 | 5.716 | 1.00 | 28.60 | A | N |
| ATOM | 1368 | CA  | SER | A | 211 | 22.938 | 52.355 | 4.435 | 1.00 | 29.73 | A | C |
| ATOM | 1369 | CB  | SER | A | 211 | 21.654 | 51.543 | 4.292 | 1.00 | 38.84 | A | C |
| ATOM | 1370 | OG  | SER | A | 211 | 20.525 | 52.400 | 4.178 | 1.00 | 39.82 | A | O |
| ATOM | 1371 | C   | SER | A | 211 | 23.032 | 53.379 | 3.321 | 1.00 | 28.13 | A | C |
| ATOM | 1372 | O   | SER | A | 211 | 23.526 | 54.492 | 3.497 | 1.00 | 28.42 | A | O |
| ATOM | 1373 | N   | LEU | A | 212 | 22.563 | 52.999 | 2.155 | 1.00 | 31.48 | A | N |
| ATOM | 1374 | CA  | LEU | A | 212 | 22.514 | 53.948 | 1.064 | 1.00 | 36.59 | A | C |
| ATOM | 1375 | CB  | LEU | A | 212 | 23.375 | 53.474 | −0.096 | 1.00 | 34.16 | A | C |
| ATOM | 1376 | CG  | LEU | A | 212 | 24.639 | 54.293 | −0.316 | 1.00 | 31.22 | A | C |
| ATOM | 1377 | CD1 | LEU | A | 212 | 25.570 | 54.141 | 0.846 | 1.00 | 29.54 | A | C |
| ATOM | 1378 | CD2 | LEU | A | 212 | 25.288 | 53.830 | −1.610 | 1.00 | 35.76 | A | C |
| ATOM | 1379 | C   | LEU | A | 212 | 21.087 | 54.012 | 0.617 | 1.00 | 42.23 | A | C |
| ATOM | 1380 | O   | LEU | A | 212 | 20.593 | 55.052 | 0.187 | 1.00 | 39.67 | A | O |
| ATOM | 1381 | N   | GLY | A | 213 | 20.433 | 52.863 | 0.739 | 1.00 | 51.39 | A | N |
| ATOM | 1382 | CA  | GLY | A | 213 | 19.085 | 52.684 | 0.248 | 1.00 | 55.69 | A | C |

TABLE 12-continued

Coordinates for pro MMP9(35-444 ΔFnII) (SEQ ID NO: 12) complex with Example 2

| ATOM | 1383 | C | GLY | A | 213 | 18.026 | 53.456 | 1.007 | 1.00 | 50.21 | A | C |
|---|---|---|---|---|---|---|---|---|---|---|---|---|
| ATOM | 1384 | O | GLY | A | 213 | 18.341 | 54.297 | 1.860 | 1.00 | 47.17 | A | O |
| ATOM | 1385 | N | LYS | A | 389 | 16.766 | 53.134 | 0.730 | 1.00 | 54.86 | A | N |
| ATOM | 1386 | CA | LYS | A | 389 | 16.398 | 51.955 | −0.074 | 1.00 | 54.61 | A | C |
| ATOM | 1387 | CB | LYS | A | 389 | 16.965 | 51.991 | −1.499 | 1.00 | 52.87 | A | C |
| ATOM | 1388 | CG | LYS | A | 389 | 16.496 | 53.187 | −2.314 | 1.00 | 55.29 | A | C |
| ATOM | 1389 | CD | LYS | A | 389 | 15.000 | 53.120 | −2.662 | 1.00 | 59.26 | A | C |
| ATOM | 1390 | CE | LYS | A | 389 | 14.740 | 52.274 | −3.919 | 1.00 | 60.06 | A | C |
| ATOM | 1391 | NZ | LYS | A | 389 | 13.600 | 52.802 | −4.749 | 1.00 | 56.51 | A | N |
| ATOM | 1392 | C | LYS | A | 389 | 16.750 | 50.645 | 0.631 | 1.00 | 53.94 | A | C |
| ATOM | 1393 | O | LYS | A | 389 | 17.919 | 50.367 | 0.944 | 1.00 | 48.23 | A | O |
| ATOM | 1394 | N | GLY | A | 390 | 15.710 | 49.850 | 0.866 | 1.00 | 49.25 | A | N |
| ATOM | 1395 | CA | GLY | A | 390 | 15.808 | 48.651 | 1.668 | 1.00 | 47.39 | A | C |
| ATOM | 1396 | C | GLY | A | 390 | 15.520 | 49.014 | 3.110 | 1.00 | 50.25 | A | C |
| ATOM | 1397 | O | GLY | A | 390 | 14.370 | 48.983 | 3.556 | 1.00 | 57.97 | A | O |
| ATOM | 1398 | N | GLN | A | 391 | 16.568 | 49.368 | 3.837 | 1.00 | 43.28 | A | N |
| ATOM | 1399 | CA | GLN | A | 391 | 16.443 | 49.761 | 5.223 | 1.00 | 40.21 | A | C |
| ATOM | 1400 | CB | GLN | A | 391 | 16.492 | 48.523 | 6.116 | 1.00 | 39.87 | A | C |
| ATOM | 1401 | CG | GLN | A | 391 | 15.254 | 47.615 | 5.924 | 1.00 | 44.25 | A | C |
| ATOM | 1402 | CD | GLN | A | 391 | 15.387 | 46.217 | 6.520 | 1.00 | 38.26 | A | C |
| ATOM | 1403 | OE1 | GLN | A | 391 | 15.910 | 46.035 | 7.622 | 1.00 | 40.73 | A | O |
| ATOM | 1404 | NE2 | GLN | A | 391 | 14.886 | 45.222 | 5.793 | 1.00 | 36.24 | A | N |
| ATOM | 1405 | C | GLN | A | 391 | 17.576 | 50.733 | 5.529 | 1.00 | 44.73 | A | C |
| ATOM | 1406 | O | GLN | A | 391 | 18.493 | 50.883 | 4.724 | 1.00 | 42.29 | A | O |
| ATOM | 1407 | N | GLY | A | 392 | 17.492 | 51.408 | 6.672 | 1.00 | 38.28 | A | N |
| ATOM | 1408 | CA | GLY | A | 392 | 18.540 | 52.297 | 7.128 | 1.00 | 30.99 | A | C |
| ATOM | 1409 | C | GLY | A | 392 | 18.477 | 53.662 | 6.481 | 1.00 | 36.64 | A | C |
| ATOM | 1410 | O | GLY | A | 392 | 17.744 | 53.871 | 5.509 | 1.00 | 34.19 | A | O |
| ATOM | 1411 | N | TYR | A | 393 | 19.260 | 54.587 | 7.032 | 1.00 | 37.67 | A | N |
| ATOM | 1412 | CA | TYR | A | 393 | 19.424 | 55.938 | 6.496 | 1.00 | 32.31 | A | C |
| ATOM | 1413 | CB | TYR | A | 393 | 19.722 | 56.900 | 7.641 | 1.00 | 30.99 | A | C |
| ATOM | 1414 | CG | TYR | A | 393 | 18.624 | 57.051 | 8.665 | 1.00 | 35.37 | A | C |
| ATOM | 1415 | CD1 | TYR | A | 393 | 17.525 | 57.869 | 8.413 | 1.00 | 34.11 | A | C |
| ATOM | 1416 | CE1 | TYR | A | 393 | 16.516 | 58.024 | 9.345 | 1.00 | 30.74 | A | C |
| ATOM | 1417 | CD2 | TYR | A | 393 | 18.696 | 56.399 | 9.895 | 1.00 | 35.46 | A | C |
| ATOM | 1418 | CE2 | TYR | A | 393 | 17.693 | 56.544 | 10.827 | 1.00 | 40.89 | A | C |
| ATOM | 1419 | CZ | TYR | A | 393 | 16.605 | 57.365 | 10.538 | 1.00 | 35.37 | A | C |
| ATOM | 1420 | OH | TYR | A | 393 | 15.609 | 57.526 | 11.454 | 1.00 | 40.33 | A | O |
| ATOM | 1421 | C | TYR | A | 393 | 20.602 | 56.036 | 5.507 | 1.00 | 33.64 | A | C |
| ATOM | 1422 | O | TYR | A | 393 | 21.625 | 55.397 | 5.695 | 1.00 | 31.02 | A | O |
| ATOM | 1423 | N | SER | A | 394 | 20.468 | 56.886 | 4.497 | 1.00 | 33.38 | A | N |
| ATOM | 1424 | CA | SER | A | 394 | 21.518 | 57.085 | 3.493 | 1.00 | 28.60 | A | C |
| ATOM | 1425 | CB | SER | A | 394 | 20.922 | 57.763 | 2.247 | 1.00 | 31.01 | A | C |
| ATOM | 1426 | OG | SER | A | 394 | 21.873 | 58.076 | 1.240 | 1.00 | 34.83 | A | O |
| ATOM | 1427 | C | SER | A | 394 | 22.697 | 57.887 | 4.046 | 1.00 | 28.77 | A | C |
| ATOM | 1428 | O | SER | A | 394 | 22.601 | 59.102 | 4.273 | 1.00 | 25.83 | A | O |
| ATOM | 1429 | N | LEU | A | 395 | 23.817 | 57.204 | 4.268 | 1.00 | 25.99 | A | N |
| ATOM | 1430 | CA | LEU | A | 395 | 25.051 | 57.898 | 4.616 | 1.00 | 30.77 | A | C |
| ATOM | 1431 | CB | LEU | A | 395 | 26.198 | 56.908 | 4.711 | 1.00 | 27.36 | A | C |
| ATOM | 1432 | CG | LEU | A | 395 | 27.474 | 57.436 | 5.354 | 1.00 | 29.25 | A | C |
| ATOM | 1433 | CD1 | LEU | A | 395 | 27.182 | 57.916 | 6.750 | 1.00 | 26.12 | A | C |
| ATOM | 1434 | CD2 | LEU | A | 395 | 28.534 | 56.341 | 5.363 | 1.00 | 23.17 | A | C |
| ATOM | 1435 | C | LEU | A | 395 | 25.391 | 58.989 | 3.598 | 1.00 | 23.86 | A | C |
| ATOM | 1436 | O | LEU | A | 395 | 25.801 | 60.080 | 3.953 | 1.00 | 31.47 | A | O |
| ATOM | 1437 | N | PHE | A | 396 | 25.198 | 58.687 | 2.331 | 1.00 | 24.58 | A | N |
| ATOM | 1438 | CA | PHE | A | 396 | 25.489 | 59.641 | 1.286 | 1.00 | 25.13 | A | C |
| ATOM | 1439 | CB | PHE | A | 396 | 25.078 | 59.066 | −0.073 | 1.00 | 24.32 | A | C |
| ATOM | 1440 | CG | PHE | A | 396 | 25.174 | 60.051 | −1.201 | 1.00 | 26.86 | A | C |
| ATOM | 1441 | CD1 | PHE | A | 396 | 26.310 | 60.862 | −1.346 | 1.00 | 29.65 | A | C |
| ATOM | 1442 | CD2 | PHE | A | 396 | 24.145 | 60.182 | −2.107 | 1.00 | 25.09 | A | C |
| ATOM | 1443 | CE1 | PHE | A | 396 | 26.409 | 61.786 | −2.379 | 1.00 | 21.52 | A | C |
| ATOM | 1444 | CE2 | PHE | A | 396 | 24.232 | 61.115 | −3.161 | 1.00 | 33.69 | A | C |
| ATOM | 1445 | CZ | PHE | A | 396 | 25.377 | 61.913 | −3.293 | 1.00 | 25.00 | A | C |
| ATOM | 1446 | C | PHE | A | 396 | 24.785 | 60.965 | 1.583 | 1.00 | 31.10 | A | C |
| ATOM | 1447 | O | PHE | A | 396 | 25.441 | 62.006 | 1.745 | 1.00 | 25.39 | A | O |
| ATOM | 1448 | N | LEU | A | 397 | 23.451 | 60.900 | 1.695 | 1.00 | 30.63 | A | N |
| ATOM | 1449 | CA | LEU | A | 397 | 22.595 | 62.077 | 1.905 | 1.00 | 28.84 | A | C |
| ATOM | 1450 | CB | LEU | A | 397 | 21.129 | 61.659 | 1.931 | 1.00 | 24.21 | A | C |
| ATOM | 1451 | CG | LEU | A | 397 | 20.585 | 61.350 | 0.541 | 1.00 | 23.84 | A | C |
| ATOM | 1452 | CD1 | LEU | A | 397 | 19.133 | 60.974 | 0.579 | 1.00 | 30.42 | A | C |
| ATOM | 1453 | CD2 | LEU | A | 397 | 20.776 | 62.580 | −0.331 | 1.00 | 29.27 | A | C |
| ATOM | 1454 | C | LEU | A | 397 | 22.920 | 62.857 | 3.158 | 1.00 | 24.45 | A | C |
| ATOM | 1455 | O | LEU | A | 397 | 23.092 | 64.072 | 3.106 | 1.00 | 25.25 | A | O |
| ATOM | 1456 | N | VAL | A | 398 | 22.992 | 62.153 | 4.281 | 1.00 | 19.58 | A | N |
| ATOM | 1457 | CA | VAL | A | 398 | 23.326 | 62.757 | 5.556 | 1.00 | 22.66 | A | C |
| ATOM | 1458 | CB | VAL | A | 398 | 23.299 | 61.671 | 6.684 | 1.00 | 25.46 | A | C |
| ATOM | 1459 | CG1 | VAL | A | 398 | 23.830 | 62.221 | 7.961 | 1.00 | 27.06 | A | C |

TABLE 12-continued

Coordinates for pro MMP9(35-444 ΔFnII) (SEQ ID NO: 12) complex with Example 2

| ATOM | 1460 | CG2 | VAL | A | 398 | 21.865 | 61.127 | 6.893 | 1.00 | 28.73 | A | C |
|---|---|---|---|---|---|---|---|---|---|---|---|---|
| ATOM | 1461 | C | VAL | A | 398 | 24.707 | 63.460 | 5.507 | 1.00 | 29.30 | A | C |
| ATOM | 1462 | O | VAL | A | 398 | 24.853 | 64.619 | 5.938 | 1.00 | 26.62 | A | O |
| ATOM | 1463 | N | ALA | A | 399 | 25.718 | 62.743 | 5.004 | 1.00 | 27.68 | A | N |
| ATOM | 1464 | CA | ALA | A | 399 | 27.063 | 63.318 | 4.832 | 1.00 | 28.70 | A | C |
| ATOM | 1465 | CB | ALA | A | 399 | 28.030 | 62.290 | 4.141 | 1.00 | 23.22 | A | C |
| ATOM | 1466 | C | ALA | A | 399 | 27.013 | 64.626 | 4.040 | 1.00 | 19.96 | A | C |
| ATOM | 1467 | O | ALA | A | 399 | 27.534 | 65.656 | 4.470 | 1.00 | 26.15 | A | O |
| ATOM | 1468 | N | ALA | A | 400 | 26.376 | 64.600 | 2.889 | 1.00 | 25.46 | A | N |
| ATOM | 1469 | CA | ALA | A | 400 | 26.204 | 65.834 | 2.118 | 1.00 | 21.78 | A | C |
| ATOM | 1470 | CB | ALA | A | 400 | 25.315 | 65.589 | 0.941 | 1.00 | 20.42 | A | C |
| ATOM | 1471 | C | ALA | A | 400 | 25.682 | 66.994 | 2.977 | 1.00 | 31.85 | A | C |
| ATOM | 1472 | O | ALA | A | 400 | 26.222 | 68.135 | 2.931 | 1.00 | 26.53 | A | O |
| ATOM | 1473 | N | HIS | A | 401 | 24.644 | 66.714 | 3.770 | 1.00 | 25.59 | A | N |
| ATOM | 1474 | CA | HIS | A | 401 | 24.075 | 67.746 | 4.636 | 1.00 | 26.62 | A | C |
| ATOM | 1475 | CB | HIS | A | 401 | 22.848 | 67.184 | 5.388 | 1.00 | 29.73 | A | C |
| ATOM | 1476 | CG | HIS | A | 401 | 22.241 | 68.139 | 6.367 | 1.00 | 23.42 | A | C |
| ATOM | 1477 | CD2 | HIS | A | 401 | 22.577 | 68.460 | 7.638 | 1.00 | 24.84 | A | C |
| ATOM | 1478 | ND1 | HIS | A | 401 | 21.121 | 68.886 | 6.069 | 1.00 | 24.58 | A | N |
| ATOM | 1479 | CE1 | HIS | A | 401 | 20.809 | 69.645 | 7.103 | 1.00 | 22.83 | A | C |
| ATOM | 1480 | NE2 | HIS | A | 401 | 21.666 | 69.400 | 8.078 | 1.00 | 18.99 | A | N |
| ATOM | 1481 | C | HIS | A | 401 | 25.113 | 68.239 | 5.621 | 1.00 | 22.18 | A | C |
| ATOM | 1482 | O | HIS | A | 401 | 25.348 | 69.446 | 5.760 | 1.00 | 22.06 | A | O |
| ATOM | 1483 | N | GLU | A | 402 | 25.731 | 67.311 | 6.339 | 1.00 | 24.84 | A | N |
| ATOM | 1484 | CA | GLU | A | 402 | 26.715 | 67.688 | 7.357 | 1.00 | 24.15 | A | C |
| ATOM | 1485 | CB | GLU | A | 402 | 27.140 | 66.479 | 8.191 | 1.00 | 26.68 | A | C |
| ATOM | 1486 | CG | GLU | A | 402 | 25.987 | 65.731 | 8.880 | 1.00 | 30.49 | A | C |
| ATOM | 1487 | CD | GLU | A | 402 | 25.229 | 66.577 | 9.878 | 1.00 | 29.67 | A | C |
| ATOM | 1488 | OE1 | GLU | A | 402 | 25.813 | 67.511 | 10.469 | 1.00 | 27.32 | A | O |
| ATOM | 1489 | OE2 | GLU | A | 402 | 24.025 | 66.294 | 10.077 | 1.00 | 35.89 | A | O |
| ATOM | 1490 | C | GLU | A | 402 | 27.985 | 68.348 | 6.783 | 1.00 | 24.01 | A | C |
| ATOM | 1491 | O | GLU | A | 402 | 28.619 | 69.151 | 7.461 | 1.00 | 25.88 | A | O |
| ATOM | 1492 | N | PHE | A | 403 | 28.373 | 68.001 | 5.560 | 1.00 | 27.66 | A | N |
| ATOM | 1493 | CA | PHE | A | 403 | 29.558 | 68.652 | 4.952 | 1.00 | 27.50 | A | C |
| ATOM | 1494 | CB | PHE | A | 403 | 30.005 | 67.930 | 3.674 | 1.00 | 22.21 | A | C |
| ATOM | 1495 | CG | PHE | A | 403 | 30.550 | 66.553 | 3.923 | 1.00 | 24.05 | A | C |
| ATOM | 1496 | CD1 | PHE | A | 403 | 30.907 | 66.163 | 5.206 | 1.00 | 28.46 | A | C |
| ATOM | 1497 | CD2 | PHE | A | 403 | 30.689 | 65.637 | 2.883 | 1.00 | 23.98 | A | C |
| ATOM | 1498 | CE1 | PHE | A | 403 | 31.382 | 64.868 | 5.456 | 1.00 | 24.96 | A | C |
| ATOM | 1499 | CE2 | PHE | A | 403 | 31.173 | 64.375 | 3.109 | 1.00 | 25.01 | A | C |
| ATOM | 1500 | CZ | PHE | A | 403 | 31.516 | 63.975 | 4.401 | 1.00 | 24.31 | A | C |
| ATOM | 1501 | C | PHE | A | 403 | 29.176 | 70.101 | 4.682 | 1.00 | 27.96 | A | C |
| ATOM | 1502 | O | PHE | A | 403 | 30.003 | 71.016 | 4.754 | 1.00 | 29.09 | A | O |
| ATOM | 1503 | N | GLY | A | 404 | 27.881 | 70.316 | 4.447 | 1.00 | 26.82 | A | N |
| ATOM | 1504 | CA | GLY | A | 404 | 27.366 | 71.661 | 4.249 | 1.00 | 19.60 | A | C |
| ATOM | 1505 | C | GLY | A | 404 | 27.593 | 72.578 | 5.428 | 1.00 | 20.79 | A | C |
| ATOM | 1506 | O | GLY | A | 404 | 27.812 | 73.788 | 5.256 | 1.00 | 27.69 | A | O |
| ATOM | 1507 | N | HIS | A | 405 | 27.515 | 72.026 | 6.629 | 1.00 | 23.53 | A | N |
| ATOM | 1508 | CA | HIS | A | 405 | 27.797 | 72.790 | 7.826 | 1.00 | 22.68 | A | C |
| ATOM | 1509 | CB | HIS | A | 405 | 27.340 | 72.040 | 9.091 | 1.00 | 26.79 | A | C |
| ATOM | 1510 | CG | HIS | A | 405 | 25.855 | 72.039 | 9.289 | 1.00 | 25.71 | A | C |
| ATOM | 1511 | CD2 | HIS | A | 405 | 24.988 | 71.027 | 9.523 | 1.00 | 23.80 | A | C |
| ATOM | 1512 | ND1 | HIS | A | 405 | 25.096 | 73.188 | 9.204 | 1.00 | 22.22 | A | N |
| ATOM | 1513 | CE1 | HIS | A | 405 | 23.821 | 72.885 | 9.398 | 1.00 | 29.49 | A | C |
| ATOM | 1514 | NE2 | HIS | A | 405 | 23.730 | 71.585 | 9.603 | 1.00 | 32.20 | A | N |
| ATOM | 1515 | C | HIS | A | 405 | 29.312 | 72.973 | 7.912 | 1.00 | 29.63 | A | C |
| ATOM | 1516 | O | HIS | A | 405 | 29.802 | 74.010 | 8.385 | 1.00 | 26.07 | A | O |
| ATOM | 1517 | N | ALA | A | 406 | 30.043 | 71.941 | 7.491 | 1.00 | 25.67 | A | N |
| ATOM | 1518 | CA | ALA | A | 406 | 31.509 | 71.945 | 7.627 | 1.00 | 29.10 | A | C |
| ATOM | 1519 | CB | ALA | A | 406 | 32.078 | 70.586 | 7.263 | 1.00 | 25.62 | A | C |
| ATOM | 1520 | C | ALA | A | 406 | 32.138 | 73.048 | 6.761 | 1.00 | 25.23 | A | C |
| ATOM | 1521 | O | ALA | A | 406 | 33.258 | 73.477 | 7.010 | 1.00 | 33.63 | A | O |
| ATOM | 1522 | N | LEU | A | 407 | 31.410 | 73.465 | 5.731 | 1.00 | 24.80 | A | N |
| ATOM | 1523 | CA | LEU | A | 407 | 31.804 | 74.571 | 4.882 | 1.00 | 24.81 | A | C |
| ATOM | 1524 | CB | LEU | A | 407 | 31.395 | 74.288 | 3.451 | 1.00 | 18.80 | A | C |
| ATOM | 1525 | CG | LEU | A | 407 | 31.986 | 72.990 | 2.914 | 1.00 | 25.53 | A | C |
| ATOM | 1526 | CD1 | LEU | A | 407 | 31.496 | 72.729 | 1.515 | 1.00 | 23.35 | A | C |
| ATOM | 1527 | CD2 | LEU | A | 407 | 33.526 | 73.038 | 2.982 | 1.00 | 22.56 | A | C |
| ATOM | 1528 | C | LEU | A | 407 | 31.223 | 75.903 | 5.296 | 1.00 | 31.44 | A | C |
| ATOM | 1529 | O | LEU | A | 407 | 31.529 | 76.915 | 4.667 | 1.00 | 33.50 | A | O |
| ATOM | 1530 | N | GLY | A | 408 | 30.370 | 75.908 | 6.326 | 1.00 | 32.79 | A | N |
| ATOM | 1531 | CA | GLY | A | 408 | 29.819 | 77.141 | 6.860 | 1.00 | 24.97 | A | C |
| ATOM | 1532 | C | GLY | A | 408 | 28.334 | 77.401 | 6.585 | 1.00 | 29.02 | A | C |
| ATOM | 1533 | O | GLY | A | 408 | 27.868 | 78.536 | 6.742 | 1.00 | 28.57 | A | O |
| ATOM | 1534 | N | LEU | A | 409 | 27.584 | 76.386 | 6.163 | 1.00 | 26.49 | A | N |
| ATOM | 1535 | CA | LEU | A | 409 | 26.151 | 76.596 | 5.877 | 1.00 | 28.63 | A | C |
| ATOM | 1536 | CB | LEU | A | 409 | 25.648 | 75.717 | 4.739 | 1.00 | 25.88 | A | C |

TABLE 12-continued

Coordinates for pro MMP9(35-444 ΔFnII) (SEQ ID NO: 12) complex with Example 2

| ATOM | 1537 | CG  | LEU | A | 409 | 26.179 | 76.061 | 3.336  | 1.00 | 22.16 | A | C |
| ---- | ---- | --- | --- | - | --- | ------ | ------ | ------ | ---- | ----- | - | - |
| ATOM | 1538 | CD1 | LEU | A | 409 | 25.633 | 75.138 | 2.283  | 1.00 | 23.06 | A | C |
| ATOM | 1539 | CD2 | LEU | A | 409 | 25.860 | 77.517 | 2.974  | 1.00 | 24.52 | A | C |
| ATOM | 1540 | C   | LEU | A | 409 | 25.303 | 76.379 | 7.126  | 1.00 | 29.23 | A | C |
| ATOM | 1541 | O   | LEU | A | 409 | 25.674 | 75.614 | 8.015  | 1.00 | 27.90 | A | O |
| ATOM | 1542 | N   | ASP | A | 410 | 24.183 | 77.095 | 7.194  | 1.00 | 36.70 | A | N |
| ATOM | 1543 | CA  | ASP | A | 410 | 23.198 | 76.915 | 8.254  | 1.00 | 31.57 | A | C |
| ATOM | 1544 | CB  | ASP | A | 410 | 22.749 | 78.251 | 8.783  | 1.00 | 28.53 | A | C |
| ATOM | 1545 | CG  | ASP | A | 410 | 23.745 | 78.849 | 9.676  | 1.00 | 27.81 | A | C |
| ATOM | 1546 | OD1 | ASP | A | 410 | 24.355 | 78.089 | 10.436 | 1.00 | 41.70 | A | O |
| ATOM | 1547 | OD2 | ASP | A | 410 | 23.948 | 80.074 | 9.607  | 1.00 | 37.66 | A | O |
| ATOM | 1548 | C   | ASP | A | 410 | 22.008 | 76.209 | 7.684  | 1.00 | 33.29 | A | C |
| ATOM | 1549 | O   | ASP | A | 410 | 21.877 | 76.097 | 6.466  | 1.00 | 29.05 | A | O |
| ATOM | 1550 | N   | HIS | A | 411 | 21.121 | 75.739 | 8.562  | 1.00 | 33.49 | A | N |
| ATOM | 1551 | CA  | HIS | A | 411 | 19.932 | 75.035 | 8.101  | 1.00 | 23.48 | A | C |
| ATOM | 1552 | CB  | HIS | A | 411 | 19.083 | 74.557 | 9.287  | 1.00 | 30.65 | A | C |
| ATOM | 1553 | CG  | HIS | A | 411 | 19.674 | 73.383 | 9.993  | 1.00 | 27.07 | A | C |
| ATOM | 1554 | CD2 | HIS | A | 411 | 20.241 | 72.251 | 9.513  | 1.00 | 22.87 | A | C |
| ATOM | 1555 | ND1 | HIS | A | 411 | 19.781 | 73.313 | 11.367 | 1.00 | 29.80 | A | N |
| ATOM | 1556 | CE1 | HIS | A | 411 | 20.361 | 72.175 | 11.703 | 1.00 | 29.66 | A | C |
| ATOM | 1557 | NE2 | HIS | A | 411 | 20.650 | 71.515 | 10.595 | 1.00 | 31.14 | A | N |
| ATOM | 1558 | C   | HIS | A | 411 | 19.128 | 75.925 | 7.199  | 1.00 | 19.82 | A | C |
| ATOM | 1559 | O   | HIS | A | 411 | 19.108 | 77.131 | 7.361  | 1.00 | 24.63 | A | O |
| ATOM | 1560 | N   | SER | A | 412 | 18.476 | 75.320 | 6.226  | 1.00 | 19.96 | A | N |
| ATOM | 1561 | CA  | SER | A | 412 | 17.523 | 76.048 | 5.422  | 1.00 | 26.83 | A | C |
| ATOM | 1562 | CB  | SER | A | 412 | 17.551 | 75.513 | 4.012  | 1.00 | 19.72 | A | C |
| ATOM | 1563 | OG  | SER | A | 412 | 16.523 | 76.112 | 3.263  | 1.00 | 22.68 | A | O |
| ATOM | 1564 | C   | SER | A | 412 | 16.117 | 75.838 | 5.968  | 1.00 | 26.56 | A | C |
| ATOM | 1565 | O   | SER | A | 412 | 15.877 | 74.859 | 6.642  | 1.00 | 25.38 | A | O |
| ATOM | 1566 | N   | SER | A | 413 | 15.208 | 76.745 | 5.626  | 1.00 | 28.86 | A | N |
| ATOM | 1567 | CA  | SER | A | 413 | 13.780 | 76.632 | 5.964  | 1.00 | 34.11 | A | C |
| ATOM | 1568 | CB  | SER | A | 413 | 13.229 | 77.980 | 6.420  | 1.00 | 28.72 | A | C |
| ATOM | 1569 | OG  | SER | A | 413 | 12.765 | 78.659 | 5.271  | 1.00 | 38.32 | A | O |
| ATOM | 1570 | C   | SER | A | 413 | 12.957 | 76.166 | 4.759  | 1.00 | 36.22 | A | C |
| ATOM | 1571 | O   | SER | A | 413 | 11.745 | 75.950 | 4.876  | 1.00 | 34.33 | A | O |
| ATOM | 1572 | N   | VAL | A | 414 | 13.596 | 76.040 | 3.591  | 1.00 | 29.78 | A | N |
| ATOM | 1573 | CA  | VAL | A | 414 | 12.951 | 75.389 | 2.461  | 1.00 | 28.33 | A | C |
| ATOM | 1574 | CB  | VAL | A | 414 | 13.719 | 75.631 | 1.172  | 1.00 | 32.14 | A | C |
| ATOM | 1575 | CG1 | VAL | A | 414 | 13.049 | 74.936 | 0.005  | 1.00 | 29.14 | A | C |
| ATOM | 1576 | CG2 | VAL | A | 414 | 13.844 | 77.126 | 0.909  | 1.00 | 32.06 | A | C |
| ATOM | 1577 | C   | VAL | A | 414 | 12.992 | 73.896 | 2.719  | 1.00 | 36.80 | A | C |
| ATOM | 1578 | O   | VAL | A | 414 | 14.080 | 73.331 | 2.783  | 1.00 | 34.84 | A | O |
| ATOM | 1579 | N   | PRO | A | 415 | 11.819 | 73.242 | 2.852  | 1.00 | 30.94 | A | N |
| ATOM | 1580 | CD  | PRO | A | 415 | 10.483 | 73.813 | 2.638  | 1.00 | 35.81 | A | C |
| ATOM | 1581 | CA  | PRO | A | 415 | 11.745 | 71.807 | 3.187  | 1.00 | 36.51 | A | C |
| ATOM | 1582 | CB  | PRO | A | 415 | 10.228 | 71.535 | 3.238  | 1.00 | 36.93 | A | C |
| ATOM | 1583 | CG  | PRO | A | 415 | 9.599  | 72.878 | 3.403  | 1.00 | 35.86 | A | C |
| ATOM | 1584 | C   | PRO | A | 415 | 12.420 | 70.846 | 2.171  | 1.00 | 31.98 | A | C |
| ATOM | 1585 | O   | PRO | A | 415 | 12.896 | 69.777 | 2.554  | 1.00 | 33.70 | A | O |
| ATOM | 1586 | N   | GLU | A | 416 | 12.448 | 71.208 | 0.897  | 1.00 | 35.67 | A | N |
| ATOM | 1587 | CA  | GLU | A | 416 | 13.086 | 70.350 | −0.116 | 1.00 | 38.69 | A | C |
| ATOM | 1588 | CB  | GLU | A | 416 | 12.481 | 70.607 | −1.502 | 1.00 | 37.34 | A | C |
| ATOM | 1589 | CG  | GLU | A | 416 | 10.949 | 70.457 | −1.572 | 1.00 | 41.72 | A | C |
| ATOM | 1590 | CD  | GLU | A | 416 | 10.188 | 71.582 | −0.866 | 1.00 | 43.34 | A | C |
| ATOM | 1591 | OE1 | GLU | A | 416 | 10.452 | 72.786 | −1.118 | 1.00 | 35.02 | A | O |
| ATOM | 1592 | OE2 | GLU | A | 416 | 9.298  | 71.250 | −0.056 | 1.00 | 53.09 | A | O |
| ATOM | 1593 | C   | GLU | A | 416 | 14.626 | 70.502 | −0.167 | 1.00 | 36.60 | A | C |
| ATOM | 1594 | O   | GLU | A | 416 | 15.341 | 69.603 | −0.615 | 1.00 | 36.47 | A | O |
| ATOM | 1595 | N   | ALA | A | 417 | 15.122 | 71.640 | 0.301  | 1.00 | 32.80 | A | N |
| ATOM | 1596 | CA  | ALA | A | 417 | 16.557 | 71.891 | 0.350  | 1.00 | 30.20 | A | C |
| ATOM | 1597 | CB  | ALA | A | 417 | 16.844 | 73.228 | 1.029  | 1.00 | 19.44 | A | C |
| ATOM | 1598 | C   | ALA | A | 417 | 17.347 | 70.773 | 1.030  | 1.00 | 29.68 | A | C |
| ATOM | 1599 | O   | ALA | A | 417 | 16.931 | 70.191 | 2.021  | 1.00 | 26.67 | A | O |
| ATOM | 1600 | N   | LEU | A | 418 | 18.537 | 70.490 | 0.506  | 1.00 | 31.63 | A | N |
| ATOM | 1601 | CA  | LEU | A | 418 | 19.458 | 69.602 | 1.215  | 1.00 | 21.47 | A | C |
| ATOM | 1602 | CB  | LEU | A | 418 | 20.747 | 69.442 | 0.396  | 1.00 | 30.03 | A | C |
| ATOM | 1603 | CG  | LEU | A | 418 | 21.841 | 68.723 | 1.155  | 1.00 | 24.23 | A | C |
| ATOM | 1604 | CD1 | LEU | A | 418 | 21.422 | 67.275 | 1.360  | 1.00 | 20.16 | A | C |
| ATOM | 1605 | CD2 | LEU | A | 418 | 23.173 | 68.855 | 0.361  | 1.00 | 25.29 | A | C |
| ATOM | 1606 | C   | LEU | A | 418 | 19.809 | 70.058 | 2.625  | 1.00 | 18.44 | A | C |
| ATOM | 1607 | O   | LEU | A | 418 | 20.031 | 69.237 | 3.514  | 1.00 | 22.59 | A | O |
| ATOM | 1608 | N   | MET | A | 419 | 19.899 | 71.369 | 2.848  | 1.00 | 19.72 | A | N |
| ATOM | 1609 | CA  | MET | A | 419 | 20.192 | 71.870 | 4.192  | 1.00 | 19.83 | A | C |
| ATOM | 1610 | CB  | MET | A | 419 | 20.943 | 73.202 | 4.118  | 1.00 | 24.42 | A | C |
| ATOM | 1611 | CG  | MET | A | 419 | 22.409 | 73.113 | 3.574  | 1.00 | 20.01 | A | C |
| ATOM | 1612 | SD  | MET | A | 419 | 23.276 | 71.676 | 4.191  | 1.00 | 22.60 | A | S |
| ATOM | 1613 | CE  | MET | A | 419 | 23.732 | 72.209 | 5.816  | 1.00 | 22.01 | A | C |

TABLE 12-continued

Coordinates for pro MMP9(35-444 ΔFnII) (SEQ ID NO: 12) complex with Example 2

| ATOM | 1614 | C | MET | A | 419 | 18.936 | 71.992 | 5.143 | 1.00 | 22.22 | A | C |
|---|---|---|---|---|---|---|---|---|---|---|---|---|
| ATOM | 1615 | O | MET | A | 419 | 19.042 | 72.478 | 6.261 | 1.00 | 23.67 | A | O |
| ATOM | 1616 | N | TYR | A | 420 | 17.767 | 71.542 | 4.708 | 1.00 | 25.58 | A | N |
| ATOM | 1617 | CA | TYR | A | 420 | 16.620 | 71.464 | 5.637 | 1.00 | 24.58 | A | C |
| ATOM | 1618 | CB | TYR | A | 420 | 15.375 | 71.015 | 4.873 | 1.00 | 29.53 | A | C |
| ATOM | 1619 | CG | TYR | A | 420 | 14.070 | 71.212 | 5.628 | 1.00 | 35.10 | A | C |
| ATOM | 1620 | CD1 | TYR | A | 420 | 13.599 | 72.491 | 5.918 | 1.00 | 34.14 | A | C |
| ATOM | 1621 | CE1 | TYR | A | 420 | 12.390 | 72.683 | 6.603 | 1.00 | 34.79 | A | C |
| ATOM | 1622 | CD2 | TYR | A | 420 | 13.303 | 70.113 | 6.051 | 1.00 | 33.62 | A | C |
| ATOM | 1623 | CE2 | TYR | A | 420 | 12.084 | 70.298 | 6.741 | 1.00 | 34.13 | A | C |
| ATOM | 1624 | CZ | TYR | A | 420 | 11.648 | 71.583 | 7.013 | 1.00 | 33.50 | A | C |
| ATOM | 1625 | OH | TYR | A | 420 | 10.472 | 71.783 | 7.688 | 1.00 | 39.71 | A | O |
| ATOM | 1626 | C | TYR | A | 420 | 16.938 | 70.478 | 6.758 | 1.00 | 25.48 | A | C |
| ATOM | 1627 | O | TYR | A | 420 | 17.379 | 69.372 | 6.490 | 1.00 | 30.68 | A | O |
| ATOM | 1628 | N | PRO | A | 421 | 16.700 | 70.858 | 8.024 | 1.00 | 28.89 | A | N |
| ATOM | 1629 | CD | PRO | A | 421 | 15.762 | 71.916 | 8.426 | 1.00 | 29.11 | A | C |
| ATOM | 1630 | CA | PRO | A | 421 | 17.162 | 70.052 | 9.169 | 1.00 | 28.03 | A | C |
| ATOM | 1631 | CB | PRO | A | 421 | 16.589 | 70.785 | 10.383 | 1.00 | 30.37 | A | C |
| ATOM | 1632 | CG | PRO | A | 421 | 16.041 | 72.091 | 9.856 | 1.00 | 30.64 | A | C |
| ATOM | 1633 | C | PRO | A | 421 | 16.705 | 68.589 | 9.220 | 1.00 | 27.99 | A | C |
| ATOM | 1634 | O | PRO | A | 421 | 17.445 | 67.763 | 9.765 | 1.00 | 27.92 | A | O |
| ATOM | 1635 | N | MET | A | 422 | 15.524 | 68.276 | 8.694 | 1.00 | 24.03 | A | N |
| ATOM | 1636 | CA | MET | A | 422 | 14.961 | 66.932 | 8.817 | 1.00 | 27.36 | A | C |
| ATOM | 1637 | CB | MET | A | 422 | 13.427 | 66.256 | 8.658 | 1.00 | 31.70 | A | C |
| ATOM | 1638 | CG | MET | A | 422 | 12.604 | 67.504 | 9.835 | 1.00 | 35.06 | A | C |
| ATOM | 1639 | SD | MET | A | 422 | 10.821 | 67.537 | 9.398 | 1.00 | 34.82 | A | S |
| ATOM | 1640 | CE | MET | A | 422 | 10.375 | 68.997 | 10.345 | 1.00 | 29.02 | A | C |
| ATOM | 1641 | C | MET | A | 422 | 15.464 | 66.027 | 7.727 | 1.00 | 29.32 | A | C |
| ATOM | 1642 | O | MET | A | 422 | 15.554 | 66.449 | 6.574 | 1.00 | 30.97 | A | O |
| ATOM | 1643 | N | TYR | A | 423 | 15.728 | 64.769 | 8.075 | 1.00 | 27.29 | A | N |
| ATOM | 1644 | CA | TYR | A | 423 | 16.030 | 63.745 | 7.080 | 1.00 | 28.66 | A | C |
| ATOM | 1645 | CB | TYR | A | 423 | 16.412 | 62.440 | 7.766 | 1.00 | 33.38 | A | C |
| ATOM | 1646 | CG | TYR | A | 423 | 16.768 | 61.352 | 6.801 | 1.00 | 31.14 | A | C |
| ATOM | 1647 | CD1 | TYR | A | 423 | 15.864 | 60.353 | 6.493 | 1.00 | 29.67 | A | C |
| ATOM | 1648 | CE1 | TYR | A | 423 | 16.180 | 59.347 | 5.604 | 1.00 | 34.36 | A | C |
| ATOM | 1649 | CD2 | TYR | A | 423 | 18.030 | 61.312 | 6.197 | 1.00 | 35.49 | A | C |
| ATOM | 1650 | CE2 | TYR | A | 423 | 18.365 | 60.300 | 5.302 | 1.00 | 25.95 | A | C |
| ATOM | 1651 | CZ | TYR | A | 423 | 17.442 | 59.317 | 5.010 | 1.00 | 31.38 | A | C |
| ATOM | 1652 | OH | TYR | A | 423 | 17.741 | 58.304 | 4.126 | 1.00 | 30.74 | A | O |
| ATOM | 1653 | C | TYR | A | 423 | 14.886 | 63.448 | 6.133 | 1.00 | 37.85 | A | C |
| ATOM | 1654 | O | TYR | A | 423 | 13.802 | 63.008 | 6.568 | 1.00 | 38.94 | A | O |
| ATOM | 1655 | N | ARG | A | 424 | 15.138 | 63.655 | 4.841 | 1.00 | 32.32 | A | N |
| ATOM | 1656 | CA | ARG | A | 424 | 14.224 | 63.234 | 3.791 | 1.00 | 32.75 | A | C |
| ATOM | 1657 | CB | ARG | A | 424 | 13.659 | 64.454 | 3.040 | 1.00 | 36.08 | A | C |
| ATOM | 1658 | CG | ARG | A | 424 | 14.396 | 64.825 | 1.730 | 1.00 | 44.57 | A | C |
| ATOM | 1659 | CD | ARG | A | 424 | 13.728 | 65.999 | 1.002 | 1.00 | 47.53 | A | C |
| ATOM | 1660 | NE | ARG | A | 424 | 14.210 | 66.217 | −0.368 | 1.00 | 45.70 | A | N |
| ATOM | 1661 | CZ | ARG | A | 424 | 13.438 | 66.149 | −1.453 | 1.00 | 49.30 | A | C |
| ATOM | 1662 | NH1 | ARG | A | 424 | 12.149 | 65.853 | −1.325 | 1.00 | 53.81 | A | N |
| ATOM | 1663 | NH2 | ARG | A | 424 | 13.941 | 66.370 | −2.670 | 1.00 | 47.77 | A | N |
| ATOM | 1664 | C | ARG | A | 424 | 15.014 | 62.372 | 2.828 | 1.00 | 36.90 | A | C |
| ATOM | 1665 | O | ARG | A | 424 | 16.003 | 62.844 | 2.254 | 1.00 | 43.64 | A | O |
| ATOM | 1666 | N | PHE | A | 425 | 14.621 | 61.115 | 2.642 | 1.00 | 33.41 | A | N |
| ATOM | 1667 | CA | PHE | A | 425 | 15.268 | 60.318 | 1.596 | 1.00 | 33.48 | A | C |
| ATOM | 1668 | CB | PHE | A | 425 | 15.102 | 58.814 | 1.789 | 1.00 | 39.00 | A | C |
| ATOM | 1669 | CG | PHE | A | 425 | 15.660 | 58.006 | 0.642 | 1.00 | 34.42 | A | C |
| ATOM | 1670 | CD1 | PHE | A | 425 | 17.013 | 57.735 | 0.568 | 1.00 | 35.68 | A | C |
| ATOM | 1671 | CD2 | PHE | A | 425 | 14.842 | 57.572 | −0.382 | 1.00 | 36.21 | A | C |
| ATOM | 1672 | CE1 | PHE | A | 425 | 17.532 | 57.005 | −0.485 | 1.00 | 38.14 | A | C |
| ATOM | 1673 | CE2 | PHE | A | 425 | 15.361 | 56.853 | −1.445 | 1.00 | 41.73 | A | C |
| ATOM | 1674 | CZ | PHE | A | 425 | 16.707 | 56.567 | −1.489 | 1.00 | 36.73 | A | C |
| ATOM | 1675 | C | PHE | A | 425 | 14.760 | 60.693 | 0.225 | 1.00 | 35.41 | A | C |
| ATOM | 1676 | O | PHE | A | 425 | 13.573 | 60.923 | 0.034 | 1.00 | 40.53 | A | O |
| ATOM | 1677 | N | THR | A | 426 | 15.673 | 60.761 | −0.735 | 1.00 | 33.23 | A | N |
| ATOM | 1678 | CA | THR | A | 426 | 15.332 | 61.059 | −2.119 | 1.00 | 34.43 | A | C |
| ATOM | 1679 | CB | THR | A | 426 | 15.378 | 62.576 | −2.410 | 1.00 | 32.58 | A | C |
| ATOM | 1680 | OG1 | THR | A | 426 | 15.125 | 62.807 | −3.800 | 1.00 | 32.27 | A | O |
| ATOM | 1681 | CG2 | THR | A | 426 | 16.720 | 63.160 | −2.040 | 1.00 | 31.56 | A | C |
| ATOM | 1682 | C | THR | A | 426 | 16.311 | 60.354 | −3.036 | 1.00 | 33.13 | A | C |
| ATOM | 1683 | O | THR | A | 426 | 17.432 | 60.082 | −2.632 | 1.00 | 31.17 | A | O |
| ATOM | 1684 | N | GLU | A | 427 | 15.876 | 60.044 | −4.251 | 1.00 | 35.91 | A | N |
| ATOM | 1685 | CA | GLU | A | 427 | 16.755 | 59.478 | −5.270 | 1.00 | 37.00 | A | C |
| ATOM | 1686 | CB | GLU | A | 427 | 16.119 | 58.245 | −5.909 | 1.00 | 43.83 | A | C |
| ATOM | 1687 | CG | GLU | A | 427 | 15.904 | 57.126 | −4.906 | 1.00 | 45.05 | A | C |
| ATOM | 1688 | CD | GLU | A | 427 | 15.774 | 55.779 | −5.551 | 1.00 | 49.23 | A | C |
| ATOM | 1689 | OE1 | GLU | A | 427 | 14.854 | 55.597 | −6.375 | 1.00 | 54.33 | A | O |
| ATOM | 1690 | OE2 | GLU | A | 427 | 16.593 | 54.900 | −5.213 | 1.00 | 56.10 | A | O |

TABLE 12-continued

Coordinates for pro MMP9(35-444 ΔFnII) (SEQ ID NO: 12) complex with Example 2

| ATOM | 1691 | C | GLU | A | 427 | 17.104 | 60.515 | −6.337 | 1.00 | 37.10 | A | C |
|---|---|---|---|---|---|---|---|---|---|---|---|---|
| ATOM | 1692 | O | GLU | A | 427 | 17.824 | 60.227 | −7.285 | 1.00 | 39.37 | A | O |
| ATOM | 1693 | N | GLY | A | 428 | 16.583 | 61.723 | −6.177 | 1.00 | 33.88 | A | N |
| ATOM | 1694 | CA | GLY | A | 428 | 16.926 | 62.814 | −7.060 | 1.00 | 32.25 | A | C |
| ATOM | 1695 | C | GLY | A | 428 | 18.179 | 63.533 | −6.592 | 1.00 | 29.40 | A | C |
| ATOM | 1696 | O | GLY | A | 428 | 18.656 | 63.315 | −5.479 | 1.00 | 33.20 | A | O |
| ATOM | 1697 | N | PRO | A | 429 | 18.739 | 64.389 | −7.459 | 1.00 | 29.47 | A | N |
| ATOM | 1698 | CD | PRO | A | 429 | 18.330 | 64.539 | −8.861 | 1.00 | 23.59 | A | C |
| ATOM | 1699 | CA | PRO | A | 429 | 19.892 | 65.232 | −7.115 | 1.00 | 30.51 | A | C |
| ATOM | 1700 | CB | PRO | A | 429 | 19.923 | 66.260 | −8.247 | 1.00 | 26.07 | A | C |
| ATOM | 1701 | CG | PRO | A | 429 | 19.297 | 65.582 | −9.387 | 1.00 | 29.55 | A | C |
| ATOM | 1702 | C | PRO | A | 429 | 19.654 | 65.940 | −5.774 | 1.00 | 31.41 | A | C |
| ATOM | 1703 | O | PRO | A | 429 | 18.658 | 66.646 | −5.627 | 1.00 | 34.49 | A | O |
| ATOM | 1704 | N | PRO | A | 430 | 20.544 | 65.726 | −4.806 | 1.00 | 25.43 | A | N |
| ATOM | 1705 | CD | PRO | A | 430 | 21.560 | 64.664 | −4.902 | 1.00 | 28.97 | A | C |
| ATOM | 1706 | CA | PRO | A | 430 | 20.481 | 66.280 | −3.457 | 1.00 | 27.18 | A | C |
| ATOM | 1707 | CB | PRO | A | 430 | 21.737 | 65.714 | −2.722 | 1.00 | 29.51 | A | C |
| ATOM | 1708 | CG | PRO | A | 430 | 21.931 | 64.412 | −3.480 | 1.00 | 26.73 | A | C |
| ATOM | 1709 | C | PRO | A | 430 | 20.498 | 67.796 | −3.371 | 1.00 | 34.62 | A | C |
| ATOM | 1710 | O | PRO | A | 430 | 19.934 | 68.319 | −2.408 | 1.00 | 27.76 | A | O |
| ATOM | 1711 | N | LEU | A | 431 | 21.109 | 68.509 | −4.312 | 1.00 | 26.02 | A | N |
| ATOM | 1712 | CA | LEU | A | 431 | 21.226 | 69.958 | −4.112 | 1.00 | 28.74 | A | C |
| ATOM | 1713 | CB | LEU | A | 431 | 22.519 | 70.527 | −4.708 | 1.00 | 27.49 | A | C |
| ATOM | 1714 | CG | LEU | A | 431 | 23.836 | 70.202 | −4.002 | 1.00 | 32.47 | A | C |
| ATOM | 1715 | CD1 | LEU | A | 431 | 25.025 | 70.610 | −4.884 | 1.00 | 29.48 | A | C |
| ATOM | 1716 | CD2 | LEU | A | 431 | 23.902 | 70.900 | −2.661 | 1.00 | 28.82 | A | C |
| ATOM | 1717 | C | LEU | A | 431 | 20.066 | 70.691 | −4.712 | 1.00 | 21.45 | A | C |
| ATOM | 1718 | O | LEU | A | 431 | 19.533 | 70.264 | −5.720 | 1.00 | 22.73 | A | O |
| ATOM | 1719 | N | HIS | A | 432 | 19.701 | 71.819 | −4.103 | 1.00 | 26.85 | A | N |
| ATOM | 1720 | CA | HIS | A | 432 | 18.648 | 72.687 | −4.646 | 1.00 | 27.16 | A | C |
| ATOM | 1721 | CB | HIS | A | 432 | 17.381 | 72.623 | −3.801 | 1.00 | 29.72 | A | C |
| ATOM | 1722 | CG | HIS | A | 432 | 16.655 | 71.326 | −3.909 | 1.00 | 28.53 | A | C |
| ATOM | 1723 | CD2 | HIS | A | 432 | 15.508 | 70.998 | −4.546 | 1.00 | 26.74 | A | C |
| ATOM | 1724 | ND1 | HIS | A | 432 | 17.115 | 70.167 | −3.317 | 1.00 | 28.99 | A | N |
| ATOM | 1725 | CE1 | HIS | A | 432 | 16.276 | 69.180 | −3.580 | 1.00 | 24.72 | A | C |
| ATOM | 1726 | NE2 | HIS | A | 432 | 15.302 | 69.655 | −4.336 | 1.00 | 24.94 | A | N |
| ATOM | 1727 | C | HIS | A | 432 | 19.086 | 74.122 | −4.668 | 1.00 | 21.22 | A | C |
| ATOM | 1728 | O | HIS | A | 432 | 20.037 | 74.492 | −4.004 | 1.00 | 27.85 | A | O |
| ATOM | 1729 | N | LYS | A | 433 | 18.358 | 74.933 | −5.417 | 1.00 | 23.69 | A | N |
| ATOM | 1730 | CA | LYS | A | 433 | 18.703 | 76.332 | −5.574 | 1.00 | 27.57 | A | C |
| ATOM | 1731 | CB | LYS | A | 433 | 17.525 | 77.102 | −6.157 | 1.00 | 23.89 | A | C |
| ATOM | 1732 | CG | LYS | A | 433 | 17.109 | 76.590 | −7.514 | 1.00 | 24.59 | A | C |
| ATOM | 1733 | CD | LYS | A | 433 | 15.835 | 77.303 | −8.007 | 1.00 | 33.37 | A | C |
| ATOM | 1734 | CE | LYS | A | 433 | 15.445 | 76.925 | −9.415 | 1.00 | 32.27 | A | C |
| ATOM | 1735 | NZ | LYS | A | 433 | 16.227 | 77.637 | −10.467 | 1.00 | 31.36 | A | N |
| ATOM | 1736 | C | LYS | A | 433 | 19.141 | 76.925 | −4.259 | 1.00 | 29.25 | A | C |
| ATOM | 1737 | O | LYS | A | 433 | 20.163 | 77.606 | −4.178 | 1.00 | 27.37 | A | O |
| ATOM | 1738 | N | ASP | A | 434 | 18.382 | 76.662 | −3.207 | 1.00 | 26.30 | A | N |
| ATOM | 1739 | CA | ASP | A | 434 | 18.692 | 77.297 | −1.938 | 1.00 | 20.16 | A | C |
| ATOM | 1740 | CB | ASP | A | 434 | 17.624 | 76.987 | −0.894 | 1.00 | 26.67 | A | C |
| ATOM | 1741 | CG | ASP | A | 434 | 17.737 | 77.888 | 0.297 | 1.00 | 21.35 | A | C |
| ATOM | 1742 | OD1 | ASP | A | 434 | 17.451 | 79.080 | 0.140 | 1.00 | 27.44 | A | O |
| ATOM | 1743 | OD2 | ASP | A | 434 | 18.156 | 77.418 | 1.365 | 1.00 | 26.80 | A | O |
| ATOM | 1744 | C | ASP | A | 434 | 20.060 | 76.894 | −1.386 | 1.00 | 22.73 | A | C |
| ATOM | 1745 | O | ASP | A | 434 | 20.696 | 77.660 | −0.650 | 1.00 | 22.33 | A | O |
| ATOM | 1746 | N | ASP | A | 435 | 20.468 | 75.667 | −1.674 | 1.00 | 20.85 | A | N |
| ATOM | 1747 | CA | ASP | A | 435 | 21.771 | 75.174 | −1.224 | 1.00 | 32.42 | A | C |
| ATOM | 1748 | CB | ASP | A | 435 | 21.843 | 73.630 | −1.291 | 1.00 | 25.84 | A | C |
| ATOM | 1749 | CG | ASP | A | 435 | 20.665 | 72.940 | −0.591 | 1.00 | 27.86 | A | C |
| ATOM | 1750 | OD1 | ASP | A | 435 | 20.477 | 73.148 | 0.626 | 1.00 | 27.89 | A | O |
| ATOM | 1751 | OD2 | ASP | A | 435 | 19.947 | 72.162 | −1.261 | 1.00 | 30.11 | A | O |
| ATOM | 1752 | C | ASP | A | 435 | 22.902 | 75.826 | −2.066 | 1.00 | 19.98 | A | C |
| ATOM | 1753 | O | ASP | A | 435 | 23.872 | 76.329 | −1.517 | 1.00 | 28.25 | A | O |
| ATOM | 1754 | N | VAL | A | 436 | 22.743 | 75.830 | −3.378 | 1.00 | 21.15 | A | N |
| ATOM | 1755 | CA | VAL | A | 436 | 23.727 | 76.448 | −4.295 | 1.00 | 25.02 | A | C |
| ATOM | 1756 | CB | VAL | A | 436 | 23.354 | 76.186 | −5.750 | 1.00 | 28.61 | A | C |
| ATOM | 1757 | CG1 | VAL | A | 436 | 24.301 | 76.936 | −6.742 | 1.00 | 24.32 | A | C |
| ATOM | 1758 | CG2 | VAL | A | 436 | 23.350 | 74.692 | −6.011 | 1.00 | 24.57 | A | C |
| ATOM | 1759 | C | VAL | A | 436 | 23.880 | 77.948 | −4.059 | 1.00 | 30.75 | A | C |
| ATOM | 1760 | O | VAL | A | 436 | 24.996 | 78.457 | −3.913 | 1.00 | 28.38 | A | O |
| ATOM | 1761 | N | ASN | A | 437 | 22.754 | 78.652 | −3.970 | 1.00 | 27.73 | A | N |
| ATOM | 1762 | CA | ASN | A | 437 | 22.786 | 80.066 | −3.658 | 1.00 | 21.15 | A | C |
| ATOM | 1763 | CB | ASN | A | 437 | 21.419 | 80.711 | −3.841 | 1.00 | 33.13 | A | C |
| ATOM | 1764 | CG | ASN | A | 437 | 21.133 | 81.049 | −5.281 | 1.00 | 38.24 | A | C |
| ATOM | 1765 | OD1 | ASN | A | 437 | 22.011 | 80.948 | −6.142 | 1.00 | 39.84 | A | O |
| ATOM | 1766 | ND2 | ASN | A | 437 | 19.905 | 81.475 | −5.559 | 1.00 | 34.85 | A | N |
| ATOM | 1767 | C | ASN | A | 437 | 23.370 | 80.360 | −2.299 | 1.00 | 25.95 | A | C |

TABLE 12-continued

Coordinates for pro MMP9(35-444 ΔFnII) (SEQ ID NO: 12) complex with Example 2

| ATOM | 1768 | O   | ASN | A | 437 | 23.998 | 81.392 | −2.111 | 1.00 | 31.39 | A | O  |
|------|------|-----|-----|---|-----|--------|--------|--------|------|-------|---|----|
| ATOM | 1769 | N   | GLY | A | 438 | 23.218 | 79.449 | −1.347 | 1.00 | 24.54 | A | N  |
| ATOM | 1770 | CA  | GLY | A | 438 | 23.779 | 79.686 | −0.028 | 1.00 | 23.95 | A | C  |
| ATOM | 1771 | C   | GLY | A | 438 | 25.306 | 79.614 | −0.064 | 1.00 | 32.24 | A | C  |
| ATOM | 1772 | O   | GLY | A | 438 | 26.022 | 80.422 | 0.529  | 1.00 | 33.98 | A | O  |
| ATOM | 1773 | N   | ILE | A | 439 | 25.807 | 78.609 | −0.761 | 1.00 | 29.61 | A | N  |
| ATOM | 1774 | CA  | ILE | A | 439 | 27.244 | 78.372 | −0.845 | 1.00 | 33.48 | A | C  |
| ATOM | 1775 | CB  | ILE | A | 439 | 27.523 | 76.938 | −1.382 | 1.00 | 28.67 | A | C  |
| ATOM | 1776 | CG2 | ILE | A | 439 | 27.394 | 76.895 | −2.888 | 1.00 | 32.67 | A | C  |
| ATOM | 1777 | CG1 | ILE | A | 439 | 28.860 | 76.398 | −0.864 | 1.00 | 30.72 | A | C  |
| ATOM | 1778 | CD1 | ILE | A | 439 | 28.959 | 76.339 | 0.649  | 1.00 | 27.98 | A | C  |
| ATOM | 1779 | C   | ILE | A | 439 | 27.899 | 79.482 | −1.694 | 1.00 | 29.89 | A | C  |
| ATOM | 1780 | O   | ILE | A | 439 | 28.927 | 80.012 | −1.321 | 1.00 | 36.80 | A | O  |
| ATOM | 1781 | N   | ARG | A | 440 | 27.270 | 79.873 | −2.795 | 1.00 | 29.08 | A | N  |
| ATOM | 1782 | CA  | ARG | A | 440 | 27.752 | 81.020 | −3.553 | 1.00 | 33.52 | A | C  |
| ATOM | 1783 | CB  | ARG | A | 440 | 26.868 | 81.329 | −4.766 | 1.00 | 30.06 | A | C  |
| ATOM | 1784 | CG  | ARG | A | 440 | 26.976 | 80.276 | −5.844 | 1.00 | 35.84 | A | C  |
| ATOM | 1785 | CD  | ARG | A | 440 | 26.382 | 80.721 | −7.163 | 1.00 | 33.90 | A | C  |
| ATOM | 1786 | NE  | ARG | A | 440 | 27.097 | 81.869 | −7.712 | 1.00 | 37.11 | A | N  |
| ATOM | 1787 | CZ  | ARG | A | 440 | 26.905 | 82.328 | −8.945 | 1.00 | 38.23 | A | C  |
| ATOM | 1788 | NH1 | ARG | A | 440 | 26.016 | 81.754 | −9.736 | 1.00 | 42.76 | A | N  |
| ATOM | 1789 | NH2 | ARG | A | 440 | 27.597 | 83.357 | −9.391 | 1.00 | 43.96 | A | N  |
| ATOM | 1790 | C   | ARG | A | 440 | 27.889 | 82.229 | −2.652 | 1.00 | 41.32 | A | C  |
| ATOM | 1791 | O   | ARG | A | 440 | 28.950 | 82.849 | −2.620 | 1.00 | 44.45 | A | O  |
| ATOM | 1792 | N   | HIS | A | 441 | 26.837 | 82.546 | −1.895 | 1.00 | 40.88 | A | N  |
| ATOM | 1793 | CA  | HIS | A | 441 | 26.853 | 83.709 | −0.994 | 1.00 | 38.08 | A | C  |
| ATOM | 1794 | CB  | HIS | A | 441 | 25.477 | 83.968 | −0.372 | 1.00 | 36.49 | A | C  |
| ATOM | 1795 | CG  | HIS | A | 441 | 24.410 | 84.259 | −1.377 | 1.00 | 36.13 | A | C  |
| ATOM | 1796 | CD2 | HIS | A | 441 | 23.066 | 84.100 | −1.322 | 1.00 | 36.79 | A | C  |
| ATOM | 1797 | ND1 | HIS | A | 441 | 24.686 | 84.787 | −2.619 | 1.00 | 39.18 | A | N  |
| ATOM | 1798 | CE1 | HIS | A | 441 | 23.557 | 84.928 | −3.295 | 1.00 | 41.38 | A | C  |
| ATOM | 1799 | NE2 | HIS | A | 441 | 22.560 | 84.527 | −2.527 | 1.00 | 42.62 | A | N  |
| ATOM | 1800 | C   | HIS | A | 441 | 27.873 | 83.605 | 0.119  | 1.00 | 38.30 | A | C  |
| ATOM | 1801 | O   | HIS | A | 441 | 27.881 | 84.437 | 1.019  | 1.00 | 39.90 | A | O  |
| ATOM | 1802 | N   | LEU | A | 442 | 28.715 | 82.580 | 0.079  | 1.00 | 37.40 | A | N  |
| ATOM | 1803 | CA  | LEU | A | 442 | 29.740 | 82.414 | 1.104  | 1.00 | 36.58 | A | C  |
| ATOM | 1804 | CB  | LEU | A | 442 | 29.554 | 81.082 | 1.836  | 1.00 | 34.94 | A | C  |
| ATOM | 1805 | CG  | LEU | A | 442 | 29.676 | 81.101 | 3.366  | 1.00 | 38.08 | A | C  |
| ATOM | 1806 | CD1 | LEU | A | 442 | 29.424 | 79.718 | 4.011  | 1.00 | 34.32 | A | C  |
| ATOM | 1807 | CD2 | LEU | A | 442 | 31.024 | 81.656 | 3.791  | 1.00 | 44.31 | A | C  |
| ATOM | 1808 | C   | LEU | A | 442 | 31.147 | 82.470 | 0.506  | 1.00 | 40.31 | A | C  |
| ATOM | 1809 | O   | LEU | A | 442 | 32.047 | 83.085 | 1.073  | 1.00 | 42.88 | A | O  |
| ATOM | 1810 | N   | TYR | A | 443 | 31.322 | 81.823 | −0.643 | 1.00 | 35.05 | A | N  |
| ATOM | 1811 | CA  | TYR | A | 443 | 32.639 | 81.653 | −1.274 | 1.00 | 40.92 | A | C  |
| ATOM | 1812 | CB  | TYR | A | 443 | 32.996 | 80.154 | −1.373 | 1.00 | 30.92 | A | C  |
| ATOM | 1813 | CG  | TYR | A | 443 | 33.294 | 79.534 | −0.027 | 1.00 | 35.32 | A | C  |
| ATOM | 1814 | CD1 | TYR | A | 443 | 32.384 | 78.681 | 0.587  | 1.00 | 32.49 | A | C  |
| ATOM | 1815 | CE1 | TYR | A | 443 | 32.655 | 78.105 | 1.823  | 1.00 | 26.61 | A | C  |
| ATOM | 1816 | CD2 | TYR | A | 443 | 34.489 | 79.811 | 0.647  | 1.00 | 34.15 | A | C  |
| ATOM | 1817 | CE2 | TYR | A | 443 | 34.755 | 79.253 | 1.884  | 1.00 | 36.38 | A | C  |
| ATOM | 1818 | CZ  | TYR | A | 443 | 33.821 | 78.403 | 2.474  | 1.00 | 31.16 | A | C  |
| ATOM | 1819 | OH  | TYR | A | 443 | 34.077 | 77.846 | 3.706  | 1.00 | 30.00 | A | O  |
| ATOM | 1820 | C   | TYR | A | 443 | 32.747 | 82.320 | −2.651 | 1.00 | 41.25 | A | C  |
| ATOM | 1821 | O   | TYR | A | 443 | 31.742 | 82.533 | −3.340 | 1.00 | 45.93 | A | O  |
| ATOM | 1822 | ZN  | ZN  | A | 500 | 22.102 | 70.114 | 9.863  | 1.00 | 30.01 | A | Zn |
| ATOM | 1823 | ZN  | ZN  | A | 501 | 30.065 | 64.798 | 18.002 | 1.00 | 39.36 | A | Zn |
| ATOM | 1824 | CA  | CA  | A | 502 | 20.282 | 58.923 | 16.938 | 1.00 | 35.28 | A | Ca |
| ATOM | 1825 | CA  | CA  | A | 504 | 38.880 | 70.297 | 12.131 | 1.00 | 51.74 | A | Ca |
| ATOM | 1826 | CA  | CA  | A | 505 | 41.748 | 78.476 | 7.140  | 1.00 | 52.17 | A | Ca |
| TER  | 1827 |     | CA  | A | 505 |        |        |        |      |       |   |    |
| ATOM | 1828 | CB  | ASP | B | 41  | 5.022  | 13.505 | 39.326 | 1.00 | 65.74 | B | C  |
| ATOM | 1829 | CG  | ASP | B | 41  | 4.163  | 13.796 | 38.118 | 1.00 | 65.95 | B | C  |
| ATOM | 1830 | OD1 | ASP | B | 41  | 4.201  | 13.001 | 37.155 | 1.00 | 59.17 | B | O  |
| ATOM | 1831 | OD2 | ASP | B | 41  | 3.464  | 14.831 | 38.126 | 1.00 | 68.82 | B | O  |
| ATOM | 1832 | C   | ASP | B | 41  | 5.571  | 15.898 | 39.892 | 1.00 | 71.04 | B | C  |
| ATOM | 1833 | O   | ASP | B | 41  | 5.670  | 16.867 | 39.134 | 1.00 | 65.93 | B | O  |
| ATOM | 1834 | N   | ASP | B | 41  | 7.108  | 14.067 | 40.496 | 1.00 | 67.20 | B | N  |
| ATOM | 1835 | CA  | ASP | B | 41  | 6.142  | 14.531 | 39.506 | 1.00 | 70.21 | B | C  |
| ATOM | 1836 | N   | ARG | B | 42  | 4.958  | 15.960 | 41.071 | 1.00 | 75.25 | B | N  |
| ATOM | 1837 | CA  | ARG | B | 42  | 4.633  | 17.236 | 41.701 | 1.00 | 74.37 | B | C  |
| ATOM | 1838 | CB  | ARG | B | 42  | 3.765  | 17.009 | 42.944 | 1.00 | 74.29 | B | C  |
| ATOM | 1839 | CG  | ARG | B | 42  | 3.788  | 18.156 | 43.960 | 1.00 | 75.37 | B | C  |
| ATOM | 1840 | CD  | ARG | B | 42  | 2.682  | 19.175 | 43.702 | 1.00 | 76.78 | B | C  |
| ATOM | 1841 | NE  | ARG | B | 42  | 2.713  | 20.283 | 44.659 | 1.00 | 78.96 | B | N  |
| ATOM | 1842 | CZ  | ARG | B | 42  | 1.761  | 21.208 | 44.768 | 1.00 | 80.51 | B | C  |
| ATOM | 1843 | NH1 | ARG | B | 42  | 0.690  | 21.153 | 43.982 | 1.00 | 80.92 | B | N  |
| ATOM | 1844 | NH2 | ARG | B | 42  | 1.874  | 22.182 | 45.665 | 1.00 | 76.45 | B | N  |

TABLE 12-continued

Coordinates for pro MMP9(35-444 ΔFnII) (SEQ ID NO: 12) complex with Example 2

| ATOM | 1845 | C | ARG | B | 42 | 5.946 | 17.924 | 42.096 | 1.00 | 74.15 | B | C |
|---|---|---|---|---|---|---|---|---|---|---|---|---|
| ATOM | 1846 | O | ARG | B | 42 | 6.054 | 19.160 | 42.079 | 1.00 | 70.08 | B | O |
| ATOM | 1847 | N | GLN | B | 43 | 6.937 | 17.098 | 42.448 | 1.00 | 72.25 | B | N |
| ATOM | 1848 | CA | GLN | B | 43 | 8.264 | 17.567 | 42.828 | 1.00 | 68.50 | B | C |
| ATOM | 1849 | CB | GLN | B | 43 | 9.092 | 16.409 | 43.394 | 1.00 | 67.70 | B | C |
| ATOM | 1850 | CG | GLN | B | 43 | 8.289 | 15.342 | 44.158 | 1.00 | 71.84 | B | C |
| ATOM | 1851 | CD | GLN | B | 43 | 7.766 | 14.228 | 43.258 | 1.00 | 71.97 | B | C |
| ATOM | 1852 | OE1 | GLN | B | 43 | 8.534 | 13.566 | 42.553 | 1.00 | 72.75 | B | O |
| ATOM | 1853 | NE2 | GLN | B | 43 | 6.456 | 14.012 | 43.285 | 1.00 | 71.19 | B | N |
| ATOM | 1854 | C | GLN | B | 43 | 8.935 | 18.101 | 41.576 | 1.00 | 67.06 | B | C |
| ATOM | 1855 | O | GLN | B | 43 | 9.571 | 19.159 | 41.573 | 1.00 | 61.43 | B | O |
| ATOM | 1856 | N | LEU | B | 44 | 8.777 | 17.344 | 40.505 | 1.00 | 63.74 | B | N |
| ATOM | 1857 | CA | LEU | B | 44 | 9.273 | 17.753 | 39.219 | 1.00 | 62.74 | B | C |
| ATOM | 1858 | CB | LEU | B | 44 | 8.858 | 16.728 | 38.172 | 1.00 | 64.04 | B | C |
| ATOM | 1859 | CG | LEU | B | 44 | 9.538 | 16.825 | 36.811 | 1.00 | 67.58 | B | C |
| ATOM | 1860 | CD1 | LEU | B | 44 | 9.472 | 15.488 | 36.057 | 1.00 | 67.66 | B | C |
| ATOM | 1861 | CD2 | LEU | B | 44 | 8.902 | 17.947 | 36.013 | 1.00 | 63.50 | B | C |
| ATOM | 1862 | C | LEU | B | 44 | 8.713 | 19.127 | 38.883 | 1.00 | 63.84 | B | C |
| ATOM | 1863 | O | LEU | B | 44 | 9.465 | 20.070 | 38.661 | 1.00 | 61.49 | B | O |
| ATOM | 1864 | N | ALA | B | 45 | 7.393 | 19.247 | 38.855 | 1.00 | 61.91 | B | N |
| ATOM | 1865 | CA | ALA | B | 45 | 6.775 | 20.505 | 38.471 | 1.00 | 58.80 | B | C |
| ATOM | 1866 | CB | ALA | B | 45 | 5.274 | 20.410 | 38.579 | 1.00 | 61.07 | B | C |
| ATOM | 1867 | C | ALA | B | 45 | 7.300 | 21.665 | 39.310 | 1.00 | 60.91 | B | C |
| ATOM | 1868 | O | ALA | B | 45 | 7.666 | 22.711 | 38.772 | 1.00 | 57.10 | B | O |
| ATOM | 1869 | N | GLU | B | 46 | 7.341 | 21.475 | 40.627 | 1.00 | 63.09 | B | N |
| ATOM | 1870 | CA | GLU | B | 46 | 7.750 | 22.538 | 41.542 | 1.00 | 59.47 | B | C |
| ATOM | 1871 | CB | GLU | B | 46 | 7.679 | 22.058 | 42.994 | 1.00 | 63.75 | B | C |
| ATOM | 1872 | CG | GLU | B | 46 | 6.283 | 22.073 | 43.593 | 1.00 | 70.09 | B | C |
| ATOM | 1873 | CD | GLU | B | 46 | 6.276 | 21.760 | 45.081 | 1.00 | 72.04 | B | C |
| ATOM | 1874 | OE1 | GLU | B | 46 | 7.247 | 21.145 | 45.577 | 1.00 | 73.57 | B | O |
| ATOM | 1875 | OE2 | GLU | B | 46 | 5.294 | 22.127 | 45.756 | 1.00 | 72.41 | B | O |
| ATOM | 1876 | C | GLU | B | 46 | 9.155 | 23.025 | 41.254 | 1.00 | 55.36 | B | C |
| ATOM | 1877 | O | GLU | B | 46 | 9.408 | 24.226 | 41.209 | 1.00 | 55.17 | B | O |
| ATOM | 1878 | N | GLU | B | 47 | 10.068 | 22.077 | 41.085 | 1.00 | 57.58 | B | N |
| ATOM | 1879 | CA | GLU | B | 47 | 11.481 | 22.367 | 40.862 | 1.00 | 59.64 | B | C |
| ATOM | 1880 | CB | GLU | B | 47 | 12.249 | 21.047 | 40.771 | 1.00 | 61.53 | B | C |
| ATOM | 1881 | CG | GLU | B | 47 | 13.714 | 21.134 | 41.132 | 1.00 | 67.83 | B | C |
| ATOM | 1882 | CD | GLU | B | 47 | 14.490 | 22.033 | 40.192 | 1.00 | 70.62 | B | C |
| ATOM | 1883 | OE1 | GLU | B | 47 | 14.383 | 21.838 | 38.955 | 1.00 | 70.87 | B | O |
| ATOM | 1884 | OE2 | GLU | B | 47 | 15.209 | 22.934 | 40.694 | 1.00 | 71.51 | B | O |
| ATOM | 1885 | C | GLU | B | 47 | 11.679 | 23.186 | 39.584 | 1.00 | 54.79 | B | C |
| ATOM | 1886 | O | GLU | B | 47 | 12.296 | 24.250 | 39.604 | 1.00 | 53.75 | B | O |
| ATOM | 1887 | N | TYR | B | 48 | 11.138 | 22.676 | 38.480 | 1.00 | 53.13 | B | N |
| ATOM | 1888 | CA | TYR | B | 48 | 11.179 | 23.342 | 37.177 | 1.00 | 51.61 | B | C |
| ATOM | 1889 | CB | TYR | B | 48 | 10.327 | 22.550 | 36.178 | 1.00 | 44.62 | B | C |
| ATOM | 1890 | CG | TYR | B | 48 | 10.500 | 22.920 | 34.719 | 1.00 | 48.44 | B | C |
| ATOM | 1891 | CD1 | TYR | B | 48 | 10.205 | 24.195 | 34.263 | 1.00 | 45.42 | B | C |
| ATOM | 1892 | CE1 | TYR | B | 48 | 10.350 | 24.536 | 32.916 | 1.00 | 43.59 | B | C |
| ATOM | 1893 | CD2 | TYR | B | 48 | 10.928 | 21.976 | 33.786 | 1.00 | 49.68 | B | C |
| ATOM | 1894 | CE2 | TYR | B | 48 | 11.072 | 22.304 | 32.434 | 1.00 | 42.42 | B | C |
| ATOM | 1895 | CZ | TYR | B | 48 | 10.790 | 23.589 | 32.012 | 1.00 | 40.58 | B | C |
| ATOM | 1896 | OH | TYR | B | 48 | 10.912 | 23.927 | 30.688 | 1.00 | 34.82 | B | O |
| ATOM | 1897 | C | TYR | B | 48 | 10.696 | 24.793 | 37.272 | 1.00 | 52.17 | B | C |
| ATOM | 1898 | O | TYR | B | 48 | 11.434 | 25.730 | 36.958 | 1.00 | 49.81 | B | O |
| ATOM | 1899 | N | LEU | B | 49 | 9.459 | 24.978 | 37.720 | 1.00 | 49.77 | B | N |
| ATOM | 1900 | CA | LEU | B | 49 | 8.882 | 26.310 | 37.832 | 1.00 | 46.45 | B | C |
| ATOM | 1901 | CB | LEU | B | 49 | 7.519 | 26.256 | 38.519 | 1.00 | 51.02 | B | C |
| ATOM | 1902 | CG | LEU | B | 49 | 6.387 | 25.614 | 37.731 | 1.00 | 53.12 | B | C |
| ATOM | 1903 | CD1 | LEU | B | 49 | 5.252 | 25.193 | 38.662 | 1.00 | 60.04 | B | C |
| ATOM | 1904 | CD2 | LEU | B | 49 | 5.901 | 26.582 | 36.681 | 1.00 | 51.92 | B | C |
| ATOM | 1905 | C | LEU | B | 49 | 9.780 | 27.225 | 38.624 | 1.00 | 46.54 | B | C |
| ATOM | 1906 | O | LEU | B | 49 | 9.854 | 28.420 | 38.350 | 1.00 | 49.92 | B | O |
| ATOM | 1907 | N | TYR | B | 50 | 10.445 | 26.685 | 39.636 | 1.00 | 42.96 | B | N |
| ATOM | 1908 | CA | TYR | B | 50 | 11.263 | 27.548 | 40.472 | 1.00 | 45.93 | B | C |
| ATOM | 1909 | CB | TYR | B | 50 | 11.610 | 26.902 | 41.815 | 1.00 | 50.35 | B | C |
| ATOM | 1910 | CG | TYR | B | 50 | 12.649 | 27.709 | 42.563 | 1.00 | 52.07 | B | C |
| ATOM | 1911 | CD1 | TYR | B | 50 | 12.288 | 28.832 | 43.292 | 1.00 | 55.31 | B | C |
| ATOM | 1912 | CE1 | TYR | B | 50 | 13.240 | 29.596 | 43.962 | 1.00 | 56.70 | B | C |
| ATOM | 1913 | CD2 | TYR | B | 50 | 13.998 | 27.374 | 42.504 | 1.00 | 54.61 | B | C |
| ATOM | 1914 | CE2 | TYR | B | 50 | 14.961 | 28.130 | 43.167 | 1.00 | 55.56 | B | C |
| ATOM | 1915 | CZ | TYR | B | 50 | 14.575 | 29.242 | 43.899 | 1.00 | 59.82 | B | C |
| ATOM | 1916 | OH | TYR | B | 50 | 15.524 | 30.003 | 44.565 | 1.00 | 65.40 | B | O |
| ATOM | 1917 | C | TYR | B | 50 | 12.538 | 27.912 | 39.736 | 1.00 | 51.95 | B | C |
| ATOM | 1918 | O | TYR | B | 50 | 12.943 | 29.081 | 39.713 | 1.00 | 51.35 | B | O |
| ATOM | 1919 | N | ARG | B | 51 | 13.160 | 26.897 | 39.136 | 1.00 | 54.54 | B | N |
| ATOM | 1920 | CA | ARG | B | 51 | 14.479 | 27.029 | 38.509 | 1.00 | 52.84 | B | C |
| ATOM | 1921 | CB | ARG | B | 51 | 14.880 | 25.711 | 37.845 | 1.00 | 49.30 | B | C |

TABLE 12-continued

Coordinates for pro MMP9(35-444 ΔFnII) (SEQ ID NO: 12) complex with Example 2

| ATOM | 1922 | CG  | ARG | B | 51 | 16.279 | 25.694 | 37.246 | 1.00 | 47.56 | B | C |
| ATOM | 1923 | CD  | ARG | B | 51 | 16.503 | 24.426 | 36.436 | 1.00 | 45.80 | B | C |
| ATOM | 1924 | NE  | ARG | B | 51 | 16.868 | 23.265 | 37.250 | 1.00 | 46.98 | B | N |
| ATOM | 1925 | CZ  | ARG | B | 51 | 18.080 | 23.053 | 37.759 | 1.00 | 50.08 | B | C |
| ATOM | 1926 | NH1 | ARG | B | 51 | 19.057 | 23.937 | 37.567 | 1.00 | 41.56 | B | N |
| ATOM | 1927 | NH2 | ARG | B | 51 | 18.314 | 21.959 | 38.480 | 1.00 | 52.18 | B | N |
| ATOM | 1928 | C   | ARG | B | 51 | 14.488 | 28.130 | 37.470 | 1.00 | 44.39 | B | C |
| ATOM | 1929 | O   | ARG | B | 51 | 15.373 | 28.992 | 37.452 | 1.00 | 40.15 | B | O |
| ATOM | 1930 | N   | TYR | B | 52 | 13.480 | 28.105 | 36.616 | 1.00 | 43.93 | B | N |
| ATOM | 1931 | CA  | TYR | B | 52 | 13.486 | 28.956 | 35.448 | 1.00 | 40.69 | B | C |
| ATOM | 1932 | CB  | TYR | B | 52 | 12.863 | 28.216 | 34.270 | 1.00 | 43.23 | B | C |
| ATOM | 1933 | CG  | TYR | B | 52 | 13.625 | 26.934 | 33.970 | 1.00 | 44.97 | B | C |
| ATOM | 1934 | CD1 | TYR | B | 52 | 13.067 | 25.690 | 34.227 | 1.00 | 41.85 | B | C |
| ATOM | 1935 | CE1 | TYR | B | 52 | 13.770 | 24.517 | 33.967 | 1.00 | 44.90 | B | C |
| ATOM | 1936 | CD2 | TYR | B | 52 | 14.921 | 26.976 | 33.465 | 1.00 | 39.45 | B | C |
| ATOM | 1937 | CE2 | TYR | B | 52 | 15.638 | 25.809 | 33.215 | 1.00 | 38.75 | B | C |
| ATOM | 1938 | CZ  | TYR | B | 52 | 15.055 | 24.582 | 33.457 | 1.00 | 44.77 | B | C |
| ATOM | 1939 | OH  | TYR | B | 52 | 15.756 | 23.417 | 33.201 | 1.00 | 47.32 | B | O |
| ATOM | 1940 | C   | TYR | B | 52 | 12.871 | 30.317 | 35.680 | 1.00 | 44.92 | B | C |
| ATOM | 1941 | O   | TYR | B | 52 | 12.693 | 31.070 | 34.730 | 1.00 | 38.50 | B | O |
| ATOM | 1942 | N   | GLY | B | 53 | 12.547 | 30.617 | 36.946 | 1.00 | 52.40 | B | N |
| ATOM | 1943 | CA  | GLY | B | 53 | 12.119 | 31.953 | 37.375 | 1.00 | 52.23 | B | C |
| ATOM | 1944 | C   | GLY | B | 53 | 10.620 | 32.214 | 37.516 | 1.00 | 53.39 | B | C |
| ATOM | 1945 | O   | GLY | B | 53 | 10.201 | 33.341 | 37.800 | 1.00 | 51.02 | B | O |
| ATOM | 1946 | N   | TYR | B | 54 | 9.818  | 31.170 | 37.329 | 1.00 | 46.47 | B | N |
| ATOM | 1947 | CA  | TYR | B | 54 | 8.361  | 31.285 | 37.312 | 1.00 | 53.09 | B | C |
| ATOM | 1948 | CB  | TYR | B | 54 | 7.752  | 29.995 | 36.748 | 1.00 | 48.72 | B | C |
| ATOM | 1949 | CG  | TYR | B | 54 | 8.006  | 29.871 | 35.269 | 1.00 | 49.41 | B | C |
| ATOM | 1950 | CD1 | TYR | B | 54 | 8.884  | 28.910 | 34.753 | 1.00 | 52.68 | B | C |
| ATOM | 1951 | CE1 | TYR | B | 54 | 9.131  | 28.830 | 33.389 | 1.00 | 42.25 | B | C |
| ATOM | 1952 | CD2 | TYR | B | 54 | 7.406  | 30.751 | 34.386 | 1.00 | 47.29 | B | C |
| ATOM | 1953 | CE2 | TYR | B | 54 | 7.643  | 30.681 | 33.043 | 1.00 | 48.96 | B | C |
| ATOM | 1954 | CZ  | TYR | B | 54 | 8.499  | 29.725 | 32.547 | 1.00 | 46.11 | B | C |
| ATOM | 1955 | OH  | TYR | B | 54 | 8.698  | 29.695 | 31.195 | 1.00 | 44.01 | B | O |
| ATOM | 1956 | C   | TYR | B | 54 | 7.735  | 31.652 | 38.670 | 1.00 | 58.21 | B | C |
| ATOM | 1957 | O   | TYR | B | 54 | 7.173  | 32.743 | 38.850 | 1.00 | 51.66 | B | O |
| ATOM | 1958 | N   | THR | B | 55 | 7.826  | 30.736 | 39.620 | 1.00 | 52.97 | B | N |
| ATOM | 1959 | CA  | THR | B | 55 | 7.336  | 31.011 | 40.950 | 1.00 | 54.51 | B | C |
| ATOM | 1960 | CB  | THR | B | 55 | 7.827  | 29.949 | 41.923 | 1.00 | 53.92 | B | C |
| ATOM | 1961 | OG1 | THR | B | 55 | 9.163  | 30.268 | 42.319 | 1.00 | 57.98 | B | O |
| ATOM | 1962 | CG2 | THR | B | 55 | 7.798  | 28.557 | 41.265 | 1.00 | 43.39 | B | C |
| ATOM | 1963 | C   | THR | B | 55 | 7.804  | 32.403 | 41.409 | 1.00 | 61.71 | B | C |
| ATOM | 1964 | O   | THR | B | 55 | 7.003  | 33.235 | 41.845 | 1.00 | 65.02 | B | O |
| ATOM | 1965 | N   | ARG | B | 56 | 9.098  | 32.662 | 41.284 | 1.00 | 57.06 | B | N |
| ATOM | 1966 | CA  | ARG | B | 56 | 9.700  | 33.907 | 41.764 | 1.00 | 63.01 | B | C |
| ATOM | 1967 | CB  | ARG | B | 56 | 11.191 | 33.901 | 41.422 | 1.00 | 66.89 | B | C |
| ATOM | 1968 | CG  | ARG | B | 56 | 11.964 | 35.173 | 41.742 | 1.00 | 72.53 | B | C |
| ATOM | 1969 | CD  | ARG | B | 56 | 13.434 | 34.976 | 41.357 | 1.00 | 77.67 | B | C |
| ATOM | 1970 | NE  | ARG | B | 56 | 14.348 | 35.771 | 42.171 | 1.00 | 81.82 | B | N |
| ATOM | 1971 | CZ  | ARG | B | 56 | 15.591 | 35.402 | 42.465 | 1.00 | 79.88 | B | C |
| ATOM | 1972 | NH1 | ARG | B | 56 | 16.066 | 34.244 | 42.016 | 1.00 | 73.79 | B | N |
| ATOM | 1973 | NH2 | ARG | B | 56 | 16.356 | 36.187 | 43.216 | 1.00 | 78.98 | B | N |
| ATOM | 1974 | C   | ARG | B | 56 | 9.049  | 35.165 | 41.191 | 1.00 | 63.81 | B | C |
| ATOM | 1975 | O   | ARG | B | 56 | 9.086  | 36.231 | 41.797 | 1.00 | 64.42 | B | O |
| ATOM | 1976 | N   | VAL | B | 57 | 8.470  | 35.046 | 40.008 | 1.00 | 63.79 | B | N |
| ATOM | 1977 | CA  | VAL | B | 57 | 7.896  | 36.200 | 39.352 | 1.00 | 61.30 | B | C |
| ATOM | 1978 | CB  | VAL | B | 57 | 8.110  | 36.147 | 37.840 | 1.00 | 59.39 | B | C |
| ATOM | 1979 | CG1 | VAL | B | 57 | 7.166  | 37.099 | 37.134 | 1.00 | 64.11 | B | C |
| ATOM | 1980 | CG2 | VAL | B | 57 | 9.564  | 36.482 | 37.514 | 1.00 | 58.75 | B | C |
| ATOM | 1981 | C   | VAL | B | 57 | 6.424  | 36.235 | 39.668 | 1.00 | 66.96 | B | C |
| ATOM | 1982 | O   | VAL | B | 57 | 5.817  | 37.306 | 39.733 | 1.00 | 71.03 | B | O |
| ATOM | 1983 | N   | ALA | B | 58 | 5.852  | 35.054 | 39.876 | 1.00 | 64.11 | B | N |
| ATOM | 1984 | CA  | ALA | B | 58 | 4.482  | 34.954 | 40.352 | 1.00 | 61.65 | B | C |
| ATOM | 1985 | CB  | ALA | B | 58 | 4.073  | 33.503 | 40.486 | 1.00 | 65.52 | B | C |
| ATOM | 1986 | C   | ALA | B | 58 | 4.388  | 35.677 | 41.696 | 1.00 | 67.74 | B | C |
| ATOM | 1987 | O   | ALA | B | 58 | 3.712  | 36.699 | 41.812 | 1.00 | 67.71 | B | O |
| ATOM | 1988 | N   | GLU | B | 59 | 5.081  | 35.149 | 42.702 | 1.00 | 67.67 |   | N |
| ATOM | 1989 | CA  | GLU | B | 59 | 5.206  | 35.834 | 43.982 | 1.00 | 65.60 |   | C |
| ATOM | 1990 | C   | GLU | B | 59 | 5.372  | 37.325 | 43.727 | 1.00 | 67.86 |   | C |
| ATOM | 1991 | CB  | GLU | B | 59 | 6.413  | 35.307 | 44.765 | 1.00 | 58.06 |   | C |
| ATOM | 1992 | CG  | GLU | B | 59 | 6.392  | 33.812 | 45.045 | 1.00 | 59.37 |   | C |
| ATOM | 1993 | CD  | GLU | B | 59 | 7.649  | 33.339 | 45.772 | 1.00 | 60.63 |   | C |
| ATOM | 1994 | OE1 | GLU | B | 59 | 8.658  | 34.084 | 45.773 | 1.00 | 63.25 |   | O |
| ATOM | 1995 | OE2 | GLU | B | 59 | 7.634  | 32.227 | 46.347 | 1.00 | 56.75 |   | O |
| ATOM | 1996 | O   | GLU | B | 59 | 4.413  | 38.086 | 43.784 | 1.00 | 73.68 |   | O |
| ATOM | 1997 | N   | MET | B | 60 | 6.600  | 37.730 | 43.427 | 1.00 | 67.55 |   | N |
| ATOM | 1998 | CA  | MET | B | 60 | 6.918  | 39.118 | 43.114 | 1.00 | 69.87 |   | C |

TABLE 12-continued

Coordinates for pro MMP9(35-444 ΔFnII) (SEQ ID NO: 12) complex with Example 2

| ATOM | 1999 | C | MET | B | 60 | 5.934 | 39.739 | 42.141 | 1.00 | 76.80 | | C |
|---|---|---|---|---|---|---|---|---|---|---|---|---|
| ATOM | 2000 | CB | MET | B | 60 | 8.324 | 39.204 | 42.515 | 1.00 | 79.28 | | C |
| ATOM | 2001 | CG | MET | B | 60 | 8.656 | 40.537 | 41.849 | 1.00 | 83.24 | | C |
| ATOM | 2002 | SD | MET | B | 60 | 10.117 | 40.403 | 40.796 | 1.00 | 89.28 | | S |
| ATOM | 2003 | CE | MET | B | 60 | 10.466 | 42.135 | 40.471 | 1.00 | 84.15 | | C |
| ATOM | 2004 | O | MET | B | 60 | 6.051 | 39.531 | 40.931 | 1.00 | 76.81 | | O |
| ATOM | 2005 | N | ARG | B | 61 | 4.971 | 40.483 | 42.689 | 1.00 | 80.76 | | N |
| ATOM | 2006 | CA | ARG | B | 61 | 4.034 | 41.338 | 41.941 | 1.00 | 80.02 | | C |
| ATOM | 2007 | C | ARG | B | 61 | 2.561 | 40.920 | 42.057 | 1.00 | 82.28 | | C |
| ATOM | 2008 | CB | ARG | B | 61 | 4.445 | 41.534 | 40.462 | 1.00 | 85.16 | | C |
| ATOM | 2009 | CG | ARG | B | 61 | 3.930 | 40.470 | 39.477 | 1.00 | 80.22 | | C |
| ATOM | 2010 | CD | ARG | B | 61 | 4.384 | 40.760 | 38.050 | 1.00 | 78.02 | | C |
| ATOM | 2011 | NE | ARG | B | 61 | 3.909 | 39.753 | 37.099 | 1.00 | 80.81 | | N |
| ATOM | 2012 | CZ | ARG | B | 61 | 3.946 | 39.897 | 35.775 | 1.00 | 78.21 | | C |
| ATOM | 2013 | NH1 | ARG | B | 61 | 4.436 | 41.010 | 35.241 | 1.00 | 80.01 | | N |
| ATOM | 2014 | NH2 | ARG | B | 61 | 3.491 | 38.930 | 34.985 | 1.00 | 66.52 | | N |
| ATOM | 2015 | O | ARG | B | 61 | 1.690 | 41.768 | 42.261 | 1.00 | 84.66 | | O |
| ATOM | 2016 | N | GLY | B | 62 | 2.283 | 39.625 | 41.936 | 1.00 | 79.93 | | N |
| ATOM | 2017 | CA | GLY | B | 62 | 0.906 | 39.176 | 41.832 | 1.00 | 83.57 | | C |
| ATOM | 2018 | C | GLY | B | 62 | 0.499 | 38.021 | 42.726 | 1.00 | 88.38 | | C |
| ATOM | 2019 | O | GLY | B | 62 | −0.004 | 37.003 | 42.237 | 1.00 | 91.14 | | O |
| ATOM | 2020 | O | ALA | B | 63 | 1.504 | 35.177 | 45.204 | 1.00 | 83.74 | | O |
| ATOM | 2021 | N | ALA | B | 63 | 0.710 | 38.179 | 44.032 | 1.00 | 87.30 | | N |
| ATOM | 2022 | CA | ALA | B | 63 | 0.235 | 37.217 | 45.036 | 1.00 | 84.21 | | C |
| ATOM | 2023 | C | ALA | B | 63 | 0.522 | 35.744 | 44.716 | 1.00 | 82.02 | | C |
| ATOM | 2024 | CB | ALA | B | 63 | −1.256 | 37.424 | 45.314 | 1.00 | 81.80 | | C |
| ATOM | 2025 | O | ALA | B | 64 | 0.555 | 32.582 | 45.554 | 1.00 | 82.36 | | O |
| ATOM | 2026 | N | ALA | B | 64 | −0.349 | 35.131 | 43.916 | 1.00 | 80.13 | | N |
| ATOM | 2027 | CA | ALA | B | 64 | −0.246 | 33.712 | 43.575 | 1.00 | 79.65 | | C |
| ATOM | 2028 | C | ALA | B | 64 | −0.398 | 32.794 | 44.795 | 1.00 | 80.69 | | C |
| ATOM | 2029 | CB | ALA | B | 64 | 1.060 | 33.432 | 42.845 | 1.00 | 79.23 | | C |
| ATOM | 2030 | O | ALA | B | 65 | −0.096 | 29.771 | 46.514 | 1.00 | 75.70 | | O |
| ATOM | 2031 | N | ALA | B | 65 | −1.597 | 32.244 | 44.975 | 1.00 | 77.24 | | N |
| ATOM | 2032 | CA | ALA | B | 65 | −1.867 | 31.342 | 46.091 | 1.00 | 78.75 | | C |
| ATOM | 2033 | C | ALA | B | 65 | −1.150 | 30.003 | 45.914 | 1.00 | 76.00 | | C |
| ATOM | 2034 | CB | ALA | B | 65 | −3.373 | 31.134 | 46.259 | 1.00 | 78.89 | | C |
| ATOM | 2035 | N | SER | B | 66 | −1.722 | 29.129 | 45.091 | 1.00 | 74.14 | | N |
| ATOM | 2036 | CA | SER | B | 66 | −1.083 | 27.859 | 44.752 | 1.00 | 76.20 | | C |
| ATOM | 2037 | C | SER | B | 66 | −0.200 | 28.045 | 43.526 | 1.00 | 76.11 | | C |
| ATOM | 2038 | CB | SER | B | 66 | −2.126 | 26.790 | 44.437 | 1.00 | 74.06 | | C |
| ATOM | 2039 | OG | SER | B | 66 | −2.584 | 26.917 | 43.099 | 1.00 | 72.23 | | O |
| ATOM | 2040 | O | SER | B | 66 | −0.069 | 29.156 | 43.011 | 1.00 | 75.48 | | O |
| ATOM | 2041 | N | LEU | B | 67 | 0.396 | 26.958 | 43.049 | 1.00 | 73.68 | | N |
| ATOM | 2042 | CA | LEU | B | 67 | 1.195 | 27.032 | 41.831 | 1.00 | 73.20 | | C |
| ATOM | 2043 | C | LEU | B | 67 | 0.316 | 26.958 | 40.571 | 1.00 | 71.75 | | C |
| ATOM | 2044 | CB | LEU | B | 67 | 2.321 | 25.984 | 41.827 | 1.00 | 70.14 | | C |
| ATOM | 2045 | CG | LEU | B | 67 | 2.049 | 24.531 | 42.229 | 1.00 | 72.69 | | C |
| ATOM | 2046 | CD1 | LEU | B | 67 | 1.458 | 23.735 | 41.074 | 1.00 | 66.99 | | C |
| ATOM | 2047 | CD2 | LEU | B | 67 | 3.336 | 23.886 | 42.713 | 1.00 | 69.48 | | C |
| ATOM | 2048 | O | LEU | B | 67 | 0.685 | 26.334 | 39.576 | 1.00 | 69.22 | | O |
| ATOM | 2049 | N | GLY | B | 68 | −0.842 | 27.616 | 40.629 | 1.00 | 71.30 | B | N |
| ATOM | 2050 | CA | GLY | B | 68 | −1.745 | 27.727 | 39.493 | 1.00 | 63.45 | B | C |
| ATOM | 2051 | C | GLY | B | 68 | −1.452 | 28.943 | 38.628 | 1.00 | 66.35 | B | C |
| ATOM | 2052 | O | GLY | B | 68 | −1.557 | 28.865 | 37.402 | 1.00 | 64.85 | B | O |
| ATOM | 2053 | N | PRO | B | 69 | −1.115 | 30.084 | 39.261 | 1.00 | 68.38 | B | N |
| ATOM | 2054 | CD | PRO | B | 69 | −1.466 | 30.386 | 40.660 | 1.00 | 70.73 | B | C |
| ATOM | 2055 | CA | PRO | B | 69 | −0.577 | 31.268 | 38.577 | 1.00 | 69.12 | B | C |
| ATOM | 2056 | CB | PRO | B | 69 | −0.463 | 32.302 | 39.708 | 1.00 | 71.10 | B | C |
| ATOM | 2057 | CG | PRO | B | 69 | −1.480 | 31.889 | 40.692 | 1.00 | 71.67 | B | C |
| ATOM | 2058 | C | PRO | B | 69 | 0.804 | 31.023 | 37.942 | 1.00 | 62.19 | B | C |
| ATOM | 2059 | O | PRO | B | 69 | 0.985 | 31.287 | 36.753 | 1.00 | 56.18 | B | O |
| ATOM | 2060 | N | ALA | B | 70 | 1.758 | 30.529 | 38.726 | 1.00 | 61.70 | B | N |
| ATOM | 2061 | CA | ALA | B | 70 | 3.081 | 30.203 | 38.202 | 1.00 | 57.78 | B | C |
| ATOM | 2062 | CB | ALA | B | 70 | 3.980 | 29.643 | 39.296 | 1.00 | 55.65 | B | C |
| ATOM | 2063 | C | ALA | B | 70 | 3.022 | 29.245 | 37.014 | 1.00 | 57.58 | B | C |
| ATOM | 2064 | O | ALA | B | 70 | 3.912 | 29.260 | 36.167 | 1.00 | 58.50 | B | O |
| ATOM | 2065 | N | LEU | B | 71 | 1.979 | 28.423 | 36.937 | 1.00 | 58.37 | B | N |
| ATOM | 2066 | CA | LEU | B | 71 | 1.845 | 27.484 | 35.825 | 1.00 | 54.20 | B | C |
| ATOM | 2067 | CB | LEU | B | 71 | 0.981 | 26.293 | 36.217 | 1.00 | 57.73 | B | C |
| ATOM | 2068 | CG | LEU | B | 71 | 1.740 | 25.038 | 36.643 | 1.00 | 61.95 | B | C |
| ATOM | 2069 | CD1 | LEU | B | 71 | 0.804 | 23.995 | 37.236 | 1.00 | 63.87 | B | C |
| ATOM | 2070 | CD2 | LEU | B | 71 | 2.474 | 24.462 | 35.456 | 1.00 | 60.55 | B | C |
| ATOM | 2071 | C | LEU | B | 71 | 1.301 | 28.114 | 34.547 | 1.00 | 57.56 | B | C |
| ATOM | 2072 | O | LEU | B | 71 | 1.513 | 27.594 | 33.449 | 1.00 | 54.38 | B | O |
| ATOM | 2073 | N | LEU | B | 72 | 0.585 | 29.225 | 34.679 | 1.00 | 59.26 | B | N |
| ATOM | 2074 | CA | LEU | B | 72 | 0.057 | 29.892 | 33.494 | 1.00 | 58.25 | B | C |
| ATOM | 2075 | CB | LEU | B | 72 | −1.160 | 30.759 | 33.833 | 1.00 | 52.93 | B | C |

TABLE 12-continued

Coordinates for pro MMP9(35-444 ΔFnII) (SEQ ID NO: 12) complex with Example 2

| ATOM | 2076 | CG | LEU | B | 72 | −2.275 | 30.715 | 32.782 | 1.00 | 58.95 | B | C |
|------|------|-----|-----|---|----|--------|--------|--------|------|-------|---|---|
| ATOM | 2077 | CD1 | LEU | B | 72 | −3.393 | 31.721 | 33.058 | 1.00 | 59.88 | B | C |
| ATOM | 2078 | CD2 | LEU | B | 72 | −2.843 | 29.307 | 32.668 | 1.00 | 59.13 | B | C |
| ATOM | 2079 | C | LEU | B | 72 | 1.150 | 30.731 | 32.842 | 1.00 | 49.05 | B | C |
| ATOM | 2080 | O | LEU | B | 72 | 1.232 | 30.816 | 31.624 | 1.00 | 51.22 | B | O |
| ATOM | 2081 | N | LEU | B | 73 | 1.974 | 31.364 | 33.666 | 1.00 | 52.29 | B | N |
| ATOM | 2082 | CA | LEU | B | 73 | 3.126 | 32.094 | 33.169 | 1.00 | 50.42 | B | C |
| ATOM | 2083 | CB | LEU | B | 73 | 3.957 | 32.621 | 34.330 | 1.00 | 43.90 | B | C |
| ATOM | 2084 | CG | LEU | B | 73 | 3.362 | 33.801 | 35.082 | 1.00 | 47.42 | B | C |
| ATOM | 2085 | CD1 | LEU | B | 73 | 4.385 | 34.352 | 36.050 | 1.00 | 47.82 | B | C |
| ATOM | 2086 | CD2 | LEU | B | 73 | 2.892 | 34.867 | 34.104 | 1.00 | 45.81 | B | C |
| ATOM | 2087 | C | LEU | B | 73 | 3.975 | 31.151 | 32.324 | 1.00 | 48.66 | B | C |
| ATOM | 2088 | O | LEU | B | 73 | 4.338 | 31.459 | 31.195 | 1.00 | 39.99 | B | O |
| ATOM | 2089 | N | LEU | B | 74 | 4.274 | 29.988 | 32.889 | 1.00 | 46.40 | B | N |
| ATOM | 2090 | CA | LEU | B | 74 | 5.084 | 29.002 | 32.200 | 1.00 | 47.76 | B | C |
| ATOM | 2091 | CB | LEU | B | 74 | 5.289 | 27.770 | 33.072 | 1.00 | 46.03 | B | C |
| ATOM | 2092 | CG | LEU | B | 74 | 5.643 | 26.549 | 32.238 | 1.00 | 48.51 | B | C |
| ATOM | 2093 | CD1 | LEU | B | 74 | 6.809 | 25.776 | 32.853 | 1.00 | 50.36 | B | C |
| ATOM | 2094 | CD2 | LEU | B | 74 | 4.422 | 25.677 | 32.046 | 1.00 | 46.77 | B | C |
| ATOM | 2095 | C | LEU | B | 74 | 4.473 | 28.603 | 30.872 | 1.00 | 50.10 | B | C |
| ATOM | 2096 | O | LEU | B | 74 | 5.164 | 28.538 | 29.854 | 1.00 | 49.27 | B | O |
| ATOM | 2097 | N | GLN | B | 75 | 3.175 | 28.337 | 30.886 | 1.00 | 48.13 | B | N |
| ATOM | 2098 | CA | GLN | B | 75 | 2.471 | 27.924 | 29.687 | 1.00 | 46.79 | B | C |
| ATOM | 2099 | CB | GLN | B | 75 | 1.044 | 27.513 | 30.033 | 1.00 | 55.32 | B | C |
| ATOM | 2100 | CG | GLN | B | 75 | 0.961 | 26.281 | 30.922 | 1.00 | 55.15 | B | C |
| ATOM | 2101 | CD | GLN | B | 75 | −0.454 | 26.005 | 31.381 | 1.00 | 59.47 | B | C |
| ATOM | 2102 | OE1 | GLN | B | 75 | −1.109 | 26.868 | 31.983 | 1.00 | 54.32 | B | O |
| ATOM | 2103 | NE2 | GLN | B | 75 | −0.935 | 24.801 | 31.099 | 1.00 | 59.22 | B | N |
| ATOM | 2104 | C | GLN | B | 75 | 2.451 | 29.056 | 28.679 | 1.00 | 45.24 | B | C |
| ATOM | 2105 | O | GLN | B | 75 | 2.353 | 28.823 | 27.475 | 1.00 | 44.89 | B | O |
| ATOM | 2106 | N | LYS | B | 76 | 2.526 | 30.285 | 29.169 | 1.00 | 43.52 | B | N |
| ATOM | 2107 | CA | LYS | B | 76 | 2.630 | 31.416 | 28.261 | 1.00 | 48.29 | B | C |
| ATOM | 2108 | CB | LYS | B | 76 | 2.364 | 32.740 | 28.976 | 1.00 | 52.99 | B | C |
| ATOM | 2109 | CG | LYS | B | 76 | 0.887 | 32.980 | 29.294 | 1.00 | 59.68 | B | C |
| ATOM | 2110 | CD | LYS | B | 76 | 0.614 | 34.454 | 29.615 | 1.00 | 69.17 | B | C |
| ATOM | 2111 | CE | LYS | B | 76 | −0.829 | 34.682 | 30.086 | 1.00 | 67.84 | B | C |
| ATOM | 2112 | NZ | LYS | B | 76 | −1.075 | 34.064 | 31.420 | 1.00 | 62.54 | B | N |
| ATOM | 2113 | C | LYS | B | 76 | 4.006 | 31.425 | 27.587 | 1.00 | 46.35 | B | C |
| ATOM | 2114 | O | LYS | B | 76 | 4.089 | 31.387 | 26.365 | 1.00 | 41.00 | B | O |
| ATOM | 2115 | N | GLN | B | 77 | 5.068 | 31.454 | 28.388 | 1.00 | 47.54 | B | N |
| ATOM | 2116 | CA | GLN | B | 77 | 6.447 | 31.453 | 27.867 | 1.00 | 50.61 | B | C |
| ATOM | 2117 | CB | GLN | B | 77 | 7.463 | 31.323 | 29.002 | 1.00 | 48.68 | B | C |
| ATOM | 2118 | CG | GLN | B | 77 | 7.977 | 32.651 | 29.524 | 1.00 | 55.06 | B | C |
| ATOM | 2119 | CD | GLN | B | 77 | 8.596 | 33.511 | 28.434 | 1.00 | 56.24 | B | C |
| ATOM | 2120 | OE1 | GLN | B | 77 | 8.521 | 34.741 | 28.478 | 1.00 | 59.18 | B | O |
| ATOM | 2121 | NE2 | GLN | B | 77 | 9.215 | 32.866 | 27.448 | 1.00 | 53.94 | B | N |
| ATOM | 2122 | C | GLN | B | 77 | 6.746 | 30.377 | 26.823 | 1.00 | 46.16 | B | C |
| ATOM | 2123 | O | GLN | B | 77 | 7.472 | 30.630 | 25.880 | 1.00 | 49.02 | B | O |
| ATOM | 2124 | N | LEU | B | 78 | 6.188 | 29.183 | 26.993 | 1.00 | 43.35 | B | N |
| ATOM | 2125 | CA | LEU | B | 78 | 6.489 | 28.067 | 26.106 | 1.00 | 43.42 | B | C |
| ATOM | 2126 | CB | LEU | B | 78 | 6.595 | 26.769 | 26.903 | 1.00 | 41.38 | B | C |
| ATOM | 2127 | CG | LEU | B | 78 | 7.361 | 26.948 | 28.208 | 1.00 | 39.55 | B | C |
| ATOM | 2128 | CD1 | LEU | B | 78 | 7.865 | 25.622 | 28.707 | 1.00 | 40.76 | B | C |
| ATOM | 2129 | CD2 | LEU | B | 78 | 8.508 | 27.929 | 28.019 | 1.00 | 42.89 | B | C |
| ATOM | 2130 | C | LEU | B | 78 | 5.436 | 27.917 | 25.030 | 1.00 | 42.27 | B | C |
| ATOM | 2131 | O | LEU | B | 78 | 5.441 | 26.948 | 24.270 | 1.00 | 38.83 | B | O |
| ATOM | 2132 | N | SER | B | 79 | 4.539 | 28.891 | 24.959 | 1.00 | 41.22 | B | N |
| ATOM | 2133 | CA | SER | B | 79 | 3.379 | 28.785 | 24.087 | 1.00 | 43.16 | B | C |
| ATOM | 2134 | CB | SER | B | 79 | 3.756 | 29.107 | 22.647 | 1.00 | 42.01 | B | C |
| ATOM | 2135 | OG | SER | B | 79 | 3.905 | 30.508 | 22.521 | 1.00 | 46.07 | B | C |
| ATOM | 2136 | C | SER | B | 79 | 2.725 | 27.414 | 24.210 | 1.00 | 38.43 | B | C |
| ATOM | 2137 | O | SER | B | 79 | 2.514 | 26.712 | 23.213 | 1.00 | 39.79 | B | O |
| ATOM | 2138 | N | LEU | B | 80 | 2.435 | 27.044 | 25.460 | 1.00 | 43.42 | B | N |
| ATOM | 2139 | CA | LEU | B | 80 | 1.599 | 25.882 | 25.806 | 1.00 | 50.55 | B | C |
| ATOM | 2140 | CB | LEU | B | 80 | 2.082 | 25.257 | 27.113 | 1.00 | 45.61 | B | C |
| ATOM | 2141 | CG | LEU | B | 80 | 3.505 | 24.727 | 27.060 | 1.00 | 43.90 | B | C |
| ATOM | 2142 | CD1 | LEU | B | 80 | 3.922 | 24.228 | 28.424 | 1.00 | 44.53 | B | C |
| ATOM | 2143 | CD2 | LEU | B | 80 | 3.613 | 23.627 | 26.000 | 1.00 | 48.00 | B | C |
| ATOM | 2144 | C | LEU | B | 80 | 0.142 | 26.301 | 25.989 | 1.00 | 45.27 | B | C |
| ATOM | 2145 | O | LEU | B | 80 | −0.128 | 27.484 | 26.200 | 1.00 | 45.06 | B | O |
| ATOM | 2146 | N | PRO | B | 81 | −0.798 | 25.336 | 25.913 | 1.00 | 48.19 | B | N |
| ATOM | 2147 | CD | PRO | B | 81 | −0.655 | 23.918 | 25.539 | 1.00 | 53.09 | B | C |
| ATOM | 2148 | CA | PRO | B | 81 | −2.180 | 25.655 | 26.285 | 1.00 | 57.06 | B | C |
| ATOM | 2149 | CB | PRO | B | 81 | −2.870 | 24.285 | 26.296 | 1.00 | 56.36 | B | C |
| ATOM | 2150 | CG | PRO | B | 81 | −2.083 | 23.460 | 25.359 | 1.00 | 53.06 | B | C |
| ATOM | 2151 | C | PRO | B | 81 | −2.183 | 26.250 | 27.684 | 1.00 | 54.09 | B | C |
| ATOM | 2152 | O | PRO | B | 81 | −1.569 | 25.671 | 28.595 | 1.00 | 53.23 | B | O |

TABLE 12-continued

Coordinates for pro MMP9(35-444 ΔFnII) (SEQ ID NO: 12) complex with Example 2

| ATOM | 2153 | N | GLU | B | 82 | −2.837 | 27.400 | 27.835 | 1.00 | 52.51 | B | N |
|------|------|------|-----|---|----|--------|--------|--------|------|-------|---|---|
| ATOM | 2154 | CA | GLU | B | 82 | −2.826 | 28.132 | 29.090 | 1.00 | 55.86 | B | C |
| ATOM | 2155 | CB | GLU | B | 82 | −2.993 | 29.620 | 28.812 | 1.00 | 58.20 | B | C |
| ATOM | 2156 | CG | GLU | B | 82 | −2.190 | 30.111 | 27.630 | 1.00 | 54.39 | B | C |
| ATOM | 2157 | CD | GLU | B | 82 | −2.002 | 31.608 | 27.662 | 1.00 | 59.82 | B | C |
| ATOM | 2158 | OE1 | GLU | B | 82 | −2.005 | 32.164 | 28.778 | 1.00 | 61.53 | B | O |
| ATOM | 2159 | OE2 | GLU | B | 82 | −1.853 | 32.227 | 26.583 | 1.00 | 58.32 | B | O |
| ATOM | 2160 | C | GLU | B | 82 | −3.926 | 27.630 | 30.026 | 1.00 | 58.62 | B | C |
| ATOM | 2161 | O | GLU | B | 82 | −4.807 | 28.383 | 30.439 | 1.00 | 56.46 | B | O |
| ATOM | 2162 | N | THR | B | 83 | −3.861 | 26.348 | 30.357 | 1.00 | 58.32 | B | N |
| ATOM | 2163 | CA | THR | B | 83 | −4.911 | 25.711 | 31.133 | 1.00 | 57.05 | B | C |
| ATOM | 2164 | CB | THR | B | 83 | −4.912 | 24.169 | 30.938 | 1.00 | 53.64 | B | C |
| ATOM | 2165 | OG1 | THR | B | 83 | −3.769 | 23.590 | 31.571 | 1.00 | 57.63 | B | O |
| ATOM | 2166 | CG2 | THR | B | 83 | −4.912 | 23.814 | 29.466 | 1.00 | 51.79 | B | C |
| ATOM | 2167 | C | THR | B | 83 | −4.845 | 26.080 | 32.620 | 1.00 | 59.66 | B | C |
| ATOM | 2168 | O | THR | B | 83 | −5.875 | 26.166 | 33.285 | 1.00 | 67.34 | B | O |
| ATOM | 2169 | N | GLY | B | 84 | −3.644 | 26.326 | 33.131 | 1.00 | 56.50 | B | N |
| ATOM | 2170 | CA | GLY | B | 84 | −3.456 | 26.611 | 34.545 | 1.00 | 56.74 | B | C |
| ATOM | 2171 | C | GLY | B | 84 | −3.260 | 25.327 | 35.334 | 1.00 | 64.07 | B | C |
| ATOM | 2172 | O | GLY | B | 84 | −2.985 | 25.345 | 36.540 | 1.00 | 60.41 | B | O |
| ATOM | 2173 | N | GLU | B | 85 | −3.397 | 24.206 | 34.631 | 1.00 | 63.09 | B | N |
| ATOM | 2174 | CA | GLU | B | 85 | −3.299 | 22.879 | 35.216 | 1.00 | 59.41 | B | C |
| ATOM | 2175 | CB | GLU | B | 85 | −4.203 | 21.924 | 34.438 | 1.00 | 60.22 | B | C |
| ATOM | 2176 | CG | GLU | B | 85 | −5.690 | 22.246 | 34.529 | 1.00 | 64.91 | B | C |
| ATOM | 2177 | CD | GLU | B | 85 | −6.257 | 21.974 | 35.910 | 1.00 | 68.91 | B | C |
| ATOM | 2178 | OE1 | GLU | B | 85 | −6.095 | 20.834 | 36.405 | 1.00 | 65.55 | B | O |
| ATOM | 2179 | OE2 | GLU | B | 85 | −6.862 | 22.899 | 36.499 | 1.00 | 65.89 | B | O |
| ATOM | 2180 | C | GLU | B | 85 | −1.864 | 22.337 | 35.199 | 1.00 | 66.58 | B | C |
| ATOM | 2181 | O | GLU | B | 85 | −0.923 | 23.040 | 34.844 | 1.00 | 66.29 | B | O |
| ATOM | 2182 | N | LEU | B | 86 | −1.711 | 21.079 | 35.597 | 1.00 | 62.57 | B | N |
| ATOM | 2183 | CA | LEU | B | 86 | −0.455 | 20.359 | 35.478 | 1.00 | 60.61 | B | C |
| ATOM | 2184 | CB | LEU | B | 86 | −0.009 | 19.849 | 36.847 | 1.00 | 60.27 | B | C |
| ATOM | 2185 | CG | LEU | B | 86 | 1.439 | 19.435 | 37.129 | 1.00 | 60.52 | B | C |
| ATOM | 2186 | CD1 | LEU | B | 86 | 2.416 | 20.381 | 36.467 | 1.00 | 61.87 | B | C |
| ATOM | 2187 | CD2 | LEU | B | 86 | 1.696 | 18.008 | 36.690 | 1.00 | 64.51 | B | C |
| ATOM | 2188 | C | LEU | B | 86 | −0.737 | 19.200 | 34.535 | 1.00 | 63.39 | B | C |
| ATOM | 2189 | O | LEU | B | 86 | −0.506 | 18.037 | 34.861 | 1.00 | 65.16 | B | O |
| ATOM | 2190 | N | ASP | B | 87 | −1.256 | 19.537 | 33.359 | 1.00 | 61.64 | B | N |
| ATOM | 2191 | CA | ASP | B | 87 | −1.770 | 18.542 | 32.429 | 1.00 | 61.56 | B | C |
| ATOM | 2192 | CB | ASP | B | 87 | −2.658 | 19.199 | 31.371 | 1.00 | 65.92 | B | C |
| ATOM | 2193 | CG | ASP | B | 87 | −2.119 | 20.538 | 30.902 | 1.00 | 66.43 | B | C |
| ATOM | 2194 | OD1 | ASP | B | 87 | −1.771 | 20.640 | 29.702 | 1.00 | 68.19 | B | O |
| ATOM | 2195 | OD2 | ASP | B | 87 | −2.053 | 21.480 | 31.729 | 1.00 | 63.74 | B | O |
| ATOM | 2196 | C | ASP | B | 87 | −0.688 | 17.744 | 31.737 | 1.00 | 64.47 | B | C |
| ATOM | 2197 | O | ASP | B | 87 | 0.489 | 17.864 | 32.049 | 1.00 | 65.31 | B | O |
| ATOM | 2198 | N | SER | B | 88 | −1.105 | 16.928 | 30.780 | 1.00 | 63.17 | B | N |
| ATOM | 2199 | CA | SER | B | 88 | −0.168 | 16.115 | 30.044 | 1.00 | 62.88 | B | C |
| ATOM | 2200 | CB | SER | B | 88 | −0.904 | 15.192 | 29.075 | 1.00 | 67.00 | B | C |
| ATOM | 2201 | OG | SER | B | 88 | −0.027 | 14.214 | 28.543 | 1.00 | 72.17 | B | O |
| ATOM | 2202 | C | SER | B | 88 | 0.825 | 17.000 | 29.297 | 1.00 | 66.18 | B | C |
| ATOM | 2203 | O | SER | B | 88 | 2.032 | 16.910 | 29.516 | 1.00 | 64.60 | B | O |
| ATOM | 2204 | N | ALA | B | 89 | 0.322 | 17.861 | 28.421 | 1.00 | 62.37 | B | N |
| ATOM | 2205 | CA | ALA | B | 89 | 1.207 | 18.666 | 27.589 | 1.00 | 63.00 | B | C |
| ATOM | 2206 | CB | ALA | B | 89 | 0.403 | 19.591 | 26.690 | 1.00 | 64.46 | B | C |
| ATOM | 2207 | C | ALA | B | 89 | 2.189 | 19.460 | 28.444 | 1.00 | 61.89 | B | C |
| ATOM | 2208 | O | ALA | B | 89 | 3.393 | 19.508 | 28.166 | 1.00 | 62.14 | B | O |
| ATOM | 2209 | N | THR | B | 90 | 1.673 | 20.071 | 29.498 | 1.00 | 58.56 | B | N |
| ATOM | 2210 | CA | THR | B | 90 | 2.496 | 20.895 | 30.363 | 1.00 | 55.92 | B | C |
| ATOM | 2211 | CB | THR | B | 90 | 1.623 | 21.644 | 31.390 | 1.00 | 56.32 | B | C |
| ATOM | 2212 | OG1 | THR | B | 90 | 0.735 | 22.539 | 30.700 | 1.00 | 60.70 | B | O |
| ATOM | 2213 | CG2 | THR | B | 90 | 2.470 | 22.436 | 32.354 | 1.00 | 54.76 | B | C |
| ATOM | 2214 | C | THR | B | 90 | 3.548 | 20.040 | 31.057 | 1.00 | 55.44 | B | C |
| ATOM | 2215 | O | THR | B | 90 | 4.555 | 20.545 | 31.540 | 1.00 | 54.24 | B | O |
| ATOM | 2216 | N | LEU | B | 91 | 3.317 | 18.733 | 31.074 | 1.00 | 57.13 | B | N |
| ATOM | 2217 | CA | LEU | B | 91 | 4.183 | 17.796 | 31.781 | 1.00 | 57.20 | B | C |
| ATOM | 2218 | CB | LEU | B | 91 | 3.326 | 16.688 | 32.402 | 1.00 | 60.86 | B | C |
| ATOM | 2219 | CG | LEU | B | 91 | 3.697 | 16.121 | 33.775 | 1.00 | 61.80 | B | C |
| ATOM | 2220 | CD1 | LEU | B | 91 | 4.118 | 17.229 | 34.706 | 1.00 | 61.04 | B | C |
| ATOM | 2221 | CD2 | LEU | B | 91 | 2.531 | 15.335 | 34.374 | 1.00 | 62.79 | B | C |
| ATOM | 2222 | C | LEU | B | 91 | 5.246 | 17.207 | 30.834 | 1.00 | 54.07 | B | C |
| ATOM | 2223 | O | LEU | B | 91 | 6.413 | 17.035 | 31.200 | 1.00 | 49.01 | B | O |
| ATOM | 2224 | N | LYS | B | 92 | 4.834 | 16.896 | 29.610 | 1.00 | 55.13 | B | N |
| ATOM | 2225 | CA | LYS | B | 92 | 5.795 | 16.529 | 28.583 | 1.00 | 58.62 | B | C |
| ATOM | 2226 | CB | LYS | B | 92 | 5.094 | 16.299 | 27.239 | 1.00 | 56.97 | B | C |
| ATOM | 2227 | CG | LYS | B | 92 | 6.013 | 15.851 | 26.100 | 1.00 | 58.61 | B | C |
| ATOM | 2228 | CD | LYS | B | 92 | 5.333 | 16.040 | 24.735 | 1.00 | 60.82 | B | C |
| ATOM | 2229 | CE | LYS | B | 92 | 6.324 | 16.044 | 23.570 | 1.00 | 59.76 | B | C |

TABLE 12-continued

Coordinates for pro MMP9(35-444 ΔFnII) (SEQ ID NO: 12) complex with Example 2

| ATOM | 2230 | NZ | LYS | B | 92 | 7.265 | 17.209 | 23.604 | 1.00 | 59.11 | B | N |
|---|---|---|---|---|---|---|---|---|---|---|---|---|
| ATOM | 2231 | C | LYS | B | 92 | 6.832 | 17.657 | 28.491 | 1.00 | 52.92 | B | C |
| ATOM | 2232 | O | LYS | B | 92 | 8.037 | 17.401 | 28.499 | 1.00 | 54.82 | B | O |
| ATOM | 2233 | N | ALA | B | 93 | 6.349 | 18.898 | 28.446 | 1.00 | 47.56 | B | N |
| ATOM | 2234 | CA | ALA | B | 93 | 7.199 | 20.076 | 28.376 | 1.00 | 45.69 | B | C |
| ATOM | 2235 | CB | ALA | B | 93 | 6.359 | 21.333 | 28.533 | 1.00 | 48.59 | B | C |
| ATOM | 2236 | C | ALA | B | 93 | 8.303 | 20.047 | 29.429 | 1.00 | 50.95 | B | C |
| ATOM | 2237 | O | ALA | B | 93 | 9.500 | 20.085 | 29.105 | 1.00 | 50.16 | B | O |
| ATOM | 2238 | N | MET | B | 94 | 7.893 | 19.988 | 30.691 | 1.00 | 49.16 | B | N |
| ATOM | 2239 | CA | MET | B | 94 | 8.820 | 19.986 | 31.817 | 1.00 | 46.96 | B | C |
| ATOM | 2240 | CB | MET | B | 94 | 8.056 | 19.991 | 33.146 | 1.00 | 45.86 | B | C |
| ATOM | 2241 | CG | MET | B | 94 | 7.453 | 21.338 | 33.536 | 1.00 | 54.49 | B | C |
| ATOM | 2242 | SD | MET | B | 94 | 6.100 | 21.201 | 34.749 | 1.00 | 56.31 | B | S |
| ATOM | 2243 | CE | MET | B | 94 | 6.440 | 22.596 | 35.824 | 1.00 | 45.62 | B | C |
| ATOM | 2244 | C | MET | B | 94 | 9.815 | 18.821 | 31.790 | 1.00 | 47.82 | B | C |
| ATOM | 2245 | O | MET | B | 94 | 10.853 | 18.882 | 32.450 | 1.00 | 46.72 | B | O |
| ATOM | 2246 | N | ARG | B | 95 | 9.501 | 17.764 | 31.041 | 1.00 | 45.03 | B | N |
| ATOM | 2247 | CA | ARG | B | 95 | 10.415 | 16.626 | 30.920 | 1.00 | 44.41 | B | C |
| ATOM | 2248 | CB | ARG | B | 95 | 9.643 | 15.310 | 30.780 | 1.00 | 52.40 | B | C |
| ATOM | 2249 | CG | ARG | B | 95 | 9.744 | 14.393 | 32.000 | 1.00 | 54.06 | B | C |
| ATOM | 2250 | CD | ARG | B | 95 | 8.447 | 13.649 | 32.232 | 1.00 | 51.63 | B | C |
| ATOM | 2251 | NE | ARG | B | 95 | 7.745 | 13.408 | 30.979 | 1.00 | 55.01 | B | N |
| ATOM | 2252 | CZ | ARG | B | 95 | 6.564 | 12.805 | 30.894 | 1.00 | 62.66 | B | C |
| ATOM | 2253 | NH1 | ARG | B | 95 | 5.957 | 12.376 | 31.998 | 1.00 | 58.00 | B | N |
| ATOM | 2254 | NH2 | ARG | B | 95 | 5.992 | 12.625 | 29.704 | 1.00 | 59.92 | B | N |
| ATOM | 2255 | C | ARG | B | 95 | 11.418 | 16.755 | 29.774 | 1.00 | 44.64 | B | C |
| ATOM | 2256 | O | ARG | B | 95 | 12.330 | 15.938 | 29.652 | 1.00 | 41.99 | B | O |
| ATOM | 2257 | N | THR | B | 96 | 11.242 | 17.764 | 28.929 | 1.00 | 37.49 | B | N |
| ATOM | 2258 | CA | THR | B | 96 | 12.109 | 17.918 | 27.781 | 1.00 | 40.66 | B | C |
| ATOM | 2259 | CB | THR | B | 96 | 11.421 | 18.679 | 26.644 | 1.00 | 41.09 | B | C |
| ATOM | 2260 | OG1 | THR | B | 96 | 10.229 | 17.979 | 26.272 | 1.00 | 48.42 | B | O |
| ATOM | 2261 | CG2 | THR | B | 96 | 12.318 | 18.742 | 25.425 | 1.00 | 41.04 | B | C |
| ATOM | 2262 | C | THR | B | 96 | 13.430 | 18.573 | 28.173 | 1.00 | 38.47 | B | C |
| ATOM | 2263 | O | THR | B | 96 | 13.455 | 19.581 | 28.887 | 1.00 | 37.15 | B | O |
| ATOM | 2264 | N | PRO | B | 97 | 14.544 | 17.977 | 27.722 | 1.00 | 41.30 | B | N |
| ATOM | 2265 | CD | PRO | B | 97 | 14.609 | 16.741 | 26.934 | 1.00 | 37.26 | B | C |
| ATOM | 2266 | CA | PRO | B | 97 | 15.864 | 18.582 | 27.902 | 1.00 | 32.37 | B | C |
| ATOM | 2267 | CB | PRO | B | 97 | 16.752 | 17.701 | 27.038 | 1.00 | 39.42 | B | C |
| ATOM | 2268 | CG | PRO | B | 97 | 16.039 | 16.382 | 27.030 | 1.00 | 44.04 | B | C |
| ATOM | 2269 | C | PRO | B | 97 | 15.821 | 20.000 | 27.357 | 1.00 | 31.26 | B | C |
| ATOM | 2270 | O | PRO | B | 97 | 15.135 | 20.244 | 26.371 | 1.00 | 33.06 | B | O |
| ATOM | 2271 | N | ARG | B | 98 | 16.530 | 20.927 | 27.986 | 1.00 | 34.30 | B | N |
| ATOM | 2272 | CA | ARG | B | 98 | 16.362 | 22.322 | 27.649 | 1.00 | 30.20 | B | C |
| ATOM | 2273 | CB | ARG | B | 98 | 15.155 | 22.862 | 28.396 | 1.00 | 34.40 | B | C |
| ATOM | 2274 | CG | ARG | B | 98 | 15.544 | 23.357 | 29.782 | 1.00 | 35.93 | B | C |
| ATOM | 2275 | CD | ARG | B | 98 | 14.373 | 23.612 | 30.695 | 1.00 | 37.63 | B | C |
| ATOM | 2276 | NE | ARG | B | 98 | 13.403 | 24.596 | 30.218 | 1.00 | 39.37 | B | N |
| ATOM | 2277 | CZ | ARG | B | 98 | 13.571 | 25.918 | 30.221 | 1.00 | 38.21 | B | C |
| ATOM | 2278 | NH1 | ARG | B | 98 | 12.594 | 26.699 | 29.806 | 1.00 | 34.09 | B | N |
| ATOM | 2279 | NH2 | ARG | B | 98 | 14.709 | 26.461 | 30.612 | 1.00 | 37.91 | B | N |
| ATOM | 2280 | C | ARG | B | 98 | 17.584 | 23.142 | 28.056 | 1.00 | 33.56 | B | C |
| ATOM | 2281 | O | ARG | B | 98 | 18.464 | 22.657 | 28.769 | 1.00 | 33.78 | B | O |
| ATOM | 2282 | N | CYS | B | 99 | 17.609 | 24.404 | 27.631 | 1.00 | 32.32 | B | N |
| ATOM | 2283 | CA | CYS | B | 99 | 18.677 | 25.310 | 28.017 | 1.00 | 29.79 | B | C |
| ATOM | 2284 | CB | CYS | B | 99 | 18.662 | 26.576 | 27.139 | 1.00 | 25.97 | B | C |
| ATOM | 2285 | SG | CYS | B | 99 | 19.716 | 27.860 | 27.793 | 1.00 | 30.26 | B | S |
| ATOM | 2286 | C | CYS | B | 99 | 18.533 | 25.649 | 29.500 | 1.00 | 36.85 | B | C |
| ATOM | 2287 | O | CYS | B | 99 | 17.427 | 25.843 | 30.000 | 1.00 | 40.02 | B | O |
| ATOM | 2288 | N | GLY | B | 100 | 19.646 | 25.724 | 30.213 | 1.00 | 31.95 | B | N |
| ATOM | 2289 | CA | GLY | B | 100 | 19.602 | 25.975 | 31.640 | 1.00 | 37.37 | B | C |
| ATOM | 2290 | C | GLY | B | 100 | 19.406 | 27.427 | 32.037 | 1.00 | 37.12 | B | C |
| ATOM | 2291 | O | GLY | B | 100 | 19.360 | 27.744 | 33.222 | 1.00 | 36.76 | B | O |
| ATOM | 2292 | N | VAL | B | 101 | 19.317 | 28.323 | 31.061 | 1.00 | 35.23 | B | N |
| ATOM | 2293 | CA | VAL | B | 101 | 19.163 | 29.733 | 31.389 | 1.00 | 38.21 | B | C |
| ATOM | 2294 | CB | VAL | B | 101 | 19.641 | 30.620 | 30.233 | 1.00 | 33.41 | B | C |
| ATOM | 2295 | CG1 | VAL | B | 101 | 19.398 | 32.095 | 30.526 | 1.00 | 34.44 | B | C |
| ATOM | 2296 | CG2 | VAL | B | 101 | 21.123 | 30.387 | 29.976 | 1.00 | 35.63 | B | C |
| ATOM | 2297 | C | VAL | B | 101 | 17.696 | 30.034 | 31.768 | 1.00 | 35.02 | B | C |
| ATOM | 2298 | O | VAL | B | 101 | 16.779 | 29.555 | 31.117 | 1.00 | 31.26 | B | O |
| ATOM | 2299 | N | PRO | B | 102 | 17.485 | 30.798 | 32.845 | 1.00 | 35.27 | B | N |
| ATOM | 2300 | CA | PRO | B | 102 | 16.121 | 31.112 | 33.291 | 1.00 | 39.50 | B | C |
| ATOM | 2301 | C | PRO | B | 102 | 15.288 | 31.771 | 32.208 | 1.00 | 40.68 | B | C |
| ATOM | 2302 | CB | PRO | B | 102 | 16.351 | 32.076 | 34.456 | 1.00 | 39.74 | B | C |
| ATOM | 2303 | CG | PRO | B | 102 | 17.670 | 31.628 | 35.047 | 1.00 | 43.17 | B | C |
| ATOM | 2304 | CD | PRO | B | 102 | 18.501 | 31.207 | 33.836 | 1.00 | 41.03 | B | C |
| ATOM | 2305 | O | PRO | B | 102 | 15.811 | 32.558 | 31.429 | 1.00 | 40.54 | B | O |
| ATOM | 2306 | N | ASP | B | 103 | 14.008 | 31.422 | 32.145 | 1.00 | 36.84 | B | N |

TABLE 12-continued

Coordinates for pro MMP9(35-444 ΔFnII) (SEQ ID NO: 12) complex with Example 2

| ATOM | 2307 | CA | ASP | B | 103 | 13.083 | 32.068 | 31.216 | 1.00 | 39.42 | B | C |
|------|------|-----|-----|---|-----|--------|--------|--------|------|-------|---|---|
| ATOM | 2308 | C | ASP | B | 103 | 12.660 | 33.443 | 31.725 | 1.00 | 36.78 | B | C |
| ATOM | 2309 | CB | ASP | B | 103 | 11.851 | 31.193 | 30.996 | 1.00 | 37.22 | B | C |
| ATOM | 2310 | CG | ASP | B | 103 | 12.208 | 29.807 | 30.507 | 1.00 | 42.54 | B | C |
| ATOM | 2311 | OD1 | ASP | B | 103 | 13.074 | 29.716 | 29.619 | 1.00 | 37.92 | B | O |
| ATOM | 2312 | OD2 | ASP | B | 103 | 11.638 | 28.810 | 31.009 | 1.00 | 36.72 | B | O |
| ATOM | 2313 | O | ASP | B | 103 | 12.338 | 34.335 | 30.942 | 1.00 | 31.02 | B | O |
| ATOM | 2314 | N | LEU | B | 104 | 12.650 | 33.597 | 33.047 | 1.00 | 44.87 | B | N |
| ATOM | 2315 | CA | LEU | B | 104 | 12.336 | 34.881 | 33.680 | 1.00 | 48.54 | B | C |
| ATOM | 2316 | C | LEU | B | 104 | 13.281 | 35.151 | 34.848 | 1.00 | 42.34 | B | C |
| ATOM | 2317 | CB | LEU | B | 104 | 10.884 | 34.908 | 34.176 | 1.00 | 49.26 | B | C |
| ATOM | 2318 | CG | LEU | B | 104 | 9.764 | 34.533 | 33.201 | 1.00 | 48.04 | B | C |
| ATOM | 2319 | CD1 | LEU | B | 104 | 8.467 | 34.213 | 33.956 | 1.00 | 47.38 | B | C |
| ATOM | 2320 | CD2 | LEU | B | 104 | 9.532 | 35.624 | 32.167 | 1.00 | 42.58 | B | C |
| ATOM | 2321 | O | LEU | B | 104 | 13.403 | 36.286 | 35.311 | 1.00 | 41.60 | B | O |
| ATOM | 2322 | N | VAL | B | 109 | 22.008 | 39.187 | 39.070 | 1.00 | 45.74 | B | N |
| ATOM | 2323 | CA | VAL | B | 109 | 22.331 | 40.533 | 38.609 | 1.00 | 52.19 | B | C |
| ATOM | 2324 | C | VAL | B | 109 | 23.699 | 40.598 | 37.934 | 1.00 | 55.61 | B | C |
| ATOM | 2325 | CB | VAL | B | 109 | 22.264 | 41.571 | 39.749 | 1.00 | 56.64 | B | C |
| ATOM | 2326 | CG1 | VAL | B | 109 | 23.101 | 42.794 | 39.393 | 1.00 | 50.47 | B | C |
| ATOM | 2327 | CG2 | VAL | B | 109 | 22.724 | 40.955 | 41.073 | 1.00 | 57.06 | B | C |
| ATOM | 2328 | O | VAL | B | 109 | 24.692 | 40.098 | 38.466 | 1.00 | 52.03 | B | O |
| ATOM | 2329 | N | PHE | B | 110 | 23.732 | 41.214 | 36.755 | 1.00 | 55.16 | B | N |
| ATOM | 2330 | CA | PHE | B | 110 | 24.940 | 41.285 | 35.936 | 1.00 | 50.88 | B | C |
| ATOM | 2331 | C | PHE | B | 110 | 25.427 | 42.699 | 35.806 | 1.00 | 52.10 | B | C |
| ATOM | 2332 | CB | PHE | B | 110 | 24.670 | 40.755 | 34.540 | 1.00 | 43.64 | B | C |
| ATOM | 2333 | CG | PHE | B | 110 | 24.383 | 39.310 | 34.517 | 1.00 | 44.34 | B | C |
| ATOM | 2334 | CD1 | PHE | B | 110 | 25.360 | 38.405 | 34.874 | 1.00 | 46.49 | B | C |
| ATOM | 2335 | CD2 | PHE | B | 110 | 23.138 | 38.849 | 34.175 | 1.00 | 47.06 | B | C |
| ATOM | 2336 | CE1 | PHE | B | 110 | 25.105 | 37.059 | 34.876 | 1.00 | 46.52 | B | C |
| ATOM | 2337 | CE2 | PHE | B | 110 | 22.879 | 37.504 | 34.176 | 1.00 | 49.10 | B | C |
| ATOM | 2338 | CZ | PHE | B | 110 | 23.870 | 36.608 | 34.527 | 1.00 | 43.61 | B | C |
| ATOM | 2339 | O | PHE | B | 110 | 24.817 | 43.631 | 36.337 | 1.00 | 53.58 | B | O |
| ATOM | 2340 | N | GLU | B | 111 | 26.511 | 42.864 | 35.062 | 1.00 | 48.54 | B | N |
| ATOM | 2341 | CA | GLU | B | 111 | 27.093 | 44.180 | 34.919 | 1.00 | 46.97 | B | C |
| ATOM | 2342 | CB | GLU | B | 111 | 28.569 | 44.155 | 35.305 | 1.00 | 48.79 | B | C |
| ATOM | 2343 | CG | GLU | B | 111 | 29.137 | 45.507 | 35.687 | 1.00 | 55.89 | B | C |
| ATOM | 2344 | CD | GLU | B | 111 | 30.622 | 45.431 | 36.052 | 1.00 | 69.12 | B | C |
| ATOM | 2345 | OE1 | GLU | B | 111 | 31.026 | 44.445 | 36.710 | 1.00 | 64.56 | B | O |
| ATOM | 2346 | OE2 | GLU | B | 111 | 31.383 | 46.358 | 35.680 | 1.00 | 69.29 | B | O |
| ATOM | 2347 | C | GLU | B | 111 | 26.888 | 44.768 | 33.532 | 1.00 | 49.19 | B | C |
| ATOM | 2348 | O | GLU | B | 111 | 27.020 | 44.092 | 32.508 | 1.00 | 49.50 | B | O |
| ATOM | 2349 | N | GLY | B | 112 | 26.516 | 46.040 | 33.526 | 1.00 | 52.86 | B | N |
| ATOM | 2350 | CA | GLY | B | 112 | 26.493 | 46.829 | 32.316 | 1.00 | 48.52 | B | C |
| ATOM | 2351 | C | GLY | B | 112 | 25.278 | 46.701 | 31.425 | 1.00 | 48.74 | B | C |
| ATOM | 2352 | O | GLY | B | 112 | 24.242 | 46.154 | 31.790 | 1.00 | 40.11 | B | O |
| ATOM | 2353 | N | ASP | B | 113 | 25.458 | 47.213 | 30.215 | 1.00 | 50.85 | B | N |
| ATOM | 2354 | CA | ASP | B | 113 | 24.442 | 47.323 | 29.187 | 1.00 | 45.47 | B | C |
| ATOM | 2355 | CB | ASP | B | 113 | 25.071 | 48.097 | 28.035 | 1.00 | 43.86 | B | C |
| ATOM | 2356 | CG | ASP | B | 113 | 24.055 | 48.727 | 27.147 | 1.00 | 49.66 | B | C |
| ATOM | 2357 | OD1 | ASP | B | 113 | 22.980 | 48.121 | 26.953 | 1.00 | 54.15 | B | O |
| ATOM | 2358 | OD2 | ASP | B | 113 | 24.331 | 49.833 | 26.636 | 1.00 | 53.69 | B | O |
| ATOM | 2359 | C | ASP | B | 113 | 23.894 | 45.979 | 28.666 | 1.00 | 41.91 | B | C |
| ATOM | 2360 | O | ASP | B | 113 | 22.840 | 45.939 | 28.032 | 1.00 | 34.00 | B | O |
| ATOM | 2361 | N | LEU | B | 114 | 24.626 | 44.895 | 28.918 | 1.00 | 40.10 | B | N |
| ATOM | 2362 | CA | LEU | B | 114 | 24.281 | 43.550 | 28.430 | 1.00 | 41.53 | B | C |
| ATOM | 2363 | CB | LEU | B | 114 | 22.955 | 43.050 | 29.021 | 1.00 | 45.57 | B | C |
| ATOM | 2364 | CG | LEU | B | 114 | 22.843 | 42.933 | 30.547 | 1.00 | 43.84 | B | C |
| ATOM | 2365 | CD1 | LEU | B | 114 | 21.670 | 42.018 | 30.913 | 1.00 | 48.45 | B | C |
| ATOM | 2366 | CD2 | LEU | B | 114 | 24.128 | 42.425 | 31.169 | 1.00 | 42.72 | B | C |
| ATOM | 2367 | C | LEU | B | 114 | 24.268 | 43.413 | 26.902 | 1.00 | 41.02 | B | C |
| ATOM | 2368 | O | LEU | B | 114 | 23.618 | 42.514 | 26.359 | 1.00 | 41.54 | B | O |
| ATOM | 2369 | N | LYS | B | 115 | 24.973 | 44.332 | 26.238 | 1.00 | 43.71 | B | N |
| ATOM | 2370 | CA | LYS | B | 115 | 25.375 | 44.254 | 24.824 | 1.00 | 41.78 | B | C |
| ATOM | 2371 | CB | LYS | B | 115 | 24.869 | 45.484 | 24.073 | 1.00 | 39.99 | B | C |
| ATOM | 2372 | CG | LYS | B | 115 | 23.562 | 45.328 | 23.356 | 1.00 | 41.16 | B | C |
| ATOM | 2373 | CD | LYS | B | 115 | 22.989 | 46.706 | 22.987 | 1.00 | 46.05 | B | C |
| ATOM | 2374 | CE | LYS | B | 115 | 24.022 | 47.624 | 22.348 | 1.00 | 44.60 | B | C |
| ATOM | 2375 | NZ | LYS | B | 115 | 23.891 | 47.743 | 20.860 | 1.00 | 40.73 | B | N |
| ATOM | 2376 | C | LYS | B | 115 | 26.916 | 44.264 | 24.730 | 1.00 | 40.31 | B | C |
| ATOM | 2377 | O | LYS | B | 115 | 27.602 | 44.652 | 25.685 | 1.00 | 37.72 | B | O |
| ATOM | 2378 | N | TRP | B | 116 | 27.454 | 43.850 | 23.580 | 1.00 | 37.67 | B | N |
| ATOM | 2379 | CA | TRP | B | 116 | 28.865 | 44.086 | 23.262 | 1.00 | 35.96 | B | C |
| ATOM | 2380 | CB | TRP | B | 116 | 29.353 | 43.077 | 22.214 | 1.00 | 29.76 | B | C |
| ATOM | 2381 | CG | TRP | B | 116 | 29.391 | 41.695 | 22.762 | 1.00 | 27.68 | B | C |
| ATOM | 2382 | CD2 | TRP | B | 116 | 30.206 | 41.228 | 23.839 | 1.00 | 26.56 | B | C |
| ATOM | 2383 | CE2 | TRP | B | 116 | 29.893 | 39.873 | 24.040 | 1.00 | 28.20 | B | C |

TABLE 12-continued

Coordinates for pro MMP9(35-444 ΔFnII) (SEQ ID NO: 12) complex with Example 2

| ATOM | 2384 | CE3 | TRP | B | 116 | 31.175 | 41.822 | 24.646 | 1.00 | 28.86 | B | C |
|---|---|---|---|---|---|---|---|---|---|---|---|---|
| ATOM | 2385 | CD1 | TRP | B | 116 | 28.635 | 40.636 | 22.364 | 1.00 | 27.78 | B | C |
| ATOM | 2386 | NE1 | TRP | B | 116 | 28.929 | 39.536 | 23.127 | 1.00 | 30.44 | B | N |
| ATOM | 2387 | CZ2 | TRP | B | 116 | 30.511 | 39.101 | 25.015 | 1.00 | 29.79 | B | C |
| ATOM | 2388 | CZ3 | TRP | B | 116 | 31.785 | 41.053 | 25.608 | 1.00 | 34.12 | B | C |
| ATOM | 2389 | CH2 | TRP | B | 116 | 31.453 | 39.704 | 25.784 | 1.00 | 31.09 | B | C |
| ATOM | 2390 | C | TRP | B | 116 | 29.029 | 45.495 | 22.718 | 1.00 | 33.35 | B | C |
| ATOM | 2391 | O | TRP | B | 116 | 28.212 | 45.937 | 21.927 | 1.00 | 32.94 | B | O |
| ATOM | 2392 | N | HIS | B | 117 | 30.089 | 46.190 | 23.113 | 1.00 | 39.27 | B | N |
| ATOM | 2393 | CA | HIS | B | 117 | 30.341 | 47.528 | 22.569 | 1.00 | 39.86 | B | C |
| ATOM | 2394 | CB | HIS | B | 117 | 30.302 | 48.566 | 23.684 | 1.00 | 40.72 | B | C |
| ATOM | 2395 | CG | HIS | B | 117 | 28.932 | 48.762 | 24.245 | 1.00 | 44.42 | B | C |
| ATOM | 2396 | CD2 | HIS | B | 117 | 27.849 | 49.403 | 23.743 | 1.00 | 45.91 | B | C |
| ATOM | 2397 | ND1 | HIS | B | 117 | 28.530 | 48.199 | 25.438 | 1.00 | 48.45 | B | N |
| ATOM | 2398 | CE1 | HIS | B | 117 | 27.265 | 48.514 | 25.664 | 1.00 | 47.33 | B | C |
| ATOM | 2399 | NE2 | HIS | B | 117 | 26.829 | 49.243 | 24.650 | 1.00 | 48.08 | B | N |
| ATOM | 2400 | C | HIS | B | 117 | 31.601 | 47.692 | 21.690 | 1.00 | 45.47 | B | C |
| ATOM | 2401 | O | HIS | B | 117 | 32.283 | 48.734 | 21.737 | 1.00 | 34.01 | B | O |
| ATOM | 2402 | N | HIS | B | 118 | 31.867 | 46.676 | 20.869 | 1.00 | 38.19 | B | N |
| ATOM | 2403 | CA | HIS | B | 118 | 32.989 | 46.667 | 19.936 | 1.00 | 39.90 | B | C |
| ATOM | 2404 | CB | HIS | B | 118 | 34.305 | 46.463 | 20.687 | 1.00 | 40.02 | B | C |
| ATOM | 2405 | CG | HIS | B | 118 | 34.370 | 45.178 | 21.455 | 1.00 | 41.12 | B | C |
| ATOM | 2406 | CD2 | HIS | B | 118 | 34.645 | 43.915 | 21.055 | 1.00 | 38.22 | B | C |
| ATOM | 2407 | ND1 | HIS | B | 118 | 34.133 | 45.106 | 22.813 | 1.00 | 40.38 | B | N |
| ATOM | 2408 | CE1 | HIS | B | 118 | 34.260 | 43.853 | 23.216 | 1.00 | 39.36 | B | C |
| ATOM | 2409 | NE2 | HIS | B | 118 | 34.574 | 43.111 | 22.168 | 1.00 | 38.13 | B | N |
| ATOM | 2410 | C | HIS | B | 118 | 32.742 | 45.523 | 18.953 | 1.00 | 38.80 | B | C |
| ATOM | 2411 | O | HIS | B | 118 | 32.082 | 44.563 | 19.298 | 1.00 | 37.79 | B | O |
| ATOM | 2412 | N | HIS | B | 119 | 33.265 | 45.608 | 17.738 | 1.00 | 39.43 | B | N |
| ATOM | 2413 | CA | HIS | B | 119 | 32.796 | 44.720 | 16.669 | 1.00 | 38.70 | B | C |
| ATOM | 2414 | CB | HIS | B | 119 | 32.924 | 45.409 | 15.308 | 1.00 | 45.75 | B | C |
| ATOM | 2415 | CG | HIS | B | 119 | 34.154 | 46.260 | 15.174 | 1.00 | 57.55 | B | C |
| ATOM | 2416 | CD2 | HIS | B | 119 | 34.578 | 47.333 | 15.887 | 1.00 | 56.67 | B | C |
| ATOM | 2417 | ND1 | HIS | B | 119 | 35.115 | 46.041 | 14.207 | 1.00 | 60.13 | B | N |
| ATOM | 2418 | CE1 | HIS | B | 119 | 36.075 | 46.943 | 14.330 | 1.00 | 61.35 | B | C |
| ATOM | 2419 | NE2 | HIS | B | 119 | 35.776 | 47.736 | 15.345 | 1.00 | 61.01 | B | N |
| ATOM | 2420 | C | HIS | B | 119 | 33.440 | 43.332 | 16.616 | 1.00 | 36.49 | B | C |
| ATOM | 2421 | O | HIS | B | 119 | 32.850 | 42.380 | 16.095 | 1.00 | 30.07 | B | O |
| ATOM | 2422 | N | ASN | B | 120 | 34.657 | 43.203 | 17.125 | 1.00 | 41.60 | B | N |
| ATOM | 2423 | CA | ASN | B | 120 | 35.355 | 41.931 | 16.949 | 1.00 | 39.10 | B | C |
| ATOM | 2424 | CB | ASN | B | 120 | 36.772 | 42.093 | 16.388 | 1.00 | 42.04 | B | C |
| ATOM | 2425 | CG | ASN | B | 120 | 37.470 | 40.741 | 16.175 | 1.00 | 44.33 | B | C |
| ATOM | 2426 | OD1 | ASN | B | 120 | 36.899 | 39.807 | 15.576 | 1.00 | 36.73 | B | O |
| ATOM | 2427 | ND2 | ASN | B | 120 | 38.706 | 40.630 | 16.677 | 1.00 | 46.50 | B | N |
| ATOM | 2428 | C | ASN | B | 120 | 35.362 | 41.096 | 18.203 | 1.00 | 35.56 | B | C |
| ATOM | 2429 | O | ASN | B | 120 | 36.104 | 41.357 | 19.149 | 1.00 | 33.58 | B | O |
| ATOM | 2430 | N | ILE | B | 121 | 34.549 | 40.053 | 18.191 | 1.00 | 32.05 | B | N |
| ATOM | 2431 | CA | ILE | B | 121 | 34.357 | 39.308 | 19.415 | 1.00 | 33.64 | B | C |
| ATOM | 2432 | CB | ILE | B | 121 | 32.877 | 38.874 | 19.601 | 1.00 | 31.41 | B | C |
| ATOM | 2433 | CG2 | ILE | B | 121 | 32.687 | 38.297 | 20.985 | 1.00 | 26.58 | B | C |
| ATOM | 2434 | CG1 | ILE | B | 121 | 31.959 | 40.067 | 19.374 | 1.00 | 26.86 | B | C |
| ATOM | 2435 | CD1 | ILE | B | 121 | 32.202 | 41.223 | 20.384 | 1.00 | 32.55 | B | C |
| ATOM | 2436 | C | ILE | B | 121 | 35.271 | 38.122 | 19.420 | 1.00 | 26.01 | B | C |
| ATOM | 2437 | O | ILE | B | 121 | 35.263 | 37.334 | 18.488 | 1.00 | 33.42 | B | O |
| ATOM | 2438 | N | THR | B | 122 | 36.056 | 37.993 | 20.476 | 1.00 | 29.39 | B | N |
| ATOM | 2439 | CA | THR | B | 122 | 37.045 | 36.922 | 20.549 | 1.00 | 31.05 | B | C |
| ATOM | 2440 | CB | THR | B | 122 | 38.384 | 37.439 | 21.087 | 1.00 | 34.89 | B | C |
| ATOM | 2441 | OG1 | THR | B | 122 | 38.229 | 37.876 | 22.445 | 1.00 | 32.45 | B | O |
| ATOM | 2442 | CG2 | THR | B | 122 | 38.903 | 38.605 | 20.217 | 1.00 | 35.85 | B | C |
| ATOM | 2443 | C | THR | B | 122 | 36.584 | 35.812 | 21.464 | 1.00 | 32.51 | B | C |
| ATOM | 2444 | O | THR | B | 122 | 36.083 | 36.073 | 22.561 | 1.00 | 33.63 | B | O |
| ATOM | 2445 | N | TYR | B | 123 | 36.784 | 34.573 | 21.035 | 1.00 | 33.68 | B | N |
| ATOM | 2446 | CA | TYR | B | 123 | 36.412 | 33.424 | 21.851 | 1.00 | 34.92 | B | C |
| ATOM | 2447 | CB | TYR | B | 123 | 35.156 | 32.783 | 21.273 | 1.00 | 28.78 | B | C |
| ATOM | 2448 | CG | TYR | B | 123 | 35.310 | 32.067 | 19.945 | 1.00 | 26.40 | B | C |
| ATOM | 2449 | CD1 | TYR | B | 123 | 35.170 | 32.737 | 18.738 | 1.00 | 23.69 | B | C |
| ATOM | 2450 | CE1 | TYR | B | 123 | 35.278 | 32.067 | 17.534 | 1.00 | 25.64 | B | C |
| ATOM | 2451 | CD2 | TYR | B | 123 | 35.549 | 30.701 | 19.912 | 1.00 | 31.15 | B | C |
| ATOM | 2452 | CE2 | TYR | B | 123 | 35.666 | 30.014 | 18.715 | 1.00 | 29.96 | B | C |
| ATOM | 2453 | CZ | TYR | B | 123 | 35.531 | 30.695 | 17.538 | 1.00 | 33.85 | B | C |
| ATOM | 2454 | OH | TYR | B | 123 | 35.630 | 29.976 | 16.376 | 1.00 | 29.81 | B | O |
| ATOM | 2455 | C | TYR | B | 123 | 37.507 | 32.364 | 22.073 | 1.00 | 34.86 | B | C |
| ATOM | 2456 | O | TYR | B | 123 | 38.266 | 32.044 | 21.170 | 1.00 | 33.65 | B | O |
| ATOM | 2457 | N | TRP | B | 124 | 37.554 | 31.803 | 23.278 | 1.00 | 38.28 | B | N |
| ATOM | 2458 | CA | TRP | B | 124 | 38.542 | 30.787 | 23.624 | 1.00 | 35.70 | B | C |
| ATOM | 2459 | CB | TRP | B | 124 | 39.401 | 31.293 | 24.782 | 1.00 | 40.41 | B | C |
| ATOM | 2460 | CG | TRP | B | 124 | 40.420 | 30.312 | 25.249 | 1.00 | 39.86 | B | C |

TABLE 12-continued

Coordinates for pro MMP9(35-444 ΔFnII) (SEQ ID NO: 12) complex with Example 2

| ATOM | 2461 | CD2 | TRP | B | 124 | 40.850 | 30.103 | 26.597 | 1.00 | 44.32 | B | C |
|---|---|---|---|---|---|---|---|---|---|---|---|---|
| ATOM | 2462 | CE2 | TRP | B | 124 | 41.835 | 29.096 | 26.569 | 1.00 | 40.40 | B | C |
| ATOM | 2463 | CE3 | TRP | B | 124 | 40.496 | 30.670 | 27.828 | 1.00 | 45.84 | B | C |
| ATOM | 2464 | CD1 | TRP | B | 124 | 41.142 | 29.451 | 24.477 | 1.00 | 40.68 | B | C |
| ATOM | 2465 | NE1 | TRP | B | 124 | 41.992 | 28.712 | 25.265 | 1.00 | 42.22 | B | N |
| ATOM | 2466 | CZ2 | TRP | B | 124 | 42.467 | 28.636 | 27.725 | 1.00 | 44.51 | B | C |
| ATOM | 2467 | CZ3 | TRP | B | 124 | 41.123 | 30.220 | 28.973 | 1.00 | 47.21 | B | C |
| ATOM | 2468 | CH2 | TRP | B | 124 | 42.100 | 29.210 | 28.914 | 1.00 | 50.81 | B | C |
| ATOM | 2469 | C | TRP | B | 124 | 37.945 | 29.425 | 23.981 | 1.00 | 41.05 | B | C |
| ATOM | 2470 | O | TRP | B | 124 | 37.325 | 29.270 | 25.026 | 1.00 | 44.41 | B | O |
| ATOM | 2471 | N | ILE | B | 125 | 38.149 | 28.431 | 23.122 | 1.00 | 37.85 | B | N |
| ATOM | 2472 | CA | ILE | B | 125 | 37.737 | 27.068 | 23.419 | 1.00 | 34.16 | B | C |
| ATOM | 2473 | CB | ILE | B | 125 | 37.859 | 26.197 | 22.186 | 1.00 | 36.18 | B | C |
| ATOM | 2474 | CG2 | ILE | B | 125 | 37.370 | 24.786 | 22.469 | 1.00 | 41.36 | B | C |
| ATOM | 2475 | CG1 | ILE | B | 125 | 37.111 | 26.846 | 21.029 | 1.00 | 32.68 | B | C |
| ATOM | 2476 | CD1 | ILE | B | 125 | 36.908 | 25.944 | 19.856 | 1.00 | 37.45 | B | C |
| ATOM | 2477 | C | ILE | B | 125 | 38.621 | 26.484 | 24.486 | 1.00 | 42.02 | B | C |
| ATOM | 2478 | O | ILE | B | 125 | 39.591 | 25.799 | 24.181 | 1.00 | 44.71 | B | O |
| ATOM | 2479 | N | GLN | B | 126 | 38.274 | 26.749 | 25.740 | 1.00 | 42.74 | B | N |
| ATOM | 2480 | CA | GLN | B | 126 | 39.124 | 26.447 | 26.882 | 1.00 | 40.60 | B | C |
| ATOM | 2481 | CB | GLN | B | 126 | 38.487 | 27.000 | 28.158 | 1.00 | 42.12 | B | C |
| ATOM | 2482 | CG | GLN | B | 126 | 39.413 | 27.042 | 29.346 | 1.00 | 46.23 | B | C |
| ATOM | 2483 | CD | GLN | B | 126 | 38.727 | 27.578 | 30.596 | 1.00 | 56.73 | B | C |
| ATOM | 2484 | OE1 | GLN | B | 126 | 37.949 | 26.871 | 31.253 | 1.00 | 56.80 | B | O |
| ATOM | 2485 | NE2 | GLN | B | 126 | 39.019 | 28.836 | 30.937 | 1.00 | 53.02 | B | N |
| ATOM | 2486 | C | GLN | B | 126 | 39.433 | 24.968 | 27.070 | 1.00 | 41.42 | B | C |
| ATOM | 2487 | O | GLN | B | 126 | 40.489 | 24.623 | 27.579 | 1.00 | 45.51 | B | O |
| ATOM | 2488 | N | ASN | B | 127 | 38.499 | 24.100 | 26.711 | 1.00 | 40.04 | B | N |
| ATOM | 2489 | CA | ASN | B | 127 | 38.713 | 22.651 | 26.812 | 1.00 | 40.78 | B | C |
| ATOM | 2490 | CB | ASN | B | 127 | 38.693 | 22.133 | 28.267 | 1.00 | 41.99 | B | C |
| ATOM | 2491 | CG | ASN | B | 127 | 37.336 | 22.289 | 28.953 | 1.00 | 45.31 | B | C |
| ATOM | 2492 | OD1 | ASN | B | 127 | 36.324 | 22.570 | 28.320 | 1.00 | 40.92 | B | O |
| ATOM | 2493 | ND2 | ASN | B | 127 | 37.321 | 22.091 | 30.263 | 1.00 | 38.46 | B | N |
| ATOM | 2494 | C | ASN | B | 127 | 37.769 | 21.890 | 25.886 | 1.00 | 39.75 | B | C |
| ATOM | 2495 | O | ASN | B | 127 | 36.944 | 22.522 | 25.232 | 1.00 | 39.13 | B | O |
| ATOM | 2496 | N | TYR | B | 128 | 37.934 | 20.565 | 25.780 | 1.00 | 41.63 | B | N |
| ATOM | 2497 | CA | TYR | B | 128 | 37.200 | 19.743 | 24.799 | 1.00 | 39.72 | B | C |
| ATOM | 2498 | CB | TYR | B | 128 | 38.128 | 19.246 | 23.688 | 1.00 | 41.35 | B | C |
| ATOM | 2499 | CG | TYR | B | 128 | 38.617 | 20.315 | 22.748 | 1.00 | 43.51 | B | C |
| ATOM | 2500 | CD1 | TYR | B | 128 | 38.046 | 20.478 | 21.501 | 1.00 | 38.99 | B | C |
| ATOM | 2501 | CE1 | TYR | B | 128 | 38.494 | 21.453 | 20.644 | 1.00 | 41.32 | B | C |
| ATOM | 2502 | CD2 | TYR | B | 128 | 39.659 | 21.154 | 23.111 | 1.00 | 46.44 | B | C |
| ATOM | 2503 | CE2 | TYR | B | 128 | 40.111 | 22.128 | 22.263 | 1.00 | 42.42 | B | C |
| ATOM | 2504 | CZ | TYR | B | 128 | 39.528 | 22.268 | 21.034 | 1.00 | 40.18 | B | C |
| ATOM | 2505 | OH | TYR | B | 128 | 39.987 | 23.238 | 20.184 | 1.00 | 48.91 | B | O |
| ATOM | 2506 | C | TYR | B | 128 | 36.593 | 18.508 | 25.428 | 1.00 | 43.39 | B | C |
| ATOM | 2507 | O | TYR | B | 128 | 37.197 | 17.906 | 26.317 | 1.00 | 47.74 | B | O |
| ATOM | 2508 | N | SER | B | 129 | 35.425 | 18.109 | 24.934 | 1.00 | 41.54 | B | N |
| ATOM | 2509 | CA | SER | B | 129 | 34.770 | 16.896 | 25.403 | 1.00 | 42.63 | B | C |
| ATOM | 2510 | CB | SER | B | 129 | 33.251 | 17.013 | 25.214 | 1.00 | 38.24 | B | C |
| ATOM | 2511 | OG | SER | B | 129 | 32.690 | 15.778 | 24.798 | 1.00 | 40.30 | B | O |
| ATOM | 2512 | C | SER | B | 129 | 35.298 | 15.690 | 24.638 | 1.00 | 40.68 | B | C |
| ATOM | 2513 | O | SER | B | 129 | 35.601 | 15.783 | 23.458 | 1.00 | 39.80 | B | O |
| ATOM | 2514 | N | GLU | B | 130 | 35.378 | 14.546 | 25.306 | 1.00 | 46.04 | B | N |
| ATOM | 2515 | CA | GLU | B | 130 | 35.923 | 13.343 | 24.681 | 1.00 | 43.54 | B | C |
| ATOM | 2516 | CB | GLU | B | 130 | 36.183 | 12.256 | 25.729 | 1.00 | 46.66 | B | C |
| ATOM | 2517 | CG | GLU | B | 130 | 37.410 | 12.505 | 26.599 | 1.00 | 48.87 | B | C |
| ATOM | 2518 | CD | GLU | B | 130 | 38.697 | 12.625 | 25.785 | 1.00 | 56.90 | B | C |
| ATOM | 2519 | OE1 | GLU | B | 130 | 38.981 | 11.713 | 24.977 | 1.00 | 64.25 | B | O |
| ATOM | 2520 | OE2 | GLU | B | 130 | 39.430 | 13.628 | 25.958 | 1.00 | 57.04 | B | O |
| ATOM | 2521 | C | GLU | B | 130 | 35.036 | 12.784 | 23.580 | 1.00 | 44.55 | B | C |
| ATOM | 2522 | O | GLU | B | 130 | 35.470 | 11.935 | 22.790 | 1.00 | 48.00 | B | O |
| ATOM | 2523 | N | ASP | B | 131 | 33.802 | 13.261 | 23.513 | 1.00 | 42.33 | B | N |
| ATOM | 2524 | CA | ASP | B | 131 | 32.802 | 12.604 | 22.679 | 1.00 | 38.51 | B | C |
| ATOM | 2525 | CB | ASP | B | 131 | 31.395 | 13.020 | 23.110 | 1.00 | 45.73 | B | C |
| ATOM | 2526 | CG | ASP | B | 131 | 31.133 | 12.723 | 24.577 | 1.00 | 45.01 | B | C |
| ATOM | 2527 | OD1 | ASP | B | 131 | 31.554 | 11.635 | 25.050 | 1.00 | 43.17 | B | O |
| ATOM | 2528 | OD2 | ASP | B | 131 | 30.526 | 13.580 | 25.256 | 1.00 | 47.36 | B | O |
| ATOM | 2529 | C | ASP | B | 131 | 32.993 | 12.798 | 21.182 | 1.00 | 44.35 | B | C |
| ATOM | 2530 | O | ASP | B | 131 | 32.362 | 12.093 | 20.383 | 1.00 | 44.17 | B | O |
| ATOM | 2531 | N | LEU | B | 132 | 33.865 | 13.739 | 20.810 | 1.00 | 40.28 | B | N |
| ATOM | 2532 | CA | LEU | B | 132 | 34.128 | 14.063 | 19.405 | 1.00 | 38.93 | B | C |
| ATOM | 2533 | CB | LEU | B | 132 | 33.193 | 15.177 | 18.934 | 1.00 | 40.27 | B | C |
| ATOM | 2534 | CG | LEU | B | 132 | 31.675 | 14.957 | 18.881 | 1.00 | 38.56 | B | C |
| ATOM | 2535 | CD1 | LEU | B | 132 | 30.947 | 16.213 | 19.275 | 1.00 | 35.37 | B | C |
| ATOM | 2536 | CD2 | LEU | B | 132 | 31.224 | 14.514 | 17.517 | 1.00 | 34.79 | B | C |
| ATOM | 2537 | C | LEU | B | 132 | 35.577 | 14.522 | 19.194 | 1.00 | 42.01 | B | C |

TABLE 12-continued

Coordinates for pro MMP9(35-444 ΔFnII) (SEQ ID NO: 12) complex with Example 2

| ATOM | 2538 | O | LEU | B | 132 | 36.236 | 14.987 | 20.137 | 1.00 | 36.91 | B | O |
|------|------|------|-----|---|-----|--------|--------|--------|------|-------|---|---|
| ATOM | 2539 | N | PRO | B | 133 | 36.073 | 14.408 | 17.945 | 1.00 | 40.13 | B | N |
| ATOM | 2540 | CD | PRO | B | 133 | 35.467 | 13.656 | 16.833 | 1.00 | 37.38 | B | C |
| ATOM | 2541 | CA | PRO | B | 133 | 37.388 | 14.957 | 17.587 | 1.00 | 36.50 | B | C |
| ATOM | 2542 | CB | PRO | B | 133 | 37.469 | 14.688 | 16.085 | 1.00 | 37.78 | B | C |
| ATOM | 2543 | CG | PRO | B | 133 | 36.613 | 13.461 | 15.884 | 1.00 | 41.15 | B | C |
| ATOM | 2544 | C | PRO | B | 133 | 37.457 | 16.464 | 17.863 | 1.00 | 41.04 | B | C |
| ATOM | 2545 | O | PRO | B | 133 | 36.484 | 17.184 | 17.629 | 1.00 | 41.40 | B | O |
| ATOM | 2546 | N | ARG | B | 134 | 38.598 | 16.926 | 18.355 | 1.00 | 34.23 | B | N |
| ATOM | 2547 | CA | ARG | B | 134 | 38.801 | 18.329 | 18.673 | 1.00 | 36.89 | B | C |
| ATOM | 2548 | CB | ARG | B | 134 | 40.243 | 18.565 | 19.135 | 1.00 | 37.59 | B | C |
| ATOM | 2549 | CG | ARG | B | 134 | 40.576 | 17.987 | 20.478 | 1.00 | 38.06 | B | C |
| ATOM | 2550 | CD | ARG | B | 134 | 41.658 | 18.785 | 21.146 | 1.00 | 40.03 | B | C |
| ATOM | 2551 | NE | ARG | B | 134 | 41.908 | 18.317 | 22.505 | 1.00 | 45.68 | B | N |
| ATOM | 2552 | CZ | ARG | B | 134 | 42.793 | 18.866 | 23.333 | 1.00 | 49.76 | B | C |
| ATOM | 2553 | NH1 | ARG | B | 134 | 43.517 | 19.913 | 22.945 | 1.00 | 56.93 | B | N |
| ATOM | 2554 | NH2 | ARG | B | 134 | 42.948 | 18.375 | 24.555 | 1.00 | 52.95 | B | N |
| ATOM | 2555 | C | ARG | B | 134 | 38.455 | 19.305 | 17.538 | 1.00 | 40.52 | B | C |
| ATOM | 2556 | O | ARG | B | 134 | 38.081 | 20.454 | 17.806 | 1.00 | 38.77 | B | O |
| ATOM | 2557 | N | ALA | B | 135 | 38.594 | 18.867 | 16.286 | 1.00 | 40.56 | B | N |
| ATOM | 2558 | CA | ALA | B | 135 | 38.337 | 19.746 | 15.146 | 1.00 | 39.73 | B | C |
| ATOM | 2559 | CB | ALA | B | 135 | 39.242 | 19.389 | 13.993 | 1.00 | 39.64 | B | C |
| ATOM | 2560 | C | ALA | B | 135 | 36.872 | 19.686 | 14.703 | 1.00 | 38.66 | B | C |
| ATOM | 2561 | O | ALA | B | 135 | 36.360 | 20.583 | 14.024 | 1.00 | 36.34 | B | O |
| ATOM | 2562 | N | VAL | B | 136 | 36.206 | 18.601 | 15.045 | 1.00 | 35.13 | B | N |
| ATOM | 2563 | CA | VAL | B | 136 | 34.779 | 18.532 | 14.784 | 1.00 | 36.49 | B | C |
| ATOM | 2564 | CB | VAL | B | 136 | 34.297 | 17.089 | 14.899 | 1.00 | 35.30 | B | C |
| ATOM | 2565 | CG1 | VAL | B | 136 | 32.801 | 16.998 | 14.689 | 1.00 | 35.19 | B | C |
| ATOM | 2566 | CG2 | VAL | B | 136 | 35.028 | 16.238 | 13.863 | 1.00 | 31.26 | B | C |
| ATOM | 2567 | C | VAL | B | 136 | 34.095 | 19.513 | 15.772 | 1.00 | 30.51 | B | C |
| ATOM | 2568 | O | VAL | B | 136 | 33.201 | 20.276 | 15.416 | 1.00 | 33.64 | B | O |
| ATOM | 2569 | N | ILE | B | 137 | 34.597 | 19.544 | 16.989 | 1.00 | 29.92 | B | N |
| ATOM | 2570 | CA | ILE | B | 137 | 34.167 | 20.532 | 17.959 | 1.00 | 33.71 | B | C |
| ATOM | 2571 | CB | ILE | B | 137 | 34.764 | 20.218 | 19.325 | 1.00 | 32.97 | B | C |
| ATOM | 2572 | CG2 | ILE | B | 137 | 34.639 | 21.401 | 20.239 | 1.00 | 37.27 | B | C |
| ATOM | 2573 | CG1 | ILE | B | 137 | 34.068 | 18.979 | 19.921 | 1.00 | 36.00 | B | C |
| ATOM | 2574 | CD1 | ILE | B | 137 | 34.770 | 18.423 | 21.129 | 1.00 | 32.61 | B | C |
| ATOM | 2575 | C | ILE | B | 137 | 34.509 | 21.963 | 17.524 | 1.00 | 37.21 | B | C |
| ATOM | 2576 | O | ILE | B | 137 | 33.600 | 22.800 | 17.344 | 1.00 | 34.33 | B | O |
| ATOM | 2577 | N | ASP | B | 138 | 35.808 | 22.234 | 17.357 | 1.00 | 31.17 | B | N |
| ATOM | 2578 | CA | ASP | B | 138 | 36.296 | 23.498 | 16.799 | 1.00 | 32.57 | B | C |
| ATOM | 2579 | CB | ASP | B | 138 | 37.703 | 23.326 | 16.197 | 1.00 | 33.14 | B | C |
| ATOM | 2580 | CG | ASP | B | 138 | 38.758 | 23.067 | 17.240 | 1.00 | 39.79 | B | C |
| ATOM | 2581 | OD1 | ASP | B | 138 | 38.456 | 23.245 | 18.438 | 1.00 | 45.17 | B | O |
| ATOM | 2582 | OD2 | ASP | B | 138 | 39.890 | 22.685 | 16.863 | 1.00 | 46.04 | B | O |
| ATOM | 2583 | C | ASP | B | 138 | 35.402 | 23.988 | 15.682 | 1.00 | 25.16 | B | C |
| ATOM | 2584 | O | ASP | B | 138 | 35.117 | 25.179 | 15.577 | 1.00 | 29.98 | B | O |
| ATOM | 2585 | N | ASP | B | 139 | 34.965 | 23.064 | 14.837 | 1.00 | 27.40 | B | N |
| ATOM | 2586 | CA | ASP | B | 139 | 34.217 | 23.418 | 13.636 | 1.00 | 28.27 | B | C |
| ATOM | 2587 | CB | ASP | B | 139 | 34.277 | 22.260 | 12.650 | 1.00 | 29.54 | B | C |
| ATOM | 2588 | CG | ASP | B | 139 | 33.304 | 22.421 | 11.514 | 1.00 | 33.04 | B | C |
| ATOM | 2589 | OD1 | ASP | B | 139 | 33.534 | 23.304 | 10.656 | 1.00 | 36.55 | B | O |
| ATOM | 2590 | OD2 | ASP | B | 139 | 32.316 | 21.655 | 11.453 | 1.00 | 31.94 | B | O |
| ATOM | 2591 | C | ASP | B | 139 | 32.741 | 23.736 | 13.934 | 1.00 | 33.68 | B | C |
| ATOM | 2592 | O | ASP | B | 139 | 32.113 | 24.596 | 13.279 | 1.00 | 28.11 | B | O |
| ATOM | 2593 | N | ALA | B | 140 | 32.190 | 23.021 | 14.913 | 1.00 | 31.25 | B | N |
| ATOM | 2594 | CA | ALA | B | 140 | 30.785 | 23.214 | 15.297 | 1.00 | 31.70 | B | C |
| ATOM | 2595 | CB | ALA | B | 140 | 30.321 | 22.089 | 16.230 | 1.00 | 27.54 | B | C |
| ATOM | 2596 | C | ALA | B | 140 | 30.642 | 24.574 | 15.963 | 1.00 | 23.86 | B | C |
| ATOM | 2597 | O | ALA | B | 140 | 29.762 | 25.348 | 15.633 | 1.00 | 27.33 | B | O |
| ATOM | 2598 | N | PHE | B | 141 | 31.524 | 24.875 | 16.900 | 1.00 | 25.73 | B | N |
| ATOM | 2599 | CA | PHE | B | 141 | 31.568 | 26.228 | 17.432 | 1.00 | 27.06 | B | C |
| ATOM | 2600 | CB | PHE | B | 141 | 32.652 | 26.366 | 18.487 | 1.00 | 27.20 | B | C |
| ATOM | 2601 | CG | PHE | B | 141 | 32.457 | 25.479 | 19.664 | 1.00 | 31.72 | B | C |
| ATOM | 2602 | CD1 | PHE | B | 141 | 31.184 | 25.022 | 20.003 | 1.00 | 32.52 | B | C |
| ATOM | 2603 | CD2 | PHE | B | 141 | 33.539 | 25.118 | 20.465 | 1.00 | 30.15 | B | C |
| ATOM | 2604 | CE1 | PHE | B | 141 | 31.002 | 24.204 | 21.113 | 1.00 | 31.73 | B | C |
| ATOM | 2605 | CE2 | PHE | B | 141 | 33.372 | 24.300 | 21.574 | 1.00 | 33.44 | B | C |
| ATOM | 2606 | CZ | PHE | B | 141 | 32.098 | 23.841 | 21.899 | 1.00 | 34.20 | B | C |
| ATOM | 2607 | C | PHE | B | 141 | 31.742 | 27.302 | 16.345 | 1.00 | 33.52 | B | C |
| ATOM | 2608 | O | PHE | B | 141 | 31.188 | 28.408 | 16.462 | 1.00 | 34.64 | B | O |
| ATOM | 2609 | N | ALA | B | 142 | 32.495 | 26.994 | 15.289 | 1.00 | 31.95 | B | N |
| ATOM | 2610 | CA | ALA | B | 142 | 32.710 | 27.984 | 14.215 | 1.00 | 29.67 | B | C |
| ATOM | 2611 | CB | ALA | B | 142 | 33.850 | 27.524 | 13.265 | 1.00 | 30.45 | B | C |
| ATOM | 2612 | C | ALA | B | 142 | 31.455 | 28.252 | 13.409 | 1.00 | 24.46 | B | C |
| ATOM | 2613 | O | ALA | B | 142 | 31.068 | 29.405 | 13.170 | 1.00 | 21.93 | B | O |
| ATOM | 2614 | N | ARG | B | 143 | 30.862 | 27.172 | 12.926 | 1.00 | 25.94 | B | N |

TABLE 12-continued

Coordinates for pro MMP9(35-444 ΔFnII) (SEQ ID NO: 12) complex with Example 2

| | | | | | | | | | | | |
|---|---|---|---|---|---|---|---|---|---|---|---|
| ATOM | 2615 | CA | ARG | B | 143 | 29.576 | 27.232 | 12.241 | 1.00 | 29.70 B | C |
| ATOM | 2616 | CB | ARG | B | 143 | 29.109 | 25.828 | 11.911 | 1.00 | 23.86 B | C |
| ATOM | 2617 | CG | ARG | B | 143 | 29.870 | 25.200 | 10.739 | 1.00 | 32.24 B | C |
| ATOM | 2618 | CD | ARG | B | 143 | 29.975 | 23.700 | 10.929 | 1.00 | 34.53 B | C |
| ATOM | 2619 | NE | ARG | B | 143 | 28.646 | 23.151 | 10.856 | 1.00 | 41.14 B | N |
| ATOM | 2620 | CZ | ARG | B | 143 | 28.192 | 22.148 | 11.587 | 1.00 | 35.61 B | C |
| ATOM | 2621 | NH1 | ARG | B | 143 | 28.965 | 21.533 | 12.473 | 1.00 | 34.83 B | N |
| ATOM | 2622 | NH2 | ARG | B | 143 | 26.942 | 21.773 | 11.414 | 1.00 | 37.65 B | N |
| ATOM | 2623 | C | ARG | B | 143 | 28.518 | 27.948 | 13.097 | 1.00 | 25.15 B | C |
| ATOM | 2624 | O | ARG | B | 143 | 27.696 | 28.710 | 12.591 | 1.00 | 27.67 B | O |
| ATOM | 2625 | N | ALA | B | 144 | 28.555 | 27.692 | 14.391 | 1.00 | 22.96 B | N |
| ATOM | 2626 | CA | ALA | B | 144 | 27.612 | 28.318 | 15.279 | 1.00 | 28.85 B | C |
| ATOM | 2627 | CB | ALA | B | 144 | 27.855 | 27.838 | 16.699 | 1.00 | 26.99 B | C |
| ATOM | 2628 | C | ALA | B | 144 | 27.742 | 29.844 | 15.174 | 1.00 | 29.28 B | C |
| ATOM | 2629 | O | ALA | B | 144 | 26.748 | 30.553 | 14.960 | 1.00 | 24.56 B | O |
| ATOM | 2630 | N | PHE | B | 145 | 28.966 | 30.350 | 15.308 | 1.00 | 23.93 B | N |
| ATOM | 2631 | CA | PHE | B | 145 | 29.188 | 31.798 | 15.233 | 1.00 | 27.09 B | C |
| ATOM | 2632 | CB | PHE | B | 145 | 30.632 | 32.160 | 15.597 | 1.00 | 23.43 B | C |
| ATOM | 2633 | CG | PHE | B | 145 | 30.929 | 32.071 | 17.047 | 1.00 | 25.14 B | C |
| ATOM | 2634 | CD1 | PHE | B | 145 | 30.432 | 33.019 | 17.931 | 1.00 | 27.69 B | C |
| ATOM | 2635 | CD2 | PHE | B | 145 | 31.729 | 31.060 | 17.543 | 1.00 | 25.48 B | C |
| ATOM | 2636 | CE1 | PHE | B | 145 | 30.726 | 32.934 | 19.289 | 1.00 | 23.37 B | C |
| ATOM | 2637 | CE2 | PHE | B | 145 | 32.044 | 30.990 | 18.885 | 1.00 | 24.74 B | C |
| ATOM | 2638 | CZ | PHE | B | 145 | 31.544 | 31.924 | 19.759 | 1.00 | 26.91 B | C |
| ATOM | 2639 | C | PHE | B | 145 | 28.855 | 32.350 | 13.859 | 1.00 | 26.73 B | C |
| ATOM | 2640 | O | PHE | B | 145 | 28.362 | 33.482 | 13.729 | 1.00 | 26.48 B | O |
| ATOM | 2641 | N | ALA | B | 146 | 29.126 | 31.558 | 12.822 | 1.00 | 28.34 B | N |
| ATOM | 2642 | CA | ALA | B | 146 | 28.839 | 32.010 | 11.468 | 1.00 | 24.97 B | C |
| ATOM | 2643 | CB | ALA | B | 146 | 29.211 | 30.975 | 10.489 | 1.00 | 24.79 B | C |
| ATOM | 2644 | C | ALA | B | 146 | 27.368 | 32.372 | 11.292 | 1.00 | 27.63 B | C |
| ATOM | 2645 | O | ALA | B | 146 | 27.035 | 33.248 | 10.477 | 1.00 | 20.89 B | O |
| ATOM | 2646 | N | LEU | B | 147 | 26.471 | 31.672 | 12.001 | 1.00 | 29.36 B | N |
| ATOM | 2647 | CA | LEU | B | 147 | 25.037 | 32.000 | 11.883 | 1.00 | 20.93 B | C |
| ATOM | 2648 | CB | LEU | B | 147 | 24.177 | 31.116 | 12.787 | 1.00 | 27.60 B | C |
| ATOM | 2649 | CG | LEU | B | 147 | 23.976 | 29.660 | 12.369 | 1.00 | 26.34 B | C |
| ATOM | 2650 | CD1 | LEU | B | 147 | 23.644 | 28.788 | 13.567 | 1.00 | 30.17 B | C |
| ATOM | 2651 | CD2 | LEU | B | 147 | 22.914 | 29.520 | 11.287 | 1.00 | 28.65 B | C |
| ATOM | 2652 | C | LEU | B | 147 | 24.863 | 33.461 | 12.277 | 1.00 | 15.44 B | C |
| ATOM | 2653 | O | LEU | B | 147 | 24.330 | 34.246 | 11.525 | 1.00 | 23.60 B | O |
| ATOM | 2654 | N | TRP | B | 148 | 25.350 | 33.813 | 13.456 | 1.00 | 20.89 B | N |
| ATOM | 2655 | CA | TRP | B | 148 | 25.208 | 35.149 | 14.002 | 1.00 | 25.33 B | C |
| ATOM | 2656 | CB | TRP | B | 148 | 25.555 | 35.119 | 15.497 | 1.00 | 29.18 B | C |
| ATOM | 2657 | CG | TRP | B | 148 | 24.630 | 34.219 | 16.326 | 1.00 | 37.59 B | C |
| ATOM | 2658 | CD2 | TRP | B | 148 | 23.223 | 34.413 | 16.571 | 1.00 | 29.17 B | C |
| ATOM | 2659 | CE2 | TRP | B | 148 | 22.781 | 33.341 | 17.371 | 1.00 | 34.19 B | C |
| ATOM | 2660 | CE3 | TRP | B | 148 | 22.298 | 35.390 | 16.186 | 1.00 | 30.19 B | C |
| ATOM | 2661 | CD1 | TRP | B | 148 | 24.967 | 33.059 | 16.979 | 1.00 | 37.03 B | C |
| ATOM | 2662 | NE1 | TRP | B | 148 | 23.859 | 32.531 | 17.609 | 1.00 | 33.28 B | N |
| ATOM | 2663 | CZ2 | TRP | B | 148 | 21.447 | 33.225 | 17.805 | 1.00 | 33.60 B | C |
| ATOM | 2664 | CZ3 | TRP | B | 148 | 20.968 | 35.263 | 16.612 | 1.00 | 32.19 B | C |
| ATOM | 2665 | CH2 | TRP | B | 148 | 20.564 | 34.189 | 17.403 | 1.00 | 29.62 B | C |
| ATOM | 2666 | C | TRP | B | 148 | 26.060 | 36.207 | 13.278 | 1.00 | 29.92 B | C |
| ATOM | 2667 | O | TRP | B | 148 | 25.779 | 37.404 | 13.337 | 1.00 | 20.03 B | O |
| ATOM | 2668 | N | SER | B | 149 | 27.118 | 35.782 | 12.590 | 1.00 | 32.08 B | N |
| ATOM | 2669 | CA | SER | B | 149 | 27.994 | 36.785 | 12.000 | 1.00 | 25.83 B | C |
| ATOM | 2670 | CB | SER | B | 149 | 29.308 | 36.163 | 11.508 | 1.00 | 30.48 B | C |
| ATOM | 2671 | OG | SER | B | 149 | 30.227 | 37.211 | 11.257 | 1.00 | 35.92 B | O |
| ATOM | 2672 | C | SER | B | 149 | 27.278 | 37.441 | 10.851 | 1.00 | 22.19 B | C |
| ATOM | 2673 | O | SER | B | 149 | 27.379 | 38.646 | 10.609 | 1.00 | 24.42 B | O |
| ATOM | 2674 | N | ALA | B | 150 | 26.544 | 36.630 | 10.122 | 1.00 | 18.70 B | N |
| ATOM | 2675 | CA | ALA | B | 150 | 25.912 | 37.099 | 8.906 | 1.00 | 19.08 B | C |
| ATOM | 2676 | CB | ALA | B | 150 | 25.380 | 35.906 | 8.138 | 1.00 | 21.25 B | C |
| ATOM | 2677 | C | ALA | B | 150 | 24.783 | 38.107 | 9.146 | 1.00 | 26.52 B | C |
| ATOM | 2678 | O | ALA | B | 150 | 24.435 | 38.885 | 8.244 | 1.00 | 21.90 B | O |
| ATOM | 2679 | N | VAL | B | 151 | 24.184 | 38.069 | 10.342 | 1.00 | 22.69 B | N |
| ATOM | 2680 | CA | VAL | B | 151 | 22.967 | 38.856 | 10.601 | 1.00 | 25.66 B | C |
| ATOM | 2681 | CB | VAL | B | 151 | 21.826 | 37.970 | 11.140 | 1.00 | 22.60 B | C |
| ATOM | 2682 | CG1 | VAL | B | 151 | 21.342 | 37.016 | 10.079 | 1.00 | 20.46 B | C |
| ATOM | 2683 | CG2 | VAL | B | 151 | 22.273 | 37.209 | 12.378 | 1.00 | 22.58 B | C |
| ATOM | 2684 | C | VAL | B | 151 | 23.221 | 39.981 | 11.597 | 1.00 | 29.63 B | C |
| ATOM | 2685 | O | VAL | B | 151 | 22.276 | 40.520 | 12.176 | 1.00 | 29.66 B | O |
| ATOM | 2686 | N | THR | B | 152 | 24.501 | 40.309 | 11.799 | 1.00 | 28.93 B | N |
| ATOM | 2687 | CA | THR | B | 152 | 24.941 | 41.357 | 12.717 | 1.00 | 29.43 B | C |
| ATOM | 2688 | CB | THR | B | 152 | 25.256 | 40.788 | 14.106 | 1.00 | 33.71 B | C |
| ATOM | 2689 | OG1 | THR | B | 152 | 26.504 | 40.101 | 14.062 | 1.00 | 33.49 B | O |
| ATOM | 2690 | CG2 | THR | B | 152 | 24.163 | 39.817 | 14.593 | 1.00 | 27.41 B | C |
| ATOM | 2691 | C | THR | B | 152 | 26.237 | 42.032 | 12.217 | 1.00 | 33.69 B | C |

TABLE 12-continued

Coordinates for pro MMP9(35-444 ΔFnII) (SEQ ID NO: 12) complex with Example 2

| ATOM | 2692 | O | THR | B | 152 | 26.902 | 41.515 | 11.317 | 1.00 | 30.17 | B | O |
|------|------|-----|-----|---|-----|--------|--------|--------|------|-------|---|---|
| ATOM | 2693 | N | PRO | B | 153 | 26.577 | 43.200 | 12.786 | 1.00 | 32.70 | B | N |
| ATOM | 2694 | CD | PRO | B | 153 | 25.618 | 44.040 | 13.517 | 1.00 | 33.25 | B | C |
| ATOM | 2695 | CA | PRO | B | 153 | 27.803 | 43.951 | 12.506 | 1.00 | 34.26 | B | C |
| ATOM | 2696 | CB | PRO | B | 153 | 27.469 | 45.359 | 13.024 | 1.00 | 34.92 | B | C |
| ATOM | 2697 | CG | PRO | B | 153 | 25.997 | 45.414 | 13.067 | 1.00 | 32.81 | B | C |
| ATOM | 2698 | C | PRO | B | 153 | 29.001 | 43.426 | 13.275 | 1.00 | 33.52 | B | C |
| ATOM | 2699 | O | PRO | B | 153 | 29.914 | 44.199 | 13.547 | 1.00 | 34.26 | B | O |
| ATOM | 2700 | N | LEU | B | 154 | 28.989 | 42.147 | 13.637 | 1.00 | 31.11 | B | N |
| ATOM | 2701 | CA | LEU | B | 154 | 30.037 | 41.578 | 14.472 | 1.00 | 31.11 | B | C |
| ATOM | 2702 | CB | LEU | B | 154 | 29.406 | 40.920 | 15.688 | 1.00 | 31.84 | B | C |
| ATOM | 2703 | CG | LEU | B | 154 | 28.482 | 41.786 | 16.543 | 1.00 | 34.46 | B | C |
| ATOM | 2704 | CD1 | LEU | B | 154 | 27.740 | 40.913 | 17.531 | 1.00 | 35.26 | B | C |
| ATOM | 2705 | CD2 | LEU | B | 154 | 29.272 | 42.842 | 17.271 | 1.00 | 27.29 | B | C |
| ATOM | 2706 | C | LEU | B | 154 | 30.829 | 40.501 | 13.740 | 1.00 | 28.09 | B | C |
| ATOM | 2707 | O | LEU | B | 154 | 30.322 | 39.902 | 12.809 | 1.00 | 25.88 | B | O |
| ATOM | 2708 | N | THR | B | 155 | 32.050 | 40.241 | 14.203 | 1.00 | 28.45 | B | N |
| ATOM | 2709 | CA | THR | B | 155 | 32.831 | 39.116 | 13.715 | 1.00 | 27.19 | B | C |
| ATOM | 2710 | CB | THR | B | 155 | 34.036 | 39.558 | 12.864 | 1.00 | 28.36 | B | C |
| ATOM | 2711 | OG1 | THR | B | 155 | 34.977 | 40.242 | 13.705 | 1.00 | 36.24 | B | O |
| ATOM | 2712 | CG2 | THR | B | 155 | 33.598 | 40.474 | 11.776 | 1.00 | 25.25 | B | C |
| ATOM | 2713 | C | THR | B | 155 | 33.369 | 38.377 | 14.898 | 1.00 | 25.14 | B | C |
| ATOM | 2714 | O | THR | B | 155 | 33.595 | 38.947 | 15.954 | 1.00 | 31.29 | B | O |
| ATOM | 2715 | N | PHE | B | 156 | 33.600 | 37.094 | 14.710 | 1.00 | 23.88 | B | N |
| ATOM | 2716 | CA | PHE | B | 156 | 34.074 | 36.258 | 15.781 | 1.00 | 24.06 | B | C |
| ATOM | 2717 | CB | PHE | B | 156 | 33.034 | 35.184 | 16.049 | 1.00 | 26.77 | B | C |
| ATOM | 2718 | CG | PHE | B | 156 | 31.668 | 35.775 | 16.357 | 1.00 | 26.24 | B | C |
| ATOM | 2719 | CD1 | PHE | B | 156 | 30.754 | 35.987 | 15.347 | 1.00 | 27.83 | B | C |
| ATOM | 2720 | CD2 | PHE | B | 156 | 31.365 | 36.206 | 17.643 | 1.00 | 25.27 | B | C |
| ATOM | 2721 | CE1 | PHE | B | 156 | 29.519 | 36.579 | 15.615 | 1.00 | 29.83 | B | C |
| ATOM | 2722 | CE2 | PHE | B | 156 | 30.129 | 36.804 | 17.929 | 1.00 | 26.39 | B | C |
| ATOM | 2723 | CZ | PHE | B | 156 | 29.213 | 36.984 | 16.921 | 1.00 | 28.36 | B | C |
| ATOM | 2724 | C | PHE | B | 156 | 35.433 | 35.668 | 15.397 | 1.00 | 31.54 | B | C |
| ATOM | 2725 | O | PHE | B | 156 | 35.611 | 35.127 | 14.317 | 1.00 | 30.27 | B | O |
| ATOM | 2726 | N | THR | B | 157 | 36.375 | 35.796 | 16.305 | 1.00 | 30.81 | B | N |
| ATOM | 2727 | CA | THR | B | 157 | 37.737 | 35.414 | 16.044 | 1.00 | 31.27 | B | C |
| ATOM | 2728 | CB | THR | B | 157 | 38.659 | 36.642 | 16.147 | 1.00 | 31.97 | B | C |
| ATOM | 2729 | OG1 | THR | B | 157 | 38.450 | 37.504 | 15.023 | 1.00 | 37.50 | B | O |
| ATOM | 2730 | CG2 | THR | B | 157 | 40.110 | 36.204 | 16.181 | 1.00 | 35.24 | B | C |
| ATOM | 2731 | C | THR | B | 157 | 38.154 | 34.462 | 17.128 | 1.00 | 26.84 | B | C |
| ATOM | 2732 | O | THR | B | 157 | 38.189 | 34.828 | 18.307 | 1.00 | 31.93 | B | O |
| ATOM | 2733 | N | ARG | B | 158 | 38.506 | 33.247 | 16.746 | 1.00 | 33.28 | B | N |
| ATOM | 2734 | CA | ARG | B | 158 | 39.042 | 32.299 | 17.718 | 1.00 | 33.83 | B | C |
| ATOM | 2735 | CB | ARG | B | 158 | 39.174 | 30.923 | 17.064 | 1.00 | 29.38 | B | C |
| ATOM | 2736 | CG | ARG | B | 158 | 39.559 | 29.843 | 18.025 | 1.00 | 32.76 | B | C |
| ATOM | 2737 | CD | ARG | B | 158 | 39.663 | 28.473 | 17.356 | 1.00 | 32.09 | B | C |
| ATOM | 2738 | NE | ARG | B | 158 | 40.269 | 27.545 | 18.304 | 1.00 | 31.08 | B | N |
| ATOM | 2739 | CZ | ARG | B | 158 | 40.513 | 26.260 | 18.064 | 1.00 | 30.48 | B | C |
| ATOM | 2740 | NH1 | ARG | B | 158 | 40.206 | 25.722 | 16.888 | 1.00 | 30.78 | B | N |
| ATOM | 2741 | NH2 | ARG | B | 158 | 41.062 | 25.514 | 19.013 | 1.00 | 33.64 | B | N |
| ATOM | 2742 | C | ARG | B | 158 | 40.400 | 32.767 | 18.251 | 1.00 | 34.81 | B | C |
| ATOM | 2743 | O | ARG | B | 158 | 41.279 | 33.151 | 17.466 | 1.00 | 38.61 | B | O |
| ATOM | 2744 | N | VAL | B | 159 | 40.578 | 32.758 | 19.570 | 1.00 | 34.09 | B | N |
| ATOM | 2745 | CA | VAL | B | 159 | 41.900 | 33.002 | 20.150 | 1.00 | 34.95 | B | C |
| ATOM | 2746 | CB | VAL | B | 159 | 42.018 | 34.411 | 20.789 | 1.00 | 30.65 | B | C |
| ATOM | 2747 | CG1 | VAL | B | 159 | 41.650 | 35.492 | 19.751 | 1.00 | 33.82 | B | C |
| ATOM | 2748 | CG2 | VAL | B | 159 | 41.142 | 34.532 | 22.032 | 1.00 | 38.78 | B | C |
| ATOM | 2749 | C | VAL | B | 159 | 42.369 | 31.868 | 21.092 | 1.00 | 38.83 | B | C |
| ATOM | 2750 | O | VAL | B | 159 | 41.704 | 30.831 | 21.203 | 1.00 | 39.69 | B | O |
| ATOM | 2751 | N | TYR | B | 160 | 43.509 | 32.048 | 21.758 | 1.00 | 35.17 | B | N |
| ATOM | 2752 | CA | TYR | B | 160 | 44.125 | 30.933 | 22.484 | 1.00 | 34.52 | B | C |
| ATOM | 2753 | CB | TYR | B | 160 | 45.218 | 30.211 | 21.627 | 1.00 | 34.78 | B | C |
| ATOM | 2754 | CG | TYR | B | 160 | 44.662 | 29.508 | 20.385 | 1.00 | 29.89 | B | C |
| ATOM | 2755 | CD1 | TYR | B | 160 | 44.311 | 30.231 | 19.260 | 1.00 | 32.01 | B | C |
| ATOM | 2756 | CE1 | TYR | B | 160 | 43.772 | 29.619 | 18.151 | 1.00 | 29.18 | B | C |
| ATOM | 2757 | CD2 | TYR | B | 160 | 44.458 | 28.131 | 20.357 | 1.00 | 27.82 | B | C |
| ATOM | 2758 | CE2 | TYR | B | 160 | 43.925 | 27.510 | 19.234 | 1.00 | 22.88 | B | C |
| ATOM | 2759 | CZ | TYR | B | 160 | 43.580 | 28.265 | 18.148 | 1.00 | 28.40 | B | C |
| ATOM | 2760 | OH | TYR | B | 160 | 43.048 | 27.687 | 17.024 | 1.00 | 33.31 | B | O |
| ATOM | 2761 | C | TYR | B | 160 | 44.639 | 31.331 | 23.866 | 1.00 | 36.10 | B | C |
| ATOM | 2762 | O | TYR | B | 160 | 45.389 | 30.588 | 24.487 | 1.00 | 45.76 | B | O |
| ATOM | 2763 | N | SER | B | 161 | 44.232 | 32.495 | 24.360 | 1.00 | 34.77 | B | N |
| ATOM | 2764 | CA | SER | B | 161 | 44.494 | 32.854 | 25.754 | 1.00 | 40.41 | B | C |
| ATOM | 2765 | CB | SER | B | 161 | 45.403 | 34.072 | 25.832 | 1.00 | 37.53 | B | C |
| ATOM | 2766 | OG | SER | B | 161 | 44.716 | 35.213 | 25.345 | 1.00 | 48.82 | B | O |
| ATOM | 2767 | C | SER | B | 161 | 43.182 | 33.194 | 26.477 | 1.00 | 42.79 | B | C |
| ATOM | 2768 | O | SER | B | 161 | 42.154 | 33.396 | 25.837 | 1.00 | 40.86 | B | O |

TABLE 12-continued

Coordinates for pro MMP9(35-444 ΔFnII) (SEQ ID NO: 12) complex with Example 2

| ATOM | 2769 | N | ARG | B | 162 | 43.232 | 33.285 | 27.805 | 1.00 | 43.77 | B | N |
|------|------|-----|-----|---|-----|--------|--------|--------|------|-------|---|---|
| ATOM | 2770 | CA | ARG | B | 162 | 42.076 | 33.737 | 28.598 | 1.00 | 50.22 | B | C |
| ATOM | 2771 | CB | ARG | B | 162 | 42.367 | 33.644 | 30.100 | 1.00 | 51.70 | B | C |
| ATOM | 2772 | CG | ARG | B | 162 | 43.710 | 34.232 | 30.543 | 1.00 | 56.16 | B | C |
| ATOM | 2773 | CD | ARG | B | 162 | 43.652 | 35.740 | 30.775 | 1.00 | 60.42 | B | C |
| ATOM | 2774 | NE | ARG | B | 162 | 44.988 | 36.296 | 31.010 | 1.00 | 63.52 | B | N |
| ATOM | 2775 | CZ | ARG | B | 162 | 45.233 | 37.502 | 31.518 | 1.00 | 67.95 | B | C |
| ATOM | 2776 | NH1 | ARG | B | 162 | 44.230 | 38.302 | 31.866 | 1.00 | 71.00 | B | N |
| ATOM | 2777 | NH2 | ARG | B | 162 | 46.489 | 37.905 | 31.687 | 1.00 | 66.17 | B | N |
| ATOM | 2778 | C | ARG | B | 162 | 41.657 | 35.154 | 28.244 | 1.00 | 48.43 | B | C |
| ATOM | 2779 | O | ARG | B | 162 | 40.556 | 35.576 | 28.550 | 1.00 | 52.70 | B | O |
| ATOM | 2780 | N | ASP | B | 163 | 42.565 | 35.898 | 27.626 | 1.00 | 51.35 | B | N |
| ATOM | 2781 | CA | ASP | B | 163 | 42.243 | 37.200 | 27.071 | 1.00 | 53.37 | B | C |
| ATOM | 2782 | CB | ASP | B | 163 | 43.534 | 37.922 | 26.629 | 1.00 | 58.34 | B | C |
| ATOM | 2783 | CG | ASP | B | 163 | 43.306 | 39.389 | 26.244 | 1.00 | 67.51 | B | C |
| ATOM | 2784 | OD1 | ASP | B | 163 | 42.497 | 40.077 | 26.902 | 1.00 | 70.67 | B | O |
| ATOM | 2785 | OD2 | ASP | B | 163 | 43.960 | 39.866 | 25.289 | 1.00 | 66.93 | B | O |
| ATOM | 2786 | C | ASP | B | 163 | 41.300 | 36.949 | 25.892 | 1.00 | 50.04 | B | C |
| ATOM | 2787 | O | ASP | B | 163 | 41.725 | 36.868 | 24.743 | 1.00 | 48.16 | B | O |
| ATOM | 2788 | N | ALA | B | 164 | 40.017 | 36.787 | 26.195 | 1.00 | 45.53 | B | N |
| ATOM | 2789 | CA | ALA | B | 164 | 38.984 | 36.624 | 25.169 | 1.00 | 42.59 | B | C |
| ATOM | 2790 | CB | ALA | B | 164 | 38.929 | 35.171 | 24.690 | 1.00 | 37.81 | B | C |
| ATOM | 2791 | C | ALA | B | 164 | 37.621 | 37.064 | 25.724 | 1.00 | 37.38 | B | C |
| ATOM | 2792 | O | ALA | B | 164 | 37.386 | 36.972 | 26.930 | 1.00 | 43.20 | B | O |
| ATOM | 2793 | N | ASP | B | 165 | 36.732 | 37.538 | 24.856 | 1.00 | 33.30 | B | N |
| ATOM | 2794 | CA | ASP | B | 165 | 35.390 | 37.973 | 25.286 | 1.00 | 38.79 | B | C |
| ATOM | 2795 | CB | ASP | B | 165 | 34.654 | 38.653 | 24.149 | 1.00 | 30.05 | B | C |
| ATOM | 2796 | CG | ASP | B | 165 | 35.290 | 39.954 | 23.739 | 1.00 | 31.15 | B | C |
| ATOM | 2797 | OD1 | ASP | B | 165 | 35.786 | 40.676 | 24.626 | 1.00 | 39.03 | B | O |
| ATOM | 2798 | OD2 | ASP | B | 165 | 35.261 | 40.259 | 22.526 | 1.00 | 31.72 | B | O |
| ATOM | 2799 | C | ASP | B | 165 | 34.520 | 36.818 | 25.771 | 1.00 | 36.71 | B | C |
| ATOM | 2800 | O | ASP | B | 165 | 33.952 | 36.874 | 26.853 | 1.00 | 40.46 | B | O |
| ATOM | 2801 | N | ILE | B | 166 | 34.399 | 35.793 | 24.936 | 1.00 | 33.51 | B | N |
| ATOM | 2802 | CA | ILE | B | 166 | 33.629 | 34.603 | 25.244 | 1.00 | 36.10 | B | C |
| ATOM | 2803 | CB | ILE | B | 166 | 32.727 | 34.239 | 24.066 | 1.00 | 36.93 | B | C |
| ATOM | 2804 | CG2 | ILE | B | 166 | 32.037 | 32.897 | 24.317 | 1.00 | 37.36 | B | C |
| ATOM | 2805 | CG1 | ILE | B | 166 | 31.760 | 35.393 | 23.767 | 1.00 | 31.10 | B | C |
| ATOM | 2806 | CD1 | ILE | B | 166 | 30.897 | 35.199 | 22.510 | 1.00 | 31.74 | B | C |
| ATOM | 2807 | C | ILE | B | 166 | 34.534 | 33.399 | 25.477 | 1.00 | 37.88 | B | C |
| ATOM | 2808 | O | ILE | B | 166 | 35.193 | 32.932 | 24.554 | 1.00 | 39.73 | B | O |
| ATOM | 2809 | N | VAL | B | 167 | 34.553 | 32.901 | 26.711 | 1.00 | 35.51 | B | N |
| ATOM | 2810 | CA | VAL | B | 167 | 35.275 | 31.687 | 27.044 | 1.00 | 34.20 | B | C |
| ATOM | 2811 | CB | VAL | B | 167 | 35.854 | 31.753 | 28.450 | 1.00 | 33.45 | B | C |
| ATOM | 2812 | CG1 | VAL | B | 167 | 36.393 | 30.391 | 28.856 | 1.00 | 38.45 | B | C |
| ATOM | 2813 | CG2 | VAL | B | 167 | 36.946 | 32.782 | 28.503 | 1.00 | 37.14 | B | C |
| ATOM | 2814 | C | VAL | B | 167 | 34.340 | 30.490 | 26.993 | 1.00 | 38.39 | B | C |
| ATOM | 2815 | O | VAL | B | 167 | 33.381 | 30.416 | 27.767 | 1.00 | 41.11 | B | O |
| ATOM | 2816 | N | ILE | B | 168 | 34.611 | 29.565 | 26.081 | 1.00 | 33.64 | B | N |
| ATOM | 2817 | CA | ILE | B | 168 | 33.850 | 28.328 | 25.966 | 1.00 | 32.63 | B | C |
| ATOM | 2818 | CB | ILE | B | 168 | 33.837 | 27.878 | 24.534 | 1.00 | 33.03 | B | C |
| ATOM | 2819 | CG2 | ILE | B | 168 | 33.331 | 26.458 | 24.408 | 1.00 | 36.57 | B | C |
| ATOM | 2820 | CG1 | ILE | B | 168 | 32.967 | 28.824 | 23.731 | 1.00 | 32.62 | B | C |
| ATOM | 2821 | CD1 | ILE | B | 168 | 33.118 | 28.660 | 22.256 | 1.00 | 35.92 | B | C |
| ATOM | 2822 | C | ILE | B | 168 | 34.433 | 27.224 | 26.853 | 1.00 | 40.68 | B | C |
| ATOM | 2823 | O | ILE | B | 168 | 35.648 | 27.108 | 26.977 | 1.00 | 42.84 | B | O |
| ATOM | 2824 | N | GLN | B | 169 | 33.571 | 26.418 | 27.469 | 1.00 | 33.87 | B | N |
| ATOM | 2825 | CA | GLN | B | 169 | 34.005 | 25.461 | 28.486 | 1.00 | 31.82 | B | C |
| ATOM | 2826 | CB | GLN | B | 169 | 34.164 | 26.179 | 29.829 | 1.00 | 37.77 | B | C |
| ATOM | 2827 | CG | GLN | B | 169 | 34.136 | 25.288 | 31.051 | 1.00 | 37.07 | B | C |
| ATOM | 2828 | CD | GLN | B | 169 | 34.544 | 26.018 | 32.329 | 1.00 | 46.28 | B | C |
| ATOM | 2829 | OE1 | GLN | B | 169 | 34.969 | 27.179 | 32.304 | 1.00 | 51.90 | B | O |
| ATOM | 2830 | NE2 | GLN | B | 169 | 34.425 | 25.330 | 33.454 | 1.00 | 51.39 | B | N |
| ATOM | 2831 | C | GLN | B | 169 | 33.071 | 24.248 | 28.623 | 1.00 | 39.40 | B | C |
| ATOM | 2832 | O | GLN | B | 169 | 31.838 | 24.386 | 28.597 | 1.00 | 38.98 | B | O |
| ATOM | 2833 | N | PHE | B | 170 | 33.656 | 23.062 | 28.741 | 1.00 | 32.22 | B | N |
| ATOM | 2834 | CA | PHE | B | 170 | 32.894 | 21.844 | 28.962 | 1.00 | 33.84 | B | C |
| ATOM | 2835 | CB | PHE | B | 170 | 33.427 | 20.682 | 28.136 | 1.00 | 38.39 | B | C |
| ATOM | 2836 | CG | PHE | B | 170 | 33.008 | 20.684 | 26.689 | 1.00 | 39.53 | B | C |
| ATOM | 2837 | CD1 | PHE | B | 170 | 33.814 | 21.262 | 25.719 | 1.00 | 35.87 | B | C |
| ATOM | 2838 | CD2 | PHE | B | 170 | 31.837 | 20.060 | 26.291 | 1.00 | 37.03 | B | C |
| ATOM | 2839 | CE1 | PHE | B | 170 | 33.457 | 21.233 | 24.386 | 1.00 | 34.34 | B | C |
| ATOM | 2840 | CE2 | PHE | B | 170 | 31.472 | 20.033 | 24.958 | 1.00 | 36.58 | B | C |
| ATOM | 2841 | CZ | PHE | B | 170 | 32.290 | 20.622 | 24.001 | 1.00 | 38.24 | B | C |
| ATOM | 2842 | C | PHE | B | 170 | 33.098 | 21.507 | 30.415 | 1.00 | 38.06 | B | C |
| ATOM | 2843 | O | PHE | B | 170 | 34.212 | 21.621 | 30.922 | 1.00 | 35.38 | B | O |
| ATOM | 2844 | N | GLY | B | 171 | 32.035 | 21.094 | 31.098 | 1.00 | 36.47 | B | N |
| ATOM | 2845 | CA | GLY | B | 171 | 32.110 | 20.867 | 32.535 | 1.00 | 36.82 | B | C |

TABLE 12-continued

Coordinates for pro MMP9(35-444 ΔFnII) (SEQ ID NO: 12) complex with Example 2

| ATOM | 2846 | C | GLY | B | 171 | 30.980 | 19.977 | 33.039 | 1.00 | 40.48 | B | C |
| --- | --- | --- | --- | --- | --- | --- | --- | --- | --- | --- | --- | --- |
| ATOM | 2847 | O | GLY | B | 171 | 30.031 | 19.694 | 32.290 | 1.00 | 37.14 | B | O |
| ATOM | 2848 | N | VAL | B | 172 | 31.076 | 19.528 | 34.291 | 1.00 | 36.07 | B | N |
| ATOM | 2849 | CA | VAL | B | 172 | 30.040 | 18.660 | 34.868 | 1.00 | 38.81 | B | C |
| ATOM | 2850 | CB | VAL | B | 172 | 30.392 | 17.151 | 34.767 | 1.00 | 39.31 | B | C |
| ATOM | 2851 | CG1 | VAL | B | 172 | 30.119 | 16.631 | 33.387 | 1.00 | 40.55 | B | C |
| ATOM | 2852 | CG2 | VAL | B | 172 | 31.826 | 16.903 | 35.167 | 1.00 | 39.57 | B | C |
| ATOM | 2853 | C | VAL | B | 172 | 29.751 | 19.006 | 36.324 | 1.00 | 43.55 | B | C |
| ATOM | 2854 | O | VAL | B | 172 | 30.633 | 19.481 | 37.051 | 1.00 | 41.87 | B | O |
| ATOM | 2855 | N | ALA | B | 173 | 28.514 | 18.767 | 36.748 | 1.00 | 43.08 | B | N |
| ATOM | 2856 | CA | ALA | B | 173 | 28.101 | 19.134 | 38.091 | 1.00 | 41.48 | B | C |
| ATOM | 2857 | CB | ALA | B | 173 | 28.686 | 18.175 | 39.087 | 1.00 | 50.34 | B | C |
| ATOM | 2858 | C | ALA | B | 173 | 28.569 | 20.553 | 38.385 | 1.00 | 45.54 | B | C |
| ATOM | 2859 | O | ALA | B | 173 | 28.352 | 21.454 | 37.590 | 1.00 | 50.50 | B | O |
| ATOM | 2860 | N | GLU | B | 174 | 29.215 | 20.765 | 39.523 | 1.00 | 48.20 | B | N |
| ATOM | 2861 | CA | GLU | B | 174 | 29.789 | 22.076 | 39.788 | 1.00 | 50.01 | B | C |
| ATOM | 2862 | CB | GLU | B | 174 | 30.018 | 22.328 | 41.278 | 1.00 | 50.93 | B | C |
| ATOM | 2863 | CG | GLU | B | 174 | 30.380 | 23.774 | 41.575 | 1.00 | 52.28 | B | C |
| ATOM | 2864 | CD | GLU | B | 174 | 29.307 | 24.755 | 41.106 | 1.00 | 56.72 | B | C |
| ATOM | 2865 | OE1 | GLU | B | 174 | 28.743 | 25.455 | 41.975 | 1.00 | 56.03 | B | O |
| ATOM | 2866 | OE2 | GLU | B | 174 | 29.018 | 24.821 | 39.881 | 1.00 | 57.63 | B | O |
| ATOM | 2867 | C | GLU | B | 174 | 31.092 | 22.209 | 39.017 | 1.00 | 52.56 | B | C |
| ATOM | 2868 | O | GLU | B | 174 | 32.022 | 21.412 | 39.178 | 1.00 | 48.11 | B | O |
| ATOM | 2869 | N | HIS | B | 175 | 31.128 | 23.214 | 38.155 | 1.00 | 54.27 | B | N |
| ATOM | 2870 | CA | HIS | B | 175 | 32.256 | 23.429 | 37.280 | 1.00 | 45.01 | B | C |
| ATOM | 2871 | CB | HIS | B | 175 | 31.837 | 23.255 | 35.822 | 1.00 | 42.39 | B | C |
| ATOM | 2872 | CG | HIS | B | 175 | 30.551 | 23.938 | 35.468 | 1.00 | 42.79 | B | C |
| ATOM | 2873 | CD2 | HIS | B | 175 | 30.304 | 25.053 | 34.740 | 1.00 | 38.83 | B | C |
| ATOM | 2874 | ND1 | HIS | B | 175 | 29.320 | 23.455 | 35.853 | 1.00 | 43.53 | B | N |
| ATOM | 2875 | CE1 | HIS | B | 175 | 28.370 | 24.241 | 35.377 | 1.00 | 41.82 | B | C |
| ATOM | 2876 | NE2 | HIS | B | 175 | 28.942 | 25.220 | 34.700 | 1.00 | 37.89 | B | N |
| ATOM | 2877 | C | HIS | B | 175 | 32.845 | 24.801 | 37.523 | 1.00 | 48.59 | B | C |
| ATOM | 2878 | O | HIS | B | 175 | 33.521 | 25.352 | 36.661 | 1.00 | 49.15 | B | O |
| ATOM | 2879 | N | GLY | B | 176 | 32.577 | 25.357 | 38.702 | 1.00 | 51.45 | B | N |
| ATOM | 2880 | CA | GLY | B | 176 | 33.286 | 26.542 | 39.155 | 1.00 | 49.63 | B | C |
| ATOM | 2881 | C | GLY | B | 176 | 32.624 | 27.886 | 38.940 | 1.00 | 50.18 | B | C |
| ATOM | 2882 | O | GLY | B | 176 | 33.298 | 28.919 | 39.029 | 1.00 | 51.50 | B | O |
| ATOM | 2883 | N | ASP | B | 177 | 31.320 | 27.887 | 38.653 | 1.00 | 52.35 | B | N |
| ATOM | 2884 | CA | ASP | B | 177 | 30.550 | 29.139 | 38.585 | 1.00 | 47.14 | B | C |
| ATOM | 2885 | CB | ASP | B | 177 | 30.149 | 29.496 | 37.151 | 1.00 | 43.40 | B | C |
| ATOM | 2886 | CG | ASP | B | 177 | 29.155 | 28.522 | 36.553 | 1.00 | 43.27 | B | C |
| ATOM | 2887 | OD1 | ASP | B | 177 | 28.780 | 27.540 | 37.238 | 1.00 | 40.59 | B | O |
| ATOM | 2888 | OD2 | ASP | B | 177 | 28.773 | 28.746 | 35.380 | 1.00 | 37.09 | B | O |
| ATOM | 2889 | C | ASP | B | 177 | 29.310 | 29.152 | 39.463 | 1.00 | 51.31 | B | C |
| ATOM | 2890 | O | ASP | B | 177 | 28.497 | 30.073 | 39.377 | 1.00 | 50.90 | B | O |
| ATOM | 2891 | N | GLY | B | 178 | 29.160 | 28.137 | 40.303 | 1.00 | 50.16 | B | N |
| ATOM | 2892 | CA | GLY | B | 178 | 28.044 | 28.102 | 41.225 | 1.00 | 50.32 | B | C |
| ATOM | 2893 | C | GLY | B | 178 | 26.692 | 28.045 | 40.540 | 1.00 | 55.05 | B | C |
| ATOM | 2894 | O | GLY | B | 178 | 25.672 | 28.442 | 41.116 | 1.00 | 56.87 | B | O |
| ATOM | 2895 | N | TYR | B | 179 | 26.683 | 27.571 | 39.300 | 1.00 | 47.19 | B | N |
| ATOM | 2896 | CA | TYR | B | 179 | 25.444 | 27.233 | 38.636 | 1.00 | 42.38 | B | C |
| ATOM | 2897 | CB | TYR | B | 179 | 25.163 | 28.190 | 37.497 | 1.00 | 44.49 | B | C |
| ATOM | 2898 | CG | TYR | B | 179 | 24.949 | 29.629 | 37.912 | 1.00 | 49.32 | B | C |
| ATOM | 2899 | CD1 | TYR | B | 179 | 26.024 | 30.469 | 38.140 | 1.00 | 52.07 | B | C |
| ATOM | 2900 | CE1 | TYR | B | 179 | 25.837 | 31.796 | 38.500 | 1.00 | 52.63 | B | C |
| ATOM | 2901 | CD2 | TYR | B | 179 | 23.672 | 30.159 | 38.033 | 1.00 | 51.27 | B | C |
| ATOM | 2902 | CE2 | TYR | B | 179 | 23.473 | 31.490 | 38.396 | 1.00 | 52.62 | B | C |
| ATOM | 2903 | CZ | TYR | B | 179 | 24.564 | 32.305 | 38.628 | 1.00 | 51.35 | B | C |
| ATOM | 2904 | OH | TYR | B | 179 | 24.395 | 33.631 | 38.985 | 1.00 | 52.11 | B | O |
| ATOM | 2905 | C | TYR | B | 179 | 25.586 | 25.820 | 38.113 | 1.00 | 44.27 | B | C |
| ATOM | 2906 | O | TYR | B | 179 | 25.620 | 25.591 | 36.914 | 1.00 | 44.14 | B | O |
| ATOM | 2907 | N | PRO | B | 180 | 25.671 | 24.860 | 39.030 | 1.00 | 48.54 | B | N |
| ATOM | 2908 | CD | PRO | B | 180 | 25.399 | 25.091 | 40.462 | 1.00 | 45.44 | B | C |
| ATOM | 2909 | CA | PRO | B | 180 | 25.988 | 23.461 | 38.729 | 1.00 | 46.01 | B | C |
| ATOM | 2910 | CB | PRO | B | 180 | 25.725 | 22.757 | 40.066 | 1.00 | 48.44 | B | C |
| ATOM | 2911 | CG | PRO | B | 180 | 25.862 | 23.829 | 41.106 | 1.00 | 47.77 | B | C |
| ATOM | 2912 | C | PRO | B | 180 | 25.110 | 22.843 | 37.637 | 1.00 | 48.67 | B | C |
| ATOM | 2913 | O | PRO | B | 180 | 23.923 | 23.167 | 37.564 | 1.00 | 52.52 | B | O |
| ATOM | 2914 | N | PHE | B | 181 | 25.677 | 21.970 | 36.802 | 1.00 | 42.24 | B | N |
| ATOM | 2915 | CA | PHE | B | 181 | 24.857 | 21.140 | 35.918 | 1.00 | 42.54 | B | C |
| ATOM | 2916 | C | PHE | B | 181 | 24.301 | 19.944 | 36.689 | 1.00 | 45.49 | B | C |
| ATOM | 2917 | CB | PHE | B | 181 | 25.641 | 20.652 | 34.703 | 1.00 | 43.26 | B | C |
| ATOM | 2918 | CG | PHE | B | 181 | 26.056 | 21.754 | 33.757 | 1.00 | 45.88 | B | C |
| ATOM | 2919 | CD1 | PHE | B | 181 | 25.114 | 22.630 | 33.234 | 1.00 | 43.60 | B | C |
| ATOM | 2920 | CD2 | PHE | B | 181 | 27.391 | 21.901 | 33.380 | 1.00 | 42.30 | B | C |
| ATOM | 2921 | CE1 | PHE | B | 181 | 25.493 | 23.651 | 32.359 | 1.00 | 43.75 | B | C |
| ATOM | 2922 | CE2 | PHE | B | 181 | 27.780 | 22.914 | 32.506 | 1.00 | 40.86 | B | C |

TABLE 12-continued

Coordinates for pro MMP9(35-444 ΔFnII) (SEQ ID NO: 12) complex with Example 2

| | | | | | | | | | | |
|---|---|---|---|---|---|---|---|---|---|---|
| ATOM | 2923 | CZ | PHE | B | 181 | 26.831 | 23.790 | 31.993 | 1.00 | 42.98 B C |
| ATOM | 2924 | O | PHE | B | 181 | 24.555 | 19.796 | 37.884 | 1.00 | 46.37 B O |
| ATOM | 2925 | N | ASP | B | 182 | 23.574 | 19.078 | 35.988 | 1.00 | 46.91 B N |
| ATOM | 2926 | CA | ASP | B | 182 | 22.711 | 18.091 | 36.637 | 1.00 | 45.91 B C |
| ATOM | 2927 | CB | ASP | B | 182 | 21.260 | 18.581 | 36.575 | 1.00 | 45.38 B C |
| ATOM | 2928 | CG | ASP | B | 182 | 20.749 | 18.667 | 35.152 | 1.00 | 44.42 B C |
| ATOM | 2929 | OD1 | ASP | B | 182 | 21.598 | 18.820 | 34.265 | 1.00 | 49.75 B O |
| ATOM | 2930 | OD2 | ASP | B | 182 | 19.527 | 18.587 | 34.904 | 1.00 | 49.13 B O |
| ATOM | 2931 | C | ASP | B | 182 | 22.746 | 16.711 | 35.999 | 1.00 | 48.78 B C |
| ATOM | 2932 | O | ASP | B | 182 | 21.694 | 16.094 | 35.821 | 1.00 | 50.00 B O |
| ATOM | 2933 | N | GLY | B | 183 | 23.927 | 16.224 | 35.635 | 1.00 | 43.04 B N |
| ATOM | 2934 | CA | GLY | B | 183 | 24.036 | 14.888 | 35.071 | 1.00 | 43.30 B C |
| ATOM | 2935 | C | GLY | B | 183 | 23.263 | 14.737 | 33.778 | 1.00 | 42.37 B C |
| ATOM | 2936 | O | GLY | B | 183 | 22.953 | 15.731 | 33.139 | 1.00 | 41.54 B O |
| ATOM | 2937 | N | LYS | B | 184 | 22.932 | 13.504 | 33.399 | 1.00 | 41.17 B N |
| ATOM | 2938 | CA | LYS | B | 184 | 22.303 | 13.259 | 32.098 | 1.00 | 42.93 B C |
| ATOM | 2939 | CB | LYS | B | 184 | 22.133 | 11.753 | 31.817 | 1.00 | 41.28 B C |
| ATOM | 2940 | CG | LYS | B | 184 | 21.253 | 11.453 | 30.586 | 1.00 | 51.91 B C |
| ATOM | 2941 | CD | LYS | B | 184 | 21.660 | 10.175 | 29.813 | 1.00 | 53.07 B C |
| ATOM | 2942 | CE | LYS | B | 184 | 21.712 | 8.940 | 30.709 | 1.00 | 54.49 B C |
| ATOM | 2943 | NZ | LYS | B | 184 | 22.066 | 7.685 | 29.958 | 1.00 | 55.79 B N |
| ATOM | 2944 | C | LYS | B | 184 | 20.975 | 13.987 | 31.935 | 1.00 | 45.56 B C |
| ATOM | 2945 | O | LYS | B | 184 | 20.243 | 14.176 | 32.903 | 1.00 | 47.59 B O |
| ATOM | 2946 | N | ASP | B | 185 | 20.681 | 14.395 | 30.704 | 1.00 | 41.73 B N |
| ATOM | 2947 | CA | ASP | B | 185 | 19.447 | 15.111 | 30.379 | 1.00 | 44.67 B C |
| ATOM | 2948 | CB | ASP | B | 185 | 18.273 | 14.134 | 30.383 | 1.00 | 42.84 B C |
| ATOM | 2949 | CG | ASP | B | 185 | 18.481 | 12.999 | 29.406 | 1.00 | 53.23 B C |
| ATOM | 2950 | OD1 | ASP | B | 185 | 19.340 | 13.158 | 28.503 | 1.00 | 47.75 B O |
| ATOM | 2951 | OD2 | ASP | B | 185 | 17.808 | 11.952 | 29.538 | 1.00 | 53.77 B O |
| ATOM | 2952 | C | ASP | B | 185 | 19.175 | 16.335 | 31.268 | 1.00 | 41.45 B C |
| ATOM | 2953 | O | ASP | B | 185 | 20.021 | 16.756 | 32.045 | 1.00 | 42.42 B O |
| ATOM | 2954 | N | GLY | B | 186 | 17.990 | 16.914 | 31.144 | 1.00 | 42.46 B N |
| ATOM | 2955 | CA | GLY | B | 186 | 17.666 | 18.111 | 31.902 | 1.00 | 42.84 B C |
| ATOM | 2956 | C | GLY | B | 186 | 18.273 | 19.360 | 31.282 | 1.00 | 41.30 B C |
| ATOM | 2957 | O | GLY | B | 186 | 18.042 | 19.652 | 30.108 | 1.00 | 40.00 B O |
| ATOM | 2958 | N | LEU | B | 187 | 19.036 | 20.103 | 32.078 | 1.00 | 41.00 B N |
| ATOM | 2959 | CA | LEU | B | 187 | 19.799 | 21.233 | 31.574 | 1.00 | 40.83 B C |
| ATOM | 2960 | CB | LEU | B | 187 | 20.457 | 21.995 | 32.721 | 1.00 | 41.33 B C |
| ATOM | 2961 | CG | LEU | B | 187 | 19.595 | 22.570 | 33.835 | 1.00 | 47.32 B C |
| ATOM | 2962 | CD1 | LEU | B | 187 | 18.987 | 21.451 | 34.647 | 1.00 | 42.96 B C |
| ATOM | 2963 | CD2 | LEU | B | 187 | 20.452 | 23.475 | 34.723 | 1.00 | 46.90 B C |
| ATOM | 2964 | C | LEU | B | 187 | 20.903 | 20.706 | 30.661 | 1.00 | 41.47 B C |
| ATOM | 2965 | O | LEU | B | 187 | 21.597 | 19.771 | 31.010 | 1.00 | 42.18 B O |
| ATOM | 2966 | N | LEU | B | 188 | 21.072 | 21.303 | 29.493 | 1.00 | 34.96 B N |
| ATOM | 2967 | CA | LEU | B | 188 | 22.124 | 20.867 | 28.589 | 1.00 | 34.14 B C |
| ATOM | 2968 | CB | LEU | B | 188 | 21.597 | 20.849 | 27.174 | 1.00 | 34.39 B C |
| ATOM | 2969 | CG | LEU | B | 188 | 20.481 | 19.826 | 27.034 | 1.00 | 36.61 B C |
| ATOM | 2970 | CD1 | LEU | B | 188 | 19.993 | 19.749 | 25.590 | 1.00 | 25.87 B C |
| ATOM | 2971 | CD2 | LEU | B | 188 | 20.972 | 18.481 | 27.562 | 1.00 | 34.33 B C |
| ATOM | 2972 | C | LEU | B | 188 | 23.377 | 21.739 | 28.660 | 1.00 | 37.74 B C |
| ATOM | 2973 | O | LEU | B | 188 | 24.502 | 21.221 | 28.574 | 1.00 | 42.51 B O |
| ATOM | 2974 | N | ALA | B | 189 | 23.173 | 23.047 | 28.814 | 1.00 | 28.57 B N |
| ATOM | 2975 | CA | ALA | B | 189 | 24.244 | 24.019 | 28.886 | 1.00 | 34.98 B C |
| ATOM | 2976 | CB | ALA | B | 189 | 24.861 | 24.178 | 27.499 | 1.00 | 33.52 B C |
| ATOM | 2977 | C | ALA | B | 189 | 23.662 | 25.352 | 29.344 | 1.00 | 35.36 B C |
| ATOM | 2978 | O | ALA | B | 189 | 22.458 | 25.490 | 29.425 | 1.00 | 32.68 B O |
| ATOM | 2979 | N | HIS | B | 190 | 24.511 | 26.340 | 29.613 | 1.00 | 34.99 B N |
| ATOM | 2980 | CA | HIS | B | 190 | 24.052 | 27.720 | 29.782 | 1.00 | 35.10 B C |
| ATOM | 2981 | CB | HIS | B | 190 | 23.672 | 27.993 | 31.239 | 1.00 | 39.22 B C |
| ATOM | 2982 | CG | HIS | B | 190 | 24.739 | 27.639 | 32.224 | 1.00 | 39.62 B C |
| ATOM | 2983 | CD2 | HIS | B | 190 | 25.894 | 28.266 | 32.550 | 1.00 | 42.64 B C |
| ATOM | 2984 | ND1 | HIS | B | 190 | 24.675 | 26.520 | 33.024 | 1.00 | 44.16 B N |
| ATOM | 2985 | CE1 | HIS | B | 190 | 25.748 | 26.467 | 33.794 | 1.00 | 40.97 B C |
| ATOM | 2986 | NE2 | HIS | B | 190 | 26.504 | 27.512 | 33.521 | 1.00 | 38.34 B N |
| ATOM | 2987 | C | HIS | B | 190 | 25.096 | 28.737 | 29.310 | 1.00 | 37.47 B C |
| ATOM | 2988 | O | HIS | B | 190 | 26.249 | 28.390 | 29.111 | 1.00 | 41.54 B O |
| ATOM | 2989 | N | ALA | B | 191 | 24.685 | 29.987 | 29.140 | 1.00 | 33.77 B N |
| ATOM | 2990 | CA | ALA | B | 191 | 25.578 | 31.068 | 28.731 | 1.00 | 36.92 B C |
| ATOM | 2991 | CB | ALA | B | 191 | 25.452 | 31.331 | 27.240 | 1.00 | 31.78 B C |
| ATOM | 2992 | C | ALA | B | 191 | 25.216 | 32.329 | 29.501 | 1.00 | 42.41 B C |
| ATOM | 2993 | O | ALA | B | 191 | 24.136 | 32.408 | 30.077 | 1.00 | 33.21 B O |
| ATOM | 2994 | N | PHE | B | 192 | 26.112 | 33.312 | 29.480 | 1.00 | 33.88 B N |
| ATOM | 2995 | CA | PHE | B | 192 | 25.912 | 34.565 | 30.186 | 1.00 | 36.62 B C |
| ATOM | 2996 | CB | PHE | B | 192 | 26.979 | 34.708 | 31.256 | 1.00 | 34.58 B C |
| ATOM | 2997 | CG | PHE | B | 192 | 27.083 | 33.515 | 32.129 | 1.00 | 37.95 B C |
| ATOM | 2998 | CD1 | PHE | B | 192 | 26.493 | 33.507 | 33.392 | 1.00 | 40.25 B C |
| ATOM | 2999 | CD2 | PHE | B | 192 | 27.712 | 32.371 | 31.678 | 1.00 | 36.45 B C |

TABLE 12-continued

Coordinates for pro MMP9(35-444 ΔFnII) (SEQ ID NO: 12) complex with Example 2

| ATOM | 3000 | CE1 | PHE | B | 192 | 26.565 | 32.382 | 34.203 | 1.00 | 42.49 | B | C |
|---|---|---|---|---|---|---|---|---|---|---|---|---|
| ATOM | 3001 | CE2 | PHE | B | 192 | 27.792 | 31.250 | 32.481 | 1.00 | 38.85 | B | C |
| ATOM | 3002 | CZ | PHE | B | 192 | 27.225 | 31.253 | 33.746 | 1.00 | 40.62 | B | C |
| ATOM | 3003 | C | PHE | B | 192 | 25.947 | 35.753 | 29.237 | 1.00 | 37.12 | B | C |
| ATOM | 3004 | O | PHE | B | 192 | 26.662 | 35.738 | 28.252 | 1.00 | 38.76 | B | O |
| ATOM | 3005 | N | PRO | B | 193 | 25.177 | 36.800 | 29.543 | 1.00 | 41.07 | B | N |
| ATOM | 3006 | CD | PRO | B | 193 | 24.538 | 37.049 | 30.839 | 1.00 | 39.75 | B | C |
| ATOM | 3007 | CA | PRO | B | 193 | 25.047 | 37.953 | 28.652 | 1.00 | 40.07 | B | C |
| ATOM | 3008 | CB | PRO | B | 193 | 24.021 | 38.841 | 29.375 | 1.00 | 40.84 | B | C |
| ATOM | 3009 | CG | PRO | B | 193 | 23.484 | 38.012 | 30.470 | 1.00 | 42.48 | B | C |
| ATOM | 3010 | C | PRO | B | 193 | 26.365 | 38.707 | 28.538 | 1.00 | 35.24 | B | C |
| ATOM | 3011 | O | PRO | B | 193 | 27.202 | 38.590 | 29.428 | 1.00 | 31.73 | B | O |
| ATOM | 3012 | N | PRO | B | 194 | 26.527 | 39.484 | 27.461 | 1.00 | 33.02 | B | N |
| ATOM | 3013 | CD | PRO | B | 194 | 25.529 | 39.630 | 26.389 | 1.00 | 32.41 | B | C |
| ATOM | 3014 | CA | PRO | B | 194 | 27.748 | 40.239 | 27.176 | 1.00 | 33.35 | B | C |
| ATOM | 3015 | CB | PRO | B | 194 | 27.321 | 41.182 | 26.037 | 1.00 | 32.05 | B | C |
| ATOM | 3016 | CG | PRO | B | 194 | 26.262 | 40.445 | 25.319 | 1.00 | 31.10 | B | C |
| ATOM | 3017 | C | PRO | B | 194 | 28.185 | 41.054 | 28.368 | 1.00 | 37.65 | B | C |
| ATOM | 3018 | O | PRO | B | 194 | 27.358 | 41.591 | 29.096 | 1.00 | 37.17 | B | O |
| ATOM | 3019 | N | GLY | B | 195 | 29.492 | 41.149 | 28.561 | 1.00 | 34.70 | B | N |
| ATOM | 3020 | CA | GLY | B | 195 | 30.031 | 42.008 | 29.593 | 1.00 | 41.16 | B | C |
| ATOM | 3021 | C | GLY | B | 195 | 31.357 | 41.466 | 30.087 | 1.00 | 42.46 | B | C |
| ATOM | 3022 | O | GLY | B | 195 | 31.996 | 40.650 | 29.424 | 1.00 | 43.29 | B | O |
| ATOM | 3023 | N | PRO | B | 196 | 31.768 | 41.899 | 31.272 | 1.00 | 42.13 | B | N |
| ATOM | 3024 | CD | PRO | B | 196 | 31.010 | 42.804 | 32.148 | 1.00 | 47.27 | B | C |
| ATOM | 3025 | CA | PRO | B | 196 | 33.068 | 41.538 | 31.834 | 1.00 | 39.61 | B | C |
| ATOM | 3026 | CB | PRO | B | 196 | 33.280 | 42.593 | 32.926 | 1.00 | 47.06 | B | C |
| ATOM | 3027 | CG | PRO | B | 196 | 32.089 | 43.537 | 32.843 | 1.00 | 47.56 | B | C |
| ATOM | 3028 | C | PRO | B | 196 | 33.049 | 40.165 | 32.487 | 1.00 | 44.19 | B | C |
| ATOM | 3029 | O | PRO | B | 196 | 31.984 | 39.620 | 32.805 | 1.00 | 45.41 | B | O |
| ATOM | 3030 | N | GLY | B | 197 | 34.241 | 39.619 | 32.689 | 1.00 | 45.98 | B | N |
| ATOM | 3031 | CA | GLY | B | 197 | 34.420 | 38.425 | 33.490 | 1.00 | 42.22 | B | C |
| ATOM | 3032 | C | GLY | B | 197 | 33.757 | 37.220 | 32.880 | 1.00 | 39.45 | B | C |
| ATOM | 3033 | O | GLY | B | 197 | 33.944 | 36.934 | 31.719 | 1.00 | 39.75 | B | O |
| ATOM | 3034 | N | ILE | B | 198 | 32.978 | 36.511 | 33.678 | 1.00 | 38.61 | B | N |
| ATOM | 3035 | CA | ILE | B | 198 | 32.254 | 35.355 | 33.194 | 1.00 | 40.78 | B | C |
| ATOM | 3036 | CB | ILE | B | 198 | 31.513 | 34.687 | 34.353 | 1.00 | 43.65 | B | C |
| ATOM | 3037 | CG2 | ILE | B | 198 | 30.187 | 35.421 | 34.639 | 1.00 | 36.35 | B | C |
| ATOM | 3038 | CG1 | ILE | B | 198 | 31.262 | 33.212 | 34.051 | 1.00 | 46.65 | B | C |
| ATOM | 3039 | CD1 | ILE | B | 198 | 30.392 | 32.540 | 35.100 | 1.00 | 37.85 | B | C |
| ATOM | 3040 | C | ILE | B | 198 | 31.223 | 35.763 | 32.136 | 1.00 | 38.67 | B | C |
| ATOM | 3041 | O | ILE | B | 198 | 30.701 | 34.930 | 31.391 | 1.00 | 36.53 | B | O |
| ATOM | 3042 | N | GLN | B | 199 | 30.913 | 37.050 | 32.079 | 1.00 | 36.92 | B | N |
| ATOM | 3043 | CA | GLN | B | 199 | 29.867 | 37.478 | 31.175 | 1.00 | 37.29 | B | C |
| ATOM | 3044 | CB | GLN | B | 199 | 29.408 | 38.905 | 31.502 | 1.00 | 39.10 | B | C |
| ATOM | 3045 | CG | GLN | B | 199 | 28.591 | 38.915 | 32.799 | 1.00 | 34.92 | B | C |
| ATOM | 3046 | CD | GLN | B | 199 | 28.220 | 40.301 | 33.318 | 1.00 | 44.31 | B | C |
| ATOM | 3047 | OE1 | GLN | B | 199 | 27.630 | 41.131 | 32.608 | 1.00 | 45.51 | B | O |
| ATOM | 3048 | NE2 | GLN | B | 199 | 28.520 | 40.538 | 34.592 | 1.00 | 42.78 | B | N |
| ATOM | 3049 | C | GLN | B | 199 | 30.302 | 37.278 | 29.733 | 1.00 | 38.45 | B | C |
| ATOM | 3050 | O | GLN | B | 199 | 31.410 | 37.642 | 29.367 | 1.00 | 39.31 | B | O |
| ATOM | 3051 | N | GLY | B | 200 | 29.430 | 36.670 | 28.934 | 1.00 | 31.44 | B | N |
| ATOM | 3052 | CA | GLY | B | 200 | 29.751 | 36.292 | 27.574 | 1.00 | 32.42 | B | C |
| ATOM | 3053 | C | GLY | B | 200 | 30.086 | 34.819 | 27.374 | 1.00 | 33.22 | B | C |
| ATOM | 3054 | O | GLY | B | 200 | 29.985 | 34.297 | 26.268 | 1.00 | 35.53 | B | O |
| ATOM | 3055 | N | ASP | B | 201 | 30.485 | 34.133 | 28.437 | 1.00 | 35.18 | B | N |
| ATOM | 3056 | CA | ASP | B | 201 | 30.908 | 32.740 | 28.306 | 1.00 | 33.99 | B | C |
| ATOM | 3057 | CB | ASP | B | 201 | 31.666 | 32.302 | 29.548 | 1.00 | 35.20 | B | C |
| ATOM | 3058 | CG | ASP | B | 201 | 32.805 | 33.219 | 29.874 | 1.00 | 38.12 | B | C |
| ATOM | 3059 | OD1 | ASP | B | 201 | 33.031 | 34.185 | 29.113 | 1.00 | 35.69 | B | O |
| ATOM | 3060 | OD2 | ASP | B | 201 | 33.468 | 32.976 | 30.901 | 1.00 | 38.63 | B | O |
| ATOM | 3061 | C | ASP | B | 201 | 29.766 | 31.766 | 28.048 | 1.00 | 37.51 | B | C |
| ATOM | 3062 | O | ASP | B | 201 | 28.589 | 32.091 | 28.265 | 1.00 | 39.30 | B | O |
| ATOM | 3063 | N | ALA | B | 202 | 30.126 | 30.569 | 27.596 | 1.00 | 34.77 | B | N |
| ATOM | 3064 | CA | ALA | B | 202 | 29.177 | 29.494 | 27.301 | 1.00 | 26.22 | B | C |
| ATOM | 3065 | CB | ALA | B | 202 | 28.957 | 29.382 | 25.824 | 1.00 | 31.45 | B | C |
| ATOM | 3066 | C | ALA | B | 202 | 29.745 | 28.202 | 27.837 | 1.00 | 38.74 | B | C |
| ATOM | 3067 | O | ALA | B | 202 | 30.921 | 27.899 | 27.630 | 1.00 | 42.37 | B | O |
| ATOM | 3068 | N | HIS | B | 203 | 28.919 | 27.436 | 28.534 | 1.00 | 33.06 | B | N |
| ATOM | 3069 | CA | HIS | B | 203 | 29.345 | 26.190 | 29.151 | 1.00 | 33.01 | B | C |
| ATOM | 3070 | CB | HIS | B | 203 | 29.311 | 26.342 | 30.681 | 1.00 | 36.46 | B | C |
| ATOM | 3071 | CG | HIS | B | 203 | 30.163 | 27.466 | 31.181 | 1.00 | 34.12 | B | C |
| ATOM | 3072 | CD2 | HIS | B | 203 | 30.691 | 28.533 | 30.537 | 1.00 | 37.81 | B | C |
| ATOM | 3073 | ND1 | HIS | B | 203 | 30.601 | 27.555 | 32.483 | 1.00 | 38.52 | B | N |
| ATOM | 3074 | CE1 | HIS | B | 203 | 31.339 | 28.641 | 32.629 | 1.00 | 33.78 | B | C |
| ATOM | 3075 | NE2 | HIS | B | 203 | 31.413 | 29.249 | 31.460 | 1.00 | 32.52 | B | N |
| ATOM | 3076 | C | HIS | B | 203 | 28.442 | 25.054 | 28.676 | 1.00 | 36.26 | B | C |

TABLE 12-continued

Coordinates for pro MMP9(35-444 ΔFnII) (SEQ ID NO: 12) complex with Example 2

| ATOM | 3077 | O   | HIS | B | 203 | 27.268 | 25.282 | 28.325 | 1.00 | 34.09 | B | O |
|------|------|-----|-----|---|-----|--------|--------|--------|------|-------|---|---|
| ATOM | 3078 | N   | PHE | B | 204 | 28.980 | 23.840 | 28.656 | 1.00 | 27.51 | B | N |
| ATOM | 3079 | CA  | PHE | B | 204 | 28.246 | 22.704 | 28.131 | 1.00 | 30.16 | B | C |
| ATOM | 3080 | CB  | PHE | B | 204 | 28.752 | 22.319 | 26.740 | 1.00 | 34.46 | B | C |
| ATOM | 3081 | CG  | PHE | B | 204 | 28.611 | 23.416 | 25.731 | 1.00 | 34.96 | B | C |
| ATOM | 3082 | CD1 | PHE | B | 204 | 29.542 | 24.439 | 25.670 | 1.00 | 29.64 | B | C |
| ATOM | 3083 | CD2 | PHE | B | 204 | 27.534 | 23.442 | 24.861 | 1.00 | 28.33 | B | C |
| ATOM | 3084 | CE1 | PHE | B | 204 | 29.405 | 25.464 | 24.758 | 1.00 | 27.71 | B | C |
| ATOM | 3085 | CE2 | PHE | B | 204 | 27.392 | 24.474 | 23.948 | 1.00 | 28.25 | B | C |
| ATOM | 3086 | CZ  | PHE | B | 204 | 28.334 | 25.491 | 23.910 | 1.00 | 24.48 | B | C |
| ATOM | 3087 | C   | PHE | B | 204 | 28.400 | 21.545 | 29.094 | 1.00 | 37.56 | B | C |
| ATOM | 3088 | O   | PHE | B | 204 | 29.490 | 21.310 | 29.613 | 1.00 | 40.20 | B | O |
| ATOM | 3089 | N   | ASP | B | 205 | 27.307 | 20.822 | 29.329 | 1.00 | 34.11 | B | N |
| ATOM | 3090 | CA  | ASP | B | 205 | 27.298 | 19.746 | 30.310 | 1.00 | 37.49 | B | C |
| ATOM | 3091 | CB  | ASP | B | 205 | 25.860 | 19.484 | 30.784 | 1.00 | 39.62 | B | C |
| ATOM | 3092 | CG  | ASP | B | 205 | 25.802 | 18.579 | 32.016 | 1.00 | 45.97 | B | C |
| ATOM | 3093 | OD1 | ASP | B | 205 | 26.819 | 17.938 | 32.376 | 1.00 | 40.17 | B | O |
| ATOM | 3094 | OD2 | ASP | B | 205 | 24.726 | 18.519 | 32.643 | 1.00 | 44.26 | B | O |
| ATOM | 3095 | C   | ASP | B | 205 | 27.865 | 18.484 | 29.694 | 1.00 | 33.20 | B | C |
| ATOM | 3096 | O   | ASP | B | 205 | 27.275 | 17.914 | 28.792 | 1.00 | 34.42 | B | O |
| ATOM | 3097 | N   | ASP | B | 206 | 29.008 | 18.036 | 30.188 | 1.00 | 38.02 | B | N |
| ATOM | 3098 | CA  | ASP | B | 206 | 29.715 | 16.950 | 29.515 | 1.00 | 39.83 | B | C |
| ATOM | 3099 | CB  | ASP | B | 206 | 31.211 | 17.002 | 29.826 | 1.00 | 41.15 | B | C |
| ATOM | 3100 | CG  | ASP | B | 206 | 32.074 | 16.492 | 28.674 | 1.00 | 40.58 | B | C |
| ATOM | 3101 | OD1 | ASP | B | 206 | 31.515 | 16.015 | 27.654 | 1.00 | 38.67 | B | O |
| ATOM | 3102 | OD2 | ASP | B | 206 | 33.319 | 16.572 | 28.807 | 1.00 | 39.98 | B | O |
| ATOM | 3103 | C   | ASP | B | 206 | 29.111 | 15.622 | 29.929 | 1.00 | 43.00 | B | C |
| ATOM | 3104 | O   | ASP | B | 206 | 29.428 | 14.570 | 29.370 | 1.00 | 45.91 | B | O |
| ATOM | 3105 | N   | ASP | B | 207 | 28.231 | 15.692 | 30.923 | 1.00 | 46.26 | B | N |
| ATOM | 3106 | CA  | ASP | B | 207 | 27.409 | 14.560 | 31.325 | 1.00 | 45.80 | B | C |
| ATOM | 3107 | CB  | ASP | B | 207 | 26.651 | 14.882 | 32.616 | 1.00 | 41.52 | B | C |
| ATOM | 3108 | CG  | ASP | B | 207 | 27.472 | 14.576 | 33.850 | 1.00 | 45.84 | B | C |
| ATOM | 3109 | OD1 | ASP | B | 207 | 28.160 | 13.528 | 33.841 | 1.00 | 47.58 | B | O |
| ATOM | 3110 | OD2 | ASP | B | 207 | 27.446 | 15.376 | 34.817 | 1.00 | 47.58 | B | O |
| ATOM | 3111 | C   | ASP | B | 207 | 26.471 | 14.151 | 30.191 | 1.00 | 38.49 | B | C |
| ATOM | 3112 | O   | ASP | B | 207 | 26.070 | 12.995 | 30.092 | 1.00 | 32.42 | B | O |
| ATOM | 3113 | N   | GLU | B | 208 | 26.147 | 15.099 | 29.318 | 1.00 | 36.13 | B | N |
| ATOM | 3114 | CA  | GLU | B | 208 | 25.439 | 14.773 | 28.090 | 1.00 | 36.42 | B | C |
| ATOM | 3115 | CB  | GLU | B | 208 | 24.850 | 16.038 | 27.461 | 1.00 | 37.00 | B | C |
| ATOM | 3116 | CG  | GLU | B | 208 | 23.924 | 16.800 | 28.371 | 1.00 | 39.43 | B | C |
| ATOM | 3117 | CD  | GLU | B | 208 | 22.985 | 15.880 | 29.121 | 1.00 | 39.41 | B | C |
| ATOM | 3118 | OE1 | GLU | B | 208 | 22.556 | 14.830 | 28.587 | 1.00 | 38.21 | B | O |
| ATOM | 3119 | OE2 | GLU | B | 208 | 22.692 | 16.200 | 30.270 | 1.00 | 42.04 | B | O |
| ATOM | 3120 | C   | GLU | B | 208 | 26.382 | 14.101 | 27.078 | 1.00 | 39.69 | B | C |
| ATOM | 3121 | O   | GLU | B | 208 | 27.585 | 14.336 | 27.090 | 1.00 | 42.35 | B | O |
| ATOM | 3122 | N   | LEU | B | 209 | 25.818 | 13.276 | 26.206 | 1.00 | 41.72 | B | N |
| ATOM | 3123 | CA  | LEU | B | 209 | 26.534 | 12.742 | 25.063 | 1.00 | 44.33 | B | C |
| ATOM | 3124 | CB  | LEU | B | 209 | 25.969 | 11.393 | 24.632 | 1.00 | 43.52 | B | C |
| ATOM | 3125 | CG  | LEU | B | 209 | 26.387 | 10.963 | 23.221 | 1.00 | 41.71 | B | C |
| ATOM | 3126 | CD1 | LEU | B | 209 | 27.884 | 10.602 | 23.164 | 1.00 | 43.79 | B | C |
| ATOM | 3127 | CD2 | LEU | B | 209 | 25.540 | 9.806  | 22.746 | 1.00 | 45.11 | B | C |
| ATOM | 3128 | C   | LEU | B | 209 | 26.425 | 13.713 | 23.897 | 1.00 | 45.40 | B | C |
| ATOM | 3129 | O   | LEU | B | 209 | 25.339 | 13.904 | 23.328 | 1.00 | 46.63 | B | O |
| ATOM | 3130 | N   | TRP | B | 210 | 27.559 | 14.310 | 23.540 | 1.00 | 38.00 | B | N |
| ATOM | 3131 | CA  | TRP | B | 210 | 27.586 | 15.372 | 22.551 | 1.00 | 38.65 | B | C |
| ATOM | 3132 | CB  | TRP | B | 210 | 28.549 | 16.456 | 23.008 | 1.00 | 36.01 | B | C |
| ATOM | 3133 | CG  | TRP | B | 210 | 27.948 | 17.363 | 24.051 | 1.00 | 35.06 | B | C |
| ATOM | 3134 | CD2 | TRP | B | 210 | 26.845 | 18.253 | 23.864 | 1.00 | 33.87 | B | C |
| ATOM | 3135 | CE2 | TRP | B | 210 | 26.618 | 18.902 | 25.093 | 1.00 | 35.01 | B | C |
| ATOM | 3136 | CE3 | TRP | B | 210 | 26.026 | 18.566 | 22.773 | 1.00 | 33.99 | B | C |
| ATOM | 3137 | CD1 | TRP | B | 210 | 28.331 | 17.496 | 25.361 | 1.00 | 36.44 | B | C |
| ATOM | 3138 | NE1 | TRP | B | 210 | 27.539 | 18.426 | 25.992 | 1.00 | 34.15 | B | N |
| ATOM | 3139 | CZ2 | TRP | B | 210 | 25.607 | 19.842 | 25.257 | 1.00 | 33.41 | B | C |
| ATOM | 3140 | CZ3 | TRP | B | 210 | 25.030 | 19.505 | 22.935 | 1.00 | 32.07 | B | C |
| ATOM | 3141 | CH2 | TRP | B | 210 | 24.828 | 20.130 | 24.170 | 1.00 | 32.94 | B | C |
| ATOM | 3142 | C   | TRP | B | 210 | 27.969 | 14.832 | 21.176 | 1.00 | 40.52 | B | C |
| ATOM | 3143 | O   | TRP | B | 210 | 29.028 | 14.221 | 21.011 | 1.00 | 40.95 | B | O |
| ATOM | 3144 | N   | SER | B | 211 | 27.087 | 15.033 | 20.202 | 1.00 | 35.72 | B | N |
| ATOM | 3145 | CA  | SER | B | 211 | 27.306 | 14.522 | 18.859 | 1.00 | 41.69 | B | C |
| ATOM | 3146 | CB  | SER | B | 211 | 26.590 | 13.180 | 18.671 | 1.00 | 44.90 | B | C |
| ATOM | 3147 | OG  | SER | B | 211 | 25.185 | 13.349 | 18.615 | 1.00 | 49.12 | B | O |
| ATOM | 3148 | C   | SER | B | 211 | 26.826 | 15.558 | 17.847 | 1.00 | 38.57 | B | C |
| ATOM | 3149 | O   | SER | B | 211 | 26.815 | 16.749 | 18.147 | 1.00 | 37.98 | B | O |
| ATOM | 3150 | N   | LEU | B | 212 | 26.434 | 15.124 | 16.658 | 1.00 | 38.78 | B | N |
| ATOM | 3151 | CA  | LEU | B | 212 | 25.892 | 16.057 | 15.677 | 1.00 | 44.25 | B | C |
| ATOM | 3152 | CB  | LEU | B | 212 | 26.713 | 16.070 | 14.389 | 1.00 | 50.61 | B | C |
| ATOM | 3153 | CG  | LEU | B | 212 | 28.037 | 16.815 | 14.539 | 1.00 | 48.05 | B | C |

TABLE 12-continued

Coordinates for pro MMP9(35-444 ΔFnII) (SEQ ID NO: 12) complex with Example 2

| ATOM | 3154 | CD1 | LEU | B | 212 | 28.470 | 17.403 | 13.193 | 1.00 | 49.93 | B | C |
|------|------|-----|-----|---|-----|--------|--------|--------|------|-------|---|---|
| ATOM | 3155 | CD2 | LEU | B | 212 | 27.915 | 17.912 | 15.583 | 1.00 | 37.67 | B | C |
| ATOM | 3156 | C | LEU | B | 212 | 24.426 | 15.818 | 15.370 | 1.00 | 51.56 | B | C |
| ATOM | 3157 | O | LEU | B | 212 | 23.968 | 16.096 | 14.251 | 1.00 | 49.50 | B | O |
| ATOM | 3158 | N | GLY | B | 213 | 23.713 | 15.291 | 16.373 | 1.00 | 52.23 | B | N |
| ATOM | 3159 | CA | GLY | B | 213 | 22.260 | 15.324 | 16.430 | 1.00 | 49.49 | B | C |
| ATOM | 3160 | C | GLY | B | 213 | 21.511 | 14.283 | 15.625 | 1.00 | 54.16 | B | C |
| ATOM | 3161 | O | GLY | B | 213 | 20.353 | 13.976 | 15.927 | 1.00 | 51.68 | B | O |
| ATOM | 3162 | N | LYS | B | 389 | 22.164 | 13.759 | 14.593 | 1.00 | 52.27 | B | N |
| ATOM | 3163 | CA | LYS | B | 389 | 21.566 | 12.778 | 13.686 | 1.00 | 56.63 | B | C |
| ATOM | 3164 | CB | LYS | B | 389 | 22.573 | 12.460 | 12.579 | 1.00 | 60.09 | B | C |
| ATOM | 3165 | CG | LYS | B | 389 | 24.045 | 12.643 | 13.009 | 1.00 | 60.47 | B | C |
| ATOM | 3166 | CD | LYS | B | 389 | 24.464 | 11.640 | 14.083 | 1.00 | 56.80 | B | C |
| ATOM | 3167 | CE | LYS | B | 389 | 25.926 | 11.784 | 14.463 | 1.00 | 59.61 | B | C |
| ATOM | 3168 | NZ | LYS | B | 389 | 26.162 | 13.042 | 15.215 | 1.00 | 53.01 | B | N |
| ATOM | 3169 | C | LYS | B | 389 | 21.128 | 11.485 | 14.405 | 1.00 | 61.48 | B | C |
| ATOM | 3170 | O | LYS | B | 389 | 21.870 | 10.490 | 14.433 | 1.00 | 60.81 | B | O |
| ATOM | 3171 | N | GLY | B | 390 | 19.928 | 11.496 | 14.988 | 1.00 | 59.41 | B | N |
| ATOM | 3172 | CA | GLY | B | 390 | 19.482 | 10.386 | 15.821 | 1.00 | 56.46 | B | C |
| ATOM | 3173 | C | GLY | B | 390 | 20.453 | 10.114 | 16.962 | 1.00 | 56.43 | B | C |
| ATOM | 3174 | O | GLY | B | 390 | 20.263 | 9.205 | 17.775 | 1.00 | 49.80 | B | O |
| ATOM | 3175 | N | GLN | B | 391 | 21.507 | 10.922 | 17.021 | 1.00 | 57.20 | B | N |
| ATOM | 3176 | CA | GLN | B | 391 | 22.551 | 10.743 | 18.015 | 1.00 | 57.51 | B | C |
| ATOM | 3177 | CB | GLN | B | 391 | 23.921 | 11.060 | 17.414 | 1.00 | 53.13 | B | C |
| ATOM | 3178 | CG | GLN | B | 391 | 25.014 | 10.267 | 18.077 | 1.00 | 53.52 | B | C |
| ATOM | 3179 | CD | GLN | B | 391 | 24.686 | 8.800 | 18.057 | 1.00 | 55.50 | B | C |
| ATOM | 3180 | OE1 | GLN | B | 391 | 24.690 | 8.117 | 19.093 | 1.00 | 57.06 | B | O |
| ATOM | 3181 | NE2 | GLN | B | 391 | 24.364 | 8.299 | 16.864 | 1.00 | 59.92 | B | N |
| ATOM | 3182 | C | GLN | B | 391 | 22.318 | 11.611 | 19.255 | 1.00 | 58.15 | B | C |
| ATOM | 3183 | O | GLN | B | 391 | 22.374 | 11.115 | 20.387 | 1.00 | 53.47 | B | O |
| ATOM | 3184 | N | GLY | B | 392 | 22.064 | 12.904 | 19.014 | 1.00 | 57.43 | B | N |
| ATOM | 3185 | CA | GLY | B | 392 | 21.851 | 13.901 | 20.052 | 1.00 | 36.70 | B | C |
| ATOM | 3186 | C | GLY | B | 392 | 22.909 | 13.818 | 21.113 | 1.00 | 39.24 | B | C |
| ATOM | 3187 | O | GLY | B | 392 | 23.521 | 12.762 | 21.309 | 1.00 | 46.92 | B | O |
| ATOM | 3188 | N | TYR | B | 393 | 23.152 | 14.921 | 21.809 | 1.00 | 41.14 | B | N |
| ATOM | 3189 | CA | TYR | B | 393 | 22.562 | 16.222 | 21.521 | 1.00 | 39.08 | B | C |
| ATOM | 3190 | CB | TYR | B | 393 | 22.434 | 17.033 | 22.827 | 1.00 | 39.25 | B | C |
| ATOM | 3191 | CG | TYR | B | 393 | 21.457 | 16.434 | 23.838 | 1.00 | 43.00 | B | C |
| ATOM | 3192 | CD1 | TYR | B | 393 | 20.080 | 16.479 | 23.616 | 1.00 | 42.80 | B | C |
| ATOM | 3193 | CE1 | TYR | B | 393 | 19.183 | 15.935 | 24.519 | 1.00 | 39.67 | B | C |
| ATOM | 3194 | CD2 | TYR | B | 393 | 21.913 | 15.824 | 24.992 | 1.00 | 34.26 | B | C |
| ATOM | 3195 | CE2 | TYR | B | 393 | 21.028 | 15.266 | 25.897 | 1.00 | 47.67 | B | C |
| ATOM | 3196 | CZ | TYR | B | 393 | 19.657 | 15.329 | 25.655 | 1.00 | 46.74 | B | C |
| ATOM | 3197 | OH | TYR | B | 393 | 18.770 | 14.777 | 26.556 | 1.00 | 41.69 | B | O |
| ATOM | 3198 | C | TYR | B | 393 | 23.511 | 16.947 | 20.569 | 1.00 | 36.11 | B | C |
| ATOM | 3199 | O | TYR | B | 393 | 24.718 | 16.872 | 20.753 | 1.00 | 37.03 | B | O |
| ATOM | 3200 | N | SER | B | 394 | 22.992 | 17.644 | 19.567 | 1.00 | 32.97 | B | N |
| ATOM | 3201 | CA | SER | B | 394 | 23.878 | 18.344 | 18.637 | 1.00 | 35.15 | B | C |
| ATOM | 3202 | CB | SER | B | 394 | 23.152 | 18.813 | 17.387 | 1.00 | 33.71 | B | C |
| ATOM | 3203 | OG | SER | B | 394 | 23.768 | 20.013 | 16.940 | 1.00 | 34.93 | B | O |
| ATOM | 3204 | C | SER | B | 394 | 24.579 | 19.536 | 19.283 | 1.00 | 36.67 | B | C |
| ATOM | 3205 | O | SER | B | 394 | 23.963 | 20.575 | 19.554 | 1.00 | 31.67 | B | O |
| ATOM | 3206 | N | LEU | B | 395 | 25.877 | 19.384 | 19.523 | 1.00 | 33.16 | B | N |
| ATOM | 3207 | CA | LEU | B | 395 | 26.670 | 20.481 | 20.031 | 1.00 | 32.02 | B | C |
| ATOM | 3208 | CB | LEU | B | 395 | 28.143 | 20.076 | 20.135 | 1.00 | 34.49 | B | C |
| ATOM | 3209 | CG | LEU | B | 395 | 29.158 | 21.076 | 20.678 | 1.00 | 34.38 | B | C |
| ATOM | 3210 | CD1 | LEU | B | 395 | 28.951 | 21.360 | 22.150 | 1.00 | 30.69 | B | C |
| ATOM | 3211 | CD2 | LEU | B | 395 | 30.595 | 20.525 | 20.437 | 1.00 | 35.97 | B | C |
| ATOM | 3212 | C | LEU | B | 395 | 26.496 | 21.693 | 19.141 | 1.00 | 24.57 | B | C |
| ATOM | 3213 | O | LEU | B | 395 | 26.593 | 22.819 | 19.610 | 1.00 | 34.81 | B | O |
| ATOM | 3214 | N | PHE | B | 396 | 26.242 | 21.478 | 17.858 | 1.00 | 29.04 | B | N |
| ATOM | 3215 | CA | PHE | B | 396 | 26.064 | 22.597 | 16.922 | 1.00 | 31.77 | B | C |
| ATOM | 3216 | CB | PHE | B | 396 | 25.973 | 22.103 | 15.468 | 1.00 | 24.07 | B | C |
| ATOM | 3217 | CG | PHE | B | 396 | 25.634 | 23.206 | 14.478 | 1.00 | 25.77 | B | C |
| ATOM | 3218 | CD1 | PHE | B | 396 | 26.396 | 24.366 | 14.427 | 1.00 | 27.51 | B | C |
| ATOM | 3219 | CD2 | PHE | B | 396 | 24.572 | 23.093 | 13.617 | 1.00 | 22.89 | B | C |
| ATOM | 3220 | CE1 | PHE | B | 396 | 26.099 | 25.390 | 13.525 | 1.00 | 23.33 | B | C |
| ATOM | 3221 | CE2 | PHE | B | 396 | 24.271 | 24.112 | 12.715 | 1.00 | 25.89 | B | C |
| ATOM | 3222 | CZ | PHE | B | 396 | 25.036 | 25.258 | 12.667 | 1.00 | 24.21 | B | C |
| ATOM | 3223 | C | PHE | B | 396 | 24.853 | 23.496 | 17.233 | 1.00 | 29.41 | B | C |
| ATOM | 3224 | O | PHE | B | 396 | 24.990 | 24.714 | 17.403 | 1.00 | 27.93 | B | O |
| ATOM | 3225 | N | LEU | B | 397 | 23.666 | 22.883 | 17.242 | 1.00 | 36.58 | B | N |
| ATOM | 3226 | CA | LEU | B | 397 | 22.423 | 23.553 | 17.646 | 1.00 | 30.40 | B | C |
| ATOM | 3227 | CB | LEU | B | 397 | 21.272 | 22.562 | 17.655 | 1.00 | 29.23 | B | C |
| ATOM | 3228 | CG | LEU | B | 397 | 20.903 | 21.985 | 16.296 | 1.00 | 31.77 | B | C |
| ATOM | 3229 | CD1 | LEU | B | 397 | 19.727 | 21.029 | 16.413 | 1.00 | 33.74 | B | C |
| ATOM | 3230 | CD2 | LEU | B | 397 | 20.627 | 23.099 | 15.318 | 1.00 | 28.80 | B | C |

TABLE 12-continued

Coordinates for pro MMP9(35-444 ΔFnII) (SEQ ID NO: 12) complex with Example 2

| ATOM | 3231 | C | LEU | B | 397 | 22.555 | 24.145 | 19.031 | 1.00 | 27.75 | B | C |
|---|---|---|---|---|---|---|---|---|---|---|---|---|
| ATOM | 3232 | O | LEU | B | 397 | 22.298 | 25.325 | 19.236 | 1.00 | 26.18 | B | O |
| ATOM | 3233 | N | VAL | B | 398 | 22.976 | 23.344 | 19.995 | 1.00 | 25.57 | B | N |
| ATOM | 3234 | CA | VAL | B | 398 | 23.065 | 23.883 | 21.339 | 1.00 | 25.14 | B | C |
| ATOM | 3235 | CB | VAL | B | 398 | 23.449 | 22.821 | 22.392 | 1.00 | 31.51 | B | C |
| ATOM | 3236 | CG1 | VAL | B | 398 | 23.750 | 23.491 | 23.733 | 1.00 | 27.68 | B | C |
| ATOM | 3237 | CG2 | VAL | B | 398 | 22.335 | 21.763 | 22.533 | 1.00 | 24.83 | B | C |
| ATOM | 3238 | C | VAL | B | 398 | 24.019 | 25.078 | 21.402 | 1.00 | 32.26 | B | C |
| ATOM | 3239 | O | VAL | B | 398 | 23.665 | 26.105 | 21.984 | 1.00 | 28.99 | B | O |
| ATOM | 3240 | N | ALA | B | 399 | 25.213 | 24.972 | 20.799 | 1.00 | 26.23 | B | N |
| ATOM | 3241 | CA | ALA | B | 399 | 26.165 | 26.093 | 20.883 | 1.00 | 27.75 | B | C |
| ATOM | 3242 | CB | ALA | B | 399 | 27.527 | 25.759 | 20.237 | 1.00 | 29.02 | B | C |
| ATOM | 3243 | C | ALA | B | 399 | 25.569 | 27.322 | 20.243 | 1.00 | 23.86 | B | C |
| ATOM | 3244 | O | ALA | B | 399 | 25.733 | 28.441 | 20.744 | 1.00 | 29.38 | B | O |
| ATOM | 3245 | N | ALA | B | 400 | 24.865 | 27.126 | 19.140 | 1.00 | 23.86 | B | N |
| ATOM | 3246 | CA | ALA | B | 400 | 24.244 | 28.252 | 18.453 | 1.00 | 27.86 | B | C |
| ATOM | 3247 | CB | ALA | B | 400 | 23.542 | 27.777 | 17.185 | 1.00 | 24.17 | B | C |
| ATOM | 3248 | C | ALA | B | 400 | 23.267 | 28.970 | 19.400 | 1.00 | 29.05 | B | C |
| ATOM | 3249 | O | ALA | B | 400 | 23.268 | 30.200 | 19.528 | 1.00 | 30.71 | B | O |
| ATOM | 3250 | N | HIS | B | 401 | 22.447 | 28.178 | 20.080 | 1.00 | 31.44 | B | N |
| ATOM | 3251 | CA | HIS | B | 401 | 21.517 | 28.697 | 21.076 | 1.00 | 31.79 | B | C |
| ATOM | 3252 | CB | HIS | B | 401 | 20.813 | 27.557 | 21.815 | 1.00 | 28.75 | B | C |
| ATOM | 3253 | CG | HIS | B | 401 | 19.799 | 28.042 | 22.810 | 1.00 | 34.11 | B | C |
| ATOM | 3254 | CD2 | HIS | B | 401 | 19.920 | 28.405 | 24.112 | 1.00 | 31.51 | B | C |
| ATOM | 3255 | ND1 | HIS | B | 401 | 18.478 | 28.251 | 22.477 | 1.00 | 31.07 | B | N |
| ATOM | 3256 | CE1 | HIS | B | 401 | 17.826 | 28.713 | 23.530 | 1.00 | 31.23 | B | C |
| ATOM | 3257 | NE2 | HIS | B | 401 | 18.673 | 28.804 | 24.539 | 1.00 | 28.38 | B | N |
| ATOM | 3258 | C | HIS | B | 401 | 22.240 | 29.532 | 22.103 | 1.00 | 27.22 | B | C |
| ATOM | 3259 | O | HIS | B | 401 | 21.939 | 30.711 | 22.286 | 1.00 | 28.31 | B | O |
| ATOM | 3260 | N | GLU | B | 402 | 23.175 | 28.898 | 22.788 | 1.00 | 28.63 | B | N |
| ATOM | 3261 | CA | GLU | B | 402 | 23.911 | 29.553 | 23.853 | 1.00 | 33.61 | B | C |
| ATOM | 3262 | CB | GLU | B | 402 | 24.972 | 28.616 | 24.435 | 1.00 | 30.91 | B | C |
| ATOM | 3263 | CG | GLU | B | 402 | 24.439 | 27.366 | 25.151 | 1.00 | 34.69 | B | C |
| ATOM | 3264 | CD | GLU | B | 402 | 23.326 | 27.652 | 26.174 | 1.00 | 35.87 | B | C |
| ATOM | 3265 | OE1 | GLU | B | 402 | 23.416 | 28.651 | 26.927 | 1.00 | 31.21 | B | O |
| ATOM | 3266 | OE2 | GLU | B | 402 | 22.366 | 26.849 | 26.214 | 1.00 | 32.20 | B | O |
| ATOM | 3267 | C | GLU | B | 402 | 24.586 | 30.829 | 23.370 | 1.00 | 33.75 | B | C |
| ATOM | 3268 | O | GLU | B | 402 | 24.649 | 31.832 | 24.101 | 1.00 | 33.88 | B | O |
| ATOM | 3269 | N | PHE | B | 403 | 25.112 | 30.787 | 22.150 | 1.00 | 31.20 | B | N |
| ATOM | 3270 | CA | PHE | B | 403 | 25.869 | 31.920 | 21.626 | 1.00 | 29.83 | B | C |
| ATOM | 3271 | CB | PHE | B | 403 | 26.560 | 31.581 | 20.289 | 1.00 | 30.07 | B | C |
| ATOM | 3272 | CG | PHE | B | 403 | 27.773 | 30.644 | 20.426 | 1.00 | 26.45 | B | C |
| ATOM | 3273 | CD1 | PHE | B | 403 | 28.333 | 30.375 | 21.661 | 1.00 | 26.41 | B | C |
| ATOM | 3274 | CD2 | PHE | B | 403 | 28.361 | 30.076 | 19.302 | 1.00 | 31.44 | B | C |
| ATOM | 3275 | CE1 | PHE | B | 403 | 29.441 | 29.516 | 21.791 | 1.00 | 35.79 | B | C |
| ATOM | 3276 | CE2 | PHE | B | 403 | 29.468 | 29.229 | 19.413 | 1.00 | 27.00 | B | C |
| ATOM | 3277 | CZ | PHE | B | 403 | 30.007 | 28.940 | 20.652 | 1.00 | 28.81 | B | C |
| ATOM | 3278 | C | PHE | B | 403 | 24.907 | 33.085 | 21.481 | 1.00 | 33.20 | B | C |
| ATOM | 3279 | O | PHE | B | 403 | 25.305 | 34.239 | 21.572 | 1.00 | 30.19 | B | O |
| ATOM | 3280 | N | GLY | B | 404 | 23.631 | 32.765 | 21.274 | 1.00 | 31.92 | B | N |
| ATOM | 3281 | CA | GLY | B | 404 | 22.560 | 33.756 | 21.295 | 1.00 | 28.28 | B | C |
| ATOM | 3282 | C | GLY | B | 404 | 22.577 | 34.563 | 22.580 | 1.00 | 26.84 | B | C |
| ATOM | 3283 | O | GLY | B | 404 | 22.588 | 35.780 | 22.552 | 1.00 | 26.56 | B | O |
| ATOM | 3284 | N | HIS | B | 405 | 22.628 | 33.876 | 23.707 | 1.00 | 29.62 | B | N |
| ATOM | 3285 | CA | HIS | B | 405 | 22.698 | 34.517 | 25.016 | 1.00 | 31.65 | B | C |
| ATOM | 3286 | CB | HIS | B | 405 | 22.652 | 33.459 | 26.133 | 1.00 | 30.34 | B | C |
| ATOM | 3287 | CG | HIS | B | 405 | 21.352 | 32.708 | 26.238 | 1.00 | 36.49 | B | C |
| ATOM | 3288 | CD2 | HIS | B | 405 | 21.090 | 31.412 | 26.550 | 1.00 | 32.52 | B | C |
| ATOM | 3289 | ND1 | HIS | B | 405 | 20.125 | 33.317 | 26.091 | 1.00 | 34.57 | B | N |
| ATOM | 3290 | CE1 | HIS | B | 405 | 19.165 | 32.429 | 26.291 | 1.00 | 32.79 | B | C |
| ATOM | 3291 | NE2 | HIS | B | 405 | 19.721 | 31.270 | 26.578 | 1.00 | 27.14 | B | N |
| ATOM | 3292 | C | HIS | B | 405 | 23.996 | 35.293 | 25.172 | 1.00 | 35.90 | B | C |
| ATOM | 3293 | O | HIS | B | 405 | 24.027 | 36.363 | 25.792 | 1.00 | 33.62 | B | O |
| ATOM | 3294 | N | ALA | B | 406 | 25.088 | 34.737 | 24.650 | 1.00 | 32.66 | B | N |
| ATOM | 3295 | CA | ALA | B | 406 | 26.389 | 35.382 | 24.831 | 1.00 | 31.44 | B | C |
| ATOM | 3296 | CB | ALA | B | 406 | 27.506 | 34.498 | 24.328 | 1.00 | 31.27 | B | C |
| ATOM | 3297 | C | ALA | B | 406 | 26.366 | 36.708 | 24.092 | 1.00 | 31.80 | B | C |
| ATOM | 3298 | O | ALA | B | 406 | 27.172 | 37.600 | 24.348 | 1.00 | 33.25 | B | O |
| ATOM | 3299 | N | LEU | B | 407 | 25.423 | 36.834 | 23.169 | 1.00 | 26.21 | B | N |
| ATOM | 3300 | CA | LEU | B | 407 | 25.283 | 38.072 | 22.421 | 1.00 | 27.94 | B | C |
| ATOM | 3301 | CB | LEU | B | 407 | 24.863 | 37.759 | 20.999 | 1.00 | 26.53 | B | C |
| ATOM | 3302 | CG | LEU | B | 407 | 25.988 | 37.110 | 20.198 | 1.00 | 27.30 | B | C |
| ATOM | 3303 | CD1 | LEU | B | 407 | 25.639 | 37.205 | 18.751 | 1.00 | 30.22 | B | C |
| ATOM | 3304 | CD2 | LEU | B | 407 | 27.315 | 37.798 | 20.477 | 1.00 | 29.21 | B | C |
| ATOM | 3305 | C | LEU | B | 407 | 24.290 | 39.049 | 23.054 | 1.00 | 33.13 | B | C |
| ATOM | 3306 | O | LEU | B | 407 | 24.176 | 40.191 | 22.607 | 1.00 | 31.07 | B | O |
| ATOM | 3307 | N | GLY | B | 408 | 23.581 | 38.582 | 24.086 | 1.00 | 33.28 | B | N |

TABLE 12-continued

Coordinates for pro MMP9(35-444 ΔFnII) (SEQ ID NO: 12) complex with Example 2

| ATOM | 3308 | CA | GLY | B | 408 | 22.586 | 39.373 | 24.805 | 1.00 | 34.97 | B | C |
|------|------|------|-----|---|-----|--------|--------|--------|------|-------|---|---|
| ATOM | 3309 | C | GLY | B | 408 | 21.120 | 39.030 | 24.515 | 1.00 | 34.84 | B | C |
| ATOM | 3310 | O | GLY | B | 408 | 20.238 | 39.854 | 24.743 | 1.00 | 32.85 | B | O |
| ATOM | 3311 | N | LEU | B | 409 | 20.846 | 37.822 | 24.021 | 1.00 | 25.84 | B | N |
| ATOM | 3312 | CA | LEU | B | 409 | 19.476 | 37.460 | 23.675 | 1.00 | 34.40 | B | C |
| ATOM | 3313 | CB | LEU | B | 409 | 19.414 | 36.622 | 22.403 | 1.00 | 34.50 | B | C |
| ATOM | 3314 | CG | LEU | B | 409 | 19.693 | 37.293 | 21.065 | 1.00 | 29.08 | B | C |
| ATOM | 3315 | CD1 | LEU | B | 409 | 19.490 | 36.245 | 19.974 | 1.00 | 23.23 | B | C |
| ATOM | 3316 | CD2 | LEU | B | 409 | 18.788 | 38.500 | 20.841 | 1.00 | 24.33 | B | C |
| ATOM | 3317 | C | LEU | B | 409 | 18.857 | 36.668 | 24.805 | 1.00 | 35.13 | B | C |
| ATOM | 3318 | O | LEU | B | 409 | 19.558 | 35.967 | 25.530 | 1.00 | 32.49 | B | O |
| ATOM | 3319 | N | ASP | B | 410 | 17.538 | 36.775 | 24.944 | 1.00 | 38.05 | B | N |
| ATOM | 3320 | CA | ASP | B | 410 | 16.812 | 35.984 | 25.936 | 1.00 | 36.91 | B | C |
| ATOM | 3321 | CB | ASP | B | 410 | 15.870 | 36.877 | 26.732 | 1.00 | 35.50 | B | C |
| ATOM | 3322 | CG | ASP | B | 410 | 16.621 | 37.808 | 27.628 | 1.00 | 41.41 | B | C |
| ATOM | 3323 | OD1 | ASP | B | 410 | 17.375 | 37.265 | 28.455 | 1.00 | 46.89 | B | O |
| ATOM | 3324 | OD2 | ASP | B | 410 | 16.495 | 39.053 | 27.489 | 1.00 | 41.79 | B | O |
| ATOM | 3325 | C | ASP | B | 410 | 16.040 | 34.899 | 25.238 | 1.00 | 35.50 | B | C |
| ATOM | 3326 | O | ASP | B | 410 | 16.116 | 34.776 | 24.024 | 1.00 | 30.42 | B | O |
| ATOM | 3327 | N | HIS | B | 411 | 15.278 | 34.119 | 25.993 | 1.00 | 32.52 | B | N |
| ATOM | 3328 | CA | HIS | B | 411 | 14.511 | 33.050 | 25.374 | 1.00 | 31.15 | B | C |
| ATOM | 3329 | CB | HIS | B | 411 | 14.037 | 32.051 | 26.417 | 1.00 | 38.06 | B | C |
| ATOM | 3330 | CG | HIS | B | 411 | 15.098 | 31.088 | 26.829 | 1.00 | 35.86 | B | C |
| ATOM | 3331 | CD2 | HIS | B | 411 | 16.040 | 30.446 | 26.103 | 1.00 | 33.28 | B | C |
| ATOM | 3332 | ND1 | HIS | B | 411 | 15.295 | 30.704 | 28.138 | 1.00 | 35.23 | B | N |
| ATOM | 3333 | CE1 | HIS | B | 411 | 16.299 | 29.849 | 28.198 | 1.00 | 33.38 | B | C |
| ATOM | 3334 | NE2 | HIS | B | 411 | 16.764 | 29.674 | 26.975 | 1.00 | 34.56 | B | N |
| ATOM | 3335 | C | HIS | B | 411 | 13.352 | 33.574 | 24.548 | 1.00 | 32.41 | B | C |
| ATOM | 3336 | O | HIS | B | 411 | 12.838 | 34.662 | 24.778 | 1.00 | 35.20 | B | O |
| ATOM | 3337 | N | SER | B | 412 | 12.964 | 32.798 | 23.557 | 1.00 | 31.56 | B | N |
| ATOM | 3338 | CA | SER | B | 412 | 11.826 | 33.128 | 22.733 | 1.00 | 31.59 | B | C |
| ATOM | 3339 | CB | SER | B | 412 | 12.217 | 32.963 | 21.264 | 1.00 | 26.45 | B | C |
| ATOM | 3340 | OG | SER | B | 412 | 11.120 | 32.684 | 20.419 | 1.00 | 22.22 | B | O |
| ATOM | 3341 | C | SER | B | 412 | 10.630 | 32.229 | 23.105 | 1.00 | 32.63 | B | C |
| ATOM | 3342 | O | SER | B | 412 | 10.792 | 31.113 | 23.612 | 1.00 | 35.31 | B | O |
| ATOM | 3343 | N | SER | B | 413 | 9.430 | 32.708 | 22.823 | 1.00 | 31.37 | B | N |
| ATOM | 3344 | CA | SER | B | 413 | 8.251 | 31.890 | 23.071 | 1.00 | 38.71 | B | C |
| ATOM | 3345 | CB | SER | B | 413 | 7.137 | 32.710 | 23.710 | 1.00 | 34.94 | B | C |
| ATOM | 3346 | OG | SER | B | 413 | 6.641 | 33.658 | 22.798 | 1.00 | 45.15 | B | O |
| ATOM | 3347 | C | SER | B | 413 | 7.765 | 31.229 | 21.802 | 1.00 | 42.59 | B | C |
| ATOM | 3348 | O | SER | B | 413 | 6.761 | 30.515 | 21.830 | 1.00 | 43.20 | B | O |
| ATOM | 3349 | N | VAL | B | 414 | 8.471 | 31.445 | 20.685 | 1.00 | 38.36 | B | N |
| ATOM | 3350 | CA | VAL | B | 414 | 8.154 | 30.701 | 19.457 | 1.00 | 34.96 | B | C |
| ATOM | 3351 | CB | VAL | B | 414 | 8.552 | 31.430 | 18.168 | 1.00 | 33.22 | B | C |
| ATOM | 3352 | CG1 | VAL | B | 414 | 8.069 | 30.631 | 16.963 | 1.00 | 32.38 | B | C |
| ATOM | 3353 | CG2 | VAL | B | 414 | 7.972 | 32.819 | 18.133 | 1.00 | 26.89 | B | C |
| ATOM | 3354 | C | VAL | B | 414 | 8.810 | 29.333 | 19.455 | 1.00 | 37.88 | B | C |
| ATOM | 3355 | O | VAL | B | 414 | 10.032 | 29.215 | 19.408 | 1.00 | 36.44 | B | O |
| ATOM | 3356 | N | PRO | B | 415 | 7.990 | 28.287 | 19.495 | 1.00 | 38.18 | B | N |
| ATOM | 3357 | CD | PRO | B | 415 | 6.537 | 28.316 | 19.262 | 1.00 | 41.23 | B | C |
| ATOM | 3358 | CA | PRO | B | 415 | 8.496 | 26.937 | 19.727 | 1.00 | 41.04 | B | C |
| ATOM | 3359 | CB | PRO | B | 415 | 7.255 | 26.055 | 19.542 | 1.00 | 37.81 | B | C |
| ATOM | 3360 | CG | PRO | B | 415 | 6.099 | 26.982 | 19.750 | 1.00 | 41.90 | B | C |
| ATOM | 3361 | C | PRO | B | 415 | 9.556 | 26.564 | 18.710 | 1.00 | 39.22 | B | C |
| ATOM | 3362 | O | PRO | B | 415 | 10.471 | 25.825 | 19.049 | 1.00 | 40.11 | B | O |
| ATOM | 3363 | N | GLU | B | 416 | 9.441 | 27.054 | 17.485 | 1.00 | 36.64 | B | N |
| ATOM | 3364 | CA | GLU | B | 416 | 10.411 | 26.645 | 16.473 | 1.00 | 44.82 | B | C |
| ATOM | 3365 | CB | GLU | B | 416 | 9.736 | 26.280 | 15.137 | 1.00 | 45.54 | B | C |
| ATOM | 3366 | CG | GLU | B | 416 | 8.642 | 27.245 | 14.668 | 1.00 | 56.24 | B | C |
| ATOM | 3367 | CD | GLU | B | 416 | 7.343 | 27.115 | 15.454 | 1.00 | 47.39 | B | C |
| ATOM | 3368 | OE1 | GLU | B | 416 | 6.947 | 25.975 | 15.782 | 1.00 | 50.92 | B | O |
| ATOM | 3369 | OE2 | GLU | B | 416 | 6.721 | 28.160 | 15.732 | 1.00 | 48.08 | B | O |
| ATOM | 3370 | C | GLU | B | 416 | 11.594 | 27.618 | 16.290 | 1.00 | 43.63 | B | C |
| ATOM | 3371 | O | GLU | B | 416 | 12.440 | 27.404 | 15.421 | 1.00 | 40.00 | B | O |
| ATOM | 3372 | N | ALA | B | 417 | 11.662 | 28.659 | 17.121 | 1.00 | 37.37 | B | N |
| ATOM | 3373 | CA | ALA | B | 417 | 12.782 | 29.595 | 17.077 | 1.00 | 35.20 | B | C |
| ATOM | 3374 | CB | ALA | B | 417 | 12.429 | 30.904 | 17.753 | 1.00 | 30.24 | B | C |
| ATOM | 3375 | C | ALA | B | 417 | 14.021 | 28.994 | 17.721 | 1.00 | 34.09 | B | C |
| ATOM | 3376 | O | ALA | B | 417 | 13.929 | 28.217 | 18.669 | 1.00 | 31.19 | B | O |
| ATOM | 3377 | N | LEU | B | 418 | 15.191 | 29.370 | 17.208 | 1.00 | 34.15 | B | N |
| ATOM | 3378 | CA | LEU | B | 418 | 16.447 | 28.911 | 17.805 | 1.00 | 33.75 | B | C |
| ATOM | 3379 | CB | LEU | B | 418 | 17.636 | 29.556 | 17.079 | 1.00 | 29.86 | B | C |
| ATOM | 3380 | CG | LEU | B | 418 | 18.987 | 29.289 | 17.732 | 1.00 | 27.52 | B | C |
| ATOM | 3381 | CD1 | LEU | B | 418 | 19.249 | 27.796 | 17.765 | 1.00 | 27.43 | B | C |
| ATOM | 3382 | CD2 | LEU | B | 418 | 20.121 | 30.042 | 16.998 | 1.00 | 27.87 | B | C |
| ATOM | 3383 | C | LEU | B | 418 | 16.525 | 29.233 | 19.305 | 1.00 | 26.38 | B | C |
| ATOM | 3384 | O | LEU | B | 418 | 17.068 | 28.454 | 20.115 | 1.00 | 23.36 | B | O |

TABLE 12-continued

Coordinates for pro MMP9(35-444 ΔFnII) (SEQ ID NO: 12) complex with Example 2

| ATOM | 3385 | N | MET | B | 419 | 16.022 | 30.404 | 19.674 | 1.00 | 28.01 | B | N |
|------|------|------|-----|---|-----|--------|--------|--------|------|-------|---|---|
| ATOM | 3386 | CA | MET | B | 419 | 16.149 | 30.840 | 21.060 | 1.00 | 27.85 | B | C |
| ATOM | 3387 | CB | MET | B | 419 | 16.239 | 32.359 | 21.178 | 1.00 | 26.67 | B | C |
| ATOM | 3388 | CG | MET | B | 419 | 17.565 | 32.969 | 20.639 | 1.00 | 28.74 | B | C |
| ATOM | 3389 | SD | MET | B | 419 | 19.079 | 32.027 | 21.011 | 1.00 | 25.96 | B | S |
| ATOM | 3390 | CE | MET | B | 419 | 19.342 | 32.299 | 22.738 | 1.00 | 24.53 | B | C |
| ATOM | 3391 | C | MET | B | 419 | 15.053 | 30.245 | 21.998 | 1.00 | 31.91 | B | C |
| ATOM | 3392 | O | MET | B | 419 | 15.073 | 30.488 | 23.195 | 1.00 | 36.09 | B | O |
| ATOM | 3393 | N | TYR | B | 420 | 14.143 | 29.437 | 21.461 | 1.00 | 30.26 | B | N |
| ATOM | 3394 | CA | TYR | B | 420 | 13.263 | 28.613 | 22.315 | 1.00 | 30.76 | B | C |
| ATOM | 3395 | CB | TYR | B | 420 | 12.407 | 27.707 | 21.449 | 1.00 | 33.96 | B | C |
| ATOM | 3396 | CG | TYR | B | 420 | 11.161 | 27.135 | 22.119 | 1.00 | 44.14 | B | C |
| ATOM | 3397 | CD1 | TYR | B | 420 | 10.048 | 27.939 | 22.397 | 1.00 | 38.43 | B | C |
| ATOM | 3398 | CE1 | TYR | B | 420 | 8.902 | 27.401 | 22.996 | 1.00 | 41.12 | B | C |
| ATOM | 3399 | CD2 | TYR | B | 420 | 11.093 | 25.786 | 22.447 | 1.00 | 39.78 | B | C |
| ATOM | 3400 | CE2 | TYR | B | 420 | 9.951 | 25.241 | 23.040 | 1.00 | 39.43 | B | C |
| ATOM | 3401 | CZ | TYR | B | 420 | 8.867 | 26.049 | 23.308 | 1.00 | 43.36 | B | C |
| ATOM | 3402 | OH | TYR | B | 420 | 7.761 | 25.487 | 23.907 | 1.00 | 46.01 | B | O |
| ATOM | 3403 | C | TYR | B | 420 | 14.122 | 27.762 | 23.219 | 1.00 | 33.37 | B | C |
| ATOM | 3404 | O | TYR | B | 420 | 15.105 | 27.182 | 22.765 | 1.00 | 34.51 | B | O |
| ATOM | 3405 | N | PRO | B | 421 | 13.756 | 27.668 | 24.508 | 1.00 | 34.99 | B | N |
| ATOM | 3406 | CD | PRO | B | 421 | 12.463 | 28.132 | 25.048 | 1.00 | 38.45 | B | C |
| ATOM | 3407 | CA | PRO | B | 421 | 14.595 | 27.046 | 25.542 | 1.00 | 33.82 | B | C |
| ATOM | 3408 | CB | PRO | B | 421 | 13.849 | 27.367 | 26.851 | 1.00 | 39.33 | B | C |
| ATOM | 3409 | CG | PRO | B | 421 | 12.759 | 28.354 | 26.480 | 1.00 | 39.11 | B | C |
| ATOM | 3410 | C | PRO | B | 421 | 14.755 | 25.536 | 25.440 | 1.00 | 32.34 | B | C |
| ATOM | 3411 | O | PRO | B | 421 | 15.707 | 24.996 | 26.024 | 1.00 | 32.23 | B | O |
| ATOM | 3412 | N | MET | B | 422 | 13.835 | 24.867 | 24.755 | 1.00 | 34.19 | B | N |
| ATOM | 3413 | CA | MET | B | 422 | 13.806 | 23.413 | 24.752 | 1.00 | 34.43 | B | C |
| ATOM | 3414 | CB | MET | B | 422 | 12.381 | 22.910 | 24.572 | 1.00 | 38.61 | B | C |
| ATOM | 3415 | CG | MET | B | 422 | 11.456 | 22.986 | 25.777 | 1.00 | 42.46 | B | C |
| ATOM | 3416 | SD | MET | B | 422 | 9.965 | 22.018 | 25.380 | 1.00 | 45.95 | B | S |
| ATOM | 3417 | CE | MET | B | 422 | 8.697 | 23.251 | 25.705 | 1.00 | 41.72 | B | C |
| ATOM | 3418 | C | MET | B | 422 | 14.594 | 22.881 | 23.585 | 1.00 | 36.25 | B | C |
| ATOM | 3419 | O | MET | B | 422 | 14.440 | 23.358 | 22.459 | 1.00 | 36.62 | B | O |
| ATOM | 3420 | N | TYR | B | 423 | 15.397 | 21.856 | 23.841 | 1.00 | 40.39 | B | N |
| ATOM | 3421 | CA | TYR | B | 423 | 16.185 | 21.237 | 22.786 | 1.00 | 35.65 | B | C |
| ATOM | 3422 | CB | TYR | B | 423 | 17.085 | 20.144 | 23.323 | 1.00 | 40.41 | B | C |
| ATOM | 3423 | CG | TYR | B | 423 | 17.856 | 19.485 | 22.211 | 1.00 | 43.35 | B | C |
| ATOM | 3424 | CD1 | TYR | B | 423 | 17.482 | 18.245 | 21.722 | 1.00 | 37.50 | B | C |
| ATOM | 3425 | CE1 | TYR | B | 423 | 18.179 | 17.649 | 20.697 | 1.00 | 37.38 | B | C |
| ATOM | 3426 | CD2 | TYR | B | 423 | 18.943 | 20.130 | 21.615 | 1.00 | 39.34 | B | C |
| ATOM | 3427 | CE2 | TYR | B | 423 | 19.651 | 19.534 | 20.587 | 1.00 | 38.36 | B | C |
| ATOM | 3428 | CZ | TYR | B | 423 | 19.263 | 18.299 | 20.126 | 1.00 | 39.14 | B | C |
| ATOM | 3429 | OH | TYR | B | 423 | 19.964 | 17.701 | 19.106 | 1.00 | 32.27 | B | O |
| ATOM | 3430 | C | TYR | B | 423 | 15.288 | 20.621 | 21.760 | 1.00 | 40.86 | B | C |
| ATOM | 3431 | O | TYR | B | 423 | 14.314 | 19.941 | 22.100 | 1.00 | 44.88 | B | O |
| ATOM | 3432 | N | ARG | B | 424 | 15.621 | 20.845 | 20.501 | 1.00 | 37.73 | B | N |
| ATOM | 3433 | CA | ARG | B | 424 | 14.796 | 20.380 | 19.415 | 1.00 | 41.11 | B | C |
| ATOM | 3434 | CB | ARG | B | 424 | 13.683 | 21.392 | 19.122 | 1.00 | 41.89 | B | C |
| ATOM | 3435 | CG | ARG | B | 424 | 12.771 | 20.938 | 17.998 | 1.00 | 43.79 | B | C |
| ATOM | 3436 | CD | ARG | B | 424 | 11.867 | 22.039 | 17.491 | 1.00 | 53.41 | B | C |
| ATOM | 3437 | NE | ARG | B | 424 | 12.597 | 23.173 | 16.921 | 1.00 | 55.24 | B | N |
| ATOM | 3438 | CZ | ARG | B | 424 | 12.866 | 23.319 | 15.626 | 1.00 | 54.90 | B | C |
| ATOM | 3439 | NH1 | ARG | B | 424 | 12.478 | 22.383 | 14.759 | 1.00 | 55.37 | B | N |
| ATOM | 3440 | NH2 | ARG | B | 424 | 13.521 | 24.401 | 15.198 | 1.00 | 47.69 | B | N |
| ATOM | 3441 | C | ARG | B | 424 | 15.638 | 20.199 | 18.166 | 1.00 | 41.08 | B | C |
| ATOM | 3442 | O | ARG | B | 424 | 16.002 | 21.172 | 17.519 | 1.00 | 39.68 | B | O |
| ATOM | 3443 | N | PHE | B | 425 | 15.916 | 18.952 | 17.818 | 1.00 | 41.93 | B | N |
| ATOM | 3444 | CA | PHE | B | 425 | 16.744 | 18.648 | 16.659 | 1.00 | 37.65 | B | C |
| ATOM | 3445 | CB | PHE | B | 425 | 17.153 | 17.178 | 16.694 | 1.00 | 42.16 | B | C |
| ATOM | 3446 | CG | PHE | B | 425 | 17.997 | 16.770 | 15.542 | 1.00 | 39.36 | B | C |
| ATOM | 3447 | CD1 | PHE | B | 425 | 19.376 | 16.926 | 15.587 | 1.00 | 44.56 | B | C |
| ATOM | 3448 | CD2 | PHE | B | 425 | 17.418 | 16.250 | 14.402 | 1.00 | 40.07 | B | C |
| ATOM | 3449 | CE1 | PHE | B | 425 | 20.163 | 16.570 | 14.504 | 1.00 | 46.39 | B | C |
| ATOM | 3450 | CE2 | PHE | B | 425 | 18.199 | 15.888 | 13.319 | 1.00 | 48.81 | B | C |
| ATOM | 3451 | CZ | PHE | B | 425 | 19.575 | 16.047 | 13.375 | 1.00 | 47.79 | B | C |
| ATOM | 3452 | C | PHE | B | 425 | 16.067 | 18.993 | 15.326 | 1.00 | 37.74 | B | C |
| ATOM | 3453 | O | PHE | B | 425 | 14.929 | 18.601 | 15.069 | 1.00 | 42.44 | B | O |
| ATOM | 3454 | N | THR | B | 426 | 16.774 | 19.743 | 14.487 | 1.00 | 41.03 | B | N |
| ATOM | 3455 | CA | THR | B | 426 | 16.342 | 20.005 | 13.110 | 1.00 | 42.02 | B | C |
| ATOM | 3456 | CB | THR | B | 426 | 15.735 | 21.430 | 12.944 | 1.00 | 40.51 | B | C |
| ATOM | 3457 | OG1 | THR | B | 426 | 15.104 | 21.553 | 11.656 | 1.00 | 35.09 | B | O |
| ATOM | 3458 | CG2 | THR | B | 426 | 16.802 | 22.509 | 13.088 | 1.00 | 35.93 | B | C |
| ATOM | 3459 | C | THR | B | 426 | 17.508 | 19.832 | 12.129 | 1.00 | 43.76 | B | C |
| ATOM | 3460 | O | THR | B | 426 | 18.678 | 19.899 | 12.517 | 1.00 | 37.99 | B | O |
| ATOM | 3461 | N | GLU | B | 427 | 17.175 | 19.594 | 10.864 | 1.00 | 47.40 | B | N |

TABLE 12-continued

Coordinates for pro MMP9(35-444 ΔFnII) (SEQ ID NO: 12) complex with Example 2

| ATOM | 3462 | CA  | GLU | B | 427 | 18.155 | 19.540 | 9.785  | 1.00 | 45.24 | B | C |
| ---- | ---- | --- | --- | - | --- | ------ | ------ | ------ | ---- | ----- | - | - |
| ATOM | 3463 | CB  | GLU | B | 427 | 17.763 | 18.469 | 8.770  | 1.00 | 50.25 | B | C |
| ATOM | 3464 | CG  | GLU | B | 427 | 17.391 | 17.124 | 9.365  | 1.00 | 58.90 | B | C |
| ATOM | 3465 | CD  | GLU | B | 427 | 18.469 | 16.068 | 9.184  | 1.00 | 56.72 | B | C |
| ATOM | 3466 | OE1 | GLU | B | 427 | 19.539 | 16.171 | 9.825  | 1.00 | 61.62 | B | O |
| ATOM | 3467 | OE2 | GLU | B | 427 | 18.235 | 15.123 | 8.403  | 1.00 | 55.13 | B | O |
| ATOM | 3468 | C   | GLU | B | 427 | 18.184 | 20.886 | 9.062  | 1.00 | 46.83 | B | C |
| ATOM | 3469 | O   | GLU | B | 427 | 19.130 | 21.187 | 8.299  | 1.00 | 42.48 | B | O |
| ATOM | 3470 | N   | GLY | B | 428 | 17.130 | 21.674 | 9.282  | 1.00 | 31.53 | B | N |
| ATOM | 3471 | CA  | GLY | B | 428 | 16.942 | 22.930 | 8.581  | 1.00 | 31.53 | B | C |
| ATOM | 3472 | C   | GLY | B | 428 | 17.801 | 24.062 | 9.110  | 1.00 | 28.85 | B | C |
| ATOM | 3473 | O   | GLY | B | 428 | 18.440 | 23.931 | 10.163 | 1.00 | 30.01 | B | O |
| ATOM | 3474 | N   | PRO | B | 429 | 17.809 | 25.192 | 8.391  | 1.00 | 23.94 | B | N |
| ATOM | 3475 | CD  | PRO | B | 429 | 16.997 | 25.457 | 7.203  | 1.00 | 22.51 | B | C |
| ATOM | 3476 | CA  | PRO | B | 429 | 18.495 | 26.391 | 8.874  | 1.00 | 25.81 | B | C |
| ATOM | 3477 | CB  | PRO | B | 429 | 18.016 | 27.483 | 7.912  | 1.00 | 22.99 | B | C |
| ATOM | 3478 | CG  | PRO | B | 429 | 17.578 | 26.710 | 6.694  | 1.00 | 26.40 | B | C |
| ATOM | 3479 | C   | PRO | B | 429 | 17.976 | 26.683 | 10.270 | 1.00 | 25.78 | B | C |
| ATOM | 3480 | O   | PRO | B | 429 | 16.767 | 26.840 | 10.457 | 1.00 | 31.58 | B | O |
| ATOM | 3481 | N   | PRO | B | 430 | 18.878 | 26.758 | 11.236 | 1.00 | 27.15 | B | N |
| ATOM | 3482 | CD  | PRO | B | 430 | 20.336 | 26.636 | 11.045 | 1.00 | 24.41 | B | C |
| ATOM | 3483 | CA  | PRO | B | 430 | 18.516 | 27.006 | 12.636 | 1.00 | 29.50 | B | C |
| ATOM | 3484 | CB  | PRO | B | 430 | 19.867 | 26.909 | 13.365 | 1.00 | 33.21 | B | C |
| ATOM | 3485 | CG  | PRO | B | 430 | 20.799 | 26.159 | 12.366 | 1.00 | 25.62 | B | C |
| ATOM | 3486 | C   | PRO | B | 430 | 17.848 | 28.370 | 12.896 | 1.00 | 36.36 | B | C |
| ATOM | 3487 | O   | PRO | B | 430 | 16.947 | 28.413 | 13.728 | 1.00 | 35.88 | B | O |
| ATOM | 3488 | N   | LEU | B | 431 | 18.261 | 29.457 | 12.243 | 1.00 | 26.72 | B | N |
| ATOM | 3489 | CA  | LEU | B | 431 | 17.698 | 30.759 | 12.598 | 1.00 | 29.21 | B | C |
| ATOM | 3490 | CB  | LEU | B | 431 | 18.506 | 31.909 | 11.991 | 1.00 | 31.16 | B | C |
| ATOM | 3491 | CG  | LEU | B | 431 | 19.935 | 32.097 | 12.489 | 1.00 | 35.04 | B | C |
| ATOM | 3492 | CD1 | LEU | B | 431 | 20.520 | 33.336 | 11.872 | 1.00 | 23.70 | B | C |
| ATOM | 3493 | CD2 | LEU | B | 431 | 19.970 | 32.183 | 14.006 | 1.00 | 27.87 | B | C |
| ATOM | 3494 | C   | LEU | B | 431 | 16.265 | 30.896 | 12.111 | 1.00 | 30.49 | B | C |
| ATOM | 3495 | O   | LEU | B | 431 | 15.949 | 30.488 | 10.990 | 1.00 | 27.06 | B | O |
| ATOM | 3496 | N   | HIS | B | 432 | 15.412 | 31.504 | 12.934 | 1.00 | 31.54 | B | N |
| ATOM | 3497 | CA  | HIS | B | 432 | 14.067 | 31.887 | 12.493 | 1.00 | 27.52 | B | C |
| ATOM | 3498 | CB  | HIS | B | 432 | 13.021 | 31.125 | 13.309 | 1.00 | 31.55 | B | C |
| ATOM | 3499 | CG  | HIS | B | 432 | 12.848 | 29.699 | 12.881 | 1.00 | 28.77 | B | C |
| ATOM | 3500 | CD2 | HIS | B | 432 | 11.915 | 29.112 | 12.096 | 1.00 | 30.65 | B | C |
| ATOM | 3501 | ND1 | HIS | B | 432 | 13.717 | 28.697 | 13.261 | 1.00 | 29.33 | B | N |
| ATOM | 3502 | CE1 | HIS | B | 432 | 13.319 | 27.551 | 12.734 | 1.00 | 33.00 | B | C |
| ATOM | 3503 | NE2 | HIS | B | 432 | 12.229 | 27.775 | 12.022 | 1.00 | 27.70 | B | N |
| ATOM | 3504 | C   | HIS | B | 432 | 13.831 | 33.405 | 12.580 | 1.00 | 23.89 | B | C |
| ATOM | 3505 | O   | HIS | B | 432 | 14.578 | 34.121 | 13.247 | 1.00 | 24.79 | B | O |
| ATOM | 3506 | N   | LYS | B | 433 | 12.777 | 33.885 | 11.929 | 1.00 | 25.84 | B | N |
| ATOM | 3507 | CA  | LYS | B | 433 | 12.457 | 35.315 | 11.938 | 1.00 | 27.89 | B | C |
| ATOM | 3508 | CB  | LYS | B | 433 | 11.037 | 35.558 | 11.422 | 1.00 | 26.05 | B | C |
| ATOM | 3509 | CG  | LYS | B | 433 | 10.819 | 35.221 | 9.955  | 1.00 | 34.94 | B | C |
| ATOM | 3510 | CD  | LYS | B | 433 | 9.353  | 35.319 | 9.559  | 1.00 | 35.41 | B | C |
| ATOM | 3511 | CE  | LYS | B | 433 | 9.151  | 35.007 | 8.087  | 1.00 | 35.38 | B | C |
| ATOM | 3512 | NZ  | LYS | B | 433 | 9.425  | 36.203 | 7.247  | 1.00 | 34.82 | B | N |
| ATOM | 3513 | C   | LYS | B | 433 | 12.571 | 35.905 | 13.327 | 1.00 | 27.17 | B | C |
| ATOM | 3514 | O   | LYS | B | 433 | 13.058 | 37.028 | 13.502 | 1.00 | 29.29 | B | O |
| ATOM | 3515 | N   | ASP | B | 434 | 12.145 | 35.143 | 14.330 | 1.00 | 25.80 | B | N |
| ATOM | 3516 | CA  | ASP | B | 434 | 12.099 | 35.683 | 15.701 | 1.00 | 30.13 | B | C |
| ATOM | 3517 | CB  | ASP | B | 434 | 11.186 | 34.867 | 16.662 | 1.00 | 23.63 | B | C |
| ATOM | 3518 | CG  | ASP | B | 434 | 10.951 | 35.604 | 17.975 | 1.00 | 22.61 | B | C |
| ATOM | 3519 | OD1 | ASP | B | 434 | 10.276 | 36.676 | 17.960 | 1.00 | 25.59 | B | O |
| ATOM | 3520 | OD2 | ASP | B | 434 | 11.499 | 35.164 | 18.999 | 1.00 | 23.53 | B | O |
| ATOM | 3521 | C   | ASP | B | 434 | 13.480 | 35.877 | 16.306 | 1.00 | 26.91 | B | C |
| ATOM | 3522 | O   | ASP | B | 434 | 13.722 | 36.834 | 17.039 | 1.00 | 28.29 | B | O |
| ATOM | 3523 | N   | ASP | B | 435 | 14.374 | 34.948 | 16.013 | 1.00 | 28.16 | B | N |
| ATOM | 3524 | CA  | ASP | B | 435 | 15.783 | 35.115 | 16.332 | 1.00 | 30.27 | B | C |
| ATOM | 3525 | CB  | ASP | B | 435 | 16.529 | 33.855 | 15.928 | 1.00 | 31.09 | B | C |
| ATOM | 3526 | CG  | ASP | B | 435 | 15.925 | 32.607 | 16.536 | 1.00 | 30.39 | B | C |
| ATOM | 3527 | OD1 | ASP | B | 435 | 15.911 | 32.491 | 17.789 | 1.00 | 29.43 | B | O |
| ATOM | 3528 | OD2 | ASP | B | 435 | 15.492 | 31.738 | 15.758 | 1.00 | 28.40 | B | O |
| ATOM | 3529 | C   | ASP | B | 435 | 16.413 | 36.335 | 15.635 | 1.00 | 19.99 | B | C |
| ATOM | 3530 | O   | ASP | B | 435 | 17.167 | 37.084 | 16.245 | 1.00 | 27.70 | B | O |
| ATOM | 3531 | N   | VAL | B | 436 | 16.099 | 36.546 | 14.373 | 1.00 | 24.03 | B | N |
| ATOM | 3532 | CA  | VAL | B | 436 | 16.714 | 37.665 | 13.644 | 1.00 | 27.92 | B | C |
| ATOM | 3533 | CB  | VAL | B | 436 | 16.443 | 37.579 | 12.118 | 1.00 | 27.14 | B | C |
| ATOM | 3534 | CG1 | VAL | B | 436 | 17.001 | 38.786 | 11.392 | 1.00 | 27.02 | B | C |
| ATOM | 3535 | CG2 | VAL | B | 436 | 17.043 | 36.297 | 11.546 | 1.00 | 28.95 | B | C |
| ATOM | 3536 | C   | VAL | B | 436 | 16.234 | 38.997 | 14.209 | 1.00 | 31.84 | B | C |
| ATOM | 3537 | O   | VAL | B | 436 | 17.033 | 39.897 | 14.521 | 1.00 | 27.16 | B | O |
| ATOM | 3538 | N   | ASN | B | 437 | 14.916 | 39.115 | 14.361 | 1.00 | 31.95 | B | N |

TABLE 12-continued

Coordinates for pro MMP9(35-444 ΔFnII) (SEQ ID NO: 12) complex with Example 2

| ATOM | 3539 | CA  | ASN | B | 437 | 14.333 | 40.309 | 14.974 | 1.00 | 28.82 | B | C  |
|------|------|-----|-----|---|-----|--------|--------|--------|------|-------|---|----|
| ATOM | 3540 | CB  | ASN | B | 437 | 12.823 | 40.133 | 15.158 | 1.00 | 32.65 | B | C  |
| ATOM | 3541 | CG  | ASN | B | 437 | 12.094 | 40.041 | 13.844 | 1.00 | 34.13 | B | C  |
| ATOM | 3542 | OD1 | ASN | B | 437 | 12.465 | 40.688 | 12.858 | 1.00 | 35.07 | B | O  |
| ATOM | 3543 | ND2 | ASN | B | 437 | 11.034 | 39.248 | 13.821 | 1.00 | 38.57 | B | N  |
| ATOM | 3544 | C   | ASN | B | 437 | 14.977 | 40.605 | 16.298 | 1.00 | 19.64 | B | C  |
| ATOM | 3545 | O   | ASN | B | 437 | 15.404 | 41.715 | 16.551 | 1.00 | 27.86 | B | O  |
| ATOM | 3546 | N   | GLY | B | 438 | 15.051 | 39.605 | 17.151 | 1.00 | 19.87 | B | N  |
| ATOM | 3547 | CA  | GLY | B | 438 | 15.685 | 39.802 | 18.442 | 1.00 | 22.69 | B | C  |
| ATOM | 3548 | C   | GLY | B | 438 | 17.097 | 40.337 | 18.260 | 1.00 | 28.94 | B | C  |
| ATOM | 3549 | O   | GLY | B | 438 | 17.526 | 41.302 | 18.903 | 1.00 | 25.63 | B | O  |
| ATOM | 3550 | N   | ILE | B | 439 | 17.842 | 39.736 | 17.346 | 1.00 | 31.08 | B | N  |
| ATOM | 3551 | CA  | ILE | B | 439 | 19.247 | 40.143 | 17.249 | 1.00 | 28.32 | B | C  |
| ATOM | 3552 | CB  | ILE | B | 439 | 20.108 | 39.117 | 16.489 | 1.00 | 26.70 | B | C  |
| ATOM | 3553 | CG2 | ILE | B | 439 | 19.835 | 39.185 | 14.990 | 1.00 | 23.81 | B | C  |
| ATOM | 3554 | CG1 | ILE | B | 439 | 21.577 | 39.275 | 16.900 | 1.00 | 24.32 | B | C  |
| ATOM | 3555 | CD1 | ILE | B | 439 | 21.792 | 39.033 | 18.376 | 1.00 | 25.13 | B | C  |
| ATOM | 3556 | C   | ILE | B | 439 | 19.332 | 41.539 | 16.658 | 1.00 | 23.79 | B | C  |
| ATOM | 3557 | O   | ILE | B | 439 | 20.128 | 42.356 | 17.100 | 1.00 | 30.30 | B | O  |
| ATOM | 3558 | N   | ARG | B | 440 | 18.476 | 41.843 | 15.698 | 1.00 | 26.32 | B | N  |
| ATOM | 3559 | CA  | ARG | B | 440 | 18.511 | 43.177 | 15.130 | 1.00 | 26.31 | B | C  |
| ATOM | 3560 | CB  | ARG | B | 440 | 17.645 | 43.276 | 13.890 | 1.00 | 28.74 | B | C  |
| ATOM | 3561 | CG  | ARG | B | 440 | 18.211 | 42.518 | 12.722 | 1.00 | 28.48 | B | C  |
| ATOM | 3562 | CD  | ARG | B | 440 | 17.453 | 42.780 | 11.465 | 1.00 | 35.18 | B | C  |
| ATOM | 3563 | NE  | ARG | B | 440 | 17.744 | 41.768 | 10.460 | 1.00 | 34.95 | B | N  |
| ATOM | 3564 | CZ  | ARG | B | 440 | 17.278 | 41.788 | 9.215  | 1.00 | 36.37 | B | C  |
| ATOM | 3565 | NH1 | ARG | B | 440 | 16.502 | 42.784 | 8.791  | 1.00 | 33.80 | B | N  |
| ATOM | 3566 | NH2 | ARG | B | 440 | 17.609 | 40.813 | 8.382  | 1.00 | 33.22 | B | N  |
| ATOM | 3567 | C   | ARG | B | 440 | 18.105 | 44.227 | 16.145 | 1.00 | 33.33 | B | C  |
| ATOM | 3568 | O   | ARG | B | 440 | 18.507 | 45.382 | 16.039 | 1.00 | 32.00 | B | O  |
| ATOM | 3569 | N   | HIS | B | 441 | 17.307 | 43.840 | 17.136 | 1.00 | 33.60 | B | N  |
| ATOM | 3570 | CA  | HIS | B | 441 | 16.853 | 44.837 | 18.102 | 1.00 | 34.46 | B | C  |
| ATOM | 3571 | CB  | HIS | B | 441 | 15.657 | 44.342 | 18.921 | 1.00 | 36.90 | B | C  |
| ATOM | 3572 | CG  | HIS | B | 441 | 15.270 | 45.282 | 20.021 | 1.00 | 42.77 | B | C  |
| ATOM | 3573 | CD2 | HIS | B | 441 | 14.648 | 46.487 | 19.987 | 1.00 | 41.09 | B | C  |
| ATOM | 3574 | ND1 | HIS | B | 441 | 15.578 | 45.046 | 21.345 | 1.00 | 43.46 | B | N  |
| ATOM | 3575 | CE1 | HIS | B | 441 | 15.147 | 46.057 | 22.083 | 1.00 | 45.60 | B | C  |
| ATOM | 3576 | NE2 | HIS | B | 441 | 14.582 | 46.944 | 21.283 | 1.00 | 50.21 | B | N  |
| ATOM | 3577 | C   | HIS | B | 441 | 18.011 | 45.263 | 19.008 | 1.00 | 35.34 | B | C  |
| ATOM | 3578 | O   | HIS | B | 441 | 18.034 | 46.394 | 19.517 | 1.00 | 38.38 | B | O  |
| ATOM | 3579 | N   | LEU | B | 442 | 18.984 | 44.372 | 19.194 | 1.00 | 33.75 | B | N  |
| ATOM | 3580 | CA  | LEU | B | 442 | 20.206 | 44.726 | 19.934 | 1.00 | 32.13 | B | C  |
| ATOM | 3581 | CB  | LEU | B | 442 | 20.847 | 43.484 | 20.573 | 1.00 | 31.05 | B | C  |
| ATOM | 3582 | CG  | LEU | B | 442 | 20.248 | 43.004 | 21.896 | 1.00 | 35.48 | B | C  |
| ATOM | 3583 | CD1 | LEU | B | 442 | 18.726 | 42.961 | 21.850 | 1.00 | 37.69 | B | C  |
| ATOM | 3584 | CD2 | LEU | B | 442 | 20.790 | 41.655 | 22.276 | 1.00 | 34.25 | B | C  |
| ATOM | 3585 | C   | LEU | B | 442 | 21.251 | 45.476 | 19.078 | 1.00 | 34.07 | B | C  |
| ATOM | 3586 | O   | LEU | B | 442 | 21.749 | 46.527 | 19.484 | 1.00 | 38.06 | B | O  |
| ATOM | 3587 | N   | TYR | B | 443 | 21.569 | 44.941 | 17.898 | 1.00 | 32.79 | B | N  |
| ATOM | 3588 | CA  | TYR | B | 443 | 22.693 | 45.443 | 17.088 | 1.00 | 34.58 | B | C  |
| ATOM | 3589 | CB  | TYR | B | 443 | 23.695 | 44.298 | 16.815 | 1.00 | 29.55 | B | C  |
| ATOM | 3590 | CG  | TYR | B | 443 | 24.254 | 43.709 | 18.095 | 1.00 | 27.01 | B | C  |
| ATOM | 3591 | CD1 | TYR | B | 443 | 23.824 | 42.479 | 18.578 | 1.00 | 25.66 | B | C  |
| ATOM | 3592 | CE1 | TYR | B | 443 | 24.318 | 41.970 | 19.756 | 1.00 | 20.51 | B | C  |
| ATOM | 3593 | CD2 | TYR | B | 443 | 25.162 | 44.419 | 18.850 | 1.00 | 28.32 | B | C  |
| ATOM | 3594 | CE2 | TYR | B | 443 | 25.666 | 43.916 | 20.032 | 1.00 | 29.77 | B | C  |
| ATOM | 3595 | CZ  | TYR | B | 443 | 25.241 | 42.693 | 20.479 | 1.00 | 27.46 | B | C  |
| ATOM | 3596 | OH  | TYR | B | 443 | 25.774 | 42.212 | 21.663 | 1.00 | 31.04 | B | O  |
| ATOM | 3597 | C   | TYR | B | 443 | 22.303 | 46.151 | 15.785 | 1.00 | 35.90 | B | C  |
| ATOM | 3598 | O   | TYR | B | 443 | 23.150 | 46.763 | 15.115 | 1.00 | 35.10 | B | O  |
| ATOM | 3599 | N   | GLY | B | 444 | 21.033 | 46.045 | 15.409 | 1.00 | 29.94 | B | N  |
| ATOM | 3600 | CA  | GLY | B | 444 | 20.502 | 46.798 | 14.287 | 1.00 | 23.72 | B | C  |
| ATOM | 3601 | C   | GLY | B | 444 | 20.229 | 45.972 | 13.058 | 1.00 | 24.22 | B | C  |
| ATOM | 3602 | O   | GLY | B | 444 | 19.712 | 46.519 | 12.086 | 1.00 | 33.74 | B | O  |
| ATOM | 3603 | ZN  | ZN  | B | 500 | 18.926 | 29.347 | 26.591 | 1.00 | 32.37 | B | Zn |
| ATOM | 3604 | ZN  | ZN  | B | 501 | 28.572 | 27.259 | 34.032 | 1.00 | 42.34 | B | Zn |
| ATOM | 3605 | CA  | CA  | B | 502 | 22.431 | 17.803 | 31.961 | 1.00 | 41.66 | B | Ca |
| ATOM | 3606 | CA  | CA  | B | 504 | 33.866 | 36.697 | 29.276 | 1.00 | 49.72 | B | Ca |
| ATOM | 3607 | CA  | CA  | B | 505 | 32.637 | 45.904 | 25.506 | 1.00 | 54.30 | B | Ca |
| TER  | 3608 |     | CA  | B | 505 |        |        |        |      |       |   |    |
| ATOM | 3609 | C01 | LIG | C | 1   | 20.376 | 35.685 | 28.031 | 1.00 | 46.05 | A | C  |
| ATOM | 3610 | O02 | LIG | C | 1   | 20.646 | 37.080 | 28.151 | 1.00 | 52.57 | A | O  |
| ATOM | 3611 | C03 | LIG | C | 1   | 20.132 | 37.822 | 29.196 | 1.00 | 50.59 | A | C  |
| ATOM | 3612 | C04 | LIG | C | 1   | 19.422 | 39.029 | 29.001 | 1.00 | 51.04 | A | C  |
| ATOM | 3613 | C05 | LIG | C | 1   | 18.941 | 39.808 | 30.065 | 1.00 | 53.55 | A | C  |
| ATOM | 3614 | C06 | LIG | C | 1   | 19.160 | 39.419 | 31.392 | 1.00 | 57.54 | A | C  |
| ATOM | 3615 | C07 | LIG | C | 1   | 19.883 | 38.203 | 31.580 | 1.00 | 54.92 | A | C  |

TABLE 12-continued

Coordinates for pro MMP9(35-444 ΔFnII) (SEQ ID NO: 12) complex with Example 2

| | | | | | | | | | | | |
|---|---|---|---|---|---|---|---|---|---|---|---|
| ATOM | 3616 | C08 | LIG | C | 1 | 20.397 | 37.354 | 30.544 | 1.00 | 47.25 A | C |
| ATOM | 3617 | N09 | LIG | C | 1 | 21.104 | 36.090 | 30.869 | 1.00 | 48.66 A | N |
| ATOM | 3618 | C10 | LIG | C | 1 | 21.199 | 35.094 | 31.916 | 1.00 | 51.94 A | C |
| ATOM | 3619 | C11 | LIG | C | 1 | 20.523 | 35.259 | 33.182 | 1.00 | 42.58 A | C |
| ATOM | 3620 | C12 | LIG | C | 1 | 20.667 | 34.362 | 34.200 | 1.00 | 46.59 A | C |
| ATOM | 3621 | C13 | LIG | C | 1 | 21.489 | 33.217 | 34.066 | 1.00 | 46.36 A | C |
| ATOM | 3622 | C14 | LIG | C | 1 | 21.639 | 32.281 | 35.133 | 1.00 | 46.01 A | C |
| ATOM | 3623 | C15 | LIG | C | 1 | 22.417 | 31.179 | 34.989 | 1.00 | 52.78 A | C |
| ATOM | 3624 | C16 | LIG | C | 1 | 23.099 | 30.994 | 33.754 | 1.00 | 48.48 A | C |
| ATOM | 3625 | C17 | LIG | C | 1 | 22.981 | 31.886 | 32.722 | 1.00 | 44.53 A | C |
| ATOM | 3626 | C18 | LIG | C | 1 | 22.149 | 33.071 | 32.817 | 1.00 | 48.43 A | C |
| ATOM | 3627 | N19 | LIG | C | 1 | 22.023 | 33.989 | 31.739 | 1.00 | 42.50 A | N |
| ATOM | 3628 | C20 | LIG | C | 1 | 18.588 | 40.255 | 32.553 | 1.00 | 59.78 A | C |
| ATOM | 3629 | N21 | LIG | C | 1 | 17.265 | 40.099 | 32.948 | 1.00 | 61.09 A | N |
| ATOM | 3630 | O22 | LIG | C | 1 | 19.264 | 40.992 | 33.279 | 1.00 | 56.39 A | O |
| END | | | | | | | | | | | |

TABLE 13

Coordinates for proMMP9(35-444 ΔFnII) (SEQ ID NO: 12) complex with Example 3

| | | | | | | | | | | | |
|---|---|---|---|---|---|---|---|---|---|---|---|
| ATOM | 1 | N | THR | A | 40 | 3.707 | 63.329 | 27.801 | 1.00 | 65.23 A | N |
| ATOM | 2 | CA | THR | A | 40 | 5.111 | 63.406 | 27.409 | 1.00 | 56.43 A | C |
| ATOM | 3 | C | THR | A | 40 | 5.284 | 63.878 | 25.958 | 1.00 | 57.40 A | C |
| ATOM | 4 | CB | THR | A | 40 | 5.845 | 62.067 | 27.633 | 1.00 | 47.95 A | C |
| ATOM | 5 | OG1 | THR | A | 40 | 7.241 | 62.314 | 27.838 | 1.00 | 57.95 A | O |
| ATOM | 6 | CG2 | THR | A | 40 | 5.661 | 61.147 | 26.439 | 1.00 | 44.46 A | C |
| ATOM | 7 | O | THR | A | 40 | 6.406 | 64.094 | 25.499 | 1.00 | 63.74 A | O |
| ATOM | 8 | CB | ASP | A | 41 | 2.876 | 64.686 | 23.248 | 1.00 | 48.39 A | C |
| ATOM | 9 | CG | ASP | A | 41 | 2.712 | 63.464 | 22.366 | 1.00 | 54.52 A | C |
| ATOM | 10 | OD1 | ASP | A | 41 | 3.690 | 62.694 | 22.225 | 1.00 | 51.80 A | O |
| ATOM | 11 | OD2 | ASP | A | 41 | 1.610 | 63.279 | 21.804 | 1.00 | 53.68 A | O |
| ATOM | 12 | C | ASP | A | 41 | 4.631 | 66.150 | 24.272 | 1.00 | 52.10 A | C |
| ATOM | 13 | O | ASP | A | 41 | 5.612 | 66.667 | 23.751 | 1.00 | 51.97 A | O |
| ATOM | 14 | N | ASP | A | 41 | 4.182 | 64.024 | 25.230 | 1.00 | 51.04 A | N |
| ATOM | 15 | CA | ASP | A | 41 | 4.231 | 64.721 | 23.952 | 1.00 | 53.17 A | C |
| ATOM | 16 | N | ARG | A | 42 | 3.863 | 66.771 | 25.155 | 1.00 | 49.17 A | N |
| ATOM | 17 | CA | ARG | A | 42 | 4.240 | 68.030 | 25.777 | 1.00 | 52.85 A | C |
| ATOM | 18 | CB | ARG | A | 42 | 3.368 | 68.245 | 27.023 | 1.00 | 41.01 A | C |
| ATOM | 19 | CG | ARG | A | 42 | 3.845 | 69.335 | 27.960 | 1.00 | 53.00 A | C |
| ATOM | 20 | CD | ARG | A | 42 | 3.256 | 70.701 | 27.619 | 1.00 | 50.04 A | C |
| ATOM | 21 | NE | ARG | A | 42 | 3.930 | 71.767 | 28.356 | 1.00 | 49.06 A | N |
| ATOM | 22 | CZ | ARG | A | 42 | 3.431 | 72.983 | 28.562 | 1.00 | 51.93 A | C |
| ATOM | 23 | NH1 | ARG | A | 42 | 2.225 | 73.308 | 28.105 | 1.00 | 53.17 A | N |
| ATOM | 24 | NH2 | ARG | A | 42 | 4.144 | 73.875 | 29.233 | 1.00 | 47.20 A | N |
| ATOM | 25 | C | ARG | A | 42 | 5.734 | 68.051 | 26.152 | 1.00 | 49.50 A | C |
| ATOM | 26 | O | ARG | A | 42 | 6.405 | 69.071 | 25.997 | 1.00 | 44.17 A | O |
| ATOM | 27 | N | GLN | A | 43 | 6.238 | 66.919 | 26.642 | 1.00 | 51.53 A | N |
| ATOM | 28 | CA | GLN | A | 43 | 7.625 | 66.782 | 27.102 | 1.00 | 48.90 A | C |
| ATOM | 29 | CB | GLN | A | 43 | 7.793 | 65.464 | 27.868 | 1.00 | 54.47 A | C |
| ATOM | 30 | CG | GLN | A | 43 | 7.214 | 65.410 | 29.305 | 1.00 | 62.36 A | C |
| ATOM | 31 | CD | GLN | A | 43 | 5.885 | 66.144 | 29.493 | 1.00 | 65.21 A | C |
| ATOM | 32 | OE1 | GLN | A | 43 | 4.865 | 65.789 | 28.894 | 1.00 | 63.86 A | O |
| ATOM | 33 | NE2 | GLN | A | 43 | 5.892 | 67.162 | 30.351 | 1.00 | 58.16 A | N |
| ATOM | 34 | C | GLN | A | 43 | 8.592 | 66.797 | 25.917 | 1.00 | 51.40 A | C |
| ATOM | 35 | O | GLN | A | 43 | 9.657 | 67.409 | 25.962 | 1.00 | 47.08 A | O |
| ATOM | 36 | N | LEU | A | 44 | 8.201 | 66.098 | 24.858 | 1.00 | 53.65 A | N |
| ATOM | 37 | CA | LEU | A | 44 | 8.953 | 66.048 | 23.617 | 1.00 | 45.75 A | C |
| ATOM | 38 | CB | LEU | A | 44 | 8.167 | 65.224 | 22.603 | 1.00 | 45.32 A | C |
| ATOM | 39 | CG | LEU | A | 44 | 8.902 | 64.533 | 21.466 | 1.00 | 38.28 A | C |
| ATOM | 40 | CD1 | LEU | A | 44 | 9.509 | 63.235 | 21.970 | 1.00 | 39.36 A | C |
| ATOM | 41 | CD2 | LEU | A | 44 | 7.938 | 64.266 | 20.328 | 1.00 | 37.71 A | C |
| ATOM | 42 | C | LEU | A | 44 | 9.173 | 67.453 | 23.062 | 1.00 | 40.29 A | C |
| ATOM | 43 | O | LEU | A | 44 | 10.231 | 67.758 | 22.526 | 1.00 | 43.14 A | O |
| ATOM | 44 | N | ALA | A | 45 | 8.165 | 68.304 | 23.200 | 1.00 | 37.38 A | N |
| ATOM | 45 | CA | ALA | A | 45 | 8.202 | 69.650 | 22.647 | 1.00 | 38.15 A | C |
| ATOM | 46 | CB | ALA | A | 45 | 6.812 | 70.232 | 22.602 | 1.00 | 40.95 A | C |
| ATOM | 47 | C | ALA | A | 45 | 9.141 | 70.580 | 23.410 | 1.00 | 44.99 A | C |
| ATOM | 48 | O | ALA | A | 45 | 9.820 | 71.414 | 22.815 | 1.00 | 46.69 A | O |
| ATOM | 49 | N | GLU | A | 46 | 9.191 | 70.433 | 24.726 | 1.00 | 45.22 A | N |
| ATOM | 50 | CA | GLU | A | 46 | 10.050 | 71.285 | 25.538 | 1.00 | 44.34 A | C |
| ATOM | 51 | CB | GLU | A | 46 | 9.692 | 71.124 | 27.019 | 1.00 | 44.15 A | C |
| ATOM | 52 | CG | GLU | A | 46 | 8.385 | 71.828 | 27.386 | 1.00 | 47.21 A | C |

TABLE 13-continued

Coordinates for proMMP9(35-444 ΔFnII) (SEQ ID NO: 12) complex with Example 3

| ATOM | 53 | CD | GLU | A | 46 | 7.645 | 71.193 | 28.563 | 1.00 | 58.84 | A | C |
|---|---|---|---|---|---|---|---|---|---|---|---|---|
| ATOM | 54 | OE1 | GLU | A | 46 | 8.281 | 70.551 | 29.428 | 1.00 | 66.08 | A | O |
| ATOM | 55 | OE2 | GLU | A | 46 | 6.409 | 71.350 | 28.627 | 1.00 | 57.46 | A | O |
| ATOM | 56 | C | GLU | A | 46 | 11.540 | 71.018 | 25.283 | 1.00 | 44.91 | A | C |
| ATOM | 57 | O | GLU | A | 46 | 12.347 | 71.950 | 25.183 | 1.00 | 43.32 | A | O |
| ATOM | 58 | N | GLU | A | 47 | 11.887 | 69.740 | 25.171 | 1.00 | 41.42 | A | N |
| ATOM | 59 | CA | GLU | A | 47 | 13.264 | 69.311 | 24.987 | 1.00 | 43.32 | A | C |
| ATOM | 60 | CB | GLU | A | 47 | 13.383 | 67.812 | 25.301 | 1.00 | 49.05 | A | C |
| ATOM | 61 | CG | GLU | A | 47 | 14.672 | 67.144 | 24.839 | 1.00 | 51.28 | A | C |
| ATOM | 62 | CD | GLU | A | 47 | 15.921 | 67.781 | 25.426 | 1.00 | 59.60 | A | C |
| ATOM | 63 | OE1 | GLU | A | 47 | 15.867 | 68.273 | 26.578 | 1.00 | 61.96 | A | O |
| ATOM | 64 | OE2 | GLU | A | 47 | 16.961 | 67.786 | 24.731 | 1.00 | 54.90 | A | O |
| ATOM | 65 | C | GLU | A | 47 | 13.710 | 69.605 | 23.561 | 1.00 | 48.70 | A | C |
| ATOM | 66 | O | GLU | A | 47 | 14.872 | 69.925 | 23.303 | 1.00 | 44.84 | A | O |
| ATOM | 67 | N | TYR | A | 48 | 12.767 | 69.511 | 22.635 | 1.00 | 47.27 | A | N |
| ATOM | 68 | CA | TYR | A | 48 | 13.035 | 69.817 | 21.243 | 1.00 | 36.23 | A | C |
| ATOM | 69 | CB | TYR | A | 48 | 11.916 | 69.259 | 20.389 | 1.00 | 38.13 | A | C |
| ATOM | 70 | CG | TYR | A | 48 | 12.139 | 69.351 | 18.914 | 1.00 | 34.88 | A | C |
| ATOM | 71 | CD1 | TYR | A | 48 | 12.052 | 70.572 | 18.248 | 1.00 | 34.98 | A | C |
| ATOM | 72 | CE1 | TYR | A | 48 | 12.240 | 70.647 | 16.876 | 1.00 | 36.21 | A | C |
| ATOM | 73 | CD2 | TYR | A | 48 | 12.393 | 68.213 | 18.171 | 1.00 | 33.55 | A | C |
| ATOM | 74 | CE2 | TYR | A | 48 | 12.580 | 68.279 | 16.809 | 1.00 | 32.78 | A | C |
| ATOM | 75 | CZ | TYR | A | 48 | 12.502 | 69.494 | 16.165 | 1.00 | 31.59 | A | C |
| ATOM | 76 | OH | TYR | A | 48 | 12.690 | 69.542 | 14.809 | 1.00 | 34.86 | A | O |
| ATOM | 77 | C | TYR | A | 48 | 13.126 | 71.317 | 21.044 | 1.00 | 40.70 | A | C |
| ATOM | 78 | O | TYR | A | 48 | 14.001 | 71.798 | 20.336 | 1.00 | 46.73 | A | O |
| ATOM | 79 | N | LEU | A | 49 | 12.220 | 72.070 | 21.650 | 1.00 | 39.93 | A | N |
| ATOM | 80 | CA | LEU | A | 49 | 12.303 | 73.515 | 21.518 | 1.00 | 42.14 | A | C |
| ATOM | 81 | CB | LEU | A | 49 | 11.097 | 74.204 | 22.142 | 1.00 | 40.66 | A | C |
| ATOM | 82 | CG | LEU | A | 49 | 9.752 | 74.009 | 21.448 | 1.00 | 40.53 | A | C |
| ATOM | 83 | CD1 | LEU | A | 49 | 8.636 | 74.595 | 22.310 | 1.00 | 36.70 | A | C |
| ATOM | 84 | CD2 | LEU | A | 49 | 9.769 | 74.625 | 20.066 | 1.00 | 36.54 | A | C |
| ATOM | 85 | C | LEU | A | 49 | 13.582 | 74.009 | 22.172 | 1.00 | 43.88 | A | C |
| ATOM | 86 | O | LEU | A | 49 | 14.243 | 74.921 | 21.664 | 1.00 | 41.86 | A | O |
| ATOM | 87 | N | TYR | A | 50 | 13.941 | 73.410 | 23.301 | 1.00 | 45.31 | A | N |
| ATOM | 88 | CA | TYR | A | 50 | 15.121 | 73.882 | 24.013 | 1.00 | 44.52 | A | C |
| ATOM | 89 | CB | TYR | A | 50 | 15.235 | 73.292 | 25.428 | 1.00 | 39.30 | A | C |
| ATOM | 90 | CG | TYR | A | 50 | 16.641 | 73.371 | 25.971 | 1.00 | 38.74 | A | C |
| ATOM | 91 | CD1 | TYR | A | 50 | 17.109 | 74.527 | 26.583 | 1.00 | 42.78 | A | C |
| ATOM | 92 | CE1 | TYR | A | 50 | 18.408 | 74.611 | 27.061 | 1.00 | 38.89 | A | C |
| ATOM | 93 | CD2 | TYR | A | 50 | 17.518 | 72.298 | 25.833 | 1.00 | 46.42 | A | C |
| ATOM | 94 | CE2 | TYR | A | 50 | 18.821 | 72.370 | 26.303 | 1.00 | 42.93 | A | C |
| ATOM | 95 | CZ | TYR | A | 50 | 19.257 | 73.529 | 26.919 | 1.00 | 45.61 | A | C |
| ATOM | 96 | OH | TYR | A | 50 | 20.549 | 73.600 | 27.390 | 1.00 | 52.91 | A | O |
| ATOM | 97 | C | TYR | A | 50 | 16.340 | 73.537 | 23.195 | 1.00 | 38.67 | A | C |
| ATOM | 98 | O | TYR | A | 50 | 17.150 | 74.399 | 22.882 | 1.00 | 41.01 | A | O |
| ATOM | 99 | N | ARG | A | 51 | 16.438 | 72.263 | 22.838 | 1.00 | 41.08 | A | N |
| ATOM | 100 | CA | ARG | A | 51 | 17.605 | 71.724 | 22.160 | 1.00 | 37.70 | A | C |
| ATOM | 101 | CB | ARG | A | 51 | 17.371 | 70.255 | 21.805 | 1.00 | 35.94 | A | C |
| ATOM | 102 | CG | ARG | A | 51 | 18.378 | 69.677 | 20.844 | 1.00 | 40.07 | A | C |
| ATOM | 103 | CD | ARG | A | 51 | 17.995 | 68.272 | 20.403 | 1.00 | 40.13 | A | C |
| ATOM | 104 | NE | ARG | A | 51 | 18.320 | 67.268 | 21.413 | 1.00 | 44.72 | A | N |
| ATOM | 105 | CZ | ARG | A | 51 | 19.548 | 66.813 | 21.647 | 1.00 | 44.49 | A | C |
| ATOM | 106 | NH1 | ARG | A | 51 | 20.572 | 67.286 | 20.944 | 1.00 | 45.84 | A | N |
| ATOM | 107 | NH2 | ARG | A | 51 | 19.756 | 65.896 | 22.589 | 1.00 | 36.35 | A | N |
| ATOM | 108 | C | ARG | A | 51 | 17.978 | 72.510 | 20.909 | 1.00 | 42.20 | A | C |
| ATOM | 109 | O | ARG | A | 51 | 19.153 | 72.815 | 20.698 | 1.00 | 48.01 | A | O |
| ATOM | 110 | N | TYR | A | 52 | 16.991 | 72.845 | 20.084 | 1.00 | 34.17 | A | N |
| ATOM | 111 | CA | TYR | A | 52 | 17.291 | 73.442 | 18.789 | 1.00 | 35.47 | A | C |
| ATOM | 112 | CB | TYR | A | 52 | 16.398 | 72.841 | 17.708 | 1.00 | 35.15 | A | C |
| ATOM | 113 | CG | TYR | A | 52 | 16.722 | 71.388 | 17.508 | 1.00 | 34.30 | A | C |
| ATOM | 114 | CD1 | TYR | A | 52 | 15.791 | 70.411 | 17.776 | 1.00 | 34.22 | A | C |
| ATOM | 115 | CE1 | TYR | A | 52 | 16.093 | 69.080 | 17.622 | 1.00 | 35.92 | A | C |
| ATOM | 116 | CD2 | TYR | A | 52 | 17.991 | 70.993 | 17.107 | 1.00 | 35.72 | A | C |
| ATOM | 117 | CE2 | TYR | A | 52 | 18.309 | 69.660 | 16.949 | 1.00 | 34.68 | A | C |
| ATOM | 118 | CZ | TYR | A | 52 | 17.351 | 68.709 | 17.207 | 1.00 | 40.38 | A | C |
| ATOM | 119 | OH | TYR | A | 52 | 17.645 | 67.377 | 17.058 | 1.00 | 42.46 | A | O |
| ATOM | 120 | C | TYR | A | 52 | 17.323 | 74.971 | 18.742 | 1.00 | 39.45 | A | C |
| ATOM | 121 | O | TYR | A | 52 | 17.451 | 75.562 | 17.667 | 1.00 | 36.86 | A | O |
| ATOM | 122 | N | GLY | A | 53 | 17.234 | 75.605 | 19.909 | 1.00 | 38.15 | A | N |
| ATOM | 123 | CA | GLY | A | 53 | 17.515 | 77.028 | 20.020 | 1.00 | 37.95 | A | C |
| ATOM | 124 | C | GLY | A | 53 | 16.310 | 77.936 | 20.156 | 1.00 | 42.61 | A | C |
| ATOM | 125 | O | GLY | A | 53 | 16.452 | 79.141 | 20.332 | 1.00 | 47.74 | A | O |
| ATOM | 126 | N | TYR | A | 54 | 15.120 | 77.352 | 20.103 | 1.00 | 46.81 | A | N |
| ATOM | 127 | CA | TYR | A | 54 | 13.881 | 78.124 | 20.086 | 1.00 | 45.99 | A | C |
| ATOM | 128 | CB | TYR | A | 54 | 12.750 | 77.251 | 19.573 | 1.00 | 40.94 | A | C |
| ATOM | 129 | CG | TYR | A | 54 | 13.018 | 76.671 | 18.213 | 1.00 | 39.27 | A | C |

TABLE 13-continued

Coordinates for proMMP9(35-444 ΔFnII) (SEQ ID NO: 12) complex with Example 3

| ATOM | 130 | CD1 | TYR | A | 54 | 13.372 | 75.340 | 18.066 | 1.00 | 36.86 | A | C |
|---|---|---|---|---|---|---|---|---|---|---|---|---|
| ATOM | 131 | CE1 | TYR | A | 54 | 13.607 | 74.804 | 16.826 | 1.00 | 37.65 | A | C |
| ATOM | 132 | CD2 | TYR | A | 54 | 12.911 | 77.454 | 17.073 | 1.00 | 37.01 | A | C |
| ATOM | 133 | CE2 | TYR | A | 54 | 13.145 | 76.927 | 15.828 | 1.00 | 38.04 | A | C |
| ATOM | 134 | CZ | TYR | A | 54 | 13.491 | 75.604 | 15.714 | 1.00 | 37.87 | A | C |
| ATOM | 135 | OH | TYR | A | 54 | 13.723 | 75.078 | 14.480 | 1.00 | 41.55 | A | O |
| ATOM | 136 | C | TYR | A | 54 | 13.480 | 78.768 | 21.419 | 1.00 | 45.13 | A | C |
| ATOM | 137 | O | TYR | A | 54 | 13.330 | 79.983 | 21.496 | 1.00 | 48.34 | A | O |
| ATOM | 138 | N | THR | A | 55 | 13.283 | 77.957 | 22.451 | 1.00 | 39.98 | A | N |
| ATOM | 139 | CA | THR | A | 55 | 12.883 | 78.475 | 23.749 | 1.00 | 42.41 | A | C |
| ATOM | 140 | CB | THR | A | 55 | 12.871 | 77.379 | 24.818 | 1.00 | 36.38 | A | C |
| ATOM | 141 | OG1 | THR | A | 55 | 14.215 | 77.073 | 25.189 | 1.00 | 40.11 | A | O |
| ATOM | 142 | CG2 | THR | A | 55 | 12.225 | 76.137 | 24.290 | 1.00 | 42.64 | A | C |
| ATOM | 143 | C | THR | A | 55 | 13.821 | 79.579 | 24.229 | 1.00 | 53.13 | A | C |
| ATOM | 144 | O | THR | A | 55 | 13.397 | 80.471 | 24.967 | 1.00 | 51.47 | A | O |
| ATOM | 145 | N | ARG | A | 56 | 15.088 | 79.511 | 23.809 | 1.00 | 49.05 | A | N |
| ATOM | 146 | CA | ARG | A | 56 | 16.118 | 80.454 | 24.248 | 1.00 | 45.72 | A | C |
| ATOM | 147 | CB | ARG | A | 56 | 17.508 | 79.927 | 23.874 | 1.00 | 44.73 | A | C |
| ATOM | 148 | CG | ARG | A | 56 | 17.645 | 78.396 | 23.966 | 1.00 | 54.70 | A | C |
| ATOM | 149 | CD | ARG | A | 56 | 18.930 | 77.900 | 23.294 | 1.00 | 61.19 | A | C |
| ATOM | 150 | NE | ARG | A | 56 | 19.387 | 76.606 | 23.808 | 1.00 | 64.09 | A | N |
| ATOM | 151 | CZ | ARG | A | 56 | 20.237 | 75.792 | 23.178 | 1.00 | 57.07 | A | C |
| ATOM | 152 | NH1 | ARG | A | 56 | 20.725 | 76.115 | 21.987 | 1.00 | 57.51 | A | N |
| ATOM | 153 | NH2 | ARG | A | 56 | 20.592 | 74.640 | 23.736 | 1.00 | 45.98 | A | N |
| ATOM | 154 | C | ARG | A | 56 | 15.887 | 81.835 | 23.630 | 1.00 | 50.10 | A | C |
| ATOM | 155 | O | ARG | A | 56 | 15.978 | 82.858 | 24.306 | 1.00 | 52.08 | A | O |
| ATOM | 156 | N | VAL | A | 57 | 15.585 | 81.847 | 22.336 | 1.00 | 51.08 | A | N |
| ATOM | 157 | CA | VAL | A | 57 | 15.222 | 83.060 | 21.625 | 1.00 | 49.27 | A | C |
| ATOM | 158 | CB | VAL | A | 57 | 15.099 | 82.789 | 20.103 | 1.00 | 56.69 | A | C |
| ATOM | 159 | CG1 | VAL | A | 57 | 14.731 | 84.064 | 19.340 | 1.00 | 54.91 | A | C |
| ATOM | 160 | CG2 | VAL | A | 57 | 16.394 | 82.194 | 19.566 | 1.00 | 43.94 | A | C |
| ATOM | 161 | C | VAL | A | 57 | 13.899 | 83.589 | 22.174 | 1.00 | 49.15 | A | C |
| ATOM | 162 | O | VAL | A | 57 | 13.679 | 84.796 | 22.227 | 1.00 | 52.68 | A | O |
| ATOM | 163 | N | GLY | A | 58 | 13.025 | 82.675 | 22.584 | 1.00 | 47.80 | A | N |
| ATOM | 164 | CA | GLY | A | 58 | 11.768 | 83.037 | 23.215 | 1.00 | 44.98 | A | C |
| ATOM | 165 | C | GLY | A | 58 | 12.023 | 83.814 | 24.491 | 1.00 | 53.75 | A | C |
| ATOM | 166 | O | GLY | A | 58 | 11.510 | 84.919 | 24.671 | 1.00 | 53.91 | A | O |
| ATOM | 167 | N | GLU | A | 59 | 12.826 | 83.234 | 25.379 | 1.00 | 51.54 | A | N |
| ATOM | 168 | CA | GLU | A | 59 | 13.218 | 83.901 | 26.615 | 1.00 | 49.19 | A | C |
| ATOM | 169 | C | GLU | A | 59 | 13.735 | 85.282 | 26.300 | 1.00 | 55.60 | A | C |
| ATOM | 170 | CB | GLU | A | 59 | 14.347 | 83.132 | 27.296 | 1.00 | 47.68 | A | C |
| ATOM | 171 | CG | GLU | A | 59 | 14.141 | 81.643 | 27.349 | 1.00 | 50.21 | A | C |
| ATOM | 172 | CD | GLU | A | 59 | 15.143 | 80.961 | 28.245 | 1.00 | 58.44 | A | C |
| ATOM | 173 | OE1 | GLU | A | 59 | 16.266 | 81.495 | 28.394 | 1.00 | 56.06 | A | O |
| ATOM | 174 | OE2 | GLU | A | 59 | 14.806 | 79.895 | 28.802 | 1.00 | 62.38 | A | O |
| ATOM | 175 | O | GLU | A | 59 | 13.220 | 86.292 | 26.782 | 1.00 | 54.05 | A | O |
| ATOM | 176 | N | MET | A | 60 | 14.777 | 85.288 | 25.474 | 1.00 | 57.94 | A | N |
| ATOM | 177 | CA | MET | A | 60 | 15.540 | 86.467 | 25.103 | 1.00 | 53.60 | A | C |
| ATOM | 178 | C | MET | A | 60 | 14.707 | 87.434 | 24.255 | 1.00 | 57.73 | A | C |
| ATOM | 179 | CB | MET | A | 60 | 16.770 | 85.983 | 24.335 | 1.00 | 52.36 | A | C |
| ATOM | 180 | CG | MET | A | 60 | 17.784 | 87.027 | 23.942 | 1.00 | 55.17 | A | C |
| ATOM | 181 | SD | MET | A | 60 | 18.841 | 86.339 | 22.662 | 1.00 | 52.76 | A | S |
| ATOM | 182 | CE | MET | A | 60 | 19.242 | 84.752 | 23.384 | 1.00 | 48.99 | A | C |
| ATOM | 183 | O | MET | A | 60 | 15.226 | 88.095 | 23.357 | 1.00 | 63.84 | A | O |
| ATOM | 184 | N | ARG | A | 61 | 13.419 | 87.528 | 24.570 | 1.00 | 55.96 | A | N |
| ATOM | 185 | CA | ARG | A | 61 | 12.448 | 88.220 | 23.730 | 1.00 | 56.54 | A | C |
| ATOM | 186 | C | ARG | A | 61 | 11.158 | 88.410 | 24.534 | 1.00 | 60.43 | A | C |
| ATOM | 187 | CB | ARG | A | 61 | 12.182 | 87.383 | 22.481 | 1.00 | 54.80 | A | C |
| ATOM | 188 | CG | ARG | A | 61 | 11.736 | 88.146 | 21.253 | 1.00 | 59.48 | A | C |
| ATOM | 189 | CD | ARG | A | 61 | 12.204 | 87.421 | 19.990 | 1.00 | 57.07 | A | C |
| ATOM | 190 | NE | ARG | A | 61 | 11.202 | 87.438 | 18.926 | 1.00 | 58.22 | A | N |
| ATOM | 191 | CZ | ARG | A | 61 | 11.414 | 87.004 | 17.685 | 1.00 | 64.87 | A | C |
| ATOM | 192 | NH1 | ARG | A | 61 | 10.435 | 87.055 | 16.789 | 1.00 | 61.16 | A | N |
| ATOM | 193 | NH2 | ARG | A | 61 | 12.605 | 86.523 | 17.337 | 1.00 | 61.86 | A | N |
| ATOM | 194 | O | ARG | A | 61 | 10.160 | 88.936 | 24.031 | 1.00 | 53.44 | A | O |
| ATOM | 195 | N | GLY | A | 62 | 11.197 | 87.957 | 25.787 | 1.00 | 53.17 | A | N |
| ATOM | 196 | CA | GLY | A | 62 | 10.123 | 88.171 | 26.741 | 1.00 | 60.34 | A | C |
| ATOM | 197 | C | GLY | A | 62 | 9.047 | 87.098 | 26.791 | 1.00 | 61.87 | A | C |
| ATOM | 198 | O | GLY | A | 62 | 8.042 | 87.270 | 27.474 | 1.00 | 59.04 | A | O |
| ATOM | 199 | N | GLU | A | 63 | 9.264 | 85.986 | 26.093 | 1.00 | 62.54 | A | N |
| ATOM | 200 | CA | GLU | A | 63 | 8.200 | 85.009 | 25.873 | 1.00 | 59.19 | A | C |
| ATOM | 201 | C | GLU | A | 63 | 8.506 | 83.570 | 26.294 | 1.00 | 61.94 | A | C |
| ATOM | 202 | CB | GLU | A | 63 | 7.785 | 85.023 | 24.404 | 1.00 | 58.65 | A | C |
| ATOM | 203 | CG | GLU | A | 63 | 7.089 | 86.292 | 23.961 | 1.00 | 57.73 | A | C |
| ATOM | 204 | CD | GLU | A | 63 | 7.172 | 86.491 | 22.462 | 1.00 | 61.60 | A | C |
| ATOM | 205 | OE1 | GLU | A | 63 | 8.286 | 86.370 | 21.909 | 1.00 | 67.13 | A | O |
| ATOM | 206 | OE2 | GLU | A | 63 | 6.131 | 86.776 | 21.836 | 1.00 | 62.49 | A | O |

TABLE 13-continued

Coordinates for proMMP9(35-444 ΔFnII) (SEQ ID NO: 12) complex with Example 3

| ATOM | 207 | O   | GLU | A | 63 | 8.559  | 82.673 | 25.459 | 1.00 | 59.46 | A | O |
|------|-----|-----|-----|---|----|--------|--------|--------|------|-------|---|---|
| ATOM | 208 | N   | SER | A | 64 | 8.681  | 83.353 | 27.594 | 1.00 | 71.87 | A | N |
| ATOM | 209 | CA  | SER | A | 64 | 8.763  | 82.006 | 28.153 | 1.00 | 66.90 | A | C |
| ATOM | 210 | C   | SER | A | 64 | 7.548  | 81.809 | 29.057 | 1.00 | 60.96 | A | C |
| ATOM | 211 | CB  | SER | A | 64 | 10.069 | 81.830 | 28.929 | 1.00 | 70.73 | A | C |
| ATOM | 212 | OG  | SER | A | 64 | 10.329 | 82.952 | 29.759 | 1.00 | 72.39 | A | O |
| ATOM | 213 | O   | SER | A | 64 | 7.672  | 81.640 | 30.268 | 1.00 | 51.29 | A | O |
| ATOM | 214 | N   | LYS | A | 65 | 6.375  | 81.802 | 28.432 | 1.00 | 66.64 | A | N |
| ATOM | 215 | CA  | LYS | A | 65 | 5.108  | 82.112 | 29.084 | 1.00 | 65.93 | A | C |
| ATOM | 216 | C   | LYS | A | 65 | 4.017  | 81.243 | 28.474 | 1.00 | 72.49 | A | C |
| ATOM | 217 | CB  | LYS | A | 65 | 4.780  | 83.555 | 28.736 | 1.00 | 61.06 | A | C |
| ATOM | 218 | CG  | LYS | A | 65 | 5.005  | 83.818 | 27.239 | 1.00 | 58.47 | A | C |
| ATOM | 219 | CD  | LYS | A | 65 | 5.102  | 85.283 | 26.908 | 1.00 | 60.32 | A | C |
| ATOM | 220 | CE  | LYS | A | 65 | 3.817  | 85.805 | 26.318 | 1.00 | 65.09 | A | C |
| ATOM | 221 | NZ  | LYS | A | 65 | 3.809  | 87.291 | 26.344 | 1.00 | 70.67 | A | N |
| ATOM | 222 | O   | LYS | A | 65 | 3.080  | 81.765 | 27.856 | 1.00 | 68.17 | A | O |
| ATOM | 223 | N   | SER | A | 66 | 4.130  | 79.930 | 28.652 | 1.00 | 65.46 | A | N |
| ATOM | 224 | CA  | SER | A | 66 | 3.504  | 78.993 | 27.728 | 1.00 | 61.84 | A | C |
| ATOM | 225 | C   | SER | A | 66 | 4.508  | 78.806 | 26.589 | 1.00 | 62.00 | A | C |
| ATOM | 226 | CB  | SER | A | 66 | 2.168  | 79.530 | 27.213 | 1.00 | 53.77 | A | C |
| ATOM | 227 | OG  | SER | A | 66 | 2.067  | 79.390 | 25.811 | 1.00 | 60.68 | A | O |
| ATOM | 228 | O   | SER | A | 66 | 5.559  | 79.453 | 26.573 | 1.00 | 55.56 | A | O |
| ATOM | 229 | N   | LEU | A | 67 | 4.201  | 77.925 | 25.648 | 1.00 | 57.21 | A | N |
| ATOM | 230 | CA  | LEU | A | 67 | 5.158  | 77.597 | 24.604 | 1.00 | 54.60 | A | C |
| ATOM | 231 | C   | LEU | A | 67 | 4.724  | 78.157 | 23.258 | 1.00 | 49.73 | A | C |
| ATOM | 232 | CB  | LEU | A | 67 | 5.340  | 76.077 | 24.503 | 1.00 | 51.02 | A | C |
| ATOM | 233 | CG  | LEU | A | 67 | 6.051  | 75.307 | 25.621 | 1.00 | 48.25 | A | C |
| ATOM | 234 | CD1 | LEU | A | 67 | 5.685  | 75.802 | 27.023 | 1.00 | 53.44 | A | C |
| ATOM | 235 | CD2 | LEU | A | 67 | 5.737  | 73.826 | 25.472 | 1.00 | 44.47 | A | C |
| ATOM | 236 | O   | LEU | A | 67 | 5.334  | 77.853 | 22.239 | 1.00 | 44.39 | A | O |
| ATOM | 237 | N   | GLY | A | 68 | 3.671  | 78.971 | 23.257 | 1.00 | 56.41 | A | N |
| ATOM | 238 | CA  | GLY | A | 68 | 3.156  | 79.533 | 22.022 | 1.00 | 52.56 | A | C |
| ATOM | 239 | C   | GLY | A | 68 | 4.252  | 80.149 | 21.182 | 1.00 | 48.73 | A | C |
| ATOM | 240 | O   | GLY | A | 68 | 4.491  | 79.725 | 20.051 | 1.00 | 51.09 | A | O |
| ATOM | 241 | N   | PRO | A | 69 | 4.938  | 81.152 | 21.739 | 1.00 | 52.52 | A | N |
| ATOM | 242 | CD  | PRO | A | 69 | 4.705  | 81.745 | 23.066 | 1.00 | 52.37 | A | C |
| ATOM | 243 | CA  | PRO | A | 69 | 5.993  | 81.854 | 21.008 | 1.00 | 44.37 | A | C |
| ATOM | 244 | CB  | PRO | A | 69 | 6.572  | 82.794 | 22.065 | 1.00 | 53.19 | A | C |
| ATOM | 245 | CG  | PRO | A | 69 | 5.437  | 83.054 | 22.976 | 1.00 | 54.17 | A | C |
| ATOM | 246 | C   | PRO | A | 69 | 7.061  | 80.911 | 20.466 | 1.00 | 44.95 | A | C |
| ATOM | 247 | O   | PRO | A | 69 | 7.338  | 80.958 | 19.268 | 1.00 | 52.80 | A | O |
| ATOM | 248 | N   | ALA | A | 70 | 7.646  | 80.072 | 21.317 | 1.00 | 47.10 | A | N |
| ATOM | 249 | CA  | ALA | A | 70 | 8.710  | 79.166 | 20.881 | 1.00 | 40.79 | A | C |
| ATOM | 250 | CB  | ALA | A | 70 | 9.208  | 78.324 | 22.034 | 1.00 | 38.89 | A | C |
| ATOM | 251 | C   | ALA | A | 70 | 8.237  | 78.278 | 19.736 | 1.00 | 46.20 | A | C |
| ATOM | 252 | O   | ALA | A | 70 | 8.973  | 78.039 | 18.782 | 1.00 | 46.93 | A | O |
| ATOM | 253 | N   | LEU | A | 71 | 7.003  | 77.800 | 19.837 | 1.00 | 42.27 | A | N |
| ATOM | 254 | CA  | LEU | A | 71 | 6.393  | 77.027 | 18.771 | 1.00 | 44.29 | A | C |
| ATOM | 255 | CB  | LEU | A | 71 | 4.963  | 76.645 | 19.144 | 1.00 | 42.21 | A | C |
| ATOM | 256 | CG  | LEU | A | 71 | 4.844  | 75.574 | 20.219 | 1.00 | 38.82 | A | C |
| ATOM | 257 | CD1 | LEU | A | 71 | 3.438  | 75.547 | 20.809 | 1.00 | 41.13 | A | C |
| ATOM | 258 | CD2 | LEU | A | 71 | 5.233  | 74.229 | 19.639 | 1.00 | 34.24 | A | C |
| ATOM | 259 | C   | LEU | A | 71 | 6.370  | 77.835 | 17.488 | 1.00 | 47.61 | A | C |
| ATOM | 260 | O   | LEU | A | 71 | 6.820  | 77.370 | 16.439 | 1.00 | 47.28 | A | O |
| ATOM | 261 | N   | LEU | A | 72 | 5.836  | 79.048 | 17.576 | 1.00 | 48.24 | A | N |
| ATOM | 262 | CA  | LEU | A | 72 | 5.681  | 79.885 | 16.397 | 1.00 | 46.29 | A | C |
| ATOM | 263 | CB  | LEU | A | 72 | 5.092  | 81.249 | 16.767 | 1.00 | 48.28 | A | C |
| ATOM | 264 | CG  | LEU | A | 72 | 4.490  | 82.110 | 15.650 | 1.00 | 47.91 | A | C |
| ATOM | 265 | CD1 | LEU | A | 72 | 3.097  | 81.631 | 15.273 | 1.00 | 39.63 | A | C |
| ATOM | 266 | CD2 | LEU | A | 72 | 4.448  | 83.570 | 16.075 | 1.00 | 41.74 | A | C |
| ATOM | 267 | C   | LEU | A | 72 | 7.031  | 80.032 | 15.713 | 1.00 | 46.30 | A | C |
| ATOM | 268 | O   | LEU | A | 72 | 7.120  | 79.991 | 14.487 | 1.00 | 48.18 | A | O |
| ATOM | 269 | N   | LEU | A | 73 | 8.085  | 80.175 | 16.508 | 1.00 | 47.36 | A | N |
| ATOM | 270 | CA  | LEU | A | 73 | 9.426  | 80.315 | 15.953 | 1.00 | 46.67 | A | C |
| ATOM | 271 | CB  | LEU | A | 73 | 10.445 | 80.638 | 17.044 | 1.00 | 44.51 | A | C |
| ATOM | 272 | CG  | LEU | A | 73 | 10.371 | 81.989 | 17.751 | 1.00 | 49.16 | A | C |
| ATOM | 273 | CD1 | LEU | A | 73 | 11.323 | 81.992 | 18.935 | 1.00 | 54.05 | A | C |
| ATOM | 274 | CD2 | LEU | A | 73 | 10.682 | 83.138 | 16.801 | 1.00 | 44.48 | A | C |
| ATOM | 275 | C   | LEU | A | 73 | 9.823  | 79.030 | 15.240 | 1.00 | 51.69 | A | C |
| ATOM | 276 | O   | LEU | A | 73 | 10.521 | 79.055 | 14.218 | 1.00 | 46.37 | A | O |
| ATOM | 277 | N   | LEU | A | 74 | 9.384  | 77.902 | 15.784 | 1.00 | 46.06 | A | N |
| ATOM | 278 | CA  | LEU | A | 74 | 9.675  | 76.632 | 15.149 | 1.00 | 41.97 | A | C |
| ATOM | 279 | CB  | LEU | A | 74 | 9.329  | 75.465 | 16.075 | 1.00 | 42.09 | A | C |
| ATOM | 280 | CG  | LEU | A | 74 | 9.562  | 74.031 | 15.592 | 1.00 | 41.73 | A | C |
| ATOM | 281 | CD1 | LEU | A | 74 | 9.754  | 73.109 | 16.775 | 1.00 | 36.01 | A | C |
| ATOM | 282 | CD2 | LEU | A | 74 | 8.393  | 73.548 | 14.742 | 1.00 | 43.31 | A | C |
| ATOM | 283 | C   | LEU | A | 74 | 8.900  | 76.557 | 13.846 | 1.00 | 44.15 | A | C |

TABLE 13-continued

Coordinates for proMMP9(35-444 ΔFnII) (SEQ ID NO: 12) complex with Example 3

| ATOM | 284 | O   | LEU | A | 74 | 9.457  | 76.227 | 12.806 | 1.00 | 43.84 | A | O |
|------|-----|-----|-----|---|----|--------|--------|--------|------|-------|---|---|
| ATOM | 285 | N   | GLN | A | 75 | 7.614  | 76.889 | 13.900 | 1.00 | 45.23 | A | N |
| ATOM | 286 | CA  | GLN | A | 75 | 6.742  | 76.711 | 12.744 | 1.00 | 41.99 | A | C |
| ATOM | 287 | CB  | GLN | A | 75 | 5.307  | 77.069 | 13.108 | 1.00 | 40.56 | A | C |
| ATOM | 288 | CG  | GLN | A | 75 | 4.529  | 75.897 | 13.681 | 1.00 | 43.57 | A | C |
| ATOM | 289 | CD  | GLN | A | 75 | 3.625  | 76.285 | 14.835 | 1.00 | 42.71 | A | C |
| ATOM | 290 | OE1 | GLN | A | 75 | 2.987  | 77.347 | 14.828 | 1.00 | 39.21 | A | O |
| ATOM | 291 | NE2 | GLN | A | 75 | 3.569  | 75.420 | 15.839 | 1.00 | 37.01 | A | N |
| ATOM | 292 | C   | GLN | A | 75 | 7.203  | 77.478 | 11.503 | 1.00 | 44.30 | A | C |
| ATOM | 293 | O   | GLN | A | 75 | 7.018  | 77.028 | 10.369 | 1.00 | 36.77 | A | O |
| ATOM | 294 | N   | LYS | A | 76 | 7.811  | 78.635 | 11.713 | 1.00 | 42.66 | A | N |
| ATOM | 295 | CA  | LYS | A | 76 | 8.264  | 79.414 | 10.584 | 1.00 | 38.57 | A | C |
| ATOM | 296 | CB  | LYS | A | 76 | 8.047  | 80.901 | 10.837 | 1.00 | 37.77 | A | C |
| ATOM | 297 | CG  | LYS | A | 76 | 9.137  | 81.562 | 11.635 | 1.00 | 47.53 | A | C |
| ATOM | 298 | CD  | LYS | A | 76 | 8.702  | 82.950 | 12.067 | 1.00 | 55.62 | A | C |
| ATOM | 299 | CE  | LYS | A | 76 | 7.307  | 82.906 | 12.687 | 1.00 | 51.90 | A | C |
| ATOM | 300 | NZ  | LYS | A | 76 | 7.133  | 83.934 | 13.738 | 1.00 | 48.00 | A | N |
| ATOM | 301 | C   | LYS | A | 76 | 9.723  | 79.089 | 10.256 | 1.00 | 45.83 | A | C |
| ATOM | 302 | O   | LYS | A | 76 | 10.206 | 79.408 | 9.169  | 1.00 | 42.00 | A | O |
| ATOM | 303 | N   | GLN | A | 77 | 10.413 | 78.434 | 11.188 | 1.00 | 45.01 | A | N |
| ATOM | 304 | CA  | GLN | A | 77 | 11.765 | 77.936 | 10.937 | 1.00 | 38.91 | A | C |
| ATOM | 305 | CB  | GLN | A | 77 | 12.488 | 77.632 | 12.250 | 1.00 | 44.46 | A | C |
| ATOM | 306 | CG  | GLN | A | 77 | 13.946 | 77.217 | 12.084 | 1.00 | 42.93 | A | C |
| ATOM | 307 | CD  | GLN | A | 77 | 14.792 | 78.311 | 11.457 | 1.00 | 45.59 | A | C |
| ATOM | 308 | OE1 | GLN | A | 77 | 14.518 | 79.494 | 11.642 | 1.00 | 40.71 | A | O |
| ATOM | 309 | NE2 | GLN | A | 77 | 15.821 | 77.918 | 10.706 | 1.00 | 38.13 | A | N |
| ATOM | 310 | C   | GLN | A | 77 | 11.766 | 76.685 | 10.065 | 1.00 | 41.36 | A | C |
| ATOM | 311 | O   | GLN | A | 77 | 12.745 | 76.414 | 9.363  | 1.00 | 43.69 | A | O |
| ATOM | 312 | N   | LEU | A | 78 | 10.678 | 75.919 | 10.108 | 1.00 | 38.12 | A | N |
| ATOM | 313 | CA  | LEU | A | 78 | 10.592 | 74.685 | 9.326  | 1.00 | 40.35 | A | C |
| ATOM | 314 | CB  | LEU | A | 78 | 10.240 | 73.488 | 10.209 | 1.00 | 34.67 | A | C |
| ATOM | 315 | CG  | LEU | A | 78 | 11.131 | 73.169 | 11.405 | 1.00 | 38.97 | A | C |
| ATOM | 316 | CD1 | LEU | A | 78 | 10.377 | 72.316 | 12.408 | 1.00 | 36.89 | A | C |
| ATOM | 317 | CD2 | LEU | A | 78 | 12.394 | 72.473 | 10.964 | 1.00 | 40.72 | A | C |
| ATOM | 318 | C   | LEU | A | 78 | 9.572  | 74.807 | 8.202  | 1.00 | 42.99 | A | C |
| ATOM | 319 | O   | LEU | A | 78 | 9.306  | 73.842 | 7.477  | 1.00 | 41.21 | A | O |
| ATOM | 320 | N   | SER | A | 79 | 9.005  | 75.999 | 8.061  | 1.00 | 41.64 | A | N |
| ATOM | 321 | CA  | SER | A | 79 | 7.973  | 76.243 | 7.057  | 1.00 | 39.68 | A | C |
| ATOM | 322 | CB  | SER | A | 79 | 8.511  | 76.008 | 5.644  | 1.00 | 41.37 | A | C |
| ATOM | 323 | OG  | SER | A | 79 | 9.484  | 76.990 | 5.307  | 1.00 | 42.49 | A | O |
| ATOM | 324 | C   | SER | A | 79 | 6.721  | 75.414 | 7.322  | 1.00 | 40.28 | A | C |
| ATOM | 325 | O   | SER | A | 79 | 6.159  | 74.795 | 6.417  | 1.00 | 43.37 | A | O |
| ATOM | 326 | N   | LEU | A | 80 | 6.302  | 75.405 | 8.584  | 1.00 | 41.47 | A | N |
| ATOM | 327 | CA  | LEU | A | 80 | 5.019  | 74.838 | 8.984  | 1.00 | 36.49 | A | C |
| ATOM | 328 | CB  | LEU | A | 80 | 5.170  | 74.045 | 10.281 | 1.00 | 35.90 | A | C |
| ATOM | 329 | CG  | LEU | A | 80 | 6.199  | 72.910 | 10.326 | 1.00 | 37.28 | A | C |
| ATOM | 330 | CD1 | LEU | A | 80 | 6.037  | 72.099 | 11.606 | 1.00 | 45.14 | A | C |
| ATOM | 331 | CD2 | LEU | A | 80 | 6.067  | 72.006 | 9.122  | 1.00 | 36.95 | A | C |
| ATOM | 332 | C   | LEU | A | 80 | 4.048  | 75.996 | 9.183  | 1.00 | 37.89 | A | C |
| ATOM | 333 | O   | LEU | A | 80 | 4.482  | 77.124 | 9.432  | 1.00 | 46.12 | A | O |
| ATOM | 334 | N   | PRO | A | 81 | 2.737  | 75.740 | 9.050  | 1.00 | 34.45 | A | N |
| ATOM | 335 | CD  | PRO | A | 81 | 2.099  | 74.500 | 8.578  | 1.00 | 34.04 | A | C |
| ATOM | 336 | CA  | PRO | A | 81 | 1.755  | 76.810 | 9.283  | 1.00 | 35.92 | A | C |
| ATOM | 337 | CB  | PRO | A | 81 | 0.411  | 76.099 | 9.122  | 1.00 | 26.58 | A | C |
| ATOM | 338 | CG  | PRO | A | 81 | 0.705  | 74.954 | 8.216  | 1.00 | 36.31 | A | C |
| ATOM | 339 | C   | PRO | A | 81 | 1.884  | 77.393 | 10.682 | 1.00 | 39.62 | A | C |
| ATOM | 340 | O   | PRO | A | 81 | 1.992  | 76.654 | 11.666 | 1.00 | 41.86 | A | O |
| ATOM | 341 | N   | GLU | A | 82 | 1.876  | 78.715 | 10.770 | 1.00 | 41.52 | A | N |
| ATOM | 342 | CA  | GLU | A | 82 | 2.152  | 79.380 | 12.041 | 1.00 | 46.69 | A | C |
| ATOM | 343 | CB  | GLU | A | 82 | 2.876  | 80.706 | 11.792 | 1.00 | 47.67 | A | C |
| ATOM | 344 | CG  | GLU | A | 82 | 4.288  | 80.492 | 11.259 | 1.00 | 39.26 | A | C |
| ATOM | 345 | CD  | GLU | A | 82 | 4.626  | 81.374 | 10.067 | 1.00 | 53.08 | A | C |
| ATOM | 346 | OE1 | GLU | A | 82 | 4.754  | 82.606 | 10.244 | 1.00 | 53.45 | A | O |
| ATOM | 347 | OE2 | GLU | A | 82 | 4.785  | 80.827 | 8.952  | 1.00 | 52.78 | A | O |
| ATOM | 348 | C   | GLU | A | 82 | 0.893  | 79.529 | 12.898 | 1.00 | 47.19 | A | C |
| ATOM | 349 | O   | GLU | A | 82 | 0.006  | 80.340 | 12.615 | 1.00 | 46.15 | A | O |
| ATOM | 350 | N   | THR | A | 83 | 0.818  | 78.708 | 13.941 | 1.00 | 47.88 | A | N |
| ATOM | 351 | CA  | THR | A | 83 | −0.410 | 78.563 | 14.713 | 1.00 | 41.85 | A | C |
| ATOM | 352 | CB  | THR | A | 83 | −0.992 | 77.147 | 14.564 | 1.00 | 39.04 | A | C |
| ATOM | 353 | OG1 | THR | A | 83 | −0.123 | 76.203 | 15.204 | 1.00 | 39.94 | A | O |
| ATOM | 354 | CG2 | THR | A | 83 | −1.142 | 76.780 | 13.099 | 1.00 | 39.15 | A | C |
| ATOM | 355 | C   | THR | A | 83 | −0.179 | 78.807 | 16.190 | 1.00 | 41.05 | A | C |
| ATOM | 356 | O   | THR | A | 83 | −1.128 | 79.012 | 16.942 | 1.00 | 44.79 | A | O |
| ATOM | 357 | N   | GLY | A | 84 | 1.080  | 78.768 | 16.609 | 1.00 | 39.14 | A | N |
| ATOM | 358 | CA  | GLY | A | 84 | 1.409  | 78.942 | 18.008 | 1.00 | 40.11 | A | C |
| ATOM | 359 | C   | GLY | A | 84 | 0.847  | 77.822 | 18.858 | 1.00 | 42.86 | A | C |
| ATOM | 360 | O   | GLY | A | 84 | 0.738  | 77.947 | 20.080 | 1.00 | 44.14 | A | O |

TABLE 13-continued

Coordinates for proMMP9(35-444 ΔFnII) (SEQ ID NO: 12) complex with Example 3

| ATOM | 361 | N | GLU | A | 85 | 0.492 | 76.720 | 18.206 | 1.00 | 41.60 | A | N |
|---|---|---|---|---|---|---|---|---|---|---|---|---|
| ATOM | 362 | CA | GLU | A | 85 | −0.072 | 75.576 | 18.907 | 1.00 | 45.16 | A | C |
| ATOM | 363 | CB | GLU | A | 85 | −1.525 | 75.330 | 18.470 | 1.00 | 42.75 | A | C |
| ATOM | 364 | CG | GLU | A | 85 | −2.426 | 76.556 | 18.443 | 1.00 | 41.12 | A | C |
| ATOM | 365 | CD | GLU | A | 85 | −2.875 | 77.006 | 19.825 | 1.00 | 46.34 | A | C |
| ATOM | 366 | OE1 | GLU | A | 85 | −2.701 | 76.241 | 20.799 | 1.00 | 41.93 | A | O |
| ATOM | 367 | OE2 | GLU | A | 85 | −3.405 | 78.132 | 19.932 | 1.00 | 44.81 | A | O |
| ATOM | 368 | C | GLU | A | 85 | 0.740 | 74.306 | 18.663 | 1.00 | 43.44 | A | C |
| ATOM | 369 | O | GLU | A | 85 | 1.125 | 74.014 | 17.531 | 1.00 | 42.30 | A | O |
| ATOM | 370 | N | LEU | A | 86 | 0.995 | 73.558 | 19.732 | 1.00 | 40.86 | A | N |
| ATOM | 371 | CA | LEU | A | 86 | 1.474 | 72.194 | 19.615 | 1.00 | 37.12 | A | C |
| ATOM | 372 | CB | LEU | A | 86 | 1.751 | 71.595 | 20.996 | 1.00 | 32.50 | A | C |
| ATOM | 373 | CG | LEU | A | 86 | 2.253 | 70.145 | 21.098 | 1.00 | 33.94 | A | C |
| ATOM | 374 | CD1 | LEU | A | 86 | 3.431 | 69.888 | 20.177 | 1.00 | 37.84 | A | C |
| ATOM | 375 | CD2 | LEU | A | 86 | 2.621 | 69.784 | 22.535 | 1.00 | 34.35 | A | C |
| ATOM | 376 | C | LEU | A | 86 | 0.364 | 71.426 | 18.927 | 1.00 | 43.66 | A | C |
| ATOM | 377 | O | LEU | A | 86 | −0.450 | 70.775 | 19.582 | 1.00 | 44.05 | A | O |
| ATOM | 378 | N | ASP | A | 87 | 0.317 | 71.521 | 17.602 | 1.00 | 44.33 | A | N |
| ATOM | 379 | CA | ASP | A | 87 | −0.721 | 70.850 | 16.836 | 1.00 | 39.30 | A | C |
| ATOM | 380 | CB | ASP | A | 87 | −1.364 | 71.825 | 15.858 | 1.00 | 38.35 | A | C |
| ATOM | 381 | CG | ASP | A | 87 | −0.345 | 72.563 | 15.018 | 1.00 | 43.68 | A | C |
| ATOM | 382 | OD1 | ASP | A | 87 | 0.785 | 72.056 | 14.886 | 1.00 | 44.30 | A | O |
| ATOM | 383 | OD2 | ASP | A | 87 | −0.673 | 73.645 | 14.484 | 1.00 | 43.81 | A | O |
| ATOM | 384 | C | ASP | A | 87 | −0.175 | 69.617 | 16.115 | 1.00 | 42.17 | A | C |
| ATOM | 385 | O | ASP | A | 87 | 0.998 | 69.265 | 16.266 | 1.00 | 38.75 | A | O |
| ATOM | 386 | N | SER | A | 88 | −1.035 | 68.959 | 15.344 | 1.00 | 41.03 | A | N |
| ATOM | 387 | CA | SER | A | 88 | −0.663 | 67.722 | 14.660 | 1.00 | 44.22 | A | C |
| ATOM | 388 | CB | SER | A | 88 | −1.838 | 67.168 | 13.844 | 1.00 | 44.49 | A | C |
| ATOM | 389 | OG | SER | A | 88 | −2.694 | 66.373 | 14.648 | 1.00 | 44.75 | A | O |
| ATOM | 390 | C | SER | A | 88 | 0.557 | 67.883 | 13.765 | 1.00 | 40.43 | A | C |
| ATOM | 391 | O | SER | A | 88 | 1.443 | 67.032 | 13.767 | 1.00 | 41.50 | A | O |
| ATOM | 392 | N | ALA | A | 89 | 0.600 | 68.967 | 12.997 | 1.00 | 35.28 | A | N |
| ATOM | 393 | CA | ALA | A | 89 | 1.719 | 69.195 | 12.092 | 1.00 | 34.20 | A | C |
| ATOM | 394 | CB | ALA | A | 89 | 1.454 | 70.378 | 11.179 | 1.00 | 26.35 | A | C |
| ATOM | 395 | C | ALA | A | 89 | 3.003 | 69.417 | 12.864 | 1.00 | 36.73 | A | C |
| ATOM | 396 | O | ALA | A | 89 | 4.073 | 68.988 | 12.439 | 1.00 | 41.09 | A | O |
| ATOM | 397 | N | THR | A | 90 | 2.899 | 70.089 | 14.001 | 1.00 | 34.29 | A | N |
| ATOM | 398 | CA | THR | A | 90 | 4.090 | 70.460 | 14.747 | 1.00 | 35.74 | A | C |
| ATOM | 399 | CB | THR | A | 90 | 3.832 | 71.680 | 15.632 | 1.00 | 36.64 | A | C |
| ATOM | 400 | OG1 | THR | A | 90 | 3.580 | 72.820 | 14.797 | 1.00 | 36.02 | A | O |
| ATOM | 401 | CG2 | THR | A | 90 | 5.023 | 71.948 | 16.531 | 1.00 | 31.50 | A | C |
| ATOM | 402 | C | THR | A | 90 | 4.675 | 69.305 | 15.555 | 1.00 | 36.10 | A | C |
| ATOM | 403 | O | THR | A | 90 | 5.892 | 69.205 | 15.707 | 1.00 | 34.37 | A | O |
| ATOM | 404 | N | LEU | A | 91 | 3.811 | 68.424 | 16.050 | 1.00 | 39.61 | A | N |
| ATOM | 405 | CA | LEU | A | 91 | 4.266 | 67.251 | 16.796 | 1.00 | 38.55 | A | C |
| ATOM | 406 | CB | LEU | A | 91 | 3.153 | 66.678 | 17.677 | 1.00 | 38.66 | A | C |
| ATOM | 407 | CG | LEU | A | 91 | 3.515 | 65.476 | 18.560 | 1.00 | 46.50 | A | C |
| ATOM | 408 | CD1 | LEU | A | 91 | 4.836 | 65.676 | 19.301 | 1.00 | 40.95 | A | C |
| ATOM | 409 | CD2 | LEU | A | 91 | 2.392 | 65.184 | 19.539 | 1.00 | 43.02 | A | C |
| ATOM | 410 | C | LEU | A | 91 | 4.792 | 66.199 | 15.834 | 1.00 | 39.88 | A | C |
| ATOM | 411 | O | LEU | A | 91 | 5.803 | 65.547 | 16.100 | 1.00 | 43.03 | A | O |
| ATOM | 412 | N | LYS | A | 92 | 4.109 | 66.042 | 14.709 | 1.00 | 37.79 | A | N |
| ATOM | 413 | CA | LYS | A | 92 | 4.614 | 65.180 | 13.654 | 1.00 | 38.93 | A | C |
| ATOM | 414 | CB | LYS | A | 92 | 3.788 | 65.368 | 12.381 | 1.00 | 42.69 | A | C |
| ATOM | 415 | CG | LYS | A | 92 | 4.378 | 64.754 | 11.130 | 1.00 | 38.78 | A | C |
| ATOM | 416 | CD | LYS | A | 92 | 3.413 | 64.896 | 9.962 | 1.00 | 52.75 | A | C |
| ATOM | 417 | CE | LYS | A | 92 | 3.911 | 64.149 | 8.724 | 1.00 | 60.93 | A | C |
| ATOM | 418 | NZ | LYS | A | 92 | 2.860 | 64.036 | 7.665 | 1.00 | 61.49 | A | N |
| ATOM | 419 | C | LYS | A | 92 | 6.078 | 65.539 | 13.407 | 1.00 | 42.82 | A | C |
| ATOM | 420 | O | LYS | A | 92 | 6.970 | 64.710 | 13.595 | 1.00 | 45.15 | A | O |
| ATOM | 421 | N | ALA | A | 93 | 6.310 | 66.788 | 13.005 | 1.00 | 39.05 | A | N |
| ATOM | 422 | CA | ALA | A | 93 | 7.652 | 67.310 | 12.755 | 1.00 | 40.24 | A | C |
| ATOM | 423 | CB | ALA | A | 93 | 7.597 | 68.828 | 12.543 | 1.00 | 41.52 | A | C |
| ATOM | 424 | C | ALA | A | 93 | 8.651 | 66.968 | 13.863 | 1.00 | 38.04 | A | C |
| ATOM | 425 | O | ALA | A | 93 | 9.719 | 66.431 | 13.605 | 1.00 | 42.76 | A | O |
| ATOM | 426 | N | MET | A | 94 | 8.298 | 67.287 | 15.099 | 1.00 | 41.25 | A | N |
| ATOM | 427 | CA | MET | A | 94 | 9.168 | 67.016 | 16.238 | 1.00 | 40.33 | A | C |
| ATOM | 428 | CB | MET | A | 94 | 8.474 | 67.465 | 17.535 | 1.00 | 39.65 | A | C |
| ATOM | 429 | CG | MET | A | 94 | 8.283 | 68.968 | 17.640 | 1.00 | 35.07 | A | C |
| ATOM | 430 | SD | MET | A | 94 | 7.436 | 69.463 | 19.153 | 1.00 | 43.06 | A | S |
| ATOM | 431 | CE | MET | A | 94 | 7.655 | 71.238 | 19.182 | 1.00 | 29.54 | A | C |
| ATOM | 432 | C | MET | A | 94 | 9.608 | 65.544 | 16.337 | 1.00 | 37.24 | A | C |
| ATOM | 433 | O | MET | A | 94 | 10.681 | 65.253 | 16.853 | 1.00 | 39.64 | A | O |
| ATOM | 434 | N | ARG | A | 95 | 8.775 | 64.630 | 15.844 | 1.00 | 42.55 | A | N |
| ATOM | 435 | CA | ARG | A | 95 | 9.060 | 63.193 | 15.871 | 1.00 | 37.31 | A | C |
| ATOM | 436 | CB | ARG | A | 95 | 7.761 | 62.373 | 15.867 | 1.00 | 47.18 | A | C |
| ATOM | 437 | CG | ARG | A | 95 | 7.059 | 62.199 | 17.222 | 1.00 | 54.29 | A | C |

TABLE 13-continued

Coordinates for proMMP9(35-444 ΔFnII) (SEQ ID NO: 12) complex with Example 3

| | | | | | | | | | | | |
|---|---|---|---|---|---|---|---|---|---|---|---|
| ATOM | 438 | CD | ARG | A | 95 | 5.888 | 61.206 | 17.110 | 1.00 | 46.18 A | C |
| ATOM | 439 | NE | ARG | A | 95 | 5.024 | 61.226 | 18.292 | 1.00 | 65.38 A | N |
| ATOM | 440 | CZ | ARG | A | 95 | 3.735 | 61.573 | 18.288 | 1.00 | 65.21 A | C |
| ATOM | 441 | NH1 | ARG | A | 95 | 3.132 | 61.924 | 17.157 | 1.00 | 60.76 A | N |
| ATOM | 442 | NH2 | ARG | A | 95 | 3.039 | 61.560 | 19.419 | 1.00 | 58.47 A | N |
| ATOM | 443 | C | ARG | A | 95 | 9.868 | 62.769 | 14.664 | 1.00 | 45.34 A | C |
| ATOM | 444 | O | ARG | A | 95 | 10.150 | 61.584 | 14.486 | 1.00 | 50.76 A | O |
| ATOM | 445 | N | THR | A | 96 | 10.212 | 63.724 | 13.808 | 1.00 | 45.88 A | N |
| ATOM | 446 | CA | THR | A | 96 | 11.005 | 63.408 | 12.629 | 1.00 | 41.71 A | C |
| ATOM | 447 | CB | THR | A | 96 | 10.732 | 64.403 | 11.491 | 1.00 | 39.84 A | C |
| ATOM | 448 | OG1 | THR | A | 96 | 9.431 | 64.152 | 10.957 | 1.00 | 42.90 A | O |
| ATOM | 449 | CG2 | THR | A | 96 | 11.742 | 64.241 | 10.379 | 1.00 | 46.83 A | C |
| ATOM | 450 | C | THR | A | 96 | 12.499 | 63.340 | 12.957 | 1.00 | 43.04 A | C |
| ATOM | 451 | O | THR | A | 96 | 13.011 | 64.178 | 13.704 | 1.00 | 45.82 A | O |
| ATOM | 452 | N | PRO | A | 97 | 13.190 | 62.310 | 12.429 | 1.00 | 45.54 A | N |
| ATOM | 453 | CD | PRO | A | 97 | 12.565 | 61.128 | 11.809 | 1.00 | 42.78 A | C |
| ATOM | 454 | CA | PRO | A | 97 | 14.651 | 62.173 | 12.513 | 1.00 | 45.20 A | C |
| ATOM | 455 | CB | PRO | A | 97 | 14.919 | 60.835 | 11.818 | 1.00 | 36.85 A | C |
| ATOM | 456 | CG | PRO | A | 97 | 13.630 | 60.096 | 11.918 | 1.00 | 41.64 A | C |
| ATOM | 457 | C | PRO | A | 97 | 15.330 | 63.301 | 11.752 | 1.00 | 43.25 A | C |
| ATOM | 458 | O | PRO | A | 97 | 14.884 | 63.658 | 10.663 | 1.00 | 43.49 A | O |
| ATOM | 459 | N | ARG | A | 98 | 16.397 | 63.851 | 12.316 | 1.00 | 41.91 A | N |
| ATOM | 460 | CA | ARG | A | 98 | 16.975 | 65.066 | 11.780 | 1.00 | 37.38 A | C |
| ATOM | 461 | CB | ARG | A | 98 | 16.145 | 66.274 | 12.218 | 1.00 | 36.18 A | C |
| ATOM | 462 | CG | ARG | A | 98 | 16.084 | 66.448 | 13.730 | 1.00 | 36.05 A | C |
| ATOM | 463 | CD | ARG | A | 98 | 15.636 | 67.854 | 14.098 | 1.00 | 33.12 A | C |
| ATOM | 464 | NE | ARG | A | 98 | 16.707 | 68.829 | 13.948 | 1.00 | 35.92 A | N |
| ATOM | 465 | CZ | ARG | A | 98 | 16.526 | 70.140 | 13.804 | 1.00 | 35.03 A | C |
| ATOM | 466 | NH1 | ARG | A | 98 | 15.307 | 70.658 | 13.785 | 1.00 | 32.81 A | N |
| ATOM | 467 | NH2 | ARG | A | 98 | 17.574 | 70.935 | 13.679 | 1.00 | 32.79 A | N |
| ATOM | 468 | C | ARG | A | 98 | 18.400 | 65.256 | 12.255 | 1.00 | 36.84 A | C |
| ATOM | 469 | O | ARG | A | 98 | 18.973 | 64.379 | 12.896 | 1.00 | 36.01 A | O |
| ATOM | 470 | N | CYS | A | 99 | 18.941 | 66.431 | 11.944 | 1.00 | 30.25 A | N |
| ATOM | 471 | CA | CYS | A | 99 | 20.302 | 66.801 | 12.269 | 1.00 | 29.21 A | C |
| ATOM | 472 | CB | CYS | A | 99 | 20.784 | 67.807 | 11.235 | 1.00 | 29.65 A | C |
| ATOM | 473 | SG | CYS | A | 99 | 22.438 | 68.453 | 11.472 | 1.00 | 39.09 A | S |
| ATOM | 474 | C | CYS | A | 99 | 20.404 | 67.404 | 13.672 | 1.00 | 36.23 A | C |
| ATOM | 475 | O | CYS | A | 99 | 19.572 | 68.217 | 14.073 | 1.00 | 35.02 A | O |
| ATOM | 476 | N | GLY | A | 100 | 21.439 | 67.018 | 14.411 | 1.00 | 34.92 A | N |
| ATOM | 477 | CA | GLY | A | 100 | 21.625 | 67.501 | 15.768 | 1.00 | 36.71 A | C |
| ATOM | 478 | C | GLY | A | 100 | 22.009 | 68.964 | 15.852 | 1.00 | 34.96 A | C |
| ATOM | 479 | O | GLY | A | 100 | 22.090 | 69.547 | 16.940 | 1.00 | 31.46 A | O |
| ATOM | 480 | N | VAL | A | 101 | 22.250 | 69.567 | 14.698 | 1.00 | 31.30 A | N |
| ATOM | 481 | CA | VAL | A | 101 | 22.680 | 70.953 | 14.665 | 1.00 | 34.55 A | C |
| ATOM | 482 | CB | VAL | A | 101 | 23.280 | 71.336 | 13.280 | 1.00 | 34.11 A | C |
| ATOM | 483 | CG1 | VAL | A | 101 | 23.762 | 72.781 | 13.277 | 1.00 | 36.93 A | C |
| ATOM | 484 | CG2 | VAL | A | 101 | 24.423 | 70.434 | 12.942 | 1.00 | 30.91 A | C |
| ATOM | 485 | C | VAL | A | 101 | 21.504 | 71.853 | 15.004 | 1.00 | 34.16 A | C |
| ATOM | 486 | O | VAL | A | 101 | 20.467 | 71.791 | 14.345 | 1.00 | 39.80 A | O |
| ATOM | 487 | N | PRO | A | 102 | 21.648 | 72.672 | 16.054 | 1.00 | 32.79 A | N |
| ATOM | 488 | CD | PRO | A | 102 | 22.619 | 72.475 | 17.142 | 1.00 | 36.55 A | C |
| ATOM | 489 | CA | PRO | A | 102 | 20.676 | 73.715 | 16.385 | 1.00 | 34.05 A | C |
| ATOM | 490 | CB | PRO | A | 102 | 21.415 | 74.532 | 17.442 | 1.00 | 34.33 A | C |
| ATOM | 491 | CG | PRO | A | 102 | 22.226 | 73.515 | 18.156 | 1.00 | 33.48 A | C |
| ATOM | 492 | C | PRO | A | 102 | 20.294 | 74.597 | 15.199 | 1.00 | 30.76 A | C |
| ATOM | 493 | O | PRO | A | 102 | 21.170 | 75.067 | 14.489 | 1.00 | 32.23 A | O |
| ATOM | 494 | N | ASP | A | 103 | 18.992 | 74.808 | 15.005 | 1.00 | 34.22 A | N |
| ATOM | 495 | CA | ASP | A | 103 | 18.460 | 75.705 | 13.975 | 1.00 | 35.08 A | C |
| ATOM | 496 | CB | ASP | A | 103 | 16.975 | 75.434 | 13.744 | 1.00 | 35.75 A | C |
| ATOM | 497 | CG | ASP | A | 103 | 16.686 | 73.985 | 13.525 | 1.00 | 36.11 A | C |
| ATOM | 498 | OD1 | ASP | A | 103 | 17.478 | 73.330 | 12.820 | 1.00 | 43.71 A | O |
| ATOM | 499 | OD2 | ASP | A | 103 | 15.674 | 73.502 | 14.055 | 1.00 | 31.30 A | O |
| ATOM | 500 | C | ASP | A | 103 | 18.589 | 77.178 | 14.326 | 1.00 | 34.69 A | C |
| ATOM | 501 | O | ASP | A | 103 | 18.498 | 78.038 | 13.451 | 1.00 | 34.52 A | O |
| ATOM | 502 | N | LEU | A | 104 | 18.760 | 77.481 | 15.605 | 1.00 | 33.07 A | N |
| ATOM | 503 | CA | LEU | A | 104 | 18.752 | 78.875 | 16.017 | 1.00 | 39.54 A | C |
| ATOM | 504 | CB | LEU | A | 104 | 17.404 | 79.289 | 16.630 | 1.00 | 40.92 A | C |
| ATOM | 505 | CG | LEU | A | 104 | 16.449 | 80.077 | 15.728 | 1.00 | 38.00 A | C |
| ATOM | 506 | CD1 | LEU | A | 104 | 15.205 | 80.462 | 16.499 | 1.00 | 42.68 A | C |
| ATOM | 507 | CD2 | LEU | A | 104 | 17.128 | 81.326 | 15.188 | 1.00 | 34.79 A | C |
| ATOM | 508 | C | LEU | A | 104 | 19.883 | 79.207 | 16.952 | 1.00 | 43.50 A | C |
| ATOM | 509 | O | LEU | A | 104 | 19.958 | 78.714 | 18.077 | 1.00 | 41.39 A | O |
| ATOM | 510 | N | GLY | A | 105 | 20.766 | 80.063 | 16.456 | 1.00 | 54.30 A | N |
| ATOM | 511 | CA | GLY | A | 105 | 21.885 | 80.530 | 17.231 | 1.00 | 57.99 A | C |
| ATOM | 512 | C | GLY | A | 105 | 22.937 | 79.486 | 17.540 | 1.00 | 58.30 A | C |
| ATOM | 513 | O | GLY | A | 105 | 23.255 | 78.635 | 16.713 | 1.00 | 48.55 A | O |
| ATOM | 514 | N | ARG | A | 106 | 23.455 | 79.557 | 18.762 | 1.00 | 63.75 A | N |

TABLE 13-continued

Coordinates for proMMP9(35-444 ΔFnII) (SEQ ID NO: 12) complex with Example 3

| ATOM | 515 | CA | ARG | A | 106 | 24.797 | 79.077 | 19.067 | 1.00 | 68.31 | A | C |
|---|---|---|---|---|---|---|---|---|---|---|---|---|
| ATOM | 516 | CB | ARG | A | 106 | 25.445 | 79.940 | 20.174 | 1.00 | 63.33 | A | C |
| ATOM | 517 | CG | ARG | A | 106 | 26.657 | 80.816 | 19.724 | 1.00 | 74.03 | A | C |
| ATOM | 518 | CD | ARG | A | 106 | 26.603 | 81.494 | 18.313 | 1.00 | 80.90 | A | C |
| ATOM | 519 | NE | ARG | A | 106 | 26.088 | 82.878 | 18.300 | 1.00 | 82.99 | A | N |
| ATOM | 520 | CZ | ARG | A | 106 | 25.131 | 83.328 | 17.471 | 1.00 | 70.56 | A | C |
| ATOM | 521 | NH1 | ARG | A | 106 | 24.567 | 82.512 | 16.590 | 1.00 | 66.59 | A | N |
| ATOM | 522 | NH2 | ARG | A | 106 | 24.696 | 84.583 | 17.524 | 1.00 | 59.21 | A | N |
| ATOM | 523 | C | ARG | A | 106 | 24.883 | 77.580 | 19.359 | 1.00 | 61.94 | A | C |
| ATOM | 524 | O | ARG | A | 106 | 24.626 | 77.123 | 20.471 | 1.00 | 61.07 | A | O |
| ATOM | 525 | N | PHE | A | 107 | 25.224 | 76.826 | 18.322 | 1.00 | 54.56 | A | N |
| ATOM | 526 | CA | PHE | A | 107 | 25.719 | 75.480 | 18.493 | 1.00 | 54.78 | A | C |
| ATOM | 527 | CB | PHE | A | 107 | 26.266 | 74.968 | 17.156 | 1.00 | 52.25 | A | C |
| ATOM | 528 | CG | PHE | A | 107 | 26.527 | 73.502 | 17.135 | 1.00 | 51.95 | A | C |
| ATOM | 529 | CD1 | PHE | A | 107 | 26.105 | 72.710 | 18.180 | 1.00 | 45.55 | A | C |
| ATOM | 530 | CD2 | PHE | A | 107 | 27.167 | 72.909 | 16.059 | 1.00 | 52.01 | A | C |
| ATOM | 531 | CE1 | PHE | A | 107 | 26.325 | 71.351 | 18.176 | 1.00 | 50.09 | A | C |
| ATOM | 532 | CE2 | PHE | A | 107 | 27.390 | 71.542 | 16.048 | 1.00 | 47.98 | A | C |
| ATOM | 533 | CZ | PHE | A | 107 | 26.969 | 70.761 | 17.110 | 1.00 | 45.27 | A | C |
| ATOM | 534 | C | PHE | A | 107 | 26.819 | 75.554 | 19.557 | 1.00 | 59.06 | A | C |
| ATOM | 535 | O | PHE | A | 107 | 27.275 | 74.526 | 20.046 | 1.00 | 58.03 | A | O |
| ATOM | 536 | N | GLN | A | 108 | 27.216 | 76.790 | 19.893 | 1.00 | 63.09 | A | N |
| ATOM | 537 | CA | GLN | A | 108 | 28.173 | 77.160 | 20.958 | 1.00 | 60.52 | A | C |
| ATOM | 538 | CB | GLN | A | 108 | 29.050 | 75.992 | 21.401 | 1.00 | 55.63 | A | C |
| ATOM | 539 | CG | GLN | A | 108 | 30.384 | 75.979 | 20.699 | 1.00 | 50.74 | A | C |
| ATOM | 540 | CD | GLN | A | 108 | 31.216 | 74.775 | 21.038 | 1.00 | 56.80 | A | C |
| ATOM | 541 | OE1 | GLN | A | 108 | 30.734 | 73.822 | 21.655 | 1.00 | 62.20 | A | O |
| ATOM | 542 | NE2 | GLN | A | 108 | 32.479 | 74.802 | 20.630 | 1.00 | 50.38 | A | N |
| ATOM | 543 | C | GLN | A | 108 | 29.070 | 78.279 | 20.426 | 1.00 | 57.91 | A | C |
| ATOM | 544 | O | GLN | A | 108 | 29.054 | 78.555 | 19.226 | 1.00 | 57.93 | A | O |
| ATOM | 545 | N | THR | A | 109 | 29.854 | 78.912 | 21.300 | 1.00 | 53.71 | A | N |
| ATOM | 546 | CA | THR | A | 109 | 30.806 | 79.951 | 20.870 | 1.00 | 58.95 | A | C |
| ATOM | 547 | CB | THR | A | 109 | 31.276 | 80.831 | 22.047 | 1.00 | 62.47 | A | C |
| ATOM | 548 | OG1 | THR | A | 109 | 31.177 | 80.091 | 23.273 | 1.00 | 66.77 | A | O |
| ATOM | 549 | CG2 | THR | A | 109 | 30.433 | 82.098 | 22.135 | 1.00 | 51.24 | A | C |
| ATOM | 550 | C | THR | A | 109 | 32.041 | 79.404 | 20.140 | 1.00 | 54.70 | A | C |
| ATOM | 551 | O | THR | A | 109 | 32.784 | 78.590 | 20.687 | 1.00 | 50.69 | A | O |
| ATOM | 552 | N | PHE | A | 110 | 32.261 | 79.876 | 18.913 | 1.00 | 53.50 | A | N |
| ATOM | 553 | CA | PHE | A | 110 | 33.299 | 79.328 | 18.037 | 1.00 | 47.66 | A | C |
| ATOM | 554 | CB | PHE | A | 110 | 32.679 | 78.819 | 16.735 | 1.00 | 40.12 | A | C |
| ATOM | 555 | CG | PHE | A | 110 | 31.764 | 77.636 | 16.910 | 1.00 | 48.25 | A | C |
| ATOM | 556 | CD1 | PHE | A | 110 | 30.406 | 77.756 | 16.689 | 1.00 | 44.39 | A | C |
| ATOM | 557 | CD2 | PHE | A | 110 | 32.264 | 76.401 | 17.280 | 1.00 | 49.53 | A | C |
| ATOM | 558 | CE1 | PHE | A | 110 | 29.571 | 76.673 | 16.834 | 1.00 | 45.82 | A | C |
| ATOM | 559 | CE2 | PHE | A | 110 | 31.430 | 75.314 | 17.426 | 1.00 | 42.36 | A | C |
| ATOM | 560 | CZ | PHE | A | 110 | 30.084 | 75.451 | 17.205 | 1.00 | 45.97 | A | C |
| ATOM | 561 | C | PHE | A | 110 | 34.401 | 80.341 | 17.708 | 1.00 | 45.08 | A | C |
| ATOM | 562 | O | PHE | A | 110 | 34.219 | 81.546 | 17.858 | 1.00 | 49.08 | A | O |
| ATOM | 563 | N | GLU | A | 111 | 35.544 | 79.852 | 17.252 | 1.00 | 42.73 | A | N |
| ATOM | 564 | CA | GLU | A | 111 | 36.605 | 80.747 | 16.818 | 1.00 | 51.42 | A | C |
| ATOM | 565 | CB | GLU | A | 111 | 37.977 | 80.142 | 17.101 | 1.00 | 54.54 | A | C |
| ATOM | 566 | CG | GLU | A | 111 | 38.406 | 80.235 | 18.548 | 1.00 | 54.80 | A | C |
| ATOM | 567 | CD | GLU | A | 111 | 39.369 | 79.132 | 18.919 | 1.00 | 65.07 | A | C |
| ATOM | 568 | OE1 | GLU | A | 111 | 40.402 | 78.985 | 18.224 | 1.00 | 68.54 | A | O |
| ATOM | 569 | OE2 | GLU | A | 111 | 39.085 | 78.406 | 19.897 | 1.00 | 69.05 | A | O |
| ATOM | 570 | C | GLU | A | 111 | 36.494 | 81.071 | 15.338 | 1.00 | 53.82 | A | C |
| ATOM | 571 | O | GLU | A | 111 | 36.142 | 80.206 | 14.525 | 1.00 | 50.49 | A | O |
| ATOM | 572 | N | GLY | A | 112 | 36.778 | 82.330 | 15.007 | 1.00 | 47.86 | A | N |
| ATOM | 573 | CA | GLY | A | 112 | 36.965 | 82.752 | 13.633 | 1.00 | 43.93 | A | C |
| ATOM | 574 | C | GLY | A | 112 | 35.750 | 83.121 | 12.798 | 1.00 | 45.88 | A | C |
| ATOM | 575 | O | GLY | A | 112 | 34.634 | 83.272 | 13.291 | 1.00 | 40.08 | A | O |
| ATOM | 576 | N | ASP | A | 113 | 36.008 | 83.247 | 11.502 | 1.00 | 48.37 | A | N |
| ATOM | 577 | CA | ASP | A | 113 | 35.051 | 83.671 | 10.491 | 1.00 | 48.26 | A | C |
| ATOM | 578 | CB | ASP | A | 113 | 35.811 | 83.830 | 9.170 | 1.00 | 41.51 | A | C |
| ATOM | 579 | CG | ASP | A | 113 | 35.220 | 84.884 | 8.290 | 1.00 | 56.76 | A | C |
| ATOM | 580 | OD1 | ASP | A | 113 | 34.353 | 85.637 | 8.780 | 1.00 | 72.22 | A | O |
| ATOM | 581 | OD2 | ASP | A | 113 | 35.621 | 84.967 | 7.111 | 1.00 | 67.55 | A | O |
| ATOM | 582 | C | ASP | A | 113 | 33.884 | 82.690 | 10.283 | 1.00 | 51.11 | A | C |
| ATOM | 583 | O | ASP | A | 113 | 32.767 | 83.103 | 9.957 | 1.00 | 45.30 | A | O |
| ATOM | 584 | N | LEU | A | 114 | 34.164 | 81.399 | 10.466 | 1.00 | 45.57 | A | N |
| ATOM | 585 | CA | LEU | A | 114 | 33.242 | 80.300 | 10.145 | 1.00 | 45.38 | A | C |
| ATOM | 586 | CB | LEU | A | 114 | 31.840 | 80.506 | 10.730 | 1.00 | 36.97 | A | C |
| ATOM | 587 | CG | LEU | A | 114 | 31.800 | 80.702 | 12.254 | 1.00 | 42.71 | A | C |
| ATOM | 588 | CD1 | LEU | A | 114 | 30.479 | 80.256 | 12.815 | 1.00 | 31.50 | A | C |
| ATOM | 589 | CD2 | LEU | A | 114 | 32.934 | 79.956 | 12.944 | 1.00 | 43.31 | A | C |
| ATOM | 590 | C | LEU | A | 114 | 33.201 | 80.050 | 8.643 | 1.00 | 44.68 | A | C |
| ATOM | 591 | O | LEU | A | 114 | 32.243 | 79.493 | 8.106 | 1.00 | 46.16 | A | O |

TABLE 13-continued

Coordinates for proMMP9(35-444 ΔFnII) (SEQ ID NO: 12) complex with Example 3

| ATOM | 592 | N | LYS | A | 115 | 34.280 | 80.458 | 7.987 | 1.00 | 50.35 | A | N |
|---|---|---|---|---|---|---|---|---|---|---|---|---|
| ATOM | 593 | CA | LYS | A | 115 | 34.495 | 80.254 | 6.559 | 1.00 | 47.90 | A | C |
| ATOM | 594 | CB | LYS | A | 115 | 34.465 | 81.612 | 5.850 | 1.00 | 49.67 | A | C |
| ATOM | 595 | CG | LYS | A | 115 | 34.366 | 81.567 | 4.340 | 1.00 | 50.19 | A | C |
| ATOM | 596 | CD | LYS | A | 115 | 34.593 | 82.945 | 3.718 | 1.00 | 52.12 | A | C |
| ATOM | 597 | CE | LYS | A | 115 | 33.517 | 83.934 | 4.148 | 1.00 | 63.18 | A | C |
| ATOM | 598 | NZ | LYS | A | 115 | 33.513 | 85.166 | 3.300 | 1.00 | 67.09 | A | N |
| ATOM | 599 | C | LYS | A | 115 | 35.874 | 79.610 | 6.414 | 1.00 | 44.14 | A | C |
| ATOM | 600 | O | LYS | A | 115 | 36.776 | 79.899 | 7.201 | 1.00 | 44.44 | A | O |
| ATOM | 601 | N | TRP | A | 116 | 36.043 | 78.723 | 5.440 | 1.00 | 42.76 | A | N |
| ATOM | 602 | CA | TRP | A | 116 | 37.372 | 78.169 | 5.187 | 1.00 | 42.86 | A | C |
| ATOM | 603 | CB | TRP | A | 116 | 37.327 | 76.914 | 4.309 | 1.00 | 42.08 | A | C |
| ATOM | 604 | CG | TRP | A | 116 | 36.880 | 75.699 | 5.072 | 1.00 | 46.23 | A | C |
| ATOM | 605 | CD2 | TRP | A | 116 | 37.519 | 75.128 | 6.217 | 1.00 | 40.23 | A | C |
| ATOM | 606 | CE2 | TRP | A | 116 | 36.752 | 74.024 | 6.615 | 1.00 | 34.56 | A | C |
| ATOM | 607 | CE3 | TRP | A | 116 | 38.672 | 75.443 | 6.938 | 1.00 | 45.84 | A | C |
| ATOM | 608 | CD1 | TRP | A | 116 | 35.772 | 74.944 | 4.837 | 1.00 | 39.43 | A | C |
| ATOM | 609 | NE1 | TRP | A | 116 | 35.691 | 73.932 | 5.757 | 1.00 | 39.54 | A | N |
| ATOM | 610 | CZ2 | TRP | A | 116 | 37.096 | 73.230 | 7.698 | 1.00 | 40.54 | A | C |
| ATOM | 611 | CZ3 | TRP | A | 116 | 39.011 | 74.655 | 8.019 | 1.00 | 51.52 | A | C |
| ATOM | 612 | CH2 | TRP | A | 116 | 38.222 | 73.564 | 8.392 | 1.00 | 47.95 | A | C |
| ATOM | 613 | C | TRP | A | 116 | 38.200 | 79.229 | 4.521 | 1.00 | 46.35 | A | C |
| ATOM | 614 | O | TRP | A | 116 | 37.724 | 79.908 | 3.614 | 1.00 | 52.09 | A | O |
| ATOM | 615 | N | HIS | A | 117 | 39.439 | 79.388 | 4.972 | 1.00 | 48.59 | A | N |
| ATOM | 616 | CA | HIS | A | 117 | 40.289 | 80.412 | 4.386 | 1.00 | 51.18 | A | C |
| ATOM | 617 | CB | HIS | A | 117 | 40.743 | 81.436 | 5.429 | 1.00 | 47.66 | A | C |
| ATOM | 618 | CG | HIS | A | 117 | 39.714 | 82.486 | 5.711 | 1.00 | 50.85 | A | C |
| ATOM | 619 | CD2 | HIS | A | 117 | 39.347 | 83.585 | 5.009 | 1.00 | 52.70 | A | C |
| ATOM | 620 | ND1 | HIS | A | 117 | 38.895 | 82.450 | 6.820 | 1.00 | 58.35 | A | N |
| ATOM | 621 | CE1 | HIS | A | 117 | 38.080 | 83.488 | 6.798 | 1.00 | 55.30 | A | C |
| ATOM | 622 | NE2 | HIS | A | 117 | 38.332 | 84.193 | 5.710 | 1.00 | 60.46 | A | N |
| ATOM | 623 | C | HIS | A | 117 | 41.435 | 79.843 | 3.573 | 1.00 | 42.60 | A | C |
| ATOM | 624 | O | HIS | A | 117 | 42.403 | 80.529 | 3.284 | 1.00 | 44.06 | A | O |
| ATOM | 625 | N | HIS | A | 118 | 41.311 | 78.579 | 3.197 | 1.00 | 42.91 | A | N |
| ATOM | 626 | CA | HIS | A | 118 | 42.121 | 78.053 | 2.105 | 1.00 | 45.00 | A | C |
| ATOM | 627 | CB | HIS | A | 118 | 43.251 | 77.132 | 2.584 | 1.00 | 41.60 | A | C |
| ATOM | 628 | CG | HIS | A | 118 | 42.827 | 76.082 | 3.566 | 1.00 | 46.24 | A | C |
| ATOM | 629 | CD2 | HIS | A | 118 | 42.928 | 74.734 | 3.520 | 1.00 | 41.68 | A | C |
| ATOM | 630 | ND1 | HIS | A | 118 | 42.269 | 76.387 | 4.791 | 1.00 | 43.49 | A | N |
| ATOM | 631 | CE1 | HIS | A | 118 | 42.024 | 75.266 | 5.446 | 1.00 | 44.79 | A | C |
| ATOM | 632 | NE2 | HIS | A | 118 | 42.413 | 74.249 | 4.699 | 1.00 | 43.60 | A | N |
| ATOM | 633 | C | HIS | A | 118 | 41.247 | 77.375 | 1.063 | 1.00 | 44.65 | A | C |
| ATOM | 634 | O | HIS | A | 118 | 40.052 | 77.185 | 1.264 | 1.00 | 41.37 | A | O |
| ATOM | 635 | N | HIS | A | 119 | 41.853 | 77.032 | −0.062 | 1.00 | 46.23 | A | N |
| ATOM | 636 | CA | HIS | A | 119 | 41.120 | 76.457 | −1.171 | 1.00 | 46.67 | A | C |
| ATOM | 637 | CB | HIS | A | 119 | 41.836 | 76.777 | −2.484 | 1.00 | 45.49 | A | C |
| ATOM | 638 | CG | HIS | A | 119 | 41.185 | 76.192 | −3.698 | 1.00 | 57.97 | A | C |
| ATOM | 639 | CD2 | HIS | A | 119 | 41.632 | 75.283 | −4.600 | 1.00 | 62.64 | A | C |
| ATOM | 640 | ND1 | HIS | A | 119 | 39.926 | 76.563 | −4.122 | 1.00 | 56.61 | A | N |
| ATOM | 641 | CE1 | HIS | A | 119 | 39.617 | 75.896 | −5.220 | 1.00 | 55.90 | A | C |
| ATOM | 642 | NE2 | HIS | A | 119 | 40.636 | 75.112 | −5.533 | 1.00 | 57.65 | A | N |
| ATOM | 643 | C | HIS | A | 119 | 40.996 | 74.956 | −0.973 | 1.00 | 47.84 | A | C |
| ATOM | 644 | O | HIS | A | 119 | 39.942 | 74.374 | −1.231 | 1.00 | 50.64 | A | O |
| ATOM | 645 | N | ASN | A | 120 | 42.063 | 74.323 | −0.499 | 1.00 | 46.57 | A | N |
| ATOM | 646 | CA | ASN | A | 120 | 42.055 | 72.869 | −0.430 | 1.00 | 46.05 | A | C |
| ATOM | 647 | CB | ASN | A | 120 | 43.344 | 72.252 | −0.918 | 1.00 | 44.36 | A | C |
| ATOM | 648 | CG | ASN | A | 120 | 43.275 | 70.763 | −0.892 | 1.00 | 46.23 | A | C |
| ATOM | 649 | OD1 | ASN | A | 120 | 42.256 | 70.193 | −1.269 | 1.00 | 44.96 | A | O |
| ATOM | 650 | ND2 | ASN | A | 120 | 44.331 | 70.114 | −0.423 | 1.00 | 45.24 | A | N |
| ATOM | 651 | C | ASN | A | 120 | 41.758 | 72.311 | 0.937 | 1.00 | 49.66 | A | C |
| ATOM | 652 | O | ASN | A | 120 | 42.558 | 72.433 | 1.864 | 1.00 | 50.18 | A | O |
| ATOM | 653 | N | ILE | A | 121 | 40.610 | 71.657 | 1.031 | 1.00 | 45.74 | A | N |
| ATOM | 654 | CA | ILE | A | 121 | 40.099 | 71.191 | 2.297 | 1.00 | 45.02 | A | C |
| ATOM | 655 | CB | ILE | A | 121 | 38.581 | 71.506 | 2.395 | 1.00 | 46.43 | A | C |
| ATOM | 656 | CG2 | ILE | A | 121 | 38.049 | 71.292 | 3.806 | 1.00 | 37.70 | A | C |
| ATOM | 657 | CG1 | ILE | A | 121 | 38.309 | 72.944 | 1.922 | 1.00 | 35.20 | A | C |
| ATOM | 658 | CD1 | ILE | A | 121 | 39.030 | 74.000 | 2.707 | 1.00 | 33.05 | A | C |
| ATOM | 659 | C | ILE | A | 121 | 40.420 | 69.702 | 2.441 | 1.00 | 41.90 | A | C |
| ATOM | 660 | O | ILE | A | 121 | 40.025 | 68.888 | 1.606 | 1.00 | 40.05 | A | O |
| ATOM | 661 | N | THR | A | 122 | 41.179 | 69.360 | 3.479 | 1.00 | 43.18 | A | N |
| ATOM | 662 | CA | THR | A | 122 | 41.568 | 67.975 | 3.722 | 1.00 | 40.86 | A | C |
| ATOM | 663 | CB | THR | A | 122 | 42.943 | 67.869 | 4.405 | 1.00 | 35.11 | A | C |
| ATOM | 664 | OG1 | THR | A | 122 | 42.979 | 68.743 | 5.536 | 1.00 | 48.07 | A | O |
| ATOM | 665 | CG2 | THR | A | 122 | 44.049 | 68.250 | 3.461 | 1.00 | 33.19 | A | C |
| ATOM | 666 | C | THR | A | 122 | 40.548 | 67.334 | 4.636 | 1.00 | 40.12 | A | C |
| ATOM | 667 | O | THR | A | 122 | 39.945 | 68.016 | 5.454 | 1.00 | 43.82 | A | O |
| ATOM | 668 | N | TYR | A | 123 | 40.356 | 66.025 | 4.501 | 1.00 | 39.73 | A | N |

TABLE 13-continued

Coordinates for proMMP9(35-444 ΔFnII) (SEQ ID NO: 12) complex with Example 3

| ATOM | 669 | CA | TYR | A | 123 | 39.430 | 65.296 | 5.361 | 1.00 | 39.89 | A | C |
|---|---|---|---|---|---|---|---|---|---|---|---|---|
| ATOM | 670 | CB | TYR | A | 123 | 38.043 | 65.205 | 4.722 | 1.00 | 34.84 | A | C |
| ATOM | 671 | CG | TYR | A | 123 | 37.931 | 64.269 | 3.534 | 1.00 | 38.86 | A | C |
| ATOM | 672 | CD1 | TYR | A | 123 | 38.134 | 64.728 | 2.237 | 1.00 | 36.98 | A | C |
| ATOM | 673 | CE1 | TYR | A | 123 | 38.009 | 63.880 | 1.153 | 1.00 | 37.63 | A | C |
| ATOM | 674 | CD2 | TYR | A | 123 | 37.591 | 62.930 | 3.711 | 1.00 | 37.72 | A | C |
| ATOM | 675 | CE2 | TYR | A | 123 | 37.467 | 62.074 | 2.640 | 1.00 | 37.69 | A | C |
| ATOM | 676 | CZ | TYR | A | 123 | 37.678 | 62.550 | 1.361 | 1.00 | 45.19 | A | C |
| ATOM | 677 | OH | TYR | A | 123 | 37.558 | 61.690 | 0.291 | 1.00 | 40.14 | A | O |
| ATOM | 678 | C | TYR | A | 123 | 39.947 | 63.909 | 5.748 | 1.00 | 44.56 | A | C |
| ATOM | 679 | O | TYR | A | 123 | 40.570 | 63.210 | 4.941 | 1.00 | 45.12 | A | O |
| ATOM | 680 | N | TRP | A | 124 | 39.685 | 63.516 | 6.990 | 1.00 | 41.48 | A | N |
| ATOM | 681 | CA | TRP | A | 124 | 40.177 | 62.248 | 7.497 | 1.00 | 38.27 | A | C |
| ATOM | 682 | CB | TRP | A | 124 | 41.233 | 62.475 | 8.568 | 1.00 | 42.08 | A | C |
| ATOM | 683 | CG | TRP | A | 124 | 41.707 | 61.211 | 9.188 | 1.00 | 45.22 | A | C |
| ATOM | 684 | CD2 | TRP | A | 124 | 42.016 | 60.995 | 10.569 | 1.00 | 41.57 | A | C |
| ATOM | 685 | CE2 | TRP | A | 124 | 42.432 | 59.661 | 10.698 | 1.00 | 38.26 | A | C |
| ATOM | 686 | CE3 | TRP | A | 124 | 41.979 | 61.803 | 11.708 | 1.00 | 45.45 | A | C |
| ATOM | 687 | CD1 | TRP | A | 124 | 41.953 | 60.035 | 8.552 | 1.00 | 49.25 | A | C |
| ATOM | 688 | NE1 | TRP | A | 124 | 42.387 | 59.095 | 9.452 | 1.00 | 46.46 | A | N |
| ATOM | 689 | CZ2 | TRP | A | 124 | 42.812 | 59.114 | 11.917 | 1.00 | 42.80 | A | C |
| ATOM | 690 | CZ3 | TRP | A | 124 | 42.351 | 61.258 | 12.919 | 1.00 | 46.72 | A | C |
| ATOM | 691 | CH2 | TRP | A | 124 | 42.766 | 59.927 | 13.014 | 1.00 | 46.39 | A | C |
| ATOM | 692 | C | TRP | A | 124 | 39.070 | 61.402 | 8.069 | 1.00 | 41.98 | A | C |
| ATOM | 693 | O | TRP | A | 124 | 38.401 | 61.802 | 9.018 | 1.00 | 42.33 | A | O |
| ATOM | 694 | N | ILE | A | 125 | 38.887 | 60.222 | 7.488 | 1.00 | 48.44 | A | N |
| ATOM | 695 | CA | ILE | A | 125 | 37.915 | 59.255 | 7.981 | 1.00 | 39.99 | A | C |
| ATOM | 696 | CB | ILE | A | 125 | 37.565 | 58.238 | 6.888 | 1.00 | 41.05 | A | C |
| ATOM | 697 | CG2 | ILE | A | 125 | 36.412 | 57.348 | 7.330 | 1.00 | 43.17 | A | C |
| ATOM | 698 | CG1 | ILE | A | 125 | 37.262 | 58.969 | 5.571 | 1.00 | 39.02 | A | C |
| ATOM | 699 | CD1 | ILE | A | 125 | 36.780 | 58.068 | 4.447 | 1.00 | 37.03 | A | C |
| ATOM | 700 | C | ILE | A | 125 | 38.511 | 58.530 | 9.177 | 1.00 | 40.49 | A | C |
| ATOM | 701 | O | ILE | A | 125 | 39.200 | 57.530 | 9.016 | 1.00 | 42.25 | A | O |
| ATOM | 702 | N | GLN | A | 126 | 38.234 | 59.043 | 10.373 | 1.00 | 45.62 | A | N |
| ATOM | 703 | CA | GLN | A | 126 | 38.873 | 58.584 | 11.608 | 1.00 | 43.03 | A | C |
| ATOM | 704 | CB | GLN | A | 126 | 38.700 | 59.635 | 12.703 | 1.00 | 42.12 | A | C |
| ATOM | 705 | CG | GLN | A | 126 | 39.554 | 59.419 | 13.941 | 1.00 | 43.31 | A | C |
| ATOM | 706 | CD | GLN | A | 126 | 39.107 | 60.293 | 15.100 | 1.00 | 49.29 | A | C |
| ATOM | 707 | OE1 | GLN | A | 126 | 37.912 | 60.562 | 15.260 | 1.00 | 49.63 | A | O |
| ATOM | 708 | NE2 | GLN | A | 126 | 40.060 | 60.740 | 15.915 | 1.00 | 36.45 | A | N |
| ATOM | 709 | C | GLN | A | 126 | 38.388 | 57.220 | 12.116 | 1.00 | 48.28 | A | C |
| ATOM | 710 | O | GLN | A | 126 | 38.934 | 56.692 | 13.079 | 1.00 | 57.07 | A | O |
| ATOM | 711 | N | ASN | A | 127 | 37.370 | 56.656 | 11.478 | 1.00 | 44.99 | A | N |
| ATOM | 712 | CA | ASN | A | 127 | 36.925 | 55.303 | 11.804 | 1.00 | 48.02 | A | C |
| ATOM | 713 | CB | ASN | A | 127 | 36.533 | 55.191 | 13.276 | 1.00 | 45.59 | A | C |
| ATOM | 714 | CG | ASN | A | 127 | 35.253 | 55.923 | 13.589 | 1.00 | 49.16 | A | C |
| ATOM | 715 | OD1 | ASN | A | 127 | 34.777 | 56.723 | 12.789 | 1.00 | 46.12 | A | O |
| ATOM | 716 | ND2 | ASN | A | 127 | 34.683 | 55.651 | 14.758 | 1.00 | 50.93 | A | N |
| ATOM | 717 | C | ASN | A | 127 | 35.781 | 54.843 | 10.904 | 1.00 | 46.99 | A | C |
| ATOM | 718 | O | ASN | A | 127 | 35.571 | 55.409 | 9.834 | 1.00 | 46.92 | A | O |
| ATOM | 719 | N | TYR | A | 128 | 35.048 | 53.818 | 11.330 | 1.00 | 42.92 | A | N |
| ATOM | 720 | CA | TYR | A | 128 | 33.965 | 53.284 | 10.509 | 1.00 | 45.61 | A | C |
| ATOM | 721 | CB | TYR | A | 128 | 34.508 | 52.239 | 9.534 | 1.00 | 36.76 | A | C |
| ATOM | 722 | CG | TYR | A | 128 | 35.362 | 52.784 | 8.419 | 1.00 | 43.64 | A | C |
| ATOM | 723 | CD1 | TYR | A | 128 | 34.822 | 53.035 | 7.161 | 1.00 | 46.43 | A | C |
| ATOM | 724 | CE1 | TYR | A | 128 | 35.613 | 53.520 | 6.121 | 1.00 | 45.63 | A | C |
| ATOM | 725 | CD2 | TYR | A | 128 | 36.722 | 53.014 | 8.606 | 1.00 | 50.16 | A | C |
| ATOM | 726 | CE2 | TYR | A | 128 | 37.521 | 53.497 | 7.571 | 1.00 | 46.03 | A | C |
| ATOM | 727 | CZ | TYR | A | 128 | 36.962 | 53.745 | 6.332 | 1.00 | 42.81 | A | C |
| ATOM | 728 | OH | TYR | A | 128 | 37.752 | 54.229 | 5.309 | 1.00 | 35.57 | A | O |
| ATOM | 729 | C | TYR | A | 128 | 32.808 | 52.656 | 11.297 | 1.00 | 46.13 | A | C |
| ATOM | 730 | O | TYR | A | 128 | 33.008 | 52.111 | 12.382 | 1.00 | 49.50 | A | O |
| ATOM | 731 | N | SER | A | 129 | 31.601 | 52.739 | 10.735 | 1.00 | 40.60 | A | N |
| ATOM | 732 | CA | SER | A | 129 | 30.493 | 51.872 | 11.128 | 1.00 | 37.94 | A | C |
| ATOM | 733 | CB | SER | A | 129 | 29.157 | 52.513 | 10.748 | 1.00 | 38.93 | A | C |
| ATOM | 734 | OG | SER | A | 129 | 28.186 | 51.537 | 10.390 | 1.00 | 40.49 | A | O |
| ATOM | 735 | C | SER | A | 129 | 30.653 | 50.530 | 10.405 | 1.00 | 40.81 | A | C |
| ATOM | 736 | O | SER | A | 129 | 31.276 | 50.466 | 9.352 | 1.00 | 44.54 | A | O |
| ATOM | 737 | N | GLU | A | 130 | 30.103 | 49.459 | 10.966 | 1.00 | 40.43 | A | N |
| ATOM | 738 | CA | GLU | A | 130 | 30.216 | 48.136 | 10.349 | 1.00 | 43.33 | A | C |
| ATOM | 739 | CB | GLU | A | 130 | 30.562 | 47.064 | 11.396 | 1.00 | 41.96 | A | C |
| ATOM | 740 | CG | GLU | A | 130 | 31.942 | 47.224 | 12.040 | 1.00 | 50.00 | A | C |
| ATOM | 741 | CD | GLU | A | 130 | 33.099 | 46.872 | 11.096 | 1.00 | 55.87 | A | C |
| ATOM | 742 | OE1 | GLU | A | 130 | 32.875 | 46.139 | 10.109 | 1.00 | 54.14 | A | O |
| ATOM | 743 | OE2 | GLU | A | 130 | 34.240 | 47.320 | 11.348 | 1.00 | 56.47 | A | O |
| ATOM | 744 | C | GLU | A | 130 | 28.946 | 47.749 | 9.581 | 1.00 | 43.69 | A | C |
| ATOM | 745 | O | GLU | A | 130 | 28.829 | 46.629 | 9.081 | 1.00 | 33.63 | A | O |

TABLE 13-continued

Coordinates for proMMP9(35-444 ΔFnII) (SEQ ID NO: 12) complex with Example 3

| | | | | | | | | | | | |
|---|---|---|---|---|---|---|---|---|---|---|---|
| ATOM | 746 | N | ASP | A | 131 | 27.991 | 48.675 | 9.504 | 1.00 | 45.42 A | N |
| ATOM | 747 | CA | ASP | A | 131 | 26.832 | 48.496 | 8.635 | 1.00 | 39.84 A | C |
| ATOM | 748 | CB | ASP | A | 131 | 25.942 | 49.739 | 8.649 | 1.00 | 42.08 A | C |
| ATOM | 749 | CG | ASP | A | 131 | 25.477 | 50.118 | 10.033 | 1.00 | 44.96 A | C |
| ATOM | 750 | OD1 | ASP | A | 131 | 25.244 | 49.217 | 10.865 | 1.00 | 41.61 A | O |
| ATOM | 751 | OD2 | ASP | A | 131 | 25.334 | 51.335 | 10.275 | 1.00 | 50.01 A | O |
| ATOM | 752 | C | ASP | A | 131 | 27.252 | 48.257 | 7.187 | 1.00 | 41.77 A | C |
| ATOM | 753 | O | ASP | A | 131 | 26.551 | 47.579 | 6.439 | 1.00 | 43.53 A | O |
| ATOM | 754 | N | LEU | A | 132 | 28.389 | 48.831 | 6.790 | 1.00 | 40.67 A | N |
| ATOM | 755 | CA | LEU | A | 132 | 28.741 | 48.929 | 5.379 | 1.00 | 35.56 A | C |
| ATOM | 756 | CB | LEU | A | 132 | 28.396 | 50.327 | 4.868 | 1.00 | 30.94 A | C |
| ATOM | 757 | CG | LEU | A | 132 | 26.916 | 50.667 | 4.717 | 1.00 | 44.13 A | C |
| ATOM | 758 | CD1 | LEU | A | 132 | 26.676 | 52.183 | 4.642 | 1.00 | 39.18 A | C |
| ATOM | 759 | CD2 | LEU | A | 132 | 26.358 | 49.960 | 3.492 | 1.00 | 47.17 A | C |
| ATOM | 760 | C | LEU | A | 132 | 30.217 | 48.650 | 5.118 | 1.00 | 40.06 A | C |
| ATOM | 761 | O | LEU | A | 132 | 31.069 | 48.964 | 5.948 | 1.00 | 49.88 A | O |
| ATOM | 762 | N | PRO | A | 133 | 30.528 | 48.072 | 3.949 | 1.00 | 31.65 A | N |
| ATOM | 763 | CD | PRO | A | 133 | 29.563 | 47.638 | 2.927 | 1.00 | 37.73 A | C |
| ATOM | 764 | CA | PRO | A | 133 | 31.917 | 47.847 | 3.533 | 1.00 | 39.27 A | C |
| ATOM | 765 | CB | PRO | A | 133 | 31.777 | 47.317 | 2.097 | 1.00 | 35.31 A | C |
| ATOM | 766 | CG | PRO | A | 133 | 30.391 | 46.779 | 2.016 | 1.00 | 35.63 A | C |
| ATOM | 767 | C | PRO | A | 133 | 32.716 | 49.148 | 3.514 | 1.00 | 42.95 A | C |
| ATOM | 768 | O | PRO | A | 133 | 32.296 | 50.108 | 2.872 | 1.00 | 46.67 A | O |
| ATOM | 769 | N | ARG | A | 134 | 33.858 | 49.170 | 4.190 | 1.00 | 40.02 A | N |
| ATOM | 770 | CA | ARG | A | 134 | 34.685 | 50.368 | 4.248 | 1.00 | 40.97 A | C |
| ATOM | 771 | CB | ARG | A | 134 | 36.033 | 50.052 | 4.887 | 1.00 | 42.84 A | C |
| ATOM | 772 | CG | ARG | A | 134 | 35.937 | 49.671 | 6.349 | 1.00 | 52.35 A | C |
| ATOM | 773 | CD | ARG | A | 134 | 37.262 | 49.885 | 7.038 | 1.00 | 52.29 A | C |
| ATOM | 774 | NE | ARG | A | 134 | 37.275 | 49.358 | 8.395 | 1.00 | 54.19 A | N |
| ATOM | 775 | CZ | ARG | A | 134 | 38.368 | 49.304 | 9.148 | 1.00 | 60.82 A | C |
| ATOM | 776 | NH1 | ARG | A | 134 | 39.526 | 49.742 | 8.664 | 1.00 | 54.36 A | N |
| ATOM | 777 | NH2 | ARG | A | 134 | 38.308 | 48.814 | 10.380 | 1.00 | 65.72 A | N |
| ATOM | 778 | C | ARG | A | 134 | 34.898 | 51.034 | 2.890 | 1.00 | 40.42 A | C |
| ATOM | 779 | O | ARG | A | 134 | 35.014 | 52.252 | 2.802 | 1.00 | 44.90 A | O |
| ATOM | 780 | N | ALA | A | 135 | 34.963 | 50.244 | 1.829 | 1.00 | 40.83 A | N |
| ATOM | 781 | CA | ALA | A | 135 | 35.088 | 50.826 | 0.503 | 1.00 | 45.18 A | C |
| ATOM | 782 | CB | ALA | A | 135 | 35.290 | 49.749 | −0.543 | 1.00 | 40.69 A | C |
| ATOM | 783 | C | ALA | A | 135 | 33.841 | 51.660 | 0.200 | 1.00 | 49.47 A | C |
| ATOM | 784 | O | ALA | A | 135 | 33.942 | 52.805 | −0.240 | 1.00 | 49.60 A | O |
| ATOM | 785 | N | VAL | A | 136 | 32.667 | 51.093 | 0.462 | 1.00 | 42.93 A | N |
| ATOM | 786 | CA | VAL | A | 136 | 31.419 | 51.795 | 0.177 | 1.00 | 44.82 A | C |
| ATOM | 787 | CB | VAL | A | 136 | 30.214 | 50.834 | 0.179 | 1.00 | 45.28 A | C |
| ATOM | 788 | CG1 | VAL | A | 136 | 28.904 | 51.607 | 0.168 | 1.00 | 43.53 A | C |
| ATOM | 789 | CG2 | VAL | A | 136 | 30.292 | 49.913 | −1.020 | 1.00 | 41.86 A | C |
| ATOM | 790 | C | VAL | A | 136 | 31.151 | 53.011 | 1.075 | 1.00 | 38.60 A | C |
| ATOM | 791 | O | VAL | A | 136 | 30.336 | 53.857 | 0.738 | 1.00 | 36.43 A | O |
| ATOM | 792 | N | ILE | A | 137 | 31.836 | 53.102 | 2.209 | 1.00 | 41.57 A | N |
| ATOM | 793 | CA | ILE | A | 137 | 31.736 | 54.292 | 3.052 | 1.00 | 40.82 A | C |
| ATOM | 794 | CB | ILE | A | 137 | 32.122 | 54.006 | 4.529 | 1.00 | 41.43 A | C |
| ATOM | 795 | CG2 | ILE | A | 137 | 32.339 | 55.302 | 5.291 | 1.00 | 35.32 A | C |
| ATOM | 796 | CG1 | ILE | A | 137 | 31.035 | 53.179 | 5.226 | 1.00 | 40.62 A | C |
| ATOM | 797 | CD1 | ILE | A | 137 | 31.238 | 53.011 | 6.733 | 1.00 | 34.08 A | C |
| ATOM | 798 | C | ILE | A | 137 | 32.663 | 55.357 | 2.475 | 1.00 | 42.18 A | C |
| ATOM | 799 | O | ILE | A | 137 | 32.322 | 56.541 | 2.404 | 1.00 | 41.58 A | O |
| ATOM | 800 | N | ASP | A | 138 | 33.836 | 54.909 | 2.045 | 1.00 | 40.62 A | N |
| ATOM | 801 | CA | ASP | A | 138 | 34.812 | 55.768 | 1.397 | 1.00 | 38.08 A | C |
| ATOM | 802 | CB | ASP | A | 138 | 36.018 | 54.932 | 0.966 | 1.00 | 37.43 A | C |
| ATOM | 803 | CG | ASP | A | 138 | 36.833 | 54.422 | 2.144 | 1.00 | 43.62 A | C |
| ATOM | 804 | OD1 | ASP | A | 138 | 36.385 | 54.574 | 3.301 | 1.00 | 37.62 A | O |
| ATOM | 805 | OD2 | ASP | A | 138 | 37.931 | 53.870 | 1.906 | 1.00 | 43.96 A | O |
| ATOM | 806 | C | ASP | A | 138 | 34.228 | 56.481 | 0.177 | 1.00 | 40.95 A | C |
| ATOM | 807 | O | ASP | A | 138 | 34.522 | 57.655 | −0.076 | 1.00 | 42.39 A | O |
| ATOM | 808 | N | ASP | A | 139 | 33.412 | 55.761 | −0.586 | 1.00 | 37.43 A | N |
| ATOM | 809 | CA | ASP | A | 139 | 32.832 | 56.301 | −1.808 | 1.00 | 39.64 A | C |
| ATOM | 810 | CB | ASP | A | 139 | 32.382 | 55.169 | −2.725 | 1.00 | 40.52 A | C |
| ATOM | 811 | CG | ASP | A | 139 | 31.724 | 55.674 | −3.992 | 1.00 | 41.98 A | C |
| ATOM | 812 | OD1 | ASP | A | 139 | 32.451 | 56.114 | −4.914 | 1.00 | 45.33 A | O |
| ATOM | 813 | OD2 | ASP | A | 139 | 30.480 | 55.617 | −4.071 | 1.00 | 33.52 A | O |
| ATOM | 814 | C | ASP | A | 139 | 31.650 | 57.216 | −1.522 | 1.00 | 43.20 A | C |
| ATOM | 815 | O | ASP | A | 139 | 31.386 | 58.150 | −2.277 | 1.00 | 42.92 A | O |
| ATOM | 816 | N | ALA | A | 140 | 30.925 | 56.935 | −0.444 | 1.00 | 40.69 A | N |
| ATOM | 817 | CA | ALA | A | 140 | 29.761 | 57.741 | −0.089 | 1.00 | 43.22 A | C |
| ATOM | 818 | CB | ALA | A | 140 | 28.922 | 57.048 | 0.982 | 1.00 | 38.02 A | C |
| ATOM | 819 | C | ALA | A | 140 | 30.177 | 59.140 | 0.368 | 1.00 | 43.38 A | C |
| ATOM | 820 | O | ALA | A | 140 | 29.471 | 60.115 | 0.136 | 1.00 | 41.16 A | O |
| ATOM | 821 | N | PHE | A | 141 | 31.325 | 59.248 | 1.021 | 1.00 | 45.71 A | N |
| ATOM | 822 | CA | PHE | A | 141 | 31.790 | 60.564 | 1.433 | 1.00 | 46.15 A | C |

TABLE 13-continued

Coordinates for proMMP9(35-444 ΔFnII) (SEQ ID NO: 12) complex with Example 3

| ATOM | 823 | CB | PHE | A | 141 | 32.862 | 60.467 | 2.520 | 1.00 | 43.69 | A | C |
|------|-----|-----|-----|---|-----|--------|--------|--------|------|-------|---|---|
| ATOM | 824 | CG | PHE | A | 141 | 32.351 | 59.947 | 3.839 | 1.00 | 41.91 | A | C |
| ATOM | 825 | CD1 | PHE | A | 141 | 31.160 | 60.410 | 4.374 | 1.00 | 47.14 | A | C |
| ATOM | 826 | CD2 | PHE | A | 141 | 33.077 | 59.013 | 4.562 | 1.00 | 44.69 | A | C |
| ATOM | 827 | CE1 | PHE | A | 141 | 30.694 | 59.935 | 5.608 | 1.00 | 39.29 | A | C |
| ATOM | 828 | CE2 | PHE | A | 141 | 32.617 | 58.541 | 5.788 | 1.00 | 38.94 | A | C |
| ATOM | 829 | CZ | PHE | A | 141 | 31.432 | 59.005 | 6.309 | 1.00 | 31.58 | A | C |
| ATOM | 830 | C | PHE | A | 141 | 32.307 | 61.325 | 0.218 | 1.00 | 42.72 | A | C |
| ATOM | 831 | O | PHE | A | 141 | 31.998 | 62.509 | 0.036 | 1.00 | 41.23 | A | O |
| ATOM | 832 | N | ALA | A | 142 | 33.072 | 60.628 | −0.620 | 1.00 | 42.88 | A | N |
| ATOM | 833 | CA | ALA | A | 142 | 33.656 | 61.217 | −1.830 | 1.00 | 41.56 | A | C |
| ATOM | 834 | CB | ALA | A | 142 | 34.419 | 60.160 | −2.620 | 1.00 | 38.11 | A | C |
| ATOM | 835 | C | ALA | A | 142 | 32.593 | 61.865 | −2.707 | 1.00 | 36.22 | A | C |
| ATOM | 836 | O | ALA | A | 142 | 32.711 | 63.031 | −3.091 | 1.00 | 33.19 | A | O |
| ATOM | 837 | N | ARG | A | 143 | 31.557 | 61.092 | −3.013 | 1.00 | 38.42 | A | N |
| ATOM | 838 | CA | ARG | A | 143 | 30.433 | 61.562 | −3.809 | 1.00 | 35.08 | A | C |
| ATOM | 839 | CB | ARG | A | 143 | 29.424 | 60.441 | −3.997 | 1.00 | 35.80 | A | C |
| ATOM | 840 | CG | ARG | A | 143 | 29.831 | 59.351 | −4.964 | 1.00 | 30.32 | A | C |
| ATOM | 841 | CD | ARG | A | 143 | 29.156 | 58.058 | −4.546 | 1.00 | 40.76 | A | C |
| ATOM | 842 | NE | ARG | A | 143 | 27.710 | 58.232 | −4.379 | 1.00 | 45.34 | A | N |
| ATOM | 843 | CZ | ARG | A | 143 | 26.940 | 57.502 | −3.572 | 1.00 | 43.79 | A | C |
| ATOM | 844 | NH1 | ARG | A | 143 | 27.462 | 56.542 | −2.815 | 1.00 | 40.55 | A | N |
| ATOM | 845 | NH2 | ARG | A | 143 | 25.640 | 57.746 | −3.512 | 1.00 | 45.12 | A | N |
| ATOM | 846 | C | ARG | A | 143 | 29.754 | 62.732 | −3.117 | 1.00 | 35.96 | A | C |
| ATOM | 847 | O | ARG | A | 143 | 29.196 | 63.610 | −3.769 | 1.00 | 35.25 | A | O |
| ATOM | 848 | N | ALA | A | 144 | 29.809 | 62.733 | −1.789 | 1.00 | 37.43 | A | N |
| ATOM | 849 | CA | ALA | A | 144 | 29.154 | 63.763 | −0.999 | 1.00 | 38.17 | A | C |
| ATOM | 850 | CB | ALA | A | 144 | 29.075 | 63.344 | 0.458 | 1.00 | 37.91 | A | C |
| ATOM | 851 | C | ALA | A | 144 | 29.899 | 65.082 | −1.144 | 1.00 | 40.95 | A | C |
| ATOM | 852 | O | ALA | A | 144 | 29.282 | 66.151 | −1.265 | 1.00 | 36.68 | A | O |
| ATOM | 853 | N | PHE | A | 145 | 31.230 | 64.994 | −1.129 | 1.00 | 42.51 | A | N |
| ATOM | 854 | CA | PHE | A | 145 | 32.092 | 66.142 | −1.388 | 1.00 | 32.53 | A | C |
| ATOM | 855 | CB | PHE | A | 145 | 33.539 | 65.829 | −1.029 | 1.00 | 35.94 | A | C |
| ATOM | 856 | CG | PHE | A | 145 | 33.834 | 65.883 | 0.443 | 1.00 | 37.74 | A | C |
| ATOM | 857 | CD1 | PHE | A | 145 | 33.538 | 67.018 | 1.185 | 1.00 | 35.05 | A | C |
| ATOM | 858 | CD2 | PHE | A | 145 | 34.440 | 64.803 | 1.080 | 1.00 | 33.17 | A | C |
| ATOM | 859 | CE1 | PHE | A | 145 | 33.831 | 67.069 | 2.541 | 1.00 | 37.52 | A | C |
| ATOM | 860 | CE2 | PHE | A | 145 | 34.730 | 64.841 | 2.429 | 1.00 | 29.05 | A | C |
| ATOM | 861 | CZ | PHE | A | 145 | 34.431 | 65.976 | 3.163 | 1.00 | 36.76 | A | C |
| ATOM | 862 | C | PHE | A | 145 | 32.021 | 66.498 | −2.858 | 1.00 | 31.13 | A | C |
| ATOM | 863 | O | PHE | A | 145 | 32.093 | 67.665 | −3.231 | 1.00 | 38.12 | A | O |
| ATOM | 864 | N | ALA | A | 146 | 31.881 | 65.487 | −3.698 | 1.00 | 29.39 | A | N |
| ATOM | 865 | CA | ALA | A | 146 | 31.830 | 65.727 | −5.130 | 1.00 | 32.09 | A | C |
| ATOM | 866 | CB | ALA | A | 146 | 31.694 | 64.419 | −5.886 | 1.00 | 25.89 | A | C |
| ATOM | 867 | C | ALA | A | 146 | 30.701 | 66.694 | −5.492 | 1.00 | 33.03 | A | C |
| ATOM | 868 | O | ALA | A | 146 | 30.708 | 67.283 | −6.569 | 1.00 | 39.49 | A | O |
| ATOM | 869 | N | LEU | A | 147 | 29.735 | 66.857 | −4.595 | 1.00 | 31.00 | A | N |
| ATOM | 870 | CA | LEU | A | 147 | 28.639 | 67.805 | −4.824 | 1.00 | 40.30 | A | C |
| ATOM | 871 | CB | LEU | A | 147 | 27.421 | 67.467 | −3.959 | 1.00 | 33.31 | A | C |
| ATOM | 872 | CG | LEU | A | 147 | 26.682 | 66.141 | −4.094 | 1.00 | 36.71 | A | C |
| ATOM | 873 | CD1 | LEU | A | 147 | 25.711 | 66.008 | −2.925 | 1.00 | 37.37 | A | C |
| ATOM | 874 | CD2 | LEU | A | 147 | 25.950 | 66.036 | −5.418 | 1.00 | 26.22 | A | C |
| ATOM | 875 | C | LEU | A | 147 | 29.038 | 69.257 | −4.541 | 1.00 | 38.47 | A | C |
| ATOM | 876 | O | LEU | A | 147 | 28.702 | 70.161 | −5.295 | 1.00 | 35.87 | A | O |
| ATOM | 877 | N | TRP | A | 148 | 29.725 | 69.476 | −3.430 | 1.00 | 36.50 | A | N |
| ATOM | 878 | CA | TRP | A | 148 | 30.039 | 70.819 | −3.010 | 1.00 | 35.94 | A | C |
| ATOM | 879 | CB | TRP | A | 148 | 30.357 | 70.848 | −1.514 | 1.00 | 39.58 | A | C |
| ATOM | 880 | CG | TRP | A | 148 | 29.176 | 70.543 | −0.590 | 1.00 | 44.37 | A | C |
| ATOM | 881 | CD2 | TRP | A | 148 | 27.969 | 71.309 | −0.444 | 1.00 | 38.36 | A | C |
| ATOM | 882 | CE2 | TRP | A | 148 | 27.174 | 70.661 | 0.521 | 1.00 | 41.11 | A | C |
| ATOM | 883 | CE3 | TRP | A | 148 | 27.481 | 72.476 | −1.037 | 1.00 | 36.75 | A | C |
| ATOM | 884 | CD1 | TRP | A | 148 | 29.066 | 69.497 | 0.286 | 1.00 | 38.34 | A | C |
| ATOM | 885 | NE1 | TRP | A | 148 | 27.864 | 69.556 | 0.950 | 1.00 | 36.28 | A | N |
| ATOM | 886 | CZ2 | TRP | A | 148 | 25.924 | 71.147 | 0.908 | 1.00 | 37.91 | A | C |
| ATOM | 887 | CZ3 | TRP | A | 148 | 26.231 | 72.946 | −0.658 | 1.00 | 27.33 | A | C |
| ATOM | 888 | CH2 | TRP | A | 148 | 25.477 | 72.291 | 0.305 | 1.00 | 27.25 | A | C |
| ATOM | 889 | C | TRP | A | 148 | 31.218 | 71.360 | −3.812 | 1.00 | 45.39 | A | C |
| ATOM | 890 | O | TRP | A | 148 | 31.389 | 72.570 | −3.951 | 1.00 | 47.98 | A | O |
| ATOM | 891 | N | SER | A | 149 | 32.042 | 70.468 | −4.342 | 1.00 | 39.84 | A | N |
| ATOM | 892 | CA | SER | A | 149 | 33.196 | 70.922 | −5.097 | 1.00 | 39.66 | A | C |
| ATOM | 893 | CB | SER | A | 149 | 34.214 | 69.797 | −5.261 | 1.00 | 35.74 | A | C |
| ATOM | 894 | OG | SER | A | 149 | 33.849 | 68.947 | −6.328 | 1.00 | 38.64 | A | O |
| ATOM | 895 | C | SER | A | 149 | 32.790 | 71.496 | −6.461 | 1.00 | 41.43 | A | C |
| ATOM | 896 | O | SER | A | 149 | 33.298 | 72.535 | −6.877 | 1.00 | 44.16 | A | O |
| ATOM | 897 | N | ALA | A | 150 | 31.869 | 70.831 | −7.149 | 1.00 | 34.70 | A | N |
| ATOM | 898 | CA | ALA | A | 150 | 31.451 | 71.284 | −8.469 | 1.00 | 38.94 | A | C |
| ATOM | 899 | CB | ALA | A | 150 | 30.457 | 70.311 | −9.076 | 1.00 | 35.49 | A | C |

TABLE 13-continued

Coordinates for proMMP9(35-444 ΔFnII) (SEQ ID NO: 12) complex with Example 3

| ATOM | 900 | C | ALA | A | 150 | 30.876 | 72.703 | −8.459 | 1.00 | 41.16 | A | C |
|---|---|---|---|---|---|---|---|---|---|---|---|---|
| ATOM | 901 | O | ALA | A | 150 | 30.783 | 73.356 | −9.503 | 1.00 | 41.26 | A | O |
| ATOM | 902 | N | VAL | A | 151 | 30.504 | 73.183 | −7.279 | 1.00 | 42.06 | A | N |
| ATOM | 903 | CA | VAL | A | 151 | 29.802 | 74.459 | −7.163 | 1.00 | 41.64 | A | C |
| ATOM | 904 | CB | VAL | A | 151 | 28.369 | 74.248 | −6.673 | 1.00 | 37.55 | A | C |
| ATOM | 905 | CG1 | VAL | A | 151 | 27.622 | 73.366 | −7.645 | 1.00 | 31.20 | A | C |
| ATOM | 906 | CG2 | VAL | A | 151 | 28.377 | 73.620 | −5.285 | 1.00 | 41.04 | A | C |
| ATOM | 907 | C | VAL | A | 151 | 30.519 | 75.451 | −6.245 | 1.00 | 42.34 | A | C |
| ATOM | 908 | O | VAL | A | 151 | 30.004 | 76.525 | −5.955 | 1.00 | 42.81 | A | O |
| ATOM | 909 | N | THR | A | 152 | 31.713 | 75.081 | −5.798 | 1.00 | 38.65 | A | N |
| ATOM | 910 | CA | THR | A | 152 | 32.527 | 75.962 | −4.984 | 1.00 | 41.50 | A | C |
| ATOM | 911 | CB | THR | A | 152 | 32.632 | 75.469 | −3.530 | 1.00 | 47.07 | A | C |
| ATOM | 912 | OG1 | THR | A | 152 | 33.112 | 74.119 | −3.521 | 1.00 | 47.18 | A | O |
| ATOM | 913 | CG2 | THR | A | 152 | 31.286 | 75.537 | −2.824 | 1.00 | 45.18 | A | C |
| ATOM | 914 | C | THR | A | 152 | 33.936 | 75.991 | −5.543 | 1.00 | 47.37 | A | C |
| ATOM | 915 | O | THR | A | 152 | 34.374 | 75.038 | −6.182 | 1.00 | 44.00 | A | O |
| ATOM | 916 | N | PRO | A | 153 | 34.644 | 77.104 | −5.326 | 1.00 | 48.44 | A | N |
| ATOM | 917 | CD | PRO | A | 153 | 34.103 | 78.454 | −5.096 | 1.00 | 43.82 | A | C |
| ATOM | 918 | CA | PRO | A | 153 | 36.090 | 77.136 | −5.536 | 1.00 | 47.51 | A | C |
| ATOM | 919 | CB | PRO | A | 153 | 36.413 | 78.627 | −5.411 | 1.00 | 47.79 | A | C |
| ATOM | 920 | CG | PRO | A | 153 | 35.281 | 79.168 | −4.550 | 1.00 | 45.42 | A | C |
| ATOM | 921 | C | PRO | A | 153 | 36.771 | 76.374 | −4.407 | 1.00 | 47.92 | A | C |
| ATOM | 922 | O | PRO | A | 153 | 37.545 | 76.968 | −3.662 | 1.00 | 54.80 | A | O |
| ATOM | 923 | N | LEU | A | 154 | 36.466 | 75.088 | −4.265 | 1.00 | 48.13 | A | N |
| ATOM | 924 | CA | LEU | A | 154 | 37.070 | 74.261 | −3.224 | 1.00 | 44.42 | A | C |
| ATOM | 925 | CB | LEU | A | 154 | 36.127 | 74.137 | −2.025 | 1.00 | 45.56 | A | C |
| ATOM | 926 | CG | LEU | A | 154 | 35.774 | 75.362 | −1.172 | 1.00 | 46.87 | A | C |
| ATOM | 927 | CD1 | LEU | A | 154 | 34.857 | 74.954 | −0.035 | 1.00 | 41.76 | A | C |
| ATOM | 928 | CD2 | LEU | A | 154 | 37.009 | 76.035 | −0.621 | 1.00 | 40.70 | A | C |
| ATOM | 929 | C | LEU | A | 154 | 37.384 | 72.866 | −3.743 | 1.00 | 42.40 | A | C |
| ATOM | 930 | O | LEU | A | 154 | 36.636 | 72.317 | −4.552 | 1.00 | 43.63 | A | O |
| ATOM | 931 | N | THR | A | 155 | 38.485 | 72.288 | −3.272 | 1.00 | 41.09 | A | N |
| ATOM | 932 | CA | THR | A | 155 | 38.779 | 70.880 | −3.534 | 1.00 | 35.89 | A | C |
| ATOM | 933 | CB | THR | A | 155 | 40.135 | 70.676 | −4.236 | 1.00 | 37.39 | A | C |
| ATOM | 934 | OG1 | THR | A | 155 | 41.108 | 71.559 | −3.664 | 1.00 | 47.03 | A | O |
| ATOM | 935 | CG2 | THR | A | 155 | 40.009 | 70.947 | −5.720 | 1.00 | 39.81 | A | C |
| ATOM | 936 | C | THR | A | 155 | 38.800 | 70.084 | −2.240 | 1.00 | 39.71 | A | C |
| ATOM | 937 | O | THR | A | 155 | 39.094 | 70.615 | −1.169 | 1.00 | 41.35 | A | O |
| ATOM | 938 | N | PHE | A | 156 | 38.505 | 68.797 | −2.342 | 1.00 | 37.31 | A | N |
| ATOM | 939 | CA | PHE | A | 156 | 38.477 | 67.959 | −1.162 | 1.00 | 39.59 | A | C |
| ATOM | 940 | CB | PHE | A | 156 | 37.042 | 67.515 | −0.853 | 1.00 | 37.81 | A | C |
| ATOM | 941 | CG | PHE | A | 156 | 36.093 | 68.664 | −0.701 | 1.00 | 38.38 | A | C |
| ATOM | 942 | CD1 | PHE | A | 156 | 35.306 | 69.072 | −1.760 | 1.00 | 37.70 | A | C |
| ATOM | 943 | CD2 | PHE | A | 156 | 36.021 | 69.367 | 0.490 | 1.00 | 38.34 | A | C |
| ATOM | 944 | CE1 | PHE | A | 156 | 34.457 | 70.137 | −1.632 | 1.00 | 32.30 | A | C |
| ATOM | 945 | CE2 | PHE | A | 156 | 35.169 | 70.435 | 0.618 | 1.00 | 37.95 | A | C |
| ATOM | 946 | CZ | PHE | A | 156 | 34.388 | 70.818 | −0.448 | 1.00 | 34.11 | A | C |
| ATOM | 947 | C | PHE | A | 156 | 39.435 | 66.789 | −1.308 | 1.00 | 39.55 | A | C |
| ATOM | 948 | O | PHE | A | 156 | 39.335 | 65.977 | −2.226 | 1.00 | 39.02 | A | O |
| ATOM | 949 | N | THR | A | 157 | 40.376 | 66.723 | −0.386 | 1.00 | 37.75 | A | N |
| ATOM | 950 | CA | THR | A | 157 | 41.458 | 65.771 | −0.474 | 1.00 | 40.55 | A | C |
| ATOM | 951 | CB | THR | A | 157 | 42.796 | 66.513 | −0.666 | 1.00 | 43.34 | A | C |
| ATOM | 952 | OG1 | THR | A | 157 | 42.926 | 66.909 | −2.036 | 1.00 | 41.00 | A | O |
| ATOM | 953 | CG2 | THR | A | 157 | 43.947 | 65.631 | −0.293 | 1.00 | 40.02 | A | C |
| ATOM | 954 | C | THR | A | 157 | 41.503 | 64.939 | 0.796 | 1.00 | 43.28 | A | C |
| ATOM | 955 | O | THR | A | 157 | 41.546 | 65.482 | 1.902 | 1.00 | 37.87 | A | O |
| ATOM | 956 | N | ARG | A | 158 | 41.483 | 63.619 | 0.629 | 1.00 | 45.97 | A | N |
| ATOM | 957 | CA | ARG | A | 158 | 41.479 | 62.698 | 1.763 | 1.00 | 48.13 | A | C |
| ATOM | 958 | CB | ARG | A | 158 | 40.867 | 61.358 | 1.362 | 1.00 | 41.11 | A | C |
| ATOM | 959 | CG | ARG | A | 158 | 41.072 | 60.287 | 2.395 | 1.00 | 36.93 | A | C |
| ATOM | 960 | CD | ARG | A | 158 | 40.627 | 58.948 | 1.872 | 1.00 | 38.87 | A | C |
| ATOM | 961 | NE | ARG | A | 158 | 40.686 | 57.931 | 2.914 | 1.00 | 39.75 | A | N |
| ATOM | 962 | CZ | ARG | A | 158 | 40.205 | 56.701 | 2.776 | 1.00 | 41.47 | A | C |
| ATOM | 963 | NH1 | ARG | A | 158 | 39.619 | 56.340 | 1.638 | 1.00 | 32.69 | A | N |
| ATOM | 964 | NH2 | ARG | A | 158 | 40.304 | 55.837 | 3.779 | 1.00 | 36.91 | A | N |
| ATOM | 965 | C | ARG | A | 158 | 42.879 | 62.474 | 2.336 | 1.00 | 45.23 | A | C |
| ATOM | 966 | O | ARG | A | 158 | 43.847 | 62.342 | 1.591 | 1.00 | 42.73 | A | O |
| ATOM | 967 | N | VAL | A | 159 | 42.973 | 62.438 | 3.662 | 1.00 | 47.17 | A | N |
| ATOM | 968 | CA | VAL | A | 159 | 44.249 | 62.238 | 4.347 | 1.00 | 51.53 | A | C |
| ATOM | 969 | CB | VAL | A | 159 | 44.802 | 63.561 | 4.903 | 1.00 | 44.96 | A | C |
| ATOM | 970 | CG1 | VAL | A | 159 | 44.743 | 64.642 | 3.836 | 1.00 | 41.71 | A | C |
| ATOM | 971 | CG2 | VAL | A | 159 | 44.023 | 63.976 | 6.132 | 1.00 | 41.47 | A | C |
| ATOM | 972 | C | VAL | A | 159 | 44.109 | 61.230 | 5.495 | 1.00 | 57.18 | A | C |
| ATOM | 973 | O | VAL | A | 159 | 43.022 | 60.673 | 5.720 | 1.00 | 53.41 | A | O |
| ATOM | 974 | N | TYR | A | 160 | 45.199 | 61.003 | 6.228 | 1.00 | 51.13 | A | N |
| ATOM | 975 | CA | TYR | A | 160 | 45.196 | 59.957 | 7.248 | 1.00 | 46.79 | A | C |
| ATOM | 976 | CB | TYR | A | 160 | 45.963 | 58.737 | 6.737 | 1.00 | 40.00 | A | C |

TABLE 13-continued

Coordinates for proMMP9(35-444 ΔFnII) (SEQ ID NO: 12) complex with Example 3

| ATOM | 977 | CG | TYR | A | 160 | 45.255 | 58.088 | 5.573 | 1.00 | 45.10 | A | C |
|---|---|---|---|---|---|---|---|---|---|---|---|---|
| ATOM | 978 | CD1 | TYR | A | 160 | 45.457 | 58.528 | 4.265 | 1.00 | 49.58 | A | C |
| ATOM | 979 | CE1 | TYR | A | 160 | 44.780 | 57.936 | 3.198 | 1.00 | 41.76 | A | C |
| ATOM | 980 | CD2 | TYR | A | 160 | 44.351 | 57.060 | 5.781 | 1.00 | 44.65 | A | C |
| ATOM | 981 | CE2 | TYR | A | 160 | 43.679 | 56.468 | 4.729 | 1.00 | 42.75 | A | C |
| ATOM | 982 | CZ | TYR | A | 160 | 43.891 | 56.908 | 3.446 | 1.00 | 38.36 | A | C |
| ATOM | 983 | OH | TYR | A | 160 | 43.202 | 56.301 | 2.424 | 1.00 | 42.28 | A | O |
| ATOM | 984 | C | TYR | A | 160 | 45.699 | 60.414 | 8.613 | 1.00 | 49.65 | A | C |
| ATOM | 985 | O | TYR | A | 160 | 46.354 | 59.659 | 9.334 | 1.00 | 50.66 | A | O |
| ATOM | 986 | N | SER | A | 161 | 45.356 | 61.645 | 8.975 | 1.00 | 46.05 | A | N |
| ATOM | 987 | CA | SER | A | 161 | 45.850 | 62.251 | 10.203 | 1.00 | 48.54 | A | C |
| ATOM | 988 | CB | SER | A | 161 | 47.191 | 62.947 | 9.944 | 1.00 | 55.90 | A | C |
| ATOM | 989 | OG | SER | A | 161 | 47.049 | 64.009 | 9.006 | 1.00 | 60.58 | A | O |
| ATOM | 990 | C | SER | A | 161 | 44.853 | 63.257 | 10.777 | 1.00 | 53.00 | A | C |
| ATOM | 991 | O | SER | A | 161 | 43.921 | 63.685 | 10.097 | 1.00 | 48.39 | A | O |
| ATOM | 222 | N | ARG | A | 162 | 45.065 | 63.636 | 12.032 | 1.00 | 50.80 | A | N |
| ATOM | 993 | CA | ARG | A | 162 | 44.215 | 64.609 | 12.698 | 1.00 | 52.52 | A | C |
| ATOM | 994 | CB | ARG | A | 162 | 44.490 | 64.588 | 14.202 | 1.00 | 66.58 | A | C |
| ATOM | 995 | CG | ARG | A | 162 | 44.693 | 65.953 | 14.843 | 1.00 | 68.63 | A | C |
| ATOM | 996 | CD | ARG | A | 162 | 45.694 | 65.838 | 15.979 | 1.00 | 68.43 | A | C |
| ATOM | 997 | NE | ARG | A | 162 | 46.759 | 64.900 | 15.632 | 1.00 | 72.12 | A | N |
| ATOM | 998 | CZ | ARG | A | 162 | 47.586 | 64.341 | 16.509 | 1.00 | 80.60 | A | C |
| ATOM | 999 | NH1 | ARG | A | 162 | 47.476 | 64.621 | 17.804 | 1.00 | 73.93 | A | N |
| ATOM | 1000 | NH2 | ARG | A | 162 | 48.522 | 63.496 | 16.090 | 1.00 | 68.46 | A | N |
| ATOM | 1001 | C | ARG | A | 162 | 44.437 | 66.003 | 12.144 | 1.00 | 54.65 | A | C |
| ATOM | 1002 | O | ARG | A | 162 | 43.697 | 66.930 | 12.452 | 1.00 | 57.84 | A | O |
| ATOM | 1003 | N | ASP | A | 163 | 45.456 | 66.149 | 11.309 | 1.00 | 65.80 | A | N |
| ATOM | 1004 | CA | ASP | A | 163 | 45.811 | 67.456 | 10.767 | 1.00 | 66.90 | A | C |
| ATOM | 1005 | CB | ASP | A | 163 | 47.256 | 67.442 | 10.267 | 1.00 | 69.55 | A | C |
| ATOM | 1006 | CG | ASP | A | 163 | 47.919 | 68.799 | 10.378 | 1.00 | 77.87 | A | C |
| ATOM | 1007 | OD1 | ASP | A | 163 | 47.834 | 69.406 | 11.469 | 1.00 | 72.47 | A | O |
| ATOM | 1008 | OD2 | ASP | A | 163 | 48.524 | 69.252 | 9.379 | 1.00 | 76.64 | A | O |
| ATOM | 1009 | C | ASP | A | 163 | 44.870 | 67.923 | 9.645 | 1.00 | 59.97 | A | C |
| ATOM | 1010 | O | ASP | A | 163 | 45.092 | 68.970 | 9.033 | 1.00 | 54.83 | A | O |
| ATOM | 1011 | N | ALA | A | 164 | 43.820 | 67.152 | 9.382 | 1.00 | 52.59 | A | N |
| ATOM | 1012 | CA | ALA | A | 164 | 42.890 | 67.497 | 8.315 | 1.00 | 46.75 | A | C |
| ATOM | 1013 | CB | ALA | A | 164 | 42.177 | 66.262 | 7.823 | 1.00 | 45.52 | A | C |
| ATOM | 1014 | C | ALA | A | 164 | 41.883 | 68.554 | 8.765 | 1.00 | 50.10 | A | C |
| ATOM | 1015 | O | ALA | A | 164 | 41.469 | 68.580 | 9.924 | 1.00 | 45.67 | A | O |
| ATOM | 1016 | N | ASP | A | 165 | 41.505 | 69.431 | 7.840 | 1.00 | 49.12 | A | N |
| ATOM | 1017 | CA | ASP | A | 165 | 40.475 | 70.430 | 8.098 | 1.00 | 46.81 | A | C |
| ATOM | 1018 | CB | ASP | A | 165 | 40.153 | 71.212 | 6.823 | 1.00 | 48.31 | A | C |
| ATOM | 1019 | CG | ASP | A | 165 | 41.389 | 71.683 | 6.092 | 1.00 | 49.96 | A | C |
| ATOM | 1020 | OD1 | ASP | A | 165 | 42.307 | 72.202 | 6.761 | 1.00 | 57.10 | A | O |
| ATOM | 1021 | OD2 | ASP | A | 165 | 41.434 | 71.551 | 4.848 | 1.00 | 40.05 | A | O |
| ATOM | 1022 | C | ASP | A | 165 | 39.193 | 69.765 | 8.584 | 1.00 | 49.76 | A | C |
| ATOM | 1023 | O | ASP | A | 165 | 38.471 | 70.320 | 9.416 | 1.00 | 51.93 | A | O |
| ATOM | 1024 | N | ILE | A | 166 | 38.900 | 68.582 | 8.045 | 1.00 | 46.34 | A | N |
| ATOM | 1025 | CA | ILE | A | 166 | 37.658 | 67.882 | 8.369 | 1.00 | 47.71 | A | C |
| ATOM | 1026 | CB | ILE | A | 166 | 36.702 | 67.839 | 7.160 | 1.00 | 42.91 | A | C |
| ATOM | 1027 | CG2 | ILE | A | 166 | 35.365 | 67.232 | 7.559 | 1.00 | 44.34 | A | C |
| ATOM | 1028 | CG1 | ILE | A | 166 | 36.495 | 69.234 | 6.583 | 1.00 | 42.84 | A | C |
| ATOM | 1029 | CD1 | ILE | A | 166 | 35.255 | 69.345 | 5.710 | 1.00 | 43.27 | A | C |
| ATOM | 1030 | C | ILE | A | 166 | 37.866 | 66.447 | 8.862 | 1.00 | 43.66 | A | C |
| ATOM | 1031 | O | ILE | A | 166 | 38.131 | 65.547 | 8.070 | 1.00 | 38.28 | A | O |
| ATOM | 1032 | N | VAL | A | 167 | 37.730 | 66.242 | 10.171 | 1.00 | 43.55 | A | N |
| ATOM | 1033 | CA | VAL | A | 167 | 37.807 | 64.902 | 10.753 | 1.00 | 43.31 | A | C |
| ATOM | 1034 | CB | VAL | A | 167 | 38.393 | 64.932 | 12.167 | 1.00 | 49.52 | A | C |
| ATOM | 1035 | CG1 | VAL | A | 167 | 38.624 | 63.514 | 12.670 | 1.00 | 48.56 | A | C |
| ATOM | 1036 | CG2 | VAL | A | 167 | 39.684 | 65.733 | 12.184 | 1.00 | 44.69 | A | C |
| ATOM | 1037 | C | VAL | A | 167 | 36.432 | 64.233 | 10.805 | 1.00 | 40.56 | A | C |
| ATOM | 1038 | O | VAL | A | 167 | 35.483 | 64.767 | 11.370 | 1.00 | 43.26 | A | O |
| ATOM | 1039 | N | ILE | A | 168 | 36.338 | 63.057 | 10.206 | 1.00 | 39.85 | A | N |
| ATOM | 1040 | CA | ILE | A | 168 | 35.070 | 62.362 | 10.062 | 1.00 | 39.18 | A | C |
| ATOM | 1041 | CB | ILE | A | 168 | 34.849 | 61.946 | 8.588 | 1.00 | 36.61 | A | C |
| ATOM | 1042 | CG2 | ILE | A | 168 | 33.826 | 60.833 | 8.460 | 1.00 | 35.97 | A | C |
| ATOM | 1043 | CG1 | ILE | A | 168 | 34.427 | 63.161 | 7.762 | 1.00 | 39.08 | A | C |
| ATOM | 1044 | CD1 | ILE | A | 168 | 34.124 | 62.833 | 6.313 | 1.00 | 44.23 | A | C |
| ATOM | 1045 | C | ILE | A | 168 | 35.024 | 61.159 | 10.999 | 1.00 | 38.30 | A | C |
| ATOM | 1046 | O | ILE | A | 168 | 35.902 | 60.299 | 10.972 | 1.00 | 36.56 | A | O |
| ATOM | 1047 | N | GLN | A | 169 | 33.994 | 61.108 | 11.833 | 1.00 | 41.28 | A | N |
| ATOM | 1048 | CA | GLN | A | 169 | 33.959 | 60.134 | 12.919 | 1.00 | 45.36 | A | C |
| ATOM | 1049 | CB | GLN | A | 169 | 34.496 | 60.779 | 14.199 | 1.00 | 49.64 | A | C |
| ATOM | 1050 | CG | GLN | A | 169 | 34.184 | 60.038 | 15.479 | 1.00 | 47.23 | A | C |
| ATOM | 1051 | CD | GLN | A | 169 | 34.877 | 60.675 | 16.666 | 1.00 | 50.98 | A | C |
| ATOM | 1052 | OE1 | GLN | A | 169 | 35.772 | 61.505 | 16.497 | 1.00 | 50.74 | A | O |
| ATOM | 1053 | NE2 | GLN | A | 169 | 34.471 | 60.292 | 17.871 | 1.00 | 52.60 | A | N |

TABLE 13-continued

Coordinates for proMMP9(35-444 ΔFnII) (SEQ ID NO: 12) complex with Example 3

| ATOM | 1054 | C   | GLN | A | 169 | 32.575 | 59.554 | 13.158 | 1.00 | 37.52 | A | C |
|------|------|-----|-----|---|-----|--------|--------|--------|------|-------|---|---|
| ATOM | 1055 | O   | GLN | A | 169 | 31.577 | 60.252 | 13.065 | 1.00 | 44.21 | A | O |
| ATOM | 1056 | N   | PHE | A | 170 | 32.529 | 58.260 | 13.438 | 1.00 | 38.70 | A | N |
| ATOM | 1057 | CA  | PHE | A | 170 | 31.301 | 57.604 | 13.854 | 1.00 | 41.18 | A | C |
| ATOM | 1058 | CB  | PHE | A | 170 | 31.206 | 56.210 | 13.232 | 1.00 | 39.26 | A | C |
| ATOM | 1059 | CG  | PHE | A | 170 | 31.041 | 56.216 | 11.730 | 1.00 | 38.08 | A | C |
| ATOM | 1060 | CD1 | PHE | A | 170 | 32.117 | 56.497 | 10.896 | 1.00 | 41.99 | A | C |
| ATOM | 1061 | CD2 | PHE | A | 170 | 29.816 | 55.921 | 11.151 | 1.00 | 35.22 | A | C |
| ATOM | 1062 | CE1 | PHE | A | 170 | 31.974 | 56.498 | 9.508  | 1.00 | 38.90 | A | C |
| ATOM | 1063 | CE2 | PHE | A | 170 | 29.667 | 55.918 | 9.757  | 1.00 | 43.81 | A | C |
| ATOM | 1064 | CZ  | PHE | A | 170 | 30.749 | 56.210 | 8.939  | 1.00 | 37.30 | A | C |
| ATOM | 1065 | C   | PHE | A | 170 | 31.265 | 57.521 | 15.391 | 1.00 | 42.97 | A | C |
| ATOM | 1066 | O   | PHE | A | 170 | 32.291 | 57.332 | 16.041 | 1.00 | 38.89 | A | O |
| ATOM | 1067 | N   | GLY | A | 171 | 30.089 | 57.676 | 15.978 | 1.00 | 39.22 | A | N |
| ATOM | 1068 | CA  | GLY | A | 171 | 30.006 | 57.652 | 17.422 | 1.00 | 43.04 | A | C |
| ATOM | 1069 | C   | GLY | A | 171 | 28.637 | 57.277 | 17.930 | 1.00 | 46.38 | A | C |
| ATOM | 1070 | O   | GLY | A | 171 | 27.653 | 57.360 | 17.195 | 1.00 | 43.66 | A | O |
| ATOM | 1071 | N   | VAL | A | 172 | 28.583 | 56.838 | 19.185 | 1.00 | 44.13 | A | N |
| ATOM | 1072 | CA  | VAL | A | 172 | 27.317 | 56.613 | 19.866 | 1.00 | 40.95 | A | C |
| ATOM | 1073 | CB  | VAL | A | 172 | 27.027 | 55.109 | 20.107 | 1.00 | 40.62 | A | C |
| ATOM | 1074 | CG1 | VAL | A | 172 | 26.959 | 54.354 | 18.789 | 1.00 | 41.88 | A | C |
| ATOM | 1075 | CG2 | VAL | A | 172 | 28.076 | 54.503 | 21.011 | 1.00 | 47.38 | A | C |
| ATOM | 1076 | C   | VAL | A | 172 | 27.349 | 57.356 | 21.192 | 1.00 | 42.87 | A | C |
| ATOM | 1077 | O   | VAL | A | 172 | 28.384 | 57.415 | 21.852 | 1.00 | 42.41 | A | O |
| ATOM | 1078 | N   | ALA | A | 173 | 26.223 | 57.943 | 21.570 | 1.00 | 45.71 | A | N |
| ATOM | 1079 | CA  | ALA | A | 173 | 26.135 | 58.615 | 22.856 | 1.00 | 48.78 | A | C |
| ATOM | 1080 | CB  | ALA | A | 173 | 26.176 | 57.598 | 23.978 | 1.00 | 46.11 | A | C |
| ATOM | 1081 | C   | ALA | A | 173 | 27.269 | 59.622 | 23.003 | 1.00 | 48.28 | A | C |
| ATOM | 1082 | O   | ALA | A | 173 | 27.528 | 60.400 | 22.089 | 1.00 | 49.88 | A | O |
| ATOM | 1083 | N   | GLU | A | 174 | 27.943 | 59.613 | 24.150 | 1.00 | 49.13 | A | N |
| ATOM | 1084 | CA  | GLU | A | 174 | 29.070 | 60.522 | 24.362 | 1.00 | 58.08 | A | C |
| ATOM | 1085 | CB  | GLU | A | 174 | 29.282 | 60.808 | 25.852 | 1.00 | 52.66 | A | C |
| ATOM | 1086 | CG  | GLU | A | 174 | 30.548 | 61.610 | 26.154 | 1.00 | 58.78 | A | C |
| ATOM | 1087 | CD  | GLU | A | 174 | 30.548 | 63.002 | 25.534 | 1.00 | 59.48 | A | C |
| ATOM | 1088 | OE1 | GLU | A | 174 | 29.465 | 63.499 | 25.151 | 1.00 | 55.88 | A | O |
| ATOM | 1089 | OE2 | GLU | A | 174 | 31.641 | 63.603 | 25.435 | 1.00 | 60.46 | A | O |
| ATOM | 1090 | C   | GLU | A | 174 | 30.358 | 59.995 | 23.721 | 1.00 | 53.01 | A | C |
| ATOM | 1091 | O   | GLU | A | 174 | 30.834 | 58.904 | 24.045 | 1.00 | 51.94 | A | O |
| ATOM | 1092 | N   | HIS | A | 175 | 30.919 | 60.787 | 22.819 | 1.00 | 50.40 | A | N |
| ATOM | 1093 | CA  | HIS | A | 175 | 32.053 | 60.349 | 22.006 | 1.00 | 50.47 | A | C |
| ATOM | 1094 | CB  | HIS | A | 175 | 31.581 | 60.067 | 20.581 | 1.00 | 48.12 | A | C |
| ATOM | 1095 | CG  | HIS | A | 175 | 30.635 | 61.100 | 20.059 | 1.00 | 47.64 | A | C |
| ATOM | 1096 | CD2 | HIS | A | 175 | 30.852 | 62.243 | 19.366 | 1.00 | 48.22 | A | C |
| ATOM | 1097 | ND1 | HIS | A | 175 | 29.277 | 61.034 | 20.272 | 1.00 | 45.89 | A | N |
| ATOM | 1098 | CE1 | HIS | A | 175 | 28.695 | 62.082 | 19.717 | 1.00 | 45.76 | A | C |
| ATOM | 1099 | NE2 | HIS | A | 175 | 29.627 | 62.829 | 19.159 | 1.00 | 39.11 | A | N |
| ATOM | 1100 | C   | HIS | A | 175 | 33.192 | 61.368 | 21.978 | 1.00 | 45.82 | A | C |
| ATOM | 1101 | O   | HIS | A | 175 | 33.998 | 61.377 | 21.050 | 1.00 | 47.84 | A | O |
| ATOM | 1102 | N   | GLY | A | 176 | 33.238 | 62.237 | 22.983 | 1.00 | 49.29 | A | N |
| ATOM | 1103 | CA  | GLY | A | 176 | 34.398 | 63.077 | 23.204 | 1.00 | 43.18 | A | C |
| ATOM | 1104 | C   | GLY | A | 176 | 34.253 | 64.565 | 22.945 | 1.00 | 46.89 | A | C |
| ATOM | 1105 | O   | GLY | A | 176 | 35.266 | 65.263 | 22.790 | 1.00 | 37.40 | A | O |
| ATOM | 1106 | N   | ASP | A | 177 | 33.023 | 65.073 | 22.909 | 1.00 | 46.04 | A | N |
| ATOM | 1107 | CA  | ASP | A | 177 | 32.844 | 66.487 | 22.563 | 1.00 | 46.91 | A | C |
| ATOM | 1108 | CB  | ASP | A | 177 | 32.640 | 66.660 | 21.053 | 1.00 | 43.92 | A | C |
| ATOM | 1109 | CG  | ASP | A | 177 | 31.303 | 66.121 | 20.572 | 1.00 | 44.98 | A | C |
| ATOM | 1110 | OD1 | ASP | A | 177 | 30.543 | 65.547 | 21.382 | 1.00 | 43.91 | A | O |
| ATOM | 1111 | OD2 | ASP | A | 177 | 31.016 | 66.279 | 19.368 | 1.00 | 40.34 | A | O |
| ATOM | 1112 | C   | ASP | A | 177 | 31.743 | 67.228 | 23.309 | 1.00 | 49.54 | A | C |
| ATOM | 1113 | O   | ASP | A | 177 | 31.454 | 68.377 | 22.986 | 1.00 | 59.49 | A | O |
| ATOM | 1114 | N   | GLY | A | 178 | 31.129 | 66.581 | 24.293 | 1.00 | 50.91 | A | N |
| ATOM | 1115 | CA  | GLY | A | 178 | 30.082 | 67.220 | 25.070 | 1.00 | 51.44 | A | C |
| ATOM | 1116 | C   | GLY | A | 178 | 28.811 | 67.524 | 24.297 | 1.00 | 48.15 | A | C |
| ATOM | 1117 | O   | GLY | A | 178 | 28.058 | 68.435 | 24.645 | 1.00 | 53.49 | A | O |
| ATOM | 1118 | N   | TYR | A | 179 | 28.588 | 66.774 | 23.226 | 1.00 | 49.83 | A | N |
| ATOM | 1119 | CA  | TYR | A | 179 | 27.300 | 66.750 | 22.551 | 1.00 | 48.79 | A | C |
| ATOM | 1120 | CB  | TYR | A | 179 | 27.331 | 67.557 | 21.259 | 1.00 | 43.85 | A | C |
| ATOM | 1121 | CG  | TYR | A | 179 | 27.400 | 69.049 | 21.467 | 1.00 | 45.92 | A | C |
| ATOM | 1122 | CD1 | TYR | A | 179 | 28.611 | 69.676 | 21.734 | 1.00 | 51.48 | A | C |
| ATOM | 1123 | CE1 | TYR | A | 179 | 28.681 | 71.043 | 21.917 | 1.00 | 50.00 | A | C |
| ATOM | 1124 | CD2 | TYR | A | 179 | 26.261 | 69.836 | 21.376 | 1.00 | 43.94 | A | C |
| ATOM | 1125 | CE2 | TYR | A | 179 | 26.321 | 71.201 | 21.553 | 1.00 | 41.37 | A | C |
| ATOM | 1126 | CZ  | TYR | A | 179 | 27.532 | 71.797 | 21.826 | 1.00 | 45.57 | A | C |
| ATOM | 1127 | OH  | TYR | A | 179 | 27.602 | 73.155 | 22.007 | 1.00 | 50.59 | A | O |
| ATOM | 1128 | C   | TYR | A | 179 | 26.987 | 65.293 | 22.255 | 1.00 | 51.91 | A | C |
| ATOM | 1129 | O   | TYR | A | 179 | 27.276 | 64.793 | 21.170 | 1.00 | 51.33 | A | O |
| ATOM | 1130 | N   | PRO | A | 180 | 26.410 | 64.597 | 23.237 | 1.00 | 49.18 | A | N |

TABLE 13-continued

Coordinates for proMMP9(35-444 ΔFnII) (SEQ ID NO: 12) complex with Example 3

| ATOM | 1131 | CD  | PRO | A | 180 | 25.960 | 65.088 | 24.550 | 1.00 | 44.48 A | C |
|------|------|-----|-----|---|-----|--------|--------|--------|------|---------|---|
| ATOM | 1132 | CA  | PRO | A | 180 | 26.210 | 63.158 | 23.085 | 1.00 | 48.80 A | C |
| ATOM | 1133 | CB  | PRO | A | 180 | 25.728 | 62.726 | 24.477 | 1.00 | 45.89 A | C |
| ATOM | 1134 | CG  | PRO | A | 180 | 26.098 | 63.873 | 25.405 | 1.00 | 46.52 A | C |
| ATOM | 1135 | C   | PRO | A | 180 | 25.146 | 62.875 | 22.044 | 1.00 | 46.04 A | C |
| ATOM | 1136 | O   | PRO | A | 180 | 24.287 | 63.721 | 21.816 | 1.00 | 48.93 A | O |
| ATOM | 1137 | N   | PHE | A | 181 | 25.220 | 61.714 | 21.404 | 1.00 | 47.43 A | N |
| ATOM | 1138 | CA  | PHE | A | 181 | 24.157 | 61.268 | 20.513 | 1.00 | 44.84 A | C |
| ATOM | 1139 | CB  | PHE | A | 181 | 24.682 | 60.254 | 19.494 | 1.00 | 44.55 A | C |
| ATOM | 1140 | CG  | PHE | A | 181 | 25.570 | 60.850 | 18.437 | 1.00 | 43.70 A | C |
| ATOM | 1141 | CD1 | PHE | A | 181 | 25.205 | 62.010 | 17.773 | 1.00 | 47.73 A | C |
| ATOM | 1142 | CD2 | PHE | A | 181 | 26.764 | 60.231 | 18.084 | 1.00 | 46.36 A | C |
| ATOM | 1143 | CE1 | PHE | A | 181 | 26.031 | 62.551 | 16.782 | 1.00 | 48.34 A | C |
| ATOM | 1144 | CE2 | PHE | A | 181 | 27.589 | 60.768 | 17.097 | 1.00 | 43.09 A | C |
| ATOM | 1145 | CZ  | PHE | A | 181 | 27.222 | 61.926 | 16.448 | 1.00 | 39.86 A | C |
| ATOM | 1146 | C   | PHE | A | 181 | 23.079 | 60.645 | 21.383 | 1.00 | 40.91 A | C |
| ATOM | 1147 | O   | PHE | A | 181 | 23.260 | 60.537 | 22.593 | 1.00 | 39.38 A | O |
| ATOM | 1148 | N   | ASP | A | 182 | 21.979 | 60.205 | 20.775 | 1.00 | 40.48 A | N |
| ATOM | 1149 | CA  | ASP | A | 182 | 20.780 | 59.868 | 21.544 | 1.00 | 32.94 A | C |
| ATOM | 1150 | CB  | ASP | A | 182 | 19.733 | 60.963 | 21.337 | 1.00 | 30.65 A | C |
| ATOM | 1151 | CG  | ASP | A | 182 | 19.144 | 60.948 | 19.934 | 1.00 | 38.96 A | C |
| ATOM | 1152 | OD1 | ASP | A | 182 | 19.320 | 59.953 | 19.218 | 1.00 | 43.10 A | O |
| ATOM | 1153 | OD2 | ASP | A | 182 | 18.491 | 61.923 | 19.538 | 1.00 | 45.36 A | O |
| ATOM | 1154 | C   | ASP | A | 182 | 20.148 | 58.490 | 21.258 | 1.00 | 41.29 A | C |
| ATOM | 1155 | O   | ASP | A | 182 | 18.933 | 58.318 | 21.393 | 1.00 | 40.40 A | O |
| ATOM | 1156 | N   | GLY | A | 183 | 20.954 | 57.505 | 20.874 | 1.00 | 38.80 A | N |
| ATOM | 1157 | CA  | GLY | A | 183 | 20.415 | 56.187 | 20.582 | 1.00 | 42.57 A | C |
| ATOM | 1158 | C   | GLY | A | 183 | 19.895 | 56.138 | 19.159 | 1.00 | 45.31 A | C |
| ATOM | 1159 | O   | GLY | A | 183 | 20.280 | 56.953 | 18.339 | 1.00 | 42.68 A | O |
| ATOM | 1160 | N   | LYS | A | 184 | 19.020 | 55.193 | 18.852 | 1.00 | 44.75 A | N |
| ATOM | 1161 | CA  | LYS | A | 184 | 18.493 | 55.111 | 17.496 | 1.00 | 46.56 A | C |
| ATOM | 1162 | CB  | LYS | A | 184 | 17.885 | 53.737 | 17.229 | 1.00 | 47.90 A | C |
| ATOM | 1163 | CG  | LYS | A | 184 | 17.828 | 53.399 | 15.757 | 1.00 | 51.43 A | C |
| ATOM | 1164 | CD  | LYS | A | 184 | 17.063 | 52.123 | 15.508 | 1.00 | 43.50 A | C |
| ATOM | 1165 | CE  | LYS | A | 184 | 15.609 | 52.311 | 15.832 | 1.00 | 44.30 A | C |
| ATOM | 1166 | NZ  | LYS | A | 184 | 14.780 | 51.494 | 14.917 | 1.00 | 44.04 A | N |
| ATOM | 1167 | C   | LYS | A | 184 | 17.460 | 56.206 | 17.230 | 1.00 | 49.04 A | C |
| ATOM | 1168 | O   | LYS | A | 184 | 16.738 | 56.623 | 18.139 | 1.00 | 49.51 A | O |
| ATOM | 1169 | N   | ASP | A | 185 | 17.399 | 56.656 | 15.976 | 1.00 | 49.36 A | N |
| ATOM | 1170 | CA  | ASP | A | 185 | 16.516 | 57.746 | 15.543 | 1.00 | 46.30 A | C |
| ATOM | 1171 | CB  | ASP | A | 185 | 15.049 | 57.327 | 15.646 | 1.00 | 45.98 A | C |
| ATOM | 1172 | CG  | ASP | A | 185 | 14.745 | 56.085 | 14.838 | 1.00 | 47.99 A | C |
| ATOM | 1173 | OD1 | ASP | A | 185 | 15.291 | 55.959 | 13.718 | 1.00 | 42.26 A | O |
| ATOM | 1174 | OD2 | ASP | A | 185 | 13.967 | 55.234 | 15.325 | 1.00 | 47.18 A | O |
| ATOM | 1175 | C   | ASP | A | 185 | 16.761 | 59.067 | 16.286 | 1.00 | 48.11 A | C |
| ATOM | 1176 | O   | ASP | A | 185 | 17.532 | 59.125 | 17.236 | 1.00 | 50.32 A | O |
| ATOM | 1177 | N   | GLY | A | 186 | 16.093 | 60.130 | 15.856 | 1.00 | 54.19 A | N |
| ATOM | 1178 | CA  | GLY | A | 186 | 16.308 | 61.436 | 16.457 | 1.00 | 50.40 A | C |
| ATOM | 1179 | C   | GLY | A | 186 | 17.568 | 62.043 | 15.881 | 1.00 | 48.45 A | C |
| ATOM | 1180 | O   | GLY | A | 186 | 17.758 | 62.041 | 14.667 | 1.00 | 50.84 A | O |
| ATOM | 1181 | N   | LEU | A | 187 | 18.430 | 62.559 | 16.749 | 1.00 | 42.98 A | N |
| ATOM | 1182 | CA  | LEU | A | 187 | 19.743 | 63.044 | 16.336 | 1.00 | 42.88 A | C |
| ATOM | 1183 | CB  | LEU | A | 187 | 20.606 | 63.276 | 17.571 | 1.00 | 41.34 A | C |
| ATOM | 1184 | CG  | LEU | A | 187 | 20.675 | 64.673 | 18.166 | 1.00 | 43.23 A | C |
| ATOM | 1185 | CD1 | LEU | A | 187 | 19.445 | 65.449 | 17.810 | 1.00 | 42.58 A | C |
| ATOM | 1186 | CD2 | LEU | A | 187 | 20.847 | 64.565 | 19.681 | 1.00 | 44.87 A | C |
| ATOM | 1187 | C   | LEU | A | 187 | 20.488 | 62.062 | 15.430 | 1.00 | 45.38 A | C |
| ATOM | 1188 | O   | LEU | A | 187 | 21.133 | 61.148 | 15.931 | 1.00 | 52.68 A | O |
| ATOM | 1189 | N   | LEU | A | 188 | 20.447 | 62.267 | 14.114 | 1.00 | 38.62 A | N |
| ATOM | 1190 | CA  | LEU | A | 188 | 21.155 | 61.385 | 13.185 | 1.00 | 39.56 A | C |
| ATOM | 1191 | CB  | LEU | A | 188 | 20.529 | 61.459 | 11.794 | 1.00 | 38.44 A | C |
| ATOM | 1192 | CG  | LEU | A | 188 | 19.057 | 61.055 | 11.716 | 1.00 | 40.21 A | C |
| ATOM | 1193 | CD1 | LEU | A | 188 | 18.620 | 60.886 | 10.258 | 1.00 | 32.66 A | C |
| ATOM | 1194 | CD2 | LEU | A | 188 | 18.826 | 59.778 | 12.521 | 1.00 | 40.60 A | C |
| ATOM | 1195 | C   | LEU | A | 188 | 22.661 | 61.657 | 13.077 | 1.00 | 43.46 A | C |
| ATOM | 1196 | O   | LEU | A | 188 | 23.427 | 60.771 | 12.683 | 1.00 | 40.76 A | O |
| ATOM | 1197 | N   | ALA | A | 189 | 23.075 | 62.873 | 13.433 | 1.00 | 41.09 A | N |
| ATOM | 1198 | CA  | ALA | A | 189 | 24.455 | 63.319 | 13.241 | 1.00 | 36.56 A | C |
| ATOM | 1199 | CB  | ALA | A | 189 | 24.957 | 62.871 | 11.885 | 1.00 | 35.84 A | C |
| ATOM | 1200 | C   | ALA | A | 189 | 24.586 | 64.848 | 13.366 | 1.00 | 40.35 A | C |
| ATOM | 1201 | O   | ALA | A | 189 | 23.588 | 65.574 | 13.359 | 1.00 | 38.41 A | O |
| ATOM | 1202 | N   | HIS | A | 190 | 25.818 | 65.336 | 13.474 | 1.00 | 37.22 A | N |
| ATOM | 1203 | CA  | HIS | A | 190 | 26.054 | 66.772 | 13.517 | 1.00 | 38.14 A | C |
| ATOM | 1204 | CB  | HIS | A | 190 | 25.901 | 67.332 | 14.934 | 1.00 | 33.23 A | C |
| ATOM | 1205 | CG  | HIS | A | 190 | 26.741 | 66.638 | 15.954 | 1.00 | 38.68 A | C |
| ATOM | 1206 | CD2 | HIS | A | 190 | 27.971 | 66.082 | 15.868 | 1.00 | 41.77 A | C |
| ATOM | 1207 | ND1 | HIS | A | 190 | 26.325 | 66.451 | 17.255 | 1.00 | 46.93 A | N |

TABLE 13-continued

Coordinates for proMMP9(35-444 ΔFnII) (SEQ ID NO: 12) complex with Example 3

| ATOM | 1208 | CE1 | HIS | A | 190 | 27.267 | 65.816 | 17.929 | 1.00 | 43.47 | A | C |
|------|------|-----|-----|---|-----|--------|--------|--------|------|-------|---|---|
| ATOM | 1209 | NE2 | HIS | A | 190 | 28.275 | 65.578 | 17.109 | 1.00 | 44.52 | A | N |
| ATOM | 1210 | C | HIS | A | 190 | 27.418 | 67.147 | 12.959 | 1.00 | 39.39 | A | C |
| ATOM | 1211 | O | HIS | A | 190 | 28.196 | 66.285 | 12.572 | 1.00 | 39.30 | A | O |
| ATOM | 1212 | N | ALA | A | 191 | 27.696 | 68.445 | 12.926 | 1.00 | 40.82 | A | N |
| ATOM | 1213 | CA | ALA | A | 191 | 28.949 | 68.946 | 12.386 | 1.00 | 42.76 | A | C |
| ATOM | 1214 | CB | ALA | A | 191 | 28.918 | 68.931 | 10.858 | 1.00 | 33.63 | A | C |
| ATOM | 1215 | C | ALA | A | 191 | 29.203 | 70.354 | 12.894 | 1.00 | 43.32 | A | C |
| ATOM | 1216 | O | ALA | A | 191 | 28.283 | 71.040 | 13.336 | 1.00 | 39.36 | A | O |
| ATOM | 1217 | N | PHE | A | 192 | 30.455 | 70.783 | 12.808 | 1.00 | 40.08 | A | N |
| ATOM | 1218 | CA | PHE | A | 192 | 30.836 | 72.113 | 13.264 | 1.00 | 47.02 | A | C |
| ATOM | 1219 | CB | PHE | A | 192 | 31.853 | 72.003 | 14.398 | 1.00 | 52.19 | A | C |
| ATOM | 1220 | CG | PHE | A | 192 | 31.477 | 70.994 | 15.459 | 1.00 | 50.96 | A | C |
| ATOM | 1221 | CD1 | PHE | A | 192 | 31.128 | 71.401 | 16.752 | 1.00 | 42.41 | A | C |
| ATOM | 1222 | CD2 | PHE | A | 192 | 31.410 | 69.641 | 15.159 | 1.00 | 45.70 | A | C |
| ATOM | 1223 | CE1 | PHE | A | 192 | 30.872 | 70.483 | 17.721 | 1.00 | 46.17 | A | C |
| ATOM | 1224 | CE2 | PHE | A | 192 | 31.076 | 68.721 | 16.123 | 1.00 | 46.33 | A | C |
| ATOM | 1225 | CZ | PHE | A | 192 | 30.808 | 69.141 | 17.409 | 1.00 | 51.20 | A | C |
| ATOM | 1226 | C | PHE | A | 192 | 31.390 | 72.957 | 12.110 | 1.00 | 45.78 | A | C |
| ATOM | 1227 | O | PHE | A | 192 | 31.872 | 72.416 | 11.114 | 1.00 | 40.80 | A | O |
| ATOM | 1228 | N | PRO | A | 193 | 31.317 | 74.289 | 12.243 | 1.00 | 43.17 | A | N |
| ATOM | 1229 | CD | PRO | A | 193 | 30.983 | 75.020 | 13.472 | 1.00 | 38.91 | A | C |
| ATOM | 1230 | CA | PRO | A | 193 | 31.669 | 75.196 | 11.147 | 1.00 | 43.15 | A | C |
| ATOM | 1231 | CB | PRO | A | 193 | 31.036 | 76.530 | 11.570 | 1.00 | 39.55 | A | C |
| ATOM | 1232 | CG | PRO | A | 193 | 30.417 | 76.290 | 12.941 | 1.00 | 44.50 | A | C |
| ATOM | 1233 | C | PRO | A | 193 | 33.173 | 75.379 | 11.011 | 1.00 | 46.27 | A | C |
| ATOM | 1234 | O | PRO | A | 193 | 33.916 | 75.105 | 11.955 | 1.00 | 44.43 | A | O |
| ATOM | 1235 | N | PRO | A | 194 | 33.618 | 75.849 | 9.837 | 1.00 | 47.37 | A | N |
| ATOM | 1236 | CD | PRO | A | 194 | 32.765 | 76.132 | 8.668 | 1.00 | 44.45 | A | C |
| ATOM | 1237 | CA | PRO | A | 194 | 35.019 | 76.172 | 9.572 | 1.00 | 46.13 | A | C |
| ATOM | 1238 | CB | PRO | A | 194 | 34.917 | 77.145 | 8.401 | 1.00 | 47.86 | A | C |
| ATOM | 1239 | CG | PRO | A | 194 | 33.743 | 76.649 | 7.640 | 1.00 | 43.53 | A | C |
| ATOM | 1240 | C | PRO | A | 194 | 35.691 | 76.845 | 10.764 | 1.00 | 44.39 | A | C |
| ATOM | 1241 | O | PRO | A | 194 | 35.095 | 77.705 | 11.407 | 1.00 | 46.02 | A | O |
| ATOM | 1242 | N | GLY | A | 195 | 36.927 | 76.438 | 11.038 | 1.00 | 48.80 | A | N |
| ATOM | 1243 | CA | GLY | A | 195 | 37.696 | 76.932 | 12.164 | 1.00 | 44.23 | A | C |
| ATOM | 1244 | C | GLY | A | 195 | 38.759 | 75.929 | 12.589 | 1.00 | 41.82 | A | C |
| ATOM | 1245 | O | GLY | A | 195 | 38.971 | 74.914 | 11.924 | 1.00 | 44.40 | A | O |
| ATOM | 1246 | N | PRO | A | 196 | 39.426 | 76.196 | 13.716 | 1.00 | 39.23 | A | N |
| ATOM | 1247 | CD | PRO | A | 196 | 39.130 | 77.260 | 14.684 | 1.00 | 41.48 | A | C |
| ATOM | 1248 | CA | PRO | A | 196 | 40.522 | 75.343 | 14.172 | 1.00 | 37.87 | A | C |
| ATOM | 1249 | CB | PRO | A | 196 | 41.296 | 76.261 | 15.124 | 1.00 | 44.70 | A | C |
| ATOM | 1250 | CG | PRO | A | 196 | 40.459 | 77.532 | 15.272 | 1.00 | 45.30 | A | C |
| ATOM | 1251 | C | PRO | A | 196 | 40.049 | 74.124 | 14.961 | 1.00 | 45.46 | A | C |
| ATOM | 1252 | O | PRO | A | 196 | 39.067 | 74.191 | 15.701 | 1.00 | 50.75 | A | O |
| ATOM | 1253 | N | GLY | A | 197 | 40.754 | 73.015 | 14.805 | 1.00 | 41.97 | A | N |
| ATOM | 1254 | CA | GLY | A | 197 | 40.621 | 71.909 | 15.729 | 1.00 | 46.98 | A | C |
| ATOM | 1255 | C | GLY | A | 197 | 39.394 | 71.058 | 15.530 | 1.00 | 51.92 | A | C |
| ATOM | 1256 | O | GLY | A | 197 | 39.311 | 70.297 | 14.574 | 1.00 | 59.06 | A | O |
| ATOM | 1257 | N | ILE | A | 198 | 38.445 | 71.172 | 16.447 | 1.00 | 53.68 | A | N |
| ATOM | 1258 | CA | ILE | A | 198 | 37.214 | 70.397 | 16.358 | 1.00 | 51.83 | A | C |
| ATOM | 1259 | CB | ILE | A | 198 | 36.466 | 70.367 | 17.705 | 1.00 | 45.75 | A | C |
| ATOM | 1260 | CG2 | ILE | A | 198 | 35.817 | 71.730 | 17.994 | 1.00 | 43.76 | A | C |
| ATOM | 1261 | CG1 | ILE | A | 198 | 35.433 | 69.243 | 17.709 | 1.00 | 48.71 | A | C |
| ATOM | 1262 | CD1 | ILE | A | 198 | 34.522 | 69.261 | 18.916 | 1.00 | 45.63 | A | C |
| ATOM | 1263 | C | ILE | A | 198 | 36.292 | 70.965 | 15.276 | 1.00 | 54.74 | A | C |
| ATOM | 1264 | O | ILE | A | 198 | 35.532 | 70.228 | 14.645 | 1.00 | 51.87 | A | O |
| ATOM | 1265 | N | GLN | A | 199 | 36.358 | 72.278 | 15.067 | 1.00 | 46.95 | A | N |
| ATOM | 1266 | CA | GLN | A | 199 | 35.524 | 72.909 | 14.061 | 1.00 | 48.44 | A | C |
| ATOM | 1267 | CB | GLN | A | 199 | 35.799 | 74.411 | 14.008 | 1.00 | 47.85 | A | C |
| ATOM | 1268 | CG | GLN | A | 199 | 35.732 | 75.074 | 15.373 | 1.00 | 46.69 | A | C |
| ATOM | 1269 | CD | GLN | A | 199 | 35.703 | 76.593 | 15.312 | 1.00 | 45.00 | A | C |
| ATOM | 1270 | OE1 | GLN | A | 199 | 35.431 | 77.181 | 14.269 | 1.00 | 40.14 | A | O |
| ATOM | 1271 | NE2 | GLN | A | 199 | 35.978 | 77.232 | 16.443 | 1.00 | 44.81 | A | N |
| ATOM | 1272 | C | GLN | A | 199 | 35.802 | 72.239 | 12.722 | 1.00 | 47.45 | A | C |
| ATOM | 1273 | O | GLN | A | 199 | 36.880 | 71.705 | 12.517 | 1.00 | 50.18 | A | O |
| ATOM | 1274 | N | GLY | A | 200 | 34.822 | 72.236 | 11.826 | 1.00 | 44.72 | A | N |
| ATOM | 1275 | CA | GLY | A | 200 | 34.968 | 71.560 | 10.552 | 1.00 | 39.34 | A | C |
| ATOM | 1276 | C | GLY | A | 200 | 34.668 | 70.070 | 10.619 | 1.00 | 43.86 | A | C |
| ATOM | 1277 | O | GLY | A | 200 | 34.507 | 69.426 | 9.577 | 1.00 | 40.38 | A | O |
| ATOM | 1278 | N | ASP | A | 201 | 34.601 | 69.526 | 11.837 | 1.00 | 36.55 | A | N |
| ATOM | 1279 | CA | ASP | A | 201 | 34.309 | 68.105 | 12.061 | 1.00 | 40.58 | A | C |
| ATOM | 1280 | CB | ASP | A | 201 | 34.674 | 67.692 | 13.489 | 1.00 | 45.61 | A | C |
| ATOM | 1281 | CG | ASP | A | 201 | 36.158 | 67.587 | 13.705 | 1.00 | 49.67 | A | C |
| ATOM | 1282 | OD1 | ASP | A | 201 | 36.911 | 67.743 | 12.722 | 1.00 | 52.73 | A | O |
| ATOM | 1283 | OD2 | ASP | A | 201 | 36.569 | 67.346 | 14.865 | 1.00 | 53.94 | A | O |
| ATOM | 1284 | C | ASP | A | 201 | 32.852 | 67.684 | 11.810 | 1.00 | 37.16 | A | C |

TABLE 13-continued

Coordinates for proMMP9(35-444 ΔFnII) (SEQ ID NO: 12) complex with Example 3

| ATOM | 1285 | O   | ASP | A | 201 | 31.915 | 68.452 | 11.995 | 1.00 | 34.15 | A | O |
|------|------|-----|-----|---|-----|--------|--------|--------|------|-------|---|---|
| ATOM | 1286 | N   | ALA | A | 202 | 32.688 | 66.429 | 11.420 | 1.00 | 38.87 | A | N |
| ATOM | 1287 | CA  | ALA | A | 202 | 31.381 | 65.855 | 11.159 | 1.00 | 42.26 | A | C |
| ATOM | 1288 | CB  | ALA | A | 202 | 31.188 | 65.672 | 9.650  | 1.00 | 38.60 | A | C |
| ATOM | 1289 | C   | ALA | A | 202 | 31.266 | 64.516 | 11.884 | 1.00 | 36.65 | A | C |
| ATOM | 1290 | O   | ALA | A | 202 | 32.114 | 63.644 | 11.722 | 1.00 | 41.29 | A | O |
| ATOM | 1291 | N   | HIS | A | 203 | 30.232 | 64.348 | 12.692 | 1.00 | 35.83 | A | N |
| ATOM | 1292 | CA  | HIS | A | 203 | 30.055 | 63.082 | 13.405 | 1.00 | 41.65 | A | C |
| ATOM | 1293 | CB  | HIS | A | 203 | 30.212 | 63.288 | 14.913 | 1.00 | 41.30 | A | C |
| ATOM | 1294 | CG  | HIS | A | 203 | 31.529 | 63.882 | 15.303 | 1.00 | 42.82 | A | C |
| ATOM | 1295 | CD2 | HIS | A | 203 | 32.759 | 63.760 | 14.751 | 1.00 | 47.56 | A | C |
| ATOM | 1296 | ND1 | HIS | A | 203 | 31.676 | 64.734 | 16.376 | 1.00 | 46.26 | A | N |
| ATOM | 1297 | CE1 | HIS | A | 203 | 32.939 | 65.106 | 16.474 | 1.00 | 49.13 | A | C |
| ATOM | 1298 | NE2 | HIS | A | 203 | 33.618 | 64.532 | 15.497 | 1.00 | 53.43 | A | N |
| ATOM | 1299 | C   | HIS | A | 203 | 28.719 | 62.418 | 13.095 | 1.00 | 38.12 | A | C |
| ATOM | 1300 | O   | HIS | A | 203 | 27.703 | 63.097 | 12.963 | 1.00 | 36.17 | A | O |
| ATOM | 1301 | N   | PHE | A | 204 | 28.726 | 61.092 | 12.985 | 1.00 | 35.39 | A | N |
| ATOM | 1302 | CA  | PHE | A | 204 | 27.510 | 60.331 | 12.684 | 1.00 | 39.06 | A | C |
| ATOM | 1303 | CB  | PHE | A | 204 | 27.654 | 59.584 | 11.357 | 1.00 | 39.49 | A | C |
| ATOM | 1304 | CG  | PHE | A | 204 | 28.072 | 60.465 | 10.216 | 1.00 | 39.87 | A | C |
| ATOM | 1305 | CD1 | PHE | A | 204 | 29.403 | 60.616 | 9.894  | 1.00 | 41.52 | A | C |
| ATOM | 1306 | CD2 | PHE | A | 204 | 27.134 | 61.156 | 9.479  | 1.00 | 38.67 | A | C |
| ATOM | 1307 | CE1 | PHE | A | 204 | 29.790 | 61.438 | 8.850  | 1.00 | 41.34 | A | C |
| ATOM | 1308 | CE2 | PHE | A | 204 | 27.518 | 61.976 | 8.433  | 1.00 | 38.86 | A | C |
| ATOM | 1309 | CZ  | PHE | A | 204 | 28.844 | 62.114 | 8.120  | 1.00 | 38.16 | A | C |
| ATOM | 1310 | C   | PHE | A | 204 | 27.138 | 59.351 | 13.798 | 1.00 | 43.64 | A | C |
| ATOM | 1311 | O   | PHE | A | 204 | 28.002 | 58.645 | 14.329 | 1.00 | 41.07 | A | O |
| ATOM | 1312 | N   | ASP | A | 205 | 25.848 | 59.315 | 14.140 | 1.00 | 43.29 | A | N |
| ATOM | 1313 | CA  | ASP | A | 205 | 25.339 | 58.443 | 15.198 | 1.00 | 42.38 | A | C |
| ATOM | 1314 | CB  | ASP | A | 205 | 23.923 | 58.858 | 15.622 | 1.00 | 47.87 | A | C |
| ATOM | 1315 | CG  | ASP | A | 205 | 23.453 | 58.154 | 16.901 | 1.00 | 44.18 | A | C |
| ATOM | 1316 | OD1 | ASP | A | 205 | 24.003 | 57.092 | 17.264 | 1.00 | 41.91 | A | O |
| ATOM | 1317 | OD2 | ASP | A | 205 | 22.532 | 58.674 | 17.554 | 1.00 | 37.51 | A | O |
| ATOM | 1318 | C   | ASP | A | 205 | 25.331 | 56.978 | 14.776 | 1.00 | 46.02 | A | C |
| ATOM | 1319 | O   | ASP | A | 205 | 24.429 | 56.535 | 14.060 | 1.00 | 40.67 | A | O |
| ATOM | 1320 | N   | ASP | A | 206 | 26.326 | 56.230 | 15.257 | 1.00 | 47.23 | A | N |
| ATOM | 1321 | CA  | ASP | A | 206 | 26.441 | 54.804 | 14.973 | 1.00 | 44.05 | A | C |
| ATOM | 1322 | CB  | ASP | A | 206 | 27.816 | 54.288 | 15.396 | 1.00 | 43.66 | A | C |
| ATOM | 1323 | CG  | ASP | A | 206 | 28.418 | 53.324 | 14.380 | 1.00 | 43.20 | A | C |
| ATOM | 1324 | OD1 | ASP | A | 206 | 27.718 | 52.933 | 13.412 | 1.00 | 31.90 | A | O |
| ATOM | 1325 | OD2 | ASP | A | 206 | 29.605 | 52.966 | 14.553 | 1.00 | 46.28 | A | O |
| ATOM | 1326 | C   | ASP | A | 206 | 25.335 | 53.942 | 15.604 | 1.00 | 42.55 | A | C |
| ATOM | 1327 | O   | ASP | A | 206 | 25.268 | 52.742 | 15.356 | 1.00 | 45.05 | A | O |
| ATOM | 1328 | N   | ASP | A | 207 | 24.468 | 54.536 | 16.415 | 1.00 | 39.56 | A | N |
| ATOM | 1329 | CA  | ASP | A | 207 | 23.284 | 53.807 | 16.845 | 1.00 | 39.78 | A | C |
| ATOM | 1330 | CB  | ASP | A | 207 | 22.637 | 54.431 | 18.089 | 1.00 | 42.04 | A | C |
| ATOM | 1331 | CG  | ASP | A | 207 | 23.291 | 53.965 | 19.400 | 1.00 | 44.62 | A | C |
| ATOM | 1332 | OD1 | ASP | A | 207 | 23.795 | 52.822 | 19.459 | 1.00 | 40.99 | A | O |
| ATOM | 1333 | OD2 | ASP | A | 207 | 23.291 | 54.742 | 20.382 | 1.00 | 41.45 | A | O |
| ATOM | 1334 | C   | ASP | A | 207 | 22.300 | 53.735 | 15.680 | 1.00 | 43.55 | A | C |
| ATOM | 1335 | O   | ASP | A | 207 | 21.325 | 52.997 | 15.734 | 1.00 | 50.68 | A | O |
| ATOM | 1336 | N   | GLU | A | 208 | 22.563 | 54.489 | 14.616 | 1.00 | 39.96 | A | N |
| ATOM | 1337 | CA  | GLU | A | 208 | 21.743 | 54.390 | 13.407 | 1.00 | 40.53 | A | C |
| ATOM | 1338 | CB  | GLU | A | 208 | 21.750 | 55.700 | 12.622 | 1.00 | 43.15 | A | C |
| ATOM | 1339 | CG  | GLU | A | 208 | 21.248 | 56.888 | 13.398 | 1.00 | 46.47 | A | C |
| ATOM | 1340 | CD  | GLU | A | 208 | 19.883 | 56.640 | 13.985 | 1.00 | 48.59 | A | C |
| ATOM | 1341 | OE1 | GLU | A | 208 | 19.107 | 55.870 | 13.378 | 1.00 | 49.85 | A | O |
| ATOM | 1342 | OE2 | GLU | A | 208 | 19.590 | 57.213 | 15.050 | 1.00 | 43.79 | A | O |
| ATOM | 1343 | C   | GLU | A | 208 | 22.225 | 53.280 | 12.493 | 1.00 | 39.47 | A | C |
| ATOM | 1344 | O   | GLU | A | 208 | 23.420 | 52.991 | 12.428 | 1.00 | 40.89 | A | O |
| ATOM | 1345 | N   | LEU | A | 209 | 21.289 | 52.656 | 11.788 | 1.00 | 38.73 | A | N |
| ATOM | 1346 | CA  | LEU | A | 209 | 21.639 | 51.702 | 10.749 | 1.00 | 33.34 | A | C |
| ATOM | 1347 | CB  | LEU | A | 209 | 20.471 | 50.771 | 10.448 | 1.00 | 34.57 | A | C |
| ATOM | 1348 | CG  | LEU | A | 209 | 20.713 | 49.720 | 9.360  | 1.00 | 38.77 | A | C |
| ATOM | 1349 | CD1 | LEU | A | 209 | 21.624 | 48.607 | 9.880  | 1.00 | 37.95 | A | C |
| ATOM | 1350 | CD2 | LEU | A | 209 | 19.393 | 49.156 | 8.832  | 1.00 | 38.30 | A | C |
| ATOM | 1351 | C   | LEU | A | 209 | 21.994 | 52.495 | 9.501  | 1.00 | 42.87 | A | C |
| ATOM | 1352 | O   | LEU | A | 209 | 21.135 | 53.146 | 8.899  | 1.00 | 41.83 | A | O |
| ATOM | 1353 | N   | TRP | A | 210 | 23.261 | 52.447 | 9.112  | 1.00 | 38.25 | A | N |
| ATOM | 1354 | CA  | TRP | A | 210 | 23.705 | 53.226 | 7.973  | 1.00 | 43.88 | A | C |
| ATOM | 1355 | CB  | TRP | A | 210 | 25.107 | 53.788 | 8.224  | 1.00 | 41.32 | A | C |
| ATOM | 1356 | CG  | TRP | A | 210 | 25.041 | 54.876 | 9.226  | 1.00 | 37.97 | A | C |
| ATOM | 1357 | CD2 | TRP | A | 210 | 24.492 | 56.182 | 9.023  | 1.00 | 43.27 | A | C |
| ATOM | 1358 | CE2 | TRP | A | 210 | 24.596 | 56.872 | 10.245 | 1.00 | 41.98 | A | C |
| ATOM | 1359 | CE3 | TRP | A | 210 | 23.931 | 56.841 | 7.916  | 1.00 | 39.09 | A | C |
| ATOM | 1360 | CD1 | TRP | A | 210 | 25.421 | 54.817 | 10.528 | 1.00 | 37.80 | A | C |
| ATOM | 1361 | NE1 | TRP | A | 210 | 25.170 | 56.016 | 11.149 | 1.00 | 39.60 | A | N |

TABLE 13-continued

Coordinates for proMMP9(35-444 ΔFnII) (SEQ ID NO: 12) complex with Example 3

| ATOM | 1362 | CZ2 | TRP | A | 210 | 24.162 | 58.194 | 10.395 | 1.00 | 41.39 | A | C |
|---|---|---|---|---|---|---|---|---|---|---|---|---|
| ATOM | 1363 | CZ3 | TRP | A | 210 | 23.507 | 58.150 | 8.067 | 1.00 | 32.20 | A | C |
| ATOM | 1364 | CH2 | TRP | A | 210 | 23.621 | 58.812 | 9.294 | 1.00 | 32.06 | A | C |
| ATOM | 1365 | C | TRP | A | 210 | 23.608 | 52.440 | 6.676 | 1.00 | 41.51 | A | C |
| ATOM | 1366 | O | TRP | A | 210 | 24.072 | 51.310 | 6.593 | 1.00 | 45.91 | A | O |
| ATOM | 1367 | N | SER | A | 211 | 22.970 | 53.039 | 5.679 | 1.00 | 33.23 | A | N |
| ATOM | 1368 | CA | SER | A | 211 | 22.859 | 52.413 | 4.373 | 1.00 | 40.21 | A | C |
| ATOM | 1369 | CB | SER | A | 211 | 21.563 | 51.611 | 4.262 | 1.00 | 39.68 | A | C |
| ATOM | 1370 | OG | SER | A | 211 | 20.471 | 52.457 | 3.942 | 1.00 | 46.06 | A | O |
| ATOM | 1371 | C | SER | A | 211 | 22.926 | 53.451 | 3.255 | 1.00 | 41.77 | A | C |
| ATOM | 1372 | O | SER | A | 211 | 23.502 | 54.530 | 3.421 | 1.00 | 34.06 | A | O |
| ATOM | 1373 | N | LEU | A | 212 | 22.327 | 53.112 | 2.116 | 1.00 | 42.77 | A | N |
| ATOM | 1374 | CA | LEU | A | 212 | 22.343 | 53.979 | 0.946 | 1.00 | 43.28 | A | C |
| ATOM | 1375 | CB | LEU | A | 212 | 23.289 | 53.407 | −0.114 | 1.00 | 35.29 | A | C |
| ATOM | 1376 | CG | LEU | A | 212 | 24.523 | 54.233 | −0.457 | 1.00 | 41.29 | A | C |
| ATOM | 1377 | CD1 | LEU | A | 212 | 25.467 | 54.349 | 0.731 | 1.00 | 40.19 | A | C |
| ATOM | 1378 | CD2 | LEU | A | 212 | 25.231 | 53.616 | −1.647 | 1.00 | 46.67 | A | C |
| ATOM | 1379 | C | LEU | A | 212 | 20.962 | 54.171 | 0.325 | 1.00 | 46.44 | A | C |
| ATOM | 1380 | O | LEU | A | 212 | 20.837 | 54.163 | −0.902 | 1.00 | 44.76 | A | O |
| ATOM | 1381 | N | GLY | A | 213 | 19.920 | 54.339 | 1.140 | 1.00 | 48.27 | A | N |
| ATOM | 1382 | CA | GLY | A | 213 | 18.593 | 54.474 | 0.560 | 1.00 | 51.11 | A | C |
| ATOM | 1383 | C | GLY | A | 213 | 17.354 | 54.371 | 1.428 | 1.00 | 52.93 | A | C |
| ATOM | 1384 | O | GLY | A | 213 | 17.194 | 55.173 | 2.347 | 1.00 | 61.33 | A | O |
| ATOM | 1385 | N | LYS | A | 389 | 16.439 | 53.437 | 1.155 | 1.00 | 58.93 | A | N |
| ATOM | 1386 | CA | LYS | A | 389 | 16.470 | 52.396 | 0.104 | 1.00 | 58.71 | A | C |
| ATOM | 1387 | CB | LYS | A | 389 | 17.362 | 52.711 | −1.093 | 1.00 | 52.00 | A | C |
| ATOM | 1388 | CG | LYS | A | 389 | 16.677 | 53.601 | −2.103 | 1.00 | 60.52 | A | C |
| ATOM | 1389 | CD | LYS | A | 389 | 15.224 | 53.196 | −2.304 | 1.00 | 56.32 | A | C |
| ATOM | 1390 | CE | LYS | A | 389 | 15.117 | 51.936 | −3.140 | 1.00 | 61.88 | A | C |
| ATOM | 1391 | NZ | LYS | A | 389 | 13.757 | 51.780 | −3.721 | 1.00 | 64.90 | A | N |
| ATOM | 1392 | C | LYS | A | 389 | 16.751 | 51.010 | 0.664 | 1.00 | 56.01 | A | C |
| ATOM | 1393 | O | LYS | A | 389 | 17.906 | 50.625 | 0.866 | 1.00 | 52.42 | A | O |
| ATOM | 1394 | N | GLY | A | 390 | 15.668 | 50.274 | 0.902 | 1.00 | 48.41 | A | N |
| ATOM | 1395 | CA | GLY | A | 390 | 15.726 | 49.005 | 1.594 | 1.00 | 48.24 | A | C |
| ATOM | 1396 | C | GLY | A | 390 | 15.502 | 49.218 | 3.077 | 1.00 | 49.81 | A | C |
| ATOM | 1397 | O | GLY | A | 390 | 14.417 | 48.961 | 3.589 | 1.00 | 55.54 | A | O |
| ATOM | 1398 | N | GLN | A | 391 | 16.533 | 49.711 | 3.757 | 1.00 | 46.03 | A | N |
| ATOM | 1399 | CA | GLN | A | 391 | 16.502 | 49.937 | 5.197 | 1.00 | 48.33 | A | C |
| ATOM | 1400 | CB | GLN | A | 391 | 16.599 | 48.607 | 5.951 | 1.00 | 45.33 | A | C |
| ATOM | 1401 | CG | GLN | A | 391 | 15.323 | 47.776 | 5.913 | 1.00 | 49.10 | A | C |
| ATOM | 1402 | CD | GLN | A | 391 | 15.502 | 46.379 | 6.468 | 1.00 | 44.75 | A | C |
| ATOM | 1403 | OE1 | GLN | A | 391 | 16.220 | 46.165 | 7.443 | 1.00 | 46.20 | A | O |
| ATOM | 1404 | NE2 | GLN | A | 391 | 14.845 | 45.415 | 5.844 | 1.00 | 45.38 | A | N |
| ATOM | 1405 | C | GLN | A | 391 | 17.666 | 50.842 | 5.596 | 1.00 | 50.46 | A | C |
| ATOM | 1406 | O | GLN | A | 391 | 18.653 | 50.940 | 4.874 | 1.00 | 50.22 | A | O |
| ATOM | 1407 | N | GLY | A | 392 | 17.555 | 51.498 | 6.746 | 1.00 | 50.15 | A | N |
| ATOM | 1408 | CA | GLY | A | 392 | 18.629 | 52.347 | 7.231 | 1.00 | 45.79 | A | C |
| ATOM | 1409 | C | GLY | A | 392 | 18.619 | 53.734 | 6.623 | 1.00 | 47.75 | A | C |
| ATOM | 1410 | O | GLY | A | 392 | 17.886 | 53.998 | 5.668 | 1.00 | 50.03 | A | O |
| ATOM | 1411 | N | TYR | A | 393 | 19.437 | 54.622 | 7.182 | 1.00 | 49.59 | A | N |
| ATOM | 1412 | CA | TYR | A | 393 | 19.568 | 55.989 | 6.675 | 1.00 | 45.46 | A | C |
| ATOM | 1413 | CB | TYR | A | 393 | 19.813 | 56.964 | 7.820 | 1.00 | 40.78 | A | C |
| ATOM | 1414 | CG | TYR | A | 393 | 18.657 | 57.133 | 8.777 | 1.00 | 44.25 | A | C |
| ATOM | 1415 | CD1 | TYR | A | 393 | 17.579 | 57.955 | 8.462 | 1.00 | 39.29 | A | C |
| ATOM | 1416 | CE1 | TYR | A | 393 | 16.535 | 58.120 | 9.339 | 1.00 | 36.38 | A | C |
| ATOM | 1417 | CD2 | TYR | A | 393 | 18.657 | 56.491 | 10.011 | 1.00 | 47.87 | A | C |
| ATOM | 1418 | CE2 | TYR | A | 393 | 17.619 | 56.653 | 10.894 | 1.00 | 43.12 | A | C |
| ATOM | 1419 | CZ | TYR | A | 393 | 16.563 | 57.470 | 10.554 | 1.00 | 43.29 | A | C |
| ATOM | 1420 | OH | TYR | A | 393 | 15.527 | 57.625 | 11.439 | 1.00 | 50.95 | A | O |
| ATOM | 1421 | C | TYR | A | 393 | 20.721 | 56.117 | 5.689 | 1.00 | 40.40 | A | C |
| ATOM | 1422 | O | TYR | A | 393 | 21.827 | 55.646 | 5.959 | 1.00 | 44.20 | A | O |
| ATOM | 1423 | N | SER | A | 394 | 20.460 | 56.776 | 4.564 | 1.00 | 34.38 | A | N |
| ATOM | 1424 | CA | SER | A | 394 | 21.477 | 57.012 | 3.546 | 1.00 | 36.71 | A | C |
| ATOM | 1425 | CB | SER | A | 394 | 20.864 | 57.725 | 2.337 | 1.00 | 40.29 | A | C |
| ATOM | 1426 | OG | SER | A | 394 | 21.831 | 57.964 | 1.326 | 1.00 | 35.94 | A | O |
| ATOM | 1427 | C | SER | A | 394 | 22.685 | 57.800 | 4.068 | 1.00 | 35.66 | A | C |
| ATOM | 1428 | O | SER | A | 394 | 22.607 | 59.006 | 4.312 | 1.00 | 37.53 | A | O |
| ATOM | 1429 | N | LEU | A | 395 | 23.805 | 57.107 | 4.233 | 1.00 | 35.78 | A | N |
| ATOM | 1430 | CA | LEU | A | 395 | 25.043 | 57.747 | 4.647 | 1.00 | 35.26 | A | C |
| ATOM | 1431 | CB | LEU | A | 395 | 26.175 | 56.722 | 4.706 | 1.00 | 30.65 | A | C |
| ATOM | 1432 | CG | LEU | A | 395 | 27.525 | 57.239 | 5.202 | 1.00 | 32.19 | A | C |
| ATOM | 1433 | CD1 | LEU | A | 395 | 27.367 | 57.950 | 6.534 | 1.00 | 32.51 | A | C |
| ATOM | 1434 | CD2 | LEU | A | 395 | 28.504 | 56.096 | 5.315 | 1.00 | 32.07 | A | C |
| ATOM | 1435 | C | LEU | A | 395 | 25.411 | 58.861 | 3.676 | 1.00 | 35.39 | A | C |
| ATOM | 1436 | O | LEU | A | 395 | 25.864 | 59.935 | 4.078 | 1.00 | 34.99 | A | O |
| ATOM | 1437 | N | PHE | A | 396 | 25.224 | 58.588 | 2.392 | 1.00 | 32.75 | A | N |
| ATOM | 1438 | CA | PHE | A | 396 | 25.540 | 59.556 | 1.357 | 1.00 | 35.29 | A | C |

TABLE 13-continued

Coordinates for proMMP9(35-444 ΔFnII) (SEQ ID NO: 12) complex with Example 3

| ATOM | 1439 | CB | PHE | A | 396 | 25.197 | 58.986 | −0.030 | 1.00 | 36.22 | A | C |
|---|---|---|---|---|---|---|---|---|---|---|---|---|
| ATOM | 1440 | CG | PHE | A | 396 | 25.196 | 60.011 | −1.126 | 1.00 | 32.91 | A | C |
| ATOM | 1441 | CD1 | PHE | A | 396 | 26.307 | 60.815 | −1.348 | 1.00 | 35.89 | A | C |
| ATOM | 1442 | CD2 | PHE | A | 396 | 24.089 | 60.172 | −1.936 | 1.00 | 32.31 | A | C |
| ATOM | 1443 | CE1 | PHE | A | 396 | 26.310 | 61.766 | −2.359 | 1.00 | 36.84 | A | C |
| ATOM | 1444 | CE2 | PHE | A | 396 | 24.081 | 61.117 | −2.953 | 1.00 | 34.84 | A | C |
| ATOM | 1445 | CZ | PHE | A | 396 | 25.194 | 61.919 | −3.163 | 1.00 | 33.16 | A | C |
| ATOM | 1446 | C | PHE | A | 396 | 24.810 | 60.873 | 1.619 | 1.00 | 34.29 | A | C |
| ATOM | 1447 | O | PHE | A | 396 | 25.432 | 61.934 | 1.703 | 1.00 | 34.28 | A | O |
| ATOM | 1448 | N | LEU | A | 397 | 23.494 | 60.792 | 1.783 | 1.00 | 35.67 | A | N |
| ATOM | 1449 | CA | LEU | A | 397 | 22.660 | 61.981 | 1.950 | 1.00 | 35.88 | A | C |
| ATOM | 1450 | CB | LEU | A | 397 | 21.180 | 61.615 | 1.870 | 1.00 | 34.40 | A | C |
| ATOM | 1451 | CG | LEU | A | 397 | 20.674 | 61.326 | 0.452 | 1.00 | 34.88 | A | C |
| ATOM | 1452 | CD1 | LEU | A | 397 | 19.210 | 60.907 | 0.469 | 1.00 | 40.43 | A | C |
| ATOM | 1453 | CD2 | LEU | A | 397 | 20.865 | 62.540 | −0.438 | 1.00 | 34.70 | A | C |
| ATOM | 1454 | C | LEU | A | 397 | 22.960 | 62.777 | 3.218 | 1.00 | 31.17 | A | C |
| ATOM | 1455 | O | LEU | A | 397 | 23.138 | 63.988 | 3.157 | 1.00 | 31.77 | A | O |
| ATOM | 1456 | N | VAL | A | 398 | 23.021 | 62.100 | 4.359 | 1.00 | 28.52 | A | N |
| ATOM | 1457 | CA | VAL | A | 398 | 23.309 | 62.773 | 5.619 | 1.00 | 28.45 | A | C |
| ATOM | 1458 | CB | VAL | A | 398 | 23.225 | 61.791 | 6.828 | 1.00 | 29.92 | A | C |
| ATOM | 1459 | CG1 | VAL | A | 398 | 23.804 | 62.410 | 8.076 | 1.00 | 27.08 | A | C |
| ATOM | 1460 | CG2 | VAL | A | 398 | 21.787 | 61.371 | 7.084 | 1.00 | 28.79 | A | C |
| ATOM | 1461 | C | VAL | A | 398 | 24.676 | 63.469 | 5.558 | 1.00 | 36.34 | A | C |
| ATOM | 1462 | O | VAL | A | 398 | 24.859 | 64.556 | 6.123 | 1.00 | 33.44 | A | O |
| ATOM | 1463 | N | ALA | A | 399 | 25.624 | 62.855 | 4.849 | 1.00 | 34.76 | A | N |
| ATOM | 1464 | CA | ALA | A | 399 | 26.975 | 63.407 | 4.736 | 1.00 | 33.33 | A | C |
| ATOM | 1465 | CB | ALA | A | 399 | 27.932 | 62.401 | 4.105 | 1.00 | 29.37 | A | C |
| ATOM | 1466 | C | ALA | A | 399 | 26.984 | 64.714 | 3.956 | 1.00 | 34.30 | A | C |
| ATOM | 1467 | O | ALA | A | 399 | 27.700 | 65.648 | 4.311 | 1.00 | 34.81 | A | O |
| ATOM | 1468 | N | ALA | A | 400 | 26.201 | 64.772 | 2.885 | 1.00 | 34.76 | A | N |
| ATOM | 1469 | CA | ALA | A | 400 | 26.103 | 65.991 | 2.098 | 1.00 | 31.73 | A | C |
| ATOM | 1470 | CB | ALA | A | 400 | 25.190 | 65.781 | 0.910 | 1.00 | 26.46 | A | C |
| ATOM | 1471 | C | ALA | A | 400 | 25.593 | 67.126 | 2.992 | 1.00 | 36.30 | A | C |
| ATOM | 1472 | O | ALA | A | 400 | 26.113 | 68.252 | 2.974 | 1.00 | 33.48 | A | O |
| ATOM | 1473 | N | HIS | A | 401 | 24.587 | 66.814 | 3.796 | 1.00 | 31.57 | A | N |
| ATOM | 1474 | CA | HIS | A | 401 | 24.048 | 67.796 | 4.720 | 1.00 | 35.82 | A | C |
| ATOM | 1475 | CB | HIS | A | 401 | 22.845 | 67.210 | 5.459 | 1.00 | 33.23 | A | C |
| ATOM | 1476 | CG | HIS | A | 401 | 22.192 | 68.171 | 6.395 | 1.00 | 36.48 | A | C |
| ATOM | 1477 | CD2 | HIS | A | 401 | 22.381 | 68.395 | 7.719 | 1.00 | 33.26 | A | C |
| ATOM | 1478 | ND1 | HIS | A | 401 | 21.207 | 69.047 | 5.992 | 1.00 | 34.67 | A | N |
| ATOM | 1479 | CE1 | HIS | A | 401 | 20.825 | 69.777 | 7.026 | 1.00 | 37.95 | A | C |
| ATOM | 1480 | NE2 | HIS | A | 401 | 21.517 | 69.396 | 8.086 | 1.00 | 31.50 | A | N |
| ATOM | 1481 | C | HIS | A | 401 | 25.112 | 68.285 | 5.714 | 1.00 | 35.06 | A | C |
| ATOM | 1482 | O | HIS | A | 401 | 25.343 | 69.492 | 5.846 | 1.00 | 33.07 | A | O |
| ATOM | 1483 | N | GLU | A | 402 | 25.764 | 67.344 | 6.395 | 1.00 | 30.51 | A | N |
| ATOM | 1484 | CA | GLU | A | 402 | 26.746 | 67.674 | 7.421 | 1.00 | 26.51 | A | C |
| ATOM | 1485 | CB | GLU | A | 402 | 27.220 | 66.417 | 8.146 | 1.00 | 33.83 | A | C |
| ATOM | 1486 | CG | GLU | A | 402 | 26.123 | 65.652 | 8.851 | 1.00 | 29.47 | A | C |
| ATOM | 1487 | CD | GLU | A | 402 | 25.396 | 66.497 | 9.863 | 1.00 | 32.53 | A | C |
| ATOM | 1488 | OE1 | GLU | A | 402 | 25.936 | 67.550 | 10.265 | 1.00 | 31.93 | A | O |
| ATOM | 1489 | OE2 | GLU | A | 402 | 24.282 | 66.106 | 10.262 | 1.00 | 36.15 | A | O |
| ATOM | 1490 | C | GLU | A | 402 | 27.943 | 68.424 | 6.877 | 1.00 | 30.27 | A | C |
| ATOM | 1491 | O | GLU | A | 402 | 28.324 | 69.440 | 7.438 | 1.00 | 35.27 | A | O |
| ATOM | 1492 | N | PHE | A | 403 | 28.544 | 67.915 | 5.797 | 1.00 | 35.22 | A | N |
| ATOM | 1493 | CA | PHE | A | 403 | 29.620 | 68.621 | 5.089 | 1.00 | 33.75 | A | C |
| ATOM | 1494 | CB | PHE | A | 403 | 30.033 | 67.890 | 3.805 | 1.00 | 33.76 | A | C |
| ATOM | 1495 | CG | PHE | A | 403 | 30.615 | 66.515 | 4.037 | 1.00 | 40.84 | A | C |
| ATOM | 1496 | CD1 | PHE | A | 403 | 31.083 | 66.141 | 5.292 | 1.00 | 39.95 | A | C |
| ATOM | 1497 | CD2 | PHE | A | 403 | 30.711 | 65.604 | 2.992 | 1.00 | 35.68 | A | C |
| ATOM | 1498 | CE1 | PHE | A | 403 | 31.607 | 64.883 | 5.502 | 1.00 | 38.52 | A | C |
| ATOM | 1499 | CE2 | PHE | A | 403 | 31.239 | 64.344 | 3.193 | 1.00 | 34.41 | A | C |
| ATOM | 1500 | CZ | PHE | A | 403 | 31.690 | 63.982 | 4.446 | 1.00 | 40.32 | A | C |
| ATOM | 1501 | C | PHE | A | 403 | 29.212 | 70.047 | 4.745 | 1.00 | 34.69 | A | C |
| ATOM | 1502 | O | PHE | A | 403 | 30.019 | 70.976 | 4.832 | 1.00 | 36.13 | A | O |
| ATOM | 1503 | N | GLY | A | 404 | 27.957 | 70.214 | 4.341 | 1.00 | 32.69 | A | N |
| ATOM | 1504 | CA | GLY | A | 404 | 27.398 | 71.536 | 4.146 | 1.00 | 35.84 | A | C |
| ATOM | 1505 | C | GLY | A | 404 | 27.670 | 72.414 | 5.351 | 1.00 | 34.68 | A | C |
| ATOM | 1506 | O | GLY | A | 404 | 28.132 | 73.543 | 5.213 | 1.00 | 35.36 | A | O |
| ATOM | 1507 | N | HIS | A | 405 | 27.381 | 71.893 | 6.538 | 1.00 | 36.75 | A | N |
| ATOM | 1508 | CA | HIS | A | 405 | 27.696 | 72.603 | 7.769 | 1.00 | 35.94 | A | C |
| ATOM | 1509 | CB | HIS | A | 405 | 27.244 | 71.805 | 8.984 | 1.00 | 36.35 | A | C |
| ATOM | 1510 | CG | HIS | A | 405 | 25.796 | 71.964 | 9.299 | 1.00 | 30.48 | A | C |
| ATOM | 1511 | CD2 | HIS | A | 405 | 24.846 | 71.053 | 9.602 | 1.00 | 30.12 | A | C |
| ATOM | 1512 | ND1 | HIS | A | 405 | 25.181 | 73.194 | 9.339 | 1.00 | 36.08 | A | N |
| ATOM | 1513 | CE1 | HIS | A | 405 | 23.905 | 73.034 | 9.646 | 1.00 | 35.21 | A | C |
| ATOM | 1514 | NE2 | HIS | A | 405 | 23.677 | 71.746 | 9.811 | 1.00 | 33.13 | A | N |
| ATOM | 1515 | C | HIS | A | 405 | 29.189 | 72.823 | 7.865 | 1.00 | 40.98 | A | C |

TABLE 13-continued

Coordinates for proMMP9(35-444 ΔFnII) (SEQ ID NO: 12) complex with Example 3

| | | | | | | | | | | | |
|---|---|---|---|---|---|---|---|---|---|---|---|
| ATOM | 1516 | O | HIS | A | 405 | 29.660 | 73.921 | 8.208 | 1.00 | 41.09 A | O |
| ATOM | 1517 | N | ALA | A | 406 | 29.925 | 71.759 | 7.566 | 1.00 | 37.81 A | N |
| ATOM | 1518 | CA | ALA | A | 406 | 31.376 | 71.763 | 7.651 | 1.00 | 35.81 A | C |
| ATOM | 1519 | CB | ALA | A | 406 | 31.918 | 70.404 | 7.251 | 1.00 | 35.22 A | C |
| ATOM | 1520 | C | ALA | A | 406 | 32.030 | 72.878 | 6.821 | 1.00 | 35.82 A | C |
| ATOM | 1521 | O | ALA | A | 406 | 33.148 | 73.295 | 7.115 | 1.00 | 41.89 A | O |
| ATOM | 1522 | N | LEU | A | 407 | 31.340 | 73.357 | 5.793 | 1.00 | 32.88 A | N |
| ATOM | 1523 | CA | LEU | A | 407 | 31.863 | 74.450 | 4.971 | 1.00 | 37.46 A | C |
| ATOM | 1524 | CB | LEU | A | 407 | 31.448 | 74.287 | 3.509 | 1.00 | 33.28 A | C |
| ATOM | 1525 | CG | LEU | A | 407 | 31.871 | 73.041 | 2.753 | 1.00 | 36.50 A | C |
| ATOM | 1526 | CD1 | LEU | A | 407 | 31.136 | 73.008 | 1.437 | 1.00 | 40.30 A | C |
| ATOM | 1527 | CD2 | LEU | A | 407 | 33.383 | 73.006 | 2.544 | 1.00 | 38.27 A | C |
| ATOM | 1528 | C | LEU | A | 407 | 31.381 | 75.813 | 5.444 | 1.00 | 38.99 A | C |
| ATOM | 1529 | O | LEU | A | 407 | 31.879 | 76.839 | 4.992 | 1.00 | 43.22 A | O |
| ATOM | 1530 | N | GLY | A | 408 | 30.380 | 75.824 | 6.316 | 1.00 | 40.95 A | N |
| ATOM | 1531 | CA | GLY | A | 408 | 29.880 | 77.069 | 6.862 | 1.00 | 39.97 A | C |
| ATOM | 1532 | C | GLY | A | 408 | 28.403 | 77.337 | 6.620 | 1.00 | 39.95 A | C |
| ATOM | 1533 | O | GLY | A | 408 | 27.949 | 78.459 | 6.841 | 1.00 | 42.55 A | O |
| ATOM | 1534 | N | LEU | A | 409 | 27.649 | 76.330 | 6.178 | 1.00 | 36.74 A | N |
| ATOM | 1535 | CA | LEU | A | 409 | 26.213 | 76.522 | 5.920 | 1.00 | 34.59 A | C |
| ATOM | 1536 | CB | LEU | A | 409 | 25.705 | 75.606 | 4.803 | 1.00 | 35.58 A | C |
| ATOM | 1537 | CG | LEU | A | 409 | 26.195 | 75.953 | 3.391 | 1.00 | 39.33 A | C |
| ATOM | 1538 | CD1 | LEU | A | 409 | 25.795 | 74.878 | 2.384 | 1.00 | 30.99 A | C |
| ATOM | 1539 | CD2 | LEU | A | 409 | 25.714 | 77.345 | 2.953 | 1.00 | 30.29 A | C |
| ATOM | 1540 | C | LEU | A | 409 | 25.341 | 76.352 | 7.150 | 1.00 | 34.47 A | C |
| ATOM | 1541 | O | LEU | A | 409 | 25.643 | 75.564 | 8.041 | 1.00 | 38.48 A | O |
| ATOM | 1542 | N | ASP | A | 410 | 24.251 | 77.109 | 7.184 | 1.00 | 39.57 A | N |
| ATOM | 1543 | CA | ASP | A | 410 | 23.232 | 76.980 | 8.220 | 1.00 | 35.25 A | C |
| ATOM | 1544 | CB | ASP | A | 410 | 22.804 | 78.354 | 8.704 | 1.00 | 30.26 A | C |
| ATOM | 1545 | CG | ASP | A | 410 | 23.705 | 78.887 | 9.762 | 1.00 | 35.55 A | C |
| ATOM | 1546 | OD1 | ASP | A | 410 | 24.120 | 78.089 | 10.635 | 1.00 | 35.70 A | O |
| ATOM | 1547 | OD2 | ASP | A | 410 | 23.993 | 80.098 | 9.724 | 1.00 | 38.32 A | O |
| ATOM | 1548 | C | ASP | A | 410 | 22.019 | 76.277 | 7.656 | 1.00 | 35.49 A | C |
| ATOM | 1549 | O | ASP | A | 410 | 21.814 | 76.260 | 6.443 | 1.00 | 39.27 A | O |
| ATOM | 1550 | N | HIS | A | 411 | 21.196 | 75.716 | 8.531 | 1.00 | 40.76 A | N |
| ATOM | 1551 | CA | HIS | A | 411 | 20.007 | 75.014 | 8.071 | 1.00 | 34.38 A | C |
| ATOM | 1552 | CB | HIS | A | 411 | 19.138 | 74.561 | 9.240 | 1.00 | 34.73 A | C |
| ATOM | 1553 | CG | HIS | A | 411 | 19.667 | 73.356 | 9.949 | 1.00 | 37.49 A | C |
| ATOM | 1554 | CD2 | HIS | A | 411 | 20.366 | 72.289 | 9.493 | 1.00 | 33.75 A | C |
| ATOM | 1555 | ND1 | HIS | A | 411 | 19.511 | 73.162 | 11.307 | 1.00 | 38.96 A | N |
| ATOM | 1556 | CE1 | HIS | A | 411 | 20.083 | 72.024 | 11.656 | 1.00 | 35.88 A | C |
| ATOM | 1557 | NE2 | HIS | A | 411 | 20.607 | 71.474 | 10.574 | 1.00 | 40.17 A | N |
| ATOM | 1558 | C | HIS | A | 411 | 19.201 | 75.897 | 7.153 | 1.00 | 31.87 A | C |
| ATOM | 1559 | O | HIS | A | 411 | 19.191 | 77.116 | 7.297 | 1.00 | 30.11 A | O |
| ATOM | 1560 | N | SER | A | 412 | 18.540 | 75.266 | 6.196 | 1.00 | 35.46 A | N |
| ATOM | 1561 | CA | SER | A | 412 | 17.551 | 75.935 | 5.371 | 1.00 | 36.69 A | C |
| ATOM | 1562 | CB | SER | A | 412 | 17.599 | 75.383 | 3.953 | 1.00 | 34.02 A | C |
| ATOM | 1563 | OG | SER | A | 412 | 16.485 | 75.838 | 3.220 | 1.00 | 41.39 A | O |
| ATOM | 1564 | C | SER | A | 412 | 16.154 | 75.735 | 5.958 | 1.00 | 38.27 A | C |
| ATOM | 1565 | O | SER | A | 412 | 15.934 | 74.848 | 6.780 | 1.00 | 38.18 A | O |
| ATOM | 1566 | N | SER | A | 413 | 15.208 | 76.567 | 5.544 | 1.00 | 41.43 A | N |
| ATOM | 1567 | CA | SER | A | 413 | 13.829 | 76.406 | 5.986 | 1.00 | 39.44 A | C |
| ATOM | 1568 | CB | SER | A | 413 | 13.278 | 77.712 | 6.557 | 1.00 | 36.34 A | C |
| ATOM | 1569 | OG | SER | A | 413 | 13.008 | 78.639 | 5.530 | 1.00 | 39.77 A | O |
| ATOM | 1570 | C | SER | A | 413 | 12.984 | 75.913 | 4.818 | 1.00 | 44.11 A | C |
| ATOM | 1571 | O | SER | A | 413 | 11.820 | 75.531 | 4.990 | 1.00 | 40.30 A | O |
| ATOM | 1572 | N | VAL | A | 414 | 13.594 | 75.925 | 3.631 | 1.00 | 42.19 A | N |
| ATOM | 1573 | CA | VAL | A | 414 | 13.012 | 75.326 | 2.438 | 1.00 | 36.85 A | C |
| ATOM | 1574 | CB | VAL | A | 414 | 13.850 | 75.658 | 1.181 | 1.00 | 38.32 A | C |
| ATOM | 1575 | CG1 | VAL | A | 414 | 13.476 | 74.753 | 0.007 | 1.00 | 32.58 A | C |
| ATOM | 1576 | CG2 | VAL | A | 414 | 13.685 | 77.114 | 0.805 | 1.00 | 32.39 A | C |
| ATOM | 1577 | C | VAL | A | 414 | 12.990 | 73.823 | 2.643 | 1.00 | 37.90 A | C |
| ATOM | 1578 | O | VAL | A | 414 | 14.043 | 73.199 | 2.720 | 1.00 | 42.69 A | O |
| ATOM | 1579 | N | PRO | A | 415 | 11.788 | 73.237 | 2.734 | 1.00 | 38.26 A | N |
| ATOM | 1580 | CD | PRO | A | 415 | 10.518 | 73.943 | 2.526 | 1.00 | 36.50 A | C |
| ATOM | 1581 | CA | PRO | A | 415 | 11.576 | 71.817 | 3.043 | 1.00 | 40.79 A | C |
| ATOM | 1582 | CB | PRO | A | 415 | 10.057 | 71.659 | 2.921 | 1.00 | 38.57 A | C |
| ATOM | 1583 | CG | PRO | A | 415 | 9.523 | 73.019 | 3.138 | 1.00 | 33.99 A | C |
| ATOM | 1584 | C | PRO | A | 415 | 12.286 | 70.844 | 2.095 | 1.00 | 36.31 A | C |
| ATOM | 1585 | O | PRO | A | 415 | 12.826 | 69.838 | 2.552 | 1.00 | 34.21 A | O |
| ATOM | 1586 | N | GLU | A | 416 | 12.283 | 71.133 | 0.798 | 1.00 | 38.92 A | N |
| ATOM | 1587 | CA | GLU | A | 416 | 12.909 | 70.234 | −0.181 | 1.00 | 44.14 A | C |
| ATOM | 1588 | CB | GLU | A | 416 | 12.311 | 70.428 | −1.581 | 1.00 | 37.57 A | C |
| ATOM | 1589 | CG | GLU | A | 416 | 10.792 | 70.326 | −1.633 | 1.00 | 37.51 A | C |
| ATOM | 1590 | CD | GLU | A | 416 | 10.089 | 71.522 | −1.001 | 1.00 | 39.22 A | C |
| ATOM | 1591 | OE1 | GLU | A | 416 | 10.711 | 72.601 | −0.898 | 1.00 | 40.32 A | O |
| ATOM | 1592 | OE2 | GLU | A | 416 | 8.908 | 71.384 | −0.607 | 1.00 | 47.65 A | O |

TABLE 13-continued

Coordinates for proMMP9(35-444 ΔFnII) (SEQ ID NO: 12) complex with Example 3

| ATOM | 1593 | C   | GLU | A | 416 | 14.435 | 70.375 | -0.232 | 1.00 | 37.98 | A | C |
| ---- | ---- | --- | --- | - | --- | ------ | ------ | ------ | ---- | ----- | - | - |
| ATOM | 1594 | O   | GLU | A | 416 | 15.136 | 69.429 | -0.581 | 1.00 | 40.50 | A | O |
| ATOM | 1595 | N   | ALA | A | 417 | 14.939 | 71.548 | 0.123  | 1.00 | 31.10 | A | N |
| ATOM | 1596 | CA  | ALA | A | 417 | 16.375 | 71.785 | 0.151  | 1.00 | 35.99 | A | C |
| ATOM | 1597 | CB  | ALA | A | 417 | 16.669 | 73.189 | 0.659  | 1.00 | 36.83 | A | C |
| ATOM | 1598 | C   | ALA | A | 417 | 17.118 | 70.763 | 0.999  | 1.00 | 35.13 | A | C |
| ATOM | 1599 | O   | ALA | A | 417 | 16.601 | 70.277 | 2.001  | 1.00 | 36.76 | A | O |
| ATOM | 1600 | N   | LEU | A | 418 | 18.349 | 70.473 | 0.590  | 1.00 | 35.37 | A | N |
| ATOM | 1601 | CA  | LEU | A | 418 | 19.268 | 69.594 | 1.312  | 1.00 | 35.31 | A | C |
| ATOM | 1602 | CB  | LEU | A | 418 | 20.560 | 69.442 | 0.503  | 1.00 | 30.84 | A | C |
| ATOM | 1603 | CG  | LEU | A | 418 | 21.670 | 68.685 | 1.230  | 1.00 | 39.17 | A | C |
| ATOM | 1604 | CD1 | LEU | A | 418 | 21.404 | 67.189 | 1.167  | 1.00 | 31.67 | A | C |
| ATOM | 1605 | CD2 | LEU | A | 418 | 23.048 | 69.015 | 0.675  | 1.00 | 28.61 | A | C |
| ATOM | 1606 | C   | LEU | A | 418 | 19.621 | 70.045 | 2.744  | 1.00 | 35.70 | A | C |
| ATOM | 1607 | O   | LEU | A | 418 | 19.780 | 69.218 | 3.640  | 1.00 | 35.62 | A | O |
| ATOM | 1608 | N   | MET | A | 419 | 19.778 | 71.349 | 2.949  | 1.00 | 36.62 | A | N |
| ATOM | 1609 | CA  | MET | A | 419 | 20.157 | 71.868 | 4.257  | 1.00 | 33.19 | A | C |
| ATOM | 1610 | CB  | MET | A | 419 | 20.875 | 73.212 | 4.134  | 1.00 | 32.16 | A | C |
| ATOM | 1611 | CG  | MET | A | 419 | 22.229 | 73.126 | 3.477  | 1.00 | 32.84 | A | C |
| ATOM | 1612 | SD  | MET | A | 419 | 23.266 | 71.786 | 4.102  | 1.00 | 35.07 | A | S |
| ATOM | 1613 | CE  | MET | A | 419 | 23.403 | 72.198 | 5.842  | 1.00 | 36.84 | A | C |
| ATOM | 1614 | C   | MET | A | 419 | 18.945 | 72.006 | 5.157  | 1.00 | 35.59 | A | C |
| ATOM | 1615 | O   | MET | A | 419 | 19.041 | 72.518 | 6.267  | 1.00 | 39.45 | A | O |
| ATOM | 1616 | N   | TYR | A | 420 | 17.796 | 71.556 | 4.676  | 1.00 | 38.14 | A | N |
| ATOM | 1617 | CA  | TYR | A | 420 | 16.644 | 71.415 | 5.543  | 1.00 | 35.51 | A | C |
| ATOM | 1618 | CB  | TYR | A | 420 | 15.441 | 70.916 | 4.761  | 1.00 | 34.18 | A | C |
| ATOM | 1619 | CG  | TYR | A | 420 | 14.145 | 71.071 | 5.523  | 1.00 | 42.18 | A | C |
| ATOM | 1620 | CD1 | TYR | A | 420 | 13.590 | 72.327 | 5.727  | 1.00 | 39.06 | A | C |
| ATOM | 1621 | CE1 | TYR | A | 420 | 12.412 | 72.479 | 6.416  | 1.00 | 38.71 | A | C |
| ATOM | 1622 | CD2 | TYR | A | 420 | 13.477 | 69.966 | 6.039  | 1.00 | 39.92 | A | C |
| ATOM | 1623 | CE2 | TYR | A | 420 | 12.293 | 70.112 | 6.732  | 1.00 | 36.93 | A | C |
| ATOM | 1624 | CZ  | TYR | A | 420 | 11.767 | 71.372 | 6.919  | 1.00 | 36.74 | A | C |
| ATOM | 1625 | OH  | TYR | A | 420 | 10.589 | 71.533 | 7.612  | 1.00 | 38.81 | A | O |
| ATOM | 1626 | C   | TYR | A | 420 | 17.004 | 70.399 | 6.603  | 1.00 | 35.69 | A | C |
| ATOM | 1627 | O   | TYR | A | 420 | 17.462 | 69.311 | 6.266  | 1.00 | 34.24 | A | O |
| ATOM | 1628 | N   | PRO | A | 421 | 16.763 | 70.741 | 7.883  | 1.00 | 39.38 | A | N |
| ATOM | 1629 | CD  | PRO | A | 421 | 15.884 | 71.863 | 8.249  | 1.00 | 36.94 | A | C |
| ATOM | 1630 | CA  | PRO | A | 421 | 17.209 | 69.995 | 9.068  | 1.00 | 35.47 | A | C |
| ATOM | 1631 | CB  | PRO | A | 421 | 16.575 | 70.768 | 10.234 | 1.00 | 34.12 | A | C |
| ATOM | 1632 | CG  | PRO | A | 421 | 16.228 | 72.096 | 9.684  | 1.00 | 35.68 | A | C |
| ATOM | 1633 | C   | PRO | A | 421 | 16.718 | 68.555 | 9.104  | 1.00 | 36.41 | A | C |
| ATOM | 1634 | O   | PRO | A | 421 | 17.453 | 67.681 | 9.551  | 1.00 | 37.42 | A | O |
| ATOM | 1635 | N   | MET | A | 422 | 15.493 | 68.306 | 8.660  | 1.00 | 34.14 | A | N |
| ATOM | 1636 | CA  | MET | A | 422 | 14.938 | 66.958 | 8.753  | 1.00 | 42.16 | A | C |
| ATOM | 1637 | CB  | MET | A | 422 | 13.408 | 66.980 | 8.679  | 1.00 | 41.55 | A | C |
| ATOM | 1638 | CG  | MET | A | 422 | 12.720 | 67.703 | 9.835  | 1.00 | 35.20 | A | C |
| ATOM | 1639 | SD  | MET | A | 422 | 10.927 | 67.599 | 9.674  | 1.00 | 42.41 | A | S |
| ATOM | 1640 | CE  | MET | A | 422 | 10.417 | 69.202 | 10.291 | 1.00 | 31.39 | A | C |
| ATOM | 1641 | C   | MET | A | 422 | 15.488 | 66.022 | 7.686  | 1.00 | 41.20 | A | C |
| ATOM | 1642 | O   | MET | A | 422 | 15.939 | 66.467 | 6.632  | 1.00 | 43.90 | A | O |
| ATOM | 1643 | N   | TYR | A | 423 | 15.444 | 64.722 | 7.970  | 1.00 | 45.04 | A | N |
| ATOM | 1644 | CA  | TYR | A | 423 | 15.819 | 63.704 | 6.989  | 1.00 | 42.31 | A | C |
| ATOM | 1645 | CB  | TYR | A | 423 | 16.338 | 62.446 | 7.677  | 1.00 | 40.32 | A | C |
| ATOM | 1646 | CG  | TYR | A | 423 | 16.737 | 61.371 | 6.704  | 1.00 | 35.85 | A | C |
| ATOM | 1647 | CD1 | TYR | A | 423 | 15.805 | 60.468 | 6.216  | 1.00 | 39.70 | A | C |
| ATOM | 1648 | CE1 | TYR | A | 423 | 16.164 | 59.484 | 5.319  | 1.00 | 37.36 | A | C |
| ATOM | 1649 | CD2 | TYR | A | 423 | 18.042 | 61.262 | 6.262  | 1.00 | 33.86 | A | C |
| ATOM | 1650 | CE2 | TYR | A | 423 | 18.414 | 60.273 | 5.366  | 1.00 | 36.65 | A | C |
| ATOM | 1651 | CZ  | TYR | A | 423 | 17.471 | 59.390 | 4.900  | 1.00 | 34.05 | A | C |
| ATOM | 1652 | OH  | TYR | A | 423 | 17.833 | 58.410 | 4.015  | 1.00 | 34.60 | A | O |
| ATOM | 1653 | C   | TYR | A | 423 | 14.662 | 63.325 | 6.067  | 1.00 | 40.38 | A | C |
| ATOM | 1654 | O   | TYR | A | 423 | 13.587 | 62.928 | 6.517  | 1.00 | 33.70 | A | O |
| ATOM | 1655 | N   | ARG | A | 424 | 14.908 | 63.461 | 4.770  | 1.00 | 43.26 | A | N |
| ATOM | 1656 | CA  | ARG | A | 424 | 13.969 | 63.074 | 3.730  | 1.00 | 33.79 | A | C |
| ATOM | 1657 | CB  | ARG | A | 424 | 13.484 | 64.311 | 2.969  | 1.00 | 36.54 | A | C |
| ATOM | 1658 | CG  | ARG | A | 424 | 14.398 | 64.745 | 1.800  | 1.00 | 43.63 | A | C |
| ATOM | 1659 | CD  | ARG | A | 424 | 14.172 | 66.204 | 1.401  | 1.00 | 49.92 | A | C |
| ATOM | 1660 | NE  | ARG | A | 424 | 14.486 | 66.468 | -0.005 | 1.00 | 40.25 | A | N |
| ATOM | 1661 | CZ  | ARG | A | 424 | 13.690 | 66.141 | -1.023 | 1.00 | 41.63 | A | C |
| ATOM | 1662 | NH1 | ARG | A | 424 | 12.539 | 65.524 | -0.796 | 1.00 | 43.84 | A | N |
| ATOM | 1663 | NH2 | ARG | A | 424 | 14.042 | 66.423 | -2.271 | 1.00 | 43.80 | A | N |
| ATOM | 1664 | C   | ARG | A | 424 | 14.787 | 62.212 | 2.800  | 1.00 | 38.38 | A | C |
| ATOM | 1665 | O   | ARG | A | 424 | 15.917 | 62.567 | 2.459  | 1.00 | 43.07 | A | O |
| ATOM | 1666 | N   | PHE | A | 425 | 14.269 | 61.066 | 2.394  | 1.00 | 35.52 | A | N |
| ATOM | 1667 | CA  | PHE | A | 425 | 15.027 | 60.312 | 1.416  | 1.00 | 34.46 | A | C |
| ATOM | 1668 | CB  | PHE | A | 425 | 15.026 | 58.812 | 1.672  | 1.00 | 35.53 | A | C |
| ATOM | 1669 | CG  | PHE | A | 425 | 15.590 | 58.034 | 0.523  | 1.00 | 36.58 | A | C |

TABLE 13-continued

Coordinates for proMMP9(35-444 ΔFnII) (SEQ ID NO: 12) complex with Example 3

| ATOM | 1670 | CD1 | PHE | A | 425 | 16.958 | 57.965 | 0.328 | 1.00 | 33.57 | A | C |
|---|---|---|---|---|---|---|---|---|---|---|---|---|
| ATOM | 1671 | CD2 | PHE | A | 425 | 14.757 | 57.430 | −0.395 | 1.00 | 37.30 | A | C |
| ATOM | 1672 | CE1 | PHE | A | 425 | 17.485 | 57.272 | −0.731 | 1.00 | 39.85 | A | C |
| ATOM | 1673 | CE2 | PHE | A | 425 | 15.283 | 56.740 | −1.471 | 1.00 | 48.72 | A | C |
| ATOM | 1674 | CZ | PHE | A | 425 | 16.653 | 56.661 | −1.635 | 1.00 | 45.38 | A | C |
| ATOM | 1675 | C | PHE | A | 425 | 14.520 | 60.586 | 0.016 | 1.00 | 36.12 | A | C |
| ATOM | 1676 | O | PHE | A | 425 | 13.326 | 60.498 | −0.252 | 1.00 | 43.15 | A | O |
| ATOM | 1677 | N | THR | A | 426 | 15.443 | 60.911 | −0.875 | 1.00 | 34.43 | A | N |
| ATOM | 1678 | CA | THR | A | 426 | 15.116 | 61.156 | −2.267 | 1.00 | 38.75 | A | C |
| ATOM | 1679 | CB | THR | A | 426 | 15.326 | 62.641 | −2.635 | 1.00 | 39.94 | A | C |
| ATOM | 1680 | OG1 | THR | A | 426 | 15.113 | 62.830 | −4.034 | 1.00 | 39.18 | A | O |
| ATOM | 1681 | CG2 | THR | A | 426 | 16.728 | 63.090 | −2.286 | 1.00 | 28.57 | A | C |
| ATOM | 1682 | C | THR | A | 426 | 16.017 | 60.299 | −3.135 | 1.00 | 39.06 | A | C |
| ATOM | 1683 | O | THR | A | 426 | 17.018 | 59.768 | −2.660 | 1.00 | 31.83 | A | O |
| ATOM | 1684 | N | GLU | A | 427 | 15.653 | 60.151 | −4.402 | 1.00 | 42.55 | A | N |
| ATOM | 1685 | CA | GLU | A | 427 | 16.572 | 59.571 | −5.371 | 1.00 | 42.35 | A | C |
| ATOM | 1686 | CB | GLU | A | 427 | 15.968 | 58.353 | −6.051 | 1.00 | 42.41 | A | C |
| ATOM | 1687 | CG | GLU | A | 427 | 15.487 | 57.330 | −5.068 | 1.00 | 52.95 | A | C |
| ATOM | 1688 | CD | GLU | A | 427 | 15.779 | 55.931 | −5.517 | 1.00 | 55.58 | A | C |
| ATOM | 1689 | OE1 | GLU | A | 427 | 14.967 | 55.373 | −6.288 | 1.00 | 54.06 | A | O |
| ATOM | 1690 | OE2 | GLU | A | 427 | 16.821 | 55.394 | −5.083 | 1.00 | 55.76 | A | O |
| ATOM | 1691 | C | GLU | A | 427 | 16.982 | 60.619 | −6.393 | 1.00 | 44.48 | A | C |
| ATOM | 1692 | O | GLU | A | 427 | 17.865 | 60.388 | −7.214 | 1.00 | 50.98 | A | O |
| ATOM | 1693 | N | GLY | A | 428 | 16.343 | 61.781 | −6.327 | 1.00 | 39.41 | A | N |
| ATOM | 1694 | CA | GLY | A | 428 | 16.704 | 62.885 | −7.188 | 1.00 | 38.09 | A | C |
| ATOM | 1695 | C | GLY | A | 428 | 18.002 | 63.502 | −6.723 | 1.00 | 39.67 | A | C |
| ATOM | 1696 | O | GLY | A | 428 | 18.466 | 63.207 | −5.617 | 1.00 | 39.35 | A | O |
| ATOM | 1697 | N | PRO | A | 429 | 18.599 | 64.360 | −7.567 | 1.00 | 42.88 | A | N |
| ATOM | 1698 | CD | PRO | A | 429 | 18.070 | 64.730 | −8.891 | 1.00 | 34.17 | A | C |
| ATOM | 1699 | CA | PRO | A | 429 | 19.814 | 65.112 | −7.233 | 1.00 | 33.35 | A | C |
| ATOM | 1700 | CB | PRO | A | 429 | 19.894 | 66.154 | −8.350 | 1.00 | 28.70 | A | C |
| ATOM | 1701 | CG | PRO | A | 429 | 19.162 | 65.572 | −9.466 | 1.00 | 32.70 | A | C |
| ATOM | 1702 | C | PRO | A | 429 | 19.663 | 65.817 | −5.882 | 1.00 | 38.50 | A | C |
| ATOM | 1703 | O | PRO | A | 429 | 18.720 | 66.579 | −5.681 | 1.00 | 39.95 | A | O |
| ATOM | 1704 | N | PRO | A | 430 | 20.588 | 65.566 | −4.957 | 1.00 | 36.40 | A | N |
| ATOM | 1705 | CD | PRO | A | 430 | 21.687 | 64.587 | −5.041 | 1.00 | 22.80 | A | C |
| ATOM | 1706 | CA | PRO | A | 430 | 20.441 | 66.139 | −3.614 | 1.00 | 33.48 | A | C |
| ATOM | 1707 | CB | PRO | A | 430 | 21.652 | 65.575 | −2.861 | 1.00 | 36.60 | A | C |
| ATOM | 1708 | CG | PRO | A | 430 | 22.007 | 64.309 | −3.612 | 1.00 | 30.54 | A | C |
| ATOM | 1709 | C | PRO | A | 430 | 20.402 | 67.677 | −3.525 | 1.00 | 30.49 | A | C |
| ATOM | 1710 | O | PRO | A | 430 | 19.786 | 68.175 | −2.599 | 1.00 | 44.03 | A | O |
| ATOM | 1711 | N | LEU | A | 431 | 21.019 | 68.418 | −4.435 | 1.00 | 33.03 | A | N |
| ATOM | 1712 | CA | LEU | A | 431 | 21.093 | 69.882 | −4.285 | 1.00 | 32.86 | A | C |
| ATOM | 1713 | CB | LEU | A | 431 | 22.426 | 70.420 | −4.794 | 1.00 | 37.62 | A | C |
| ATOM | 1714 | CG | LEU | A | 431 | 23.661 | 70.087 | −3.963 | 1.00 | 43.53 | A | C |
| ATOM | 1715 | CD1 | LEU | A | 431 | 24.907 | 70.687 | −4.602 | 1.00 | 32.68 | A | C |
| ATOM | 1716 | CD2 | LEU | A | 431 | 23.471 | 70.590 | −2.546 | 1.00 | 34.80 | A | C |
| ATOM | 1717 | C | LEU | A | 431 | 19.966 | 70.652 | −4.964 | 1.00 | 35.94 | A | C |
| ATOM | 1718 | O | LEU | A | 431 | 19.527 | 70.301 | −6.051 | 1.00 | 37.09 | A | O |
| ATOM | 1719 | N | HIS | A | 432 | 19.514 | 71.718 | −4.312 | 1.00 | 36.54 | A | N |
| ATOM | 1720 | CA | HIS | A | 432 | 18.453 | 72.563 | −4.845 | 1.00 | 33.66 | A | C |
| ATOM | 1721 | CB | HIS | A | 432 | 17.163 | 72.399 | −4.027 | 1.00 | 33.15 | A | C |
| ATOM | 1722 | CG | HIS | A | 432 | 16.640 | 70.996 | −3.994 | 1.00 | 33.59 | A | C |
| ATOM | 1723 | CD2 | HIS | A | 432 | 15.543 | 70.439 | −4.556 | 1.00 | 30.52 | A | C |
| ATOM | 1724 | ND1 | HIS | A | 432 | 17.274 | 69.981 | −3.306 | 1.00 | 35.78 | A | N |
| ATOM | 1725 | CE1 | HIS | A | 432 | 16.596 | 68.857 | −3.459 | 1.00 | 33.45 | A | C |
| ATOM | 1726 | NE2 | HIS | A | 432 | 15.540 | 69.108 | −4.209 | 1.00 | 36.07 | A | N |
| ATOM | 1727 | C | HIS | A | 432 | 18.924 | 74.014 | −4.818 | 1.00 | 34.10 | A | C |
| ATOM | 1728 | O | HIS | A | 432 | 19.929 | 74.328 | −4.183 | 1.00 | 34.51 | A | O |
| ATOM | 1729 | N | LYS | A | 433 | 18.196 | 74.889 | −5.509 | 1.00 | 34.35 | A | N |
| ATOM | 1730 | CA | LYS | A | 433 | 18.593 | 76.287 | −5.678 | 1.00 | 32.83 | A | C |
| ATOM | 1731 | CB | LYS | A | 433 | 17.442 | 77.107 | −6.276 | 1.00 | 34.11 | A | C |
| ATOM | 1732 | CG | LYS | A | 433 | 17.169 | 76.814 | −7.751 | 1.00 | 41.26 | A | C |
| ATOM | 1733 | CD | LYS | A | 433 | 15.725 | 77.134 | −8.145 | 1.00 | 33.94 | A | C |
| ATOM | 1734 | CE | LYS | A | 433 | 15.461 | 76.868 | −9.628 | 1.00 | 35.87 | A | C |
| ATOM | 1735 | NZ | LYS | A | 433 | 16.383 | 77.614 | −10.533 | 1.00 | 32.69 | A | N |
| ATOM | 1736 | C | LYS | A | 433 | 19.061 | 76.918 | −4.376 | 1.00 | 36.35 | A | C |
| ATOM | 1737 | O | LYS | A | 433 | 20.087 | 77.594 | −4.336 | 1.00 | 35.06 | A | O |
| ATOM | 1738 | N | ASP | A | 434 | 18.313 | 76.680 | −3.306 | 1.00 | 33.37 | A | N |
| ATOM | 1739 | CA | ASP | A | 434 | 18.646 | 77.261 | −2.019 | 1.00 | 30.23 | A | C |
| ATOM | 1740 | CB | ASP | A | 434 | 17.562 | 76.969 | −0.979 | 1.00 | 33.14 | A | C |
| ATOM | 1741 | CG | ASP | A | 434 | 17.698 | 77.847 | 0.248 | 1.00 | 34.72 | A | C |
| ATOM | 1742 | OD1 | ASP | A | 434 | 17.418 | 79.056 | 0.137 | 1.00 | 31.97 | A | O |
| ATOM | 1743 | OD2 | ASP | A | 434 | 18.106 | 77.337 | 1.312 | 1.00 | 35.18 | A | O |
| ATOM | 1744 | C | ASP | A | 434 | 20.004 | 76.814 | −1.493 | 1.00 | 30.02 | A | C |
| ATOM | 1745 | O | ASP | A | 434 | 20.721 | 77.601 | −0.898 | 1.00 | 32.63 | A | O |
| ATOM | 1746 | N | ASP | A | 435 | 20.352 | 75.550 | −1.698 | 1.00 | 32.63 | A | N |

TABLE 13-continued

Coordinates for proMMP9(35-444 ΔFnII) (SEQ ID NO: 12) complex with Example 3

| ATOM | 1747 | CA | ASP | A | 435 | 21.655 | 75.053 | −1.269 | 1.00 | 33.52 | A | C |
|---|---|---|---|---|---|---|---|---|---|---|---|---|
| ATOM | 1748 | CB | ASP | A | 435 | 21.712 | 73.521 | −1.338 | 1.00 | 30.37 | A | C |
| ATOM | 1749 | CG | ASP | A | 435 | 20.584 | 72.850 | −0.569 | 1.00 | 38.23 | A | C |
| ATOM | 1750 | OD1 | ASP | A | 435 | 20.380 | 73.171 | 0.628 | 1.00 | 37.21 | A | O |
| ATOM | 1751 | OD2 | ASP | A | 435 | 19.907 | 71.979 | −1.164 | 1.00 | 41.09 | A | O |
| ATOM | 1752 | C | ASP | A | 435 | 22.800 | 75.684 | −2.090 | 1.00 | 35.28 | A | C |
| ATOM | 1753 | O | ASP | A | 435 | 23.788 | 76.153 | −1.523 | 1.00 | 32.93 | A | O |
| ATOM | 1754 | N | VAL | A | 436 | 22.656 | 75.695 | −3.417 | 1.00 | 32.42 | A | N |
| ATOM | 1755 | CA | VAL | A | 436 | 23.667 | 76.278 | −4.303 | 1.00 | 33.19 | A | C |
| ATOM | 1756 | CB | VAL | A | 436 | 23.277 | 76.114 | −5.794 | 1.00 | 39.80 | A | C |
| ATOM | 1757 | CG1 | VAL | A | 436 | 24.230 | 76.895 | −6.701 | 1.00 | 34.36 | A | C |
| ATOM | 1758 | CG2 | VAL | A | 436 | 23.242 | 74.657 | −6.178 | 1.00 | 31.56 | A | C |
| ATOM | 1759 | C | VAL | A | 436 | 23.884 | 77.765 | −4.020 | 1.00 | 35.14 | A | C |
| ATOM | 1760 | O | VAL | A | 436 | 25.018 | 78.228 | −3.889 | 1.00 | 36.16 | A | O |
| ATOM | 1761 | N | ASN | A | 437 | 22.787 | 78.509 | −3.932 | 1.00 | 33.33 | A | N |
| ATOM | 1762 | CA | ASN | A | 437 | 22.857 | 79.933 | −3.660 | 1.00 | 36.01 | A | C |
| ATOM | 1763 | CB | ASN | A | 437 | 21.482 | 80.582 | −3.788 | 1.00 | 34.26 | A | C |
| ATOM | 1764 | CG | ASN | A | 437 | 21.054 | 80.734 | −5.230 | 1.00 | 38.90 | A | C |
| ATOM | 1765 | OD1 | ASN | A | 437 | 21.797 | 80.381 | −6.146 | 1.00 | 49.61 | A | O |
| ATOM | 1766 | ND2 | ASN | A | 437 | 19.863 | 81.259 | −5.444 | 1.00 | 33.73 | A | N |
| ATOM | 1767 | C | ASN | A | 437 | 23.456 | 80.212 | −2.303 | 1.00 | 39.47 | A | C |
| ATOM | 1768 | O | ASN | A | 437 | 24.252 | 81.136 | −2.148 | 1.00 | 40.70 | A | O |
| ATOM | 1769 | N | GLY | A | 438 | 23.078 | 79.404 | −1.319 | 1.00 | 40.20 | A | N |
| ATOM | 1770 | CA | GLY | A | 438 | 23.609 | 79.560 | 0.020 | 1.00 | 39.49 | A | C |
| ATOM | 1771 | C | GLY | A | 438 | 25.117 | 79.471 | −0.032 | 1.00 | 40.21 | A | C |
| ATOM | 1772 | O | GLY | A | 438 | 25.822 | 80.411 | 0.344 | 1.00 | 48.20 | A | O |
| ATOM | 1773 | N | ILE | A | 439 | 25.616 | 78.343 | −0.521 | 1.00 | 37.01 | A | N |
| ATOM | 1774 | CA | ILE | A | 439 | 27.065 | 78.146 | −0.663 | 1.00 | 46.85 | A | C |
| ATOM | 1775 | CB | ILE | A | 439 | 27.423 | 76.690 | −1.089 | 1.00 | 38.61 | A | C |
| ATOM | 1776 | CG2 | ILE | A | 439 | 27.312 | 76.523 | −2.584 | 1.00 | 37.75 | A | C |
| ATOM | 1777 | CG1 | ILE | A | 439 | 28.824 | 76.314 | −0.608 | 1.00 | 40.92 | A | C |
| ATOM | 1778 | CD1 | ILE | A | 439 | 29.037 | 76.507 | 0.864 | 1.00 | 36.99 | A | C |
| ATOM | 1779 | C | ILE | A | 439 | 27.757 | 79.186 | −1.574 | 1.00 | 41.38 | A | C |
| ATOM | 1780 | O | ILE | A | 439 | 28.900 | 79.552 | −1.322 | 1.00 | 39.86 | A | O |
| ATOM | 1781 | N | ARG | A | 440 | 27.073 | 79.676 | −2.610 | 1.00 | 39.37 | A | N |
| ATOM | 1782 | CA | ARG | A | 440 | 27.633 | 80.779 | −3.408 | 1.00 | 41.04 | A | C |
| ATOM | 1783 | CB | ARG | A | 440 | 26.747 | 81.136 | −4.605 | 1.00 | 33.93 | A | C |
| ATOM | 1784 | CG | ARG | A | 440 | 26.634 | 80.047 | −5.641 | 1.00 | 40.37 | A | C |
| ATOM | 1785 | CD | ARG | A | 440 | 26.017 | 80.567 | −6.926 | 1.00 | 42.98 | A | C |
| ATOM | 1786 | NE | ARG | A | 440 | 26.963 | 81.332 | −7.737 | 1.00 | 45.89 | A | N |
| ATOM | 1787 | CZ | ARG | A | 440 | 26.641 | 81.941 | −8.874 | 1.00 | 44.46 | A | C |
| ATOM | 1788 | NH1 | ARG | A | 440 | 25.398 | 81.879 | −9.323 | 1.00 | 36.67 | A | N |
| ATOM | 1789 | NH2 | ARG | A | 440 | 27.557 | 82.609 | −9.564 | 1.00 | 46.47 | A | N |
| ATOM | 1790 | C | ARG | A | 440 | 27.832 | 82.027 | −2.558 | 1.00 | 43.16 | A | C |
| ATOM | 1791 | O | ARG | A | 440 | 28.902 | 82.626 | −2.563 | 1.00 | 45.45 | A | O |
| ATOM | 1792 | N | HIS | A | 441 | 26.789 | 82.414 | −1.831 | 1.00 | 47.75 | A | N |
| ATOM | 1793 | CA | HIS | A | 441 | 26.806 | 83.640 | −1.040 | 1.00 | 47.84 | A | C |
| ATOM | 1794 | CB | HIS | A | 441 | 25.402 | 83.969 | −0.535 | 1.00 | 44.88 | A | C |
| ATOM | 1795 | CG | HIS | A | 441 | 24.419 | 84.235 | −1.631 | 1.00 | 42.35 | A | C |
| ATOM | 1796 | CD2 | HIS | A | 441 | 23.066 | 84.160 | −1.648 | 1.00 | 43.42 | A | C |
| ATOM | 1797 | ND1 | HIS | A | 441 | 24.804 | 84.652 | −2.881 | 1.00 | 43.18 | A | N |
| ATOM | 1798 | CE1 | HIS | A | 441 | 23.726 | 84.811 | −3.640 | 1.00 | 48.88 | A | C |
| ATOM | 1799 | NE2 | HIS | A | 441 | 22.665 | 84.525 | −2.914 | 1.00 | 50.69 | A | N |
| ATOM | 1800 | C | HIS | A | 441 | 27.740 | 83.545 | 0.149 | 1.00 | 43.15 | A | C |
| ATOM | 1801 | O | HIS | A | 441 | 27.494 | 84.162 | 1.173 | 1.00 | 47.16 | A | O |
| ATOM | 1802 | N | LEU | A | 442 | 28.807 | 82.770 | 0.005 | 1.00 | 43.63 | A | N |
| ATOM | 1803 | CA | LEU | A | 442 | 29.724 | 82.515 | 1.098 | 1.00 | 42.86 | A | C |
| ATOM | 1804 | CB | LEU | A | 442 | 29.351 | 81.201 | 1.790 | 1.00 | 44.66 | A | C |
| ATOM | 1805 | CG | LEU | A | 442 | 29.809 | 80.979 | 3.235 | 1.00 | 47.04 | A | C |
| ATOM | 1806 | CD1 | LEU | A | 442 | 28.896 | 79.993 | 3.962 | 1.00 | 39.21 | A | C |
| ATOM | 1807 | CD2 | LEU | A | 442 | 31.249 | 80.512 | 3.280 | 1.00 | 51.09 | A | C |
| ATOM | 1808 | C | LEU | A | 442 | 31.133 | 82.438 | 0.542 | 1.00 | 49.04 | A | C |
| ATOM | 1809 | O | LEU | A | 442 | 32.074 | 82.938 | 1.152 | 1.00 | 56.86 | A | O |
| ATOM | 1810 | N | TYR | A | 443 | 31.260 | 81.809 | −0.625 | 1.00 | 49.44 | A | N |
| ATOM | 1811 | CA | TYR | A | 443 | 32.537 | 81.655 | −1.325 | 1.00 | 48.15 | A | C |
| ATOM | 1812 | CB | TYR | A | 443 | 32.930 | 80.172 | −1.425 | 1.00 | 43.21 | A | C |
| ATOM | 1813 | CG | TYR | A | 443 | 33.289 | 79.557 | −0.098 | 1.00 | 43.91 | A | C |
| ATOM | 1814 | CD1 | TYR | A | 443 | 32.441 | 78.656 | 0.523 | 1.00 | 46.34 | A | C |
| ATOM | 1815 | CE1 | TYR | A | 443 | 32.763 | 78.095 | 1.743 | 1.00 | 44.55 | A | C |
| ATOM | 1816 | CD2 | TYR | A | 443 | 34.471 | 79.890 | 0.542 | 1.00 | 45.27 | A | C |
| ATOM | 1817 | CE2 | TYR | A | 443 | 34.801 | 79.337 | 1.763 | 1.00 | 47.19 | A | C |
| ATOM | 1818 | CZ | TYR | A | 443 | 33.943 | 78.443 | 2.361 | 1.00 | 44.06 | A | C |
| ATOM | 1819 | OH | TYR | A | 443 | 34.266 | 77.895 | 3.582 | 1.00 | 39.32 | A | O |
| ATOM | 1820 | C | TYR | A | 443 | 32.462 | 82.263 | −2.724 | 1.00 | 47.20 | A | C |
| ATOM | 1821 | O | TYR | A | 443 | 31.551 | 81.952 | −3.497 | 1.00 | 43.08 | A | O |
| ATOM | 1822 | ZN | ZN | A | 500 | 22.173 | 70.201 | 9.953 | 1.00 | 41.19 | A | Zn |
| ATOM | 1823 | ZN | ZN | A | 501 | 30.204 | 64.830 | 18.023 | 1.00 | 47.86 | A | Zn |

TABLE 13-continued

Coordinates for proMMP9(35-444 ΔFnII) (SEQ ID NO: 12) complex with Example 3

| ATOM | 1824 | CA | CA | A | 502 | 20.082 | 59.015 | 16.980 | 1.00 | 50.81 | A | Ca |
|------|------|-----|-----|---|-----|--------|--------|--------|------|-------|---|-----|
| ATOM | 1825 | CA | CA | A | 504 | 39.043 | 69.999 | 12.033 | 1.00 | 67.22 | A | Ca |
| ATOM | 1826 | CB | ASP | B | 41 | 4.353 | 14.442 | 39.527 | 1.00 | 77.43 | B | C |
| ATOM | 1827 | CG | ASP | B | 41 | 3.555 | 14.867 | 38.310 | 1.00 | 77.58 | B | C |
| ATOM | 1828 | OD1 | ASP | B | 41 | 3.156 | 13.983 | 37.522 | 1.00 | 71.95 | B | O |
| ATOM | 1829 | OD2 | ASP | B | 41 | 3.343 | 16.086 | 38.135 | 1.00 | 69.04 | B | O |
| ATOM | 1830 | C | ASP | B | 41 | 5.421 | 16.608 | 40.239 | 1.00 | 68.23 | B | C |
| ATOM | 1831 | O | ASP | B | 41 | 5.803 | 17.606 | 39.631 | 1.00 | 68.27 | B | O |
| ATOM | 1832 | N | ASP | B | 41 | 6.629 | 14.446 | 40.443 | 1.00 | 62.78 | B | N |
| ATOM | 1833 | CA | ASP | B | 41 | 5.667 | 15.211 | 39.661 | 1.00 | 71.10 | B | C |
| ATOM | 1834 | N | ARG | B | 42 | 4.771 | 16.679 | 41.399 | 1.00 | 68.75 | B | N |
| ATOM | 1835 | CA | ARG | B | 42 | 4.596 | 17.954 | 42.097 | 1.00 | 68.25 | B | C |
| ATOM | 1836 | CB | ARG | B | 42 | 3.877 | 17.752 | 43.430 | 1.00 | 63.43 | B | C |
| ATOM | 1837 | CG | ARG | B | 42 | 3.790 | 19.016 | 44.288 | 1.00 | 67.79 | B | C |
| ATOM | 1838 | CD | ARG | B | 42 | 2.493 | 19.782 | 44.032 | 1.00 | 73.81 | B | C |
| ATOM | 1839 | NE | ARG | B | 42 | 2.448 | 21.075 | 44.718 | 1.00 | 72.77 | B | N |
| ATOM | 1840 | CZ | ARG | B | 42 | 1.338 | 21.792 | 44.890 | 1.00 | 68.09 | B | C |
| ATOM | 1841 | NH1 | ARG | B | 42 | 0.174 | 21.340 | 44.434 | 1.00 | 60.94 | B | N |
| ATOM | 1842 | NH2 | ARG | B | 42 | 1.390 | 22.959 | 45.521 | 1.00 | 53.99 | B | N |
| ATOM | 1843 | C | ARG | B | 42 | 5.965 | 18.560 | 42.368 | 1.00 | 71.79 | B | C |
| ATOM | 1844 | O | ARG | B | 42 | 6.167 | 19.774 | 42.263 | 1.00 | 61.68 | B | O |
| ATOM | 1845 | N | GLN | B | 43 | 6.900 | 17.690 | 42.734 | 1.00 | 70.14 | B | N |
| ATOM | 1846 | CA | GLN | B | 43 | 8.270 | 18.091 | 42.989 | 1.00 | 66.96 | B | C |
| ATOM | 1847 | CB | GLN | B | 43 | 9.109 | 16.868 | 43.356 | 1.00 | 68.64 | B | C |
| ATOM | 1848 | CG | GLN | B | 43 | 8.321 | 15.762 | 44.064 | 1.00 | 74.42 | B | C |
| ATOM | 1849 | CD | GLN | B | 43 | 7.705 | 14.759 | 43.098 | 1.00 | 73.04 | B | C |
| ATOM | 1850 | OE1 | GLN | B | 43 | 8.386 | 14.220 | 42.221 | 1.00 | 67.06 | B | O |
| ATOM | 1851 | NE2 | GLN | B | 43 | 6.413 | 14.493 | 43.269 | 1.00 | 65.67 | B | N |
| ATOM | 1852 | C | GLN | B | 43 | 8.808 | 18.728 | 41.721 | 1.00 | 68.43 | B | C |
| ATOM | 1853 | O | GLN | B | 43 | 9.313 | 19.856 | 41.734 | 1.00 | 63.99 | B | O |
| ATOM | 1854 | N | LEU | B | 44 | 8.679 | 17.997 | 40.620 | 1.00 | 62.80 | B | N |
| ATOM | 1855 | CA | LEU | B | 44 | 9.126 | 18.495 | 39.339 | 1.00 | 58.41 | B | C |
| ATOM | 1856 | CB | LEU | B | 44 | 8.786 | 17.510 | 38.220 | 1.00 | 59.98 | B | C |
| ATOM | 1857 | CG | LEU | B | 44 | 9.578 | 17.675 | 36.918 | 1.00 | 64.99 | B | C |
| ATOM | 1858 | CD1 | LEU | B | 44 | 9.738 | 16.341 | 36.184 | 1.00 | 59.70 | B | C |
| ATOM | 1859 | CD2 | LEU | B | 44 | 8.941 | 18.726 | 36.020 | 1.00 | 56.49 | B | C |
| ATOM | 1860 | C | LEU | B | 44 | 8.471 | 19.846 | 39.107 | 1.00 | 61.51 | B | C |
| ATOM | 1861 | O | LEU | B | 44 | 9.121 | 20.883 | 39.218 | 1.00 | 65.64 | B | O |
| ATOM | 1862 | N | ALA | B | 45 | 7.178 | 19.831 | 38.814 | 1.00 | 62.18 | B | N |
| ATOM | 1863 | CA | ALA | B | 45 | 6.447 | 21.060 | 38.565 | 1.00 | 60.13 | B | C |
| ATOM | 1864 | CB | ALA | B | 45 | 4.983 | 20.878 | 38.910 | 1.00 | 64.37 | B | C |
| ATOM | 1865 | C | ALA | B | 45 | 7.052 | 22.209 | 39.363 | 1.00 | 61.16 | B | C |
| ATOM | 1866 | O | ALA | B | 45 | 7.513 | 23.191 | 38.788 | 1.00 | 60.58 | B | O |
| ATOM | 1867 | N | GLU | B | 46 | 7.074 | 22.065 | 40.686 | 1.00 | 65.00 | B | N |
| ATOM | 1868 | CA | GLU | B | 46 | 7.570 | 23.112 | 41.580 | 1.00 | 61.96 | B | C |
| ATOM | 1869 | CB | GLU | B | 46 | 7.503 | 22.655 | 43.042 | 1.00 | 53.91 | B | C |
| ATOM | 1870 | CG | GLU | B | 46 | 6.146 | 22.859 | 43.699 | 1.00 | 59.21 | B | C |
| ATOM | 1871 | CD | GLU | B | 46 | 6.047 | 22.212 | 45.076 | 1.00 | 68.20 | B | C |
| ATOM | 1872 | OE1 | GLU | B | 46 | 6.660 | 21.144 | 45.290 | 1.00 | 66.18 | B | O |
| ATOM | 1873 | OE2 | GLU | B | 46 | 5.348 | 22.771 | 45.946 | 1.00 | 67.92 | B | O |
| ATOM | 1874 | C | GLU | B | 46 | 8.987 | 23.563 | 41.240 | 1.00 | 58.57 | B | C |
| ATOM | 1875 | O | GLU | B | 46 | 9.227 | 24.739 | 40.958 | 1.00 | 57.82 | B | O |
| ATOM | 1876 | N | GLU | B | 47 | 9.925 | 22.625 | 41.280 | 1.00 | 55.71 | B | N |
| ATOM | 1877 | CA | GLU | B | 47 | 11.328 | 22.941 | 41.057 | 1.00 | 58.64 | B | C |
| ATOM | 1878 | CB | GLU | B | 47 | 12.159 | 21.656 | 41.061 | 1.00 | 67.19 | B | C |
| ATOM | 1879 | CG | GLU | B | 47 | 13.631 | 21.863 | 41.360 | 1.00 | 70.42 | B | C |
| ATOM | 1880 | CD | GLU | B | 47 | 14.331 | 22.674 | 40.292 | 1.00 | 70.30 | B | C |
| ATOM | 1881 | OE1 | GLU | B | 47 | 14.058 | 22.436 | 39.095 | 1.00 | 71.02 | B | O |
| ATOM | 1882 | OE2 | GLU | B | 47 | 15.155 | 23.547 | 40.649 | 1.00 | 73.47 | B | O |
| ATOM | 1883 | C | GLU | B | 47 | 11.512 | 23.691 | 39.737 | 1.00 | 63.42 | B | C |
| ATOM | 1884 | O | GLU | B | 47 | 12.242 | 24.682 | 39.672 | 1.00 | 61.20 | B | O |
| ATOM | 1885 | N | TYR | B | 48 | 10.841 | 23.209 | 38.693 | 1.00 | 57.55 | B | N |
| ATOM | 1886 | CA | TYR | B | 48 | 10.898 | 23.827 | 37.374 | 1.00 | 60.26 | B | C |
| ATOM | 1887 | CB | TYR | B | 48 | 10.009 | 23.051 | 36.397 | 1.00 | 57.66 | B | C |
| ATOM | 1888 | CG | TYR | B | 48 | 10.236 | 23.366 | 34.934 | 1.00 | 57.89 | B | C |
| ATOM | 1889 | CD1 | TYR | B | 48 | 9.789 | 24.559 | 34.380 | 1.00 | 58.94 | B | C |
| ATOM | 1890 | CE1 | TYR | B | 48 | 9.994 | 24.848 | 33.031 | 1.00 | 59.51 | B | C |
| ATOM | 1891 | CD2 | TYR | B | 48 | 10.883 | 22.455 | 34.098 | 1.00 | 61.36 | B | C |
| ATOM | 1892 | CE2 | TYR | B | 48 | 11.090 | 22.731 | 32.746 | 1.00 | 55.33 | B | C |
| ATOM | 1893 | CZ | TYR | B | 48 | 10.642 | 23.931 | 32.220 | 1.00 | 57.84 | B | C |
| ATOM | 1894 | OH | TYR | B | 48 | 10.835 | 24.218 | 30.884 | 1.00 | 53.72 | B | O |
| ATOM | 1895 | C | TYR | B | 48 | 10.470 | 25.294 | 37.425 | 1.00 | 58.81 | B | C |
| ATOM | 1896 | O | TYR | B | 48 | 11.147 | 26.170 | 36.893 | 1.00 | 61.87 | B | O |
| ATOM | 1897 | N | LEU | B | 49 | 9.346 | 25.557 | 38.075 | 1.00 | 56.00 | B | N |
| ATOM | 1898 | CA | LEU | B | 49 | 8.805 | 26.900 | 38.135 | 1.00 | 54.19 | B | C |
| ATOM | 1899 | CB | LEU | B | 49 | 7.429 | 26.878 | 38.788 | 1.00 | 61.61 | B | C |
| ATOM | 1900 | CG | LEU | B | 49 | 6.417 | 25.970 | 38.096 | 1.00 | 62.24 | B | C |

TABLE 13-continued

Coordinates for proMMP9(35-444 ΔFnII) (SEQ ID NO: 12) complex with Example 3

| ATOM | 1901 | CD1 | LEU | B | 49 | 5.155 | 25.809 | 38.943 | 1.00 | 60.49 | B | C |
|------|------|-----|-----|---|----|-------|--------|--------|------|-------|---|---|
| ATOM | 1902 | CD2 | LEU | B | 49 | 6.095 | 26.522 | 36.720 | 1.00 | 60.19 | B | C |
| ATOM | 1903 | C | LEU | B | 49 | 9.725 | 27.833 | 38.906 | 1.00 | 57.61 | B | C |
| ATOM | 1904 | O | LEU | B | 49 | 9.804 | 29.025 | 38.613 | 1.00 | 59.27 | B | O |
| ATOM | 1905 | N | TYR | B | 50 | 10.421 | 27.307 | 39.902 | 1.00 | 52.94 | B | N |
| ATOM | 1906 | CA | TYR | B | 50 | 11.322 | 28.164 | 40.652 | 1.00 | 54.50 | B | C |
| ATOM | 1907 | CB | TYR | B | 50 | 11.625 | 27.603 | 42.047 | 1.00 | 51.82 | B | C |
| ATOM | 1908 | CG | TYR | B | 50 | 12.663 | 28.438 | 42.749 | 1.00 | 51.29 | B | C |
| ATOM | 1909 | CD1 | TYR | B | 50 | 12.301 | 29.582 | 43.439 | 1.00 | 55.78 | B | C |
| ATOM | 1910 | CE1 | TYR | B | 50 | 13.250 | 30.372 | 44.057 | 1.00 | 62.06 | B | C |
| ATOM | 1911 | CD2 | TYR | B | 50 | 14.015 | 28.120 | 42.666 | 1.00 | 53.44 | B | C |
| ATOM | 1912 | CE2 | TYR | B | 50 | 14.972 | 28.903 | 43.276 | 1.00 | 55.28 | B | C |
| ATOM | 1913 | CZ | TYR | B | 50 | 14.584 | 30.028 | 43.973 | 1.00 | 58.76 | B | C |
| ATOM | 1914 | OH | TYR | B | 50 | 15.527 | 30.817 | 44.595 | 1.00 | 60.81 | B | O |
| ATOM | 1915 | C | TYR | B | 50 | 12.623 | 28.428 | 39.884 | 1.00 | 56.14 | B | C |
| ATOM | 1916 | O | TYR | B | 50 | 13.121 | 29.554 | 39.848 | 1.00 | 55.56 | B | O |
| ATOM | 1917 | N | ARG | B | 51 | 13.167 | 27.383 | 39.270 | 1.00 | 58.15 | B | N |
| ATOM | 1918 | CA | ARG | B | 51 | 14.458 | 27.477 | 38.600 | 1.00 | 55.92 | B | C |
| ATOM | 1919 | CB | ARG | B | 51 | 14.850 | 26.126 | 38.009 | 1.00 | 56.07 | B | C |
| ATOM | 1920 | CG | ARG | B | 51 | 16.194 | 26.148 | 37.321 | 1.00 | 48.94 | B | C |
| ATOM | 1921 | CD | ARG | B | 51 | 16.380 | 24.960 | 36.395 | 1.00 | 51.62 | B | C |
| ATOM | 1922 | NE | ARG | B | 51 | 16.550 | 23.693 | 37.094 | 1.00 | 50.21 | B | N |
| ATOM | 1923 | CZ | ARG | B | 51 | 17.631 | 23.368 | 37.792 | 1.00 | 54.62 | B | C |
| ATOM | 1924 | NH1 | ARG | B | 51 | 18.630 | 24.230 | 37.908 | 1.00 | 47.29 | B | N |
| ATOM | 1925 | NH2 | ARG | B | 51 | 17.707 | 22.187 | 38.388 | 1.00 | 63.33 | B | N |
| ATOM | 1926 | C | ARG | B | 51 | 14.470 | 28.519 | 37.495 | 1.00 | 54.18 | B | C |
| ATOM | 1927 | O | ARG | B | 51 | 15.403 | 29.315 | 37.384 | 1.00 | 50.10 | B | O |
| ATOM | 1928 | N | TYR | B | 52 | 13.432 | 28.507 | 36.672 | 1.00 | 53.51 | B | N |
| ATOM | 1929 | CA | TYR | B | 52 | 13.431 | 29.336 | 35.477 | 1.00 | 49.85 | B | C |
| ATOM | 1930 | CB | TYR | B | 52 | 12.780 | 28.584 | 34.310 | 1.00 | 44.56 | B | C |
| ATOM | 1931 | CG | TYR | B | 52 | 13.525 | 27.295 | 34.025 | 1.00 | 43.22 | B | C |
| ATOM | 1932 | CD1 | TYR | B | 52 | 12.927 | 26.060 | 34.199 | 1.00 | 44.80 | B | C |
| ATOM | 1933 | CE1 | TYR | B | 52 | 13.629 | 24.894 | 33.962 | 1.00 | 48.47 | B | C |
| ATOM | 1934 | CD2 | TYR | B | 52 | 14.858 | 27.326 | 33.631 | 1.00 | 42.01 | B | C |
| ATOM | 1935 | CE2 | TYR | B | 52 | 15.562 | 26.179 | 33.391 | 1.00 | 37.31 | B | C |
| ATOM | 1936 | CZ | TYR | B | 52 | 14.953 | 24.964 | 33.555 | 1.00 | 48.17 | B | C |
| ATOM | 1937 | OH | TYR | B | 52 | 15.680 | 23.819 | 33.312 | 1.00 | 49.11 | B | O |
| ATOM | 1938 | C | TYR | B | 52 | 12.817 | 30.699 | 35.744 | 1.00 | 49.91 | B | C |
| ATOM | 1939 | O | TYR | B | 52 | 12.577 | 31.476 | 34.823 | 1.00 | 52.36 | B | O |
| ATOM | 1940 | N | GLY | B | 53 | 12.580 | 30.976 | 37.024 | 1.00 | 53.69 | B | N |
| ATOM | 1941 | CA | GLY | B | 53 | 12.175 | 32.295 | 37.484 | 1.00 | 58.02 | B | C |
| ATOM | 1942 | C | GLY | B | 53 | 10.683 | 32.558 | 37.592 | 1.00 | 61.60 | B | C |
| ATOM | 1943 | O | GLY | B | 53 | 10.271 | 33.694 | 37.815 | 1.00 | 65.26 | B | O |
| ATOM | 1944 | N | TYR | B | 54 | 9.869 | 31.521 | 37.443 | 1.00 | 55.74 | B | N |
| ATOM | 1945 | CA | TYR | B | 54 | 8.420 | 31.703 | 37.411 | 1.00 | 60.33 | B | C |
| ATOM | 1946 | CB | TYR | B | 54 | 7.731 | 30.462 | 36.841 | 1.00 | 60.45 | B | C |
| ATOM | 1947 | CG | TYR | B | 54 | 7.995 | 30.296 | 35.369 | 1.00 | 60.36 | B | C |
| ATOM | 1948 | CD1 | TYR | B | 54 | 8.746 | 29.231 | 34.892 | 1.00 | 61.28 | B | C |
| ATOM | 1949 | CE1 | TYR | B | 54 | 9.001 | 29.088 | 33.539 | 1.00 | 59.44 | B | C |
| ATOM | 1950 | CD2 | TYR | B | 54 | 7.522 | 31.228 | 34.457 | 1.00 | 58.87 | B | C |
| ATOM | 1951 | CE2 | TYR | B | 54 | 7.773 | 31.094 | 33.106 | 1.00 | 59.34 | B | C |
| ATOM | 1952 | CZ | TYR | B | 54 | 8.513 | 30.023 | 32.653 | 1.00 | 55.15 | B | C |
| ATOM | 1953 | OH | TYR | B | 54 | 8.765 | 29.892 | 31.309 | 1.00 | 58.06 | B | O |
| ATOM | 1954 | C | TYR | B | 54 | 7.809 | 32.073 | 38.759 | 1.00 | 63.37 | B | C |
| ATOM | 1955 | O | TYR | B | 54 | 7.066 | 33.047 | 38.862 | 1.00 | 65.68 | B | O |
| ATOM | 1956 | N | THR | B | 55 | 8.113 | 31.289 | 39.785 | 1.00 | 62.80 | B | N |
| ATOM | 1957 | CA | THR | B | 55 | 7.536 | 31.513 | 41.105 | 1.00 | 63.55 | B | C |
| ATOM | 1958 | CB | THR | B | 55 | 8.090 | 30.510 | 42.143 | 1.00 | 61.62 | B | C |
| ATOM | 1959 | OG1 | THR | B | 55 | 9.521 | 30.565 | 42.142 | 1.00 | 70.91 | B | O |
| ATOM | 1960 | CG2 | THR | B | 55 | 7.657 | 29.091 | 41.809 | 1.00 | 57.64 | B | C |
| ATOM | 1961 | C | THR | B | 55 | 7.781 | 32.943 | 41.595 | 1.00 | 69.37 | B | C |
| ATOM | 1962 | O | THR | B | 55 | 6.851 | 33.646 | 41.998 | 1.00 | 70.84 | B | O |
| ATOM | 1963 | N | ARG | B | 56 | 9.036 | 33.375 | 41.545 | 1.00 | 66.80 | B | N |
| ATOM | 1964 | CA | ARG | B | 56 | 9.431 | 34.656 | 42.120 | 1.00 | 64.68 | B | C |
| ATOM | 1965 | CB | ARG | B | 56 | 10.957 | 34.752 | 42.177 | 1.00 | 74.06 | B | C |
| ATOM | 1966 | CG | ARG | B | 56 | 11.501 | 36.077 | 42.685 | 1.00 | 84.37 | B | C |
| ATOM | 1967 | CD | ARG | B | 56 | 12.951 | 35.934 | 43.122 | 1.00 | 85.54 | B | C |
| ATOM | 1968 | NE | ARG | B | 56 | 13.703 | 37.172 | 42.943 | 1.00 | 87.12 | B | N |
| ATOM | 1969 | CZ | ARG | B | 56 | 15.001 | 37.296 | 43.202 | 1.00 | 86.97 | B | C |
| ATOM | 1970 | NH1 | ARG | B | 56 | 15.687 | 36.255 | 43.659 | 1.00 | 81.08 | B | N |
| ATOM | 1971 | NH2 | ARG | B | 56 | 15.612 | 38.459 | 43.006 | 1.00 | 81.03 | B | N |
| ATOM | 1972 | C | ARG | B | 56 | 8.834 | 35.860 | 41.389 | 1.00 | 64.25 | B | C |
| ATOM | 1973 | O | ARG | B | 56 | 8.856 | 36.978 | 41.898 | 1.00 | 66.74 | B | O |
| ATOM | 1974 | N | VAL | B | 57 | 8.298 | 35.632 | 40.197 | 1.00 | 65.37 | B | N |
| ATOM | 1975 | CA | VAL | B | 57 | 7.650 | 36.699 | 39.445 | 1.00 | 60.53 | B | C |
| ATOM | 1976 | CB | VAL | B | 57 | 7.718 | 36.430 | 37.933 | 1.00 | 59.91 | B | C |
| ATOM | 1977 | CG1 | VAL | B | 57 | 6.939 | 37.474 | 37.159 | 1.00 | 60.10 | B | C |

TABLE 13-continued

Coordinates for proMMP9(35-444 ΔFnII) (SEQ ID NO: 12) complex with Example 3

| ATOM | 1978 | CG2 | VAL | B | 57 | 9.161 | 36.412 | 37.480 | 1.00 | 62.14 | B | C |
|---|---|---|---|---|---|---|---|---|---|---|---|---|
| ATOM | 1979 | C | VAL | B | 57 | 6.197 | 36.859 | 39.901 | 1.00 | 70.86 | B | C |
| ATOM | 1980 | O | VAL | B | 57 | 5.637 | 37.961 | 39.877 | 1.00 | 65.59 | B | O |
| ATOM | 1981 | N | ALA | B | 58 | 5.601 | 35.751 | 40.334 | 1.00 | 70.38 | B | N |
| ATOM | 1982 | CA | ALA | B | 58 | 4.243 | 35.761 | 40.863 | 1.00 | 66.51 | B | C |
| ATOM | 1983 | CB | ALA | B | 58 | 3.443 | 34.599 | 40.290 | 1.00 | 66.23 | B | C |
| ATOM | 1984 | C | ALA | B | 58 | 4.244 | 35.709 | 42.390 | 1.00 | 63.44 | B | C |
| ATOM | 1985 | O | ALA | B | 58 | 5.012 | 36.411 | 43.050 | 1.00 | 64.10 | B | O |
| ATOM | 1986 | N | GLY | B | 68 | −0.478 | 27.631 | 40.155 | 1.00 | 63.44 | B | N |
| ATOM | 1987 | CA | GLY | B | 68 | −1.756 | 28.210 | 39.773 | 1.00 | 62.59 | B | C |
| ATOM | 1988 | C | GLY | B | 68 | −1.601 | 29.438 | 38.898 | 1.00 | 68.63 | B | C |
| ATOM | 1989 | O | GLY | B | 68 | −1.904 | 29.392 | 37.704 | 1.00 | 70.46 | B | O |
| ATOM | 1990 | N | PRO | B | 69 | −1.140 | 30.554 | 39.491 | 1.00 | 69.84 | B | N |
| ATOM | 1991 | CD | PRO | B | 69 | −1.008 | 30.783 | 40.938 | 1.00 | 69.42 | B | C |
| ATOM | 1992 | CA | PRO | B | 69 | −0.793 | 31.750 | 38.719 | 1.00 | 69.14 | B | C |
| ATOM | 1993 | CB | PRO | B | 69 | −0.533 | 32.811 | 39.800 | 1.00 | 62.23 | B | C |
| ATOM | 1994 | CG | PRO | B | 69 | −1.140 | 32.268 | 41.045 | 1.00 | 63.43 | B | C |
| ATOM | 1995 | C | PRO | B | 69 | 0.481 | 31.499 | 37.918 | 1.00 | 63.39 | B | C |
| ATOM | 1996 | O | PRO | B | 69 | 0.449 | 31.537 | 36.690 | 1.00 | 58.81 | B | O |
| ATOM | 1997 | N | ALA | B | 70 | 1.576 | 31.230 | 38.626 | 1.00 | 62.91 | B | N |
| ATOM | 1998 | CA | ALA | B | 70 | 2.873 | 30.931 | 38.022 | 1.00 | 58.68 | B | C |
| ATOM | 1999 | CB | ALA | B | 70 | 3.832 | 30.383 | 39.077 | 1.00 | 51.53 | B | C |
| ATOM | 2000 | C | ALA | B | 70 | 2.798 | 29.970 | 36.834 | 1.00 | 58.45 | B | C |
| ATOM | 2001 | O | ALA | B | 70 | 3.622 | 30.044 | 35.924 | 1.00 | 54.87 | B | O |
| ATOM | 2002 | N | LEU | B | 71 | 1.820 | 29.068 | 36.845 | 1.00 | 60.52 | B | N |
| ATOM | 2003 | CA | LEU | B | 71 | 1.701 | 28.070 | 35.783 | 1.00 | 59.07 | B | C |
| ATOM | 2004 | CB | LEU | B | 71 | 0.834 | 26.900 | 36.235 | 1.00 | 60.35 | B | C |
| ATOM | 2005 | CG | LEU | B | 71 | 1.654 | 25.740 | 36.788 | 1.00 | 67.52 | B | C |
| ATOM | 2006 | CD1 | LEU | B | 71 | 0.773 | 24.747 | 37.541 | 1.00 | 63.12 | B | C |
| ATOM | 2007 | CD2 | LEU | B | 71 | 2.439 | 25.057 | 35.670 | 1.00 | 56.79 | B | C |
| ATOM | 2008 | C | LEU | B | 71 | 1.176 | 28.631 | 34.466 | 1.00 | 62.30 | B | C |
| ATOM | 2009 | O | LEU | B | 71 | 1.462 | 28.094 | 33.397 | 1.00 | 58.91 | B | O |
| ATOM | 2010 | N | LEU | B | 72 | 0.396 | 29.702 | 34.541 | 1.00 | 65.72 | B | N |
| ATOM | 2011 | CA | LEU | B | 72 | −0.087 | 30.341 | 33.331 | 1.00 | 61.97 | B | C |
| ATOM | 2012 | CB | LEU | B | 72 | −1.323 | 31.192 | 33.622 | 1.00 | 57.06 | B | C |
| ATOM | 2013 | CG | LEU | B | 72 | −2.488 | 30.872 | 32.689 | 1.00 | 58.07 | B | C |
| ATOM | 2014 | CD1 | LEU | B | 72 | −3.810 | 31.205 | 33.337 | 1.00 | 64.14 | B | C |
| ATOM | 2015 | CD2 | LEU | B | 72 | −2.426 | 29.408 | 32.343 | 1.00 | 62.65 | B | C |
| ATOM | 2016 | C | LEU | B | 72 | 1.051 | 31.175 | 32.771 | 1.00 | 58.95 | B | C |
| ATOM | 2017 | O | LEU | B | 72 | 1.229 | 31.276 | 31.556 | 1.00 | 63.17 | B | O |
| ATOM | 2018 | N | LEU | B | 73 | 1.839 | 31.744 | 33.675 | 1.00 | 51.63 | B | N |
| ATOM | 2019 | CA | LEU | B | 73 | 3.030 | 32.469 | 33.293 | 1.00 | 52.68 | B | C |
| ATOM | 2020 | CB | LEU | B | 73 | 3.800 | 32.887 | 34.538 | 1.00 | 52.13 | B | C |
| ATOM | 2021 | CG | LEU | B | 73 | 3.214 | 34.073 | 35.289 | 1.00 | 57.76 | B | C |
| ATOM | 2022 | CD1 | LEU | B | 73 | 4.083 | 34.435 | 36.485 | 1.00 | 56.21 | B | C |
| ATOM | 2023 | CD2 | LEU | B | 73 | 3.065 | 35.251 | 34.341 | 1.00 | 54.00 | B | C |
| ATOM | 2024 | C | LEU | B | 73 | 3.903 | 31.578 | 32.421 | 1.00 | 55.69 | B | C |
| ATOM | 2025 | O | LEU | B | 73 | 4.357 | 31.979 | 31.349 | 1.00 | 53.22 | B | O |
| ATOM | 2026 | N | LEU | B | 74 | 4.129 | 30.359 | 32.895 | 1.00 | 56.01 | B | N |
| ATOM | 2027 | CA | LEU | B | 74 | 4.998 | 29.419 | 32.209 | 1.00 | 56.68 | B | C |
| ATOM | 2028 | CB | LEU | B | 74 | 5.294 | 28.207 | 33.091 | 1.00 | 52.74 | B | C |
| ATOM | 2029 | CG | LEU | B | 74 | 5.912 | 27.025 | 32.347 | 1.00 | 52.55 | B | C |
| ATOM | 2030 | CD1 | LEU | B | 74 | 6.913 | 26.293 | 33.215 | 1.00 | 58.39 | B | C |
| ATOM | 2031 | CD2 | LEU | B | 74 | 4.832 | 26.084 | 31.855 | 1.00 | 53.12 | B | C |
| ATOM | 2032 | C | LEU | B | 74 | 4.408 | 28.967 | 30.890 | 1.00 | 55.52 | B | C |
| ATOM | 2033 | O | LEU | B | 74 | 5.138 | 28.647 | 29.959 | 1.00 | 58.29 | B | O |
| ATOM | 2034 | N | GLN | B | 75 | 3.084 | 28.935 | 30.816 | 1.00 | 58.82 | B | N |
| ATOM | 2035 | CA | GLN | B | 75 | 2.409 | 28.488 | 29.608 | 1.00 | 60.75 | B | C |
| ATOM | 2036 | CB | GLN | B | 75 | 1.036 | 27.911 | 29.953 | 1.00 | 64.75 | B | C |
| ATOM | 2037 | CG | GLN | B | 75 | 1.094 | 26.628 | 30.780 | 1.00 | 59.69 | B | C |
| ATOM | 2038 | CD | GLN | B | 75 | −0.278 | 26.166 | 31.244 | 1.00 | 65.31 | B | C |
| ATOM | 2039 | OE1 | GLN | B | 75 | −1.069 | 26.956 | 31.768 | 1.00 | 60.62 | B | O |
| ATOM | 2040 | NE2 | GLN | B | 75 | −0.567 | 24.881 | 31.054 | 1.00 | 63.22 | B | N |
| ATOM | 2041 | C | GLN | B | 75 | 2.295 | 29.634 | 28.606 | 1.00 | 62.51 | B | C |
| ATOM | 2042 | O | GLN | B | 75 | 2.010 | 29.420 | 27.428 | 1.00 | 62.06 | B | O |
| ATOM | 2043 | N | LYS | B | 76 | 2.520 | 30.853 | 29.087 | 1.00 | 58.37 | B | N |
| ATOM | 2044 | CA | LYS | B | 76 | 2.634 | 32.010 | 28.213 | 1.00 | 60.04 | B | C |
| ATOM | 2045 | CB | LYS | B | 76 | 2.409 | 33.314 | 28.989 | 1.00 | 62.09 | B | C |
| ATOM | 2046 | CG | LYS | B | 76 | 0.952 | 33.643 | 29.276 | 1.00 | 60.25 | B | C |
| ATOM | 2047 | CD | LYS | B | 76 | 0.776 | 35.119 | 29.624 | 1.00 | 71.62 | B | C |
| ATOM | 2048 | CE | LYS | B | 76 | −0.702 | 35.504 | 29.793 | 1.00 | 69.25 | B | C |
| ATOM | 2049 | NZ | LYS | B | 76 | −1.297 | 34.977 | 31.054 | 1.00 | 59.05 | B | N |
| ATOM | 2050 | C | LYS | B | 76 | 4.016 | 32.020 | 27.560 | 1.00 | 60.31 | B | C |
| ATOM | 2051 | O | LYS | B | 76 | 4.131 | 32.040 | 26.334 | 1.00 | 56.69 | B | O |
| ATOM | 2052 | N | GLN | B | 77 | 5.058 | 32.002 | 28.391 | 1.00 | 58.08 | B | N |
| ATOM | 2053 | CA | GLN | B | 77 | 6.439 | 31.968 | 27.914 | 1.00 | 54.06 | B | C |
| ATOM | 2054 | CB | GLN | B | 77 | 7.419 | 31.724 | 29.069 | 1.00 | 59.51 | B | C |

TABLE 13-continued

Coordinates for proMMP9(35-444 ΔFnII) (SEQ ID NO: 12) complex with Example 3

| ATOM | 2055 | CG  | GLN | B | 77 | 7.915  | 32.974 | 29.772 | 1.00 | 63.26 | B | C |
|------|------|-----|-----|---|----|--------|--------|--------|------|-------|---|---|
| ATOM | 2056 | CD  | GLN | B | 77 | 8.706  | 33.893 | 28.859 | 1.00 | 63.95 | B | C |
| ATOM | 2057 | OE1 | GLN | B | 77 | 8.493  | 35.106 | 28.849 | 1.00 | 67.19 | B | O |
| ATOM | 2058 | NE2 | GLN | B | 77 | 9.623  | 33.319 | 28.084 | 1.00 | 60.61 | B | N |
| ATOM | 2059 | C   | GLN | B | 77 | 6.653  | 30.890 | 26.865 | 1.00 | 53.18 | B | C |
| ATOM | 2060 | O   | GLN | B | 77 | 7.160  | 31.166 | 25.789 | 1.00 | 56.68 | B | O |
| ATOM | 2061 | N   | LEU | B | 78 | 6.277  | 29.657 | 27.186 | 1.00 | 52.31 | B | N |
| ATOM | 2062 | CA  | LEU | B | 78 | 6.558  | 28.529 | 26.308 | 1.00 | 53.52 | B | C |
| ATOM | 2063 | CB  | LEU | B | 78 | 6.668  | 27.235 | 27.115 | 1.00 | 56.76 | B | C |
| ATOM | 2064 | CG  | LEU | B | 78 | 7.468  | 27.277 | 28.418 | 1.00 | 55.60 | B | C |
| ATOM | 2065 | CD1 | LEU | B | 78 | 7.738  | 25.865 | 28.916 | 1.00 | 53.16 | B | C |
| ATOM | 2066 | CD2 | LEU | B | 78 | 8.771  | 28.036 | 28.237 | 1.00 | 49.17 | B | C |
| ATOM | 2067 | C   | LEU | B | 78 | 5.503  | 28.361 | 25.223 | 1.00 | 53.79 | B | C |
| ATOM | 2068 | O   | LEU | B | 78 | 5.584  | 27.435 | 24.420 | 1.00 | 50.25 | B | O |
| ATOM | 2069 | N   | SER | B | 79 | 4.517  | 29.256 | 25.204 | 1.00 | 58.17 | B | N |
| ATOM | 2070 | CA  | SER | B | 79 | 3.403  | 29.156 | 24.262 | 1.00 | 54.14 | B | C |
| ATOM | 2071 | CB  | SER | B | 79 | 3.870  | 29.384 | 22.824 | 1.00 | 49.92 | B | C |
| ATOM | 2072 | OG  | SER | B | 79 | 3.766  | 30.752 | 22.486 | 1.00 | 48.45 | B | O |
| ATOM | 2073 | C   | SER | B | 79 | 2.707  | 27.811 | 24.385 | 1.00 | 53.97 | B | C |
| ATOM | 2074 | O   | SER | B | 79 | 2.625  | 27.041 | 23.421 | 1.00 | 50.65 | B | O |
| ATOM | 2075 | N   | LEU | B | 80 | 2.216  | 27.539 | 25.591 | 1.00 | 60.28 | B | N |
| ATOM | 2076 | CA  | LEU | B | 80 | 1.456  | 26.330 | 25.880 | 1.00 | 62.42 | B | C |
| ATOM | 2077 | CB  | LEU | B | 80 | 2.010  | 25.649 | 27.131 | 1.00 | 58.16 | B | C |
| ATOM | 2078 | CG  | LEU | B | 80 | 3.369  | 24.973 | 27.010 | 1.00 | 55.91 | B | C |
| ATOM | 2079 | CD1 | LEU | B | 80 | 3.724  | 24.297 | 28.322 | 1.00 | 57.99 | B | C |
| ATOM | 2080 | CD2 | LEU | B | 80 | 3.352  | 23.967 | 25.873 | 1.00 | 60.66 | B | C |
| ATOM | 2081 | C   | LEU | B | 80 | −0.006 | 26.687 | 26.114 | 1.00 | 57.37 | B | C |
| ATOM | 2082 | O   | LEU | B | 80 | −0.303 | 27.796 | 26.557 | 1.00 | 60.13 | B | O |
| ATOM | 2083 | N   | PRO | B | 81 | −0.922 | 25.750 | 25.814 | 1.00 | 61.97 | B | N |
| ATOM | 2084 | CD  | PRO | B | 81 | −0.686 | 24.474 | 25.111 | 1.00 | 61.25 | B | C |
| ATOM | 2085 | CA  | PRO | B | 81 | −2.330 | 25.909 | 26.189 | 1.00 | 60.47 | B | C |
| ATOM | 2086 | CB  | PRO | B | 81 | −2.847 | 24.472 | 26.167 | 1.00 | 57.27 | B | C |
| ATOM | 2087 | CG  | PRO | B | 81 | −2.064 | 23.831 | 25.078 | 1.00 | 48.71 | B | C |
| ATOM | 2088 | C   | PRO | B | 81 | −2.434 | 26.484 | 27.594 | 1.00 | 62.47 | B | C |
| ATOM | 2089 | O   | PRO | B | 81 | −2.095 | 25.797 | 28.562 | 1.00 | 61.09 | B | O |
| ATOM | 2090 | N   | GLU | B | 82 | −2.890 | 27.732 | 27.688 | 1.00 | 59.56 | B | N |
| ATOM | 2091 | CA  | GLU | B | 82 | −2.887 | 28.479 | 28.942 | 1.00 | 58.94 | B | C |
| ATOM | 2092 | CB  | GLU | B | 82 | −3.020 | 29.981 | 28.662 | 1.00 | 60.91 | B | C |
| ATOM | 2093 | CG  | GLU | B | 82 | −2.035 | 30.517 | 27.637 | 1.00 | 64.84 | B | C |
| ATOM | 2094 | CD  | GLU | B | 82 | −1.922 | 32.032 | 27.667 | 1.00 | 72.77 | B | C |
| ATOM | 2095 | OE1 | GLU | B | 82 | −2.023 | 32.608 | 28.773 | 1.00 | 70.95 | B | O |
| ATOM | 2096 | OE2 | GLU | B | 82 | −1.721 | 32.643 | 26.590 | 1.00 | 66.58 | B | O |
| ATOM | 2097 | C   | GLU | B | 82 | −3.989 | 28.019 | 29.901 | 1.00 | 62.99 | B | C |
| ATOM | 2098 | O   | GLU | B | 82 | −4.970 | 28.730 | 30.128 | 1.00 | 54.76 | B | O |
| ATOM | 2099 | N   | THR | B | 83 | −3.814 | 26.831 | 30.470 | 1.00 | 64.82 | B | N |
| ATOM | 2100 | CA  | THR | B | 83 | −4.801 | 26.272 | 31.383 | 1.00 | 63.98 | B | C |
| ATOM | 2101 | CB  | THR | B | 83 | −4.758 | 24.737 | 31.388 | 1.00 | 57.18 | B | C |
| ATOM | 2102 | OG1 | THR | B | 83 | −3.444 | 24.298 | 31.739 | 1.00 | 60.21 | B | O |
| ATOM | 2103 | CG2 | THR | B | 83 | −5.110 | 24.195 | 30.022 | 1.00 | 52.46 | B | C |
| ATOM | 2104 | C   | THR | B | 83 | −4.642 | 26.799 | 32.813 | 1.00 | 62.61 | B | C |
| ATOM | 2105 | O   | THR | B | 83 | −5.580 | 27.350 | 33.378 | 1.00 | 71.68 | B | O |
| ATOM | 2106 | N   | GLY | B | 84 | −3.454 | 26.641 | 33.386 | 1.00 | 62.09 | B | N |
| ATOM | 2107 | CA  | GLY | B | 84 | −3.214 | 26.994 | 34.778 | 1.00 | 60.11 | B | C |
| ATOM | 2108 | C   | GLY | B | 84 | −3.079 | 25.715 | 35.581 | 1.00 | 63.64 | B | C |
| ATOM | 2109 | O   | GLY | B | 84 | −2.949 | 25.725 | 36.804 | 1.00 | 60.72 | B | O |
| ATOM | 2110 | N   | GLU | B | 85 | −3.096 | 24.604 | 34.855 | 1.00 | 67.12 | B | N |
| ATOM | 2111 | CA  | GLU | B | 85 | −3.132 | 23.270 | 35.428 | 1.00 | 64.23 | B | C |
| ATOM | 2112 | CB  | GLU | B | 85 | −4.035 | 22.398 | 34.561 | 1.00 | 70.24 | B | C |
| ATOM | 2113 | CG  | GLU | B | 85 | −5.422 | 22.978 | 34.354 | 1.00 | 68.25 | B | C |
| ATOM | 2114 | CD  | GLU | B | 85 | −6.416 | 22.450 | 35.365 | 1.00 | 71.42 | B | C |
| ATOM | 2115 | OE1 | GLU | B | 85 | −6.710 | 21.237 | 35.302 | 1.00 | 61.20 | B | O |
| ATOM | 2116 | OE2 | GLU | B | 85 | −6.896 | 23.239 | 36.214 | 1.00 | 63.85 | B | O |
| ATOM | 2117 | C   | GLU | B | 85 | −1.747 | 22.635 | 35.509 | 1.00 | 67.75 | B | C |
| ATOM | 2118 | O   | GLU | B | 85 | −0.748 | 23.313 | 35.714 | 1.00 | 73.21 | B | O |
| ATOM | 2119 | N   | LEU | B | 86 | −1.698 | 21.321 | 35.341 | 1.00 | 67.78 | B | N |
| ATOM | 2120 | CA  | LEU | B | 86 | −0.445 | 20.580 | 35.385 | 1.00 | 71.96 | B | C |
| ATOM | 2121 | CB  | LEU | B | 86 | −0.131 | 20.158 | 36.820 | 1.00 | 72.41 | B | C |
| ATOM | 2122 | CG  | LEU | B | 86 | 1.294  | 19.762 | 37.207 | 1.00 | 66.28 | B | C |
| ATOM | 2123 | CD1 | LEU | B | 86 | 2.309  | 20.531 | 36.383 | 1.00 | 68.71 | B | C |
| ATOM | 2124 | CD2 | LEU | B | 86 | 1.495  | 18.272 | 37.056 | 1.00 | 72.56 | B | C |
| ATOM | 2125 | C   | LEU | B | 86 | −0.640 | 19.379 | 34.477 | 1.00 | 71.46 | B | C |
| ATOM | 2126 | O   | LEU | B | 86 | −0.585 | 18.227 | 34.908 | 1.00 | 74.91 | B | O |
| ATOM | 2127 | N   | ASP | B | 87 | −0.860 | 19.684 | 33.204 | 1.00 | 70.75 | B | N |
| ATOM | 2128 | CA  | ASP | B | 87 | −1.421 | 18.751 | 32.237 | 1.00 | 68.01 | B | C |
| ATOM | 2129 | CB  | ASP | B | 87 | −2.387 | 19.523 | 31.344 | 1.00 | 72.56 | B | C |
| ATOM | 2130 | CG  | ASP | B | 87 | −2.110 | 21.018 | 31.358 | 1.00 | 70.64 | B | C |
| ATOM | 2131 | OD1 | ASP | B | 87 | −1.054 | 21.436 | 30.836 | 1.00 | 73.81 | B | O |

TABLE 13-continued

Coordinates for proMMP9(35-444 ΔFnII) (SEQ ID NO: 12) complex with Example 3

| ATOM | 2132 | OD2 | ASP | B | 87 | −2.940 | 21.774 | 31.902 | 1.00 | 65.94 | B | O |
|---|---|---|---|---|---|---|---|---|---|---|---|---|
| ATOM | 2133 | C | ASP | B | 87 | −0.397 | 18.013 | 31.378 | 1.00 | 71.38 | B | C |
| ATOM | 2134 | O | ASP | B | 87 | 0.804 | 18.265 | 31.460 | 1.00 | 73.55 | B | O |
| ATOM | 2135 | N | SER | B | 88 | −0.895 | 17.101 | 30.547 | 1.00 | 71.40 | B | N |
| ATOM | 2136 | CA | SER | B | 88 | −0.058 | 16.322 | 29.638 | 1.00 | 76.17 | B | C |
| ATOM | 2137 | CB | SER | B | 88 | −0.914 | 15.285 | 28.901 | 1.00 | 81.14 | B | C |
| ATOM | 2138 | OG | SER | B | 88 | −0.200 | 14.680 | 27.836 | 1.00 | 97.89 | B | O |
| ATOM | 2139 | C | SER | B | 88 | 0.682 | 17.211 | 28.634 | 1.00 | 76.49 | B | C |
| ATOM | 2140 | O | SER | B | 88 | 1.407 | 16.724 | 27.756 | 1.00 | 71.22 | B | O |
| ATOM | 2141 | N | ALA | B | 89 | 0.483 | 18.518 | 28.763 | 1.00 | 73.00 | B | N |
| ATOM | 2142 | CA | ALA | B | 89 | 1.181 | 19.488 | 27.937 | 1.00 | 67.00 | B | C |
| ATOM | 2143 | CB | ALA | B | 89 | 0.220 | 20.561 | 27.450 | 1.00 | 66.96 | B | C |
| ATOM | 2144 | C | ALA | B | 89 | 2.306 | 20.106 | 28.757 | 1.00 | 65.13 | B | C |
| ATOM | 2145 | O | ALA | B | 89 | 3.464 | 20.100 | 28.343 | 1.00 | 70.19 | B | O |
| ATOM | 2146 | N | THR | B | 90 | 1.958 | 20.624 | 29.928 | 1.00 | 62.06 | B | N |
| ATOM | 2147 | CA | THR | B | 90 | 2.939 | 21.232 | 30.813 | 1.00 | 61.02 | B | C |
| ATOM | 2148 | CB | THR | B | 90 | 2.265 | 22.093 | 31.904 | 1.00 | 60.52 | B | C |
| ATOM | 2149 | OG1 | THR | B | 90 | 1.360 | 23.020 | 31.295 | 1.00 | 54.25 | B | O |
| ATOM | 2150 | CG2 | THR | B | 90 | 3.301 | 22.870 | 32.691 | 1.00 | 58.17 | B | C |
| ATOM | 2151 | C | THR | B | 90 | 3.824 | 20.168 | 31.461 | 1.00 | 65.81 | B | C |
| ATOM | 2152 | O | THR | B | 90 | 4.880 | 20.478 | 32.010 | 1.00 | 65.96 | B | O |
| ATOM | 2153 | N | LEU | B | 91 | 3.397 | 18.910 | 31.392 | 1.00 | 67.51 | B | N |
| ATOM | 2154 | CA | LEU | B | 91 | 4.199 | 17.810 | 31.924 | 1.00 | 68.60 | B | C |
| ATOM | 2155 | CB | LEU | B | 91 | 3.320 | 16.618 | 32.297 | 1.00 | 72.84 | B | C |
| ATOM | 2156 | CG | LEU | B | 91 | 2.967 | 16.597 | 33.781 | 1.00 | 70.90 | B | C |
| ATOM | 2157 | CD1 | LEU | B | 91 | 2.895 | 18.017 | 34.272 | 1.00 | 67.17 | B | C |
| ATOM | 2158 | CD2 | LEU | B | 91 | 1.663 | 15.854 | 34.042 | 1.00 | 74.75 | B | C |
| ATOM | 2159 | C | LEU | B | 91 | 5.283 | 17.391 | 30.944 | 1.00 | 64.01 | B | C |
| ATOM | 2160 | O | LEU | B | 91 | 6.462 | 17.305 | 31.299 | 1.00 | 58.07 | B | O |
| ATOM | 2161 | N | LYS | B | 92 | 4.882 | 17.125 | 29.708 | 1.00 | 62.63 | B | N |
| ATOM | 2162 | CA | LYS | B | 92 | 5.862 | 16.914 | 28.663 | 1.00 | 66.15 | B | C |
| ATOM | 2163 | CB | LYS | B | 92 | 5.198 | 16.788 | 27.292 | 1.00 | 64.51 | B | C |
| ATOM | 2164 | CG | LYS | B | 92 | 6.167 | 16.403 | 26.186 | 1.00 | 61.84 | B | C |
| ATOM | 2165 | CD | LYS | B | 92 | 5.496 | 16.412 | 24.824 | 1.00 | 67.85 | B | C |
| ATOM | 2166 | CE | LYS | B | 92 | 6.528 | 16.500 | 23.711 | 1.00 | 68.24 | B | C |
| ATOM | 2167 | NZ | LYS | B | 92 | 7.446 | 17.660 | 23.914 | 1.00 | 70.30 | B | N |
| ATOM | 2168 | C | LYS | B | 92 | 6.808 | 18.108 | 28.696 | 1.00 | 63.81 | B | C |
| ATOM | 2169 | O | LYS | B | 92 | 7.995 | 17.954 | 28.967 | 1.00 | 63.68 | B | O |
| ATOM | 2170 | N | ALA | B | 93 | 6.267 | 19.299 | 28.453 | 1.00 | 56.96 | B | N |
| ATOM | 2171 | CA | ALA | B | 93 | 7.060 | 20.521 | 28.450 | 1.00 | 51.81 | B | C |
| ATOM | 2172 | CB | ALA | B | 93 | 6.152 | 21.733 | 28.527 | 1.00 | 51.49 | B | C |
| ATOM | 2173 | C | ALA | B | 93 | 8.098 | 20.551 | 29.576 | 1.00 | 57.02 | B | C |
| ATOM | 2174 | O | ALA | B | 93 | 9.286 | 20.784 | 29.336 | 1.00 | 61.50 | B | O |
| ATOM | 2175 | N | MET | B | 94 | 7.652 | 20.303 | 30.801 | 1.00 | 59.70 | B | N |
| ATOM | 2176 | CA | MET | B | 94 | 8.541 | 20.336 | 31.960 | 1.00 | 58.29 | B | C |
| ATOM | 2177 | CB | MET | B | 94 | 7.732 | 20.324 | 33.261 | 1.00 | 60.51 | B | C |
| ATOM | 2178 | CG | MET | B | 94 | 7.272 | 21.705 | 33.733 | 1.00 | 62.85 | B | C |
| ATOM | 2179 | SD | MET | B | 94 | 5.978 | 21.641 | 35.001 | 1.00 | 55.45 | B | S |
| ATOM | 2180 | CE | MET | B | 94 | 6.094 | 23.278 | 35.712 | 1.00 | 53.95 | B | C |
| ATOM | 2181 | C | MET | B | 94 | 9.591 | 19.217 | 31.965 | 1.00 | 62.12 | B | C |
| ATOM | 2182 | O | MET | B | 94 | 10.606 | 19.317 | 32.654 | 1.00 | 63.47 | B | O |
| ATOM | 2183 | N | ARG | B | 95 | 9.351 | 18.160 | 31.195 | 1.00 | 61.52 | B | N |
| ATOM | 2184 | CA | ARG | B | 95 | 10.307 | 17.059 | 31.091 | 1.00 | 56.19 | B | C |
| ATOM | 2185 | CB | ARG | B | 95 | 9.586 | 15.726 | 30.881 | 1.00 | 66.06 | B | C |
| ATOM | 2186 | CG | ARG | B | 95 | 8.885 | 15.178 | 32.097 | 1.00 | 65.13 | B | C |
| ATOM | 2187 | CD | ARG | B | 95 | 8.530 | 13.723 | 31.881 | 1.00 | 63.53 | B | C |
| ATOM | 2188 | NE | ARG | B | 95 | 7.270 | 13.378 | 32.528 | 1.00 | 70.76 | B | N |
| ATOM | 2189 | CZ | ARG | B | 95 | 6.114 | 13.271 | 31.883 | 1.00 | 72.75 | B | C |
| ATOM | 2190 | NH1 | ARG | B | 95 | 6.068 | 13.472 | 30.572 | 1.00 | 73.16 | B | N |
| ATOM | 2191 | NH2 | ARG | B | 95 | 5.000 | 12.958 | 32.545 | 1.00 | 67.06 | B | N |
| ATOM | 2192 | C | ARG | B | 95 | 11.284 | 17.244 | 29.942 | 1.00 | 53.67 | B | C |
| ATOM | 2193 | O | ARG | B | 95 | 12.251 | 16.488 | 29.817 | 1.00 | 50.81 | B | O |
| ATOM | 2194 | N | THR | B | 96 | 11.024 | 18.225 | 29.086 | 1.00 | 51.50 | B | N |
| ATOM | 2195 | CA | THR | B | 96 | 11.842 | 18.394 | 27.895 | 1.00 | 48.95 | B | C |
| ATOM | 2196 | CB | THR | B | 96 | 11.091 | 19.137 | 26.779 | 1.00 | 49.75 | B | C |
| ATOM | 2197 | OG1 | THR | B | 96 | 9.904 | 18.410 | 26.441 | 1.00 | 59.02 | B | O |
| ATOM | 2198 | CG2 | THR | B | 96 | 11.956 | 19.241 | 25.541 | 1.00 | 43.36 | B | C |
| ATOM | 2199 | C | THR | B | 96 | 13.145 | 19.104 | 28.224 | 1.00 | 48.58 | B | C |
| ATOM | 2200 | O | THR | B | 96 | 13.134 | 20.179 | 28.826 | 1.00 | 52.86 | B | O |
| ATOM | 2201 | N | PRO | B | 97 | 14.275 | 18.485 | 27.843 | 1.00 | 53.45 | B | N |
| ATOM | 2202 | CD | PRO | B | 97 | 14.299 | 17.154 | 27.216 | 1.00 | 50.12 | B | C |
| ATOM | 2203 | CA | PRO | B | 97 | 15.629 | 19.032 | 27.989 | 1.00 | 48.45 | B | C |
| ATOM | 2204 | CB | PRO | B | 97 | 16.443 | 18.165 | 27.046 | 1.00 | 45.26 | B | C |
| ATOM | 2205 | CG | PRO | B | 97 | 15.766 | 16.850 | 27.128 | 1.00 | 49.95 | B | C |
| ATOM | 2206 | C | PRO | B | 97 | 15.673 | 20.486 | 27.559 | 1.00 | 45.10 | B | C |
| ATOM | 2207 | O | PRO | B | 97 | 15.021 | 20.879 | 26.597 | 1.00 | 47.02 | B | O |
| ATOM | 2208 | N | ARG | B | 98 | 16.454 | 21.275 | 28.274 | 1.00 | 41.15 | B | N |

TABLE 13-continued

Coordinates for proMMP9(35-444 ΔFnII) (SEQ ID NO: 12) complex with Example 3

| ATOM | 2209 | CA | ARG | B | 98 | 16.255 | 22.700 | 28.259 | 1.00 | 39.57 | B | C |
|---|---|---|---|---|---|---|---|---|---|---|---|---|
| ATOM | 2210 | CB | ARG | B | 98 | 15.497 | 23.070 | 29.526 | 1.00 | 40.45 | B | C |
| ATOM | 2211 | CG | ARG | B | 98 | 14.288 | 23.919 | 29.304 | 1.00 | 48.97 | B | C |
| ATOM | 2212 | CD | ARG | B | 98 | 13.820 | 24.504 | 30.613 | 1.00 | 41.86 | B | C |
| ATOM | 2213 | NE | ARG | B | 98 | 14.341 | 25.851 | 30.795 | 1.00 | 42.00 | B | N |
| ATOM | 2214 | CZ | ARG | B | 98 | 13.643 | 26.952 | 30.547 | 1.00 | 44.30 | B | C |
| ATOM | 2215 | NH1 | ARG | B | 98 | 12.389 | 26.861 | 30.116 | 1.00 | 36.29 | B | N |
| ATOM | 2216 | NH2 | ARG | B | 98 | 14.198 | 28.142 | 30.737 | 1.00 | 43.05 | B | N |
| ATOM | 2217 | C | ARG | B | 98 | 17.575 | 23.445 | 28.288 | 1.00 | 45.87 | B | C |
| ATOM | 2218 | O | ARG | B | 98 | 18.639 | 22.871 | 28.546 | 1.00 | 41.37 | B | O |
| ATOM | 2219 | N | CYS | B | 99 | 17.490 | 24.744 | 28.043 | 1.00 | 41.10 | B | N |
| ATOM | 2220 | CA | CYS | B | 99 | 18.580 | 25.638 | 28.369 | 1.00 | 39.89 | B | C |
| ATOM | 2221 | CB | CYS | B | 99 | 18.547 | 26.865 | 27.469 | 1.00 | 35.02 | B | C |
| ATOM | 2222 | SG | CYS | B | 99 | 19.709 | 28.100 | 28.000 | 1.00 | 35.66 | B | S |
| ATOM | 2223 | C | CYS | B | 99 | 18.451 | 26.064 | 29.839 | 1.00 | 46.12 | B | C |
| ATOM | 2224 | O | CYS | B | 99 | 17.344 | 26.215 | 30.354 | 1.00 | 37.35 | B | O |
| ATOM | 2225 | N | GLY | B | 100 | 19.584 | 26.260 | 30.509 | 1.00 | 43.34 | B | N |
| ATOM | 2226 | CA | GLY | B | 100 | 19.579 | 26.584 | 31.921 | 1.00 | 40.75 | B | C |
| ATOM | 2227 | C | GLY | B | 100 | 19.165 | 28.007 | 32.236 | 1.00 | 40.76 | B | C |
| ATOM | 2228 | O | GLY | B | 100 | 18.657 | 28.297 | 33.320 | 1.00 | 41.17 | B | O |
| ATOM | 2229 | N | VAL | B | 101 | 19.387 | 28.908 | 31.290 | 1.00 | 42.65 | B | N |
| ATOM | 2230 | CA | VAL | B | 101 | 19.087 | 30.311 | 31.533 | 1.00 | 47.46 | B | C |
| ATOM | 2231 | CB | VAL | B | 101 | 19.552 | 31.197 | 30.352 | 1.00 | 39.84 | B | C |
| ATOM | 2232 | CG1 | VAL | B | 101 | 18.937 | 32.582 | 30.425 | 1.00 | 40.45 | B | C |
| ATOM | 2233 | CG2 | VAL | B | 101 | 21.059 | 31.287 | 30.338 | 1.00 | 36.80 | B | C |
| ATOM | 2234 | C | VAL | B | 101 | 17.600 | 30.494 | 31.832 | 1.00 | 42.44 | B | C |
| ATOM | 2235 | O | VAL | B | 101 | 16.759 | 29.986 | 31.105 | 1.00 | 46.63 | B | O |
| ATOM | 2236 | N | PRO | B | 102 | 17.278 | 31.198 | 32.927 | 1.00 | 44.08 | B | N |
| ATOM | 2237 | CA | PRO | B | 102 | 15.889 | 31.462 | 33.333 | 1.00 | 46.95 | B | C |
| ATOM | 2238 | C | PRO | B | 102 | 15.091 | 32.224 | 32.279 | 1.00 | 46.22 | B | C |
| ATOM | 2239 | CB | PRO | B | 102 | 16.049 | 32.306 | 34.602 | 1.00 | 49.61 | B | C |
| ATOM | 2240 | CG | PRO | B | 102 | 17.386 | 31.905 | 35.150 | 1.00 | 48.94 | B | C |
| ATOM | 2241 | CD | PRO | B | 102 | 18.246 | 31.660 | 33.936 | 1.00 | 47.68 | B | C |
| ATOM | 2242 | O | PRO | B | 102 | 15.682 | 32.891 | 31.428 | 1.00 | 43.88 | B | O |
| ATOM | 2243 | N | ASP | B | 103 | 13.764 | 32.118 | 32.342 | 1.00 | 45.75 | B | N |
| ATOM | 2244 | CA | ASP | B | 103 | 12.877 | 32.721 | 31.348 | 1.00 | 42.66 | B | C |
| ATOM | 2245 | C | ASP | B | 103 | 12.351 | 34.085 | 31.790 | 1.00 | 46.42 | B | C |
| ATOM | 2246 | CB | ASP | B | 103 | 11.708 | 31.787 | 31.039 | 1.00 | 43.94 | B | C |
| ATOM | 2247 | CG | ASP | B | 103 | 12.163 | 30.413 | 30.580 | 1.00 | 47.78 | B | C |
| ATOM | 2248 | OD1 | ASP | B | 103 | 13.226 | 30.331 | 29.932 | 1.00 | 43.44 | B | O |
| ATOM | 2249 | OD2 | ASP | B | 103 | 11.457 | 29.416 | 30.860 | 1.00 | 48.02 | B | O |
| ATOM | 2250 | O | ASP | B | 103 | 12.030 | 34.929 | 30.958 | 1.00 | 48.95 | B | O |
| ATOM | 2251 | N | LEU | B | 104 | 12.251 | 34.291 | 33.100 | 1.00 | 56.26 | B | N |
| ATOM | 2252 | CA | LEU | B | 104 | 11.881 | 35.594 | 33.656 | 1.00 | 54.57 | B | C |
| ATOM | 2253 | C | LEU | B | 104 | 12.873 | 35.926 | 34.754 | 1.00 | 62.42 | B | C |
| ATOM | 2254 | CB | LEU | B | 104 | 10.467 | 35.573 | 34.233 | 1.00 | 54.89 | B | C |
| ATOM | 2255 | CG | LEU | B | 104 | 9.386 | 34.777 | 33.493 | 1.00 | 59.53 | B | C |
| ATOM | 2256 | CD1 | LEU | B | 104 | 8.117 | 34.686 | 34.334 | 1.00 | 56.01 | B | C |
| ATOM | 2257 | CD2 | LEU | B | 104 | 9.097 | 35.378 | 32.125 | 1.00 | 53.55 | B | C |
| ATOM | 2258 | O | LEU | B | 104 | 12.626 | 35.647 | 35.929 | 1.00 | 71.10 | B | O |
| ATOM | 2259 | N | GLY | B | 105 | 13.994 | 36.528 | 34.364 | 1.00 | 70.21 | B | N |
| ATOM | 2260 | CA | GLY | B | 105 | 15.141 | 36.659 | 35.243 | 1.00 | 73.75 | B | C |
| ATOM | 2261 | C | GLY | B | 105 | 15.345 | 37.991 | 35.935 | 1.00 | 73.86 | B | C |
| ATOM | 2262 | O | GLY | B | 105 | 15.215 | 39.052 | 35.327 | 1.00 | 80.83 | B | O |
| ATOM | 2263 | N | ARG | B | 106 | 15.665 | 37.910 | 37.224 | 1.00 | 79.69 | B | N |
| ATOM | 2264 | CA | ARG | B | 106 | 16.064 | 39.047 | 38.049 | 1.00 | 74.60 | B | C |
| ATOM | 2265 | C | ARG | B | 106 | 17.383 | 39.606 | 37.527 | 1.00 | 82.15 | B | C |
| ATOM | 2266 | CB | ARG | B | 106 | 16.256 | 38.570 | 39.488 | 1.00 | 79.05 | B | C |
| ATOM | 2267 | CG | ARG | B | 106 | 17.196 | 37.361 | 39.621 | 1.00 | 76.81 | B | C |
| ATOM | 2268 | CD | ARG | B | 106 | 16.514 | 36.053 | 39.219 | 1.00 | 75.56 | B | C |
| ATOM | 2269 | NE | ARG | B | 106 | 17.464 | 34.954 | 39.059 | 1.00 | 79.25 | B | N |
| ATOM | 2270 | CZ | ARG | B | 106 | 17.115 | 33.679 | 38.897 | 1.00 | 76.89 | B | C |
| ATOM | 2271 | NH1 | ARG | B | 106 | 15.830 | 33.339 | 38.877 | 1.00 | 69.62 | B | N |
| ATOM | 2272 | NH2 | ARG | B | 106 | 18.050 | 32.743 | 38.759 | 1.00 | 62.05 | B | N |
| ATOM | 2273 | O | ARG | B | 106 | 18.369 | 39.699 | 38.268 | 1.00 | 80.20 | B | O |
| ATOM | 2274 | N | PHE | B | 107 | 17.378 | 40.008 | 36.257 | 1.00 | 85.16 | B | N |
| ATOM | 2275 | CA | PHE | B | 107 | 18.598 | 40.054 | 35.439 | 1.00 | 78.48 | B | C |
| ATOM | 2276 | C | PHE | B | 107 | 19.871 | 40.672 | 36.031 | 1.00 | 76.74 | B | C |
| ATOM | 2277 | CB | PHE | B | 107 | 18.331 | 40.533 | 33.992 | 1.00 | 75.03 | B | C |
| ATOM | 2278 | CG | PHE | B | 107 | 17.627 | 41.860 | 33.879 | 1.00 | 83.31 | B | C |
| ATOM | 2279 | CD1 | PHE | B | 107 | 16.272 | 41.978 | 34.168 | 1.00 | 82.00 | B | C |
| ATOM | 2280 | CD2 | PHE | B | 107 | 18.310 | 42.980 | 33.421 | 1.00 | 79.46 | B | C |
| ATOM | 2281 | CE1 | PHE | B | 107 | 15.622 | 43.197 | 34.041 | 1.00 | 81.08 | B | C |
| ATOM | 2282 | CE2 | PHE | B | 107 | 17.667 | 44.201 | 33.290 | 1.00 | 79.56 | B | C |
| ATOM | 2283 | CZ | PHE | B | 107 | 16.320 | 44.309 | 33.601 | 1.00 | 82.34 | B | C |
| ATOM | 2284 | O | PHE | B | 107 | 20.819 | 39.939 | 36.318 | 1.00 | 69.47 | B | O |
| ATOM | 2285 | N | GLN | B | 108 | 19.895 | 41.991 | 36.214 | 1.00 | 79.36 | B | N |

TABLE 13-continued

Coordinates for proMMP9(35-444 ΔFnII) (SEQ ID NO: 12) complex with Example 3

| ATOM | 2286 | CA  | GLN | B | 108 | 21.153 | 42.696 | 36.495 | 1.00 | 71.01 B | C |
| ---- | ---- | --- | --- | - | --- | ------ | ------ | ------ | ---- | ------- | - |
| ATOM | 2287 | C   | GLN | B | 108 | 21.945 | 42.287 | 37.756 | 1.00 | 72.52 B | C |
| ATOM | 2288 | CB  | GLN | B | 108 | 20.990 | 44.218 | 36.376 | 1.00 | 70.87 B | C |
| ATOM | 2289 | CG  | GLN | B | 108 | 21.307 | 44.738 | 34.968 | 1.00 | 73.74 B | C |
| ATOM | 2290 | CD  | GLN | B | 108 | 21.063 | 46.232 | 34.809 | 1.00 | 77.39 B | C |
| ATOM | 2291 | OE1 | GLN | B | 108 | 20.028 | 46.755 | 35.235 | 1.00 | 71.06 B | O |
| ATOM | 2292 | NE2 | GLN | B | 108 | 22.012 | 46.923 | 34.181 | 1.00 | 60.71 B | N |
| ATOM | 2293 | O   | GLN | B | 108 | 22.634 | 43.106 | 38.368 | 1.00 | 69.21 B | O |
| ATOM | 2294 | N   | VAL | B | 109 | 21.852 | 41.007 | 38.115 | 1.00 | 71.72 B | N |
| ATOM | 2295 | CA  | VAL | B | 109 | 22.927 | 40.317 | 38.813 | 1.00 | 65.27 B | C |
| ATOM | 2296 | C   | VAL | B | 109 | 24.170 | 40.545 | 37.951 | 1.00 | 60.53 B | C |
| ATOM | 2297 | CB  | VAL | B | 109 | 22.644 | 38.788 | 38.874 | 1.00 | 72.89 B | C |
| ATOM | 2298 | CG1 | VAL | B | 109 | 21.320 | 38.503 | 39.577 | 1.00 | 73.16 B | C |
| ATOM | 2299 | CG2 | VAL | B | 109 | 23.797 | 38.023 | 39.533 | 1.00 | 68.50 B | C |
| ATOM | 2300 | O   | VAL | B | 109 | 25.255 | 40.043 | 38.237 | 1.00 | 57.47 B | O |
| ATOM | 2301 | N   | PHE | B | 110 | 23.982 | 41.312 | 36.879 | 1.00 | 63.50 B | N |
| ATOM | 2302 | CA  | PHE | B | 110 | 24.991 | 41.522 | 35.850 | 1.00 | 57.69 B | C |
| ATOM | 2303 | C   | PHE | B | 110 | 25.415 | 42.977 | 35.719 | 1.00 | 51.67 B | C |
| ATOM | 2304 | CB  | PHE | B | 110 | 24.465 | 41.024 | 34.509 | 1.00 | 49.06 B | C |
| ATOM | 2305 | CG  | PHE | B | 110 | 24.123 | 39.571 | 34.510 | 1.00 | 54.61 B | C |
| ATOM | 2306 | CD1 | PHE | B | 110 | 25.062 | 38.631 | 34.895 | 1.00 | 52.85 B | C |
| ATOM | 2307 | CD2 | PHE | B | 110 | 22.868 | 39.141 | 34.130 | 1.00 | 57.14 B | C |
| ATOM | 2308 | CE1 | PHE | B | 110 | 24.761 | 37.293 | 34.899 | 1.00 | 53.90 B | C |
| ATOM | 2309 | CE2 | PHE | B | 110 | 22.558 | 37.800 | 34.137 | 1.00 | 58.98 B | C |
| ATOM | 2310 | CZ  | PHE | B | 110 | 23.506 | 36.874 | 34.522 | 1.00 | 58.60 B | C |
| ATOM | 2311 | O   | PHE | B | 110 | 24.600 | 43.894 | 35.826 | 1.00 | 55.38 B | O |
| ATOM | 2312 | N   | GLU | B | 111 | 26.701 | 43.176 | 35.468 | 1.00 | 50.32 B | N |
| ATOM | 2313 | CA  | GLU | B | 111 | 27.252 | 44.512 | 35.308 | 1.00 | 51.37 B | C |
| ATOM | 2314 | CB  | GLU | B | 111 | 28.754 | 44.500 | 35.595 | 1.00 | 50.26 B | C |
| ATOM | 2315 | CG  | GLU | B | 111 | 29.351 | 45.870 | 35.892 | 1.00 | 61.59 B | C |
| ATOM | 2316 | CD  | GLU | B | 111 | 30.847 | 45.806 | 36.182 | 1.00 | 70.62 B | C |
| ATOM | 2317 | OE1 | GLU | B | 111 | 31.246 | 45.021 | 37.074 | 1.00 | 63.54 B | O |
| ATOM | 2318 | OE2 | GLU | B | 111 | 31.619 | 46.543 | 35.518 | 1.00 | 61.97 B | O |
| ATOM | 2319 | C   | GLU | B | 111 | 26.976 | 45.074 | 33.913 | 1.00 | 48.33 B | C |
| ATOM | 2320 | O   | GLU | B | 111 | 26.871 | 44.337 | 32.935 | 1.00 | 46.73 B | O |
| ATOM | 2321 | N   | GLY | B | 112 | 26.814 | 46.387 | 33.840 | 1.00 | 51.87 B | N |
| ATOM | 2322 | CA  | GLY | B | 112 | 26.801 | 47.074 | 32.565 | 1.00 | 55.06 B | C |
| ATOM | 2323 | C   | GLY | B | 112 | 25.555 | 46.978 | 31.710 | 1.00 | 56.42 B | C |
| ATOM | 2324 | O   | GLY | B | 112 | 24.436 | 46.826 | 32.198 | 1.00 | 49.39 B | O |
| ATOM | 2325 | N   | ASP | B | 113 | 25.776 | 47.057 | 30.404 | 1.00 | 58.88 B | N |
| ATOM | 2326 | CA  | ASP | B | 113 | 24.714 | 47.287 | 29.433 | 1.00 | 56.55 B | C |
| ATOM | 2327 | CB  | ASP | B | 113 | 25.290 | 48.105 | 28.280 | 1.00 | 46.86 B | C |
| ATOM | 2328 | CG  | ASP | B | 113 | 24.233 | 48.780 | 27.477 | 1.00 | 51.13 B | C |
| ATOM | 2329 | OD1 | ASP | B | 113 | 23.112 | 48.940 | 28.001 | 1.00 | 53.14 B | O |
| ATOM | 2330 | OD2 | ASP | B | 113 | 24.525 | 49.155 | 26.326 | 1.00 | 64.56 B | O |
| ATOM | 2331 | C   | ASP | B | 113 | 24.069 | 45.999 | 28.898 | 1.00 | 53.37 B | C |
| ATOM | 2332 | O   | ASP | B | 113 | 22.924 | 46.010 | 28.431 | 1.00 | 49.47 B | O |
| ATOM | 2333 | N   | LEU | B | 114 | 24.816 | 44.899 | 28.966 | 1.00 | 47.53 B | N |
| ATOM | 2334 | CA  | LEU | B | 114 | 24.363 | 43.603 | 28.461 | 1.00 | 47.15 B | C |
| ATOM | 2335 | CB  | LEU | B | 114 | 23.022 | 43.206 | 29.080 | 1.00 | 46.85 B | C |
| ATOM | 2336 | CG  | LEU | B | 114 | 22.996 | 43.324 | 30.608 | 1.00 | 50.33 B | C |
| ATOM | 2337 | CD1 | LEU | B | 114 | 21.901 | 42.462 | 31.207 | 1.00 | 48.76 B | C |
| ATOM | 2338 | CD2 | LEU | B | 114 | 24.353 | 42.956 | 31.203 | 1.00 | 48.21 B | C |
| ATOM | 2339 | C   | LEU | B | 114 | 24.317 | 43.578 | 26.928 | 1.00 | 51.92 B | C |
| ATOM | 2340 | O   | LEU | B | 114 | 23.498 | 42.882 | 26.322 | 1.00 | 50.80 B | O |
| ATOM | 2341 | N   | LYS | B | 115 | 25.210 | 44.366 | 26.331 | 1.00 | 52.50 B | N |
| ATOM | 2342 | CA  | LYS | B | 115 | 25.484 | 44.390 | 24.900 | 1.00 | 46.97 B | C |
| ATOM | 2343 | CB  | LYS | B | 115 | 24.905 | 45.649 | 24.257 | 1.00 | 48.03 B | C |
| ATOM | 2344 | CG  | LYS | B | 115 | 23.455 | 45.569 | 23.842 | 1.00 | 49.71 B | C |
| ATOM | 2345 | CD  | LYS | B | 115 | 22.921 | 46.969 | 23.559 | 1.00 | 58.89 B | C |
| ATOM | 2346 | CE  | LYS | B | 115 | 23.887 | 47.787 | 22.699 | 1.00 | 56.85 B | C |
| ATOM | 2347 | NZ  | LYS | B | 115 | 23.534 | 47.781 | 21.249 | 1.00 | 43.43 B | N |
| ATOM | 2348 | C   | LYS | B | 115 | 26.996 | 44.444 | 24.741 | 1.00 | 48.75 B | C |
| ATOM | 2349 | O   | LYS | B | 115 | 27.725 | 44.707 | 25.709 | 1.00 | 48.65 B | O |
| ATOM | 2350 | N   | TRP | B | 116 | 27.474 | 44.211 | 23.526 | 1.00 | 42.34 B | N |
| ATOM | 2351 | CA  | TRP | B | 116 | 28.878 | 44.453 | 23.241 | 1.00 | 43.79 B | C |
| ATOM | 2352 | CB  | TRP | B | 116 | 29.413 | 43.443 | 22.235 | 1.00 | 44.73 B | C |
| ATOM | 2353 | CG  | TRP | B | 116 | 29.479 | 42.030 | 22.741 | 1.00 | 44.36 B | C |
| ATOM | 2354 | CD2 | TRP | B | 116 | 30.218 | 41.542 | 23.874 | 1.00 | 39.82 B | C |
| ATOM | 2355 | CE2 | TRP | B | 116 | 29.988 | 40.158 | 23.955 | 1.00 | 39.86 B | C |
| ATOM | 2356 | CE3 | TRP | B | 116 | 31.047 | 42.141 | 24.822 | 1.00 | 41.32 B | C |
| ATOM | 2357 | CD1 | TRP | B | 116 | 28.856 | 40.950 | 22.202 | 1.00 | 42.85 B | C |
| ATOM | 2358 | NE1 | TRP | B | 116 | 29.153 | 39.824 | 22.923 | 1.00 | 50.04 B | N |
| ATOM | 2359 | CZ2 | TRP | B | 116 | 30.553 | 39.361 | 24.945 | 1.00 | 38.59 B | C |
| ATOM | 2360 | CZ3 | TRP | B | 116 | 31.601 | 41.351 | 25.808 | 1.00 | 45.80 B | C |
| ATOM | 2361 | CH2 | TRP | B | 116 | 31.351 | 39.973 | 25.864 | 1.00 | 42.53 B | C |
| ATOM | 2362 | C   | TRP | B | 116 | 29.059 | 45.873 | 22.715 | 1.00 | 42.44 B | C |

TABLE 13-continued

Coordinates for proMMP9(35-444 ΔFnII) (SEQ ID NO: 12) complex with Example 3

| ATOM | 2363 | O | TRP | B | 116 | 28.190 | 46.403 | 22.029 | 1.00 | 41.43 B | O |
|---|---|---|---|---|---|---|---|---|---|---|---|
| ATOM | 2364 | N | HIS | B | 117 | 30.182 | 46.498 | 23.038 | 1.00 | 44.50 B | N |
| ATOM | 2365 | CA | HIS | B | 117 | 30.439 | 47.843 | 22.534 | 1.00 | 47.40 B | C |
| ATOM | 2366 | CB | HIS | B | 117 | 30.401 | 48.863 | 23.670 | 1.00 | 47.30 B | C |
| ATOM | 2367 | CG | HIS | B | 117 | 29.047 | 49.001 | 24.293 | 1.00 | 50.75 B | C |
| ATOM | 2368 | CD2 | HIS | B | 117 | 27.949 | 49.691 | 23.898 | 1.00 | 54.32 B | C |
| ATOM | 2369 | ND1 | HIS | B | 117 | 28.688 | 48.345 | 25.452 | 1.00 | 53.55 B | N |
| ATOM | 2370 | CE1 | HIS | B | 117 | 27.433 | 48.636 | 25.753 | 1.00 | 51.35 B | C |
| ATOM | 2371 | NE2 | HIS | B | 117 | 26.961 | 49.451 | 24.826 | 1.00 | 55.23 B | N |
| ATOM | 2372 | C | HIS | B | 117 | 31.723 | 47.931 | 21.707 | 1.00 | 51.10 B | C |
| ATOM | 2373 | O | HIS | B | 117 | 32.396 | 48.963 | 21.681 | 1.00 | 54.55 B | O |
| ATOM | 2374 | N | HIS | B | 118 | 32.037 | 46.822 | 21.039 | 1.00 | 45.47 B | N |
| ATOM | 2375 | CA | HIS | B | 118 | 33.109 | 46.737 | 20.053 | 1.00 | 53.46 B | C |
| ATOM | 2376 | CB | HIS | B | 118 | 34.444 | 46.420 | 20.714 | 1.00 | 49.44 B | C |
| ATOM | 2377 | CG | HIS | B | 118 | 34.449 | 45.125 | 21.461 | 1.00 | 50.04 B | C |
| ATOM | 2378 | CD2 | HIS | B | 118 | 34.854 | 43.888 | 21.096 | 1.00 | 48.01 B | C |
| ATOM | 2379 | ND1 | HIS | B | 118 | 33.980 | 45.014 | 22.753 | 1.00 | 49.91 B | N |
| ATOM | 2380 | CE1 | HIS | B | 118 | 34.105 | 43.761 | 23.154 | 1.00 | 51.40 B | C |
| ATOM | 2381 | NE2 | HIS | B | 118 | 34.633 | 43.058 | 22.169 | 1.00 | 51.26 B | N |
| ATOM | 2382 | C | HIS | B | 118 | 32.714 | 45.621 | 19.096 | 1.00 | 50.28 B | C |
| ATOM | 2383 | O | HIS | B | 118 | 32.017 | 44.696 | 19.491 | 1.00 | 46.97 B | O |
| ATOM | 2384 | N | HIS | B | 119 | 33.145 | 45.706 | 17.843 | 1.00 | 47.92 B | N |
| ATOM | 2385 | CA | HIS | B | 119 | 32.567 | 44.860 | 16.800 | 1.00 | 49.38 B | C |
| ATOM | 2386 | CB | HIS | B | 119 | 32.604 | 45.570 | 15.449 | 1.00 | 47.66 B | C |
| ATOM | 2387 | CG | HIS | B | 119 | 33.991 | 45.830 | 14.947 | 1.00 | 66.83 B | C |
| ATOM | 2388 | CD2 | HIS | B | 119 | 34.861 | 46.841 | 15.203 | 1.00 | 63.36 B | C |
| ATOM | 2389 | ND1 | HIS | B | 119 | 34.642 | 44.983 | 14.073 | 1.00 | 65.14 B | N |
| ATOM | 2390 | CE1 | HIS | B | 119 | 35.845 | 45.461 | 13.809 | 1.00 | 62.80 B | C |
| ATOM | 2391 | NE2 | HIS | B | 119 | 36.000 | 46.590 | 14.481 | 1.00 | 64.56 B | N |
| ATOM | 2392 | C | HIS | B | 119 | 33.227 | 43.493 | 16.680 | 1.00 | 48.74 B | C |
| ATOM | 2393 | O | HIS | B | 119 | 32.591 | 42.526 | 16.271 | 1.00 | 46.40 B | O |
| ATOM | 2394 | N | ASN | B | 120 | 34.505 | 43.411 | 17.019 | 1.00 | 53.45 B | N |
| ATOM | 2395 | CA | ASN | B | 120 | 35.214 | 42.148 | 16.877 | 1.00 | 49.60 B | C |
| ATOM | 2396 | CB | ASN | B | 120 | 36.614 | 42.353 | 16.299 | 1.00 | 44.14 B | C |
| ATOM | 2397 | CG | ASN | B | 120 | 37.462 | 41.099 | 16.390 | 1.00 | 51.69 B | C |
| ATOM | 2398 | OD1 | ASN | B | 120 | 37.046 | 40.011 | 15.969 | 1.00 | 45.02 B | O |
| ATOM | 2399 | ND2 | ASN | B | 120 | 38.656 | 41.239 | 16.954 | 1.00 | 50.93 B | N |
| ATOM | 2400 | C | ASN | B | 120 | 35.287 | 41.396 | 18.195 | 1.00 | 49.18 B | C |
| ATOM | 2401 | O | ASN | B | 120 | 36.098 | 41.714 | 19.066 | 1.00 | 45.24 B | O |
| ATOM | 2402 | N | ILE | B | 121 | 34.433 | 40.388 | 18.326 | 1.00 | 50.38 B | N |
| ATOM | 2403 | CA | ILE | B | 121 | 34.361 | 39.597 | 19.544 | 1.00 | 49.52 B | C |
| ATOM | 2404 | CB | ILE | B | 121 | 32.955 | 39.068 | 19.757 | 1.00 | 39.76 B | C |
| ATOM | 2405 | CG2 | ILE | B | 121 | 32.875 | 38.327 | 21.063 | 1.00 | 43.00 B | C |
| ATOM | 2406 | CG1 | ILE | B | 121 | 31.965 | 40.230 | 19.706 | 1.00 | 44.80 B | C |
| ATOM | 2407 | CD1 | ILE | B | 121 | 32.426 | 41.441 | 20.466 | 1.00 | 45.45 B | C |
| ATOM | 2408 | C | ILE | B | 121 | 35.325 | 38.423 | 19.509 | 1.00 | 43.32 B | C |
| ATOM | 2409 | O | ILE | B | 121 | 35.358 | 37.664 | 18.545 | 1.00 | 45.27 B | O |
| ATOM | 2410 | N | THR | B | 122 | 36.117 | 38.285 | 20.562 | 1.00 | 39.28 B | N |
| ATOM | 2411 | CA | THR | B | 122 | 37.082 | 37.202 | 20.643 | 1.00 | 41.93 B | C |
| ATOM | 2412 | CB | THR | B | 122 | 38.419 | 37.683 | 21.235 | 1.00 | 46.81 B | C |
| ATOM | 2413 | OG1 | THR | B | 122 | 38.216 | 38.142 | 22.577 | 1.00 | 43.28 B | O |
| ATOM | 2414 | CG2 | THR | B | 122 | 39.002 | 38.820 | 20.387 | 1.00 | 39.61 B | C |
| ATOM | 2415 | C | THR | B | 122 | 36.499 | 36.109 | 21.510 | 1.00 | 42.10 B | C |
| ATOM | 2416 | O | THR | B | 122 | 35.655 | 36.383 | 22.358 | 1.00 | 45.35 B | O |
| ATOM | 2417 | N | TYR | B | 123 | 36.929 | 34.872 | 21.285 | 1.00 | 43.44 B | N |
| ATOM | 2418 | CA | TYR | B | 123 | 36.443 | 33.739 | 22.070 | 1.00 | 39.13 B | C |
| ATOM | 2419 | CB | TYR | B | 123 | 35.156 | 33.165 | 21.475 | 1.00 | 36.63 B | C |
| ATOM | 2420 | CG | TYR | B | 123 | 35.285 | 32.416 | 20.163 | 1.00 | 36.92 B | C |
| ATOM | 2421 | CD1 | TYR | B | 123 | 35.097 | 33.065 | 18.954 | 1.00 | 39.72 B | C |
| ATOM | 2422 | CE1 | TYR | B | 123 | 35.175 | 32.388 | 17.754 | 1.00 | 38.16 B | C |
| ATOM | 2423 | CD2 | TYR | B | 123 | 35.540 | 31.050 | 20.134 | 1.00 | 40.99 B | C |
| ATOM | 2424 | CE2 | TYR | B | 123 | 35.625 | 30.358 | 18.935 | 1.00 | 34.84 B | C |
| ATOM | 2425 | CZ | TYR | B | 123 | 35.438 | 31.037 | 17.747 | 1.00 | 42.37 B | C |
| ATOM | 2426 | OH | TYR | B | 123 | 35.517 | 30.376 | 16.539 | 1.00 | 42.40 B | O |
| ATOM | 2427 | C | TYR | B | 123 | 37.484 | 32.642 | 22.282 | 1.00 | 38.07 B | C |
| ATOM | 2428 | O | TYR | B | 123 | 38.281 | 32.343 | 21.398 | 1.00 | 39.06 B | O |
| ATOM | 2429 | N | TRP | B | 124 | 37.455 | 32.039 | 23.464 | 1.00 | 40.32 B | N |
| ATOM | 2430 | CA | TRP | B | 124 | 38.491 | 31.109 | 23.883 | 1.00 | 40.84 B | C |
| ATOM | 2431 | CB | TRP | B | 124 | 39.135 | 31.638 | 25.154 | 1.00 | 43.55 B | C |
| ATOM | 2432 | CG | TRP | B | 124 | 40.249 | 30.805 | 25.670 | 1.00 | 46.76 B | C |
| ATOM | 2433 | CD2 | TRP | B | 124 | 40.619 | 30.633 | 27.043 | 1.00 | 49.46 B | C |
| ATOM | 2434 | CE2 | TRP | B | 124 | 41.751 | 29.790 | 27.067 | 1.00 | 53.85 B | C |
| ATOM | 2435 | CE3 | TRP | B | 124 | 40.105 | 31.112 | 28.256 | 1.00 | 44.96 B | C |
| ATOM | 2436 | CD1 | TRP | B | 124 | 41.149 | 30.088 | 24.935 | 1.00 | 44.04 B | C |
| ATOM | 2437 | NE1 | TRP | B | 124 | 42.052 | 29.471 | 25.766 | 1.00 | 49.43 B | N |
| ATOM | 2438 | CZ2 | TRP | B | 124 | 42.375 | 29.408 | 28.259 | 1.00 | 47.46 B | C |
| ATOM | 2439 | CZ3 | TRP | B | 124 | 40.725 | 30.734 | 29.440 | 1.00 | 45.40 B | C |

TABLE 13-continued

Coordinates for proMMP9(35-444 ΔFnII) (SEQ ID NO: 12) complex with Example 3

| ATOM | 2440 | CH2 | TRP | B | 124 | 41.848 | 29.891 | 29.431 | 1.00 | 55.02 | B | C |
|---|---|---|---|---|---|---|---|---|---|---|---|---|
| ATOM | 2441 | C | TRP | B | 124 | 37.954 | 29.719 | 24.153 | 1.00 | 41.37 | B | C |
| ATOM | 2442 | O | TRP | B | 124 | 37.390 | 29.471 | 25.209 | 1.00 | 53.15 | B | O |
| ATOM | 2443 | N | ILE | B | 125 | 38.123 | 28.808 | 23.208 | 1.00 | 37.64 | B | N |
| ATOM | 2444 | CA | ILE | B | 125 | 37.677 | 27.436 | 23.413 | 1.00 | 42.10 | B | C |
| ATOM | 2445 | CB | ILE | B | 125 | 37.799 | 26.613 | 22.124 | 1.00 | 46.72 | B | C |
| ATOM | 2446 | CG2 | ILE | B | 125 | 37.527 | 25.152 | 22.408 | 1.00 | 50.80 | B | C |
| ATOM | 2447 | CG1 | ILE | B | 125 | 36.837 | 27.155 | 21.059 | 1.00 | 46.91 | B | C |
| ATOM | 2448 | CD1 | ILE | B | 125 | 36.800 | 26.334 | 19.785 | 1.00 | 42.20 | B | C |
| ATOM | 2449 | C | ILE | B | 125 | 38.513 | 26.796 | 24.515 | 1.00 | 45.32 | B | C |
| ATOM | 2450 | O | ILE | B | 125 | 39.501 | 26.122 | 24.252 | 1.00 | 53.04 | B | O |
| ATOM | 2451 | N | GLN | B | 126 | 38.107 | 27.014 | 25.755 | 1.00 | 43.61 | B | N |
| ATOM | 2452 | CA | GLN | B | 126 | 38.965 | 26.747 | 26.903 | 1.00 | 45.07 | B | C |
| ATOM | 2453 | CB | GLN | B | 126 | 38.377 | 27.419 | 28.139 | 1.00 | 47.23 | B | C |
| ATOM | 2454 | CG | GLN | B | 126 | 39.255 | 27.384 | 29.366 | 1.00 | 46.29 | B | C |
| ATOM | 2455 | CD | GLN | B | 126 | 38.492 | 27.801 | 30.602 | 1.00 | 52.87 | B | C |
| ATOM | 2456 | OE1 | GLN | B | 126 | 37.382 | 27.318 | 30.861 | 1.00 | 52.66 | B | O |
| ATOM | 2457 | NE2 | GLN | B | 126 | 39.074 | 28.712 | 31.371 | 1.00 | 55.44 | B | N |
| ATOM | 2458 | C | GLN | B | 126 | 39.223 | 25.266 | 27.181 | 1.00 | 42.21 | B | C |
| ATOM | 2459 | O | GLN | B | 126 | 40.264 | 24.910 | 27.723 | 1.00 | 36.42 | B | O |
| ATOM | 2460 | N | ASN | B | 127 | 38.274 | 24.403 | 26.842 | 1.00 | 39.73 | B | N |
| ATOM | 2461 | CA | ASN | B | 127 | 38.502 | 22.965 | 26.981 | 1.00 | 46.07 | B | C |
| ATOM | 2462 | CB | ASN | B | 127 | 38.485 | 22.511 | 28.452 | 1.00 | 44.50 | B | C |
| ATOM | 2463 | CG | ASN | B | 127 | 37.132 | 22.690 | 29.110 | 1.00 | 46.02 | B | C |
| ATOM | 2464 | OD1 | ASN | B | 127 | 36.186 | 23.174 | 28.496 | 1.00 | 47.88 | B | O |
| ATOM | 2465 | ND2 | ASN | B | 127 | 37.038 | 22.298 | 30.369 | 1.00 | 51.76 | B | N |
| ATOM | 2466 | C | ASN | B | 127 | 37.548 | 22.148 | 26.125 | 1.00 | 43.66 | B | C |
| ATOM | 2467 | O | ASN | B | 127 | 36.642 | 22.702 | 25.515 | 1.00 | 42.64 | B | O |
| ATOM | 2468 | N | TYR | B | 128 | 37.767 | 20.837 | 26.071 | 1.00 | 42.86 | B | N |
| ATOM | 2469 | CA | TYR | B | 128 | 37.028 | 19.986 | 25.147 | 1.00 | 46.13 | B | C |
| ATOM | 2470 | CB | TYR | B | 128 | 37.914 | 19.550 | 23.988 | 1.00 | 42.01 | B | C |
| ATOM | 2471 | CG | TYR | B | 128 | 38.421 | 20.682 | 23.128 | 1.00 | 50.36 | B | C |
| ATOM | 2472 | CD1 | TYR | B | 128 | 37.748 | 21.049 | 21.972 | 1.00 | 47.28 | B | C |
| ATOM | 2473 | CE1 | TYR | B | 128 | 38.212 | 22.073 | 21.174 | 1.00 | 50.13 | B | C |
| ATOM | 2474 | CD2 | TYR | B | 128 | 39.586 | 21.374 | 23.462 | 1.00 | 52.15 | B | C |
| ATOM | 2475 | CE2 | TYR | B | 128 | 40.058 | 22.405 | 22.669 | 1.00 | 45.44 | B | C |
| ATOM | 2476 | CZ | TYR | B | 128 | 39.366 | 22.746 | 21.525 | 1.00 | 50.69 | B | C |
| ATOM | 2477 | OH | TYR | B | 128 | 39.813 | 23.769 | 20.726 | 1.00 | 55.45 | B | O |
| ATOM | 2478 | C | TYR | B | 128 | 36.451 | 18.748 | 25.803 | 1.00 | 54.02 | B | C |
| ATOM | 2479 | O | TYR | B | 128 | 37.048 | 18.173 | 26.713 | 1.00 | 57.00 | B | O |
| ATOM | 2480 | N | SER | B | 129 | 35.280 | 18.344 | 25.323 | 1.00 | 50.31 | B | N |
| ATOM | 2481 | CA | SER | B | 129 | 34.659 | 17.109 | 25.750 | 1.00 | 44.78 | B | C |
| ATOM | 2482 | CB | SER | B | 129 | 33.151 | 17.177 | 25.503 | 1.00 | 45.36 | B | C |
| ATOM | 2483 | OG | SER | B | 129 | 32.534 | 15.926 | 25.728 | 1.00 | 47.57 | B | O |
| ATOM | 2484 | C | SER | B | 129 | 35.289 | 15.980 | 24.952 | 1.00 | 43.51 | B | C |
| ATOM | 2485 | O | SER | B | 129 | 35.735 | 16.195 | 23.832 | 1.00 | 50.04 | B | O |
| ATOM | 2486 | N | GLU | B | 130 | 35.335 | 14.783 | 25.523 | 1.00 | 46.45 | B | N |
| ATOM | 2487 | CA | GLU | B | 130 | 35.942 | 13.645 | 24.842 | 1.00 | 48.02 | B | C |
| ATOM | 2488 | CB | GLU | B | 130 | 36.402 | 12.583 | 25.844 | 1.00 | 49.45 | B | C |
| ATOM | 2489 | CG | GLU | B | 130 | 37.648 | 12.964 | 26.619 | 1.00 | 56.40 | B | C |
| ATOM | 2490 | CD | GLU | B | 130 | 38.811 | 13.347 | 25.715 | 1.00 | 61.77 | B | C |
| ATOM | 2491 | OE1 | GLU | B | 130 | 39.200 | 12.527 | 24.858 | 1.00 | 71.84 | B | O |
| ATOM | 2492 | OE2 | GLU | B | 130 | 39.345 | 14.466 | 25.866 | 1.00 | 63.98 | B | O |
| ATOM | 2493 | C | GLU | B | 130 | 34.974 | 13.031 | 23.849 | 1.00 | 48.91 | B | C |
| ATOM | 2494 | O | GLU | B | 130 | 35.306 | 12.069 | 23.149 | 1.00 | 46.50 | B | O |
| ATOM | 2495 | N | ASP | B | 131 | 33.779 | 13.606 | 23.784 | 1.00 | 48.79 | B | N |
| ATOM | 2496 | CA | ASP | B | 131 | 32.689 | 13.028 | 23.010 | 1.00 | 49.17 | B | C |
| ATOM | 2497 | CB | ASP | B | 131 | 31.362 | 13.630 | 23.447 | 1.00 | 48.20 | B | C |
| ATOM | 2498 | CG | ASP | B | 131 | 30.926 | 13.123 | 24.799 | 1.00 | 54.48 | B | C |
| ATOM | 2499 | OD1 | ASP | B | 131 | 31.708 | 12.363 | 25.418 | 1.00 | 56.14 | B | O |
| ATOM | 2500 | OD2 | ASP | B | 131 | 29.807 | 13.476 | 25.236 | 1.00 | 52.94 | B | O |
| ATOM | 2501 | C | ASP | B | 131 | 32.865 | 13.180 | 21.511 | 1.00 | 53.98 | B | C |
| ATOM | 2502 | O | ASP | B | 131 | 32.403 | 12.333 | 20.742 | 1.00 | 56.76 | B | O |
| ATOM | 2503 | N | LEU | B | 132 | 33.523 | 14.264 | 21.105 | 1.00 | 51.78 | B | N |
| ATOM | 2504 | CA | LEU | B | 132 | 33.791 | 14.529 | 19.698 | 1.00 | 43.52 | B | C |
| ATOM | 2505 | CB | LEU | B | 132 | 32.954 | 15.708 | 19.207 | 1.00 | 43.67 | B | C |
| ATOM | 2506 | CG | LEU | B | 132 | 31.424 | 15.678 | 19.209 | 1.00 | 39.43 | B | C |
| ATOM | 2507 | CD1 | LEU | B | 132 | 30.910 | 17.098 | 19.066 | 1.00 | 37.86 | B | C |
| ATOM | 2508 | CD2 | LEU | B | 132 | 30.862 | 14.813 | 18.103 | 1.00 | 34.59 | B | C |
| ATOM | 2509 | C | LEU | B | 132 | 35.266 | 14.862 | 19.522 | 1.00 | 44.40 | B | C |
| ATOM | 2510 | O | LEU | B | 132 | 35.934 | 15.249 | 20.484 | 1.00 | 49.72 | B | O |
| ATOM | 2511 | N | PRO | B | 133 | 35.782 | 14.716 | 18.291 | 1.00 | 43.45 | B | N |
| ATOM | 2512 | CD | PRO | B | 133 | 35.117 | 14.075 | 17.144 | 1.00 | 43.13 | B | C |
| ATOM | 2513 | CA | PRO | B | 133 | 37.159 | 15.115 | 17.974 | 1.00 | 37.84 | B | C |
| ATOM | 2514 | CB | PRO | B | 133 | 37.319 | 14.693 | 16.514 | 1.00 | 35.64 | B | C |
| ATOM | 2515 | CG | PRO | B | 133 | 36.275 | 13.637 | 16.299 | 1.00 | 40.82 | B | C |
| ATOM | 2516 | C | PRO | B | 133 | 37.329 | 16.626 | 18.107 | 1.00 | 39.64 | B | C |

TABLE 13-continued

Coordinates for proMMP9(35-444 ΔFnII) (SEQ ID NO: 12) complex with Example 3

| ATOM | 2517 | O | PRO | B | 133 | 36.462 | 17.376 | 17.678 | 1.00 | 42.21 | B | O |
|------|------|-----|-----|---|-----|--------|--------|--------|------|-------|---|---|
| ATOM | 2518 | N | ARG | B | 134 | 38.436 | 17.056 | 18.698 | 1.00 | 39.72 | B | N |
| ATOM | 2519 | CA | ARG | B | 134 | 38.669 | 18.463 | 18.984 | 1.00 | 39.48 | B | C |
| ATOM | 2520 | CB | ARG | B | 134 | 40.135 | 18.698 | 19.350 | 1.00 | 34.26 | B | C |
| ATOM | 2521 | CG | ARG | B | 134 | 40.466 | 18.294 | 20.763 | 1.00 | 45.79 | B | C |
| ATOM | 2522 | CD | ARG | B | 134 | 41.765 | 18.916 | 21.220 | 1.00 | 52.96 | B | C |
| ATOM | 2523 | NE | ARG | B | 134 | 42.005 | 18.669 | 22.637 | 1.00 | 60.26 | B | N |
| ATOM | 2524 | CZ | ARG | B | 134 | 42.898 | 19.329 | 23.366 | 1.00 | 61.56 | B | C |
| ATOM | 2525 | NH1 | ARG | B | 134 | 43.631 | 20.286 | 22.811 | 1.00 | 57.81 | B | N |
| ATOM | 2526 | NH2 | ARG | B | 134 | 43.051 | 19.038 | 24.652 | 1.00 | 60.79 | B | N |
| ATOM | 2527 | C | ARG | B | 134 | 38.263 | 19.390 | 17.847 | 1.00 | 46.22 | B | C |
| ATOM | 2528 | O | ARG | B | 134 | 37.752 | 20.491 | 18.091 | 1.00 | 45.48 | B | O |
| ATOM | 2529 | N | ALA | B | 135 | 38.497 | 18.946 | 16.613 | 1.00 | 41.61 | B | N |
| ATOM | 2530 | CA | ALA | B | 135 | 38.189 | 19.748 | 15.430 | 1.00 | 46.44 | B | C |
| ATOM | 2531 | CB | ALA | B | 135 | 39.111 | 19.375 | 14.259 | 1.00 | 40.60 | B | C |
| ATOM | 2532 | C | ALA | B | 135 | 36.714 | 19.681 | 15.011 | 1.00 | 44.61 | B | C |
| ATOM | 2533 | O | ALA | B | 135 | 36.253 | 20.497 | 14.213 | 1.00 | 47.22 | B | O |
| ATOM | 2534 | N | VAL | B | 136 | 35.969 | 18.721 | 15.538 | 1.00 | 43.97 | B | N |
| ATOM | 2535 | CA | VAL | B | 136 | 34.528 | 18.738 | 15.314 | 1.00 | 46.49 | B | C |
| ATOM | 2536 | CB | VAL | B | 136 | 33.879 | 17.356 | 15.519 | 1.00 | 41.37 | B | C |
| ATOM | 2537 | CG1 | VAL | B | 136 | 32.398 | 17.422 | 15.220 | 1.00 | 35.84 | B | C |
| ATOM | 2538 | CG2 | VAL | B | 136 | 34.534 | 16.345 | 14.604 | 1.00 | 41.58 | B | C |
| ATOM | 2539 | C | VAL | B | 136 | 33.924 | 19.796 | 16.228 | 1.00 | 42.03 | B | C |
| ATOM | 2540 | O | VAL | B | 136 | 32.978 | 20.491 | 15.862 | 1.00 | 42.92 | B | O |
| ATOM | 2541 | N | ILE | B | 137 | 34.514 | 19.933 | 17.408 | 1.00 | 45.12 | B | N |
| ATOM | 2542 | CA | ILE | B | 137 | 34.128 | 20.967 | 18.365 | 1.00 | 41.50 | B | C |
| ATOM | 2543 | CB | ILE | B | 137 | 34.788 | 20.721 | 19.739 | 1.00 | 42.58 | B | C |
| ATOM | 2544 | CG2 | ILE | B | 137 | 34.507 | 21.870 | 20.688 | 1.00 | 39.25 | B | C |
| ATOM | 2545 | CG1 | ILE | B | 137 | 34.308 | 19.383 | 20.326 | 1.00 | 41.50 | B | C |
| ATOM | 2546 | CD1 | ILE | B | 137 | 35.181 | 18.857 | 21.454 | 1.00 | 39.48 | B | C |
| ATOM | 2547 | C | ILE | B | 137 | 34.474 | 22.369 | 17.851 | 1.00 | 40.33 | B | C |
| ATOM | 2548 | O | ILE | B | 137 | 33.595 | 23.218 | 17.719 | 1.00 | 41.84 | B | O |
| ATOM | 2549 | N | ASP | B | 138 | 35.748 | 22.605 | 17.552 | 1.00 | 42.50 | B | N |
| ATOM | 2550 | CA | ASP | B | 138 | 36.177 | 23.873 | 16.960 | 1.00 | 40.93 | B | C |
| ATOM | 2551 | CB | ASP | B | 138 | 37.592 | 23.754 | 16.371 | 1.00 | 36.85 | B | C |
| ATOM | 2552 | CG | ASP | B | 138 | 38.625 | 23.281 | 17.383 | 1.00 | 44.46 | B | C |
| ATOM | 2553 | OD1 | ASP | B | 138 | 38.298 | 23.151 | 18.579 | 1.00 | 50.63 | B | O |
| ATOM | 2554 | OD2 | ASP | B | 138 | 39.780 | 23.033 | 16.977 | 1.00 | 55.49 | B | O |
| ATOM | 2555 | C | ASP | B | 138 | 35.214 | 24.310 | 15.853 | 1.00 | 38.85 | B | C |
| ATOM | 2556 | O | ASP | B | 138 | 34.782 | 25.466 | 15.789 | 1.00 | 38.98 | B | O |
| ATOM | 2557 | N | ASP | B | 139 | 34.877 | 23.364 | 14.988 | 1.00 | 39.23 | B | N |
| ATOM | 2558 | CA | ASP | B | 139 | 34.075 | 23.641 | 13.812 | 1.00 | 38.85 | B | C |
| ATOM | 2559 | CB | ASP | B | 139 | 34.174 | 22.465 | 12.843 | 1.00 | 35.18 | B | C |
| ATOM | 2560 | CG | ASP | B | 139 | 33.258 | 22.613 | 11.661 | 1.00 | 36.65 | B | C |
| ATOM | 2561 | OD1 | ASP | B | 139 | 33.619 | 23.345 | 10.716 | 1.00 | 42.68 | B | O |
| ATOM | 2562 | OD2 | ASP | B | 139 | 32.179 | 21.987 | 11.674 | 1.00 | 37.93 | B | O |
| ATOM | 2563 | C | ASP | B | 139 | 32.610 | 23.932 | 14.147 | 1.00 | 42.00 | B | C |
| ATOM | 2564 | O | ASP | B | 139 | 31.984 | 24.792 | 13.522 | 1.00 | 41.56 | B | O |
| ATOM | 2565 | N | ALA | B | 140 | 32.058 | 23.218 | 15.125 | 1.00 | 39.23 | B | N |
| ATOM | 2566 | CA | ALA | B | 140 | 30.673 | 23.454 | 15.519 | 1.00 | 40.19 | B | C |
| ATOM | 2567 | CB | ALA | B | 140 | 30.177 | 22.368 | 16.472 | 1.00 | 44.25 | B | C |
| ATOM | 2568 | C | ALA | B | 140 | 30.530 | 24.836 | 16.151 | 1.00 | 39.77 | B | C |
| ATOM | 2569 | O | ALA | B | 140 | 29.497 | 25.493 | 16.003 | 1.00 | 38.61 | B | O |
| ATOM | 2570 | N | PHE | B | 141 | 31.566 | 25.272 | 16.860 | 1.00 | 39.21 | B | N |
| ATOM | 2571 | CA | PHE | B | 141 | 31.575 | 26.620 | 17.416 | 1.00 | 44.29 | B | C |
| ATOM | 2572 | CB | PHE | B | 141 | 32.654 | 26.776 | 18.488 | 1.00 | 40.07 | B | C |
| ATOM | 2573 | CG | PHE | B | 141 | 32.406 | 25.967 | 19.716 | 1.00 | 44.25 | B | C |
| ATOM | 2574 | CD1 | PHE | B | 141 | 31.122 | 25.786 | 20.191 | 1.00 | 40.25 | B | C |
| ATOM | 2575 | CD2 | PHE | B | 141 | 33.466 | 25.394 | 20.412 | 1.00 | 46.22 | B | C |
| ATOM | 2576 | CE1 | PHE | B | 141 | 30.900 | 25.032 | 21.337 | 1.00 | 48.37 | B | C |
| ATOM | 2577 | CE2 | PHE | B | 141 | 33.252 | 24.646 | 21.556 | 1.00 | 39.72 | B | C |
| ATOM | 2578 | CZ | PHE | B | 141 | 31.972 | 24.463 | 22.022 | 1.00 | 43.12 | B | C |
| ATOM | 2579 | C | PHE | B | 141 | 31.770 | 27.671 | 16.320 | 1.00 | 42.30 | B | C |
| ATOM | 2580 | O | PHE | B | 141 | 31.129 | 28.728 | 16.341 | 1.00 | 42.04 | B | O |
| ATOM | 2581 | N | ALA | B | 142 | 32.658 | 27.391 | 15.371 | 1.00 | 36.56 | B | N |
| ATOM | 2582 | CA | ALA | B | 142 | 32.864 | 28.318 | 14.256 | 1.00 | 42.91 | B | C |
| ATOM | 2583 | CB | ALA | B | 142 | 33.945 | 27.804 | 13.306 | 1.00 | 33.42 | B | C |
| ATOM | 2584 | C | ALA | B | 142 | 31.555 | 28.558 | 13.510 | 1.00 | 33.68 | B | C |
| ATOM | 2585 | O | ALA | B | 142 | 31.208 | 29.691 | 13.194 | 1.00 | 32.88 | B | O |
| ATOM | 2586 | N | ARG | B | 143 | 30.819 | 27.479 | 13.266 | 1.00 | 37.33 | B | N |
| ATOM | 2587 | CA | ARG | B | 143 | 29.551 | 27.541 | 12.540 | 1.00 | 34.79 | B | C |
| ATOM | 2588 | CB | ARG | B | 143 | 29.092 | 26.131 | 12.175 | 1.00 | 28.59 | B | C |
| ATOM | 2589 | CG | ARG | B | 143 | 29.982 | 25.494 | 11.128 | 1.00 | 34.05 | B | C |
| ATOM | 2590 | CD | ARG | B | 143 | 30.004 | 23.982 | 11.206 | 1.00 | 36.62 | B | C |
| ATOM | 2591 | NE | ARG | B | 143 | 28.673 | 23.424 | 11.045 | 1.00 | 39.62 | B | N |
| ATOM | 2592 | CZ | ARG | B | 143 | 28.159 | 22.499 | 11.838 | 1.00 | 39.89 | B | C |
| ATOM | 2593 | NH1 | ARG | B | 143 | 28.879 | 22.000 | 12.838 | 1.00 | 40.33 | B | N |

TABLE 13-continued

Coordinates for proMMP9(35-444 ΔFnII) (SEQ ID NO: 12) complex with Example 3

| ATOM | 2594 | NH2 | ARG | B | 143 | 26.934 | 22.060 | 11.612 | 1.00 | 43.27 | B | N |
|---|---|---|---|---|---|---|---|---|---|---|---|---|
| ATOM | 2595 | C | ARG | B | 143 | 28.461 | 28.292 | 13.301 | 1.00 | 38.47 | B | C |
| ATOM | 2596 | O | ARG | B | 143 | 27.743 | 29.111 | 12.725 | 1.00 | 43.47 | B | O |
| ATOM | 2597 | N | ALA | B | 144 | 28.329 | 28.019 | 14.592 | 1.00 | 31.03 | B | N |
| ATOM | 2598 | CA | ALA | B | 144 | 27.395 | 28.780 | 15.397 | 1.00 | 32.58 | B | C |
| ATOM | 2599 | CB | ALA | B | 144 | 27.496 | 28.366 | 16.852 | 1.00 | 42.03 | B | C |
| ATOM | 2600 | C | ALA | B | 144 | 27.615 | 30.290 | 15.247 | 1.00 | 33.31 | B | C |
| ATOM | 2601 | O | ALA | B | 144 | 26.674 | 31.045 | 14.996 | 1.00 | 37.33 | B | O |
| ATOM | 2602 | N | PHE | B | 145 | 28.856 | 30.732 | 15.402 | 1.00 | 34.57 | B | N |
| ATOM | 2603 | CA | PHE | B | 145 | 29.169 | 32.151 | 15.277 | 1.00 | 35.40 | B | C |
| ATOM | 2604 | CB | PHE | B | 145 | 30.628 | 32.425 | 15.662 | 1.00 | 34.39 | B | C |
| ATOM | 2605 | CG | PHE | B | 145 | 30.881 | 32.367 | 17.141 | 1.00 | 36.43 | B | C |
| ATOM | 2606 | CD1 | PHE | B | 145 | 30.177 | 33.181 | 18.007 | 1.00 | 32.92 | B | C |
| ATOM | 2607 | CD2 | PHE | B | 145 | 31.828 | 31.502 | 17.667 | 1.00 | 40.02 | B | C |
| ATOM | 2608 | CE1 | PHE | B | 145 | 30.402 | 33.125 | 19.368 | 1.00 | 32.33 | B | C |
| ATOM | 2609 | CE2 | PHE | B | 145 | 32.057 | 31.443 | 19.030 | 1.00 | 34.61 | B | C |
| ATOM | 2610 | CZ | PHE | B | 145 | 31.346 | 32.260 | 19.878 | 1.00 | 36.72 | B | C |
| ATOM | 2611 | C | PHE | B | 145 | 28.863 | 32.693 | 13.877 | 1.00 | 33.93 | B | C |
| ATOM | 2612 | O | PHE | B | 145 | 28.481 | 33.852 | 13.720 | 1.00 | 36.70 | B | O |
| ATOM | 2613 | N | ALA | B | 146 | 29.021 | 31.852 | 12.864 | 1.00 | 31.41 | B | N |
| ATOM | 2614 | CA | ALA | B | 146 | 28.779 | 32.279 | 11.490 | 1.00 | 31.63 | B | C |
| ATOM | 2615 | CB | ALA | B | 146 | 29.433 | 31.332 | 10.518 | 1.00 | 25.44 | B | C |
| ATOM | 2616 | C | ALA | B | 146 | 27.294 | 32.434 | 11.163 | 1.00 | 38.07 | B | C |
| ATOM | 2617 | O | ALA | B | 146 | 26.952 | 32.987 | 10.107 | 1.00 | 43.68 | B | O |
| ATOM | 2618 | N | LEU | B | 147 | 26.417 | 31.934 | 12.040 | 1.00 | 29.99 | B | N |
| ATOM | 2619 | CA | LEU | B | 147 | 24.987 | 32.219 | 11.926 | 1.00 | 29.38 | B | C |
| ATOM | 2620 | CB | LEU | B | 147 | 24.152 | 31.338 | 12.855 | 1.00 | 31.83 | B | C |
| ATOM | 2621 | CG | LEU | B | 147 | 23.960 | 29.853 | 12.561 | 1.00 | 37.60 | B | C |
| ATOM | 2622 | CD1 | LEU | B | 147 | 23.435 | 29.167 | 13.800 | 1.00 | 27.62 | B | C |
| ATOM | 2623 | CD2 | LEU | B | 147 | 23.041 | 29.627 | 11.361 | 1.00 | 26.68 | B | C |
| ATOM | 2624 | C | LEU | B | 147 | 24.746 | 33.659 | 12.319 | 1.00 | 34.14 | B | C |
| ATOM | 2625 | O | LEU | B | 147 | 24.024 | 34.391 | 11.634 | 1.00 | 33.22 | B | O |
| ATOM | 2626 | N | TRP | B | 148 | 25.356 | 34.046 | 13.439 | 1.00 | 33.33 | B | N |
| ATOM | 2627 | CA | TRP | B | 148 | 25.103 | 35.331 | 14.068 | 1.00 | 34.62 | B | C |
| ATOM | 2628 | CB | TRP | B | 148 | 25.461 | 35.273 | 15.560 | 1.00 | 33.73 | B | C |
| ATOM | 2629 | CG | TRP | B | 148 | 24.536 | 34.370 | 16.358 | 1.00 | 42.62 | B | C |
| ATOM | 2630 | CD2 | TRP | B | 148 | 23.134 | 34.578 | 16.621 | 1.00 | 34.51 | B | C |
| ATOM | 2631 | CE2 | TRP | B | 148 | 22.685 | 33.484 | 17.382 | 1.00 | 31.47 | B | C |
| ATOM | 2632 | CE3 | TRP | B | 148 | 22.220 | 35.584 | 16.288 | 1.00 | 33.64 | B | C |
| ATOM | 2633 | CD1 | TRP | B | 148 | 24.862 | 33.186 | 16.963 | 1.00 | 33.85 | B | C |
| ATOM | 2634 | NE1 | TRP | B | 148 | 23.757 | 32.653 | 17.575 | 1.00 | 33.77 | B | N |
| ATOM | 2635 | CZ2 | TRP | B | 148 | 21.362 | 33.364 | 17.820 | 1.00 | 34.08 | B | C |
| ATOM | 2636 | CZ3 | TRP | B | 148 | 20.899 | 35.459 | 16.722 | 1.00 | 33.77 | B | C |
| ATOM | 2637 | CH2 | TRP | B | 148 | 20.488 | 34.358 | 17.476 | 1.00 | 26.80 | B | C |
| ATOM | 2638 | C | TRP | B | 148 | 25.863 | 36.457 | 13.385 | 1.00 | 34.38 | B | C |
| ATOM | 2639 | O | TRP | B | 148 | 25.477 | 37.618 | 13.455 | 1.00 | 34.89 | B | O |
| ATOM | 2640 | N | SER | B | 149 | 26.952 | 36.106 | 12.725 | 1.00 | 34.89 | B | N |
| ATOM | 2641 | CA | SER | B | 149 | 27.780 | 37.102 | 12.063 | 1.00 | 37.77 | B | C |
| ATOM | 2642 | CB | SER | B | 149 | 29.110 | 36.477 | 11.654 | 1.00 | 32.84 | B | C |
| ATOM | 2643 | OG | SER | B | 149 | 29.711 | 37.242 | 10.634 | 1.00 | 44.99 | B | O |
| ATOM | 2644 | C | SER | B | 149 | 27.088 | 37.715 | 10.844 | 1.00 | 36.20 | B | C |
| ATOM | 2645 | O | SER | B | 149 | 27.028 | 38.932 | 10.699 | 1.00 | 41.48 | B | O |
| ATOM | 2646 | N | ALA | B | 150 | 26.567 | 36.865 | 9.971 | 1.00 | 33.94 | B | N |
| ATOM | 2647 | CA | ALA | B | 150 | 25.904 | 37.318 | 8.753 | 1.00 | 33.34 | B | C |
| ATOM | 2648 | CB | ALA | B | 150 | 25.418 | 36.120 | 7.963 | 1.00 | 29.49 | B | C |
| ATOM | 2649 | C | ALA | B | 150 | 24.734 | 38.261 | 9.019 | 1.00 | 35.61 | B | C |
| ATOM | 2650 | O | ALA | B | 150 | 24.268 | 38.949 | 8.107 | 1.00 | 32.62 | B | O |
| ATOM | 2651 | N | VAL | B | 151 | 24.243 | 38.269 | 10.258 | 1.00 | 33.12 | B | N |
| ATOM | 2652 | CA | VAL | B | 151 | 22.993 | 38.954 | 10.586 | 1.00 | 32.35 | B | C |
| ATOM | 2653 | CB | VAL | B | 151 | 21.948 | 37.993 | 11.202 | 1.00 | 35.06 | B | C |
| ATOM | 2654 | CG1 | VAL | B | 151 | 21.318 | 37.118 | 10.129 | 1.00 | 25.89 | B | C |
| ATOM | 2655 | CG2 | VAL | B | 151 | 22.578 | 37.160 | 12.318 | 1.00 | 31.20 | B | C |
| ATOM | 2656 | C | VAL | B | 151 | 23.200 | 40.115 | 11.543 | 1.00 | 31.88 | B | C |
| ATOM | 2657 | O | VAL | B | 151 | 22.243 | 40.797 | 11.898 | 1.00 | 32.20 | B | O |
| ATOM | 2658 | N | THR | B | 152 | 24.452 | 40.324 | 11.946 | 1.00 | 34.50 | B | N |
| ATOM | 2659 | CA | THR | B | 152 | 24.830 | 41.412 | 12.841 | 1.00 | 33.93 | B | C |
| ATOM | 2660 | CB | THR | B | 152 | 25.161 | 40.901 | 14.263 | 1.00 | 34.13 | B | C |
| ATOM | 2661 | OG1 | THR | B | 152 | 26.472 | 40.322 | 14.283 | 1.00 | 31.86 | B | O |
| ATOM | 2662 | CG2 | THR | B | 152 | 24.151 | 39.887 | 14.708 | 1.00 | 31.66 | B | C |
| ATOM | 2663 | C | THR | B | 152 | 26.060 | 42.135 | 12.309 | 1.00 | 35.18 | B | C |
| ATOM | 2664 | O | THR | B | 152 | 26.693 | 41.670 | 11.360 | 1.00 | 37.27 | B | O |
| ATOM | 2665 | N | PRO | B | 153 | 26.396 | 43.285 | 12.914 | 1.00 | 33.61 | B | N |
| ATOM | 2666 | CD | PRO | B | 153 | 25.540 | 44.083 | 13.804 | 1.00 | 35.29 | B | C |
| ATOM | 2667 | CA | PRO | B | 153 | 27.641 | 43.986 | 12.603 | 1.00 | 35.48 | B | C |
| ATOM | 2668 | CB | PRO | B | 153 | 27.373 | 45.418 | 13.099 | 1.00 | 33.59 | B | C |
| ATOM | 2669 | CG | PRO | B | 153 | 25.922 | 45.469 | 13.447 | 1.00 | 40.01 | B | C |
| ATOM | 2670 | C | PRO | B | 153 | 28.817 | 43.391 | 13.380 | 1.00 | 37.59 | B | C |

TABLE 13-continued

Coordinates for proMMP9(35-444 ΔFnII) (SEQ ID NO: 12) complex with Example 3

| ATOM | 2671 | O | PRO | B | 153 | 29.749 | 44.108 | 13.737 | 1.00 | 38.95 | B | O |
|---|---|---|---|---|---|---|---|---|---|---|---|---|
| ATOM | 2672 | N | LEU | B | 154 | 28.785 | 42.092 | 13.645 | 1.00 | 35.39 | B | N |
| ATOM | 2673 | CA | LEU | B | 154 | 29.873 | 41.494 | 14.403 | 1.00 | 37.49 | B | C |
| ATOM | 2674 | CB | LEU | B | 154 | 29.348 | 40.905 | 15.713 | 1.00 | 40.60 | B | C |
| ATOM | 2675 | CG | LEU | B | 154 | 28.620 | 41.899 | 16.616 | 1.00 | 37.22 | B | C |
| ATOM | 2676 | CD1 | LEU | B | 154 | 28.184 | 41.225 | 17.904 | 1.00 | 40.85 | B | C |
| ATOM | 2677 | CD2 | LEU | B | 154 | 29.497 | 43.094 | 16.914 | 1.00 | 34.40 | B | C |
| ATOM | 2678 | C | LEU | B | 154 | 30.698 | 40.456 | 13.635 | 1.00 | 42.35 | B | C |
| ATOM | 2679 | O | LEU | B | 154 | 30.176 | 39.727 | 12.782 | 1.00 | 40.30 | B | O |
| ATOM | 2680 | N | THR | B | 155 | 31.997 | 40.431 | 13.933 | 1.00 | 36.06 | B | N |
| ATOM | 2681 | CA | THR | B | 155 | 32.882 | 39.350 | 13.527 | 1.00 | 38.75 | B | C |
| ATOM | 2682 | CB | THR | B | 155 | 34.113 | 39.856 | 12.722 | 1.00 | 40.50 | B | C |
| ATOM | 2683 | OG1 | THR | B | 155 | 34.902 | 40.723 | 13.543 | 1.00 | 49.90 | B | O |
| ATOM | 2684 | CG2 | THR | B | 155 | 33.696 | 40.595 | 11.467 | 1.00 | 28.86 | B | C |
| ATOM | 2685 | C | THR | B | 155 | 33.381 | 38.640 | 14.782 | 1.00 | 37.09 | B | C |
| ATOM | 2686 | O | THR | B | 155 | 33.595 | 39.269 | 15.813 | 1.00 | 45.28 | B | O |
| ATOM | 2687 | N | PHE | B | 156 | 33.581 | 37.333 | 14.689 | 1.00 | 39.72 | B | N |
| ATOM | 2688 | CA | PHE | B | 156 | 34.015 | 36.538 | 15.835 | 1.00 | 41.10 | B | C |
| ATOM | 2689 | CB | PHE | B | 156 | 32.945 | 35.501 | 16.207 | 1.00 | 35.76 | B | C |
| ATOM | 2690 | CG | PHE | B | 156 | 31.583 | 36.097 | 16.472 | 1.00 | 38.58 | B | C |
| ATOM | 2691 | CD1 | PHE | B | 156 | 30.663 | 36.246 | 15.440 | 1.00 | 35.22 | B | C |
| ATOM | 2692 | CD2 | PHE | B | 156 | 31.229 | 36.514 | 17.748 | 1.00 | 33.15 | B | C |
| ATOM | 2693 | CE1 | PHE | B | 156 | 29.424 | 36.796 | 15.670 | 1.00 | 32.35 | B | C |
| ATOM | 2694 | CE2 | PHE | B | 156 | 29.985 | 37.069 | 17.991 | 1.00 | 34.02 | B | C |
| ATOM | 2695 | CZ | PHE | B | 156 | 29.080 | 37.209 | 16.949 | 1.00 | 36.26 | B | C |
| ATOM | 2696 | C | PHE | B | 156 | 35.350 | 35.843 | 15.569 | 1.00 | 40.45 | B | C |
| ATOM | 2697 | O | PHE | B | 156 | 35.433 | 34.959 | 14.730 | 1.00 | 40.21 | B | O |
| ATOM | 2698 | N | THR | B | 157 | 36.386 | 36.249 | 16.295 | 1.00 | 37.91 | B | N |
| ATOM | 2699 | CA | THR | B | 157 | 37.703 | 35.641 | 16.172 | 1.00 | 40.14 | B | C |
| ATOM | 2700 | CB | THR | B | 157 | 38.814 | 36.696 | 16.226 | 1.00 | 45.87 | B | C |
| ATOM | 2701 | OG1 | THR | B | 157 | 38.708 | 37.574 | 15.102 | 1.00 | 53.48 | B | O |
| ATOM | 2702 | CG2 | THR | B | 157 | 40.178 | 36.015 | 16.219 | 1.00 | 40.61 | B | C |
| ATOM | 2703 | C | THR | B | 157 | 37.985 | 34.690 | 17.319 | 1.00 | 45.36 | B | C |
| ATOM | 2704 | O | THR | B | 157 | 37.757 | 35.030 | 18.479 | 1.00 | 44.14 | B | O |
| ATOM | 2705 | N | ARG | B | 158 | 38.502 | 33.508 | 17.000 | 1.00 | 46.85 | B | N |
| ATOM | 2706 | CA | ARG | B | 158 | 38.929 | 32.572 | 18.033 | 1.00 | 42.93 | B | C |
| ATOM | 2707 | CB | ARG | B | 158 | 38.921 | 31.141 | 17.501 | 1.00 | 42.43 | B | C |
| ATOM | 2708 | CG | ARG | B | 158 | 39.632 | 30.170 | 18.424 | 1.00 | 43.77 | B | C |
| ATOM | 2709 | CD | ARG | B | 158 | 39.762 | 28.783 | 17.828 | 1.00 | 42.00 | B | C |
| ATOM | 2710 | NE | ARG | B | 158 | 40.458 | 27.899 | 18.757 | 1.00 | 43.13 | B | N |
| ATOM | 2711 | CZ | ARG | B | 158 | 40.652 | 26.601 | 18.554 | 1.00 | 45.87 | B | C |
| ATOM | 2712 | NH1 | ARG | B | 158 | 40.196 | 26.030 | 17.450 | 1.00 | 40.20 | B | N |
| ATOM | 2713 | NH2 | ARG | B | 158 | 41.292 | 25.871 | 19.462 | 1.00 | 48.03 | B | N |
| ATOM | 2714 | C | ARG | B | 158 | 40.335 | 32.908 | 18.510 | 1.00 | 44.60 | B | C |
| ATOM | 2715 | O | ARG | B | 158 | 41.255 | 33.010 | 17.704 | 1.00 | 46.17 | B | O |
| ATOM | 2716 | N | VAL | B | 159 | 40.505 | 33.076 | 19.816 | 1.00 | 41.59 | B | N |
| ATOM | 2717 | CA | VAL | B | 159 | 41.836 | 33.289 | 20.374 | 1.00 | 43.66 | B | C |
| ATOM | 2718 | CB | VAL | B | 159 | 41.918 | 34.632 | 21.100 | 1.00 | 41.73 | B | C |
| ATOM | 2719 | CG1 | VAL | B | 159 | 41.350 | 35.737 | 20.214 | 1.00 | 40.38 | B | C |
| ATOM | 2720 | CG2 | VAL | B | 159 | 41.168 | 34.560 | 22.416 | 1.00 | 45.42 | B | C |
| ATOM | 2721 | C | VAL | B | 159 | 42.250 | 32.155 | 21.324 | 1.00 | 44.45 | B | C |
| ATOM | 2722 | O | VAL | B | 159 | 41.452 | 31.275 | 21.643 | 1.00 | 42.73 | B | O |
| ATOM | 2723 | N | TYR | B | 160 | 43.501 | 32.176 | 21.771 | 1.00 | 43.06 | B | N |
| ATOM | 2724 | CA | TYR | B | 160 | 44.011 | 31.130 | 22.656 | 1.00 | 40.60 | B | C |
| ATOM | 2725 | CB | TYR | B | 160 | 45.095 | 30.323 | 21.943 | 1.00 | 42.08 | B | C |
| ATOM | 2726 | CG | TYR | B | 160 | 44.574 | 29.680 | 20.675 | 1.00 | 39.79 | B | C |
| ATOM | 2727 | CD1 | TYR | B | 160 | 44.348 | 30.436 | 19.537 | 1.00 | 38.54 | B | C |
| ATOM | 2728 | CE1 | TYR | B | 160 | 43.855 | 29.865 | 18.385 | 1.00 | 38.44 | B | C |
| ATOM | 2729 | CD2 | TYR | B | 160 | 44.273 | 28.333 | 20.629 | 1.00 | 36.72 | B | C |
| ATOM | 2730 | CE2 | TYR | B | 160 | 43.782 | 27.756 | 19.479 | 1.00 | 40.75 | B | C |
| ATOM | 2731 | CZ | TYR | B | 160 | 43.574 | 28.527 | 18.361 | 1.00 | 36.20 | B | C |
| ATOM | 2732 | OH | TYR | B | 160 | 43.088 | 27.956 | 17.211 | 1.00 | 37.41 | B | O |
| ATOM | 2733 | C | TYR | B | 160 | 44.502 | 31.704 | 23.988 | 1.00 | 44.59 | B | C |
| ATOM | 2734 | O | TYR | B | 160 | 45.160 | 31.028 | 24.777 | 1.00 | 46.58 | B | O |
| ATOM | 2735 | N | SER | B | 161 | 44.154 | 32.960 | 24.229 | 1.00 | 43.48 | B | N |
| ATOM | 2736 | CA | SER | B | 161 | 44.433 | 33.619 | 25.493 | 1.00 | 48.74 | B | C |
| ATOM | 2737 | CB | SER | B | 161 | 44.916 | 35.035 | 25.220 | 1.00 | 50.11 | B | C |
| ATOM | 2738 | OG | SER | B | 161 | 44.009 | 35.701 | 24.355 | 1.00 | 48.11 | B | O |
| ATOM | 2739 | C | SER | B | 161 | 43.148 | 33.680 | 26.314 | 1.00 | 51.38 | B | C |
| ATOM | 2740 | O | SER | B | 161 | 42.057 | 33.608 | 25.761 | 1.00 | 54.19 | B | O |
| ATOM | 2741 | N | ARG | B | 162 | 43.273 | 33.807 | 27.631 | 1.00 | 57.09 | B | N |
| ATOM | 2742 | CA | ARG | B | 162 | 42.109 | 34.045 | 28.483 | 1.00 | 54.46 | B | C |
| ATOM | 2743 | CB | ARG | B | 162 | 42.402 | 33.683 | 29.938 | 1.00 | 50.75 | B | C |
| ATOM | 2744 | CG | ARG | B | 162 | 43.570 | 34.421 | 30.557 | 1.00 | 54.15 | B | C |
| ATOM | 2745 | CD | ARG | B | 162 | 43.171 | 35.803 | 31.021 | 1.00 | 54.39 | B | C |
| ATOM | 2746 | NE | ARG | B | 162 | 44.338 | 36.662 | 31.160 | 1.00 | 68.06 | B | N |
| ATOM | 2747 | CZ | ARG | B | 162 | 44.284 | 37.958 | 31.437 | 1.00 | 62.11 | B | C |

TABLE 13-continued

Coordinates for proMMP9(35-444 ΔFnII) (SEQ ID NO: 12) complex with Example 3

| ATOM | 2748 | NH1 | ARG | B | 162 | 43.111 | 38.547 | 31.613 | 1.00 | 61.20 | B | N |
|------|------|-----|-----|---|-----|--------|--------|--------|------|-------|---|---|
| ATOM | 2749 | NH2 | ARG | B | 162 | 45.405 | 38.661 | 31.538 | 1.00 | 65.78 | B | N |
| ATOM | 2750 | C | ARG | B | 162 | 41.683 | 35.501 | 28.349 | 1.00 | 58.39 | B | C |
| ATOM | 2751 | O | ARG | B | 162 | 40.726 | 35.948 | 28.980 | 1.00 | 53.60 | B | O |
| ATOM | 2752 | N | ASP | B | 163 | 42.423 | 36.231 | 27.520 | 1.00 | 62.85 | B | N |
| ATOM | 2753 | CA | ASP | B | 163 | 42.030 | 37.560 | 27.079 | 1.00 | 66.16 | B | C |
| ATOM | 2754 | CB | ASP | B | 163 | 43.248 | 38.318 | 26.524 | 1.00 | 65.73 | B | C |
| ATOM | 2755 | CG | ASP | B | 163 | 42.901 | 39.724 | 26.030 | 1.00 | 80.17 | B | C |
| ATOM | 2756 | OD1 | ASP | B | 163 | 41.744 | 40.162 | 26.220 | 1.00 | 79.18 | B | O |
| ATOM | 2757 | OD2 | ASP | B | 163 | 43.789 | 40.392 | 25.452 | 1.00 | 76.77 | B | O |
| ATOM | 2758 | C | ASP | B | 163 | 40.967 | 37.389 | 25.996 | 1.00 | 63.62 | B | C |
| ATOM | 2759 | O | ASP | B | 163 | 41.266 | 37.482 | 24.796 | 1.00 | 59.65 | B | O |
| ATOM | 2760 | N | ALA | B | 164 | 39.734 | 37.117 | 26.422 | 1.00 | 51.47 | B | N |
| ATOM | 2761 | CA | ALA | B | 164 | 38.631 | 36.915 | 25.483 | 1.00 | 49.69 | B | C |
| ATOM | 2762 | CB | ALA | B | 164 | 38.626 | 35.483 | 24.956 | 1.00 | 47.46 | B | C |
| ATOM | 2763 | C | ALA | B | 164 | 37.265 | 37.271 | 26.066 | 1.00 | 51.22 | B | C |
| ATOM | 2764 | O | ALA | B | 164 | 37.022 | 37.107 | 27.263 | 1.00 | 49.18 | B | O |
| ATOM | 2765 | N | ASP | B | 165 | 36.380 | 37.752 | 25.197 | 1.00 | 49.35 | B | N |
| ATOM | 2766 | CA | ASP | B | 165 | 35.020 | 38.121 | 25.569 | 1.00 | 44.53 | B | C |
| ATOM | 2767 | CB | ASP | B | 165 | 34.349 | 38.851 | 24.399 | 1.00 | 40.89 | B | C |
| ATOM | 2768 | CG | ASP | B | 165 | 35.162 | 40.035 | 23.899 | 1.00 | 48.66 | B | C |
| ATOM | 2769 | OD1 | ASP | B | 165 | 35.631 | 40.834 | 24.738 | 1.00 | 54.11 | B | O |
| ATOM | 2770 | OD2 | ASP | B | 165 | 35.321 | 40.178 | 22.663 | 1.00 | 43.94 | B | O |
| ATOM | 2771 | C | ASP | B | 165 | 34.187 | 36.891 | 25.947 | 1.00 | 44.06 | B | C |
| ATOM | 2772 | O | ASP | B | 165 | 33.503 | 36.865 | 26.976 | 1.00 | 42.52 | B | O |
| ATOM | 2773 | N | ILE | B | 166 | 34.242 | 35.879 | 25.092 | 1.00 | 38.70 | B | N |
| ATOM | 2774 | CA | ILE | B | 166 | 33.434 | 34.681 | 25.248 | 1.00 | 40.09 | B | C |
| ATOM | 2775 | CB | ILE | B | 166 | 32.635 | 34.402 | 23.957 | 1.00 | 39.77 | B | C |
| ATOM | 2776 | CG2 | ILE | B | 166 | 32.076 | 32.962 | 23.932 | 1.00 | 32.15 | B | C |
| ATOM | 2777 | CG1 | ILE | B | 166 | 31.543 | 35.459 | 23.785 | 1.00 | 40.62 | B | C |
| ATOM | 2778 | CD1 | ILE | B | 166 | 30.969 | 35.531 | 22.382 | 1.00 | 43.36 | B | C |
| ATOM | 2779 | C | ILE | B | 166 | 34.316 | 33.481 | 25.564 | 1.00 | 43.67 | B | C |
| ATOM | 2780 | O | ILE | B | 166 | 34.941 | 32.912 | 24.669 | 1.00 | 44.03 | B | O |
| ATOM | 2781 | N | VAL | B | 167 | 34.385 | 33.099 | 26.835 | 1.00 | 40.56 | B | N |
| ATOM | 2782 | CA | VAL | B | 167 | 35.142 | 31.907 | 27.183 | 1.00 | 43.55 | B | C |
| ATOM | 2783 | CB | VAL | B | 167 | 35.820 | 32.020 | 28.548 | 1.00 | 44.36 | B | C |
| ATOM | 2784 | CG1 | VAL | B | 167 | 36.403 | 30.673 | 28.945 | 1.00 | 43.21 | B | C |
| ATOM | 2785 | CG2 | VAL | B | 167 | 36.905 | 33.079 | 28.501 | 1.00 | 42.28 | B | C |
| ATOM | 2786 | C | VAL | B | 167 | 34.244 | 30.688 | 27.162 | 1.00 | 40.78 | B | C |
| ATOM | 2787 | O | VAL | B | 167 | 33.297 | 30.603 | 27.939 | 1.00 | 45.31 | B | O |
| ATOM | 2788 | N | ILE | B | 168 | 34.536 | 29.751 | 26.263 | 1.00 | 39.57 | B | N |
| ATOM | 2789 | CA | ILE | B | 168 | 33.772 | 28.512 | 26.172 | 1.00 | 39.97 | B | C |
| ATOM | 2790 | CB | ILE | B | 168 | 33.828 | 27.938 | 24.772 | 1.00 | 42.34 | B | C |
| ATOM | 2791 | CG2 | ILE | B | 168 | 33.161 | 26.568 | 24.732 | 1.00 | 44.20 | B | C |
| ATOM | 2792 | CG1 | ILE | B | 168 | 33.180 | 28.893 | 23.776 | 1.00 | 45.33 | B | C |
| ATOM | 2793 | CD1 | ILE | B | 168 | 33.616 | 28.621 | 22.344 | 1.00 | 43.76 | B | C |
| ATOM | 2794 | C | ILE | B | 168 | 34.316 | 27.457 | 27.130 | 1.00 | 44.53 | B | C |
| ATOM | 2795 | O | ILE | B | 168 | 35.528 | 27.336 | 27.299 | 1.00 | 46.20 | B | O |
| ATOM | 2796 | N | GLN | B | 169 | 33.422 | 26.693 | 27.751 | 1.00 | 43.06 | B | N |
| ATOM | 2797 | CA | GLN | B | 169 | 33.827 | 25.700 | 28.740 | 1.00 | 44.66 | B | C |
| ATOM | 2798 | CB | GLN | B | 169 | 33.982 | 26.348 | 30.116 | 1.00 | 43.34 | B | C |
| ATOM | 2799 | CG | GLN | B | 169 | 34.202 | 25.340 | 31.236 | 1.00 | 47.07 | B | C |
| ATOM | 2800 | CD | GLN | B | 169 | 34.097 | 25.955 | 32.625 | 1.00 | 51.75 | B | C |
| ATOM | 2801 | OE1 | GLN | B | 169 | 33.675 | 27.100 | 32.782 | 1.00 | 51.62 | B | O |
| ATOM | 2802 | NE2 | GLN | B | 169 | 34.479 | 25.189 | 33.642 | 1.00 | 51.96 | B | N |
| ATOM | 2803 | C | GLN | B | 169 | 32.884 | 24.503 | 28.859 | 1.00 | 46.19 | B | C |
| ATOM | 2804 | O | GLN | B | 169 | 31.665 | 24.656 | 28.931 | 1.00 | 48.58 | B | O |
| ATOM | 2805 | N | PHE | B | 170 | 33.467 | 23.311 | 28.897 | 1.00 | 45.67 | B | N |
| ATOM | 2806 | CA | PHE | B | 170 | 32.735 | 22.102 | 29.235 | 1.00 | 40.96 | B | C |
| ATOM | 2807 | CB | PHE | B | 170 | 33.238 | 20.931 | 28.392 | 1.00 | 46.03 | B | C |
| ATOM | 2808 | CG | PHE | B | 170 | 32.888 | 21.030 | 26.934 | 1.00 | 43.00 | B | C |
| ATOM | 2809 | CD1 | PHE | B | 170 | 33.678 | 21.768 | 26.066 | 1.00 | 45.97 | B | C |
| ATOM | 2810 | CD2 | PHE | B | 170 | 31.775 | 20.379 | 26.430 | 1.00 | 42.44 | B | C |
| ATOM | 2811 | CE1 | PHE | B | 170 | 33.368 | 21.857 | 24.716 | 1.00 | 41.65 | B | C |
| ATOM | 2812 | CE2 | PHE | B | 170 | 31.452 | 20.467 | 25.083 | 1.00 | 39.21 | B | C |
| ATOM | 2813 | CZ | PHE | B | 170 | 32.256 | 21.205 | 24.226 | 1.00 | 42.19 | B | C |
| ATOM | 2814 | C | PHE | B | 170 | 32.949 | 21.796 | 30.711 | 1.00 | 43.48 | B | C |
| ATOM | 2815 | O | PHE | B | 170 | 34.080 | 21.838 | 31.196 | 1.00 | 42.06 | B | O |
| ATOM | 2816 | N | GLY | B | 171 | 31.868 | 21.488 | 31.425 | 1.00 | 44.89 | B | N |
| ATOM | 2817 | CA | GLY | B | 171 | 31.963 | 21.199 | 32.846 | 1.00 | 42.34 | B | C |
| ATOM | 2818 | C | GLY | B | 171 | 30.835 | 20.321 | 33.350 | 1.00 | 48.05 | B | C |
| ATOM | 2819 | O | GLY | B | 171 | 29.768 | 20.264 | 32.745 | 1.00 | 52.63 | B | O |
| ATOM | 2820 | N | VAL | B | 172 | 31.066 | 19.629 | 34.459 | 1.00 | 47.23 | B | N |
| ATOM | 2821 | CA | VAL | B | 172 | 30.035 | 18.765 | 35.036 | 1.00 | 50.19 | B | C |
| ATOM | 2822 | CB | VAL | B | 172 | 30.491 | 17.289 | 35.090 | 1.00 | 48.13 | B | C |
| ATOM | 2823 | CG1 | VAL | B | 172 | 30.175 | 16.581 | 33.783 | 1.00 | 46.92 | B | C |
| ATOM | 2824 | CG2 | VAL | B | 172 | 31.969 | 17.207 | 35.395 | 1.00 | 45.77 | B | C |

TABLE 13-continued

Coordinates for proMMP9(35-444 ΔFnII) (SEQ ID NO: 12) complex with Example 3

| ATOM | 2825 | C | VAL | B | 172 | 29.615 | 19.221 | 36.432 | 1.00 | 50.74 | B | C |
|------|------|------|-----|---|-----|--------|--------|--------|------|-------|---|---|
| ATOM | 2826 | O | VAL | B | 172 | 30.453 | 19.636 | 37.246 | 1.00 | 52.67 | B | O |
| ATOM | 2827 | N | ALA | B | 173 | 28.319 | 19.151 | 36.712 | 1.00 | 44.07 | B | N |
| ATOM | 2828 | CA | ALA | B | 173 | 27.835 | 19.540 | 38.028 | 1.00 | 49.14 | B | C |
| ATOM | 2829 | CB | ALA | B | 173 | 28.348 | 18.571 | 39.074 | 1.00 | 46.26 | B | C |
| ATOM | 2830 | C | ALA | B | 173 | 28.310 | 20.950 | 38.350 | 1.00 | 55.73 | B | C |
| ATOM | 2831 | O | ALA | B | 173 | 28.293 | 21.832 | 37.488 | 1.00 | 55.80 | B | O |
| ATOM | 2832 | N | GLU | B | 174 | 28.735 | 21.160 | 39.593 | 1.00 | 57.47 | B | N |
| ATOM | 2833 | CA | GLU | B | 174 | 29.381 | 22.410 | 39.976 | 1.00 | 55.99 | B | C |
| ATOM | 2834 | CB | GLU | B | 174 | 29.635 | 22.450 | 41.483 | 1.00 | 51.82 | B | C |
| ATOM | 2835 | CG | GLU | B | 174 | 30.499 | 23.608 | 41.929 | 1.00 | 54.91 | B | C |
| ATOM | 2836 | CD | GLU | B | 174 | 29.758 | 24.935 | 41.935 | 1.00 | 61.90 | B | C |
| ATOM | 2837 | OE1 | GLU | B | 174 | 28.645 | 24.998 | 42.509 | 1.00 | 57.17 | B | O |
| ATOM | 2838 | OE2 | GLU | B | 174 | 30.302 | 25.919 | 41.378 | 1.00 | 58.73 | B | O |
| ATOM | 2839 | C | GLU | B | 174 | 30.693 | 22.512 | 39.206 | 1.00 | 57.40 | B | C |
| ATOM | 2840 | O | GLU | B | 174 | 31.535 | 21.611 | 39.267 | 1.00 | 54.64 | B | O |
| ATOM | 2841 | N | HIS | B | 175 | 30.857 | 23.597 | 38.460 | 1.00 | 57.49 | B | N |
| ATOM | 2842 | CA | HIS | B | 175 | 31.982 | 23.705 | 37.543 | 1.00 | 44.72 | B | C |
| ATOM | 2843 | CB | HIS | B | 175 | 31.530 | 23.453 | 36.098 | 1.00 | 42.64 | B | C |
| ATOM | 2844 | CG | HIS | B | 175 | 30.330 | 24.252 | 35.685 | 1.00 | 45.53 | B | C |
| ATOM | 2845 | CD2 | HIS | B | 175 | 30.214 | 25.342 | 34.891 | 1.00 | 41.79 | B | C |
| ATOM | 2846 | ND1 | HIS | B | 175 | 29.051 | 23.945 | 36.099 | 1.00 | 48.06 | B | N |
| ATOM | 2847 | CE1 | HIS | B | 175 | 28.201 | 24.812 | 35.580 | 1.00 | 41.78 | B | C |
| ATOM | 2848 | NE2 | HIS | B | 175 | 28.880 | 25.671 | 34.845 | 1.00 | 39.88 | B | N |
| ATOM | 2849 | C | HIS | B | 175 | 32.689 | 25.043 | 37.677 | 1.00 | 48.27 | B | C |
| ATOM | 2850 | O | HIS | B | 175 | 33.553 | 25.380 | 36.867 | 1.00 | 50.09 | B | O |
| ATOM | 2851 | N | GLY | B | 176 | 32.321 | 25.808 | 38.702 | 1.00 | 52.16 | B | N |
| ATOM | 2852 | CA | GLY | B | 176 | 33.081 | 26.993 | 39.063 | 1.00 | 43.07 | B | C |
| ATOM | 2853 | C | GLY | B | 176 | 32.326 | 28.303 | 39.129 | 1.00 | 46.08 | B | C |
| ATOM | 2854 | O | GLY | B | 176 | 32.943 | 29.363 | 39.061 | 1.00 | 40.72 | B | O |
| ATOM | 2855 | N | ASP | B | 177 | 31.003 | 28.248 | 39.275 | 1.00 | 48.62 | B | N |
| ATOM | 2856 | CA | ASP | B | 177 | 30.197 | 29.472 | 39.279 | 1.00 | 44.01 | B | C |
| ATOM | 2857 | CB | ASP | B | 177 | 29.889 | 29.933 | 37.848 | 1.00 | 41.94 | B | C |
| ATOM | 2858 | CG | ASP | B | 177 | 29.104 | 28.905 | 37.050 | 1.00 | 47.06 | B | C |
| ATOM | 2859 | OD1 | ASP | B | 177 | 28.866 | 27.787 | 37.558 | 1.00 | 44.94 | B | O |
| ATOM | 2860 | OD2 | ASP | B | 177 | 28.727 | 29.219 | 35.901 | 1.00 | 47.72 | B | O |
| ATOM | 2861 | C | ASP | B | 177 | 28.907 | 29.359 | 40.087 | 1.00 | 51.23 | B | C |
| ATOM | 2862 | O | ASP | B | 177 | 28.091 | 30.280 | 40.107 | 1.00 | 50.83 | B | O |
| ATOM | 2863 | N | GLY | B | 178 | 28.721 | 28.230 | 40.755 | 1.00 | 51.61 | B | N |
| ATOM | 2864 | CA | GLY | B | 178 | 27.546 | 28.053 | 41.581 | 1.00 | 52.55 | B | C |
| ATOM | 2865 | C | GLY | B | 178 | 26.259 | 28.141 | 40.786 | 1.00 | 58.22 | B | C |
| ATOM | 2866 | O | GLY | B | 178 | 25.198 | 28.471 | 41.326 | 1.00 | 60.58 | B | O |
| ATOM | 2867 | N | TYR | B | 179 | 26.359 | 27.864 | 39.492 | 1.00 | 51.97 | B | N |
| ATOM | 2868 | CA | TYR | B | 179 | 25.193 | 27.567 | 38.680 | 1.00 | 46.35 | B | C |
| ATOM | 2869 | CB | TYR | B | 179 | 25.042 | 28.566 | 37.543 | 1.00 | 41.86 | B | C |
| ATOM | 2870 | CG | TYR | B | 179 | 24.706 | 29.972 | 37.965 | 1.00 | 43.83 | B | C |
| ATOM | 2871 | CD1 | TYR | B | 179 | 25.652 | 30.976 | 37.876 | 1.00 | 44.97 | B | C |
| ATOM | 2872 | CE1 | TYR | B | 179 | 25.361 | 32.270 | 38.239 | 1.00 | 44.18 | B | C |
| ATOM | 2873 | CD2 | TYR | B | 179 | 23.438 | 30.305 | 38.426 | 1.00 | 46.17 | B | C |
| ATOM | 2874 | CE2 | TYR | B | 179 | 23.134 | 31.612 | 38.795 | 1.00 | 46.68 | B | C |
| ATOM | 2875 | CZ | TYR | B | 179 | 24.109 | 32.591 | 38.697 | 1.00 | 44.80 | B | C |
| ATOM | 2876 | OH | TYR | B | 179 | 23.860 | 33.899 | 39.062 | 1.00 | 41.72 | B | O |
| ATOM | 2877 | C | TYR | B | 179 | 25.426 | 26.184 | 38.099 | 1.00 | 49.16 | B | C |
| ATOM | 2878 | O | TYR | B | 179 | 25.513 | 26.026 | 36.885 | 1.00 | 50.26 | B | O |
| ATOM | 2879 | N | PRO | B | 180 | 25.533 | 25.176 | 38.975 | 1.00 | 52.31 | B | N |
| ATOM | 2880 | CD | PRO | B | 180 | 25.049 | 25.254 | 40.364 | 1.00 | 54.19 | B | C |
| ATOM | 2881 | CA | PRO | B | 180 | 25.972 | 23.822 | 38.619 | 1.00 | 46.42 | B | C |
| ATOM | 2882 | CB | PRO | B | 180 | 25.927 | 23.072 | 39.961 | 1.00 | 55.60 | B | C |
| ATOM | 2883 | CG | PRO | B | 180 | 25.738 | 24.115 | 41.022 | 1.00 | 55.32 | B | C |
| ATOM | 2884 | C | PRO | B | 180 | 25.016 | 23.153 | 37.644 | 1.00 | 48.18 | B | C |
| ATOM | 2885 | O | PRO | B | 180 | 23.836 | 23.502 | 37.630 | 1.00 | 53.31 | B | O |
| ATOM | 2886 | N | PHE | B | 181 | 25.509 | 22.200 | 36.855 | 1.00 | 50.24 | B | N |
| ATOM | 2887 | CA | PHE | B | 181 | 24.640 | 21.419 | 35.972 | 1.00 | 48.65 | B | C |
| ATOM | 2888 | C | PHE | B | 181 | 24.031 | 20.227 | 36.712 | 1.00 | 50.88 | B | C |
| ATOM | 2889 | CB | PHE | B | 181 | 25.393 | 20.929 | 34.738 | 1.00 | 47.06 | B | C |
| ATOM | 2890 | CG | PHE | B | 181 | 25.921 | 22.030 | 33.870 | 1.00 | 47.77 | B | C |
| ATOM | 2891 | CD1 | PHE | B | 181 | 25.091 | 23.053 | 33.442 | 1.00 | 48.13 | B | C |
| ATOM | 2892 | CD2 | PHE | B | 181 | 27.251 | 22.033 | 33.466 | 1.00 | 48.92 | B | C |
| ATOM | 2893 | CE1 | PHE | B | 181 | 25.578 | 24.070 | 32.638 | 1.00 | 42.30 | B | C |
| ATOM | 2894 | CE2 | PHE | B | 181 | 27.749 | 23.047 | 32.661 | 1.00 | 42.34 | B | C |
| ATOM | 2895 | CZ | PHE | B | 181 | 26.909 | 24.068 | 32.248 | 1.00 | 46.60 | B | C |
| ATOM | 2896 | O | PHE | B | 181 | 24.172 | 20.102 | 37.928 | 1.00 | 48.68 | B | O |
| ATOM | 2897 | N | ASP | B | 182 | 23.370 | 19.345 | 35.968 | 1.00 | 52.28 | B | N |
| ATOM | 2898 | CA | ASP | B | 182 | 22.610 | 18.248 | 36.567 | 1.00 | 49.03 | B | C |
| ATOM | 2899 | CB | ASP | B | 182 | 21.123 | 18.611 | 36.604 | 1.00 | 53.03 | B | C |
| ATOM | 2900 | CG | ASP | B | 182 | 20.594 | 19.051 | 35.243 | 1.00 | 48.84 | B | C |
| ATOM | 2901 | OD1 | ASP | B | 182 | 21.001 | 20.125 | 34.769 | 1.00 | 51.57 | B | O |

TABLE 13-continued

Coordinates for proMMP9(35-444 ΔFnII) (SEQ ID NO: 12) complex with Example 3

| ATOM | 2902 | OD2 | ASP | B | 182 | 19.767 | 18.334 | 34.645 | 1.00 | 49.97 | B | O |
|------|------|-----|-----|---|-----|--------|--------|--------|------|-------|---|---|
| ATOM | 2903 | C | ASP | B | 182 | 22.770 | 16.944 | 35.797 | 1.00 | 48.62 | B | C |
| ATOM | 2904 | O | ASP | B | 182 | 21.840 | 16.498 | 35.133 | 1.00 | 56.89 | B | O |
| ATOM | 2905 | N | GLY | B | 183 | 23.944 | 16.334 | 35.876 | 1.00 | 48.83 | B | N |
| ATOM | 2906 | CA | GLY | B | 183 | 24.173 | 15.066 | 35.206 | 1.00 | 51.53 | B | C |
| ATOM | 2907 | C | GLY | B | 183 | 23.447 | 14.934 | 33.878 | 1.00 | 50.37 | B | C |
| ATOM | 2908 | O | GLY | B | 183 | 23.465 | 15.846 | 33.065 | 1.00 | 47.97 | B | O |
| ATOM | 2909 | N | LYS | B | 184 | 22.796 | 13.798 | 33.656 | 1.00 | 54.02 | B | N |
| ATOM | 2910 | CA | LYS | B | 184 | 22.202 | 13.527 | 32.351 | 1.00 | 54.69 | B | C |
| ATOM | 2911 | CB | LYS | B | 184 | 22.062 | 12.020 | 32.103 | 1.00 | 50.22 | B | C |
| ATOM | 2912 | CG | LYS | B | 184 | 21.265 | 11.700 | 30.846 | 1.00 | 55.82 | B | C |
| ATOM | 2913 | CD | LYS | B | 184 | 21.489 | 10.279 | 30.355 | 1.00 | 62.30 | B | C |
| ATOM | 2914 | CE | LYS | B | 184 | 20.546 | 9.292 | 31.014 | 1.00 | 54.49 | B | C |
| ATOM | 2915 | NZ | LYS | B | 184 | 20.863 | 7.904 | 30.565 | 1.00 | 49.38 | B | N |
| ATOM | 2916 | C | LYS | B | 184 | 20.864 | 14.228 | 32.133 | 1.00 | 50.03 | B | C |
| ATOM | 2917 | O | LYS | B | 184 | 20.000 | 14.213 | 33.001 | 1.00 | 47.67 | B | O |
| ATOM | 2918 | N | ASP | B | 185 | 20.714 | 14.838 | 30.960 | 1.00 | 52.04 | B | N |
| ATOM | 2919 | CA | ASP | B | 185 | 19.471 | 15.501 | 30.562 | 1.00 | 49.55 | B | C |
| ATOM | 2920 | CB | ASP | B | 185 | 18.334 | 14.486 | 30.491 | 1.00 | 47.32 | B | C |
| ATOM | 2921 | CG | ASP | B | 185 | 18.639 | 13.351 | 29.539 | 1.00 | 55.03 | B | C |
| ATOM | 2922 | OD1 | ASP | B | 185 | 19.783 | 13.301 | 29.034 | 1.00 | 52.08 | B | O |
| ATOM | 2923 | OD2 | ASP | B | 185 | 17.741 | 12.514 | 29.292 | 1.00 | 53.51 | B | O |
| ATOM | 2924 | C | ASP | B | 185 | 19.098 | 16.660 | 31.475 | 1.00 | 45.20 | B | C |
| ATOM | 2925 | O | ASP | B | 185 | 19.775 | 16.927 | 32.456 | 1.00 | 51.87 | B | O |
| ATOM | 2926 | N | GLY | B | 186 | 18.014 | 17.350 | 31.148 | 1.00 | 47.60 | B | N |
| ATOM | 2927 | CA | GLY | B | 186 | 17.554 | 18.456 | 31.967 | 1.00 | 49.59 | B | C |
| ATOM | 2928 | C | GLY | B | 186 | 18.143 | 19.765 | 31.485 | 1.00 | 49.74 | B | C |
| ATOM | 2929 | O | GLY | B | 186 | 17.844 | 20.212 | 30.380 | 1.00 | 44.77 | B | O |
| ATOM | 2930 | N | LEU | B | 187 | 18.971 | 20.384 | 32.320 | 1.00 | 50.57 | B | N |
| ATOM | 2931 | CA | LEU | B | 187 | 19.734 | 21.547 | 31.898 | 1.00 | 49.94 | B | C |
| ATOM | 2932 | CB | LEU | B | 187 | 20.384 | 22.243 | 33.092 | 1.00 | 49.22 | B | C |
| ATOM | 2933 | CG | LEU | B | 187 | 19.580 | 23.251 | 33.897 | 1.00 | 53.67 | B | C |
| ATOM | 2934 | CD1 | LEU | B | 187 | 18.299 | 22.608 | 34.396 | 1.00 | 55.66 | B | C |
| ATOM | 2935 | CD2 | LEU | B | 187 | 20.423 | 23.771 | 35.052 | 1.00 | 47.79 | B | C |
| ATOM | 2936 | C | LEU | B | 187 | 20.832 | 21.101 | 30.941 | 1.00 | 52.02 | B | C |
| ATOM | 2937 | O | LEU | B | 187 | 21.762 | 20.405 | 31.341 | 1.00 | 49.29 | B | O |
| ATOM | 2938 | N | LEU | B | 188 | 20.732 | 21.509 | 29.682 | 1.00 | 47.59 | B | N |
| ATOM | 2939 | CA | LEU | B | 188 | 21.762 | 21.195 | 28.710 | 1.00 | 40.48 | B | C |
| ATOM | 2940 | CB | LEU | B | 188 | 21.182 | 21.242 | 27.299 | 1.00 | 45.07 | B | C |
| ATOM | 2941 | CG | LEU | B | 188 | 20.157 | 20.123 | 27.125 | 1.00 | 50.89 | B | C |
| ATOM | 2942 | CD1 | LEU | B | 188 | 19.686 | 19.995 | 25.680 | 1.00 | 41.31 | B | C |
| ATOM | 2943 | CD2 | LEU | B | 188 | 20.755 | 18.809 | 27.636 | 1.00 | 45.67 | B | C |
| ATOM | 2944 | C | LEU | B | 188 | 22.980 | 22.110 | 28.844 | 1.00 | 41.35 | B | C |
| ATOM | 2945 | O | LEU | B | 188 | 24.117 | 21.635 | 28.890 | 1.00 | 44.85 | B | O |
| ATOM | 2946 | N | ALA | B | 189 | 22.744 | 23.415 | 28.918 | 1.00 | 33.97 | B | N |
| ATOM | 2947 | CA | ALA | B | 189 | 23.827 | 24.377 | 29.028 | 1.00 | 33.93 | B | C |
| ATOM | 2948 | CB | ALA | B | 189 | 24.556 | 24.492 | 27.699 | 1.00 | 43.52 | B | C |
| ATOM | 2949 | C | ALA | B | 189 | 23.292 | 25.732 | 29.445 | 1.00 | 35.04 | B | C |
| ATOM | 2950 | O | ALA | B | 189 | 22.086 | 25.911 | 29.566 | 1.00 | 41.17 | B | O |
| ATOM | 2951 | N | HIS | B | 190 | 24.187 | 26.689 | 29.662 | 1.00 | 36.65 | B | N |
| ATOM | 2952 | CA | HIS | B | 190 | 23.786 | 28.061 | 29.947 | 1.00 | 34.63 | B | C |
| ATOM | 2953 | CB | HIS | B | 190 | 23.386 | 28.231 | 31.422 | 1.00 | 46.41 | B | C |
| ATOM | 2954 | CG | HIS | B | 190 | 24.481 | 27.920 | 32.398 | 1.00 | 44.75 | B | C |
| ATOM | 2955 | CD2 | HIS | B | 190 | 25.548 | 28.648 | 32.803 | 1.00 | 46.86 | B | C |
| ATOM | 2956 | ND1 | HIS | B | 190 | 24.542 | 26.735 | 33.097 | 1.00 | 45.91 | B | N |
| ATOM | 2957 | CE1 | HIS | B | 190 | 25.599 | 26.745 | 33.887 | 1.00 | 43.00 | B | C |
| ATOM | 2958 | NE2 | HIS | B | 190 | 26.227 | 27.893 | 33.726 | 1.00 | 41.21 | B | N |
| ATOM | 2959 | C | HIS | B | 190 | 24.876 | 29.046 | 29.581 | 1.00 | 34.46 | B | C |
| ATOM | 2960 | O | HIS | B | 190 | 26.022 | 28.667 | 29.406 | 1.00 | 42.07 | B | O |
| ATOM | 2961 | N | ALA | B | 191 | 24.515 | 30.314 | 29.452 | 1.00 | 41.51 | B | N |
| ATOM | 2962 | CA | ALA | B | 191 | 25.484 | 31.349 | 29.090 | 1.00 | 43.48 | B | C |
| ATOM | 2963 | CB | ALA | B | 191 | 25.475 | 31.612 | 27.574 | 1.00 | 31.30 | B | C |
| ATOM | 2964 | C | ALA | B | 191 | 25.157 | 32.622 | 29.852 | 1.00 | 42.76 | B | C |
| ATOM | 2965 | O | ALA | B | 191 | 24.109 | 32.722 | 30.472 | 1.00 | 39.63 | B | O |
| ATOM | 2966 | N | PHE | B | 192 | 26.056 | 33.594 | 29.784 | 1.00 | 43.65 | B | N |
| ATOM | 2967 | CA | PHE | B | 192 | 25.905 | 34.838 | 30.517 | 1.00 | 41.11 | B | C |
| ATOM | 2968 | CB | PHE | B | 192 | 26.983 | 34.891 | 31.590 | 1.00 | 43.47 | B | C |
| ATOM | 2969 | CG | PHE | B | 192 | 27.070 | 33.625 | 32.406 | 1.00 | 44.44 | B | C |
| ATOM | 2970 | CD1 | PHE | B | 192 | 26.457 | 33.536 | 33.647 | 1.00 | 50.44 | B | C |
| ATOM | 2971 | CD2 | PHE | B | 192 | 27.736 | 32.518 | 31.921 | 1.00 | 42.77 | B | C |
| ATOM | 2972 | CE1 | PHE | B | 192 | 26.521 | 32.366 | 34.393 | 1.00 | 49.07 | B | C |
| ATOM | 2973 | CE2 | PHE | B | 192 | 27.803 | 31.351 | 32.659 | 1.00 | 46.30 | B | C |
| ATOM | 2974 | CZ | PHE | B | 192 | 27.195 | 31.275 | 33.898 | 1.00 | 49.02 | B | C |
| ATOM | 2975 | C | PHE | B | 192 | 25.984 | 36.036 | 29.565 | 1.00 | 42.69 | B | C |
| ATOM | 2976 | O | PHE | B | 192 | 26.758 | 36.018 | 28.612 | 1.00 | 41.40 | B | O |
| ATOM | 2977 | N | PRO | B | 193 | 25.174 | 37.081 | 29.812 | 1.00 | 45.64 | B | N |
| ATOM | 2978 | CD | PRO | B | 193 | 24.496 | 37.379 | 31.077 | 1.00 | 41.52 | B | C |

TABLE 13-continued

Coordinates for proMMP9(35-444 ΔFnII) (SEQ ID NO: 12) complex with Example 3

| ATOM | 2979 | CA | PRO | B | 193 | 25.053 | 38.197 | 28.862 | 1.00 | 45.70 | B | C |
|------|------|-----|-----|---|-----|--------|--------|--------|------|-------|---|---|
| ATOM | 2980 | CB | PRO | B | 193 | 24.089 | 39.160 | 29.564 | 1.00 | 41.73 | B | C |
| ATOM | 2981 | CG | PRO | B | 193 | 23.505 | 38.399 | 30.664 | 1.00 | 48.56 | B | C |
| ATOM | 2982 | C | PRO | B | 193 | 26.392 | 38.893 | 28.612 | 1.00 | 41.65 | B | C |
| ATOM | 2983 | O | PRO | B | 193 | 27.357 | 38.667 | 29.348 | 1.00 | 41.71 | B | O |
| ATOM | 2984 | N | PRO | B | 194 | 26.457 | 39.729 | 27.572 | 1.00 | 40.24 | B | N |
| ATOM | 2985 | CD | PRO | B | 194 | 25.415 | 40.011 | 26.571 | 1.00 | 44.69 | B | C |
| ATOM | 2986 | CA | PRO | B | 194 | 27.711 | 40.422 | 27.267 | 1.00 | 44.34 | B | C |
| ATOM | 2987 | CB | PRO | B | 194 | 27.315 | 41.380 | 26.135 | 1.00 | 39.44 | B | C |
| ATOM | 2988 | CG | PRO | B | 194 | 26.181 | 40.719 | 25.468 | 1.00 | 41.39 | B | C |
| ATOM | 2989 | C | PRO | B | 194 | 28.232 | 41.204 | 28.468 | 1.00 | 39.87 | B | C |
| ATOM | 2990 | O | PRO | B | 194 | 27.455 | 41.694 | 29.271 | 1.00 | 37.37 | B | O |
| ATOM | 2991 | N | GLY | B | 195 | 29.547 | 41.315 | 28.582 | 1.00 | 47.17 | B | N |
| ATOM | 2992 | CA | GLY | B | 195 | 30.145 | 42.106 | 29.639 | 1.00 | 48.71 | B | C |
| ATOM | 2993 | C | GLY | B | 195 | 31.487 | 41.570 | 30.087 | 1.00 | 41.36 | B | C |
| ATOM | 2994 | O | GLY | B | 195 | 32.113 | 40.783 | 29.379 | 1.00 | 40.69 | B | O |
| ATOM | 2995 | N | PRO | B | 196 | 31.931 | 41.996 | 31.277 | 1.00 | 43.40 | B | N |
| ATOM | 2996 | CD | PRO | B | 196 | 31.238 | 43.035 | 32.048 | 1.00 | 49.89 | B | C |
| ATOM | 2997 | CA | PRO | B | 196 | 33.208 | 41.639 | 31.899 | 1.00 | 41.10 | B | C |
| ATOM | 2998 | CB | PRO | B | 196 | 33.470 | 42.811 | 32.857 | 1.00 | 43.13 | B | C |
| ATOM | 2999 | CG | PRO | B | 196 | 32.383 | 43.818 | 32.589 | 1.00 | 51.92 | B | C |
| ATOM | 3000 | C | PRO | B | 196 | 33.119 | 40.362 | 32.719 | 1.00 | 43.41 | B | C |
| ATOM | 3001 | O | PRO | B | 196 | 32.030 | 39.894 | 33.056 | 1.00 | 42.33 | B | O |
| ATOM | 3002 | N | GLY | B | 197 | 34.279 | 39.815 | 33.049 | 1.00 | 44.29 | B | N |
| ATOM | 3003 | CA | GLY | B | 197 | 34.362 | 38.650 | 33.900 | 1.00 | 41.34 | B | C |
| ATOM | 3004 | C | GLY | B | 197 | 33.814 | 37.411 | 33.240 | 1.00 | 42.48 | B | C |
| ATOM | 3005 | O | GLY | B | 197 | 34.206 | 37.055 | 32.131 | 1.00 | 40.92 | B | O |
| ATOM | 3006 | N | ILE | B | 198 | 32.911 | 36.743 | 33.944 | 1.00 | 45.32 | B | N |
| ATOM | 3007 | CA | ILE | B | 198 | 32.280 | 35.538 | 33.438 | 1.00 | 44.02 | B | C |
| ATOM | 3008 | CB | ILE | B | 198 | 31.574 | 34.769 | 34.576 | 1.00 | 47.53 | B | C |
| ATOM | 3009 | CG2 | ILE | B | 198 | 30.283 | 35.483 | 34.997 | 1.00 | 42.88 | B | C |
| ATOM | 3010 | CG1 | ILE | B | 198 | 31.299 | 33.321 | 34.160 | 1.00 | 51.07 | B | C |
| ATOM | 3011 | CD1 | ILE | B | 198 | 30.501 | 32.524 | 35.192 | 1.00 | 50.33 | B | C |
| ATOM | 3012 | C | ILE | B | 198 | 31.266 | 35.921 | 32.362 | 1.00 | 43.76 | B | C |
| ATOM | 3013 | O | ILE | B | 198 | 30.766 | 35.073 | 31.625 | 1.00 | 43.31 | B | O |
| ATOM | 3014 | N | GLN | B | 199 | 30.975 | 37.212 | 32.273 | 1.00 | 40.37 | B | N |
| ATOM | 3015 | CA | GLN | B | 199 | 29.950 | 37.686 | 31.361 | 1.00 | 44.09 | B | C |
| ATOM | 3016 | CB | GLN | B | 199 | 29.579 | 39.138 | 31.666 | 1.00 | 47.38 | B | C |
| ATOM | 3017 | CG | GLN | B | 199 | 28.424 | 39.278 | 32.645 | 1.00 | 39.09 | B | C |
| ATOM | 3018 | CD | GLN | B | 199 | 28.287 | 40.691 | 33.171 | 1.00 | 50.69 | B | C |
| ATOM | 3019 | OE1 | GLN | B | 199 | 27.473 | 41.476 | 32.677 | 1.00 | 44.79 | B | O |
| ATOM | 3020 | NE2 | GLN | B | 199 | 29.093 | 41.029 | 34.175 | 1.00 | 51.75 | B | N |
| ATOM | 3021 | C | GLN | B | 199 | 30.332 | 37.513 | 29.901 | 1.00 | 38.27 | B | C |
| ATOM | 3022 | O | GLN | B | 199 | 31.349 | 38.020 | 29.454 | 1.00 | 43.57 | B | O |
| ATOM | 3023 | N | GLY | B | 200 | 29.491 | 36.782 | 29.177 | 1.00 | 41.59 | B | N |
| ATOM | 3024 | CA | GLY | B | 200 | 29.689 | 36.502 | 27.771 | 1.00 | 38.06 | B | C |
| ATOM | 3025 | C | GLY | B | 200 | 30.083 | 35.057 | 27.534 | 1.00 | 40.77 | B | C |
| ATOM | 3026 | O | GLY | B | 200 | 29.986 | 34.539 | 26.414 | 1.00 | 41.62 | B | O |
| ATOM | 3027 | N | ASP | B | 201 | 30.544 | 34.405 | 28.594 | 1.00 | 37.35 | B | N |
| ATOM | 3028 | CA | ASP | B | 201 | 31.047 | 33.043 | 28.486 | 1.00 | 38.32 | B | C |
| ATOM | 3029 | CB | ASP | B | 201 | 31.860 | 32.688 | 29.732 | 1.00 | 41.37 | B | C |
| ATOM | 3030 | CG | ASP | B | 201 | 33.095 | 33.570 | 29.900 | 1.00 | 48.78 | B | C |
| ATOM | 3031 | OD1 | ASP | B | 201 | 33.361 | 34.433 | 29.024 | 1.00 | 45.25 | B | O |
| ATOM | 3032 | OD2 | ASP | B | 201 | 33.809 | 33.394 | 30.914 | 1.00 | 49.28 | B | O |
| ATOM | 3033 | C | ASP | B | 201 | 29.915 | 32.035 | 28.263 | 1.00 | 43.29 | B | C |
| ATOM | 3034 | O | ASP | B | 201 | 28.756 | 32.290 | 28.624 | 1.00 | 43.73 | B | O |
| ATOM | 3035 | N | ALA | B | 202 | 30.244 | 30.897 | 27.658 | 1.00 | 38.47 | B | N |
| ATOM | 3036 | CA | ALA | B | 202 | 29.250 | 29.858 | 27.403 | 1.00 | 36.74 | B | C |
| ATOM | 3037 | CB | ALA | B | 202 | 28.935 | 29.776 | 25.922 | 1.00 | 29.17 | B | C |
| ATOM | 3038 | C | ALA | B | 202 | 29.730 | 28.512 | 27.924 | 1.00 | 40.02 | B | C |
| ATOM | 3039 | O | ALA | B | 202 | 30.844 | 28.095 | 27.638 | 1.00 | 44.61 | B | O |
| ATOM | 3040 | N | HIS | B | 203 | 28.886 | 27.836 | 28.693 | 1.00 | 40.81 | B | N |
| ATOM | 3041 | CA | HIS | B | 203 | 29.251 | 26.549 | 29.282 | 1.00 | 43.85 | B | C |
| ATOM | 3042 | CB | HIS | B | 203 | 29.166 | 26.624 | 30.808 | 1.00 | 46.78 | B | C |
| ATOM | 3043 | CG | HIS | B | 203 | 29.981 | 27.731 | 31.393 | 1.00 | 45.40 | B | C |
| ATOM | 3044 | CD2 | HIS | B | 203 | 31.289 | 28.043 | 31.251 | 1.00 | 41.37 | B | C |
| ATOM | 3045 | ND1 | HIS | B | 203 | 29.446 | 28.694 | 32.220 | 1.00 | 53.35 | B | N |
| ATOM | 3046 | CE1 | HIS | B | 203 | 30.394 | 29.541 | 32.575 | 1.00 | 51.53 | B | C |
| ATOM | 3047 | NE2 | HIS | B | 203 | 31.521 | 29.170 | 31.998 | 1.00 | 46.70 | B | N |
| ATOM | 3048 | C | HIS | B | 203 | 28.384 | 25.406 | 28.787 | 1.00 | 42.10 | B | C |
| ATOM | 3049 | O | HIS | B | 203 | 27.216 | 25.593 | 28.455 | 1.00 | 44.90 | B | O |
| ATOM | 3050 | N | PHE | B | 204 | 28.955 | 24.212 | 28.761 | 1.00 | 37.02 | B | N |
| ATOM | 3051 | CA | PHE | B | 204 | 28.222 | 23.047 | 28.302 | 1.00 | 38.68 | B | C |
| ATOM | 3052 | CB | PHE | B | 204 | 28.688 | 22.632 | 26.895 | 1.00 | 40.39 | B | C |
| ATOM | 3053 | CG | PHE | B | 204 | 28.461 | 23.692 | 25.842 | 1.00 | 37.67 | B | C |
| ATOM | 3054 | CD1 | PHE | B | 204 | 29.397 | 24.684 | 25.624 | 1.00 | 36.11 | B | C |
| ATOM | 3055 | CD2 | PHE | B | 204 | 27.303 | 23.699 | 25.083 | 1.00 | 39.00 | B | C |

TABLE 13-continued

Coordinates for proMMP9(35-444 ΔFnII) (SEQ ID NO: 12) complex with Example 3

| ATOM | 3056 | CE1 | PHE | B | 204 | 29.184 | 25.660 | 24.666 | 1.00 | 40.74 | B | C |
| --- | --- | --- | --- | --- | --- | --- | --- | --- | --- | --- | --- | --- |
| ATOM | 3057 | CE2 | PHE | B | 204 | 27.087 | 24.670 | 24.123 | 1.00 | 37.97 | B | C |
| ATOM | 3058 | CZ | PHE | B | 204 | 28.030 | 25.654 | 23.914 | 1.00 | 33.23 | B | C |
| ATOM | 3059 | C | PHE | B | 204 | 28.370 | 21.901 | 29.297 | 1.00 | 44.24 | B | C |
| ATOM | 3060 | O | PHE | B | 204 | 29.444 | 21.678 | 29.861 | 1.00 | 46.75 | B | O |
| ATOM | 3061 | N | ASP | B | 205 | 27.277 | 21.180 | 29.500 | 1.00 | 42.07 | B | N |
| ATOM | 3062 | CA | ASP | B | 205 | 27.213 | 20.107 | 30.473 | 1.00 | 39.94 | B | C |
| ATOM | 3063 | CB | ASP | B | 205 | 25.754 | 19.861 | 30.832 | 1.00 | 44.47 | B | C |
| ATOM | 3064 | CG | ASP | B | 205 | 25.596 | 19.097 | 32.115 | 1.00 | 49.98 | B | C |
| ATOM | 3065 | OD1 | ASP | B | 205 | 26.599 | 18.559 | 32.632 | 1.00 | 52.52 | B | O |
| ATOM | 3066 | OD2 | ASP | B | 205 | 24.461 | 19.037 | 32.612 | 1.00 | 50.05 | B | O |
| ATOM | 3067 | C | ASP | B | 205 | 27.841 | 18.821 | 29.949 | 1.00 | 42.30 | B | C |
| ATOM | 3068 | O | ASP | B | 205 | 27.211 | 18.071 | 29.209 | 1.00 | 44.89 | B | O |
| ATOM | 3069 | N | ASP | B | 206 | 29.079 | 18.561 | 30.352 | 1.00 | 46.34 | B | N |
| ATOM | 3070 | CA | ASP | B | 206 | 29.852 | 17.433 | 29.832 | 1.00 | 42.86 | B | C |
| ATOM | 3071 | CB | ASP | B | 206 | 31.315 | 17.552 | 30.294 | 1.00 | 48.42 | B | C |
| ATOM | 3072 | CG | ASP | B | 206 | 32.323 | 17.051 | 29.255 | 1.00 | 49.06 | B | C |
| ATOM | 3073 | OD1 | ASP | B | 206 | 31.908 | 16.570 | 28.178 | 1.00 | 48.20 | B | O |
| ATOM | 3074 | OD2 | ASP | B | 206 | 33.543 | 17.149 | 29.523 | 1.00 | 41.40 | B | O |
| ATOM | 3075 | C | ASP | B | 206 | 29.227 | 16.119 | 30.304 | 1.00 | 42.47 | B | C |
| ATOM | 3076 | O | ASP | B | 206 | 29.738 | 15.038 | 30.043 | 1.00 | 48.03 | B | O |
| ATOM | 3077 | N | ASP | B | 207 | 28.115 | 16.225 | 31.016 | 1.00 | 47.39 | B | N |
| ATOM | 3078 | CA | ASP | B | 207 | 27.352 | 15.056 | 31.423 | 1.00 | 49.53 | B | C |
| ATOM | 3079 | CB | ASP | B | 207 | 26.543 | 15.365 | 32.676 | 1.00 | 42.81 | B | C |
| ATOM | 3080 | CG | ASP | B | 207 | 27.291 | 15.019 | 33.937 | 1.00 | 53.26 | B | C |
| ATOM | 3081 | OD1 | ASP | B | 207 | 28.130 | 14.090 | 33.884 | 1.00 | 52.09 | B | O |
| ATOM | 3082 | OD2 | ASP | B | 207 | 27.043 | 15.671 | 34.978 | 1.00 | 60.99 | B | O |
| ATOM | 3083 | C | ASP | B | 207 | 26.436 | 14.617 | 30.291 | 1.00 | 48.77 | B | C |
| ATOM | 3084 | O | ASP | B | 207 | 25.770 | 13.582 | 30.361 | 1.00 | 43.44 | B | O |
| ATOM | 3085 | N | GLU | B | 208 | 26.401 | 15.431 | 29.248 | 1.00 | 46.40 | B | N |
| ATOM | 3086 | CA | GLU | B | 208 | 25.649 | 15.094 | 28.061 | 1.00 | 48.70 | B | C |
| ATOM | 3087 | CB | GLU | B | 208 | 25.062 | 16.354 | 27.417 | 1.00 | 52.00 | B | C |
| ATOM | 3088 | CG | GLU | B | 208 | 24.356 | 17.262 | 28.392 | 1.00 | 42.41 | B | C |
| ATOM | 3089 | CD | GLU | B | 208 | 23.207 | 16.572 | 29.072 | 1.00 | 47.16 | B | C |
| ATOM | 3090 | OE1 | GLU | B | 208 | 22.934 | 15.397 | 28.751 | 1.00 | 42.31 | B | O |
| ATOM | 3091 | OE2 | GLU | B | 208 | 22.574 | 17.208 | 29.930 | 1.00 | 48.75 | B | O |
| ATOM | 3092 | C | GLU | B | 208 | 26.581 | 14.402 | 27.090 | 1.00 | 44.42 | B | C |
| ATOM | 3093 | O | GLU | B | 208 | 27.790 | 14.624 | 27.111 | 1.00 | 44.16 | B | O |
| ATOM | 3094 | N | LEU | B | 209 | 26.007 | 13.545 | 26.258 | 1.00 | 46.53 | B | N |
| ATOM | 3095 | CA | LEU | B | 209 | 26.733 | 12.905 | 25.177 | 1.00 | 53.79 | B | C |
| ATOM | 3096 | CB | LEU | B | 209 | 26.104 | 11.545 | 24.869 | 1.00 | 54.25 | B | C |
| ATOM | 3097 | CG | LEU | B | 209 | 26.417 | 10.824 | 23.559 | 1.00 | 53.46 | B | C |
| ATOM | 3098 | CD1 | LEU | B | 209 | 27.911 | 10.607 | 23.394 | 1.00 | 53.00 | B | C |
| ATOM | 3099 | CD2 | LEU | B | 209 | 25.676 | 9.500 | 23.537 | 1.00 | 63.51 | B | C |
| ATOM | 3100 | C | LEU | B | 209 | 26.626 | 13.832 | 23.981 | 1.00 | 48.56 | B | C |
| ATOM | 3101 | O | LEU | B | 209 | 25.564 | 13.930 | 23.369 | 1.00 | 51.30 | B | O |
| ATOM | 3102 | N | TRP | B | 210 | 27.716 | 14.528 | 23.668 | 1.00 | 42.56 | B | N |
| ATOM | 3103 | CA | TRP | B | 210 | 27.653 | 15.641 | 22.729 | 1.00 | 44.71 | B | C |
| ATOM | 3104 | CB | TRP | B | 210 | 28.543 | 16.804 | 23.202 | 1.00 | 41.10 | B | C |
| ATOM | 3105 | CG | TRP | B | 210 | 27.918 | 17.609 | 24.323 | 1.00 | 44.96 | B | C |
| ATOM | 3106 | CD2 | TRP | B | 210 | 26.806 | 18.518 | 24.219 | 1.00 | 40.37 | B | C |
| ATOM | 3107 | CE2 | TRP | B | 210 | 26.559 | 19.027 | 25.512 | 1.00 | 39.93 | B | C |
| ATOM | 3108 | CE3 | TRP | B | 210 | 26.001 | 18.950 | 23.158 | 1.00 | 37.00 | B | C |
| ATOM | 3109 | CD1 | TRP | B | 210 | 28.280 | 17.602 | 25.645 | 1.00 | 46.51 | B | C |
| ATOM | 3110 | NE1 | TRP | B | 210 | 27.468 | 18.455 | 26.364 | 1.00 | 39.55 | B | N |
| ATOM | 3111 | CZ2 | TRP | B | 210 | 25.545 | 19.948 | 25.767 | 1.00 | 41.79 | B | C |
| ATOM | 3112 | CZ3 | TRP | B | 210 | 24.998 | 19.857 | 23.414 | 1.00 | 35.63 | B | C |
| ATOM | 3113 | CH2 | TRP | B | 210 | 24.778 | 20.349 | 24.707 | 1.00 | 41.96 | B | C |
| ATOM | 3114 | C | TRP | B | 210 | 27.975 | 15.213 | 21.300 | 1.00 | 42.85 | B | C |
| ATOM | 3115 | O | TRP | B | 210 | 29.114 | 14.891 | 20.988 | 1.00 | 53.27 | B | O |
| ATOM | 3116 | N | SER | B | 211 | 26.956 | 15.199 | 20.444 | 1.00 | 41.74 | B | N |
| ATOM | 3117 | CA | SER | B | 211 | 27.097 | 14.729 | 19.068 | 1.00 | 48.75 | B | C |
| ATOM | 3118 | CB | SER | B | 211 | 26.346 | 13.414 | 18.883 | 1.00 | 50.22 | B | C |
| ATOM | 3119 | OG | SER | B | 211 | 24.975 | 13.651 | 18.634 | 1.00 | 56.94 | B | O |
| ATOM | 3120 | C | SER | B | 211 | 26.600 | 15.775 | 18.064 | 1.00 | 48.23 | B | C |
| ATOM | 3121 | O | SER | B | 211 | 26.506 | 16.954 | 18.394 | 1.00 | 50.52 | B | O |
| ATOM | 3122 | N | LEU | B | 212 | 26.285 | 15.360 | 16.842 | 1.00 | 47.17 | B | N |
| ATOM | 3123 | CA | LEU | B | 212 | 25.782 | 16.319 | 15.862 | 1.00 | 49.28 | B | C |
| ATOM | 3124 | CB | LEU | B | 212 | 26.675 | 16.372 | 14.629 | 1.00 | 50.08 | B | C |
| ATOM | 3125 | CG | LEU | B | 212 | 27.977 | 17.107 | 14.935 | 1.00 | 56.52 | B | C |
| ATOM | 3126 | CD1 | LEU | B | 212 | 28.742 | 17.421 | 13.646 | 1.00 | 45.05 | B | C |
| ATOM | 3127 | CD2 | LEU | B | 212 | 27.701 | 18.379 | 15.740 | 1.00 | 40.62 | B | C |
| ATOM | 3128 | C | LEU | B | 212 | 24.315 | 16.119 | 15.484 | 1.00 | 55.23 | B | C |
| ATOM | 3129 | O | LEU | B | 212 | 23.937 | 16.254 | 14.315 | 1.00 | 49.99 | B | O |
| ATOM | 3130 | N | GLY | B | 213 | 23.507 | 15.819 | 16.503 | 1.00 | 58.43 | B | N |
| ATOM | 3131 | CA | GLY | B | 213 | 22.058 | 15.775 | 16.400 | 1.00 | 56.98 | B | C |
| ATOM | 3132 | C | GLY | B | 213 | 21.510 | 14.495 | 15.812 | 1.00 | 58.81 | B | C |

TABLE 13-continued

Coordinates for proMMP9(35-444 ΔFnII) (SEQ ID NO: 12) complex with Example 3

| ATOM | 3133 | O | GLY | B | 213 | 21.113 | 13.586 | 16.539 | 1.00 | 69.17 | B | O |
|---|---|---|---|---|---|---|---|---|---|---|---|---|
| ATOM | 3134 | N | LYS | B | 389 | 21.508 | 14.454 | 14.484 | 1.00 | 56.84 | B | N |
| ATOM | 3135 | CA | LYS | B | 389 | 21.175 | 13.290 | 13.654 | 1.00 | 63.38 | B | C |
| ATOM | 3136 | CB | LYS | B | 389 | 22.359 | 13.005 | 12.725 | 1.00 | 64.52 | B | C |
| ATOM | 3137 | CG | LYS | B | 389 | 23.706 | 13.534 | 13.249 | 1.00 | 66.09 | B | C |
| ATOM | 3138 | CD | LYS | B | 389 | 24.064 | 12.983 | 14.628 | 1.00 | 59.33 | B | C |
| ATOM | 3139 | CE | LYS | B | 389 | 25.050 | 11.837 | 14.532 | 1.00 | 65.09 | B | C |
| ATOM | 3140 | NZ | LYS | B | 389 | 26.283 | 12.203 | 13.771 | 1.00 | 68.86 | B | N |
| ATOM | 3141 | C | LYS | B | 389 | 20.728 | 11.956 | 14.282 | 1.00 | 72.00 | B | C |
| ATOM | 3142 | O | LYS | B | 389 | 21.012 | 10.902 | 13.720 | 1.00 | 66.08 | B | O |
| ATOM | 3143 | N | GLY | B | 390 | 20.013 | 11.967 | 15.400 | 1.00 | 69.67 | B | N |
| ATOM | 3144 | CA | GLY | B | 390 | 19.585 | 10.702 | 15.964 | 1.00 | 69.49 | B | C |
| ATOM | 3145 | C | GLY | B | 390 | 19.666 | 10.521 | 17.467 | 1.00 | 70.68 | B | C |
| ATOM | 3146 | O | GLY | B | 390 | 18.648 | 10.230 | 18.090 | 1.00 | 73.30 | B | O |
| ATOM | 3147 | N | GLN | B | 391 | 20.848 | 10.647 | 18.065 | 1.00 | 65.22 | B | N |
| ATOM | 3148 | CA | GLN | B | 391 | 20.932 | 10.334 | 19.498 | 1.00 | 75.23 | B | C |
| ATOM | 3149 | CB | GLN | B | 391 | 21.304 | 8.860 | 19.734 | 1.00 | 72.31 | B | C |
| ATOM | 3150 | CG | GLN | B | 391 | 22.394 | 8.661 | 20.768 | 1.00 | 74.64 | B | C |
| ATOM | 3151 | CD | GLN | B | 391 | 23.762 | 8.762 | 20.115 | 1.00 | 77.26 | B | C |
| ATOM | 3152 | OE1 | GLN | B | 391 | 23.907 | 8.397 | 18.964 | 1.00 | 72.38 | B | O |
| ATOM | 3153 | NE2 | GLN | B | 391 | 24.762 | 9.235 | 20.840 | 1.00 | 81.11 | B | N |
| ATOM | 3154 | C | GLN | B | 391 | 21.723 | 11.269 | 20.429 | 1.00 | 74.42 | B | C |
| ATOM | 3155 | O | GLN | B | 391 | 21.550 | 11.214 | 21.644 | 1.00 | 82.25 | B | O |
| ATOM | 3156 | N | GLY | B | 392 | 22.565 | 12.137 | 19.888 | 1.00 | 66.64 | B | N |
| ATOM | 3157 | CA | GLY | B | 392 | 23.223 | 13.111 | 20.741 | 1.00 | 56.19 | B | C |
| ATOM | 3158 | C | GLY | B | 392 | 22.435 | 14.404 | 20.847 | 1.00 | 50.71 | B | C |
| ATOM | 3159 | O | GLY | B | 392 | 21.445 | 14.585 | 20.141 | 1.00 | 53.71 | B | O |
| ATOM | 3160 | N | TYR | B | 393 | 22.853 | 15.294 | 21.744 | 1.00 | 45.50 | B | N |
| ATOM | 3161 | CA | TYR | B | 393 | 22.453 | 16.694 | 21.636 | 1.00 | 46.89 | B | C |
| ATOM | 3162 | CB | TYR | B | 393 | 22.486 | 17.423 | 22.985 | 1.00 | 41.47 | B | C |
| ATOM | 3163 | CG | TYR | B | 393 | 21.450 | 16.943 | 23.970 | 1.00 | 43.93 | B | C |
| ATOM | 3164 | CD1 | TYR | B | 393 | 20.092 | 16.991 | 23.664 | 1.00 | 46.41 | B | C |
| ATOM | 3165 | CE1 | TYR | B | 393 | 19.138 | 16.552 | 24.565 | 1.00 | 50.23 | B | C |
| ATOM | 3166 | CD2 | TYR | B | 393 | 21.824 | 16.452 | 25.210 | 1.00 | 44.54 | B | C |
| ATOM | 3167 | CE2 | TYR | B | 393 | 20.880 | 16.010 | 26.114 | 1.00 | 53.01 | B | C |
| ATOM | 3168 | CZ | TYR | B | 393 | 19.538 | 16.062 | 25.788 | 1.00 | 52.60 | B | C |
| ATOM | 3169 | OH | TYR | B | 393 | 18.599 | 15.622 | 26.692 | 1.00 | 50.57 | B | O |
| ATOM | 3170 | C | TYR | B | 393 | 23.425 | 17.351 | 20.672 | 1.00 | 46.96 | B | C |
| ATOM | 3171 | O | TYR | B | 393 | 24.641 | 17.273 | 20.864 | 1.00 | 47.65 | B | O |
| ATOM | 3172 | N | SER | B | 394 | 22.897 | 17.972 | 19.624 | 1.00 | 39.54 | B | N |
| ATOM | 3173 | CA | SER | B | 394 | 23.754 | 18.633 | 18.650 | 1.00 | 42.93 | B | C |
| ATOM | 3174 | CB | SER | B | 394 | 22.959 | 19.052 | 17.411 | 1.00 | 40.14 | B | C |
| ATOM | 3175 | OG | SER | B | 394 | 23.627 | 20.076 | 16.700 | 1.00 | 37.74 | B | O |
| ATOM | 3176 | C | SER | B | 394 | 24.443 | 19.837 | 19.282 | 1.00 | 42.72 | B | C |
| ATOM | 3177 | O | SER | B | 394 | 23.813 | 20.862 | 19.552 | 1.00 | 40.19 | B | O |
| ATOM | 3178 | N | LEU | B | 395 | 25.739 | 19.698 | 19.529 | 1.00 | 40.04 | B | N |
| ATOM | 3179 | CA | LEU | B | 395 | 26.536 | 20.804 | 20.027 | 1.00 | 35.99 | B | C |
| ATOM | 3180 | CB | LEU | B | 395 | 28.016 | 20.413 | 20.114 | 1.00 | 36.46 | B | C |
| ATOM | 3181 | CG | LEU | B | 395 | 29.004 | 21.385 | 20.778 | 1.00 | 40.88 | B | C |
| ATOM | 3182 | CD1 | LEU | B | 395 | 28.684 | 21.610 | 22.246 | 1.00 | 31.61 | B | C |
| ATOM | 3183 | CD2 | LEU | B | 395 | 30.457 | 20.905 | 20.617 | 1.00 | 38.79 | B | C |
| ATOM | 3184 | C | LEU | B | 395 | 26.346 | 21.989 | 19.102 | 1.00 | 36.37 | B | C |
| ATOM | 3185 | O | LEU | B | 395 | 26.337 | 23.138 | 19.541 | 1.00 | 39.00 | B | O |
| ATOM | 3186 | N | PHE | B | 396 | 26.176 | 21.712 | 17.813 | 1.00 | 40.97 | B | N |
| ATOM | 3187 | CA | PHE | B | 396 | 25.982 | 22.797 | 16.860 | 1.00 | 39.88 | B | C |
| ATOM | 3188 | CB | PHE | B | 396 | 25.865 | 22.284 | 15.422 | 1.00 | 34.67 | B | C |
| ATOM | 3189 | CG | PHE | B | 396 | 25.449 | 23.347 | 14.439 | 1.00 | 34.50 | B | C |
| ATOM | 3190 | CD1 | PHE | B | 396 | 26.146 | 24.540 | 14.350 | 1.00 | 33.57 | B | C |
| ATOM | 3191 | CD2 | PHE | B | 396 | 24.366 | 23.154 | 13.601 | 1.00 | 32.03 | B | C |
| ATOM | 3192 | CE1 | PHE | B | 396 | 25.766 | 25.521 | 13.453 | 1.00 | 32.32 | B | C |
| ATOM | 3193 | CE2 | PHE | B | 396 | 23.988 | 24.137 | 12.702 | 1.00 | 26.92 | B | C |
| ATOM | 3194 | CZ | PHE | B | 396 | 24.686 | 25.323 | 12.634 | 1.00 | 24.31 | B | C |
| ATOM | 3195 | C | PHE | B | 396 | 24.775 | 23.659 | 17.239 | 1.00 | 36.24 | B | C |
| ATOM | 3196 | O | PHE | B | 396 | 24.920 | 24.858 | 17.427 | 1.00 | 34.67 | B | O |
| ATOM | 3197 | N | LEU | B | 397 | 23.599 | 23.035 | 17.357 | 1.00 | 41.03 | B | N |
| ATOM | 3198 | CA | LEU | B | 397 | 22.356 | 23.728 | 17.712 | 1.00 | 36.24 | B | C |
| ATOM | 3199 | CB | LEU | B | 397 | 21.159 | 22.772 | 17.640 | 1.00 | 38.19 | B | C |
| ATOM | 3200 | CG | LEU | B | 397 | 20.795 | 22.196 | 16.267 | 1.00 | 36.80 | B | C |
| ATOM | 3201 | CD1 | LEU | B | 397 | 19.691 | 21.161 | 16.372 | 1.00 | 31.44 | B | C |
| ATOM | 3202 | CD2 | LEU | B | 397 | 20.405 | 23.294 | 15.292 | 1.00 | 30.95 | B | C |
| ATOM | 3203 | C | LEU | B | 397 | 22.412 | 24.366 | 19.100 | 1.00 | 35.79 | B | C |
| ATOM | 3204 | O | LEU | B | 397 | 22.092 | 25.539 | 19.259 | 1.00 | 37.11 | B | O |
| ATOM | 3205 | N | VAL | B | 398 | 22.820 | 23.599 | 20.105 | 1.00 | 31.08 | B | N |
| ATOM | 3206 | CA | VAL | B | 398 | 22.888 | 24.129 | 21.462 | 1.00 | 33.81 | B | C |
| ATOM | 3207 | CB | VAL | B | 398 | 23.380 | 23.084 | 22.478 | 1.00 | 38.37 | B | C |
| ATOM | 3208 | CG1 | VAL | B | 398 | 23.483 | 23.715 | 23.852 | 1.00 | 34.21 | B | C |
| ATOM | 3209 | CG2 | VAL | B | 398 | 22.448 | 21.880 | 22.509 | 1.00 | 38.52 | B | C |

TABLE 13-continued

Coordinates for proMMP9(35-444 ΔFnII) (SEQ ID NO: 12) complex with Example 3

| ATOM | 3210 | C | VAL | B | 398 | 23.791 | 25.357 | 21.561 | 1.00 | 38.89 | B | C |
|------|------|------|-----|---|-----|--------|--------|--------|------|-------|---|---|
| ATOM | 3211 | O | VAL | B | 398 | 23.507 | 26.282 | 22.329 | 1.00 | 37.30 | B | O |
| ATOM | 3212 | N | ALA | B | 399 | 24.881 | 25.364 | 20.795 | 1.00 | 38.51 | B | N |
| ATOM | 3213 | CA | ALA | B | 399 | 25.844 | 26.456 | 20.879 | 1.00 | 31.43 | B | C |
| ATOM | 3214 | CB | ALA | B | 399 | 27.173 | 26.038 | 20.372 | 1.00 | 26.45 | B | C |
| ATOM | 3215 | C | ALA | B | 399 | 25.364 | 27.712 | 20.167 | 1.00 | 36.92 | B | C |
| ATOM | 3216 | O | ALA | B | 399 | 25.670 | 28.823 | 20.597 | 1.00 | 38.41 | B | O |
| ATOM | 3217 | N | ALA | B | 400 | 24.613 | 27.546 | 19.084 | 1.00 | 35.39 | B | N |
| ATOM | 3218 | CA | ALA | B | 400 | 24.043 | 28.695 | 18.393 | 1.00 | 35.17 | B | C |
| ATOM | 3219 | CB | ALA | B | 400 | 23.318 | 28.252 | 17.134 | 1.00 | 35.09 | B | C |
| ATOM | 3220 | C | ALA | B | 400 | 23.079 | 29.382 | 19.349 | 1.00 | 35.41 | B | C |
| ATOM | 3221 | O | ALA | B | 400 | 23.059 | 30.604 | 19.486 | 1.00 | 31.98 | B | O |
| ATOM | 3222 | N | HIS | B | 401 | 22.278 | 28.567 | 20.018 | 1.00 | 39.25 | B | N |
| ATOM | 3223 | CA | HIS | B | 401 | 21.346 | 29.059 | 21.002 | 1.00 | 32.50 | B | C |
| ATOM | 3224 | CB | HIS | B | 401 | 20.632 | 27.896 | 21.679 | 1.00 | 32.17 | B | C |
| ATOM | 3225 | CG | HIS | B | 401 | 19.697 | 28.325 | 22.764 | 1.00 | 41.47 | B | C |
| ATOM | 3226 | CD2 | HIS | B | 401 | 19.869 | 28.416 | 24.107 | 1.00 | 34.97 | B | C |
| ATOM | 3227 | ND1 | HIS | B | 401 | 18.408 | 28.745 | 22.516 | 1.00 | 36.12 | B | N |
| ATOM | 3228 | CE1 | HIS | B | 401 | 17.827 | 29.075 | 23.655 | 1.00 | 37.71 | B | C |
| ATOM | 3229 | NE2 | HIS | B | 401 | 18.692 | 28.877 | 24.635 | 1.00 | 31.29 | B | N |
| ATOM | 3230 | C | HIS | B | 401 | 22.088 | 29.868 | 22.037 | 1.00 | 33.21 | B | C |
| ATOM | 3231 | O | HIS | B | 401 | 21.750 | 31.026 | 22.291 | 1.00 | 34.58 | B | O |
| ATOM | 3232 | N | GLU | B | 402 | 23.113 | 29.261 | 22.624 | 1.00 | 30.01 | B | N |
| ATOM | 3233 | CA | GLU | B | 402 | 23.811 | 29.881 | 23.747 | 1.00 | 35.43 | B | C |
| ATOM | 3234 | CB | GLU | B | 402 | 24.811 | 28.915 | 24.388 | 1.00 | 34.71 | B | C |
| ATOM | 3235 | CG | GLU | B | 402 | 24.177 | 27.680 | 25.029 | 1.00 | 34.73 | B | C |
| ATOM | 3236 | CD | GLU | B | 402 | 23.178 | 27.990 | 26.151 | 1.00 | 33.30 | B | C |
| ATOM | 3237 | OE1 | GLU | B | 402 | 23.081 | 29.151 | 26.623 | 1.00 | 30.76 | B | O |
| ATOM | 3238 | OE2 | GLU | B | 402 | 22.487 | 27.041 | 26.560 | 1.00 | 30.26 | B | O |
| ATOM | 3239 | C | GLU | B | 402 | 24.515 | 31.160 | 23.353 | 1.00 | 33.90 | B | C |
| ATOM | 3240 | O | GLU | B | 402 | 24.506 | 32.137 | 24.102 | 1.00 | 30.46 | B | O |
| ATOM | 3241 | N | PHE | B | 403 | 25.127 | 31.143 | 22.171 | 1.00 | 39.51 | B | N |
| ATOM | 3242 | CA | PHE | B | 403 | 25.824 | 32.308 | 21.656 | 1.00 | 31.16 | B | C |
| ATOM | 3243 | CB | PHE | B | 403 | 26.564 | 31.966 | 20.374 | 1.00 | 35.97 | B | C |
| ATOM | 3244 | CG | PHE | B | 403 | 27.678 | 30.974 | 20.578 | 1.00 | 38.74 | B | C |
| ATOM | 3245 | CD1 | PHE | B | 403 | 28.127 | 30.676 | 21.863 | 1.00 | 35.53 | B | C |
| ATOM | 3246 | CD2 | PHE | B | 403 | 28.287 | 30.352 | 19.496 | 1.00 | 33.75 | B | C |
| ATOM | 3247 | CE1 | PHE | B | 403 | 29.156 | 29.767 | 22.066 | 1.00 | 31.46 | B | C |
| ATOM | 3248 | CE2 | PHE | B | 403 | 29.318 | 29.443 | 19.690 | 1.00 | 37.79 | B | C |
| ATOM | 3249 | CZ | PHE | B | 403 | 29.754 | 29.149 | 20.980 | 1.00 | 36.46 | B | C |
| ATOM | 3250 | C | PHE | B | 403 | 24.847 | 33.453 | 21.464 | 1.00 | 35.76 | B | C |
| ATOM | 3251 | O | PHE | B | 403 | 25.217 | 34.617 | 21.604 | 1.00 | 37.98 | B | O |
| ATOM | 3252 | N | GLY | B | 404 | 23.592 | 33.117 | 21.182 | 1.00 | 35.10 | B | N |
| ATOM | 3253 | CA | GLY | B | 404 | 22.513 | 34.090 | 21.255 | 1.00 | 34.26 | B | C |
| ATOM | 3254 | C | GLY | B | 404 | 22.497 | 34.824 | 22.590 | 1.00 | 31.93 | B | C |
| ATOM | 3255 | O | GLY | B | 404 | 22.547 | 36.050 | 22.636 | 1.00 | 33.08 | B | O |
| ATOM | 3256 | N | HIS | B | 405 | 22.427 | 34.070 | 23.682 | 1.00 | 36.06 | B | N |
| ATOM | 3257 | CA | HIS | B | 405 | 22.444 | 34.658 | 25.022 | 1.00 | 33.87 | B | C |
| ATOM | 3258 | CB | HIS | B | 405 | 22.427 | 33.579 | 26.110 | 1.00 | 33.91 | B | C |
| ATOM | 3259 | CG | HIS | B | 405 | 21.082 | 32.963 | 26.353 | 1.00 | 35.71 | B | C |
| ATOM | 3260 | CD2 | HIS | B | 405 | 20.731 | 31.709 | 26.721 | 1.00 | 35.18 | B | C |
| ATOM | 3261 | ND1 | HIS | B | 405 | 19.906 | 33.679 | 26.272 | 1.00 | 35.49 | B | N |
| ATOM | 3262 | CE1 | HIS | B | 405 | 18.889 | 32.887 | 26.554 | 1.00 | 34.91 | B | C |
| ATOM | 3263 | NE2 | HIS | B | 405 | 19.360 | 31.685 | 26.831 | 1.00 | 31.91 | B | N |
| ATOM | 3264 | C | HIS | B | 405 | 23.692 | 35.495 | 25.195 | 1.00 | 37.58 | B | C |
| ATOM | 3265 | O | HIS | B | 405 | 23.649 | 36.568 | 25.788 | 1.00 | 33.80 | B | O |
| ATOM | 3266 | N | ALA | B | 406 | 24.806 | 34.984 | 24.668 | 1.00 | 39.66 | B | N |
| ATOM | 3267 | CA | ALA | B | 406 | 26.118 | 35.583 | 24.877 | 1.00 | 33.05 | B | C |
| ATOM | 3268 | CB | ALA | B | 406 | 27.204 | 34.634 | 24.428 | 1.00 | 34.65 | B | C |
| ATOM | 3269 | C | ALA | B | 406 | 26.234 | 36.916 | 24.148 | 1.00 | 40.07 | B | C |
| ATOM | 3270 | O | ALA | B | 406 | 27.136 | 37.719 | 24.422 | 1.00 | 39.35 | B | O |
| ATOM | 3271 | N | LEU | B | 407 | 25.321 | 37.145 | 23.210 | 1.00 | 39.74 | B | N |
| ATOM | 3272 | CA | LEU | B | 407 | 25.255 | 38.425 | 22.522 | 1.00 | 38.43 | B | C |
| ATOM | 3273 | CB | LEU | B | 407 | 24.874 | 38.239 | 21.062 | 1.00 | 35.77 | B | C |
| ATOM | 3274 | CG | LEU | B | 407 | 25.812 | 37.334 | 20.282 | 1.00 | 31.26 | B | C |
| ATOM | 3275 | CD1 | LEU | B | 407 | 25.349 | 37.260 | 18.866 | 1.00 | 34.69 | B | C |
| ATOM | 3276 | CD2 | LEU | B | 407 | 27.210 | 37.869 | 20.356 | 1.00 | 35.59 | B | C |
| ATOM | 3277 | C | LEU | B | 407 | 24.241 | 39.319 | 23.199 | 1.00 | 34.60 | B | C |
| ATOM | 3278 | O | LEU | B | 407 | 24.104 | 40.475 | 22.845 | 1.00 | 34.18 | B | O |
| ATOM | 3279 | N | GLY | B | 408 | 23.526 | 38.772 | 24.174 | 1.00 | 37.84 | B | N |
| ATOM | 3280 | CA | GLY | B | 408 | 22.543 | 39.546 | 24.909 | 1.00 | 37.26 | B | C |
| ATOM | 3281 | C | GLY | B | 408 | 21.108 | 39.315 | 24.470 | 1.00 | 32.91 | B | C |
| ATOM | 3282 | O | GLY | B | 408 | 20.272 | 40.212 | 24.555 | 1.00 | 33.74 | B | O |
| ATOM | 3283 | N | LEU | B | 409 | 20.811 | 38.111 | 23.996 | 1.00 | 32.97 | B | N |
| ATOM | 3284 | CA | LEU | B | 409 | 19.427 | 37.752 | 23.703 | 1.00 | 33.68 | B | C |
| ATOM | 3285 | CB | LEU | B | 409 | 19.340 | 36.922 | 22.428 | 1.00 | 41.86 | B | C |
| ATOM | 3286 | CG | LEU | B | 409 | 19.618 | 37.654 | 21.117 | 1.00 | 40.08 | B | C |

TABLE 13-continued

Coordinates for proMMP9(35-444 ΔFnII) (SEQ ID NO: 12) complex with Example 3

| ATOM | 3287 | CD1 | LEU | B | 409 | 19.484 | 36.675 | 19.964 | 1.00 | 36.51 | B | C |
|------|------|-----|-----|---|-----|--------|--------|--------|------|-------|---|---|
| ATOM | 3288 | CD2 | LEU | B | 409 | 18.674 | 38.851 | 20.953 | 1.00 | 25.32 | B | C |
| ATOM | 3289 | C | LEU | B | 409 | 18.801 | 36.982 | 24.852 | 1.00 | 36.03 | B | C |
| ATOM | 3290 | O | LEU | B | 409 | 19.496 | 36.308 | 25.611 | 1.00 | 36.21 | B | O |
| ATOM | 3291 | N | ASP | B | 410 | 17.483 | 37.101 | 24.978 | 1.00 | 43.30 | B | N |
| ATOM | 3292 | CA | ASP | B | 410 | 16.709 | 36.344 | 25.957 | 1.00 | 39.82 | B | C |
| ATOM | 3293 | CB | ASP | B | 410 | 15.706 | 37.253 | 26.661 | 1.00 | 39.96 | B | C |
| ATOM | 3294 | CG | ASP | B | 410 | 16.352 | 38.094 | 27.738 | 1.00 | 54.39 | B | C |
| ATOM | 3295 | OD1 | ASP | B | 410 | 17.135 | 37.520 | 28.536 | 1.00 | 56.41 | B | O |
| ATOM | 3296 | OD2 | ASP | B | 410 | 16.083 | 39.319 | 27.782 | 1.00 | 46.72 | B | O |
| ATOM | 3297 | C | ASP | B | 410 | 15.974 | 35.231 | 25.250 | 1.00 | 36.56 | B | C |
| ATOM | 3298 | O | ASP | B | 410 | 15.970 | 35.166 | 24.029 | 1.00 | 38.09 | B | O |
| ATOM | 3299 | N | HIS | B | 411 | 15.339 | 34.351 | 26.001 | 1.00 | 39.84 | B | N |
| ATOM | 3300 | CA | HIS | B | 411 | 14.574 | 33.305 | 25.345 | 1.00 | 42.76 | B | C |
| ATOM | 3301 | CB | HIS | B | 411 | 14.089 | 32.260 | 26.334 | 1.00 | 44.29 | B | C |
| ATOM | 3302 | CG | HIS | B | 411 | 15.164 | 31.330 | 26.776 | 1.00 | 40.72 | B | C |
| ATOM | 3303 | CD2 | HIS | B | 411 | 15.989 | 30.530 | 26.066 | 1.00 | 38.93 | B | C |
| ATOM | 3304 | ND1 | HIS | B | 411 | 15.525 | 31.184 | 28.096 | 1.00 | 41.16 | B | N |
| ATOM | 3305 | CE1 | HIS | B | 411 | 16.512 | 30.314 | 28.184 | 1.00 | 37.40 | B | C |
| ATOM | 3306 | NE2 | HIS | B | 411 | 16.810 | 29.900 | 26.966 | 1.00 | 40.78 | B | N |
| ATOM | 3307 | C | HIS | B | 411 | 13.408 | 33.860 | 24.555 | 1.00 | 45.16 | B | C |
| ATOM | 3308 | O | HIS | B | 411 | 13.057 | 35.034 | 24.672 | 1.00 | 44.14 | B | O |
| ATOM | 3309 | N | SER | B | 412 | 12.816 | 32.976 | 23.762 | 1.00 | 44.46 | B | N |
| ATOM | 3310 | CA | SER | B | 412 | 11.753 | 33.297 | 22.827 | 1.00 | 38.92 | B | C |
| ATOM | 3311 | CB | SER | B | 412 | 12.223 | 32.895 | 21.422 | 1.00 | 32.94 | B | C |
| ATOM | 3312 | OG | SER | B | 412 | 11.250 | 33.144 | 20.428 | 1.00 | 29.52 | B | O |
| ATOM | 3313 | C | SER | B | 412 | 10.488 | 32.516 | 23.223 | 1.00 | 38.77 | B | C |
| ATOM | 3314 | O | SER | B | 412 | 10.578 | 31.420 | 23.788 | 1.00 | 37.31 | B | O |
| ATOM | 3315 | N | SER | B | 413 | 9.310 | 33.064 | 22.939 | 1.00 | 35.12 | B | N |
| ATOM | 3316 | CA | SER | B | 413 | 8.086 | 32.290 | 23.150 | 1.00 | 35.56 | B | C |
| ATOM | 3317 | CB | SER | B | 413 | 6.948 | 33.130 | 23.749 | 1.00 | 37.57 | B | C |
| ATOM | 3318 | OG | SER | B | 413 | 6.708 | 34.318 | 23.028 | 1.00 | 42.13 | B | O |
| ATOM | 3319 | C | SER | B | 413 | 7.647 | 31.554 | 21.891 | 1.00 | 38.41 | B | C |
| ATOM | 3320 | O | SER | B | 413 | 6.968 | 30.535 | 21.972 | 1.00 | 48.24 | B | O |
| ATOM | 3321 | N | VAL | B | 414 | 8.060 | 32.055 | 20.731 | 1.00 | 40.19 | B | N |
| ATOM | 3322 | CA | VAL | B | 414 | 7.835 | 31.349 | 19.469 | 1.00 | 39.61 | B | C |
| ATOM | 3323 | CB | VAL | B | 414 | 8.314 | 32.172 | 18.253 | 1.00 | 34.60 | B | C |
| ATOM | 3324 | CG1 | VAL | B | 414 | 8.171 | 31.359 | 16.958 | 1.00 | 32.12 | B | C |
| ATOM | 3325 | CG2 | VAL | B | 414 | 7.541 | 33.480 | 18.172 | 1.00 | 25.42 | B | C |
| ATOM | 3326 | C | VAL | B | 414 | 8.553 | 30.009 | 19.485 | 1.00 | 38.87 | B | C |
| ATOM | 3327 | O | VAL | B | 414 | 9.776 | 29.959 | 19.520 | 1.00 | 44.42 | B | O |
| ATOM | 3328 | N | PRO | B | 415 | 7.788 | 28.914 | 19.453 | 1.00 | 44.19 | B | N |
| ATOM | 3329 | CD | PRO | B | 415 | 6.329 | 28.902 | 19.271 | 1.00 | 42.97 | B | C |
| ATOM | 3330 | CA | PRO | B | 415 | 8.334 | 27.563 | 19.622 | 1.00 | 44.37 | B | C |
| ATOM | 3331 | CB | PRO | B | 415 | 7.128 | 26.655 | 19.362 | 1.00 | 40.20 | B | C |
| ATOM | 3332 | CG | PRO | B | 415 | 5.955 | 27.504 | 19.669 | 1.00 | 44.24 | B | C |
| ATOM | 3333 | C | PRO | B | 415 | 9.457 | 27.229 | 18.656 | 1.00 | 43.10 | B | C |
| ATOM | 3334 | O | PRO | B | 415 | 10.465 | 26.697 | 19.104 | 1.00 | 47.86 | B | O |
| ATOM | 3335 | N | GLU | B | 416 | 9.299 | 27.518 | 17.367 | 1.00 | 45.13 | B | N |
| ATOM | 3336 | CA | GLU | B | 416 | 10.288 | 27.050 | 16.384 | 1.00 | 54.15 | B | C |
| ATOM | 3337 | CB | GLU | B | 416 | 9.669 | 26.828 | 14.992 | 1.00 | 50.62 | B | C |
| ATOM | 3338 | CG | GLU | B | 416 | 8.511 | 27.747 | 14.660 | 1.00 | 56.34 | B | C |
| ATOM | 3339 | CD | GLU | B | 416 | 7.278 | 27.412 | 15.463 | 1.00 | 57.77 | B | C |
| ATOM | 3340 | OE1 | GLU | B | 416 | 7.257 | 26.311 | 16.056 | 1.00 | 56.98 | B | O |
| ATOM | 3341 | OE2 | GLU | B | 416 | 6.338 | 28.240 | 15.504 | 1.00 | 56.48 | B | O |
| ATOM | 3342 | C | GLU | B | 416 | 11.549 | 27.910 | 16.283 | 1.00 | 47.24 | B | C |
| ATOM | 3343 | O | GLU | B | 416 | 12.517 | 27.506 | 15.639 | 1.00 | 44.81 | B | O |
| ATOM | 3344 | N | ALA | B | 417 | 11.535 | 29.080 | 16.923 | 1.00 | 45.05 | B | N |
| ATOM | 3345 | CA | ALA | B | 417 | 12.703 | 29.965 | 16.945 | 1.00 | 45.26 | B | C |
| ATOM | 3346 | CB | ALA | B | 417 | 12.363 | 31.290 | 17.620 | 1.00 | 35.21 | B | C |
| ATOM | 3347 | C | ALA | B | 417 | 13.893 | 29.308 | 17.643 | 1.00 | 40.79 | B | C |
| ATOM | 3348 | O | ALA | B | 417 | 13.718 | 28.486 | 18.538 | 1.00 | 38.86 | B | O |
| ATOM | 3349 | N | LEU | B | 418 | 15.099 | 29.686 | 17.231 | 1.00 | 37.49 | B | N |
| ATOM | 3350 | CA | LEU | B | 418 | 16.328 | 29.141 | 17.809 | 1.00 | 42.61 | B | C |
| ATOM | 3351 | CB | LEU | B | 418 | 17.547 | 29.671 | 17.049 | 1.00 | 33.35 | B | C |
| ATOM | 3352 | CG | LEU | B | 418 | 18.889 | 29.419 | 17.741 | 1.00 | 33.33 | B | C |
| ATOM | 3353 | CD1 | LEU | B | 418 | 19.255 | 27.943 | 17.664 | 1.00 | 32.39 | B | C |
| ATOM | 3354 | CD2 | LEU | B | 418 | 19.986 | 30.280 | 17.145 | 1.00 | 32.37 | B | C |
| ATOM | 3355 | C | LEU | B | 418 | 16.489 | 29.423 | 19.316 | 1.00 | 38.41 | B | C |
| ATOM | 3356 | O | LEU | B | 418 | 16.987 | 28.582 | 20.067 | 1.00 | 31.04 | B | O |
| ATOM | 3357 | N | MET | B | 419 | 16.089 | 30.620 | 19.732 | 1.00 | 38.69 | B | N |
| ATOM | 3358 | CA | MET | B | 419 | 16.199 | 31.057 | 21.120 | 1.00 | 34.98 | B | C |
| ATOM | 3359 | CB | MET | B | 419 | 16.323 | 32.576 | 21.183 | 1.00 | 29.60 | B | C |
| ATOM | 3360 | CG | MET | B | 419 | 17.549 | 33.124 | 20.486 | 1.00 | 28.78 | B | C |
| ATOM | 3361 | SD | MET | B | 419 | 19.068 | 32.447 | 21.162 | 1.00 | 31.82 | B | S |
| ATOM | 3362 | CE | MET | B | 419 | 18.776 | 32.618 | 22.928 | 1.00 | 31.73 | B | C |
| ATOM | 3363 | C | MET | B | 419 | 14.986 | 30.604 | 21.925 | 1.00 | 41.43 | B | C |

TABLE 13-continued

Coordinates for proMMP9(35-444 ΔFnII) (SEQ ID NO: 12) complex with Example 3

| ATOM | 3364 | O | MET | B | 419 | 14.568 | 31.265 | 22.870 | 1.00 | 45.23 | B | O |
|------|------|------|-----|---|-----|--------|--------|--------|------|-------|---|---|
| ATOM | 3365 | N | TYR | B | 420 | 14.406 | 29.484 | 21.518 | 1.00 | 41.58 | B | N |
| ATOM | 3366 | CA | TYR | B | 420 | 13.392 | 28.822 | 22.303 | 1.00 | 38.95 | B | C |
| ATOM | 3367 | CB | TYR | B | 420 | 12.611 | 27.862 | 21.422 | 1.00 | 37.97 | B | C |
| ATOM | 3368 | CG | TYR | B | 420 | 11.312 | 27.400 | 22.019 | 1.00 | 46.04 | B | C |
| ATOM | 3369 | CD1 | TYR | B | 420 | 10.303 | 28.309 | 22.335 | 1.00 | 44.66 | B | C |
| ATOM | 3370 | CE1 | TYR | B | 420 | 9.103 | 27.881 | 22.876 | 1.00 | 43.67 | B | C |
| ATOM | 3371 | CD2 | TYR | B | 420 | 11.081 | 26.053 | 22.263 | 1.00 | 49.41 | B | C |
| ATOM | 3372 | CE2 | TYR | B | 420 | 9.883 | 25.619 | 22.804 | 1.00 | 46.00 | B | C |
| ATOM | 3373 | CZ | TYR | B | 420 | 8.901 | 26.534 | 23.106 | 1.00 | 41.79 | B | C |
| ATOM | 3374 | OH | TYR | B | 420 | 7.717 | 26.095 | 23.648 | 1.00 | 45.79 | B | O |
| ATOM | 3375 | C | TYR | B | 420 | 14.148 | 28.045 | 23.356 | 1.00 | 39.98 | B | C |
| ATOM | 3376 | O | TYR | B | 420 | 15.175 | 27.447 | 23.054 | 1.00 | 42.50 | B | O |
| ATOM | 3377 | N | PRO | B | 421 | 13.646 | 28.046 | 24.598 | 1.00 | 45.27 | B | N |
| ATOM | 3378 | CD | PRO | B | 421 | 12.382 | 28.673 | 25.022 | 1.00 | 42.84 | B | C |
| ATOM | 3379 | CA | PRO | B | 421 | 14.357 | 27.413 | 25.717 | 1.00 | 41.10 | B | C |
| ATOM | 3380 | CB | PRO | B | 421 | 13.445 | 27.699 | 26.917 | 1.00 | 42.46 | B | C |
| ATOM | 3381 | CG | PRO | B | 421 | 12.568 | 28.835 | 26.494 | 1.00 | 42.41 | B | C |
| ATOM | 3382 | C | PRO | B | 421 | 14.542 | 25.901 | 25.556 | 1.00 | 42.27 | B | C |
| ATOM | 3383 | O | PRO | B | 421 | 15.502 | 25.342 | 26.090 | 1.00 | 43.29 | B | O |
| ATOM | 3384 | N | MET | B | 422 | 13.633 | 25.244 | 24.845 | 1.00 | 39.49 | B | N |
| ATOM | 3385 | CA | MET | B | 422 | 13.668 | 23.789 | 24.761 | 1.00 | 41.29 | B | C |
| ATOM | 3386 | CB | MET | B | 422 | 12.278 | 23.225 | 24.521 | 1.00 | 53.64 | B | C |
| ATOM | 3387 | CG | MET | B | 422 | 11.306 | 23.468 | 25.636 | 1.00 | 46.99 | B | C |
| ATOM | 3388 | SD | MET | B | 422 | 9.818 | 22.532 | 25.304 | 1.00 | 59.92 | B | S |
| ATOM | 3389 | CE | MET | B | 422 | 8.827 | 23.022 | 26.711 | 1.00 | 52.65 | B | C |
| ATOM | 3390 | C | MET | B | 422 | 14.559 | 23.342 | 23.642 | 1.00 | 42.87 | B | C |
| ATOM | 3391 | O | MET | B | 422 | 14.816 | 24.101 | 22.714 | 1.00 | 54.09 | B | O |
| ATOM | 3392 | N | TYR | B | 423 | 15.013 | 22.097 | 23.712 | 1.00 | 47.02 | B | N |
| ATOM | 3393 | CA | TYR | B | 423 | 15.942 | 21.586 | 22.710 | 1.00 | 50.60 | B | C |
| ATOM | 3394 | CB | TYR | B | 423 | 16.919 | 20.578 | 23.314 | 1.00 | 45.12 | B | C |
| ATOM | 3395 | CG | TYR | B | 423 | 17.713 | 19.850 | 22.255 | 1.00 | 45.67 | B | C |
| ATOM | 3396 | CD1 | TYR | B | 423 | 17.311 | 18.604 | 21.795 | 1.00 | 46.09 | B | C |
| ATOM | 3397 | CE1 | TYR | B | 423 | 18.022 | 17.939 | 20.815 | 1.00 | 44.01 | B | C |
| ATOM | 3398 | CD2 | TYR | B | 423 | 18.848 | 20.421 | 21.694 | 1.00 | 41.38 | B | C |
| ATOM | 3399 | CE2 | TYR | B | 423 | 19.568 | 19.760 | 20.715 | 1.00 | 43.51 | B | C |
| ATOM | 3400 | CZ | TYR | B | 423 | 19.149 | 18.518 | 20.281 | 1.00 | 41.33 | B | C |
| ATOM | 3401 | OH | TYR | B | 423 | 19.859 | 17.849 | 19.313 | 1.00 | 42.90 | B | O |
| ATOM | 3402 | C | TYR | B | 423 | 15.233 | 20.952 | 21.522 | 1.00 | 47.44 | B | C |
| ATOM | 3403 | O | TYR | B | 423 | 14.831 | 19.793 | 21.575 | 1.00 | 50.43 | B | O |
| ATOM | 3404 | N | ARG | B | 424 | 15.087 | 21.711 | 20.445 | 1.00 | 48.86 | B | N |
| ATOM | 3405 | CA | ARG | B | 424 | 14.528 | 21.158 | 19.218 | 1.00 | 51.94 | B | C |
| ATOM | 3406 | CB | ARG | B | 424 | 13.524 | 22.129 | 18.596 | 1.00 | 50.84 | B | C |
| ATOM | 3407 | CG | ARG | B | 424 | 12.703 | 21.514 | 17.477 | 1.00 | 55.24 | B | C |
| ATOM | 3408 | CD | ARG | B | 424 | 11.591 | 22.443 | 16.998 | 1.00 | 53.75 | B | C |
| ATOM | 3409 | NE | ARG | B | 424 | 12.056 | 23.468 | 16.062 | 1.00 | 61.04 | B | N |
| ATOM | 3410 | CZ | ARG | B | 424 | 12.087 | 23.320 | 14.737 | 1.00 | 65.72 | B | C |
| ATOM | 3411 | NH1 | ARG | B | 424 | 11.693 | 22.175 | 14.183 | 1.00 | 61.54 | B | N |
| ATOM | 3412 | NH2 | ARG | B | 424 | 12.517 | 24.314 | 13.965 | 1.00 | 53.10 | B | N |
| ATOM | 3413 | C | ARG | B | 424 | 15.635 | 20.844 | 18.218 | 1.00 | 43.72 | B | C |
| ATOM | 3414 | O | ARG | B | 424 | 16.232 | 21.751 | 17.655 | 1.00 | 42.89 | B | O |
| ATOM | 3415 | N | PHE | B | 425 | 15.926 | 19.566 | 18.013 | 1.00 | 41.31 | B | N |
| ATOM | 3416 | CA | PHE | B | 425 | 16.796 | 19.186 | 16.907 | 1.00 | 41.48 | B | C |
| ATOM | 3417 | CB | PHE | B | 425 | 17.237 | 17.730 | 17.009 | 1.00 | 37.91 | B | C |
| ATOM | 3418 | CG | PHE | B | 425 | 17.965 | 17.249 | 15.797 | 1.00 | 41.35 | B | C |
| ATOM | 3419 | CD1 | PHE | B | 425 | 19.319 | 17.496 | 15.643 | 1.00 | 44.97 | B | C |
| ATOM | 3420 | CD2 | PHE | B | 425 | 17.295 | 16.572 | 14.794 | 1.00 | 39.51 | B | C |
| ATOM | 3421 | CE1 | PHE | B | 425 | 19.993 | 17.074 | 14.509 | 1.00 | 44.66 | B | C |
| ATOM | 3422 | CE2 | PHE | B | 425 | 17.963 | 16.145 | 13.662 | 1.00 | 44.81 | B | C |
| ATOM | 3423 | CZ | PHE | B | 425 | 19.313 | 16.396 | 13.519 | 1.00 | 47.96 | B | C |
| ATOM | 3424 | C | PHE | B | 425 | 16.100 | 19.417 | 15.564 | 1.00 | 38.40 | B | C |
| ATOM | 3425 | O | PHE | B | 425 | 14.935 | 19.080 | 15.382 | 1.00 | 44.23 | B | O |
| ATOM | 3426 | N | THR | B | 426 | 16.820 | 20.001 | 14.626 | 1.00 | 38.81 | B | N |
| ATOM | 3427 | CA | THR | B | 426 | 16.291 | 20.214 | 13.288 | 1.00 | 43.84 | B | C |
| ATOM | 3428 | CB | THR | B | 426 | 15.650 | 21.618 | 13.140 | 1.00 | 46.19 | B | C |
| ATOM | 3429 | OG1 | THR | B | 426 | 14.864 | 21.669 | 11.939 | 1.00 | 41.44 | B | O |
| ATOM | 3430 | CG2 | THR | B | 426 | 16.727 | 22.707 | 13.102 | 1.00 | 37.03 | B | C |
| ATOM | 3431 | C | THR | B | 426 | 17.437 | 20.056 | 12.298 | 1.00 | 40.21 | B | C |
| ATOM | 3432 | O | THR | B | 426 | 18.591 | 20.275 | 12.653 | 1.00 | 34.83 | B | O |
| ATOM | 3433 | N | GLU | B | 427 | 17.120 | 19.647 | 11.073 | 1.00 | 44.75 | B | N |
| ATOM | 3434 | CA | GLU | B | 427 | 18.119 | 19.538 | 10.019 | 1.00 | 39.86 | B | C |
| ATOM | 3435 | CB | GLU | B | 427 | 17.819 | 18.357 | 9.097 | 1.00 | 37.66 | B | C |
| ATOM | 3436 | CG | GLU | B | 427 | 17.778 | 16.993 | 9.779 | 1.00 | 51.55 | B | C |
| ATOM | 3437 | CD | GLU | B | 427 | 19.155 | 16.360 | 9.958 | 1.00 | 64.43 | B | C |
| ATOM | 3438 | OE1 | GLU | B | 427 | 20.171 | 16.989 | 9.572 | 1.00 | 62.60 | B | O |
| ATOM | 3439 | OE2 | GLU | B | 427 | 19.218 | 15.226 | 10.486 | 1.00 | 63.30 | B | O |
| ATOM | 3440 | C | GLU | B | 427 | 18.111 | 20.827 | 9.219 | 1.00 | 40.92 | B | C |

TABLE 13-continued

Coordinates for proMMP9(35-444 ΔFnII) (SEQ ID NO: 12) complex with Example 3

| ATOM | 3441 | O   | GLU | B | 427 | 18.971 | 21.054 | 8.364  | 1.00 | 45.81 B | O |
|------|------|-----|-----|---|-----|--------|--------|--------|------|---------|---|
| ATOM | 3442 | N   | GLY | B | 428 | 17.132 | 21.675 | 9.506  | 1.00 | 38.95 B | N |
| ATOM | 3443 | CA  | GLY | B | 428 | 16.924 | 22.887 | 8.734  | 1.00 | 43.85 B | C |
| ATOM | 3444 | C   | GLY | B | 428 | 17.589 | 24.120 | 9.310  | 1.00 | 36.99 B | C |
| ATOM | 3445 | O   | GLY | B | 428 | 18.116 | 24.078 | 10.423 | 1.00 | 36.41 B | O |
| ATOM | 3446 | N   | PRO | B | 429 | 17.556 | 25.230 | 8.554  | 1.00 | 37.44 B | N |
| ATOM | 3447 | CD  | PRO | B | 429 | 16.822 | 25.326 | 7.278  | 1.00 | 31.00 B | C |
| ATOM | 3448 | CA  | PRO | B | 429 | 18.234 | 26.488 | 8.902  | 1.00 | 28.59 B | C |
| ATOM | 3449 | CB  | PRO | B | 429 | 17.753 | 27.451 | 7.817  | 1.00 | 31.30 B | C |
| ATOM | 3450 | CG  | PRO | B | 429 | 17.380 | 26.563 | 6.661  | 1.00 | 30.77 B | C |
| ATOM | 3451 | C   | PRO | B | 429 | 17.842 | 26.987 | 10.293 | 1.00 | 36.22 B | C |
| ATOM | 3452 | O   | PRO | B | 429 | 16.683 | 27.332 | 10.532 | 1.00 | 35.94 B | O |
| ATOM | 3453 | N   | PRO | B | 430 | 18.812 | 27.008 | 11.214 | 1.00 | 36.27 B | N |
| ATOM | 3454 | CD  | PRO | B | 430 | 20.174 | 26.527 | 10.917 | 1.00 | 28.12 B | C |
| ATOM | 3455 | CA  | PRO | B | 430 | 18.646 | 27.335 | 12.632 | 1.00 | 33.91 B | C |
| ATOM | 3456 | CB  | PRO | B | 430 | 20.092 | 27.377 | 13.135 | 1.00 | 39.95 B | C |
| ATOM | 3457 | CG  | PRO | B | 430 | 20.797 | 26.365 | 12.273 | 1.00 | 26.98 B | C |
| ATOM | 3458 | C   | PRO | B | 430 | 17.928 | 28.660 | 12.934 | 1.00 | 37.72 B | C |
| ATOM | 3459 | O   | PRO | B | 430 | 16.936 | 28.647 | 13.662 | 1.00 | 35.11 B | O |
| ATOM | 3460 | N   | LEU | B | 431 | 18.419 | 29.780 | 12.411 | 1.00 | 38.24 B | N |
| ATOM | 3461 | CA  | LEU | B | 431 | 17.819 | 31.074 | 12.739 | 1.00 | 33.69 B | C |
| ATOM | 3462 | CB  | LEU | B | 431 | 18.637 | 32.232 | 12.153 | 1.00 | 33.63 B | C |
| ATOM | 3463 | CG  | LEU | B | 431 | 20.042 | 32.555 | 12.672 | 1.00 | 28.73 B | C |
| ATOM | 3464 | CD1 | LEU | B | 431 | 20.599 | 33.734 | 11.909 | 1.00 | 23.36 B | C |
| ATOM | 3465 | CD2 | LEU | B | 431 | 20.020 | 32.864 | 14.155 | 1.00 | 31.39 B | C |
| ATOM | 3466 | C   | LEU | B | 431 | 16.385 | 31.163 | 12.233 | 1.00 | 39.12 B | C |
| ATOM | 3467 | O   | LEU | B | 431 | 16.074 | 30.676 | 11.140 | 1.00 | 41.93 B | O |
| ATOM | 3468 | N   | HIS | B | 432 | 15.521 | 31.795 | 13.027 | 1.00 | 39.31 B | N |
| ATOM | 3469 | CA  | HIS | B | 432 | 14.141 | 32.082 | 12.625 | 1.00 | 37.61 B | C |
| ATOM | 3470 | CB  | HIS | B | 432 | 13.164 | 31.295 | 13.490 | 1.00 | 36.42 B | C |
| ATOM | 3471 | CG  | HIS | B | 432 | 12.824 | 29.945 | 12.945 | 1.00 | 36.01 B | C |
| ATOM | 3472 | CD2 | HIS | B | 432 | 11.752 | 29.514 | 12.243 | 1.00 | 35.57 B | C |
| ATOM | 3473 | ND1 | HIS | B | 432 | 13.639 | 28.845 | 13.113 | 1.00 | 40.00 B | N |
| ATOM | 3474 | CE1 | HIS | B | 432 | 13.088 | 27.798 | 12.530 | 1.00 | 34.96 B | C |
| ATOM | 3475 | NE2 | HIS | B | 432 | 11.938 | 28.174 | 12.000 | 1.00 | 35.19 B | N |
| ATOM | 3476 | C   | HIS | B | 432 | 13.827 | 33.591 | 12.663 | 1.00 | 37.35 B | C |
| ATOM | 3477 | O   | HIS | B | 432 | 14.616 | 34.386 | 13.186 | 1.00 | 33.05 B | O |
| ATOM | 3478 | N   | LYS | B | 433 | 12.686 | 33.981 | 12.098 | 1.00 | 32.05 B | N |
| ATOM | 3479 | CA  | LYS | B | 433 | 12.347 | 35.401 | 11.962 | 1.00 | 34.88 B | C |
| ATOM | 3480 | CB  | LYS | B | 433 | 10.919 | 35.578 | 11.448 | 1.00 | 38.30 B | C |
| ATOM | 3481 | CG  | LYS | B | 433 | 10.759 | 35.580 | 9.934  | 1.00 | 40.80 B | C |
| ATOM | 3482 | CD  | LYS | B | 433 | 9.279  | 35.463 | 9.552  | 1.00 | 37.88 B | C |
| ATOM | 3483 | CE  | LYS | B | 433 | 9.061  | 35.315 | 8.045  | 1.00 | 40.11 B | C |
| ATOM | 3484 | NZ  | LYS | B | 433 | 8.865  | 36.616 | 7.344  | 1.00 | 38.99 B | N |
| ATOM | 3485 | C   | LYS | B | 433 | 12.501 | 36.154 | 13.276 | 1.00 | 36.47 B | C |
| ATOM | 3486 | O   | LYS | B | 433 | 12.998 | 37.282 | 13.310 | 1.00 | 37.47 B | O |
| ATOM | 3487 | N   | ASP | B | 434 | 12.072 | 35.517 | 14.359 | 1.00 | 38.85 B | N |
| ATOM | 3488 | CA  | ASP | B | 434 | 12.106 | 36.122 | 15.684 | 1.00 | 33.79 B | C |
| ATOM | 3489 | CB  | ASP | B | 434 | 11.248 | 35.315 | 16.665 | 1.00 | 34.12 B | C |
| ATOM | 3490 | CG  | ASP | B | 434 | 10.855 | 36.119 | 17.890 | 1.00 | 39.64 B | C |
| ATOM | 3491 | OD1 | ASP | B | 434 | 10.412 | 37.277 | 17.712 | 1.00 | 39.66 B | O |
| ATOM | 3492 | OD2 | ASP | B | 434 | 10.985 | 35.596 | 19.021 | 1.00 | 34.25 B | O |
| ATOM | 3493 | C   | ASP | B | 434 | 13.527 | 36.253 | 16.219 | 1.00 | 33.80 B | C |
| ATOM | 3494 | O   | ASP | B | 434 | 13.846 | 37.218 | 16.910 | 1.00 | 33.26 B | O |
| ATOM | 3495 | N   | ASP | B | 435 | 14.377 | 35.276 | 15.915 | 1.00 | 33.33 B | N |
| ATOM | 3496 | CA  | ASP | B | 435 | 15.776 | 35.376 | 16.294 | 1.00 | 29.72 B | C |
| ATOM | 3497 | CB  | ASP | B | 435 | 16.547 | 34.141 | 15.873 | 1.00 | 33.76 B | C |
| ATOM | 3498 | CG  | ASP | B | 435 | 15.885 | 32.866 | 16.299 | 1.00 | 34.51 B | C |
| ATOM | 3499 | OD1 | ASP | B | 435 | 16.106 | 32.435 | 17.444 | 1.00 | 39.97 B | O |
| ATOM | 3500 | OD2 | ASP | B | 435 | 15.159 | 32.280 | 15.478 | 1.00 | 37.24 B | O |
| ATOM | 3501 | C   | ASP | B | 435 | 16.381 | 36.596 | 15.625 | 1.00 | 34.00 B | C |
| ATOM | 3502 | O   | ASP | B | 435 | 17.136 | 37.338 | 16.239 | 1.00 | 43.44 B | O |
| ATOM | 3503 | N   | VAL | B | 436 | 16.041 | 36.812 | 14.361 | 1.00 | 36.85 B | N |
| ATOM | 3504 | CA  | VAL | B | 436 | 16.614 | 37.926 | 13.610 | 1.00 | 37.75 B | C |
| ATOM | 3505 | CB  | VAL | B | 436 | 16.300 | 37.825 | 12.092 | 1.00 | 41.65 B | C |
| ATOM | 3506 | CG1 | VAL | B | 436 | 16.767 | 39.066 | 11.357 | 1.00 | 38.72 B | C |
| ATOM | 3507 | CG2 | VAL | B | 436 | 16.957 | 36.595 | 11.502 | 1.00 | 37.20 B | C |
| ATOM | 3508 | C   | VAL | B | 436 | 16.145 | 39.261 | 14.176 | 1.00 | 38.83 B | C |
| ATOM | 3509 | O   | VAL | B | 436 | 16.967 | 40.122 | 14.495 | 1.00 | 40.16 B | O |
| ATOM | 3510 | N   | ASN | B | 437 | 14.825 | 39.419 | 14.300 | 1.00 | 41.55 B | N |
| ATOM | 3511 | CA  | ASN | B | 437 | 14.220 | 40.594 | 14.935 | 1.00 | 37.98 B | C |
| ATOM | 3512 | CB  | ASN | B | 437 | 12.734 | 40.348 | 15.228 | 1.00 | 39.82 B | C |
| ATOM | 3513 | CG  | ASN | B | 437 | 11.919 | 40.096 | 13.971 | 1.00 | 41.05 B | C |
| ATOM | 3514 | OD1 | ASN | B | 437 | 12.342 | 40.434 | 12.860 | 1.00 | 40.25 B | O |
| ATOM | 3515 | ND2 | ASN | B | 437 | 10.737 | 39.499 | 14.143 | 1.00 | 37.66 B | N |
| ATOM | 3516 | C   | ASN | B | 437 | 14.909 | 40.905 | 16.240 | 1.00 | 33.15 B | C |
| ATOM | 3517 | O   | ASN | B | 437 | 15.405 | 42.007 | 16.453 | 1.00 | 38.63 B | O |

TABLE 13-continued

Coordinates for proMMP9(35-444 ΔFnII) (SEQ ID NO: 12) complex with Example 3

| ATOM | 3518 | N | GLY | B | 438 | 14.925 | 39.914 | 17.118 | 1.00 | 34.30 | B | N |
|---|---|---|---|---|---|---|---|---|---|---|---|---|
| ATOM | 3519 | CA | GLY | B | 438 | 15.583 | 40.037 | 18.398 | 1.00 | 32.90 | B | C |
| ATOM | 3520 | C | GLY | B | 438 | 16.965 | 40.617 | 18.251 | 1.00 | 33.61 | B | C |
| ATOM | 3521 | O | GLY | B | 438 | 17.221 | 41.718 | 18.718 | 1.00 | 35.24 | B | O |
| ATOM | 3522 | N | ILE | B | 439 | 17.855 | 39.882 | 17.590 | 1.00 | 35.36 | B | N |
| ATOM | 3523 | CA | ILE | B | 439 | 19.229 | 40.340 | 17.384 | 1.00 | 35.59 | B | C |
| ATOM | 3524 | CB | ILE | B | 439 | 20.058 | 39.323 | 16.552 | 1.00 | 42.62 | B | C |
| ATOM | 3525 | CG2 | ILE | B | 439 | 19.713 | 39.414 | 15.076 | 1.00 | 37.47 | B | C |
| ATOM | 3526 | CG1 | ILE | B | 439 | 21.558 | 39.510 | 16.805 | 1.00 | 31.51 | B | C |
| ATOM | 3527 | CD1 | ILE | B | 439 | 21.955 | 39.222 | 18.229 | 1.00 | 31.55 | B | C |
| ATOM | 3528 | C | ILE | B | 439 | 19.307 | 41.745 | 16.761 | 1.00 | 38.77 | B | C |
| ATOM | 3529 | O | ILE | B | 439 | 20.010 | 42.614 | 17.278 | 1.00 | 39.77 | B | O |
| ATOM | 3530 | N | ARG | B | 440 | 18.584 | 41.973 | 15.668 | 1.00 | 34.96 | B | N |
| ATOM | 3531 | CA | ARG | B | 440 | 18.585 | 43.291 | 15.041 | 1.00 | 39.46 | B | C |
| ATOM | 3532 | CB | ARG | B | 440 | 17.640 | 43.337 | 13.843 | 1.00 | 37.61 | B | C |
| ATOM | 3533 | CG | ARG | B | 440 | 18.173 | 42.662 | 12.609 | 1.00 | 37.83 | B | C |
| ATOM | 3534 | CD | ARG | B | 440 | 17.157 | 42.741 | 11.484 | 1.00 | 44.10 | B | C |
| ATOM | 3535 | NE | ARG | B | 440 | 17.564 | 41.946 | 10.328 | 1.00 | 47.73 | B | N |
| ATOM | 3536 | CZ | ARG | B | 440 | 17.054 | 42.083 | 9.108 | 1.00 | 50.10 | B | C |
| ATOM | 3537 | NH1 | ARG | B | 440 | 16.116 | 42.994 | 8.873 | 1.00 | 50.41 | B | N |
| ATOM | 3538 | NH2 | ARG | B | 440 | 17.492 | 41.319 | 8.117 | 1.00 | 46.95 | B | N |
| ATOM | 3539 | C | ARG | B | 440 | 18.213 | 44.388 | 16.031 | 1.00 | 42.41 | B | C |
| ATOM | 3540 | O | ARG | B | 440 | 18.820 | 45.453 | 16.031 | 1.00 | 40.63 | B | O |
| ATOM | 3541 | N | HIS | B | 441 | 17.204 | 44.132 | 16.861 | 1.00 | 41.17 | B | N |
| ATOM | 3542 | CA | HIS | B | 441 | 16.827 | 45.064 | 17.922 | 1.00 | 42.17 | B | C |
| ATOM | 3543 | CB | HIS | B | 441 | 15.933 | 44.351 | 18.940 | 1.00 | 45.93 | B | C |
| ATOM | 3544 | CG | HIS | B | 441 | 15.270 | 45.260 | 19.929 | 1.00 | 53.49 | B | C |
| ATOM | 3545 | CD2 | HIS | B | 441 | 13.985 | 45.680 | 20.030 | 1.00 | 57.99 | B | C |
| ATOM | 3546 | ND1 | HIS | B | 441 | 15.938 | 45.815 | 20.999 | 1.00 | 56.29 | B | N |
| ATOM | 3547 | CE1 | HIS | B | 441 | 15.101 | 46.559 | 21.701 | 1.00 | 54.49 | B | C |
| ATOM | 3548 | NE2 | HIS | B | 441 | 13.909 | 46.491 | 21.136 | 1.00 | 50.49 | B | N |
| ATOM | 3549 | C | HIS | B | 441 | 18.094 | 45.595 | 18.596 | 1.00 | 49.37 | B | C |
| ATOM | 3550 | O | HIS | B | 441 | 18.347 | 46.802 | 18.603 | 1.00 | 52.85 | B | O |
| ATOM | 3551 | N | LEU | B | 442 | 18.902 | 44.680 | 19.129 | 1.00 | 45.59 | B | N |
| ATOM | 3552 | CA | LEU | B | 442 | 20.158 | 45.031 | 19.796 | 1.00 | 44.32 | B | C |
| ATOM | 3553 | CB | LEU | B | 442 | 20.831 | 43.773 | 20.354 | 1.00 | 40.10 | B | C |
| ATOM | 3554 | CG | LEU | B | 442 | 20.560 | 43.388 | 21.811 | 1.00 | 42.68 | B | C |
| ATOM | 3555 | CD1 | LEU | B | 442 | 19.202 | 43.882 | 22.274 | 1.00 | 41.57 | B | C |
| ATOM | 3556 | CD2 | LEU | B | 442 | 20.676 | 41.893 | 21.986 | 1.00 | 36.14 | B | C |
| ATOM | 3557 | C | LEU | B | 442 | 21.162 | 45.793 | 18.923 | 1.00 | 43.98 | B | C |
| ATOM | 3558 | O | LEU | B | 442 | 21.549 | 46.919 | 19.240 | 1.00 | 48.51 | B | O |
| ATOM | 3559 | N | TYR | B | 443 | 21.592 | 45.172 | 17.831 | 1.00 | 44.59 | B | N |
| ATOM | 3560 | CA | TYR | B | 443 | 22.728 | 45.683 | 17.076 | 1.00 | 38.25 | B | C |
| ATOM | 3561 | CB | TYR | B | 443 | 23.739 | 44.563 | 16.843 | 1.00 | 44.01 | B | C |
| ATOM | 3562 | CG | TYR | B | 443 | 24.183 | 43.874 | 18.111 | 1.00 | 40.20 | B | C |
| ATOM | 3563 | CD1 | TYR | B | 443 | 23.657 | 42.645 | 18.472 | 1.00 | 33.45 | B | C |
| ATOM | 3564 | CE1 | TYR | B | 443 | 24.054 | 42.014 | 19.622 | 1.00 | 29.70 | B | C |
| ATOM | 3565 | CD2 | TYR | B | 443 | 25.126 | 44.457 | 18.948 | 1.00 | 37.17 | B | C |
| ATOM | 3566 | CE2 | TYR | B | 443 | 25.527 | 43.835 | 20.098 | 1.00 | 37.41 | B | C |
| ATOM | 3567 | CZ | TYR | B | 443 | 24.982 | 42.610 | 20.430 | 1.00 | 37.02 | B | C |
| ATOM | 3568 | OH | TYR | B | 443 | 25.380 | 41.972 | 21.581 | 1.00 | 45.31 | B | O |
| ATOM | 3569 | C | TYR | B | 443 | 22.360 | 46.341 | 15.746 | 1.00 | 38.90 | B | C |
| ATOM | 3570 | O | TYR | B | 443 | 23.239 | 46.736 | 14.978 | 1.00 | 45.23 | B | O |
| ATOM | 3571 | N | GLY | B | 444 | 21.068 | 46.459 | 15.473 | 1.00 | 35.79 | B | N |
| ATOM | 3572 | CA | GLY | B | 444 | 20.611 | 47.107 | 14.258 | 1.00 | 35.91 | B | C |
| ATOM | 3573 | C | GLY | B | 444 | 20.677 | 46.245 | 13.015 | 1.00 | 31.37 | B | C |
| ATOM | 3574 | O | GLY | B | 444 | 19.800 | 46.341 | 12.163 | 1.00 | 33.15 | B | O |
| ATOM | 3575 | ZN | ZN | B | 500 | 18.805 | 29.746 | 26.683 | 1.00 | 42.53 | B | Zn |
| ATOM | 3576 | ZN | ZN | B | 501 | 28.409 | 27.765 | 34.203 | 1.00 | 47.53 | B | Zn |
| ATOM | 3577 | CA | CA | B | 502 | 22.234 | 18.035 | 32.429 | 1.00 | 56.15 | B | Ca |
| ATOM | 3578 | CA | CA | B | 504 | 34.346 | 37.370 | 29.501 | 1.00 | 67.64 | B | Ca |
| ATOM | 3579 | C01 | LIG | C | 1 | 23.381 | 30.840 | 34.333 | 1.00 | 53.33 | A | C |
| ATOM | 3580 | O02 | LIG | C | 1 | 22.683 | 31.724 | 33.497 | 1.00 | 49.94 | A | O |
| ATOM | 3581 | C03 | LIG | C | 1 | 21.906 | 32.725 | 34.058 | 1.00 | 50.08 | A | C |
| ATOM | 3582 | C04 | LIG | C | 1 | 21.566 | 32.691 | 35.465 | 1.00 | 57.59 | A | C |
| ATOM | 3583 | C05 | LIG | C | 1 | 20.725 | 33.749 | 36.037 | 1.00 | 58.70 | A | C |
| ATOM | 3584 | C06 | LIG | C | 1 | 20.207 | 34.888 | 35.143 | 1.00 | 64.32 | A | C |
| ATOM | 3585 | C07 | LIG | C | 1 | 20.542 | 34.923 | 33.768 | 1.00 | 53.68 | A | C |
| ATOM | 3586 | C08 | LIG | C | 1 | 21.404 | 33.836 | 33.185 | 1.00 | 51.64 | A | C |
| ATOM | 3587 | N09 | LIG | C | 1 | 21.767 | 33.805 | 31.741 | 1.00 | 47.46 | A | N |
| ATOM | 3588 | C10 | LIG | C | 1 | 21.536 | 34.934 | 30.816 | 1.00 | 48.02 | A | C |
| ATOM | 3589 | N11 | LIG | C | 1 | 20.680 | 36.173 | 31.113 | 1.00 | 57.95 | A | N |
| ATOM | 3590 | C12 | LIG | C | 1 | 20.698 | 37.157 | 29.760 | 1.00 | 58.61 | A | C |
| ATOM | 3591 | C13 | LIG | C | 1 | 21.526 | 36.525 | 28.769 | 1.00 | 51.23 | A | C |
| ATOM | 3592 | S14 | LIG | C | 1 | 22.088 | 35.049 | 29.409 | 1.00 | 45.15 | A | S |
| ATOM | 3593 | C15 | LIG | C | 1 | 20.059 | 38.393 | 29.702 | 1.00 | 55.14 | A | C |
| ATOM | 3594 | S16 | LIG | C | 1 | 19.503 | 39.228 | 28.415 | 1.00 | 59.20 | A | S |

TABLE 13-continued

Coordinates for proMMP9(35-444 ΔFnII) (SEQ ID NO: 12) complex with Example 3

| ATOM | 3595 | C17 | LIG | C | 1 | 18.848 | 40.567 | 28.978 | 1.00 | 65.97 | A | C |
|---|---|---|---|---|---|---|---|---|---|---|---|---|
| ATOM | 3596 | N18 | LIG | C | 1 | 18.212 | 41.643 | 28.212 | 1.00 | 58.41 | A | N |
| ATOM | 3597 | N19 | LIG | C | 1 | 18.973 | 40.566 | 30.481 | 1.00 | 62.23 | A | N |
| ATOM | 3598 | C20 | LIG | C | 1 | 19.749 | 39.170 | 30.915 | 1.00 | 54.08 | A | C |
| ATOM | 3599 | C21 | LIG | C | 1 | 20.110 | 38.742 | 32.348 | 1.00 | 59.61 | A | C |
| ATOM | 3600 | C22 | LIG | C | 1 | 19.297 | 35.964 | 35.750 | 1.00 | 68.76 | A | C |
| ATOM | 3601 | N23 | LIG | C | 1 | 19.723 | 36.603 | 36.969 | 1.00 | 64.88 | A | N |
| ATOM | 3602 | O24 | LIG | C | 1 | 18.141 | 35.979 | 35.457 | 1.00 | 64.69 | A | O |
| END | | | | | | | | | | | | |

TABLE 14

Coordinates for proMMP9(35-444 ΔFnII) (SEQ ID NO: 12) complex with Example 4

| ATOM | 1 | N | THR | A | 40 | 6.815 | 61.205 | 26.895 | 1.00 | 41.49 | A | N |
|---|---|---|---|---|---|---|---|---|---|---|---|---|
| ATOM | 2 | CA | THR | A | 40 | 5.541 | 61.896 | 26.714 | 1.00 | 44.51 | A | C |
| ATOM | 3 | C | THR | A | 40 | 5.611 | 62.901 | 25.558 | 1.00 | 48.92 | A | C |
| ATOM | 4 | CB | THR | A | 40 | 5.048 | 62.568 | 28.032 | 1.00 | 47.93 | A | C |
| ATOM | 5 | OG1 | THR | A | 40 | 4.274 | 63.743 | 27.739 | 1.00 | 53.72 | A | O |
| ATOM | 6 | CG2 | THR | A | 40 | 6.208 | 62.952 | 28.906 | 1.00 | 44.24 | A | C |
| ATOM | 7 | O | THR | A | 40 | 6.701 | 63.190 | 25.053 | 1.00 | 47.24 | A | O |
| ATOM | 8 | CB | ASP | A | 41 | 2.973 | 64.531 | 23.474 | 1.00 | 40.84 | A | C |
| ATOM | 9 | CG | ASP | A | 41 | 2.408 | 63.258 | 22.893 | 1.00 | 38.30 | A | C |
| ATOM | 10 | OD1 | ASP | A | 41 | 3.179 | 62.323 | 22.615 | 1.00 | 37.84 | A | O |
| ATOM | 11 | OD2 | ASP | A | 41 | 1.178 | 63.197 | 22.706 | 1.00 | 40.04 | A | O |
| ATOM | 12 | C | ASP | A | 41 | 4.883 | 65.703 | 24.519 | 1.00 | 43.31 | A | C |
| ATOM | 13 | O | ASP | A | 41 | 5.735 | 66.337 | 23.896 | 1.00 | 38.74 | A | O |
| ATOM | 14 | N | ASP | A | 41 | 4.450 | 63.393 | 25.115 | 1.00 | 46.41 | A | N |
| ATOM | 15 | CA | ASP | A | 41 | 4.396 | 64.360 | 24.016 | 1.00 | 44.76 | A | C |
| ATOM | 16 | N | ARG | A | 42 | 4.332 | 66.125 | 25.654 | 1.00 | 41.84 | A | N |
| ATOM | 17 | CA | ARG | A | 42 | 4.684 | 67.405 | 26.244 | 1.00 | 41.99 | A | C |
| ATOM | 18 | CB | ARG | A | 42 | 3.732 | 67.746 | 27.396 | 1.00 | 44.53 | A | C |
| ATOM | 19 | CG | ARG | A | 42 | 4.121 | 68.991 | 28.198 | 1.00 | 53.97 | A | C |
| ATOM | 20 | CD | ARG | A | 42 | 3.435 | 70.276 | 27.713 | 1.00 | 50.68 | A | C |
| ATOM | 21 | NE | ARG | A | 42 | 3.990 | 71.458 | 28.379 | 1.00 | 60.32 | A | N |
| ATOM | 22 | CZ | ARG | A | 42 | 3.356 | 72.624 | 28.525 | 1.00 | 59.61 | A | C |
| ATOM | 23 | NH1 | ARG | A | 42 | 2.120 | 72.785 | 28.061 | 1.00 | 51.20 | A | N |
| ATOM | 24 | NH2 | ARG | A | 42 | 3.962 | 73.634 | 29.145 | 1.00 | 56.54 | A | N |
| ATOM | 25 | C | ARG | A | 42 | 6.154 | 67.437 | 26.681 | 1.00 | 43.15 | A | C |
| ATOM | 26 | O | ARG | A | 42 | 6.772 | 68.502 | 26.715 | 1.00 | 46.76 | A | O |
| ATOM | 27 | N | GLN | A | 43 | 6.717 | 66.268 | 26.978 | 1.00 | 41.55 | A | N |
| ATOM | 28 | CA | GLN | A | 43 | 8.113 | 66.169 | 27.395 | 1.00 | 40.76 | A | C |
| ATOM | 29 | CB | GLN | A | 43 | 8.368 | 64.839 | 28.107 | 1.00 | 40.10 | A | C |
| ATOM | 30 | CG | GLN | A | 43 | 9.833 | 64.402 | 28.181 | 1.00 | 45.45 | A | C |
| ATOM | 31 | CD | GLN | A | 43 | 10.023 | 63.009 | 28.796 | 1.00 | 50.08 | A | C |
| ATOM | 32 | OE1 | GLN | A | 43 | 9.114 | 62.174 | 28.790 | 1.00 | 55.94 | A | O |
| ATOM | 33 | NE2 | GLN | A | 43 | 11.216 | 62.756 | 29.320 | 1.00 | 45.78 | A | N |
| ATOM | 34 | C | GLN | A | 43 | 9.034 | 66.265 | 26.193 | 1.00 | 41.53 | A | C |
| ATOM | 35 | O | GLN | A | 43 | 10.056 | 66.951 | 26.237 | 1.00 | 36.67 | A | O |
| ATOM | 36 | N | LEU | A | 44 | 8.674 | 65.536 | 25.135 | 1.00 | 39.20 | A | N |
| ATOM | 37 | CA | LEU | A | 44 | 9.424 | 65.531 | 23.893 | 1.00 | 37.68 | A | C |
| ATOM | 38 | CB | LEU | A | 44 | 8.786 | 64.565 | 22.890 | 1.00 | 39.15 | A | C |
| ATOM | 39 | CG | LEU | A | 44 | 9.020 | 64.713 | 21.378 | 1.00 | 40.36 | A | C |
| ATOM | 40 | CD1 | LEU | A | 44 | 10.502 | 64.746 | 20.999 | 1.00 | 41.17 | A | C |
| ATOM | 41 | CD2 | LEU | A | 44 | 8.329 | 63.588 | 20.642 | 1.00 | 37.97 | A | C |
| ATOM | 42 | C | LEU | A | 44 | 9.488 | 66.951 | 23.346 | 1.00 | 36.20 | A | C |
| ATOM | 43 | O | LEU | A | 44 | 10.530 | 67.393 | 22.870 | 1.00 | 37.28 | A | O |
| ATOM | 44 | N | ALA | A | 45 | 8.382 | 67.676 | 23.464 | 1.00 | 31.95 | A | N |
| ATOM | 45 | CA | ALA | A | 45 | 8.289 | 69.019 | 22.912 | 1.00 | 32.90 | A | C |
| ATOM | 46 | CB | ALA | A | 45 | 6.847 | 69.460 | 22.852 | 1.00 | 36.64 | A | C |
| ATOM | 47 | C | ALA | A | 45 | 9.130 | 70.030 | 23.690 | 1.00 | 38.02 | A | C |
| ATOM | 48 | O | ALA | A | 45 | 9.785 | 70.895 | 23.092 | 1.00 | 34.03 | A | O |
| ATOM | 49 | N | GLU | A | 46 | 9.104 | 69.930 | 25.020 | 1.00 | 39.34 | A | N |
| ATOM | 50 | CA | GLU | A | 46 | 9.974 | 70.757 | 25.850 | 1.00 | 37.95 | A | C |
| ATOM | 51 | CB | GLU | A | 46 | 9.734 | 70.482 | 27.341 | 1.00 | 37.81 | A | C |
| ATOM | 52 | CG | GLU | A | 46 | 8.416 | 71.068 | 27.857 | 1.00 | 48.83 | A | C |
| ATOM | 53 | CD | GLU | A | 46 | 8.024 | 70.601 | 29.271 | 1.00 | 58.46 | A | C |
| ATOM | 54 | OE1 | GLU | A | 46 | 8.888 | 70.072 | 30.013 | 1.00 | 56.20 | A | O |
| ATOM | 55 | OE2 | GLU | A | 46 | 6.838 | 70.773 | 29.638 | 1.00 | 60.95 | A | O |
| ATOM | 56 | C | GLU | A | 46 | 11.455 | 70.552 | 25.499 | 1.00 | 34.76 | A | C |
| ATOM | 57 | O | GLU | A | 46 | 12.212 | 71.514 | 25.361 | 1.00 | 32.46 | A | O |
| ATOM | 58 | N | GLU | A | 47 | 11.854 | 69.291 | 25.377 | 1.00 | 30.80 | A | N |
| ATOM | 59 | CA | GLU | A | 47 | 13.216 | 68.918 | 25.049 | 1.00 | 34.96 | A | C |
| ATOM | 60 | CB | GLU | A | 47 | 13.356 | 67.399 | 25.212 | 1.00 | 35.72 | A | C |

TABLE 14-continued

Coordinates for proMMP9(35-444 ΔFnII) (SEQ ID NO: 12) complex with Example 4

| ATOM | 61 | CG | GLU | A | 47 | 14.728 | 66.822 | 24.970 | 1.00 | 42.08 | A | C |
|---|---|---|---|---|---|---|---|---|---|---|---|---|
| ATOM | 62 | CD | GLU | A | 47 | 15.779 | 67.356 | 25.932 | 1.00 | 50.60 | A | C |
| ATOM | 63 | OE1 | GLU | A | 47 | 15.392 | 67.895 | 26.994 | 1.00 | 52.94 | A | O |
| ATOM | 64 | OE2 | GLU | A | 47 | 16.992 | 67.239 | 25.624 | 1.00 | 48.16 | A | O |
| ATOM | 65 | C | GLU | A | 47 | 13.589 | 69.357 | 23.616 | 1.00 | 34.61 | A | C |
| ATOM | 66 | O | GLU | A | 47 | 14.677 | 69.879 | 23.371 | 1.00 | 35.40 | A | O |
| ATOM | 67 | N | TYR | A | 48 | 12.684 | 69.139 | 22.671 | 1.00 | 30.60 | A | N |
| ATOM | 68 | CA | TYR | A | 48 | 12.933 | 69.525 | 21.286 | 1.00 | 31.95 | A | C |
| ATOM | 69 | CB | TYR | A | 48 | 11.777 | 69.071 | 20.419 | 1.00 | 31.53 | A | C |
| ATOM | 70 | CG | TYR | A | 48 | 12.019 | 69.102 | 18.934 | 1.00 | 26.09 | A | C |
| ATOM | 71 | CD1 | TYR | A | 48 | 11.919 | 70.290 | 18.213 | 1.00 | 24.34 | A | C |
| ATOM | 72 | CE1 | TYR | A | 48 | 12.124 | 70.306 | 16.825 | 1.00 | 27.70 | A | C |
| ATOM | 73 | CD2 | TYR | A | 48 | 12.307 | 67.929 | 18.242 | 1.00 | 26.24 | A | C |
| ATOM | 74 | CE2 | TYR | A | 48 | 12.504 | 67.931 | 16.872 | 1.00 | 26.15 | A | C |
| ATOM | 75 | CZ | TYR | A | 48 | 12.416 | 69.120 | 16.167 | 1.00 | 24.76 | A | C |
| ATOM | 76 | OH | TYR | A | 48 | 12.627 | 69.110 | 14.800 | 1.00 | 26.92 | A | O |
| ATOM | 77 | C | TYR | A | 48 | 13.101 | 71.038 | 21.185 | 1.00 | 29.96 | A | C |
| ATOM | 78 | O | TYR | A | 48 | 14.081 | 71.520 | 20.639 | 1.00 | 28.34 | A | O |
| ATOM | 79 | N | LEU | A | 49 | 12.138 | 71.779 | 21.731 | 1.00 | 31.10 | A | N |
| ATOM | 80 | CA | LEU | A | 49 | 12.200 | 73.232 | 21.725 | 1.00 | 31.20 | A | C |
| ATOM | 81 | CB | LEU | A | 49 | 10.971 | 73.829 | 22.416 | 1.00 | 29.56 | A | C |
| ATOM | 82 | CG | LEU | A | 49 | 9.648 | 73.749 | 21.650 | 1.00 | 28.86 | A | C |
| ATOM | 83 | CD1 | LEU | A | 49 | 8.503 | 74.210 | 22.530 | 1.00 | 29.67 | A | C |
| ATOM | 84 | CD2 | LEU | A | 49 | 9.719 | 74.588 | 20.347 | 1.00 | 25.11 | A | C |
| ATOM | 85 | C | LEU | A | 49 | 13.470 | 73.729 | 22.402 | 1.00 | 31.73 | A | C |
| ATOM | 86 | O | LEU | A | 49 | 14.099 | 74.696 | 21.963 | 1.00 | 30.36 | A | O |
| ATOM | 87 | N | TYR | A | 50 | 13.859 | 73.084 | 23.489 | 1.00 | 31.65 | A | N |
| ATOM | 88 | CA | TYR | A | 50 | 15.044 | 73.569 | 24.176 | 1.00 | 33.14 | A | C |
| ATOM | 89 | CB | TYR | A | 50 | 15.209 | 72.951 | 25.560 | 1.00 | 33.85 | A | C |
| ATOM | 90 | CG | TYR | A | 50 | 16.620 | 73.091 | 26.083 | 1.00 | 36.42 | A | C |
| ATOM | 91 | CD1 | TYR | A | 50 | 17.047 | 74.270 | 26.682 | 1.00 | 35.52 | A | C |
| ATOM | 92 | CE1 | TYR | A | 50 | 18.335 | 74.400 | 27.157 | 1.00 | 39.57 | A | C |
| ATOM | 93 | CD2 | TYR | A | 50 | 17.532 | 72.046 | 25.954 | 1.00 | 39.41 | A | C |
| ATOM | 94 | CE2 | TYR | A | 50 | 18.829 | 72.170 | 26.422 | 1.00 | 38.19 | A | C |
| ATOM | 95 | CZ | TYR | A | 50 | 19.221 | 73.344 | 27.025 | 1.00 | 40.79 | A | C |
| ATOM | 96 | OH | TYR | A | 50 | 20.512 | 73.459 | 27.488 | 1.00 | 50.96 | A | O |
| ATOM | 97 | C | TYR | A | 50 | 16.274 | 73.281 | 23.350 | 1.00 | 29.04 | A | C |
| ATOM | 98 | O | TYR | A | 50 | 17.092 | 74.159 | 23.120 | 1.00 | 30.30 | A | O |
| ATOM | 99 | N | ARG | A | 51 | 16.398 | 72.044 | 22.901 | 1.00 | 26.80 | A | N |
| ATOM | 100 | CA | ARG | A | 51 | 17.667 | 71.600 | 22.382 | 1.00 | 30.40 | A | C |
| ATOM | 101 | CB | ARG | A | 51 | 17.802 | 70.075 | 22.423 | 1.00 | 30.79 | A | C |
| ATOM | 102 | CG | ARG | A | 51 | 17.211 | 69.310 | 21.277 | 1.00 | 35.26 | A | C |
| ATOM | 103 | CD | ARG | A | 51 | 17.685 | 67.856 | 21.352 | 1.00 | 33.78 | A | C |
| ATOM | 104 | NE | ARG | A | 51 | 19.137 | 67.790 | 21.257 | 1.00 | 44.43 | A | N |
| ATOM | 105 | CZ | ARG | A | 51 | 19.899 | 66.819 | 21.768 | 1.00 | 47.46 | A | C |
| ATOM | 106 | NH1 | ARG | A | 51 | 21.215 | 66.875 | 21.614 | 1.00 | 41.83 | A | N |
| ATOM | 107 | NH2 | ARG | A | 51 | 19.357 | 65.802 | 22.430 | 1.00 | 43.17 | A | N |
| ATOM | 108 | C | ARG | A | 51 | 17.975 | 72.221 | 21.014 | 1.00 | 28.63 | A | C |
| ATOM | 109 | O | ARG | A | 51 | 19.120 | 72.465 | 20.709 | 1.00 | 27.12 | A | O |
| ATOM | 110 | N | TYR | A | 52 | 16.950 | 72.571 | 20.247 | 1.00 | 27.07 | A | N |
| ATOM | 111 | CA | TYR | A | 52 | 17.187 | 73.157 | 18.938 | 1.00 | 28.88 | A | C |
| ATOM | 112 | CB | TYR | A | 52 | 16.267 | 72.532 | 17.909 | 1.00 | 26.56 | A | C |
| ATOM | 113 | CG | TYR | A | 52 | 16.568 | 71.059 | 17.757 | 1.00 | 29.11 | A | C |
| ATOM | 114 | CD1 | TYR | A | 52 | 15.627 | 70.096 | 18.088 | 1.00 | 28.57 | A | C |
| ATOM | 115 | CE1 | TYR | A | 52 | 15.919 | 68.742 | 17.953 | 1.00 | 33.11 | A | C |
| ATOM | 116 | CD2 | TYR | A | 52 | 17.811 | 70.637 | 17.311 | 1.00 | 28.47 | A | C |
| ATOM | 117 | CE2 | TYR | A | 52 | 18.115 | 69.297 | 17.169 | 1.00 | 30.55 | A | C |
| ATOM | 118 | CZ | TYR | A | 52 | 17.168 | 68.349 | 17.487 | 1.00 | 32.61 | A | C |
| ATOM | 119 | OH | TYR | A | 52 | 17.471 | 67.006 | 17.350 | 1.00 | 28.55 | A | O |
| ATOM | 120 | C | TYR | A | 52 | 17.142 | 74.676 | 18.946 | 1.00 | 30.95 | A | C |
| ATOM | 121 | O | TYR | A | 52 | 17.193 | 75.317 | 17.897 | 1.00 | 25.11 | A | O |
| ATOM | 122 | N | GLY | A | 53 | 17.088 | 75.250 | 20.150 | 1.00 | 30.29 | A | N |
| ATOM | 123 | CA | GLY | A | 53 | 17.310 | 76.677 | 20.324 | 1.00 | 29.26 | A | C |
| ATOM | 124 | C | GLY | A | 53 | 16.077 | 77.544 | 20.419 | 1.00 | 29.30 | A | C |
| ATOM | 125 | O | GLY | A | 53 | 16.169 | 78.735 | 20.694 | 1.00 | 31.01 | A | O |
| ATOM | 126 | N | TYR | A | 54 | 14.910 | 76.953 | 20.203 | 1.00 | 32.20 | A | N |
| ATOM | 127 | CA | TYR | A | 54 | 13.661 | 77.715 | 20.192 | 1.00 | 29.18 | A | C |
| ATOM | 128 | CB | TYR | A | 54 | 12.528 | 76.831 | 19.684 | 1.00 | 27.83 | A | C |
| ATOM | 129 | CG | TYR | A | 54 | 12.766 | 76.344 | 18.280 | 1.00 | 31.53 | A | C |
| ATOM | 130 | CD1 | TYR | A | 54 | 13.174 | 75.038 | 18.025 | 1.00 | 30.02 | A | C |
| ATOM | 131 | CE1 | TYR | A | 54 | 13.399 | 74.604 | 16.735 | 1.00 | 25.91 | A | C |
| ATOM | 132 | CD2 | TYR | A | 54 | 12.632 | 77.211 | 17.206 | 1.00 | 29.66 | A | C |
| ATOM | 133 | CE2 | TYR | A | 54 | 12.843 | 76.790 | 15.926 | 1.00 | 26.68 | A | C |
| ATOM | 134 | CZ | TYR | A | 54 | 13.224 | 75.493 | 15.688 | 1.00 | 28.65 | A | C |
| ATOM | 135 | OH | TYR | A | 54 | 13.454 | 75.105 | 14.378 | 1.00 | 29.53 | A | O |
| ATOM | 136 | C | TYR | A | 54 | 13.275 | 78.356 | 21.537 | 1.00 | 31.81 | A | C |
| ATOM | 137 | O | TYR | A | 54 | 12.699 | 79.443 | 21.575 | 1.00 | 27.67 | A | O |
| ATOM | 138 | N | THR | A | 55 | 13.588 | 77.687 | 22.637 | 1.00 | 32.54 | A | N |

TABLE 14-continued

Coordinates for proMMP9(35-444 ΔFnII) (SEQ ID NO: 12) complex with Example 4

| ATOM | 139 | CA  | THR | A | 55 | 13.233 | 78.222 | 23.947 | 1.00 | 33.59 | A | C |
|------|-----|-----|-----|---|----|--------|--------|--------|------|-------|---|---|
| ATOM | 140 | CB  | THR | A | 55 | 13.273 | 77.132 | 25.032 | 1.00 | 33.04 | A | C |
| ATOM | 141 | OG1 | THR | A | 55 | 14.594 | 76.574 | 25.111 | 1.00 | 36.18 | A | O |
| ATOM | 142 | CG2 | THR | A | 55 | 12.316 | 76.038 | 24.671 | 1.00 | 28.50 | A | C |
| ATOM | 143 | C   | THR | A | 55 | 14.107 | 79.423 | 24.329 | 1.00 | 36.78 | A | C |
| ATOM | 144 | O   | THR | A | 55 | 13.592 | 80.444 | 24.785 | 1.00 | 38.31 | A | O |
| ATOM | 145 | N   | ARG | A | 56 | 15.418 | 79.311 | 24.125 | 1.00 | 37.42 | A | N |
| ATOM | 146 | CA  | ARG | A | 56 | 16.327 | 80.440 | 24.352 | 1.00 | 41.03 | A | C |
| ATOM | 147 | CB  | ARG | A | 56 | 17.752 | 80.070 | 23.911 | 1.00 | 39.63 | A | C |
| ATOM | 148 | CG  | ARG | A | 56 | 18.786 | 81.186 | 24.096 | 1.00 | 44.33 | A | C |
| ATOM | 149 | CD  | ARG | A | 56 | 19.274 | 81.321 | 25.543 | 1.00 | 47.51 | A | C |
| ATOM | 150 | NE  | ARG | A | 56 | 18.326 | 82.029 | 26.399 | 1.00 | 44.01 | A | N |
| ATOM | 151 | CZ  | ARG | A | 56 | 18.506 | 83.245 | 26.914 | 1.00 | 44.93 | A | C |
| ATOM | 152 | NH1 | ARG | A | 56 | 19.615 | 83.936 | 26.682 | 1.00 | 46.99 | A | N |
| ATOM | 153 | NH2 | ARG | A | 56 | 17.561 | 83.774 | 27.678 | 1.00 | 46.03 | A | N |
| ATOM | 154 | C   | ARG | A | 56 | 15.860 | 81.718 | 23.632 | 1.00 | 38.69 | A | C |
| ATOM | 155 | O   | ARG | A | 56 | 15.846 | 82.807 | 24.207 | 1.00 | 36.67 | A | O |
| ATOM | 156 | N   | VAL | A | 57 | 15.484 | 81.576 | 22.366 | 1.00 | 34.77 | A | N |
| ATOM | 157 | CA  | VAL | A | 57 | 14.980 | 82.700 | 21.584 | 1.00 | 36.17 | A | C |
| ATOM | 158 | CB  | VAL | A | 57 | 14.767 | 82.321 | 20.108 | 1.00 | 37.68 | A | C |
| ATOM | 159 | CG1 | VAL | A | 57 | 14.180 | 83.496 | 19.340 | 1.00 | 37.21 | A | C |
| ATOM | 160 | CG2 | VAL | A | 57 | 16.085 | 81.862 | 19.476 | 1.00 | 33.46 | A | C |
| ATOM | 161 | C   | VAL | A | 57 | 13.668 | 83.210 | 22.163 | 1.00 | 35.68 | A | C |
| ATOM | 162 | O   | VAL | A | 57 | 13.425 | 84.417 | 22.209 | 1.00 | 35.23 | A | O |
| ATOM | 163 | N   | GLY | A | 58 | 12.823 | 82.283 | 22.604 | 1.00 | 36.01 | A | N |
| ATOM | 164 | CA  | GLY | A | 58 | 11.559 | 82.628 | 23.238 | 1.00 | 37.49 | A | C |
| ATOM | 165 | C   | GLY | A | 58 | 11.785 | 83.511 | 24.451 | 1.00 | 36.51 | A | C |
| ATOM | 166 | O   | GLY | A | 58 | 11.165 | 84.558 | 24.597 | 1.00 | 39.55 | A | O |
| ATOM | 167 | N   | GLU | A | 59 | 12.693 | 83.086 | 25.321 | 1.00 | 38.00 | A | N |
| ATOM | 168 | CA  | GLU | A | 59 | 13.039 | 83.864 | 26.509 | 1.00 | 41.42 | A | C |
| ATOM | 169 | C   | GLU | A | 59 | 13.515 | 85.272 | 26.153 | 1.00 | 44.35 | A | C |
| ATOM | 170 | CB  | GLU | A | 59 | 14.117 | 83.153 | 27.318 | 1.00 | 38.70 | A | C |
| ATOM | 171 | CG  | GLU | A | 59 | 13.795 | 81.701 | 27.616 | 1.00 | 41.48 | A | C |
| ATOM | 172 | CD  | GLU | A | 59 | 14.887 | 81.018 | 28.402 | 1.00 | 44.95 | A | C |
| ATOM | 173 | OE1 | GLU | A | 59 | 15.975 | 81.615 | 28.550 | 1.00 | 47.60 | A | O |
| ATOM | 174 | OE2 | GLU | A | 59 | 14.664 | 79.882 | 28.871 | 1.00 | 48.93 | A | O |
| ATOM | 175 | O   | GLU | A | 59 | 13.129 | 86.245 | 26.809 | 1.00 | 44.06 | A | O |
| ATOM | 176 | N   | MET | A | 60 | 14.344 | 85.375 | 25.111 | 1.00 | 40.89 | A | N |
| ATOM | 177 | CA  | MET | A | 60 | 14.900 | 86.661 | 24.689 | 1.00 | 41.38 | A | C |
| ATOM | 178 | C   | MET | A | 60 | 13.817 | 87.619 | 24.232 | 1.00 | 40.47 | A | C |
| ATOM | 179 | CB  | MET | A | 60 | 15.904 | 86.488 | 23.547 | 1.00 | 39.66 | A | C |
| ATOM | 180 | CG  | MET | A | 60 | 17.153 | 85.711 | 23.897 | 1.00 | 40.81 | A | C |
| ATOM | 181 | SD  | MET | A | 60 | 18.251 | 85.659 | 22.464 | 1.00 | 47.39 | A | S |
| ATOM | 182 | CE  | MET | A | 60 | 19.367 | 84.356 | 22.960 | 1.00 | 44.47 | A | C |
| ATOM | 183 | O   | MET | A | 60 | 14.093 | 88.773 | 23.927 | 1.00 | 41.88 | A | O |
| ATOM | 184 | N   | ARG | A | 61 | 12.584 | 87.134 | 24.161 | 1.00 | 43.73 | A | N |
| ATOM | 185 | CA  | ARG | A | 61 | 11.482 | 87.979 | 23.725 | 1.00 | 40.85 | A | C |
| ATOM | 186 | C   | ARG | A | 61 | 10.445 | 88.115 | 24.822 | 1.00 | 42.71 | A | C |
| ATOM | 187 | CB  | ARG | A | 61 | 10.843 | 87.411 | 22.466 | 1.00 | 41.23 | A | C |
| ATOM | 188 | CG  | ARG | A | 61 | 11.835 | 87.120 | 21.353 | 1.00 | 45.78 | A | C |
| ATOM | 189 | CD  | ARG | A | 61 | 11.107 | 86.814 | 20.069 | 1.00 | 47.99 | A | C |
| ATOM | 190 | NE  | ARG | A | 61 | 12.029 | 86.518 | 18.982 | 1.00 | 50.65 | A | N |
| ATOM | 191 | CZ  | ARG | A | 61 | 11.641 | 86.262 | 17.737 | 1.00 | 50.08 | A | C |
| ATOM | 192 | NH1 | ARG | A | 61 | 12.543 | 85.997 | 16.800 | 1.00 | 43.93 | A | N |
| ATOM | 193 | NH2 | ARG | A | 61 | 10.346 | 86.271 | 17.434 | 1.00 | 49.73 | A | N |
| ATOM | 194 | O   | ARG | A | 61 | 9.344  | 88.609 | 24.580 | 1.00 | 45.46 | A | O |
| ATOM | 195 | N   | GLY | A | 62 | 10.811 | 87.670 | 26.023 | 1.00 | 43.12 | A | N |
| ATOM | 196 | CA  | GLY | A | 62 | 9.930  | 87.728 | 27.179 | 1.00 | 45.32 | A | C |
| ATOM | 197 | C   | GLY | A | 62 | 8.688  | 86.874 | 26.991 | 1.00 | 51.72 | A | C |
| ATOM | 198 | O   | GLY | A | 62 | 7.646  | 87.122 | 27.605 | 1.00 | 50.28 | A | O |
| ATOM | 199 | N   | GLU | A | 63 | 8.814  | 85.875 | 26.118 | 1.00 | 49.86 | A | N |
| ATOM | 200 | CA  | GLU | A | 63 | 7.759  | 84.908 | 25.845 | 1.00 | 51.51 | A | C |
| ATOM | 201 | C   | GLU | A | 63 | 8.138  | 83.596 | 26.499 | 1.00 | 55.34 | A | C |
| ATOM | 202 | CB  | GLU | A | 63 | 7.587  | 84.720 | 24.343 | 1.00 | 48.53 | A | C |
| ATOM | 203 | CG  | GLU | A | 63 | 6.756  | 85.811 | 23.703 | 1.00 | 53.52 | A | C |
| ATOM | 204 | CD  | GLU | A | 63 | 7.112  | 86.044 | 22.246 | 1.00 | 55.28 | A | C |
| ATOM | 205 | OE1 | GLU | A | 63 | 6.431  | 86.861 | 21.592 | 1.00 | 59.70 | A | O |
| ATOM | 206 | OE2 | GLU | A | 63 | 8.077  | 85.418 | 21.758 | 1.00 | 55.92 | A | O |
| ATOM | 207 | O   | GLU | A | 63 | 8.150  | 82.539 | 25.864 | 1.00 | 53.90 | A | O |
| ATOM | 208 | N   | SER | A | 64 | 8.420  | 83.687 | 27.794 | 1.00 | 59.35 | A | N |
| ATOM | 209 | CA  | SER | A | 64 | 9.177  | 82.663 | 28.507 | 1.00 | 58.38 | A | C |
| ATOM | 210 | C   | SER | A | 64 | 8.725  | 81.204 | 28.339 | 1.00 | 62.15 | A | C |
| ATOM | 211 | CB  | SER | A | 64 | 9.429  | 83.080 | 29.957 | 1.00 | 62.69 | A | C |
| ATOM | 212 | OG  | SER | A | 64 | 10.134 | 84.317 | 29.963 | 1.00 | 59.30 | A | O |
| ATOM | 213 | O   | SER | A | 64 | 9.396  | 80.488 | 27.592 | 1.00 | 64.10 | A | O |
| ATOM | 214 | N   | LYS | A | 65 | 7.638  | 80.718 | 28.955 | 1.00 | 61.32 | A | N |
| ATOM | 215 | CA  | LYS | A | 65 | 6.639  | 81.397 | 29.789 | 1.00 | 58.69 | A | C |
| ATOM | 216 | C   | LYS | A | 65 | 5.391  | 80.522 | 29.670 | 1.00 | 60.03 | A | C |

TABLE 14-continued

Coordinates for proMMP9(35-444 ΔFnII) (SEQ ID NO: 12) complex with Example 4

| ATOM | 217 | CB | LYS | A | 65 | 6.298 | 82.794 | 29.276 | 1.00 | 59.62 | A | C |
|---|---|---|---|---|---|---|---|---|---|---|---|---|
| ATOM | 218 | CG | LYS | A | 65 | 4.832 | 82.982 | 28.943 | 1.00 | 57.57 | A | C |
| ATOM | 219 | CD | LYS | A | 65 | 4.584 | 82.994 | 27.448 | 1.00 | 52.86 | A | C |
| ATOM | 220 | CE | LYS | A | 65 | 4.844 | 84.375 | 26.887 | 1.00 | 49.44 | A | C |
| ATOM | 221 | NZ | LYS | A | 65 | 3.838 | 84.764 | 25.860 | 1.00 | 54.03 | A | N |
| ATOM | 222 | O | LYS | A | 65 | 4.399 | 80.702 | 30.379 | 1.00 | 67.06 | A | O |
| ATOM | 223 | N | SER | A | 66 | 5.496 | 79.542 | 28.779 | 1.00 | 58.28 | A | N |
| ATOM | 224 | CA | SER | A | 66 | 4.384 | 78.819 | 28.176 | 1.00 | 52.97 | A | C |
| ATOM | 225 | C | SER | A | 66 | 4.978 | 78.372 | 26.843 | 1.00 | 50.97 | A | C |
| ATOM | 226 | CB | SER | A | 66 | 3.191 | 79.749 | 27.937 | 1.00 | 49.09 | A | C |
| ATOM | 227 | OG | SER | A | 66 | 2.503 | 79.421 | 26.735 | 1.00 | 49.00 | A | O |
| ATOM | 228 | O | SER | A | 66 | 5.879 | 79.031 | 26.332 | 1.00 | 48.04 | A | O |
| ATOM | 229 | N | LEU | A | 67 | 4.507 | 77.269 | 26.276 | 1.00 | 45.40 | A | N |
| ATOM | 230 | CA | LEU | A | 67 | 5.136 | 76.754 | 25.058 | 1.00 | 44.93 | A | C |
| ATOM | 231 | C | LEU | A | 67 | 4.783 | 77.547 | 23.799 | 1.00 | 41.46 | A | C |
| ATOM | 232 | CB | LEU | A | 67 | 4.786 | 75.278 | 24.845 | 1.00 | 45.20 | A | C |
| ATOM | 233 | CG | LEU | A | 67 | 5.407 | 74.265 | 25.799 | 1.00 | 42.42 | A | C |
| ATOM | 234 | CD1 | LEU | A | 67 | 5.026 | 72.861 | 25.393 | 1.00 | 47.76 | A | C |
| ATOM | 235 | CD2 | LEU | A | 67 | 6.900 | 74.406 | 25.819 | 1.00 | 44.45 | A | C |
| ATOM | 236 | O | LEU | A | 67 | 5.545 | 77.569 | 22.822 | 1.00 | 37.58 | A | O |
| ATOM | 237 | N | GLY | A | 68 | 3.622 | 78.185 | 23.825 | 1.00 | 39.26 | A | N |
| ATOM | 238 | CA | GLY | A | 68 | 3.069 | 78.831 | 22.651 | 1.00 | 39.10 | A | C |
| ATOM | 239 | C | GLY | A | 68 | 4.079 | 79.519 | 21.758 | 1.00 | 36.77 | A | C |
| ATOM | 240 | O | GLY | A | 68 | 4.268 | 79.129 | 20.611 | 1.00 | 39.15 | A | O |
| ATOM | 241 | N | PRO | A | 69 | 4.728 | 80.564 | 22.275 | 1.00 | 39.44 | A | N |
| ATOM | 242 | CD | PRO | A | 69 | 4.557 | 81.151 | 23.615 | 1.00 | 43.10 | A | C |
| ATOM | 243 | CA | PRO | A | 69 | 5.676 | 81.326 | 21.461 | 1.00 | 38.28 | A | C |
| ATOM | 244 | CB | PRO | A | 69 | 6.228 | 82.356 | 22.446 | 1.00 | 43.32 | A | C |
| ATOM | 245 | CG | PRO | A | 69 | 5.107 | 82.539 | 23.433 | 1.00 | 46.06 | A | C |
| ATOM | 246 | C | PRO | A | 69 | 6.785 | 80.454 | 20.871 | 1.00 | 35.43 | A | C |
| ATOM | 247 | O | PRO | A | 69 | 7.047 | 80.596 | 19.671 | 1.00 | 33.15 | A | O |
| ATOM | 248 | N | ALA | A | 70 | 7.397 | 79.572 | 21.664 | 1.00 | 32.48 | A | N |
| ATOM | 249 | CA | ALA | A | 70 | 8.448 | 78.680 | 21.152 | 1.00 | 34.98 | A | C |
| ATOM | 250 | CB | ALA | A | 70 | 9.023 | 77.802 | 22.274 | 1.00 | 28.82 | A | C |
| ATOM | 251 | C | ALA | A | 70 | 7.969 | 77.800 | 19.987 | 1.00 | 36.25 | A | C |
| ATOM | 252 | O | ALA | A | 70 | 8.706 | 77.591 | 19.008 | 1.00 | 33.30 | A | O |
| ATOM | 253 | N | LEU | A | 71 | 6.747 | 77.275 | 20.111 | 1.00 | 31.36 | A | N |
| ATOM | 254 | CA | LEU | A | 71 | 6.152 | 76.430 | 19.079 | 1.00 | 29.55 | A | C |
| ATOM | 255 | CB | LEU | A | 71 | 4.789 | 75.894 | 19.534 | 1.00 | 32.08 | A | C |
| ATOM | 256 | CG | LEU | A | 71 | 4.755 | 74.870 | 20.669 | 1.00 | 32.54 | A | C |
| ATOM | 257 | CD1 | LEU | A | 71 | 3.325 | 74.701 | 21.217 | 1.00 | 33.32 | A | C |
| ATOM | 258 | CD2 | LEU | A | 71 | 5.322 | 73.533 | 20.212 | 1.00 | 29.69 | A | C |
| ATOM | 259 | C | LEU | A | 71 | 5.970 | 77.220 | 17.795 | 1.00 | 32.24 | A | C |
| ATOM | 260 | O | LEU | A | 71 | 6.119 | 76.694 | 16.685 | 1.00 | 32.92 | A | O |
| ATOM | 261 | N | LEU | A | 72 | 5.627 | 78.489 | 17.951 | 1.00 | 33.75 | A | N |
| ATOM | 262 | CA | LEU | A | 72 | 5.405 | 79.349 | 16.806 | 1.00 | 32.89 | A | C |
| ATOM | 263 | CB | LEU | A | 72 | 4.852 | 80.697 | 17.265 | 1.00 | 33.96 | A | C |
| ATOM | 264 | CG | LEU | A | 72 | 4.169 | 81.585 | 16.228 | 1.00 | 39.41 | A | C |
| ATOM | 265 | CD1 | LEU | A | 72 | 3.125 | 80.814 | 15.447 | 1.00 | 40.95 | A | C |
| ATOM | 266 | CD2 | LEU | A | 72 | 3.539 | 82.792 | 16.914 | 1.00 | 44.13 | A | C |
| ATOM | 267 | C | LEU | A | 72 | 6.712 | 79.534 | 16.037 | 1.00 | 33.92 | A | C |
| ATOM | 268 | O | LEU | A | 72 | 6.747 | 79.385 | 14.815 | 1.00 | 32.15 | A | O |
| ATOM | 269 | N | LEU | A | 73 | 7.783 | 79.852 | 16.758 | 1.00 | 33.84 | A | N |
| ATOM | 270 | CA | LEU | A | 73 | 9.095 | 80.031 | 16.133 | 1.00 | 34.27 | A | C |
| ATOM | 271 | CB | LEU | A | 73 | 10.140 | 80.452 | 17.169 | 1.00 | 34.92 | A | C |
| ATOM | 272 | CG | LEU | A | 73 | 9.933 | 81.785 | 17.889 | 1.00 | 39.25 | A | C |
| ATOM | 273 | CD1 | LEU | A | 73 | 10.997 | 81.984 | 18.962 | 1.00 | 35.24 | A | C |
| ATOM | 274 | CD2 | LEU | A | 73 | 9.937 | 82.937 | 16.889 | 1.00 | 38.29 | A | C |
| ATOM | 275 | C | LEU | A | 73 | 9.548 | 78.745 | 15.446 | 1.00 | 33.43 | A | C |
| ATOM | 276 | O | LEU | A | 73 | 10.207 | 78.787 | 14.397 | 1.00 | 32.04 | A | O |
| ATOM | 277 | N | LEU | A | 74 | 9.209 | 77.603 | 16.045 | 1.00 | 29.42 | A | N |
| ATOM | 278 | CA | LEU | A | 74 | 9.584 | 76.317 | 15.476 | 1.00 | 30.39 | A | C |
| ATOM | 279 | CB | LEU | A | 74 | 9.325 | 75.178 | 16.467 | 1.00 | 28.90 | A | C |
| ATOM | 280 | CG | LEU | A | 74 | 9.415 | 73.715 | 16.014 | 1.00 | 29.89 | A | C |
| ATOM | 281 | CD1 | LEU | A | 74 | 9.585 | 72.775 | 17.217 | 1.00 | 29.86 | A | C |
| ATOM | 282 | CD2 | LEU | A | 74 | 8.193 | 73.295 | 15.217 | 1.00 | 27.65 | A | C |
| ATOM | 283 | C | LEU | A | 74 | 8.836 | 76.085 | 14.166 | 1.00 | 32.43 | A | C |
| ATOM | 284 | O | LEU | A | 74 | 9.418 | 75.622 | 13.184 | 1.00 | 28.46 | A | O |
| ATOM | 285 | N | GLN | A | 75 | 7.551 | 76.422 | 14.172 | 1.00 | 29.84 | A | N |
| ATOM | 286 | CA | GLN | A | 75 | 6.680 | 76.259 | 13.019 | 1.00 | 29.56 | A | C |
| ATOM | 287 | CB | GLN | A | 75 | 5.233 | 76.544 | 13.416 | 1.00 | 31.35 | A | C |
| ATOM | 288 | CG | GLN | A | 75 | 4.582 | 75.367 | 14.113 | 1.00 | 31.39 | A | C |
| ATOM | 289 | CD | GLN | A | 75 | 3.481 | 75.770 | 15.077 | 1.00 | 33.36 | A | C |
| ATOM | 290 | OE1 | GLN | A | 75 | 3.065 | 76.930 | 15.131 | 1.00 | 34.75 | A | O |
| ATOM | 291 | NE2 | GLN | A | 75 | 2.982 | 74.801 | 15.823 | 1.00 | 28.27 | A | N |
| ATOM | 292 | C | GLN | A | 75 | 7.103 | 77.154 | 11.855 | 1.00 | 32.66 | A | C |
| ATOM | 293 | O | GLN | A | 75 | 7.003 | 76.768 | 10.681 | 1.00 | 29.20 | A | O |
| ATOM | 294 | N | LYS | A | 76 | 7.567 | 78.351 | 12.192 | 1.00 | 30.39 | A | N |

TABLE 14-continued

Coordinates for proMMP9(35-444 ΔFnII) (SEQ ID NO: 12) complex with Example 4

| ATOM | 295 | CA | LYS | A | 76 | 8.144 | 79.246 | 11.203 | 1.00 | 33.96 | A | C |
|------|-----|-----|-----|---|----|-------|--------|--------|------|-------|---|---|
| ATOM | 296 | CB | LYS | A | 76 | 8.403 | 80.625 | 11.802 | 1.00 | 30.20 | A | C |
| ATOM | 297 | CG | LYS | A | 76 | 7.238 | 81.587 | 11.629 | 1.00 | 42.11 | A | C |
| ATOM | 298 | CD | LYS | A | 76 | 7.134 | 82.548 | 12.810 | 1.00 | 40.94 | A | C |
| ATOM | 299 | CE | LYS | A | 76 | 5.885 | 83.411 | 12.725 | 1.00 | 46.18 | A | C |
| ATOM | 300 | NZ | LYS | A | 76 | 5.840 | 84.366 | 13.878 | 1.00 | 57.58 | A | N |
| ATOM | 301 | C | LYS | A | 76 | 9.441 | 78.684 | 10.649 | 1.00 | 32.56 | A | C |
| ATOM | 302 | O | LYS | A | 76 | 9.651 | 78.682 | 9.442 | 1.00 | 30.30 | A | O |
| ATOM | 303 | N | GLN | A | 77 | 10.309 | 78.212 | 11.538 | 1.00 | 30.55 | A | N |
| ATOM | 304 | CA | GLN | A | 77 | 11.631 | 77.748 | 11.130 | 1.00 | 29.82 | A | C |
| ATOM | 305 | CB | GLN | A | 77 | 12.537 | 77.527 | 12.348 | 1.00 | 31.37 | A | C |
| ATOM | 306 | CG | GLN | A | 77 | 13.951 | 77.036 | 12.014 | 1.00 | 34.58 | A | C |
| ATOM | 307 | CD | GLN | A | 77 | 14.791 | 78.060 | 11.262 | 1.00 | 37.61 | A | C |
| ATOM | 308 | OE1 | GLN | A | 77 | 14.567 | 79.267 | 11.371 | 1.00 | 37.52 | A | O |
| ATOM | 309 | NE2 | GLN | A | 77 | 15.766 | 77.572 | 10.484 | 1.00 | 37.26 | A | N |
| ATOM | 310 | C | GLN | A | 77 | 11.559 | 76.488 | 10.282 | 1.00 | 32.47 | A | C |
| ATOM | 311 | O | GLN | A | 77 | 12.439 | 76.240 | 9.447 | 1.00 | 34.40 | A | O |
| ATOM | 312 | N | LEU | A | 78 | 10.503 | 75.709 | 10.458 | 1.00 | 28.33 | A | N |
| ATOM | 313 | CA | LEU | A | 78 | 10.406 | 74.429 | 9.772 | 1.00 | 28.74 | A | C |
| ATOM | 314 | CB | LEU | A | 78 | 10.133 | 73.301 | 10.759 | 1.00 | 27.70 | A | C |
| ATOM | 315 | CG | LEU | A | 78 | 11.123 | 73.108 | 11.899 | 1.00 | 31.78 | A | C |
| ATOM | 316 | CD1 | LEU | A | 78 | 10.697 | 71.913 | 12.725 | 1.00 | 31.16 | A | C |
| ATOM | 317 | CD2 | LEU | A | 78 | 12.494 | 72.895 | 11.335 | 1.00 | 31.42 | A | C |
| ATOM | 318 | C | LEU | A | 78 | 9.332 | 74.423 | 8.717 | 1.00 | 27.24 | A | C |
| ATOM | 319 | O | LEU | A | 78 | 9.042 | 73.376 | 8.141 | 1.00 | 28.52 | A | O |
| ATOM | 320 | N | SER | A | 79 | 8.729 | 75.588 | 8.479 | 1.00 | 30.48 | A | N |
| ATOM | 321 | CA | SER | A | 79 | 7.648 | 75.717 | 7.498 | 1.00 | 28.97 | A | C |
| ATOM | 322 | CB | SER | A | 79 | 8.182 | 75.493 | 6.084 | 1.00 | 28.47 | A | C |
| ATOM | 323 | OG | SER | A | 79 | 9.172 | 76.468 | 5.815 | 1.00 | 30.36 | A | O |
| ATOM | 324 | C | SER | A | 79 | 6.450 | 74.812 | 7.771 | 1.00 | 31.91 | A | C |
| ATOM | 325 | O | SER | A | 79 | 5.879 | 74.227 | 6.854 | 1.00 | 32.10 | A | O |
| ATOM | 326 | N | LEU | A | 80 | 6.072 | 74.705 | 9.036 | 1.00 | 30.77 | A | N |
| ATOM | 327 | CA | LEU | A | 80 | 4.817 | 74.069 | 9.400 | 1.00 | 31.64 | A | C |
| ATOM | 328 | CB | LEU | A | 80 | 4.956 | 73.322 | 10.726 | 1.00 | 31.22 | A | C |
| ATOM | 329 | CG | LEU | A | 80 | 6.231 | 72.500 | 10.921 | 1.00 | 33.12 | A | C |
| ATOM | 330 | CD1 | LEU | A | 80 | 6.333 | 72.011 | 12.366 | 1.00 | 28.23 | A | C |
| ATOM | 331 | CD2 | LEU | A | 80 | 6.258 | 71.337 | 9.958 | 1.00 | 30.41 | A | C |
| ATOM | 332 | C | LEU | A | 80 | 3.773 | 75.170 | 9.546 | 1.00 | 33.72 | A | C |
| ATOM | 333 | O | LEU | A | 80 | 4.124 | 76.345 | 9.608 | 1.00 | 37.46 | A | O |
| ATOM | 334 | N | PRO | A | 81 | 2.486 | 74.799 | 9.601 | 1.00 | 35.06 | A | N |
| ATOM | 335 | CD | PRO | A | 81 | 1.919 | 73.469 | 9.323 | 1.00 | 33.78 | A | C |
| ATOM | 336 | CA | PRO | A | 81 | 1.445 | 75.801 | 9.875 | 1.00 | 35.72 | A | C |
| ATOM | 337 | CB | PRO | A | 81 | 0.156 | 74.976 | 9.858 | 1.00 | 36.70 | A | C |
| ATOM | 338 | CG | PRO | A | 81 | 0.488 | 73.774 | 9.015 | 1.00 | 36.26 | A | C |
| ATOM | 339 | C | PRO | A | 81 | 1.644 | 76.494 | 11.232 | 1.00 | 34.20 | A | C |
| ATOM | 340 | O | PRO | A | 81 | 1.879 | 75.848 | 12.259 | 1.00 | 33.23 | A | O |
| ATOM | 341 | N | GLU | A | 82 | 1.542 | 77.816 | 11.218 | 1.00 | 34.37 | A | N |
| ATOM | 342 | CA | GLU | A | 82 | 1.895 | 78.637 | 12.372 | 1.00 | 35.46 | A | C |
| ATOM | 343 | CB | GLU | A | 82 | 2.529 | 79.941 | 11.890 | 1.00 | 35.12 | A | C |
| ATOM | 344 | CG | GLU | A | 82 | 3.652 | 79.643 | 10.894 | 1.00 | 36.40 | A | C |
| ATOM | 345 | CD | GLU | A | 82 | 4.218 | 80.861 | 10.214 | 1.00 | 43.11 | A | C |
| ATOM | 346 | OE1 | GLU | A | 82 | 3.978 | 81.991 | 10.690 | 1.00 | 44.74 | A | O |
| ATOM | 347 | OE2 | GLU | A | 82 | 4.922 | 80.678 | 9.192 | 1.00 | 44.33 | A | O |
| ATOM | 348 | C | GLU | A | 82 | 0.702 | 78.844 | 13.314 | 1.00 | 39.51 | A | C |
| ATOM | 349 | O | GLU | A | 82 | 0.070 | 79.905 | 13.361 | 1.00 | 39.72 | A | O |
| ATOM | 350 | N | THR | A | 83 | 0.407 | 77.784 | 14.056 | 1.00 | 36.38 | A | N |
| ATOM | 351 | CA | THR | A | 83 | −0.734 | 77.736 | 14.953 | 1.00 | 37.67 | A | C |
| ATOM | 352 | CB | THR | A | 83 | −1.317 | 76.333 | 14.944 | 1.00 | 36.43 | A | C |
| ATOM | 353 | OG1 | THR | A | 83 | −0.360 | 75.419 | 15.502 | 1.00 | 32.72 | A | O |
| ATOM | 354 | CG2 | THR | A | 83 | −1.625 | 75.915 | 13.510 | 1.00 | 31.41 | A | C |
| ATOM | 355 | C | THR | A | 83 | −0.291 | 78.064 | 16.375 | 1.00 | 37.84 | A | C |
| ATOM | 356 | O | THR | A | 83 | −1.104 | 78.405 | 17.230 | 1.00 | 36.20 | A | O |
| ATOM | 357 | N | GLY | A | 84 | 1.012 | 77.970 | 16.620 | 1.00 | 36.65 | A | N |
| ATOM | 358 | CA | GLY | A | 84 | 1.525 | 78.166 | 17.961 | 1.00 | 36.39 | A | C |
| ATOM | 359 | C | GLY | A | 84 | 0.904 | 77.158 | 18.913 | 1.00 | 36.79 | A | C |
| ATOM | 360 | O | GLY | A | 84 | 0.801 | 77.406 | 20.119 | 1.00 | 37.31 | A | O |
| ATOM | 361 | N | GLU | A | 85 | 0.491 | 76.014 | 18.372 | 1.00 | 33.76 | A | N |
| ATOM | 362 | CA | GLU | A | 85 | −0.085 | 74.950 | 19.192 | 1.00 | 36.02 | A | C |
| ATOM | 363 | CB | GLU | A | 85 | −1.542 | 74.657 | 18.783 | 1.00 | 30.97 | A | C |
| ATOM | 364 | CG | GLU | A | 85 | −2.517 | 75.831 | 18.922 | 1.00 | 31.51 | A | C |
| ATOM | 365 | CD | GLU | A | 85 | −2.953 | 76.094 | 20.377 | 1.00 | 35.89 | A | C |
| ATOM | 366 | OE1 | GLU | A | 85 | −2.576 | 75.323 | 21.298 | 1.00 | 32.12 | A | O |
| ATOM | 367 | OE2 | GLU | A | 85 | −3.691 | 77.078 | 20.596 | 1.00 | 38.22 | A | O |
| ATOM | 368 | C | GLU | A | 85 | 0.751 | 73.689 | 19.031 | 1.00 | 33.43 | A | C |
| ATOM | 369 | O | GLU | A | 85 | 1.283 | 73.428 | 17.948 | 1.00 | 33.17 | A | O |
| ATOM | 370 | N | LEU | A | 86 | 0.874 | 72.921 | 20.108 | 1.00 | 33.30 | A | N |
| ATOM | 371 | CA | LEU | A | 86 | 1.427 | 71.582 | 20.038 | 1.00 | 33.20 | A | C |
| ATOM | 372 | CB | LEU | A | 86 | 1.741 | 71.044 | 21.441 | 1.00 | 28.84 | A | C |

TABLE 14-continued

Coordinates for proMMP9(35-444 ΔFnII) (SEQ ID NO: 12) complex with Example 4

| | | | | | | | | | | | |
|---|---|---|---|---|---|---|---|---|---|---|---|
| ATOM | 373 | CG | LEU | A | 86 | 2.373 | 69.652 | 21.517 | 1.00 | 31.21 A | C |
| ATOM | 374 | CD1 | LEU | A | 86 | 3.522 | 69.515 | 20.516 | 1.00 | 33.17 A | C |
| ATOM | 375 | CD2 | LEU | A | 86 | 2.876 | 69.357 | 22.915 | 1.00 | 34.51 A | C |
| ATOM | 376 | C | LEU | A | 86 | 0.380 | 70.720 | 19.348 | 1.00 | 32.87 A | C |
| ATOM | 377 | O | LEU | A | 86 | −0.309 | 69.928 | 19.994 | 1.00 | 34.20 A | O |
| ATOM | 378 | N | ASP | A | 87 | 0.252 | 70.893 | 18.035 | 1.00 | 30.27 A | N |
| ATOM | 379 | CA | ASP | A | 87 | −0.764 | 70.188 | 17.252 | 1.00 | 30.67 A | C |
| ATOM | 380 | CB | ASP | A | 87 | −1.367 | 71.127 | 16.208 | 1.00 | 29.91 A | C |
| ATOM | 381 | CG | ASP | A | 87 | −0.307 | 71.765 | 15.320 | 1.00 | 31.84 A | C |
| ATOM | 382 | OD1 | ASP | A | 87 | 0.770 | 71.152 | 15.167 | 1.00 | 31.10 A | O |
| ATOM | 383 | OD2 | ASP | A | 87 | −0.561 | 72.867 | 14.776 | 1.00 | 31.61 A | O |
| ATOM | 384 | C | ASP | A | 87 | −0.187 | 68.938 | 16.582 | 1.00 | 33.08 A | C |
| ATOM | 385 | O | ASP | A | 87 | 0.957 | 68.556 | 16.846 | 1.00 | 27.45 A | O |
| ATOM | 386 | N | SER | A | 88 | −0.979 | 68.307 | 15.719 | 1.00 | 31.20 A | N |
| ATOM | 387 | CA | SER | A | 88 | −0.571 | 67.043 | 15.110 | 1.00 | 31.46 A | C |
| ATOM | 388 | CB | SER | A | 88 | −1.739 | 66.387 | 14.354 | 1.00 | 30.83 A | C |
| ATOM | 389 | OG | SER | A | 88 | −2.733 | 65.904 | 15.253 | 1.00 | 39.76 A | O |
| ATOM | 390 | C | SER | A | 88 | 0.654 | 67.193 | 14.198 | 1.00 | 28.33 A | C |
| ATOM | 391 | O | SER | A | 88 | 1.568 | 66.367 | 14.241 | 1.00 | 29.84 A | O |
| ATOM | 392 | N | ALA | A | 89 | 0.665 | 68.225 | 13.361 | 1.00 | 29.74 A | N |
| ATOM | 393 | CA | ALA | A | 89 | 1.796 | 68.416 | 12.449 | 1.00 | 30.30 A | C |
| ATOM | 394 | CB | ALA | A | 89 | 1.570 | 69.583 | 11.526 | 1.00 | 28.19 A | C |
| ATOM | 395 | C | ALA | A | 89 | 3.061 | 68.620 | 13.266 | 1.00 | 30.62 A | C |
| ATOM | 396 | O | ALA | A | 89 | 4.087 | 68.002 | 12.990 | 1.00 | 29.25 A | O |
| ATOM | 397 | N | THR | A | 90 | 2.975 | 69.464 | 14.293 | 1.00 | 28.12 A | N |
| ATOM | 398 | CA | THR | A | 90 | 4.161 | 69.808 | 15.080 | 1.00 | 27.36 A | C |
| ATOM | 399 | CB | THR | A | 90 | 3.911 | 71.007 | 15.992 | 1.00 | 28.15 A | C |
| ATOM | 400 | OG1 | THR | A | 90 | 3.536 | 72.133 | 15.194 | 1.00 | 28.03 A | O |
| ATOM | 401 | CG2 | THR | A | 90 | 5.153 | 71.344 | 16.783 | 1.00 | 25.06 A | C |
| ATOM | 402 | C | THR | A | 90 | 4.714 | 68.619 | 15.856 | 1.00 | 28.43 A | C |
| ATOM | 403 | O | THR | A | 90 | 5.925 | 68.418 | 15.901 | 1.00 | 29.06 A | O |
| ATOM | 404 | N | LEU | A | 91 | 3.836 | 67.812 | 16.436 | 1.00 | 25.19 A | N |
| ATOM | 405 | CA | LEU | A | 91 | 4.272 | 66.601 | 17.124 | 1.00 | 25.70 A | C |
| ATOM | 406 | CB | LEU | A | 91 | 3.077 | 65.891 | 17.735 | 1.00 | 31.92 A | C |
| ATOM | 407 | CG | LEU | A | 91 | 3.434 | 64.819 | 18.763 | 1.00 | 36.55 A | C |
| ATOM | 408 | CD1 | LEU | A | 91 | 4.507 | 65.346 | 19.698 | 1.00 | 37.27 A | C |
| ATOM | 409 | CD2 | LEU | A | 91 | 2.190 | 64.394 | 19.553 | 1.00 | 36.39 A | C |
| ATOM | 410 | C | LEU | A | 91 | 4.976 | 65.638 | 16.174 | 1.00 | 29.70 A | C |
| ATOM | 411 | O | LEU | A | 91 | 6.021 | 65.062 | 16.493 | 1.00 | 29.11 A | O |
| ATOM | 412 | N | LYS | A | 92 | 4.385 | 65.455 | 15.003 | 1.00 | 29.12 A | N |
| ATOM | 413 | CA | LYS | A | 92 | 4.922 | 64.527 | 14.041 | 1.00 | 32.10 A | C |
| ATOM | 414 | CB | LYS | A | 92 | 3.978 | 64.388 | 12.841 | 1.00 | 32.19 A | C |
| ATOM | 415 | CG | LYS | A | 92 | 4.558 | 63.538 | 11.724 | 1.00 | 39.19 A | C |
| ATOM | 416 | CD | LYS | A | 92 | 3.754 | 63.656 | 10.437 | 1.00 | 47.21 A | C |
| ATOM | 417 | CE | LYS | A | 92 | 4.629 | 63.327 | 9.219 | 1.00 | 48.85 A | C |
| ATOM | 418 | NZ | LYS | A | 92 | 3.892 | 63.445 | 7.927 | 1.00 | 52.75 A | N |
| ATOM | 419 | C | LYS | A | 92 | 6.294 | 65.063 | 13.622 | 1.00 | 31.23 A | C |
| ATOM | 420 | O | LYS | A | 92 | 7.284 | 64.325 | 13.620 | 1.00 | 28.50 A | O |
| ATOM | 421 | N | ALA | A | 93 | 6.345 | 66.355 | 13.305 | 1.00 | 25.66 A | N |
| ATOM | 422 | CA | ALA | A | 93 | 7.612 | 67.004 | 13.007 | 1.00 | 29.53 A | C |
| ATOM | 423 | CB | ALA | A | 93 | 7.451 | 68.516 | 12.884 | 1.00 | 26.65 A | C |
| ATOM | 424 | C | ALA | A | 93 | 8.632 | 66.668 | 14.084 | 1.00 | 30.38 A | C |
| ATOM | 425 | O | ALA | A | 93 | 9.711 | 66.185 | 13.771 | 1.00 | 28.12 A | O |
| ATOM | 426 | N | MET | A | 94 | 8.281 | 66.906 | 15.349 | 1.00 | 28.01 A | N |
| ATOM | 427 | CA | MET | A | 94 | 9.195 | 66.659 | 16.462 | 1.00 | 28.21 A | C |
| ATOM | 428 | CB | MET | A | 94 | 8.563 | 67.080 | 17.796 | 1.00 | 29.43 A | C |
| ATOM | 429 | CG | MET | A | 94 | 8.398 | 68.573 | 17.961 | 1.00 | 30.64 A | C |
| ATOM | 430 | SD | MET | A | 94 | 7.441 | 68.988 | 19.432 | 1.00 | 29.03 A | S |
| ATOM | 431 | CE | MET | A | 94 | 7.484 | 70.776 | 19.418 | 1.00 | 26.52 A | C |
| ATOM | 432 | C | MET | A | 94 | 9.642 | 65.205 | 16.575 | 1.00 | 29.47 A | C |
| ATOM | 433 | O | MET | A | 94 | 10.722 | 64.922 | 17.095 | 1.00 | 32.13 A | O |
| ATOM | 434 | N | ARG | A | 95 | 8.801 | 64.284 | 16.119 | 1.00 | 28.08 A | N |
| ATOM | 435 | CA | ARG | A | 95 | 9.120 | 62.860 | 16.178 | 1.00 | 27.32 A | C |
| ATOM | 436 | CB | ARG | A | 95 | 7.841 | 62.018 | 16.199 | 1.00 | 32.95 A | C |
| ATOM | 437 | CG | ARG | A | 95 | 7.044 | 61.981 | 17.510 | 1.00 | 36.73 A | C |
| ATOM | 438 | CD | ARG | A | 95 | 6.136 | 60.741 | 17.470 | 1.00 | 37.06 A | C |
| ATOM | 439 | NE | ARG | A | 95 | 4.949 | 60.838 | 18.310 | 1.00 | 50.40 A | N |
| ATOM | 440 | CZ | ARG | A | 95 | 3.719 | 61.079 | 17.855 | 1.00 | 49.89 A | C |
| ATOM | 441 | NH1 | ARG | A | 95 | 3.500 | 61.265 | 16.551 | 1.00 | 43.80 A | N |
| ATOM | 442 | NH2 | ARG | A | 95 | 2.702 | 61.143 | 18.710 | 1.00 | 48.67 A | N |
| ATOM | 443 | C | ARG | A | 95 | 9.970 | 62.399 | 14.981 | 1.00 | 29.53 A | C |
| ATOM | 444 | O | ARG | A | 95 | 10.374 | 61.245 | 14.913 | 1.00 | 30.39 A | O |
| ATOM | 445 | N | THR | A | 96 | 10.218 | 63.292 | 14.032 | 1.00 | 27.31 A | N |
| ATOM | 446 | CA | THR | A | 96 | 10.961 | 62.927 | 12.827 | 1.00 | 31.53 A | C |
| ATOM | 447 | CB | THR | A | 96 | 10.574 | 63.843 | 11.649 | 1.00 | 28.90 A | C |
| ATOM | 448 | OG1 | THR | A | 96 | 9.153 | 63.793 | 11.459 | 1.00 | 30.87 A | O |
| ATOM | 449 | CG2 | THR | A | 96 | 11.258 | 63.401 | 10.355 | 1.00 | 29.04 A | C |
| ATOM | 450 | C | THR | A | 96 | 12.476 | 62.954 | 13.094 | 1.00 | 26.66 A | C |

TABLE 14-continued

Coordinates for proMMP9(35-444 ΔFnII) (SEQ ID NO: 12) complex with Example 4

| ATOM | 451 | O   | THR | A | 96  | 12.989 | 63.919 | 13.671 | 1.00 | 25.71 | A | O |
|------|-----|-----|-----|---|-----|--------|--------|--------|------|-------|---|---|
| ATOM | 452 | N   | PRO | A | 97  | 13.189 | 61.878 | 12.706 | 1.00 | 28.60 | A | N |
| ATOM | 453 | CD  | PRO | A | 97  | 12.683 | 60.671 | 12.030 | 1.00 | 31.95 | A | C |
| ATOM | 454 | CA  | PRO | A | 97  | 14.652 | 61.843 | 12.859 | 1.00 | 30.12 | A | C |
| ATOM | 455 | CB  | PRO | A | 97  | 15.053 | 60.532 | 12.176 | 1.00 | 29.20 | A | C |
| ATOM | 456 | CG  | PRO | A | 97  | 13.813 | 59.699 | 12.198 | 1.00 | 33.13 | A | C |
| ATOM | 457 | C   | PRO | A | 97  | 15.260 | 63.030 | 12.123 | 1.00 | 29.08 | A | C |
| ATOM | 458 | O   | PRO | A | 97  | 14.713 | 63.439 | 11.109 | 1.00 | 31.50 | A | O |
| ATOM | 459 | N   | ARG | A | 98  | 16.345 | 63.593 | 12.638 | 1.00 | 29.10 | A | N |
| ATOM | 460 | CA  | ARG | A | 98  | 16.869 | 64.842 | 12.097 | 1.00 | 26.45 | A | C |
| ATOM | 461 | CB  | ARG | A | 98  | 16.047 | 66.037 | 12.577 | 1.00 | 28.80 | A | C |
| ATOM | 462 | CG  | ARG | A | 98  | 15.940 | 66.148 | 14.131 | 1.00 | 26.39 | A | C |
| ATOM | 463 | CD  | ARG | A | 98  | 15.555 | 67.566 | 14.549 | 1.00 | 25.63 | A | C |
| ATOM | 464 | NE  | ARG | A | 98  | 16.675 | 68.475 | 14.350 | 1.00 | 30.70 | A | N |
| ATOM | 465 | CZ  | ARG | A | 98  | 16.568 | 69.785 | 14.147 | 1.00 | 27.35 | A | C |
| ATOM | 466 | NH1 | ARG | A | 98  | 15.379 | 70.362 | 14.111 | 1.00 | 27.88 | A | N |
| ATOM | 467 | NH2 | ARG | A | 98  | 17.662 | 70.513 | 13.966 | 1.00 | 24.71 | A | N |
| ATOM | 468 | C   | ARG | A | 98  | 18.299 | 65.043 | 12.525 | 1.00 | 28.07 | A | C |
| ATOM | 469 | O   | ARG | A | 98  | 18.835 | 64.257 | 13.300 | 1.00 | 27.23 | A | O |
| ATOM | 470 | N   | CYS | A | 99  | 18.901 | 66.103 | 11.993 | 1.00 | 25.30 | A | N |
| ATOM | 471 | CA  | CYS | A | 99  | 20.228 | 66.549 | 12.377 | 1.00 | 28.60 | A | C |
| ATOM | 472 | CB  | CYS | A | 99  | 20.669 | 67.637 | 11.413 | 1.00 | 23.56 | A | C |
| ATOM | 473 | SG  | CYS | A | 99  | 22.289 | 68.278 | 11.777 | 1.00 | 26.28 | A | S |
| ATOM | 474 | C   | CYS | A | 99  | 20.276 | 67.127 | 13.790 | 1.00 | 25.38 | A | C |
| ATOM | 475 | O   | CYS | A | 99  | 19.424 | 67.919 | 14.164 | 1.00 | 25.26 | A | O |
| ATOM | 476 | N   | GLY | A | 100 | 21.311 | 66.783 | 14.544 | 1.00 | 28.00 | A | N |
| ATOM | 477 | CA  | GLY | A | 100 | 21.456 | 67.261 | 15.910 | 1.00 | 27.71 | A | C |
| ATOM | 478 | C   | GLY | A | 100 | 21.923 | 68.707 | 16.061 | 1.00 | 30.00 | A | C |
| ATOM | 479 | O   | GLY | A | 100 | 21.973 | 69.242 | 17.166 | 1.00 | 25.78 | A | O |
| ATOM | 480 | N   | VAL | A | 101 | 22.276 | 69.350 | 14.953 | 1.00 | 29.21 | A | N |
| ATOM | 481 | CA  | VAL | A | 101 | 22.718 | 70.742 | 15.002 | 1.00 | 27.22 | A | C |
| ATOM | 482 | CB  | VAL | A | 101 | 23.420 | 71.158 | 13.666 | 1.00 | 27.17 | A | C |
| ATOM | 483 | CG1 | VAL | A | 101 | 23.603 | 72.680 | 13.569 | 1.00 | 28.66 | A | C |
| ATOM | 484 | CG2 | VAL | A | 101 | 24.758 | 70.467 | 13.545 | 1.00 | 24.07 | A | C |
| ATOM | 485 | C   | VAL | A | 101 | 21.494 | 71.614 | 15.290 | 1.00 | 27.29 | A | C |
| ATOM | 486 | O   | VAL | A | 101 | 20.433 | 71.382 | 14.728 | 1.00 | 28.30 | A | O |
| ATOM | 487 | N   | PRO | A | 102 | 21.637 | 72.614 | 16.170 | 1.00 | 27.10 | A | N |
| ATOM | 488 | CD  | PRO | A | 102 | 22.833 | 72.839 | 16.999 | 1.00 | 32.08 | A | C |
| ATOM | 489 | CA  | PRO | A | 102 | 20.557 | 73.553 | 16.506 | 1.00 | 27.20 | A | C |
| ATOM | 490 | CB  | PRO | A | 102 | 21.243 | 74.544 | 17.444 | 1.00 | 30.08 | A | C |
| ATOM | 491 | CG  | PRO | A | 102 | 22.338 | 73.774 | 18.057 | 1.00 | 33.36 | A | C |
| ATOM | 492 | C   | PRO | A | 102 | 19.978 | 74.305 | 15.313 | 1.00 | 28.11 | A | C |
| ATOM | 493 | O   | PRO | A | 102 | 20.674 | 74.538 | 14.336 | 1.00 | 27.56 | A | O |
| ATOM | 494 | N   | ASP | A | 103 | 18.714 | 74.705 | 15.400 | 1.00 | 27.06 | A | N |
| ATOM | 495 | CA  | ASP | A | 103 | 18.112 | 75.469 | 14.314 | 1.00 | 30.43 | A | C |
| ATOM | 496 | CB  | ASP | A | 103 | 16.617 | 75.178 | 14.206 | 1.00 | 28.37 | A | C |
| ATOM | 497 | CG  | ASP | A | 103 | 16.335 | 73.742 | 13.860 | 1.00 | 25.65 | A | C |
| ATOM | 498 | OD1 | ASP | A | 103 | 17.218 | 73.081 | 13.286 | 1.00 | 26.49 | A | O |
| ATOM | 499 | OD2 | ASP | A | 103 | 15.224 | 73.269 | 14.158 | 1.00 | 25.92 | A | O |
| ATOM | 500 | C   | ASP | A | 103 | 18.321 | 76.958 | 14.520 | 1.00 | 33.99 | A | C |
| ATOM | 501 | O   | ASP | A | 103 | 18.487 | 77.708 | 13.555 | 1.00 | 27.29 | A | O |
| ATOM | 502 | N   | LEU | A | 104 | 18.274 | 77.380 | 15.783 | 1.00 | 28.21 | A | N |
| ATOM | 503 | CA  | LEU | A | 104 | 18.480 | 78.772 | 16.136 | 1.00 | 28.15 | A | C |
| ATOM | 504 | CB  | LEU | A | 104 | 17.216 | 79.367 | 16.740 | 1.00 | 32.49 | A | C |
| ATOM | 505 | CG  | LEU | A | 104 | 16.035 | 79.514 | 15.783 | 1.00 | 31.16 | A | C |
| ATOM | 506 | CD1 | LEU | A | 104 | 14.777 | 79.978 | 16.502 | 1.00 | 34.26 | A | C |
| ATOM | 507 | CD2 | LEU | A | 104 | 16.421 | 80.492 | 14.700 | 1.00 | 35.51 | A | C |
| ATOM | 508 | C   | LEU | A | 104 | 19.628 | 78.847 | 17.114 | 1.00 | 35.40 | A | C |
| ATOM | 509 | O   | LEU | A | 104 | 19.638 | 78.141 | 18.107 | 1.00 | 36.07 | A | O |
| ATOM | 510 | N   | GLY | A | 105 | 20.613 | 79.684 | 16.814 | 1.00 | 44.28 | A | N |
| ATOM | 511 | CA  | GLY | A | 105 | 21.810 | 79.746 | 17.634 | 1.00 | 41.90 | A | C |
| ATOM | 512 | C   | GLY | A | 105 | 22.809 | 78.663 | 17.270 | 1.00 | 46.32 | A | C |
| ATOM | 513 | O   | GLY | A | 105 | 22.758 | 78.068 | 16.186 | 1.00 | 41.38 | A | O |
| ATOM | 514 | N   | ARG | A | 106 | 23.733 | 78.402 | 18.183 | 1.00 | 49.26 | A | N |
| ATOM | 515 | CA  | ARG | A | 106 | 24.782 | 77.428 | 17.921 | 1.00 | 46.50 | A | C |
| ATOM | 516 | CB  | ARG | A | 106 | 26.057 | 78.123 | 17.432 | 1.00 | 47.78 | A | C |
| ATOM | 517 | CG  | ARG | A | 106 | 25.825 | 78.911 | 16.148 | 1.00 | 43.45 | A | C |
| ATOM | 518 | CD  | ARG | A | 106 | 27.103 | 79.156 | 15.360 | 1.00 | 47.73 | A | C |
| ATOM | 519 | NE  | ARG | A | 106 | 26.844 | 79.286 | 13.920 | 1.00 | 45.35 | A | N |
| ATOM | 520 | CZ  | ARG | A | 106 | 26.819 | 78.258 | 13.074 | 1.00 | 42.33 | A | C |
| ATOM | 521 | NH1 | ARG | A | 106 | 27.034 | 77.023 | 13.520 | 1.00 | 43.35 | A | N |
| ATOM | 522 | NH2 | ARG | A | 106 | 26.588 | 78.457 | 11.781 | 1.00 | 39.80 | A | N |
| ATOM | 523 | C   | ARG | A | 106 | 25.061 | 76.555 | 19.140 | 1.00 | 49.59 | A | C |
| ATOM | 524 | O   | ARG | A | 106 | 24.598 | 76.843 | 20.251 | 1.00 | 49.49 | A | O |
| ATOM | 525 | N   | PHE | A | 107 | 25.786 | 75.465 | 18.910 | 1.00 | 47.61 | A | N |
| ATOM | 526 | CA  | PHE | A | 107 | 26.213 | 74.591 | 19.989 | 1.00 | 51.46 | A | C |
| ATOM | 527 | CB  | PHE | A | 107 | 27.233 | 73.589 | 19.462 | 1.00 | 46.92 | A | C |
| ATOM | 528 | CG  | PHE | A | 107 | 26.629 | 72.371 | 18.826 | 1.00 | 45.06 | A | C |

TABLE 14-continued

Coordinates for proMMP9(35-444 ΔFnII) (SEQ ID NO: 12) complex with Example 4

| ATOM | 529 | CD1 | PHE | A | 107 | 25.675 | 71.615 | 19.503 | 1.00 | 40.50 | A | C |
|---|---|---|---|---|---|---|---|---|---|---|---|---|
| ATOM | 530 | CD2 | PHE | A | 107 | 27.056 | 71.956 | 17.567 | 1.00 | 37.67 | A | C |
| ATOM | 531 | CE1 | PHE | A | 107 | 25.130 | 70.479 | 18.916 | 1.00 | 45.47 | A | C |
| ATOM | 532 | CE2 | PHE | A | 107 | 26.536 | 70.820 | 16.981 | 1.00 | 36.50 | A | C |
| ATOM | 533 | CZ | PHE | A | 107 | 25.571 | 70.078 | 17.644 | 1.00 | 38.83 | A | C |
| ATOM | 534 | C | PHE | A | 107 | 26.871 | 75.407 | 21.098 | 1.00 | 52.66 | A | C |
| ATOM | 535 | O | PHE | A | 107 | 26.525 | 75.284 | 22.284 | 1.00 | 55.56 | A | O |
| ATOM | 536 | N | GLN | A | 108 | 27.827 | 76.237 | 20.686 | 1.00 | 49.51 | A | N |
| ATOM | 537 | CA | GLN | A | 108 | 28.694 | 76.956 | 21.600 | 1.00 | 50.29 | A | C |
| ATOM | 538 | CB | GLN | A | 108 | 29.850 | 76.043 | 22.018 | 1.00 | 46.60 | A | C |
| ATOM | 539 | CG | GLN | A | 108 | 30.602 | 75.432 | 20.850 | 1.00 | 48.74 | A | C |
| ATOM | 540 | CD | GLN | A | 108 | 31.737 | 74.511 | 21.289 | 1.00 | 52.45 | A | C |
| ATOM | 541 | OE1 | GLN | A | 108 | 31.503 | 73.386 | 21.734 | 1.00 | 52.06 | A | O |
| ATOM | 542 | NE2 | GLN | A | 108 | 32.976 | 74.984 | 21.153 | 1.00 | 50.59 | A | N |
| ATOM | 543 | C | GLN | A | 108 | 29.221 | 78.213 | 20.914 | 1.00 | 49.62 | A | C |
| ATOM | 544 | O | GLN | A | 108 | 28.945 | 78.443 | 19.736 | 1.00 | 48.83 | A | O |
| ATOM | 545 | N | THR | A | 109 | 29.956 | 79.042 | 21.645 | 1.00 | 45.71 | A | N |
| ATOM | 546 | CA | THR | A | 109 | 30.722 | 80.089 | 20.995 | 1.00 | 47.87 | A | C |
| ATOM | 547 | CB | THR | A | 109 | 31.276 | 81.113 | 21.992 | 1.00 | 50.01 | A | C |
| ATOM | 548 | OG1 | THR | A | 109 | 32.101 | 80.446 | 22.957 | 1.00 | 54.86 | A | O |
| ATOM | 549 | CG2 | THR | A | 109 | 30.139 | 81.828 | 22.688 | 1.00 | 40.16 | A | C |
| ATOM | 550 | C | THR | A | 109 | 31.884 | 79.420 | 20.273 | 1.00 | 46.68 | A | C |
| ATOM | 551 | O | THR | A | 109 | 32.538 | 78.546 | 20.831 | 1.00 | 48.02 | A | O |
| ATOM | 552 | N | PHE | A | 110 | 32.123 | 79.824 | 19.029 | 1.00 | 44.86 | A | N |
| ATOM | 553 | CA | PHE | A | 110 | 33.150 | 79.206 | 18.207 | 1.00 | 43.76 | A | C |
| ATOM | 554 | CB | PHE | A | 110 | 32.555 | 78.668 | 16.895 | 1.00 | 41.70 | A | C |
| ATOM | 555 | CG | PHE | A | 110 | 31.691 | 77.439 | 17.060 | 1.00 | 40.60 | A | C |
| ATOM | 556 | CD1 | PHE | A | 110 | 30.328 | 77.498 | 16.823 | 1.00 | 38.17 | A | C |
| ATOM | 557 | CD2 | PHE | A | 110 | 32.249 | 76.218 | 17.421 | 1.00 | 38.46 | A | C |
| ATOM | 558 | CE1 | PHE | A | 110 | 29.532 | 76.372 | 16.957 | 1.00 | 37.15 | A | C |
| ATOM | 559 | CE2 | PHE | A | 110 | 31.456 | 75.090 | 17.556 | 1.00 | 39.40 | A | C |
| ATOM | 560 | CZ | PHE | A | 110 | 30.091 | 75.172 | 17.324 | 1.00 | 36.84 | A | C |
| ATOM | 561 | C | PHE | A | 110 | 34.263 | 80.200 | 17.886 | 1.00 | 48.73 | A | C |
| ATOM | 562 | O | PHE | A | 110 | 34.116 | 81.412 | 18.074 | 1.00 | 48.74 | A | O |
| ATOM | 563 | N | GLU | A | 111 | 35.372 | 79.677 | 17.383 | 1.00 | 43.32 | A | N |
| ATOM | 564 | CA | GLU | A | 111 | 36.509 | 80.508 | 17.043 | 1.00 | 45.18 | A | C |
| ATOM | 565 | CB | GLU | A | 111 | 37.799 | 79.731 | 17.275 | 1.00 | 45.39 | A | C |
| ATOM | 566 | CG | GLU | A | 111 | 38.068 | 79.433 | 18.735 | 1.00 | 53.73 | A | C |
| ATOM | 567 | CD | GLU | A | 111 | 39.155 | 80.330 | 19.302 | 1.00 | 61.90 | A | C |
| ATOM | 568 | OE1 | GLU | A | 111 | 38.823 | 81.338 | 19.969 | 1.00 | 56.57 | A | O |
| ATOM | 569 | OE2 | GLU | A | 111 | 40.347 | 80.022 | 19.065 | 1.00 | 61.94 | A | O |
| ATOM | 570 | C | GLU | A | 111 | 36.419 | 80.944 | 15.595 | 1.00 | 45.00 | A | C |
| ATOM | 571 | O | GLU | A | 111 | 36.141 | 80.126 | 14.715 | 1.00 | 45.53 | A | O |
| ATOM | 572 | N | GLY | A | 112 | 36.644 | 82.233 | 15.354 | 1.00 | 43.11 | A | N |
| ATOM | 573 | CA | GLY | A | 112 | 36.789 | 82.741 | 14.003 | 1.00 | 38.83 | A | C |
| ATOM | 574 | C | GLY | A | 112 | 35.523 | 83.083 | 13.235 | 1.00 | 42.29 | A | C |
| ATOM | 575 | O | GLY | A | 112 | 34.457 | 83.333 | 13.801 | 1.00 | 36.82 | A | O |
| ATOM | 576 | N | ASP | A | 113 | 35.679 | 83.037 | 11.919 | 1.00 | 39.15 | A | N |
| ATOM | 577 | CA | ASP | A | 113 | 34.750 | 83.489 | 10.899 | 1.00 | 38.17 | A | C |
| ATOM | 578 | CB | ASP | A | 113 | 35.556 | 83.593 | 9.598 | 1.00 | 42.85 | A | C |
| ATOM | 579 | CG | ASP | A | 113 | 35.090 | 84.705 | 8.726 | 1.00 | 45.55 | A | C |
| ATOM | 580 | OD1 | ASP | A | 113 | 34.243 | 85.484 | 9.209 | 1.00 | 53.75 | A | O |
| ATOM | 581 | OD2 | ASP | A | 113 | 35.568 | 84.806 | 7.576 | 1.00 | 44.65 | A | O |
| ATOM | 582 | C | ASP | A | 113 | 33.590 | 82.532 | 10.608 | 1.00 | 40.89 | A | C |
| ATOM | 583 | O | ASP | A | 113 | 32.511 | 82.963 | 10.185 | 1.00 | 39.79 | A | O |
| ATOM | 584 | N | LEU | A | 114 | 33.852 | 81.236 | 10.777 | 1.00 | 37.51 | A | N |
| ATOM | 585 | CA | LEU | A | 114 | 32.932 | 80.163 | 10.392 | 1.00 | 37.69 | A | C |
| ATOM | 586 | CB | LEU | A | 114 | 31.525 | 80.398 | 10.951 | 1.00 | 35.57 | A | C |
| ATOM | 587 | CG | LEU | A | 114 | 31.544 | 80.794 | 12.432 | 1.00 | 42.35 | A | C |
| ATOM | 588 | CD1 | LEU | A | 114 | 30.129 | 81.018 | 12.965 | 1.00 | 40.76 | A | C |
| ATOM | 589 | CD2 | LEU | A | 114 | 32.308 | 79.755 | 13.272 | 1.00 | 39.56 | A | C |
| ATOM | 590 | C | LEU | A | 114 | 32.903 | 79.951 | 8.877 | 1.00 | 39.24 | A | C |
| ATOM | 591 | O | LEU | A | 114 | 31.954 | 79.383 | 8.333 | 1.00 | 35.36 | A | O |
| ATOM | 592 | N | LYS | A | 115 | 33.962 | 80.411 | 8.216 | 1.00 | 37.82 | A | N |
| ATOM | 593 | CA | LYS | A | 115 | 34.165 | 80.249 | 6.775 | 1.00 | 40.02 | A | C |
| ATOM | 594 | CB | LYS | A | 115 | 33.978 | 81.608 | 6.081 | 1.00 | 42.34 | A | C |
| ATOM | 595 | CG | LYS | A | 115 | 34.372 | 81.690 | 4.624 | 1.00 | 43.05 | A | C |
| ATOM | 596 | CD | LYS | A | 115 | 34.179 | 83.112 | 4.078 | 1.00 | 45.97 | A | C |
| ATOM | 597 | CE | LYS | A | 115 | 34.558 | 83.198 | 2.598 | 1.00 | 51.38 | A | C |
| ATOM | 598 | NZ | LYS | A | 115 | 34.230 | 84.520 | 1.963 | 1.00 | 56.46 | A | N |
| ATOM | 599 | C | LYS | A | 115 | 35.591 | 79.739 | 6.586 | 1.00 | 36.72 | A | C |
| ATOM | 600 | O | LYS | A | 115 | 36.484 | 80.160 | 7.309 | 1.00 | 38.11 | A | O |
| ATOM | 601 | N | TRP | A | 116 | 35.803 | 78.818 | 5.649 | 1.00 | 34.05 | A | N |
| ATOM | 602 | CA | TRP | A | 116 | 37.165 | 78.383 | 5.316 | 1.00 | 40.46 | A | C |
| ATOM | 603 | CB | TRP | A | 116 | 37.177 | 77.114 | 4.457 | 1.00 | 34.45 | A | C |
| ATOM | 604 | CG | TRP | A | 116 | 36.709 | 75.906 | 5.160 | 1.00 | 37.90 | A | C |
| ATOM | 605 | CD2 | TRP | A | 116 | 37.329 | 75.276 | 6.284 | 1.00 | 35.52 | A | C |
| ATOM | 606 | CE2 | TRP | A | 116 | 36.535 | 74.169 | 6.634 | 1.00 | 34.36 | A | C |

TABLE 14-continued

Coordinates for proMMP9(35-444 ΔFnII) (SEQ ID NO: 12) complex with Example 4

| ATOM | 607 | CE3 | TRP | A | 116 | 38.472 | 75.551 | 7.039 | 1.00 | 38.92 | A | C |
|---|---|---|---|---|---|---|---|---|---|---|---|---|
| ATOM | 608 | CD1 | TRP | A | 116 | 35.592 | 75.170 | 4.874 | 1.00 | 32.16 | A | C |
| ATOM | 609 | NE1 | TRP | A | 116 | 35.490 | 74.118 | 5.751 | 1.00 | 31.90 | A | N |
| ATOM | 610 | CZ2 | TRP | A | 116 | 36.854 | 73.326 | 7.690 | 1.00 | 35.38 | A | C |
| ATOM | 611 | CZ3 | TRP | A | 116 | 38.788 | 74.708 | 8.096 | 1.00 | 37.99 | A | C |
| ATOM | 612 | CH2 | TRP | A | 116 | 37.982 | 73.617 | 8.410 | 1.00 | 39.00 | A | C |
| ATOM | 613 | C | TRP | A | 116 | 37.897 | 79.471 | 4.545 | 1.00 | 43.89 | A | C |
| ATOM | 614 | O | TRP | A | 116 | 37.328 | 80.098 | 3.645 | 1.00 | 44.49 | A | O |
| ATOM | 615 | N | HIS | A | 117 | 39.165 | 79.675 | 4.880 | 1.00 | 42.33 | A | N |
| ATOM | 616 | CA | HIS | A | 117 | 39.958 | 80.683 | 4.206 | 1.00 | 40.57 | A | C |
| ATOM | 617 | CB | HIS | A | 117 | 40.439 | 81.735 | 5.202 | 1.00 | 42.81 | A | C |
| ATOM | 618 | CG | HIS | A | 117 | 39.327 | 82.542 | 5.791 | 1.00 | 44.04 | A | C |
| ATOM | 619 | CD2 | HIS | A | 117 | 38.735 | 82.490 | 7.007 | 1.00 | 44.87 | A | C |
| ATOM | 620 | ND1 | HIS | A | 117 | 38.674 | 83.531 | 5.088 | 1.00 | 43.72 | A | N |
| ATOM | 621 | CE1 | HIS | A | 117 | 37.737 | 84.064 | 5.849 | 1.00 | 46.67 | A | C |
| ATOM | 622 | NE2 | HIS | A | 117 | 37.748 | 83.447 | 7.019 | 1.00 | 44.47 | A | N |
| ATOM | 623 | C | HIS | A | 117 | 41.109 | 80.051 | 3.434 | 1.00 | 39.19 | A | C |
| ATOM | 624 | O | HIS | A | 117 | 42.160 | 80.660 | 3.255 | 1.00 | 36.97 | A | O |
| ATOM | 625 | N | HIS | A | 118 | 40.895 | 78.804 | 3.028 | 1.00 | 34.01 | A | N |
| ATOM | 626 | CA | HIS | A | 118 | 41.694 | 78.151 | 2.006 | 1.00 | 37.93 | A | C |
| ATOM | 627 | CB | HIS | A | 118 | 42.851 | 77.333 | 2.592 | 1.00 | 36.51 | A | C |
| ATOM | 628 | CG | HIS | A | 118 | 42.440 | 76.275 | 3.568 | 1.00 | 34.63 | A | C |
| ATOM | 629 | CD2 | HIS | A | 118 | 42.388 | 74.927 | 3.451 | 1.00 | 35.94 | A | C |
| ATOM | 630 | ND1 | HIS | A | 118 | 42.077 | 76.560 | 4.871 | 1.00 | 39.19 | A | N |
| ATOM | 631 | CE1 | HIS | A | 118 | 41.800 | 75.434 | 5.505 | 1.00 | 35.71 | A | C |
| ATOM | 632 | NE2 | HIS | A | 118 | 41.978 | 74.427 | 4.668 | 1.00 | 30.44 | A | N |
| ATOM | 633 | C | HIS | A | 118 | 40.766 | 77.287 | 1.157 | 1.00 | 37.75 | A | C |
| ATOM | 634 | O | HIS | A | 118 | 39.608 | 77.083 | 1.509 | 1.00 | 37.21 | A | O |
| ATOM | 635 | N | HIS | A | 119 | 41.274 | 76.777 | 0.047 | 1.00 | 39.01 | A | N |
| ATOM | 636 | CA | HIS | A | 119 | 40.419 | 76.154 | −0.948 | 1.00 | 40.69 | A | C |
| ATOM | 637 | CB | HIS | A | 119 | 40.705 | 76.716 | −2.342 | 1.00 | 43.45 | A | C |
| ATOM | 638 | CG | HIS | A | 119 | 40.031 | 78.024 | −2.609 | 1.00 | 43.38 | A | C |
| ATOM | 639 | CD2 | HIS | A | 119 | 39.996 | 78.803 | −3.718 | 1.00 | 45.46 | A | C |
| ATOM | 640 | ND1 | HIS | A | 119 | 39.284 | 78.681 | −1.656 | 1.00 | 48.21 | A | N |
| ATOM | 641 | CE1 | HIS | A | 119 | 38.811 | 79.806 | −2.168 | 1.00 | 46.37 | A | C |
| ATOM | 642 | NE2 | HIS | A | 119 | 39.231 | 79.904 | −3.415 | 1.00 | 49.26 | A | N |
| ATOM | 643 | C | HIS | A | 119 | 40.542 | 74.652 | −0.969 | 1.00 | 36.19 | A | C |
| ATOM | 644 | O | HIS | A | 119 | 39.615 | 73.964 | −1.389 | 1.00 | 34.90 | A | O |
| ATOM | 645 | N | ASN | A | 120 | 41.676 | 74.119 | −0.542 | 1.00 | 34.14 | A | N |
| ATOM | 646 | CA | ASN | A | 120 | 41.753 | 72.673 | −0.490 | 1.00 | 37.82 | A | C |
| ATOM | 647 | CB | ASN | A | 120 | 43.054 | 72.102 | −1.036 | 1.00 | 39.91 | A | C |
| ATOM | 648 | CG | ASN | A | 120 | 43.004 | 70.585 | −1.137 | 1.00 | 42.78 | A | C |
| ATOM | 649 | OD1 | ASN | A | 120 | 41.920 | 69.987 | −1.147 | 1.00 | 41.85 | A | O |
| ATOM | 650 | ND2 | ASN | A | 120 | 44.168 | 69.952 | −1.198 | 1.00 | 43.98 | A | N |
| ATOM | 651 | C | ASN | A | 120 | 41.492 | 72.159 | 0.902 | 1.00 | 38.56 | A | C |
| ATOM | 652 | O | ASN | A | 120 | 42.316 | 72.309 | 1.805 | 1.00 | 37.15 | A | O |
| ATOM | 653 | N | ILE | A | 121 | 40.324 | 71.552 | 1.062 | 1.00 | 36.47 | A | N |
| ATOM | 654 | CA | ILE | A | 121 | 39.860 | 71.125 | 2.367 | 1.00 | 35.04 | A | C |
| ATOM | 655 | CB | ILE | A | 121 | 38.342 | 71.363 | 2.486 | 1.00 | 35.92 | A | C |
| ATOM | 656 | CG2 | ILE | A | 121 | 37.870 | 71.234 | 3.931 | 1.00 | 32.74 | A | C |
| ATOM | 657 | CG1 | ILE | A | 121 | 37.999 | 72.752 | 1.926 | 1.00 | 34.55 | A | C |
| ATOM | 658 | CD1 | ILE | A | 121 | 38.622 | 73.893 | 2.721 | 1.00 | 32.69 | A | C |
| ATOM | 659 | C | ILE | A | 121 | 40.216 | 69.656 | 2.517 | 1.00 | 35.49 | A | C |
| ATOM | 660 | O | ILE | A | 121 | 39.942 | 68.845 | 1.634 | 1.00 | 37.37 | A | O |
| ATOM | 661 | N | THR | A | 122 | 40.886 | 69.322 | 3.608 | 1.00 | 33.32 | A | N |
| ATOM | 662 | CA | THR | A | 122 | 41.321 | 67.955 | 3.819 | 1.00 | 33.79 | A | C |
| ATOM | 663 | CB | THR | A | 122 | 42.725 | 67.915 | 4.405 | 1.00 | 31.56 | A | C |
| ATOM | 664 | OG1 | THR | A | 122 | 42.803 | 68.847 | 5.487 | 1.00 | 37.24 | A | O |
| ATOM | 665 | CG2 | THR | A | 122 | 43.736 | 68.330 | 3.339 | 1.00 | 37.38 | A | C |
| ATOM | 666 | C | THR | A | 122 | 40.345 | 67.304 | 4.774 | 1.00 | 33.11 | A | C |
| ATOM | 667 | O | THR | A | 122 | 39.784 | 67.965 | 5.637 | 1.00 | 33.85 | A | O |
| ATOM | 668 | N | TYR | A | 123 | 40.115 | 66.016 | 4.604 | 1.00 | 31.79 | A | N |
| ATOM | 669 | CA | TYR | A | 123 | 39.262 | 65.311 | 5.536 | 1.00 | 35.53 | A | C |
| ATOM | 670 | CB | TYR | A | 123 | 37.839 | 65.133 | 4.989 | 1.00 | 30.50 | A | C |
| ATOM | 671 | CG | TYR | A | 123 | 37.701 | 64.199 | 3.813 | 1.00 | 28.17 | A | C |
| ATOM | 672 | CD1 | TYR | A | 123 | 37.769 | 64.678 | 2.520 | 1.00 | 29.99 | A | C |
| ATOM | 673 | CE1 | TYR | A | 123 | 37.629 | 63.832 | 1.432 | 1.00 | 29.02 | A | C |
| ATOM | 674 | CD2 | TYR | A | 123 | 37.459 | 62.834 | 4.004 | 1.00 | 31.77 | A | C |
| ATOM | 675 | CE2 | TYR | A | 123 | 37.308 | 61.974 | 2.926 | 1.00 | 30.51 | A | C |
| ATOM | 676 | CZ | TYR | A | 123 | 37.395 | 62.486 | 1.638 | 1.00 | 33.72 | A | C |
| ATOM | 677 | OH | TYR | A | 123 | 37.247 | 61.656 | 0.547 | 1.00 | 31.89 | A | O |
| ATOM | 678 | C | TYR | A | 123 | 39.885 | 63.982 | 5.889 | 1.00 | 35.94 | A | C |
| ATOM | 679 | O | TYR | A | 123 | 40.608 | 63.393 | 5.080 | 1.00 | 34.12 | A | O |
| ATOM | 680 | N | TRP | A | 124 | 39.633 | 63.541 | 7.118 | 1.00 | 32.13 | A | N |
| ATOM | 681 | CA | TRP | A | 124 | 40.134 | 62.263 | 7.582 | 1.00 | 32.38 | A | C |
| ATOM | 682 | CB | TRP | A | 124 | 41.237 | 62.486 | 8.604 | 1.00 | 37.24 | A | C |
| ATOM | 683 | CG | TRP | A | 124 | 41.719 | 61.245 | 9.263 | 1.00 | 37.82 | A | C |
| ATOM | 684 | CD2 | TRP | A | 124 | 41.995 | 61.074 | 10.655 | 1.00 | 39.32 | A | C |

TABLE 14-continued

Coordinates for proMMP9(35-444 ΔFnII) (SEQ ID NO: 12) complex with Example 4

| ATOM | 685 | CE2 | TRP | A | 124 | 42.436 | 59.752 | 10.835 | 1.00 | 39.37 | A | C |
|---|---|---|---|---|---|---|---|---|---|---|---|---|
| ATOM | 686 | CE3 | TRP | A | 124 | 41.900 | 61.913 | 11.771 | 1.00 | 41.23 | A | C |
| ATOM | 687 | CD1 | TRP | A | 124 | 42.001 | 60.060 | 8.668 | 1.00 | 39.14 | A | C |
| ATOM | 688 | NE1 | TRP | A | 124 | 42.432 | 59.149 | 9.605 | 1.00 | 40.13 | A | N |
| ATOM | 689 | CZ2 | TRP | A | 124 | 42.789 | 59.245 | 12.080 | 1.00 | 41.73 | A | C |
| ATOM | 690 | CZ3 | TRP | A | 124 | 42.245 | 61.409 | 13.010 | 1.00 | 45.92 | A | C |
| ATOM | 691 | CH2 | TRP | A | 124 | 42.690 | 60.088 | 13.154 | 1.00 | 46.29 | A | C |
| ATOM | 692 | C | TRP | A | 124 | 39.006 | 61.419 | 8.159 | 1.00 | 33.61 | A | C |
| ATOM | 693 | O | TRP | A | 124 | 38.250 | 61.866 | 9.030 | 1.00 | 33.96 | A | O |
| ATOM | 694 | N | ILE | A | 125 | 38.884 | 60.203 | 7.645 | 1.00 | 32.03 | A | N |
| ATOM | 695 | CA | ILE | A | 125 | 37.904 | 59.247 | 8.145 | 1.00 | 34.71 | A | C |
| ATOM | 696 | CB | ILE | A | 125 | 37.492 | 58.241 | 7.043 | 1.00 | 35.73 | A | C |
| ATOM | 697 | CG2 | ILE | A | 125 | 36.565 | 57.177 | 7.599 | 1.00 | 32.66 | A | C |
| ATOM | 698 | CG1 | ILE | A | 125 | 36.843 | 58.989 | 5.877 | 1.00 | 33.43 | A | C |
| ATOM | 699 | CD1 | ILE | A | 125 | 36.917 | 58.248 | 4.566 | 1.00 | 38.78 | A | C |
| ATOM | 700 | C | ILE | A | 125 | 38.549 | 58.524 | 9.316 | 1.00 | 34.73 | A | C |
| ATOM | 701 | O | ILE | A | 125 | 39.291 | 57.555 | 9.133 | 1.00 | 34.48 | A | O |
| ATOM | 702 | N | GLN | A | 126 | 38.290 | 59.028 | 10.516 | 1.00 | 36.27 | A | N |
| ATOM | 703 | CA | GLN | A | 126 | 38.951 | 58.536 | 11.708 | 1.00 | 36.59 | A | C |
| ATOM | 704 | CB | GLN | A | 126 | 38.592 | 59.405 | 12.912 | 1.00 | 39.49 | A | C |
| ATOM | 705 | CG | GLN | A | 126 | 39.428 | 59.119 | 14.150 | 1.00 | 41.05 | A | C |
| ATOM | 706 | CD | GLN | A | 126 | 39.146 | 60.094 | 15.286 | 1.00 | 47.67 | A | C |
| ATOM | 707 | OE1 | GLN | A | 126 | 38.060 | 60.677 | 15.374 | 1.00 | 47.32 | A | O |
| ATOM | 708 | NE2 | GLN | A | 126 | 40.125 | 60.264 | 16.170 | 1.00 | 51.05 | A | N |
| ATOM | 709 | C | GLN | A | 126 | 38.578 | 57.083 | 11.949 | 1.00 | 38.71 | A | C |
| ATOM | 710 | O | GLN | A | 126 | 39.439 | 56.258 | 12.265 | 1.00 | 38.60 | A | O |
| ATOM | 711 | N | ASN | A | 127 | 37.302 | 56.760 | 11.768 | 1.00 | 33.96 | A | N |
| ATOM | 712 | CA | ASN | A | 127 | 36.851 | 55.387 | 11.938 | 1.00 | 35.25 | A | C |
| ATOM | 713 | CB | ASN | A | 127 | 36.582 | 55.102 | 13.423 | 1.00 | 36.32 | A | C |
| ATOM | 714 | CG | ASN | A | 127 | 35.470 | 55.974 | 13.996 | 1.00 | 38.35 | A | C |
| ATOM | 715 | OD1 | ASN | A | 127 | 34.929 | 56.842 | 13.312 | 1.00 | 36.26 | A | O |
| ATOM | 716 | ND2 | ASN | A | 127 | 35.123 | 55.739 | 15.259 | 1.00 | 38.22 | A | N |
| ATOM | 717 | C | ASN | A | 127 | 35.650 | 55.005 | 11.056 | 1.00 | 34.32 | A | C |
| ATOM | 718 | O | ASN | A | 127 | 35.150 | 55.817 | 10.280 | 1.00 | 33.29 | A | O |
| ATOM | 719 | N | TYR | A | 128 | 35.215 | 53.756 | 11.163 | 1.00 | 34.08 | A | N |
| ATOM | 720 | CA | TYR | A | 128 | 34.097 | 53.253 | 10.382 | 1.00 | 34.30 | A | C |
| ATOM | 721 | CB | TYR | A | 128 | 34.577 | 52.245 | 9.350 | 1.00 | 33.31 | A | C |
| ATOM | 722 | CG | TYR | A | 128 | 35.513 | 52.819 | 8.321 | 1.00 | 38.44 | A | C |
| ATOM | 723 | CD1 | TYR | A | 128 | 35.095 | 53.019 | 7.014 | 1.00 | 35.21 | A | C |
| ATOM | 724 | CE1 | TYR | A | 128 | 35.951 | 53.537 | 6.063 | 1.00 | 40.15 | A | C |
| ATOM | 725 | CD2 | TYR | A | 128 | 36.823 | 53.146 | 8.654 | 1.00 | 38.79 | A | C |
| ATOM | 726 | CE2 | TYR | A | 128 | 37.685 | 53.664 | 7.713 | 1.00 | 39.02 | A | C |
| ATOM | 727 | CZ | TYR | A | 128 | 37.243 | 53.860 | 6.418 | 1.00 | 39.96 | A | C |
| ATOM | 728 | OH | TYR | A | 128 | 38.098 | 54.374 | 5.477 | 1.00 | 38.78 | A | O |
| ATOM | 729 | C | TYR | A | 128 | 33.056 | 52.553 | 11.241 | 1.00 | 37.50 | A | C |
| ATOM | 730 | O | TYR | A | 128 | 33.391 | 51.911 | 12.229 | 1.00 | 39.58 | A | O |
| ATOM | 731 | N | SER | A | 129 | 31.793 | 52.664 | 10.833 | 1.00 | 33.63 | A | N |
| ATOM | 732 | CA | SER | A | 129 | 30.736 | 51.805 | 11.351 | 1.00 | 35.09 | A | C |
| ATOM | 733 | CB | SER | A | 129 | 29.369 | 52.442 | 11.109 | 1.00 | 30.54 | A | C |
| ATOM | 734 | OG | SER | A | 129 | 28.400 | 51.460 | 10.806 | 1.00 | 29.48 | A | O |
| ATOM | 735 | C | SER | A | 129 | 30.813 | 50.489 | 10.598 | 1.00 | 37.53 | A | C |
| ATOM | 736 | O | SER | A | 129 | 31.270 | 50.451 | 9.449 | 1.00 | 33.62 | A | O |
| ATOM | 737 | N | GLU | A | 130 | 30.345 | 49.415 | 11.222 | 1.00 | 34.80 | A | N |
| ATOM | 738 | CA | GLU | A | 130 | 30.433 | 48.100 | 10.605 | 1.00 | 35.34 | A | C |
| ATOM | 739 | CB | GLU | A | 130 | 30.740 | 47.039 | 11.659 | 1.00 | 40.30 | A | C |
| ATOM | 740 | CG | GLU | A | 130 | 31.972 | 47.364 | 12.508 | 1.00 | 38.06 | A | C |
| ATOM | 741 | CD | GLU | A | 130 | 33.270 | 47.212 | 11.738 | 1.00 | 45.15 | A | C |
| ATOM | 742 | OE1 | GLU | A | 130 | 33.239 | 46.639 | 10.623 | 1.00 | 44.01 | A | O |
| ATOM | 743 | OE2 | GLU | A | 130 | 34.324 | 47.654 | 12.254 | 1.00 | 50.94 | A | O |
| ATOM | 744 | C | GLU | A | 130 | 29.168 | 47.755 | 9.836 | 1.00 | 35.43 | A | C |
| ATOM | 745 | O | GLU | A | 130 | 29.002 | 46.627 | 9.376 | 1.00 | 31.50 | A | O |
| ATOM | 746 | N | ASP | A | 131 | 28.280 | 48.736 | 9.689 | 1.00 | 33.47 | A | N |
| ATOM | 747 | CA | ASP | A | 131 | 27.042 | 48.542 | 8.935 | 1.00 | 33.74 | A | C |
| ATOM | 748 | CB | ASP | A | 131 | 26.109 | 49.740 | 9.124 | 1.00 | 31.58 | A | C |
| ATOM | 749 | CG | ASP | A | 131 | 25.566 | 49.836 | 10.534 | 1.00 | 33.21 | A | C |
| ATOM | 750 | OD1 | ASP | A | 131 | 25.608 | 48.820 | 11.258 | 1.00 | 33.04 | A | O |
| ATOM | 751 | OD2 | ASP | A | 131 | 25.081 | 50.919 | 10.906 | 1.00 | 34.53 | A | O |
| ATOM | 752 | C | ASP | A | 131 | 27.270 | 48.323 | 7.435 | 1.00 | 32.07 | A | C |
| ATOM | 753 | O | ASP | A | 131 | 26.482 | 47.653 | 6.778 | 1.00 | 31.28 | A | O |
| ATOM | 754 | N | LEU | A | 132 | 28.330 | 48.917 | 6.902 | 1.00 | 30.54 | A | N |
| ATOM | 755 | CA | LEU | A | 132 | 28.610 | 48.888 | 5.461 | 1.00 | 33.69 | A | C |
| ATOM | 756 | CB | LEU | A | 132 | 28.348 | 50.269 | 4.856 | 1.00 | 33.34 | A | C |
| ATOM | 757 | CG | LEU | A | 132 | 26.899 | 50.762 | 4.777 | 1.00 | 36.27 | A | C |
| ATOM | 758 | CD1 | LEU | A | 132 | 26.813 | 52.295 | 4.611 | 1.00 | 30.58 | A | C |
| ATOM | 759 | CD2 | LEU | A | 132 | 26.179 | 50.045 | 3.637 | 1.00 | 34.05 | A | C |
| ATOM | 760 | C | LEU | A | 132 | 30.073 | 48.538 | 5.258 | 1.00 | 30.82 | A | C |
| ATOM | 761 | O | LEU | A | 132 | 30.872 | 48.727 | 6.171 | 1.00 | 31.95 | A | O |
| ATOM | 762 | N | PRO | A | 133 | 30.439 | 48.040 | 4.060 | 1.00 | 34.02 | A | N |

TABLE 14-continued

Coordinates for proMMP9(35-444 ΔFnII) (SEQ ID NO: 12) complex with Example 4

| ATOM | 763 | CD | PRO | A | 133 | 29.583 | 47.525 | 2.976 | 1.00 | 32.69 | A | C |
|---|---|---|---|---|---|---|---|---|---|---|---|---|
| ATOM | 764 | CA | PRO | A | 133 | 31.863 | 47.822 | 3.787 | 1.00 | 31.22 | A | C |
| ATOM | 765 | CB | PRO | A | 133 | 31.874 | 47.267 | 2.360 | 1.00 | 32.02 | A | C |
| ATOM | 766 | CG | PRO | A | 133 | 30.534 | 46.656 | 2.174 | 1.00 | 33.97 | A | C |
| ATOM | 767 | C | PRO | A | 133 | 32.599 | 49.148 | 3.838 | 1.00 | 35.28 | A | C |
| ATOM | 768 | O | PRO | A | 133 | 31.978 | 50.193 | 3.668 | 1.00 | 37.04 | A | O |
| ATOM | 769 | N | ARG | A | 134 | 33.906 | 49.115 | 4.062 | 1.00 | 34.27 | A | N |
| ATOM | 770 | CA | ARG | A | 134 | 34.649 | 50.350 | 4.254 | 1.00 | 34.85 | A | C |
| ATOM | 771 | CB | ARG | A | 134 | 36.015 | 50.056 | 4.860 | 1.00 | 38.63 | A | C |
| ATOM | 772 | CG | ARG | A | 134 | 35.980 | 49.663 | 6.335 | 1.00 | 41.61 | A | C |
| ATOM | 773 | CD | ARG | A | 134 | 37.396 | 49.406 | 6.835 | 1.00 | 44.68 | A | C |
| ATOM | 774 | NE | ARG | A | 134 | 37.490 | 49.388 | 8.289 | 1.00 | 52.21 | A | N |
| ATOM | 775 | CZ | ARG | A | 134 | 38.615 | 49.618 | 8.957 | 1.00 | 51.24 | A | C |
| ATOM | 776 | NH1 | ARG | A | 134 | 39.735 | 49.897 | 8.296 | 1.00 | 51.17 | A | N |
| ATOM | 777 | NH2 | ARG | A | 134 | 38.618 | 49.587 | 10.285 | 1.00 | 54.94 | A | N |
| ATOM | 778 | C | ARG | A | 134 | 34.798 | 51.118 | 2.941 | 1.00 | 35.98 | A | C |
| ATOM | 779 | O | ARG | A | 134 | 34.914 | 52.348 | 2.931 | 1.00 | 35.27 | A | O |
| ATOM | 780 | N | ALA | A | 135 | 34.796 | 50.388 | 1.833 | 1.00 | 34.04 | A | N |
| ATOM | 781 | CA | ALA | A | 135 | 34.886 | 51.009 | 0.518 | 1.00 | 34.41 | A | C |
| ATOM | 782 | CB | ALA | A | 135 | 35.159 | 49.960 | -0.531 | 1.00 | 41.14 | A | C |
| ATOM | 783 | C | ALA | A | 135 | 33.603 | 51.760 | 0.196 | 1.00 | 34.90 | A | C |
| ATOM | 784 | O | ALA | A | 135 | 33.624 | 52.844 | -0.374 | 1.00 | 34.07 | A | O |
| ATOM | 785 | N | VAL | A | 136 | 32.480 | 51.164 | 0.571 | 1.00 | 35.75 | A | N |
| ATOM | 786 | CA | VAL | A | 136 | 31.188 | 51.783 | 0.356 | 1.00 | 35.31 | A | C |
| ATOM | 787 | CB | VAL | A | 136 | 30.057 | 50.793 | 0.657 | 1.00 | 36.15 | A | C |
| ATOM | 788 | CG1 | VAL | A | 136 | 28.723 | 51.502 | 0.708 | 1.00 | 36.65 | A | C |
| ATOM | 789 | CG2 | VAL | A | 136 | 30.050 | 49.685 | -0.403 | 1.00 | 32.23 | A | C |
| ATOM | 790 | C | VAL | A | 136 | 31.067 | 53.061 | 1.184 | 1.00 | 32.70 | A | C |
| ATOM | 791 | O | VAL | A | 136 | 30.537 | 54.063 | 0.713 | 1.00 | 35.23 | A | O |
| ATOM | 792 | N | ILE | A | 137 | 31.596 | 53.025 | 2.401 | 1.00 | 34.13 | A | N |
| ATOM | 793 | CA | ILE | A | 137 | 31.633 | 54.195 | 3.278 | 1.00 | 30.87 | A | C |
| ATOM | 794 | CB | ILE | A | 137 | 32.093 | 53.805 | 4.696 | 1.00 | 31.26 | A | C |
| ATOM | 795 | CG2 | ILE | A | 137 | 32.497 | 55.048 | 5.490 | 1.00 | 29.94 | A | C |
| ATOM | 796 | CG1 | ILE | A | 137 | 30.989 | 53.014 | 5.416 | 1.00 | 32.05 | A | C |
| ATOM | 797 | CD1 | ILE | A | 137 | 31.308 | 52.643 | 6.871 | 1.00 | 31.59 | A | C |
| ATOM | 798 | C | ILE | A | 137 | 32.551 | 55.297 | 2.730 | 1.00 | 33.59 | A | C |
| ATOM | 799 | O | ILE | A | 137 | 32.182 | 56.487 | 2.705 | 1.00 | 30.17 | A | O |
| ATOM | 800 | N | ASP | A | 138 | 33.747 | 54.900 | 2.307 | 1.00 | 30.00 | A | N |
| ATOM | 801 | CA | ASP | A | 138 | 34.659 | 55.801 | 1.609 | 1.00 | 32.34 | A | C |
| ATOM | 802 | CB | ASP | A | 138 | 35.874 | 55.030 | 1.097 | 1.00 | 33.62 | A | C |
| ATOM | 803 | CG | ASP | A | 138 | 36.824 | 54.607 | 2.216 | 1.00 | 38.02 | A | C |
| ATOM | 804 | OD1 | ASP | A | 138 | 36.583 | 54.934 | 3.400 | 1.00 | 38.89 | A | O |
| ATOM | 805 | OD2 | ASP | A | 138 | 37.825 | 53.943 | 1.902 | 1.00 | 42.12 | A | O |
| ATOM | 806 | C | ASP | A | 138 | 33.985 | 56.511 | 0.432 | 1.00 | 29.33 | A | C |
| ATOM | 807 | O | ASP | A | 138 | 34.087 | 57.722 | 0.286 | 1.00 | 27.63 | A | O |
| ATOM | 808 | N | ASP | A | 139 | 33.288 | 55.752 | -0.400 | 1.00 | 28.62 | A | N |
| ATOM | 809 | CA | ASP | A | 139 | 32.706 | 56.307 | -1.613 | 1.00 | 28.03 | A | C |
| ATOM | 810 | CB | ASP | A | 139 | 32.306 | 55.181 | -2.567 | 1.00 | 32.93 | A | C |
| ATOM | 811 | CG | ASP | A | 139 | 31.431 | 55.661 | -3.713 | 1.00 | 34.02 | A | C |
| ATOM | 812 | OD1 | ASP | A | 139 | 31.945 | 56.360 | -4.614 | 1.00 | 35.82 | A | O |
| ATOM | 813 | OD2 | ASP | A | 139 | 30.231 | 55.323 | -3.718 | 1.00 | 33.21 | A | O |
| ATOM | 814 | C | ASP | A | 139 | 31.501 | 57.190 | -1.286 | 1.00 | 31.06 | A | C |
| ATOM | 815 | O | ASP | A | 139 | 31.251 | 58.192 | -1.971 | 1.00 | 27.48 | A | O |
| ATOM | 816 | N | ALA | A | 140 | 30.757 | 56.820 | -0.240 | 1.00 | 27.86 | A | N |
| ATOM | 817 | CA | ALA | A | 140 | 29.629 | 57.639 | 0.196 | 1.00 | 28.33 | A | C |
| ATOM | 818 | CB | ALA | A | 140 | 28.887 | 56.980 | 1.388 | 1.00 | 27.35 | A | C |
| ATOM | 819 | C | ALA | A | 140 | 30.114 | 59.033 | 0.568 | 1.00 | 28.15 | A | C |
| ATOM | 820 | O | ALA | A | 140 | 29.503 | 60.030 | 0.206 | 1.00 | 30.28 | A | O |
| ATOM | 821 | N | PHE | A | 141 | 31.215 | 59.104 | 1.306 | 1.00 | 25.19 | A | N |
| ATOM | 822 | CA | PHE | A | 141 | 31.743 | 60.385 | 1.751 | 1.00 | 26.39 | A | C |
| ATOM | 823 | CB | PHE | A | 141 | 32.824 | 60.184 | 2.824 | 1.00 | 27.84 | A | C |
| ATOM | 824 | CG | PHE | A | 141 | 32.284 | 59.786 | 4.167 | 1.00 | 27.54 | A | C |
| ATOM | 825 | CD1 | PHE | A | 141 | 31.086 | 60.310 | 4.636 | 1.00 | 28.49 | A | C |
| ATOM | 826 | CD2 | PHE | A | 141 | 32.984 | 58.913 | 4.977 | 1.00 | 26.64 | A | C |
| ATOM | 827 | CE1 | PHE | A | 141 | 30.591 | 59.954 | 5.883 | 1.00 | 25.61 | A | C |
| ATOM | 828 | CE2 | PHE | A | 141 | 32.494 | 58.554 | 6.213 | 1.00 | 30.05 | A | C |
| ATOM | 829 | CZ | PHE | A | 141 | 31.290 | 59.078 | 6.664 | 1.00 | 25.09 | A | C |
| ATOM | 830 | C | PHE | A | 141 | 32.324 | 61.177 | 0.582 | 1.00 | 26.34 | A | C |
| ATOM | 831 | O | PHE | A | 141 | 32.151 | 62.397 | 0.481 | 1.00 | 25.43 | A | O |
| ATOM | 832 | N | ALA | A | 142 | 33.030 | 60.469 | -0.293 | 1.00 | 28.11 | A | N |
| ATOM | 833 | CA | ALA | A | 142 | 33.593 | 61.072 | -1.498 | 1.00 | 29.78 | A | C |
| ATOM | 834 | CB | ALA | A | 142 | 34.308 | 59.996 | -2.340 | 1.00 | 28.59 | A | C |
| ATOM | 835 | C | ALA | A | 142 | 32.474 | 61.730 | -2.295 | 1.00 | 24.71 | A | C |
| ATOM | 836 | O | ALA | A | 142 | 32.543 | 62.900 | -2.659 | 1.00 | 26.50 | A | O |
| ATOM | 837 | N | ARG | A | 143 | 31.419 | 60.971 | -2.540 | 1.00 | 26.34 | A | N |
| ATOM | 838 | CA | ARG | A | 143 | 30.325 | 61.466 | -3.367 | 1.00 | 24.57 | A | C |
| ATOM | 839 | CB | ARG | A | 143 | 29.364 | 60.335 | -3.686 | 1.00 | 26.29 | A | C |
| ATOM | 840 | CG | ARG | A | 143 | 30.017 | 59.278 | -4.561 | 1.00 | 26.65 | A | C |

TABLE 14-continued

Coordinates for proMMP9(35-444 ΔFnII) (SEQ ID NO: 12) complex with Example 4

| | | | | | | | | | | | |
|---|---|---|---|---|---|---|---|---|---|---|---|
| ATOM | 841 | CD | ARG | A | 143 | 29.281 | 57.954 | −4.562 | 1.00 | 32.59 A | C |
| ATOM | 842 | NE | ARG | A | 143 | 27.856 | 58.180 | −4.577 | 1.00 | 39.33 A | N |
| ATOM | 843 | CZ | ARG | A | 143 | 26.986 | 57.684 | −3.704 | 1.00 | 32.38 A | C |
| ATOM | 844 | NH1 | ARG | A | 143 | 27.368 | 56.864 | −2.736 | 1.00 | 35.65 A | N |
| ATOM | 845 | NH2 | ARG | A | 143 | 25.712 | 57.992 | −3.838 | 1.00 | 26.09 A | N |
| ATOM | 846 | C | ARG | A | 143 | 29.637 | 62.657 | −2.715 | 1.00 | 25.78 A | C |
| ATOM | 847 | O | ARG | A | 143 | 29.191 | 63.577 | −3.400 | 1.00 | 25.47 A | O |
| ATOM | 848 | N | ALA | A | 144 | 29.578 | 62.649 | −1.384 | 1.00 | 26.55 A | N |
| ATOM | 849 | CA | ALA | A | 144 | 28.950 | 63.732 | −0.640 | 1.00 | 27.17 A | C |
| ATOM | 850 | CB | ALA | A | 144 | 28.826 | 63.374 | 0.849 | 1.00 | 23.15 A | C |
| ATOM | 851 | C | ALA | A | 144 | 29.744 | 65.029 | −0.827 | 1.00 | 28.05 A | C |
| ATOM | 852 | O | ALA | A | 144 | 29.153 | 66.095 | −1.026 | 1.00 | 27.61 A | O |
| ATOM | 853 | N | PHE | A | 145 | 31.075 | 64.926 | −0.762 | 1.00 | 25.94 A | N |
| ATOM | 854 | CA | PHE | A | 145 | 31.958 | 66.064 | −1.033 | 1.00 | 25.40 A | C |
| ATOM | 855 | CB | PHE | A | 145 | 33.420 | 65.782 | −0.635 | 1.00 | 23.53 A | C |
| ATOM | 856 | CG | PHE | A | 145 | 33.691 | 65.850 | 0.877 | 1.00 | 26.68 A | C |
| ATOM | 857 | CD1 | PHE | A | 145 | 33.483 | 67.020 | 1.588 | 1.00 | 29.09 A | C |
| ATOM | 858 | CD2 | PHE | A | 145 | 34.198 | 64.746 | 1.557 | 1.00 | 24.57 A | C |
| ATOM | 859 | CE1 | PHE | A | 145 | 33.729 | 67.079 | 2.993 | 1.00 | 30.37 A | C |
| ATOM | 860 | CE2 | PHE | A | 145 | 34.471 | 64.795 | 2.930 | 1.00 | 28.66 A | C |
| ATOM | 861 | CZ | PHE | A | 145 | 34.241 | 65.971 | 3.649 | 1.00 | 27.25 A | C |
| ATOM | 862 | C | PHE | A | 145 | 31.899 | 66.479 | −2.502 | 1.00 | 26.99 A | C |
| ATOM | 863 | O | PHE | A | 145 | 31.940 | 67.670 | −2.819 | 1.00 | 25.55 A | O |
| ATOM | 864 | N | ALA | A | 146 | 31.803 | 65.503 | −3.401 | 1.00 | 24.15 A | N |
| ATOM | 865 | CA | ALA | A | 146 | 31.693 | 65.841 | −4.820 | 1.00 | 27.56 A | C |
| ATOM | 866 | CB | ALA | A | 146 | 31.648 | 64.601 | −5.672 | 1.00 | 22.76 A | C |
| ATOM | 867 | C | ALA | A | 146 | 30.492 | 66.748 | −5.112 | 1.00 | 28.12 A | C |
| ATOM | 868 | O | ALA | A | 146 | 30.508 | 67.502 | −6.081 | 1.00 | 27.69 A | O |
| ATOM | 869 | N | LEU | A | 147 | 29.449 | 66.682 | −4.288 | 1.00 | 24.01 A | N |
| ATOM | 870 | CA | LEU | A | 147 | 28.294 | 67.562 | −4.486 | 1.00 | 26.95 A | C |
| ATOM | 871 | CB | LEU | A | 147 | 27.175 | 67.242 | −3.487 | 1.00 | 22.66 A | C |
| ATOM | 872 | CG | LEU | A | 147 | 26.432 | 65.923 | −3.640 | 1.00 | 26.53 A | C |
| ATOM | 873 | CD1 | LEU | A | 147 | 25.598 | 65.655 | −2.375 | 1.00 | 26.10 A | C |
| ATOM | 874 | CD2 | LEU | A | 147 | 25.548 | 65.957 | −4.887 | 1.00 | 23.87 A | C |
| ATOM | 875 | C | LEU | A | 147 | 28.665 | 69.020 | −4.299 | 1.00 | 26.94 A | C |
| ATOM | 876 | O | LEU | A | 147 | 28.211 | 69.885 | −5.035 | 1.00 | 28.14 A | O |
| ATOM | 877 | N | TRP | A | 148 | 29.451 | 69.288 | −3.265 | 1.00 | 26.18 A | N |
| ATOM | 878 | CA | TRP | A | 148 | 29.809 | 70.649 | −2.903 | 1.00 | 28.26 A | C |
| ATOM | 879 | CB | TRP | A | 148 | 30.171 | 70.724 | −1.415 | 1.00 | 26.25 A | C |
| ATOM | 880 | CG | TRP | A | 148 | 29.025 | 70.384 | −0.462 | 1.00 | 29.47 A | C |
| ATOM | 881 | CD2 | TRP | A | 148 | 27.813 | 71.129 | −0.269 | 1.00 | 25.31 A | C |
| ATOM | 882 | CE2 | TRP | A | 148 | 27.053 | 70.451 | 0.715 | 1.00 | 25.37 A | C |
| ATOM | 883 | CE3 | TRP | A | 148 | 27.291 | 72.303 | −0.828 | 1.00 | 24.79 A | C |
| ATOM | 884 | CD1 | TRP | A | 148 | 28.956 | 69.317 | 0.393 | 1.00 | 27.04 A | C |
| ATOM | 885 | NE1 | TRP | A | 148 | 27.768 | 69.340 | 1.090 | 1.00 | 25.97 A | N |
| ATOM | 886 | CZ2 | TRP | A | 148 | 25.803 | 70.903 | 1.145 | 1.00 | 22.37 A | C |
| ATOM | 887 | CZ3 | TRP | A | 148 | 26.046 | 72.751 | −0.401 | 1.00 | 26.23 A | C |
| ATOM | 888 | CH2 | TRP | A | 148 | 25.321 | 72.053 | 0.576 | 1.00 | 24.80 A | C |
| ATOM | 889 | C | TRP | A | 148 | 30.978 | 71.194 | −3.748 | 1.00 | 29.42 A | C |
| ATOM | 890 | O | TRP | A | 148 | 31.034 | 72.386 | −4.052 | 1.00 | 30.04 A | O |
| ATOM | 891 | N | SER | A | 149 | 31.921 | 70.343 | −4.128 | 1.00 | 28.30 A | N |
| ATOM | 892 | CA | SER | A | 149 | 33.024 | 70.868 | −4.919 | 1.00 | 30.08 A | C |
| ATOM | 893 | CB | SER | A | 149 | 34.150 | 69.843 | −5.134 | 1.00 | 32.03 A | C |
| ATOM | 894 | OG | SER | A | 149 | 33.707 | 68.744 | −5.887 | 1.00 | 31.75 A | O |
| ATOM | 895 | C | SER | A | 149 | 32.535 | 71.421 | −6.249 | 1.00 | 29.70 A | C |
| ATOM | 896 | O | SER | A | 149 | 33.095 | 72.389 | −6.746 | 1.00 | 31.03 A | O |
| ATOM | 897 | N | ALA | A | 150 | 31.482 | 70.834 | −6.814 | 1.00 | 26.31 A | N |
| ATOM | 898 | CA | ALA | A | 150 | 31.052 | 71.244 | −8.144 | 1.00 | 27.35 A | C |
| ATOM | 899 | CB | ALA | A | 150 | 30.107 | 70.225 | −8.765 | 1.00 | 25.89 A | C |
| ATOM | 900 | C | ALA | A | 150 | 30.422 | 72.619 | −8.129 | 1.00 | 26.34 A | C |
| ATOM | 901 | O | ALA | A | 150 | 30.343 | 73.274 | −9.158 | 1.00 | 28.56 A | O |
| ATOM | 902 | N | VAL | A | 151 | 29.982 | 73.068 | −6.963 | 1.00 | 30.71 A | N |
| ATOM | 903 | CA | VAL | A | 151 | 29.254 | 74.331 | −6.870 | 1.00 | 26.68 A | C |
| ATOM | 904 | CB | VAL | A | 151 | 27.846 | 74.127 | −6.289 | 1.00 | 28.01 A | C |
| ATOM | 905 | CG1 | VAL | A | 151 | 26.943 | 73.412 | −7.310 | 1.00 | 21.35 A | C |
| ATOM | 906 | CG2 | VAL | A | 151 | 27.908 | 73.364 | −4.975 | 1.00 | 24.95 A | C |
| ATOM | 907 | C | VAL | A | 151 | 30.006 | 75.365 | −6.039 | 1.00 | 28.35 A | C |
| ATOM | 908 | O | VAL | A | 151 | 29.472 | 76.423 | −5.731 | 1.00 | 28.96 A | O |
| ATOM | 909 | N | THR | A | 152 | 31.241 | 75.038 | −5.668 | 1.00 | 31.04 A | N |
| ATOM | 910 | CA | THR | A | 152 | 32.107 | 75.949 | −4.920 | 1.00 | 33.79 A | C |
| ATOM | 911 | CB | THR | A | 152 | 32.363 | 75.449 | −3.494 | 1.00 | 32.22 A | C |
| ATOM | 912 | OG1 | THR | A | 152 | 33.046 | 74.193 | −3.566 | 1.00 | 33.57 A | O |
| ATOM | 913 | CG2 | THR | A | 152 | 31.076 | 75.290 | −2.704 | 1.00 | 31.46 A | C |
| ATOM | 914 | C | THR | A | 152 | 33.492 | 75.977 | −5.553 | 1.00 | 32.36 A | C |
| ATOM | 915 | O | THR | A | 152 | 33.837 | 75.101 | −6.349 | 1.00 | 31.69 A | O |
| ATOM | 916 | N | PRO | A | 153 | 34.302 | 76.970 | −5.172 | 1.00 | 33.49 A | N |
| ATOM | 917 | CD | PRO | A | 153 | 33.901 | 78.188 | −4.442 | 1.00 | 35.31 A | C |
| ATOM | 918 | CA | PRO | A | 153 | 35.715 | 77.001 | −5.540 | 1.00 | 35.09 A | C |

TABLE 14-continued

Coordinates for proMMP9(35-444 ΔFnII) (SEQ ID NO: 12) complex with Example 4

| ATOM | 919 | CB | PRO | A | 153 | 36.063 | 78.477 | −5.401 | 1.00 | 38.04 | A | C |
|---|---|---|---|---|---|---|---|---|---|---|---|---|
| ATOM | 920 | CG | PRO | A | 153 | 35.194 | 78.942 | −4.299 | 1.00 | 37.03 | A | C |
| ATOM | 921 | C | PRO | A | 153 | 36.543 | 76.198 | −4.551 | 1.00 | 38.62 | A | C |
| ATOM | 922 | O | PRO | A | 153 | 37.699 | 76.546 | −4.303 | 1.00 | 42.36 | A | O |
| ATOM | 923 | N | LEU | A | 154 | 35.963 | 75.137 | −3.997 | 1.00 | 35.00 | A | N |
| ATOM | 924 | CA | LEU | A | 154 | 36.654 | 74.310 | −3.017 | 1.00 | 32.10 | A | C |
| ATOM | 925 | CB | LEU | A | 154 | 35.780 | 74.137 | −1.761 | 1.00 | 32.47 | A | C |
| ATOM | 926 | CG | LEU | A | 154 | 35.470 | 75.386 | −0.943 | 1.00 | 31.94 | A | C |
| ATOM | 927 | CD1 | LEU | A | 154 | 34.597 | 75.051 | 0.270 | 1.00 | 30.62 | A | C |
| ATOM | 928 | CD2 | LEU | A | 154 | 36.745 | 76.050 | −0.488 | 1.00 | 34.26 | A | C |
| ATOM | 929 | C | LEU | A | 154 | 36.986 | 72.946 | −3.593 | 1.00 | 28.38 | A | C |
| ATOM | 930 | O | LEU | A | 154 | 36.322 | 72.473 | −4.506 | 1.00 | 30.89 | A | O |
| ATOM | 931 | N | THR | A | 155 | 38.021 | 72.317 | −3.060 | 1.00 | 27.70 | A | N |
| ATOM | 932 | CA | THR | A | 155 | 38.337 | 70.936 | −3.388 | 1.00 | 31.65 | A | C |
| ATOM | 933 | CB | THR | A | 155 | 39.693 | 70.782 | −4.127 | 1.00 | 33.47 | A | C |
| ATOM | 934 | OG1 | THR | A | 155 | 40.755 | 71.266 | −3.286 | 1.00 | 34.93 | A | O |
| ATOM | 935 | CG2 | THR | A | 155 | 39.676 | 71.549 | −5.432 | 1.00 | 30.56 | A | C |
| ATOM | 936 | C | THR | A | 155 | 38.455 | 70.170 | −2.083 | 1.00 | 30.71 | A | C |
| ATOM | 937 | O | THR | A | 155 | 38.745 | 70.744 | −1.039 | 1.00 | 31.54 | A | O |
| ATOM | 938 | N | PHE | A | 156 | 38.246 | 68.867 | −2.148 | 1.00 | 30.93 | A | N |
| ATOM | 939 | CA | PHE | A | 156 | 38.257 | 68.055 | −0.958 | 1.00 | 31.65 | A | C |
| ATOM | 940 | CB | PHE | A | 156 | 36.837 | 67.566 | −0.638 | 1.00 | 29.40 | A | C |
| ATOM | 941 | CG | PHE | A | 156 | 35.862 | 68.688 | −0.436 | 1.00 | 28.75 | A | C |
| ATOM | 942 | CD1 | PHE | A | 156 | 34.955 | 69.028 | −1.424 | 1.00 | 27.60 | A | C |
| ATOM | 943 | CD2 | PHE | A | 156 | 35.877 | 69.429 | 0.739 | 1.00 | 27.89 | A | C |
| ATOM | 944 | CE1 | PHE | A | 156 | 34.068 | 70.077 | −1.239 | 1.00 | 25.20 | A | C |
| ATOM | 945 | CE2 | PHE | A | 156 | 35.015 | 70.486 | 0.919 | 1.00 | 26.59 | A | C |
| ATOM | 946 | CZ | PHE | A | 156 | 34.102 | 70.804 | −0.067 | 1.00 | 26.89 | A | C |
| ATOM | 947 | C | PHE | A | 156 | 39.206 | 66.911 | −1.183 | 1.00 | 33.31 | A | C |
| ATOM | 948 | O | PHE | A | 156 | 39.109 | 66.190 | −2.170 | 1.00 | 34.85 | A | O |
| ATOM | 949 | N | THR | A | 157 | 40.133 | 66.746 | −0.258 | 1.00 | 30.73 | A | N |
| ATOM | 950 | CA | THR | A | 157 | 41.157 | 65.747 | −0.428 | 1.00 | 34.40 | A | C |
| ATOM | 951 | CB | THR | A | 157 | 42.522 | 66.429 | −0.613 | 1.00 | 38.71 | A | C |
| ATOM | 952 | OG1 | THR | A | 157 | 42.463 | 67.319 | −1.739 | 1.00 | 35.38 | A | O |
| ATOM | 953 | CG2 | THR | A | 157 | 43.606 | 65.396 | −0.833 | 1.00 | 41.42 | A | C |
| ATOM | 954 | C | THR | A | 157 | 41.191 | 64.867 | 0.806 | 1.00 | 34.77 | A | C |
| ATOM | 955 | O | THR | A | 157 | 41.279 | 65.368 | 1.920 | 1.00 | 34.87 | A | O |
| ATOM | 956 | N | ARG | A | 158 | 41.119 | 63.558 | 0.612 | 1.00 | 34.19 | A | N |
| ATOM | 957 | CA | ARG | A | 158 | 41.209 | 62.640 | 1.743 | 1.00 | 38.15 | A | C |
| ATOM | 958 | CB | ARG | A | 158 | 40.718 | 61.253 | 1.338 | 1.00 | 34.77 | A | C |
| ATOM | 959 | CG | ARG | A | 158 | 40.683 | 60.268 | 2.485 | 1.00 | 38.04 | A | C |
| ATOM | 960 | CD | ARG | A | 158 | 40.314 | 58.890 | 1.997 | 1.00 | 37.91 | A | C |
| ATOM | 961 | NE | ARG | A | 158 | 40.310 | 57.924 | 3.095 | 1.00 | 41.14 | A | N |
| ATOM | 962 | CZ | ARG | A | 158 | 40.014 | 56.638 | 2.947 | 1.00 | 38.65 | A | C |
| ATOM | 963 | NH1 | ARG | A | 158 | 39.692 | 56.170 | 1.746 | 1.00 | 40.42 | A | N |
| ATOM | 964 | NH2 | ARG | A | 158 | 40.034 | 55.825 | 4.001 | 1.00 | 40.15 | A | N |
| ATOM | 965 | C | ARG | A | 158 | 42.642 | 62.569 | 2.291 | 1.00 | 39.05 | A | C |
| ATOM | 966 | O | ARG | A | 158 | 43.604 | 62.473 | 1.525 | 1.00 | 38.61 | A | O |
| ATOM | 967 | N | VAL | A | 159 | 42.778 | 62.652 | 3.614 | 1.00 | 39.33 | A | N |
| ATOM | 968 | CA | VAL | A | 159 | 44.079 | 62.494 | 4.280 | 1.00 | 39.96 | A | C |
| ATOM | 969 | CB | VAL | A | 159 | 44.560 | 63.800 | 4.942 | 1.00 | 38.47 | A | C |
| ATOM | 970 | CG1 | VAL | A | 159 | 44.853 | 64.863 | 3.896 | 1.00 | 36.99 | A | C |
| ATOM | 971 | CG2 | VAL | A | 159 | 43.532 | 64.302 | 5.973 | 1.00 | 40.99 | A | C |
| ATOM | 972 | C | VAL | A | 159 | 43.997 | 61.425 | 5.369 | 1.00 | 43.78 | A | C |
| ATOM | 973 | O | VAL | A | 159 | 42.917 | 60.887 | 5.648 | 1.00 | 42.78 | A | O |
| ATOM | 974 | N | TYR | A | 160 | 45.126 | 61.134 | 6.008 | 1.00 | 42.14 | A | N |
| ATOM | 975 | CA | TYR | A | 160 | 45.129 | 60.140 | 7.080 | 1.00 | 42.71 | A | C |
| ATOM | 976 | CB | TYR | A | 160 | 45.792 | 58.846 | 6.606 | 1.00 | 40.59 | A | C |
| ATOM | 977 | CG | TYR | A | 160 | 45.100 | 58.241 | 5.395 | 1.00 | 40.66 | A | C |
| ATOM | 978 | CD1 | TYR | A | 160 | 45.296 | 58.770 | 4.117 | 1.00 | 39.02 | A | C |
| ATOM | 979 | CE1 | TYR | A | 160 | 44.662 | 58.227 | 3.010 | 1.00 | 36.95 | A | C |
| ATOM | 980 | CD2 | TYR | A | 160 | 44.254 | 57.146 | 5.531 | 1.00 | 38.87 | A | C |
| ATOM | 981 | CE2 | TYR | A | 160 | 43.618 | 56.597 | 4.435 | 1.00 | 42.17 | A | C |
| ATOM | 982 | CZ | TYR | A | 160 | 43.824 | 57.140 | 3.179 | 1.00 | 39.77 | A | C |
| ATOM | 983 | OH | TYR | A | 160 | 43.188 | 56.594 | 2.097 | 1.00 | 44.98 | A | O |
| ATOM | 984 | C | TYR | A | 160 | 45.772 | 60.659 | 8.362 | 1.00 | 43.54 | A | C |
| ATOM | 985 | O | TYR | A | 160 | 46.701 | 60.055 | 8.890 | 1.00 | 53.85 | A | O |
| ATOM | 986 | N | SER | A | 161 | 45.262 | 61.775 | 8.872 | 1.00 | 47.07 | A | N |
| ATOM | 987 | CA | SER | A | 161 | 45.821 | 62.384 | 10.075 | 1.00 | 46.44 | A | C |
| ATOM | 988 | CB | SER | A | 161 | 47.077 | 63.178 | 9.722 | 1.00 | 49.30 | A | C |
| ATOM | 989 | OG | SER | A | 161 | 46.739 | 64.371 | 9.033 | 1.00 | 53.70 | A | O |
| ATOM | 990 | C | SER | A | 161 | 44.832 | 63.289 | 10.821 | 1.00 | 49.42 | A | C |
| ATOM | 991 | O | SER | A | 161 | 43.772 | 63.645 | 10.302 | 1.00 | 47.62 | A | O |
| ATOM | 992 | N | ARG | A | 162 | 45.206 | 63.680 | 12.035 | 1.00 | 48.06 | A | N |
| ATOM | 993 | CA | ARG | A | 162 | 44.319 | 64.403 | 12.932 | 1.00 | 46.94 | A | C |
| ATOM | 994 | CB | ARG | A | 162 | 44.779 | 64.225 | 14.386 | 1.00 | 53.10 | A | C |
| ATOM | 995 | CG | ARG | A | 162 | 45.835 | 65.229 | 14.844 | 1.00 | 56.44 | A | C |
| ATOM | 996 | CD | ARG | A | 162 | 46.288 | 64.968 | 16.287 | 1.00 | 59.83 | A | C |

TABLE 14-continued

Coordinates for proMMP9(35-444 ΔFnII) (SEQ ID NO: 12) complex with Example 4

| ATOM | 997 | NE | ARG | A | 162 | 47.255 | 63.874 | 16.349 | 1.00 | 61.82 | A | N |
|---|---|---|---|---|---|---|---|---|---|---|---|---|
| ATOM | 998 | CZ | ARG | A | 162 | 48.545 | 64.006 | 16.059 | 1.00 | 56.43 | A | C |
| ATOM | 999 | NH1 | ARG | A | 162 | 49.356 | 62.955 | 16.130 | 1.00 | 55.31 | A | N |
| ATOM | 1000 | NH2 | ARG | A | 162 | 49.025 | 65.192 | 15.697 | 1.00 | 53.51 | A | N |
| ATOM | 1001 | C | ARG | A | 162 | 44.179 | 65.893 | 12.610 | 1.00 | 48.76 | A | C |
| ATOM | 1002 | O | ARG | A | 162 | 43.301 | 66.569 | 13.153 | 1.00 | 53.29 | A | O |
| ATOM | 1003 | N | ASP | A | 163 | 45.039 | 66.417 | 11.745 | 1.00 | 47.82 | A | N |
| ATOM | 1004 | CA | ASP | A | 163 | 44.948 | 67.834 | 11.384 | 1.00 | 49.50 | A | C |
| ATOM | 1005 | CB | ASP | A | 163 | 46.330 | 68.480 | 11.369 | 1.00 | 49.08 | A | C |
| ATOM | 1006 | CG | ASP | A | 163 | 47.114 | 68.103 | 10.135 | 1.00 | 58.58 | A | C |
| ATOM | 1007 | OD1 | ASP | A | 163 | 47.080 | 66.898 | 9.772 | 1.00 | 58.06 | A | O |
| ATOM | 1008 | OD2 | ASP | A | 163 | 47.738 | 69.002 | 9.519 | 1.00 | 61.81 | A | O |
| ATOM | 1009 | C | ASP | A | 163 | 44.280 | 68.058 | 10.019 | 1.00 | 47.10 | A | C |
| ATOM | 1010 | O | ASP | A | 163 | 44.539 | 69.063 | 9.348 | 1.00 | 44.34 | A | O |
| ATOM | 1011 | N | ALA | A | 164 | 43.447 | 67.112 | 9.598 | 1.00 | 43.21 | A | N |
| ATOM | 1012 | CA | ALA | A | 164 | 42.572 | 67.345 | 8.462 | 1.00 | 34.44 | A | C |
| ATOM | 1013 | CB | ALA | A | 164 | 41.751 | 66.114 | 8.198 | 1.00 | 34.77 | A | C |
| ATOM | 1014 | C | ALA | A | 164 | 41.672 | 68.486 | 8.888 | 1.00 | 34.58 | A | C |
| ATOM | 1015 | O | ALA | A | 164 | 41.419 | 68.646 | 10.082 | 1.00 | 33.55 | A | O |
| ATOM | 1016 | N | ASP | A | 165 | 41.189 | 69.286 | 7.944 | 1.00 | 33.90 | A | N |
| ATOM | 1017 | CA | ASP | A | 165 | 40.210 | 70.322 | 8.291 | 1.00 | 30.64 | A | C |
| ATOM | 1018 | CB | ASP | A | 165 | 39.854 | 71.163 | 7.077 | 1.00 | 33.40 | A | C |
| ATOM | 1019 | CG | ASP | A | 165 | 41.060 | 71.862 | 6.482 | 1.00 | 34.70 | A | C |
| ATOM | 1020 | OD1 | ASP | A | 165 | 41.752 | 72.581 | 7.242 | 1.00 | 32.19 | A | O |
| ATOM | 1021 | OD2 | ASP | A | 165 | 41.306 | 71.687 | 5.267 | 1.00 | 30.63 | A | O |
| ATOM | 1022 | C | ASP | A | 165 | 38.941 | 69.676 | 8.808 | 1.00 | 34.73 | A | C |
| ATOM | 1023 | O | ASP | A | 165 | 38.314 | 70.158 | 9.766 | 1.00 | 32.92 | A | O |
| ATOM | 1024 | N | ILE | A | 166 | 38.555 | 68.591 | 8.150 | 1.00 | 28.96 | A | N |
| ATOM | 1025 | CA | ILE | A | 166 | 37.350 | 67.879 | 8.509 | 1.00 | 34.84 | A | C |
| ATOM | 1026 | CB | ILE | A | 166 | 36.383 | 67.809 | 7.299 | 1.00 | 33.41 | A | C |
| ATOM | 1027 | CG2 | ILE | A | 166 | 35.080 | 67.090 | 7.685 | 1.00 | 31.92 | A | C |
| ATOM | 1028 | CG1 | ILE | A | 166 | 36.129 | 69.229 | 6.767 | 1.00 | 33.20 | A | C |
| ATOM | 1029 | CD1 | ILE | A | 166 | 35.057 | 69.339 | 5.714 | 1.00 | 29.85 | A | C |
| ATOM | 1030 | C | ILE | A | 166 | 37.683 | 66.481 | 9.018 | 1.00 | 33.17 | A | C |
| ATOM | 1031 | O | ILE | A | 166 | 38.100 | 65.624 | 8.250 | 1.00 | 33.02 | A | O |
| ATOM | 1032 | N | VAL | A | 167 | 37.526 | 66.262 | 10.319 | 1.00 | 35.82 | A | N |
| ATOM | 1033 | CA | VAL | A | 167 | 37.659 | 64.916 | 10.866 | 1.00 | 31.91 | A | C |
| ATOM | 1034 | CB | VAL | A | 167 | 38.362 | 64.892 | 12.238 | 1.00 | 37.58 | A | C |
| ATOM | 1035 | CG1 | VAL | A | 167 | 38.541 | 63.448 | 12.704 | 1.00 | 34.82 | A | C |
| ATOM | 1036 | CG2 | VAL | A | 167 | 39.714 | 65.619 | 12.175 | 1.00 | 30.53 | A | C |
| ATOM | 1037 | C | VAL | A | 167 | 36.276 | 64.260 | 10.935 | 1.00 | 31.08 | A | C |
| ATOM | 1038 | O | VAL | A | 167 | 35.310 | 64.844 | 11.423 | 1.00 | 34.21 | A | O |
| ATOM | 1039 | N | ILE | A | 168 | 36.191 | 63.052 | 10.403 | 1.00 | 31.53 | A | N |
| ATOM | 1040 | CA | ILE | A | 168 | 34.930 | 62.341 | 10.284 | 1.00 | 31.98 | A | C |
| ATOM | 1041 | CB | ILE | A | 168 | 34.712 | 61.845 | 8.840 | 1.00 | 31.48 | A | C |
| ATOM | 1042 | CG2 | ILE | A | 168 | 33.650 | 60.751 | 8.800 | 1.00 | 31.96 | A | C |
| ATOM | 1043 | CG1 | ILE | A | 168 | 34.348 | 63.024 | 7.928 | 1.00 | 29.33 | A | C |
| ATOM | 1044 | CD1 | ILE | A | 168 | 34.362 | 62.690 | 6.436 | 1.00 | 31.27 | A | C |
| ATOM | 1045 | C | ILE | A | 168 | 34.965 | 61.160 | 11.236 | 1.00 | 33.80 | A | C |
| ATOM | 1046 | O | ILE | A | 168 | 35.932 | 60.391 | 11.247 | 1.00 | 31.48 | A | O |
| ATOM | 1047 | N | GLN | A | 169 | 33.899 | 61.013 | 12.016 | 1.00 | 32.50 | A | N |
| ATOM | 1048 | CA | GLN | A | 169 | 33.888 | 60.076 | 13.133 | 1.00 | 34.79 | A | C |
| ATOM | 1049 | CB | GLN | A | 169 | 34.226 | 60.846 | 14.413 | 1.00 | 32.85 | A | C |
| ATOM | 1050 | CG | GLN | A | 169 | 34.437 | 59.999 | 15.616 | 1.00 | 42.87 | A | C |
| ATOM | 1051 | CD | GLN | A | 169 | 34.611 | 60.831 | 16.873 | 1.00 | 46.03 | A | C |
| ATOM | 1052 | OE1 | GLN | A | 169 | 35.542 | 61.631 | 16.979 | 1.00 | 49.22 | A | O |
| ATOM | 1053 | NE2 | GLN | A | 169 | 33.707 | 60.648 | 17.828 | 1.00 | 41.49 | A | N |
| ATOM | 1054 | C | GLN | A | 169 | 32.541 | 59.377 | 13.298 | 1.00 | 30.90 | A | C |
| ATOM | 1055 | O | GLN | A | 169 | 31.493 | 60.005 | 13.182 | 1.00 | 32.96 | A | O |
| ATOM | 1056 | N | PHE | A | 170 | 32.565 | 58.076 | 13.565 | 1.00 | 28.24 | A | N |
| ATOM | 1057 | CA | PHE | A | 170 | 31.347 | 57.367 | 13.941 | 1.00 | 33.32 | A | C |
| ATOM | 1058 | CB | PHE | A | 170 | 31.269 | 56.002 | 13.262 | 1.00 | 31.41 | A | C |
| ATOM | 1059 | CG | PHE | A | 170 | 30.957 | 56.069 | 11.796 | 1.00 | 35.15 | A | C |
| ATOM | 1060 | CD1 | PHE | A | 170 | 31.965 | 56.268 | 10.862 | 1.00 | 32.14 | A | C |
| ATOM | 1061 | CD2 | PHE | A | 170 | 29.654 | 55.934 | 11.347 | 1.00 | 31.39 | A | C |
| ATOM | 1062 | CE1 | PHE | A | 170 | 31.671 | 56.333 | 9.511 | 1.00 | 33.22 | A | C |
| ATOM | 1063 | CE2 | PHE | A | 170 | 29.358 | 55.995 | 9.999 | 1.00 | 32.96 | A | C |
| ATOM | 1064 | CZ | PHE | A | 170 | 30.367 | 56.202 | 9.077 | 1.00 | 31.83 | A | C |
| ATOM | 1065 | C | PHE | A | 170 | 31.386 | 57.209 | 15.458 | 1.00 | 35.88 | A | C |
| ATOM | 1066 | O | PHE | A | 170 | 32.410 | 56.811 | 16.007 | 1.00 | 36.15 | A | O |
| ATOM | 1067 | N | GLY | A | 171 | 30.293 | 57.548 | 16.131 | 1.00 | 33.47 | A | N |
| ATOM | 1068 | CA | GLY | A | 171 | 30.241 | 57.478 | 17.585 | 1.00 | 35.91 | A | C |
| ATOM | 1069 | C | GLY | A | 171 | 28.854 | 57.173 | 18.151 | 1.00 | 36.90 | A | C |
| ATOM | 1070 | O | GLY | A | 171 | 27.850 | 57.240 | 17.431 | 1.00 | 36.90 | A | O |
| ATOM | 1071 | N | VAL | A | 172 | 28.805 | 56.819 | 19.437 | 1.00 | 34.80 | A | N |
| ATOM | 1072 | CA | VAL | A | 172 | 27.549 | 56.587 | 20.141 | 1.00 | 35.62 | A | C |
| ATOM | 1073 | CB | VAL | A | 172 | 27.295 | 55.086 | 20.379 | 1.00 | 37.59 | A | C |
| ATOM | 1074 | CG1 | VAL | A | 172 | 27.308 | 54.319 | 19.059 | 1.00 | 36.47 | A | C |

TABLE 14-continued

Coordinates for proMMP9(35-444 ΔFnII) (SEQ ID NO: 12) complex with Example 4

| ATOM | 1075 | CG2 | VAL | A | 172 | 28.327 | 54.527 | 21.335 | 1.00 | 38.39 | A | C |
|---|---|---|---|---|---|---|---|---|---|---|---|---|
| ATOM | 1076 | C | VAL | A | 172 | 27.558 | 57.293 | 21.498 | 1.00 | 39.36 | A | C |
| ATOM | 1077 | O | VAL | A | 172 | 28.621 | 57.546 | 22.065 | 1.00 | 38.19 | A | O |
| ATOM | 1078 | N | ALA | A | 173 | 26.372 | 57.594 | 22.019 | 1.00 | 35.84 | A | N |
| ATOM | 1079 | CA | ALA | A | 173 | 26.258 | 58.277 | 23.298 | 1.00 | 41.56 | A | C |
| ATOM | 1080 | CB | ALA | A | 173 | 26.413 | 57.284 | 24.457 | 1.00 | 39.79 | A | C |
| ATOM | 1081 | C | ALA | A | 173 | 27.321 | 59.363 | 23.377 | 1.00 | 43.55 | A | C |
| ATOM | 1082 | O | ALA | A | 173 | 27.575 | 60.058 | 22.385 | 1.00 | 39.83 | A | O |
| ATOM | 1083 | N | GLU | A | 174 | 27.942 | 59.510 | 24.545 | 1.00 | 39.85 | A | N |
| ATOM | 1084 | CA | GLU | A | 174 | 29.050 | 60.452 | 24.679 | 1.00 | 43.16 | A | C |
| ATOM | 1085 | CB | GLU | A | 174 | 29.381 | 60.731 | 26.144 | 1.00 | 45.98 | A | C |
| ATOM | 1086 | CG | GLU | A | 174 | 30.730 | 61.438 | 26.320 | 1.00 | 44.58 | A | C |
| ATOM | 1087 | CD | GLU | A | 174 | 30.749 | 62.827 | 25.709 | 1.00 | 44.52 | A | C |
| ATOM | 1088 | OE1 | GLU | A | 174 | 29.670 | 63.454 | 25.618 | 1.00 | 45.71 | A | O |
| ATOM | 1089 | OE2 | GLU | A | 174 | 31.847 | 63.297 | 25.328 | 1.00 | 49.52 | A | O |
| ATOM | 1090 | C | GLU | A | 174 | 30.292 | 59.926 | 23.959 | 1.00 | 42.18 | A | C |
| ATOM | 1091 | O | GLU | A | 174 | 30.823 | 58.865 | 24.290 | 1.00 | 40.68 | A | O |
| ATOM | 1092 | N | HIS | A | 175 | 30.762 | 60.679 | 22.979 | 1.00 | 43.41 | A | N |
| ATOM | 1093 | CA | HIS | A | 175 | 31.829 | 60.194 | 22.115 | 1.00 | 40.96 | A | C |
| ATOM | 1094 | CB | HIS | A | 175 | 31.276 | 59.923 | 20.729 | 1.00 | 39.18 | A | C |
| ATOM | 1095 | CG | HIS | A | 175 | 30.469 | 61.055 | 20.195 | 1.00 | 38.03 | A | C |
| ATOM | 1096 | CD2 | HIS | A | 175 | 30.781 | 62.047 | 19.334 | 1.00 | 38.32 | A | C |
| ATOM | 1097 | ND1 | HIS | A | 175 | 29.165 | 61.281 | 20.587 | 1.00 | 37.38 | A | N |
| ATOM | 1098 | CE1 | HIS | A | 175 | 28.708 | 62.354 | 19.975 | 1.00 | 39.65 | A | C |
| ATOM | 1099 | NE2 | HIS | A | 175 | 29.666 | 62.835 | 19.202 | 1.00 | 38.69 | A | N |
| ATOM | 1100 | C | HIS | A | 175 | 32.968 | 61.189 | 22.023 | 1.00 | 40.28 | A | C |
| ATOM | 1101 | O | HIS | A | 175 | 33.709 | 61.200 | 21.046 | 1.00 | 45.67 | A | O |
| ATOM | 1102 | N | GLY | A | 176 | 33.088 | 62.039 | 23.035 | 1.00 | 45.00 | A | N |
| ATOM | 1103 | CA | GLY | A | 176 | 34.286 | 62.831 | 23.212 | 1.00 | 44.18 | A | C |
| ATOM | 1104 | C | GLY | A | 176 | 34.173 | 64.324 | 22.994 | 1.00 | 41.52 | A | C |
| ATOM | 1105 | O | GLY | A | 176 | 35.176 | 65.021 | 23.087 | 1.00 | 39.80 | A | O |
| ATOM | 1106 | N | ASP | A | 177 | 32.976 | 64.833 | 22.711 | 1.00 | 41.99 | A | N |
| ATOM | 1107 | CA | ASP | A | 177 | 32.851 | 66.255 | 22.375 | 1.00 | 42.50 | A | C |
| ATOM | 1108 | CB | ASP | A | 177 | 32.550 | 66.453 | 20.880 | 1.00 | 44.74 | A | C |
| ATOM | 1109 | CG | ASP | A | 177 | 31.155 | 65.961 | 20.478 | 1.00 | 42.23 | A | C |
| ATOM | 1110 | OD1 | ASP | A | 177 | 30.459 | 65.334 | 21.302 | 1.00 | 40.45 | A | O |
| ATOM | 1111 | OD2 | ASP | A | 177 | 30.735 | 66.213 | 19.332 | 1.00 | 41.47 | A | O |
| ATOM | 1112 | C | ASP | A | 177 | 31.823 | 66.986 | 23.231 | 1.00 | 46.14 | A | C |
| ATOM | 1113 | O | ASP | A | 177 | 31.587 | 68.182 | 23.048 | 1.00 | 48.27 | A | O |
| ATOM | 1114 | N | GLY | A | 178 | 31.210 | 66.266 | 24.166 | 1.00 | 46.00 | A | N |
| ATOM | 1115 | CA | GLY | A | 178 | 30.233 | 66.874 | 25.057 | 1.00 | 43.88 | A | C |
| ATOM | 1116 | C | GLY | A | 178 | 28.883 | 67.151 | 24.411 | 1.00 | 44.06 | A | C |
| ATOM | 1117 | O | GLY | A | 178 | 28.060 | 67.876 | 24.965 | 1.00 | 45.44 | A | O |
| ATOM | 1118 | N | TYR | A | 179 | 28.660 | 66.580 | 23.233 | 1.00 | 43.05 | A | N |
| ATOM | 1119 | CA | TYR | A | 179 | 27.355 | 66.614 | 22.591 | 1.00 | 39.95 | A | C |
| ATOM | 1120 | CB | TYR | A | 179 | 27.400 | 67.459 | 21.322 | 1.00 | 43.11 | A | C |
| ATOM | 1121 | CG | TYR | A | 179 | 27.877 | 68.870 | 21.570 | 1.00 | 45.00 | A | C |
| ATOM | 1122 | CD1 | TYR | A | 179 | 29.188 | 69.245 | 21.289 | 1.00 | 47.83 | A | C |
| ATOM | 1123 | CE1 | TYR | A | 179 | 29.631 | 70.536 | 21.523 | 1.00 | 46.10 | A | C |
| ATOM | 1124 | CD2 | TYR | A | 179 | 27.021 | 69.824 | 22.106 | 1.00 | 44.61 | A | C |
| ATOM | 1125 | CE2 | TYR | A | 179 | 27.447 | 71.109 | 22.337 | 1.00 | 46.06 | A | C |
| ATOM | 1126 | CZ | TYR | A | 179 | 28.749 | 71.462 | 22.048 | 1.00 | 48.11 | A | C |
| ATOM | 1127 | OH | TYR | A | 179 | 29.165 | 72.750 | 22.287 | 1.00 | 53.97 | A | O |
| ATOM | 1128 | C | TYR | A | 179 | 26.988 | 65.174 | 22.271 | 1.00 | 42.03 | A | C |
| ATOM | 1129 | O | TYR | A | 179 | 27.153 | 64.715 | 21.136 | 1.00 | 39.70 | A | O |
| ATOM | 1130 | N | PRO | A | 180 | 26.495 | 64.444 | 23.280 | 1.00 | 39.35 | A | N |
| ATOM | 1131 | CD | PRO | A | 180 | 25.972 | 64.936 | 24.567 | 1.00 | 42.30 | A | C |
| ATOM | 1132 | CA | PRO | A | 180 | 26.338 | 62.994 | 23.139 | 1.00 | 38.35 | A | C |
| ATOM | 1133 | CB | PRO | A | 180 | 25.968 | 62.530 | 24.562 | 1.00 | 41.56 | A | C |
| ATOM | 1134 | CG | PRO | A | 180 | 26.147 | 63.743 | 25.461 | 1.00 | 45.95 | A | C |
| ATOM | 1135 | C | PRO | A | 180 | 25.211 | 62.665 | 22.184 | 1.00 | 37.72 | A | C |
| ATOM | 1136 | O | PRO | A | 180 | 24.266 | 63.438 | 22.060 | 1.00 | 32.68 | A | O |
| ATOM | 1137 | N | PHE | A | 181 | 25.317 | 61.535 | 21.503 | 1.00 | 37.23 | A | N |
| ATOM | 1138 | CA | PHE | A | 181 | 24.197 | 61.035 | 20.724 | 1.00 | 36.91 | A | C |
| ATOM | 1139 | CB | PHE | A | 181 | 24.689 | 60.083 | 19.634 | 1.00 | 35.63 | A | C |
| ATOM | 1140 | CG | PHE | A | 181 | 25.430 | 60.774 | 18.542 | 1.00 | 34.95 | A | C |
| ATOM | 1141 | CD1 | PHE | A | 181 | 24.921 | 61.939 | 17.981 | 1.00 | 37.36 | A | C |
| ATOM | 1142 | CD2 | PHE | A | 181 | 26.635 | 60.278 | 18.071 | 1.00 | 35.33 | A | C |
| ATOM | 1143 | CE1 | PHE | A | 181 | 25.607 | 62.594 | 16.958 | 1.00 | 34.44 | A | C |
| ATOM | 1144 | CE2 | PHE | A | 181 | 27.315 | 60.926 | 17.058 | 1.00 | 33.31 | A | C |
| ATOM | 1145 | CZ | PHE | A | 181 | 26.800 | 62.086 | 16.500 | 1.00 | 33.04 | A | C |
| ATOM | 1146 | C | PHE | A | 181 | 23.136 | 60.382 | 21.623 | 1.00 | 40.57 | A | C |
| ATOM | 1147 | O | PHE | A | 181 | 23.381 | 60.131 | 22.810 | 1.00 | 35.96 | A | O |
| ATOM | 1148 | N | ASP | A | 182 | 21.970 | 60.110 | 21.042 | 1.00 | 38.52 | A | N |
| ATOM | 1149 | CA | ASP | A | 182 | 20.765 | 59.796 | 21.805 | 1.00 | 40.16 | A | C |
| ATOM | 1150 | CB | ASP | A | 182 | 19.663 | 60.785 | 21.425 | 1.00 | 38.60 | A | C |
| ATOM | 1151 | CG | ASP | A | 182 | 19.304 | 60.713 | 19.947 | 1.00 | 40.33 | A | C |
| ATOM | 1152 | OD1 | ASP | A | 182 | 20.083 | 60.126 | 19.172 | 1.00 | 40.53 | A | O |

TABLE 14-continued

Coordinates for proMMP9(35-444 ΔFnII) (SEQ ID NO: 12) complex with Example 4

| ATOM | 1153 | OD2 | ASP | A | 182 | 18.259 | 61.250 | 19.546 | 1.00 | 40.77 | A | O |
|---|---|---|---|---|---|---|---|---|---|---|---|---|
| ATOM | 1154 | C | ASP | A | 182 | 20.242 | 58.380 | 21.558 | 1.00 | 41.02 | A | C |
| ATOM | 1155 | O | ASP | A | 182 | 19.026 | 58.150 | 21.601 | 1.00 | 41.40 | A | O |
| ATOM | 1156 | N | GLY | A | 183 | 21.141 | 57.436 | 21.292 | 1.00 | 38.85 | A | N |
| ATOM | 1157 | CA | GLY | A | 183 | 20.729 | 56.076 | 20.994 | 1.00 | 38.06 | A | C |
| ATOM | 1158 | C | GLY | A | 183 | 20.014 | 56.034 | 19.662 | 1.00 | 40.81 | A | C |
| ATOM | 1159 | O | GLY | A | 183 | 20.248 | 56.878 | 18.825 | 1.00 | 39.76 | A | O |
| ATOM | 1160 | N | LYS | A | 184 | 19.117 | 55.078 | 19.472 | 1.00 | 39.26 | A | N |
| ATOM | 1161 | CA | LYS | A | 184 | 18.493 | 54.887 | 18.173 | 1.00 | 39.63 | A | C |
| ATOM | 1162 | CB | LYS | A | 184 | 17.811 | 53.523 | 18.122 | 1.00 | 43.49 | A | C |
| ATOM | 1163 | CG | LYS | A | 184 | 17.448 | 53.067 | 16.724 | 1.00 | 47.35 | A | C |
| ATOM | 1164 | CD | LYS | A | 184 | 17.195 | 51.576 | 16.701 | 1.00 | 48.43 | A | C |
| ATOM | 1165 | CE | LYS | A | 184 | 16.731 | 51.137 | 15.336 | 1.00 | 49.12 | A | C |
| ATOM | 1166 | NZ | LYS | A | 184 | 15.467 | 51.830 | 14.980 | 1.00 | 56.98 | A | N |
| ATOM | 1167 | C | LYS | A | 184 | 17.513 | 55.998 | 17.764 | 1.00 | 42.01 | A | C |
| ATOM | 1168 | O | LYS | A | 184 | 16.767 | 56.506 | 18.598 | 1.00 | 43.68 | A | O |
| ATOM | 1169 | N | ASP | A | 185 | 17.539 | 56.358 | 16.473 | 1.00 | 41.05 | A | N |
| ATOM | 1170 | CA | ASP | A | 185 | 16.673 | 57.399 | 15.882 | 1.00 | 41.09 | A | C |
| ATOM | 1171 | CB | ASP | A | 185 | 15.186 | 57.015 | 15.962 | 1.00 | 40.56 | A | C |
| ATOM | 1172 | CG | ASP | A | 185 | 14.863 | 55.784 | 15.148 | 1.00 | 44.87 | A | C |
| ATOM | 1173 | OD1 | ASP | A | 185 | 15.342 | 55.696 | 13.988 | 1.00 | 40.39 | A | O |
| ATOM | 1174 | OD2 | ASP | A | 185 | 14.145 | 54.902 | 15.673 | 1.00 | 45.97 | A | O |
| ATOM | 1175 | C | ASP | A | 185 | 16.904 | 58.788 | 16.481 | 1.00 | 39.84 | A | C |
| ATOM | 1176 | O | ASP | A | 185 | 17.958 | 59.056 | 17.035 | 1.00 | 39.87 | A | O |
| ATOM | 1177 | N | GLY | A | 186 | 15.926 | 59.678 | 16.367 | 1.00 | 37.98 | A | N |
| ATOM | 1178 | CA | GLY | A | 186 | 16.124 | 61.037 | 16.856 | 1.00 | 42.09 | A | C |
| ATOM | 1179 | C | GLY | A | 186 | 17.271 | 61.730 | 16.122 | 1.00 | 35.32 | A | C |
| ATOM | 1180 | O | GLY | A | 186 | 17.203 | 61.888 | 14.908 | 1.00 | 34.38 | A | O |
| ATOM | 1181 | N | LEU | A | 187 | 18.310 | 62.133 | 16.858 | 1.00 | 35.14 | A | N |
| ATOM | 1182 | CA | LEU | A | 187 | 19.520 | 62.742 | 16.281 | 1.00 | 36.68 | A | C |
| ATOM | 1183 | CB | LEU | A | 187 | 20.445 | 63.270 | 17.384 | 1.00 | 33.87 | A | C |
| ATOM | 1184 | CG | LEU | A | 187 | 20.132 | 64.549 | 18.157 | 1.00 | 41.05 | A | C |
| ATOM | 1185 | CD1 | LEU | A | 187 | 18.816 | 64.428 | 18.889 | 1.00 | 41.96 | A | C |
| ATOM | 1186 | CD2 | LEU | A | 187 | 21.256 | 64.836 | 19.139 | 1.00 | 40.00 | A | C |
| ATOM | 1187 | C | LEU | A | 187 | 20.328 | 61.739 | 15.469 | 1.00 | 36.52 | A | C |
| ATOM | 1188 | O | LEU | A | 187 | 20.692 | 60.696 | 15.982 | 1.00 | 34.45 | A | O |
| ATOM | 1189 | N | LEU | A | 188 | 20.670 | 62.072 | 14.235 | 1.00 | 28.66 | A | N |
| ATOM | 1190 | CA | LEU | A | 188 | 21.407 | 61.123 | 13.408 | 1.00 | 32.72 | A | C |
| ATOM | 1191 | CB | LEU | A | 188 | 20.810 | 61.089 | 11.998 | 1.00 | 31.15 | A | C |
| ATOM | 1192 | CG | LEU | A | 188 | 19.303 | 60.853 | 11.947 | 1.00 | 31.13 | A | C |
| ATOM | 1193 | CD1 | LEU | A | 188 | 18.808 | 60.931 | 10.508 | 1.00 | 29.02 | A | C |
| ATOM | 1194 | CD2 | LEU | A | 188 | 18.978 | 59.509 | 12.566 | 1.00 | 31.96 | A | C |
| ATOM | 1195 | C | LEU | A | 188 | 22.911 | 61.416 | 13.335 | 1.00 | 31.76 | A | C |
| ATOM | 1196 | O | LEU | A | 188 | 23.711 | 60.546 | 12.980 | 1.00 | 30.80 | A | O |
| ATOM | 1197 | N | ALA | A | 189 | 23.284 | 62.644 | 13.671 | 1.00 | 31.31 | A | N |
| ATOM | 1198 | CA | ALA | A | 189 | 24.609 | 63.143 | 13.354 | 1.00 | 29.42 | A | C |
| ATOM | 1199 | CB | ALA | A | 189 | 24.900 | 62.920 | 11.862 | 1.00 | 25.40 | A | C |
| ATOM | 1200 | C | ALA | A | 189 | 24.666 | 64.626 | 13.656 | 1.00 | 30.99 | A | C |
| ATOM | 1201 | O | ALA | A | 189 | 23.631 | 65.277 | 13.807 | 1.00 | 30.84 | A | O |
| ATOM | 1202 | N | HIS | A | 190 | 25.879 | 65.164 | 13.744 | 1.00 | 30.53 | A | N |
| ATOM | 1203 | CA | HIS | A | 190 | 26.055 | 66.616 | 13.792 | 1.00 | 28.59 | A | C |
| ATOM | 1204 | CB | HIS | A | 190 | 25.875 | 67.173 | 15.198 | 1.00 | 30.59 | A | C |
| ATOM | 1205 | CG | HIS | A | 190 | 26.717 | 66.505 | 16.235 | 1.00 | 32.41 | A | C |
| ATOM | 1206 | CD2 | HIS | A | 190 | 27.950 | 65.943 | 16.167 | 1.00 | 32.40 | A | C |
| ATOM | 1207 | ND1 | HIS | A | 190 | 26.312 | 66.372 | 17.549 | 1.00 | 34.17 | A | N |
| ATOM | 1208 | CE1 | HIS | A | 190 | 27.249 | 65.754 | 18.239 | 1.00 | 35.39 | A | C |
| ATOM | 1209 | NE2 | HIS | A | 190 | 28.255 | 65.484 | 17.422 | 1.00 | 38.47 | A | N |
| ATOM | 1210 | C | HIS | A | 190 | 27.413 | 67.021 | 13.241 | 1.00 | 29.43 | A | C |
| ATOM | 1211 | O | HIS | A | 190 | 28.215 | 66.176 | 12.874 | 1.00 | 26.07 | A | O |
| ATOM | 1212 | N | ALA | A | 191 | 27.656 | 68.324 | 13.190 | 1.00 | 27.29 | A | N |
| ATOM | 1213 | CA | ALA | A | 191 | 28.872 | 68.833 | 12.583 | 1.00 | 33.76 | A | C |
| ATOM | 1214 | CB | ALA | A | 191 | 28.741 | 68.841 | 11.051 | 1.00 | 26.15 | A | C |
| ATOM | 1215 | C | ALA | A | 191 | 29.100 | 70.232 | 13.099 | 1.00 | 31.92 | A | C |
| ATOM | 1216 | O | ALA | A | 191 | 28.181 | 70.859 | 13.602 | 1.00 | 31.90 | A | O |
| ATOM | 1217 | N | PHE | A | 192 | 30.322 | 70.718 | 12.947 | 1.00 | 34.75 | A | N |
| ATOM | 1218 | CA | PHE | A | 192 | 30.723 | 72.020 | 13.464 | 1.00 | 35.03 | A | C |
| ATOM | 1219 | CB | PHE | A | 192 | 31.810 | 71.818 | 14.526 | 1.00 | 35.99 | A | C |
| ATOM | 1220 | CG | PHE | A | 192 | 31.422 | 70.836 | 15.602 | 1.00 | 37.81 | A | C |
| ATOM | 1221 | CD1 | PHE | A | 192 | 30.796 | 71.271 | 16.751 | 1.00 | 36.11 | A | C |
| ATOM | 1222 | CD2 | PHE | A | 192 | 31.662 | 69.478 | 15.445 | 1.00 | 37.79 | A | C |
| ATOM | 1223 | CE1 | PHE | A | 192 | 30.427 | 70.378 | 17.743 | 1.00 | 42.49 | A | C |
| ATOM | 1224 | CE2 | PHE | A | 192 | 31.294 | 68.575 | 16.440 | 1.00 | 41.71 | A | C |
| ATOM | 1225 | CZ | PHE | A | 192 | 30.677 | 69.030 | 17.592 | 1.00 | 38.38 | A | C |
| ATOM | 1226 | C | PHE | A | 192 | 31.231 | 72.932 | 12.339 | 1.00 | 33.66 | A | C |
| ATOM | 1227 | O | PHE | A | 192 | 31.881 | 72.458 | 11.398 | 1.00 | 29.02 | A | O |
| ATOM | 1228 | N | PRO | A | 193 | 30.978 | 74.251 | 12.463 | 1.00 | 30.26 | A | N |
| ATOM | 1229 | CD | PRO | A | 193 | 30.828 | 74.932 | 13.759 | 1.00 | 31.45 | A | C |
| ATOM | 1230 | CA | PRO | A | 193 | 31.310 | 75.190 | 11.386 | 1.00 | 30.62 | A | C |

TABLE 14-continued

Coordinates for proMMP9(35-444 ΔFnII) (SEQ ID NO: 12) complex with Example 4

| ATOM | 1231 | CB | PRO | A | 193 | 30.806 | 76.536 | 11.909 | 1.00 | 30.61 | A | C |
|------|------|-----|-----|---|-----|--------|--------|--------|------|-------|---|---|
| ATOM | 1232 | CG | PRO | A | 193 | 30.451 | 76.323 | 13.367 | 1.00 | 35.13 | A | C |
| ATOM | 1233 | C | PRO | A | 193 | 32.821 | 75.251 | 11.211 | 1.00 | 34.13 | A | C |
| ATOM | 1234 | O | PRO | A | 193 | 33.540 | 74.881 | 12.141 | 1.00 | 33.25 | A | O |
| ATOM | 1235 | N | PRO | A | 194 | 33.295 | 75.723 | 10.042 | 1.00 | 34.93 | A | N |
| ATOM | 1236 | CD | PRO | A | 194 | 32.486 | 76.185 | 8.898 | 1.00 | 31.83 | A | C |
| ATOM | 1237 | CA | PRO | A | 194 | 34.743 | 75.788 | 9.778 | 1.00 | 34.90 | A | C |
| ATOM | 1238 | CB | PRO | A | 194 | 34.837 | 76.546 | 8.440 | 1.00 | 34.18 | A | C |
| ATOM | 1239 | CG | PRO | A | 194 | 33.510 | 76.306 | 7.764 | 1.00 | 34.91 | A | C |
| ATOM | 1240 | C | PRO | A | 194 | 35.514 | 76.531 | 10.869 | 1.00 | 33.19 | A | C |
| ATOM | 1241 | O | PRO | A | 194 | 34.982 | 77.436 | 11.504 | 1.00 | 32.78 | A | O |
| ATOM | 1242 | N | GLY | A | 195 | 36.771 | 76.149 | 11.067 | 1.00 | 36.64 | A | N |
| ATOM | 1243 | CA | GLY | A | 195 | 37.638 | 76.834 | 12.009 | 1.00 | 34.42 | A | C |
| ATOM | 1244 | C | GLY | A | 195 | 38.572 | 75.854 | 12.679 | 1.00 | 37.39 | A | C |
| ATOM | 1245 | O | GLY | A | 195 | 38.720 | 74.733 | 12.207 | 1.00 | 36.23 | A | O |
| ATOM | 1246 | N | PRO | A | 196 | 39.161 | 76.249 | 13.819 | 1.00 | 40.63 | A | N |
| ATOM | 1247 | CD | PRO | A | 196 | 38.708 | 77.374 | 14.648 | 1.00 | 40.98 | A | C |
| ATOM | 1248 | CA | PRO | A | 196 | 40.224 | 75.492 | 14.486 | 1.00 | 41.14 | A | C |
| ATOM | 1249 | CB | PRO | A | 196 | 40.818 | 76.518 | 15.472 | 1.00 | 36.71 | A | C |
| ATOM | 1250 | CG | PRO | A | 196 | 39.966 | 77.774 | 15.350 | 1.00 | 42.03 | A | C |
| ATOM | 1251 | C | PRO | A | 196 | 39.718 | 74.289 | 15.288 | 1.00 | 44.34 | A | C |
| ATOM | 1252 | O | PRO | A | 196 | 38.612 | 74.311 | 15.844 | 1.00 | 37.75 | A | O |
| ATOM | 1253 | N | GLY | A | 197 | 40.552 | 73.258 | 15.365 | 1.00 | 40.20 | A | N |
| ATOM | 1254 | CA | GLY | A | 197 | 40.311 | 72.148 | 16.265 | 1.00 | 41.00 | A | C |
| ATOM | 1255 | C | GLY | A | 197 | 39.137 | 71.304 | 15.845 | 1.00 | 43.02 | A | C |
| ATOM | 1256 | O | GLY | A | 197 | 39.163 | 70.694 | 14.787 | 1.00 | 40.75 | A | O |
| ATOM | 1257 | N | ILE | A | 198 | 38.102 | 71.271 | 16.678 | 1.00 | 35.00 | A | N |
| ATOM | 1258 | CA | ILE | A | 198 | 36.910 | 70.468 | 16.409 | 1.00 | 38.29 | A | C |
| ATOM | 1259 | CB | ILE | A | 198 | 36.073 | 70.271 | 17.705 | 1.00 | 41.03 | A | C |
| ATOM | 1260 | CG2 | ILE | A | 198 | 35.497 | 71.596 | 18.182 | 1.00 | 39.19 | A | C |
| ATOM | 1261 | CG1 | ILE | A | 198 | 34.965 | 69.234 | 17.509 | 1.00 | 41.77 | A | C |
| ATOM | 1262 | CD1 | ILE | A | 198 | 34.163 | 68.962 | 18.783 | 1.00 | 39.77 | A | C |
| ATOM | 1263 | C | ILE | A | 198 | 36.037 | 71.097 | 15.314 | 1.00 | 39.65 | A | C |
| ATOM | 1264 | O | ILE | A | 198 | 35.235 | 70.410 | 14.668 | 1.00 | 38.07 | A | O |
| ATOM | 1265 | N | GLN | A | 199 | 36.184 | 72.404 | 15.110 | 1.00 | 36.66 | A | N |
| ATOM | 1266 | CA | GLN | A | 199 | 35.414 | 73.082 | 14.074 | 1.00 | 35.66 | A | C |
| ATOM | 1267 | CB | GLN | A | 199 | 35.703 | 74.588 | 14.078 | 1.00 | 35.95 | A | C |
| ATOM | 1268 | CG | GLN | A | 199 | 35.240 | 75.223 | 15.388 | 1.00 | 37.86 | A | C |
| ATOM | 1269 | CD | GLN | A | 199 | 35.381 | 76.731 | 15.441 | 1.00 | 42.27 | A | C |
| ATOM | 1270 | OE1 | GLN | A | 199 | 35.661 | 77.293 | 16.504 | 1.00 | 43.34 | A | O |
| ATOM | 1271 | NE2 | GLN | A | 199 | 35.194 | 77.397 | 14.299 | 1.00 | 38.38 | A | N |
| ATOM | 1272 | C | GLN | A | 199 | 35.697 | 72.427 | 12.732 | 1.00 | 39.30 | A | C |
| ATOM | 1273 | O | GLN | A | 199 | 36.833 | 72.079 | 12.435 | 1.00 | 33.33 | A | O |
| ATOM | 1274 | N | GLY | A | 200 | 34.650 | 72.220 | 11.941 | 1.00 | 37.16 | A | N |
| ATOM | 1275 | CA | GLY | A | 200 | 34.785 | 71.482 | 10.700 | 1.00 | 33.38 | A | C |
| ATOM | 1276 | C | GLY | A | 200 | 34.449 | 70.003 | 10.841 | 1.00 | 35.39 | A | C |
| ATOM | 1277 | O | GLY | A | 200 | 34.203 | 69.322 | 9.845 | 1.00 | 32.60 | A | O |
| ATOM | 1278 | N | ASP | A | 201 | 34.438 | 69.490 | 12.069 | 1.00 | 32.26 | A | N |
| ATOM | 1279 | CA | ASP | A | 201 | 34.249 | 68.056 | 12.263 | 1.00 | 33.60 | A | C |
| ATOM | 1280 | CB | ASP | A | 201 | 34.710 | 67.623 | 13.664 | 1.00 | 36.95 | A | C |
| ATOM | 1281 | CG | ASP | A | 201 | 36.213 | 67.615 | 13.792 | 1.00 | 38.19 | A | C |
| ATOM | 1282 | OD1 | ASP | A | 201 | 36.881 | 67.931 | 12.779 | 1.00 | 38.79 | A | O |
| ATOM | 1283 | OD2 | ASP | A | 201 | 36.725 | 67.292 | 14.882 | 1.00 | 37.08 | A | O |
| ATOM | 1284 | C | ASP | A | 201 | 32.808 | 67.597 | 12.000 | 1.00 | 32.00 | A | C |
| ATOM | 1285 | O | ASP | A | 201 | 31.866 | 68.372 | 12.114 | 1.00 | 27.89 | A | O |
| ATOM | 1286 | N | ALA | A | 202 | 32.669 | 66.328 | 11.631 | 1.00 | 30.52 | A | N |
| ATOM | 1287 | CA | ALA | A | 202 | 31.382 | 65.723 | 11.342 | 1.00 | 30.73 | A | C |
| ATOM | 1288 | CB | ALA | A | 202 | 31.219 | 65.538 | 9.836 | 1.00 | 28.11 | A | C |
| ATOM | 1289 | C | ALA | A | 202 | 31.260 | 64.380 | 12.066 | 1.00 | 29.74 | A | C |
| ATOM | 1290 | O | ALA | A | 202 | 32.106 | 63.495 | 11.905 | 1.00 | 30.45 | A | O |
| ATOM | 1291 | N | HIS | A | 203 | 30.217 | 64.237 | 12.872 | 1.00 | 28.51 | A | N |
| ATOM | 1292 | CA | HIS | A | 203 | 30.030 | 63.019 | 13.668 | 1.00 | 32.05 | A | C |
| ATOM | 1293 | CB | HIS | A | 203 | 29.989 | 63.342 | 15.161 | 1.00 | 30.75 | A | C |
| ATOM | 1294 | CG | HIS | A | 203 | 31.246 | 63.978 | 15.686 | 1.00 | 36.71 | A | C |
| ATOM | 1295 | CD2 | HIS | A | 203 | 32.525 | 63.552 | 15.681 | 1.00 | 40.23 | A | C |
| ATOM | 1296 | ND1 | HIS | A | 203 | 31.241 | 65.212 | 16.307 | 1.00 | 43.80 | A | N |
| ATOM | 1297 | CE1 | HIS | A | 203 | 32.471 | 65.510 | 16.682 | 1.00 | 40.13 | A | C |
| ATOM | 1298 | NE2 | HIS | A | 203 | 33.271 | 64.532 | 16.321 | 1.00 | 40.75 | A | N |
| ATOM | 1299 | C | HIS | A | 203 | 28.738 | 62.303 | 13.275 | 1.00 | 30.16 | A | C |
| ATOM | 1300 | O | HIS | A | 203 | 27.707 | 62.942 | 13.094 | 1.00 | 27.41 | A | O |
| ATOM | 1301 | N | PHE | A | 204 | 28.808 | 60.983 | 13.136 | 1.00 | 30.15 | A | N |
| ATOM | 1302 | CA | PHE | A | 204 | 27.643 | 60.176 | 12.776 | 1.00 | 32.11 | A | C |
| ATOM | 1303 | CB | PHE | A | 204 | 27.902 | 59.437 | 11.465 | 1.00 | 29.08 | A | C |
| ATOM | 1304 | CG | PHE | A | 204 | 28.249 | 60.354 | 10.335 | 1.00 | 31.22 | A | C |
| ATOM | 1305 | CD1 | PHE | A | 204 | 29.556 | 60.771 | 10.143 | 1.00 | 28.93 | A | C |
| ATOM | 1306 | CD2 | PHE | A | 204 | 27.258 | 60.838 | 9.491 | 1.00 | 31.83 | A | C |
| ATOM | 1307 | CE1 | PHE | A | 204 | 29.877 | 61.643 | 9.096 | 1.00 | 32.83 | A | C |
| ATOM | 1308 | CE2 | PHE | A | 204 | 27.566 | 61.705 | 8.450 | 1.00 | 26.40 | A | C |

TABLE 14-continued

Coordinates for proMMP9(35-444 ΔFnII) (SEQ ID NO: 12) complex with Example 4

| ATOM | 1309 | CZ  | PHE | A | 204 | 28.878 | 62.107 | 8.257  | 1.00 | 28.70 | A | C |
|------|------|-----|-----|---|-----|--------|--------|--------|------|-------|---|---|
| ATOM | 1310 | C   | PHE | A | 204 | 27.270 | 59.191 | 13.881 | 1.00 | 32.72 | A | C |
| ATOM | 1311 | O   | PHE | A | 204 | 28.121 | 58.447 | 14.375 | 1.00 | 30.18 | A | O |
| ATOM | 1312 | N   | ASP | A | 205 | 25.995 | 59.193 | 14.264 | 1.00 | 32.89 | A | N |
| ATOM | 1313 | CA  | ASP | A | 205 | 25.531 | 58.348 | 15.361 | 1.00 | 31.25 | A | C |
| ATOM | 1314 | CB  | ASP | A | 205 | 24.166 | 58.813 | 15.873 | 1.00 | 34.66 | A | C |
| ATOM | 1315 | CG  | ASP | A | 205 | 23.764 | 58.124 | 17.183 | 1.00 | 35.48 | A | C |
| ATOM | 1316 | OD1 | ASP | A | 205 | 24.413 | 57.140 | 17.591 | 1.00 | 33.68 | A | O |
| ATOM | 1317 | OD2 | ASP | A | 205 | 22.798 | 58.576 | 17.811 | 1.00 | 36.15 | A | O |
| ATOM | 1318 | C   | ASP | A | 205 | 25.447 | 56.890 | 14.942 | 1.00 | 33.25 | A | C |
| ATOM | 1319 | O   | ASP | A | 205 | 24.564 | 56.509 | 14.165 | 1.00 | 35.40 | A | O |
| ATOM | 1320 | N   | ASP | A | 206 | 26.354 | 56.075 | 15.472 | 1.00 | 32.88 | A | N |
| ATOM | 1321 | CA  | ASP | A | 206 | 26.460 | 54.679 | 15.067 | 1.00 | 32.84 | A | C |
| ATOM | 1322 | CB  | ASP | A | 206 | 27.881 | 54.164 | 15.316 | 1.00 | 35.80 | A | C |
| ATOM | 1323 | CG  | ASP | A | 206 | 28.316 | 53.090 | 14.313 | 1.00 | 32.37 | A | C |
| ATOM | 1324 | OD1 | ASP | A | 206 | 27.515 | 52.677 | 13.449 | 1.00 | 30.53 | A | O |
| ATOM | 1325 | OD2 | ASP | A | 206 | 29.479 | 52.649 | 14.400 | 1.00 | 38.85 | A | O |
| ATOM | 1326 | C   | ASP | A | 206 | 25.410 | 53.804 | 15.775 | 1.00 | 34.93 | A | C |
| ATOM | 1327 | O   | ASP | A | 206 | 25.379 | 52.598 | 15.604 | 1.00 | 32.58 | A | O |
| ATOM | 1328 | N   | ASP | A | 207 | 24.535 | 54.417 | 16.565 | 1.00 | 36.15 | A | N |
| ATOM | 1329 | CA  | ASP | A | 207 | 23.377 | 53.679 | 17.058 | 1.00 | 37.65 | A | C |
| ATOM | 1330 | CB  | ASP | A | 207 | 22.838 | 54.274 | 18.363 | 1.00 | 40.05 | A | C |
| ATOM | 1331 | CG  | ASP | A | 207 | 23.551 | 53.721 | 19.582 | 1.00 | 40.19 | A | C |
| ATOM | 1332 | OD1 | ASP | A | 207 | 24.125 | 52.614 | 19.464 | 1.00 | 34.03 | A | O |
| ATOM | 1333 | OD2 | ASP | A | 207 | 23.543 | 54.397 | 20.631 | 1.00 | 32.45 | A | O |
| ATOM | 1334 | C   | ASP | A | 207 | 22.297 | 53.647 | 15.990 | 1.00 | 37.28 | A | C |
| ATOM | 1335 | O   | ASP | A | 207 | 21.233 | 53.068 | 16.189 | 1.00 | 39.64 | A | O |
| ATOM | 1336 | N   | GLU | A | 208 | 22.567 | 54.290 | 14.860 | 1.00 | 36.27 | A | N |
| ATOM | 1337 | CA  | GLU | A | 208 | 21.682 | 54.189 | 13.708 | 1.00 | 34.34 | A | C |
| ATOM | 1338 | CB  | GLU | A | 208 | 21.610 | 55.510 | 12.940 | 1.00 | 35.14 | A | C |
| ATOM | 1339 | CG  | GLU | A | 208 | 21.270 | 56.703 | 13.783 | 1.00 | 36.32 | A | C |
| ATOM | 1340 | CD  | GLU | A | 208 | 19.932 | 56.568 | 14.456 | 1.00 | 38.56 | A | C |
| ATOM | 1341 | OE1 | GLU | A | 208 | 19.158 | 55.646 | 14.103 | 1.00 | 39.58 | A | O |
| ATOM | 1342 | OE2 | GLU | A | 208 | 19.651 | 57.395 | 15.343 | 1.00 | 40.48 | A | O |
| ATOM | 1343 | C   | GLU | A | 208 | 22.224 | 53.132 | 12.773 | 1.00 | 36.27 | A | C |
| ATOM | 1344 | O   | GLU | A | 208 | 23.437 | 52.873 | 12.737 | 1.00 | 36.67 | A | O |
| ATOM | 1345 | N   | LEU | A | 209 | 21.315 | 52.536 | 12.012 | 1.00 | 33.12 | A | N |
| ATOM | 1346 | CA  | LEU | A | 209 | 21.673 | 51.624 | 10.955 | 1.00 | 33.68 | A | C |
| ATOM | 1347 | CB  | LEU | A | 209 | 20.518 | 50.678 | 10.624 | 1.00 | 32.96 | A | C |
| ATOM | 1348 | CG  | LEU | A | 209 | 20.799 | 49.669 | 9.504  | 1.00 | 33.74 | A | C |
| ATOM | 1349 | CD1 | LEU | A | 209 | 21.829 | 48.648 | 9.982  | 1.00 | 32.63 | A | C |
| ATOM | 1350 | CD2 | LEU | A | 209 | 19.513 | 48.984 | 9.030  | 1.00 | 35.24 | A | C |
| ATOM | 1351 | C   | LEU | A | 209 | 21.990 | 52.467 | 9.729  | 1.00 | 36.11 | A | C |
| ATOM | 1352 | O   | LEU | A | 209 | 21.096 | 53.110 | 9.168  | 1.00 | 35.91 | A | O |
| ATOM | 1353 | N   | TRP | A | 210 | 23.259 | 52.463 | 9.332  | 1.00 | 32.31 | A | N |
| ATOM | 1354 | CA  | TRP | A | 210 | 23.708 | 53.173 | 8.150  | 1.00 | 30.84 | A | C |
| ATOM | 1355 | CB  | TRP | A | 210 | 25.118 | 53.736 | 8.369  | 1.00 | 26.95 | A | C |
| ATOM | 1356 | CG  | TRP | A | 210 | 25.091 | 54.779 | 9.437  | 1.00 | 29.29 | A | C |
| ATOM | 1357 | CD2 | TRP | A | 210 | 24.482 | 56.069 | 9.345  | 1.00 | 28.67 | A | C |
| ATOM | 1358 | CE2 | TRP | A | 210 | 24.648 | 56.700 | 10.592 | 1.00 | 29.44 | A | C |
| ATOM | 1359 | CE3 | TRP | A | 210 | 23.831 | 56.766 | 8.316  | 1.00 | 28.89 | A | C |
| ATOM | 1360 | CD1 | TRP | A | 210 | 25.562 | 54.667 | 10.711 | 1.00 | 32.64 | A | C |
| ATOM | 1361 | NE1 | TRP | A | 210 | 25.310 | 55.822 | 11.412 | 1.00 | 31.23 | A | N |
| ATOM | 1362 | CZ2 | TRP | A | 210 | 24.175 | 57.989 | 10.846 | 1.00 | 29.34 | A | C |
| ATOM | 1363 | CZ3 | TRP | A | 210 | 23.374 | 58.046 | 8.567  | 1.00 | 28.07 | A | C |
| ATOM | 1364 | CH2 | TRP | A | 210 | 23.547 | 58.644 | 9.821  | 1.00 | 28.71 | A | C |
| ATOM | 1365 | C   | TRP | A | 210 | 23.641 | 52.282 | 6.922  | 1.00 | 36.87 | A | C |
| ATOM | 1366 | O   | TRP | A | 210 | 24.022 | 51.107 | 6.956  | 1.00 | 34.27 | A | O |
| ATOM | 1367 | N   | SER | A | 211 | 23.125 | 52.851 | 5.842  | 1.00 | 31.60 | A | N |
| ATOM | 1368 | CA  | SER | A | 211 | 23.035 | 52.144 | 4.591  | 1.00 | 31.47 | A | C |
| ATOM | 1369 | CB  | SER | A | 211 | 21.718 | 51.360 | 4.503  | 1.00 | 32.96 | A | C |
| ATOM | 1370 | OG  | SER | A | 211 | 20.583 | 52.223 | 4.556  | 1.00 | 32.66 | A | O |
| ATOM | 1371 | C   | SER | A | 211 | 23.072 | 53.216 | 3.524  | 1.00 | 30.24 | A | C |
| ATOM | 1372 | O   | SER | A | 211 | 23.582 | 54.320 | 3.741  | 1.00 | 28.81 | A | O |
| ATOM | 1373 | N   | LEU | A | 212 | 22.493 | 52.910 | 2.378  | 1.00 | 29.74 | A | N |
| ATOM | 1374 | CA  | LEU | A | 212 | 22.322 | 53.944 | 1.381  | 1.00 | 34.63 | A | C |
| ATOM | 1375 | CB  | LEU | A | 212 | 22.904 | 53.507 | 0.042  | 1.00 | 30.11 | A | C |
| ATOM | 1376 | CG  | LEU | A | 212 | 24.425 | 53.362 | 0.170  | 1.00 | 29.06 | A | C |
| ATOM | 1377 | CD1 | LEU | A | 212 | 25.139 | 53.214 | −1.191 | 1.00 | 34.37 | A | C |
| ATOM | 1378 | CD2 | LEU | A | 212 | 25.018 | 54.547 | 0.926  | 1.00 | 29.64 | A | C |
| ATOM | 1379 | C   | LEU | A | 212 | 20.855 | 54.413 | 1.325  | 1.00 | 37.49 | A | C |
| ATOM | 1380 | O   | LEU | A | 212 | 20.390 | 54.952 | 0.314  | 1.00 | 34.59 | A | O |
| ATOM | 1381 | N   | GLY | A | 213 | 20.148 | 54.215 | 2.444  | 1.00 | 34.07 | A | N |
| ATOM | 1382 | CA  | GLY | A | 213 | 18.811 | 54.763 | 2.631  | 1.00 | 34.89 | A | C |
| ATOM | 1383 | C   | GLY | A | 213 | 17.730 | 53.901 | 2.003  | 1.00 | 40.31 | A | C |
| ATOM | 1384 | O   | GLY | A | 213 | 16.537 | 54.058 | 2.282  | 1.00 | 39.26 | A | O |
| ATOM | 1385 | N   | LYS | A | 389 | 18.161 | 52.976 | 1.142  | 1.00 | 40.84 | A | N |
| ATOM | 1386 | CA  | LYS | A | 389 | 17.224 | 52.070 | 0.484  | 1.00 | 44.47 | A | C |

TABLE 14-continued

Coordinates for proMMP9(35-444 ΔFnII) (SEQ ID NO: 12) complex with Example 4

| ATOM | 1387 | CB  | LYS | A | 389 | 17.739 | 51.721 | −0.902 | 1.00 | 47.97 | A | C |
|------|------|-----|-----|---|-----|--------|--------|--------|------|-------|---|---|
| ATOM | 1388 | CG  | LYS | A | 389 | 16.731 | 51.032 | −1.767 | 1.00 | 54.22 | A | C |
| ATOM | 1389 | CD  | LYS | A | 389 | 16.228 | 51.966 | −2.865 | 1.00 | 59.73 | A | C |
| ATOM | 1390 | CE  | LYS | A | 389 | 15.956 | 51.187 | −4.174 | 1.00 | 64.08 | A | C |
| ATOM | 1391 | NZ  | LYS | A | 389 | 17.244 | 50.652 | −4.770 | 1.00 | 59.91 | A | N |
| ATOM | 1392 | C   | LYS | A | 389 | 17.014 | 50.781 | 1.279  | 1.00 | 46.09 | A | C |
| ATOM | 1393 | O   | LYS | A | 389 | 17.956 | 50.226 | 1.848  | 1.00 | 42.92 | A | O |
| ATOM | 1394 | N   | GLY | A | 390 | 15.774 | 50.304 | 1.312  | 1.00 | 43.18 | A | N |
| ATOM | 1395 | CA  | GLY | A | 390 | 15.463 | 49.050 | 1.968  | 1.00 | 41.35 | A | C |
| ATOM | 1396 | C   | GLY | A | 390 | 15.269 | 49.252 | 3.455  | 1.00 | 44.81 | A | C |
| ATOM | 1397 | O   | GLY | A | 390 | 14.147 | 49.200 | 3.958  | 1.00 | 48.67 | A | O |
| ATOM | 1398 | N   | GLN | A | 391 | 16.371 | 49.461 | 4.158  | 1.00 | 37.85 | A | N |
| ATOM | 1399 | CA  | GLN | A | 391 | 16.341 | 49.789 | 5.573  | 1.00 | 39.08 | A | C |
| ATOM | 1400 | CB  | GLN | A | 391 | 16.397 | 48.521 | 6.429  | 1.00 | 40.91 | A | C |
| ATOM | 1401 | CG  | GLN | A | 391 | 15.207 | 47.580 | 6.249  | 1.00 | 49.33 | A | C |
| ATOM | 1402 | CD  | GLN | A | 391 | 15.457 | 46.198 | 6.831  | 1.00 | 43.68 | A | C |
| ATOM | 1403 | OE1 | GLN | A | 391 | 16.067 | 46.056 | 7.896  | 1.00 | 41.17 | A | O |
| ATOM | 1404 | NE2 | GLN | A | 391 | 14.997 | 45.168 | 6.122  | 1.00 | 43.13 | A | N |
| ATOM | 1405 | C   | GLN | A | 391 | 17.556 | 50.668 | 5.862  | 1.00 | 40.87 | A | C |
| ATOM | 1406 | O   | GLN | A | 391 | 18.532 | 50.671 | 5.088  | 1.00 | 35.63 | A | O |
| ATOM | 1407 | N   | GLY | A | 392 | 17.486 | 51.425 | 6.957  | 1.00 | 35.12 | A | N |
| ATOM | 1408 | CA  | GLY | A | 392 | 18.602 | 52.239 | 7.397  | 1.00 | 36.35 | A | C |
| ATOM | 1409 | C   | GLY | A | 392 | 18.623 | 53.646 | 6.833  | 1.00 | 34.96 | A | C |
| ATOM | 1410 | O   | GLY | A | 392 | 17.931 | 53.953 | 5.859  | 1.00 | 32.84 | A | O |
| ATOM | 1411 | N   | TYR | A | 393 | 19.418 | 54.509 | 7.455  | 1.00 | 32.10 | A | N |
| ATOM | 1412 | CA  | TYR | A | 393 | 19.563 | 55.890 | 6.994  | 1.00 | 33.29 | A | C |
| ATOM | 1413 | CB  | TYR | A | 393 | 19.867 | 56.808 | 8.170  | 1.00 | 29.08 | A | C |
| ATOM | 1414 | CG  | TYR | A | 393 | 18.738 | 56.908 | 9.161  | 1.00 | 33.18 | A | C |
| ATOM | 1415 | CD1 | TYR | A | 393 | 17.586 | 57.637 | 8.863  | 1.00 | 31.83 | A | C |
| ATOM | 1416 | CE1 | TYR | A | 393 | 16.549 | 57.739 | 9.779  | 1.00 | 32.42 | A | C |
| ATOM | 1417 | CD2 | TYR | A | 393 | 18.822 | 56.276 | 10.404 | 1.00 | 34.63 | A | C |
| ATOM | 1418 | CE2 | TYR | A | 393 | 17.797 | 56.365 | 11.320 | 1.00 | 33.36 | A | C |
| ATOM | 1419 | CZ  | TYR | A | 393 | 16.667 | 57.100 | 11.008 | 1.00 | 37.24 | A | C |
| ATOM | 1420 | OH  | TYR | A | 393 | 15.660 | 57.179 | 11.936 | 1.00 | 36.80 | A | O |
| ATOM | 1421 | C   | TYR | A | 393 | 20.673 | 56.022 | 5.955  | 1.00 | 31.36 | A | C |
| ATOM | 1422 | O   | TYR | A | 393 | 21.725 | 55.421 | 6.108  | 1.00 | 30.35 | A | O |
| ATOM | 1423 | N   | SER | A | 394 | 20.438 | 56.812 | 4.908  | 1.00 | 29.12 | A | N |
| ATOM | 1424 | CA  | SER | A | 394 | 21.460 | 57.022 | 3.886  | 1.00 | 27.20 | A | C |
| ATOM | 1425 | CB  | SER | A | 394 | 20.888 | 57.760 | 2.674  | 1.00 | 28.20 | A | C |
| ATOM | 1426 | OG  | SER | A | 394 | 21.922 | 58.127 | 1.783  | 1.00 | 29.11 | A | O |
| ATOM | 1427 | C   | SER | A | 394 | 22.660 | 57.785 | 4.435  | 1.00 | 28.00 | A | C |
| ATOM | 1428 | O   | SER | A | 394 | 22.564 | 58.969 | 4.764  | 1.00 | 24.83 | A | O |
| ATOM | 1429 | N   | LEU | A | 395 | 23.796 | 57.102 | 4.522  | 1.00 | 27.18 | A | N |
| ATOM | 1430 | CA  | LEU | A | 395 | 25.033 | 57.746 | 4.936  | 1.00 | 25.19 | A | C |
| ATOM | 1431 | CB  | LEU | A | 395 | 26.172 | 56.724 | 4.972  | 1.00 | 26.89 | A | C |
| ATOM | 1432 | CG  | LEU | A | 395 | 27.475 | 57.319 | 5.494  | 1.00 | 28.46 | A | C |
| ATOM | 1433 | CD1 | LEU | A | 395 | 27.228 | 57.961 | 6.845  | 1.00 | 28.96 | A | C |
| ATOM | 1434 | CD2 | LEU | A | 395 | 28.583 | 56.271 | 5.562  | 1.00 | 27.24 | A | C |
| ATOM | 1435 | C   | LEU | A | 395 | 25.396 | 58.861 | 3.963  | 1.00 | 28.02 | A | C |
| ATOM | 1436 | O   | LEU | A | 395 | 25.913 | 59.910 | 4.356  | 1.00 | 25.06 | A | O |
| ATOM | 1437 | N   | PHE | A | 396 | 25.146 | 58.612 | 2.683  | 1.00 | 24.74 | A | N |
| ATOM | 1438 | CA  | PHE | A | 396 | 25.446 | 59.580 | 1.643  | 1.00 | 25.16 | A | C |
| ATOM | 1439 | CB  | PHE | A | 396 | 25.053 | 59.004 | 0.272  | 1.00 | 27.27 | A | C |
| ATOM | 1440 | CG  | PHE | A | 396 | 25.060 | 60.014 | −0.849 | 1.00 | 25.95 | A | C |
| ATOM | 1441 | CD1 | PHE | A | 396 | 26.192 | 60.782 | −1.118 | 1.00 | 26.93 | A | C |
| ATOM | 1442 | CD2 | PHE | A | 396 | 23.949 | 60.170 | −1.659 | 1.00 | 26.43 | A | C |
| ATOM | 1443 | CE1 | PHE | A | 396 | 26.191 | 61.712 | −2.159 | 1.00 | 24.65 | A | C |
| ATOM | 1444 | CE2 | PHE | A | 396 | 23.948 | 61.088 | −2.713 | 1.00 | 28.53 | A | C |
| ATOM | 1445 | CZ  | PHE | A | 396 | 25.059 | 61.862 | −2.953 | 1.00 | 24.03 | A | C |
| ATOM | 1446 | C   | PHE | A | 396 | 24.710 | 60.886 | 1.932  | 1.00 | 23.05 | A | C |
| ATOM | 1447 | O   | PHE | A | 396 | 25.322 | 61.921 | 2.163  | 1.00 | 24.92 | A | O |
| ATOM | 1448 | N   | LEU | A | 397 | 23.391 | 60.818 | 1.952  | 1.00 | 24.15 | A | N |
| ATOM | 1449 | CA  | LEU | A | 397 | 22.566 | 61.990 | 2.200  | 1.00 | 23.87 | A | C |
| ATOM | 1450 | CB  | LEU | A | 397 | 21.091 | 61.593 | 2.167  | 1.00 | 20.75 | A | C |
| ATOM | 1451 | CG  | LEU | A | 397 | 20.513 | 61.106 | 0.833  | 1.00 | 23.49 | A | C |
| ATOM | 1452 | CD1 | LEU | A | 397 | 19.095 | 60.582 | 0.995  | 1.00 | 24.16 | A | C |
| ATOM | 1453 | CD2 | LEU | A | 397 | 20.545 | 62.210 | −0.236 | 1.00 | 25.17 | A | C |
| ATOM | 1454 | C   | LEU | A | 397 | 22.919 | 62.698 | 3.521  | 1.00 | 22.52 | A | C |
| ATOM | 1455 | O   | LEU | A | 397 | 23.093 | 63.908 | 3.552  | 1.00 | 22.15 | A | O |
| ATOM | 1456 | N   | VAL | A | 398 | 23.024 | 61.953 | 4.616  | 1.00 | 21.47 | A | N |
| ATOM | 1457 | CA  | VAL | A | 398 | 23.282 | 62.584 | 5.916  | 1.00 | 21.80 | A | C |
| ATOM | 1458 | CB  | VAL | A | 398 | 23.221 | 61.553 | 7.070  | 1.00 | 26.16 | A | C |
| ATOM | 1459 | CG1 | VAL | A | 398 | 23.678 | 62.173 | 8.373  | 1.00 | 23.35 | A | C |
| ATOM | 1460 | CG2 | VAL | A | 398 | 21.801 | 61.001 | 7.205  | 1.00 | 22.85 | A | C |
| ATOM | 1461 | C   | VAL | A | 398 | 24.632 | 63.306 | 5.906  | 1.00 | 26.58 | A | C |
| ATOM | 1462 | O   | VAL | A | 398 | 24.776 | 64.411 | 6.454  | 1.00 | 24.30 | A | O |
| ATOM | 1463 | N   | ALA | A | 399 | 25.610 | 62.673 | 5.262  | 1.00 | 21.81 | A | N |
| ATOM | 1464 | CA  | ALA | A | 399 | 26.953 | 63.227 | 5.168  | 1.00 | 27.72 | A | C |

TABLE 14-continued

Coordinates for proMMP9(35-444 ΔFnII) (SEQ ID NO: 12) complex with Example 4

| ATOM | 1465 | CB | ALA | A | 399 | 27.942 | 62.169 | 4.645 | 1.00 | 25.02 | A | C |
|---|---|---|---|---|---|---|---|---|---|---|---|---|
| ATOM | 1466 | C | ALA | A | 399 | 26.975 | 64.493 | 4.297 | 1.00 | 24.20 | A | C |
| ATOM | 1467 | O | ALA | A | 399 | 27.600 | 65.494 | 4.647 | 1.00 | 23.61 | A | O |
| ATOM | 1468 | N | ALA | A | 400 | 26.265 | 64.448 | 3.180 | 1.00 | 21.18 | A | N |
| ATOM | 1469 | CA | ALA | A | 400 | 26.159 | 65.621 | 2.312 | 1.00 | 25.85 | A | C |
| ATOM | 1470 | CB | ALA | A | 400 | 25.225 | 65.328 | 1.145 | 1.00 | 22.45 | A | C |
| ATOM | 1471 | C | ALA | A | 400 | 25.656 | 66.812 | 3.123 | 1.00 | 25.78 | A | C |
| ATOM | 1472 | O | ALA | A | 400 | 26.181 | 67.933 | 3.036 | 1.00 | 25.57 | A | O |
| ATOM | 1473 | N | HIS | A | 401 | 24.643 | 66.546 | 3.939 | 1.00 | 25.02 | A | N |
| ATOM | 1474 | CA | HIS | A | 401 | 24.037 | 67.572 | 4.777 | 1.00 | 21.15 | A | C |
| ATOM | 1475 | CB | HIS | A | 401 | 22.731 | 67.031 | 5.373 | 1.00 | 21.64 | A | C |
| ATOM | 1476 | CG | HIS | A | 401 | 22.119 | 67.921 | 6.401 | 1.00 | 21.81 | A | C |
| ATOM | 1477 | CD2 | HIS | A | 401 | 22.501 | 68.212 | 7.667 | 1.00 | 22.60 | A | C |
| ATOM | 1478 | ND1 | HIS | A | 401 | 20.988 | 68.665 | 6.161 | 1.00 | 21.74 | A | N |
| ATOM | 1479 | CE1 | HIS | A | 401 | 20.695 | 69.380 | 7.231 | 1.00 | 20.89 | A | C |
| ATOM | 1480 | NE2 | HIS | A | 401 | 21.591 | 69.116 | 8.163 | 1.00 | 21.45 | A | N |
| ATOM | 1481 | C | HIS | A | 401 | 25.002 | 68.077 | 5.866 | 1.00 | 22.61 | A | C |
| ATOM | 1482 | O | HIS | A | 401 | 25.174 | 69.281 | 6.035 | 1.00 | 20.12 | A | O |
| ATOM | 1483 | N | GLU | A | 402 | 25.624 | 67.156 | 6.599 | 1.00 | 20.74 | A | N |
| ATOM | 1484 | CA | GLU | A | 402 | 26.581 | 67.524 | 7.635 | 1.00 | 23.20 | A | C |
| ATOM | 1485 | CB | GLU | A | 402 | 27.007 | 66.289 | 8.431 | 1.00 | 22.77 | A | C |
| ATOM | 1486 | CG | GLU | A | 402 | 25.821 | 65.520 | 9.031 | 1.00 | 25.19 | A | C |
| ATOM | 1487 | CD | GLU | A | 402 | 25.074 | 66.302 | 10.100 | 1.00 | 24.15 | A | C |
| ATOM | 1488 | OE1 | GLU | A | 402 | 25.638 | 67.273 | 10.638 | 1.00 | 25.08 | A | O |
| ATOM | 1489 | OE2 | GLU | A | 402 | 23.915 | 65.934 | 10.409 | 1.00 | 26.52 | A | O |
| ATOM | 1490 | C | GLU | A | 402 | 27.818 | 68.277 | 7.100 | 1.00 | 22.76 | A | C |
| ATOM | 1491 | O | GLU | A | 402 | 28.285 | 69.229 | 7.725 | 1.00 | 22.99 | A | O |
| ATOM | 1492 | N | PHE | A | 403 | 28.341 | 67.846 | 5.953 | 1.00 | 24.34 | A | N |
| ATOM | 1493 | CA | PHE | A | 403 | 29.439 | 68.566 | 5.282 | 1.00 | 25.52 | A | C |
| ATOM | 1494 | CB | PHE | A | 403 | 29.884 | 67.830 | 4.015 | 1.00 | 24.24 | A | C |
| ATOM | 1495 | CG | PHE | A | 403 | 30.441 | 66.457 | 4.275 | 1.00 | 25.85 | A | C |
| ATOM | 1496 | CD1 | PHE | A | 403 | 30.769 | 66.058 | 5.557 | 1.00 | 25.75 | A | C |
| ATOM | 1497 | CD2 | PHE | A | 403 | 30.657 | 65.573 | 3.226 | 1.00 | 26.81 | A | C |
| ATOM | 1498 | CE1 | PHE | A | 403 | 31.283 | 64.796 | 5.800 | 1.00 | 27.96 | A | C |
| ATOM | 1499 | CE2 | PHE | A | 403 | 31.175 | 64.320 | 3.452 | 1.00 | 26.04 | A | C |
| ATOM | 1500 | CZ | PHE | A | 403 | 31.487 | 63.926 | 4.752 | 1.00 | 27.42 | A | C |
| ATOM | 1501 | C | PHE | A | 403 | 29.045 | 70.010 | 4.948 | 1.00 | 26.65 | A | C |
| ATOM | 1502 | O | PHE | A | 403 | 29.883 | 70.917 | 4.970 | 1.00 | 28.46 | A | O |
| ATOM | 1503 | N | GLY | A | 404 | 27.762 | 70.213 | 4.646 | 1.00 | 25.27 | A | N |
| ATOM | 1504 | CA | GLY | A | 404 | 27.202 | 71.549 | 4.490 | 1.00 | 24.54 | A | C |
| ATOM | 1505 | C | GLY | A | 404 | 27.475 | 72.444 | 5.687 | 1.00 | 26.29 | A | C |
| ATOM | 1506 | O | GLY | A | 404 | 27.891 | 73.599 | 5.540 | 1.00 | 25.47 | A | O |
| ATOM | 1507 | N | HIS | A | 405 | 27.237 | 71.917 | 6.886 | 1.00 | 27.24 | A | N |
| ATOM | 1508 | CA | HIS | A | 405 | 27.625 | 72.627 | 8.107 | 1.00 | 24.18 | A | C |
| ATOM | 1509 | CB | HIS | A | 405 | 27.174 | 71.845 | 9.341 | 1.00 | 25.29 | A | C |
| ATOM | 1510 | CG | HIS | A | 405 | 25.687 | 71.821 | 9.520 | 1.00 | 21.70 | A | C |
| ATOM | 1511 | CD2 | HIS | A | 405 | 24.838 | 70.783 | 9.748 | 1.00 | 22.91 | A | C |
| ATOM | 1512 | ND1 | HIS | A | 405 | 24.920 | 72.952 | 9.469 | 1.00 | 21.35 | A | N |
| ATOM | 1513 | CE1 | HIS | A | 405 | 23.641 | 72.627 | 9.676 | 1.00 | 26.04 | A | C |
| ATOM | 1514 | NE2 | HIS | A | 405 | 23.579 | 71.323 | 9.844 | 1.00 | 26.12 | A | N |
| ATOM | 1515 | C | HIS | A | 405 | 29.143 | 72.868 | 8.170 | 1.00 | 26.84 | A | C |
| ATOM | 1516 | O | HIS | A | 405 | 29.593 | 73.952 | 8.565 | 1.00 | 26.69 | A | O |
| ATOM | 1517 | N | ALA | A | 406 | 29.914 | 71.843 | 7.807 | 1.00 | 24.57 | A | N |
| ATOM | 1518 | CA | ALA | A | 406 | 31.375 | 71.881 | 7.873 | 1.00 | 26.21 | A | C |
| ATOM | 1519 | CB | ALA | A | 406 | 31.988 | 70.473 | 7.560 | 1.00 | 21.40 | A | C |
| ATOM | 1520 | C | ALA | A | 406 | 31.964 | 72.939 | 6.934 | 1.00 | 29.85 | A | C |
| ATOM | 1521 | O | ALA | A | 406 | 33.139 | 73.296 | 7.049 | 1.00 | 32.04 | A | O |
| ATOM | 1522 | N | LEU | A | 407 | 31.147 | 73.414 | 5.997 | 1.00 | 26.50 | A | N |
| ATOM | 1523 | CA | LEU | A | 407 | 31.556 | 74.462 | 5.080 | 1.00 | 29.86 | A | C |
| ATOM | 1524 | CB | LEU | A | 407 | 31.084 | 74.156 | 3.656 | 1.00 | 24.34 | A | C |
| ATOM | 1525 | CG | LEU | A | 407 | 31.689 | 72.909 | 3.021 | 1.00 | 26.87 | A | C |
| ATOM | 1526 | CD1 | LEU | A | 407 | 31.108 | 72.738 | 1.639 | 1.00 | 28.31 | A | C |
| ATOM | 1527 | CD2 | LEU | A | 407 | 33.238 | 72.993 | 2.978 | 1.00 | 24.97 | A | C |
| ATOM | 1528 | C | LEU | A | 407 | 30.988 | 75.791 | 5.537 | 1.00 | 28.40 | A | C |
| ATOM | 1529 | O | LEU | A | 407 | 31.241 | 76.826 | 4.915 | 1.00 | 28.98 | A | O |
| ATOM | 1530 | N | GLY | A | 408 | 30.200 | 75.753 | 6.609 | 1.00 | 29.31 | A | N |
| ATOM | 1531 | CA | GLY | A | 408 | 29.607 | 76.955 | 7.177 | 1.00 | 25.53 | A | C |
| ATOM | 1532 | C | GLY | A | 408 | 28.114 | 77.196 | 6.946 | 1.00 | 28.25 | A | C |
| ATOM | 1533 | O | GLY | A | 408 | 27.613 | 78.277 | 7.255 | 1.00 | 29.02 | A | O |
| ATOM | 1534 | N | LEU | A | 409 | 27.383 | 76.215 | 6.423 | 1.00 | 27.35 | A | N |
| ATOM | 1535 | CA | LEU | A | 409 | 25.939 | 76.420 | 6.204 | 1.00 | 25.94 | A | C |
| ATOM | 1536 | CB | LEU | A | 409 | 25.417 | 75.563 | 5.054 | 1.00 | 23.12 | A | C |
| ATOM | 1537 | CG | LEU | A | 409 | 25.981 | 75.808 | 3.648 | 1.00 | 28.27 | A | C |
| ATOM | 1538 | CD1 | LEU | A | 409 | 25.372 | 74.827 | 2.654 | 1.00 | 24.95 | A | C |
| ATOM | 1539 | CD2 | LEU | A | 409 | 25.733 | 77.239 | 3.195 | 1.00 | 23.70 | A | C |
| ATOM | 1540 | C | LEU | A | 409 | 25.096 | 76.156 | 7.451 | 1.00 | 27.11 | A | C |
| ATOM | 1541 | O | LEU | A | 409 | 25.404 | 75.267 | 8.232 | 1.00 | 30.58 | A | O |
| ATOM | 1542 | N | ASP | A | 410 | 24.032 | 76.941 | 7.624 | 1.00 | 28.33 | A | N |

TABLE 14-continued

Coordinates for proMMP9(35-444 ΔFnII) (SEQ ID NO: 12) complex with Example 4

| ATOM | 1543 | CA  | ASP | A | 410 | 23.008 | 76.693 | 8.641  | 1.00 | 31.06 | A | C |
|------|------|-----|-----|---|-----|--------|--------|--------|------|-------|---|---|
| ATOM | 1544 | CB  | ASP | A | 410 | 22.412 | 78.001 | 9.162  | 1.00 | 27.79 | A | C |
| ATOM | 1545 | CG  | ASP | A | 410 | 23.432 | 78.886 | 9.802  | 1.00 | 35.16 | A | C |
| ATOM | 1546 | OD1 | ASP | A | 410 | 24.254 | 78.365 | 10.584 | 1.00 | 32.76 | A | O |
| ATOM | 1547 | OD2 | ASP | A | 410 | 23.410 | 80.102 | 9.527  | 1.00 | 40.03 | A | O |
| ATOM | 1548 | C   | ASP | A | 410 | 21.870 | 75.923 | 8.020  | 1.00 | 29.46 | A | C |
| ATOM | 1549 | O   | ASP | A | 410 | 21.859 | 75.676 | 6.831  | 1.00 | 26.28 | A | O |
| ATOM | 1550 | N   | HIS | A | 411 | 20.874 | 75.588 | 8.833  | 1.00 | 30.88 | A | N |
| ATOM | 1551 | CA  | HIS | A | 411 | 19.693 | 74.895 | 8.332  | 1.00 | 25.74 | A | C |
| ATOM | 1552 | CB  | HIS | A | 411 | 18.847 | 74.328 | 9.488  | 1.00 | 26.57 | A | C |
| ATOM | 1553 | CG  | HIS | A | 411 | 19.465 | 73.136 | 10.152 | 1.00 | 27.70 | A | C |
| ATOM | 1554 | CD2 | HIS | A | 411 | 20.207 | 72.121 | 9.639  | 1.00 | 24.94 | A | C |
| ATOM | 1555 | ND1 | HIS | A | 411 | 19.389 | 72.915 | 11.508 | 1.00 | 27.71 | A | N |
| ATOM | 1556 | CE1 | HIS | A | 411 | 20.043 | 71.804 | 11.806 | 1.00 | 26.48 | A | C |
| ATOM | 1557 | NE2 | HIS | A | 411 | 20.552 | 71.311 | 10.702 | 1.00 | 25.41 | A | N |
| ATOM | 1558 | C   | HIS | A | 411 | 18.846 | 75.784 | 7.452  | 1.00 | 25.02 | A | C |
| ATOM | 1559 | O   | HIS | A | 411 | 18.787 | 76.986 | 7.630  | 1.00 | 28.01 | A | O |
| ATOM | 1560 | N   | SER | A | 412 | 18.182 | 75.154 | 6.498  | 1.00 | 27.13 | A | N |
| ATOM | 1561 | CA  | SER | A | 412 | 17.218 | 75.810 | 5.638  | 1.00 | 24.71 | A | C |
| ATOM | 1562 | CB  | SER | A | 412 | 17.278 | 75.186 | 4.256  | 1.00 | 23.48 | A | C |
| ATOM | 1563 | OG  | SER | A | 412 | 16.358 | 75.826 | 3.395  | 1.00 | 25.12 | A | O |
| ATOM | 1564 | C   | SER | A | 412 | 15.825 | 75.559 | 6.187  | 1.00 | 27.53 | A | C |
| ATOM | 1565 | O   | SER | A | 412 | 15.589 | 74.550 | 6.843  | 1.00 | 23.98 | A | O |
| ATOM | 1566 | N   | SER | A | 413 | 14.902 | 76.463 | 5.873  | 1.00 | 27.76 | A | N |
| ATOM | 1567 | CA  | SER | A | 413 | 13.498 | 76.285 | 6.204  | 1.00 | 25.64 | A | C |
| ATOM | 1568 | CB  | SER | A | 413 | 12.921 | 77.595 | 6.736  | 1.00 | 30.17 | A | C |
| ATOM | 1569 | OG  | SER | A | 413 | 12.916 | 78.582 | 5.723  | 1.00 | 37.76 | A | O |
| ATOM | 1570 | C   | SER | A | 413 | 12.687 | 75.761 | 5.000  | 1.00 | 30.25 | A | C |
| ATOM | 1571 | O   | SER | A | 413 | 11.485 | 75.493 | 5.093  | 1.00 | 32.18 | A | O |
| ATOM | 1572 | N   | VAL | A | 414 | 13.358 | 75.602 | 3.870  | 1.00 | 26.90 | A | N |
| ATOM | 1573 | CA  | VAL | A | 414 | 12.789 | 74.910 | 2.722  | 1.00 | 28.51 | A | C |
| ATOM | 1574 | CB  | VAL | A | 414 | 13.613 | 75.215 | 1.454  | 1.00 | 27.08 | A | C |
| ATOM | 1575 | CG1 | VAL | A | 414 | 13.077 | 74.433 | 0.260  | 1.00 | 27.63 | A | C |
| ATOM | 1576 | CG2 | VAL | A | 414 | 13.603 | 76.705 | 1.189  | 1.00 | 27.48 | A | C |
| ATOM | 1577 | C   | VAL | A | 414 | 12.860 | 73.417 | 2.985  | 1.00 | 29.36 | A | C |
| ATOM | 1578 | O   | VAL | A | 414 | 13.954 | 72.865 | 3.062  | 1.00 | 27.70 | A | O |
| ATOM | 1579 | N   | PRO | A | 415 | 11.698 | 72.750 | 3.115  | 1.00 | 29.12 | A | N |
| ATOM | 1580 | CD  | PRO | A | 415 | 10.352 | 73.314 | 2.937  | 1.00 | 29.93 | A | C |
| ATOM | 1581 | CA  | PRO | A | 415 | 11.656 | 71.326 | 3.487  | 1.00 | 30.94 | A | C |
| ATOM | 1582 | CB  | PRO | A | 415 | 10.139 | 71.032 | 3.615  | 1.00 | 30.46 | A | C |
| ATOM | 1583 | CG  | PRO | A | 415 | 9.482  | 72.375 | 3.767  | 1.00 | 27.58 | A | C |
| ATOM | 1584 | C   | PRO | A | 415 | 12.313 | 70.370 | 2.465  | 1.00 | 31.71 | A | C |
| ATOM | 1585 | O   | PRO | A | 415 | 12.746 | 69.275 | 2.832  | 1.00 | 32.24 | A | O |
| ATOM | 1586 | N   | GLU | A | 416 | 12.366 | 70.771 | 1.197  | 1.00 | 31.03 | A | N |
| ATOM | 1587 | CA  | GLU | A | 416 | 12.990 | 69.957 | 0.156  | 1.00 | 31.86 | A | C |
| ATOM | 1588 | CB  | GLU | A | 416 | 12.451 | 70.353 | −1.218 | 1.00 | 32.73 | A | C |
| ATOM | 1589 | CG  | GLU | A | 416 | 10.947 | 70.201 | −1.375 | 1.00 | 38.14 | A | C |
| ATOM | 1590 | CD  | GLU | A | 416 | 10.172 | 71.362 | −0.756 | 1.00 | 34.62 | A | C |
| ATOM | 1591 | OE1 | GLU | A | 416 | 10.652 | 72.523 | −0.824 | 1.00 | 33.64 | A | O |
| ATOM | 1592 | OE2 | GLU | A | 416 | 9.070  | 71.107 | −0.225 | 1.00 | 36.74 | A | O |
| ATOM | 1593 | C   | GLU | A | 416 | 14.516 | 70.083 | 0.126  | 1.00 | 31.87 | A | C |
| ATOM | 1594 | O   | GLU | A | 416 | 15.216 | 69.209 | −0.407 | 1.00 | 31.00 | A | O |
| ATOM | 1595 | N   | ALA | A | 417 | 15.023 | 71.181 | 0.681  | 1.00 | 27.80 | A | N |
| ATOM | 1596 | CA  | ALA | A | 417 | 16.448 | 71.475 | 0.615  | 1.00 | 30.80 | A | C |
| ATOM | 1597 | CB  | ALA | A | 417 | 16.729 | 72.872 | 1.186  | 1.00 | 25.54 | A | C |
| ATOM | 1598 | C   | ALA | A | 417 | 17.281 | 70.431 | 1.346  | 1.00 | 26.62 | A | C |
| ATOM | 1599 | O   | ALA | A | 417 | 16.853 | 69.886 | 2.367  | 1.00 | 27.97 | A | O |
| ATOM | 1600 | N   | LEU | A | 418 | 18.489 | 70.177 | 0.836  | 1.00 | 29.44 | A | N |
| ATOM | 1601 | CA  | LEU | A | 418 | 19.444 | 69.339 | 1.553  | 1.00 | 27.09 | A | C |
| ATOM | 1602 | CB  | LEU | A | 418 | 20.784 | 69.241 | 0.795  | 1.00 | 23.23 | A | C |
| ATOM | 1603 | CG  | LEU | A | 418 | 21.898 | 68.451 | 1.496  | 1.00 | 22.75 | A | C |
| ATOM | 1604 | CD1 | LEU | A | 418 | 21.472 | 67.022 | 1.759  | 1.00 | 24.61 | A | C |
| ATOM | 1605 | CD2 | LEU | A | 418 | 23.237 | 68.457 | 0.725  | 1.00 | 24.14 | A | C |
| ATOM | 1606 | C   | LEU | A | 418 | 19.677 | 69.820 | 2.998  | 1.00 | 23.84 | A | C |
| ATOM | 1607 | O   | LEU | A | 418 | 19.852 | 69.003 | 3.902  | 1.00 | 23.01 | A | O |
| ATOM | 1608 | N   | MET | A | 419 | 19.717 | 71.137 | 3.215  | 1.00 | 26.13 | A | N |
| ATOM | 1609 | CA  | MET | A | 419 | 20.058 | 71.671 | 4.542  | 1.00 | 22.55 | A | C |
| ATOM | 1610 | CB  | MET | A | 419 | 20.798 | 73.007 | 4.445  | 1.00 | 19.43 | A | C |
| ATOM | 1611 | CG  | MET | A | 419 | 22.178 | 72.936 | 3.778  | 1.00 | 21.30 | A | C |
| ATOM | 1612 | SD  | MET | A | 419 | 23.209 | 71.597 | 4.408  | 1.00 | 21.22 | A | S |
| ATOM | 1613 | CE  | MET | A | 419 | 23.484 | 72.101 | 6.120  | 1.00 | 23.60 | A | C |
| ATOM | 1614 | C   | MET | A | 419 | 18.855 | 71.782 | 5.506  | 1.00 | 24.87 | A | C |
| ATOM | 1615 | O   | MET | A | 419 | 18.979 | 72.296 | 6.622  | 1.00 | 23.86 | A | O |
| ATOM | 1616 | N   | TYR | A | 420 | 17.695 | 71.317 | 5.074  | 1.00 | 25.66 | A | N |
| ATOM | 1617 | CA  | TYR | A | 420 | 16.569 | 71.175 | 5.988  | 1.00 | 26.26 | A | C |
| ATOM | 1618 | CB  | TYR | A | 420 | 15.358 | 70.652 | 5.227  | 1.00 | 24.51 | A | C |
| ATOM | 1619 | CG  | TYR | A | 420 | 14.034 | 70.775 | 5.957  | 1.00 | 28.59 | A | C |
| ATOM | 1620 | CD1 | TYR | A | 420 | 13.454 | 72.020 | 6.204  | 1.00 | 26.59 | A | C |

TABLE 14-continued

Coordinates for proMMP9(35-444 ΔFnII) (SEQ ID NO: 12) complex with Example 4

| ATOM | 1621 | CE1 | TYR | A | 420 | 12.221 | 72.123 | 6.866 | 1.00 | 29.27 | A | C |
|---|---|---|---|---|---|---|---|---|---|---|---|---|
| ATOM | 1622 | CD2 | TYR | A | 420 | 13.338 | 69.637 | 6.359 | 1.00 | 27.63 | A | C |
| ATOM | 1623 | CE2 | TYR | A | 420 | 12.116 | 69.731 | 7.007 | 1.00 | 28.55 | A | C |
| ATOM | 1624 | CZ | TYR | A | 420 | 11.562 | 70.966 | 7.253 | 1.00 | 28.01 | A | C |
| ATOM | 1625 | OH | TYR | A | 420 | 10.348 | 71.030 | 7.894 | 1.00 | 33.11 | A | O |
| ATOM | 1626 | C | TYR | A | 420 | 16.993 | 70.194 | 7.085 | 1.00 | 26.07 | A | C |
| ATOM | 1627 | O | TYR | A | 420 | 17.688 | 69.228 | 6.815 | 1.00 | 25.89 | A | O |
| ATOM | 1628 | N | PRO | A | 421 | 16.572 | 70.437 | 8.330 | 1.00 | 29.40 | A | N |
| ATOM | 1629 | CD | PRO | A | 421 | 15.558 | 71.423 | 8.712 | 1.00 | 26.73 | A | C |
| ATOM | 1630 | CA | PRO | A | 421 | 17.047 | 69.657 | 9.482 | 1.00 | 26.14 | A | C |
| ATOM | 1631 | CB | PRO | A | 421 | 16.450 | 70.395 | 10.679 | 1.00 | 26.98 | A | C |
| ATOM | 1632 | CG | PRO | A | 421 | 15.867 | 71.644 | 10.134 | 1.00 | 27.02 | A | C |
| ATOM | 1633 | C | PRO | A | 421 | 16.572 | 68.205 | 2.486 | 1.00 | 24.25 | A | C |
| ATOM | 1634 | O | PRO | A | 421 | 17.323 | 67.336 | 9.907 | 1.00 | 26.40 | A | O |
| ATOM | 1635 | N | MET | A | 422 | 15.354 | 67.945 | 9.022 | 1.00 | 25.97 | A | N |
| ATOM | 1636 | CA | MET | A | 422 | 14.784 | 66.589 | 9.059 | 1.00 | 29.90 | A | C |
| ATOM | 1637 | CB | MET | A | 422 | 13.271 | 66.615 | 8.855 | 1.00 | 25.47 | A | C |
| ATOM | 1638 | CG | MET | A | 422 | 12.493 | 67.323 | 9.947 | 1.00 | 31.29 | A | C |
| ATOM | 1639 | SD | MET | A | 422 | 10.704 | 67.261 | 9.632 | 1.00 | 35.01 | A | S |
| ATOM | 1640 | CE | MET | A | 422 | 10.208 | 68.638 | 10.667 | 1.00 | 25.43 | A | C |
| ATOM | 1641 | C | MET | A | 422 | 15.387 | 65.680 | 7.997 | 1.00 | 32.93 | A | C |
| ATOM | 1642 | O | MET | A | 422 | 15.669 | 66.122 | 6.887 | 1.00 | 25.94 | A | O |
| ATOM | 1643 | N | TYR | A | 423 | 15.567 | 64.410 | 8.351 | 1.00 | 31.03 | A | N |
| ATOM | 1644 | CA | TYR | A | 423 | 15.959 | 63.393 | 7.391 | 1.00 | 28.30 | A | C |
| ATOM | 1645 | CB | TYR | A | 423 | 16.388 | 62.101 | 8.105 | 1.00 | 29.27 | A | C |
| ATOM | 1646 | CG | TYR | A | 423 | 16.748 | 61.005 | 7.128 | 1.00 | 32.33 | A | C |
| ATOM | 1647 | CD1 | TYR | A | 423 | 15.805 | 60.062 | 6.726 | 1.00 | 33.00 | A | C |
| ATOM | 1648 | CE1 | TYR | A | 423 | 16.129 | 59.072 | 5.812 | 1.00 | 32.64 | A | C |
| ATOM | 1649 | CD2 | TYR | A | 423 | 18.018 | 60.940 | 6.567 | 1.00 | 31.17 | A | C |
| ATOM | 1650 | CE2 | TYR | A | 423 | 18.350 | 59.949 | 5.652 | 1.00 | 29.46 | A | C |
| ATOM | 1651 | CZ | TYR | A | 423 | 17.401 | 59.026 | 5.271 | 1.00 | 30.29 | A | C |
| ATOM | 1652 | OH | TYR | A | 423 | 17.725 | 58.046 | 4.351 | 1.00 | 29.62 | A | O |
| ATOM | 1653 | C | TYR | A | 423 | 14.787 | 63.092 | 6.458 | 1.00 | 32.43 | A | C |
| ATOM | 1654 | O | TYR | A | 423 | 13.672 | 62.824 | 6.912 | 1.00 | 32.50 | A | O |
| ATOM | 1655 | N | ARG | A | 424 | 15.038 | 63.146 | 5.159 | 1.00 | 30.14 | A | N |
| ATOM | 1656 | CA | ARG | A | 424 | 14.054 | 62.721 | 4.177 | 1.00 | 34.92 | A | C |
| ATOM | 1657 | CB | ARG | A | 424 | 13.285 | 63.915 | 3.595 | 1.00 | 36.59 | A | C |
| ATOM | 1658 | CG | ARG | A | 424 | 14.093 | 64.733 | 2.590 | 1.00 | 41.10 | A | C |
| ATOM | 1659 | CD | ARG | A | 424 | 13.209 | 65.336 | 1.496 | 1.00 | 46.52 | A | C |
| ATOM | 1660 | NE | ARG | A | 424 | 14.014 | 65.973 | 0.460 | 1.00 | 40.47 | A | N |
| ATOM | 1661 | CZ | ARG | A | 424 | 13.712 | 65.984 | −0.836 | 1.00 | 43.48 | A | C |
| ATOM | 1662 | NH1 | ARG | A | 424 | 12.609 | 65.386 | −1.276 | 1.00 | 48.17 | A | N |
| ATOM | 1663 | NH2 | ARG | A | 424 | 14.524 | 66.585 | −1.698 | 1.00 | 37.23 | A | N |
| ATOM | 1664 | C | ARG | A | 424 | 14.791 | 61.993 | 3.066 | 1.00 | 34.15 | A | C |
| ATOM | 1665 | O | ARG | A | 424 | 15.629 | 62.583 | 2.378 | 1.00 | 36.98 | A | O |
| ATOM | 1666 | N | PHE | A | 425 | 14.509 | 60.707 | 2.893 | 1.00 | 33.04 | A | N |
| ATOM | 1667 | CA | PHE | A | 425 | 15.196 | 59.949 | 1.857 | 1.00 | 32.72 | A | C |
| ATOM | 1668 | CB | PHE | A | 425 | 14.980 | 58.445 | 1.990 | 1.00 | 34.73 | A | C |
| ATOM | 1669 | CG | PHE | A | 425 | 15.611 | 57.657 | 0.876 | 1.00 | 32.87 | A | C |
| ATOM | 1670 | CD1 | PHE | A | 425 | 16.973 | 57.428 | 0.862 | 1.00 | 32.99 | A | C |
| ATOM | 1671 | CD2 | PHE | A | 425 | 14.852 | 57.185 | −0.175 | 1.00 | 33.53 | A | C |
| ATOM | 1672 | CE1 | PHE | A | 425 | 17.567 | 56.717 | −0.174 | 1.00 | 34.01 | A | C |
| ATOM | 1673 | CE2 | PHE | A | 425 | 15.441 | 56.475 | −1.214 | 1.00 | 35.94 | A | C |
| ATOM | 1674 | CZ | PHE | A | 425 | 16.797 | 56.238 | −1.207 | 1.00 | 33.62 | A | C |
| ATOM | 1675 | C | PHE | A | 425 | 14.730 | 60.394 | 0.489 | 1.00 | 31.38 | A | C |
| ATOM | 1676 | O | PHE | A | 425 | 13.567 | 60.707 | 0.297 | 1.00 | 31.98 | A | O |
| ATOM | 1677 | N | THR | A | 426 | 15.653 | 60.418 | −0.465 | 1.00 | 31.59 | A | N |
| ATOM | 1678 | CA | THR | A | 426 | 15.329 | 60.773 | −1.838 | 1.00 | 31.80 | A | C |
| ATOM | 1679 | CB | THR | A | 426 | 15.512 | 62.293 | −2.081 | 1.00 | 32.79 | A | C |
| ATOM | 1680 | OG1 | THR | A | 426 | 15.015 | 62.645 | −3.380 | 1.00 | 30.88 | A | O |
| ATOM | 1681 | CG2 | THR | A | 426 | 16.975 | 62.675 | −1.987 | 1.00 | 30.39 | A | C |
| ATOM | 1682 | C | THR | A | 426 | 16.267 | 60.019 | −2.756 | 1.00 | 31.70 | A | C |
| ATOM | 1683 | O | THR | A | 426 | 17.390 | 59.698 | −2.371 | 1.00 | 28.98 | A | O |
| ATOM | 1684 | N | GLU | A | 427 | 15.810 | 59.737 | −3.972 | 1.00 | 34.15 | A | N |
| ATOM | 1685 | CA | GLU | A | 427 | 16.706 | 59.236 | −5.012 | 1.00 | 35.81 | A | C |
| ATOM | 1686 | CB | GLU | A | 427 | 16.096 | 58.031 | −5.731 | 1.00 | 40.71 | A | C |
| ATOM | 1687 | CG | GLU | A | 427 | 16.002 | 56.804 | −4.837 | 1.00 | 45.17 | A | C |
| ATOM | 1688 | CD | GLU | A | 427 | 15.363 | 55.619 | −5.519 | 1.00 | 54.28 | A | C |
| ATOM | 1689 | OE1 | GLU | A | 427 | 14.396 | 55.818 | −6.282 | 1.00 | 56.04 | A | O |
| ATOM | 1690 | OE2 | GLU | A | 427 | 15.824 | 54.485 | −5.277 | 1.00 | 60.76 | A | O |
| ATOM | 1691 | C | GLU | A | 427 | 17.068 | 60.349 | −5.995 | 1.00 | 33.37 | A | C |
| ATOM | 1692 | O | GLU | A | 427 | 17.986 | 60.203 | −6.798 | 1.00 | 35.70 | A | O |
| ATOM | 1693 | N | GLY | A | 428 | 16.351 | 61.466 | −5.920 | 1.00 | 33.02 | A | N |
| ATOM | 1694 | CA | GLY | A | 428 | 16.675 | 62.620 | −6.736 | 1.00 | 29.12 | A | C |
| ATOM | 1695 | C | GLY | A | 428 | 18.001 | 63.251 | −6.334 | 1.00 | 29.53 | A | C |
| ATOM | 1696 | O | GLY | A | 428 | 18.547 | 62.971 | −5.260 | 1.00 | 29.95 | A | O |
| ATOM | 1697 | N | PRO | A | 429 | 18.527 | 64.129 | −7.188 | 1.00 | 28.08 | A | N |
| ATOM | 1698 | CD | PRO | A | 429 | 17.978 | 64.559 | −8.492 | 1.00 | 27.74 | A | C |

TABLE 14-continued

Coordinates for proMMP9(35-444 ΔFnII) (SEQ ID NO: 12) complex with Example 4

| ATOM | 1699 | CA | PRO | A | 429 | 19.759 | 64.839 | −6.822 | 1.00 | 23.77 | A | C |
|---|---|---|---|---|---|---|---|---|---|---|---|---|
| ATOM | 1700 | CB | PRO | A | 429 | 19.944 | 65.836 | −7.973 | 1.00 | 23.62 | A | C |
| ATOM | 1701 | CG | PRO | A | 429 | 19.165 | 65.253 | −9.142 | 1.00 | 23.77 | A | C |
| ATOM | 1702 | C | PRO | A | 429 | 19.555 | 65.586 | −5.485 | 1.00 | 26.51 | A | C |
| ATOM | 1703 | O | PRO | A | 429 | 18.563 | 66.288 | −5.321 | 1.00 | 25.62 | A | O |
| ATOM | 1704 | N | PRO | A | 430 | 20.479 | 65.424 | −4.530 | 1.00 | 25.53 | A | N |
| ATOM | 1705 | CD | PRO | A | 430 | 21.665 | 64.544 | −4.578 | 1.00 | 22.21 | A | C |
| ATOM | 1706 | CA | PRO | A | 430 | 20.254 | 66.005 | −3.189 | 1.00 | 23.15 | A | C |
| ATOM | 1707 | CB | PRO | A | 430 | 21.440 | 65.468 | −2.369 | 1.00 | 22.53 | A | C |
| ATOM | 1708 | CG | PRO | A | 430 | 21.871 | 64.181 | −3.115 | 1.00 | 25.11 | A | C |
| ATOM | 1709 | C | PRO | A | 430 | 20.222 | 67.542 | −3.147 | 1.00 | 24.01 | A | C |
| ATOM | 1710 | O | PRO | A | 430 | 19.482 | 68.095 | −2.337 | 1.00 | 22.83 | A | O |
| ATOM | 1711 | N | LEU | A | 431 | 20.991 | 68.234 | −3.987 | 1.00 | 23.27 | A | N |
| ATOM | 1712 | CA | LEU | A | 431 | 21.052 | 69.701 | −3.885 | 1.00 | 25.99 | A | C |
| ATOM | 1713 | CB | LEU | A | 431 | 22.315 | 70.274 | −4.550 | 1.00 | 25.49 | A | C |
| ATOM | 1714 | CG | LEU | A | 431 | 23.675 | 69.929 | −3.939 | 1.00 | 28.77 | A | C |
| ATOM | 1715 | CD1 | LEU | A | 431 | 24.819 | 70.554 | −4.737 | 1.00 | 18.67 | A | C |
| ATOM | 1716 | CD2 | LEU | A | 431 | 23.738 | 70.396 | −2.496 | 1.00 | 22.61 | A | C |
| ATOM | 1717 | C | LEU | A | 431 | 19.823 | 70.384 | −4.476 | 1.00 | 26.35 | A | C |
| ATOM | 1718 | O | LEU | A | 431 | 19.279 | 69.940 | −5.473 | 1.00 | 24.35 | A | O |
| ATOM | 1719 | N | HIS | A | 432 | 19.393 | 71.469 | −3.842 | 1.00 | 26.81 | A | N |
| ATOM | 1720 | CA | HIS | A | 432 | 18.326 | 72.312 | −4.372 | 1.00 | 24.94 | A | C |
| ATOM | 1721 | CB | HIS | A | 432 | 17.054 | 72.196 | −3.511 | 1.00 | 25.02 | A | C |
| ATOM | 1722 | CG | HIS | A | 432 | 16.385 | 70.862 | −3.627 | 1.00 | 28.67 | A | C |
| ATOM | 1723 | CD2 | HIS | A | 432 | 15.220 | 70.495 | −4.203 | 1.00 | 27.83 | A | C |
| ATOM | 1724 | ND1 | HIS | A | 432 | 16.959 | 69.701 | −3.150 | 1.00 | 29.09 | A | N |
| ATOM | 1725 | CE1 | HIS | A | 432 | 16.165 | 68.682 | −3.419 | 1.00 | 26.93 | A | C |
| ATOM | 1726 | NE2 | HIS | A | 432 | 15.108 | 69.133 | −4.060 | 1.00 | 27.71 | A | N |
| ATOM | 1727 | C | HIS | A | 432 | 18.805 | 73.753 | −4.431 | 1.00 | 23.99 | A | C |
| ATOM | 1728 | O | HIS | A | 432 | 19.857 | 74.081 | −3.890 | 1.00 | 27.97 | A | O |
| ATOM | 1729 | N | LYS | A | 433 | 18.030 | 74.607 | −5.089 | 1.00 | 26.76 | A | N |
| ATOM | 1730 | CA | LYS | A | 433 | 18.389 | 76.008 | −5.257 | 1.00 | 26.56 | A | C |
| ATOM | 1731 | CB | LYS | A | 433 | 17.193 | 76.792 | −5.818 | 1.00 | 24.67 | A | C |
| ATOM | 1732 | CG | LYS | A | 433 | 16.782 | 76.354 | −7.227 | 1.00 | 21.91 | A | C |
| ATOM | 1733 | CD | LYS | A | 433 | 15.378 | 76.829 | −7.612 | 1.00 | 27.01 | A | C |
| ATOM | 1734 | CE | LYS | A | 433 | 15.062 | 76.579 | −9.105 | 1.00 | 30.42 | A | C |
| ATOM | 1735 | NZ | LYS | A | 433 | 16.004 | 77.295 | −10.041 | 1.00 | 23.69 | A | N |
| ATOM | 1736 | C | LYS | A | 433 | 18.859 | 76.614 | −3.940 | 1.00 | 27.97 | A | C |
| ATOM | 1737 | O | LYS | A | 433 | 19.905 | 77.264 | −3.878 | 1.00 | 27.51 | A | O |
| ATOM | 1738 | N | ASP | A | 434 | 18.102 | 76.371 | −2.876 | 1.00 | 27.28 | A | N |
| ATOM | 1739 | CA | ASP | A | 434 | 18.418 | 76.986 | −1.595 | 1.00 | 24.01 | A | C |
| ATOM | 1740 | CB | ASP | A | 434 | 17.364 | 76.648 | −0.538 | 1.00 | 27.46 | A | C |
| ATOM | 1741 | CG | ASP | A | 434 | 17.408 | 77.604 | 0.626 | 1.00 | 28.18 | A | C |
| ATOM | 1742 | OD1 | ASP | A | 434 | 17.232 | 78.811 | 0.382 | 1.00 | 29.69 | A | O |
| ATOM | 1743 | OD2 | ASP | A | 434 | 17.666 | 77.158 | 1.768 | 1.00 | 30.91 | A | O |
| ATOM | 1744 | C | ASP | A | 434 | 19.808 | 76.616 | −1.091 | 1.00 | 26.06 | A | C |
| ATOM | 1745 | O | ASP | A | 434 | 20.517 | 77.444 | −0.525 | 1.00 | 25.00 | A | O |
| ATOM | 1746 | N | ASP | A | 435 | 20.191 | 75.365 | −1.284 | 1.00 | 25.29 | A | N |
| ATOM | 1747 | CA | ASP | A | 435 | 21.499 | 74.902 | −0.845 | 1.00 | 25.22 | A | C |
| ATOM | 1748 | CB | ASP | A | 435 | 21.591 | 73.368 | −0.972 | 1.00 | 26.96 | A | C |
| ATOM | 1749 | CG | ASP | A | 435 | 20.433 | 72.643 | −0.268 | 1.00 | 24.70 | A | C |
| ATOM | 1750 | OD1 | ASP | A | 435 | 20.201 | 72.899 | 0.923 | 1.00 | 26.62 | A | O |
| ATOM | 1751 | OD2 | ASP | A | 435 | 19.762 | 71.804 | −0.901 | 1.00 | 26.76 | A | O |
| ATOM | 1752 | C | ASP | A | 435 | 22.619 | 75.575 | −1.654 | 1.00 | 26.00 | A | C |
| ATOM | 1753 | O | ASP | A | 435 | 23.652 | 75.968 | −1.098 | 1.00 | 25.44 | A | O |
| ATOM | 1754 | N | VAL | A | 436 | 22.406 | 75.688 | −2.966 | 1.00 | 27.05 | A | N |
| ATOM | 1755 | CA | VAL | A | 436 | 23.402 | 76.237 | −3.898 | 1.00 | 26.76 | A | C |
| ATOM | 1756 | CB | VAL | A | 436 | 22.992 | 75.995 | −5.366 | 1.00 | 28.44 | A | C |
| ATOM | 1757 | CG1 | VAL | A | 436 | 23.963 | 76.717 | −6.357 | 1.00 | 28.54 | A | C |
| ATOM | 1758 | CG2 | VAL | A | 436 | 22.917 | 74.476 | −5.649 | 1.00 | 25.57 | A | C |
| ATOM | 1759 | C | VAL | A | 436 | 23.628 | 77.727 | −3.654 | 1.00 | 27.87 | A | C |
| ATOM | 1760 | O | VAL | A | 436 | 24.759 | 78.181 | −3.512 | 1.00 | 30.24 | A | O |
| ATOM | 1761 | N | ASN | A | 437 | 22.539 | 78.479 | −3.600 | 1.00 | 27.85 | A | N |
| ATOM | 1762 | CA | ASN | A | 437 | 22.614 | 79.884 | −3.260 | 1.00 | 31.33 | A | C |
| ATOM | 1763 | CB | ASN | A | 437 | 21.240 | 80.533 | −3.366 | 1.00 | 32.53 | A | C |
| ATOM | 1764 | CG | ASN | A | 437 | 20.748 | 80.626 | −4.799 | 1.00 | 35.79 | A | C |
| ATOM | 1765 | OD1 | ASN | A | 437 | 21.510 | 80.422 | −5.759 | 1.00 | 35.87 | A | O |
| ATOM | 1766 | ND2 | ASN | A | 437 | 19.472 | 80.930 | −4.953 | 1.00 | 35.07 | A | N |
| ATOM | 1767 | C | ASN | A | 437 | 23.187 | 80.081 | −1.863 | 1.00 | 31.99 | A | C |
| ATOM | 1768 | O | ASN | A | 437 | 23.964 | 81.011 | −1.641 | 1.00 | 30.29 | A | O |
| ATOM | 1769 | N | GLY | A | 438 | 22.811 | 79.209 | −0.927 | 1.00 | 28.34 | A | N |
| ATOM | 1770 | CA | GLY | A | 438 | 23.367 | 79.276 | 0.419 | 1.00 | 26.93 | A | C |
| ATOM | 1771 | C | GLY | A | 438 | 24.888 | 79.230 | 0.372 | 1.00 | 32.48 | A | C |
| ATOM | 1772 | O | GLY | A | 438 | 25.576 | 80.091 | 0.920 | 1.00 | 33.32 | A | O |
| ATOM | 1773 | N | ILE | A | 439 | 25.423 | 78.228 | −0.316 | 1.00 | 29.69 | A | N |
| ATOM | 1774 | CA | ILE | A | 439 | 26.866 | 78.075 | −0.435 | 1.00 | 32.74 | A | C |
| ATOM | 1775 | CB | ILE | A | 439 | 27.243 | 76.653 | −0.928 | 1.00 | 29.49 | A | C |
| ATOM | 1776 | CG2 | ILE | A | 439 | 27.078 | 76.554 | −2.418 | 1.00 | 29.33 | A | C |

TABLE 14-continued

Coordinates for proMMP9(35-444 ΔFnII) (SEQ ID NO: 12) complex with Example 4

| ATOM | 1777 | CG1 | ILE | A | 439 | 28.658 | 76.275 | −0.481 | 1.00 | 33.29 | A | C |
|---|---|---|---|---|---|---|---|---|---|---|---|---|
| ATOM | 1778 | CD1 | ILE | A | 439 | 28.815 | 76.145 | 1.043 | 1.00 | 28.96 | A | C |
| ATOM | 1779 | C | ILE | A | 439 | 27.510 | 79.165 | −1.323 | 1.00 | 34.07 | A | C |
| ATOM | 1780 | O | ILE | A | 439 | 28.644 | 79.574 | −1.067 | 1.00 | 35.20 | A | O |
| ATOM | 1781 | N | ARG | A | 440 | 26.794 | 79.635 | −2.347 | 1.00 | 32.49 | A | N |
| ATOM | 1782 | CA | ARG | A | 440 | 27.293 | 80.720 | −3.201 | 1.00 | 36.62 | A | C |
| ATOM | 1783 | CB | ARG | A | 440 | 26.357 | 81.000 | −4.382 | 1.00 | 35.67 | A | C |
| ATOM | 1784 | CG | ARG | A | 440 | 26.545 | 80.111 | −5.586 | 1.00 | 37.21 | A | C |
| ATOM | 1785 | CD | ARG | A | 440 | 25.742 | 80.663 | −6.747 | 1.00 | 40.92 | A | C |
| ATOM | 1786 | NE | ARG | A | 440 | 26.563 | 81.391 | −7.718 | 1.00 | 39.70 | A | N |
| ATOM | 1787 | CZ | ARG | A | 440 | 26.137 | 81.726 | −8.933 | 1.00 | 37.75 | A | C |
| ATOM | 1788 | NH1 | ARG | A | 440 | 24.902 | 81.402 | −9.306 | 1.00 | 39.48 | A | N |
| ATOM | 1789 | NH2 | ARG | A | 440 | 26.935 | 82.374 | −9.778 | 1.00 | 37.83 | A | N |
| ATOM | 1790 | C | ARG | A | 440 | 27.461 | 82.007 | −2.419 | 1.00 | 38.89 | A | C |
| ATOM | 1791 | O | ARG | A | 440 | 28.368 | 82.798 | −2.693 | 1.00 | 41.04 | A | O |
| ATOM | 1792 | N | HIS | A | 441 | 26.564 | 82.218 | −1.460 | 1.00 | 38.38 | A | N |
| ATOM | 1793 | CA | HIS | A | 441 | 26.593 | 83.407 | −0.614 | 1.00 | 38.89 | A | C |
| ATOM | 1794 | CB | HIS | A | 441 | 25.220 | 83.658 | 0.016 | 1.00 | 36.58 | A | C |
| ATOM | 1795 | CG | HIS | A | 441 | 24.131 | 83.878 | −0.990 | 1.00 | 41.22 | A | C |
| ATOM | 1796 | CD2 | HIS | A | 441 | 22.784 | 83.916 | −0.851 | 1.00 | 40.64 | A | C |
| ATOM | 1797 | ND1 | HIS | A | 441 | 24.387 | 84.086 | −2.329 | 1.00 | 40.03 | A | N |
| ATOM | 1798 | CE1 | HIS | A | 441 | 23.243 | 84.245 | −2.974 | 1.00 | 35.91 | A | C |
| ATOM | 1799 | NE2 | HIS | A | 441 | 22.256 | 84.146 | −2.102 | 1.00 | 40.67 | A | N |
| ATOM | 1800 | C | HIS | A | 441 | 27.657 | 83.317 | 0.473 | 1.00 | 39.63 | A | C |
| ATOM | 1801 | O | HIS | A | 441 | 27.752 | 84.193 | 1.323 | 1.00 | 42.58 | A | O |
| ATOM | 1802 | N | LEU | A | 442 | 28.464 | 82.266 | 0.433 | 1.00 | 36.50 | A | N |
| ATOM | 1803 | CA | LEU | A | 442 | 29.542 | 82.098 | 1.396 | 1.00 | 38.88 | A | C |
| ATOM | 1804 | CB | LEU | A | 442 | 29.395 | 80.753 | 2.112 | 1.00 | 40.22 | A | C |
| ATOM | 1805 | CG | LEU | A | 442 | 29.497 | 80.700 | 3.640 | 1.00 | 42.51 | A | C |
| ATOM | 1806 | CD1 | LEU | A | 442 | 28.844 | 81.915 | 4.284 | 1.00 | 40.07 | A | C |
| ATOM | 1807 | CD2 | LEU | A | 442 | 28.865 | 79.418 | 4.164 | 1.00 | 29.38 | A | C |
| ATOM | 1808 | C | LEU | A | 442 | 30.914 | 82.175 | 0.725 | 1.00 | 40.09 | A | C |
| ATOM | 1809 | O | LEU | A | 442 | 31.822 | 82.834 | 1.230 | 1.00 | 41.93 | A | O |
| ATOM | 1810 | N | TYR | A | 443 | 31.055 | 81.492 | −0.409 | 1.00 | 36.48 | A | N |
| ATOM | 1811 | CA | TYR | A | 443 | 32.347 | 81.345 | −1.082 | 1.00 | 36.79 | A | C |
| ATOM | 1812 | CB | TYR | A | 443 | 32.706 | 79.859 | −1.193 | 1.00 | 34.33 | A | C |
| ATOM | 1813 | CG | TYR | A | 443 | 32.980 | 79.232 | 0.155 | 1.00 | 40.17 | A | C |
| ATOM | 1814 | CD1 | TYR | A | 443 | 34.209 | 79.414 | 0.786 | 1.00 | 38.32 | A | C |
| ATOM | 1815 | CE1 | TYR | A | 443 | 34.465 | 78.857 | 2.029 | 1.00 | 38.03 | A | C |
| ATOM | 1816 | CD2 | TYR | A | 443 | 32.008 | 78.479 | 0.811 | 1.00 | 35.43 | A | C |
| ATOM | 1817 | CE2 | TYR | A | 443 | 32.264 | 77.913 | 2.053 | 1.00 | 34.75 | A | C |
| ATOM | 1818 | CZ | TYR | A | 443 | 33.489 | 78.111 | 2.655 | 1.00 | 33.20 | A | C |
| ATOM | 1819 | OH | TYR | A | 443 | 33.760 | 77.551 | 3.880 | 1.00 | 34.31 | A | O |
| ATOM | 1820 | C | TYR | A | 443 | 32.404 | 82.003 | −2.460 | 1.00 | 41.08 | A | C |
| ATOM | 1821 | O | TYR | A | 443 | 31.394 | 82.093 | −3.160 | 1.00 | 45.49 | A | O |
| ATOM | 1822 | ZN | ZN | A | 500 | 21.993 | 69.936 | 10.164 | 1.00 | 28.09 | A | Zn |
| ATOM | 1823 | ZN | ZN | A | 501 | 30.069 | 64.692 | 18.116 | 1.00 | 38.01 | A | Zn |
| ATOM | 1824 | CA | CA | A | 502 | 20.361 | 58.697 | 17.246 | 1.00 | 39.90 | A | Ca |
| ATOM | 1825 | CA | CA | A | 504 | 38.504 | 70.165 | 12.384 | 1.00 | 55.43 | A | Ca |
| ATOM | 1826 | CA | CA | A | 505 | 41.479 | 78.513 | 7.460 | 1.00 | 53.78 | A | Ca |
| TER | 1827 | | CA | A | 505 | | | | | | | |
| ATOM | 1828 | CB | ASP | B | 41 | 4.599 | 14.284 | 39.348 | 1.00 | 57.62 | B | C |
| ATOM | 1829 | CG | ASP | B | 41 | 3.860 | 14.557 | 38.068 | 1.00 | 57.64 | B | C |
| ATOM | 1830 | OD1 | ASP | B | 41 | 3.948 | 13.726 | 37.138 | 1.00 | 55.33 | B | O |
| ATOM | 1831 | OD2 | ASP | B | 41 | 3.204 | 15.614 | 37.987 | 1.00 | 62.09 | B | O |
| ATOM | 1832 | C | ASP | B | 41 | 5.553 | 16.517 | 40.010 | 1.00 | 59.56 | B | C |
| ATOM | 1833 | O | ASP | B | 41 | 5.888 | 17.526 | 39.379 | 1.00 | 59.73 | B | O |
| ATOM | 1834 | N | ASP | B | 41 | 6.829 | 14.438 | 40.326 | 1.00 | 54.69 | B | N |
| ATOM | 1835 | CA | ASP | B | 41 | 5.869 | 15.118 | 39.474 | 1.00 | 56.03 | B | C |
| ATOM | 1836 | N | ARG | B | 42 | 4.909 | 16.572 | 41.172 | 1.00 | 59.41 | B | N |
| ATOM | 1837 | CA | ARG | B | 42 | 4.698 | 17.830 | 41.880 | 1.00 | 58.55 | B | C |
| ATOM | 1838 | CB | ARG | B | 42 | 3.982 | 17.574 | 43.208 | 1.00 | 62.12 | B | C |
| ATOM | 1839 | CG | ARG | B | 42 | 4.020 | 18.752 | 44.178 | 1.00 | 62.32 | B | C |
| ATOM | 1840 | CD | ARG | B | 42 | 2.617 | 19.297 | 44.434 | 1.00 | 67.97 | B | C |
| ATOM | 1841 | NE | ARG | B | 42 | 2.635 | 20.627 | 45.043 | 1.00 | 69.68 | B | N |
| ATOM | 1842 | CZ | ARG | B | 42 | 1.646 | 21.512 | 44.937 | 1.00 | 67.45 | B | C |
| ATOM | 1843 | NH1 | ARG | B | 42 | 0.558 | 21.212 | 44.236 | 1.00 | 61.67 | B | N |
| ATOM | 1844 | NH2 | ARG | B | 42 | 1.747 | 22.698 | 45.524 | 1.00 | 66.36 | B | N |
| ATOM | 1845 | C | ARG | B | 42 | 6.056 | 18.454 | 42.155 | 1.00 | 59.93 | B | C |
| ATOM | 1846 | O | ARG | B | 42 | 6.218 | 19.677 | 42.151 | 1.00 | 58.05 | B | O |
| ATOM | 1847 | N | GLN | B | 43 | 7.026 | 17.579 | 42.401 | 1.00 | 57.91 | B | N |
| ATOM | 1848 | CA | GLN | B | 43 | 8.398 | 17.965 | 42.665 | 1.00 | 55.81 | B | C |
| ATOM | 1849 | CB | GLN | B | 43 | 9.231 | 16.716 | 42.983 | 1.00 | 59.15 | B | C |
| ATOM | 1850 | CG | GLN | B | 43 | 8.508 | 15.657 | 43.840 | 1.00 | 61.71 | B | C |
| ATOM | 1851 | CD | GLN | B | 43 | 7.720 | 14.633 | 43.015 | 1.00 | 60.78 | B | C |
| ATOM | 1852 | OE1 | GLN | B | 43 | 8.284 | 13.914 | 42.185 | 1.00 | 61.04 | B | O |
| ATOM | 1853 | NE2 | GLN | B | 43 | 6.414 | 14.552 | 43.261 | 1.00 | 58.24 | B | N |
| ATOM | 1854 | C | GLN | B | 43 | 8.961 | 18.654 | 41.428 | 1.00 | 58.12 | B | C |

TABLE 14-continued

Coordinates for proMMP9(35-444 ΔFnII) (SEQ ID NO: 12) complex with Example 4

| ATOM | 1855 | O   | GLN | B | 43 | 9.605  | 19.704 | 41.508 | 1.00 | 54.51 | B | O |
| ATOM | 1856 | N   | LEU | B | 44 | 8.712  | 18.041 | 40.279 | 1.00 | 54.46 | B | N |
| ATOM | 1857 | CA  | LEU | B | 44 | 9.204  | 18.570 | 39.028 | 1.00 | 52.46 | B | C |
| ATOM | 1858 | CB  | LEU | B | 44 | 8.745  | 17.681 | 37.874 | 1.00 | 52.72 | B | C |
| ATOM | 1859 | CG  | LEU | B | 44 | 9.715  | 17.529 | 36.704 | 1.00 | 56.91 | B | C |
| ATOM | 1860 | CD1 | LEU | B | 44 | 9.225  | 16.459 | 35.728 | 1.00 | 52.04 | B | C |
| ATOM | 1861 | CD2 | LEU | B | 44 | 9.940  | 18.866 | 36.003 | 1.00 | 53.29 | B | C |
| ATOM | 1862 | C   | LEU | B | 44 | 8.686  | 19.991 | 38.839 | 1.00 | 50.96 | B | C |
| ATOM | 1863 | O   | LEU | B | 44 | 9.464  | 20.929 | 38.676 | 1.00 | 49.90 | B | O |
| ATOM | 1864 | N   | ALA | B | 45 | 7.368  | 20.147 | 38.870 | 1.00 | 50.63 | B | N |
| ATOM | 1865 | CA  | ALA | B | 45 | 6.753  | 21.432 | 38.582 | 1.00 | 47.02 | B | C |
| ATOM | 1866 | CB  | ALA | B | 45 | 5.249  | 21.324 | 38.701 | 1.00 | 51.53 | B | C |
| ATOM | 1867 | C   | ALA | B | 45 | 7.272  | 22.535 | 39.490 | 1.00 | 49.21 | B | C |
| ATOM | 1868 | O   | ALA | B | 45 | 7.424  | 23.682 | 39.067 | 1.00 | 46.48 | B | O |
| ATOM | 1869 | N   | GLU | B | 46 | 7.535  | 22.195 | 40.744 | 1.00 | 48.02 | B | N |
| ATOM | 1870 | CA  | GLU | B | 46 | 7.964  | 23.197 | 41.698 | 1.00 | 46.08 | B | C |
| ATOM | 1871 | CB  | GLU | B | 46 | 7.862  | 22.655 | 43.124 | 1.00 | 52.26 | B | C |
| ATOM | 1872 | CG  | GLU | B | 46 | 6.438  | 22.299 | 43.523 | 1.00 | 55.18 | B | C |
| ATOM | 1873 | CD  | GLU | B | 46 | 6.297  | 21.930 | 44.991 | 1.00 | 62.40 | B | C |
| ATOM | 1874 | OE1 | GLU | B | 46 | 7.317  | 21.617 | 45.650 | 1.00 | 58.01 | B | O |
| ATOM | 1875 | OE2 | GLU | B | 46 | 5.150  | 21.952 | 45.485 | 1.00 | 63.52 | B | O |
| ATOM | 1876 | C   | GLU | B | 46 | 9.376  | 23.661 | 41.396 | 1.00 | 42.57 | B | C |
| ATOM | 1877 | O   | GLU | B | 46 | 9.659  | 24.858 | 41.401 | 1.00 | 42.61 | B | O |
| ATOM | 1878 | N   | GLU | B | 47 | 10.259 | 22.706 | 41.131 | 1.00 | 44.28 | B | N |
| ATOM | 1879 | CA  | GLU | B | 47 | 11.657 | 22.990 | 40.809 | 1.00 | 49.40 | B | C |
| ATOM | 1880 | CB  | GLU | B | 47 | 12.387 | 21.659 | 40.637 | 1.00 | 51.72 | B | C |
| ATOM | 1881 | CG  | GLU | B | 47 | 13.897 | 21.735 | 40.681 | 1.00 | 56.10 | B | C |
| ATOM | 1882 | CD  | GLU | B | 47 | 14.524 | 20.387 | 41.011 | 1.00 | 66.64 | B | C |
| ATOM | 1883 | OE1 | GLU | B | 47 | 13.865 | 19.573 | 41.701 | 1.00 | 65.29 | B | O |
| ATOM | 1884 | OE2 | GLU | B | 47 | 15.677 | 20.145 | 40.587 | 1.00 | 66.73 | B | O |
| ATOM | 1885 | C   | GLU | B | 47 | 11.811 | 23.851 | 39.534 | 1.00 | 43.51 | B | C |
| ATOM | 1886 | O   | GLU | B | 47 | 12.550 | 24.836 | 39.511 | 1.00 | 37.90 | B | O |
| ATOM | 1887 | N   | TYR | B | 48 | 11.091 | 23.469 | 38.488 | 1.00 | 41.74 | B | N |
| ATOM | 1888 | CA  | TYR | B | 48 | 11.130 | 24.149 | 37.195 | 1.00 | 40.24 | B | C |
| ATOM | 1889 | CB  | TYR | B | 48 | 10.198 | 23.410 | 36.237 | 1.00 | 40.91 | B | C |
| ATOM | 1890 | CG  | TYR | B | 48 | 10.361 | 23.711 | 34.765 | 1.00 | 40.48 | B | C |
| ATOM | 1891 | CD1 | TYR | B | 48 | 9.809  | 24.858 | 34.202 | 1.00 | 39.11 | B | C |
| ATOM | 1892 | CE1 | TYR | B | 48 | 9.942  | 25.123 | 32.847 | 1.00 | 37.45 | B | C |
| ATOM | 1893 | CD2 | TYR | B | 48 | 11.028 | 22.822 | 33.929 | 1.00 | 36.30 | B | C |
| ATOM | 1894 | CE2 | TYR | B | 48 | 11.163 | 23.069 | 32.583 | 1.00 | 36.08 | B | C |
| ATOM | 1895 | CZ  | TYR | B | 48 | 10.619 | 24.219 | 32.046 | 1.00 | 38.86 | B | C |
| ATOM | 1896 | OH  | TYR | B | 48 | 10.745 | 24.464 | 30.708 | 1.00 | 33.22 | B | O |
| ATOM | 1897 | C   | TYR | B | 48 | 10.692 | 25.607 | 37.335 | 1.00 | 41.99 | B | C |
| ATOM | 1898 | O   | TYR | B | 48 | 11.426 | 26.533 | 36.979 | 1.00 | 40.32 | B | O |
| ATOM | 1899 | N   | LEU | B | 49 | 9.495  | 25.805 | 37.868 | 1.00 | 38.21 | B | N |
| ATOM | 1900 | CA  | LEU | B | 49 | 8.939  | 27.132 | 38.035 | 1.00 | 36.75 | B | C |
| ATOM | 1901 | CB  | LEU | B | 49 | 7.582  | 27.030 | 38.720 | 1.00 | 41.86 | B | C |
| ATOM | 1902 | CG  | LEU | B | 49 | 6.513  | 26.287 | 37.921 | 1.00 | 43.82 | B | C |
| ATOM | 1903 | CD1 | LEU | B | 49 | 5.430  | 25.739 | 38.829 | 1.00 | 47.45 | B | C |
| ATOM | 1904 | CD2 | LEU | B | 49 | 5.917  | 27.201 | 36.856 | 1.00 | 44.02 | B | C |
| ATOM | 1905 | C   | LEU | B | 49 | 9.856  | 28.070 | 38.813 | 1.00 | 42.56 | B | C |
| ATOM | 1906 | O   | LEU | B | 49 | 9.903  | 29.274 | 38.543 | 1.00 | 42.28 | B | O |
| ATOM | 1907 | N   | TYR | B | 50 | 10.580 | 27.541 | 39.792 | 1.00 | 39.79 | B | N |
| ATOM | 1908 | CA  | TYR | B | 50 | 11.465 | 28.403 | 40.562 | 1.00 | 40.23 | B | C |
| ATOM | 1909 | CB  | TYR | B | 50 | 11.781 | 27.805 | 41.937 | 1.00 | 44.39 | B | C |
| ATOM | 1910 | CG  | TYR | B | 50 | 13.052 | 28.356 | 42.560 | 1.00 | 43.40 | B | C |
| ATOM | 1911 | CD1 | TYR | B | 50 | 13.034 | 29.524 | 43.318 | 1.00 | 47.11 | B | C |
| ATOM | 1912 | CE1 | TYR | B | 50 | 14.203 | 30.033 | 43.890 | 1.00 | 46.40 | B | C |
| ATOM | 1913 | CD2 | TYR | B | 50 | 14.272 | 27.710 | 42.385 | 1.00 | 43.80 | B | C |
| ATOM | 1914 | CE2 | TYR | B | 50 | 15.450 | 28.207 | 42.956 | 1.00 | 47.67 | B | C |
| ATOM | 1915 | CZ  | TYR | B | 50 | 15.409 | 29.367 | 43.705 | 1.00 | 48.90 | B | C |
| ATOM | 1916 | OH  | TYR | B | 50 | 16.574 | 29.852 | 44.268 | 1.00 | 49.50 | B | O |
| ATOM | 1917 | C   | TYR | B | 50 | 12.751 | 28.635 | 39.809 | 1.00 | 39.91 | B | C |
| ATOM | 1918 | O   | TYR | B | 50 | 13.223 | 29.761 | 39.680 | 1.00 | 41.02 | B | O |
| ATOM | 1919 | N   | ARG | B | 51 | 13.331 | 27.545 | 39.335 | 1.00 | 40.60 | B | N |
| ATOM | 1920 | CA  | ARG | B | 51 | 14.602 | 27.596 | 38.635 | 1.00 | 40.66 | B | C |
| ATOM | 1921 | CB  | ARG | B | 51 | 14.938 | 26.209 | 38.109 | 1.00 | 37.44 | B | C |
| ATOM | 1922 | CG  | ARG | B | 51 | 16.150 | 26.145 | 37.267 | 1.00 | 38.53 | B | C |
| ATOM | 1923 | CD  | ARG | B | 51 | 16.238 | 24.792 | 36.596 | 1.00 | 41.46 | B | C |
| ATOM | 1924 | NE  | ARG | B | 51 | 16.714 | 23.760 | 37.504 | 1.00 | 43.17 | B | N |
| ATOM | 1925 | CZ  | ARG | B | 51 | 17.994 | 23.589 | 37.801 | 1.00 | 41.52 | B | C |
| ATOM | 1926 | NH1 | ARG | B | 51 | 18.898 | 24.399 | 37.273 | 1.00 | 44.30 | B | N |
| ATOM | 1927 | NH2 | ARG | B | 51 | 18.367 | 22.628 | 38.637 | 1.00 | 44.40 | B | N |
| ATOM | 1928 | C   | ARG | B | 51 | 14.557 | 28.585 | 37.482 | 1.00 | 37.89 | B | C |
| ATOM | 1929 | O   | ARG | B | 51 | 15.497 | 29.336 | 37.265 | 1.00 | 38.49 | B | O |
| ATOM | 1930 | N   | TYR | B | 52 | 13.450 | 28.603 | 36.752 | 1.00 | 37.43 | B | N |
| ATOM | 1931 | CA  | TYR | B | 52 | 13.388 | 29.418 | 35.543 | 1.00 | 37.67 | B | C |
| ATOM | 1932 | CB  | TYR | B | 52 | 12.773 | 28.618 | 34.386 | 1.00 | 32.61 | B | C |

TABLE 14-continued

Coordinates for proMMP9(35-444 ΔFnII) (SEQ ID NO: 12) complex with Example 4

| ATOM | 1933 | CG  | TYR | B | 52 | 13.618 | 27.405 | 34.072 | 1.00 | 33.86 | B | C |
|------|------|-----|-----|---|----|--------|--------|--------|------|-------|---|---|
| ATOM | 1934 | CD1 | TYR | B | 52 | 13.144 | 26.118 | 34.285 | 1.00 | 32.11 | B | C |
| ATOM | 1935 | CE1 | TYR | B | 52 | 13.940 | 25.013 | 34.013 | 1.00 | 33.86 | B | C |
| ATOM | 1936 | CD2 | TYR | B | 52 | 14.928 | 27.557 | 33.615 | 1.00 | 32.24 | B | C |
| ATOM | 1937 | CE2 | TYR | B | 52 | 15.723 | 26.478 | 33.348 | 1.00 | 29.22 | B | C |
| ATOM | 1938 | CZ  | TYR | B | 52 | 15.232 | 25.209 | 33.545 | 1.00 | 31.85 | B | C |
| ATOM | 1939 | OH  | TYR | B | 52 | 16.055 | 24.144 | 33.279 | 1.00 | 32.52 | B | O |
| ATOM | 1940 | C   | TYR | B | 52 | 12.732 | 30.777 | 35.744 | 1.00 | 39.64 | B | C |
| ATOM | 1941 | O   | TYR | B | 52 | 12.510 | 31.502 | 34.782 | 1.00 | 38.67 | B | O |
| ATOM | 1942 | N   | GLY | B | 53 | 12.430 | 31.116 | 37.002 | 1.00 | 41.82 | B | N |
| ATOM | 1943 | CA  | GLY | B | 53 | 11.996 | 32.458 | 37.371 | 1.00 | 42.70 | B | C |
| ATOM | 1944 | C   | GLY | B | 53 | 10.498 | 32.733 | 37.456 | 1.00 | 44.52 | B | C |
| ATOM | 1945 | O   | GLY | B | 53 | 10.075 | 33.861 | 37.720 | 1.00 | 40.63 | B | O |
| ATOM | 1946 | N   | TYR | B | 54 | 9.692  | 31.705 | 37.229 | 1.00 | 41.43 | B | N |
| ATOM | 1947 | CA  | TYR | B | 54 | 8.250  | 31.870 | 37.161 | 1.00 | 43.82 | B | C |
| ATOM | 1948 | CB  | TYR | B | 54 | 7.619  | 30.628 | 36.536 | 1.00 | 43.57 | B | C |
| ATOM | 1949 | CG  | TYR | B | 54 | 8.004  | 30.430 | 35.077 | 1.00 | 43.55 | B | C |
| ATOM | 1950 | CD1 | TYR | B | 54 | 8.997  | 29.522 | 34.704 | 1.00 | 43.54 | B | C |
| ATOM | 1951 | CE1 | TYR | B | 54 | 9.345  | 29.347 | 33.368 | 1.00 | 38.02 | B | C |
| ATOM | 1952 | CD2 | TYR | B | 54 | 7.377  | 31.160 | 34.076 | 1.00 | 43.19 | B | C |
| ATOM | 1953 | CE2 | TYR | B | 54 | 7.720  | 30.997 | 32.751 | 1.00 | 44.48 | B | C |
| ATOM | 1954 | CZ  | TYR | B | 54 | 8.699  | 30.088 | 32.400 | 1.00 | 40.27 | B | C |
| ATOM | 1955 | OH  | TYR | B | 54 | 9.021  | 29.936 | 31.074 | 1.00 | 39.85 | B | O |
| ATOM | 1956 | C   | TYR | B | 54 | 7.612  | 32.196 | 38.526 | 1.00 | 50.04 | B | C |
| ATOM | 1957 | O   | TYR | B | 54 | 6.844  | 33.156 | 38.657 | 1.00 | 44.74 | B | O |
| ATOM | 1958 | N   | THR | B | 55 | 7.935  | 31.400 | 39.538 | 1.00 | 47.55 | B | N |
| ATOM | 1959 | CA  | THR | B | 55 | 7.424  | 31.648 | 40.881 | 1.00 | 44.74 | B | C |
| ATOM | 1960 | CB  | THR | B | 55 | 7.946  | 30.601 | 41.882 | 1.00 | 43.88 | B | C |
| ATOM | 1961 | OG1 | THR | B | 55 | 9.334  | 30.833 | 42.132 | 1.00 | 53.17 | B | O |
| ATOM | 1962 | CG2 | THR | B | 55 | 7.786  | 29.196 | 41.330 | 1.00 | 39.70 | B | C |
| ATOM | 1963 | C   | THR | B | 55 | 7.790  | 33.069 | 41.341 | 1.00 | 50.30 | B | C |
| ATOM | 1964 | O   | THR | B | 55 | 6.929  | 33.818 | 41.801 | 1.00 | 51.31 | B | O |
| ATOM | 1965 | N   | ARG | B | 56 | 9.054  | 33.449 | 41.184 | 1.00 | 49.30 | B | N |
| ATOM | 1966 | CA  | ARG | B | 56 | 9.517  | 34.774 | 41.610 | 1.00 | 51.66 | B | C |
| ATOM | 1967 | CB  | ARG | B | 56 | 11.016 | 34.937 | 41.349 | 1.00 | 56.44 | B | C |
| ATOM | 1968 | CG  | ARG | B | 56 | 11.667 | 36.083 | 42.125 | 1.00 | 63.05 | B | C |
| ATOM | 1969 | CD  | ARG | B | 56 | 13.044 | 35.664 | 42.643 | 1.00 | 67.17 | B | C |
| ATOM | 1970 | NE  | ARG | B | 56 | 13.734 | 36.716 | 43.388 | 1.00 | 66.86 | B | N |
| ATOM | 1971 | CZ  | ARG | B | 56 | 15.058 | 36.833 | 43.456 | 1.00 | 70.07 | B | C |
| ATOM | 1972 | NH1 | ARG | B | 56 | 15.835 | 35.970 | 42.808 | 1.00 | 68.46 | B | N |
| ATOM | 1973 | NH2 | ARG | B | 56 | 15.609 | 37.818 | 44.159 | 1.00 | 70.07 | B | N |
| ATOM | 1974 | C   | ARG | B | 56 | 8.747  | 35.928 | 40.962 | 1.00 | 57.09 | B | C |
| ATOM | 1975 | O   | ARG | B | 56 | 8.488  | 36.944 | 41.602 | 1.00 | 54.17 | B | O |
| ATOM | 1976 | N   | VAL | B | 57 | 8.398  | 35.780 | 39.689 | 1.00 | 54.28 | B | N |
| ATOM | 1977 | CA  | VAL | B | 57 | 7.579  | 36.784 | 39.023 | 1.00 | 54.64 | B | C |
| ATOM | 1978 | CB  | VAL | B | 57 | 7.458  | 36.516 | 37.529 | 1.00 | 52.07 | B | C |
| ATOM | 1979 | CG1 | VAL | B | 57 | 6.487  | 37.490 | 36.911 | 1.00 | 52.20 | B | C |
| ATOM | 1980 | CG2 | VAL | B | 57 | 8.801  | 36.629 | 36.872 | 1.00 | 50.30 | B | C |
| ATOM | 1981 | C   | VAL | B | 57 | 6.173  | 36.771 | 39.599 | 1.00 | 58.23 | B | C |
| ATOM | 1982 | O   | VAL | B | 57 | 5.616  | 37.817 | 39.946 | 1.00 | 59.62 | B | O |
| ATOM | 1983 | N   | ALA | B | 58 | 5.605  | 35.571 | 39.677 | 1.00 | 54.58 | B | N |
| ATOM | 1984 | CA  | ALA | B | 58 | 4.266  | 35.371 | 40.216 | 1.00 | 54.29 | B | C |
| ATOM | 1985 | CB  | ALA | B | 58 | 3.945  | 33.891 | 40.273 | 1.00 | 48.36 | B | C |
| ATOM | 1986 | C   | ALA | B | 58 | 4.143  | 35.998 | 41.599 | 1.00 | 56.31 | B | C |
| ATOM | 1987 | O   | ALA | B | 58 | 3.115  | 36.582 | 41.933 | 1.00 | 61.38 | B | O |
| ATOM | 1988 | O   | GLU | B | 59 | 4.760  | 38.678 | 44.521 | 1.00 | 56.15 | B | O |
| ATOM | 1989 | N   | GLU | B | 59 | 5.201  | 35.873 | 42.394 | 1.00 | 53.35 | B | N |
| ATOM | 1990 | CA  | GLU | B | 59 | 5.266  | 36.483 | 43.719 | 1.00 | 54.16 | B | C |
| ATOM | 1991 | C   | GLU | B | 59 | 5.296  | 38.002 | 43.646 | 1.00 | 56.99 | B | C |
| ATOM | 1992 | CB  | GLU | B | 59 | 6.499  | 35.986 | 44.480 | 1.00 | 47.99 | B | C |
| ATOM | 1993 | CG  | GLU | B | 59 | 6.509  | 34.479 | 44.677 | 1.00 | 50.29 | B | C |
| ATOM | 1994 | CD  | GLU | B | 59 | 7.631  | 33.986 | 45.573 | 1.00 | 46.44 | B | C |
| ATOM | 1995 | OE1 | GLU | B | 59 | 8.714  | 34.627 | 45.624 | 1.00 | 44.75 | B | O |
| ATOM | 1996 | OE2 | GLU | B | 59 | 7.409  | 32.944 | 46.229 | 1.00 | 47.26 | B | O |
| ATOM | 1997 | O   | MET | B | 60 | 4.516  | 41.810 | 42.438 | 1.00 | 62.55 | B | O |
| ATOM | 1998 | N   | MET | B | 60 | 5.941  | 38.532 | 42.609 | 1.00 | 58.91 | B | N |
| ATOM | 1999 | CA  | MET | B | 60 | 6.063  | 39.975 | 42.429 | 1.00 | 58.55 | B | C |
| ATOM | 2000 | C   | MET | B | 60 | 4.710  | 40.624 | 42.167 | 1.00 | 62.24 | B | C |
| ATOM | 2001 | CB  | MET | B | 60 | 7.020  | 40.299 | 41.277 | 1.00 | 61.94 | B | C |
| ATOM | 2002 | CG  | MET | B | 60 | 8.484  | 39.994 | 41.569 | 1.00 | 63.88 | B | C |
| ATOM | 2003 | SD  | MET | B | 60 | 9.574  | 40.298 | 40.156 | 1.00 | 75.33 | B | S |
| ATOM | 2004 | CE  | MET | B | 60 | 10.580 | 41.639 | 40.788 | 1.00 | 68.61 | B | C |
| ATOM | 2005 | O   | ARG | B | 61 | 0.316  | 39.387 | 41.767 | 1.00 | 68.92 | B | O |
| ATOM | 2006 | N   | ARG | B | 61 | 3.774  | 39.841 | 41.641 | 1.00 | 64.10 | B | N |
| ATOM | 2007 | CA  | ARG | B | 61 | 2.460  | 40.358 | 41.274 | 1.00 | 66.40 | B | C |
| ATOM | 2008 | C   | ARG | B | 61 | 1.377  | 39.830 | 42.212 | 1.00 | 66.89 | B | C |
| ATOM | 2009 | CB  | ARG | B | 61 | 2.137  | 39.967 | 39.832 | 1.00 | 65.83 | B | C |
| ATOM | 2010 | CG  | ARG | B | 61 | 3.197  | 40.391 | 38.818 | 1.00 | 64.20 | B | C |

TABLE 14-continued

Coordinates for proMMP9(35-444 ΔFnII) (SEQ ID NO: 12) complex with Example 4

| ATOM | 2011 | CD | ARG | B | 61 | 3.435 | 39.299 | 37.784 | 1.00 | 63.60 | B | C |
|------|------|-----|-----|---|----|-------|--------|--------|------|-------|---|---|
| ATOM | 2012 | NE | ARG | B | 61 | 4.201 | 39.774 | 36.635 | 1.00 | 67.07 | B | N |
| ATOM | 2013 | CZ | ARG | B | 61 | 3.667 | 40.089 | 35.458 | 1.00 | 71.36 | B | C |
| ATOM | 2014 | NH1 | ARG | B | 61 | 2.356 | 39.978 | 35.271 | 1.00 | 69.85 | B | N |
| ATOM | 2015 | NH2 | ARG | B | 61 | 4.441 | 40.511 | 34.463 | 1.00 | 71.44 | B | N |
| ATOM | 2016 | O | GLY | B | 62 | 1.784 | 37.218 | 43.983 | 1.00 | 67.43 | B | O |
| ATOM | 2017 | N | GLY | B | 62 | 1.643 | 39.884 | 43.513 | 1.00 | 65.11 | B | N |
| ATOM | 2018 | CA | GLY | B | 62 | 0.736 | 39.304 | 44.484 | 1.00 | 65.49 | B | C |
| ATOM | 2019 | C | GLY | B | 62 | 0.772 | 37.789 | 44.386 | 1.00 | 68.91 | B | C |
| ATOM | 2020 | O | GLU | B | 63 | 0.939 | 33.877 | 45.731 | 1.00 | 69.33 | B | O |
| ATOM | 2021 | N | GLU | B | 63 | −0.333 | 37.137 | 44.737 | 1.00 | 71.67 | B | N |
| ATOM | 2022 | CA | GLU | B | 63 | −0.380 | 35.675 | 44.791 | 1.00 | 70.54 | B | C |
| ATOM | 2023 | C | GLU | B | 63 | 0.748 | 35.098 | 45.654 | 1.00 | 68.20 | B | C |
| ATOM | 2024 | CB | GLU | B | 63 | −0.343 | 35.061 | 43.387 | 1.00 | 63.60 | B | C |
| ATOM | 2025 | CG | GLU | B | 63 | −0.594 | 33.553 | 43.391 | 1.00 | 65.59 | B | C |
| ATOM | 2026 | CD | GLU | B | 63 | −1.981 | 33.172 | 43.937 | 1.00 | 63.90 | B | C |
| ATOM | 2027 | OE1 | GLU | B | 63 | −2.960 | 33.896 | 43.649 | 1.00 | 57.75 | B | O |
| ATOM | 2028 | OE2 | GLU | B | 63 | −2.095 | 32.139 | 44.638 | 1.00 | 60.45 | B | O |
| ATOM | 2029 | O | ALA | B | 66 | −1.271 | 26.997 | 42.798 | 1.00 | 69.51 | B | O |
| ATOM | 2030 | N | ALA | B | 66 | −2.081 | 28.983 | 44.548 | 1.00 | 54.43 | B | N |
| ATOM | 2031 | CA | ALA | B | 66 | −0.668 | 28.661 | 44.417 | 1.00 | 61.59 | B | C |
| ATOM | 2032 | C | ALA | B | 66 | −0.425 | 27.807 | 43.179 | 1.00 | 63.17 | B | C |
| ATOM | 2033 | CB | ALA | B | 66 | −0.161 | 27.950 | 45.665 | 1.00 | 62.88 | B | C |
| ATOM | 2034 | O | LEU | B | 67 | 0.913 | 28.041 | 39.043 | 1.00 | 53.98 | B | O |
| ATOM | 2035 | N | LEU | B | 67 | 0.737 | 27.995 | 42.563 | 1.00 | 59.81 | B | N |
| ATOM | 2036 | CA | LEU | B | 67 | 1.110 | 27.299 | 41.327 | 1.00 | 61.14 | B | C |
| ATOM | 2037 | C | LEU | B | 67 | 0.327 | 27.783 | 40.097 | 1.00 | 58.49 | B | C |
| ATOM | 2038 | CB | LEU | B | 67 | 0.992 | 25.777 | 41.483 | 1.00 | 57.74 | B | C |
| ATOM | 2039 | CG | LEU | B | 67 | 2.318 | 25.013 | 41.456 | 1.00 | 56.56 | B | C |
| ATOM | 2040 | CD1 | LEU | B | 67 | 3.208 | 25.435 | 42.608 | 1.00 | 54.76 | B | C |
| ATOM | 2041 | CD2 | LEU | B | 67 | 2.090 | 23.511 | 41.478 | 1.00 | 55.06 | B | C |
| ATOM | 2042 | N | GLY | B | 68 | −0.992 | 27.905 | 40.244 | 1.00 | 55.51 | B | N |
| ATOM | 2043 | CA | GLY | B | 68 | −1.868 | 28.317 | 39.157 | 1.00 | 53.27 | B | C |
| ATOM | 2044 | C | GLY | B | 68 | −1.391 | 29.539 | 38.394 | 1.00 | 58.72 | B | C |
| ATOM | 2045 | O | GLY | B | 68 | −1.251 | 29.497 | 37.163 | 1.00 | 57.37 | B | O |
| ATOM | 2046 | N | PRO | B | 69 | −1.147 | 30.645 | 39.116 | 1.00 | 58.22 | B | N |
| ATOM | 2047 | CD | PRO | B | 69 | −1.449 | 30.823 | 40.548 | 1.00 | 59.15 | B | C |
| ATOM | 2048 | CA | PRO | B | 69 | −0.615 | 31.871 | 38.512 | 1.00 | 51.74 | B | C |
| ATOM | 2049 | CB | PRO | B | 69 | −0.397 | 32.784 | 39.720 | 1.00 | 58.75 | B | C |
| ATOM | 2050 | CG | PRO | B | 69 | −1.387 | 32.309 | 40.721 | 1.00 | 58.35 | B | C |
| ATOM | 2051 | C | PRO | B | 69 | 0.712 | 31.605 | 37.806 | 1.00 | 53.95 | B | C |
| ATOM | 2052 | O | PRO | B | 69 | 0.822 | 31.835 | 36.605 | 1.00 | 53.13 | B | O |
| ATOM | 2053 | N | ALA | B | 70 | 1.700 | 31.118 | 38.547 | 1.00 | 52.50 | B | N |
| ATOM | 2054 | CA | ALA | B | 70 | 3.008 | 30.835 | 37.982 | 1.00 | 49.69 | B | C |
| ATOM | 2055 | CB | ALA | B | 70 | 3.928 | 30.202 | 39.030 | 1.00 | 42.95 | B | C |
| ATOM | 2056 | C | ALA | B | 70 | 2.881 | 29.938 | 36.754 | 1.00 | 50.92 | B | C |
| ATOM | 2057 | O | ALA | B | 70 | 3.554 | 30.160 | 35.746 | 1.00 | 50.97 | B | O |
| ATOM | 2058 | N | LEU | B | 71 | 2.003 | 28.943 | 36.836 | 1.00 | 49.67 | B | N |
| ATOM | 2059 | CA | LEU | B | 71 | 1.803 | 28.001 | 35.741 | 1.00 | 49.52 | B | C |
| ATOM | 2060 | CB | LEU | B | 71 | 0.764 | 26.948 | 36.116 | 1.00 | 51.84 | B | C |
| ATOM | 2061 | CG | LEU | B | 71 | 1.259 | 25.674 | 36.790 | 1.00 | 53.46 | B | C |
| ATOM | 2062 | CD1 | LEU | B | 71 | 0.344 | 24.526 | 36.415 | 1.00 | 54.90 | B | C |
| ATOM | 2063 | CD2 | LEU | B | 71 | 2.666 | 25.357 | 36.370 | 1.00 | 49.49 | B | C |
| ATOM | 2064 | C | LEU | B | 71 | 1.356 | 28.688 | 34.454 | 1.00 | 50.77 | B | C |
| ATOM | 2065 | O | LEU | B | 71 | 1.780 | 28.317 | 33.355 | 1.00 | 44.45 | B | O |
| ATOM | 2066 | N | LEU | B | 72 | 0.469 | 29.669 | 34.595 | 1.00 | 51.46 | B | N |
| ATOM | 2067 | CA | LEU | B | 72 | −0.071 | 30.370 | 33.437 | 1.00 | 53.21 | B | C |
| ATOM | 2068 | CB | LEU | B | 72 | −1.257 | 31.250 | 33.835 | 1.00 | 49.12 | B | C |
| ATOM | 2069 | CG | LEU | B | 72 | −2.442 | 31.203 | 32.867 | 1.00 | 53.99 | B | C |
| ATOM | 2070 | CD1 | LEU | B | 72 | −2.909 | 29.774 | 32.661 | 1.00 | 54.77 | B | C |
| ATOM | 2071 | CD2 | LEU | B | 72 | −3.588 | 32.073 | 33.352 | 1.00 | 61.28 | B | C |
| ATOM | 2072 | C | LEU | B | 72 | 1.017 | 31.219 | 32.795 | 1.00 | 48.74 | B | C |
| ATOM | 2073 | O | LEU | B | 72 | 1.030 | 31.415 | 31.586 | 1.00 | 47.12 | B | O |
| ATOM | 2074 | N | LEU | B | 73 | 1.913 | 31.733 | 33.629 | 1.00 | 45.48 | B | N |
| ATOM | 2075 | CA | LEU | B | 73 | 3.025 | 32.541 | 33.166 | 1.00 | 49.85 | B | C |
| ATOM | 2076 | CB | LEU | B | 73 | 3.795 | 33.108 | 34.358 | 1.00 | 45.75 | B | C |
| ATOM | 2077 | CG | LEU | B | 73 | 3.137 | 34.282 | 35.081 | 1.00 | 49.62 | B | C |
| ATOM | 2078 | CD1 | LEU | B | 73 | 4.088 | 34.861 | 36.110 | 1.00 | 52.10 | B | C |
| ATOM | 2079 | CD2 | LEU | B | 73 | 2.722 | 35.344 | 34.074 | 1.00 | 52.25 | B | C |
| ATOM | 2080 | C | LEU | B | 73 | 3.949 | 31.690 | 32.308 | 1.00 | 44.51 | B | C |
| ATOM | 2081 | O | LEU | B | 73 | 4.547 | 32.164 | 31.350 | 1.00 | 40.49 | B | O |
| ATOM | 2082 | N | LEU | B | 74 | 4.043 | 30.423 | 32.678 | 1.00 | 44.12 | B | N |
| ATOM | 2083 | CA | LEU | B | 74 | 4.913 | 29.470 | 32.015 | 1.00 | 45.83 | B | C |
| ATOM | 2084 | CB | LEU | B | 74 | 5.113 | 28.263 | 32.926 | 1.00 | 40.02 | B | C |
| ATOM | 2085 | CG | LEU | B | 74 | 5.880 | 27.067 | 32.408 | 1.00 | 40.81 | B | C |
| ATOM | 2086 | CD1 | LEU | B | 74 | 6.625 | 26.415 | 33.563 | 1.00 | 41.20 | B | C |
| ATOM | 2087 | CD2 | LEU | B | 74 | 4.934 | 26.087 | 31.752 | 1.00 | 42.10 | B | C |
| ATOM | 2088 | C | LEU | B | 74 | 4.323 | 29.037 | 30.685 | 1.00 | 44.15 | B | C |

TABLE 14-continued

Coordinates for proMMP9(35-444 ΔFnII) (SEQ ID NO: 12) complex with Example 4

| ATOM | 2089 | O   | LEU | B | 74 | 5.023  | 28.947 | 29.678 | 1.00 | 40.39 | B | O |
|------|------|-----|-----|---|----|--------|--------|--------|------|-------|---|---|
| ATOM | 2090 | N   | GLN | B | 75 | 3.026  | 28.760 | 30.696 | 1.00 | 43.25 | B | N |
| ATOM | 2091 | CA  | GLN | B | 75 | 2.317  | 28.344 | 29.496 | 1.00 | 42.66 | B | C |
| ATOM | 2092 | CB  | GLN | B | 75 | 0.886  | 27.922 | 29.836 | 1.00 | 46.75 | B | C |
| ATOM | 2093 | CG  | GLN | B | 75 | 0.777  | 26.503 | 30.373 | 1.00 | 48.30 | B | C |
| ATOM | 2094 | CD  | GLN | B | 75 | −0.382 | 26.327 | 31.337 | 1.00 | 54.90 | B | C |
| ATOM | 2095 | OE1 | GLN | B | 75 | −1.137 | 27.264 | 31.605 | 1.00 | 51.44 | B | O |
| ATOM | 2096 | NE2 | GLN | B | 75 | −0.522 | 25.120 | 31.870 | 1.00 | 55.25 | B | N |
| ATOM | 2097 | C   | GLN | B | 75 | 2.309  | 29.456 | 28.458 | 1.00 | 41.94 | B | C |
| ATOM | 2098 | O   | GLN | B | 75 | 2.416  | 29.189 | 27.266 | 1.00 | 42.70 | B | O |
| ATOM | 2099 | N   | LYS | B | 76 | 2.174  | 30.697 | 28.909 | 1.00 | 41.54 | B | N |
| ATOM | 2100 | CA  | LYS | B | 76 | 2.229  | 31.837 | 27.996 | 1.00 | 43.18 | B | C |
| ATOM | 2101 | CB  | LYS | B | 76 | 1.822  | 33.138 | 28.696 | 1.00 | 42.56 | B | C |
| ATOM | 2102 | CG  | LYS | B | 76 | 0.399  | 33.151 | 29.238 | 1.00 | 53.22 | B | C |
| ATOM | 2103 | CD  | LYS | B | 76 | 0.061  | 34.488 | 29.890 | 1.00 | 57.10 | B | C |
| ATOM | 2104 | CE  | LYS | B | 76 | −1.406 | 34.558 | 30.309 | 1.00 | 55.64 | B | C |
| ATOM | 2105 | NZ  | LYS | B | 76 | −1.683 | 35.807 | 31.069 | 1.00 | 61.58 | B | N |
| ATOM | 2106 | C   | LYS | B | 76 | 3.652  | 31.979 | 27.477 | 1.00 | 41.32 | B | C |
| ATOM | 2107 | O   | LYS | B | 76 | 3.878  | 32.250 | 26.298 | 1.00 | 41.61 | B | O |
| ATOM | 2108 | N   | GLN | B | 77 | 4.608  | 31.788 | 28.377 | 1.00 | 39.90 | B | N |
| ATOM | 2109 | CA  | GLN | B | 77 | 6.016  | 31.950 | 28.051 | 1.00 | 43.73 | B | C |
| ATOM | 2110 | CB  | GLN | B | 77 | 6.853  | 31.963 | 29.338 | 1.00 | 41.93 | B | C |
| ATOM | 2111 | CG  | GLN | B | 77 | 8.316  | 32.325 | 29.142 | 1.00 | 42.12 | B | C |
| ATOM | 2112 | CD  | GLN | B | 77 | 8.520  | 33.702 | 28.508 | 1.00 | 48.35 | B | C |
| ATOM | 2113 | OE1 | GLN | B | 77 | 7.685  | 34.605 | 28.647 | 1.00 | 53.58 | B | O |
| ATOM | 2114 | NE2 | GLN | B | 77 | 9.640  | 33.860 | 27.804 | 1.00 | 44.79 | B | N |
| ATOM | 2115 | C   | GLN | B | 77 | 6.508  | 30.872 | 27.071 | 1.00 | 41.80 | B | C |
| ATOM | 2116 | O   | GLN | B | 77 | 7.310  | 31.157 | 26.196 | 1.00 | 36.58 | B | O |
| ATOM | 2117 | N   | LEU | B | 78 | 6.007  | 29.646 | 27.203 | 1.00 | 40.14 | B | N |
| ATOM | 2118 | CA  | LEU | B | 78 | 6.451  | 28.538 | 26.358 | 1.00 | 37.10 | B | C |
| ATOM | 2119 | CB  | LEU | B | 78 | 6.571  | 27.261 | 27.185 | 1.00 | 36.20 | B | C |
| ATOM | 2120 | CG  | LEU | B | 78 | 7.575  | 27.327 | 28.334 | 1.00 | 36.69 | B | C |
| ATOM | 2121 | CD1 | LEU | B | 78 | 7.725  | 25.968 | 28.977 | 1.00 | 38.24 | B | C |
| ATOM | 2122 | CD2 | LEU | B | 78 | 8.931  | 27.811 | 27.825 | 1.00 | 35.45 | B | C |
| ATOM | 2123 | C   | LEU | B | 78 | 5.521  | 28.302 | 25.163 | 1.00 | 39.24 | B | C |
| ATOM | 2124 | O   | LEU | B | 78 | 5.641  | 27.307 | 24.444 | 1.00 | 34.26 | B | O |
| ATOM | 2125 | N   | SER | B | 79 | 4.604  | 29.238 | 24.953 | 1.00 | 42.34 | B | N |
| ATOM | 2126 | CA  | SER | B | 79 | 3.545  | 29.062 | 23.972 | 1.00 | 43.21 | B | C |
| ATOM | 2127 | CB  | SER | B | 79 | 4.099  | 29.225 | 22.561 | 1.00 | 39.70 | B | C |
| ATOM | 2128 | OG  | SER | B | 79 | 4.344  | 30.600 | 22.323 | 1.00 | 39.11 | B | O |
| ATOM | 2129 | C   | SER | B | 79 | 2.807  | 27.732 | 24.144 | 1.00 | 41.66 | B | C |
| ATOM | 2130 | O   | SER | B | 79 | 2.634  | 26.968 | 23.191 | 1.00 | 39.61 | B | O |
| ATOM | 2131 | N   | LEU | B | 80 | 2.382  | 27.468 | 25.377 | 1.00 | 44.88 | B | N |
| ATOM | 2132 | CA  | LEU | B | 80 | 1.550  | 26.307 | 25.694 | 1.00 | 47.95 | B | C |
| ATOM | 2133 | CB  | LEU | B | 80 | 2.054  | 25.611 | 26.957 | 1.00 | 45.82 | B | C |
| ATOM | 2134 | CG  | LEU | B | 80 | 3.454  | 25.020 | 26.931 | 1.00 | 42.34 | B | C |
| ATOM | 2135 | CD1 | LEU | B | 80 | 3.738  | 24.371 | 28.272 | 1.00 | 46.00 | B | C |
| ATOM | 2136 | CD2 | LEU | B | 80 | 3.592  | 24.014 | 25.784 | 1.00 | 39.25 | B | C |
| ATOM | 2137 | C   | LEU | B | 80 | 0.113  | 26.755 | 25.917 | 1.00 | 45.17 | B | C |
| ATOM | 2138 | O   | LEU | B | 80 | −0.125 | 27.922 | 26.221 | 1.00 | 46.92 | B | O |
| ATOM | 2139 | N   | PRO | B | 81 | −0.846 | 25.829 | 25.760 | 1.00 | 46.80 | B | N |
| ATOM | 2140 | CD  | PRO | B | 81 | −0.628 | 24.483 | 25.198 | 1.00 | 50.68 | B | C |
| ATOM | 2141 | CA  | PRO | B | 81 | −2.256 | 26.057 | 26.103 | 1.00 | 51.00 | B | C |
| ATOM | 2142 | CB  | PRO | B | 81 | −2.848 | 24.648 | 26.056 | 1.00 | 53.70 | B | C |
| ATOM | 2143 | CG  | PRO | B | 81 | −2.026 | 23.943 | 25.033 | 1.00 | 53.27 | B | C |
| ATOM | 2144 | C   | PRO | B | 81 | −2.366 | 26.610 | 27.518 | 1.00 | 50.89 | B | C |
| ATOM | 2145 | O   | PRO | B | 81 | −1.925 | 25.939 | 28.457 | 1.00 | 53.09 | B | O |
| ATOM | 2146 | N   | GLU | B | 82 | −2.949 | 27.799 | 27.664 | 1.00 | 49.69 | B | N |
| ATOM | 2147 | CA  | GLU | B | 82 | −2.903 | 28.538 | 28.923 | 1.00 | 51.37 | B | C |
| ATOM | 2148 | CB  | GLU | B | 82 | −2.983 | 30.031 | 28.625 | 1.00 | 52.24 | B | C |
| ATOM | 2149 | CG  | GLU | B | 82 | −2.193 | 30.402 | 27.385 | 1.00 | 50.97 | B | C |
| ATOM | 2150 | CD  | GLU | B | 82 | −1.935 | 31.888 | 27.253 | 1.00 | 55.70 | B | C |
| ATOM | 2151 | OE1 | GLU | B | 82 | −2.318 | 32.637 | 28.173 | 1.00 | 55.48 | B | O |
| ATOM | 2152 | OE2 | GLU | B | 82 | −1.336 | 32.306 | 26.231 | 1.00 | 57.32 | B | O |
| ATOM | 2153 | C   | GLU | B | 82 | −3.976 | 28.102 | 29.930 | 1.00 | 57.05 | B | C |
| ATOM | 2154 | O   | GLU | B | 82 | −4.798 | 28.904 | 30.380 | 1.00 | 56.14 | B | O |
| ATOM | 2155 | N   | THR | B | 83 | −3.942 | 26.823 | 30.289 | 1.00 | 55.88 | B | N |
| ATOM | 2156 | CA  | THR | B | 83 | −4.939 | 26.237 | 31.170 | 1.00 | 55.16 | B | C |
| ATOM | 2157 | CB  | THR | B | 83 | −4.854 | 24.705 | 31.141 | 1.00 | 52.64 | B | C |
| ATOM | 2158 | OG1 | THR | B | 83 | −3.620 | 24.282 | 31.730 | 1.00 | 53.23 | B | O |
| ATOM | 2159 | CG2 | THR | B | 83 | −4.936 | 24.198 | 29.725 | 1.00 | 48.41 | B | C |
| ATOM | 2160 | C   | THR | B | 83 | −4.792 | 26.708 | 32.618 | 1.00 | 59.57 | B | C |
| ATOM | 2161 | O   | THR | B | 83 | −5.785 | 26.977 | 33.307 | 1.00 | 56.85 | B | O |
| ATOM | 2162 | N   | GLY | B | 84 | −3.551 | 26.798 | 33.082 | 1.00 | 57.88 | B | N |
| ATOM | 2163 | CA  | GLY | B | 84 | −3.293 | 27.156 | 34.462 | 1.00 | 53.25 | B | C |
| ATOM | 2164 | C   | GLY | B | 84 | −3.178 | 25.904 | 35.300 | 1.00 | 58.09 | B | C |
| ATOM | 2165 | O   | GLY | B | 84 | −3.139 | 25.963 | 36.530 | 1.00 | 56.84 | B | O |
| ATOM | 2166 | N   | GLU | B | 85 | −3.118 | 24.759 | 34.628 | 1.00 | 57.50 | B | N |

TABLE 14-continued

Coordinates for proMMP9(35-444 ΔFnII) (SEQ ID NO: 12) complex with Example 4

| ATOM | 2167 | CA  | GLU | B | 85 | −3.043 | 23.483 | 35.323 | 1.00 | 56.58 | B | C |
| ATOM | 2168 | CB  | GLU | B | 85 | −4.232 | 22.610 | 34.952 | 1.00 | 57.69 | B | C |
| ATOM | 2169 | CG  | GLU | B | 85 | −5.548 | 23.118 | 35.486 | 1.00 | 60.69 | B | C |
| ATOM | 2170 | CD  | GLU | B | 85 | −6.626 | 22.069 | 35.380 | 1.00 | 68.60 | B | C |
| ATOM | 2171 | OE1 | GLU | B | 85 | −6.329 | 20.988 | 34.822 | 1.00 | 64.33 | B | O |
| ATOM | 2172 | OE2 | GLU | B | 85 | −7.758 | 22.320 | 35.850 | 1.00 | 66.09 | B | O |
| ATOM | 2173 | C   | GLU | B | 85 | −1.754 | 22.729 | 35.033 | 1.00 | 57.49 | B | C |
| ATOM | 2174 | O   | GLU | B | 85 | −1.144 | 22.896 | 33.976 | 1.00 | 57.69 | B | O |
| ATOM | 2175 | N   | LEU | B | 86 | −1.348 | 21.900 | 35.987 | 1.00 | 51.25 | B | N |
| ATOM | 2176 | CA  | LEU | B | 86 | −0.186 | 21.048 | 35.825 | 1.00 | 57.10 | B | C |
| ATOM | 2177 | CB  | LEU | B | 86 | 0.321  | 20.579 | 37.191 | 1.00 | 52.95 | B | C |
| ATOM | 2178 | CG  | LEU | B | 86 | 1.685  | 19.890 | 37.227 | 1.00 | 56.27 | B | C |
| ATOM | 2179 | CD1 | LEU | B | 86 | 2.152  | 19.687 | 38.661 | 1.00 | 55.47 | B | C |
| ATOM | 2180 | CD2 | LEU | B | 86 | 2.692  | 20.714 | 36.449 | 1.00 | 55.68 | B | C |
| ATOM | 2181 | C   | LEU | B | 86 | −0.564 | 19.866 | 34.937 | 1.00 | 59.82 | B | C |
| ATOM | 2182 | O   | LEU | B | 86 | −0.310 | 18.707 | 35.272 | 1.00 | 58.79 | B | O |
| ATOM | 2183 | N   | ASP | B | 87 | −1.166 | 20.181 | 33.794 | 1.00 | 57.78 | B | N |
| ATOM | 2184 | CA  | ASP | B | 87 | −1.700 | 19.176 | 32.888 | 1.00 | 54.79 | B | C |
| ATOM | 2185 | CB  | ASP | B | 87 | −2.772 | 19.801 | 31.991 | 1.00 | 58.32 | B | C |
| ATOM | 2186 | CG  | ASP | B | 87 | −2.245 | 20.966 | 31.178 | 1.00 | 58.74 | B | C |
| ATOM | 2187 | OD1 | ASP | B | 87 | −2.875 | 22.048 | 31.210 | 1.00 | 58.51 | B | O |
| ATOM | 2188 | OD2 | ASP | B | 87 | −1.199 | 20.803 | 30.512 | 1.00 | 61.56 | B | O |
| ATOM | 2189 | C   | ASP | B | 87 | −0.643 | 18.489 | 32.028 | 1.00 | 58.98 | B | C |
| ATOM | 2190 | O   | ASP | B | 87 | 0.559  | 18.720 | 32.171 | 1.00 | 60.39 | B | O |
| ATOM | 2191 | N   | SER | B | 88 | −1.119 | 17.657 | 31.112 | 1.00 | 58.32 | B | N |
| ATOM | 2192 | CA  | SER | B | 88 | −0.268 | 16.819 | 30.285 | 1.00 | 55.29 | B | C |
| ATOM | 2193 | CB  | SER | B | 88 | −1.146 | 15.907 | 29.427 | 1.00 | 56.71 | B | C |
| ATOM | 2194 | OG  | SER | B | 88 | −0.367 | 15.042 | 28.619 | 1.00 | 60.79 | B | O |
| ATOM | 2195 | C   | SER | B | 88 | 0.694  | 17.614 | 29.395 | 1.00 | 55.84 | B | C |
| ATOM | 2196 | O   | SER | B | 88 | 1.862  | 17.254 | 29.261 | 1.00 | 53.72 | B | O |
| ATOM | 2197 | N   | ALA | B | 89 | 0.202  | 18.680 | 28.776 | 1.00 | 57.35 | B | N |
| ATOM | 2198 | CA  | ALA | B | 89 | 1.035  | 19.471 | 27.874 | 1.00 | 56.74 | B | C |
| ATOM | 2199 | CB  | ALA | B | 89 | 0.233  | 20.606 | 27.261 | 1.00 | 50.94 | B | C |
| ATOM | 2200 | C   | ALA | B | 89 | 2.203  | 20.030 | 28.654 | 1.00 | 53.67 | B | C |
| ATOM | 2201 | O   | ALA | B | 89 | 3.359  | 19.941 | 28.235 | 1.00 | 54.21 | B | O |
| ATOM | 2202 | N   | THR | B | 90 | 1.875  | 20.607 | 29.802 | 1.00 | 51.49 | B | N |
| ATOM | 2203 | CA  | THR | B | 90 | 2.837  | 21.285 | 30.648 | 1.00 | 51.97 | B | C |
| ATOM | 2204 | CB  | THR | B | 90 | 2.132  | 21.947 | 31.835 | 1.00 | 53.28 | B | C |
| ATOM | 2205 | OG1 | THR | B | 90 | 0.985  | 22.678 | 31.367 | 1.00 | 51.93 | B | O |
| ATOM | 2206 | CG2 | THR | B | 90 | 3.082  | 22.884 | 32.549 | 1.00 | 51.40 | B | C |
| ATOM | 2207 | C   | THR | B | 90 | 3.910  | 20.332 | 31.162 | 1.00 | 50.55 | B | C |
| ATOM | 2208 | O   | THR | B | 90 | 5.096  | 20.640 | 31.124 | 1.00 | 45.84 | B | O |
| ATOM | 2209 | N   | LEU | B | 91 | 3.480  | 19.172 | 31.641 | 1.00 | 51.37 | B | N |
| ATOM | 2210 | CA  | LEU | B | 91 | 4.390  | 18.161 | 32.164 | 1.00 | 48.46 | B | C |
| ATOM | 2211 | CB  | LEU | B | 91 | 3.586  | 16.970 | 32.679 | 1.00 | 57.50 | B | C |
| ATOM | 2212 | CG  | LEU | B | 91 | 3.634  | 16.648 | 34.172 | 1.00 | 51.59 | B | C |
| ATOM | 2213 | CD1 | LEU | B | 91 | 3.506  | 17.911 | 34.993 | 1.00 | 54.20 | B | C |
| ATOM | 2214 | CD2 | LEU | B | 91 | 2.533  | 15.660 | 34.521 | 1.00 | 55.95 | B | C |
| ATOM | 2215 | C   | LEU | B | 91 | 5.406  | 17.681 | 31.122 | 1.00 | 48.37 | B | C |
| ATOM | 2216 | O   | LEU | B | 91 | 6.588  | 17.491 | 31.425 | 1.00 | 46.48 | B | O |
| ATOM | 2217 | N   | LYS | B | 92 | 4.942  | 17.461 | 29.899 | 1.00 | 46.74 | B | N |
| ATOM | 2218 | CA  | LYS | B | 92 | 5.848  | 17.070 | 28.836 | 1.00 | 49.90 | B | C |
| ATOM | 2219 | CB  | LYS | B | 92 | 5.086  | 16.765 | 27.553 | 1.00 | 51.13 | B | C |
| ATOM | 2220 | CG  | LYS | B | 92 | 5.925  | 16.062 | 26.507 | 1.00 | 52.28 | B | C |
| ATOM | 2221 | CD  | LYS | B | 92 | 5.457  | 16.428 | 25.111 | 1.00 | 56.69 | B | C |
| ATOM | 2222 | CE  | LYS | B | 92 | 6.514  | 16.117 | 24.067 | 1.00 | 54.23 | B | C |
| ATOM | 2223 | NZ  | LYS | B | 92 | 6.375  | 17.000 | 22.878 | 1.00 | 51.65 | B | N |
| ATOM | 2224 | C   | LYS | B | 92 | 6.845  | 18.204 | 28.606 | 1.00 | 45.28 | B | C |
| ATOM | 2225 | O   | LYS | B | 92 | 8.039  | 17.972 | 28.517 | 1.00 | 47.11 | B | O |
| ATOM | 2226 | N   | ALA | B | 93 | 6.343  | 19.433 | 28.528 | 1.00 | 44.61 | B | N |
| ATOM | 2227 | CA  | ALA | B | 93 | 7.201  | 20.602 | 28.418 | 1.00 | 42.10 | B | C |
| ATOM | 2228 | CB  | ALA | B | 93 | 6.371  | 21.861 | 28.496 | 1.00 | 41.42 | B | C |
| ATOM | 2229 | C   | ALA | B | 93 | 8.286  | 20.608 | 29.501 | 1.00 | 41.89 | B | C |
| ATOM | 2230 | O   | ALA | B | 93 | 9.484  | 20.698 | 29.196 | 1.00 | 38.77 | B | O |
| ATOM | 2231 | N   | MET | B | 94 | 7.860  | 20.519 | 30.762 | 1.00 | 43.36 | B | N |
| ATOM | 2232 | CA  | MET | B | 94 | 8.781  | 20.508 | 31.903 | 1.00 | 40.24 | B | C |
| ATOM | 2233 | CB  | MET | B | 94 | 8.014  | 20.483 | 33.226 | 1.00 | 41.12 | B | C |
| ATOM | 2234 | CG  | MET | B | 94 | 7.304  | 21.792 | 33.572 | 1.00 | 44.34 | B | C |
| ATOM | 2235 | SD  | MET | B | 94 | 6.190  | 21.619 | 34.992 | 1.00 | 42.55 | B | S |
| ATOM | 2236 | CE  | MET | B | 94 | 5.646  | 23.308 | 35.253 | 1.00 | 40.03 | B | C |
| ATOM | 2237 | C   | MET | B | 94 | 9.813  | 19.372 | 31.887 | 1.00 | 38.62 | B | C |
| ATOM | 2238 | O   | MET | B | 94 | 10.893 | 19.521 | 32.451 | 1.00 | 39.23 | B | O |
| ATOM | 2239 | N   | ARG | B | 95 | 9.481  | 18.247 | 31.261 | 1.00 | 40.53 | B | N |
| ATOM | 2240 | CA  | ARG | B | 95 | 10.413 | 17.118 | 31.144 | 1.00 | 40.27 | B | C |
| ATOM | 2241 | CB  | ARG | B | 95 | 9.673  | 15.801 | 30.880 | 1.00 | 43.17 | B | C |
| ATOM | 2242 | CG  | ARG | B | 95 | 8.940  | 15.194 | 32.059 | 1.00 | 50.81 | B | C |
| ATOM | 2243 | CD  | ARG | B | 95 | 8.274  | 13.896 | 31.627 | 1.00 | 50.30 | B | C |
| ATOM | 2244 | NE  | ARG | B | 95 | 7.020  | 13.664 | 32.332 | 1.00 | 59.49 | B | N |

TABLE 14-continued

Coordinates for proMMP9(35-444 ΔFnII) (SEQ ID NO: 12) complex with Example 4

| ATOM | 2245 | CZ | ARG | B | 95 | 5.899 | 13.255 | 31.746 | 1.00 | 59.61 | B | C |
|---|---|---|---|---|---|---|---|---|---|---|---|---|
| ATOM | 2246 | NH1 | ARG | B | 95 | 5.874 | 13.023 | 30.437 | 1.00 | 57.56 | B | N |
| ATOM | 2247 | NH2 | ARG | B | 95 | 4.805 | 13.072 | 32.471 | 1.00 | 61.42 | B | N |
| ATOM | 2248 | C | ARG | B | 95 | 11.408 | 17.302 | 30.008 | 1.00 | 38.25 | B | C |
| ATOM | 2249 | O | ARG | B | 95 | 12.346 | 16.522 | 29.883 | 1.00 | 36.11 | B | O |
| ATOM | 2250 | N | THR | B | 96 | 11.192 | 18.305 | 29.161 | 1.00 | 36.88 | B | N |
| ATOM | 2251 | CA | THR | B | 96 | 12.015 | 18.445 | 27.957 | 1.00 | 37.14 | B | C |
| ATOM | 2252 | CB | THR | B | 96 | 11.305 | 19.267 | 26.886 | 1.00 | 35.78 | B | C |
| ATOM | 2253 | OG1 | THR | B | 96 | 9.949 | 18.827 | 26.798 | 1.00 | 40.76 | B | O |
| ATOM | 2254 | CG2 | THR | B | 96 | 11.968 | 19.067 | 25.534 | 1.00 | 38.38 | B | C |
| ATOM | 2255 | C | THR | B | 96 | 13.357 | 19.072 | 28.284 | 1.00 | 34.10 | B | C |
| ATOM | 2256 | O | THR | B | 96 | 13.415 | 20.161 | 28.872 | 1.00 | 33.78 | B | O |
| ATOM | 2257 | N | PRO | B | 97 | 14.444 | 18.373 | 27.928 | 1.00 | 34.31 | B | N |
| ATOM | 2258 | CD | PRO | B | 97 | 14.487 | 17.020 | 27.355 | 1.00 | 35.18 | B | C |
| ATOM | 2259 | CA | PRO | B | 97 | 15.783 | 18.947 | 28.072 | 1.00 | 33.33 | B | C |
| ATOM | 2260 | CB | PRO | B | 97 | 16.645 | 18.013 | 27.237 | 1.00 | 32.50 | B | C |
| ATOM | 2261 | CG | PRO | B | 97 | 15.964 | 16.704 | 27.367 | 1.00 | 38.80 | B | C |
| ATOM | 2262 | C | PRO | B | 97 | 15.788 | 20.358 | 27.504 | 1.00 | 31.56 | B | C |
| ATOM | 2263 | O | PRO | B | 97 | 15.038 | 20.643 | 26.571 | 1.00 | 28.23 | B | O |
| ATOM | 2264 | N | ARG | B | 98 | 16.603 | 21.235 | 28.077 | 1.00 | 31.15 | B | N |
| ATOM | 2265 | CA | ARG | B | 98 | 16.493 | 22.647 | 27.759 | 1.00 | 30.35 | B | C |
| ATOM | 2266 | CB | ARG | B | 98 | 15.224 | 23.217 | 28.382 | 1.00 | 27.02 | B | C |
| ATOM | 2267 | CG | ARG | B | 98 | 15.302 | 23.336 | 29.922 | 1.00 | 28.86 | B | C |
| ATOM | 2268 | CD | ARG | B | 98 | 14.234 | 24.293 | 30.464 | 1.00 | 29.57 | B | C |
| ATOM | 2269 | NE | ARG | B | 98 | 14.723 | 25.670 | 30.487 | 1.00 | 31.34 | B | N |
| ATOM | 2270 | CZ | ARG | B | 98 | 13.945 | 26.748 | 30.426 | 1.00 | 29.53 | B | C |
| ATOM | 2271 | NH1 | ARG | B | 98 | 12.635 | 26.614 | 30.334 | 1.00 | 27.65 | B | N |
| ATOM | 2272 | NH2 | ARG | B | 98 | 14.478 | 27.966 | 30.443 | 1.00 | 29.12 | B | N |
| ATOM | 2273 | C | ARG | B | 98 | 17.683 | 23.456 | 28.261 | 1.00 | 30.67 | B | C |
| ATOM | 2274 | O | ARG | B | 98 | 18.568 | 22.940 | 28.946 | 1.00 | 29.63 | B | O |
| ATOM | 2275 | N | CYS | B | 99 | 17.664 | 24.744 | 27.934 | 1.00 | 27.83 | B | N |
| ATOM | 2276 | CA | CYS | B | 99 | 18.707 | 25.665 | 28.341 | 1.00 | 27.69 | B | C |
| ATOM | 2277 | CB | CYS | B | 99 | 18.637 | 26.907 | 27.468 | 1.00 | 26.53 | B | C |
| ATOM | 2278 | SG | CYS | B | 99 | 19.786 | 28.177 | 27.936 | 1.00 | 25.26 | B | S |
| ATOM | 2279 | C | CYS | B | 99 | 18.566 | 26.044 | 29.823 | 1.00 | 29.26 | B | C |
| ATOM | 2280 | O | CYS | B | 99 | 17.451 | 26.169 | 30.329 | 1.00 | 28.86 | B | O |
| ATOM | 2281 | N | GLY | B | 100 | 19.701 | 26.223 | 30.505 | 1.00 | 28.11 | B | N |
| ATOM | 2282 | CA | GLY | B | 100 | 19.718 | 26.506 | 31.931 | 1.00 | 29.95 | B | C |
| ATOM | 2283 | C | GLY | B | 100 | 19.348 | 27.929 | 32.292 | 1.00 | 32.78 | B | C |
| ATOM | 2284 | O | GLY | B | 100 | 18.956 | 28.202 | 33.430 | 1.00 | 32.99 | B | O |
| ATOM | 2285 | N | VAL | B | 101 | 19.463 | 28.843 | 31.325 | 1.00 | 28.73 | B | N |
| ATOM | 2286 | CA | VAL | B | 101 | 19.168 | 30.254 | 31.569 | 1.00 | 29.95 | B | C |
| ATOM | 2287 | CB | VAL | B | 101 | 19.536 | 31.116 | 30.347 | 1.00 | 26.43 | B | C |
| ATOM | 2288 | CG1 | VAL | B | 101 | 19.136 | 32.585 | 30.560 | 1.00 | 23.85 | B | C |
| ATOM | 2289 | CG2 | VAL | B | 101 | 21.039 | 30.976 | 30.027 | 1.00 | 26.00 | B | C |
| ATOM | 2290 | C | VAL | B | 101 | 17.687 | 30.453 | 31.905 | 1.00 | 28.98 | B | C |
| ATOM | 2291 | O | VAL | B | 101 | 16.834 | 29.785 | 31.341 | 1.00 | 27.42 | B | O |
| ATOM | 2292 | N | PRO | B | 102 | 17.378 | 31.374 | 32.831 | 1.00 | 31.96 | B | N |
| ATOM | 2293 | CA | PRO | B | 102 | 15.965 | 31.518 | 33.222 | 1.00 | 34.34 | B | C |
| ATOM | 2294 | C | PRO | B | 102 | 15.104 | 32.146 | 32.124 | 1.00 | 35.79 | B | C |
| ATOM | 2295 | CB | PRO | B | 102 | 16.028 | 32.418 | 34.475 | 1.00 | 35.45 | B | C |
| ATOM | 2296 | CG | PRO | B | 102 | 17.413 | 32.192 | 35.036 | 1.00 | 35.25 | B | C |
| ATOM | 2297 | CD | PRO | B | 102 | 18.287 | 32.040 | 33.780 | 1.00 | 34.60 | B | C |
| ATOM | 2298 | O | PRO | B | 102 | 15.635 | 32.753 | 31.202 | 1.00 | 30.44 | B | O |
| ATOM | 2299 | N | ASP | B | 103 | 13.787 | 31.995 | 32.231 | 1.00 | 31.78 | B | N |
| ATOM | 2300 | CA | ASP | B | 103 | 12.867 | 32.577 | 31.258 | 1.00 | 35.82 | B | C |
| ATOM | 2301 | C | ASP | B | 103 | 12.401 | 33.944 | 31.736 | 1.00 | 37.44 | B | C |
| ATOM | 2302 | CB | ASP | B | 103 | 11.662 | 31.651 | 31.041 | 1.00 | 34.70 | B | C |
| ATOM | 2303 | CG | ASP | B | 103 | 12.073 | 30.279 | 30.558 | 1.00 | 33.62 | B | C |
| ATOM | 2304 | OD1 | ASP | B | 103 | 13.118 | 30.202 | 29.875 | 1.00 | 29.22 | B | O |
| ATOM | 2305 | OD2 | ASP | B | 103 | 11.370 | 29.281 | 30.841 | 1.00 | 29.60 | B | O |
| ATOM | 2306 | O | ASP | B | 103 | 12.142 | 34.842 | 30.935 | 1.00 | 34.45 | B | O |
| ATOM | 2307 | N | LEU | B | 104 | 12.305 | 34.095 | 33.055 | 1.00 | 39.78 | B | N |
| ATOM | 2308 | CA | LEU | B | 104 | 11.885 | 35.358 | 33.675 | 1.00 | 47.25 | B | C |
| ATOM | 2309 | C | LEU | B | 104 | 12.743 | 35.701 | 34.898 | 1.00 | 46.92 | B | C |
| ATOM | 2310 | CB | LEU | B | 104 | 10.416 | 35.278 | 34.094 | 1.00 | 46.98 | B | C |
| ATOM | 2311 | CG | LEU | B | 104 | 9.376 | 35.036 | 33.000 | 1.00 | 45.54 | B | C |
| ATOM | 2312 | CD1 | LEU | B | 104 | 8.016 | 34.802 | 33.640 | 1.00 | 49.06 | B | C |
| ATOM | 2313 | CD2 | LEU | B | 104 | 9.329 | 36.210 | 32.048 | 1.00 | 43.04 | B | C |
| ATOM | 2314 | O | LEU | B | 104 | 13.745 | 35.044 | 35.169 | 1.00 | 48.47 | B | O |
| ATOM | 2315 | N | GLY | B | 105 | 12.346 | 36.725 | 35.646 | 1.00 | 56.26 | B | N |
| ATOM | 2316 | CA | GLY | B | 105 | 13.111 | 37.132 | 36.815 | 1.00 | 62.60 | B | C |
| ATOM | 2317 | C | GLY | B | 105 | 12.274 | 37.397 | 38.056 | 1.00 | 61.85 | B | C |
| ATOM | 2318 | O | GLY | B | 105 | 11.059 | 37.541 | 37.947 | 1.00 | 64.62 | B | O |
| ATOM | 2319 | N | ARG | B | 106 | 12.887 | 37.443 | 39.241 | 1.00 | 64.34 | B | N |
| ATOM | 2320 | CA | ARG | B | 106 | 14.291 | 37.073 | 39.490 | 1.00 | 68.00 | B | C |
| ATOM | 2321 | C | ARG | B | 106 | 15.414 | 38.029 | 39.068 | 1.00 | 69.98 | B | C |
| ATOM | 2322 | CB | ARG | B | 106 | 14.599 | 35.656 | 38.997 | 1.00 | 64.01 | B | C |

TABLE 14-continued

Coordinates for proMMP9(35-444 ΔFnII) (SEQ ID NO: 12) complex with Example 4

| ATOM | 2323 | CG  | ARG | B | 106 | 14.373 | 34.590 | 40.041 | 1.00 | 60.91 | B | C |
| ---- | ---- | --- | --- | - | --- | ------ | ------ | ------ | ---- | ----- | - | - |
| ATOM | 2324 | CD  | ARG | B | 106 | 14.361 | 33.228 | 39.411 | 1.00 | 58.01 | B | C |
| ATOM | 2325 | NE  | ARG | B | 106 | 15.674 | 32.863 | 38.902 | 1.00 | 59.26 | B | N |
| ATOM | 2326 | CZ  | ARG | B | 106 | 16.560 | 32.170 | 39.605 | 1.00 | 60.73 | B | C |
| ATOM | 2327 | NH1 | ARG | B | 106 | 16.251 | 31.772 | 40.837 | 1.00 | 59.87 | B | N |
| ATOM | 2328 | NH2 | ARG | B | 106 | 17.742 | 31.870 | 39.082 | 1.00 | 56.57 | B | N |
| ATOM | 2329 | O   | ARG | B | 106 | 15.365 | 38.695 | 38.030 | 1.00 | 69.79 | B | O |
| ATOM | 2330 | N   | PHE | B | 107 | 16.430 | 38.058 | 39.921 | 1.00 | 70.43 | B | N |
| ATOM | 2331 | CA  | PHE | B | 107 | 17.674 | 38.755 | 39.669 | 1.00 | 67.30 | B | C |
| ATOM | 2332 | C   | PHE | B | 107 | 18.686 | 37.751 | 39.194 | 1.00 | 65.37 | B | C |
| ATOM | 2333 | CB  | PHE | B | 107 | 18.254 | 39.269 | 40.985 | 1.00 | 70.53 | B | C |
| ATOM | 2334 | CG  | PHE | B | 107 | 17.720 | 40.591 | 41.421 | 1.00 | 73.01 | B | C |
| ATOM | 2335 | CD1 | PHE | B | 107 | 18.525 | 41.453 | 42.142 | 1.00 | 69.47 | B | C |
| ATOM | 2336 | CD2 | PHE | B | 107 | 16.424 | 40.975 | 41.124 | 1.00 | 74.54 | B | C |
| ATOM | 2337 | CE1 | PHE | B | 107 | 18.059 | 42.668 | 42.555 | 1.00 | 68.88 | B | C |
| ATOM | 2338 | CE2 | PHE | B | 107 | 15.946 | 42.202 | 41.537 | 1.00 | 72.52 | B | C |
| ATOM | 2339 | CZ  | PHE | B | 107 | 16.767 | 43.050 | 42.256 | 1.00 | 72.60 | B | C |
| ATOM | 2340 | O   | PHE | B | 107 | 18.511 | 36.548 | 39.362 | 1.00 | 65.58 | B | O |
| ATOM | 2341 | N   | GLN | B | 108 | 19.727 | 38.286 | 38.572 | 1.00 | 67.17 | B | N |
| ATOM | 2342 | CA  | GLN | B | 108 | 21.110 | 37.858 | 38.747 | 1.00 | 59.93 | B | C |
| ATOM | 2343 | C   | GLN | B | 108 | 21.775 | 39.113 | 38.266 | 1.00 | 57.96 | B | C |
| ATOM | 2344 | CB  | GLN | B | 108 | 21.515 | 36.672 | 37.875 | 1.00 | 56.10 | B | C |
| ATOM | 2345 | CG  | GLN | B | 108 | 21.024 | 35.331 | 38.391 | 1.00 | 57.59 | B | C |
| ATOM | 2346 | CD  | GLN | B | 108 | 19.635 | 34.986 | 37.875 | 1.00 | 62.64 | B | C |
| ATOM | 2347 | OE1 | GLN | B | 108 | 19.184 | 35.519 | 36.846 | 1.00 | 60.16 | B | O |
| ATOM | 2348 | NE2 | GLN | B | 108 | 18.942 | 34.102 | 38.593 | 1.00 | 55.66 | B | N |
| ATOM | 2349 | O   | GLN | B | 108 | 22.091 | 39.234 | 37.082 | 1.00 | 61.09 | B | O |
| ATOM | 2350 | N   | VAL | B | 109 | 21.905 | 40.087 | 39.159 | 1.00 | 57.62 | B | N |
| ATOM | 2351 | CA  | VAL | B | 109 | 22.386 | 41.387 | 38.734 | 1.00 | 57.73 | B | C |
| ATOM | 2352 | C   | VAL | B | 109 | 23.626 | 41.185 | 37.866 | 1.00 | 54.43 | B | C |
| ATOM | 2353 | CB  | VAL | B | 109 | 22.653 | 42.349 | 39.916 | 1.00 | 57.85 | B | C |
| ATOM | 2354 | CG1 | VAL | B | 109 | 24.142 | 42.696 | 40.012 | 1.00 | 56.19 | B | C |
| ATOM | 2355 | CG2 | VAL | B | 109 | 22.103 | 41.772 | 41.229 | 1.00 | 60.46 | B | C |
| ATOM | 2356 | O   | VAL | B | 109 | 24.575 | 40.490 | 38.246 | 1.00 | 50.27 | B | O |
| ATOM | 2357 | N   | PHE | B | 110 | 23.568 | 41.743 | 36.667 | 1.00 | 51.11 | B | N |
| ATOM | 2358 | CA  | PHE | B | 110 | 24.698 | 41.701 | 35.758 | 1.00 | 47.89 | B | C |
| ATOM | 2359 | C   | PHE | B | 110 | 25.233 | 43.096 | 35.582 | 1.00 | 45.68 | B | C |
| ATOM | 2360 | CB  | PHE | B | 110 | 24.305 | 41.089 | 34.413 | 1.00 | 41.35 | B | C |
| ATOM | 2361 | CG  | PHE | B | 110 | 24.221 | 39.602 | 34.451 | 1.00 | 42.00 | B | C |
| ATOM | 2362 | CD1 | PHE | B | 110 | 23.023 | 38.955 | 34.211 | 1.00 | 42.08 | B | C |
| ATOM | 2363 | CD2 | PHE | B | 110 | 25.342 | 38.848 | 34.767 | 1.00 | 41.87 | B | C |
| ATOM | 2364 | CE1 | PHE | B | 110 | 22.942 | 37.576 | 34.269 | 1.00 | 41.08 | B | C |
| ATOM | 2365 | CE2 | PHE | B | 110 | 25.278 | 37.468 | 34.819 | 1.00 | 41.35 | B | C |
| ATOM | 2366 | CZ  | PHE | B | 110 | 24.067 | 36.830 | 34.578 | 1.00 | 40.11 | B | C |
| ATOM | 2367 | O   | PHE | B | 110 | 24.529 | 44.079 | 35.802 | 1.00 | 49.71 | B | O |
| ATOM | 2368 | N   | GLU | B | 111 | 26.490 | 43.184 | 35.193 | 1.00 | 44.15 | B | N |
| ATOM | 2369 | CA  | GLU | B | 111 | 27.118 | 44.476 | 35.068 | 1.00 | 42.39 | B | C |
| ATOM | 2370 | CB  | GLU | B | 111 | 28.595 | 44.364 | 35.423 | 1.00 | 45.58 | B | C |
| ATOM | 2371 | CG  | GLU | B | 111 | 29.372 | 45.650 | 35.302 | 1.00 | 54.45 | B | C |
| ATOM | 2372 | CD  | GLU | B | 111 | 30.736 | 45.542 | 35.948 | 1.00 | 61.76 | B | C |
| ATOM | 2373 | OE1 | GLU | B | 111 | 30.987 | 44.510 | 36.615 | 1.00 | 64.13 | B | O |
| ATOM | 2374 | OE2 | GLU | B | 111 | 31.546 | 46.483 | 35.798 | 1.00 | 64.21 | B | O |
| ATOM | 2375 | C   | GLU | B | 111 | 26.938 | 45.027 | 33.665 | 1.00 | 45.59 | B | C |
| ATOM | 2376 | O   | GLU | B | 111 | 27.110 | 44.317 | 32.674 | 1.00 | 41.99 | B | O |
| ATOM | 2377 | N   | GLY | B | 112 | 26.568 | 46.298 | 33.592 | 1.00 | 44.08 | B | N |
| ATOM | 2378 | CA  | GLY | B | 112 | 26.615 | 47.031 | 32.346 | 1.00 | 36.40 | B | C |
| ATOM | 2379 | C   | GLY | B | 112 | 25.395 | 46.886 | 31.464 | 1.00 | 41.12 | B | C |
| ATOM | 2380 | O   | GLY | B | 112 | 24.319 | 46.502 | 31.903 | 1.00 | 38.89 | B | O |
| ATOM | 2381 | N   | ASP | B | 113 | 25.613 | 47.183 | 30.191 | 1.00 | 39.05 | B | N |
| ATOM | 2382 | CA  | ASP | B | 113 | 24.588 | 47.286 | 29.167 | 1.00 | 42.01 | B | C |
| ATOM | 2383 | CB  | ASP | B | 113 | 25.272 | 47.851 | 27.926 | 1.00 | 38.42 | B | C |
| ATOM | 2384 | CG  | ASP | B | 113 | 24.418 | 48.805 | 27.207 | 1.00 | 39.78 | B | C |
| ATOM | 2385 | OD1 | ASP | B | 113 | 23.389 | 49.203 | 27.790 | 1.00 | 45.34 | B | O |
| ATOM | 2386 | OD2 | ASP | B | 113 | 24.765 | 49.152 | 26.070 | 1.00 | 41.96 | B | O |
| ATOM | 2387 | C   | ASP | B | 113 | 23.895 | 45.975 | 28.757 | 1.00 | 37.89 | B | C |
| ATOM | 2388 | O   | ASP | B | 113 | 22.781 | 45.984 | 28.224 | 1.00 | 33.57 | B | O |
| ATOM | 2389 | N   | LEU | B | 114 | 24.590 | 44.865 | 28.961 | 1.00 | 32.28 | B | N |
| ATOM | 2390 | CA  | LEU | B | 114 | 24.180 | 43.572 | 28.427 | 1.00 | 35.12 | B | C |
| ATOM | 2391 | CB  | LEU | B | 114 | 22.798 | 43.150 | 28.948 | 1.00 | 33.15 | B | C |
| ATOM | 2392 | CG  | LEU | B | 114 | 22.605 | 43.190 | 30.469 | 1.00 | 38.09 | B | C |
| ATOM | 2393 | CD1 | LEU | B | 114 | 21.431 | 42.276 | 30.879 | 1.00 | 37.51 | B | C |
| ATOM | 2394 | CD2 | LEU | B | 114 | 23.880 | 42.812 | 31.215 | 1.00 | 34.18 | B | C |
| ATOM | 2395 | C   | LEU | B | 114 | 24.236 | 43.511 | 26.893 | 1.00 | 33.88 | B | C |
| ATOM | 2396 | O   | LEU | B | 114 | 23.598 | 42.658 | 26.288 | 1.00 | 34.87 | B | O |
| ATOM | 2397 | N   | LYS | B | 115 | 25.001 | 44.423 | 26.284 | 1.00 | 37.42 | B | N |
| ATOM | 2398 | CA  | LYS | B | 115 | 25.389 | 44.342 | 24.871 | 1.00 | 35.10 | B | C |
| ATOM | 2399 | CB  | LYS | B | 115 | 24.737 | 45.455 | 24.043 | 1.00 | 37.98 | B | C |
| ATOM | 2400 | CG  | LYS | B | 115 | 23.245 | 45.293 | 23.859 | 1.00 | 40.88 | B | C |

TABLE 14-continued

Coordinates for proMMP9(35-444 ΔFnII) (SEQ ID NO: 12) complex with Example 4

| ATOM | 2401 | CD | LYS | B | 115 | 22.741 | 46.117 | 22.691 | 1.00 | 43.17 | B | C |
|------|------|-----|-----|---|-----|--------|--------|--------|------|-------|---|---|
| ATOM | 2402 | CE | LYS | B | 115 | 22.973 | 47.609 | 22.880 | 1.00 | 46.08 | B | C |
| ATOM | 2403 | NZ | LYS | B | 115 | 21.908 | 48.379 | 22.139 | 1.00 | 48.01 | B | N |
| ATOM | 2404 | C | LYS | B | 115 | 26.899 | 44.498 | 24.758 | 1.00 | 36.32 | B | C |
| ATOM | 2405 | O | LYS | B | 115 | 27.529 | 45.033 | 25.682 | 1.00 | 32.62 | B | O |
| ATOM | 2406 | N | TRP | B | 116 | 27.475 | 44.033 | 23.643 | 1.00 | 28.18 | B | N |
| ATOM | 2407 | CA | TRP | B | 116 | 28.880 | 44.311 | 23.346 | 1.00 | 29.82 | B | C |
| ATOM | 2408 | CB | TRP | B | 116 | 29.487 | 43.276 | 22.386 | 1.00 | 29.96 | B | C |
| ATOM | 2409 | CG | TRP | B | 116 | 29.522 | 41.888 | 22.923 | 1.00 | 26.83 | B | C |
| ATOM | 2410 | CD2 | TRP | B | 116 | 30.284 | 41.413 | 24.038 | 1.00 | 30.05 | B | C |
| ATOM | 2411 | CE2 | TRP | B | 116 | 30.002 | 40.039 | 24.180 | 1.00 | 31.33 | B | C |
| ATOM | 2412 | CE3 | TRP | B | 116 | 31.182 | 42.013 | 24.925 | 1.00 | 30.16 | B | C |
| ATOM | 2413 | CD1 | TRP | B | 116 | 28.832 | 40.810 | 22.442 | 1.00 | 29.79 | B | C |
| ATOM | 2414 | NE1 | TRP | B | 116 | 29.123 | 39.697 | 23.186 | 1.00 | 33.82 | B | N |
| ATOM | 2415 | CZ2 | TRP | B | 116 | 30.572 | 39.256 | 25.184 | 1.00 | 27.66 | B | C |
| ATOM | 2416 | CZ3 | TRP | B | 116 | 31.755 | 41.229 | 25.915 | 1.00 | 33.01 | B | C |
| ATOM | 2417 | CH2 | TRP | B | 116 | 31.447 | 39.866 | 26.034 | 1.00 | 32.26 | B | C |
| ATOM | 2418 | C | TRP | B | 116 | 29.029 | 45.691 | 22.720 | 1.00 | 34.26 | B | C |
| ATOM | 2419 | O | TRP | B | 116 | 28.147 | 46.155 | 21.991 | 1.00 | 32.27 | B | O |
| ATOM | 2420 | N | HIS | B | 117 | 30.168 | 46.326 | 22.973 | 1.00 | 35.09 | B | N |
| ATOM | 2421 | CA | HIS | B | 117 | 30.416 | 47.673 | 22.467 | 1.00 | 33.70 | B | C |
| ATOM | 2422 | CB | HIS | B | 117 | 30.415 | 48.670 | 23.615 | 1.00 | 31.37 | B | C |
| ATOM | 2423 | CG | HIS | B | 117 | 29.103 | 48.735 | 24.315 | 1.00 | 36.76 | B | C |
| ATOM | 2424 | CD2 | HIS | B | 117 | 28.652 | 48.106 | 25.422 | 1.00 | 35.38 | B | C |
| ATOM | 2425 | ND1 | HIS | B | 117 | 28.047 | 49.480 | 23.835 | 1.00 | 39.73 | B | N |
| ATOM | 2426 | CE1 | HIS | B | 117 | 27.007 | 49.329 | 24.635 | 1.00 | 38.20 | B | C |
| ATOM | 2427 | NE2 | HIS | B | 117 | 27.348 | 48.500 | 25.608 | 1.00 | 42.19 | B | N |
| ATOM | 2428 | C | HIS | B | 117 | 31.689 | 47.787 | 21.649 | 1.00 | 35.31 | B | C |
| ATOM | 2429 | O | HIS | B | 117 | 32.334 | 48.834 | 21.623 | 1.00 | 35.80 | B | O |
| ATOM | 2430 | N | HIS | B | 118 | 32.034 | 46.685 | 20.992 | 1.00 | 34.07 | B | N |
| ATOM | 2431 | CA | HIS | B | 118 | 33.114 | 46.633 | 20.026 | 1.00 | 34.15 | B | C |
| ATOM | 2432 | CB | HIS | B | 118 | 34.450 | 46.389 | 20.724 | 1.00 | 36.66 | B | C |
| ATOM | 2433 | CG | HIS | B | 118 | 34.565 | 45.050 | 21.382 | 1.00 | 34.47 | B | C |
| ATOM | 2434 | CD2 | HIS | B | 118 | 35.045 | 43.868 | 20.922 | 1.00 | 35.49 | B | C |
| ATOM | 2435 | ND1 | HIS | B | 118 | 34.190 | 44.829 | 22.691 | 1.00 | 31.81 | B | N |
| ATOM | 2436 | CE1 | HIS | B | 118 | 34.426 | 43.565 | 23.007 | 1.00 | 33.82 | B | C |
| ATOM | 2437 | NE2 | HIS | B | 118 | 34.947 | 42.962 | 21.954 | 1.00 | 33.20 | B | N |
| ATOM | 2438 | C | HIS | B | 118 | 32.762 | 45.504 | 19.064 | 1.00 | 33.10 | B | C |
| ATOM | 2439 | O | HIS | B | 118 | 32.016 | 44.602 | 19.425 | 1.00 | 32.47 | B | O |
| ATOM | 2440 | N | HIS | B | 119 | 33.269 | 45.543 | 17.842 | 1.00 | 32.23 | B | N |
| ATOM | 2441 | CA | HIS | B | 119 | 32.701 | 44.661 | 16.820 | 1.00 | 34.01 | B | C |
| ATOM | 2442 | CB | HIS | B | 119 | 32.573 | 45.379 | 15.477 | 1.00 | 38.72 | B | C |
| ATOM | 2443 | CG | HIS | B | 119 | 33.697 | 45.095 | 14.535 | 1.00 | 42.44 | B | C |
| ATOM | 2444 | CD2 | HIS | B | 119 | 33.760 | 44.310 | 13.429 | 1.00 | 43.84 | B | C |
| ATOM | 2445 | ND1 | HIS | B | 119 | 34.948 | 45.661 | 14.675 | 1.00 | 45.99 | B | N |
| ATOM | 2446 | CE1 | HIS | B | 119 | 35.730 | 45.232 | 13.701 | 1.00 | 47.41 | B | C |
| ATOM | 2447 | NE2 | HIS | B | 119 | 35.037 | 44.412 | 12.932 | 1.00 | 42.40 | B | N |
| ATOM | 2448 | C | HIS | B | 119 | 33.401 | 43.318 | 16.639 | 1.00 | 33.32 | B | C |
| ATOM | 2449 | O | HIS | B | 119 | 32.782 | 42.351 | 16.187 | 1.00 | 30.35 | B | O |
| ATOM | 2450 | N | ASN | B | 120 | 34.686 | 43.249 | 16.964 | 1.00 | 35.94 | B | N |
| ATOM | 2451 | CA | ASN | B | 120 | 35.372 | 41.973 | 16.855 | 1.00 | 34.45 | B | C |
| ATOM | 2452 | CB | ASN | B | 120 | 36.817 | 42.122 | 16.408 | 1.00 | 37.17 | B | C |
| ATOM | 2453 | CG | ASN | B | 120 | 37.501 | 40.763 | 16.180 | 1.00 | 42.30 | B | C |
| ATOM | 2454 | OD1 | ASN | B | 120 | 36.856 | 39.763 | 15.812 | 1.00 | 33.27 | B | O |
| ATOM | 2455 | ND2 | ASN | B | 120 | 38.815 | 40.727 | 16.396 | 1.00 | 42.16 | B | N |
| ATOM | 2456 | C | ASN | B | 120 | 35.308 | 41.216 | 18.167 | 1.00 | 34.97 | B | C |
| ATOM | 2457 | O | ASN | B | 120 | 36.062 | 41.488 | 19.096 | 1.00 | 31.76 | B | O |
| ATOM | 2458 | N | ILE | B | 121 | 34.408 | 40.246 | 18.224 | 1.00 | 31.32 | B | N |
| ATOM | 2459 | CA | ILE | B | 121 | 34.237 | 39.473 | 19.437 | 1.00 | 31.99 | B | C |
| ATOM | 2460 | CB | ILE | B | 121 | 32.798 | 39.030 | 19.602 | 1.00 | 26.89 | B | C |
| ATOM | 2461 | CG2 | ILE | B | 121 | 32.600 | 38.432 | 20.970 | 1.00 | 26.28 | B | C |
| ATOM | 2462 | CG1 | ILE | B | 121 | 31.871 | 40.219 | 19.363 | 1.00 | 30.44 | B | C |
| ATOM | 2463 | CD1 | ILE | B | 121 | 32.062 | 41.359 | 20.353 | 1.00 | 30.61 | B | C |
| ATOM | 2464 | C | ILE | B | 121 | 35.157 | 38.277 | 19.388 | 1.00 | 30.91 | B | C |
| ATOM | 2465 | O | ILE | B | 121 | 35.188 | 37.551 | 18.395 | 1.00 | 31.79 | B | O |
| ATOM | 2466 | N | THR | B | 122 | 35.928 | 38.096 | 20.451 | 1.00 | 28.28 | B | N |
| ATOM | 2467 | CA | THR | B | 122 | 36.887 | 37.008 | 20.510 | 1.00 | 27.84 | B | C |
| ATOM | 2468 | CB | THR | B | 122 | 38.238 | 37.487 | 21.040 | 1.00 | 29.87 | B | C |
| ATOM | 2469 | OG1 | THR | B | 122 | 38.073 | 37.969 | 22.380 | 1.00 | 29.34 | B | O |
| ATOM | 2470 | CG2 | THR | B | 122 | 38.796 | 38.606 | 20.159 | 1.00 | 27.39 | B | C |
| ATOM | 2471 | C | THR | B | 122 | 36.379 | 35.926 | 21.436 | 1.00 | 29.16 | B | C |
| ATOM | 2472 | O | THR | B | 122 | 35.688 | 36.203 | 22.424 | 1.00 | 26.04 | B | O |
| ATOM | 2473 | N | TYR | B | 123 | 36.740 | 34.686 | 21.136 | 1.00 | 28.30 | B | N |
| ATOM | 2474 | CA | TYR | B | 123 | 36.300 | 33.577 | 21.966 | 1.00 | 28.28 | B | C |
| ATOM | 2475 | CB | TYR | B | 123 | 35.039 | 32.936 | 21.394 | 1.00 | 28.24 | B | C |
| ATOM | 2476 | CG | TYR | B | 123 | 35.183 | 32.226 | 20.054 | 1.00 | 28.94 | B | C |
| ATOM | 2477 | CD1 | TYR | B | 123 | 35.043 | 32.914 | 18.856 | 1.00 | 25.71 | B | C |
| ATOM | 2478 | CE1 | TYR | B | 123 | 35.141 | 32.252 | 17.634 | 1.00 | 26.95 | B | C |

TABLE 14-continued

Coordinates for proMMP9(35-444 ΔFnII) (SEQ ID NO: 12) complex with Example 4

| ATOM | 2479 | CD2 | TYR | B | 123 | 35.432 | 30.854 | 20.000 | 1.00 | 29.89 | B | C |
|------|------|-----|-----|---|-----|--------|--------|--------|------|-------|---|---|
| ATOM | 2480 | CE2 | TYR | B | 123 | 35.539 | 30.187 | 18.800 | 1.00 | 24.71 | B | C |
| ATOM | 2481 | CZ | TYR | B | 123 | 35.395 | 30.892 | 17.625 | 1.00 | 29.20 | B | C |
| ATOM | 2482 | OH | TYR | B | 123 | 35.486 | 30.213 | 16.446 | 1.00 | 29.90 | B | O |
| ATOM | 2483 | C | TYR | B | 123 | 37.381 | 32.535 | 22.163 | 1.00 | 28.54 | B | C |
| ATOM | 2484 | O | TYR | B | 123 | 38.149 | 32.250 | 21.253 | 1.00 | 27.88 | B | O |
| ATOM | 2485 | N | TRP | B | 124 | 37.429 | 31.971 | 23.365 | 1.00 | 31.22 | B | N |
| ATOM | 2486 | CA | TRP | B | 124 | 38.419 | 30.973 | 23.702 | 1.00 | 28.09 | B | C |
| ATOM | 2487 | CB | TRP | B | 124 | 39.264 | 31.460 | 24.882 | 1.00 | 31.90 | B | C |
| ATOM | 2488 | CG | TRP | B | 124 | 40.312 | 30.498 | 25.331 | 1.00 | 32.37 | B | C |
| ATOM | 2489 | CD2 | TRP | B | 124 | 40.767 | 30.287 | 26.674 | 1.00 | 37.67 | B | C |
| ATOM | 2490 | CE2 | TRP | B | 124 | 41.780 | 29.301 | 26.623 | 1.00 | 34.69 | B | C |
| ATOM | 2491 | CE3 | TRP | B | 124 | 40.418 | 30.831 | 27.916 | 1.00 | 36.22 | B | C |
| ATOM | 2492 | CD1 | TRP | B | 124 | 41.049 | 29.658 | 24.541 | 1.00 | 36.33 | B | C |
| ATOM | 2493 | NE1 | TRP | B | 124 | 41.929 | 28.932 | 25.312 | 1.00 | 37.02 | B | N |
| ATOM | 2494 | CZ2 | TRP | B | 124 | 42.443 | 28.854 | 27.760 | 1.00 | 36.24 | B | C |
| ATOM | 2495 | CZ3 | TRP | B | 124 | 41.079 | 30.384 | 29.043 | 1.00 | 38.16 | B | C |
| ATOM | 2496 | CH2 | TRP | B | 124 | 42.081 | 29.407 | 28.958 | 1.00 | 38.34 | B | C |
| ATOM | 2497 | C | TRP | B | 124 | 37.751 | 29.660 | 24.059 | 1.00 | 32.28 | B | C |
| ATOM | 2498 | O | TRP | B | 124 | 36.956 | 29.585 | 24.997 | 1.00 | 33.08 | B | O |
| ATOM | 2499 | N | ILE | B | 125 | 38.075 | 28.620 | 23.308 | 1.00 | 31.43 | B | N |
| ATOM | 2500 | CA | ILE | B | 125 | 37.652 | 27.288 | 23.686 | 1.00 | 31.79 | B | C |
| ATOM | 2501 | CB | ILE | B | 125 | 37.652 | 26.334 | 22.490 | 1.00 | 36.01 | B | C |
| ATOM | 2502 | CG2 | ILE | B | 125 | 37.029 | 25.016 | 22.887 | 1.00 | 35.00 | B | C |
| ATOM | 2503 | CG1 | ILE | B | 125 | 36.928 | 26.987 | 21.304 | 1.00 | 35.74 | B | C |
| ATOM | 2504 | CD1 | ILE | B | 125 | 36.826 | 26.127 | 20.068 | 1.00 | 30.71 | B | C |
| ATOM | 2505 | C | ILE | B | 125 | 38.607 | 26.813 | 24.771 | 1.00 | 34.87 | B | C |
| ATOM | 2506 | O | ILE | B | 125 | 39.768 | 26.518 | 24.515 | 1.00 | 35.69 | B | O |
| ATOM | 2507 | N | GLN | B | 126 | 38.115 | 26.782 | 25.996 | 1.00 | 33.98 | B | N |
| ATOM | 2508 | CA | GLN | B | 126 | 38.959 | 26.609 | 27.167 | 1.00 | 37.38 | B | C |
| ATOM | 2509 | CB | GLN | B | 126 | 38.274 | 27.289 | 28.361 | 1.00 | 37.02 | B | C |
| ATOM | 2510 | CG | GLN | B | 126 | 38.952 | 27.162 | 29.700 | 1.00 | 41.93 | B | C |
| ATOM | 2511 | CD | GLN | B | 126 | 38.232 | 27.964 | 30.770 | 1.00 | 41.63 | B | C |
| ATOM | 2512 | OE1 | GLN | B | 126 | 37.202 | 27.536 | 31.306 | 1.00 | 41.92 | B | O |
| ATOM | 2513 | NE2 | GLN | B | 126 | 38.770 | 29.137 | 31.083 | 1.00 | 43.54 | B | N |
| ATOM | 2514 | C | GLN | B | 126 | 39.237 | 25.125 | 27.421 | 1.00 | 37.09 | B | C |
| ATOM | 2515 | O | GLN | B | 126 | 40.247 | 24.772 | 28.021 | 1.00 | 40.10 | B | O |
| ATOM | 2516 | N | ASN | B | 127 | 38.339 | 24.259 | 26.958 | 1.00 | 37.26 | B | N |
| ATOM | 2517 | CA | ASN | B | 127 | 38.549 | 22.809 | 27.027 | 1.00 | 32.95 | B | C |
| ATOM | 2518 | CB | ASN | B | 127 | 38.472 | 22.291 | 28.472 | 1.00 | 36.15 | B | C |
| ATOM | 2519 | CG | ASN | B | 127 | 37.059 | 22.302 | 29.034 | 1.00 | 36.13 | B | C |
| ATOM | 2520 | OD1 | ASN | B | 127 | 36.209 | 23.060 | 28.589 | 1.00 | 34.82 | B | O |
| ATOM | 2521 | ND2 | ASN | B | 127 | 36.808 | 21.448 | 30.020 | 1.00 | 35.31 | B | N |
| ATOM | 2522 | C | ASN | B | 127 | 37.614 | 22.050 | 26.073 | 1.00 | 36.87 | B | C |
| ATOM | 2523 | O | ASN | B | 127 | 36.801 | 22.676 | 25.381 | 1.00 | 36.09 | B | O |
| ATOM | 2524 | N | TYR | B | 128 | 37.739 | 20.720 | 26.014 | 1.00 | 34.17 | B | N |
| ATOM | 2525 | CA | TYR | B | 128 | 37.004 | 19.921 | 25.031 | 1.00 | 30.92 | B | C |
| ATOM | 2526 | CB | TYR | B | 128 | 37.945 | 19.435 | 23.934 | 1.00 | 34.44 | B | C |
| ATOM | 2527 | CG | TYR | B | 128 | 38.473 | 20.504 | 23.041 | 1.00 | 35.03 | B | C |
| ATOM | 2528 | CD1 | TYR | B | 128 | 37.872 | 20.760 | 21.826 | 1.00 | 33.74 | B | C |
| ATOM | 2529 | CE1 | TYR | B | 128 | 38.356 | 21.727 | 20.990 | 1.00 | 33.23 | B | C |
| ATOM | 2530 | CD2 | TYR | B | 128 | 39.589 | 21.250 | 23.400 | 1.00 | 36.71 | B | C |
| ATOM | 2531 | CE2 | TYR | B | 128 | 40.081 | 22.231 | 22.564 | 1.00 | 36.37 | B | C |
| ATOM | 2532 | CZ | TYR | B | 128 | 39.456 | 22.459 | 21.357 | 1.00 | 35.71 | B | C |
| ATOM | 2533 | OH | TYR | B | 128 | 39.929 | 23.427 | 20.498 | 1.00 | 37.79 | B | O |
| ATOM | 2534 | C | TYR | B | 128 | 36.360 | 18.678 | 25.588 | 1.00 | 34.96 | B | C |
| ATOM | 2535 | O | TYR | B | 128 | 37.002 | 17.916 | 26.302 | 1.00 | 41.28 | B | O |
| ATOM | 2536 | N | SER | B | 129 | 35.111 | 18.440 | 25.209 | 1.00 | 30.87 | B | N |
| ATOM | 2537 | CA | SER | B | 129 | 34.449 | 17.185 | 25.529 | 1.00 | 33.97 | B | C |
| ATOM | 2538 | CB | SER | B | 129 | 32.953 | 17.263 | 25.218 | 1.00 | 31.60 | B | C |
| ATOM | 2539 | OG | SER | B | 129 | 32.406 | 15.967 | 25.067 | 1.00 | 32.67 | B | O |
| ATOM | 2540 | C | SER | B | 129 | 35.084 | 16.038 | 24.750 | 1.00 | 37.85 | B | C |
| ATOM | 2541 | O | SER | B | 129 | 35.600 | 16.231 | 23.644 | 1.00 | 39.17 | B | O |
| ATOM | 2542 | N | GLU | B | 130 | 35.030 | 14.840 | 25.318 | 1.00 | 37.05 | B | N |
| ATOM | 2543 | CA | GLU | B | 130 | 35.640 | 13.674 | 24.689 | 1.00 | 36.25 | B | C |
| ATOM | 2544 | CB | GLU | B | 130 | 36.103 | 12.676 | 25.750 | 1.00 | 38.16 | B | C |
| ATOM | 2545 | CG | GLU | B | 130 | 37.297 | 13.165 | 26.536 | 1.00 | 43.44 | B | C |
| ATOM | 2546 | CD | GLU | B | 130 | 38.477 | 13.517 | 25.632 | 1.00 | 53.48 | B | C |
| ATOM | 2547 | OE1 | GLU | B | 130 | 38.849 | 12.670 | 24.785 | 1.00 | 55.72 | B | O |
| ATOM | 2548 | OE2 | GLU | B | 130 | 39.029 | 14.641 | 25.759 | 1.00 | 56.89 | B | O |
| ATOM | 2549 | C | GLU | B | 130 | 34.716 | 12.985 | 23.702 | 1.00 | 37.68 | B | C |
| ATOM | 2550 | O | GLU | B | 130 | 35.088 | 11.979 | 23.093 | 1.00 | 40.60 | B | O |
| ATOM | 2551 | N | ASP | B | 131 | 33.511 | 13.515 | 23.541 | 1.00 | 34.46 | B | N |
| ATOM | 2552 | CA | ASP | B | 131 | 32.526 | 12.858 | 22.697 | 1.00 | 35.34 | B | C |
| ATOM | 2553 | CB | ASP | B | 131 | 31.124 | 13.308 | 23.069 | 1.00 | 34.35 | B | C |
| ATOM | 2554 | CG | ASP | B | 131 | 30.834 | 13.135 | 24.540 | 1.00 | 37.96 | B | C |
| ATOM | 2555 | OD1 | ASP | B | 131 | 31.581 | 12.391 | 25.223 | 1.00 | 37.43 | B | O |
| ATOM | 2556 | OD2 | ASP | B | 131 | 29.856 | 13.754 | 25.007 | 1.00 | 36.10 | B | O |

TABLE 14-continued

Coordinates for proMMP9(35-444 ΔFnII) (SEQ ID NO: 12) complex with Example 4

| ATOM | 2557 | C | ASP | B | 131 | 32.747 | 13.093 | 21.207 | 1.00 | 34.52 | B | C |
|---|---|---|---|---|---|---|---|---|---|---|---|---|
| ATOM | 2558 | O | ASP | B | 131 | 32.189 | 12.367 | 20.385 | 1.00 | 32.42 | B | O |
| ATOM | 2559 | N | LEU | B | 132 | 33.544 | 14.107 | 20.872 | 1.00 | 34.53 | B | N |
| ATOM | 2560 | CA | LEU | B | 132 | 33.798 | 14.496 | 19.484 | 1.00 | 31.14 | B | C |
| ATOM | 2561 | CB | LEU | B | 132 | 32.890 | 15.676 | 19.085 | 1.00 | 32.96 | B | C |
| ATOM | 2562 | CG | LEU | B | 132 | 31.383 | 15.412 | 18.953 | 1.00 | 33.73 | B | C |
| ATOM | 2563 | CD1 | LEU | B | 132 | 30.544 | 16.680 | 19.076 | 1.00 | 27.93 | B | C |
| ATOM | 2564 | CD2 | LEU | B | 132 | 31.112 | 14.705 | 17.621 | 1.00 | 31.04 | B | C |
| ATOM | 2565 | C | LEU | B | 132 | 35.252 | 14.895 | 19.266 | 1.00 | 32.34 | B | C |
| ATOM | 2566 | O | LEU | B | 132 | 35.893 | 15.446 | 20.167 | 1.00 | 34.88 | B | O |
| ATOM | 2567 | N | PRO | B | 133 | 35.776 | 14.646 | 18.054 | 1.00 | 32.97 | B | N |
| ATOM | 2568 | CD | PRO | B | 133 | 35.129 | 13.947 | 16.930 | 1.00 | 30.43 | B | C |
| ATOM | 2569 | CA | PRO | B | 133 | 37.109 | 15.142 | 17.707 | 1.00 | 30.83 | B | C |
| ATOM | 2570 | CB | PRO | B | 133 | 37.170 | 14.937 | 16.190 | 1.00 | 29.25 | B | C |
| ATOM | 2571 | CG | PRO | B | 133 | 36.244 | 13.803 | 15.920 | 1.00 | 28.79 | B | C |
| ATOM | 2572 | C | PRO | B | 133 | 37.179 | 16.629 | 18.022 | 1.00 | 33.06 | B | C |
| ATOM | 2573 | O | PRO | B | 133 | 36.149 | 17.300 | 17.954 | 1.00 | 32.75 | B | O |
| ATOM | 2574 | N | ARG | B | 134 | 38.361 | 17.138 | 18.349 | 1.00 | 30.39 | B | N |
| ATOM | 2575 | CA | ARG | B | 134 | 38.512 | 18.561 | 18.605 | 1.00 | 31.73 | B | C |
| ATOM | 2576 | CB | ARG | B | 134 | 39.927 | 18.889 | 19.077 | 1.00 | 35.29 | B | C |
| ATOM | 2577 | CG | ARG | B | 134 | 40.282 | 18.233 | 20.392 | 1.00 | 37.20 | B | C |
| ATOM | 2578 | CD | ARG | B | 134 | 41.492 | 18.895 | 21.019 | 1.00 | 42.64 | B | C |
| ATOM | 2579 | NE | ARG | B | 134 | 41.608 | 18.524 | 22.425 | 1.00 | 46.65 | B | N |
| ATOM | 2580 | CZ | ARG | B | 134 | 42.493 | 19.037 | 23.271 | 1.00 | 48.63 | B | C |
| ATOM | 2581 | NH1 | ARG | B | 134 | 43.360 | 19.955 | 22.855 | 1.00 | 46.45 | B | N |
| ATOM | 2582 | NH2 | ARG | B | 134 | 42.509 | 18.630 | 24.541 | 1.00 | 47.56 | B | N |
| ATOM | 2583 | C | ARG | B | 134 | 38.162 | 19.405 | 17.394 | 1.00 | 33.90 | B | C |
| ATOM | 2584 | O | ARG | B | 134 | 37.568 | 20.476 | 17.535 | 1.00 | 34.24 | B | O |
| ATOM | 2585 | N | ALA | B | 135 | 38.535 | 18.930 | 16.207 | 1.00 | 31.53 | B | N |
| ATOM | 2586 | CA | ALA | B | 135 | 38.304 | 19.691 | 14.984 | 1.00 | 33.19 | B | C |
| ATOM | 2587 | CB | ALA | B | 135 | 38.973 | 19.007 | 13.782 | 1.00 | 28.43 | B | C |
| ATOM | 2588 | C | ALA | B | 135 | 36.809 | 19.859 | 14.735 | 1.00 | 32.71 | B | C |
| ATOM | 2589 | O | ALA | B | 135 | 36.359 | 20.893 | 14.236 | 1.00 | 34.13 | B | O |
| ATOM | 2590 | N | VAL | B | 136 | 36.045 | 18.827 | 15.075 | 1.00 | 33.83 | B | N |
| ATOM | 2591 | CA | VAL | B | 136 | 34.599 | 18.857 | 14.897 | 1.00 | 30.82 | B | C |
| ATOM | 2592 | CB | VAL | B | 136 | 33.979 | 17.456 | 15.052 | 1.00 | 31.74 | B | C |
| ATOM | 2593 | CG1 | VAL | B | 136 | 32.494 | 17.510 | 14.789 | 1.00 | 31.08 | B | C |
| ATOM | 2594 | CG2 | VAL | B | 136 | 34.631 | 16.484 | 14.088 | 1.00 | 32.80 | B | C |
| ATOM | 2595 | C | VAL | B | 136 | 33.967 | 19.844 | 15.890 | 1.00 | 27.26 | B | C |
| ATOM | 2596 | O | VAL | B | 136 | 33.031 | 20.577 | 15.551 | 1.00 | 28.06 | B | O |
| ATOM | 2597 | N | ILE | B | 137 | 34.494 | 19.864 | 17.109 | 1.00 | 27.08 | B | N |
| ATOM | 2598 | CA | ILE | B | 137 | 34.052 | 20.816 | 18.123 | 1.00 | 26.33 | B | C |
| ATOM | 2599 | CB | ILE | B | 137 | 34.680 | 20.513 | 19.499 | 1.00 | 28.51 | B | C |
| ATOM | 2600 | CG2 | ILE | B | 137 | 34.515 | 21.715 | 20.431 | 1.00 | 30.04 | B | C |
| ATOM | 2601 | CG1 | ILE | B | 137 | 34.035 | 19.251 | 20.107 | 1.00 | 32.07 | B | C |
| ATOM | 2602 | CD1 | ILE | B | 137 | 34.739 | 18.692 | 21.351 | 1.00 | 29.01 | B | C |
| ATOM | 2603 | C | ILE | B | 137 | 34.356 | 22.253 | 17.677 | 1.00 | 27.46 | B | C |
| ATOM | 2604 | O | ILE | B | 137 | 33.450 | 23.090 | 17.586 | 1.00 | 29.77 | B | O |
| ATOM | 2605 | N | ASP | B | 138 | 35.623 | 22.525 | 17.390 | 1.00 | 24.64 | B | N |
| ATOM | 2606 | CA | ASP | B | 138 | 36.045 | 23.787 | 16.790 | 1.00 | 28.63 | B | C |
| ATOM | 2607 | CB | ASP | B | 138 | 37.464 | 23.659 | 16.227 | 1.00 | 27.81 | B | C |
| ATOM | 2608 | CG | ASP | B | 138 | 38.513 | 23.510 | 17.313 | 1.00 | 36.90 | B | C |
| ATOM | 2609 | OD1 | ASP | B | 138 | 38.142 | 23.617 | 18.511 | 1.00 | 33.26 | B | O |
| ATOM | 2610 | OD2 | ASP | B | 138 | 39.707 | 23.290 | 16.968 | 1.00 | 33.17 | B | O |
| ATOM | 2611 | C | ASP | B | 138 | 35.117 | 24.218 | 15.658 | 1.00 | 26.40 | B | C |
| ATOM | 2612 | O | ASP | B | 138 | 34.696 | 25.364 | 15.576 | 1.00 | 27.46 | B | O |
| ATOM | 2613 | N | ASP | B | 139 | 34.817 | 23.289 | 14.766 | 1.00 | 27.90 | B | N |
| ATOM | 2614 | CA | ASP | B | 139 | 34.027 | 23.623 | 13.602 | 1.00 | 27.65 | B | C |
| ATOM | 2615 | CB | ASP | B | 139 | 34.138 | 22.519 | 12.556 | 1.00 | 30.62 | B | C |
| ATOM | 2616 | CG | ASP | B | 139 | 33.228 | 22.758 | 11.374 | 1.00 | 32.90 | B | C |
| ATOM | 2617 | OD1 | ASP | B | 139 | 33.567 | 23.594 | 10.510 | 1.00 | 34.57 | B | O |
| ATOM | 2618 | OD2 | ASP | B | 139 | 32.163 | 22.115 | 11.322 | 1.00 | 31.46 | B | O |
| ATOM | 2619 | C | ASP | B | 139 | 32.570 | 23.868 | 13.969 | 1.00 | 27.13 | B | C |
| ATOM | 2620 | O | ASP | B | 139 | 31.918 | 24.722 | 13.380 | 1.00 | 25.46 | B | O |
| ATOM | 2621 | N | ALA | B | 140 | 32.057 | 23.130 | 14.955 | 1.00 | 26.68 | B | N |
| ATOM | 2622 | CA | ALA | B | 140 | 30.689 | 23.377 | 15.434 | 1.00 | 26.01 | B | C |
| ATOM | 2623 | CB | ALA | B | 140 | 30.262 | 22.319 | 16.461 | 1.00 | 20.34 | B | C |
| ATOM | 2624 | C | ALA | B | 140 | 30.544 | 24.785 | 16.017 | 1.00 | 25.12 | B | C |
| ATOM | 2625 | O | ALA | B | 140 | 29.569 | 25.498 | 15.749 | 1.00 | 20.71 | B | O |
| ATOM | 2626 | N | PHE | B | 141 | 31.498 | 25.179 | 16.846 | 1.00 | 25.84 | B | N |
| ATOM | 2627 | CA | PHE | B | 141 | 31.434 | 26.518 | 17.420 | 1.00 | 25.66 | B | C |
| ATOM | 2628 | CB | PHE | B | 141 | 32.465 | 26.715 | 18.535 | 1.00 | 22.52 | B | C |
| ATOM | 2629 | CG | PHE | B | 141 | 32.263 | 25.836 | 19.734 | 1.00 | 27.19 | B | C |
| ATOM | 2630 | CD1 | PHE | B | 141 | 31.002 | 25.543 | 20.203 | 1.00 | 26.26 | B | C |
| ATOM | 2631 | CD2 | PHE | B | 141 | 33.353 | 25.325 | 20.411 | 1.00 | 24.11 | B | C |
| ATOM | 2632 | CE1 | PHE | B | 141 | 30.841 | 24.737 | 21.324 | 1.00 | 30.27 | B | C |
| ATOM | 2633 | CE2 | PHE | B | 141 | 33.202 | 24.532 | 21.510 | 1.00 | 27.64 | B | C |
| ATOM | 2634 | CZ | PHE | B | 141 | 31.956 | 24.228 | 21.977 | 1.00 | 24.85 | B | C |

TABLE 14-continued

Coordinates for proMMP9(35-444 ΔFnII) (SEQ ID NO: 12) complex with Example 4

| ATOM | 2635 | C | PHE | B | 141 | 31.614 | 27.588 | 16.316 | 1.00 | 24.97 | B | C |
|---|---|---|---|---|---|---|---|---|---|---|---|---|
| ATOM | 2636 | O | PHE | B | 141 | 30.932 | 28.601 | 16.330 | 1.00 | 26.56 | B | O |
| ATOM | 2637 | N | ALA | B | 142 | 32.529 | 27.378 | 15.366 | 1.00 | 25.52 | B | N |
| ATOM | 2638 | CA | ALA | B | 142 | 32.709 | 28.385 | 14.309 | 1.00 | 25.90 | B | C |
| ATOM | 2639 | CB | ALA | B | 142 | 33.884 | 28.018 | 13.384 | 1.00 | 27.24 | B | C |
| ATOM | 2640 | C | ALA | B | 142 | 31.429 | 28.578 | 13.487 | 1.00 | 26.71 | B | C |
| ATOM | 2641 | O | ALA | B | 142 | 31.058 | 29.691 | 13.127 | 1.00 | 23.88 | B | O |
| ATOM | 2642 | N | ARG | B | 143 | 30.772 | 27.468 | 13.178 | 1.00 | 27.10 | B | N |
| ATOM | 2643 | CA | ARG | B | 143 | 29.542 | 27.488 | 12.397 | 1.00 | 25.43 | B | C |
| ATOM | 2644 | CB | ARG | B | 143 | 29.134 | 26.060 | 12.047 | 1.00 | 26.35 | B | C |
| ATOM | 2645 | CG | ARG | B | 143 | 30.161 | 25.370 | 11.124 | 1.00 | 26.97 | B | C |
| ATOM | 2646 | CD | ARG | B | 143 | 30.068 | 23.848 | 11.280 | 1.00 | 33.61 | B | C |
| ATOM | 2647 | NE | ARG | B | 143 | 28.716 | 23.469 | 10.975 | 1.00 | 34.98 | B | N |
| ATOM | 2648 | CZ | ARG | B | 143 | 28.004 | 22.534 | 11.575 | 1.00 | 27.34 | B | C |
| ATOM | 2649 | NH1 | ARG | B | 143 | 28.494 | 21.757 | 12.538 | 1.00 | 28.40 | B | N |
| ATOM | 2650 | NH2 | ARG | B | 143 | 26.768 | 22.373 | 11.155 | 1.00 | 30.14 | B | N |
| ATOM | 2651 | C | ARG | B | 143 | 28.427 | 28.189 | 13.161 | 1.00 | 26.18 | B | C |
| ATOM | 2652 | O | ARG | B | 143 | 27.677 | 28.989 | 12.604 | 1.00 | 24.56 | B | O |
| ATOM | 2653 | N | ALA | B | 144 | 28.319 | 27.898 | 14.450 | 1.00 | 23.96 | B | N |
| ATOM | 2654 | CA | ALA | B | 144 | 27.351 | 28.615 | 15.261 | 1.00 | 24.95 | B | C |
| ATOM | 2655 | CB | ALA | B | 144 | 27.309 | 28.050 | 16.690 | 1.00 | 23.20 | B | C |
| ATOM | 2656 | C | ALA | B | 144 | 27.593 | 30.136 | 15.255 | 1.00 | 22.91 | B | C |
| ATOM | 2657 | O | ALA | B | 144 | 26.644 | 30.911 | 15.173 | 1.00 | 21.81 | B | O |
| ATOM | 2658 | N | PHE | B | 145 | 28.849 | 30.573 | 15.332 | 1.00 | 22.75 | B | N |
| ATOM | 2659 | CA | PHE | B | 145 | 29.124 | 32.012 | 15.243 | 1.00 | 24.22 | B | C |
| ATOM | 2660 | CB | PHE | B | 145 | 30.582 | 32.328 | 15.596 | 1.00 | 22.90 | B | C |
| ATOM | 2661 | CG | PHE | B | 145 | 30.859 | 32.342 | 17.076 | 1.00 | 22.99 | B | C |
| ATOM | 2662 | CD1 | PHE | B | 145 | 30.178 | 33.217 | 17.920 | 1.00 | 26.40 | B | C |
| ATOM | 2663 | CD2 | PHE | B | 145 | 31.777 | 31.465 | 17.634 | 1.00 | 23.15 | B | C |
| ATOM | 2664 | CE1 | PHE | B | 145 | 30.428 | 33.222 | 19.304 | 1.00 | 22.82 | B | C |
| ATOM | 2665 | CE2 | PHE | B | 145 | 32.032 | 31.472 | 19.001 | 1.00 | 24.46 | B | C |
| ATOM | 2666 | CZ | PHE | B | 145 | 31.349 | 32.353 | 19.833 | 1.00 | 22.76 | B | C |
| ATOM | 2667 | C | PHE | B | 145 | 28.776 | 32.590 | 13.864 | 1.00 | 28.53 | B | C |
| ATOM | 2668 | O | PHE | B | 145 | 28.271 | 33.716 | 13.744 | 1.00 | 25.58 | B | O |
| ATOM | 2669 | N | ALA | B | 146 | 29.063 | 31.830 | 12.807 | 1.00 | 28.95 | B | N |
| ATOM | 2670 | CA | ALA | B | 146 | 28.777 | 32.325 | 11.460 | 1.00 | 25.57 | B | C |
| ATOM | 2671 | CB | ALA | B | 146 | 29.259 | 31.347 | 10.400 | 1.00 | 26.71 | B | C |
| ATOM | 2672 | C | ALA | B | 146 | 27.299 | 32.625 | 11.276 | 1.00 | 24.70 | B | C |
| ATOM | 2673 | O | ALA | B | 146 | 26.943 | 33.476 | 10.457 | 1.00 | 26.26 | B | O |
| ATOM | 2674 | N | LEU | B | 147 | 26.430 | 31.929 | 12.012 | 1.00 | 26.21 | B | N |
| ATOM | 2675 | CA | LEU | B | 147 | 24.997 | 32.236 | 11.945 | 1.00 | 23.60 | B | C |
| ATOM | 2676 | CB | LEU | B | 147 | 24.157 | 31.335 | 12.859 | 1.00 | 25.21 | B | C |
| ATOM | 2677 | CG | LEU | B | 147 | 23.940 | 29.861 | 12.560 | 1.00 | 25.66 | B | C |
| ATOM | 2678 | CD1 | LEU | B | 147 | 23.246 | 29.167 | 13.762 | 1.00 | 23.23 | B | C |
| ATOM | 2679 | CD2 | LEU | B | 147 | 23.132 | 29.692 | 11.275 | 1.00 | 24.27 | B | C |
| ATOM | 2680 | C | LEU | B | 147 | 24.787 | 33.679 | 12.382 | 1.00 | 26.09 | B | C |
| ATOM | 2681 | O | LEU | B | 147 | 24.070 | 34.452 | 11.738 | 1.00 | 24.52 | B | O |
| ATOM | 2682 | N | TRP | B | 148 | 25.407 | 34.039 | 13.496 | 1.00 | 22.61 | B | N |
| ATOM | 2683 | CA | TRP | B | 148 | 25.198 | 35.363 | 14.057 | 1.00 | 24.85 | B | C |
| ATOM | 2684 | CB | TRP | B | 148 | 25.552 | 35.358 | 15.547 | 1.00 | 24.53 | B | C |
| ATOM | 2685 | CG | TRP | B | 148 | 24.604 | 34.494 | 16.333 | 1.00 | 22.25 | B | C |
| ATOM | 2686 | CD2 | TRP | B | 148 | 23.202 | 34.728 | 16.543 | 1.00 | 25.90 | B | C |
| ATOM | 2687 | CE2 | TRP | B | 148 | 22.711 | 33.662 | 17.328 | 1.00 | 26.23 | B | C |
| ATOM | 2688 | CE3 | TRP | B | 148 | 22.314 | 35.740 | 16.164 | 1.00 | 22.79 | B | C |
| ATOM | 2689 | CD1 | TRP | B | 148 | 24.895 | 33.311 | 16.965 | 1.00 | 24.08 | B | C |
| ATOM | 2690 | NE1 | TRP | B | 148 | 23.764 | 32.810 | 17.566 | 1.00 | 21.99 | B | N |
| ATOM | 2691 | CZ2 | TRP | B | 148 | 21.373 | 33.582 | 17.738 | 1.00 | 24.20 | B | C |
| ATOM | 2692 | CZ3 | TRP | B | 148 | 20.983 | 35.655 | 16.562 | 1.00 | 25.88 | B | C |
| ATOM | 2693 | CH2 | TRP | B | 148 | 20.526 | 34.583 | 17.332 | 1.00 | 22.01 | B | C |
| ATOM | 2694 | C | TRP | B | 148 | 25.975 | 36.427 | 13.305 | 1.00 | 25.10 | B | C |
| ATOM | 2695 | O | TRP | B | 148 | 25.538 | 37.570 | 13.199 | 1.00 | 25.33 | B | O |
| ATOM | 2696 | N | SER | B | 149 | 27.125 | 36.038 | 12.765 | 1.00 | 23.03 | B | N |
| ATOM | 2697 | CA | SER | B | 149 | 27.979 | 36.965 | 12.045 | 1.00 | 23.74 | B | C |
| ATOM | 2698 | CB | SER | B | 149 | 29.180 | 36.204 | 11.470 | 1.00 | 25.15 | B | C |
| ATOM | 2699 | OG | SER | B | 149 | 30.216 | 37.096 | 11.161 | 1.00 | 31.30 | B | O |
| ATOM | 2700 | C | SER | B | 149 | 27.215 | 37.598 | 10.893 | 1.00 | 24.77 | B | C |
| ATOM | 2701 | O | SER | B | 149 | 27.318 | 38.794 | 10.632 | 1.00 | 24.27 | B | O |
| ATOM | 2702 | N | ALA | B | 150 | 26.466 | 36.775 | 10.176 | 1.00 | 21.84 | B | N |
| ATOM | 2703 | CA | ALA | B | 150 | 25.823 | 37.239 | 8.954 | 1.00 | 24.59 | B | C |
| ATOM | 2704 | CB | ALA | B | 150 | 25.260 | 36.067 | 8.161 | 1.00 | 22.47 | B | C |
| ATOM | 2705 | C | ALA | B | 150 | 24.739 | 38.286 | 9.202 | 1.00 | 24.53 | B | C |
| ATOM | 2706 | O | ALA | B | 150 | 24.445 | 39.073 | 8.310 | 1.00 | 23.31 | B | O |
| ATOM | 2707 | N | VAL | B | 151 | 24.151 | 38.295 | 10.407 | 1.00 | 23.53 | B | N |
| ATOM | 2708 | CA | VAL | B | 151 | 22.973 | 39.132 | 10.682 | 1.00 | 25.98 | B | C |
| ATOM | 2709 | CB | VAL | B | 151 | 21.795 | 38.299 | 11.231 | 1.00 | 29.35 | B | C |
| ATOM | 2710 | CG1 | VAL | B | 151 | 21.184 | 37.409 | 10.129 | 1.00 | 21.18 | B | C |
| ATOM | 2711 | CG2 | VAL | B | 151 | 22.256 | 37.462 | 12.436 | 1.00 | 26.13 | B | C |
| ATOM | 2712 | C | VAL | B | 151 | 23.251 | 40.261 | 11.675 | 1.00 | 28.03 | B | C |

TABLE 14-continued

Coordinates for proMMP9(35-444 ΔFnII) (SEQ ID NO: 12) complex with Example 4

| ATOM | 2713 | O   | VAL | B | 151 | 22.325 | 40.871 | 12.181 | 1.00 | 25.95 | B | O |
|------|------|-----|-----|---|-----|--------|--------|--------|------|-------|---|---|
| ATOM | 2714 | N   | THR | B | 152 | 24.526 | 40.522 | 11.954 | 1.00 | 28.10 | B | N |
| ATOM | 2715 | CA  | THR | B | 152 | 24.916 | 41.578 | 12.883 | 1.00 | 27.38 | B | C |
| ATOM | 2716 | CB  | THR | B | 152 | 25.350 | 41.002 | 14.222 | 1.00 | 27.21 | B | C |
| ATOM | 2717 | OG1 | THR | B | 152 | 26.576 | 40.292 | 14.036 | 1.00 | 28.58 | B | O |
| ATOM | 2718 | CG2 | THR | B | 152 | 24.291 | 40.053 | 14.785 | 1.00 | 27.38 | B | C |
| ATOM | 2719 | C   | THR | B | 152 | 26.167 | 42.242 | 12.332 | 1.00 | 29.69 | B | C |
| ATOM | 2720 | O   | THR | B | 152 | 26.803 | 41.696 | 11.436 | 1.00 | 29.80 | B | O |
| ATOM | 2721 | N   | PRO | B | 153 | 26.523 | 43.414 | 12.876 | 1.00 | 28.16 | B | N |
| ATOM | 2722 | CD  | PRO | B | 153 | 25.662 | 44.244 | 13.735 | 1.00 | 29.79 | B | C |
| ATOM | 2723 | CA  | PRO | B | 153 | 27.788 | 44.087 | 12.577 | 1.00 | 31.90 | B | C |
| ATOM | 2724 | CB  | PRO | B | 153 | 27.545 | 45.528 | 13.066 | 1.00 | 29.62 | B | C |
| ATOM | 2725 | CG  | PRO | B | 153 | 26.072 | 45.616 | 13.352 | 1.00 | 32.20 | B | C |
| ATOM | 2726 | C   | PRO | B | 153 | 28.961 | 43.482 | 13.349 | 1.00 | 31.33 | B | C |
| ATOM | 2727 | O   | PRO | B | 153 | 29.987 | 44.136 | 13.526 | 1.00 | 33.17 | B | O |
| ATOM | 2728 | N   | LEU | B | 154 | 28.824 | 42.249 | 13.808 | 1.00 | 27.28 | B | N |
| ATOM | 2729 | CA  | LEU | B | 154 | 29.898 | 41.662 | 14.576 | 1.00 | 27.94 | B | C |
| ATOM | 2730 | CB  | LEU | B | 154 | 29.356 | 41.010 | 15.849 | 1.00 | 28.66 | B | C |
| ATOM | 2731 | CG  | LEU | B | 154 | 28.459 | 41.877 | 16.723 | 1.00 | 25.37 | B | C |
| ATOM | 2732 | CD1 | LEU | B | 154 | 27.870 | 41.007 | 17.805 | 1.00 | 26.39 | B | C |
| ATOM | 2733 | CD2 | LEU | B | 154 | 29.255 | 43.029 | 17.309 | 1.00 | 27.92 | B | C |
| ATOM | 2734 | C   | LEU | B | 154 | 30.671 | 40.626 | 13.791 | 1.00 | 27.39 | B | C |
| ATOM | 2735 | O   | LEU | B | 154 | 30.124 | 39.973 | 12.903 | 1.00 | 27.85 | B | O |
| ATOM | 2736 | N   | THR | B | 155 | 31.940 | 40.466 | 14.145 | 1.00 | 24.79 | B | N |
| ATOM | 2737 | CA  | THR | B | 155 | 32.719 | 39.338 | 13.662 | 1.00 | 29.99 | B | C |
| ATOM | 2738 | CB  | THR | B | 155 | 33.955 | 39.749 | 12.835 | 1.00 | 29.11 | B | C |
| ATOM | 2739 | OG1 | THR | B | 155 | 34.854 | 40.480 | 13.668 | 1.00 | 35.35 | B | O |
| ATOM | 2740 | CG2 | THR | B | 155 | 33.559 | 40.599 | 11.637 | 1.00 | 27.55 | B | C |
| ATOM | 2741 | C   | THR | B | 155 | 33.198 | 38.549 | 14.860 | 1.00 | 29.95 | B | C |
| ATOM | 2742 | O   | THR | B | 155 | 33.312 | 39.074 | 15.975 | 1.00 | 30.51 | B | O |
| ATOM | 2743 | N   | PHE | B | 156 | 33.477 | 37.281 | 14.629 | 1.00 | 24.60 | B | N |
| ATOM | 2744 | CA  | PHE | B | 156 | 33.935 | 36.423 | 15.704 | 1.00 | 26.60 | B | C |
| ATOM | 2745 | CB  | PHE | B | 156 | 32.865 | 35.373 | 16.003 | 1.00 | 23.69 | B | C |
| ATOM | 2746 | CG  | PHE | B | 156 | 31.556 | 35.994 | 16.453 | 1.00 | 23.37 | B | C |
| ATOM | 2747 | CD1 | PHE | B | 156 | 30.553 | 36.268 | 15.535 | 1.00 | 23.79 | B | C |
| ATOM | 2748 | CD2 | PHE | B | 156 | 31.372 | 36.379 | 17.774 | 1.00 | 23.42 | B | C |
| ATOM | 2749 | CE1 | PHE | B | 156 | 29.370 | 36.860 | 15.927 | 1.00 | 25.80 | B | C |
| ATOM | 2750 | CE2 | PHE | B | 156 | 30.180 | 36.984 | 18.188 | 1.00 | 25.22 | B | C |
| ATOM | 2751 | CZ  | PHE | B | 156 | 29.182 | 37.228 | 17.273 | 1.00 | 25.13 | B | C |
| ATOM | 2752 | C   | PHE | B | 156 | 35.293 | 35.822 | 15.365 | 1.00 | 31.67 | B | C |
| ATOM | 2753 | O   | PHE | B | 156 | 35.500 | 35.315 | 14.264 | 1.00 | 27.33 | B | O |
| ATOM | 2754 | N   | THR | B | 157 | 36.219 | 35.925 | 16.313 | 1.00 | 28.54 | B | N |
| ATOM | 2755 | CA  | THR | B | 157 | 37.558 | 35.407 | 16.134 | 1.00 | 27.69 | B | C |
| ATOM | 2756 | CB  | THR | B | 157 | 38.584 | 36.546 | 16.047 | 1.00 | 30.70 | B | C |
| ATOM | 2757 | OG1 | THR | B | 157 | 38.215 | 37.437 | 14.988 | 1.00 | 29.98 | B | O |
| ATOM | 2758 | CG2 | THR | B | 157 | 39.958 | 35.973 | 15.782 | 1.00 | 29.68 | B | C |
| ATOM | 2759 | C   | THR | B | 157 | 37.989 | 34.495 | 17.263 | 1.00 | 25.50 | B | C |
| ATOM | 2760 | O   | THR | B | 157 | 38.026 | 34.891 | 18.425 | 1.00 | 26.65 | B | O |
| ATOM | 2761 | N   | ARG | B | 158 | 38.349 | 33.275 | 16.902 | 1.00 | 29.35 | B | N |
| ATOM | 2762 | CA  | ARG | B | 158 | 38.915 | 32.324 | 17.835 | 1.00 | 29.60 | B | C |
| ATOM | 2763 | CB  | ARG | B | 158 | 39.000 | 30.949 | 17.181 | 1.00 | 27.91 | B | C |
| ATOM | 2764 | CG  | ARG | B | 158 | 39.496 | 29.883 | 18.130 | 1.00 | 34.73 | B | C |
| ATOM | 2765 | CD  | ARG | B | 158 | 39.527 | 28.529 | 17.476 | 1.00 | 34.77 | B | C |
| ATOM | 2766 | NE  | ARG | B | 158 | 40.155 | 27.541 | 18.346 | 1.00 | 37.19 | B | N |
| ATOM | 2767 | CZ  | ARG | B | 158 | 40.381 | 26.285 | 17.981 | 1.00 | 39.32 | B | C |
| ATOM | 2768 | NH1 | ARG | B | 158 | 40.017 | 25.883 | 16.764 | 1.00 | 36.71 | B | N |
| ATOM | 2769 | NH2 | ARG | B | 158 | 40.957 | 25.431 | 18.823 | 1.00 | 38.34 | B | N |
| ATOM | 2770 | C   | ARG | B | 158 | 40.315 | 32.755 | 18.261 | 1.00 | 32.28 | B | C |
| ATOM | 2771 | O   | ARG | B | 158 | 41.173 | 33.025 | 17.415 | 1.00 | 29.12 | B | O |
| ATOM | 2772 | N   | VAL | B | 159 | 40.535 | 32.810 | 19.568 | 1.00 | 28.37 | B | N |
| ATOM | 2773 | CA  | VAL | B | 159 | 41.842 | 33.141 | 20.132 | 1.00 | 27.72 | B | C |
| ATOM | 2774 | CB  | VAL | B | 159 | 41.823 | 34.529 | 20.753 | 1.00 | 28.76 | B | C |
| ATOM | 2775 | CG1 | VAL | B | 159 | 41.332 | 35.520 | 19.736 | 1.00 | 28.39 | B | C |
| ATOM | 2776 | CG2 | VAL | B | 159 | 40.915 | 34.536 | 21.969 | 1.00 | 30.12 | B | C |
| ATOM | 2777 | C   | VAL | B | 159 | 42.216 | 32.118 | 21.206 | 1.00 | 32.99 | B | C |
| ATOM | 2778 | O   | VAL | B | 159 | 41.384 | 31.314 | 21.621 | 1.00 | 31.96 | B | O |
| ATOM | 2779 | N   | TYR | B | 160 | 43.461 | 32.148 | 21.667 | 1.00 | 32.91 | B | N |
| ATOM | 2780 | CA  | TYR | B | 160 | 43.928 | 31.090 | 22.545 | 1.00 | 32.04 | B | C |
| ATOM | 2781 | CB  | TYR | B | 160 | 44.975 | 30.222 | 21.839 | 1.00 | 35.20 | B | C |
| ATOM | 2782 | CG  | TYR | B | 160 | 44.429 | 29.590 | 20.566 | 1.00 | 37.07 | B | C |
| ATOM | 2783 | CD1 | TYR | B | 160 | 44.273 | 30.344 | 19.412 | 1.00 | 31.16 | B | C |
| ATOM | 2784 | CE1 | TYR | B | 160 | 43.751 | 29.793 | 18.256 | 1.00 | 31.39 | B | C |
| ATOM | 2785 | CD2 | TYR | B | 160 | 44.039 | 28.249 | 20.530 | 1.00 | 34.44 | B | C |
| ATOM | 2786 | CE2 | TYR | B | 160 | 43.524 | 27.686 | 19.365 | 1.00 | 35.45 | B | C |
| ATOM | 2787 | CZ  | TYR | B | 160 | 43.386 | 28.466 | 18.231 | 1.00 | 32.61 | B | C |
| ATOM | 2788 | OH  | TYR | B | 160 | 42.882 | 27.945 | 17.057 | 1.00 | 36.36 | B | O |
| ATOM | 2789 | C   | TYR | B | 160 | 44.431 | 31.622 | 23.875 | 1.00 | 35.22 | B | C |
| ATOM | 2790 | O   | TYR | B | 160 | 45.254 | 30.985 | 24.535 | 1.00 | 45.29 | B | O |

TABLE 14-continued

Coordinates for proMMP9(35-444 ΔFnII) (SEQ ID NO: 12) complex with Example 4

| ATOM | 2791 | N   | SER | B | 161 | 43.902 | 32.772 | 24.275 | 1.00 | 34.87 | B | N |
| --- | --- | --- | --- | --- | --- | --- | --- | --- | --- | --- | --- | --- |
| ATOM | 2792 | CA  | SER | B | 161 | 44.270 | 33.417 | 25.533 | 1.00 | 41.12 | B | C |
| ATOM | 2793 | CB  | SER | B | 161 | 44.785 | 34.821 | 25.247 | 1.00 | 38.82 | B | C |
| ATOM | 2794 | OG  | SER | B | 161 | 43.920 | 35.463 | 24.308 | 1.00 | 42.28 | B | O |
| ATOM | 2795 | C   | SER | B | 161 | 43.061 | 33.547 | 26.459 | 1.00 | 40.99 | B | C |
| ATOM | 2796 | O   | SER | B | 161 | 41.936 | 33.706 | 25.988 | 1.00 | 38.87 | B | O |
| ATOM | 2797 | N   | ARG | B | 162 | 43.313 | 33.506 | 27.773 | 1.00 | 39.83 | B | N |
| ATOM | 2798 | CA  | ARG | B | 162 | 42.322 | 33.843 | 28.807 | 1.00 | 43.33 | B | C |
| ATOM | 2799 | CB  | ARG | B | 162 | 43.006 | 33.990 | 30.176 | 1.00 | 39.96 | B | C |
| ATOM | 2800 | CG  | ARG | B | 162 | 44.114 | 32.973 | 30.432 | 1.00 | 45.70 | B | C |
| ATOM | 2801 | CD  | ARG | B | 162 | 44.435 | 32.830 | 31.923 | 1.00 | 46.09 | B | C |
| ATOM | 2802 | NE  | ARG | B | 162 | 44.847 | 31.467 | 32.254 | 1.00 | 42.10 | B | N |
| ATOM | 2803 | CZ  | ARG | B | 162 | 46.093 | 31.006 | 32.152 | 1.00 | 48.05 | B | C |
| ATOM | 2804 | NH1 | ARG | B | 162 | 46.361 | 29.744 | 32.469 | 1.00 | 42.62 | B | N |
| ATOM | 2805 | NH2 | ARG | B | 162 | 47.073 | 31.796 | 31.722 | 1.00 | 52.85 | B | N |
| ATOM | 2806 | C   | ARG | B | 162 | 41.680 | 35.168 | 28.447 | 1.00 | 38.45 | B | C |
| ATOM | 2807 | O   | ARG | B | 162 | 40.586 | 35.487 | 28.870 | 1.00 | 40.31 | B | O |
| ATOM | 2808 | N   | ASP | B | 163 | 42.408 | 35.934 | 27.652 | 1.00 | 42.88 | B | N |
| ATOM | 2809 | CA  | ASP | B | 163 | 41.986 | 37.227 | 27.157 | 1.00 | 45.44 | B | C |
| ATOM | 2810 | CB  | ASP | B | 163 | 43.235 | 37.960 | 26.659 | 1.00 | 50.05 | B | C |
| ATOM | 2811 | CG  | ASP | B | 163 | 43.003 | 39.428 | 26.411 | 1.00 | 57.19 | B | C |
| ATOM | 2812 | OD1 | ASP | B | 163 | 41.911 | 39.931 | 26.753 | 1.00 | 57.70 | B | O |
| ATOM | 2813 | OD2 | ASP | B | 163 | 43.928 | 40.082 | 25.876 | 1.00 | 61.70 | B | O |
| ATOM | 2814 | C   | ASP | B | 163 | 40.995 | 37.049 | 26.001 | 1.00 | 44.87 | B | C |
| ATOM | 2815 | O   | ASP | B | 163 | 41.383 | 37.127 | 24.830 | 1.00 | 47.11 | B | O |
| ATOM | 2816 | N   | ALA | B | 164 | 39.727 | 36.804 | 26.321 | 1.00 | 36.45 | B | N |
| ATOM | 2817 | CA  | ALA | B | 164 | 38.688 | 36.707 | 25.289 | 1.00 | 35.94 | B | C |
| ATOM | 2818 | CB  | ALA | B | 164 | 38.566 | 35.275 | 24.760 | 1.00 | 31.47 | B | C |
| ATOM | 2819 | C   | ALA | B | 164 | 37.348 | 37.180 | 25.827 | 1.00 | 32.25 | B | C |
| ATOM | 2820 | O   | ALA | B | 164 | 37.060 | 36.997 | 27.014 | 1.00 | 31.97 | B | O |
| ATOM | 2821 | N   | ASP | B | 165 | 36.536 | 37.778 | 24.961 | 1.00 | 26.78 | B | N |
| ATOM | 2822 | CA  | ASP | B | 165 | 35.185 | 38.212 | 25.330 | 1.00 | 28.79 | B | C |
| ATOM | 2823 | CB  | ASP | B | 165 | 34.497 | 38.892 | 24.155 | 1.00 | 26.89 | B | C |
| ATOM | 2824 | CG  | ASP | B | 165 | 35.208 | 40.140 | 23.718 | 1.00 | 30.96 | B | C |
| ATOM | 2825 | OD1 | ASP | B | 165 | 35.601 | 40.923 | 24.611 | 1.00 | 34.09 | B | O |
| ATOM | 2826 | OD2 | ASP | B | 165 | 35.362 | 40.341 | 22.497 | 1.00 | 30.82 | B | O |
| ATOM | 2827 | C   | ASP | B | 165 | 34.325 | 37.042 | 25.777 | 1.00 | 29.43 | B | C |
| ATOM | 2828 | O   | ASP | B | 165 | 33.646 | 37.109 | 26.791 | 1.00 | 31.68 | B | O |
| ATOM | 2829 | N   | ILE | B | 166 | 34.355 | 35.973 | 24.996 | 1.00 | 29.02 | B | N |
| ATOM | 2830 | CA  | ILE | B | 166 | 33.544 | 34.796 | 25.263 | 1.00 | 29.87 | B | C |
| ATOM | 2831 | CB  | ILE | B | 166 | 32.663 | 34.454 | 24.058 | 1.00 | 28.39 | B | C |
| ATOM | 2832 | CG2 | ILE | B | 166 | 31.974 | 33.093 | 24.262 | 1.00 | 28.15 | B | C |
| ATOM | 2833 | CG1 | ILE | B | 166 | 31.653 | 35.578 | 23.812 | 1.00 | 27.02 | B | C |
| ATOM | 2834 | CD1 | ILE | B | 166 | 30.960 | 35.504 | 22.444 | 1.00 | 28.61 | B | C |
| ATOM | 2835 | C   | ILE | B | 166 | 34.430 | 33.601 | 25.559 | 1.00 | 32.24 | B | C |
| ATOM | 2836 | O   | ILE | B | 166 | 35.155 | 33.123 | 24.682 | 1.00 | 31.05 | B | O |
| ATOM | 2837 | N   | VAL | B | 167 | 34.382 | 33.127 | 26.798 | 1.00 | 28.53 | B | N |
| ATOM | 2838 | CA  | VAL | B | 167 | 35.070 | 31.902 | 27.137 | 1.00 | 27.88 | B | C |
| ATOM | 2839 | CB  | VAL | B | 167 | 35.752 | 31.963 | 28.509 | 1.00 | 31.01 | B | C |
| ATOM | 2840 | CG1 | VAL | B | 167 | 36.429 | 30.631 | 28.812 | 1.00 | 30.45 | B | C |
| ATOM | 2841 | CG2 | VAL | B | 167 | 36.764 | 33.092 | 28.541 | 1.00 | 31.73 | B | C |
| ATOM | 2842 | C   | VAL | B | 167 | 34.096 | 30.745 | 27.088 | 1.00 | 30.88 | B | C |
| ATOM | 2843 | O   | VAL | B | 167 | 32.980 | 30.826 | 27.606 | 1.00 | 29.36 | B | O |
| ATOM | 2844 | N   | ILE | B | 168 | 34.538 | 29.672 | 26.450 | 1.00 | 33.42 | B | N |
| ATOM | 2845 | CA  | ILE | B | 168 | 33.734 | 28.485 | 26.215 | 1.00 | 31.33 | B | C |
| ATOM | 2846 | CB  | ILE | B | 168 | 33.719 | 28.145 | 24.728 | 1.00 | 29.99 | B | C |
| ATOM | 2847 | CG2 | ILE | B | 168 | 33.089 | 26.781 | 24.494 | 1.00 | 32.16 | B | C |
| ATOM | 2848 | CG1 | ILE | B | 168 | 32.948 | 29.208 | 23.947 | 1.00 | 30.82 | B | C |
| ATOM | 2849 | CD1 | ILE | B | 168 | 33.193 | 29.134 | 22.443 | 1.00 | 28.53 | B | C |
| ATOM | 2850 | C   | ILE | B | 168 | 34.316 | 27.303 | 26.980 | 1.00 | 31.59 | B | C |
| ATOM | 2851 | O   | ILE | B | 168 | 35.510 | 27.000 | 26.865 | 1.00 | 29.89 | B | O |
| ATOM | 2852 | N   | GLN | B | 169 | 33.458 | 26.631 | 27.736 | 1.00 | 29.41 | B | N |
| ATOM | 2853 | CA  | GLN | B | 169 | 33.884 | 25.618 | 28.687 | 1.00 | 31.97 | B | C |
| ATOM | 2854 | CB  | GLN | B | 169 | 33.955 | 26.236 | 30.092 | 1.00 | 32.01 | B | C |
| ATOM | 2855 | CG  | GLN | B | 169 | 34.303 | 25.259 | 31.203 | 1.00 | 32.93 | B | C |
| ATOM | 2856 | CD  | GLN | B | 169 | 33.967 | 25.804 | 32.593 | 1.00 | 38.34 | B | C |
| ATOM | 2857 | OE1 | GLN | B | 169 | 33.703 | 27.001 | 32.770 | 1.00 | 36.87 | B | O |
| ATOM | 2858 | NE2 | GLN | B | 169 | 33.970 | 24.921 | 33.586 | 1.00 | 41.49 | B | N |
| ATOM | 2859 | C   | GLN | B | 169 | 32.915 | 24.439 | 28.711 | 1.00 | 32.73 | B | C |
| ATOM | 2860 | O   | GLN | B | 169 | 31.687 | 24.612 | 28.685 | 1.00 | 30.74 | B | O |
| ATOM | 2861 | N   | PHE | B | 170 | 33.471 | 23.239 | 28.758 | 1.00 | 26.71 | B | N |
| ATOM | 2862 | CA  | PHE | B | 170 | 32.683 | 22.054 | 29.036 | 1.00 | 28.25 | B | C |
| ATOM | 2863 | CB  | PHE | B | 170 | 33.167 | 20.870 | 28.213 | 1.00 | 30.26 | B | C |
| ATOM | 2864 | CG  | PHE | B | 170 | 32.809 | 20.949 | 26.755 | 1.00 | 30.60 | B | C |
| ATOM | 2865 | CD1 | PHE | B | 170 | 33.677 | 21.527 | 25.845 | 1.00 | 30.32 | B | C |
| ATOM | 2866 | CD2 | PHE | B | 170 | 31.599 | 20.449 | 26.297 | 1.00 | 25.64 | B | C |
| ATOM | 2867 | CE1 | PHE | B | 170 | 33.348 | 21.595 | 24.492 | 1.00 | 29.60 | B | C |
| ATOM | 2868 | CE2 | PHE | B | 170 | 31.262 | 20.515 | 24.952 | 1.00 | 28.27 | B | C |

TABLE 14-continued

Coordinates for proMMP9(35-444 ΔFnII) (SEQ ID NO: 12) complex with Example 4

| ATOM | 2869 | CZ  | PHE | B | 170 | 32.145 | 21.084 | 24.047 | 1.00 | 26.92 | B | C |
| ---- | ---- | --- | --- | - | --- | ------ | ------ | ------ | ---- | ----- | - | - |
| ATOM | 2870 | C   | PHE | B | 170 | 32.873 | 21.752 | 30.512 | 1.00 | 32.69 | B | C |
| ATOM | 2871 | O   | PHE | B | 170 | 33.985 | 21.841 | 31.034 | 1.00 | 29.75 | B | O |
| ATOM | 2872 | N   | GLY | B | 171 | 31.793 | 21.402 | 31.189 | 1.00 | 27.89 | B | N |
| ATOM | 2873 | CA  | GLY | B | 171 | 31.866 | 21.155 | 32.622 | 1.00 | 34.82 | B | C |
| ATOM | 2874 | C   | GLY | B | 171 | 30.762 | 20.228 | 33.079 | 1.00 | 31.42 | B | C |
| ATOM | 2875 | O   | GLY | B | 171 | 29.810 | 19.990 | 32.344 | 1.00 | 33.00 | B | O |
| ATOM | 2876 | N   | VAL | B | 172 | 30.894 | 19.689 | 34.283 | 1.00 | 32.50 | B | N |
| ATOM | 2877 | CA  | VAL | B | 172 | 29.854 | 18.850 | 34.861 | 1.00 | 32.40 | B | C |
| ATOM | 2878 | CB  | VAL | B | 172 | 30.270 | 17.362 | 34.879 | 1.00 | 36.95 | B | C |
| ATOM | 2879 | CG1 | VAL | B | 172 | 30.585 | 16.866 | 33.473 | 1.00 | 37.14 | B | C |
| ATOM | 2880 | CG2 | VAL | B | 172 | 31.474 | 17.166 | 35.768 | 1.00 | 36.23 | B | C |
| ATOM | 2881 | C   | VAL | B | 172 | 29.578 | 19.318 | 36.288 | 1.00 | 38.27 | B | C |
| ATOM | 2882 | O   | VAL | B | 172 | 30.458 | 19.889 | 36.951 | 1.00 | 37.37 | B | O |
| ATOM | 2883 | N   | ALA | B | 173 | 28.355 | 19.091 | 36.754 | 1.00 | 35.47 | B | N |
| ATOM | 2884 | CA  | ALA | B | 173 | 27.990 | 19.458 | 38.111 | 1.00 | 39.26 | B | C |
| ATOM | 2885 | CB  | ALA | B | 173 | 28.642 | 18.499 | 39.099 | 1.00 | 44.27 | B | C |
| ATOM | 2886 | C   | ALA | B | 173 | 28.405 | 20.893 | 38.423 | 1.00 | 39.51 | B | C |
| ATOM | 2887 | O   | ALA | B | 173 | 28.210 | 21.804 | 37.626 | 1.00 | 34.77 | B | O |
| ATOM | 2888 | N   | GLU | B | 174 | 28.972 | 21.101 | 39.602 | 1.00 | 42.22 | B | N |
| ATOM | 2889 | CA  | GLU | B | 174 | 29.447 | 22.433 | 39.939 | 1.00 | 39.75 | B | C |
| ATOM | 2890 | CB  | GLU | B | 174 | 29.559 | 22.624 | 41.451 | 1.00 | 40.66 | B | C |
| ATOM | 2891 | CG  | GLU | B | 174 | 30.347 | 23.854 | 41.828 | 1.00 | 41.08 | B | C |
| ATOM | 2892 | CD  | GLU | B | 174 | 29.686 | 25.146 | 41.383 | 1.00 | 43.32 | B | C |
| ATOM | 2893 | OE1 | GLU | B | 174 | 28.449 | 25.296 | 41.555 | 1.00 | 42.55 | B | O |
| ATOM | 2894 | OE2 | GLU | B | 174 | 30.420 | 26.024 | 40.872 | 1.00 | 49.18 | B | O |
| ATOM | 2895 | C   | GLU | B | 174 | 30.788 | 22.613 | 39.265 | 1.00 | 41.68 | B | C |
| ATOM | 2896 | O   | GLU | B | 174 | 31.723 | 21.851 | 39.502 | 1.00 | 44.37 | B | O |
| ATOM | 2897 | N   | HIS | B | 175 | 30.882 | 23.617 | 38.408 | 1.00 | 39.73 | B | N |
| ATOM | 2898 | CA  | HIS | B | 175 | 32.017 | 23.708 | 37.513 | 1.00 | 38.47 | B | C |
| ATOM | 2899 | CB  | HIS | B | 175 | 31.579 | 23.330 | 36.109 | 1.00 | 35.46 | B | C |
| ATOM | 2900 | CG  | HIS | B | 175 | 30.422 | 24.137 | 35.627 | 1.00 | 34.72 | B | C |
| ATOM | 2901 | CD2 | HIS | B | 175 | 30.364 | 25.274 | 34.895 | 1.00 | 28.68 | B | C |
| ATOM | 2902 | ND1 | HIS | B | 175 | 29.116 | 23.819 | 35.936 | 1.00 | 34.27 | B | N |
| ATOM | 2903 | CE1 | HIS | B | 175 | 28.305 | 24.715 | 35.402 | 1.00 | 32.11 | B | C |
| ATOM | 2904 | NE2 | HIS | B | 175 | 29.042 | 25.607 | 34.765 | 1.00 | 32.38 | B | N |
| ATOM | 2905 | C   | HIS | B | 175 | 32.554 | 25.118 | 37.497 | 1.00 | 38.59 | B | C |
| ATOM | 2906 | O   | HIS | B | 175 | 33.083 | 25.565 | 36.479 | 1.00 | 35.90 | B | O |
| ATOM | 2907 | N   | GLY | B | 176 | 32.382 | 25.829 | 38.611 | 1.00 | 39.98 | B | N |
| ATOM | 2908 | CA  | GLY | B | 176 | 33.099 | 27.074 | 38.824 | 1.00 | 39.34 | B | C |
| ATOM | 2909 | C   | GLY | B | 176 | 32.338 | 28.386 | 38.747 | 1.00 | 39.39 | B | C |
| ATOM | 2910 | O   | GLY | B | 176 | 32.966 | 29.447 | 38.761 | 1.00 | 44.45 | B | O |
| ATOM | 2911 | N   | ASP | B | 177 | 31.010 | 28.344 | 38.665 | 1.00 | 40.58 | B | N |
| ATOM | 2912 | CA  | ASP | B | 177 | 30.244 | 29.593 | 38.590 | 1.00 | 37.71 | B | C |
| ATOM | 2913 | CB  | ASP | B | 177 | 29.842 | 29.936 | 37.153 | 1.00 | 35.17 | B | C |
| ATOM | 2914 | CG  | ASP | B | 177 | 28.959 | 28.876 | 36.508 | 1.00 | 35.44 | B | C |
| ATOM | 2915 | OD1 | ASP | B | 177 | 28.653 | 29.054 | 35.309 | 1.00 | 37.17 | B | O |
| ATOM | 2916 | OD2 | ASP | B | 177 | 28.580 | 27.883 | 37.165 | 1.00 | 32.28 | B | O |
| ATOM | 2917 | C   | ASP | B | 177 | 29.027 | 29.634 | 39.484 | 1.00 | 37.13 | B | C |
| ATOM | 2918 | O   | ASP | B | 177 | 28.307 | 30.631 | 39.515 | 1.00 | 40.45 | B | O |
| ATOM | 2919 | N   | GLY | B | 178 | 28.780 | 28.553 | 40.208 | 1.00 | 39.36 | B | N |
| ATOM | 2920 | CA  | GLY | B | 178 | 27.684 | 28.547 | 41.166 | 1.00 | 41.81 | B | C |
| ATOM | 2921 | C   | GLY | B | 178 | 26.330 | 28.247 | 40.559 | 1.00 | 42.36 | B | C |
| ATOM | 2922 | O   | GLY | B | 178 | 25.317 | 28.264 | 41.255 | 1.00 | 39.75 | B | O |
| ATOM | 2923 | N   | TYR | B | 179 | 26.305 | 27.971 | 39.257 | 1.00 | 40.36 | B | N |
| ATOM | 2924 | CA  | TYR | B | 179 | 25.076 | 27.534 | 38.608 | 1.00 | 35.46 | B | C |
| ATOM | 2925 | CB  | TYR | B | 179 | 24.731 | 28.441 | 37.443 | 1.00 | 36.29 | B | C |
| ATOM | 2926 | CG  | TYR | B | 179 | 24.408 | 29.847 | 37.863 | 1.00 | 38.04 | B | C |
| ATOM | 2927 | CD1 | TYR | B | 179 | 25.372 | 30.836 | 37.829 | 1.00 | 37.78 | B | C |
| ATOM | 2928 | CE1 | TYR | B | 179 | 25.082 | 32.127 | 38.214 | 1.00 | 41.09 | B | C |
| ATOM | 2929 | CD2 | TYR | B | 179 | 23.133 | 30.187 | 38.304 | 1.00 | 42.02 | B | C |
| ATOM | 2930 | CE2 | TYR | B | 179 | 22.835 | 31.482 | 38.695 | 1.00 | 42.04 | B | C |
| ATOM | 2931 | CZ  | TYR | B | 179 | 23.818 | 32.448 | 38.642 | 1.00 | 39.14 | B | C |
| ATOM | 2932 | OH  | TYR | B | 179 | 23.546 | 33.743 | 39.015 | 1.00 | 40.80 | B | O |
| ATOM | 2933 | C   | TYR | B | 179 | 25.286 | 26.115 | 38.135 | 1.00 | 37.63 | B | C |
| ATOM | 2934 | O   | TYR | B | 179 | 25.366 | 25.852 | 36.937 | 1.00 | 36.12 | B | O |
| ATOM | 2935 | N   | PRO | B | 180 | 25.386 | 25.186 | 39.086 | 1.00 | 36.78 | B | N |
| ATOM | 2936 | CD  | PRO | B | 180 | 24.780 | 25.319 | 40.422 | 1.00 | 37.76 | B | C |
| ATOM | 2937 | CA  | PRO | B | 180 | 25.804 | 23.816 | 38.765 | 1.00 | 37.27 | B | C |
| ATOM | 2938 | CB  | PRO | B | 180 | 25.582 | 23.044 | 40.078 | 1.00 | 36.28 | B | C |
| ATOM | 2939 | CG  | PRO | B | 180 | 25.089 | 24.019 | 41.088 | 1.00 | 36.47 | B | C |
| ATOM | 2940 | C   | PRO | B | 180 | 24.935 | 23.184 | 37.690 | 1.00 | 35.05 | B | C |
| ATOM | 2941 | O   | PRO | B | 180 | 23.726 | 23.441 | 37.661 | 1.00 | 35.80 | B | O |
| ATOM | 2942 | N   | PHE | B | 181 | 25.531 | 22.356 | 36.834 | 1.00 | 31.34 | B | N |
| ATOM | 2943 | CA  | PHE | B | 181 | 24.750 | 21.494 | 35.952 | 1.00 | 33.39 | B | C |
| ATOM | 2944 | C   | PHE | B | 181 | 24.185 | 20.320 | 36.756 | 1.00 | 39.31 | B | C |
| ATOM | 2945 | CB  | PHE | B | 181 | 25.596 | 20.993 | 34.779 | 1.00 | 35.46 | B | C |
| ATOM | 2946 | CG  | PHE | B | 181 | 25.874 | 22.054 | 33.741 | 1.00 | 33.22 | B | C |

TABLE 14-continued

Coordinates for proMMP9(35-444 ΔFnII) (SEQ ID NO: 12) complex with Example 4

| ATOM | 2947 | CD1 | PHE | B | 181 | 24.874 | 22.924 | 33.339 | 1.00 | 30.55 | B | C |
|------|------|-----|-----|---|-----|--------|--------|--------|------|-------|---|---|
| ATOM | 2948 | CD2 | PHE | B | 181 | 27.130 | 22.176 | 33.170 | 1.00 | 31.64 | B | C |
| ATOM | 2949 | CE1 | PHE | B | 181 | 25.120 | 23.910 | 32.390 | 1.00 | 29.68 | B | C |
| ATOM | 2950 | CE2 | PHE | B | 181 | 27.387 | 23.162 | 32.223 | 1.00 | 32.74 | B | C |
| ATOM | 2951 | CZ  | PHE | B | 181 | 26.380 | 24.027 | 31.835 | 1.00 | 28.01 | B | C |
| ATOM | 2952 | O   | PHE | B | 181 | 24.538 | 20.140 | 37.929 | 1.00 | 38.42 | B | O |
| ATOM | 2953 | N   | ASP | B | 182 | 23.342 | 19.512 | 36.115 | 1.00 | 35.36 | B | N |
| ATOM | 2954 | CA  | ASP | B | 182 | 22.515 | 18.528 | 36.814 | 1.00 | 40.36 | B | C |
| ATOM | 2955 | CB  | ASP | B | 182 | 21.027 | 18.898 | 36.670 | 1.00 | 40.75 | B | C |
| ATOM | 2956 | CG  | ASP | B | 182 | 20.598 | 19.042 | 35.203 | 1.00 | 39.50 | B | C |
| ATOM | 2957 | OD1 | ASP | B | 182 | 21.490 | 19.130 | 34.344 | 1.00 | 38.34 | B | O |
| ATOM | 2958 | OD2 | ASP | B | 182 | 19.382 | 19.069 | 34.910 | 1.00 | 36.39 | B | O |
| ATOM | 2959 | C   | ASP | B | 182 | 22.696 | 17.097 | 36.315 | 1.00 | 40.67 | B | C |
| ATOM | 2960 | O   | ASP | B | 182 | 21.728 | 16.343 | 36.243 | 1.00 | 44.49 | B | O |
| ATOM | 2961 | N   | GLY | B | 183 | 23.911 | 16.707 | 35.964 | 1.00 | 39.11 | B | N |
| ATOM | 2962 | CA  | GLY | B | 183 | 24.082 | 15.379 | 35.404 | 1.00 | 39.73 | B | C |
| ATOM | 2963 | C   | GLY | B | 183 | 23.279 | 15.266 | 34.117 | 1.00 | 41.17 | B | C |
| ATOM | 2964 | O   | GLY | B | 183 | 22.825 | 16.270 | 33.588 | 1.00 | 38.13 | B | O |
| ATOM | 2965 | N   | LYS | B | 184 | 23.078 | 14.048 | 33.626 | 1.00 | 42.72 | B | N |
| ATOM | 2966 | CA  | LYS | B | 184 | 22.506 | 13.844 | 32.294 | 1.00 | 42.30 | B | C |
| ATOM | 2967 | CB  | LYS | B | 184 | 22.756 | 12.402 | 31.826 | 1.00 | 41.63 | B | C |
| ATOM | 2968 | CG  | LYS | B | 184 | 21.534 | 11.513 | 31.664 | 1.00 | 41.85 | B | C |
| ATOM | 2969 | CD  | LYS | B | 184 | 21.970 | 10.175 | 31.071 | 1.00 | 48.21 | B | C |
| ATOM | 2970 | CE  | LYS | B | 184 | 20.803 | 9.297  | 30.632 | 1.00 | 53.57 | B | C |
| ATOM | 2971 | NZ  | LYS | B | 184 | 21.302 | 7.981  | 30.099 | 1.00 | 55.55 | B | N |
| ATOM | 2972 | C   | LYS | B | 184 | 21.039 | 14.286 | 32.117 | 1.00 | 42.70 | B | C |
| ATOM | 2973 | O   | LYS | B | 184 | 20.227 | 14.166 | 33.033 | 1.00 | 43.78 | B | O |
| ATOM | 2974 | N   | ASP | B | 185 | 20.728 | 14.809 | 30.929 | 1.00 | 41.43 | B | N |
| ATOM | 2975 | CA  | ASP | B | 185 | 19.416 | 15.381 | 30.616 | 1.00 | 42.41 | B | C |
| ATOM | 2976 | CB  | ASP | B | 185 | 18.311 | 14.348 | 30.780 | 1.00 | 41.58 | B | C |
| ATOM | 2977 | CG  | ASP | B | 185 | 18.282 | 13.367 | 29.636 | 1.00 | 45.03 | B | C |
| ATOM | 2978 | OD1 | ASP | B | 185 | 19.179 | 13.445 | 28.763 | 1.00 | 48.74 | B | O |
| ATOM | 2979 | OD2 | ASP | B | 185 | 17.369 | 12.519 | 29.608 | 1.00 | 51.18 | B | O |
| ATOM | 2980 | C   | ASP | B | 185 | 19.109 | 16.637 | 31.419 | 1.00 | 39.33 | B | C |
| ATOM | 2981 | O   | ASP | B | 185 | 19.977 | 17.176 | 32.066 | 1.00 | 42.69 | B | O |
| ATOM | 2982 | N   | GLY | B | 186 | 17.877 | 17.118 | 31.372 | 1.00 | 39.95 | B | N |
| ATOM | 2983 | CA  | GLY | B | 186 | 17.560 | 18.371 | 32.042 | 1.00 | 38.62 | B | C |
| ATOM | 2984 | C   | GLY | B | 186 | 18.232 | 19.576 | 31.383 | 1.00 | 39.16 | B | C |
| ATOM | 2985 | O   | GLY | B | 186 | 18.030 | 19.823 | 30.188 | 1.00 | 36.26 | B | O |
| ATOM | 2986 | N   | LEU | B | 187 | 19.000 | 20.336 | 32.168 | 1.00 | 35.71 | B | N |
| ATOM | 2987 | CA  | LEU | B | 187 | 19.750 | 21.486 | 31.660 | 1.00 | 36.50 | B | C |
| ATOM | 2988 | CB  | LEU | B | 187 | 20.459 | 22.226 | 32.796 | 1.00 | 38.70 | B | C |
| ATOM | 2989 | CG  | LEU | B | 187 | 19.679 | 22.963 | 33.874 | 1.00 | 39.93 | B | C |
| ATOM | 2990 | CD1 | LEU | B | 187 | 18.897 | 21.982 | 34.675 | 1.00 | 37.98 | B | C |
| ATOM | 2991 | CD2 | LEU | B | 187 | 20.653 | 23.721 | 34.761 | 1.00 | 41.27 | B | C |
| ATOM | 2992 | C   | LEU | B | 187 | 20.830 | 21.000 | 30.722 | 1.00 | 36.17 | B | C |
| ATOM | 2993 | O   | LEU | B | 187 | 21.590 | 20.129 | 31.095 | 1.00 | 33.95 | B | O |
| ATOM | 2994 | N   | LEU | B | 188 | 20.941 | 21.589 | 29.536 | 1.00 | 31.56 | B | N |
| ATOM | 2995 | CA  | LEU | B | 188 | 21.957 | 21.147 | 28.584 | 1.00 | 30.02 | B | C |
| ATOM | 2996 | CB  | LEU | B | 188 | 21.368 | 21.099 | 27.175 | 1.00 | 33.46 | B | C |
| ATOM | 2997 | CG  | LEU | B | 188 | 20.261 | 20.051 | 27.020 | 1.00 | 33.86 | B | C |
| ATOM | 2998 | CD1 | LEU | B | 188 | 19.708 | 20.032 | 25.599 | 1.00 | 27.68 | B | C |
| ATOM | 2999 | CD2 | LEU | B | 188 | 20.791 | 18.670 | 27.437 | 1.00 | 32.75 | B | C |
| ATOM | 3000 | C   | LEU | B | 188 | 23.206 | 22.028 | 28.593 | 1.00 | 30.77 | B | C |
| ATOM | 3001 | O   | LEU | B | 188 | 24.313 | 21.559 | 28.296 | 1.00 | 30.19 | B | O |
| ATOM | 3002 | N   | ALA | B | 189 | 23.016 | 23.297 | 28.942 | 1.00 | 26.98 | B | N |
| ATOM | 3003 | CA  | ALA | B | 189 | 24.068 | 24.288 | 28.844 | 1.00 | 29.14 | B | C |
| ATOM | 3004 | CB  | ALA | B | 189 | 24.494 | 24.443 | 27.368 | 1.00 | 25.83 | B | C |
| ATOM | 3005 | C   | ALA | B | 189 | 23.495 | 25.596 | 29.351 | 1.00 | 28.17 | B | C |
| ATOM | 3006 | O   | ALA | B | 189 | 22.294 | 25.699 | 29.571 | 1.00 | 25.95 | B | O |
| ATOM | 3007 | N   | HIS | B | 190 | 24.342 | 26.608 | 29.509 | 1.00 | 26.71 | B | N |
| ATOM | 3008 | CA  | HIS | B | 190 | 23.846 | 27.942 | 29.818 | 1.00 | 26.54 | B | C |
| ATOM | 3009 | CB  | HIS | B | 190 | 23.406 | 28.039 | 31.296 | 1.00 | 25.95 | B | C |
| ATOM | 3010 | CG  | HIS | B | 190 | 24.508 | 27.769 | 32.280 | 1.00 | 28.88 | B | C |
| ATOM | 3011 | CD2 | HIS | B | 190 | 25.842 | 27.979 | 32.194 | 1.00 | 29.68 | B | C |
| ATOM | 3012 | ND1 | HIS | B | 190 | 24.285 | 27.236 | 33.534 | 1.00 | 29.27 | B | N |
| ATOM | 3013 | CE1 | HIS | B | 190 | 25.434 | 27.118 | 34.171 | 1.00 | 26.95 | B | C |
| ATOM | 3014 | NE2 | HIS | B | 190 | 26.394 | 27.562 | 33.385 | 1.00 | 32.38 | B | N |
| ATOM | 3015 | C   | HIS | B | 190 | 24.904 | 28.970 | 29.469 | 1.00 | 23.85 | B | C |
| ATOM | 3016 | O   | HIS | B | 190 | 26.034 | 28.615 | 29.188 | 1.00 | 29.09 | B | O |
| ATOM | 3017 | N   | ALA | B | 191 | 24.545 | 30.244 | 29.474 | 1.00 | 27.11 | B | N |
| ATOM | 3018 | CA  | ALA | B | 191 | 25.490 | 31.283 | 29.081 | 1.00 | 27.02 | B | C |
| ATOM | 3019 | CB  | ALA | B | 191 | 25.479 | 31.463 | 27.556 | 1.00 | 25.05 | B | C |
| ATOM | 3020 | C   | ALA | B | 191 | 25.149 | 32.598 | 29.781 | 1.00 | 30.46 | B | C |
| ATOM | 3021 | O   | ALA | B | 191 | 24.083 | 32.729 | 30.370 | 1.00 | 29.13 | B | O |
| ATOM | 3022 | N   | PHE | B | 192 | 26.050 | 33.570 | 29.689 | 1.00 | 28.27 | B | N |
| ATOM | 3023 | CA  | PHE | B | 192 | 25.913 | 34.835 | 30.395 | 1.00 | 30.24 | B | C |
| ATOM | 3024 | CB  | PHE | B | 192 | 27.062 | 34.975 | 31.387 | 1.00 | 30.73 | B | C |

TABLE 14-continued

Coordinates for proMMP9(35-444 ΔFnII) (SEQ ID NO: 12) complex with Example 4

| | | | | | | | | | | | |
|---|---|---|---|---|---|---|---|---|---|---|---|
| ATOM | 3025 | CG | PHE | B | 192 | 27.161 | 33.818 | 32.331 | 1.00 | 35.41 | B | C |
| ATOM | 3026 | CD1 | PHE | B | 192 | 26.489 | 33.837 | 33.553 | 1.00 | 37.09 | B | C |
| ATOM | 3027 | CD2 | PHE | B | 192 | 27.870 | 32.685 | 31.984 | 1.00 | 31.08 | B | C |
| ATOM | 3028 | CE1 | PHE | B | 192 | 26.557 | 32.742 | 34.419 | 1.00 | 37.81 | B | C |
| ATOM | 3029 | CE2 | PHE | B | 192 | 27.935 | 31.587 | 32.844 | 1.00 | 32.68 | B | C |
| ATOM | 3030 | CZ | PHE | B | 192 | 27.295 | 31.617 | 34.055 | 1.00 | 33.09 | B | C |
| ATOM | 3031 | C | PHE | B | 192 | 25.899 | 35.992 | 29.401 | 1.00 | 32.03 | B | C |
| ATOM | 3032 | O | PHE | B | 192 | 26.529 | 35.904 | 28.355 | 1.00 | 29.16 | B | O |
| ATOM | 3033 | N | PRO | B | 193 | 25.156 | 37.067 | 29.708 | 1.00 | 30.58 | B | N |
| ATOM | 3034 | CD | PRO | B | 193 | 24.405 | 37.324 | 30.946 | 1.00 | 32.89 | B | C |
| ATOM | 3035 | CA | PRO | B | 193 | 25.027 | 38.166 | 28.743 | 1.00 | 29.36 | B | C |
| ATOM | 3036 | CB | PRO | B | 193 | 23.961 | 39.068 | 29.382 | 1.00 | 30.69 | B | C |
| ATOM | 3037 | CG | PRO | B | 193 | 24.074 | 38.784 | 30.836 | 1.00 | 36.85 | B | C |
| ATOM | 3038 | C | PRO | B | 193 | 26.340 | 38.918 | 28.580 | 1.00 | 30.03 | B | C |
| ATOM | 3039 | O | PRO | B | 193 | 27.234 | 38.781 | 29.406 | 1.00 | 33.29 | B | O |
| ATOM | 3040 | N | PRO | B | 194 | 26.464 | 39.708 | 27.512 | 1.00 | 30.53 | B | N |
| ATOM | 3041 | CD | PRO | B | 194 | 25.441 | 39.966 | 26.488 | 1.00 | 30.19 | B | C |
| ATOM | 3042 | CA | PRO | B | 194 | 27.711 | 40.424 | 27.241 | 1.00 | 28.06 | B | C |
| ATOM | 3043 | CB | PRO | B | 194 | 27.341 | 41.321 | 26.053 | 1.00 | 29.96 | B | C |
| ATOM | 3044 | CG | PRO | B | 194 | 26.230 | 40.597 | 25.370 | 1.00 | 26.21 | B | C |
| ATOM | 3045 | C | PRO | B | 194 | 28.139 | 41.277 | 28.426 | 1.00 | 31.83 | B | C |
| ATOM | 3046 | O | PRO | B | 194 | 27.302 | 41.781 | 29.180 | 1.00 | 30.07 | B | O |
| ATOM | 3047 | N | GLY | B | 195 | 29.446 | 41.437 | 28.588 | 1.00 | 34.84 | B | N |
| ATOM | 3048 | CA | GLY | B | 195 | 29.979 | 42.215 | 29.690 | 1.00 | 36.64 | B | C |
| ATOM | 3049 | C | GLY | B | 195 | 31.275 | 41.626 | 30.201 | 1.00 | 34.71 | B | C |
| ATOM | 3050 | O | GLY | B | 195 | 31.883 | 40.804 | 29.521 | 1.00 | 36.67 | B | O |
| ATOM | 3051 | N | PRO | B | 196 | 31.690 | 42.031 | 31.410 | 1.00 | 34.14 | B | N |
| ATOM | 3052 | CD | PRO | B | 196 | 30.951 | 42.975 | 32.258 | 1.00 | 40.61 | B | C |
| ATOM | 3053 | CA | PRO | B | 196 | 33.012 | 41.727 | 31.964 | 1.00 | 39.50 | B | C |
| ATOM | 3054 | CB | PRO | B | 196 | 33.202 | 42.801 | 33.047 | 1.00 | 40.08 | B | C |
| ATOM | 3055 | CG | PRO | B | 196 | 32.053 | 43.760 | 32.887 | 1.00 | 43.18 | B | C |
| ATOM | 3056 | C | PRO | B | 196 | 33.095 | 40.350 | 32.601 | 1.00 | 37.52 | B | C |
| ATOM | 3057 | O | PRO | B | 196 | 32.083 | 39.772 | 32.960 | 1.00 | 36.46 | B | O |
| ATOM | 3058 | N | GLY | B | 197 | 34.314 | 39.836 | 32.720 | 1.00 | 44.77 | B | N |
| ATOM | 3059 | CA | GLY | B | 197 | 34.567 | 38.593 | 33.425 | 1.00 | 42.13 | B | C |
| ATOM | 3060 | C | GLY | B | 197 | 33.804 | 37.404 | 32.886 | 1.00 | 38.29 | B | C |
| ATOM | 3061 | O | GLY | B | 197 | 34.083 | 36.921 | 31.801 | 1.00 | 40.29 | B | O |
| ATOM | 3062 | N | ILE | B | 198 | 32.843 | 36.921 | 33.656 | 1.00 | 38.79 | B | N |
| ATOM | 3063 | CA | ILE | B | 198 | 32.120 | 35.714 | 33.288 | 1.00 | 39.25 | B | C |
| ATOM | 3064 | CB | ILE | B | 198 | 31.498 | 35.051 | 34.522 | 1.00 | 39.24 | B | C |
| ATOM | 3065 | CG2 | ILE | B | 198 | 30.209 | 35.775 | 34.951 | 1.00 | 39.98 | B | C |
| ATOM | 3066 | CG1 | ILE | B | 198 | 31.254 | 33.566 | 34.257 | 1.00 | 38.75 | B | C |
| ATOM | 3067 | CD1 | ILE | B | 198 | 30.582 | 32.855 | 35.417 | 1.00 | 37.74 | B | C |
| ATOM | 3068 | C | ILE | B | 198 | 31.048 | 36.020 | 32.241 | 1.00 | 37.80 | B | C |
| ATOM | 3069 | O | ILE | B | 198 | 30.555 | 35.126 | 31.550 | 1.00 | 35.85 | B | O |
| ATOM | 3070 | N | GLN | B | 199 | 30.715 | 37.297 | 32.120 | 1.00 | 35.98 | B | N |
| ATOM | 3071 | CA | GLN | B | 199 | 29.706 | 37.732 | 31.178 | 1.00 | 34.37 | B | C |
| ATOM | 3072 | CB | GLN | B | 199 | 29.303 | 39.182 | 31.454 | 1.00 | 34.35 | B | C |
| ATOM | 3073 | CG | GLN | B | 199 | 28.569 | 39.310 | 32.787 | 1.00 | 36.08 | B | C |
| ATOM | 3074 | CD | GLN | B | 199 | 28.184 | 40.741 | 33.139 | 1.00 | 42.98 | B | C |
| ATOM | 3075 | OE1 | GLN | B | 199 | 28.174 | 41.113 | 34.318 | 1.00 | 36.41 | B | O |
| ATOM | 3076 | NE2 | GLN | B | 199 | 27.862 | 41.549 | 32.120 | 1.00 | 36.93 | B | N |
| ATOM | 3077 | C | GLN | B | 199 | 30.177 | 37.526 | 29.754 | 1.00 | 30.87 | B | C |
| ATOM | 3078 | O | GLN | B | 199 | 31.272 | 37.936 | 29.395 | 1.00 | 33.70 | B | O |
| ATOM | 3079 | N | GLY | B | 200 | 29.329 | 36.889 | 28.956 | 1.00 | 30.36 | B | N |
| ATOM | 3080 | CA | GLY | B | 200 | 29.661 | 36.497 | 27.599 | 1.00 | 28.96 | B | C |
| ATOM | 3081 | C | GLY | B | 200 | 30.033 | 35.028 | 27.460 | 1.00 | 27.79 | B | C |
| ATOM | 3082 | O | GLY | B | 200 | 29.979 | 34.472 | 26.376 | 1.00 | 30.58 | B | O |
| ATOM | 3083 | N | ASP | B | 201 | 30.426 | 34.400 | 28.559 | 1.00 | 31.76 | B | N |
| ATOM | 3084 | CA | ASP | B | 201 | 30.848 | 33.002 | 28.544 | 1.00 | 30.84 | B | C |
| ATOM | 3085 | CB | ASP | B | 201 | 31.503 | 32.636 | 29.879 | 1.00 | 30.86 | B | C |
| ATOM | 3086 | CG | ASP | B | 201 | 32.795 | 33.364 | 30.093 | 1.00 | 35.26 | B | C |
| ATOM | 3087 | OD1 | ASP | B | 201 | 33.144 | 34.167 | 29.205 | 1.00 | 34.12 | B | O |
| ATOM | 3088 | OD2 | ASP | B | 201 | 33.468 | 33.125 | 31.118 | 1.00 | 39.43 | B | O |
| ATOM | 3089 | C | ASP | B | 201 | 29.702 | 32.038 | 28.293 | 1.00 | 31.82 | B | C |
| ATOM | 3090 | O | ASP | B | 201 | 28.540 | 32.327 | 28.609 | 1.00 | 32.85 | B | O |
| ATOM | 3091 | N | ALA | B | 202 | 30.051 | 30.865 | 27.776 | 1.00 | 29.49 | B | N |
| ATOM | 3092 | CA | ALA | B | 202 | 29.078 | 29.833 | 27.454 | 1.00 | 28.11 | B | C |
| ATOM | 3093 | CB | ALA | B | 202 | 28.860 | 29.773 | 25.917 | 1.00 | 26.32 | B | C |
| ATOM | 3094 | C | ALA | B | 202 | 29.623 | 28.516 | 27.969 | 1.00 | 29.83 | B | C |
| ATOM | 3095 | O | ALA | B | 202 | 30.775 | 28.171 | 27.702 | 1.00 | 32.20 | B | O |
| ATOM | 3096 | N | HIS | B | 203 | 28.801 | 27.785 | 28.712 | 1.00 | 27.70 | B | N |
| ATOM | 3097 | CA | HIS | B | 203 | 29.207 | 26.518 | 29.307 | 1.00 | 28.19 | B | C |
| ATOM | 3098 | CB | HIS | B | 203 | 29.130 | 26.632 | 30.834 | 1.00 | 31.66 | B | C |
| ATOM | 3099 | CG | HIS | B | 203 | 29.961 | 27.743 | 31.398 | 1.00 | 33.16 | B | C |
| ATOM | 3100 | CD2 | HIS | B | 203 | 30.914 | 28.518 | 30.829 | 1.00 | 28.58 | B | C |
| ATOM | 3101 | ND1 | HIS | B | 203 | 29.854 | 28.159 | 32.711 | 1.00 | 32.21 | B | N |
| ATOM | 3102 | CE1 | HIS | B | 203 | 30.710 | 29.146 | 32.923 | 1.00 | 35.07 | B | C |

TABLE 14-continued

Coordinates for proMMP9(35-444 ΔFnII) (SEQ ID NO: 12) complex with Example 4

| ATOM | 3103 | NE2 | HIS | B | 203 | 31.369 | 29.374 | 31.807 | 1.00 | 36.96 | B | N |
|---|---|---|---|---|---|---|---|---|---|---|---|---|
| ATOM | 3104 | C | HIS | B | 203 | 28.291 | 25.390 | 28.831 | 1.00 | 28.56 | B | C |
| ATOM | 3105 | O | HIS | B | 203 | 27.097 | 25.594 | 28.644 | 1.00 | 29.79 | B | O |
| ATOM | 3106 | N | PHE | B | 204 | 28.849 | 24.200 | 28.661 | 1.00 | 28.04 | B | N |
| ATOM | 3107 | CA | PHE | B | 204 | 28.108 | 23.060 | 28.147 | 1.00 | 28.14 | B | C |
| ATOM | 3108 | CB | PHE | B | 204 | 28.627 | 22.670 | 26.745 | 1.00 | 29.02 | B | C |
| ATOM | 3109 | CG | PHE | B | 204 | 28.512 | 23.787 | 25.731 | 1.00 | 30.78 | B | C |
| ATOM | 3110 | CD1 | PHE | B | 204 | 29.478 | 24.776 | 25.657 | 1.00 | 28.76 | B | C |
| ATOM | 3111 | CD2 | PHE | B | 204 | 27.416 | 23.874 | 24.887 | 1.00 | 28.07 | B | C |
| ATOM | 3112 | CE1 | PHE | B | 204 | 29.360 | 25.818 | 24.755 | 1.00 | 24.40 | B | C |
| ATOM | 3113 | CE2 | PHE | B | 204 | 27.296 | 24.917 | 23.985 | 1.00 | 22.92 | B | C |
| ATOM | 3114 | CZ | PHE | B | 204 | 28.260 | 25.890 | 23.926 | 1.00 | 25.26 | B | C |
| ATOM | 3115 | C | PHE | B | 204 | 28.238 | 21.902 | 29.132 | 1.00 | 31.14 | B | C |
| ATOM | 3116 | O | PHE | B | 204 | 29.319 | 21.627 | 29.650 | 1.00 | 29.11 | B | O |
| ATOM | 3117 | N | ASP | B | 205 | 27.129 | 21.231 | 29.399 | 1.00 | 29.08 | B | N |
| ATOM | 3118 | CA | ASP | B | 205 | 27.124 | 20.161 | 30.376 | 1.00 | 30.87 | B | C |
| ATOM | 3119 | CB | ASP | B | 205 | 25.705 | 19.933 | 30.880 | 1.00 | 31.10 | B | C |
| ATOM | 3120 | CG | ASP | B | 205 | 25.637 | 18.921 | 32.010 | 1.00 | 34.12 | B | C |
| ATOM | 3121 | OD1 | ASP | B | 205 | 26.656 | 18.283 | 32.354 | 1.00 | 36.27 | B | O |
| ATOM | 3122 | OD2 | ASP | B | 205 | 24.540 | 18.762 | 32.559 | 1.00 | 34.71 | B | O |
| ATOM | 3123 | C | ASP | B | 205 | 27.682 | 18.887 | 29.782 | 1.00 | 30.35 | B | C |
| ATOM | 3124 | O | ASP | B | 205 | 27.051 | 18.251 | 28.945 | 1.00 | 32.08 | B | O |
| ATOM | 3125 | N | ASP | B | 206 | 28.862 | 18.496 | 30.229 | 1.00 | 32.42 | B | N |
| ATOM | 3126 | CA | ASP | B | 206 | 29.558 | 17.393 | 29.588 | 1.00 | 31.21 | B | C |
| ATOM | 3127 | CB | ASP | B | 206 | 31.065 | 17.545 | 29.755 | 1.00 | 32.15 | B | C |
| ATOM | 3128 | CG | ASP | B | 206 | 31.858 | 16.886 | 28.627 | 1.00 | 33.18 | B | C |
| ATOM | 3129 | OD1 | ASP | B | 206 | 31.242 | 16.355 | 27.669 | 1.00 | 32.03 | B | O |
| ATOM | 3130 | OD2 | ASP | B | 206 | 33.109 | 16.918 | 28.704 | 1.00 | 35.29 | B | O |
| ATOM | 3131 | C | ASP | B | 206 | 29.078 | 16.045 | 30.109 | 1.00 | 34.11 | B | C |
| ATOM | 3132 | O | ASP | B | 206 | 29.625 | 14.996 | 29.758 | 1.00 | 32.87 | B | O |
| ATOM | 3133 | N | ASP | B | 207 | 28.060 | 16.085 | 30.962 | 1.00 | 35.08 | B | N |
| ATOM | 3134 | CA | ASP | B | 207 | 27.328 | 14.882 | 31.335 | 1.00 | 37.04 | B | C |
| ATOM | 3135 | CB | ASP | B | 207 | 26.629 | 15.057 | 32.684 | 1.00 | 37.43 | B | C |
| ATOM | 3136 | CG | ASP | B | 207 | 27.485 | 14.599 | 33.837 | 1.00 | 38.06 | B | C |
| ATOM | 3137 | OD1 | ASP | B | 207 | 28.325 | 13.686 | 33.628 | 1.00 | 36.41 | B | O |
| ATOM | 3138 | OD2 | ASP | B | 207 | 27.319 | 15.161 | 34.941 | 1.00 | 34.60 | B | O |
| ATOM | 3139 | C | ASP | B | 207 | 26.306 | 14.540 | 30.261 | 1.00 | 35.39 | B | C |
| ATOM | 3140 | O | ASP | B | 207 | 25.656 | 13.508 | 30.327 | 1.00 | 33.03 | B | O |
| ATOM | 3141 | N | GLU | B | 208 | 26.154 | 15.427 | 29.283 | 1.00 | 34.95 | B | N |
| ATOM | 3142 | CA | GLU | B | 208 | 25.394 | 15.091 | 28.084 | 1.00 | 33.46 | B | C |
| ATOM | 3143 | CB | GLU | B | 208 | 24.770 | 16.336 | 27.450 | 1.00 | 33.55 | B | C |
| ATOM | 3144 | CG | GLU | B | 208 | 24.120 | 17.248 | 28.408 | 1.00 | 34.83 | B | C |
| ATOM | 3145 | CD | GLU | B | 208 | 22.953 | 16.598 | 29.113 | 1.00 | 38.78 | B | C |
| ATOM | 3146 | OE1 | GLU | B | 208 | 22.615 | 15.423 | 28.823 | 1.00 | 37.38 | B | O |
| ATOM | 3147 | OE2 | GLU | B | 208 | 22.363 | 17.288 | 29.949 | 1.00 | 38.50 | B | O |
| ATOM | 3148 | C | GLU | B | 208 | 26.317 | 14.474 | 27.054 | 1.00 | 32.20 | B | C |
| ATOM | 3149 | O | GLU | B | 208 | 27.492 | 14.823 | 26.973 | 1.00 | 33.36 | B | O |
| ATOM | 3150 | N | LEU | B | 209 | 25.769 | 13.574 | 26.251 | 1.00 | 32.49 | B | N |
| ATOM | 3151 | CA | LEU | B | 209 | 26.462 | 13.086 | 25.077 | 1.00 | 37.30 | B | C |
| ATOM | 3152 | CB | LEU | B | 209 | 25.850 | 11.774 | 24.606 | 1.00 | 38.67 | B | C |
| ATOM | 3153 | CG | LEU | B | 209 | 26.411 | 11.176 | 23.322 | 1.00 | 41.31 | B | C |
| ATOM | 3154 | CD1 | LEU | B | 209 | 27.776 | 10.551 | 23.573 | 1.00 | 36.31 | B | C |
| ATOM | 3155 | CD2 | LEU | B | 209 | 25.430 | 10.145 | 22.776 | 1.00 | 44.11 | B | C |
| ATOM | 3156 | C | LEU | B | 209 | 26.337 | 14.141 | 23.985 | 1.00 | 36.94 | B | C |
| ATOM | 3157 | O | LEU | B | 209 | 25.226 | 14.478 | 23.545 | 1.00 | 35.07 | B | O |
| ATOM | 3158 | N | TRP | B | 210 | 27.484 | 14.667 | 23.572 | 1.00 | 34.18 | B | N |
| ATOM | 3159 | CA | TRP | B | 210 | 27.541 | 15.716 | 22.568 | 1.00 | 34.84 | B | C |
| ATOM | 3160 | CB | TRP | B | 210 | 28.582 | 16.776 | 22.967 | 1.00 | 31.76 | B | C |
| ATOM | 3161 | CG | TRP | B | 210 | 28.096 | 17.586 | 24.115 | 1.00 | 29.94 | B | C |
| ATOM | 3162 | CD2 | TRP | B | 210 | 26.982 | 18.486 | 24.106 | 1.00 | 28.55 | B | C |
| ATOM | 3163 | CE2 | TRP | B | 210 | 26.849 | 18.997 | 25.412 | 1.00 | 31.19 | B | C |
| ATOM | 3164 | CE3 | TRP | B | 210 | 26.084 | 18.909 | 23.117 | 1.00 | 28.31 | B | C |
| ATOM | 3165 | CD1 | TRP | B | 210 | 28.572 | 17.575 | 25.397 | 1.00 | 28.82 | B | C |
| ATOM | 3166 | NE1 | TRP | B | 210 | 27.838 | 18.426 | 26.178 | 1.00 | 26.55 | B | N |
| ATOM | 3167 | CZ2 | TRP | B | 210 | 25.860 | 19.920 | 25.756 | 1.00 | 28.51 | B | C |
| ATOM | 3168 | CZ3 | TRP | B | 210 | 25.107 | 19.825 | 23.453 | 1.00 | 26.86 | B | C |
| ATOM | 3169 | CH2 | TRP | B | 210 | 24.998 | 20.318 | 24.767 | 1.00 | 28.13 | B | C |
| ATOM | 3170 | C | TRP | B | 210 | 27.853 | 15.126 | 21.206 | 1.00 | 31.28 | B | C |
| ATOM | 3171 | O | TRP | B | 210 | 28.832 | 14.405 | 21.043 | 1.00 | 28.86 | B | O |
| ATOM | 3172 | N | SER | B | 211 | 26.987 | 15.405 | 20.244 | 1.00 | 28.84 | B | N |
| ATOM | 3173 | CA | SER | B | 211 | 27.204 | 14.955 | 18.874 | 1.00 | 35.53 | B | C |
| ATOM | 3174 | CB | SER | B | 211 | 26.470 | 13.642 | 18.592 | 1.00 | 34.48 | B | C |
| ATOM | 3175 | OG | SER | B | 211 | 25.077 | 13.771 | 18.818 | 1.00 | 36.46 | B | O |
| ATOM | 3176 | C | SER | B | 211 | 26.719 | 16.031 | 17.918 | 1.00 | 33.41 | B | C |
| ATOM | 3177 | O | SER | B | 211 | 26.546 | 17.188 | 18.310 | 1.00 | 29.51 | B | O |
| ATOM | 3178 | N | LEU | B | 212 | 26.482 | 15.651 | 16.671 | 1.00 | 31.49 | B | N |
| ATOM | 3179 | CA | LEU | B | 212 | 25.926 | 16.612 | 15.747 | 1.00 | 34.36 | B | C |
| ATOM | 3180 | CB | LEU | B | 212 | 26.575 | 16.530 | 14.372 | 1.00 | 37.26 | B | C |

TABLE 14-continued

Coordinates for proMMP9(35-444 ΔFnII) (SEQ ID NO: 12) complex with Example 4

| ATOM | 3181 | CG | LEU | B | 212 | 28.009 | 17.022 | 14.531 | 1.00 | 35.51 | B | C |
|---|---|---|---|---|---|---|---|---|---|---|---|---|
| ATOM | 3182 | CD1 | LEU | B | 212 | 28.600 | 17.446 | 13.193 | 1.00 | 39.28 | B | C |
| ATOM | 3183 | CD2 | LEU | B | 212 | 28.016 | 18.191 | 15.496 | 1.00 | 32.06 | B | C |
| ATOM | 3184 | C | LEU | B | 212 | 24.426 | 16.495 | 15.715 | 1.00 | 38.47 | B | C |
| ATOM | 3185 | O | LEU | B | 212 | 23.780 | 16.959 | 14.769 | 1.00 | 42.85 | B | O |
| ATOM | 3186 | N | GLY | B | 213 | 23.902 | 15.898 | 16.794 | 1.00 | 38.85 | B | N |
| ATOM | 3187 | CA | GLY | B | 213 | 22.479 | 15.725 | 17.036 | 1.00 | 37.81 | B | C |
| ATOM | 3188 | C | GLY | B | 213 | 21.926 | 15.085 | 15.792 | 1.00 | 47.47 | B | C |
| ATOM | 3189 | O | GLY | B | 213 | 22.020 | 15.643 | 14.707 | 1.00 | 52.52 | B | O |
| ATOM | 3190 | N | LYS | B | 389 | 21.387 | 13.889 | 15.901 | 1.00 | 49.94 | B | N |
| ATOM | 3191 | CA | LYS | B | 389 | 21.121 | 13.140 | 14.677 | 1.00 | 52.59 | B | C |
| ATOM | 3192 | CB | LYS | B | 389 | 22.429 | 12.954 | 13.907 | 1.00 | 56.45 | B | C |
| ATOM | 3193 | CG | LYS | B | 389 | 22.389 | 13.449 | 12.480 | 1.00 | 55.44 | B | C |
| ATOM | 3194 | CD | LYS | B | 389 | 21.878 | 12.368 | 11.574 | 1.00 | 60.22 | B | C |
| ATOM | 3195 | CE | LYS | B | 389 | 22.573 | 12.447 | 10.225 | 1.00 | 63.58 | B | C |
| ATOM | 3196 | NZ | LYS | B | 389 | 22.625 | 11.084 | 9.603 | 1.00 | 66.66 | B | N |
| ATOM | 3197 | C | LYS | B | 389 | 20.481 | 11.787 | 14.970 | 1.00 | 50.63 | B | C |
| ATOM | 3198 | O | LYS | B | 389 | 19.587 | 11.340 | 14.260 | 1.00 | 52.27 | B | O |
| ATOM | 3199 | N | GLY | B | 390 | 20.943 | 11.154 | 16.041 | 1.00 | 50.77 | B | N |
| ATOM | 3200 | CA | GLY | B | 390 | 20.368 | 9.918 | 16.531 | 1.00 | 47.84 | B | C |
| ATOM | 3201 | C | GLY | B | 390 | 20.434 | 10.091 | 18.024 | 1.00 | 45.87 | B | C |
| ATOM | 3202 | O | GLY | B | 390 | 19.566 | 10.722 | 18.621 | 1.00 | 48.47 | B | O |
| ATOM | 3203 | N | GLN | B | 391 | 21.488 | 9.563 | 18.623 | 1.00 | 47.37 | B | N |
| ATOM | 3204 | CA | GLN | B | 391 | 21.785 | 9.856 | 20.013 | 1.00 | 52.04 | B | C |
| ATOM | 3205 | CB | GLN | B | 391 | 22.799 | 8.840 | 20.564 | 1.00 | 52.03 | B | C |
| ATOM | 3206 | CG | GLN | B | 391 | 24.135 | 8.775 | 19.769 | 1.00 | 50.55 | B | C |
| ATOM | 3207 | CD | GLN | B | 391 | 25.103 | 7.711 | 20.291 | 1.00 | 49.48 | B | C |
| ATOM | 3208 | OE1 | GLN | B | 391 | 24.694 | 6.740 | 20.930 | 1.00 | 58.51 | B | O |
| ATOM | 3209 | NE2 | GLN | B | 391 | 26.394 | 7.893 | 20.017 | 1.00 | 52.67 | B | N |
| ATOM | 3210 | C | GLN | B | 391 | 22.378 | 11.261 | 20.015 | 1.00 | 48.44 | B | C |
| ATOM | 3211 | O | GLN | B | 391 | 22.596 | 11.854 | 18.957 | 1.00 | 52.11 | B | O |
| ATOM | 3212 | N | GLY | B | 392 | 22.639 | 11.800 | 21.194 | 1.00 | 46.69 | B | N |
| ATOM | 3213 | CA | GLY | B | 392 | 23.388 | 13.034 | 21.280 | 1.00 | 39.31 | B | C |
| ATOM | 3214 | C | GLY | B | 392 | 22.590 | 14.300 | 21.032 | 1.00 | 37.93 | B | C |
| ATOM | 3215 | O | GLY | B | 392 | 21.698 | 14.365 | 20.183 | 1.00 | 36.55 | B | O |
| ATOM | 3216 | N | TYR | B | 393 | 22.923 | 15.315 | 21.815 | 1.00 | 36.88 | B | N |
| ATOM | 3217 | CA | TYR | B | 393 | 22.419 | 16.652 | 21.598 | 1.00 | 33.09 | B | C |
| ATOM | 3218 | CB | TYR | B | 393 | 22.347 | 17.404 | 22.933 | 1.00 | 27.70 | B | C |
| ATOM | 3219 | CG | TYR | B | 393 | 21.340 | 16.780 | 23.887 | 1.00 | 32.72 | B | C |
| ATOM | 3220 | CD1 | TYR | B | 393 | 19.980 | 17.039 | 23.751 | 1.00 | 30.68 | B | C |
| ATOM | 3221 | CE1 | TYR | B | 393 | 19.048 | 16.468 | 24.605 | 1.00 | 34.50 | B | C |
| ATOM | 3222 | CD2 | TYR | B | 393 | 21.746 | 15.923 | 24.905 | 1.00 | 29.49 | B | C |
| ATOM | 3223 | CE2 | TYR | B | 393 | 20.818 | 15.337 | 25.758 | 1.00 | 36.98 | B | C |
| ATOM | 3224 | CZ | TYR | B | 393 | 19.470 | 15.615 | 25.605 | 1.00 | 35.78 | B | C |
| ATOM | 3225 | OH | TYR | B | 393 | 18.542 | 15.052 | 26.456 | 1.00 | 38.17 | B | O |
| ATOM | 3226 | C | TYR | B | 393 | 23.399 | 17.323 | 20.645 | 1.00 | 28.88 | B | C |
| ATOM | 3227 | O | TYR | B | 393 | 24.604 | 17.169 | 20.788 | 1.00 | 28.18 | B | O |
| ATOM | 3228 | N | SER | B | 394 | 22.879 | 18.040 | 19.662 | 1.00 | 28.09 | B | N |
| ATOM | 3229 | CA | SER | B | 394 | 23.734 | 18.691 | 18.678 | 1.00 | 29.57 | B | C |
| ATOM | 3230 | CB | SER | B | 394 | 22.907 | 19.206 | 17.507 | 1.00 | 26.45 | B | C |
| ATOM | 3231 | OG | SER | B | 394 | 23.600 | 20.276 | 16.887 | 1.00 | 29.83 | B | O |
| ATOM | 3232 | C | SER | B | 394 | 24.473 | 19.862 | 19.319 | 1.00 | 28.00 | B | C |
| ATOM | 3233 | O | SER | B | 394 | 23.858 | 20.875 | 19.702 | 1.00 | 22.92 | B | O |
| ATOM | 3234 | N | LEU | B | 395 | 25.787 | 19.730 | 19.438 | 1.00 | 22.52 | B | N |
| ATOM | 3235 | CA | LEU | B | 395 | 26.575 | 20.812 | 20.013 | 1.00 | 24.75 | B | C |
| ATOM | 3236 | CB | LEU | B | 395 | 28.044 | 20.400 | 20.135 | 1.00 | 25.19 | B | C |
| ATOM | 3237 | CG | LEU | B | 395 | 29.044 | 21.415 | 20.681 | 1.00 | 27.43 | B | C |
| ATOM | 3238 | CD1 | LEU | B | 395 | 28.716 | 21.782 | 22.104 | 1.00 | 24.39 | B | C |
| ATOM | 3239 | CD2 | LEU | B | 395 | 30.477 | 20.863 | 20.581 | 1.00 | 22.97 | B | C |
| ATOM | 3240 | C | LEU | B | 395 | 26.423 | 22.043 | 19.134 | 1.00 | 23.50 | B | C |
| ATOM | 3241 | O | LEU | B | 395 | 26.467 | 23.173 | 19.609 | 1.00 | 23.15 | B | O |
| ATOM | 3242 | N | PHE | B | 396 | 26.238 | 21.828 | 17.836 | 1.00 | 23.81 | B | N |
| ATOM | 3243 | CA | PHE | B | 396 | 26.094 | 22.962 | 16.920 | 1.00 | 22.27 | B | C |
| ATOM | 3244 | CB | PHE | B | 396 | 25.959 | 22.497 | 15.461 | 1.00 | 21.83 | B | C |
| ATOM | 3245 | CG | PHE | B | 396 | 25.510 | 23.591 | 14.512 | 1.00 | 23.05 | B | C |
| ATOM | 3246 | CD1 | PHE | B | 396 | 26.271 | 24.756 | 14.353 | 1.00 | 23.29 | B | C |
| ATOM | 3247 | CD2 | PHE | B | 396 | 24.354 | 23.450 | 13.765 | 1.00 | 22.05 | B | C |
| ATOM | 3248 | CE1 | PHE | B | 396 | 25.868 | 25.763 | 13.467 | 1.00 | 23.00 | B | C |
| ATOM | 3249 | CE2 | PHE | B | 396 | 23.938 | 24.451 | 12.876 | 1.00 | 21.28 | B | C |
| ATOM | 3250 | CZ | PHE | B | 396 | 24.707 | 25.608 | 12.721 | 1.00 | 24.29 | B | C |
| ATOM | 3251 | C | PHE | B | 396 | 24.871 | 23.783 | 17.326 | 1.00 | 23.65 | B | C |
| ATOM | 3252 | O | PHE | B | 396 | 24.962 | 24.984 | 17.554 | 1.00 | 21.22 | B | O |
| ATOM | 3253 | N | LEU | B | 397 | 23.724 | 23.115 | 17.432 | 1.00 | 24.99 | B | N |
| ATOM | 3254 | CA | LEU | B | 397 | 22.476 | 23.813 | 17.692 | 1.00 | 26.82 | B | C |
| ATOM | 3255 | CB | LEU | B | 397 | 21.287 | 22.864 | 17.524 | 1.00 | 31.00 | B | C |
| ATOM | 3256 | CG | LEU | B | 397 | 21.005 | 22.351 | 16.104 | 1.00 | 26.82 | B | C |
| ATOM | 3257 | CD1 | LEU | B | 397 | 19.863 | 21.341 | 16.151 | 1.00 | 30.67 | B | C |
| ATOM | 3258 | CD2 | LEU | B | 397 | 20.663 | 23.508 | 15.147 | 1.00 | 23.55 | B | C |

TABLE 14-continued

Coordinates for proMMP9(35-444 ΔFnII) (SEQ ID NO: 12) complex with Example 4

| ATOM | 3259 | C   | LEU | B | 397 | 22.471 | 24.461 | 19.081 | 1.00 | 26.40 | B | C |
| ATOM | 3260 | O   | LEU | B | 397 | 22.021 | 25.589 | 19.239 | 1.00 | 24.64 | B | O |
| ATOM | 3261 | N   | VAL | B | 398 | 22.973 | 23.745 | 20.081 | 1.00 | 24.73 | B | N |
| ATOM | 3262 | CA  | VAL | B | 398 | 22.951 | 24.284 | 21.434 | 1.00 | 28.98 | B | C |
| ATOM | 3263 | CB  | VAL | B | 398 | 23.287 | 23.228 | 22.512 | 1.00 | 29.57 | B | C |
| ATOM | 3264 | CG1 | VAL | B | 398 | 23.466 | 23.904 | 23.872 | 1.00 | 23.81 | B | C |
| ATOM | 3265 | CG2 | VAL | B | 398 | 22.202 | 22.158 | 22.573 | 1.00 | 28.14 | B | C |
| ATOM | 3266 | C   | VAL | B | 398 | 23.928 | 25.451 | 21.519 | 1.00 | 26.33 | B | C |
| ATOM | 3267 | O   | VAL | B | 398 | 23.656 | 26.443 | 22.195 | 1.00 | 26.03 | B | O |
| ATOM | 3268 | N   | ALA | B | 399 | 25.071 | 25.321 | 20.848 | 1.00 | 24.27 | B | N |
| ATOM | 3269 | CA  | ALA | B | 399 | 26.041 | 26.419 | 20.763 | 1.00 | 23.73 | B | C |
| ATOM | 3270 | CB  | ALA | B | 399 | 27.277 | 25.994 | 19.977 | 1.00 | 25.97 | B | C |
| ATOM | 3271 | C   | ALA | B | 399 | 25.436 | 27.673 | 20.141 | 1.00 | 25.18 | B | C |
| ATOM | 3272 | O   | ALA | B | 399 | 25.627 | 28.782 | 20.652 | 1.00 | 25.18 | B | O |
| ATOM | 3273 | N   | ALA | B | 400 | 24.715 | 27.507 | 19.035 | 1.00 | 23.76 | B | N |
| ATOM | 3274 | CA  | ALA | B | 400 | 24.093 | 28.654 | 18.367 | 1.00 | 24.92 | B | C |
| ATOM | 3275 | CB  | ALA | B | 400 | 23.365 | 28.219 | 17.123 | 1.00 | 23.60 | B | C |
| ATOM | 3276 | C   | ALA | B | 400 | 23.133 | 29.336 | 19.324 | 1.00 | 24.65 | B | C |
| ATOM | 3277 | O   | ALA | B | 400 | 23.055 | 30.562 | 19.394 | 1.00 | 25.21 | B | O |
| ATOM | 3278 | N   | HIS | B | 401 | 22.403 | 28.525 | 20.068 | 1.00 | 23.72 | B | N |
| ATOM | 3279 | CA  | HIS | B | 401 | 21.474 | 29.045 | 21.060 | 1.00 | 25.25 | B | C |
| ATOM | 3280 | CB  | HIS | B | 401 | 20.700 | 27.917 | 21.726 | 1.00 | 24.20 | B | C |
| ATOM | 3281 | CG  | HIS | B | 401 | 19.732 | 28.392 | 22.774 | 1.00 | 23.09 | B | C |
| ATOM | 3282 | CD2 | HIS | B | 401 | 19.911 | 28.670 | 24.095 | 1.00 | 23.50 | B | C |
| ATOM | 3283 | ND1 | HIS | B | 401 | 18.412 | 28.637 | 22.512 | 1.00 | 25.12 | B | N |
| ATOM | 3284 | CE1 | HIS | B | 401 | 17.799 | 29.050 | 23.610 | 1.00 | 24.70 | B | C |
| ATOM | 3285 | NE2 | HIS | B | 401 | 18.699 | 29.064 | 24.589 | 1.00 | 23.34 | B | N |
| ATOM | 3286 | C   | HIS | B | 401 | 22.194 | 29.850 | 22.124 | 1.00 | 22.09 | B | C |
| ATOM | 3287 | O   | HIS | B | 401 | 21.842 | 31.001 | 22.382 | 1.00 | 23.91 | B | O |
| ATOM | 3288 | N   | GLU | B | 402 | 23.191 | 29.232 | 22.749 | 1.00 | 21.08 | B | N |
| ATOM | 3289 | CA  | GLU | B | 402 | 23.896 | 29.855 | 23.863 | 1.00 | 23.01 | B | C |
| ATOM | 3290 | CB  | GLU | B | 402 | 24.852 | 28.873 | 24.533 | 1.00 | 22.75 | B | C |
| ATOM | 3291 | CG  | GLU | B | 402 | 24.175 | 27.633 | 25.065 | 1.00 | 23.67 | B | C |
| ATOM | 3292 | CD  | GLU | B | 402 | 23.192 | 27.919 | 26.207 | 1.00 | 26.49 | B | C |
| ATOM | 3293 | OE1 | GLU | B | 402 | 23.290 | 28.999 | 26.849 | 1.00 | 21.30 | B | O |
| ATOM | 3294 | OE2 | GLU | B | 402 | 22.327 | 27.046 | 26.447 | 1.00 | 24.68 | B | O |
| ATOM | 3295 | C   | GLU | B | 402 | 24.659 | 31.099 | 23.431 | 1.00 | 25.15 | B | C |
| ATOM | 3296 | O   | GLU | B | 402 | 24.734 | 32.066 | 24.198 | 1.00 | 27.11 | B | O |
| ATOM | 3297 | N   | PHE | B | 403 | 25.232 | 31.069 | 22.223 | 1.00 | 25.23 | B | N |
| ATOM | 3298 | CA  | PHE | B | 403 | 25.943 | 32.226 | 21.674 | 1.00 | 22.98 | B | C |
| ATOM | 3299 | CB  | PHE | B | 403 | 26.638 | 31.901 | 20.333 | 1.00 | 25.21 | B | C |
| ATOM | 3300 | CG  | PHE | B | 403 | 27.778 | 30.900 | 20.436 | 1.00 | 23.91 | B | C |
| ATOM | 3301 | CD1 | PHE | B | 403 | 28.251 | 30.476 | 21.665 | 1.00 | 26.23 | B | C |
| ATOM | 3302 | CD2 | PHE | B | 403 | 28.376 | 30.390 | 19.286 | 1.00 | 26.21 | B | C |
| ATOM | 3303 | CE1 | PHE | B | 403 | 29.296 | 29.548 | 21.755 | 1.00 | 29.58 | B | C |
| ATOM | 3304 | CE2 | PHE | B | 403 | 29.429 | 29.478 | 19.363 | 1.00 | 25.67 | B | C |
| ATOM | 3305 | CZ  | PHE | B | 403 | 29.886 | 29.051 | 20.602 | 1.00 | 23.72 | B | C |
| ATOM | 3306 | C   | PHE | B | 403 | 24.945 | 33.388 | 21.506 | 1.00 | 24.86 | B | C |
| ATOM | 3307 | O   | PHE | B | 403 | 25.314 | 34.555 | 21.567 | 1.00 | 22.93 | B | O |
| ATOM | 3308 | N   | GLY | B | 404 | 23.678 | 33.052 | 21.284 | 1.00 | 24.77 | B | N |
| ATOM | 3309 | CA  | GLY | B | 404 | 22.611 | 34.043 | 21.259 | 1.00 | 26.05 | B | C |
| ATOM | 3310 | C   | GLY | B | 404 | 22.558 | 34.847 | 22.556 | 1.00 | 25.61 | B | C |
| ATOM | 3311 | O   | GLY | B | 404 | 22.502 | 36.074 | 22.529 | 1.00 | 22.37 | B | O |
| ATOM | 3312 | N   | HIS | B | 405 | 22.588 | 34.149 | 23.690 | 1.00 | 25.09 | B | N |
| ATOM | 3313 | CA  | HIS | B | 405 | 22.668 | 34.801 | 25.010 | 1.00 | 27.23 | B | C |
| ATOM | 3314 | CB  | HIS | B | 405 | 22.603 | 33.775 | 26.147 | 1.00 | 24.75 | B | C |
| ATOM | 3315 | CG  | HIS | B | 405 | 21.289 | 33.070 | 26.287 | 1.00 | 26.55 | B | C |
| ATOM | 3316 | CD2 | HIS | B | 405 | 20.995 | 31.770 | 26.542 | 1.00 | 25.45 | B | C |
| ATOM | 3317 | ND1 | HIS | B | 405 | 20.078 | 33.727 | 26.223 | 1.00 | 27.85 | B | N |
| ATOM | 3318 | CE1 | HIS | B | 405 | 19.095 | 32.860 | 26.413 | 1.00 | 27.79 | B | C |
| ATOM | 3319 | NE2 | HIS | B | 405 | 19.632 | 31.668 | 26.606 | 1.00 | 24.97 | B | N |
| ATOM | 3320 | C   | HIS | B | 405 | 23.968 | 35.604 | 25.167 | 1.00 | 27.09 | B | C |
| ATOM | 3321 | O   | HIS | B | 405 | 23.951 | 36.710 | 25.699 | 1.00 | 23.77 | B | O |
| ATOM | 3322 | N   | ALA | B | 406 | 25.090 | 35.025 | 24.733 | 1.00 | 24.99 | B | N |
| ATOM | 3323 | CA  | ALA | B | 406 | 26.406 | 35.685 | 24.842 | 1.00 | 25.43 | B | C |
| ATOM | 3324 | CB  | ALA | B | 406 | 27.508 | 34.778 | 24.318 | 1.00 | 25.46 | B | C |
| ATOM | 3325 | C   | ALA | B | 406 | 26.431 | 37.010 | 24.086 | 1.00 | 28.22 | B | C |
| ATOM | 3326 | O   | ALA | B | 406 | 27.327 | 37.839 | 24.272 | 1.00 | 27.95 | B | O |
| ATOM | 3327 | N   | LEU | B | 407 | 25.448 | 37.197 | 23.217 | 1.00 | 24.41 | B | N |
| ATOM | 3328 | CA  | LEU | B | 407 | 25.351 | 38.430 | 22.460 | 1.00 | 28.36 | B | C |
| ATOM | 3329 | CB  | LEU | B | 407 | 24.969 | 38.132 | 21.011 | 1.00 | 27.77 | B | C |
| ATOM | 3330 | CG  | LEU | B | 407 | 26.015 | 37.382 | 20.193 | 1.00 | 26.79 | B | C |
| ATOM | 3331 | CD1 | LEU | B | 407 | 25.579 | 37.346 | 18.731 | 1.00 | 23.59 | B | C |
| ATOM | 3332 | CD2 | LEU | B | 407 | 27.392 | 38.038 | 20.336 | 1.00 | 26.56 | B | C |
| ATOM | 3333 | C   | LEU | B | 407 | 24.319 | 39.355 | 23.078 | 1.00 | 28.67 | B | C |
| ATOM | 3334 | O   | LEU | B | 407 | 24.175 | 40.497 | 22.656 | 1.00 | 33.15 | B | O |
| ATOM | 3335 | N   | GLY | B | 408 | 23.579 | 38.833 | 24.052 | 1.00 | 28.62 | B | N |
| ATOM | 3336 | CA  | GLY | B | 408 | 22.600 | 39.622 | 24.777 | 1.00 | 30.08 | B | C |

TABLE 14-continued

Coordinates for proMMP9(35-444 ΔFnII) (SEQ ID NO: 12) complex with Example 4

| ATOM | 3337 | C | GLY | B | 408 | 21.142 | 39.282 | 24.523 | 1.00 | 30.37 | B | C |
|---|---|---|---|---|---|---|---|---|---|---|---|---|
| ATOM | 3338 | O | GLY | B | 408 | 20.283 | 40.100 | 24.837 | 1.00 | 28.46 | B | O |
| ATOM | 3339 | N | LEU | B | 409 | 20.848 | 38.100 | 23.969 | 1.00 | 26.51 | B | N |
| ATOM | 3340 | CA | LEU | B | 409 | 19.449 | 37.711 | 23.719 | 1.00 | 27.84 | B | C |
| ATOM | 3341 | CB | LEU | B | 409 | 19.311 | 36.884 | 22.438 | 1.00 | 27.28 | B | C |
| ATOM | 3342 | CG | LEU | B | 409 | 19.671 | 37.550 | 21.114 | 1.00 | 25.10 | B | C |
| ATOM | 3343 | CD1 | LEU | B | 409 | 19.694 | 36.481 | 20.019 | 1.00 | 25.82 | B | C |
| ATOM | 3344 | CD2 | LEU | B | 409 | 18.698 | 38.689 | 20.787 | 1.00 | 23.83 | B | C |
| ATOM | 3345 | C | LEU | B | 409 | 18.828 | 36.923 | 24.852 | 1.00 | 27.95 | B | C |
| ATOM | 3346 | O | LEU | B | 409 | 19.496 | 36.070 | 25.444 | 1.00 | 28.79 | B | O |
| ATOM | 3347 | N | ASP | B | 410 | 17.543 | 37.185 | 25.114 | 1.00 | 28.91 | B | N |
| ATOM | 3348 | CA | ASP | B | 410 | 16.740 | 36.418 | 26.086 | 1.00 | 30.81 | B | C |
| ATOM | 3349 | CB | ASP | B | 410 | 15.637 | 37.277 | 26.705 | 1.00 | 29.17 | B | C |
| ATOM | 3350 | CG | ASP | B | 410 | 16.174 | 38.494 | 27.414 | 1.00 | 38.66 | B | C |
| ATOM | 3351 | OD1 | ASP | B | 410 | 17.229 | 38.384 | 28.080 | 1.00 | 40.33 | B | O |
| ATOM | 3352 | OD2 | ASP | B | 410 | 15.536 | 39.566 | 27.317 | 1.00 | 45.38 | B | O |
| ATOM | 3353 | C | ASP | B | 410 | 16.059 | 35.277 | 25.367 | 1.00 | 32.04 | B | C |
| ATOM | 3354 | O | ASP | B | 410 | 16.233 | 35.099 | 24.165 | 1.00 | 28.03 | B | O |
| ATOM | 3355 | N | HIS | B | 411 | 15.248 | 34.518 | 26.087 | 1.00 | 26.05 | B | N |
| ATOM | 3356 | CA | HIS | B | 411 | 14.541 | 33.439 | 25.427 | 1.00 | 29.13 | B | C |
| ATOM | 3357 | CB | HIS | B | 411 | 14.105 | 32.352 | 26.409 | 1.00 | 33.92 | B | C |
| ATOM | 3358 | CG | HIS | B | 411 | 15.174 | 31.352 | 26.675 | 1.00 | 32.03 | B | C |
| ATOM | 3359 | CD2 | HIS | B | 411 | 16.406 | 31.204 | 26.119 | 1.00 | 30.56 | B | C |
| ATOM | 3360 | ND1 | HIS | B | 411 | 15.065 | 30.356 | 27.629 | 1.00 | 34.61 | B | N |
| ATOM | 3361 | CE1 | HIS | B | 411 | 16.179 | 29.641 | 27.638 | 1.00 | 33.82 | B | C |
| ATOM | 3362 | NE2 | HIS | B | 411 | 17.004 | 30.138 | 26.735 | 1.00 | 28.06 | B | N |
| ATOM | 3363 | C | HIS | B | 411 | 13.378 | 33.924 | 24.583 | 1.00 | 31.23 | B | C |
| ATOM | 3364 | O | HIS | B | 411 | 12.819 | 35.001 | 24.807 | 1.00 | 28.64 | B | O |
| ATOM | 3365 | N | SER | B | 412 | 13.055 | 33.114 | 23.585 | 1.00 | 31.15 | B | N |
| ATOM | 3366 | CA | SER | B | 412 | 11.911 | 33.352 | 22.734 | 1.00 | 30.15 | B | C |
| ATOM | 3367 | CB | SER | B | 412 | 12.273 | 32.994 | 21.295 | 1.00 | 27.70 | B | C |
| ATOM | 3368 | OG | SER | B | 412 | 11.135 | 33.102 | 20.475 | 1.00 | 24.43 | B | O |
| ATOM | 3369 | C | SER | B | 412 | 10.753 | 32.473 | 23.186 | 1.00 | 31.37 | B | C |
| ATOM | 3370 | O | SER | B | 412 | 10.966 | 31.356 | 23.656 | 1.00 | 29.87 | B | O |
| ATOM | 3371 | N | SER | B | 413 | 9.531 | 32.968 | 23.007 | 1.00 | 26.71 | B | N |
| ATOM | 3372 | CA | SER | B | 413 | 8.338 | 32.153 | 23.202 | 1.00 | 31.03 | B | C |
| ATOM | 3373 | CB | SER | B | 413 | 7.214 | 33.002 | 23.798 | 1.00 | 34.38 | B | C |
| ATOM | 3374 | OG | SER | B | 413 | 7.092 | 34.216 | 23.082 | 1.00 | 40.76 | B | O |
| ATOM | 3375 | C | SER | B | 413 | 7.855 | 31.468 | 21.913 | 1.00 | 32.05 | B | C |
| ATOM | 3376 | O | SER | B | 413 | 6.850 | 30.763 | 21.925 | 1.00 | 30.78 | B | O |
| ATOM | 3377 | N | VAL | B | 414 | 8.576 | 31.651 | 20.808 | 1.00 | 32.95 | B | N |
| ATOM | 3378 | CA | VAL | B | 414 | 8.260 | 30.929 | 19.567 | 1.00 | 29.80 | B | C |
| ATOM | 3379 | CB | VAL | B | 414 | 8.646 | 31.728 | 18.307 | 1.00 | 28.99 | B | C |
| ATOM | 3380 | CG1 | VAL | B | 414 | 8.342 | 30.928 | 17.032 | 1.00 | 32.17 | B | C |
| ATOM | 3381 | CG2 | VAL | B | 414 | 7.928 | 33.053 | 18.288 | 1.00 | 25.65 | B | C |
| ATOM | 3382 | C | VAL | B | 414 | 8.936 | 29.573 | 19.556 | 1.00 | 29.19 | B | C |
| ATOM | 3383 | O | VAL | B | 414 | 10.163 | 29.480 | 19.481 | 1.00 | 31.01 | B | O |
| ATOM | 3384 | N | PRO | B | 415 | 8.136 | 28.506 | 19.624 | 1.00 | 30.90 | B | N |
| ATOM | 3385 | CD | PRO | B | 415 | 6.665 | 28.520 | 19.734 | 1.00 | 35.68 | B | C |
| ATOM | 3386 | CA | PRO | B | 415 | 8.688 | 27.151 | 19.743 | 1.00 | 34.21 | B | C |
| ATOM | 3387 | CB | PRO | B | 415 | 7.455 | 26.260 | 19.613 | 1.00 | 34.44 | B | C |
| ATOM | 3388 | CG | PRO | B | 415 | 6.346 | 27.117 | 20.174 | 1.00 | 33.30 | B | C |
| ATOM | 3389 | C | PRO | B | 415 | 9.731 | 26.799 | 18.681 | 1.00 | 36.96 | B | C |
| ATOM | 3390 | O | PRO | B | 415 | 10.642 | 26.033 | 18.989 | 1.00 | 36.03 | B | O |
| ATOM | 3391 | N | GLU | B | 416 | 9.621 | 27.335 | 17.472 | 1.00 | 33.99 | B | N |
| ATOM | 3392 | CA | GLU | B | 416 | 10.605 | 26.978 | 16.440 | 1.00 | 36.21 | B | C |
| ATOM | 3393 | CB | GLU | B | 416 | 9.965 | 26.823 | 15.047 | 1.00 | 39.77 | B | C |
| ATOM | 3394 | CG | GLU | B | 416 | 8.764 | 27.722 | 14.784 | 1.00 | 44.91 | B | C |
| ATOM | 3395 | CD | GLU | B | 416 | 7.540 | 27.311 | 15.585 | 1.00 | 44.16 | B | C |
| ATOM | 3396 | OE1 | GLU | B | 416 | 7.320 | 26.092 | 15.768 | 1.00 | 46.86 | B | O |
| ATOM | 3397 | OE2 | GLU | B | 416 | 6.799 | 28.211 | 16.030 | 1.00 | 46.25 | B | O |
| ATOM | 3398 | C | GLU | B | 416 | 11.814 | 27.909 | 16.377 | 1.00 | 33.72 | B | C |
| ATOM | 3399 | O | GLU | B | 416 | 12.801 | 27.592 | 15.697 | 1.00 | 34.67 | B | O |
| ATOM | 3400 | N | ALA | B | 417 | 11.749 | 29.041 | 17.081 | 1.00 | 30.95 | B | N |
| ATOM | 3401 | CA | ALA | B | 417 | 12.873 | 29.981 | 17.100 | 1.00 | 32.49 | B | C |
| ATOM | 3402 | CB | ALA | B | 417 | 12.506 | 31.267 | 17.825 | 1.00 | 30.28 | B | C |
| ATOM | 3403 | C | ALA | B | 417 | 14.073 | 29.331 | 17.764 | 1.00 | 28.91 | B | C |
| ATOM | 3404 | O | ALA | B | 417 | 13.911 | 28.494 | 18.645 | 1.00 | 29.34 | B | O |
| ATOM | 3405 | N | LEU | B | 418 | 15.273 | 29.711 | 17.332 | 1.00 | 28.81 | B | N |
| ATOM | 3406 | CA | LEU | B | 418 | 16.503 | 29.209 | 17.940 | 1.00 | 26.35 | B | C |
| ATOM | 3407 | CB | LEU | B | 418 | 17.726 | 29.817 | 17.247 | 1.00 | 24.92 | B | C |
| ATOM | 3408 | CG | LEU | B | 418 | 19.110 | 29.453 | 17.785 | 1.00 | 25.05 | B | C |
| ATOM | 3409 | CD1 | LEU | B | 418 | 19.303 | 27.943 | 17.800 | 1.00 | 22.22 | B | C |
| ATOM | 3410 | CD2 | LEU | B | 418 | 20.215 | 30.131 | 16.971 | 1.00 | 24.84 | B | C |
| ATOM | 3411 | C | LEU | B | 418 | 16.574 | 29.502 | 19.446 | 1.00 | 25.86 | B | C |
| ATOM | 3412 | O | LEU | B | 418 | 17.052 | 28.677 | 20.224 | 1.00 | 22.75 | B | O |
| ATOM | 3413 | N | MET | B | 419 | 16.135 | 30.696 | 19.839 | 1.00 | 26.37 | B | N |
| ATOM | 3414 | CA | MET | B | 419 | 16.231 | 31.126 | 21.237 | 1.00 | 26.28 | B | C |

TABLE 14-continued

Coordinates for proMMP9(35-444 ΔFnII) (SEQ ID NO: 12) complex with Example 4

| ATOM | 3415 | CB  | MET | B | 419 | 16.311 | 32.649 | 21.336 | 1.00 | 24.00 | B | C |
|------|------|-----|-----|---|-----|--------|--------|--------|------|-------|---|---|
| ATOM | 3416 | CG  | MET | B | 419 | 17.577 | 33.226 | 20.708 | 1.00 | 21.44 | B | C |
| ATOM | 3417 | SD  | MET | B | 419 | 19.076 | 32.367 | 21.215 | 1.00 | 22.87 | B | S |
| ATOM | 3418 | CE  | MET | B | 419 | 18.917 | 32.454 | 23.007 | 1.00 | 24.01 | B | C |
| ATOM | 3419 | C   | MET | B | 419 | 15.104 | 30.567 | 22.121 | 1.00 | 28.16 | B | C |
| ATOM | 3420 | O   | MET | B | 419 | 15.009 | 30.886 | 23.314 | 1.00 | 26.98 | B | O |
| ATOM | 3421 | N   | TYR | B | 420 | 14.257 | 29.726 | 21.539 | 1.00 | 28.79 | B | N |
| ATOM | 3422 | CA  | TYR | B | 420 | 13.312 | 28.959 | 22.344 | 1.00 | 28.91 | B | C |
| ATOM | 3423 | CB  | TYR | B | 420 | 12.507 | 28.025 | 21.467 | 1.00 | 28.00 | B | C |
| ATOM | 3424 | CG  | TYR | B | 420 | 11.261 | 27.502 | 22.142 | 1.00 | 31.87 | B | C |
| ATOM | 3425 | CD1 | TYR | B | 420 | 10.208 | 28.351 | 22.458 | 1.00 | 27.19 | B | C |
| ATOM | 3426 | CE1 | TYR | B | 420 | 9.065  | 27.868 | 23.062 | 1.00 | 35.06 | B | C |
| ATOM | 3427 | CD2 | TYR | B | 420 | 11.133 | 26.157 | 22.447 | 1.00 | 31.74 | B | C |
| ATOM | 3428 | CE2 | TYR | B | 420 | 10.002 | 25.667 | 23.054 | 1.00 | 34.36 | B | C |
| ATOM | 3429 | CZ  | TYR | B | 420 | 8.974  | 26.519 | 23.354 | 1.00 | 34.05 | B | C |
| ATOM | 3430 | OH  | TYR | B | 420 | 7.861  | 26.011 | 23.951 | 1.00 | 40.79 | B | O |
| ATOM | 3431 | C   | TYR | B | 420 | 14.135 | 28.148 | 23.324 | 1.00 | 29.44 | B | C |
| ATOM | 3432 | O   | TYR | B | 420 | 15.106 | 27.509 | 22.928 | 1.00 | 28.98 | B | O |
| ATOM | 3433 | N   | PRO | B | 421 | 13.766 | 28.182 | 24.615 | 1.00 | 33.20 | B | N |
| ATOM | 3434 | CD  | PRO | B | 421 | 12.658 | 28.983 | 25.162 | 1.00 | 30.72 | B | C |
| ATOM | 3435 | CA  | PRO | B | 421 | 14.518 | 27.509 | 25.685 | 1.00 | 30.59 | B | C |
| ATOM | 3436 | CB  | PRO | B | 421 | 13.665 | 27.791 | 26.936 | 1.00 | 30.50 | B | C |
| ATOM | 3437 | CG  | PRO | B | 421 | 12.325 | 28.240 | 26.411 | 1.00 | 32.68 | B | C |
| ATOM | 3438 | C   | PRO | B | 421 | 14.667 | 25.993 | 25.533 | 1.00 | 30.03 | B | C |
| ATOM | 3439 | O   | PRO | B | 421 | 15.673 | 25.453 | 25.974 | 1.00 | 27.93 | B | O |
| ATOM | 3440 | N   | MET | B | 422 | 13.676 | 25.309 | 24.973 | 1.00 | 29.71 | B | N |
| ATOM | 3441 | CA  | MET | B | 422 | 13.721 | 23.849 | 24.941 | 1.00 | 28.60 | B | C |
| ATOM | 3442 | CB  | MET | B | 422 | 12.332 | 23.258 | 24.728 | 1.00 | 32.16 | B | C |
| ATOM | 3443 | CG  | MET | B | 422 | 11.365 | 23.451 | 25.872 | 1.00 | 36.01 | B | C |
| ATOM | 3444 | SD  | MET | B | 422 | 9.923  | 22.435 | 25.550 | 1.00 | 42.48 | B | S |
| ATOM | 3445 | CE  | MET | B | 422 | 8.632  | 23.501 | 26.177 | 1.00 | 36.39 | B | C |
| ATOM | 3446 | C   | MET | B | 422 | 14.592 | 23.390 | 23.813 | 1.00 | 31.30 | B | C |
| ATOM | 3447 | O   | MET | B | 422 | 14.645 | 24.042 | 22.779 | 1.00 | 30.45 | B | O |
| ATOM | 3448 | N   | TYR | B | 423 | 15.270 | 22.264 | 24.011 | 1.00 | 34.86 | B | N |
| ATOM | 3449 | CA  | TYR | B | 423 | 16.026 | 21.644 | 22.938 | 1.00 | 30.71 | B | C |
| ATOM | 3450 | CB  | TYR | B | 423 | 16.916 | 20.519 | 23.450 | 1.00 | 32.97 | B | C |
| ATOM | 3451 | CG  | TYR | B | 423 | 17.697 | 19.851 | 22.337 | 1.00 | 30.50 | B | C |
| ATOM | 3452 | CD1 | TYR | B | 423 | 17.351 | 18.583 | 21.872 | 1.00 | 32.84 | B | C |
| ATOM | 3453 | CE1 | TYR | B | 423 | 18.070 | 17.970 | 20.838 | 1.00 | 29.38 | B | C |
| ATOM | 3454 | CD2 | TYR | B | 423 | 18.757 | 20.503 | 21.724 | 1.00 | 31.81 | B | C |
| ATOM | 3455 | CE2 | TYR | B | 423 | 19.473 | 19.909 | 20.684 | 1.00 | 29.92 | B | C |
| ATOM | 3456 | CZ  | TYR | B | 423 | 19.130 | 18.648 | 20.250 | 1.00 | 31.11 | B | C |
| ATOM | 3457 | OH  | TYR | B | 423 | 19.854 | 18.061 | 19.237 | 1.00 | 26.55 | B | O |
| ATOM | 3458 | C   | TYR | B | 423 | 15.053 | 21.068 | 21.933 | 1.00 | 35.03 | B | C |
| ATOM | 3459 | O   | TYR | B | 423 | 14.051 | 20.457 | 22.304 | 1.00 | 31.33 | B | O |
| ATOM | 3460 | N   | ARG | B | 424 | 15.350 | 21.272 | 20.657 | 1.00 | 33.05 | B | N |
| ATOM | 3461 | CA  | ARG | B | 424 | 14.511 | 20.760 | 19.591 | 1.00 | 33.16 | B | C |
| ATOM | 3462 | CB  | ARG | B | 424 | 13.358 | 21.725 | 19.300 | 1.00 | 35.92 | B | C |
| ATOM | 3463 | CG  | ARG | B | 424 | 12.530 | 21.327 | 18.091 | 1.00 | 39.58 | B | C |
| ATOM | 3464 | CD  | ARG | B | 424 | 11.908 | 22.537 | 17.387 | 1.00 | 48.60 | B | C |
| ATOM | 3465 | NE  | ARG | B | 424 | 12.880 | 23.347 | 16.640 | 1.00 | 45.15 | B | N |
| ATOM | 3466 | CZ  | ARG | B | 424 | 12.726 | 23.701 | 15.366 | 1.00 | 49.86 | B | C |
| ATOM | 3467 | NH1 | ARG | B | 424 | 11.646 | 23.303 | 14.696 | 1.00 | 50.15 | B | N |
| ATOM | 3468 | NH2 | ARG | B | 424 | 13.646 | 24.451 | 14.753 | 1.00 | 48.73 | B | N |
| ATOM | 3469 | C   | ARG | B | 424 | 15.383 | 20.591 | 18.356 | 1.00 | 34.45 | B | C |
| ATOM | 3470 | O   | ARG | B | 424 | 15.770 | 21.576 | 17.727 | 1.00 | 33.91 | B | O |
| ATOM | 3471 | N   | PHE | B | 425 | 15.704 | 19.345 | 18.017 | 1.00 | 28.87 | B | N |
| ATOM | 3472 | CA  | PHE | B | 425 | 16.628 | 19.105 | 16.919 | 1.00 | 33.27 | B | C |
| ATOM | 3473 | CB  | PHE | B | 425 | 17.119 | 17.663 | 16.916 | 1.00 | 29.57 | B | C |
| ATOM | 3474 | CG  | PHE | B | 425 | 17.965 | 17.338 | 15.738 | 1.00 | 34.93 | B | C |
| ATOM | 3475 | CD1 | PHE | B | 425 | 19.295 | 17.727 | 15.700 | 1.00 | 34.03 | B | C |
| ATOM | 3476 | CD2 | PHE | B | 425 | 17.426 | 16.676 | 14.639 | 1.00 | 36.58 | B | C |
| ATOM | 3477 | CE1 | PHE | B | 425 | 20.078 | 17.451 | 14.584 | 1.00 | 39.42 | B | C |
| ATOM | 3478 | CE2 | PHE | B | 425 | 18.211 | 16.392 | 13.520 | 1.00 | 35.31 | B | C |
| ATOM | 3479 | CZ  | PHE | B | 425 | 19.535 | 16.781 | 13.499 | 1.00 | 39.08 | B | C |
| ATOM | 3480 | C   | PHE | B | 425 | 16.012 | 19.470 | 15.562 | 1.00 | 34.13 | B | C |
| ATOM | 3481 | O   | PHE | B | 425 | 14.815 | 19.316 | 15.346 | 1.00 | 29.55 | B | O |
| ATOM | 3482 | N   | THR | B | 426 | 16.838 | 19.972 | 14.657 | 1.00 | 33.63 | B | N |
| ATOM | 3483 | CA  | THR | B | 426 | 16.377 | 20.304 | 13.314 | 1.00 | 34.53 | B | C |
| ATOM | 3484 | CB  | THR | B | 426 | 15.741 | 21.715 | 13.263 | 1.00 | 34.39 | B | C |
| ATOM | 3485 | OG1 | THR | B | 426 | 15.209 | 21.964 | 11.953 | 1.00 | 31.61 | B | O |
| ATOM | 3486 | CG2 | THR | B | 426 | 16.768 | 22.796 | 13.635 | 1.00 | 29.09 | B | C |
| ATOM | 3487 | C   | THR | B | 426 | 17.528 | 20.203 | 12.325 | 1.00 | 34.34 | B | C |
| ATOM | 3488 | O   | THR | B | 426 | 18.688 | 20.384 | 12.702 | 1.00 | 30.85 | B | O |
| ATOM | 3489 | N   | GLU | B | 427 | 17.208 | 19.885 | 11.068 | 1.00 | 38.18 | B | N |
| ATOM | 3490 | CA  | GLU | B | 427 | 18.199 | 19.886 | 9.992  | 1.00 | 35.10 | B | C |
| ATOM | 3491 | CB  | GLU | B | 427 | 18.016 | 18.683 | 9.066  | 1.00 | 44.11 | B | C |
| ATOM | 3492 | CG  | GLU | B | 427 | 18.074 | 17.335 | 9.772  | 1.00 | 47.56 | B | C |

TABLE 14-continued

Coordinates for proMMP9(35-444 ΔFnII) (SEQ ID NO: 12) complex with Example 4

| ATOM | 3493 | CD  | GLU | B | 427 | 19.021 | 16.355 | 9.097  | 1.00 | 53.94 | B | C |
|------|------|-----|-----|---|-----|--------|--------|--------|------|-------|---|---|
| ATOM | 3494 | OE1 | GLU | B | 427 | 20.241 | 16.630 | 9.045  | 1.00 | 57.20 | B | O |
| ATOM | 3495 | OE2 | GLU | B | 427 | 18.545 | 15.304 | 8.623  | 1.00 | 61.87 | B | O |
| ATOM | 3496 | C   | GLU | B | 427 | 18.084 | 21.166 | 9.181  | 1.00 | 35.94 | B | C |
| ATOM | 3497 | O   | GLU | B | 427 | 18.903 | 21.432 | 8.285  | 1.00 | 34.79 | B | O |
| ATOM | 3498 | N   | GLY | B | 428 | 17.053 | 21.953 | 9.484  | 1.00 | 31.88 | B | N |
| ATOM | 3499 | CA  | GLY | B | 428 | 16.831 | 23.212 | 8.797  | 1.00 | 32.26 | B | C |
| ATOM | 3500 | C   | GLY | B | 428 | 17.721 | 24.347 | 9.281  | 1.00 | 31.02 | B | C |
| ATOM | 3501 | O   | GLY | B | 428 | 18.388 | 24.227 | 10.314 | 1.00 | 29.01 | B | O |
| ATOM | 3502 | N   | PRO | B | 429 | 17.731 | 25.466 | 8.541  | 1.00 | 28.00 | B | N |
| ATOM | 3503 | CD  | PRO | B | 429 | 17.036 | 25.694 | 7.259  | 1.00 | 28.13 | B | C |
| ATOM | 3504 | CA  | PRO | B | 429 | 18.463 | 26.652 | 9.001  | 1.00 | 24.79 | B | C |
| ATOM | 3505 | CB  | PRO | B | 429 | 18.006 | 27.732 | 8.034  | 1.00 | 21.89 | B | C |
| ATOM | 3506 | CG  | PRO | B | 429 | 17.687 | 26.944 | 6.745  | 1.00 | 27.05 | B | C |
| ATOM | 3507 | C   | PRO | B | 429 | 18.045 | 27.006 | 10.430 | 1.00 | 22.34 | B | C |
| ATOM | 3508 | O   | PRO | B | 429 | 16.851 | 27.123 | 10.689 | 1.00 | 22.46 | B | O |
| ATOM | 3509 | N   | PRO | B | 430 | 19.012 | 27.184 | 11.343 | 1.00 | 22.20 | B | N |
| ATOM | 3510 | CD  | PRO | B | 430 | 20.471 | 26.972 | 11.196 | 1.00 | 21.29 | B | C |
| ATOM | 3511 | CA  | PRO | B | 430 | 18.586 | 27.379 | 12.747 | 1.00 | 24.42 | B | C |
| ATOM | 3512 | CB  | PRO | B | 430 | 19.892 | 27.242 | 13.557 | 1.00 | 20.22 | B | C |
| ATOM | 3513 | CG  | PRO | B | 430 | 20.894 | 26.505 | 12.572 | 1.00 | 22.79 | B | C |
| ATOM | 3514 | C   | PRO | B | 430 | 17.891 | 28.718 | 13.020 | 1.00 | 23.73 | B | C |
| ATOM | 3515 | O   | PRO | B | 430 | 16.994 | 28.727 | 13.841 | 1.00 | 25.76 | B | O |
| ATOM | 3516 | N   | LEU | B | 431 | 18.259 | 29.816 | 12.363 | 1.00 | 20.50 | B | N |
| ATOM | 3517 | CA  | LEU | B | 431 | 17.653 | 31.106 | 12.705 | 1.00 | 22.28 | B | C |
| ATOM | 3518 | CB  | LEU | B | 431 | 18.480 | 32.290 | 12.191 | 1.00 | 24.19 | B | C |
| ATOM | 3519 | CG  | LEU | B | 431 | 19.945 | 32.411 | 12.638 | 1.00 | 29.39 | B | C |
| ATOM | 3520 | CD1 | LEU | B | 431 | 20.636 | 33.593 | 11.971 | 1.00 | 20.80 | B | C |
| ATOM | 3521 | CD2 | LEU | B | 431 | 20.016 | 32.542 | 14.144 | 1.00 | 21.09 | B | C |
| ATOM | 3522 | C   | LEU | B | 431 | 16.231 | 31.235 | 12.158 | 1.00 | 29.53 | B | C |
| ATOM | 3523 | O   | LEU | B | 431 | 15.957 | 30.845 | 11.020 | 1.00 | 28.39 | B | O |
| ATOM | 3524 | N   | HIS | B | 432 | 15.349 | 31.817 | 12.968 | 1.00 | 25.81 | B | N |
| ATOM | 3525 | CA  | HIS | B | 432 | 14.011 | 32.189 | 12.542 | 1.00 | 24.87 | B | C |
| ATOM | 3526 | CB  | HIS | B | 432 | 12.975 | 31.405 | 13.350 | 1.00 | 28.63 | B | C |
| ATOM | 3527 | CG  | HIS | B | 432 | 12.981 | 29.943 | 13.032 | 1.00 | 29.15 | B | C |
| ATOM | 3528 | CD2 | HIS | B | 432 | 12.096 | 29.170 | 12.367 | 1.00 | 27.14 | B | C |
| ATOM | 3529 | ND1 | HIS | B | 432 | 14.041 | 29.119 | 13.361 | 1.00 | 34.09 | B | N |
| ATOM | 3530 | CE1 | HIS | B | 432 | 13.789 | 27.894 | 12.935 | 1.00 | 31.79 | B | C |
| ATOM | 3531 | NE2 | HIS | B | 432 | 12.619 | 27.899 | 12.323 | 1.00 | 29.89 | B | N |
| ATOM | 3532 | C   | HIS | B | 432 | 13.826 | 33.695 | 12.639 | 1.00 | 24.60 | B | C |
| ATOM | 3533 | O   | HIS | B | 432 | 14.700 | 34.395 | 13.160 | 1.00 | 25.43 | B | O |
| ATOM | 3534 | N   | LYS | B | 433 | 12.719 | 34.195 | 12.092 | 1.00 | 26.75 | B | N |
| ATOM | 3535 | CA  | LYS | B | 433 | 12.449 | 35.633 | 12.069 | 1.00 | 24.46 | B | C |
| ATOM | 3536 | CB  | LYS | B | 433 | 11.038 | 35.897 | 11.550 | 1.00 | 30.73 | B | C |
| ATOM | 3537 | CG  | LYS | B | 433 | 10.808 | 35.658 | 10.068 | 1.00 | 26.94 | B | C |
| ATOM | 3538 | CD  | LYS | B | 433 | 9.301  | 35.741 | 9.777  | 1.00 | 34.47 | B | C |
| ATOM | 3539 | CE  | LYS | B | 433 | 8.990  | 35.459 | 8.307  | 1.00 | 31.01 | B | C |
| ATOM | 3540 | NZ  | LYS | B | 433 | 9.534  | 36.551 | 7.443  | 1.00 | 28.86 | B | N |
| ATOM | 3541 | C   | LYS | B | 433 | 12.580 | 36.245 | 13.467 | 1.00 | 26.90 | B | C |
| ATOM | 3542 | O   | LYS | B | 433 | 13.096 | 37.347 | 13.625 | 1.00 | 27.29 | B | O |
| ATOM | 3543 | N   | ASP | B | 434 | 12.116 | 35.524 | 14.484 | 1.00 | 25.77 | B | N |
| ATOM | 3544 | CA  | ASP | B | 434 | 12.135 | 36.061 | 15.856 | 1.00 | 25.26 | B | C |
| ATOM | 3545 | CB  | ASP | B | 434 | 11.363 | 35.174 | 16.829 | 1.00 | 22.07 | B | C |
| ATOM | 3546 | CG  | ASP | B | 434 | 11.123 | 35.869 | 18.167 | 1.00 | 26.22 | B | C |
| ATOM | 3547 | OD1 | ASP | B | 434 | 10.510 | 36.958 | 18.162 | 1.00 | 23.93 | B | O |
| ATOM | 3548 | OD2 | ASP | B | 434 | 11.590 | 35.349 | 19.201 | 1.00 | 22.23 | B | O |
| ATOM | 3549 | C   | ASP | B | 434 | 13.546 | 36.281 | 16.376 | 1.00 | 24.03 | B | C |
| ATOM | 3550 | O   | ASP | B | 434 | 13.819 | 37.290 | 17.016 | 1.00 | 25.85 | B | O |
| ATOM | 3551 | N   | ASP | B | 435 | 14.436 | 35.334 | 16.087 | 1.00 | 25.46 | B | N |
| ATOM | 3552 | CA  | ASP | B | 435 | 15.846 | 35.428 | 16.458 | 1.00 | 23.99 | B | C |
| ATOM | 3553 | CB  | ASP | B | 435 | 16.582 | 34.166 | 15.999 | 1.00 | 25.35 | B | C |
| ATOM | 3554 | CG  | ASP | B | 435 | 15.922 | 32.885 | 16.498 | 1.00 | 30.42 | B | C |
| ATOM | 3555 | OD1 | ASP | B | 435 | 15.716 | 32.758 | 17.722 | 1.00 | 25.09 | B | O |
| ATOM | 3556 | OD2 | ASP | B | 435 | 15.602 | 32.015 | 15.663 | 1.00 | 26.77 | B | O |
| ATOM | 3557 | C   | ASP | B | 435 | 16.497 | 36.645 | 15.824 | 1.00 | 24.01 | B | C |
| ATOM | 3558 | O   | ASP | B | 435 | 17.255 | 37.356 | 16.475 | 1.00 | 25.34 | B | O |
| ATOM | 3559 | N   | VAL | B | 436 | 16.211 | 36.859 | 14.542 | 1.00 | 25.85 | B | N |
| ATOM | 3560 | CA  | VAL | B | 436 | 16.793 | 37.966 | 13.772 | 1.00 | 26.06 | B | C |
| ATOM | 3561 | CB  | VAL | B | 436 | 16.571 | 37.782 | 12.238 | 1.00 | 27.51 | B | C |
| ATOM | 3562 | CG1 | VAL | B | 436 | 17.201 | 38.941 | 11.445 | 1.00 | 27.33 | B | C |
| ATOM | 3563 | CG2 | VAL | B | 436 | 17.158 | 36.451 | 11.766 | 1.00 | 27.17 | B | C |
| ATOM | 3564 | C   | VAL | B | 436 | 16.235 | 39.320 | 14.240 | 1.00 | 29.15 | B | C |
| ATOM | 3565 | O   | VAL | B | 436 | 16.995 | 40.286 | 14.407 | 1.00 | 28.58 | B | O |
| ATOM | 3566 | N   | ASN | B | 437 | 14.914 | 39.387 | 14.444 | 1.00 | 26.57 | B | N |
| ATOM | 3567 | CA  | ASN | B | 437 | 14.293 | 40.585 | 15.020 | 1.00 | 29.07 | B | C |
| ATOM | 3568 | CB  | ASN | B | 437 | 12.796 | 40.372 | 15.294 | 1.00 | 28.34 | B | C |
| ATOM | 3569 | CG  | ASN | B | 437 | 11.974 | 40.208 | 14.019 | 1.00 | 33.61 | B | C |
| ATOM | 3570 | OD1 | ASN | B | 437 | 12.366 | 40.679 | 12.949 | 1.00 | 32.14 | B | O |

TABLE 14-continued

Coordinates for proMMP9(35-444 ΔFnII) (SEQ ID NO: 12) complex with Example 4

| | | | | | | | | | | | |
|---|---|---|---|---|---|---|---|---|---|---|---|
| ATOM | 3571 | ND2 | ASN | B | 437 | 10.823 | 39.536 | 14.132 | 1.00 | 30.32 B | N |
| ATOM | 3572 | C | ASN | B | 437 | 15.001 | 40.955 | 16.316 | 1.00 | 25.22 B | C |
| ATOM | 3573 | O | ASN | B | 437 | 15.465 | 42.078 | 16.495 | 1.00 | 28.31 B | O |
| ATOM | 3574 | N | GLY | B | 438 | 15.122 | 39.981 | 17.199 | 1.00 | 24.42 B | N |
| ATOM | 3575 | CA | GLY | B | 438 | 15.808 | 40.189 | 18.463 | 1.00 | 27.50 B | C |
| ATOM | 3576 | C | GLY | B | 438 | 17.217 | 40.728 | 18.329 | 1.00 | 28.51 B | C |
| ATOM | 3577 | O | GLY | B | 438 | 17.596 | 41.698 | 18.981 | 1.00 | 27.54 B | O |
| ATOM | 3578 | N | ILE | B | 439 | 18.018 | 40.096 | 17.486 | 1.00 | 26.65 B | N |
| ATOM | 3579 | CA | ILE | B | 439 | 19.408 | 40.484 | 17.420 | 1.00 | 26.26 B | C |
| ATOM | 3580 | CB | ILE | B | 439 | 20.273 | 39.432 | 16.674 | 1.00 | 26.21 B | C |
| ATOM | 3581 | CG2 | ILE | B | 439 | 20.083 | 39.535 | 15.161 | 1.00 | 25.28 B | C |
| ATOM | 3582 | CG1 | ILE | B | 439 | 21.747 | 39.555 | 17.081 | 1.00 | 24.32 B | C |
| ATOM | 3583 | CD1 | ILE | B | 439 | 21.980 | 39.393 | 18.563 | 1.00 | 26.87 B | C |
| ATOM | 3584 | C | ILE | B | 439 | 19.498 | 41.885 | 16.794 | 1.00 | 30.94 B | C |
| ATOM | 3585 | O | ILE | B | 439 | 20.248 | 42.742 | 17.265 | 1.00 | 30.45 B | O |
| ATOM | 3586 | N | ARG | B | 440 | 18.696 | 42.128 | 15.766 | 1.00 | 26.81 B | N |
| ATOM | 3587 | CA | ARG | B | 440 | 18.649 | 43.449 | 15.147 | 1.00 | 30.84 B | C |
| ATOM | 3588 | CB | ARG | B | 440 | 17.696 | 43.437 | 13.961 | 1.00 | 30.25 B | C |
| ATOM | 3589 | CG | ARG | B | 440 | 18.273 | 42.741 | 12.762 | 1.00 | 33.60 B | C |
| ATOM | 3590 | CD | ARG | B | 440 | 17.303 | 42.728 | 11.595 | 1.00 | 37.68 B | C |
| ATOM | 3591 | NE | ARG | B | 440 | 17.919 | 42.074 | 10.451 | 1.00 | 35.24 B | N |
| ATOM | 3592 | CZ | ARG | B | 440 | 17.278 | 41.727 | 9.340 | 1.00 | 38.70 B | C |
| ATOM | 3593 | NH1 | ARG | B | 440 | 15.976 | 41.973 | 9.206 | 1.00 | 36.90 B | N |
| ATOM | 3594 | NH2 | ARG | B | 440 | 17.950 | 41.128 | 8.358 | 1.00 | 31.03 B | N |
| ATOM | 3595 | C | ARG | B | 440 | 18.207 | 44.528 | 16.133 | 1.00 | 33.72 B | C |
| ATOM | 3596 | O | ARG | B | 440 | 18.595 | 45.695 | 16.007 | 1.00 | 33.48 B | O |
| ATOM | 3597 | N | HIS | B | 441 | 17.377 | 44.146 | 17.101 | 1.00 | 31.14 B | N |
| ATOM | 3598 | CA | HIS | B | 441 | 16.892 | 45.111 | 18.085 | 1.00 | 32.92 B | C |
| ATOM | 3599 | CB | HIS | B | 441 | 15.733 | 44.537 | 18.907 | 1.00 | 34.49 B | C |
| ATOM | 3600 | CG | HIS | B | 441 | 15.268 | 45.445 | 20.003 | 1.00 | 45.53 B | C |
| ATOM | 3601 | CD2 | HIS | B | 441 | 14.319 | 46.411 | 20.018 | 1.00 | 48.79 B | C |
| ATOM | 3602 | ND1 | HIS | B | 441 | 15.817 | 45.428 | 21.271 | 1.00 | 46.98 B | N |
| ATOM | 3603 | CE1 | HIS | B | 441 | 15.220 | 46.338 | 22.019 | 1.00 | 50.20 B | C |
| ATOM | 3604 | NE2 | HIS | B | 441 | 14.301 | 46.946 | 21.285 | 1.00 | 51.16 B | N |
| ATOM | 3605 | C | HIS | B | 441 | 18.041 | 45.529 | 18.995 | 1.00 | 38.57 B | C |
| ATOM | 3606 | O | HIS | B | 441 | 18.026 | 46.615 | 19.571 | 1.00 | 40.14 B | O |
| ATOM | 3607 | N | LEU | B | 442 | 19.046 | 44.660 | 19.103 | 1.00 | 32.63 B | N |
| ATOM | 3608 | CA | LEU | B | 442 | 20.229 | 44.928 | 19.917 | 1.00 | 30.97 B | C |
| ATOM | 3609 | CB | LEU | B | 442 | 20.781 | 43.623 | 20.488 | 1.00 | 28.63 B | C |
| ATOM | 3610 | CG | LEU | B | 442 | 20.372 | 43.210 | 21.898 | 1.00 | 34.83 B | C |
| ATOM | 3611 | CD1 | LEU | B | 442 | 18.883 | 43.388 | 22.080 | 1.00 | 36.94 B | C |
| ATOM | 3612 | CD2 | LEU | B | 442 | 20.786 | 41.782 | 22.183 | 1.00 | 29.80 B | C |
| ATOM | 3613 | C | LEU | B | 442 | 21.341 | 45.635 | 19.137 | 1.00 | 35.56 B | C |
| ATOM | 3614 | O | LEU | B | 442 | 22.005 | 46.529 | 19.666 | 1.00 | 36.63 B | O |
| ATOM | 3615 | N | TYR | B | 443 | 21.544 | 45.228 | 17.884 | 1.00 | 30.53 B | N |
| ATOM | 3616 | CA | TYR | B | 443 | 22.701 | 45.667 | 17.114 | 1.00 | 32.78 B | C |
| ATOM | 3617 | CB | TYR | B | 443 | 23.627 | 44.476 | 16.854 | 1.00 | 31.82 B | C |
| ATOM | 3618 | CG | TYR | B | 443 | 24.198 | 43.893 | 18.124 | 1.00 | 29.74 B | C |
| ATOM | 3619 | CD1 | TYR | B | 443 | 23.709 | 42.706 | 18.659 | 1.00 | 30.39 B | C |
| ATOM | 3620 | CE1 | TYR | B | 443 | 24.240 | 42.177 | 19.839 | 1.00 | 27.91 B | C |
| ATOM | 3621 | CD2 | TYR | B | 443 | 25.219 | 44.548 | 18.802 | 1.00 | 30.48 B | C |
| ATOM | 3622 | CE2 | TYR | B | 443 | 25.752 | 44.037 | 19.968 | 1.00 | 30.86 B | C |
| ATOM | 3623 | CZ | TYR | B | 443 | 25.260 | 42.859 | 20.488 | 1.00 | 29.82 B | C |
| ATOM | 3624 | OH | TYR | B | 443 | 25.805 | 42.376 | 21.659 | 1.00 | 31.08 B | O |
| ATOM | 3625 | C | TYR | B | 443 | 22.357 | 46.398 | 15.807 | 1.00 | 34.22 B | C |
| ATOM | 3626 | O | TYR | B | 443 | 23.237 | 46.916 | 15.127 | 1.00 | 32.66 B | O |
| ATOM | 3627 | N | GLY | B | 444 | 21.077 | 46.457 | 15.471 | 1.00 | 34.41 B | N |
| ATOM | 3628 | CA | GLY | B | 444 | 20.648 | 47.198 | 14.300 | 1.00 | 31.44 B | C |
| ATOM | 3629 | C | GLY | B | 444 | 20.413 | 46.304 | 13.097 | 1.00 | 31.12 B | C |
| ATOM | 3630 | O | GLY | B | 444 | 19.615 | 46.666 | 12.230 | 1.00 | 35.92 B | O |
| ATOM | 3631 | ZN | ZN | B | 500 | 18.910 | 29.703 | 26.678 | 1.00 | 27.12 B | Zn |
| ATOM | 3632 | ZN | ZN | B | 501 | 28.355 | 27.403 | 34.053 | 1.00 | 34.65 B | Zn |
| ATOM | 3633 | CA | CA | B | 502 | 22.163 | 18.142 | 32.164 | 1.00 | 39.48 B | Ca |
| ATOM | 3634 | CA | CA | B | 504 | 33.559 | 36.767 | 29.256 | 1.00 | 47.51 B | Ca |
| ATOM | 3635 | CA | CA | B | 505 | 32.672 | 45.975 | 25.669 | 1.00 | 44.27 B | Ca |
| TER | 3636 | | CA | B | 505 | | | | | | |
| ATOM | 3637 | C01 | LIG | C | 1 | 24.110 | 30.449 | 33.901 | 1.00 | 34.08 A | C |
| ATOM | 3638 | O02 | LIG | C | 1 | 23.352 | 31.511 | 33.335 | 1.00 | 36.24 A | O |
| ATOM | 3639 | C03 | LIG | C | 1 | 22.501 | 32.268 | 34.080 | 1.00 | 40.44 A | C |
| ATOM | 3640 | C04 | LIG | C | 1 | 22.146 | 31.902 | 35.391 | 1.00 | 42.42 A | C |
| ATOM | 3641 | C05 | LIG | C | 1 | 21.275 | 32.763 | 36.114 | 1.00 | 47.88 A | C |
| ATOM | 3642 | N06 | LIG | C | 1 | 20.815 | 33.897 | 35.556 | 1.00 | 46.45 A | N |
| ATOM | 3643 | C07 | LIG | C | 1 | 21.172 | 34.235 | 34.287 | 1.00 | 41.20 A | C |
| ATOM | 3644 | C08 | LIG | C | 1 | 22.041 | 33.467 | 33.454 | 1.00 | 42.18 A | C |
| ATOM | 3645 | N09 | LIG | C | 1 | 22.379 | 33.897 | 32.063 | 1.00 | 35.32 A | N |
| ATOM | 3646 | C10 | LIG | C | 1 | 21.935 | 34.914 | 31.145 | 1.00 | 32.60 A | C |
| ATOM | 3647 | N11 | LIG | C | 1 | 21.214 | 36.003 | 31.535 | 1.00 | 34.30 A | N |
| ATOM | 3648 | C12 | LIG | C | 1 | 20.852 | 36.958 | 30.444 | 1.00 | 34.71 A | C |

TABLE 14-continued

Coordinates for proMMP9(35-444 ΔFnII) (SEQ ID NO: 12) complex with Example 4

| ATOM | 3649 | C13 | LIG | C | 1 | 21.346 | 36.484 | 29.224 | 1.00 | 33.87 | A | C |
| --- | --- | --- | --- | --- | --- | --- | --- | --- | --- | --- | --- | --- |
| ATOM | 3650 | C14 | LIG | C | 1 | 21.188 | 37.139 | 27.983 | 1.00 | 32.44 | A | C |
| ATOM | 3651 | C15 | LIG | C | 1 | 20.479 | 38.352 | 27.896 | 1.00 | 36.08 | A | C |
| ATOM | 3652 | C16 | LIG | C | 1 | 19.947 | 38.903 | 29.089 | 1.00 | 35.28 | A | C |
| ATOM | 3653 | C17 | LIG | C | 1 | 20.112 | 38.250 | 30.340 | 1.00 | 32.01 | A | C |
| ATOM | 3654 | N18 | LIG | C | 1 | 19.466 | 39.070 | 31.289 | 1.00 | 35.21 | A | N |
| ATOM | 3655 | C19 | LIG | C | 1 | 18.911 | 40.190 | 30.667 | 1.00 | 34.92 | A | C |
| ATOM | 3656 | N20 | LIG | C | 1 | 19.218 | 40.103 | 29.259 | 1.00 | 36.38 | A | N |
| ATOM | 3657 | C21 | LIG | C | 1 | 18.734 | 41.214 | 28.408 | 1.00 | 32.86 | A | C |
| ATOM | 3658 | S22 | LIG | C | 1 | 22.226 | 34.937 | 29.381 | 1.00 | 33.80 | A | S |
| TER | 3659 | | LIG | C | 1 | | | | | | | |
| END | | | | | | | | | | | | |

TABLE 15

Coordinates for apo form of proMMP9(35-444 ΔFnII) (SEQ ID NO: 12)

| ATOM | 1 | N | THR | A | 40 | 4.483 | 62.393 | 28.469 | 1.00 | 40.90 | A | N |
| --- | --- | --- | --- | --- | --- | --- | --- | --- | --- | --- | --- | --- |
| ATOM | 2 | CA | THR | A | 40 | 5.618 | 62.127 | 27.595 | 1.00 | 36.29 | A | C |
| ATOM | 3 | C | THR | A | 40 | 5.484 | 62.867 | 26.258 | 1.00 | 40.20 | A | C |
| ATOM | 4 | CB | THR | A | 40 | 5.833 | 60.616 | 27.364 | 1.00 | 37.71 | A | C |
| ATOM | 5 | OG1 | THR | A | 40 | 7.107 | 60.389 | 26.747 | 1.00 | 50.31 | A | O |
| ATOM | 6 | CG2 | THR | A | 40 | 4.734 | 60.029 | 26.479 | 1.00 | 45.76 | A | C |
| ATOM | 7 | O | THR | A | 40 | 6.491 | 63.196 | 25.628 | 1.00 | 37.63 | A | O |
| ATOM | 8 | CB | ASP | A | 41 | 2.518 | 64.003 | 24.285 | 1.00 | 34.93 | A | C |
| ATOM | 9 | CG | ASP | A | 41 | 2.131 | 62.918 | 23.300 | 1.00 | 31.19 | A | C |
| ATOM | 10 | OD1 | ASP | A | 41 | 3.028 | 62.258 | 22.743 | 1.00 | 26.69 | A | O |
| ATOM | 11 | OD2 | ASP | A | 41 | 0.918 | 62.729 | 23.073 | 1.00 | 41.82 | A | O |
| ATOM | 12 | C | ASP | A | 41 | 4.493 | 65.371 | 24.963 | 1.00 | 33.68 | A | C |
| ATOM | 13 | O | ASP | A | 41 | 5.296 | 65.925 | 24.212 | 1.00 | 29.75 | A | O |
| ATOM | 14 | N | ASP | A | 41 | 4.246 | 63.118 | 25.825 | 1.00 | 38.23 | A | N |
| ATOM | 15 | CA | ASP | A | 41 | 4.000 | 63.964 | 24.656 | 1.00 | 32.68 | A | C |
| ATOM | 16 | N | ARG | A | 42 | 4.038 | 65.931 | 26.083 | 1.00 | 31.38 | A | N |
| ATOM | 17 | CA | ARG | A | 42 | 4.503 | 67.242 | 26.511 | 1.00 | 34.49 | A | C |
| ATOM | 18 | CB | ARG | A | 42 | 3.591 | 67.845 | 27.590 | 1.00 | 31.03 | A | C |
| ATOM | 19 | CG | ARG | A | 42 | 3.781 | 69.351 | 27.770 | 1.00 | 46.76 | A | C |
| ATOM | 20 | CD | ARG | A | 42 | 3.426 | 69.828 | 29.177 | 1.00 | 49.89 | A | C |
| ATOM | 21 | NE | ARG | A | 42 | 4.144 | 71.051 | 29.539 | 1.00 | 47.62 | A | N |
| ATOM | 22 | CZ | ARG | A | 42 | 3.681 | 72.282 | 29.340 | 1.00 | 50.03 | A | C |
| ATOM | 23 | NH1 | ARG | A | 42 | 2.490 | 72.466 | 28.780 | 1.00 | 44.68 | A | N |
| ATOM | 24 | NH2 | ARG | A | 42 | 4.411 | 73.334 | 29.699 | 1.00 | 52.81 | A | N |
| ATOM | 25 | C | ARG | A | 42 | 5.950 | 67.164 | 26.995 | 1.00 | 33.54 | A | C |
| ATOM | 26 | O | ARG | A | 42 | 6.609 | 68.189 | 27.179 | 1.00 | 39.68 | A | O |
| ATOM | 27 | N | GLN | A | 43 | 6.450 | 65.946 | 27.165 | 1.00 | 30.55 | A | N |
| ATOM | 28 | CA | GLN | A | 43 | 7.819 | 65.733 | 27.610 | 1.00 | 31.28 | A | C |
| ATOM | 29 | CB | GLN | A | 43 | 7.954 | 64.351 | 28.241 | 1.00 | 35.35 | A | C |
| ATOM | 30 | CG | GLN | A | 43 | 9.378 | 63.942 | 28.602 | 1.00 | 34.39 | A | C |
| ATOM | 31 | CD | GLN | A | 43 | 9.451 | 62.551 | 29.232 | 1.00 | 43.96 | A | C |
| ATOM | 32 | OE1 | GLN | A | 43 | 8.458 | 61.815 | 29.268 | 1.00 | 48.25 | A | O |
| ATOM | 33 | NE2 | GLN | A | 43 | 10.631 | 62.186 | 29.728 | 1.00 | 37.47 | A | N |
| ATOM | 34 | C | GLN | A | 43 | 8.768 | 65.838 | 26.429 | 1.00 | 34.66 | A | C |
| ATOM | 35 | O | GLN | A | 43 | 9.805 | 66.506 | 26.495 | 1.00 | 25.95 | A | O |
| ATOM | 36 | N | LEU | A | 44 | 8.419 | 65.146 | 25.351 | 1.00 | 29.54 | A | N |
| ATOM | 37 | CA | LEU | A | 44 | 9.218 | 65.196 | 24.146 | 1.00 | 29.84 | A | C |
| ATOM | 38 | CB | LEU | A | 44 | 8.694 | 64.183 | 23.120 | 1.00 | 29.32 | A | C |
| ATOM | 39 | CG | LEU | A | 44 | 8.738 | 64.503 | 21.630 | 1.00 | 28.05 | A | C |
| ATOM | 40 | CD1 | LEU | A | 44 | 8.553 | 63.245 | 20.831 | 1.00 | 35.77 | A | C |
| ATOM | 41 | CD2 | LEU | A | 44 | 7.648 | 65.503 | 21.285 | 1.00 | 32.67 | A | C |
| ATOM | 42 | C | LEU | A | 44 | 9.247 | 66.633 | 23.619 | 1.00 | 27.22 | A | C |
| ATOM | 43 | O | LEU | A | 44 | 10.297 | 67.124 | 23.210 | 1.00 | 29.06 | A | O |
| ATOM | 44 | N | ALA | A | 45 | 8.106 | 67.313 | 23.684 | 1.00 | 22.68 | A | N |
| ATOM | 45 | CA | ALA | A | 45 | 7.982 | 68.678 | 23.175 | 1.00 | 22.75 | A | C |
| ATOM | 46 | CB | ALA | A | 45 | 6.540 | 69.090 | 23.124 | 1.00 | 24.95 | A | C |
| ATOM | 47 | C | ALA | A | 45 | 8.811 | 69.683 | 23.960 | 1.00 | 30.88 | A | C |
| ATOM | 48 | O | ALA | A | 45 | 9.348 | 70.651 | 23.404 | 1.00 | 27.08 | A | O |
| ATOM | 49 | N | GLU | A | 46 | 8.929 | 69.454 | 25.258 | 1.00 | 30.19 | A | N |
| ATOM | 50 | CA | GLU | A | 46 | 9.782 | 70.296 | 26.068 | 1.00 | 31.83 | A | C |
| ATOM | 51 | CB | GLU | A | 46 | 9.548 | 70.032 | 27.544 | 1.00 | 29.47 | A | C |
| ATOM | 52 | CG | GLU | A | 46 | 8.265 | 70.601 | 28.040 | 1.00 | 38.13 | A | C |
| ATOM | 53 | CD | GLU | A | 46 | 8.135 | 70.466 | 29.541 | 1.00 | 46.63 | A | C |
| ATOM | 54 | OE1 | GLU | A | 46 | 9.165 | 70.197 | 30.209 | 1.00 | 45.80 | A | O |
| ATOM | 55 | OE2 | GLU | A | 46 | 7.004 | 70.631 | 30.044 | 1.00 | 51.36 | A | O |
| ATOM | 56 | C | GLU | A | 46 | 11.245 | 70.082 | 25.741 | 1.00 | 29.61 | A | C |
| ATOM | 57 | O | GLU | A | 46 | 12.006 | 71.039 | 25.644 | 1.00 | 31.21 | A | O |
| ATOM | 58 | N | GLU | A | 47 | 11.636 | 68.825 | 25.583 | 1.00 | 28.18 | A | N |

TABLE 15-continued

| | | | | | | | | | | | |
|---|---|---|---|---|---|---|---|---|---|---|---|
| Coordinates for apo form of proMMP9(35-444 ΔFnII) (SEQ ID NO: 12) | | | | | | | | | | | |
| ATOM | 59 | CA | GLU | A | 47 | 13.024 | 68.495 | 25.296 | 1.00 | 27.62 A | C |
| ATOM | 60 | CB | GLU | A | 47 | 13.270 | 67.002 | 25.551 | 1.00 | 30.67 A | C |
| ATOM | 61 | CG | GLU | A | 47 | 14.678 | 66.510 | 25.234 | 1.00 | 38.26 A | C |
| ATOM | 62 | CD | GLU | A | 47 | 15.740 | 67.068 | 26.188 | 1.00 | 46.31 A | C |
| ATOM | 63 | OE1 | GLU | A | 47 | 15.510 | 67.060 | 27.421 | 1.00 | 47.56 A | O |
| ATOM | 64 | OE2 | GLU | A | 47 | 16.810 | 67.507 | 25.701 | 1.00 | 41.49 A | O |
| ATOM | 65 | C | GLU | A | 47 | 13.419 | 68.872 | 23.862 | 1.00 | 30.84 A | C |
| ATOM | 66 | O | GLU | A | 47 | 14.592 | 69.133 | 23.571 | 1.00 | 30.11 A | O |
| ATOM | 67 | N | TYR | A | 48 | 12.446 | 68.887 | 22.959 | 1.00 | 28.21 A | N |
| ATOM | 68 | CA | TYR | A | 48 | 12.713 | 69.269 | 21.581 | 1.00 | 25.17 A | C |
| ATOM | 69 | CB | TYR | A | 48 | 11.562 | 68.817 | 20.675 | 1.00 | 25.52 A | C |
| ATOM | 70 | CG | TYR | A | 48 | 11.836 | 68.853 | 19.184 | 1.00 | 20.18 A | C |
| ATOM | 71 | CD1 | TYR | A | 48 | 11.754 | 70.038 | 18.451 | 1.00 | 23.22 A | C |
| ATOM | 72 | CE1 | TYR | A | 48 | 11.981 | 70.048 | 17.053 | 1.00 | 20.40 A | C |
| ATOM | 73 | CD2 | TYR | A | 48 | 12.117 | 67.684 | 18.495 | 1.00 | 18.19 A | C |
| ATOM | 74 | CE2 | TYR | A | 48 | 12.331 | 67.684 | 17.134 | 1.00 | 22.38 A | C |
| ATOM | 75 | CZ | TYR | A | 48 | 12.281 | 68.869 | 16.410 | 1.00 | 20.91 A | C |
| ATOM | 76 | OH | TYR | A | 48 | 12.501 | 68.817 | 15.036 | 1.00 | 19.25 A | O |
| ATOM | 77 | C | TYR | A | 48 | 12.871 | 70.778 | 21.507 | 1.00 | 25.72 A | C |
| ATOM | 78 | O | TYR | A | 48 | 13.844 | 71.299 | 20.944 | 1.00 | 23.40 A | O |
| ATOM | 79 | N | LEU | A | 49 | 11.898 | 71.482 | 22.067 | 1.00 | 25.98 A | N |
| ATOM | 80 | CA | LEU | A | 49 | 11.923 | 72.927 | 22.043 | 1.00 | 24.08 A | C |
| ATOM | 81 | CB | LEU | A | 49 | 10.672 | 73.494 | 22.710 | 1.00 | 29.21 A | C |
| ATOM | 82 | CG | LEU | A | 49 | 9.377 | 73.249 | 21.937 | 1.00 | 28.10 A | C |
| ATOM | 83 | CD1 | LEU | A | 49 | 8.170 | 73.560 | 22.819 | 1.00 | 22.99 A | C |
| ATOM | 84 | CD2 | LEU | A | 49 | 9.366 | 74.093 | 20.665 | 1.00 | 22.02 A | C |
| ATOM | 85 | C | LEU | A | 49 | 13.176 | 73.441 | 22.720 | 1.00 | 25.30 A | C |
| ATOM | 86 | O | LEU | A | 49 | 13.756 | 74.437 | 22.298 | 1.00 | 24.37 A | O |
| ATOM | 87 | N | TYR | A | 50 | 13.594 | 72.771 | 23.785 | 1.00 | 32.10 A | N |
| ATOM | 88 | CA | TYR | A | 50 | 14.774 | 73.222 | 24.498 | 1.00 | 29.27 A | C |
| ATOM | 89 | CB | TYR | A | 50 | 14.887 | 72.579 | 25.877 | 1.00 | 27.89 A | C |
| ATOM | 90 | CG | TYR | A | 50 | 16.308 | 72.587 | 26.375 | 1.00 | 28.86 A | C |
| ATOM | 91 | CD1 | TYR | A | 50 | 16.845 | 73.720 | 26.983 | 1.00 | 34.49 A | C |
| ATOM | 92 | CE1 | TYR | A | 50 | 18.158 | 73.741 | 27.419 | 1.00 | 30.57 A | C |
| ATOM | 93 | CD2 | TYR | A | 50 | 17.132 | 71.484 | 26.196 | 1.00 | 26.45 A | C |
| ATOM | 94 | CE2 | TYR | A | 50 | 18.450 | 71.496 | 26.632 | 1.00 | 32.25 A | C |
| ATOM | 95 | CZ | TYR | A | 50 | 18.953 | 72.627 | 27.245 | 1.00 | 30.20 A | C |
| ATOM | 96 | OH | TYR | A | 50 | 20.258 | 72.645 | 27.674 | 1.00 | 39.22 A | O |
| ATOM | 97 | C | TYR | A | 50 | 16.030 | 72.929 | 23.710 | 1.00 | 26.53 A | C |
| ATOM | 98 | O | TYR | A | 50 | 16.894 | 73.789 | 23.571 | 1.00 | 25.74 A | O |
| ATOM | 99 | N | ARG | A | 51 | 16.115 | 71.705 | 23.195 | 1.00 | 23.80 A | N |
| ATOM | 100 | CA | ARG | A | 51 | 17.332 | 71.199 | 22.598 | 1.00 | 25.93 A | C |
| ATOM | 101 | CB | ARG | A | 51 | 17.181 | 69.698 | 22.315 | 1.00 | 24.27 A | C |
| ATOM | 102 | CG | ARG | A | 51 | 18.402 | 69.017 | 21.768 | 1.00 | 28.40 A | C |
| ATOM | 103 | CD | ARG | A | 51 | 18.058 | 67.675 | 21.116 | 1.00 | 25.29 A | C |
| ATOM | 104 | NE | ARG | A | 51 | 18.224 | 66.552 | 22.031 | 1.00 | 23.90 A | N |
| ATOM | 105 | CZ | ARG | A | 51 | 19.401 | 66.032 | 22.365 | 1.00 | 30.22 A | C |
| ATOM | 106 | NH1 | ARG | A | 51 | 20.526 | 66.542 | 21.859 | 1.00 | 24.09 A | N |
| ATOM | 107 | NH2 | ARG | A | 51 | 19.455 | 65.012 | 23.217 | 1.00 | 28.39 A | N |
| ATOM | 108 | C | ARG | A | 51 | 17.651 | 71.974 | 21.317 | 1.00 | 24.58 A | C |
| ATOM | 109 | O | ARG | A | 51 | 18.804 | 72.207 | 20.991 | 1.00 | 22.58 A | O |
| ATOM | 110 | N | TYR | A | 52 | 16.620 | 72.396 | 20.599 | 1.00 | 24.72 A | N |
| ATOM | 111 | CA | TYR | A | 52 | 16.851 | 73.005 | 19.300 | 1.00 | 20.25 A | C |
| ATOM | 112 | CB | TYR | A | 52 | 15.935 | 72.375 | 18.252 | 1.00 | 17.52 A | C |
| ATOM | 113 | CG | TYR | A | 52 | 16.246 | 70.910 | 18.046 | 1.00 | 22.29 A | C |
| ATOM | 114 | CD1 | TYR | A | 52 | 15.281 | 69.933 | 18.239 | 1.00 | 22.95 A | C |
| ATOM | 115 | CE1 | TYR | A | 52 | 15.583 | 68.587 | 18.066 | 1.00 | 21.99 A | C |
| ATOM | 116 | CD2 | TYR | A | 52 | 17.527 | 70.504 | 17.672 | 1.00 | 20.02 A | C |
| ATOM | 117 | CE2 | TYR | A | 52 | 17.831 | 69.172 | 17.480 | 1.00 | 24.00 A | C |
| ATOM | 118 | CZ | TYR | A | 52 | 16.857 | 68.222 | 17.677 | 1.00 | 20.03 A | C |
| ATOM | 119 | OH | TYR | A | 52 | 17.163 | 66.903 | 17.492 | 1.00 | 24.36 A | O |
| ATOM | 120 | C | TYR | A | 52 | 16.787 | 74.533 | 19.334 | 1.00 | 22.92 A | C |
| ATOM | 121 | O | TYR | A | 52 | 16.763 | 75.195 | 18.290 | 1.00 | 25.08 A | O |
| ATOM | 122 | N | GLY | A | 53 | 16.786 | 75.081 | 20.550 | 1.00 | 24.92 A | N |
| ATOM | 123 | CA | GLY | A | 53 | 16.982 | 76.505 | 20.762 | 1.00 | 24.54 A | C |
| ATOM | 124 | C | GLY | A | 53 | 15.734 | 77.342 | 20.950 | 1.00 | 24.30 A | C |
| ATOM | 125 | O | GLY | A | 53 | 15.818 | 78.510 | 21.302 | 1.00 | 29.51 A | O |
| ATOM | 126 | N | TYR | A | 54 | 14.570 | 76.752 | 20.728 | 1.00 | 25.19 A | N |
| ATOM | 127 | CA | TYR | A | 54 | 13.324 | 77.519 | 20.682 | 1.00 | 22.92 A | C |
| ATOM | 128 | CB | TYR | A | 54 | 12.204 | 76.652 | 20.136 | 1.00 | 26.90 A | C |
| ATOM | 129 | CG | TYR | A | 54 | 12.432 | 76.241 | 18.709 | 1.00 | 24.65 A | C |
| ATOM | 130 | CD1 | TYR | A | 54 | 12.849 | 74.954 | 18.397 | 1.00 | 25.06 A | C |
| ATOM | 131 | CE1 | TYR | A | 54 | 13.063 | 74.574 | 17.088 | 1.00 | 21.40 A | C |
| ATOM | 132 | CD2 | TYR | A | 54 | 12.253 | 77.151 | 17.674 | 1.00 | 21.87 A | C |
| ATOM | 133 | CE2 | TYR | A | 54 | 12.469 | 76.783 | 16.360 | 1.00 | 19.39 A | C |
| ATOM | 134 | CZ | TYR | A | 54 | 12.875 | 75.492 | 16.079 | 1.00 | 21.02 A | C |
| ATOM | 135 | OH | TYR | A | 54 | 13.093 | 75.116 | 14.778 | 1.00 | 17.04 A | O |
| ATOM | 136 | C | TYR | A | 54 | 12.894 | 78.111 | 22.021 | 1.00 | 24.21 A | C |

TABLE 15-continued

| Coordinates for apo form of proMMP9(35-444 ΔFnII) (SEQ ID NO: 12) | | | | | | | | | | | |
|---|---|---|---|---|---|---|---|---|---|---|---|
| ATOM | 137 | O | TYR | A | 54 | 12.323 | 79.187 | 22.064 | 1.00 | 27.10 A | O |
| ATOM | 138 | N | THR | A | 55 | 13.142 | 77.399 | 23.109 | 1.00 | 27.82 A | N |
| ATOM | 139 | CA | THR | A | 55 | 12.651 | 77.860 | 24.406 | 1.00 | 31.86 A | C |
| ATOM | 140 | CB | THR | A | 55 | 12.746 | 76.760 | 25.481 | 1.00 | 32.13 A | C |
| ATOM | 141 | OG1 | THR | A | 55 | 14.120 | 76.495 | 25.783 | 1.00 | 39.86 A | O |
| ATOM | 142 | CG2 | THR | A | 55 | 12.098 | 75.489 | 25.001 | 1.00 | 25.96 A | C |
| ATOM | 143 | C | THR | A | 55 | 13.450 | 79.079 | 24.848 | 1.00 | 33.75 A | C |
| ATOM | 144 | O | THR | A | 55 | 12.886 | 80.098 | 25.262 | 1.00 | 33.26 A | O |
| ATOM | 145 | N | ARG | A | 56 | 14.771 | 78.968 | 24.738 | 1.00 | 32.93 A | N |
| ATOM | 146 | CA | ARG | A | 56 | 15.676 | 80.054 | 25.085 | 1.00 | 30.97 A | C |
| ATOM | 147 | CB | ARG | A | 56 | 17.114 | 79.641 | 24.766 | 1.00 | 33.53 A | C |
| ATOM | 148 | CG | ARG | A | 56 | 18.149 | 80.659 | 25.186 | 1.00 | 35.77 A | C |
| ATOM | 149 | CD | ARG | A | 56 | 17.908 | 81.157 | 26.608 | 1.00 | 31.00 A | C |
| ATOM | 150 | NE | ARG | A | 56 | 18.586 | 82.431 | 26.815 | 1.00 | 32.41 A | N |
| ATOM | 151 | CZ | ARG | A | 56 | 18.158 | 83.405 | 27.611 | 1.00 | 33.08 A | C |
| ATOM | 152 | NH1 | ARG | A | 56 | 17.037 | 83.263 | 28.305 | 1.00 | 33.98 A | N |
| ATOM | 153 | NH2 | ARG | A | 56 | 18.859 | 84.529 | 27.706 | 1.00 | 32.57 A | N |
| ATOM | 154 | C | ARG | A | 56 | 15.308 | 81.326 | 24.322 | 1.00 | 33.59 A | C |
| ATOM | 155 | O | ARG | A | 56 | 15.260 | 82.419 | 24.876 | 1.00 | 31.90 A | O |
| ATOM | 156 | N | VAL | A | 57 | 15.041 | 81.175 | 23.036 | 1.00 | 31.11 A | N |
| ATOM | 157 | CA | VAL | A | 57 | 14.621 | 82.309 | 22.222 | 1.00 | 31.66 A | C |
| ATOM | 158 | CB | VAL | A | 57 | 14.572 | 81.920 | 20.735 | 1.00 | 26.54 A | C |
| ATOM | 159 | CG1 | VAL | A | 57 | 14.095 | 83.089 | 19.881 | 1.00 | 30.64 A | C |
| ATOM | 160 | CG2 | VAL | A | 57 | 15.950 | 81.457 | 20.288 | 1.00 | 32.62 A | C |
| ATOM | 161 | C | VAL | A | 57 | 13.274 | 82.856 | 22.690 | 1.00 | 30.02 A | C |
| ATOM | 162 | O | VAL | A | 57 | 13.071 | 84.069 | 22.738 | 1.00 | 29.28 A | O |
| ATOM | 163 | N | GLY | A | 58 | 12.353 | 81.961 | 23.036 | 1.00 | 26.98 A | N |
| ATOM | 164 | CA | GLY | A | 58 | 11.062 | 82.364 | 23.568 | 1.00 | 29.77 A | C |
| ATOM | 165 | C | GLY | A | 58 | 11.222 | 83.166 | 24.852 | 1.00 | 32.88 A | C |
| ATOM | 166 | O | GLY | A | 58 | 10.517 | 84.150 | 25.086 | 1.00 | 34.39 A | O |
| ATOM | 167 | N | GLU | A | 59 | 12.162 | 82.736 | 25.689 | 1.00 | 34.03 A | N |
| ATOM | 168 | CA | GLU | A | 59 | 12.502 | 83.455 | 26.914 | 1.00 | 35.29 A | C |
| ATOM | 169 | C | GLU | A | 59 | 13.006 | 84.860 | 26.623 | 1.00 | 34.85 A | C |
| ATOM | 170 | CB | GLU | A | 59 | 13.569 | 82.697 | 27.692 | 1.00 | 33.35 A | C |
| ATOM | 171 | CG | GLU | A | 59 | 13.140 | 81.327 | 28.148 | 1.00 | 41.75 A | C |
| ATOM | 172 | CD | GLU | A | 59 | 14.127 | 80.706 | 29.113 | 1.00 | 44.85 A | C |
| ATOM | 173 | OE1 | GLU | A | 59 | 15.233 | 81.273 | 29.285 | 1.00 | 40.01 A | O |
| ATOM | 174 | OE2 | GLU | A | 59 | 13.793 | 79.654 | 29.699 | 1.00 | 43.89 A | O |
| ATOM | 175 | O | GLU | A | 59 | 12.522 | 85.830 | 27.209 | 1.00 | 32.29 A | O |
| ATOM | 176 | N | MET | A | 60 | 13.982 | 84.960 | 25.716 | 1.00 | 35.10 A | N |
| ATOM | 177 | CA | MET | A | 60 | 14.541 | 86.246 | 25.285 | 1.00 | 30.26 A | C |
| ATOM | 178 | C | MET | A | 60 | 13.464 | 87.213 | 24.802 | 1.00 | 28.22 A | C |
| ATOM | 179 | CB | MET | A | 60 | 15.574 | 86.056 | 24.158 | 1.00 | 23.03 A | C |
| ATOM | 180 | CG | MET | A | 60 | 16.825 | 85.292 | 24.548 | 1.00 | 29.72 A | C |
| ATOM | 181 | SD | MET | A | 60 | 17.965 | 85.001 | 23.171 | 1.00 | 38.67 A | S |
| ATOM | 182 | CE | MET | A | 60 | 18.982 | 83.719 | 23.890 | 1.00 | 36.29 A | C |
| ATOM | 183 | O | MET | A | 60 | 13.692 | 88.418 | 24.729 | 1.00 | 29.93 A | O |
| ATOM | 184 | N | ARG | A | 61 | 12.298 | 86.692 | 24.447 | 1.00 | 31.47 A | N |
| ATOM | 185 | CA | ARG | A | 61 | 11.228 | 87.556 | 23.959 | 1.00 | 30.85 A | C |
| ATOM | 186 | C | ARG | A | 61 | 10.194 | 87.835 | 25.036 | 1.00 | 32.84 A | C |
| ATOM | 187 | CB | ARG | A | 61 | 10.571 | 86.959 | 22.720 | 1.00 | 35.78 A | C |
| ATOM | 188 | CG | ARG | A | 61 | 11.559 | 86.625 | 21.608 | 1.00 | 36.76 A | C |
| ATOM | 189 | CD | ARG | A | 61 | 10.834 | 86.421 | 20.297 | 1.00 | 43.82 A | C |
| ATOM | 190 | NE | ARG | A | 61 | 11.733 | 86.024 | 19.221 | 1.00 | 45.48 A | N |
| ATOM | 191 | CZ | ARG | A | 61 | 11.376 | 85.985 | 17.943 | 1.00 | 45.71 A | C |
| ATOM | 192 | NH1 | ARG | A | 61 | 12.249 | 85.612 | 17.019 | 1.00 | 43.23 A | N |
| ATOM | 193 | NH2 | ARG | A | 61 | 10.139 | 86.322 | 17.593 | 1.00 | 50.16 A | N |
| ATOM | 194 | O | ARG | A | 61 | 9.127 | 88.392 | 24.751 | 1.00 | 41.35 A | O |
| ATOM | 195 | N | GLY | A | 62 | 10.523 | 87.445 | 26.268 | 1.00 | 34.73 A | N |
| ATOM | 196 | CA | GLY | A | 62 | 9.660 | 87.656 | 27.421 | 1.00 | 36.71 A | C |
| ATOM | 197 | C | GLY | A | 62 | 8.474 | 86.701 | 27.440 | 1.00 | 45.80 A | C |
| ATOM | 198 | O | GLY | A | 62 | 7.471 | 86.933 | 28.137 | 1.00 | 31.18 A | O |
| ATOM | 199 | N | GLU | A | 63 | 8.597 | 85.631 | 26.656 | 1.00 | 38.06 A | N |
| ATOM | 200 | CA | GLU | A | 63 | 7.580 | 84.594 | 26.572 | 1.00 | 44.09 A | C |
| ATOM | 201 | C | GLU | A | 63 | 8.126 | 83.266 | 27.104 | 1.00 | 51.66 A | C |
| ATOM | 202 | CB | GLU | A | 63 | 7.091 | 84.450 | 25.128 | 1.00 | 40.71 A | C |
| ATOM | 203 | CG | GLU | A | 63 | 6.637 | 85.778 | 24.515 | 1.00 | 43.80 A | C |
| ATOM | 204 | CD | GLU | A | 63 | 6.009 | 85.628 | 23.138 | 1.00 | 49.57 A | C |
| ATOM | 205 | OE1 | GLU | A | 63 | 6.567 | 86.184 | 22.166 | 1.00 | 46.80 A | O |
| ATOM | 206 | OE2 | GLU | A | 63 | 4.953 | 84.963 | 23.024 | 1.00 | 51.70 A | O |
| ATOM | 207 | O | GLU | A | 63 | 8.194 | 82.266 | 26.378 | 1.00 | 44.27 A | O |
| ATOM | 208 | N | SER | A | 64 | 8.530 | 83.273 | 28.376 | 1.00 | 52.59 A | N |
| ATOM | 209 | CA | SER | A | 64 | 8.997 | 82.063 | 29.055 | 1.00 | 51.91 A | C |
| ATOM | 210 | C | SER | A | 64 | 7.817 | 81.467 | 29.807 | 1.00 | 56.18 A | C |
| ATOM | 211 | CB | SER | A | 64 | 10.161 | 82.374 | 30.004 | 1.00 | 51.80 A | C |
| ATOM | 212 | OG | SER | A | 64 | 9.914 | 83.555 | 30.757 | 1.00 | 57.31 A | O |
| ATOM | 213 | O | SER | A | 64 | 7.962 | 80.600 | 30.673 | 1.00 | 56.45 A | O |
| ATOM | 214 | N | LYS | A | 65 | 6.641 | 81.962 | 29.448 | 1.00 | 55.59 A | N |

TABLE 15-continued

| | | | | | | | | | | | |
|---|---|---|---|---|---|---|---|---|---|---|---|
| Coordinates for apo form of proMMP9(35-444 ΔFnII) (SEQ ID NO: 12) | | | | | | | | | | | |
| ATOM | 215 | CA | LYS | A | 65 | 5.382 | 81.514 | 30.007 | 1.00 | 52.13 A | C |
| ATOM | 216 | C | LYS | A | 65 | 5.177 | 80.029 | 29.710 | 1.00 | 51.19 A | C |
| ATOM | 217 | CB | LYS | A | 65 | 4.265 | 82.330 | 29.361 | 1.00 | 50.23 A | C |
| ATOM | 218 | CG | LYS | A | 65 | 4.317 | 82.257 | 27.839 | 1.00 | 47.29 A | C |
| ATOM | 219 | CD | LYS | A | 65 | 3.363 | 83.215 | 27.181 | 1.00 | 49.48 A | C |
| ATOM | 220 | CE | LYS | A | 65 | 4.017 | 84.562 | 26.957 | 1.00 | 45.84 A | C |
| ATOM | 221 | NZ | LYS | A | 65 | 3.033 | 85.498 | 26.366 | 1.00 | 49.66 A | N |
| ATOM | 222 | O | LYS | A | 65 | 5.910 | 79.179 | 30.211 | 1.00 | 54.91 A | O |
| ATOM | 223 | N | SER | A | 66 | 4.178 | 79.733 | 28.880 | 1.00 | 48.71 A | N |
| ATOM | 224 | CA | SER | A | 66 | 3.850 | 78.371 | 28.480 | 1.00 | 40.20 A | C |
| ATOM | 225 | C | SER | A | 66 | 4.672 | 77.907 | 27.276 | 1.00 | 44.34 A | C |
| ATOM | 226 | CB | SER | A | 66 | 2.361 | 78.275 | 28.144 | 1.00 | 39.36 A | C |
| ATOM | 227 | OG | SER | A | 66 | 2.087 | 78.785 | 26.851 | 1.00 | 34.18 A | O |
| ATOM | 228 | O | SER | A | 66 | 5.731 | 78.457 | 26.973 | 1.00 | 40.20 A | O |
| ATOM | 229 | N | LEU | A | 67 | 4.164 | 76.889 | 26.592 | 1.00 | 33.76 A | N |
| ATOM | 230 | CA | LEU | A | 67 | 4.824 | 76.313 | 25.432 | 1.00 | 35.53 A | C |
| ATOM | 231 | C | LEU | A | 67 | 4.461 | 77.043 | 24.135 | 1.00 | 31.78 A | C |
| ATOM | 232 | CB | LEU | A | 67 | 4.421 | 74.839 | 25.310 | 1.00 | 31.23 A | C |
| ATOM | 233 | CG | LEU | A | 67 | 5.468 | 73.743 | 25.499 | 1.00 | 33.63 A | C |
| ATOM | 234 | CD1 | LEU | A | 67 | 6.291 | 73.951 | 26.746 | 1.00 | 33.37 A | C |
| ATOM | 235 | CD2 | LEU | A | 67 | 4.763 | 72.392 | 25.534 | 1.00 | 34.78 A | C |
| ATOM | 236 | O | LEU | A | 67 | 5.205 | 76.995 | 23.152 | 1.00 | 31.32 A | O |
| ATOM | 237 | N | GLY | A | 68 | 3.314 | 77.711 | 24.134 | 1.00 | 31.62 A | N |
| ATOM | 238 | CA | GLY | A | 68 | 2.761 | 78.287 | 22.917 | 1.00 | 29.84 A | C |
| ATOM | 239 | C | GLY | A | 68 | 3.694 | 79.115 | 22.047 | 1.00 | 29.31 A | C |
| ATOM | 240 | O | GLY | A | 68 | 3.815 | 78.873 | 20.849 | 1.00 | 33.24 A | O |
| ATOM | 241 | N | PRO | A | 69 | 4.351 | 80.115 | 22.638 | 1.00 | 34.73 A | N |
| ATOM | 242 | CD | PRO | A | 69 | 4.232 | 80.539 | 24.040 | 1.00 | 31.89 A | C |
| ATOM | 243 | CA | PRO | A | 69 | 5.248 | 80.985 | 21.868 | 1.00 | 31.91 A | C |
| ATOM | 244 | CB | PRO | A | 69 | 5.774 | 81.966 | 22.919 | 1.00 | 37.73 A | C |
| ATOM | 245 | CG | PRO | A | 69 | 4.731 | 81.948 | 23.994 | 1.00 | 38.02 A | C |
| ATOM | 246 | C | PRO | A | 69 | 6.405 | 80.221 | 21.229 | 1.00 | 28.12 A | C |
| ATOM | 247 | O | PRO | A | 69 | 6.737 | 80.486 | 20.067 | 1.00 | 28.21 A | O |
| ATOM | 248 | N | ALA | A | 70 | 6.986 | 79.281 | 21.968 | 1.00 | 31.12 A | N |
| ATOM | 249 | CA | ALA | A | 70 | 8.093 | 78.460 | 21.479 | 1.00 | 26.40 A | C |
| ATOM | 250 | CB | ALA | A | 70 | 8.701 | 77.662 | 22.626 | 1.00 | 22.85 A | C |
| ATOM | 251 | C | ALA | A | 70 | 7.660 | 77.512 | 20.363 | 1.00 | 28.06 A | C |
| ATOM | 252 | O | ALA | A | 70 | 8.433 | 77.226 | 19.442 | 1.00 | 25.01 A | O |
| ATOM | 253 | N | LEU | A | 71 | 6.425 | 77.024 | 20.443 | 1.00 | 26.95 A | N |
| ATOM | 254 | CA | LEU | A | 71 | 5.882 | 76.165 | 19.403 | 1.00 | 24.95 A | C |
| ATOM | 255 | CB | LEU | A | 71 | 4.580 | 75.509 | 19.865 | 1.00 | 28.51 A | C |
| ATOM | 256 | CG | LEU | A | 71 | 4.649 | 74.454 | 20.967 | 1.00 | 21.74 A | C |
| ATOM | 257 | CD1 | LEU | A | 71 | 3.252 | 74.226 | 21.480 | 1.00 | 24.96 A | C |
| ATOM | 258 | CD2 | LEU | A | 71 | 5.263 | 73.141 | 20.483 | 1.00 | 28.93 A | C |
| ATOM | 259 | C | LEU | A | 71 | 5.643 | 76.954 | 18.115 | 1.00 | 26.22 A | C |
| ATOM | 260 | O | LEU | A | 71 | 5.836 | 76.432 | 17.014 | 1.00 | 27.53 A | O |
| ATOM | 261 | N | LEU | A | 72 | 5.213 | 78.206 | 18.249 | 1.00 | 22.00 A | N |
| ATOM | 262 | CA | LEU | A | 72 | 5.059 | 79.084 | 17.084 | 1.00 | 27.23 A | C |
| ATOM | 263 | CB | LEU | A | 72 | 4.465 | 80.434 | 17.485 | 1.00 | 27.24 A | C |
| ATOM | 264 | CG | LEU | A | 72 | 3.816 | 81.234 | 16.354 | 1.00 | 34.35 A | C |
| ATOM | 265 | CD1 | LEU | A | 72 | 2.577 | 80.523 | 15.831 | 1.00 | 31.76 A | C |
| ATOM | 266 | CD2 | LEU | A | 72 | 3.464 | 82.643 | 16.821 | 1.00 | 36.81 A | C |
| ATOM | 267 | C | LEU | A | 72 | 6.393 | 79.313 | 16.375 | 1.00 | 25.92 A | C |
| ATOM | 268 | O | LEU | A | 72 | 6.478 | 79.272 | 15.146 | 1.00 | 24.25 A | O |
| ATOM | 269 | N | LEU | A | 73 | 7.434 | 79.565 | 17.159 | 1.00 | 27.76 A | N |
| ATOM | 270 | CA | LEU | A | 73 | 8.762 | 79.750 | 16.594 | 1.00 | 27.24 A | C |
| ATOM | 271 | CB | LEU | A | 73 | 9.770 | 80.064 | 17.693 | 1.00 | 30.21 A | C |
| ATOM | 272 | CG | LEU | A | 73 | 9.709 | 81.473 | 18.277 | 1.00 | 31.62 A | C |
| ATOM | 273 | CD1 | LEU | A | 73 | 10.776 | 81.651 | 19.341 | 1.00 | 30.89 A | C |
| ATOM | 274 | CD2 | LEU | A | 73 | 9.852 | 82.503 | 17.175 | 1.00 | 32.28 A | C |
| ATOM | 275 | C | LEU | A | 73 | 9.199 | 78.508 | 15.831 | 1.00 | 25.05 A | C |
| ATOM | 276 | O | LEU | A | 73 | 9.771 | 78.597 | 14.749 | 1.00 | 27.36 A | O |
| ATOM | 277 | N | LEU | A | 74 | 8.933 | 77.343 | 16.401 | 1.00 | 27.96 A | N |
| ATOM | 278 | CA | LEU | A | 74 | 9.321 | 76.098 | 15.762 | 1.00 | 22.54 A | C |
| ATOM | 279 | CB | LEU | A | 74 | 9.126 | 74.931 | 16.724 | 1.00 | 25.45 A | C |
| ATOM | 280 | CG | LEU | A | 74 | 9.242 | 73.492 | 16.222 | 1.00 | 21.94 A | C |
| ATOM | 281 | CD1 | LEU | A | 74 | 9.418 | 72.592 | 17.425 | 1.00 | 27.44 A | C |
| ATOM | 282 | CD2 | LEU | A | 74 | 7.998 | 73.082 | 15.437 | 1.00 | 27.42 A | C |
| ATOM | 283 | C | LEU | A | 74 | 8.532 | 75.897 | 14.474 | 1.00 | 25.51 A | C |
| ATOM | 284 | O | LEU | A | 74 | 9.113 | 75.559 | 13.441 | 1.00 | 23.54 A | O |
| ATOM | 285 | N | GLN | A | 75 | 7.217 | 76.117 | 14.535 | 1.00 | 25.11 A | N |
| ATOM | 286 | CA | GLN | A | 75 | 6.342 | 75.965 | 13.372 | 1.00 | 23.19 A | C |
| ATOM | 287 | CB | GLN | A | 75 | 4.883 | 76.232 | 13.756 | 1.00 | 23.73 A | C |
| ATOM | 288 | CG | GLN | A | 75 | 4.264 | 75.077 | 14.536 | 1.00 | 29.44 A | C |
| ATOM | 289 | CD | GLN | A | 75 | 3.127 | 75.504 | 15.456 | 1.00 | 26.10 A | C |
| ATOM | 290 | OE1 | GLN | A | 75 | 2.794 | 76.683 | 15.552 | 1.00 | 26.71 A | O |
| ATOM | 291 | NE2 | GLN | A | 75 | 2.513 | 74.534 | 16.115 | 1.00 | 21.02 A | N |
| ATOM | 292 | C | GLN | A | 75 | 6.762 | 76.895 | 12.238 | 1.00 | 27.74 A | C |

TABLE 15-continued

| | | | | | | | | | | | |
|---|---|---|---|---|---|---|---|---|---|---|---|
| | Coordinates for apo form of proMMP9(35-444 ΔFnII) (SEQ ID NO: 12) |

| ATOM | 293 | O | GLN | A | 75 | 6.651 | 76.555 | 11.061 | 1.00 | 24.99 A | O |
| ATOM | 294 | N | LYS | A | 76 | 7.237 | 78.071 | 12.613 | 1.00 | 23.48 A | N |
| ATOM | 295 | CA | LYS | A | 76 | 7.755 | 79.040 | 11.665 | 1.00 | 27.81 A | C |
| ATOM | 296 | CB | LYS | A | 76 | 7.950 | 80.384 | 12.364 | 1.00 | 25.62 A | C |
| ATOM | 297 | CG | LYS | A | 76 | 7.953 | 81.579 | 11.436 | 1.00 | 40.17 A | C |
| ATOM | 298 | CD | LYS | A | 76 | 7.964 | 82.875 | 12.237 | 1.00 | 44.17 A | C |
| ATOM | 299 | CE | LYS | A | 76 | 6.947 | 82.836 | 13.381 | 1.00 | 42.30 A | C |
| ATOM | 300 | NZ | LYS | A | 76 | 5.519 | 82.808 | 12.921 | 1.00 | 40.55 A | N |
| ATOM | 301 | C | LYS | A | 76 | 9.082 | 78.529 | 11.103 | 1.00 | 28.69 A | C |
| ATOM | 302 | O | LYS | A | 76 | 9.265 | 78.450 | 9.885 | 1.00 | 23.58 A | O |
| ATOM | 303 | N | GLN | A | 77 | 9.989 | 78.153 | 11.999 | 1.00 | 24.27 A | N |
| ATOM | 304 | CA | GLN | A | 77 | 11.310 | 77.653 | 11.598 | 1.00 | 25.73 A | C |
| ATOM | 305 | CB | GLN | A | 77 | 12.196 | 77.389 | 12.826 | 1.00 | 22.10 A | C |
| ATOM | 306 | CG | GLN | A | 77 | 13.624 | 76.905 | 12.500 | 1.00 | 23.74 A | C |
| ATOM | 307 | CD | GLN | A | 77 | 14.475 | 77.998 | 11.878 | 1.00 | 29.08 A | C |
| ATOM | 308 | OE1 | GLN | A | 77 | 14.185 | 79.180 | 12.044 | 1.00 | 31.00 A | O |
| ATOM | 309 | NE2 | GLN | A | 77 | 15.531 | 77.607 | 11.154 | 1.00 | 29.46 A | N |
| ATOM | 310 | C | GLN | A | 77 | 11.260 | 76.416 | 10.704 | 1.00 | 21.82 A | C |
| ATOM | 311 | O | GLN | A | 77 | 12.100 | 76.264 | 9.813 | 1.00 | 27.38 A | O |
| ATOM | 312 | N | LEU | A | 78 | 10.271 | 75.547 | 10.919 | 1.00 | 20.18 A | N |
| ATOM | 313 | CA | LEU | A | 78 | 10.136 | 74.299 | 10.161 | 1.00 | 21.85 A | C |
| ATOM | 314 | CB | LEU | A | 78 | 9.817 | 73.129 | 11.088 | 1.00 | 19.16 A | C |
| ATOM | 315 | CG | LEU | A | 78 | 10.877 | 72.756 | 12.125 | 1.00 | 21.84 A | C |
| ATOM | 316 | CD1 | LEU | A | 78 | 10.281 | 71.843 | 13.192 | 1.00 | 22.17 A | C |
| ATOM | 317 | CD2 | LEU | A | 78 | 12.033 | 72.084 | 11.438 | 1.00 | 20.71 A | C |
| ATOM | 318 | C | LEU | A | 78 | 9.076 | 74.326 | 9.061 | 1.00 | 23.71 A | C |
| ATOM | 319 | O | LEU | A | 78 | 8.832 | 73.311 | 8.410 | 1.00 | 24.84 A | O |
| ATOM | 320 | N | SER | A | 79 | 8.429 | 75.473 | 8.882 | 1.00 | 28.66 A | N |
| ATOM | 321 | CA | SER | A | 79 | 7.352 | 75.637 | 7.897 | 1.00 | 26.88 A | C |
| ATOM | 322 | CB | SER | A | 79 | 7.887 | 75.551 | 6.465 | 1.00 | 25.58 A | C |
| ATOM | 323 | OG | SER | A | 79 | 8.801 | 76.605 | 6.225 | 1.00 | 30.77 A | O |
| ATOM | 324 | C | SER | A | 79 | 6.140 | 74.718 | 8.074 | 1.00 | 25.97 A | C |
| ATOM | 325 | O | SER | A | 79 | 5.649 | 74.127 | 7.111 | 1.00 | 24.96 A | O |
| ATOM | 326 | N | LEU | A | 80 | 5.654 | 74.622 | 9.308 | 1.00 | 26.48 A | N |
| ATOM | 327 | CA | LEU | A | 80 | 4.383 | 73.981 | 9.600 | 1.00 | 23.40 A | C |
| ATOM | 328 | CB | LEU | A | 80 | 4.528 | 73.111 | 10.847 | 1.00 | 29.53 A | C |
| ATOM | 329 | CG | LEU | A | 80 | 5.787 | 72.252 | 10.937 | 1.00 | 30.61 A | C |
| ATOM | 330 | CD1 | LEU | A | 80 | 5.914 | 71.644 | 12.329 | 1.00 | 26.91 A | C |
| ATOM | 331 | CD2 | LEU | A | 80 | 5.732 | 71.171 | 9.879 | 1.00 | 28.75 A | C |
| ATOM | 332 | C | LEU | A | 80 | 3.385 | 75.092 | 9.892 | 1.00 | 27.46 A | C |
| ATOM | 333 | O | LEU | A | 80 | 3.790 | 76.221 | 10.158 | 1.00 | 28.99 A | O |
| ATOM | 334 | N | PRO | A | 81 | 2.077 | 74.777 | 9.896 | 1.00 | 30.34 A | N |
| ATOM | 335 | CD | PRO | A | 81 | 1.427 | 73.466 | 9.732 | 1.00 | 29.21 A | C |
| ATOM | 336 | CA | PRO | A | 81 | 1.102 | 75.836 | 10.194 | 1.00 | 26.61 A | C |
| ATOM | 337 | CB | PRO | A | 81 | −0.235 | 75.081 | 10.231 | 1.00 | 29.96 A | C |
| ATOM | 338 | CG | PRO | A | 81 | 0.011 | 73.840 | 9.419 | 1.00 | 29.47 A | C |
| ATOM | 339 | C | PRO | A | 81 | 1.387 | 76.491 | 11.549 | 1.00 | 26.37 A | C |
| ATOM | 340 | O | PRO | A | 81 | 1.567 | 75.797 | 12.552 | 1.00 | 28.00 A | O |
| ATOM | 341 | N | GLU | A | 82 | 1.460 | 77.816 | 11.564 | 1.00 | 29.90 A | N |
| ATOM | 342 | CA | GLU | A | 82 | 1.761 | 78.543 | 12.791 | 1.00 | 28.90 A | C |
| ATOM | 343 | CB | GLU | A | 82 | 2.394 | 79.895 | 12.454 | 1.00 | 30.37 A | C |
| ATOM | 344 | CG | GLU | A | 82 | 3.764 | 79.707 | 11.786 | 1.00 | 30.26 A | C |
| ATOM | 345 | CD | GLU | A | 82 | 4.040 | 80.715 | 10.698 | 1.00 | 37.75 A | C |
| ATOM | 346 | OE1 | GLU | A | 82 | 3.758 | 81.910 | 10.929 | 1.00 | 37.32 A | O |
| ATOM | 347 | OE2 | GLU | A | 82 | 4.549 | 80.313 | 9.619 | 1.00 | 35.51 A | O |
| ATOM | 348 | C | GLU | A | 82 | 0.507 | 78.642 | 13.666 | 1.00 | 27.68 A | C |
| ATOM | 349 | O | GLU | A | 82 | −0.243 | 79.613 | 13.615 | 1.00 | 33.78 A | O |
| ATOM | 350 | N | THR | A | 83 | 0.280 | 77.588 | 14.445 | 1.00 | 28.57 A | N |
| ATOM | 351 | CA | THR | A | 83 | −0.920 | 77.465 | 15.255 | 1.00 | 29.86 A | C |
| ATOM | 352 | CB | THR | A | 83 | −1.521 | 76.052 | 15.160 | 1.00 | 27.90 A | C |
| ATOM | 353 | OG1 | THR | A | 83 | −0.664 | 75.119 | 15.839 | 1.00 | 28.17 A | O |
| ATOM | 354 | CG2 | THR | A | 83 | −1.686 | 75.628 | 13.700 | 1.00 | 22.38 A | C |
| ATOM | 355 | C | THR | A | 83 | −0.595 | 77.732 | 16.717 | 1.00 | 32.70 A | C |
| ATOM | 356 | O | THR | A | 83 | −1.491 | 77.968 | 17.519 | 1.00 | 26.87 A | O |
| ATOM | 357 | N | GLY | A | 84 | 0.689 | 77.690 | 17.060 | 1.00 | 30.42 A | N |
| ATOM | 358 | CA | GLY | A | 84 | 1.110 | 77.918 | 18.433 | 1.00 | 27.94 A | C |
| ATOM | 359 | C | GLY | A | 84 | 0.631 | 76.843 | 19.393 | 1.00 | 25.62 A | C |
| ATOM | 360 | O | GLY | A | 84 | 0.670 | 77.018 | 20.617 | 1.00 | 22.97 A | O |
| ATOM | 361 | N | GLU | A | 85 | 0.183 | 75.723 | 18.840 | 1.00 | 23.69 A | N |
| ATOM | 362 | CA | GLU | A | 85 | −0.402 | 74.651 | 19.640 | 1.00 | 27.78 A | C |
| ATOM | 363 | CB | GLU | A | 85 | −1.841 | 74.374 | 19.171 | 1.00 | 27.91 A | C |
| ATOM | 364 | CG | GLU | A | 85 | −2.822 | 75.518 | 19.398 | 1.00 | 22.36 A | C |
| ATOM | 365 | CD | GLU | A | 85 | −3.233 | 75.628 | 20.864 | 1.00 | 27.57 A | C |
| ATOM | 366 | OE1 | GLU | A | 85 | −2.995 | 74.656 | 21.617 | 1.00 | 25.47 A | O |
| ATOM | 367 | OE2 | GLU | A | 85 | −3.802 | 76.674 | 21.260 | 1.00 | 24.16 A | O |
| ATOM | 368 | C | GLU | A | 85 | 0.410 | 73.385 | 19.478 | 1.00 | 27.48 A | C |
| ATOM | 369 | O | GLU | A | 85 | 0.862 | 73.092 | 18.382 | 1.00 | 28.76 A | O |
| ATOM | 370 | N | LEU | A | 86 | 0.600 | 72.630 | 20.558 | 1.00 | 24.11 A | N |

TABLE 15-continued

Coordinates for apo form of proMMP9(35-444 ΔFnII) (SEQ ID NO: 12)

| ATOM | 371 | CA | LEU | A | 86 | 1.129 | 71.287 | 20.418 | 1.00 | 24.45 | A | C |
|---|---|---|---|---|---|---|---|---|---|---|---|---|
| ATOM | 372 | CB | LEU | A | 86 | 1.515 | 70.691 | 21.768 | 1.00 | 25.59 | A | C |
| ATOM | 373 | CG | LEU | A | 86 | 2.261 | 69.348 | 21.801 | 1.00 | 22.97 | A | C |
| ATOM | 374 | CD1 | LEU | A | 86 | 3.599 | 69.366 | 21.040 | 1.00 | 22.83 | A | C |
| ATOM | 375 | CD2 | LEU | A | 86 | 2.491 | 68.925 | 23.235 | 1.00 | 27.52 | A | C |
| ATOM | 376 | C | LEU | A | 86 | 0.072 | 70.450 | 19.704 | 1.00 | 26.07 | A | C |
| ATOM | 377 | O | LEU | A | 86 | −0.600 | 69.619 | 20.309 | 1.00 | 28.12 | A | O |
| ATOM | 378 | N | ASP | A | 87 | −0.064 | 70.673 | 18.399 | 1.00 | 25.93 | A | N |
| ATOM | 379 | CA | ASP | A | 87 | −1.026 | 69.927 | 17.596 | 1.00 | 24.07 | A | C |
| ATOM | 380 | CB | ASP | A | 87 | −1.690 | 70.835 | 16.556 | 1.00 | 26.04 | A | C |
| ATOM | 381 | CG | ASP | A | 87 | −0.683 | 71.526 | 15.638 | 1.00 | 26.21 | A | C |
| ATOM | 382 | OD1 | ASP | A | 87 | 0.404 | 70.954 | 15.379 | 1.00 | 26.36 | A | O |
| ATOM | 383 | OD2 | ASP | A | 87 | −0.995 | 72.639 | 15.157 | 1.00 | 23.51 | A | O |
| ATOM | 384 | C | ASP | A | 87 | −0.373 | 68.722 | 16.929 | 1.00 | 28.57 | A | C |
| ATOM | 385 | O | ASP | A | 87 | 0.806 | 68.441 | 17.155 | 1.00 | 22.71 | A | O |
| ATOM | 386 | N | SER | A | 88 | −1.155 | 68.021 | 16.111 | 1.00 | 34.59 | A | N |
| ATOM | 387 | CA | SER | A | 88 | −0.740 | 66.749 | 15.519 | 1.00 | 28.50 | A | C |
| ATOM | 388 | CB | SER | A | 88 | −1.915 | 66.071 | 14.793 | 1.00 | 32.79 | A | C |
| ATOM | 389 | OG | SER | A | 88 | −2.824 | 65.447 | 15.702 | 1.00 | 33.96 | A | O |
| ATOM | 390 | C | SER | A | 88 | 0.437 | 66.915 | 14.562 | 1.00 | 27.18 | A | C |
| ATOM | 391 | O | SER | A | 88 | 1.353 | 66.094 | 14.559 | 1.00 | 29.01 | A | O |
| ATOM | 392 | N | ALA | A | 89 | 0.402 | 67.962 | 13.749 | 1.00 | 23.17 | A | N |
| ATOM | 393 | CA | ALA | A | 89 | 1.488 | 68.217 | 12.817 | 1.00 | 28.25 | A | C |
| ATOM | 394 | CB | ALA | A | 89 | 1.186 | 69.420 | 11.920 | 1.00 | 21.62 | A | C |
| ATOM | 395 | C | ALA | A | 89 | 2.767 | 68.441 | 13.600 | 1.00 | 28.75 | A | C |
| ATOM | 396 | O | ALA | A | 89 | 3.809 | 67.892 | 13.258 | 1.00 | 23.14 | A | O |
| ATOM | 397 | N | THR | A | 90 | 2.686 | 69.234 | 14.664 | 1.00 | 23.35 | A | N |
| ATOM | 398 | CA | THR | A | 90 | 3.880 | 69.571 | 15.429 | 1.00 | 20.82 | A | C |
| ATOM | 399 | CB | THR | A | 90 | 3.626 | 70.741 | 16.392 | 1.00 | 19.14 | A | C |
| ATOM | 400 | OG1 | THR | A | 90 | 3.176 | 71.869 | 15.637 | 1.00 | 23.92 | A | O |
| ATOM | 401 | CG2 | THR | A | 90 | 4.907 | 71.113 | 17.119 | 1.00 | 25.30 | A | C |
| ATOM | 402 | C | THR | A | 90 | 4.430 | 68.368 | 16.164 | 1.00 | 21.65 | A | C |
| ATOM | 403 | O | THR | A | 90 | 5.641 | 68.189 | 16.282 | 1.00 | 22.36 | A | O |
| ATOM | 404 | N | LEU | A | 91 | 3.540 | 67.517 | 16.649 | 1.00 | 22.58 | A | N |
| ATOM | 405 | CA | LEU | A | 91 | 3.973 | 66.313 | 17.334 | 1.00 | 19.93 | A | C |
| ATOM | 406 | CB | LEU | A | 91 | 2.772 | 65.631 | 17.974 | 1.00 | 25.21 | A | C |
| ATOM | 407 | CG | LEU | A | 91 | 3.086 | 64.714 | 19.145 | 1.00 | 26.78 | A | C |
| ATOM | 408 | CD1 | LEU | A | 91 | 4.108 | 65.380 | 20.059 | 1.00 | 28.04 | A | C |
| ATOM | 409 | CD2 | LEU | A | 91 | 1.804 | 64.336 | 19.901 | 1.00 | 27.37 | A | C |
| ATOM | 410 | C | LEU | A | 91 | 4.653 | 65.367 | 16.351 | 1.00 | 25.26 | A | C |
| ATOM | 411 | O | LEU | A | 91 | 5.725 | 64.808 | 16.623 | 1.00 | 25.97 | A | O |
| ATOM | 412 | N | LYS | A | 92 | 4.034 | 65.186 | 15.197 | 1.00 | 28.01 | A | N |
| ATOM | 413 | CA | LYS | A | 92 | 4.626 | 64.321 | 14.197 | 1.00 | 28.92 | A | C |
| ATOM | 414 | CB | LYS | A | 92 | 3.739 | 64.224 | 12.963 | 1.00 | 25.40 | A | C |
| ATOM | 415 | CG | LYS | A | 92 | 4.396 | 63.504 | 11.809 | 1.00 | 32.03 | A | C |
| ATOM | 416 | CD | LYS | A | 92 | 3.534 | 63.572 | 10.555 | 1.00 | 41.71 | A | C |
| ATOM | 417 | CE | LYS | A | 92 | 4.261 | 62.992 | 9.348 | 1.00 | 36.44 | A | C |
| ATOM | 418 | NZ | LYS | A | 92 | 3.447 | 63.149 | 8.118 | 1.00 | 46.89 | A | N |
| ATOM | 419 | C | LYS | A | 92 | 5.995 | 64.874 | 13.829 | 1.00 | 26.09 | A | C |
| ATOM | 420 | O | LYS | A | 92 | 6.960 | 64.122 | 13.711 | 1.00 | 26.22 | A | O |
| ATOM | 421 | N | ALA | A | 93 | 6.071 | 66.187 | 13.641 | 1.00 | 22.82 | A | N |
| ATOM | 422 | CA | ALA | A | 93 | 7.339 | 66.822 | 13.303 | 1.00 | 24.35 | A | C |
| ATOM | 423 | CB | ALA | A | 93 | 7.162 | 68.323 | 13.117 | 1.00 | 22.54 | A | C |
| ATOM | 424 | C | ALA | A | 93 | 8.397 | 66.536 | 14.367 | 1.00 | 23.91 | A | C |
| ATOM | 425 | O | ALA | A | 93 | 9.517 | 66.131 | 14.049 | 1.00 | 21.21 | A | O |
| ATOM | 426 | N | MET | A | 94 | 8.048 | 66.765 | 15.627 | 1.00 | 21.87 | A | N |
| ATOM | 427 | CA | MET | A | 94 | 8.961 | 66.475 | 16.725 | 1.00 | 24.00 | A | C |
| ATOM | 428 | CB | MET | A | 94 | 8.326 | 66.828 | 18.064 | 1.00 | 24.43 | A | C |
| ATOM | 429 | CG | MET | A | 94 | 8.464 | 68.288 | 18.431 | 1.00 | 26.48 | A | C |
| ATOM | 430 | SD | MET | A | 94 | 7.149 | 68.800 | 19.538 | 1.00 | 27.58 | A | S |
| ATOM | 431 | CE | MET | A | 94 | 7.516 | 70.533 | 19.810 | 1.00 | 23.38 | A | C |
| ATOM | 432 | C | MET | A | 94 | 9.442 | 65.023 | 16.760 | 1.00 | 26.34 | A | C |
| ATOM | 433 | O | MET | A | 94 | 10.568 | 64.763 | 17.189 | 1.00 | 23.15 | A | O |
| ATOM | 434 | N | ARG | A | 95 | 8.587 | 64.085 | 16.344 | 1.00 | 22.91 | A | N |
| ATOM | 435 | CA | ARG | A | 95 | 8.961 | 62.670 | 16.306 | 1.00 | 25.19 | A | C |
| ATOM | 436 | CB | ARG | A | 95 | 7.724 | 61.773 | 16.257 | 1.00 | 31.12 | A | C |
| ATOM | 437 | CG | ARG | A | 95 | 6.903 | 61.732 | 17.537 | 1.00 | 31.41 | A | C |
| ATOM | 438 | CD | ARG | A | 95 | 5.955 | 60.542 | 17.487 | 1.00 | 35.25 | A | C |
| ATOM | 439 | NE | ARG | A | 95 | 4.930 | 60.586 | 18.522 | 1.00 | 39.54 | A | N |
| ATOM | 440 | CZ | ARG | A | 95 | 3.678 | 60.979 | 18.306 | 1.00 | 40.06 | A | C |
| ATOM | 441 | NH1 | ARG | A | 95 | 3.309 | 61.371 | 17.088 | 1.00 | 36.14 | A | N |
| ATOM | 442 | NH2 | ARG | A | 95 | 2.800 | 60.982 | 19.304 | 1.00 | 40.43 | A | N |
| ATOM | 443 | C | ARG | A | 95 | 9.876 | 62.272 | 15.143 | 1.00 | 23.08 | A | C |
| ATOM | 444 | O | ARG | A | 95 | 10.451 | 61.189 | 15.153 | 1.00 | 28.13 | A | O |
| ATOM | 445 | N | THR | A | 96 | 10.000 | 63.123 | 14.137 | 1.00 | 23.62 | A | N |
| ATOM | 446 | CA | THR | A | 96 | 10.764 | 62.759 | 12.950 | 1.00 | 24.74 | A | C |
| ATOM | 447 | CB | THR | A | 96 | 10.371 | 63.653 | 11.763 | 1.00 | 21.66 | A | C |
| ATOM | 448 | OG1 | THR | A | 96 | 8.945 | 63.611 | 11.610 | 1.00 | 21.51 | A | O |

TABLE 15-continued

| | | | | | | | | | | | |
|---|---|---|---|---|---|---|---|---|---|---|---|
| \multicolumn{12}{|l|}{Coordinates for apo form of proMMP9(35-444 ΔFnII) (SEQ ID NO: 12)} |

| ATOM | 449 | CG2 | THR | A | 96 | 11.021 | 63.166 | 10.483 | 1.00 | 21.81 A | C |
|---|---|---|---|---|---|---|---|---|---|---|---|
| ATOM | 450 | C | THR | A | 96 | 12.278 | 62.807 | 13.196 | 1.00 | 22.45 A | C |
| ATOM | 451 | O | THR | A | 96 | 12.785 | 63.733 | 13.816 | 1.00 | 21.54 A | O |
| ATOM | 452 | N | PRO | A | 97 | 12.991 | 61.774 | 12.738 | 1.00 | 17.96 A | N |
| ATOM | 453 | CD | PRO | A | 97 | 12.376 | 60.507 | 12.300 | 1.00 | 20.54 A | C |
| ATOM | 454 | CA | PRO | A | 97 | 14.456 | 61.697 | 12.801 | 1.00 | 19.25 A | C |
| ATOM | 455 | CB | PRO | A | 97 | 14.760 | 60.380 | 12.081 | 1.00 | 22.39 A | C |
| ATOM | 456 | CG | PRO | A | 97 | 13.519 | 59.542 | 12.323 | 1.00 | 28.44 A | C |
| ATOM | 457 | C | PRO | A | 97 | 15.107 | 62.880 | 12.082 | 1.00 | 15.76 A | C |
| ATOM | 458 | O | PRO | A | 97 | 14.641 | 63.315 | 11.035 | 1.00 | 18.84 A | O |
| ATOM | 459 | N | ARG | A | 98 | 16.168 | 63.429 | 12.648 | 1.00 | 17.73 A | N |
| ATOM | 460 | CA | ARG | A | 98 | 16.698 | 64.682 | 12.131 | 1.00 | 15.49 A | C |
| ATOM | 461 | CB | ARG | A | 98 | 15.841 | 65.851 | 12.601 | 1.00 | 12.82 A | C |
| ATOM | 462 | CG | ARG | A | 98 | 15.782 | 65.902 | 14.167 | 1.00 | 19.50 A | C |
| ATOM | 463 | CD | ARG | A | 98 | 15.436 | 67.283 | 14.674 | 1.00 | 18.83 A | C |
| ATOM | 464 | NE | ARG | A | 98 | 16.535 | 68.221 | 14.453 | 1.00 | 18.64 A | N |
| ATOM | 465 | CZ | ARG | A | 98 | 16.374 | 69.529 | 14.298 | 1.00 | 19.76 A | C |
| ATOM | 466 | NH1 | ARG | A | 98 | 15.157 | 70.046 | 14.330 | 1.00 | 17.16 A | N |
| ATOM | 467 | NH2 | ARG | A | 98 | 17.427 | 70.314 | 14.113 | 1.00 | 13.23 A | N |
| ATOM | 468 | C | ARG | A | 98 | 18.102 | 64.935 | 12.624 | 1.00 | 17.30 A | C |
| ATOM | 469 | O | ARG | A | 98 | 18.639 | 64.166 | 13.406 | 1.00 | 16.57 A | O |
| ATOM | 470 | N | CYS | A | 99 | 18.665 | 66.043 | 12.151 | 1.00 | 14.78 A | N |
| ATOM | 471 | CA | CYS | A | 99 | 19.983 | 66.523 | 12.550 | 1.00 | 18.24 A | C |
| ATOM | 472 | CB | CYS | A | 99 | 20.435 | 67.603 | 11.565 | 1.00 | 17.84 A | C |
| ATOM | 473 | SG | CYS | A | 99 | 22.057 | 68.259 | 11.917 | 1.00 | 17.65 A | S |
| ATOM | 474 | C | CYS | A | 99 | 20.034 | 67.083 | 13.976 | 1.00 | 20.82 A | C |
| ATOM | 475 | O | CYS | A | 99 | 19.140 | 67.801 | 14.413 | 1.00 | 19.67 A | O |
| ATOM | 476 | N | GLY | A | 100 | 21.101 | 66.761 | 14.697 | 1.00 | 17.62 A | N |
| ATOM | 477 | CA | GLY | A | 100 | 21.229 | 67.208 | 16.061 | 1.00 | 21.71 A | C |
| ATOM | 478 | C | GLY | A | 100 | 21.768 | 68.620 | 16.173 | 1.00 | 23.33 A | C |
| ATOM | 479 | O | GLY | A | 100 | 21.884 | 69.144 | 17.274 | 1.00 | 19.10 A | O |
| ATOM | 480 | N | VAL | A | 101 | 22.095 | 69.249 | 15.049 | 1.00 | 21.53 A | N |
| ATOM | 481 | CA | VAL | A | 101 | 22.501 | 70.656 | 15.120 | 1.00 | 20.35 A | C |
| ATOM | 482 | CB | VAL | A | 101 | 23.186 | 71.150 | 13.802 | 1.00 | 19.16 A | C |
| ATOM | 483 | CG1 | VAL | A | 101 | 23.367 | 72.678 | 13.807 | 1.00 | 24.25 A | C |
| ATOM | 484 | CG2 | VAL | A | 101 | 24.518 | 70.500 | 13.650 | 1.00 | 19.32 A | C |
| ATOM | 485 | C | VAL | A | 101 | 21.282 | 71.498 | 15.492 | 1.00 | 22.25 A | C |
| ATOM | 486 | O | VAL | A | 101 | 20.188 | 71.295 | 14.962 | 1.00 | 20.99 A | O |
| ATOM | 487 | N | PRO | A | 102 | 21.448 | 72.424 | 16.444 | 1.00 | 19.27 A | N |
| ATOM | 488 | CD | PRO | A | 102 | 22.645 | 72.646 | 17.271 | 1.00 | 22.08 A | C |
| ATOM | 489 | CA | PRO | A | 102 | 20.342 | 73.315 | 16.812 | 1.00 | 21.40 A | C |
| ATOM | 490 | CB | PRO | A | 102 | 20.983 | 74.258 | 17.836 | 1.00 | 25.88 A | C |
| ATOM | 491 | CG | PRO | A | 102 | 22.114 | 73.459 | 18.421 | 1.00 | 28.33 A | C |
| ATOM | 492 | C | PRO | A | 102 | 19.800 | 74.124 | 15.637 | 1.00 | 19.41 A | C |
| ATOM | 493 | O | PRO | A | 102 | 20.509 | 74.405 | 14.675 | 1.00 | 23.26 A | O |
| ATOM | 494 | N | ASP | A | 103 | 18.541 | 74.518 | 15.741 | 1.00 | 20.14 A | N |
| ATOM | 495 | CA | ASP | A | 103 | 17.871 | 75.290 | 14.706 | 1.00 | 17.24 A | C |
| ATOM | 496 | CB | ASP | A | 103 | 16.384 | 74.973 | 14.717 | 1.00 | 16.86 A | C |
| ATOM | 497 | CG | ASP | A | 103 | 16.081 | 73.599 | 14.206 | 1.00 | 15.29 A | C |
| ATOM | 498 | OD1 | ASP | A | 103 | 16.976 | 72.968 | 13.597 | 1.00 | 19.58 A | O |
| ATOM | 499 | OD2 | ASP | A | 103 | 14.932 | 73.156 | 14.390 | 1.00 | 20.17 A | O |
| ATOM | 500 | C | ASP | A | 103 | 18.037 | 76.790 | 14.895 | 1.00 | 22.99 A | C |
| ATOM | 501 | O | ASP | A | 103 | 18.147 | 77.541 | 13.922 | 1.00 | 20.29 A | O |
| ATOM | 502 | N | LEU | A | 104 | 18.005 | 77.226 | 16.149 | 1.00 | 21.05 A | N |
| ATOM | 503 | CA | LEU | A | 104 | 18.171 | 78.636 | 16.491 | 1.00 | 25.44 A | C |
| ATOM | 504 | CB | LEU | A | 104 | 16.881 | 79.187 | 17.106 | 1.00 | 25.74 A | C |
| ATOM | 505 | CG | LEU | A | 104 | 15.710 | 79.464 | 16.156 | 1.00 | 22.13 A | C |
| ATOM | 506 | CD1 | LEU | A | 104 | 14.425 | 79.771 | 16.925 | 1.00 | 26.55 A | C |
| ATOM | 507 | CD2 | LEU | A | 104 | 16.046 | 80.642 | 15.253 | 1.00 | 21.34 A | C |
| ATOM | 508 | C | LEU | A | 104 | 19.316 | 78.710 | 17.487 | 1.00 | 29.77 A | C |
| ATOM | 509 | O | LEU | A | 104 | 19.272 | 78.068 | 18.525 | 1.00 | 32.01 A | O |
| ATOM | 510 | N | GLY | A | 105 | 20.351 | 79.482 | 17.181 | 1.00 | 36.14 A | N |
| ATOM | 511 | CA | GLY | A | 105 | 21.592 | 79.355 | 17.927 | 1.00 | 39.27 A | C |
| ATOM | 512 | C | GLY | A | 105 | 22.438 | 78.298 | 17.241 | 1.00 | 39.73 A | C |
| ATOM | 513 | O | GLY | A | 105 | 22.106 | 77.951 | 16.108 | 1.00 | 41.34 A | O |
| ATOM | 514 | N | ARG | A | 106 | 23.512 | 77.763 | 17.833 | 1.00 | 43.54 A | N |
| ATOM | 515 | CA | ARG | A | 106 | 24.089 | 78.038 | 19.155 | 1.00 | 44.07 A | C |
| ATOM | 516 | CB | ARG | A | 106 | 23.253 | 78.977 | 20.034 | 1.00 | 42.88 A | C |
| ATOM | 517 | CG | ARG | A | 106 | 23.802 | 80.424 | 20.166 | 1.00 | 41.91 A | C |
| ATOM | 518 | CD | ARG | A | 106 | 23.829 | 81.167 | 18.821 | 1.00 | 44.85 A | C |
| ATOM | 519 | NE | ARG | A | 106 | 23.718 | 82.622 | 18.950 | 1.00 | 42.04 A | N |
| ATOM | 520 | CZ | ARG | A | 106 | 23.550 | 83.452 | 17.923 | 1.00 | 36.44 A | C |
| ATOM | 521 | NH1 | ARG | A | 106 | 23.459 | 84.757 | 18.124 | 1.00 | 38.36 A | N |
| ATOM | 522 | NH2 | ARG | A | 106 | 23.469 | 82.979 | 16.692 | 1.00 | 41.73 A | N |
| ATOM | 523 | C | ARG | A | 106 | 24.391 | 76.713 | 19.875 | 1.00 | 39.64 A | C |
| ATOM | 524 | O | ARG | A | 106 | 23.813 | 76.423 | 20.925 | 1.00 | 35.55 A | O |
| ATOM | 525 | N | PHE | A | 107 | 25.274 | 75.901 | 19.286 | 1.00 | 35.00 A | N |
| ATOM | 526 | CA | PHE | A | 107 | 25.849 | 74.755 | 19.989 | 1.00 | 34.23 A | C |

TABLE 15-continued

Coordinates for apo form of proMMP9(35-444 ΔFnII) (SEQ ID NO: 12)

| ATOM | 527 | CB | PHE | A | 107 | 26.867 | 74.040 | 19.106 | 1.00 | 34.59 | A | C |
|---|---|---|---|---|---|---|---|---|---|---|---|---|
| ATOM | 528 | CG | PHE | A | 107 | 26.439 | 72.668 | 18.648 | 1.00 | 30.45 | A | C |
| ATOM | 529 | CD1 | PHE | A | 107 | 25.581 | 71.894 | 19.414 | 1.00 | 29.91 | A | C |
| ATOM | 530 | CD2 | PHE | A | 107 | 26.940 | 72.142 | 17.466 | 1.00 | 24.85 | A | C |
| ATOM | 531 | CE1 | PHE | A | 107 | 25.197 | 70.625 | 18.983 | 1.00 | 35.05 | A | C |
| ATOM | 532 | CE2 | PHE | A | 107 | 26.580 | 70.878 | 17.034 | 1.00 | 21.61 | A | C |
| ATOM | 533 | CZ | PHE | A | 107 | 25.711 | 70.116 | 17.783 | 1.00 | 28.46 | A | C |
| ATOM | 534 | C | PHE | A | 107 | 26.588 | 75.291 | 21.207 | 1.00 | 40.86 | A | C |
| ATOM | 535 | O | PHE | A | 107 | 26.453 | 74.793 | 22.338 | 1.00 | 41.15 | A | O |
| ATOM | 536 | N | GLN | A | 108 | 27.387 | 76.317 | 20.937 | 1.00 | 36.20 | A | N |
| ATOM | 537 | CA | GLN | A | 108 | 28.185 | 77.007 | 21.925 | 1.00 | 36.81 | A | C |
| ATOM | 538 | CB | GLN | A | 108 | 29.350 | 76.121 | 22.371 | 1.00 | 35.59 | A | C |
| ATOM | 539 | CG | GLN | A | 108 | 30.246 | 75.678 | 21.241 | 1.00 | 33.01 | A | C |
| ATOM | 540 | CD | GLN | A | 108 | 31.218 | 74.577 | 21.660 | 1.00 | 44.05 | A | C |
| ATOM | 541 | OE1 | GLN | A | 108 | 30.809 | 73.474 | 22.038 | 1.00 | 39.08 | A | O |
| ATOM | 542 | NE2 | GLN | A | 108 | 32.515 | 74.869 | 21.580 | 1.00 | 42.04 | A | N |
| ATOM | 543 | C | GLN | A | 108 | 28.677 | 78.229 | 21.172 | 1.00 | 36.68 | A | C |
| ATOM | 544 | O | GLN | A | 108 | 28.313 | 78.414 | 20.007 | 1.00 | 33.95 | A | O |
| ATOM | 545 | N | THR | A | 109 | 29.468 | 79.086 | 21.805 | 1.00 | 36.38 | A | N |
| ATOM | 546 | CA | THR | A | 109 | 30.136 | 80.112 | 21.024 | 1.00 | 30.02 | A | C |
| ATOM | 547 | CB | THR | A | 109 | 30.514 | 81.344 | 21.852 | 1.00 | 36.60 | A | C |
| ATOM | 548 | OG1 | THR | A | 109 | 31.385 | 80.958 | 22.920 | 1.00 | 38.46 | A | O |
| ATOM | 549 | CG2 | THR | A | 109 | 29.272 | 81.975 | 22.416 | 1.00 | 24.66 | A | C |
| ATOM | 550 | C | THR | A | 109 | 31.366 | 79.484 | 20.400 | 1.00 | 35.20 | A | C |
| ATOM | 551 | O | THR | A | 109 | 32.056 | 78.678 | 21.037 | 1.00 | 35.53 | A | O |
| ATOM | 552 | N | PHE | A | 110 | 31.613 | 79.827 | 19.141 | 1.00 | 30.25 | A | N |
| ATOM | 553 | CA | PHE | A | 110 | 32.679 | 79.210 | 18.369 | 1.00 | 30.77 | A | C |
| ATOM | 554 | CB | PHE | A | 110 | 32.108 | 78.592 | 17.091 | 1.00 | 25.57 | A | C |
| ATOM | 555 | CG | PHE | A | 110 | 31.391 | 77.289 | 17.313 | 1.00 | 29.18 | A | C |
| ATOM | 556 | CD1 | PHE | A | 110 | 30.023 | 77.188 | 17.120 | 1.00 | 25.98 | A | C |
| ATOM | 557 | CD2 | PHE | A | 110 | 32.090 | 76.164 | 17.710 | 1.00 | 24.26 | A | C |
| ATOM | 558 | CE1 | PHE | A | 110 | 29.374 | 75.988 | 17.301 | 1.00 | 26.02 | A | C |
| ATOM | 559 | CE2 | PHE | A | 110 | 31.443 | 74.961 | 17.901 | 1.00 | 26.73 | A | C |
| ATOM | 560 | CZ | PHE | A | 110 | 30.083 | 74.872 | 17.700 | 1.00 | 28.94 | A | C |
| ATOM | 561 | C | PHE | A | 110 | 33.748 | 80.231 | 18.010 | 1.00 | 30.51 | A | C |
| ATOM | 562 | O | PHE | A | 110 | 33.516 | 81.435 | 18.102 | 1.00 | 29.17 | A | O |
| ATOM | 563 | N | GLU | A | 111 | 34.913 | 79.744 | 17.595 | 1.00 | 29.42 | A | N |
| ATOM | 564 | CA | GLU | A | 111 | 35.996 | 80.609 | 17.170 | 1.00 | 28.87 | A | C |
| ATOM | 565 | CB | GLU | A | 111 | 37.347 | 79.931 | 17.387 | 1.00 | 29.93 | A | C |
| ATOM | 566 | CG | GLU | A | 111 | 37.750 | 79.731 | 18.835 | 1.00 | 39.56 | A | C |
| ATOM | 567 | CD | GLU | A | 111 | 39.236 | 79.414 | 18.972 | 1.00 | 43.87 | A | C |
| ATOM | 568 | OE1 | GLU | A | 111 | 40.009 | 79.790 | 18.064 | 1.00 | 53.02 | A | O |
| ATOM | 569 | OE2 | GLU | A | 111 | 39.635 | 78.802 | 19.983 | 1.00 | 45.00 | A | O |
| ATOM | 570 | C | GLU | A | 111 | 35.878 | 80.994 | 15.704 | 1.00 | 34.76 | A | C |
| ATOM | 571 | O | GLU | A | 111 | 35.593 | 80.152 | 14.845 | 1.00 | 32.30 | A | O |
| ATOM | 572 | N | GLY | A | 112 | 36.120 | 82.272 | 15.425 | 1.00 | 30.28 | A | N |
| ATOM | 573 | CA | GLY | A | 112 | 36.220 | 82.759 | 14.061 | 1.00 | 33.11 | A | C |
| ATOM | 574 | C | GLY | A | 112 | 34.901 | 83.226 | 13.485 | 1.00 | 28.91 | A | C |
| ATOM | 575 | O | GLY | A | 112 | 33.892 | 83.273 | 14.189 | 1.00 | 28.66 | A | O |
| ATOM | 576 | N | ASP | A | 113 | 34.917 | 83.569 | 12.202 | 1.00 | 27.21 | A | N |
| ATOM | 577 | CA | ASP | A | 113 | 33.716 | 83.982 | 11.476 | 1.00 | 28.09 | A | C |
| ATOM | 578 | CB | ASP | A | 113 | 34.094 | 85.017 | 10.418 | 1.00 | 29.22 | A | C |
| ATOM | 579 | CG | ASP | A | 113 | 34.862 | 84.410 | 9.253 | 1.00 | 27.67 | A | C |
| ATOM | 580 | OD1 | ASP | A | 113 | 35.125 | 83.193 | 9.263 | 1.00 | 32.88 | A | O |
| ATOM | 581 | OD2 | ASP | A | 113 | 35.201 | 85.157 | 8.322 | 1.00 | 29.35 | A | O |
| ATOM | 582 | C | ASP | A | 113 | 32.926 | 82.825 | 10.820 | 1.00 | 25.49 | A | C |
| ATOM | 583 | O | ASP | A | 113 | 31.950 | 83.061 | 10.111 | 1.00 | 25.86 | A | O |
| ATOM | 584 | N | LEU | A | 114 | 33.388 | 81.595 | 11.024 | 1.00 | 23.45 | A | N |
| ATOM | 585 | CA | LEU | A | 114 | 32.653 | 80.373 | 10.640 | 1.00 | 28.12 | A | C |
| ATOM | 586 | CB | LEU | A | 114 | 31.266 | 80.336 | 11.276 | 1.00 | 23.09 | A | C |
| ATOM | 587 | CG | LEU | A | 114 | 31.208 | 80.655 | 12.770 | 1.00 | 31.83 | A | C |
| ATOM | 588 | CD1 | LEU | A | 114 | 29.760 | 80.725 | 13.206 | 1.00 | 26.63 | A | C |
| ATOM | 589 | CD2 | LEU | A | 114 | 31.979 | 79.623 | 13.603 | 1.00 | 28.05 | A | C |
| ATOM | 590 | C | LEU | A | 114 | 32.526 | 80.089 | 9.148 | 1.00 | 28.25 | A | C |
| ATOM | 591 | O | LEU | A | 114 | 31.556 | 79.454 | 8.699 | 1.00 | 23.52 | A | O |
| ATOM | 592 | N | LYS | A | 115 | 33.504 | 80.545 | 8.379 | 1.00 | 26.54 | A | N |
| ATOM | 593 | CA | LYS | A | 115 | 33.674 | 80.049 | 7.024 | 1.00 | 27.29 | A | C |
| ATOM | 594 | CB | LYS | A | 115 | 33.165 | 81.056 | 5.986 | 1.00 | 30.13 | A | C |
| ATOM | 595 | CG | LYS | A | 115 | 34.153 | 82.148 | 5.595 | 1.00 | 28.06 | A | C |
| ATOM | 596 | CD | LYS | A | 115 | 33.579 | 82.997 | 4.462 | 1.00 | 33.60 | A | C |
| ATOM | 597 | CE | LYS | A | 115 | 34.669 | 83.734 | 3.712 | 1.00 | 31.03 | A | C |
| ATOM | 598 | NZ | LYS | A | 115 | 34.111 | 84.528 | 2.581 | 1.00 | 44.10 | A | N |
| ATOM | 599 | C | LYS | A | 115 | 35.146 | 79.749 | 6.851 | 1.00 | 23.25 | A | C |
| ATOM | 600 | O | LYS | A | 115 | 35.967 | 80.286 | 7.580 | 1.00 | 27.93 | A | O |
| ATOM | 601 | N | TRP | A | 116 | 35.476 | 78.871 | 5.913 | 1.00 | 21.61 | A | N |
| ATOM | 602 | CA | TRP | A | 116 | 36.874 | 78.514 | 5.643 | 1.00 | 28.50 | A | C |
| ATOM | 603 | CB | TRP | A | 116 | 36.952 | 77.241 | 4.794 | 1.00 | 23.28 | A | C |
| ATOM | 604 | CG | TRP | A | 116 | 36.449 | 76.035 | 5.495 | 1.00 | 24.16 | A | C |

TABLE 15-continued

Coordinates for apo form of proMMP9(35-444 ΔFnII) (SEQ ID NO: 12)

| ATOM | 605 | CD2 | TRP | A | 116 | 37.053 | 75.392 | 6.617 | 1.00 | 21.27 | A | C |
|---|---|---|---|---|---|---|---|---|---|---|---|---|
| ATOM | 606 | CE2 | TRP | A | 116 | 36.248 | 74.292 | 6.952 | 1.00 | 21.43 | A | C |
| ATOM | 607 | CE3 | TRP | A | 116 | 38.190 | 75.656 | 7.385 | 1.00 | 23.79 | A | C |
| ATOM | 608 | CD1 | TRP | A | 116 | 35.332 | 75.315 | 5.196 | 1.00 | 19.51 | A | C |
| ATOM | 609 | NE1 | TRP | A | 116 | 35.201 | 74.266 | 6.069 | 1.00 | 18.49 | A | N |
| ATOM | 610 | CZ2 | TRP | A | 116 | 36.544 | 73.445 | 8.019 | 1.00 | 23.72 | A | C |
| ATOM | 611 | CZ3 | TRP | A | 116 | 38.490 | 74.802 | 8.444 | 1.00 | 27.02 | A | C |
| ATOM | 612 | CH2 | TRP | A | 116 | 37.665 | 73.716 | 8.749 | 1.00 | 23.04 | A | C |
| ATOM | 613 | C | TRP | A | 116 | 37.596 | 79.626 | 4.901 | 1.00 | 30.80 | A | C |
| ATOM | 614 | O | TRP | A | 116 | 37.009 | 80.275 | 4.029 | 1.00 | 28.73 | A | O |
| ATOM | 615 | N | HIS | A | 117 | 38.876 | 79.818 | 5.215 | 1.00 | 28.53 | A | N |
| ATOM | 616 | CA | HIS | A | 117 | 39.682 | 80.804 | 4.500 | 1.00 | 32.77 | A | C |
| ATOM | 617 | CB | HIS | A | 117 | 40.125 | 81.925 | 5.449 | 1.00 | 29.30 | A | C |
| ATOM | 618 | CG | HIS | A | 117 | 38.989 | 82.738 | 5.976 | 1.00 | 30.21 | A | C |
| ATOM | 619 | CD2 | HIS | A | 117 | 38.261 | 83.725 | 5.405 | 1.00 | 30.22 | A | C |
| ATOM | 620 | ND1 | HIS | A | 117 | 38.460 | 82.550 | 7.235 | 1.00 | 36.49 | A | N |
| ATOM | 621 | CE1 | HIS | A | 117 | 37.462 | 83.394 | 7.422 | 1.00 | 31.51 | A | C |
| ATOM | 622 | NE2 | HIS | A | 117 | 37.320 | 84.118 | 6.326 | 1.00 | 32.15 | A | N |
| ATOM | 623 | C | HIS | A | 117 | 40.860 | 80.191 | 3.718 | 1.00 | 30.79 | A | C |
| ATOM | 624 | O | HIS | A | 117 | 41.897 | 80.833 | 3.505 | 1.00 | 27.54 | A | O |
| ATOM | 625 | N | HIS | A | 118 | 40.679 | 78.940 | 3.309 | 1.00 | 21.23 | A | N |
| ATOM | 626 | CA | HIS | A | 118 | 41.492 | 78.315 | 2.281 | 1.00 | 25.23 | A | C |
| ATOM | 627 | CB | HIS | A | 118 | 42.600 | 77.427 | 2.851 | 1.00 | 23.56 | A | C |
| ATOM | 628 | CG | HIS | A | 118 | 42.113 | 76.357 | 3.778 | 1.00 | 20.78 | A | C |
| ATOM | 629 | CD2 | HIS | A | 118 | 42.084 | 75.009 | 3.652 | 1.00 | 22.92 | A | C |
| ATOM | 630 | ND1 | HIS | A | 118 | 41.622 | 76.635 | 5.036 | 1.00 | 25.15 | A | N |
| ATOM | 631 | CE1 | HIS | A | 118 | 41.284 | 75.504 | 5.633 | 1.00 | 26.08 | A | C |
| ATOM | 632 | NE2 | HIS | A | 118 | 41.559 | 74.502 | 4.818 | 1.00 | 20.92 | A | N |
| ATOM | 633 | C | HIS | A | 118 | 40.559 | 77.509 | 1.396 | 1.00 | 24.66 | A | C |
| ATOM | 634 | O | HIS | A | 118 | 39.361 | 77.428 | 1.661 | 1.00 | 28.91 | A | O |
| ATOM | 635 | N | HIS | A | 119 | 41.134 | 76.885 | 0.378 | 1.00 | 27.88 | A | N |
| ATOM | 636 | CA | HIS | A | 119 | 40.392 | 76.358 | −0.750 | 1.00 | 27.48 | A | C |
| ATOM | 637 | CB | HIS | A | 119 | 41.043 | 76.887 | −2.038 | 1.00 | 30.54 | A | C |
| ATOM | 638 | CG | HIS | A | 119 | 40.661 | 76.152 | −3.285 | 1.00 | 36.56 | A | C |
| ATOM | 639 | CD2 | HIS | A | 119 | 41.226 | 75.086 | −3.905 | 1.00 | 38.04 | A | C |
| ATOM | 640 | ND1 | HIS | A | 119 | 39.610 | 76.544 | −4.090 | 1.00 | 41.04 | A | N |
| ATOM | 641 | CE1 | HIS | A | 119 | 39.522 | 75.731 | −5.128 | 1.00 | 34.65 | A | C |
| ATOM | 642 | NE2 | HIS | A | 119 | 40.492 | 74.837 | −5.041 | 1.00 | 34.66 | A | N |
| ATOM | 643 | C | HIS | A | 119 | 40.361 | 74.848 | −0.730 | 1.00 | 27.23 | A | C |
| ATOM | 644 | O | HIS | A | 119 | 39.333 | 74.240 | −1.031 | 1.00 | 31.66 | A | O |
| ATOM | 645 | N | ASN | A | 120 | 41.487 | 74.232 | −0.399 | 1.00 | 21.91 | A | N |
| ATOM | 646 | CA | ASN | A | 120 | 41.519 | 72.792 | −0.342 | 1.00 | 25.25 | A | C |
| ATOM | 647 | CB | ASN | A | 120 | 42.858 | 72.233 | −0.814 | 1.00 | 28.33 | A | C |
| ATOM | 648 | CG | ASN | A | 120 | 42.839 | 70.722 | −0.921 | 1.00 | 34.17 | A | C |
| ATOM | 649 | OD1 | ASN | A | 120 | 41.774 | 70.095 | −0.887 | 1.00 | 31.52 | A | O |
| ATOM | 650 | ND2 | ASN | A | 120 | 44.021 | 70.121 | −1.026 | 1.00 | 33.79 | A | N |
| ATOM | 651 | C | ASN | A | 120 | 41.203 | 72.312 | 1.066 | 1.00 | 25.06 | A | C |
| ATOM | 652 | O | ASN | A | 120 | 42.040 | 72.378 | 1.965 | 1.00 | 29.38 | A | O |
| ATOM | 653 | N | ILE | A | 121 | 39.980 | 71.837 | 1.245 | 1.00 | 26.62 | A | N |
| ATOM | 654 | CA | ILE | A | 121 | 39.536 | 71.330 | 2.530 | 1.00 | 22.88 | A | C |
| ATOM | 655 | CB | ILE | A | 121 | 38.016 | 71.479 | 2.675 | 1.00 | 23.40 | A | C |
| ATOM | 656 | CG2 | ILE | A | 121 | 37.577 | 71.230 | 4.120 | 1.00 | 19.11 | A | C |
| ATOM | 657 | CG1 | ILE | A | 121 | 37.597 | 72.885 | 2.228 | 1.00 | 25.97 | A | C |
| ATOM | 658 | CD1 | ILE | A | 121 | 38.220 | 73.994 | 3.050 | 1.00 | 24.47 | A | C |
| ATOM | 659 | C | ILE | A | 121 | 39.939 | 69.878 | 2.606 | 1.00 | 22.59 | A | C |
| ATOM | 660 | O | ILE | A | 121 | 39.642 | 69.089 | 1.707 | 1.00 | 24.78 | A | O |
| ATOM | 661 | N | THR | A | 122 | 40.643 | 69.514 | 3.667 | 1.00 | 23.63 | A | N |
| ATOM | 662 | CA | THR | A | 122 | 41.092 | 68.142 | 3.800 | 1.00 | 21.19 | A | C |
| ATOM | 663 | CB | THR | A | 122 | 42.549 | 68.078 | 4.267 | 1.00 | 17.91 | A | C |
| ATOM | 664 | OG1 | THR | A | 122 | 42.669 | 68.769 | 5.514 | 1.00 | 25.42 | A | O |
| ATOM | 665 | CG2 | THR | A | 122 | 43.440 | 68.775 | 3.248 | 1.00 | 23.17 | A | C |
| ATOM | 666 | C | THR | A | 122 | 40.177 | 67.478 | 4.804 | 1.00 | 22.00 | A | C |
| ATOM | 667 | O | THR | A | 122 | 39.612 | 68.141 | 5.664 | 1.00 | 23.82 | A | O |
| ATOM | 668 | N | TYR | A | 123 | 39.980 | 66.176 | 4.671 | 1.00 | 24.37 | A | N |
| ATOM | 669 | CA | TYR | A | 123 | 39.085 | 65.491 | 5.584 | 1.00 | 22.56 | A | C |
| ATOM | 670 | CB | TYR | A | 123 | 37.672 | 65.358 | 5.006 | 1.00 | 19.38 | A | C |
| ATOM | 671 | CG | TYR | A | 123 | 37.555 | 64.439 | 3.813 | 1.00 | 18.63 | A | C |
| ATOM | 672 | CD1 | TYR | A | 123 | 37.655 | 64.937 | 2.528 | 1.00 | 20.49 | A | C |
| ATOM | 673 | CE1 | TYR | A | 123 | 37.541 | 64.117 | 1.424 | 1.00 | 22.04 | A | C |
| ATOM | 674 | CD2 | TYR | A | 123 | 37.292 | 63.079 | 3.971 | 1.00 | 22.95 | A | C |
| ATOM | 675 | CE2 | TYR | A | 123 | 37.161 | 62.241 | 2.869 | 1.00 | 22.24 | A | C |
| ATOM | 676 | CZ | TYR | A | 123 | 37.292 | 62.767 | 1.597 | 1.00 | 22.45 | A | C |
| ATOM | 677 | OH | TYR | A | 123 | 37.150 | 61.963 | 0.486 | 1.00 | 25.84 | A | O |
| ATOM | 678 | C | TYR | A | 123 | 39.642 | 64.128 | 5.925 | 1.00 | 21.92 | A | C |
| ATOM | 679 | O | TYR | A | 123 | 40.284 | 63.497 | 5.107 | 1.00 | 21.37 | A | O |
| ATOM | 680 | N | TRP | A | 124 | 39.387 | 63.693 | 7.150 | 1.00 | 21.82 | A | N |
| ATOM | 681 | CA | TRP | A | 124 | 39.923 | 62.437 | 7.632 | 1.00 | 23.65 | A | C |
| ATOM | 682 | CB | TRP | A | 124 | 40.901 | 62.706 | 8.764 | 1.00 | 24.93 | A | C |

TABLE 15-continued

Coordinates for apo form of proMMP9(35-444 ΔFnII) (SEQ ID NO: 12)

| ATOM | 683 | CG | TRP | A | 124 | 41.506 | 61.467 | 9.350 | 1.00 | 26.30 | A | C |
|---|---|---|---|---|---|---|---|---|---|---|---|---|
| ATOM | 684 | CD2 | TRP | A | 124 | 41.930 | 61.284 | 10.704 | 1.00 | 29.98 | A | C |
| ATOM | 685 | CE2 | TRP | A | 124 | 42.453 | 59.982 | 10.806 | 1.00 | 30.27 | A | C |
| ATOM | 686 | CE3 | TRP | A | 124 | 41.916 | 62.094 | 11.841 | 1.00 | 32.92 | A | C |
| ATOM | 687 | CD1 | TRP | A | 124 | 41.789 | 60.315 | 8.703 | 1.00 | 28.63 | A | C |
| ATOM | 688 | NE1 | TRP | A | 124 | 42.348 | 59.405 | 9.571 | 1.00 | 27.65 | A | N |
| ATOM | 689 | CZ2 | TRP | A | 124 | 42.962 | 59.472 | 11.998 | 1.00 | 28.60 | A | C |
| ATOM | 690 | CZ3 | TRP | A | 124 | 42.419 | 61.588 | 13.019 | 1.00 | 34.96 | A | C |
| ATOM | 691 | CH2 | TRP | A | 124 | 42.928 | 60.285 | 13.091 | 1.00 | 30.56 | A | C |
| ATOM | 692 | C | TRP | A | 124 | 38.802 | 61.545 | 8.116 | 1.00 | 19.47 | A | C |
| ATOM | 693 | O | TRP | A | 124 | 38.008 | 61.944 | 8.967 | 1.00 | 25.79 | A | O |
| ATOM | 694 | N | ILE | A | 125 | 38.721 | 60.337 | 7.573 | 1.00 | 23.99 | A | N |
| ATOM | 695 | CA | ILE | A | 125 | 37.727 | 59.384 | 8.049 | 1.00 | 20.20 | A | C |
| ATOM | 696 | CB | ILE | A | 125 | 37.313 | 58.407 | 6.942 | 1.00 | 26.29 | A | C |
| ATOM | 697 | CG2 | ILE | A | 125 | 36.308 | 57.415 | 7.464 | 1.00 | 20.06 | A | C |
| ATOM | 698 | CG1 | ILE | A | 125 | 36.704 | 59.168 | 5.766 | 1.00 | 23.59 | A | C |
| ATOM | 699 | CD1 | ILE | A | 125 | 36.810 | 58.436 | 4.463 | 1.00 | 24.73 | A | C |
| ATOM | 700 | C | ILE | A | 125 | 38.314 | 58.627 | 9.249 | 1.00 | 24.20 | A | C |
| ATOM | 701 | O | ILE | A | 125 | 38.996 | 57.618 | 9.078 | 1.00 | 26.23 | A | O |
| ATOM | 702 | N | GLN | A | 126 | 38.046 | 59.127 | 10.455 | 1.00 | 27.66 | A | N |
| ATOM | 703 | CA | GLN | A | 126 | 38.759 | 58.688 | 11.657 | 1.00 | 28.10 | A | C |
| ATOM | 704 | CB | GLN | A | 126 | 38.502 | 59.638 | 12.831 | 1.00 | 29.85 | A | C |
| ATOM | 705 | CG | GLN | A | 126 | 39.200 | 59.189 | 14.113 | 1.00 | 32.51 | A | C |
| ATOM | 706 | CD | GLN | A | 126 | 39.023 | 60.147 | 15.283 | 1.00 | 37.58 | A | C |
| ATOM | 707 | OE1 | GLN | A | 126 | 38.010 | 60.847 | 15.406 | 1.00 | 36.41 | A | O |
| ATOM | 708 | NE2 | GLN | A | 126 | 40.009 | 60.160 | 16.170 | 1.00 | 39.88 | A | N |
| ATOM | 709 | C | GLN | A | 126 | 38.436 | 57.258 | 12.077 | 1.00 | 27.75 | A | C |
| ATOM | 710 | O | GLN | A | 126 | 39.290 | 56.554 | 12.610 | 1.00 | 31.90 | A | O |
| ATOM | 711 | N | ASN | A | 127 | 37.193 | 56.849 | 11.858 | 1.00 | 23.85 | A | N |
| ATOM | 712 | CA | ASN | A | 127 | 36.773 | 55.484 | 12.117 | 1.00 | 22.94 | A | C |
| ATOM | 713 | CB | ASN | A | 127 | 36.465 | 55.248 | 13.613 | 1.00 | 23.45 | A | C |
| ATOM | 714 | CG | ASN | A | 127 | 35.238 | 56.007 | 14.112 | 1.00 | 24.46 | A | C |
| ATOM | 715 | OD1 | ASN | A | 127 | 34.630 | 56.789 | 13.387 | 1.00 | 21.59 | A | O |
| ATOM | 716 | ND2 | ASN | A | 127 | 34.880 | 55.783 | 15.379 | 1.00 | 21.93 | A | N |
| ATOM | 717 | C | ASN | A | 127 | 35.617 | 55.130 | 11.195 | 1.00 | 22.01 | A | C |
| ATOM | 718 | O | ASN | A | 127 | 35.219 | 55.947 | 10.367 | 1.00 | 22.97 | A | O |
| ATOM | 719 | N | TYR | A | 128 | 35.105 | 53.914 | 11.313 | 1.00 | 22.09 | A | N |
| ATOM | 720 | CA | TYR | A | 128 | 34.068 | 53.418 | 10.425 | 1.00 | 22.49 | A | C |
| ATOM | 721 | CB | TYR | A | 128 | 34.654 | 52.387 | 9.469 | 1.00 | 24.51 | A | C |
| ATOM | 722 | CG | TYR | A | 128 | 35.541 | 52.949 | 8.380 | 1.00 | 27.71 | A | C |
| ATOM | 723 | CD1 | TYR | A | 128 | 35.026 | 53.224 | 7.127 | 1.00 | 25.18 | A | C |
| ATOM | 724 | CE1 | TYR | A | 128 | 35.824 | 53.722 | 6.111 | 1.00 | 29.94 | A | C |
| ATOM | 725 | CD2 | TYR | A | 128 | 36.897 | 53.179 | 8.600 | 1.00 | 26.61 | A | C |
| ATOM | 726 | CE2 | TYR | A | 128 | 37.712 | 53.691 | 7.588 | 1.00 | 26.46 | A | C |
| ATOM | 727 | CZ | TYR | A | 128 | 37.162 | 53.956 | 6.346 | 1.00 | 31.21 | A | C |
| ATOM | 728 | OH | TYR | A | 128 | 37.938 | 54.453 | 5.332 | 1.00 | 22.97 | A | O |
| ATOM | 729 | C | TYR | A | 128 | 32.951 | 52.733 | 11.201 | 1.00 | 28.11 | A | C |
| ATOM | 730 | O | TYR | A | 128 | 33.210 | 52.104 | 12.233 | 1.00 | 26.32 | A | O |
| ATOM | 731 | N | SER | A | 129 | 31.720 | 52.842 | 10.696 | 1.00 | 22.44 | A | N |
| ATOM | 732 | CA | SER | A | 129 | 30.648 | 51.940 | 11.108 | 1.00 | 21.32 | A | C |
| ATOM | 733 | CB | SER | A | 129 | 29.288 | 52.521 | 10.706 | 1.00 | 22.95 | A | C |
| ATOM | 734 | OG | SER | A | 129 | 28.258 | 51.540 | 10.740 | 1.00 | 24.54 | A | O |
| ATOM | 735 | C | SER | A | 129 | 30.839 | 50.588 | 10.421 | 1.00 | 26.13 | A | C |
| ATOM | 736 | O | SER | A | 129 | 31.322 | 50.540 | 9.292 | 1.00 | 25.04 | A | O |
| ATOM | 737 | N | GLU | A | 130 | 30.443 | 49.501 | 11.090 | 1.00 | 23.70 | A | N |
| ATOM | 738 | CA | GLU | A | 130 | 30.492 | 48.165 | 10.503 | 1.00 | 26.52 | A | C |
| ATOM | 739 | CB | GLU | A | 130 | 30.730 | 47.102 | 11.586 | 1.00 | 31.69 | A | C |
| ATOM | 740 | CG | GLU | A | 130 | 31.987 | 47.301 | 12.406 | 1.00 | 28.11 | A | C |
| ATOM | 741 | CD | GLU | A | 130 | 33.237 | 47.299 | 11.561 | 1.00 | 37.73 | A | C |
| ATOM | 742 | OE1 | GLU | A | 130 | 33.404 | 46.368 | 10.738 | 1.00 | 35.94 | A | O |
| ATOM | 743 | OE2 | GLU | A | 130 | 34.061 | 48.222 | 11.736 | 1.00 | 38.46 | A | O |
| ATOM | 744 | C | GLU | A | 130 | 29.202 | 47.834 | 9.769 | 1.00 | 29.13 | A | C |
| ATOM | 745 | O | GLU | A | 130 | 28.977 | 46.692 | 9.370 | 1.00 | 26.77 | A | O |
| ATOM | 746 | N | ASP | A | 131 | 28.334 | 48.826 | 9.601 | 1.00 | 27.87 | A | N |
| ATOM | 747 | CA | ASP | A | 131 | 27.070 | 48.579 | 8.918 | 1.00 | 24.17 | A | C |
| ATOM | 748 | CB | ASP | A | 131 | 26.066 | 49.710 | 9.188 | 1.00 | 23.88 | A | C |
| ATOM | 749 | CG | ASP | A | 131 | 25.510 | 49.667 | 10.594 | 1.00 | 26.68 | A | C |
| ATOM | 750 | OD1 | ASP | A | 131 | 25.543 | 48.580 | 11.211 | 1.00 | 26.57 | A | O |
| ATOM | 751 | OD2 | ASP | A | 131 | 25.014 | 50.707 | 11.084 | 1.00 | 26.71 | A | O |
| ATOM | 752 | C | ASP | A | 131 | 27.253 | 48.360 | 7.406 | 1.00 | 25.89 | A | C |
| ATOM | 753 | O | ASP | A | 131 | 26.508 | 47.599 | 6.799 | 1.00 | 24.26 | A | O |
| ATOM | 754 | N | LEU | A | 132 | 28.256 | 49.017 | 6.823 | 1.00 | 24.14 | A | N |
| ATOM | 755 | CA | LEU | A | 132 | 28.532 | 48.965 | 5.395 | 1.00 | 24.32 | A | C |
| ATOM | 756 | CB | LEU | A | 132 | 28.200 | 50.314 | 4.757 | 1.00 | 24.53 | A | C |
| ATOM | 757 | CG | LEU | A | 132 | 26.768 | 50.837 | 4.865 | 1.00 | 29.64 | A | C |
| ATOM | 758 | CD1 | LEU | A | 132 | 26.745 | 52.368 | 4.845 | 1.00 | 21.15 | A | C |
| ATOM | 759 | CD2 | LEU | A | 132 | 25.924 | 50.256 | 3.723 | 1.00 | 26.72 | A | C |
| ATOM | 760 | C | LEU | A | 132 | 30.027 | 48.696 | 5.195 | 1.00 | 25.31 | A | C |

TABLE 15-continued

Coordinates for apo form of proMMP9(35-444 ΔFnII) (SEQ ID NO: 12)

| ATOM | 761 | O | LEU | A | 132 | 30.831 | 48.980 | 6.078 | 1.00 | 24.25 | A | O |
|---|---|---|---|---|---|---|---|---|---|---|---|---|
| ATOM | 762 | N | PRO | A | 133 | 30.408 | 48.168 | 4.023 | 1.00 | 26.12 | A | N |
| ATOM | 763 | CD | PRO | A | 133 | 29.553 | 47.651 | 2.948 | 1.00 | 24.69 | A | C |
| ATOM | 764 | CA | PRO | A | 133 | 31.829 | 47.979 | 3.719 | 1.00 | 26.34 | A | C |
| ATOM | 765 | CB | PRO | A | 133 | 31.808 | 47.364 | 2.320 | 1.00 | 23.15 | A | C |
| ATOM | 766 | CG | PRO | A | 133 | 30.473 | 46.729 | 2.227 | 1.00 | 17.02 | A | C |
| ATOM | 767 | C | PRO | A | 133 | 32.540 | 49.312 | 3.702 | 1.00 | 26.05 | A | C |
| ATOM | 768 | O | PRO | A | 133 | 31.908 | 50.337 | 3.447 | 1.00 | 22.01 | A | O |
| ATOM | 769 | N | ARG | A | 134 | 33.837 | 49.300 | 3.986 | 1.00 | 21.09 | A | N |
| ATOM | 770 | CA | ARG | A | 134 | 34.578 | 50.536 | 4.127 | 1.00 | 25.51 | A | C |
| ATOM | 771 | CB | ARG | A | 134 | 35.943 | 50.260 | 4.724 | 1.00 | 28.49 | A | C |
| ATOM | 772 | CG | ARG | A | 134 | 35.878 | 49.879 | 6.187 | 1.00 | 33.05 | A | C |
| ATOM | 773 | CD | ARG | A | 134 | 37.274 | 49.784 | 6.784 | 1.00 | 36.72 | A | C |
| ATOM | 774 | NE | ARG | A | 134 | 37.235 | 49.774 | 8.240 | 1.00 | 37.75 | A | N |
| ATOM | 775 | CZ | ARG | A | 134 | 38.288 | 50.026 | 9.007 | 1.00 | 38.85 | A | C |
| ATOM | 776 | NH1 | ARG | A | 134 | 39.460 | 50.312 | 8.444 | 1.00 | 40.15 | A | N |
| ATOM | 777 | NH2 | ARG | A | 134 | 38.171 | 50.005 | 10.329 | 1.00 | 34.77 | A | N |
| ATOM | 778 | C | ARG | A | 134 | 34.719 | 51.294 | 2.806 | 1.00 | 25.23 | A | C |
| ATOM | 779 | O | ARG | A | 134 | 34.850 | 52.519 | 2.795 | 1.00 | 24.77 | A | O |
| ATOM | 780 | N | ALA | A | 135 | 34.698 | 50.569 | 1.696 | 1.00 | 21.16 | A | N |
| ATOM | 781 | CA | ALA | A | 135 | 34.763 | 51.209 | 0.387 | 1.00 | 22.34 | A | C |
| ATOM | 782 | CB | ALA | A | 135 | 34.998 | 50.183 | −0.688 | 1.00 | 28.75 | A | C |
| ATOM | 783 | C | ALA | A | 135 | 33.483 | 52.002 | 0.109 | 1.00 | 20.44 | A | C |
| ATOM | 784 | O | ALA | A | 135 | 33.517 | 53.068 | −0.490 | 1.00 | 25.81 | A | O |
| ATOM | 785 | N | VAL | A | 136 | 32.365 | 51.481 | 0.588 | 1.00 | 25.86 | A | N |
| ATOM | 786 | CA | VAL | A | 136 | 31.062 | 52.060 | 0.329 | 1.00 | 26.18 | A | C |
| ATOM | 787 | CB | VAL | A | 136 | 29.950 | 51.033 | 0.614 | 1.00 | 24.57 | A | C |
| ATOM | 788 | CG1 | VAL | A | 136 | 28.587 | 51.703 | 0.699 | 1.00 | 26.39 | A | C |
| ATOM | 789 | CG2 | VAL | A | 136 | 29.956 | 49.965 | −0.460 | 1.00 | 22.04 | A | C |
| ATOM | 790 | C | VAL | A | 136 | 30.867 | 53.308 | 1.165 | 1.00 | 22.89 | A | C |
| ATOM | 791 | O | VAL | A | 136 | 30.134 | 54.212 | 0.771 | 1.00 | 22.68 | A | O |
| ATOM | 792 | N | ILE | A | 137 | 31.552 | 53.339 | 2.304 | 1.00 | 22.18 | A | N |
| ATOM | 793 | CA | ILE | A | 137 | 31.563 | 54.472 | 3.224 | 1.00 | 21.81 | A | C |
| ATOM | 794 | CB | ILE | A | 137 | 31.997 | 54.012 | 4.635 | 1.00 | 23.27 | A | C |
| ATOM | 795 | CG2 | ILE | A | 137 | 32.328 | 55.220 | 5.535 | 1.00 | 21.30 | A | C |
| ATOM | 796 | CG1 | ILE | A | 137 | 30.935 | 53.104 | 5.254 | 1.00 | 21.83 | A | C |
| ATOM | 797 | CD1 | ILE | A | 137 | 31.244 | 52.666 | 6.674 | 1.00 | 27.08 | A | C |
| ATOM | 798 | C | ILE | A | 137 | 32.516 | 55.558 | 2.716 | 1.00 | 22.09 | A | C |
| ATOM | 799 | O | ILE | A | 137 | 32.184 | 56.764 | 2.731 | 1.00 | 19.52 | A | O |
| ATOM | 800 | N | ASP | A | 138 | 33.685 | 55.132 | 2.241 | 1.00 | 15.51 | A | N |
| ATOM | 801 | CA | ASP | A | 138 | 34.601 | 56.057 | 1.577 | 1.00 | 21.68 | A | C |
| ATOM | 802 | CB | ASP | A | 138 | 35.863 | 55.343 | 1.091 | 1.00 | 20.32 | A | C |
| ATOM | 803 | CG | ASP | A | 138 | 36.688 | 54.746 | 2.231 | 1.00 | 27.56 | A | C |
| ATOM | 804 | OD1 | ASP | A | 138 | 36.316 | 54.934 | 3.402 | 1.00 | 28.65 | A | O |
| ATOM | 805 | OD2 | ASP | A | 138 | 37.711 | 54.080 | 1.950 | 1.00 | 26.14 | A | O |
| ATOM | 806 | C | ASP | A | 138 | 33.898 | 56.727 | 0.400 | 1.00 | 19.81 | A | C |
| ATOM | 807 | O | ASP | A | 138 | 33.959 | 57.949 | 0.236 | 1.00 | 21.48 | A | O |
| ATOM | 808 | N | ASP | A | 139 | 33.211 | 55.934 | −0.409 | 1.00 | 18.72 | A | N |
| ATOM | 809 | CA | ASP | A | 139 | 32.572 | 56.469 | −1.603 | 1.00 | 23.38 | A | C |
| ATOM | 810 | CB | ASP | A | 139 | 32.219 | 55.348 | −2.578 | 1.00 | 23.62 | A | C |
| ATOM | 811 | CG | ASP | A | 139 | 31.236 | 55.791 | −3.651 | 1.00 | 23.82 | A | C |
| ATOM | 812 | OD1 | ASP | A | 139 | 31.668 | 56.378 | −4.666 | 1.00 | 25.26 | A | O |
| ATOM | 813 | OD2 | ASP | A | 139 | 30.025 | 55.530 | −3.484 | 1.00 | 32.34 | A | O |
| ATOM | 814 | C | ASP | A | 139 | 31.335 | 57.310 | −1.280 | 1.00 | 19.58 | A | C |
| ATOM | 815 | O | ASP | A | 139 | 31.004 | 58.260 | −2.011 | 1.00 | 19.11 | A | O |
| ATOM | 816 | N | ALA | A | 140 | 30.648 | 56.963 | −0.198 | 1.00 | 21.49 | A | N |
| ATOM | 817 | CA | ALA | A | 140 | 29.490 | 57.745 | 0.237 | 1.00 | 17.36 | A | C |
| ATOM | 818 | CB | ALA | A | 140 | 28.784 | 57.056 | 1.416 | 1.00 | 22.48 | A | C |
| ATOM | 819 | C | ALA | A | 140 | 29.920 | 59.165 | 0.616 | 1.00 | 19.30 | A | C |
| ATOM | 820 | O | ALA | A | 140 | 29.294 | 60.155 | 0.224 | 1.00 | 19.66 | A | O |
| ATOM | 821 | N | PHE | A | 141 | 30.995 | 59.262 | 1.381 | 1.00 | 19.18 | A | N |
| ATOM | 822 | CA | PHE | A | 141 | 31.532 | 60.558 | 1.795 | 1.00 | 21.07 | A | C |
| ATOM | 823 | CB | PHE | A | 141 | 32.600 | 60.367 | 2.884 | 1.00 | 19.86 | A | C |
| ATOM | 824 | CG | PHE | A | 141 | 32.040 | 59.924 | 4.219 | 1.00 | 17.04 | A | C |
| ATOM | 825 | CD1 | PHE | A | 141 | 30.872 | 60.474 | 4.714 | 1.00 | 20.55 | A | C |
| ATOM | 826 | CD2 | PHE | A | 141 | 32.702 | 58.985 | 4.985 | 1.00 | 24.18 | A | C |
| ATOM | 827 | CE1 | PHE | A | 141 | 30.359 | 60.079 | 5.952 | 1.00 | 19.03 | A | C |
| ATOM | 828 | CE2 | PHE | A | 141 | 32.194 | 58.586 | 6.219 | 1.00 | 21.80 | A | C |
| ATOM | 829 | CZ | PHE | A | 141 | 31.020 | 59.138 | 6.691 | 1.00 | 13.78 | A | C |
| ATOM | 830 | C | PHE | A | 141 | 32.112 | 61.351 | 0.615 | 1.00 | 19.94 | A | C |
| ATOM | 831 | O | PHE | A | 141 | 31.947 | 62.570 | 0.527 | 1.00 | 20.51 | A | O |
| ATOM | 832 | N | ALA | A | 142 | 32.802 | 60.653 | −0.277 | 1.00 | 22.37 | A | N |
| ATOM | 833 | CA | ALA | A | 142 | 33.400 | 61.287 | −1.436 | 1.00 | 24.59 | A | C |
| ATOM | 834 | CB | ALA | A | 142 | 34.276 | 60.303 | −2.202 | 1.00 | 21.91 | A | C |
| ATOM | 835 | C | ALA | A | 142 | 32.301 | 61.874 | −2.322 | 1.00 | 21.92 | A | C |
| ATOM | 836 | O | ALA | A | 142 | 32.423 | 62.998 | −2.783 | 1.00 | 21.29 | A | O |
| ATOM | 837 | N | ARG | A | 143 | 31.207 | 61.135 | −2.510 | 1.00 | 22.50 | A | N |
| ATOM | 838 | CA | ARG | A | 143 | 30.099 | 61.604 | −3.362 | 1.00 | 20.60 | A | C |

TABLE 15-continued

| | | | | | | | | | | | |
|---|---|---|---|---|---|---|---|---|---|---|---|
| Coordinates for apo form of proMMP9(35-444 ΔFnII) (SEQ ID NO: 12) | | | | | | | | | | | |
| ATOM | 839 | CB | ARG | A | 143 | 29.129 | 60.449 | −3.665 | 1.00 | 18.06 A | C |
| ATOM | 840 | CG | ARG | A | 143 | 29.738 | 59.327 | −4.535 | 1.00 | 19.78 A | C |
| ATOM | 841 | CD | ARG | A | 143 | 28.945 | 58.014 | −4.469 | 1.00 | 26.88 A | C |
| ATOM | 842 | NE | ARG | A | 143 | 27.532 | 58.329 | −4.385 | 1.00 | 29.07 A | N |
| ATOM | 843 | CZ | ARG | A | 143 | 26.652 | 57.801 | −3.536 | 1.00 | 22.70 A | C |
| ATOM | 844 | NH1 | ARG | A | 143 | 26.973 | 56.855 | −2.654 | 1.00 | 24.34 A | N |
| ATOM | 845 | NH2 | ARG | A | 143 | 25.409 | 58.239 | −3.593 | 1.00 | 20.42 A | N |
| ATOM | 846 | C | ARG | A | 143 | 29.388 | 62.787 | −2.681 | 1.00 | 22.44 A | C |
| ATOM | 847 | O | ARG | A | 143 | 28.975 | 63.757 | −3.337 | 1.00 | 19.75 A | O |
| ATOM | 848 | N | ALA | A | 144 | 29.287 | 62.723 | −1.356 | 1.00 | 20.57 A | N |
| ATOM | 849 | CA | ALA | A | 144 | 28.703 | 63.805 | −0.580 | 1.00 | 18.59 A | C |
| ATOM | 850 | CB | ALA | A | 144 | 28.615 | 63.420 | 0.941 | 1.00 | 17.49 A | C |
| ATOM | 851 | C | ALA | A | 144 | 29.482 | 65.102 | −0.760 | 1.00 | 19.82 A | C |
| ATOM | 852 | O | ALA | A | 144 | 28.890 | 66.182 | −0.895 | 1.00 | 18.09 A | O |
| ATOM | 853 | N | PHE | A | 145 | 30.808 | 64.994 | −0.753 | 1.00 | 17.79 A | N |
| ATOM | 854 | CA | PHE | A | 145 | 31.673 | 66.151 | −0.979 | 1.00 | 16.91 A | C |
| ATOM | 855 | CB | PHE | A | 145 | 33.136 | 65.837 | −0.647 | 1.00 | 17.02 A | C |
| ATOM | 856 | CG | PHE | A | 145 | 33.444 | 65.824 | 0.846 | 1.00 | 17.43 A | C |
| ATOM | 857 | CD1 | PHE | A | 145 | 33.142 | 66.919 | 1.645 | 1.00 | 17.74 A | C |
| ATOM | 858 | CD2 | PHE | A | 145 | 34.071 | 64.733 | 1.429 | 1.00 | 16.59 A | C |
| ATOM | 859 | CE1 | PHE | A | 145 | 33.436 | 66.909 | 3.020 | 1.00 | 22.03 A | C |
| ATOM | 860 | CE2 | PHE | A | 145 | 34.375 | 64.714 | 2.783 | 1.00 | 21.56 A | C |
| ATOM | 861 | CZ | PHE | A | 145 | 34.061 | 65.803 | 3.582 | 1.00 | 18.75 A | C |
| ATOM | 862 | C | PHE | A | 145 | 31.571 | 66.666 | −2.402 | 1.00 | 19.26 A | C |
| ATOM | 863 | O | PHE | A | 145 | 31.534 | 67.878 | −2.619 | 1.00 | 16.59 A | O |
| ATOM | 864 | N | ALA | A | 146 | 31.532 | 65.746 | −3.366 | 1.00 | 18.45 A | N |
| ATOM | 865 | CA | ALA | A | 146 | 31.446 | 66.129 | −4.768 | 1.00 | 20.68 A | C |
| ATOM | 866 | CB | ALA | A | 146 | 31.413 | 64.900 | −5.667 | 1.00 | 14.76 A | C |
| ATOM | 867 | C | ALA | A | 146 | 30.222 | 67.013 | −5.009 | 1.00 | 19.39 A | C |
| ATOM | 868 | O | ALA | A | 146 | 30.253 | 67.886 | −5.851 | 1.00 | 21.00 A | O |
| ATOM | 869 | N | LEU | A | 147 | 29.146 | 66.785 | −4.270 | 1.00 | 18.32 A | N |
| ATOM | 870 | CA | LEU | A | 147 | 28.000 | 67.679 | −4.374 | 1.00 | 17.77 A | C |
| ATOM | 871 | CB | LEU | A | 147 | 26.916 | 67.309 | −3.382 | 1.00 | 15.53 A | C |
| ATOM | 872 | CG | LEU | A | 147 | 26.243 | 65.948 | −3.556 | 1.00 | 15.55 A | C |
| ATOM | 873 | CD1 | LEU | A | 147 | 25.377 | 65.646 | −2.350 | 1.00 | 19.53 A | C |
| ATOM | 874 | CD2 | LEU | A | 147 | 25.400 | 65.930 | −4.859 | 1.00 | 16.11 A | C |
| ATOM | 875 | C | LEU | A | 147 | 28.423 | 69.129 | −4.151 | 1.00 | 20.88 A | C |
| ATOM | 876 | O | LEU | A | 147 | 28.063 | 70.003 | −4.940 | 1.00 | 19.37 A | O |
| ATOM | 877 | N | TRP | A | 148 | 29.163 | 69.380 | −3.067 | 1.00 | 18.54 A | N |
| ATOM | 878 | CA | TRP | A | 148 | 29.527 | 70.747 | −2.691 | 1.00 | 17.49 A | C |
| ATOM | 879 | CB | TRP | A | 148 | 29.852 | 70.856 | −1.183 | 1.00 | 18.66 A | C |
| ATOM | 880 | CG | TRP | A | 148 | 28.655 | 70.553 | −0.315 | 1.00 | 15.04 A | C |
| ATOM | 881 | CD2 | TRP | A | 148 | 27.478 | 71.355 | −0.173 | 1.00 | 18.67 A | C |
| ATOM | 882 | CE2 | TRP | A | 148 | 26.606 | 70.671 | 0.710 | 1.00 | 16.56 A | C |
| ATOM | 883 | CE3 | TRP | A | 148 | 27.080 | 72.592 | −0.694 | 1.00 | 17.02 A | C |
| ATOM | 884 | CD1 | TRP | A | 148 | 28.444 | 69.431 | 0.446 | 1.00 | 17.21 A | C |
| ATOM | 885 | NE1 | TRP | A | 148 | 27.218 | 69.500 | 1.066 | 1.00 | 19.54 A | N |
| ATOM | 886 | CZ2 | TRP | A | 148 | 25.360 | 71.184 | 1.083 | 1.00 | 21.39 A | C |
| ATOM | 887 | CZ3 | TRP | A | 148 | 25.843 | 73.100 | −0.324 | 1.00 | 17.16 A | C |
| ATOM | 888 | CH2 | TRP | A | 148 | 24.992 | 72.389 | 0.545 | 1.00 | 15.76 A | C |
| ATOM | 889 | C | TRP | A | 148 | 30.646 | 71.333 | −3.554 | 1.00 | 19.17 A | C |
| ATOM | 890 | O | TRP | A | 148 | 30.642 | 72.526 | −3.856 | 1.00 | 14.64 A | O |
| ATOM | 891 | N | SER | A | 149 | 31.589 | 70.512 | −4.001 | 1.00 | 16.53 A | N |
| ATOM | 892 | CA | SER | A | 149 | 32.681 | 71.102 | −4.774 | 1.00 | 18.98 A | C |
| ATOM | 893 | CB | SER | A | 149 | 33.875 | 70.146 | −4.913 | 1.00 | 23.81 A | C |
| ATOM | 894 | OG | SER | A | 149 | 33.494 | 68.992 | −5.614 | 1.00 | 22.01 A | O |
| ATOM | 895 | C | SER | A | 149 | 32.268 | 71.655 | −6.141 | 1.00 | 18.12 A | C |
| ATOM | 896 | O | SER | A | 149 | 32.865 | 72.619 | −6.601 | 1.00 | 19.16 A | O |
| ATOM | 897 | N | ALA | A | 150 | 31.242 | 71.083 | −6.764 | 1.00 | 15.01 A | N |
| ATOM | 898 | CA | ALA | A | 150 | 30.808 | 71.535 | −8.085 | 1.00 | 19.55 A | C |
| ATOM | 899 | CB | ALA | A | 150 | 29.875 | 70.524 | −8.756 | 1.00 | 16.88 A | C |
| ATOM | 900 | C | ALA | A | 150 | 30.149 | 72.905 | −8.027 | 1.00 | 17.82 A | C |
| ATOM | 901 | O | ALA | A | 150 | 30.080 | 73.600 | −9.029 | 1.00 | 18.82 A | O |
| ATOM | 902 | N | VAL | A | 151 | 29.714 | 73.304 | −6.841 | 1.00 | 21.26 A | N |
| ATOM | 903 | CA | VAL | A | 151 | 28.990 | 74.555 | −6.679 | 1.00 | 21.12 A | C |
| ATOM | 904 | CB | VAL | A | 151 | 27.551 | 74.294 | −6.138 | 1.00 | 22.39 A | C |
| ATOM | 905 | CG1 | VAL | A | 151 | 26.724 | 73.564 | −7.191 | 1.00 | 15.09 A | C |
| ATOM | 906 | CG2 | VAL | A | 151 | 27.589 | 73.488 | −4.847 | 1.00 | 22.46 A | C |
| ATOM | 907 | C | VAL | A | 151 | 29.726 | 75.561 | −5.794 | 1.00 | 24.00 A | C |
| ATOM | 908 | O | VAL | A | 151 | 29.165 | 76.590 | −5.422 | 1.00 | 20.32 A | O |
| ATOM | 909 | N | THR | A | 152 | 30.985 | 75.266 | −5.461 | 1.00 | 19.95 A | N |
| ATOM | 910 | CA | THR | A | 152 | 31.787 | 76.178 | −4.653 | 1.00 | 22.13 A | C |
| ATOM | 911 | CB | THR | A | 152 | 31.895 | 75.712 | −3.177 | 1.00 | 22.56 A | C |
| ATOM | 912 | OG1 | THR | A | 152 | 32.371 | 74.367 | −3.132 | 1.00 | 24.29 A | O |
| ATOM | 913 | CG2 | THR | A | 152 | 30.576 | 75.786 | −2.480 | 1.00 | 22.50 A | C |
| ATOM | 914 | C | THR | A | 152 | 33.199 | 76.271 | −5.207 | 1.00 | 21.01 A | C |
| ATOM | 915 | O | THR | A | 152 | 33.628 | 75.390 | −5.958 | 1.00 | 21.18 A | O |
| ATOM | 916 | N | PRO | A | 153 | 33.924 | 77.345 | −4.853 | 1.00 | 23.41 A | N |

TABLE 15-continued

| Coordinates for apo form of proMMP9(35-444 ΔFnII) (SEQ ID NO: 12) | | | | | | | | | | |
|---|---|---|---|---|---|---|---|---|---|---|
| ATOM | 917 | CD | PRO | A | 153 | 33.424 | 78.620 | −4.308 | 1.00 | 26.04 A | C |
| ATOM | 918 | CA | PRO | A | 153 | 35.357 | 77.406 | −5.154 | 1.00 | 25.29 A | C |
| ATOM | 919 | CB | PRO | A | 153 | 35.703 | 78.880 | −4.916 | 1.00 | 27.46 A | C |
| ATOM | 920 | CG | PRO | A | 153 | 34.690 | 79.352 | −3.953 | 1.00 | 29.44 A | C |
| ATOM | 921 | C | PRO | A | 153 | 36.177 | 76.560 | −4.193 | 1.00 | 28.79 A | C |
| ATOM | 922 | O | PRO | A | 153 | 37.287 | 76.958 | −3.860 | 1.00 | 30.08 A | O |
| ATOM | 923 | N | LEU | A | 154 | 35.647 | 75.428 | −3.746 | 1.00 | 28.02 A | N |
| ATOM | 924 | CA | LEU | A | 154 | 36.356 | 74.583 | −2.786 | 1.00 | 25.26 A | C |
| ATOM | 925 | CB | LEU | A | 154 | 35.519 | 74.411 | −1.510 | 1.00 | 23.27 A | C |
| ATOM | 926 | CG | LEU | A | 154 | 35.060 | 75.704 | −0.833 | 1.00 | 26.66 A | C |
| ATOM | 927 | CD1 | LEU | A | 154 | 34.172 | 75.446 | 0.373 | 1.00 | 20.65 A | C |
| ATOM | 928 | CD2 | LEU | A | 154 | 36.260 | 76.543 | −0.442 | 1.00 | 21.94 A | C |
| ATOM | 929 | C | LEU | A | 154 | 36.667 | 73.218 | −3.376 | 1.00 | 23.28 A | C |
| ATOM | 930 | O | LEU | A | 154 | 35.938 | 72.736 | −4.251 | 1.00 | 19.71 A | O |
| ATOM | 931 | N | THR | A | 155 | 37.754 | 72.606 | −2.902 | 1.00 | 21.82 A | N |
| ATOM | 932 | CA | THR | A | 155 | 38.078 | 71.216 | −3.204 | 1.00 | 22.32 A | C |
| ATOM | 933 | CB | THR | A | 155 | 39.382 | 71.052 | −4.018 | 1.00 | 25.18 A | C |
| ATOM | 934 | OG1 | THR | A | 155 | 40.504 | 71.342 | −3.175 | 1.00 | 28.22 A | O |
| ATOM | 935 | CG2 | THR | A | 155 | 39.399 | 71.963 | −5.234 | 1.00 | 23.93 A | C |
| ATOM | 936 | C | THR | A | 155 | 38.259 | 70.441 | −1.894 | 1.00 | 21.67 A | C |
| ATOM | 937 | O | THR | A | 155 | 38.593 | 71.008 | −0.859 | 1.00 | 22.99 A | O |
| ATOM | 938 | N | PHE | A | 156 | 38.035 | 69.138 | −1.946 | 1.00 | 16.51 A | N |
| ATOM | 939 | CA | PHE | A | 156 | 38.069 | 68.327 | −0.751 | 1.00 | 19.08 A | C |
| ATOM | 940 | CB | PHE | A | 156 | 36.664 | 67.789 | −0.448 | 1.00 | 21.82 A | C |
| ATOM | 941 | CG | PHE | A | 156 | 35.641 | 68.873 | −0.291 | 1.00 | 14.85 A | C |
| ATOM | 942 | CD1 | PHE | A | 156 | 34.723 | 69.134 | −1.293 | 1.00 | 17.28 A | C |
| ATOM | 943 | CD2 | PHE | A | 156 | 35.638 | 69.666 | 0.831 | 1.00 | 14.11 A | C |
| ATOM | 944 | CE1 | PHE | A | 156 | 33.807 | 70.157 | −1.163 | 1.00 | 16.58 A | C |
| ATOM | 945 | CE2 | PHE | A | 156 | 34.729 | 70.688 | 0.968 | 1.00 | 20.33 A | C |
| ATOM | 946 | CZ | PHE | A | 156 | 33.809 | 70.931 | −0.030 | 1.00 | 16.27 A | C |
| ATOM | 947 | C | PHE | A | 156 | 39.066 | 67.215 | −1.003 | 1.00 | 17.66 A | C |
| ATOM | 948 | O | PHE | A | 156 | 39.067 | 66.611 | −2.067 | 1.00 | 22.61 A | O |
| ATOM | 949 | N | THR | A | 157 | 39.943 | 66.968 | −0.044 | 1.00 | 19.73 A | N |
| ATOM | 950 | CA | THR | A | 157 | 41.010 | 66.015 | −0.261 | 1.00 | 15.88 A | C |
| ATOM | 951 | CB | THR | A | 157 | 42.369 | 66.742 | −0.465 | 1.00 | 24.96 A | C |
| ATOM | 952 | OG1 | THR | A | 157 | 42.304 | 67.586 | −1.625 | 1.00 | 20.50 A | O |
| ATOM | 953 | CG2 | THR | A | 157 | 43.490 | 65.735 | −0.671 | 1.00 | 26.22 A | C |
| ATOM | 954 | C | THR | A | 157 | 41.108 | 65.109 | 0.950 | 1.00 | 22.51 A | C |
| ATOM | 955 | O | THR | A | 157 | 41.269 | 65.595 | 2.068 | 1.00 | 23.47 A | O |
| ATOM | 956 | N | ARG | A | 158 | 41.018 | 63.799 | 0.735 | 1.00 | 24.17 A | N |
| ATOM | 957 | CA | ARG | A | 158 | 41.112 | 62.840 | 1.844 | 1.00 | 28.87 A | C |
| ATOM | 958 | CB | ARG | A | 158 | 40.607 | 61.452 | 1.418 | 1.00 | 21.39 A | C |
| ATOM | 959 | CG | ARG | A | 158 | 40.527 | 60.423 | 2.547 | 1.00 | 22.64 A | C |
| ATOM | 960 | CD | ARG | A | 158 | 40.130 | 59.037 | 2.041 | 1.00 | 22.61 A | C |
| ATOM | 961 | NE | ARG | A | 158 | 40.122 | 58.055 | 3.125 | 1.00 | 27.27 A | N |
| ATOM | 962 | CZ | ARG | A | 158 | 39.852 | 56.758 | 2.986 | 1.00 | 25.98 A | C |
| ATOM | 963 | NH1 | ARG | A | 158 | 39.544 | 56.245 | 1.802 | 1.00 | 24.16 A | N |
| ATOM | 964 | NH2 | ARG | A | 158 | 39.891 | 55.958 | 4.046 | 1.00 | 23.22 A | N |
| ATOM | 965 | C | ARG | A | 158 | 42.546 | 62.743 | 2.377 | 1.00 | 25.83 A | C |
| ATOM | 966 | O | ARG | A | 158 | 43.489 | 62.524 | 1.612 | 1.00 | 27.48 A | O |
| ATOM | 967 | N | VAL | A | 159 | 42.699 | 62.926 | 3.685 | 1.00 | 29.22 A | N |
| ATOM | 968 | CA | VAL | A | 159 | 43.993 | 62.759 | 4.357 | 1.00 | 28.73 A | C |
| ATOM | 969 | CB | VAL | A | 159 | 44.488 | 64.082 | 4.959 | 1.00 | 28.39 A | C |
| ATOM | 970 | CG1 | VAL | A | 159 | 44.775 | 65.083 | 3.852 | 1.00 | 23.39 A | C |
| ATOM | 971 | CG2 | VAL | A | 159 | 43.465 | 64.634 | 5.951 | 1.00 | 28.13 A | C |
| ATOM | 972 | C | VAL | A | 159 | 43.917 | 61.732 | 5.479 | 1.00 | 29.18 A | C |
| ATOM | 973 | O | VAL | A | 159 | 42.921 | 61.007 | 5.623 | 1.00 | 30.14 A | O |
| ATOM | 974 | N | TYR | A | 160 | 44.957 | 61.673 | 6.296 | 1.00 | 31.38 A | N |
| ATOM | 975 | CA | TYR | A | 160 | 44.953 | 60.716 | 7.394 | 1.00 | 30.83 A | C |
| ATOM | 976 | CB | TYR | A | 160 | 45.637 | 59.421 | 6.943 | 1.00 | 26.82 A | C |
| ATOM | 977 | CG | TYR | A | 160 | 45.034 | 58.828 | 5.675 | 1.00 | 30.50 A | C |
| ATOM | 978 | CD1 | TYR | A | 160 | 45.425 | 59.276 | 4.410 | 1.00 | 25.38 A | C |
| ATOM | 979 | CE1 | TYR | A | 160 | 44.859 | 58.743 | 3.250 | 1.00 | 28.31 A | C |
| ATOM | 980 | CD2 | TYR | A | 160 | 44.079 | 57.818 | 5.745 | 1.00 | 30.67 A | C |
| ATOM | 981 | CE2 | TYR | A | 160 | 43.521 | 57.271 | 4.598 | 1.00 | 30.78 A | C |
| ATOM | 982 | CZ | TYR | A | 160 | 43.910 | 57.741 | 3.357 | 1.00 | 31.93 A | C |
| ATOM | 983 | OH | TYR | A | 160 | 43.349 | 57.192 | 2.236 | 1.00 | 29.22 A | O |
| ATOM | 984 | C | TYR | A | 160 | 45.573 | 61.261 | 8.685 | 1.00 | 34.04 A | C |
| ATOM | 985 | O | TYR | A | 160 | 46.532 | 60.693 | 9.194 | 1.00 | 44.70 A | O |
| ATOM | 986 | N | SER | A | 161 | 45.018 | 62.351 | 9.215 | 1.00 | 36.71 A | N |
| ATOM | 987 | CA | SER | A | 161 | 45.527 | 62.962 | 10.449 | 1.00 | 32.72 A | C |
| ATOM | 988 | CB | SER | A | 161 | 46.819 | 63.740 | 10.168 | 1.00 | 40.57 A | C |
| ATOM | 989 | OG | SER | A | 161 | 46.658 | 64.646 | 9.078 | 1.00 | 39.16 A | O |
| ATOM | 990 | C | SER | A | 161 | 44.515 | 63.895 | 11.116 | 1.00 | 39.89 A | C |
| ATOM | 991 | O | SER | A | 161 | 43.554 | 64.337 | 10.491 | 1.00 | 36.50 A | O |
| ATOM | 992 | N | ARG | A | 162 | 44.756 | 64.214 | 12.385 | 1.00 | 33.48 A | N |
| ATOM | 993 | CA | ARG | A | 162 | 43.918 | 65.157 | 13.127 | 1.00 | 39.43 A | C |
| ATOM | 994 | CB | ARG | A | 162 | 44.330 | 65.171 | 14.605 | 1.00 | 42.01 A | C |

TABLE 15-continued

Coordinates for apo form of proMMP9(35-444 ΔFnII) (SEQ ID NO: 12)

| ATOM | 995 | CG | ARG | A | 162 | 45.575 | 66.031 | 14.863 | 1.00 | 44.84 | A | C |
|------|-----|-----|-----|---|-----|--------|--------|--------|------|-------|---|---|
| ATOM | 996 | CD | ARG | A | 162 | 46.168 | 65.824 | 16.253 | 1.00 | 50.09 | A | C |
| ATOM | 997 | NE | ARG | A | 162 | 46.783 | 64.507 | 16.395 | 1.00 | 52.45 | A | N |
| ATOM | 998 | CZ | ARG | A | 162 | 48.072 | 64.250 | 16.181 | 1.00 | 51.61 | A | C |
| ATOM | 999 | NH1 | ARG | A | 162 | 48.533 | 63.015 | 16.335 | 1.00 | 51.46 | A | N |
| ATOM | 1000 | NH2 | ARG | A | 162 | 48.899 | 65.225 | 15.812 | 1.00 | 39.55 | A | N |
| ATOM | 1001 | C | ARG | A | 162 | 44.046 | 66.576 | 12.549 | 1.00 | 36.20 | A | C |
| ATOM | 1002 | O | ARG | A | 162 | 43.399 | 67.522 | 13.012 | 1.00 | 40.05 | A | O |
| ATOM | 1003 | N | ASP | A | 163 | 44.917 | 66.713 | 11.556 | 1.00 | 42.73 | A | N |
| ATOM | 1004 | CA | ASP | A | 163 | 45.217 | 67.996 | 10.912 | 1.00 | 45.93 | A | C |
| ATOM | 1005 | CB | ASP | A | 163 | 46.588 | 67.911 | 10.238 | 1.00 | 41.96 | A | C |
| ATOM | 1006 | CG | ASP | A | 163 | 47.344 | 69.228 | 10.257 | 1.00 | 55.09 | A | C |
| ATOM | 1007 | OD1 | ASP | A | 163 | 46.792 | 70.250 | 10.715 | 1.00 | 59.47 | A | O |
| ATOM | 1008 | OD2 | ASP | A | 163 | 48.510 | 69.234 | 9.809 | 1.00 | 58.61 | A | O |
| ATOM | 1009 | C | ASP | A | 163 | 44.167 | 68.369 | 9.865 | 1.00 | 38.29 | A | C |
| ATOM | 1010 | O | ASP | A | 163 | 44.094 | 69.519 | 9.419 | 1.00 | 36.95 | A | O |
| ATOM | 1011 | N | ALA | A | 164 | 43.365 | 67.385 | 9.470 | 1.00 | 32.89 | A | N |
| ATOM | 1012 | CA | ALA | A | 164 | 42.277 | 67.600 | 8.532 | 1.00 | 23.19 | A | C |
| ATOM | 1013 | CB | ALA | A | 164 | 41.453 | 66.341 | 8.416 | 1.00 | 24.02 | A | C |
| ATOM | 1014 | C | ALA | A | 164 | 41.398 | 68.733 | 9.019 | 1.00 | 23.13 | A | C |
| ATOM | 1015 | O | ALA | A | 164 | 41.179 | 68.874 | 10.222 | 1.00 | 26.24 | A | O |
| ATOM | 1016 | N | ASP | A | 165 | 40.891 | 69.540 | 8.095 | 1.00 | 22.62 | A | N |
| ATOM | 1017 | CA | ASP | A | 165 | 39.921 | 70.573 | 8.455 | 1.00 | 23.86 | A | C |
| ATOM | 1018 | CB | ASP | A | 165 | 39.555 | 71.397 | 7.222 | 1.00 | 23.54 | A | C |
| ATOM | 1019 | CG | ASP | A | 165 | 40.737 | 72.176 | 6.672 | 1.00 | 23.48 | A | C |
| ATOM | 1020 | OD1 | ASP | A | 165 | 41.461 | 72.806 | 7.477 | 1.00 | 25.03 | A | O |
| ATOM | 1021 | OD2 | ASP | A | 165 | 40.941 | 72.157 | 5.441 | 1.00 | 20.18 | A | O |
| ATOM | 1022 | C | ASP | A | 165 | 38.671 | 69.911 | 9.019 | 1.00 | 23.22 | A | C |
| ATOM | 1023 | O | ASP | A | 165 | 38.095 | 70.360 | 10.011 | 1.00 | 24.16 | A | O |
| ATOM | 1024 | N | ILE | A | 166 | 38.286 | 68.820 | 8.374 | 1.00 | 26.16 | A | N |
| ATOM | 1025 | CA | ILE | A | 166 | 37.083 | 68.091 | 8.694 | 1.00 | 22.84 | A | C |
| ATOM | 1026 | CB | ILE | A | 166 | 36.175 | 68.003 | 7.450 | 1.00 | 21.31 | A | C |
| ATOM | 1027 | CG2 | ILE | A | 166 | 35.010 | 67.062 | 7.698 | 1.00 | 20.91 | A | C |
| ATOM | 1028 | CG1 | ILE | A | 166 | 35.659 | 69.402 | 7.076 | 1.00 | 17.04 | A | C |
| ATOM | 1029 | CD1 | ILE | A | 166 | 34.902 | 69.488 | 5.766 | 1.00 | 15.49 | A | C |
| ATOM | 1030 | C | ILE | A | 166 | 37.407 | 66.677 | 9.190 | 1.00 | 22.77 | A | C |
| ATOM | 1031 | O | ILE | A | 166 | 37.779 | 65.812 | 8.410 | 1.00 | 21.75 | A | O |
| ATOM | 1032 | N | VAL | A | 167 | 37.243 | 66.439 | 10.484 | 1.00 | 23.93 | A | N |
| ATOM | 1033 | CA | VAL | A | 167 | 37.380 | 65.084 | 11.003 | 1.00 | 24.64 | A | C |
| ATOM | 1034 | CB | VAL | A | 167 | 38.104 | 65.043 | 12.354 | 1.00 | 26.50 | A | C |
| ATOM | 1035 | CG1 | VAL | A | 167 | 38.240 | 63.597 | 12.832 | 1.00 | 26.08 | A | C |
| ATOM | 1036 | CG2 | VAL | A | 167 | 39.477 | 65.697 | 12.244 | 1.00 | 21.76 | A | C |
| ATOM | 1037 | C | VAL | A | 167 | 36.007 | 64.408 | 11.089 | 1.00 | 22.00 | A | C |
| ATOM | 1038 | O | VAL | A | 167 | 35.061 | 64.954 | 11.658 | 1.00 | 22.63 | A | O |
| ATOM | 1039 | N | ILE | A | 168 | 35.921 | 63.234 | 10.477 | 1.00 | 20.73 | A | N |
| ATOM | 1040 | CA | ILE | A | 168 | 34.695 | 62.459 | 10.356 | 1.00 | 20.64 | A | C |
| ATOM | 1041 | CB | ILE | A | 168 | 34.527 | 61.889 | 8.922 | 1.00 | 17.98 | A | C |
| ATOM | 1042 | CG2 | ILE | A | 168 | 33.370 | 60.871 | 8.874 | 1.00 | 22.07 | A | C |
| ATOM | 1043 | CG1 | ILE | A | 168 | 34.331 | 63.034 | 7.906 | 1.00 | 20.58 | A | C |
| ATOM | 1044 | CD1 | ILE | A | 168 | 34.342 | 62.626 | 6.434 | 1.00 | 18.81 | A | C |
| ATOM | 1045 | C | ILE | A | 168 | 34.777 | 61.303 | 11.344 | 1.00 | 21.36 | A | C |
| ATOM | 1046 | O | ILE | A | 168 | 35.805 | 60.637 | 11.430 | 1.00 | 17.41 | A | O |
| ATOM | 1047 | N | GLN | A | 169 | 33.688 | 61.055 | 12.063 | 1.00 | 18.99 | A | N |
| ATOM | 1048 | CA | GLN | A | 169 | 33.705 | 60.132 | 13.190 | 1.00 | 21.15 | A | C |
| ATOM | 1049 | CB | GLN | A | 169 | 34.006 | 60.945 | 14.454 | 1.00 | 22.26 | A | C |
| ATOM | 1050 | CG | GLN | A | 169 | 34.634 | 60.205 | 15.581 | 1.00 | 25.51 | A | C |
| ATOM | 1051 | CD | GLN | A | 169 | 34.727 | 61.067 | 16.833 | 1.00 | 31.76 | A | C |
| ATOM | 1052 | OE1 | GLN | A | 169 | 35.681 | 61.824 | 17.010 | 1.00 | 36.50 | A | O |
| ATOM | 1053 | NE2 | GLN | A | 169 | 33.725 | 60.960 | 17.702 | 1.00 | 29.33 | A | N |
| ATOM | 1054 | C | GLN | A | 169 | 32.351 | 59.444 | 13.352 | 1.00 | 20.36 | A | C |
| ATOM | 1055 | O | GLN | A | 169 | 31.312 | 60.086 | 13.255 | 1.00 | 17.36 | A | O |
| ATOM | 1056 | N | PHE | A | 170 | 32.369 | 58.131 | 13.557 | 1.00 | 15.98 | A | N |
| ATOM | 1057 | CA | PHE | A | 170 | 31.188 | 57.393 | 13.959 | 1.00 | 20.47 | A | C |
| ATOM | 1058 | CB | PHE | A | 170 | 31.150 | 56.031 | 13.249 | 1.00 | 20.08 | A | C |
| ATOM | 1059 | CG | PHE | A | 170 | 30.867 | 56.127 | 11.776 | 1.00 | 19.04 | A | C |
| ATOM | 1060 | CD1 | PHE | A | 170 | 31.908 | 56.211 | 10.850 | 1.00 | 21.45 | A | C |
| ATOM | 1061 | CD2 | PHE | A | 170 | 29.562 | 56.169 | 11.312 | 1.00 | 19.97 | A | C |
| ATOM | 1062 | CE1 | PHE | A | 170 | 31.641 | 56.312 | 9.503 | 1.00 | 20.80 | A | C |
| ATOM | 1063 | CE2 | PHE | A | 170 | 29.291 | 56.278 | 9.959 | 1.00 | 21.54 | A | C |
| ATOM | 1064 | CZ | PHE | A | 170 | 30.326 | 56.356 | 9.054 | 1.00 | 22.29 | A | C |
| ATOM | 1065 | C | PHE | A | 170 | 31.290 | 57.193 | 15.477 | 1.00 | 20.46 | A | C |
| ATOM | 1066 | O | PHE | A | 170 | 32.304 | 56.682 | 15.965 | 1.00 | 20.44 | A | O |
| ATOM | 1067 | N | GLY | A | 171 | 30.263 | 57.604 | 16.213 | 1.00 | 16.45 | A | N |
| ATOM | 1068 | CA | GLY | A | 171 | 30.231 | 57.431 | 17.664 | 1.00 | 21.87 | A | C |
| ATOM | 1069 | C | GLY | A | 171 | 28.841 | 57.114 | 18.199 | 1.00 | 24.66 | A | C |
| ATOM | 1070 | O | GLY | A | 171 | 27.859 | 57.165 | 17.450 | 1.00 | 24.42 | A | O |
| ATOM | 1071 | N | VAL | A | 172 | 28.752 | 56.763 | 19.484 | 1.00 | 23.94 | A | N |
| ATOM | 1072 | CA | VAL | A | 172 | 27.467 | 56.549 | 20.131 | 1.00 | 21.54 | A | C |

TABLE 15-continued

| | | | | | | | | | | | |
|---|---|---|---|---|---|---|---|---|---|---|---|
| \multicolumn{12}{|c|}{Coordinates for apo form of proMMP9(35-444 ΔFnII) (SEQ ID NO: 12)} |

| | | | | | | | | | | | |
|---|---|---|---|---|---|---|---|---|---|---|---|
| ATOM | 1073 | CB | VAL | A | 172 | 27.153 | 55.052 | 20.311 | 1.00 | 19.09 A | C |
| ATOM | 1074 | CG1 | VAL | A | 172 | 27.279 | 54.319 | 18.985 | 1.00 | 23.71 A | C |
| ATOM | 1075 | CG2 | VAL | A | 172 | 28.047 | 54.434 | 21.387 | 1.00 | 20.03 A | C |
| ATOM | 1076 | C | VAL | A | 172 | 27.410 | 57.207 | 21.506 | 1.00 | 24.46 A | C |
| ATOM | 1077 | O | VAL | A | 172 | 28.443 | 57.496 | 22.125 | 1.00 | 21.92 A | O |
| ATOM | 1078 | N | ALA | A | 173 | 26.192 | 57.405 | 21.990 | 1.00 | 25.40 A | N |
| ATOM | 1079 | CA | ALA | A | 173 | 25.977 | 58.023 | 23.284 | 1.00 | 27.47 A | C |
| ATOM | 1080 | CB | ALA | A | 173 | 26.108 | 56.993 | 24.398 | 1.00 | 18.62 A | C |
| ATOM | 1081 | C | ALA | A | 173 | 27.018 | 59.116 | 23.435 | 1.00 | 26.51 A | C |
| ATOM | 1082 | O | ALA | A | 173 | 27.181 | 59.940 | 22.532 | 1.00 | 22.93 A | O |
| ATOM | 1083 | N | GLU | A | 174 | 27.726 | 59.126 | 24.567 | 1.00 | 25.79 A | N |
| ATOM | 1084 | CA | GLU | A | 174 | 28.790 | 60.109 | 24.765 | 1.00 | 25.15 A | C |
| ATOM | 1085 | CB | GLU | A | 174 | 29.057 | 60.374 | 26.249 | 1.00 | 28.27 A | C |
| ATOM | 1086 | CG | GLU | A | 174 | 30.341 | 61.161 | 26.496 | 1.00 | 30.28 A | C |
| ATOM | 1087 | CD | GLU | A | 174 | 30.341 | 62.511 | 25.800 | 1.00 | 29.38 A | C |
| ATOM | 1088 | OE1 | GLU | A | 174 | 29.243 | 63.051 | 25.559 | 1.00 | 30.98 A | O |
| ATOM | 1089 | OE2 | GLU | A | 174 | 31.437 | 63.041 | 25.502 | 1.00 | 35.72 A | O |
| ATOM | 1090 | C | GLU | A | 174 | 30.075 | 59.680 | 24.061 | 1.00 | 28.92 A | C |
| ATOM | 1091 | O | GLU | A | 174 | 30.625 | 58.608 | 24.327 | 1.00 | 29.37 A | O |
| ATOM | 1092 | N | HIS | A | 175 | 30.569 | 60.527 | 23.170 | 1.00 | 27.57 A | N |
| ATOM | 1093 | CA | HIS | A | 175 | 31.654 | 60.107 | 22.298 | 1.00 | 26.42 A | C |
| ATOM | 1094 | CB | HIS | A | 175 | 31.128 | 59.795 | 20.901 | 1.00 | 25.80 A | C |
| ATOM | 1095 | CG | HIS | A | 175 | 30.433 | 60.946 | 20.254 | 1.00 | 21.89 A | C |
| ATOM | 1096 | CD2 | HIS | A | 175 | 30.850 | 61.834 | 19.321 | 1.00 | 25.03 A | C |
| ATOM | 1097 | ND1 | HIS | A | 175 | 29.139 | 61.296 | 20.562 | 1.00 | 25.33 A | N |
| ATOM | 1098 | CE1 | HIS | A | 175 | 28.782 | 62.345 | 19.842 | 1.00 | 24.26 A | C |
| ATOM | 1099 | NE2 | HIS | A | 175 | 29.805 | 62.694 | 19.084 | 1.00 | 25.74 A | N |
| ATOM | 1100 | C | HIS | A | 175 | 32.794 | 61.113 | 22.212 | 1.00 | 27.03 A | C |
| ATOM | 1101 | O | HIS | A | 175 | 33.512 | 61.142 | 21.229 | 1.00 | 31.03 A | O |
| ATOM | 1102 | N | GLY | A | 176 | 32.951 | 61.938 | 23.237 | 1.00 | 27.04 A | N |
| ATOM | 1103 | CA | GLY | A | 176 | 34.168 | 62.709 | 23.374 | 1.00 | 26.17 A | C |
| ATOM | 1104 | C | GLY | A | 176 | 34.046 | 64.183 | 23.082 | 1.00 | 26.62 A | C |
| ATOM | 1105 | O | GLY | A | 176 | 35.063 | 64.869 | 23.002 | 1.00 | 31.64 A | O |
| ATOM | 1106 | N | ASP | A | 177 | 32.823 | 64.681 | 22.913 | 1.00 | 25.02 A | N |
| ATOM | 1107 | CA | ASP | A | 177 | 32.656 | 66.120 | 22.664 | 1.00 | 32.43 A | C |
| ATOM | 1108 | CB | ASP | A | 177 | 32.493 | 66.409 | 21.172 | 1.00 | 30.69 A | C |
| ATOM | 1109 | CG | ASP | A | 177 | 31.181 | 65.895 | 20.608 | 1.00 | 29.03 A | C |
| ATOM | 1110 | OD1 | ASP | A | 177 | 30.301 | 65.460 | 21.387 | 1.00 | 26.59 A | O |
| ATOM | 1111 | OD2 | ASP | A | 177 | 31.035 | 65.941 | 19.371 | 1.00 | 22.89 A | O |
| ATOM | 1112 | C | ASP | A | 177 | 31.558 | 66.821 | 23.465 | 1.00 | 31.59 A | C |
| ATOM | 1113 | O | ASP | A | 177 | 31.284 | 67.998 | 23.235 | 1.00 | 32.48 A | O |
| ATOM | 1114 | N | GLY | A | 178 | 30.934 | 66.103 | 24.395 | 1.00 | 31.64 A | N |
| ATOM | 1115 | CA | GLY | A | 178 | 29.968 | 66.707 | 25.302 | 1.00 | 29.02 A | C |
| ATOM | 1116 | C | GLY | A | 178 | 28.656 | 67.051 | 24.629 | 1.00 | 28.26 A | C |
| ATOM | 1117 | O | GLY | A | 178 | 27.855 | 67.832 | 25.145 | 1.00 | 25.98 A | O |
| ATOM | 1118 | N | TYR | A | 179 | 28.447 | 66.466 | 23.455 | 1.00 | 27.08 A | N |
| ATOM | 1119 | CA | TYR | A | 179 | 27.180 | 66.545 | 22.756 | 1.00 | 26.03 A | C |
| ATOM | 1120 | CB | TYR | A | 179 | 27.313 | 67.416 | 21.519 | 1.00 | 29.37 A | C |
| ATOM | 1121 | CG | TYR | A | 179 | 27.610 | 68.871 | 21.804 | 1.00 | 27.70 A | C |
| ATOM | 1122 | CD1 | TYR | A | 179 | 28.908 | 69.364 | 21.750 | 1.00 | 31.62 A | C |
| ATOM | 1123 | CE1 | TYR | A | 179 | 29.181 | 70.705 | 22.000 | 1.00 | 26.67 A | C |
| ATOM | 1124 | CD2 | TYR | A | 179 | 26.586 | 69.751 | 22.115 | 1.00 | 28.47 A | C |
| ATOM | 1125 | CE2 | TYR | A | 179 | 26.839 | 71.076 | 22.370 | 1.00 | 29.60 A | C |
| ATOM | 1126 | CZ | TYR | A | 179 | 28.138 | 71.551 | 22.312 | 1.00 | 31.08 A | C |
| ATOM | 1127 | OH | TYR | A | 179 | 28.370 | 72.881 | 22.563 | 1.00 | 34.24 A | O |
| ATOM | 1128 | C | TYR | A | 179 | 26.820 | 65.123 | 22.367 | 1.00 | 27.64 A | C |
| ATOM | 1129 | O | TYR | A | 179 | 26.949 | 64.736 | 21.208 | 1.00 | 30.56 A | O |
| ATOM | 1130 | N | PRO | A | 180 | 26.384 | 64.331 | 23.350 | 1.00 | 30.40 A | N |
| ATOM | 1131 | CD | PRO | A | 180 | 25.938 | 64.833 | 24.657 | 1.00 | 28.80 A | C |
| ATOM | 1132 | CA | PRO | A | 180 | 26.185 | 62.884 | 23.224 | 1.00 | 28.18 A | C |
| ATOM | 1133 | CB | PRO | A | 180 | 25.701 | 62.469 | 24.626 | 1.00 | 29.17 A | C |
| ATOM | 1134 | CG | PRO | A | 180 | 25.999 | 63.609 | 25.507 | 1.00 | 33.85 A | C |
| ATOM | 1135 | C | PRO | A | 180 | 25.092 | 62.543 | 22.236 | 1.00 | 23.80 A | C |
| ATOM | 1136 | O | PRO | A | 180 | 24.120 | 63.284 | 22.106 | 1.00 | 25.16 A | O |
| ATOM | 1137 | N | PHE | A | 181 | 25.221 | 61.405 | 21.576 | 1.00 | 23.75 A | N |
| ATOM | 1138 | CA | PHE | A | 181 | 24.139 | 60.935 | 20.736 | 1.00 | 21.48 A | C |
| ATOM | 1139 | CB | PHE | A | 181 | 24.646 | 59.990 | 19.635 | 1.00 | 20.65 A | C |
| ATOM | 1140 | CG | PHE | A | 181 | 25.433 | 60.696 | 18.565 | 1.00 | 22.27 A | C |
| ATOM | 1141 | CD1 | PHE | A | 181 | 24.922 | 61.838 | 17.959 | 1.00 | 23.26 A | C |
| ATOM | 1142 | CD2 | PHE | A | 181 | 26.680 | 60.240 | 18.174 | 1.00 | 22.25 A | C |
| ATOM | 1143 | CE1 | PHE | A | 181 | 25.640 | 62.509 | 16.986 | 1.00 | 24.95 A | C |
| ATOM | 1144 | CE2 | PHE | A | 181 | 27.401 | 60.907 | 17.199 | 1.00 | 21.51 A | C |
| ATOM | 1145 | CZ | PHE | A | 181 | 26.868 | 62.044 | 16.599 | 1.00 | 21.75 A | C |
| ATOM | 1146 | C | PHE | A | 181 | 23.056 | 60.328 | 21.629 | 1.00 | 25.40 A | C |
| ATOM | 1147 | O | PHE | A | 181 | 23.206 | 60.294 | 22.857 | 1.00 | 27.74 A | O |
| ATOM | 1148 | N | ASP | A | 182 | 21.970 | 59.864 | 21.028 | 1.00 | 25.30 A | N |
| ATOM | 1149 | CA | ASP | A | 182 | 20.772 | 59.531 | 21.795 | 1.00 | 24.75 A | C |
| ATOM | 1150 | CB | ASP | A | 182 | 19.677 | 60.563 | 21.502 | 1.00 | 26.43 A | C |

TABLE 15-continued

| | | | | | | | | | | | |
|---|---|---|---|---|---|---|---|---|---|---|---|
| \multicolumn{12}{l}{Coordinates for apo form of proMMP9(35-444 ΔFnII) (SEQ ID NO: 12)} |
| ATOM | 1151 | CG | ASP | A | 182 | 19.255 | 60.557 | 20.041 | 1.00 | 23.66 A | C |
| ATOM | 1152 | OD1 | ASP | A | 182 | 20.051 | 60.077 | 19.228 | 1.00 | 23.71 A | O |
| ATOM | 1153 | OD2 | ASP | A | 182 | 18.150 | 61.038 | 19.693 | 1.00 | 24.88 A | O |
| ATOM | 1154 | C | ASP | A | 182 | 20.220 | 58.116 | 21.535 | 1.00 | 24.89 A | C |
| ATOM | 1155 | O | ASP | A | 182 | 19.043 | 57.850 | 21.794 | 1.00 | 27.79 A | O |
| ATOM | 1156 | N | GLY | A | 183 | 21.059 | 57.216 | 21.026 | 1.00 | 28.78 A | N |
| ATOM | 1157 | CA | GLY | A | 183 | 20.625 | 55.863 | 20.707 | 1.00 | 23.34 A | C |
| ATOM | 1158 | C | GLY | A | 183 | 19.751 | 55.870 | 19.470 | 1.00 | 26.40 A | C |
| ATOM | 1159 | O | GLY | A | 183 | 19.487 | 56.927 | 18.924 | 1.00 | 28.91 A | O |
| ATOM | 1160 | N | LYS | A | 184 | 19.291 | 54.705 | 19.033 | 1.00 | 26.72 A | N |
| ATOM | 1161 | CA | LYS | A | 184 | 18.527 | 54.585 | 17.788 | 1.00 | 26.75 A | C |
| ATOM | 1162 | CB | LYS | A | 184 | 17.783 | 53.248 | 17.744 | 1.00 | 26.28 A | C |
| ATOM | 1163 | CG | LYS | A | 184 | 17.536 | 52.738 | 16.326 | 1.00 | 35.08 A | C |
| ATOM | 1164 | CD | LYS | A | 184 | 16.824 | 51.397 | 16.316 | 1.00 | 26.86 A | C |
| ATOM | 1165 | CE | LYS | A | 184 | 15.321 | 51.594 | 16.222 | 1.00 | 41.57 A | C |
| ATOM | 1166 | NZ | LYS | A | 184 | 14.921 | 52.092 | 14.870 | 1.00 | 31.43 A | N |
| ATOM | 1167 | C | LYS | A | 184 | 17.538 | 55.745 | 17.534 | 1.00 | 30.13 A | C |
| ATOM | 1168 | O | LYS | A | 184 | 16.801 | 56.142 | 18.430 | 1.00 | 28.80 A | O |
| ATOM | 1169 | N | ASP | A | 185 | 17.551 | 56.275 | 16.307 | 1.00 | 30.45 A | N |
| ATOM | 1170 | CA | ASP | A | 185 | 16.660 | 57.367 | 15.876 | 1.00 | 26.69 A | C |
| ATOM | 1171 | CB | ASP | A | 185 | 15.197 | 56.930 | 15.905 | 1.00 | 26.70 A | C |
| ATOM | 1172 | CG | ASP | A | 185 | 14.956 | 55.681 | 15.092 | 1.00 | 30.55 A | C |
| ATOM | 1173 | OD1 | ASP | A | 185 | 15.399 | 55.635 | 13.914 | 1.00 | 28.80 A | O |
| ATOM | 1174 | OD2 | ASP | A | 185 | 14.331 | 54.742 | 15.630 | 1.00 | 30.45 A | O |
| ATOM | 1175 | C | ASP | A | 185 | 16.855 | 58.676 | 16.642 | 1.00 | 26.48 A | C |
| ATOM | 1176 | O | ASP | A | 185 | 17.875 | 58.882 | 17.261 | 1.00 | 28.97 A | O |
| ATOM | 1177 | N | GLY | A | 186 | 15.874 | 59.569 | 16.609 | 1.00 | 27.98 A | N |
| ATOM | 1178 | CA | GLY | A | 186 | 16.090 | 60.883 | 17.192 | 1.00 | 25.10 A | C |
| ATOM | 1179 | C | GLY | A | 186 | 17.177 | 61.591 | 16.393 | 1.00 | 21.86 A | C |
| ATOM | 1180 | O | GLY | A | 186 | 17.041 | 61.743 | 15.180 | 1.00 | 24.55 A | O |
| ATOM | 1181 | N | LEU | A | 187 | 18.256 | 62.006 | 17.054 | 1.00 | 20.45 A | N |
| ATOM | 1182 | CA | LEU | A | 187 | 19.370 | 62.689 | 16.371 | 1.00 | 24.60 A | C |
| ATOM | 1183 | CB | LEU | A | 187 | 20.355 | 63.292 | 17.383 | 1.00 | 20.25 A | C |
| ATOM | 1184 | CG | LEU | A | 187 | 19.797 | 64.154 | 18.501 | 1.00 | 31.73 A | C |
| ATOM | 1185 | CD1 | LEU | A | 187 | 20.934 | 64.715 | 19.345 | 1.00 | 27.75 A | C |
| ATOM | 1186 | CD2 | LEU | A | 187 | 18.991 | 65.260 | 17.882 | 1.00 | 28.29 A | C |
| ATOM | 1187 | C | LEU | A | 187 | 20.139 | 61.685 | 15.569 | 1.00 | 23.90 A | C |
| ATOM | 1188 | O | LEU | A | 187 | 20.523 | 60.665 | 16.116 | 1.00 | 24.81 A | O |
| ATOM | 1189 | N | LEU | A | 188 | 20.410 | 61.983 | 14.300 | 1.00 | 17.67 A | N |
| ATOM | 1190 | CA | LEU | A | 188 | 21.114 | 61.051 | 13.424 | 1.00 | 24.25 A | C |
| ATOM | 1191 | CB | LEU | A | 188 | 20.531 | 61.093 | 12.012 | 1.00 | 16.41 A | C |
| ATOM | 1192 | CG | LEU | A | 188 | 19.035 | 60.808 | 11.896 | 1.00 | 16.39 A | C |
| ATOM | 1193 | CD1 | LEU | A | 188 | 18.563 | 61.034 | 10.457 | 1.00 | 19.02 A | C |
| ATOM | 1194 | CD2 | LEU | A | 188 | 18.724 | 59.401 | 12.334 | 1.00 | 19.43 A | C |
| ATOM | 1195 | C | LEU | A | 188 | 22.600 | 61.362 | 13.345 | 1.00 | 20.59 A | C |
| ATOM | 1196 | O | LEU | A | 188 | 23.420 | 60.480 | 13.115 | 1.00 | 20.66 A | O |
| ATOM | 1197 | N | ALA | A | 189 | 22.939 | 62.630 | 13.529 | 1.00 | 21.50 A | N |
| ATOM | 1198 | CA | ALA | A | 189 | 24.299 | 63.079 | 13.305 | 1.00 | 21.34 A | C |
| ATOM | 1199 | CB | ALA | A | 189 | 24.676 | 62.906 | 11.813 | 1.00 | 16.40 A | C |
| ATOM | 1200 | C | ALA | A | 189 | 24.429 | 64.538 | 13.705 | 1.00 | 18.84 A | C |
| ATOM | 1201 | O | ALA | A | 189 | 23.437 | 65.228 | 13.935 | 1.00 | 20.92 A | O |
| ATOM | 1202 | N | HIS | A | 190 | 25.657 | 65.024 | 13.791 | 1.00 | 22.95 A | N |
| ATOM | 1203 | CA | HIS | A | 190 | 25.837 | 66.464 | 13.922 | 1.00 | 20.72 A | C |
| ATOM | 1204 | CB | HIS | A | 190 | 25.577 | 66.965 | 15.342 | 1.00 | 22.21 A | C |
| ATOM | 1205 | CG | HIS | A | 190 | 26.439 | 66.344 | 16.391 | 1.00 | 20.39 A | C |
| ATOM | 1206 | CD2 | HIS | A | 190 | 27.660 | 65.767 | 16.326 | 1.00 | 24.43 A | C |
| ATOM | 1207 | ND1 | HIS | A | 190 | 26.062 | 66.297 | 17.715 | 1.00 | 24.65 A | N |
| ATOM | 1208 | CE1 | HIS | A | 190 | 27.008 | 65.707 | 18.420 | 1.00 | 26.85 A | C |
| ATOM | 1209 | NE2 | HIS | A | 190 | 27.982 | 65.364 | 17.599 | 1.00 | 23.35 A | N |
| ATOM | 1210 | C | HIS | A | 190 | 27.188 | 66.908 | 13.416 | 1.00 | 22.43 A | C |
| ATOM | 1211 | O | HIS | A | 190 | 28.005 | 66.081 | 13.008 | 1.00 | 20.43 A | O |
| ATOM | 1212 | N | ALA | A | 191 | 27.406 | 68.219 | 13.415 | 1.00 | 18.09 A | N |
| ATOM | 1213 | CA | ALA | A | 191 | 28.596 | 68.769 | 12.784 | 1.00 | 23.36 A | C |
| ATOM | 1214 | CB | ALA | A | 191 | 28.425 | 68.806 | 11.258 | 1.00 | 21.01 A | C |
| ATOM | 1215 | C | ALA | A | 191 | 28.839 | 70.161 | 13.318 | 1.00 | 21.11 A | C |
| ATOM | 1216 | O | ALA | A | 191 | 27.946 | 70.761 | 13.891 | 1.00 | 22.47 A | O |
| ATOM | 1217 | N | PHE | A | 192 | 30.050 | 70.667 | 13.116 | 1.00 | 21.67 A | N |
| ATOM | 1218 | CA | PHE | A | 192 | 30.451 | 71.971 | 13.635 | 1.00 | 26.13 A | C |
| ATOM | 1219 | CB | PHE | A | 192 | 31.518 | 71.769 | 14.723 | 1.00 | 25.80 A | C |
| ATOM | 1220 | CG | PHE | A | 192 | 31.134 | 70.712 | 15.739 | 1.00 | 23.93 A | C |
| ATOM | 1221 | CD1 | PHE | A | 192 | 30.282 | 71.017 | 16.792 | 1.00 | 27.38 A | C |
| ATOM | 1222 | CD2 | PHE | A | 192 | 31.574 | 69.402 | 15.600 | 1.00 | 27.60 A | C |
| ATOM | 1223 | CE1 | PHE | A | 192 | 29.889 | 70.040 | 17.703 | 1.00 | 26.70 A | C |
| ATOM | 1224 | CE2 | PHE | A | 192 | 31.190 | 68.422 | 16.516 | 1.00 | 29.79 A | C |
| ATOM | 1225 | CZ | PHE | A | 192 | 30.357 | 68.745 | 17.572 | 1.00 | 26.29 A | C |
| ATOM | 1226 | C | PHE | A | 192 | 30.934 | 72.912 | 12.515 | 1.00 | 24.39 A | C |
| ATOM | 1227 | O | PHE | A | 192 | 31.520 | 72.471 | 11.520 | 1.00 | 19.81 A | O |
| ATOM | 1228 | N | PRO | A | 193 | 30.674 | 74.215 | 12.673 | 1.00 | 22.54 A | N |

TABLE 15-continued

Coordinates for apo form of proMMP9(35-444 ΔFnII) (SEQ ID NO: 12)

| ATOM | 1229 | CD | PRO | A | 193 | 30.110 | 74.812 | 13.898 | 1.00 | 19.32 | A | C |
|------|------|-----|-----|---|-----|--------|--------|--------|------|-------|---|---|
| ATOM | 1230 | CA | PRO | A | 193 | 30.993 | 75.238 | 11.664 | 1.00 | 19.16 | A | C |
| ATOM | 1231 | CB | PRO | A | 193 | 30.422 | 76.515 | 12.286 | 1.00 | 23.22 | A | C |
| ATOM | 1232 | CG | PRO | A | 193 | 30.485 | 76.256 | 13.758 | 1.00 | 28.21 | A | C |
| ATOM | 1233 | C | PRO | A | 193 | 32.495 | 75.378 | 11.469 | 1.00 | 24.38 | A | C |
| ATOM | 1234 | O | PRO | A | 193 | 33.245 | 75.121 | 12.413 | 1.00 | 24.91 | A | O |
| ATOM | 1235 | N | PRO | A | 194 | 32.930 | 75.785 | 10.260 | 1.00 | 29.17 | A | N |
| ATOM | 1236 | CD | PRO | A | 194 | 32.086 | 76.297 | 9.164 | 1.00 | 22.00 | A | C |
| ATOM | 1237 | CA | PRO | A | 194 | 34.361 | 75.866 | 9.938 | 1.00 | 22.91 | A | C |
| ATOM | 1238 | CB | PRO | A | 194 | 34.383 | 76.672 | 8.640 | 1.00 | 22.42 | A | C |
| ATOM | 1239 | CG | PRO | A | 194 | 33.054 | 76.432 | 8.017 | 1.00 | 23.54 | A | C |
| ATOM | 1240 | C | PRO | A | 194 | 35.131 | 76.599 | 11.022 | 1.00 | 22.56 | A | C |
| ATOM | 1241 | O | PRO | A | 194 | 34.621 | 77.567 | 11.586 | 1.00 | 26.04 | A | O |
| ATOM | 1242 | N | GLY | A | 195 | 36.328 | 76.117 | 11.328 | 1.00 | 22.70 | A | N |
| ATOM | 1243 | CA | GLY | A | 195 | 37.185 | 76.782 | 12.284 | 1.00 | 23.27 | A | C |
| ATOM | 1244 | C | GLY | A | 195 | 38.234 | 75.848 | 12.857 | 1.00 | 30.20 | A | C |
| ATOM | 1245 | O | GLY | A | 195 | 38.473 | 74.769 | 12.319 | 1.00 | 27.56 | A | O |
| ATOM | 1246 | N | PRO | A | 196 | 38.860 | 76.259 | 13.967 | 1.00 | 25.85 | A | N |
| ATOM | 1247 | CD | PRO | A | 196 | 38.541 | 77.505 | 14.674 | 1.00 | 29.35 | A | C |
| ATOM | 1248 | CA | PRO | A | 196 | 39.933 | 75.506 | 14.622 | 1.00 | 32.15 | A | C |
| ATOM | 1249 | CB | PRO | A | 196 | 40.544 | 76.525 | 15.591 | 1.00 | 29.63 | A | C |
| ATOM | 1250 | CG | PRO | A | 196 | 39.814 | 77.827 | 15.362 | 1.00 | 33.83 | A | C |
| ATOM | 1251 | C | PRO | A | 196 | 39.400 | 74.341 | 15.443 | 1.00 | 34.18 | A | C |
| ATOM | 1252 | O | PRO | A | 196 | 38.258 | 74.383 | 15.914 | 1.00 | 31.65 | A | O |
| ATOM | 1253 | N | GLY | A | 197 | 40.242 | 73.331 | 15.633 | 1.00 | 28.73 | A | N |
| ATOM | 1254 | CA | GLY | A | 197 | 39.962 | 72.265 | 16.572 | 1.00 | 35.57 | A | C |
| ATOM | 1255 | C | GLY | A | 197 | 38.790 | 71.426 | 16.128 | 1.00 | 37.34 | A | C |
| ATOM | 1256 | O | GLY | A | 197 | 38.791 | 70.921 | 15.016 | 1.00 | 30.91 | A | O |
| ATOM | 1257 | N | ILE | A | 198 | 37.779 | 71.288 | 16.981 | 1.00 | 25.71 | A | N |
| ATOM | 1258 | CA | ILE | A | 198 | 36.635 | 70.459 | 16.622 | 1.00 | 30.08 | A | C |
| ATOM | 1259 | CB | ILE | A | 198 | 35.768 | 70.110 | 17.825 | 1.00 | 28.72 | A | C |
| ATOM | 1260 | CG2 | ILE | A | 198 | 34.847 | 71.268 | 18.179 | 1.00 | 31.56 | A | C |
| ATOM | 1261 | CG1 | ILE | A | 198 | 34.959 | 68.851 | 17.532 | 1.00 | 31.98 | A | C |
| ATOM | 1262 | CD1 | ILE | A | 198 | 33.786 | 68.685 | 18.420 | 1.00 | 30.63 | A | C |
| ATOM | 1263 | C | ILE | A | 198 | 35.753 | 71.108 | 15.554 | 1.00 | 30.39 | A | C |
| ATOM | 1264 | O | ILE | A | 198 | 34.929 | 70.439 | 14.924 | 1.00 | 31.90 | A | O |
| ATOM | 1265 | N | GLN | A | 199 | 35.908 | 72.410 | 15.352 | 1.00 | 31.18 | A | N |
| ATOM | 1266 | CA | GLN | A | 199 | 35.105 | 73.073 | 14.339 | 1.00 | 29.84 | A | C |
| ATOM | 1267 | CB | GLN | A | 199 | 35.352 | 74.579 | 14.370 | 1.00 | 25.60 | A | C |
| ATOM | 1268 | CG | GLN | A | 199 | 34.920 | 75.144 | 15.718 | 1.00 | 28.40 | A | C |
| ATOM | 1269 | CD | GLN | A | 199 | 34.975 | 76.647 | 15.815 | 1.00 | 31.87 | A | C |
| ATOM | 1270 | OE1 | GLN | A | 199 | 34.604 | 77.355 | 14.880 | 1.00 | 29.19 | A | O |
| ATOM | 1271 | NE2 | GLN | A | 199 | 35.420 | 77.149 | 16.970 | 1.00 | 26.73 | A | N |
| ATOM | 1272 | C | GLN | A | 199 | 35.366 | 72.418 | 12.986 | 1.00 | 29.89 | A | C |
| ATOM | 1273 | O | GLN | A | 199 | 36.479 | 71.976 | 12.717 | 1.00 | 27.68 | A | O |
| ATOM | 1274 | N | GLY | A | 200 | 34.323 | 72.310 | 12.163 | 1.00 | 26.78 | A | N |
| ATOM | 1275 | CA | GLY | A | 200 | 34.416 | 71.606 | 10.896 | 1.00 | 21.24 | A | C |
| ATOM | 1276 | C | GLY | A | 200 | 34.180 | 70.091 | 10.944 | 1.00 | 25.64 | A | C |
| ATOM | 1277 | O | GLY | A | 200 | 34.025 | 69.433 | 9.897 | 1.00 | 18.55 | A | O |
| ATOM | 1278 | N | ASP | A | 201 | 34.161 | 69.518 | 12.143 | 1.00 | 24.11 | A | N |
| ATOM | 1279 | CA | ASP | A | 201 | 33.989 | 68.073 | 12.263 | 1.00 | 20.38 | A | C |
| ATOM | 1280 | CB | ASP | A | 201 | 34.490 | 67.580 | 13.624 | 1.00 | 26.18 | A | C |
| ATOM | 1281 | CG | ASP | A | 201 | 35.981 | 67.665 | 13.734 | 1.00 | 24.98 | A | C |
| ATOM | 1282 | OD1 | ASP | A | 201 | 36.605 | 67.919 | 12.683 | 1.00 | 27.56 | A | O |
| ATOM | 1283 | OD2 | ASP | A | 201 | 36.520 | 67.497 | 14.849 | 1.00 | 22.34 | A | O |
| ATOM | 1284 | C | ASP | A | 201 | 32.549 | 67.620 | 12.060 | 1.00 | 21.02 | A | C |
| ATOM | 1285 | O | ASP | A | 201 | 31.613 | 68.378 | 12.297 | 1.00 | 19.68 | A | O |
| ATOM | 1286 | N | ALA | A | 202 | 32.395 | 66.365 | 11.650 | 1.00 | 20.34 | A | N |
| ATOM | 1287 | CA | ALA | A | 202 | 31.093 | 65.782 | 11.383 | 1.00 | 19.03 | A | C |
| ATOM | 1288 | CB | ALA | A | 202 | 30.919 | 65.596 | 9.865 | 1.00 | 16.44 | A | C |
| ATOM | 1289 | C | ALA | A | 202 | 30.977 | 64.435 | 12.092 | 1.00 | 17.95 | A | C |
| ATOM | 1290 | O | ALA | A | 202 | 31.754 | 63.527 | 11.818 | 1.00 | 20.14 | A | O |
| ATOM | 1291 | N | HIS | A | 203 | 30.008 | 64.296 | 12.983 | 1.00 | 18.96 | A | N |
| ATOM | 1292 | CA | HIS | A | 203 | 29.849 | 63.040 | 13.715 | 1.00 | 22.20 | A | C |
| ATOM | 1293 | CB | HIS | A | 203 | 29.923 | 63.290 | 15.225 | 1.00 | 20.47 | A | C |
| ATOM | 1294 | CG | HIS | A | 203 | 31.199 | 63.937 | 15.666 | 1.00 | 18.78 | A | C |
| ATOM | 1295 | CD2 | HIS | A | 203 | 32.321 | 64.256 | 14.978 | 1.00 | 23.70 | A | C |
| ATOM | 1296 | ND1 | HIS | A | 203 | 31.422 | 64.340 | 16.966 | 1.00 | 27.81 | A | N |
| ATOM | 1297 | CE1 | HIS | A | 203 | 32.622 | 64.885 | 17.058 | 1.00 | 27.49 | A | C |
| ATOM | 1298 | NE2 | HIS | A | 203 | 33.186 | 64.850 | 15.865 | 1.00 | 22.82 | A | N |
| ATOM | 1299 | C | HIS | A | 203 | 28.546 | 62.329 | 13.345 | 1.00 | 23.25 | A | C |
| ATOM | 1300 | O | HIS | A | 203 | 27.489 | 62.963 | 13.203 | 1.00 | 19.33 | A | O |
| ATOM | 1301 | N | PHE | A | 204 | 28.633 | 61.010 | 13.198 | 1.00 | 19.60 | A | N |
| ATOM | 1302 | CA | PHE | A | 204 | 27.492 | 60.199 | 12.779 | 1.00 | 21.49 | A | C |
| ATOM | 1303 | CB | PHE | A | 204 | 27.821 | 59.516 | 11.456 | 1.00 | 21.59 | A | C |
| ATOM | 1304 | CG | PHE | A | 204 | 28.095 | 60.485 | 10.334 | 1.00 | 22.75 | A | C |
| ATOM | 1305 | CD1 | PHE | A | 204 | 29.365 | 61.003 | 10.129 | 1.00 | 19.92 | A | C |
| ATOM | 1306 | CD2 | PHE | A | 204 | 27.067 | 60.901 | 9.512 | 1.00 | 19.75 | A | C |

TABLE 15-continued

Coordinates for apo form of proMMP9(35-444 ΔFnII) (SEQ ID NO: 12)

| ATOM | 1307 | CE1 | PHE | A | 204 | 29.617 | 61.912 | 9.092 | 1.00 | 19.21 | A | C |
|---|---|---|---|---|---|---|---|---|---|---|---|---|
| ATOM | 1308 | CE2 | PHE | A | 204 | 27.294 | 61.801 | 8.479 | 1.00 | 15.45 | A | C |
| ATOM | 1309 | CZ | PHE | A | 204 | 28.571 | 62.312 | 8.266 | 1.00 | 17.79 | A | C |
| ATOM | 1310 | C | PHE | A | 204 | 27.139 | 59.163 | 13.846 | 1.00 | 22.85 | A | C |
| ATOM | 1311 | O | PHE | A | 204 | 28.011 | 58.429 | 14.314 | 1.00 | 19.45 | A | O |
| ATOM | 1312 | N | ASP | A | 205 | 25.860 | 59.117 | 14.230 | 1.00 | 23.70 | A | N |
| ATOM | 1313 | CA | ASP | A | 205 | 25.403 | 58.305 | 15.362 | 1.00 | 19.94 | A | C |
| ATOM | 1314 | CB | ASP | A | 205 | 24.048 | 58.820 | 15.874 | 1.00 | 23.02 | A | C |
| ATOM | 1315 | CG | ASP | A | 205 | 23.531 | 58.044 | 17.097 | 1.00 | 24.12 | A | C |
| ATOM | 1316 | OD1 | ASP | A | 205 | 24.156 | 57.055 | 17.522 | 1.00 | 23.68 | A | O |
| ATOM | 1317 | OD2 | ASP | A | 205 | 22.492 | 58.438 | 17.652 | 1.00 | 19.54 | A | O |
| ATOM | 1318 | C | ASP | A | 205 | 25.300 | 56.842 | 14.972 | 1.00 | 22.65 | A | C |
| ATOM | 1319 | O | ASP | A | 205 | 24.382 | 56.439 | 14.236 | 1.00 | 24.59 | A | O |
| ATOM | 1320 | N | ASP | A | 206 | 26.233 | 56.040 | 15.471 | 1.00 | 21.76 | A | N |
| ATOM | 1321 | CA | ASP | A | 206 | 26.348 | 54.682 | 14.988 | 1.00 | 22.23 | A | C |
| ATOM | 1322 | CB | ASP | A | 206 | 27.761 | 54.146 | 15.171 | 1.00 | 20.72 | A | C |
| ATOM | 1323 | CG | ASP | A | 206 | 28.092 | 53.036 | 14.187 | 1.00 | 18.65 | A | C |
| ATOM | 1324 | OD1 | ASP | A | 206 | 27.285 | 52.770 | 13.271 | 1.00 | 22.02 | A | O |
| ATOM | 1325 | OD2 | ASP | A | 206 | 29.175 | 52.433 | 14.326 | 1.00 | 22.24 | A | O |
| ATOM | 1326 | C | ASP | A | 206 | 25.346 | 53.774 | 15.663 | 1.00 | 23.45 | A | C |
| ATOM | 1327 | O | ASP | A | 206 | 25.384 | 52.577 | 15.466 | 1.00 | 24.62 | A | O |
| ATOM | 1328 | N | ASP | A | 207 | 24.461 | 54.346 | 16.473 | 1.00 | 22.69 | A | N |
| ATOM | 1329 | CA | ASP | A | 207 | 23.316 | 53.601 | 16.967 | 1.00 | 22.44 | A | C |
| ATOM | 1330 | CB | ASP | A | 207 | 22.773 | 54.212 | 18.276 | 1.00 | 23.50 | A | C |
| ATOM | 1331 | CG | ASP | A | 207 | 23.460 | 53.648 | 19.527 | 1.00 | 26.19 | A | C |
| ATOM | 1332 | OD1 | ASP | A | 207 | 24.074 | 52.571 | 19.436 | 1.00 | 19.67 | A | O |
| ATOM | 1333 | OD2 | ASP | A | 207 | 23.380 | 54.277 | 20.606 | 1.00 | 24.21 | A | O |
| ATOM | 1334 | C | ASP | A | 207 | 22.229 | 53.549 | 15.892 | 1.00 | 22.53 | A | C |
| ATOM | 1335 | O | ASP | A | 207 | 21.194 | 52.909 | 16.077 | 1.00 | 26.89 | A | O |
| ATOM | 1336 | N | GLU | A | 208 | 22.450 | 54.235 | 14.771 | 1.00 | 22.42 | A | N |
| ATOM | 1337 | CA | GLU | A | 208 | 21.602 | 54.035 | 13.595 | 1.00 | 19.67 | A | C |
| ATOM | 1338 | CB | GLU | A | 208 | 21.558 | 55.279 | 12.722 | 1.00 | 22.24 | A | C |
| ATOM | 1339 | CG | GLU | A | 208 | 21.338 | 56.558 | 13.437 | 1.00 | 19.10 | A | C |
| ATOM | 1340 | CD | GLU | A | 208 | 20.128 | 56.522 | 14.310 | 1.00 | 21.30 | A | C |
| ATOM | 1341 | OE1 | GLU | A | 208 | 19.215 | 55.715 | 14.030 | 1.00 | 23.81 | A | O |
| ATOM | 1342 | OE2 | GLU | A | 208 | 20.086 | 57.306 | 15.286 | 1.00 | 25.29 | A | O |
| ATOM | 1343 | C | GLU | A | 208 | 22.194 | 52.947 | 12.730 | 1.00 | 21.97 | A | C |
| ATOM | 1344 | O | GLU | A | 208 | 23.410 | 52.811 | 12.669 | 1.00 | 24.08 | A | O |
| ATOM | 1345 | N | LEU | A | 209 | 21.332 | 52.203 | 12.040 | 1.00 | 17.26 | A | N |
| ATOM | 1346 | CA | LEU | A | 209 | 21.743 | 51.370 | 10.921 | 1.00 | 23.11 | A | C |
| ATOM | 1347 | CB | LEU | A | 209 | 20.619 | 50.405 | 10.513 | 1.00 | 19.69 | A | C |
| ATOM | 1348 | CG | LEU | A | 209 | 20.855 | 49.552 | 9.252 | 1.00 | 22.75 | A | C |
| ATOM | 1349 | CD1 | LEU | A | 209 | 21.952 | 48.533 | 9.519 | 1.00 | 20.86 | A | C |
| ATOM | 1350 | CD2 | LEU | A | 209 | 19.567 | 48.860 | 8.761 | 1.00 | 20.19 | A | C |
| ATOM | 1351 | C | LEU | A | 209 | 22.034 | 52.299 | 9.748 | 1.00 | 22.51 | A | C |
| ATOM | 1352 | O | LEU | A | 209 | 21.125 | 52.943 | 9.237 | 1.00 | 19.37 | A | O |
| ATOM | 1353 | N | TRP | A | 210 | 23.293 | 52.380 | 9.332 | 1.00 | 24.64 | A | N |
| ATOM | 1354 | CA | TRP | A | 210 | 23.635 | 53.141 | 8.133 | 1.00 | 21.60 | A | C |
| ATOM | 1355 | CB | TRP | A | 210 | 24.999 | 53.833 | 8.283 | 1.00 | 23.45 | A | C |
| ATOM | 1356 | CG | TRP | A | 210 | 24.970 | 54.842 | 9.392 | 1.00 | 23.31 | A | C |
| ATOM | 1357 | CD2 | TRP | A | 210 | 24.338 | 56.129 | 9.367 | 1.00 | 25.13 | A | C |
| ATOM | 1358 | CE2 | TRP | A | 210 | 24.537 | 56.714 | 10.629 | 1.00 | 23.45 | A | C |
| ATOM | 1359 | CE3 | TRP | A | 210 | 23.637 | 56.848 | 8.393 | 1.00 | 22.49 | A | C |
| ATOM | 1360 | CD1 | TRP | A | 210 | 25.488 | 54.696 | 10.644 | 1.00 | 23.29 | A | C |
| ATOM | 1361 | NE1 | TRP | A | 210 | 25.244 | 55.821 | 11.390 | 1.00 | 20.62 | A | N |
| ATOM | 1362 | CZ2 | TRP | A | 210 | 24.049 | 57.986 | 10.948 | 1.00 | 23.89 | A | C |
| ATOM | 1363 | CZ3 | TRP | A | 210 | 23.158 | 58.103 | 8.711 | 1.00 | 21.43 | A | C |
| ATOM | 1364 | CH2 | TRP | A | 210 | 23.380 | 58.667 | 9.967 | 1.00 | 16.83 | A | C |
| ATOM | 1365 | C | TRP | A | 210 | 23.594 | 52.257 | 6.893 | 1.00 | 27.23 | A | C |
| ATOM | 1366 | O | TRP | A | 210 | 24.038 | 51.101 | 6.918 | 1.00 | 23.47 | A | O |
| ATOM | 1367 | N | SER | A | 211 | 23.022 | 52.808 | 5.826 | 1.00 | 25.99 | A | N |
| ATOM | 1368 | CA | SER | A | 211 | 22.995 | 52.162 | 4.520 | 1.00 | 23.44 | A | C |
| ATOM | 1369 | CB | SER | A | 211 | 21.750 | 51.279 | 4.370 | 1.00 | 21.90 | A | C |
| ATOM | 1370 | OG | SER | A | 211 | 20.552 | 52.052 | 4.396 | 1.00 | 20.73 | A | O |
| ATOM | 1371 | C | SER | A | 211 | 23.001 | 53.243 | 3.447 | 1.00 | 22.35 | A | C |
| ATOM | 1372 | O | SER | A | 211 | 23.518 | 54.347 | 3.657 | 1.00 | 18.50 | A | O |
| ATOM | 1373 | N | LEU | A | 212 | 22.425 | 52.932 | 2.292 | 1.00 | 24.80 | A | N |
| ATOM | 1374 | CA | LEU | A | 212 | 22.223 | 53.955 | 1.287 | 1.00 | 27.49 | A | C |
| ATOM | 1375 | CB | LEU | A | 212 | 22.809 | 53.529 | −0.055 | 1.00 | 24.56 | A | C |
| ATOM | 1376 | CG | LEU | A | 212 | 24.330 | 53.402 | 0.044 | 1.00 | 27.84 | A | C |
| ATOM | 1377 | CD1 | LEU | A | 212 | 24.992 | 53.043 | −1.291 | 1.00 | 28.51 | A | C |
| ATOM | 1378 | CD2 | LEU | A | 212 | 24.912 | 54.693 | 0.610 | 1.00 | 23.59 | A | C |
| ATOM | 1379 | C | LEU | A | 212 | 20.756 | 54.391 | 1.174 | 1.00 | 27.71 | A | C |
| ATOM | 1380 | O | LEU | A | 212 | 20.349 | 54.936 | 0.153 | 1.00 | 27.60 | A | O |
| ATOM | 1381 | N | GLY | A | 213 | 19.982 | 54.158 | 2.235 | 1.00 | 26.13 | A | N |
| ATOM | 1382 | CA | GLY | A | 213 | 18.612 | 54.648 | 2.335 | 1.00 | 26.04 | A | C |
| ATOM | 1383 | C | GLY | A | 213 | 17.517 | 53.792 | 1.700 | 1.00 | 31.54 | A | C |
| ATOM | 1384 | O | GLY | A | 213 | 16.324 | 54.013 | 1.938 | 1.00 | 26.88 | A | O |

TABLE 15-continued

Coordinates for apo form of proMMP9(35-444 ΔFnII) (SEQ ID NO: 12)

| ATOM | 1385 | N | LYS | A | 389 | 17.915 | 52.828 | 0.879 | 1.00 | 31.49 | A | N |
|---|---|---|---|---|---|---|---|---|---|---|---|---|
| ATOM | 1386 | CA | LYS | A | 389 | 16.964 | 51.890 | 0.298 | 1.00 | 33.93 | A | C |
| ATOM | 1387 | CB | LYS | A | 389 | 17.379 | 51.488 | −1.111 | 1.00 | 36.04 | A | C |
| ATOM | 1388 | CG | LYS | A | 389 | 17.116 | 52.553 | −2.151 | 1.00 | 40.69 | A | C |
| ATOM | 1389 | CD | LYS | A | 389 | 15.619 | 52.827 | −2.276 | 1.00 | 45.66 | A | C |
| ATOM | 1390 | CE | LYS | A | 389 | 14.884 | 51.640 | −2.897 | 1.00 | 50.54 | A | C |
| ATOM | 1391 | NZ | LYS | A | 389 | 13.457 | 51.966 | −3.186 | 1.00 | 50.29 | A | N |
| ATOM | 1392 | C | LYS | A | 389 | 16.834 | 50.642 | 1.153 | 1.00 | 35.52 | A | C |
| ATOM | 1393 | O | LYS | A | 389 | 17.830 | 50.101 | 1.643 | 1.00 | 30.72 | A | O |
| ATOM | 1394 | N | GLY | A | 390 | 15.595 | 50.195 | 1.312 | 1.00 | 29.44 | A | N |
| ATOM | 1395 | CA | GLY | A | 390 | 15.293 | 48.971 | 2.027 | 1.00 | 32.26 | A | C |
| ATOM | 1396 | C | GLY | A | 390 | 15.127 | 49.211 | 3.512 | 1.00 | 33.50 | A | C |
| ATOM | 1397 | O | GLY | A | 390 | 14.021 | 49.120 | 4.053 | 1.00 | 44.73 | A | O |
| ATOM | 1398 | N | GLN | A | 391 | 16.234 | 49.496 | 4.181 | 1.00 | 28.66 | A | N |
| ATOM | 1399 | CA | GLN | A | 391 | 16.227 | 49.742 | 5.617 | 1.00 | 29.78 | A | C |
| ATOM | 1400 | CB | GLN | A | 391 | 16.327 | 48.421 | 6.399 | 1.00 | 30.83 | A | C |
| ATOM | 1401 | CG | GLN | A | 391 | 15.479 | 47.268 | 5.844 | 1.00 | 31.95 | A | C |
| ATOM | 1402 | CD | GLN | A | 391 | 15.385 | 46.078 | 6.787 | 1.00 | 32.46 | A | C |
| ATOM | 1403 | OE1 | GLN | A | 391 | 15.724 | 46.173 | 7.968 | 1.00 | 33.53 | A | O |
| ATOM | 1404 | NE2 | GLN | A | 391 | 14.908 | 44.950 | 6.268 | 1.00 | 41.33 | A | N |
| ATOM | 1405 | C | GLN | A | 391 | 17.424 | 50.624 | 5.946 | 1.00 | 26.24 | A | C |
| ATOM | 1406 | O | GLN | A | 391 | 18.430 | 50.592 | 5.236 | 1.00 | 27.65 | A | O |
| ATOM | 1407 | N | GLY | A | 392 | 17.310 | 51.413 | 7.012 | 1.00 | 23.37 | A | N |
| ATOM | 1408 | CA | GLY | A | 392 | 18.429 | 52.183 | 7.523 | 1.00 | 20.75 | A | C |
| ATOM | 1409 | C | GLY | A | 392 | 18.471 | 53.588 | 6.951 | 1.00 | 26.82 | A | C |
| ATOM | 1410 | O | GLY | A | 392 | 17.734 | 53.910 | 6.011 | 1.00 | 22.43 | A | O |
| ATOM | 1411 | N | TYR | A | 393 | 19.337 | 54.427 | 7.511 | 1.00 | 21.44 | A | N |
| ATOM | 1412 | CA | TYR | A | 393 | 19.488 | 55.797 | 7.012 | 1.00 | 23.82 | A | C |
| ATOM | 1413 | CB | TYR | A | 393 | 19.759 | 56.765 | 8.164 | 1.00 | 22.67 | A | C |
| ATOM | 1414 | CG | TYR | A | 393 | 18.634 | 56.845 | 9.164 | 1.00 | 22.03 | A | C |
| ATOM | 1415 | CD1 | TYR | A | 393 | 17.542 | 57.698 | 8.958 | 1.00 | 22.60 | A | C |
| ATOM | 1416 | CE1 | TYR | A | 393 | 16.504 | 57.770 | 9.884 | 1.00 | 22.47 | A | C |
| ATOM | 1417 | CD2 | TYR | A | 393 | 18.657 | 56.074 | 10.329 | 1.00 | 26.89 | A | C |
| ATOM | 1418 | CE2 | TYR | A | 393 | 17.623 | 56.146 | 11.257 | 1.00 | 24.45 | A | C |
| ATOM | 1419 | CZ | TYR | A | 393 | 16.556 | 56.995 | 11.029 | 1.00 | 23.23 | A | C |
| ATOM | 1420 | OH | TYR | A | 393 | 15.535 | 57.055 | 11.963 | 1.00 | 30.46 | A | O |
| ATOM | 1421 | C | TYR | A | 393 | 20.600 | 55.907 | 5.988 | 1.00 | 22.06 | A | C |
| ATOM | 1422 | O | TYR | A | 393 | 21.663 | 55.306 | 6.159 | 1.00 | 21.23 | A | O |
| ATOM | 1423 | N | SER | A | 394 | 20.355 | 56.677 | 4.926 | 1.00 | 20.20 | A | N |
| ATOM | 1424 | CA | SER | A | 394 | 21.381 | 56.940 | 3.933 | 1.00 | 22.18 | A | C |
| ATOM | 1425 | CB | SER | A | 394 | 20.808 | 57.702 | 2.722 | 1.00 | 19.88 | A | C |
| ATOM | 1426 | OG | SER | A | 394 | 21.860 | 58.105 | 1.856 | 1.00 | 17.16 | A | O |
| ATOM | 1427 | C | SER | A | 394 | 22.533 | 57.749 | 4.509 | 1.00 | 18.58 | A | C |
| ATOM | 1428 | O | SER | A | 394 | 22.377 | 58.923 | 4.849 | 1.00 | 18.50 | A | O |
| ATOM | 1429 | N | LEU | A | 395 | 23.698 | 57.126 | 4.592 | 1.00 | 16.64 | A | N |
| ATOM | 1430 | CA | LEU | A | 395 | 24.920 | 57.840 | 4.911 | 1.00 | 19.19 | A | C |
| ATOM | 1431 | CB | LEU | A | 395 | 26.060 | 56.839 | 5.004 | 1.00 | 20.92 | A | C |
| ATOM | 1432 | CG | LEU | A | 395 | 27.405 | 57.412 | 5.419 | 1.00 | 15.52 | A | C |
| ATOM | 1433 | CD1 | LEU | A | 395 | 27.309 | 58.000 | 6.798 | 1.00 | 18.24 | A | C |
| ATOM | 1434 | CD2 | LEU | A | 395 | 28.419 | 56.284 | 5.382 | 1.00 | 16.12 | A | C |
| ATOM | 1435 | C | LEU | A | 395 | 25.299 | 58.920 | 3.883 | 1.00 | 20.72 | A | C |
| ATOM | 1436 | O | LEU | A | 395 | 25.887 | 59.948 | 4.226 | 1.00 | 17.03 | A | O |
| ATOM | 1437 | N | PHE | A | 396 | 25.020 | 58.668 | 2.612 | 1.00 | 19.09 | A | N |
| ATOM | 1438 | CA | PHE | A | 396 | 25.335 | 59.646 | 1.587 | 1.00 | 14.85 | A | C |
| ATOM | 1439 | CB | PHE | A | 396 | 25.028 | 59.073 | 0.196 | 1.00 | 16.67 | A | C |
| ATOM | 1440 | CG | PHE | A | 396 | 24.979 | 60.102 | −0.900 | 1.00 | 18.43 | A | C |
| ATOM | 1441 | CD1 | PHE | A | 396 | 26.044 | 60.976 | −1.116 | 1.00 | 16.10 | A | C |
| ATOM | 1442 | CD2 | PHE | A | 396 | 23.882 | 60.165 | −1.747 | 1.00 | 19.50 | A | C |
| ATOM | 1443 | CE1 | PHE | A | 396 | 25.988 | 61.914 | −2.137 | 1.00 | 17.21 | A | C |
| ATOM | 1444 | CE2 | PHE | A | 396 | 23.829 | 61.105 | −2.779 | 1.00 | 17.18 | A | C |
| ATOM | 1445 | CZ | PHE | A | 396 | 24.868 | 61.980 | −2.966 | 1.00 | 16.87 | A | C |
| ATOM | 1446 | C | PHE | A | 396 | 24.580 | 60.959 | 1.847 | 1.00 | 17.39 | A | C |
| ATOM | 1447 | O | PHE | A | 396 | 25.187 | 62.022 | 1.872 | 1.00 | 15.92 | A | O |
| ATOM | 1448 | N | LEU | A | 397 | 23.268 | 60.879 | 2.070 | 1.00 | 14.77 | A | N |
| ATOM | 1449 | CA | LEU | A | 397 | 22.436 | 62.090 | 2.251 | 1.00 | 18.57 | A | C |
| ATOM | 1450 | CB | LEU | A | 397 | 20.945 | 61.756 | 2.114 | 1.00 | 10.89 | A | C |
| ATOM | 1451 | CG | LEU | A | 397 | 20.395 | 61.299 | 0.763 | 1.00 | 16.80 | A | C |
| ATOM | 1452 | CD1 | LEU | A | 397 | 19.022 | 60.664 | 0.921 | 1.00 | 14.99 | A | C |
| ATOM | 1453 | CD2 | LEU | A | 397 | 20.359 | 62.464 | −0.238 | 1.00 | 16.45 | A | C |
| ATOM | 1454 | C | LEU | A | 397 | 22.675 | 62.803 | 3.592 | 1.00 | 16.09 | A | C |
| ATOM | 1455 | O | LEU | A | 397 | 22.695 | 64.033 | 3.662 | 1.00 | 16.68 | A | O |
| ATOM | 1456 | N | VAL | A | 398 | 22.822 | 62.030 | 4.659 | 1.00 | 13.58 | A | N |
| ATOM | 1457 | CA | VAL | A | 398 | 23.151 | 62.601 | 5.968 | 1.00 | 11.85 | A | C |
| ATOM | 1458 | CB | VAL | A | 398 | 23.104 | 61.544 | 7.112 | 1.00 | 18.88 | A | C |
| ATOM | 1459 | CG1 | VAL | A | 398 | 23.622 | 62.122 | 8.402 | 1.00 | 15.54 | A | C |
| ATOM | 1460 | CG2 | VAL | A | 398 | 21.672 | 61.023 | 7.310 | 1.00 | 18.70 | A | C |
| ATOM | 1461 | C | VAL | A | 398 | 24.513 | 63.274 | 5.925 | 1.00 | 17.07 | A | C |
| ATOM | 1462 | O | VAL | A | 398 | 24.664 | 64.397 | 6.422 | 1.00 | 17.67 | A | O |

TABLE 15-continued

| | | | | | | | | | | | |
|---|---|---|---|---|---|---|---|---|---|---|---|
| ATOM | 1463 | N | ALA | A | 399 | 25.508 | 62.597 | 5.343 | 1.00 | 16.28 A | N |
| ATOM | 1464 | CA | ALA | A | 399 | 26.814 | 63.214 | 5.143 | 1.00 | 21.17 A | C |
| ATOM | 1465 | CB | ALA | A | 399 | 27.797 | 62.248 | 4.481 | 1.00 | 13.68 A | C |
| ATOM | 1466 | C | ALA | A | 399 | 26.726 | 64.519 | 4.339 | 1.00 | 18.09 A | C |
| ATOM | 1467 | O | ALA | A | 399 | 27.328 | 65.520 | 4.718 | 1.00 | 22.97 A | O |
| ATOM | 1468 | N | ALA | A | 400 | 25.993 | 64.510 | 3.233 | 1.00 | 15.39 A | N |
| ATOM | 1469 | CA | ALA | A | 400 | 25.894 | 65.714 | 2.409 | 1.00 | 14.82 A | C |
| ATOM | 1470 | CB | ALA | A | 400 | 25.043 | 65.458 | 1.184 | 1.00 | 14.15 A | C |
| ATOM | 1471 | C | ALA | A | 400 | 25.340 | 66.891 | 3.232 | 1.00 | 18.84 A | C |
| ATOM | 1472 | O | ALA | A | 400 | 25.832 | 68.024 | 3.135 | 1.00 | 16.89 A | O |
| ATOM | 1473 | N | HIS | A | 401 | 24.327 | 66.614 | 4.048 | 1.00 | 16.48 A | N |
| ATOM | 1474 | CA | HIS | A | 401 | 23.727 | 67.641 | 4.911 | 1.00 | 14.00 A | C |
| ATOM | 1475 | CB | HIS | A | 401 | 22.417 | 67.127 | 5.527 | 1.00 | 14.73 A | C |
| ATOM | 1476 | CG | HIS | A | 401 | 21.875 | 67.968 | 6.646 | 1.00 | 14.40 A | C |
| ATOM | 1477 | CD2 | HIS | A | 401 | 22.265 | 68.099 | 7.942 | 1.00 | 16.05 A | C |
| ATOM | 1478 | ND1 | HIS | A | 401 | 20.771 | 68.780 | 6.499 | 1.00 | 13.21 A | N |
| ATOM | 1479 | CE1 | HIS | A | 401 | 20.504 | 69.382 | 7.644 | 1.00 | 14.56 A | C |
| ATOM | 1480 | NE2 | HIS | A | 401 | 21.399 | 68.993 | 8.536 | 1.00 | 15.39 A | N |
| ATOM | 1481 | C | HIS | A | 401 | 24.727 | 68.102 | 5.965 | 1.00 | 14.98 A | C |
| ATOM | 1482 | O | HIS | A | 401 | 24.928 | 69.303 | 6.140 | 1.00 | 14.19 A | O |
| ATOM | 1483 | N | GLU | A | 402 | 25.382 | 67.150 | 6.633 | 1.00 | 13.72 A | N |
| ATOM | 1484 | CA | GLU | A | 402 | 26.338 | 67.489 | 7.673 | 1.00 | 17.13 A | C |
| ATOM | 1485 | CB | GLU | A | 402 | 26.778 | 66.248 | 8.459 | 1.00 | 18.13 A | C |
| ATOM | 1486 | CG | GLU | A | 402 | 25.642 | 65.519 | 9.133 | 1.00 | 20.00 A | C |
| ATOM | 1487 | CD | GLU | A | 402 | 24.947 | 66.325 | 10.221 | 1.00 | 21.44 A | C |
| ATOM | 1488 | OE1 | GLU | A | 402 | 25.441 | 67.409 | 10.608 | 1.00 | 16.77 A | O |
| ATOM | 1489 | OE2 | GLU | A | 402 | 23.905 | 65.846 | 10.717 | 1.00 | 19.15 A | O |
| ATOM | 1490 | C | GLU | A | 402 | 27.553 | 68.251 | 7.154 | 1.00 | 16.87 A | C |
| ATOM | 1491 | O | GLU | A | 402 | 28.076 | 69.126 | 7.844 | 1.00 | 21.18 A | O |
| ATOM | 1492 | N | PHE | A | 403 | 27.999 | 67.929 | 5.943 | 1.00 | 22.04 A | N |
| ATOM | 1493 | CA | PHE | A | 403 | 29.135 | 68.628 | 5.344 | 1.00 | 17.59 A | C |
| ATOM | 1494 | CB | PHE | A | 403 | 29.607 | 67.908 | 4.081 | 1.00 | 18.84 A | C |
| ATOM | 1495 | CG | PHE | A | 403 | 30.211 | 66.547 | 4.344 | 1.00 | 15.71 A | C |
| ATOM | 1496 | CD1 | PHE | A | 403 | 30.533 | 66.152 | 5.640 | 1.00 | 18.70 A | C |
| ATOM | 1497 | CD2 | PHE | A | 403 | 30.462 | 65.673 | 3.304 | 1.00 | 15.16 A | C |
| ATOM | 1498 | CE1 | PHE | A | 403 | 31.084 | 64.894 | 5.885 | 1.00 | 21.21 A | C |
| ATOM | 1499 | CE2 | PHE | A | 403 | 31.025 | 64.434 | 3.527 | 1.00 | 18.09 A | C |
| ATOM | 1500 | CZ | PHE | A | 403 | 31.331 | 64.032 | 4.827 | 1.00 | 18.47 A | C |
| ATOM | 1501 | C | PHE | A | 403 | 28.802 | 70.099 | 5.051 | 1.00 | 19.68 A | C |
| ATOM | 1502 | O | PHE | A | 403 | 29.678 | 70.954 | 5.086 | 1.00 | 19.50 A | O |
| ATOM | 1503 | N | GLY | A | 404 | 27.537 | 70.374 | 4.748 | 1.00 | 19.48 A | N |
| ATOM | 1504 | CA | GLY | A | 404 | 27.058 | 71.738 | 4.590 | 1.00 | 21.80 A | C |
| ATOM | 1505 | C | GLY | A | 404 | 27.250 | 72.589 | 5.836 | 1.00 | 19.26 A | C |
| ATOM | 1506 | O | GLY | A | 404 | 27.681 | 73.748 | 5.751 | 1.00 | 16.35 A | O |
| ATOM | 1507 | N | HIS | A | 405 | 26.935 | 72.026 | 6.999 | 1.00 | 16.52 A | N |
| ATOM | 1508 | CA | HIS | A | 405 | 27.262 | 72.708 | 8.253 | 1.00 | 19.54 A | C |
| ATOM | 1509 | CB | HIS | A | 405 | 26.822 | 71.907 | 9.494 | 1.00 | 14.74 A | C |
| ATOM | 1510 | CG | HIS | A | 405 | 25.348 | 71.859 | 9.698 | 1.00 | 17.78 A | C |
| ATOM | 1511 | CD2 | HIS | A | 405 | 24.528 | 70.834 | 10.038 | 1.00 | 12.73 A | C |
| ATOM | 1512 | ND1 | HIS | A | 405 | 24.544 | 72.973 | 9.589 | 1.00 | 16.78 A | N |
| ATOM | 1513 | CE1 | HIS | A | 405 | 23.293 | 72.632 | 9.835 | 1.00 | 19.11 A | C |
| ATOM | 1514 | NE2 | HIS | A | 405 | 23.260 | 71.341 | 10.112 | 1.00 | 13.33 A | N |
| ATOM | 1515 | C | HIS | A | 405 | 28.760 | 72.945 | 8.337 | 1.00 | 17.13 A | C |
| ATOM | 1516 | O | HIS | A | 405 | 29.202 | 73.961 | 8.883 | 1.00 | 23.80 A | O |
| ATOM | 1517 | N | ALA | A | 406 | 29.539 | 72.000 | 7.815 | 1.00 | 16.56 A | N |
| ATOM | 1518 | CA | ALA | A | 406 | 30.975 | 71.982 | 8.042 | 1.00 | 14.45 A | C |
| ATOM | 1519 | CB | ALA | A | 406 | 31.531 | 70.568 | 7.875 | 1.00 | 19.51 A | C |
| ATOM | 1520 | C | ALA | A | 406 | 31.665 | 72.953 | 7.088 | 1.00 | 21.47 A | C |
| ATOM | 1521 | O | ALA | A | 406 | 32.869 | 73.170 | 7.192 | 1.00 | 18.14 A | O |
| ATOM | 1522 | N | LEU | A | 407 | 30.877 | 73.512 | 6.167 | 1.00 | 16.93 A | N |
| ATOM | 1523 | CA | LEU | A | 407 | 31.311 | 74.572 | 5.267 | 1.00 | 18.49 A | C |
| ATOM | 1524 | CB | LEU | A | 407 | 30.833 | 74.281 | 3.837 | 1.00 | 16.07 A | C |
| ATOM | 1525 | CG | LEU | A | 407 | 31.341 | 72.992 | 3.177 | 1.00 | 19.22 A | C |
| ATOM | 1526 | CD1 | LEU | A | 407 | 30.919 | 72.942 | 1.697 | 1.00 | 18.00 A | C |
| ATOM | 1527 | CD2 | LEU | A | 407 | 32.869 | 72.878 | 3.321 | 1.00 | 13.08 A | C |
| ATOM | 1528 | C | LEU | A | 407 | 30.752 | 75.925 | 5.710 | 1.00 | 17.72 A | C |
| ATOM | 1529 | O | LEU | A | 407 | 31.103 | 76.962 | 5.143 | 1.00 | 17.69 A | O |
| ATOM | 1530 | N | GLY | A | 408 | 29.858 | 75.903 | 6.695 | 1.00 | 22.14 A | N |
| ATOM | 1531 | CA | GLY | A | 408 | 29.282 | 77.121 | 7.255 | 1.00 | 19.75 A | C |
| ATOM | 1532 | C | GLY | A | 408 | 27.759 | 77.246 | 7.200 | 1.00 | 20.64 A | C |
| ATOM | 1533 | O | GLY | A | 408 | 27.196 | 78.189 | 7.758 | 1.00 | 22.87 A | O |
| ATOM | 1534 | N | LEU | A | 409 | 27.084 | 76.313 | 6.534 | 1.00 | 17.60 A | N |
| ATOM | 1535 | CA | LEU | A | 409 | 25.632 | 76.446 | 6.322 | 1.00 | 20.50 A | C |
| ATOM | 1536 | CB | LEU | A | 409 | 25.131 | 75.556 | 5.170 | 1.00 | 15.17 A | C |
| ATOM | 1537 | CG | LEU | A | 409 | 25.675 | 75.867 | 3.768 | 1.00 | 20.40 A | C |
| ATOM | 1538 | CD1 | LEU | A | 409 | 25.071 | 74.939 | 2.679 | 1.00 | 17.45 A | C |
| ATOM | 1539 | CD2 | LEU | A | 409 | 25.410 | 77.329 | 3.420 | 1.00 | 18.87 A | C |
| ATOM | 1540 | C | LEU | A | 409 | 24.819 | 76.139 | 7.568 | 1.00 | 21.48 A | C |

TABLE 15-continued

Coordinates for apo form of proMMP9(35-444 ΔFnII) (SEQ ID NO: 12)

| ATOM | 1541 | O | LEU | A | 409 | 25.130 | 75.221 | 8.311 | 1.00 | 19.29 | A | O |
|---|---|---|---|---|---|---|---|---|---|---|---|---|
| ATOM | 1542 | N | ASP | A | 410 | 23.757 | 76.910 | 7.764 | 1.00 | 21.66 | A | N |
| ATOM | 1543 | CA | ASP | A | 410 | 22.773 | 76.666 | 8.809 | 1.00 | 23.58 | A | C |
| ATOM | 1544 | CB | ASP | A | 410 | 22.197 | 78.001 | 9.298 | 1.00 | 23.76 | A | C |
| ATOM | 1545 | CG | ASP | A | 410 | 23.159 | 78.776 | 10.171 | 1.00 | 33.81 | A | C |
| ATOM | 1546 | OD1 | ASP | A | 410 | 24.149 | 78.190 | 10.656 | 1.00 | 26.62 | A | O |
| ATOM | 1547 | OD2 | ASP | A | 410 | 22.916 | 79.984 | 10.382 | 1.00 | 38.25 | A | O |
| ATOM | 1548 | C | ASP | A | 410 | 21.610 | 75.858 | 8.248 | 1.00 | 22.92 | A | C |
| ATOM | 1549 | O | ASP | A | 410 | 21.516 | 75.639 | 7.047 | 1.00 | 21.45 | A | O |
| ATOM | 1550 | N | HIS | A | 411 | 20.675 | 75.476 | 9.106 | 1.00 | 23.41 | A | N |
| ATOM | 1551 | CA | HIS | A | 411 | 19.474 | 74.823 | 8.599 | 1.00 | 17.58 | A | C |
| ATOM | 1552 | CB | HIS | A | 411 | 18.621 | 74.265 | 9.730 | 1.00 | 20.90 | A | C |
| ATOM | 1553 | CG | HIS | A | 411 | 19.184 | 73.018 | 10.327 | 1.00 | 19.34 | A | C |
| ATOM | 1554 | CD2 | HIS | A | 411 | 19.806 | 71.963 | 9.751 | 1.00 | 17.17 | A | C |
| ATOM | 1555 | ND1 | HIS | A | 411 | 19.197 | 72.783 | 11.683 | 1.00 | 18.38 | A | N |
| ATOM | 1556 | CE1 | HIS | A | 411 | 19.781 | 71.621 | 11.921 | 1.00 | 17.55 | A | C |
| ATOM | 1557 | NE2 | HIS | A | 411 | 20.155 | 71.103 | 10.765 | 1.00 | 17.29 | A | N |
| ATOM | 1558 | C | HIS | A | 411 | 18.645 | 75.734 | 7.709 | 1.00 | 21.00 | A | C |
| ATOM | 1559 | O | HIS | A | 411 | 18.748 | 76.950 | 7.774 | 1.00 | 24.03 | A | O |
| ATOM | 1560 | N | SER | A | 412 | 17.825 | 75.111 | 6.876 | 1.00 | 18.89 | A | N |
| ATOM | 1561 | CA | SER | A | 412 | 16.922 | 75.807 | 5.980 | 1.00 | 23.36 | A | C |
| ATOM | 1562 | CB | SER | A | 412 | 17.091 | 75.240 | 4.570 | 1.00 | 17.48 | A | C |
| ATOM | 1563 | OG | SER | A | 412 | 16.056 | 75.677 | 3.716 | 1.00 | 20.87 | A | O |
| ATOM | 1564 | C | SER | A | 412 | 15.497 | 75.568 | 6.448 | 1.00 | 18.23 | A | C |
| ATOM | 1565 | O | SER | A | 412 | 15.211 | 74.544 | 7.061 | 1.00 | 16.35 | A | O |
| ATOM | 1566 | N | SER | A | 413 | 14.599 | 76.492 | 6.122 | 1.00 | 23.17 | A | N |
| ATOM | 1567 | CA | SER | A | 413 | 13.185 | 76.340 | 6.450 | 1.00 | 18.90 | A | C |
| ATOM | 1568 | CB | SER | A | 413 | 12.604 | 77.678 | 6.939 | 1.00 | 22.40 | A | C |
| ATOM | 1569 | OG | SER | A | 413 | 12.647 | 78.641 | 5.901 | 1.00 | 35.17 | A | O |
| ATOM | 1570 | C | SER | A | 413 | 12.385 | 75.756 | 5.272 | 1.00 | 23.12 | A | C |
| ATOM | 1571 | O | SER | A | 413 | 11.220 | 75.382 | 5.415 | 1.00 | 26.66 | A | O |
| ATOM | 1572 | N | VAL | A | 414 | 13.033 | 75.653 | 4.119 | 1.00 | 21.85 | A | N |
| ATOM | 1573 | CA | VAL | A | 414 | 12.472 | 74.956 | 2.967 | 1.00 | 26.76 | A | C |
| ATOM | 1574 | CB | VAL | A | 414 | 13.204 | 75.398 | 1.675 | 1.00 | 22.83 | A | C |
| ATOM | 1575 | CG1 | VAL | A | 414 | 12.639 | 74.718 | 0.451 | 1.00 | 18.19 | A | C |
| ATOM | 1576 | CG2 | VAL | A | 414 | 13.122 | 76.916 | 1.538 | 1.00 | 24.67 | A | C |
| ATOM | 1577 | C | VAL | A | 414 | 12.565 | 73.443 | 3.175 | 1.00 | 23.41 | A | C |
| ATOM | 1578 | O | VAL | A | 414 | 13.664 | 72.893 | 3.231 | 1.00 | 20.83 | A | O |
| ATOM | 1579 | N | PRO | A | 415 | 11.409 | 72.763 | 3.296 | 1.00 | 20.31 | A | N |
| ATOM | 1580 | CD | PRO | A | 415 | 10.056 | 73.326 | 3.175 | 1.00 | 24.76 | A | C |
| ATOM | 1581 | CA | PRO | A | 415 | 11.373 | 71.350 | 3.706 | 1.00 | 21.38 | A | C |
| ATOM | 1582 | CB | PRO | A | 415 | 9.871 | 71.077 | 3.936 | 1.00 | 22.42 | A | C |
| ATOM | 1583 | CG | PRO | A | 415 | 9.244 | 72.431 | 4.080 | 1.00 | 21.16 | A | C |
| ATOM | 1584 | C | PRO | A | 415 | 11.952 | 70.352 | 2.695 | 1.00 | 22.35 | A | C |
| ATOM | 1585 | O | PRO | A | 415 | 12.340 | 69.250 | 3.090 | 1.00 | 22.46 | A | O |
| ATOM | 1586 | N | GLU | A | 416 | 12.031 | 70.735 | 1.423 | 1.00 | 25.51 | A | N |
| ATOM | 1587 | CA | GLU | A | 416 | 12.565 | 69.850 | 0.393 | 1.00 | 21.45 | A | C |
| ATOM | 1588 | CB | GLU | A | 416 | 11.907 | 70.150 | −0.959 | 1.00 | 26.61 | A | C |
| ATOM | 1589 | CG | GLU | A | 416 | 10.385 | 69.967 | −0.982 | 1.00 | 32.11 | A | C |
| ATOM | 1590 | CD | GLU | A | 416 | 9.613 | 71.152 | −0.379 | 1.00 | 32.29 | A | C |
| ATOM | 1591 | OE1 | GLU | A | 416 | 10.112 | 72.306 | −0.406 | 1.00 | 31.31 | A | O |
| ATOM | 1592 | OE2 | GLU | A | 416 | 8.488 | 70.922 | 0.109 | 1.00 | 31.77 | A | O |
| ATOM | 1593 | C | GLU | A | 416 | 14.093 | 69.964 | 0.271 | 1.00 | 24.20 | A | C |
| ATOM | 1594 | O | GLU | A | 416 | 14.750 | 69.125 | −0.358 | 1.00 | 24.70 | A | O |
| ATOM | 1595 | N | ALA | A | 417 | 14.641 | 70.992 | 0.901 | 1.00 | 16.48 | A | N |
| ATOM | 1596 | CA | ALA | A | 417 | 16.057 | 71.323 | 0.826 | 1.00 | 19.74 | A | C |
| ATOM | 1597 | CB | ALA | A | 417 | 16.278 | 72.751 | 1.340 | 1.00 | 16.73 | A | C |
| ATOM | 1598 | C | ALA | A | 417 | 16.929 | 70.371 | 1.618 | 1.00 | 19.17 | A | C |
| ATOM | 1599 | O | ALA | A | 417 | 16.522 | 69.870 | 2.658 | 1.00 | 17.34 | A | O |
| ATOM | 1600 | N | LEU | A | 418 | 18.152 | 70.156 | 1.135 | 1.00 | 22.37 | A | N |
| ATOM | 1601 | CA | LEU | A | 418 | 19.131 | 69.340 | 1.852 | 1.00 | 19.50 | A | C |
| ATOM | 1602 | CB | LEU | A | 418 | 20.429 | 69.238 | 1.038 | 1.00 | 14.34 | A | C |
| ATOM | 1603 | CG | LEU | A | 418 | 21.578 | 68.518 | 1.750 | 1.00 | 18.12 | A | C |
| ATOM | 1604 | CD1 | LEU | A | 418 | 21.310 | 67.015 | 1.863 | 1.00 | 14.68 | A | C |
| ATOM | 1605 | CD2 | LEU | A | 418 | 22.902 | 68.776 | 1.061 | 1.00 | 17.98 | A | C |
| ATOM | 1606 | C | LEU | A | 418 | 19.415 | 69.841 | 3.289 | 1.00 | 18.40 | A | C |
| ATOM | 1607 | O | LEU | A | 418 | 19.559 | 69.035 | 4.209 | 1.00 | 19.39 | A | O |
| ATOM | 1608 | N | MET | A | 419 | 19.513 | 71.160 | 3.482 | 1.00 | 15.39 | A | N |
| ATOM | 1609 | CA | MET | A | 419 | 19.840 | 71.714 | 4.796 | 1.00 | 15.22 | A | C |
| ATOM | 1610 | CB | MET | A | 419 | 20.550 | 73.080 | 4.697 | 1.00 | 14.77 | A | C |
| ATOM | 1611 | CG | MET | A | 419 | 21.913 | 73.039 | 4.023 | 1.00 | 12.11 | A | C |
| ATOM | 1612 | SD | MET | A | 419 | 22.888 | 71.579 | 4.499 | 1.00 | 16.87 | A | S |
| ATOM | 1613 | CE | MET | A | 419 | 23.188 | 71.955 | 6.237 | 1.00 | 16.41 | A | C |
| ATOM | 1614 | C | MET | A | 419 | 18.604 | 71.803 | 5.703 | 1.00 | 20.28 | A | C |
| ATOM | 1615 | O | MET | A | 419 | 18.671 | 72.284 | 6.831 | 1.00 | 17.99 | A | O |
| ATOM | 1616 | N | TYR | A | 420 | 17.469 | 71.318 | 5.214 | 1.00 | 18.67 | A | N |
| ATOM | 1617 | CA | TYR | A | 420 | 16.341 | 71.135 | 6.098 | 1.00 | 20.33 | A | C |
| ATOM | 1618 | CB | TYR | A | 420 | 15.129 | 70.638 | 5.335 | 1.00 | 21.73 | A | C |

TABLE 15-continued

Coordinates for apo form of proMMP9(35-444 ΔFnII) (SEQ ID NO: 12)

| ATOM | 1619 | CG  | TYR | A | 420 | 13.834 | 70.762 | 6.105  | 1.00 | 22.01 | A | C |
|------|------|-----|-----|---|-----|--------|--------|--------|------|-------|---|---|
| ATOM | 1620 | CD1 | TYR | A | 420 | 13.279 | 72.007 | 6.398  | 1.00 | 20.60 | A | C |
| ATOM | 1621 | CE1 | TYR | A | 420 | 12.084 | 72.102 | 7.096  | 1.00 | 22.90 | A | C |
| ATOM | 1622 | CD2 | TYR | A | 420 | 13.163 | 69.634 | 6.541  | 1.00 | 19.51 | A | C |
| ATOM | 1623 | CE2 | TYR | A | 420 | 11.973 | 69.722 | 7.233  | 1.00 | 17.63 | A | C |
| ATOM | 1624 | CZ  | TYR | A | 420 | 11.433 | 70.950 | 7.517  | 1.00 | 21.67 | A | C |
| ATOM | 1625 | OH  | TYR | A | 420 | 10.230 | 71.017 | 8.228  | 1.00 | 17.31 | A | O |
| ATOM | 1626 | C   | TYR | A | 420 | 16.764 | 70.133 | 7.163  | 1.00 | 19.53 | A | C |
| ATOM | 1627 | O   | TYR | A | 420 | 17.453 | 69.159 | 6.875  | 1.00 | 17.97 | A | O |
| ATOM | 1628 | N   | PRO | A | 421 | 16.371 | 70.379 | 8.412  | 1.00 | 19.34 | A | N |
| ATOM | 1629 | CD  | PRO | A | 421 | 15.598 | 71.526 | 8.915  | 1.00 | 18.90 | A | C |
| ATOM | 1630 | CA  | PRO | A | 421 | 16.927 | 69.559 | 9.494  | 1.00 | 17.69 | A | C |
| ATOM | 1631 | CB  | PRO | A | 421 | 16.589 | 70.367 | 10.748 | 1.00 | 16.91 | A | C |
| ATOM | 1632 | CG  | PRO | A | 421 | 15.395 | 71.177 | 10.357 | 1.00 | 18.01 | A | C |
| ATOM | 1633 | C   | PRO | A | 421 | 16.361 | 68.126 | 9.574  | 1.00 | 14.43 | A | C |
| ATOM | 1634 | O   | PRO | A | 421 | 17.083 | 67.244 | 9.999  | 1.00 | 16.67 | A | O |
| ATOM | 1635 | N   | MET | A | 422 | 15.129 | 67.881 | 9.142  | 1.00 | 20.28 | A | N |
| ATOM | 1636 | CA  | MET | A | 422 | 14.602 | 66.514 | 9.184  | 1.00 | 21.94 | A | C |
| ATOM | 1637 | CB  | MET | A | 422 | 13.083 | 66.473 | 9.066  | 1.00 | 19.96 | A | C |
| ATOM | 1638 | CG  | MET | A | 422 | 12.345 | 67.350 | 10.048 | 1.00 | 24.76 | A | C |
| ATOM | 1639 | SD  | MET | A | 422 | 10.575 | 67.036 | 9.965  | 1.00 | 26.36 | A | S |
| ATOM | 1640 | CE  | MET | A | 422 | 9.943  | 68.445 | 10.880 | 1.00 | 18.38 | A | C |
| ATOM | 1641 | C   | MET | A | 422 | 15.200 | 65.618 | 8.102  | 1.00 | 19.89 | A | C |
| ATOM | 1642 | O   | MET | A | 422 | 15.536 | 66.072 | 7.015  | 1.00 | 22.68 | A | O |
| ATOM | 1643 | N   | TYR | A | 423 | 15.329 | 64.337 | 8.423  | 1.00 | 19.74 | A | N |
| ATOM | 1644 | CA  | TYR | A | 423 | 15.749 | 63.350 | 7.453  | 1.00 | 21.11 | A | C |
| ATOM | 1645 | CB  | TYR | A | 423 | 16.180 | 62.044 | 8.140  | 1.00 | 21.72 | A | C |
| ATOM | 1646 | CG  | TYR | A | 423 | 16.533 | 60.962 | 7.136  | 1.00 | 21.32 | A | C |
| ATOM | 1647 | CD1 | TYR | A | 423 | 15.599 | 60.007 | 6.738  | 1.00 | 18.43 | A | C |
| ATOM | 1648 | CE1 | TYR | A | 423 | 15.931 | 59.027 | 5.795  | 1.00 | 20.32 | A | C |
| ATOM | 1649 | CD2 | TYR | A | 423 | 17.791 | 60.921 | 6.556  | 1.00 | 22.39 | A | C |
| ATOM | 1650 | CE2 | TYR | A | 423 | 18.124 | 59.958 | 5.616  | 1.00 | 20.32 | A | C |
| ATOM | 1651 | CZ  | TYR | A | 423 | 17.192 | 59.009 | 5.240  | 1.00 | 20.13 | A | C |
| ATOM | 1652 | OH  | TYR | A | 423 | 17.536 | 58.064 | 4.290  | 1.00 | 19.72 | A | O |
| ATOM | 1653 | C   | TYR | A | 423 | 14.565 | 63.073 | 6.543  | 1.00 | 23.33 | A | C |
| ATOM | 1654 | O   | TYR | A | 423 | 13.453 | 62.853 | 7.033  | 1.00 | 23.69 | A | O |
| ATOM | 1655 | N   | ARG | A | 424 | 14.805 | 63.087 | 5.231  | 1.00 | 22.96 | A | N |
| ATOM | 1656 | CA  | ARG | A | 424 | 13.835 | 62.611 | 4.248  | 1.00 | 23.79 | A | C |
| ATOM | 1657 | CB  | ARG | A | 424 | 13.025 | 63.771 | 3.664  | 1.00 | 26.70 | A | C |
| ATOM | 1658 | CG  | ARG | A | 424 | 13.783 | 64.513 | 2.566  | 1.00 | 33.42 | A | C |
| ATOM | 1659 | CD  | ARG | A | 424 | 12.923 | 65.521 | 1.823  | 1.00 | 37.37 | A | C |
| ATOM | 1660 | NE  | ARG | A | 424 | 13.678 | 66.124 | 0.735  | 1.00 | 33.14 | A | N |
| ATOM | 1661 | CZ  | ARG | A | 424 | 13.331 | 66.047 | −0.544 | 1.00 | 30.07 | A | C |
| ATOM | 1662 | NH1 | ARG | A | 424 | 12.225 | 65.404 | −0.897 | 1.00 | 35.26 | A | N |
| ATOM | 1663 | NH2 | ARG | A | 424 | 14.092 | 66.613 | −1.469 | 1.00 | 32.21 | A | N |
| ATOM | 1664 | C   | ARG | A | 424 | 14.582 | 61.906 | 3.115  | 1.00 | 27.22 | A | C |
| ATOM | 1665 | O   | ARG | A | 424 | 15.349 | 62.540 | 2.377  | 1.00 | 29.66 | A | O |
| ATOM | 1666 | N   | PHE | A | 425 | 14.388 | 60.598 | 2.971  | 1.00 | 21.31 | A | N |
| ATOM | 1667 | CA  | PHE | A | 425 | 15.125 | 59.896 | 1.935  | 1.00 | 20.42 | A | C |
| ATOM | 1668 | CB  | PHE | A | 425 | 15.053 | 58.381 | 2.108  | 1.00 | 17.81 | A | C |
| ATOM | 1669 | CG  | PHE | A | 425 | 15.552 | 57.621 | 0.925  | 1.00 | 17.63 | A | C |
| ATOM | 1670 | CD1 | PHE | A | 425 | 16.899 | 57.348 | 0.777  | 1.00 | 20.28 | A | C |
| ATOM | 1671 | CD2 | PHE | A | 425 | 14.677 | 57.191 | −0.052 | 1.00 | 18.22 | A | C |
| ATOM | 1672 | CE1 | PHE | A | 425 | 17.362 | 56.639 | −0.338 | 1.00 | 21.79 | A | C |
| ATOM | 1673 | CE2 | PHE | A | 425 | 15.130 | 56.485 | −1.151 | 1.00 | 23.43 | A | C |
| ATOM | 1674 | CZ  | PHE | A | 425 | 16.476 | 56.208 | −1.288 | 1.00 | 21.36 | A | C |
| ATOM | 1675 | C   | PHE | A | 425 | 14.587 | 60.317 | 0.575  | 1.00 | 20.67 | A | C |
| ATOM | 1676 | O   | PHE | A | 425 | 13.435 | 60.731 | 0.453  | 1.00 | 26.14 | A | O |
| ATOM | 1677 | N   | THR | A | 426 | 15.438 | 60.234 | −0.433 | 1.00 | 22.83 | A | N |
| ATOM | 1678 | CA  | THR | A | 426 | 15.074 | 60.615 | −1.790 | 1.00 | 23.78 | A | C |
| ATOM | 1679 | CB  | THR | A | 426 | 15.106 | 62.145 | −1.959 | 1.00 | 27.93 | A | C |
| ATOM | 1680 | OG1 | THR | A | 426 | 14.661 | 62.488 | −3.273 | 1.00 | 26.52 | A | O |
| ATOM | 1681 | CG2 | THR | A | 426 | 16.521 | 62.676 | −1.760 | 1.00 | 27.57 | A | C |
| ATOM | 1682 | C   | THR | A | 426 | 16.073 | 60.005 | −2.746 | 1.00 | 22.46 | A | C |
| ATOM | 1683 | O   | THR | A | 426 | 17.226 | 59.791 | −2.373 | 1.00 | 24.24 | A | O |
| ATOM | 1684 | N   | GLU | A | 427 | 15.636 | 59.714 | −3.972 | 1.00 | 24.46 | A | N |
| ATOM | 1685 | CA  | GLU | A | 427 | 16.543 | 59.234 | −5.004 | 1.00 | 25.45 | A | C |
| ATOM | 1686 | CB  | GLU | A | 427 | 15.923 | 58.072 | −5.785 | 1.00 | 24.88 | A | C |
| ATOM | 1687 | CG  | GLU | A | 427 | 16.068 | 56.718 | −5.090 | 1.00 | 25.39 | A | C |
| ATOM | 1688 | CD  | GLU | A | 427 | 14.999 | 55.717 | −5.484 | 1.00 | 41.36 | A | C |
| ATOM | 1689 | OE1 | GLU | A | 427 | 13.957 | 56.130 | −6.046 | 1.00 | 46.52 | A | O |
| ATOM | 1690 | OE2 | GLU | A | 427 | 15.195 | 54.511 | −5.220 | 1.00 | 44.76 | A | O |
| ATOM | 1691 | C   | GLU | A | 427 | 16.906 | 60.398 | −5.924 | 1.00 | 25.02 | A | C |
| ATOM | 1692 | O   | GLU | A | 427 | 17.839 | 60.308 | −6.709 | 1.00 | 22.84 | A | O |
| ATOM | 1693 | N   | GLY | A | 428 | 16.174 | 61.501 | −5.806 | 1.00 | 27.58 | A | N |
| ATOM | 1694 | CA  | GLY | A | 428 | 16.474 | 62.688 | −6.596 | 1.00 | 19.87 | A | C |
| ATOM | 1695 | C   | GLY | A | 428 | 17.800 | 63.325 | −6.213 | 1.00 | 22.23 | A | C |
| ATOM | 1696 | O   | GLY | A | 428 | 18.373 | 63.026 | −5.144 | 1.00 | 20.97 | A | O |

TABLE 15-continued

Coordinates for apo form of proMMP9(35-444 ΔFnII) (SEQ ID NO: 12)

| ATOM | 1697 | N   | PRO | A | 429 | 18.308 | 64.219 | −7.081 | 1.00 | 18.13 | A | N |
|------|------|-----|-----|---|-----|--------|--------|--------|------|-------|---|---|
| ATOM | 1698 | CD  | PRO | A | 429 | 17.707 | 64.651 | −8.362 | 1.00 | 18.91 | A | C |
| ATOM | 1699 | CA  | PRO | A | 429 | 19.518 | 64.967 | −6.756 | 1.00 | 17.84 | A | C |
| ATOM | 1700 | CB  | PRO | A | 429 | 19.645 | 65.969 | −7.917 | 1.00 | 16.81 | A | C |
| ATOM | 1701 | CG  | PRO | A | 429 | 18.854 | 65.325 | −9.058 | 1.00 | 19.09 | A | C |
| ATOM | 1702 | C   | PRO | A | 429 | 19.333 | 65.700 | −5.430 | 1.00 | 16.73 | A | C |
| ATOM | 1703 | O   | PRO | A | 429 | 18.336 | 66.402 | −5.220 | 1.00 | 15.42 | A | O |
| ATOM | 1704 | N   | PRO | A | 430 | 20.291 | 65.527 | −4.522 | 1.00 | 18.66 | A | N |
| ATOM | 1705 | CD  | PRO | A | 430 | 21.387 | 64.540 | −4.588 | 1.00 | 16.46 | A | C |
| ATOM | 1706 | CA  | PRO | A | 430 | 20.121 | 66.058 | −3.167 | 1.00 | 16.69 | A | C |
| ATOM | 1707 | CB  | PRO | A | 430 | 21.356 | 65.520 | −2.436 | 1.00 | 19.56 | A | C |
| ATOM | 1708 | CG  | PRO | A | 430 | 21.615 | 64.208 | −3.109 | 1.00 | 13.45 | A | C |
| ATOM | 1709 | C   | PRO | A | 430 | 20.029 | 67.595 | −3.057 | 1.00 | 18.52 | A | C |
| ATOM | 1710 | O   | PRO | A | 430 | 19.242 | 68.080 | −2.247 | 1.00 | 14.26 | A | O |
| ATOM | 1711 | N   | LEU | A | 431 | 20.780 | 68.344 | −3.859 | 1.00 | 12.35 | A | N |
| ATOM | 1712 | CA  | LEU | A | 431 | 20.774 | 69.793 | −3.716 | 1.00 | 16.93 | A | C |
| ATOM | 1713 | CB  | LEU | A | 431 | 22.038 | 70.414 | −4.317 | 1.00 | 13.30 | A | C |
| ATOM | 1714 | CG  | LEU | A | 431 | 23.347 | 69.980 | −3.668 | 1.00 | 18.77 | A | C |
| ATOM | 1715 | CD1 | LEU | A | 431 | 24.550 | 70.368 | −4.530 | 1.00 | 12.81 | A | C |
| ATOM | 1716 | CD2 | LEU | A | 431 | 23.462 | 70.536 | −2.254 | 1.00 | 16.61 | A | C |
| ATOM | 1717 | C   | LEU | A | 431 | 19.548 | 70.484 | −4.305 | 1.00 | 17.06 | A | C |
| ATOM | 1718 | O   | LEU | A | 431 | 19.010 | 70.073 | −5.331 | 1.00 | 15.66 | A | O |
| ATOM | 1719 | N   | HIS | A | 432 | 19.124 | 71.548 | −3.638 | 1.00 | 17.17 | A | N |
| ATOM | 1720 | CA  | HIS | A | 432 | 18.039 | 72.394 | −4.120 | 1.00 | 18.04 | A | C |
| ATOM | 1721 | CB  | HIS | A | 432 | 16.814 | 72.264 | −3.194 | 1.00 | 17.82 | A | C |
| ATOM | 1722 | CO  | HIS | A | 432 | 16.084 | 70.965 | −3.360 | 1.00 | 16.24 | A | C |
| ATOM | 1723 | CD2 | HIS | A | 432 | 14.880 | 70.683 | −3.909 | 1.00 | 17.82 | A | C |
| ATOM | 1724 | ND1 | HIS | A | 432 | 16.628 | 69.751 | −2.987 | 1.00 | 19.06 | A | N |
| ATOM | 1725 | CE1 | HIS | A | 432 | 15.780 | 68.781 | −3.286 | 1.00 | 17.03 | A | C |
| ATOM | 1726 | NE2 | HIS | A | 432 | 14.712 | 69.321 | −3.847 | 1.00 | 20.61 | A | N |
| ATOM | 1727 | C   | HIS | A | 432 | 18.531 | 73.831 | −4.207 | 1.00 | 16.84 | A | C |
| ATOM | 1728 | O   | HIS | A | 432 | 19.624 | 74.144 | −3.737 | 1.00 | 15.57 | A | O |
| ATOM | 1729 | N   | LYS | A | 433 | 17.729 | 74.697 | −4.816 | 1.00 | 15.30 | A | N |
| ATOM | 1730 | CA  | LYS | A | 433 | 18.089 | 76.092 | −5.013 | 1.00 | 18.53 | A | C |
| ATOM | 1731 | CB  | LYS | A | 433 | 16.885 | 76.848 | −5.567 | 1.00 | 16.42 | A | C |
| ATOM | 1732 | CG  | LYS | A | 433 | 16.437 | 76.421 | −6.965 | 1.00 | 16.12 | A | C |
| ATOM | 1733 | CD  | LYS | A | 433 | 15.053 | 76.999 | −7.263 | 1.00 | 17.15 | A | C |
| ATOM | 1734 | CE  | LYS | A | 433 | 14.558 | 76.604 | −8.661 | 1.00 | 23.44 | A | C |
| ATOM | 1735 | NZ  | LYS | A | 433 | 15.422 | 77.208 | −9.710 | 1.00 | 17.67 | A | N |
| ATOM | 1736 | C   | LYS | A | 433 | 18.524 | 76.771 | −3.724 | 1.00 | 19.85 | A | C |
| ATOM | 1737 | O   | LYS | A | 433 | 19.440 | 77.611 | −3.720 | 1.00 | 19.71 | A | O |
| ATOM | 1738 | N   | ASP | A | 434 | 17.815 | 76.458 | −2.646 | 1.00 | 19.72 | A | N |
| ATOM | 1739 | CA  | ASP | A | 434 | 18.094 | 77.050 | −1.345 | 1.00 | 17.66 | A | C |
| ATOM | 1740 | CB  | ASP | A | 434 | 17.073 | 76.577 | −0.325 | 1.00 | 17.41 | A | C |
| ATOM | 1741 | CG  | ASP | A | 434 | 17.021 | 77.467 | 0.873  | 1.00 | 20.80 | A | C |
| ATOM | 1742 | OD1 | ASP | A | 434 | 16.602 | 78.637 | 0.709  | 1.00 | 19.19 | A | O |
| ATOM | 1743 | OD2 | ASP | A | 434 | 17.414 | 77.005 | 1.967  | 1.00 | 23.04 | A | O |
| ATOM | 1744 | C   | ASP | A | 434 | 19.498 | 76.716 | −0.852 | 1.00 | 16.49 | A | C |
| ATOM | 1745 | O   | ASP | A | 434 | 20.231 | 77.598 | −0.366 | 1.00 | 16.36 | A | O |
| ATOM | 1746 | N   | ASP | A | 435 | 19.873 | 75.444 | −0.969 | 1.00 | 15.24 | A | N |
| ATOM | 1747 | CA  | ASP | A | 435 | 21.215 | 75.011 | −0.571 | 1.00 | 13.76 | A | C |
| ATOM | 1748 | CB  | ASP | A | 435 | 21.361 | 73.474 | −0.635 | 1.00 | 13.65 | A | C |
| ATOM | 1749 | CG  | ASP | A | 435 | 20.186 | 72.742 | −0.018 | 1.00 | 14.94 | A | C |
| ATOM | 1750 | OD1 | ASP | A | 435 | 19.962 | 72.882 | 1.207  | 1.00 | 16.15 | A | O |
| ATOM | 1751 | OD2 | ASP | A | 435 | 19.484 | 72.015 | −0.758 | 1.00 | 20.89 | A | O |
| ATOM | 1752 | C   | ASP | A | 435 | 22.295 | 75.671 | −1.445 | 1.00 | 16.71 | A | C |
| ATOM | 1753 | O   | ASP | A | 435 | 23.352 | 76.082 | −0.945 | 1.00 | 21.20 | A | O |
| ATOM | 1754 | N   | VAL | A | 436 | 22.052 | 75.756 | −2.747 | 1.00 | 20.97 | A | N |
| ATOM | 1755 | CA  | VAL | A | 436 | 23.092 | 76.273 | −3.655 | 1.00 | 16.69 | A | C |
| ATOM | 1756 | CB  | VAL | A | 436 | 22.788 | 75.979 | −5.133 | 1.00 | 17.52 | A | C |
| ATOM | 1757 | CG1 | VAL | A | 436 | 23.832 | 76.659 | −6.038 | 1.00 | 13.35 | A | C |
| ATOM | 1758 | CG2 | VAL | A | 436 | 22.697 | 74.436 | −5.414 | 1.00 | 11.72 | A | C |
| ATOM | 1759 | C   | VAL | A | 436 | 23.264 | 77.787 | −3.433 | 1.00 | 15.65 | A | C |
| ATOM | 1760 | O   | VAL | A | 436 | 24.379 | 78.310 | −3.327 | 1.00 | 17.23 | A | O |
| ATOM | 1761 | N   | ASN | A | 437 | 22.144 | 78.483 | −3.353 | 1.00 | 18.51 | A | N |
| ATOM | 1762 | CA  | ASN | A | 437 | 22.162 | 79.899 | −3.057 | 1.00 | 17.03 | A | C |
| ATOM | 1763 | CB  | ASN | A | 437 | 20.752 | 80.467 | −3.168 | 1.00 | 23.11 | A | C |
| ATOM | 1764 | CG  | ASN | A | 437 | 20.297 | 80.595 | −4.609 | 1.00 | 23.27 | A | C |
| ATOM | 1765 | OD1 | ASN | A | 437 | 21.090 | 80.420 | −5.538 | 1.00 | 23.74 | A | O |
| ATOM | 1766 | ND2 | ASN | A | 437 | 19.018 | 80.883 | −4.809 | 1.00 | 26.53 | A | N |
| ATOM | 1767 | C   | ASN | A | 437 | 22.781 | 80.167 | −1.685 | 1.00 | 23.58 | A | C |
| ATOM | 1768 | O   | ASN | A | 437 | 23.538 | 81.123 | −1.512 | 1.00 | 21.25 | A | O |
| ATOM | 1769 | N   | GLY | A | 438 | 22.500 | 79.284 | −0.728 | 1.00 | 17.14 | A | N |
| ATOM | 1770 | CA  | GLY | A | 438 | 23.045 | 79.422 | 0.610  | 1.00 | 20.64 | A | C |
| ATOM | 1771 | C   | GLY | A | 438 | 24.559 | 79.422 | 0.573  | 1.00 | 26.22 | A | C |
| ATOM | 1772 | O   | GLY | A | 438 | 25.225 | 80.279 | 1.170  | 1.00 | 27.43 | A | O |
| ATOM | 1773 | N   | ILE | A | 439 | 25.117 | 78.456 | −0.139 | 1.00 | 20.58 | A | N |
| ATOM | 1774 | CA  | ILE | A | 439 | 26.559 | 78.329 | −0.217 | 1.00 | 24.44 | A | C |

TABLE 15-continued

Coordinates for apo form of proMMP9(35-444 ΔFnII) (SEQ ID NO: 12)

| ATOM | 1775 | CB | ILE | A | 439 | 26.980 | 76.891 | −0.645 | 1.00 | 23.24 | A | C |
|---|---|---|---|---|---|---|---|---|---|---|---|---|
| ATOM | 1776 | CG2 | ILE | A | 439 | 26.913 | 76.722 | −2.141 | 1.00 | 22.12 | A | C |
| ATOM | 1777 | CG1 | ILE | A | 439 | 28.360 | 76.538 | −0.086 | 1.00 | 23.37 | A | C |
| ATOM | 1778 | CD1 | ILE | A | 439 | 28.421 | 76.519 | 1.447 | 1.00 | 21.30 | A | C |
| ATOM | 1779 | C | ILE | A | 439 | 27.180 | 79.417 | −1.117 | 1.00 | 25.93 | A | C |
| ATOM | 1780 | O | ILE | A | 439 | 28.270 | 79.909 | −0.830 | 1.00 | 25.28 | A | O |
| ATOM | 1781 | N | ARG | A | 440 | 26.486 | 79.800 | −2.186 | 1.00 | 25.31 | A | N |
| ATOM | 1782 | CA | ARG | A | 440 | 26.980 | 80.874 | −3.047 | 1.00 | 26.15 | A | C |
| ATOM | 1783 | CB | ARG | A | 440 | 26.077 | 81.092 | −4.262 | 1.00 | 25.27 | A | C |
| ATOM | 1784 | CG | ARG | A | 440 | 26.093 | 79.982 | −5.282 | 1.00 | 25.92 | A | C |
| ATOM | 1785 | CD | ARG | A | 440 | 25.257 | 80.362 | −6.486 | 1.00 | 29.79 | A | C |
| ATOM | 1786 | NE | ARG | A | 440 | 25.934 | 81.336 | −7.350 | 1.00 | 24.11 | A | N |
| ATOM | 1787 | CZ | ARG | A | 440 | 25.541 | 81.611 | −8.588 | 1.00 | 27.82 | A | C |
| ATOM | 1788 | NH1 | ARG | A | 440 | 24.475 | 80.993 | −9.088 | 1.00 | 26.26 | A | N |
| ATOM | 1789 | NH2 | ARG | A | 440 | 26.207 | 82.491 | −9.328 | 1.00 | 21.28 | A | N |
| ATOM | 1790 | C | ARG | A | 440 | 27.090 | 82.178 | −2.267 | 1.00 | 27.53 | A | C |
| ATOM | 1791 | O | ARG | A | 440 | 28.041 | 82.946 | −2.453 | 1.00 | 31.84 | A | O |
| ATOM | 1792 | N | HIS | A | 441 | 26.106 | 82.424 | −1.403 | 1.00 | 29.10 | A | N |
| ATOM | 1793 | CA | HIS | A | 441 | 26.079 | 83.619 | −0.569 | 1.00 | 28.90 | A | C |
| ATOM | 1794 | CB | HIS | A | 441 | 24.697 | 83.808 | 0.068 | 1.00 | 30.71 | A | C |
| ATOM | 1795 | CG | HIS | A | 441 | 23.591 | 84.022 | −0.914 | 1.00 | 30.92 | A | C |
| ATOM | 1796 | CD2 | HIS | A | 441 | 22.246 | 84.039 | −0.748 | 1.00 | 26.53 | A | C |
| ATOM | 1797 | ND1 | HIS | A | 441 | 23.814 | 84.252 | −2.255 | 1.00 | 24.41 | A | N |
| ATOM | 1798 | CE1 | HIS | A | 441 | 22.656 | 84.410 | −2.871 | 1.00 | 25.22 | A | C |
| ATOM | 1799 | NE2 | HIS | A | 441 | 21.688 | 84.276 | −1.981 | 1.00 | 29.06 | A | N |
| ATOM | 1800 | C | HIS | A | 441 | 27.129 | 83.545 | 0.540 | 1.00 | 30.68 | A | C |
| ATOM | 1801 | O | HIS | A | 441 | 27.157 | 84.395 | 1.425 | 1.00 | 29.55 | A | O |
| ATOM | 1802 | N | LEU | A | 442 | 27.975 | 82.520 | 0.490 | 1.00 | 28.39 | A | N |
| ATOM | 1803 | CA | LEU | A | 442 | 28.982 | 82.289 | 1.514 | 1.00 | 28.94 | A | C |
| ATOM | 1804 | CB | LEU | A | 442 | 28.710 | 80.953 | 2.208 | 1.00 | 34.10 | A | C |
| ATOM | 1805 | CG | LEU | A | 442 | 29.489 | 80.668 | 3.488 | 1.00 | 36.13 | A | C |
| ATOM | 1806 | CD1 | LEU | A | 442 | 29.759 | 81.966 | 4.233 | 1.00 | 32.27 | A | C |
| ATOM | 1807 | CD2 | LEU | A | 442 | 28.721 | 79.680 | 4.353 | 1.00 | 25.97 | A | C |
| ATOM | 1808 | C | LEU | A | 442 | 30.413 | 82.301 | 0.981 | 1.00 | 32.13 | A | C |
| ATOM | 1809 | O | LEU | A | 442 | 31.315 | 82.872 | 1.598 | 1.00 | 32.29 | A | O |
| ATOM | 1810 | N | TYR | A | 443 | 30.629 | 81.652 | −0.157 | 1.00 | 30.74 | A | N |
| ATOM | 1811 | CA | TYR | A | 443 | 31.968 | 81.531 | −0.714 | 1.00 | 28.94 | A | C |
| ATOM | 1812 | CB | TYR | A | 443 | 32.384 | 80.051 | −0.830 | 1.00 | 30.85 | A | C |
| ATOM | 1813 | CG | TYR | A | 443 | 32.712 | 79.388 | 0.502 | 1.00 | 29.82 | A | C |
| ATOM | 1814 | CD1 | TYR | A | 443 | 31.787 | 78.569 | 1.144 | 1.00 | 26.51 | A | C |
| ATOM | 1815 | CE1 | TYR | A | 443 | 32.084 | 77.967 | 2.360 | 1.00 | 23.42 | A | C |
| ATOM | 1816 | CD2 | TYR | A | 443 | 33.949 | 79.583 | 1.115 | 1.00 | 28.80 | A | C |
| ATOM | 1817 | CE2 | TYR | A | 443 | 34.259 | 78.981 | 2.343 | 1.00 | 23.90 | A | C |
| ATOM | 1818 | CZ | TYR | A | 443 | 33.316 | 78.177 | 2.961 | 1.00 | 20.93 | A | C |
| ATOM | 1819 | OH | TYR | A | 443 | 33.598 | 77.574 | 4.179 | 1.00 | 25.03 | A | O |
| ATOM | 1820 | C | TYR | A | 443 | 32.024 | 82.214 | −2.080 | 1.00 | 38.07 | A | C |
| ATOM | 1821 | O | TYR | A | 443 | 31.212 | 81.921 | −2.959 | 1.00 | 33.93 | A | O |
| ATOM | 1822 | ZN | ZN | A | 500 | 21.724 | 69.882 | 10.344 | 1.00 | 19.81 | A | Zn |
| ATOM | 1823 | ZN | ZN | A | 501 | 29.842 | 64.678 | 18.223 | 1.00 | 27.41 | A | Zn |
| ATOM | 1824 | CA | CA | A | 502 | 20.215 | 58.596 | 17.390 | 1.00 | 28.51 | A | Ca |
| ATOM | 1825 | CA | CA | A | 504 | 38.342 | 70.185 | 12.627 | 1.00 | 41.48 | A | Ca |
| ATOM | 1826 | CA | CA | A | 505 | 41.195 | 78.710 | 7.741 | 1.00 | 45.09 | A | Ca |
| TER | 1827 | | CA | A | 505 | | | | | | | |
| END | | | | | | | | | | | | |

The invention claimed is:

1. A method for designing, selecting and/or optimizing a chemical entity that binds to an allosteric binding site of proMMP9 comprising the steps of:

a. employing the structural coordinates of proMMP9 according to any one of Tables 11-14 to generate a three-dimensional model of said proMMP9 on a computer, wherein said computer comprises the means for generating said three-dimensional model;

b. identifying three-dimensional structural information of an allosteric binding site of proMMP9, wherein said allosteric binding site comprises amino acid residues 100-102, 110, 114, 177-179, 190-193, and 405-410, and wherein said allosteric binding site comprises a region of space that is occupied by phenylalanine (Phe) 107 in the apo form of proMMP9, numbering taken from full-length human matrix metalloproteinase-9 precursor, proMMP9(1-707) (SEQ ID NO:1);

c. employing the three-dimensional structural information identified in (b) to design, select and/or optimize said chemical entity by performing a fitting operation between said chemical entity and said three-dimensional structural information of all or part of said allosteric binding site.

2. A method for evaluating the ability of a chemical entity to associate with all or part of an allosteric binding site of proMMP9 comprising the steps of:

a. employing the structural coordinates of proMMP9 according to any to any one of Tables 11-14 to generate a three-dimensional model of said proMMP9 on a computer, wherein said computer comprises the means for generating said three-dimensional model;

b. identifying three-dimensional structural information of an allosteric binding site for said chemical entity, wherein said allosteric binding site comprises amino acid residues 100-102, 110, 114, 177-179, 190-193, and 405-410, and wherein said binding site comprises a region of space that is occupied by Phe 107 in the apo form of proMMP9, numbering taken from full-length human matrix metalloproteinase-9 precursor, proMMP9(1-707) (SEQ ID NO:1);

c. employing computational means to perform a fitting operation between the chemical entity and said three-dimensional structural information of all or part of the allosteric binding site identified in (b); and d. analyzing the results of said fitting operation to quantitate the association between the chemical entity and all or part of the allosteric binding site.

3. A method of employing a computer for evaluating the ability of a chemical entity to associate with all or part of an allosteric binding site of proMMP9, wherein said computer comprises a machine-readable data storage medium comprising a data storage material encoded with the structure coordinates of said proMMP9 according to any one of Tables 11-14 and means for generating a three-dimensional graphical representation of said proMMP9, and wherein said method comprises the steps of:

a. employing the structural coordinates of said proMMP9 according to any one of Tables 11-14 to generate a three-dimensional model of said proMMP9 on said computer;

b. identifying three-dimensional structural information of an allosteric binding site for said chemical entity, wherein said allosteric binding site comprises amino acid residues 100-102, 110, 114, 177-179, 190-193, and 405-410, and wherein said binding site comprises a region of space that is occupied by Phe 107 in the apo form of proMMP9;

c. employing computational means to perform a fitting operation between the chemical entity and said three-dimensional structural information of all or part of the allosteric binding site identified in (b); and d. analyzing the results of said fitting operation to quantitate the association between said chemical entity and said three-dimensional structural information of all or part of the allosteric binding site.

4. The method according to claim 3, further comprising the steps of:

(e) repeating steps (a) through (d) with a second chemical entity; and (f) selecting at least one part of said first or second chemical entity that associates with said three-dimensional structural information of all or part of said allosteric binding site based on said quantitated association of said first or second chemical entity.

* * * * *